US012545886B2

(12) United States Patent
Falb et al.

(10) Patent No.: US 12,545,886 B2

(45) **Date of Patent: *Feb. 10, 2026**

(54) BACTERIA FOR THE TREATMENT OF DISORDERS

(71) Applicant: Synlogic Operating Company, Inc., Cambridge, MA (US)

(72) Inventors: Dean Falb, Sherborn, MA (US); Adam B. Fisher, Cambridge, MA (US); Vincent M. Isabella, Medford, MA (US); Jonathan W. Kotula, Berkeley, CA (US); David Lubkowicz, Somerville, MA (US); Paul F. Miller, Salem, CT (US); Yves Millet, Newton, MA (US); Sarah Elizabeth Rowe, Durham, NC (US)

(73) Assignee: Synlogic Operating Company, Inc., Winchester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/512,389

(22) Filed: Nov. 17, 2023

(65) Prior Publication Data

US 2024/0368531 A1 Nov. 7, 2024

Related U.S. Application Data

(63) Continuation of application No. 16/621,792, filed as application No. PCT/US2018/038840 on Jun. 21, 2018, now Pat. No. 11,879,123.

(60) Provisional application No. 62/624,299, filed on Jan. 31, 2018, provisional application No. 62/614,213, filed on Jan. 5, 2018, provisional application No. 62/552,829, filed on Aug. 31, 2017, provisional application No. 62/552,785, filed on Aug. 31, 2017, provisional application No. 62/523,225, filed on Jun. 21, 2017, provisional application No. 62/523,202, filed on Jun. 21, 2017.

(51) Int. Cl.

| | |
|---|---|
| ***A61K 9/00*** | (2006.01) |
| ***A61K 35/74*** | (2015.01) |
| ***A61K 35/741*** | (2015.01) |
| ***C07K 14/245*** | (2006.01) |
| ***C12N 1/20*** | (2006.01) |
| ***C12N 15/63*** | (2006.01) |
| ***C12Q 1/527*** | (2006.01) |

(52) U.S. Cl.

CPC .............. *C12N 1/20* (2013.01); *A61K 9/0053* (2013.01); *A61K 35/74* (2013.01); *A61K 35/741* (2013.01); *C07K 14/245* (2013.01); *C12N 15/63* (2013.01); *C12N 2510/00* (2013.01); *C12N 2795/00021* (2013.01); *C12N 2800/202* (2013.01); *C12Q 1/527* (2013.01)

(58) Field of Classification Search

CPC .... A61K 9/0053; A61K 35/74; A61K 35/741; C07K 14/245; C12N 1/20; C12N 9/0022; C12N 9/88; C12N 15/63; C12N 2510/00; C12N 2795/00021; C12N 2800/202; C12Q 1/527

See application file for complete search history.

(56) References Cited

U.S. PATENT DOCUMENTS

| | | | |
|---|---|---|---|
| 5,589,168 | A | 12/1996 | Allen et al. |
| 5,989,463 | A | 11/1999 | Tracy et al. |
| 6,203,797 | B1 | 3/2001 | Perry |
| 6,835,376 | B1 | 12/2004 | Neeser et al. |
| 7,314,974 | B2 | 1/2008 | Cao et al. |
| 7,731,976 | B2 | 6/2010 | Cobb et al. |
| 8,541,208 | B1 | 9/2013 | Plesch et al. |
| 8,735,107 | B2 | 5/2014 | Weiner et al. |
| 9,150,845 | B2 | 10/2015 | Weiner et al. |
| 9,688,967 | B2 | 6/2017 | Falb et al. |
| 9,889,164 | B2 | 2/2018 | Falb et al. |
| 9,943,555 | B2 | 4/2018 | Falb et al. |
| 10,195,234 | B2 | 2/2019 | Falb et al. |
| 10,294,499 | B2 | 5/2019 | Simon Vecilla et al. |
| 10,610,546 | B2 | 4/2020 | Falb et al. |
| 10,883,115 | B2 | 1/2021 | Ayal et al. |
| 11,060,073 | B2 | 7/2021 | Falb et al. |
| 11,618,894 | B2 | 4/2023 | Falb et al. |
| 11,766,463 | B2 | 9/2023 | Adolfsen et al. |
| 11,879,123 | B2 | 1/2024 | Falb et al. |
| 2013/0230893 | A1 | 9/2013 | Ruebling-Jass et al. |
| 2014/0079701 | A1 | 3/2014 | Miller et al. |
| 2014/0314843 | A1 | 10/2014 | Huisman et al. |
| 2015/0238545 | A1 | 8/2015 | Borody |
| 2015/0246085 | A1 | 9/2015 | Al-Hafid et al. |
| 2015/0359894 | A1 | 12/2015 | Weinrich et al. |
| 2016/0068832 | A1 | 3/2016 | Weiner et al. |

(Continued)

FOREIGN PATENT DOCUMENTS

| | | | |
|---|---|---|---|
| CN | 1154845 | A | 7/1997 |
| CN | 1341715 | A | 3/2002 |

(Continued)

OTHER PUBLICATIONS

Anderson et al., Genetic separation of high- and low-affinity transport systems for branched-chain amino acids in *Escherichia coli* K-12. J Bacteriol. Oct. 1978;136(1):168-74.

Arai et al., Expression of the nir and nor genes for denitrification of Pseudomonas aeruginosa requires a novel CRP/FNR-related transcriptional regulator, DNR, in addition to ANR. FEBS Lett. Aug. 28, 1995;371(1):73-6.

Archer et al., Engineered *E. coli* that detect and respond to gut inflammation through nitric oxide sensing. ACS Synth Biol. Oct. 19, 2012;1(10):451-7.

(Continued)

*Primary Examiner* — Melenie L Gordon
*Assistant Examiner* — Deepa Mishra
(74) *Attorney, Agent, or Firm* — McCarter & English, LLP; Marcie B. Clarke

(57) ABSTRACT

Modified probiotics, pharmaceutical compositions thereof, and methods of modulating and treating disorders are disclosed.

20 Claims, 58 Drawing Sheets

Specification includes a Sequence Listing.

(56) References Cited

U.S. PATENT DOCUMENTS

| | | | |
|---|---|---|---|
| 2016/0177274 A1 | 6/2016 | Falb et al. |
| 2017/0136073 A1 | 5/2017 | Falb et al. |
| 2017/0216370 A1 | 8/2017 | Falb et al. |
| 2017/0232043 A1 | 8/2017 | Falb et al. |
| 2020/0172857 A1 | 6/2020 | Falb et al. |
| 2020/0246394 A1 | 8/2020 | Falb et al. |
| 2024/0076645 A1 | 3/2024 | Falb et al. |
| 2024/0082316 A1 | 3/2024 | Adolfsen et al. |

FOREIGN PATENT DOCUMENTS

| | | | |
|---|---|---|---|
| CN | 101068919 | A | 11/2007 |
| CN | 101586111 | A | 11/2009 |
| EP | 1383897 | B1 | 6/2006 |
| EP | 1666588 | A1 | 6/2006 |
| EP | 2344626 | B1 | 3/2017 |
| WO | 2006/034373 | A2 | 3/2006 |
| WO | 2006/079790 | A2 | 8/2006 |
| WO | 2008/073148 | A2 | 6/2008 |
| WO | 2008/118176 | A2 | 10/2008 |
| WO | 2009/004595 | A2 | 1/2009 |
| WO | 2011/080505 | A2 | 7/2011 |
| WO | 2011/106874 | A1 | 9/2011 |
| WO | 2012/078311 | A1 | 6/2012 |
| WO | 2013/134174 | A2 | 9/2013 |
| WO | 2013/175358 | A1 | 11/2013 |
| WO | 2013/192543 | A2 | 12/2013 |
| WO | 2014/018832 | A1 | 1/2014 |
| WO | 2014/066945 | A1 | 5/2014 |
| WO | 2014/093852 | A1 | 6/2014 |
| WO | 2014/138324 | A1 | 9/2014 |
| WO | 2014/172541 | A2 | 10/2014 |
| WO | 2016/183531 | A1 | 11/2016 |
| WO | 2016/183532 | A1 | 11/2016 |
| WO | 2016/210373 | A2 | 12/2016 |
| WO | 2017/216704 | A1 | 12/2017 |
| WO | 2018/237198 | A1 | 12/2018 |
| WO | 2020/013951 | A1 | 1/2020 |
| WO | 2021/188819 | A1 | 9/2021 |

OTHER PUBLICATIONS

Argos et al., A possible homology between immunodeficiency virus p24 core protein and picornaviral VP2 coat protein: prediction of HIV p24 antigenic sites. EMBO J. Mar. 1989;8(3):779-85.

Arrach et al., *Salmonella* promoters preferentially activated inside tumors. Cancer Res. Jun. 15, 2008;68(12):4827-32.

Arthur et al., Intestinal inflammation targets cancer-inducing activity of the microbiota. Science. Oct. 5, 2012;338(6103):120-3.

Ashida et al., Bacteria and host interactions in the gut epithelial barrier. Nat Chem Biol. Dec. 15, 2011;8(1):36-45.

Baek et al., Expression and characterization of a second L-amino acid deaminase isolated from Proteus mirabilis in *Escherichia coli*. J Basic Microbiol. Apr. 2011;51(2):129-35.

Barel et al., The complex amino acid diet of Francisella in infected macrophages. Front Cell Infect Microbiol. Feb. 6, 2015;5:9. 5 pages.

Bearden et al., The Yfe system of Yersinia pestis transports iron and manganese and is required for full virulence of plague. Mol Microbiol. Apr. 1999;32(2):403-14.

Becker et al., O2 as the regulatory signal for FNR-dependent gene regulation in *Escherichia coli*. J Bacteriol. Aug. 1996;178(15):4515-21.

Becker et al., Regulatory O2 tensions for the synthesis of fermentation products in *Escherichia coli* and relation to aerobic respiration. Arch Microbiol. Oct. 1997;168(4):290-6.

Bifulco et al., A thermostable L-aspartate oxidase: a new tool for biotechnological applications. Appl Microbiol Biotechnol. Aug. 2013;97(16):7285-95.

Bikandi et al., In silico analysis of complete bacterial genomes: PCR, AFLP-PCR and endonuclease restriction. Bioinformatics. Mar. 22, 2004;20(5):798-9.

Blau et al., Alternative therapies to address the unmet medical needs of patients with phenylketonuria. Expert Opin Pharmacother. Apr. 2015;16(6):791-800.

Bobay et al., Pervasive domestication of defective prophages by bacteria. Proc Natl Acad Sci U S A. Aug. 19, 2014;111(33):12127-32.

Boysen et al., Translational regulation of gene expression by an anaerobically induced small non-coding RNA in *Escherichia coli*. J Biol Chem. Apr. 2, 2010;285(14):10690-702.

Braat et al., A phase I trial with transgenic bacteria expressing interleukin-10 in Crohn's disease. Clin Gastroenterol Hepatol. Jun. 2006;4(6):754-9.

Brophy et al., Principles of genetic circuit design. Nat Methods. May 2014;11(5):508-20.

Bucarey et al., The *Salmonella enterica* serovar Typhi tsx gene, encoding a nucleoside-specific porin, is essential for prototrophic growth in the absence of nucleosides. Infect Immun. Oct. 2005;73(10):6210-9.

Cabrita et al., Molecular biology and regulation of nucleoside and nucleobase transporter proteins in eukaryotes and prokaryotes. Biochem Cell Biol. 2002;80(5):623-38.

Caldara et al., ArgR-dependent repression of arginine and histidine transport genes in *Escherichia coli* K-12. J Mol Biol. Oct. 19, 2007;373(2):251-67.

Callura et al., Tracking, tuning, and terminating microbial physiology using synthetic riboregulators. Proc Natl Acad Sci U S A. Sep. 7, 2010;107(36):15898-903.

Castiglione et al., The transcription factor DNR from Pseudomonas aeruginosa specifically requires nitric oxide and haem for the activation of a target promoter in *Escherichia coli*. Microbiology. Sep. 2009; 155(Pt 9):2838-44.

Celis, Properties of an *Escherichia coli* K-12 mutant defective in the transport of arginine and ornithine. J Bacteriol. Jun. 1977;130(3):1234-43.

Cellier et al., Resistance to intracellular infections: comparative genomic analysis of Nramp. Trends Genet. Jun. 1996;12(6):201-4.

Chang et al., Phenylketonuria: Genetic Defect in Enzyme Phenylalanine Hydroxylase. Artifical Cells. Regenerative Medicine Artificial Cells and Nanomedicine. World Scientific. pp. 147-159, (2007).

Charbonneau et al., Developing a new class of engineered live bacterial therapeutics to treat human diseases. Nat Commun. Apr. 8, 2020;11(1):1738, 11 pages.

Chen et al., High-level Expression of Phenylalanine Ammonia-lyase in Lactococcus lactis via Synthesized Sequence Based on Bias Codons. Chinese Journal of Biotechnology. 22(2):187-90.

Christodoulou et al., Enzyme substitution therapy for phenylketonuria delivered orally using a genetically modified probiotic: proof of principle. Retrieved online at: http://abstracts.ashg.org/cgi-bin/2012/ashg12s?author=christodoulou&sort=ptimes&sbutton=detail&absno=120121743&SID=137345. Metabolic Disease Discoveries. 1 page, Abstract 166.

Chye et al., Transcription control of the aroP gene in *Escherichia coli* K-12: analysis of operator mutants. J Bacteriol. Jan. 1987;169(1):386-93.

Clarkson et al., Diaminopimelic acid and lysine auxotrophs of Pseudomonas aeruginosa 8602. J Gen Microbiol. May 1971;66(2):161-9.

Coban et al., Screening of phenylpyruvic acid producers and optimization of culture conditions in bench scale bioreactors. Bioprocess Biosyst Eng. Nov. 2014;37(11):2343-52.

Collinson et al., Channel crossing: how are proteins shipped across the bacterial plasma membrane? Philos Trans R Soc Lond B Biol Sci. Oct. 5, 2015;370(1679):20150025, 13 pages.

Cosgriff et al., A study of AroP-PheP chimeric proteins and identification of a residue involved in tryptophan transport. J Bacteriol. Apr. 2000;182(8):2207-17.

Costa et al., Secretion systems in Gram-negative bacteria: structural and mechanistic insights. Nat Rev Microbiol. Jun. 2015;13(6):343-59.

Cuevas-Ramos et al., *Escherichia coli* induces DNA damage in vivo and triggers genomic instability in mammalian cells. Proc Natl Acad Sci U S A. Jun. 22, 2010;107(25):11537-42.

(56) References Cited

OTHER PUBLICATIONS

Danino et al., Programmable probiotics for detection of cancer in urine. Sci Transl Med. May 27, 2015;7(289):289ra84, 12 pages.
De Ruyter et al., Controlled gene expression systems for Lactococcus lactis with the food-grade inducer nisin. Appl Environ Microbiol. Oct. 1996;62(10):3662-7.
Den Hengst et al., Identification and functional characterization of the Lactococcus lactis CodY-regulated branched-chain amino acid permease BcaP (CtrA). J Bacteriol. May 2006;188(9):3280-9.
Deutscher et al., The mechanisms of carbon catabolite repression in bacteria. Curr Opin Microbiol. Apr. 2008;11(2):87-93.
Dinleyici et al., Saccharomyces boulardii CNCM I-745 in different clinical conditions. Expert Opin Biol Ther. Nov. 2014;14(11):1593-609.
Dobbelaere et al., Evaluation of nutritional status and pathophysiology of growth retardation in patients with phenylketonuria. J Inherit Metab Dis. 2003;26(1):1-11.
Drouault et al., Oral treatment with Lactococcus lactis expressing *Staphylococcus hyicus* lipase enhances lipid digestion in pigs with induced pancreatic insufficiency. Appl Environ Microbiol. Jun. 2002;68(6):3166-8.
Duan et al., Secretion of insulinotropic proteins by commensal bacteria: rewiring the gut to treat diabetes. Appl Environ Microbiol. Dec. 2008;74(23):7437-8.
Duarte et al., PerR vs OhrR: selective peroxide sensing in Bacillus subtilis. Mol Biosyst. Feb. 2010;6(2):316-23.
Dubbs et al., Peroxide-sensing transcriptional regulators in bacteria. J Bacteriol. Oct. 2012;194(20):5495-503.
Duerre et al., 1-amino acid oxidases of Proteus rettgeri. J Bacteriol. Feb. 1975;121(2):656-63.
Dunn et al., The alternative oxidase (AOX) gene in Vibrio fischeri is controlled by NsrR and upregulated in response to nitric oxide. Mol Microbiol. Jul. 1, 2010;77(1):44-55.
Durand et al., Reprogramming of anaerobic metabolism by the FnrS small RNA. Mol Microbiol. Mar. 2010;75(5):1215-31.
Durrer et al., Genetically engineered probiotic for the treatment of phenylketonuria (PKU); assessment of a novel treatment in vitro and in the PAHenu2 mouse model of Pku. Plos One. May 17, 2017;12(5):e0176286, 17 pages.
Eiglmeier et al., Molecular genetic analysis of FNR-dependent promoters. Mol Microbiol. Jul. 1989;3(7):869-78.
Elkins et al., Genes encoding bile salt hydrolases and conjugated bile salt transporters in Lactobacillus johnsonii 100-100 and other Lactobacillus species. Microbiology. Dec. 2001;147(Pt 12):3403-12.
Estrem et al., Identification of an UP element consensus sequence for bacterial promoters. Proc Natl Acad Sci U S A. Aug. 18, 1998;95(17):9761-6.
Folling, The discovery of phenylketonuria. Acta Paediatr Suppl. Dec. 1994;407:4-10.
Forbes, Engineering the perfect (bacterial) cancer therapy. Nat Rev Cancer. Nov. 2010;10(11):785-94.
Galimand et al., Positive FNR-like control of anaerobic arginine degradation and nitrate respiration in Pseudomonas aeruginosa. J Bacteriol. Mar. 1991;173(5):1598-606.
Gardner et al., Construction of a genetic toggle switch in *Escherichia coli*. Nature. Jan. 20, 2000;403(6767):339-42.
Genbank Accession No. AAA86752, amino acid deaminase [Proteus mirabilis HI4320. 1 page, Feb. 3, 1996.
Genbank Accession No. AAH26251, Phenylalanine hydroxylase [*Homo sapiens*]. 2 pages, Jul. 15, 2006.
Genbank Accession No. ABA23593, histidine ammonia-lyase [Anabaena variabilis ATCC 29413]. 2 pages, Jan. 28, 2014.
Genbank Accession No. ACD36582, L-amino acid deaminase [Proteus mirabilis]. 1 page, Aug. 15, 2011.
Genbank Accession No. BAA90864, L-amino acid deaminase [Proteus vulgaris]. 1 page, Feb. 18, 2000.
Genbank Accession No. CAE15566, Histidine ammonia-lyase (histidase) [*Photorhabdus luminescens* subsp. laumondii TT01]. 2 pages, Feb. 27, 2015.
Genbank Accession No. EDV65095, arromatic amino acid transport protein AroP [*Escherichia coli* F11]. 2 pages, Jun. 20, 2008.
Genbank Accession No. EU669819, Proteus mirabilis L-amino acid deaminase gene, complete cds. 2 pages, Aug. 15, 2011.
Genbank Accession No. U35383, Proteus mirabilis amino acid deaminase (aad) gene, complete cds. 2 pages, Feb. 3, 1996.
GenBank. *Escherichia coli* Nissle 1917, complete genome. GenBank No. CP007799.1. Jun. 25, 2015.
Gerdes et al., Essential genes on metabolic maps. Curr Opin Biotechnol. Oct. 2006;17(5):448-56.
Gilbert et al., Molecular cloning of the phenylalanine ammonia lyase gene from Rhodosporidium toruloides in *Escherichia coli* K-12. J Bacteriol. Jan. 1985;161(1):314-20.
Gorke et al., Carbon catabolite repression in bacteria: many ways to make the most out of nutrients. Nat Rev Microbiol. Aug. 2008;6(8):613-24.
Gouzy et al., *Mycobacterium tuberculosis* exploits asparagine to assimilate nitrogen and resist acid stress during infection. PLOS Pathog. Feb. 20, 2014;10(2):e1003928. 14 pages.
Grothe et al., Proline transport and osmotic stress response in *Escherichia coli* K-12. J Bacteriol. Apr. 1986;166(1):253-9.
Guardiola et al., *Escherichia coli* K-12 mutants altered in the transport of branched-chain amino acids. J Bacteriol. Dec. 1971;108(3):1034-44.
Guardiola et al., Mutations affecting the different transport systems for isoleucine, leucine, and valine in *Escherichia coli* K-12. J Bacteriol. Feb. 1974;117(2):393-405.
Guarner et al., Gut flora in health and disease. Lancet. Feb. 8, 2003;361(9356):512-9.
Haney et al., Lrp, a leucine-responsive protein, regulates branched-chain amino acid transport genes in Escherichia coli. J Bacteriol. Jan. 1992;174(1):108-15.
Hasegawa et al., Activation of a consensus FNR-dependent promoter by DNR of Pseudomonas aeruginosa in response to nitrite. FEMS Microbiol Lett. Sep. 15, 1998;166(2):213-7.
He et al., Noninvasive measurement of anatomic structure and intraluminal oxygenation in the gastrointestinal tract of living mice with spatial and spectral EPR imaging. Proc Natl Acad Sci U S A. Apr. 13, 1999;96(8):4586-91.
Heatwole et al., The tryptophan-specific permease gene, mtr, is differentially regulated by the tryptophan and tyrosine repressors in *Escherichia coli* K-12. J Bacteriol. Jun. 1991;173(11):3601-4.
Higgins, ABC transporters: from microorganisms to man. Annu Rev Cell Biol. 1992;8:67-113.
Ho et al., Phenylketonuria: translating research into novel therapies. Transl Pediatr. Apr. 2014;3(2):49-62.
Hoeks et al., Adult issues in phenylketonuria. Neth J Med. Jan. 2009;67(1):2-7.
Hoeren et al., Sequence and expression of the gene encoding the respiratory nitrous-oxide reductase from Paracoccus denitrificans. New and conserved structural and regulatory motifs. Eur J Biochem. Nov. 15, 1993;218(1):49-57.
Horsburgh et al., MntR modulates expression of the PerR regulon and superoxide resistance in *Staphylococcus aureus* through control of manganese uptake. Mol Microbiol. Jun. 2002;44(5):1269-86.
Horsburgh et al., PheP, a putative amino acid permease of *Staphylococcus aureus*, contributes to survival in vivo and during starvation. Infect Immun. May 2004;72(5):3073-6.
Hosseini et al., Propionate as a health-promoting microbial metabolite in the human gut. Nutr Rev. May 2011;69(5):245-58.
Hou et al., Production of phenylpyruvic acid from L-phenylalanine using an L-amino acid deaminase from Proteus mirabilis: comparison of enzymatic and whole-cell biotransformation approaches. Appl Microbiol Biotechnol. Oct. 2015;99(20):8391-402.
Hu et al., Membrane topology of the *Escherichia coli* gamma-aminobutyrate transporter: implications on the topography and mechanism of prokaryotic and eukaryotic transporters from the APC superfamily. Biochem J. Nov. 15, 1998;336 ( Pt 1):69-76.
Huibregtse et al., Genetically Modified Lactococcus lactis for Delivery of Human Interleukin-10 to Dendritic Cells. Gastroenterol Res Pract. 2012;2012:639291. 8 pages.

(56) References Cited

OTHER PUBLICATIONS

Isabella et al., Deep sequencing-based analysis of the anaerobic stimulon in Neisseria gonorrhoeae. BMC Genomics. Jan. 20, 2011 ;12:51. 24 pages.
Isabella et al., Functional analysis of NsrR, a nitric oxide-sensing Rrf2 repressor in Neisseria gonorrhoeae. Mol Microbiol. Jan. 2009;71(1):227-39.
Isabella et al., Identification of a conserved protein involved in anaerobic unsaturated fatty acid synthesis in Neiserria gonorrhoeae: implications for facultative and obligate anaerobes that lack FabA. Mol Microbiol. Oct. 2011;82(2):489-501.
Ivanovska et al., Pediatric drug formulations: a review of challenges and progress. Pediatrics. Aug. 2014;134(2):361-72.
Jack et al., The amino acid/polyamine/organocation (APC) superfamily of transporters specific for amino acids, polyamines and organocations. Microbiology. Aug. 2000; 146 ( Pt 8):1797-814.
Jennings et al., Cloning and molecular analysis of the *Salmonella enterica* ansP gene, encoding an L-asparagine permease. Microbiology. Jan. 1995;141 ( Pt 1):141-6.
Jensen et al., Manganese Transport, Trafficking and Function in Invertebrates. Issues in Toxicology No. 22, Manganese in Health and Disease. Lucio G. Costa (Ed.). The Royal Society of Chemistry. Chapter 1, pp. 1-33 (2015).
Jia et al., A new strategy of gene therapy for hyperphenylalaninemia rats. Zhonghua Yi Xue Za Zhi. Jun. 2000;80(6):464-7.
Jolkver et al., Identification and characterization of a bacterial transport system for the uptake of pyruvate, propionate, and acetate in Corynebacterium glutamicum. J Bacteriol. Feb. 2009;191(3):940-8.
Kadaba et al., The high-affinity *E. coli* methionine ABC transporter: structure and allosteric regulation. Science. Jul. 11, 2008;321(5886):250-3.
Kadner et al., Methionine transport in *Escherichia coli:* physiological and genetic evidence for two uptake systems. J Bacteriol. Aug. 1974;119(2):401-9.
Kang et al., Converting an injectable protein therapeutic into an oral form: phenylalanine ammonia lyase for phenylketonuria. Mol Genet Metab. Jan. 2010;99(1):4-9.
Kehres et al., SitABCD Is the Alkaline $Mn^{2+}$ Transporter of *Salmonella enterica* Serovar Typhimurium. Journal of Bacteriology. Jun. 2002;184(12):3159-3166.
Kobe et al., Regulation and crystallization of phosphorylated and dephosphorylated forms of truncated dimeric phenylalanine hydroxylase. Protein Sci. Jun. 1997;6(6):1352-7.
Koo et al., A reducing system of the superoxide sensor SoxR in *Escherichia coli.* EMBO J. Jun. 2, 2003;22(11):2614-22.
Kovacs et al., Expression and properties of the highly alkalophilic phenylalanine ammonia-lyase of thermophilic Rubrobacter xylanophilus. PLoS One. Jan. 27, 2014;9(1):e85943, 10 pages.
Landick et al., The complete nucleotide sequences of the *Escherichia coli* LIV-BP and LS-BP genes. Implications for the mechanism of high-affinity branched-chain amino acid transport. J Biol Chem. Jul. 15, 1985;260(14):8257-61.
Lee et al., Cumulative number of cell divisions as a meaningful timescale for adaptive laboratory evolution of *Escherichia coli.* PLoS One. 2011;6(10):e26172, 8 pages.
Lee et al., Systems metabolic engineering of microorganisms for natural and non-natural chemicals. Nat Chem Biol. May 17, 2012;8(6):536-46.
Leonard, Disorders of the Urea Cycle and Related Enzymes. Inborn Metabolic Diseases. J. Fernandes (Ed.) Springer, Berlin. pp. 263-272, (2006).
Levanon et al., Effect of oxygen on the *Escherichia coli* ArcA and FNR regulation systems and metabolic responses. Biotechnol Bioeng. Mar. 5, 2005;89(5):556-64.
Li et al., Monomeric state and ligand binding of recombinant GABA transporter from *Escherichia coli.* FEBS Lett. Apr. 13, 2001;494(3):165-9.
Liu et al., Study on a novel strategy to treatment of phenylketonuria. Artif Cells Blood Substit Immobil Biotechnol. Jul. 2002;30(4):243-57.
Longo et al., Single-dose, subcutaneous recombinant phenylalanine ammonia lyase conjugated with polyethylene glycol in adult patients with phenylketonuria: an open-label, multicentre, phase 1 dose-escalation trial. Lancet. Jul. 5, 2014;384(9937):37-44.
Lopez et al., Synthetic Auxotrophs with Ligand-Dependent Essential Genes for a BL21(DE3) Biosafety Strain. ACS Synth Biol. Dec. 18, 2015;4(12):1279-86.
Ma et al., Oral administration of recombinant Lactococcus lactis expressing HSP65 and tandemly repeated P277 reduces the incidence of type I diabetes in non-obese diabetic mice. PLoS One. Aug. 26, 2014;9(8):e105701, 10 pages.
Macdonald et al., A modern view of phenylalanine ammonia lyase. Biochem Cell Biol. Jun. 2007;85(3):273-82.
Macleod et al., Nutritional Management of Phenylketonuria. Ann Nestle Eng. Jun. 2010;68(2):58-69.
Marbach et al., lac operon induction in *Escherichia coli:* Systematic comparison of IPTG and TMG induction and influence of the transacetylase LacA. J Biotechnol. Jan. 2012;157(1):82-8.
Matano et al., Engineering of Corynebacterium glutamicum for growth and L-lysine and lycopene production from N-acetyl-glucosamine. Appl Microbiol Biotechnol. Jun. 2014;98(12):5633-43.
McAllister et al., Molecular analysis of the psa permease complex of *Streptococcus pneumoniae.* Mol Microbiol. Aug. 2004;53(3):889-901.
McEwen et al., Engineering Synechococcus elongatus PCC 7942 for continuous growth under diurnal conditions. Appl Environ Microbiol. Mar. 2013;79(5):1668-75.
Meadow et al., Biosynthesis of diaminopimelic acid and lysine in *Escherichia coli.* 1. The incorporation of C from various organic precursors into the diaminopimelic acid of a lysine-requiring mutant. Biochem J. Jul. 1959;72(3):396-400.
Mengesha et al., Development of a flexible and potent hypoxia-inducible promoter for tumor-targeted gene expression in attenuated *Salmonella.* Cancer Biol Ther. 2006;5(9):1120-8.
Menzel et al., Purification of the putA gene product. A bifunctional membrane-bound protein from Salmonella typhimurium responsible for the two-step oxidation of proline to glutamate. J Biol Chem. Sep. 25, 1981;256(18):9755-61.
Merlin et al., The *Escherichia coli* metD locus encodes an ABC transporter which includes Abc (MetN), YaeE (MetI), and YaeC (MetQ). J Bacteriol. Oct. 2002;184(19):5513-7.
Mironov et al., Computer analysis of transcription regulatory patterns in completely sequenced bacterial genomes. Nucleic Acids Res. Jul. 15, 1999;27(14):2981-9.
Moffitt et al., Discovery of two cyanobacterial phenylalanine ammonia lyases: kinetic and structural characterization. Biochemistry. Jan. 30, 2007;46(4):1004-12.
Moore et al., Regulation of FNR dimerization by subunit charge repulsion. J Biol Chem. Nov. 3, 2006;281(44):33268-75.
Nazos et al., Cloning and characterization of livH, the structural gene encoding a component of the leucine transport system in *Escherichia coli.* J Bacteriol. May 1986;166(2):565-73.
Nazos et al., Identification of livG, a membrane-associated component of the branched-chain amino acid transport in *Escherichia coli.* J Bacteriol. Sep. 1985;163(3):1196-202.
Nji et al., Cloning, expression, purification, crystallization and preliminary X-ray diffraction of a lysine-specific permease from Pseudomonas aeruginosa. Acta Crystallogr F Struct Biol Commun. Oct. 2014;70(Pt 10):1362-7.
Norholm et al., Specificity and topology of the *Escherichia coli* xanthosine permease, a representative of the NHS subfamily of the major facilitator superfamily. J Bacteriol. Aug. 2001;183(16):4900-4.
Nougayrede et al., *Escherichia coli* induces DNA double-strand breaks in eukaryotic cells. Science. Aug. 11, 2006;313(5788):848-51.
Ogawa et al., Cloning and expression of the gene for the Na+-coupled serine transporter from *Escherichia coli* and characteristics of the transporter. J Bacteriol. Dec. 1998;180(24):6749-52.

(56) References Cited

OTHER PUBLICATIONS

Ogawa et al., Isolation and characterization of an *Escherichia coli* mutant lacking the major serine transporter, and cloning of a serine transporter gene. J Biochem. Dec. 1997;122(6):1241-5.
Oh et al., Structural basis for multiple ligand specificity of the periplasmic lysine-, arginine-, ornithine- binding protein. J Biol Chem. Oct. 21, 1994;269(42):26323-30.
Ohnishi et al., Cloning and nucleotide sequence of the brnQ gene, the structural gene for a membrane-associated component of the LIV-II transport system for branched-chain amino acids in *Salmonella typhimurium.* Jpn J Genet. Aug. 1988;63(4):343-57.
Olier et al., Genotoxicity of *Escherichia coli* Nissle 1917 strain cannot be dissociated from its probiotic activity. Gut Microbes. Nov.-Dec. 2012;3(6):501-9.
Ortuno-Olea et al., The L-asparagine operon of Rhizobium etli contains a gene encoding an atypical asparaginase. FEMS Microbiol Lett. Aug. 15, 2000;189(2):177-82.
Ostrovsky De Spicer et al., PutA protein, a membrane-associated flavin dehydrogenase, acts as a redox-dependent transcriptional regulator. Proc Natl Acad Sci U S A. May 1, 1993;90(9):4295-8.
Ou et al., Genetic engineering of probiotic *Escherichia coli* Nissle 1917 for clinical application. Appl Microbiol Biotechnol. Oct. 2016;100(20):8693-9.
Oxender et al., Structural and functional analysis of cloned DNA containing genes responsible for branched-chain amino acid transport in *Escherichia coli.* Proc Natl Acad Sci U S A. Mar. 1980;77(3):1412-6.
Pelmont et al., L-amino acid oxidases of Proteus mirabilis: general properties. Biochimie. 1972;54(10):1359-74.
Pi et al., Cloning and sequencing of the pheP gene, which encodes the phenylalanine-specific transport system of *Escherichia coli.* J Bacteriol. Jun. 1991;173(12):3622-9.
Pi et al., Functional consequences of changing proline residues in the phenylalanine-specific permease of *Escherichia coli.* J Bacteriol. Nov. 1998;180(21):5515-9.
Pi et al., Topology of the phenylalanine-specific permease of *Escherichia coli.* J Bacteriol. May 1996;178(9):2650-5.
Porcheron et al., Iron, copper, zinc, and manganese transport and regulation in pathogenic Enterobacteria: correlations between strains, site of infection and the relative importance of the different metal transport systems for virulence. Front Cell Infect Microbiol. Dec. 5, 2013;3:90.
Pugsley. The complete general secretory pathway in gram-negative bacteria. Microbiol Rev. Mar. 1993;57(1):50-108.
Purcell et al., Towards a whole-cell modeling approach for synthetic biology. Chaos. Jun. 2013;23(2):025112, 8 pages.
Quay et al., Role of transport systems in amino acid metabolism: leucine toxicity and the branched- chain amino acid transport systems. J Bacteriol. Mar. 1977;129(3):1257-65.
Que et al., Manganese homeostasis in Bacillus subtilis is regulated by MntR, a bifunctional regulator related to the diphtheria toxin repressor family of proteins. Mol Microbiol. Mar. 2000;35(6):1454-68.
Rahmanian et al., Multiplicity of leucine transport systems in *Escherichia coli* K-12. J Bacteriol. Dec. 1973;116(3):1258-66.
Ray et al., The effects of mutation of the anr gene on the aerobic respiratory chain of Pseudomonas aeruginosa. FEMS Microbiol Lett. Nov. 15, 1997;156(2):227-32.
Rees et al., ABC transporters: The power to change. Nat Rev Mol Cell Biol. Mar. 2009;10(3):218-227.
Reeves et al., Engineering *Escherichia coli* into a protein delivery system for mammalian cells. ACS Synth Biol. May 15, 2015;4(5):644-54.
RefSeq Accession No. NP_415108, phenylalanine transporter [*Escherichia coli* str. K-12 substr. MG1655]. 3 pages, Dec. 16, 2014.
RefSeq Accession No. WP_011146484, histidine ammonia-lyase [Photorhabdus luminescens]. 1 page, May 24, 2013.
Reister et al., Complete genome sequence of the gram-negative probiotic *Escherichia coli* strain Nissle 1917. J Biotechnol. Oct. 10, 2014;187:106-7.
Rembacken et al., Non-pathogenic *Escherichia coli* versus mesalazine for the treatment of ulcerative colitis: a randomised trial. Lancet. Aug. 21, 1999;354(9179):635-9.
Rigel et al., A new twist on an old pathway—accessory Sec [corrected] systems. Mol Microbiol. Jul. 2008;69(2):291-302.
Rodionov et al., Regulation of lysine biosynthesis and transport genes in bacteria: yet another RNA riboswitch? Nucleic Acids Res. Dec. 1, 2003;31(23):6748-57.
Roquet et al., Digital and analog gene circuits for biotechnology. Biotechnol J. May 2014;9(5):597-608.
Rosen, Basic amino acid transport in *Escherichia coli.* J Biol Chem. Jun. 10, 1971;246(11):3653-62.
Ryan et al., Bacterial delivery of a novel cytolysin to hypoxic areas of solid tumors. Gene Ther. Mar. 2009;16(3):329-39.
Ryan et al., The uncoupled chloride conductance of a bacterial glutamate transporter homolog. Nat Struct Mol Biol. May 2007;14(5):365-71.
Saier, Protein secretion and membrane insertion systems in gram-negative bacteria. J Membr Biol. 2006;214(2):75-90.
Salmon et al., Global gene expression profiling in *Escherichia coli* K12. The effects of oxygen availability and Fnr. J Biol Chem. Aug. 8, 2003;278(32):29837-55.
Sarkissian et al., A different approach to treatment of phenylketonuria: Phenylalanine degradation with recombinant phenylalanine ammonia lyase. Proc Natl Acad Sci USA. Mar. 1999;96:2339-44.
Sarkissian et al., Evaluation of orally administered PEGylated phenylalanine ammonia lyase in mice for the treatment of Phenylketonuria. Mol Genet Metab. Nov. 2011;104(3):249-54.
Sarkissian et al., Quantitation of phenylalanine and its trans-cinnamic, benzoic and hippuric acid metabolites in biological fluids in a single GC-MS analysis. J Mass Spectrom. Jun. 2007;42(6):811-7.
Sat et al., The *Escherichia coli* mazEF suicide module mediates thymineless death. J Bacteriol. Mar. 2003;185(6):1803-7.
Sawers, Identification and molecular characterization of a transcriptional regulator from Pseudomonas aeruginosa PAO1 exhibiting structural and functional similarity to the FNR protein of *Escherichia coli.* Mol Microbiol. Jun. 1991;5(6):1469-81.
Schultz. Clinical use of *E. coli* Nissle 1917 in inflammatory bowel disease. Inflamm Bowel Dis. Jul. 2008;14(7):1012-8.
Seep-Feldhaus et al., Molecular analysis of the Corynebacterium glutamicum lysl gene involved in lysine uptake. Mol Microbiol. Dec. 1991;5(12):2995-3005.
Shao et al., Sequencing and characterization of the sdaC gene and identification of the sdaCB operon in *Escherichia coli* K12. Eur J Biochem. Jun. 15, 1994;222(3):901-7.
Sheehan et al., Heterologous expression of BetL, a betaine uptake system, enhances the stress tolerance of Lactobacillus salivarius UCC118. Appl Environ Microbiol. Mar. 2006;72(3):2170-7.
Silhavy et al., The bacterial cell envelope. Cold Spring Harb Perspect Biol. May 2010;2(5):a000414, 16 pages.
Siuti et al., Engineering genetic circuits that compute and remember. Nat Protoc. 2014;9(6):1292-300.
Sleator et al., Rational design of improved pharmabiotics. J Biomed Biotechnol. 2009;2009:275287, 7 pages.
Slotboom et al., Structural features of the glutamate transporter family. Microbiol Mol Biol Rev. Jun. 1999;63(2):293-307.
Sonnenborn et al., The non-pathogenic *Escherichia coli* strain Nissle 1917—features of a versatile probiotic. Microbial Ecology in Health and Disease. 2009;21(3-4):122-158.
Stanley et al., Acute infection and macrophage subversion by *Mycobacterium tuberculosis* require a specialized secretion system. Proc Natl Acad Sci U S A. Oct. 28, 2003;100(22):13001-6.
Steele, Blood-brain barrier transport of the alpha-keto acid analogs of amino acids. Fed Proc. Jun. 1986;45(7):2060-4.
Steffes et al., The lysP gene encodes the lysine-specific permease. J Bacteriol. May 1992;174(10):3242-9.
Steidler et al., Biological containment of genetically modified Lactococcus lactis for intestinal delivery of human interleukin 10. Nat Biotechnol. Jul. 2003;21(7):785-9.

(56) References Cited

OTHER PUBLICATIONS

Strauch et al., Oxygen regulation in *Salmonella typhimurium.* J Bacteriol. Feb. 1985;161(2):673-80.
Sun et al., Genomic peculiarity of coding sequences and metabolic potential of probiotic *Escherichia coli* strain Nissle 1917 inferred from raw genome data. J Biotechnol. May 4, 2005;117(2):147-61.
Takahashi et al., Multiple Functions of Glutamate Uptake via Meningococcal GltT-GltM L-Glutamate ABC Transporter in Neisseria meningitidis Internalization into Human Brain Microvascular Endothelial Cells. Infect Immun. Sep. 2015;83(9):3555-67.
Tolner et al., Characterization and functional expression in *Escherichia coli* of the sodium/proton/glutamate symport proteins of Bacillus stearothermophilus and Bacillus caldotenax. Mol Microbiol. Oct. 1992;6(19):2845-56.
Trip et al., Cloning, expression, and functional characterization of secondary amino acid transporters of Lactococcus lactis. J Bacteriol. Jan. 2013;195(2):340-50.
Trotschel et al., Characterization of methionine export in Corynebacterium glutamicum. J Bacteriol. Jun. 2005;187(11):3786-94.
Trunk et al., Anaerobic adaptation in Pseudomonas aeruginosa: definition of the Anr and Dnr regulons. Environ Microbiol. Jun. 2010;12(6):1719-33.
Ukena et al., Probiotic *Escherichia coli* Nissle 1917 inhibits leaky gut by enhancing mucosal integrity. PLoS One. Dec. 12, 2007;2(12):e1308. 9 pages.
Unden et al., Alternative respiratory pathways of *Escherichia coli:* energetics and transcriptional regulation in response to electron acceptors. Biochim Biophys Acta. Jul. 4, 1997;1320(3):217-34.
Unden et al., Control of FNR function of *Escherichia coli* by O2 and reducing conditions. J Mol Microbiol Biotechnol. May 2002;4(3):263-8.
UniProtKB/Swiss-Prot Accession No. Q3M5Z3, RecName: Full= Phenylalanine ammonia-lyase. 7 pages, Nov. 11, 2015.
Van Der Meer et al., Where microbiology meets microengineering: design and applications of reporter bacteria. Nat Rev Microbiol. Jul. 2010;8(7):511-22.
Vaziri et al., Use of molecular modelling to probe the mechanism of the nucleoside transporter NupG. Mol Membr Biol. Mar. 2013;30(2):114-28.
Vockley et al., Phenylalanine hydroxylase deficiency: diagnosis and management guideline. Genet Med. Feb. 2014;16(2):188-200.
Wanner et al., The phenylalanine ammonia-lyase gene family in *Arabidopsis thaliana.* Plant Mol Biol. Jan. 1995;27(2):327-38.
Weisser et al., Functional expression of the glucose transporter of Zymomonas mobilis leads to restoration of glucose and fructose uptake in *Escherichia coli* mutants and provides evidence for its facilitator action. J Bacteriol. Jun. 1995;177(11):3351-4.
Widhalm et al., Identification of a plastidial phenylalanine exporter that influences flux distribution through the phenylalanine biosynthetic network. Nat Commun. Sep. 10, 2015;6:8142, 11 pages.
Williams et al., The gene stlA encodes a phenylalanine ammonia-lyase that is involved in the production of a stilbene antibiotic in Photorhabdus luminescens TT01. Microbiology (Reading). Aug. 2005;151(Pt 8):2543-2550.
Willis et al., L-asparagine uptake in *Escherichia coli.* J Bacteriol. Sep. 1975;123(3):937-45.
Winteler et al., The homologous regulators ANR of Pseudomonas aeruginosa and FNR of *Escherichia coli* have overlapping but distinct specificities for anaerobically inducible promoters. Microbiology. Mar. 1996;142 ( Pt 3):685-93.
Wissenbach et al., A third periplasmic transport system for L-arginine in *Escherichia coli*: molecular characterization of the artPIQMJ genes, arginine binding and transport. Mol Microbiol. Aug. 1995;17(4):675-86.
Wissenbach et al., Physical map location of the new artPIQMJ genes of *Escherichia coli,* encoding a periplasmic arginine transport system. J Bacteriol. Jun. 1993;175(11):3687-8.
Wolken et al., The mechanism of the tyrosine transporter TyrP supports a proton motive tyrosine decarboxylation pathway in Lactobacillus brevis. J Bacteriol. Mar. 2006;188(6):2198-206.
Wood, Leucine transport in *Escherichia coli.* The resolution of multiple transport systems and their coupling to metabolic energy. J Biol Chem. Jun. 25, 1975;250(12):4477-85.
Wright et al., GeneGuard: A modular plasmid system designed for biosafety. ACS Synth Biol. Mar. 20, 2015;4(3):307-16.
Wu et al., Direct regulation of the natural competence regulator gene tfoX by cyclic AMP (cAMP) and CAMP receptor protein (CRP) in Vibrios. Sci Rep. Oct. 7, 2015;5:14921.
Xiang et al., Biochemical characterization of a prokaryotic phenylalanine ammonia lyase. J Bacteriol. Jun. 2005;187(12):4286-9.
Yamato et al., Genetic and biochemical studies of transport systems for branched-chain amino acids in *Escherichia coli* K-12: isolation and properties of mutants defective in leucine-repressible transport activities. J Bacteriol. Oct. 1980;144(1):36-44.
Yamato et al., Genetic and biochemical studies of transport systems for branched-chain amino acids in *Escherichia coli.* J Bacteriol. Apr. 1979;138(1):24-32.
Yanofsky et al., Physiological studies of tryptophan transport and tryptophanase operon induction in *Escherichia coli.* J Bacteriol. Oct. 1991;173(19):6009-17.
Zaprasis et al., Uptake of amino acids and their metabolic conversion into the compatible solute proline confers osmoprotection to Bacillus subtilis. Appl Environ Microbiol. Jan. 2015;81(1):250-9.
Zhang et al., Construction of Prophage CP-933Y Deletion Mutant Strain of Enter-hemorrhagic *E. coli* O157:H7. Lett. Biotech. Nov. 2016;27(6):804-7.
Zhang et al., DEG 5.0, a database of essential genes in both prokaryotes and eukaryotes. Nucleic Acids Res. Jan. 2009;37(Database issue):D455-8.
Zhou et al., *Salmonella typhimurium* encodes a putative iron transport system within the centisome 63 pathogenicity island. Infect Immun. Apr. 1999;67(4):1974-81.
U.S. Appl. No. 62/183,935, filed Jun. 24, 2015, by Kotula et al.
U.S. Appl. No. 62/184,811, filed Jun. 25, 2015 by Falb et al.
U.S. Appl. No. 62/263,329, filed Dec. 4, 2015, by Kotula et al.
U.S. Appl. No. 15/154,934, filed May 13, 2016, U.S. Pat. No. 10,610,546, Issued.
U.S. Appl. No. 15/260,211, filed Sep. 8, 2016, U.S. Pat. No. 9,943,555, Issued.
U.S. Appl. No. 15/301,324, filed Sep. 30, 2016, U.S. Pat. No. 10,195,234, Issued.
U.S. Appl. No. 16/788,458, filed Feb. 12, 2020, Publication No. 2020-0246394, Published.
U.S. Appl. No. 15/775,936, filed May 14, 2018, U.S. Pat. No. 11,618,894, Issued.
U.S. Appl. No. 18/068,004, filed Dec. 19, 2022, Publication No. 2024-0076645, Published.
U.S. Appl. No. 16/621,792, filed Dec. 12, 2019, U.S. Pat. No. 11,879,123, Issued.
U.S. Appl. No. 17/832,487, filed Jun. 3, 2022, U.S. Pat. No. 11,766,463, Issued.
U.S. Appl. No. 18/446,970, filed Aug. 9, 2023, Publication No. 2024-0082316, Published.
U.S. Appl. No. 18/270,102, filed Jun. 28, 2023, Pending.
Adams et al., Nucleotide sequence and genetic characterization reveal six essential genes for the LIV-I and LS transport systems of *Escherichia coli.* J Biol Chem. Jul. 15, 1990;265(20):11436-43.
Al Hafid et al., Phenylketonuria: a review of current and future treatments. Transl Pediatr. Oct. 2015;4(4):304-17.
Albiniak et al., High-level secretion of a recombinant protein to the culture medium with a Bacillus subtilis twin-arginine translocation system in *Escherichia coli.* FEBS J. Aug. 2013;280(16):3810-21.
Altenhoefer et al., The probiotic *Escherichia coli* strain Nissle 1917 interferes with invasion of human intestinal epithelial cells by different enteroinvasive bacterial pathogens. FEMS Immunol Med Microbiol. Apr. 9, 2004;40(3):223-9.
Andersen et al., Uracil uptake in *Escherichia coli* K-12: isolation of uraA mutants and cloning of the gene. J Bacteriol. Apr. 1995;177(8):2008-13.

(56) References Cited

OTHER PUBLICATIONS

Anderson et al., Environmentally controlled invasion of cancer cells by engineered bacteria. J Mol Biol. Jan. 27, 2006;355(4):619-27.
Anderson et al., *Escherichia coli* transport mutants lacking binding protein and other components of the branched-chain amino acid transport systems. J Bacteriol. Apr. 1977;130(1):384-92.
Song et al., Molecular cloning, expression and characterization of a phenylalanine ammonia-lyase gene (SmPAL1) from Salvia miltiorrhiza. Mol Biol Rep. May 2009;36(5):939-52.
Wang et al., Structural and biochemical characterization of the therapeutic Anabaena variabilis phenylalanine ammonia lyase. J Mol Biol. Jul. 18, 2008;380(4):623-35.
Zhang et al., Multifaceted regulations of gateway enzyme phenylalanine ammonia-lyase in the biosynthesis of phenylpropanoids. Mol Plant. Jan. 2015;8(1):17-27.
Zimmerman et al., Engineering and Application of LOV2-Based Photoswitches. Methods Enzymol. 2016;580:169-90.
European Office Action for Application No. 16728448.8, dated Dec. 20, 2020, 9 pages.
European Office Action for Application No. 22167588.7, dated Oct. 14, 2022, 19 pages.
International Search Report and Written Opinion for Application No. PCT/US2016/032562, dated Aug. 22, 2016, 12 pages.
International Search Report and Written Opinion for Application No. PCT/US2016/032565, dated Aug. 5, 2016.
International Search Report and Written Opinion for Application No. PCT/US2016/062369, dated Mar. 10, 2017, 14 pages.
International Search Report and Written Opinion for Application No. PCT/US2018/038840, dated Nov. 21, 2018, 17 pages.
International Search Report and Written Opinion for Application No. PCT/US2021/063976, dated Apr. 21, 2022, 11 pages.
Duerre et al., I-amino acid oxidases of Proteus rettgeri. J Bacteriol. Feb. 1975;121(2):656-63.
Hwang et al., Engineered probiotic *Escherichia coli* can eliminate and prevent Pseudomonas aeruginosa gut infection in animal models. Nat Commun. Apr. 11, 2017;8:15028.
Isabella et al., Development of a synthetic live bacterial therapeutic for the human metabolic disease phenylketonuria. Nat Biotechnol. Oct. 2018;36(9):857-864.
Purcell et al., Rule-based design of synthetic transcription factors in eukaryotes. ACS Synth Biol. Oct. 17, 2014;3(10):737-44.
Rajagopal et al., Use of inducible feedback-resistant N-acetylglutamate synthetase (argA) genes for enhanced arginine biosynthesis by genetically engineered *Escherichia coli* K-12 strains. Appl Environ Microbiol. May 1998;64(5):1805-11.
Reichert, Antibodies to watch in 2016. MAbs. 2016;8(2):197-204.
Saier et al., Protein Secretion Systems in Gram-Negative Bacteria. Gram-negative bacteria possess many protein secretion-membrane insertion systems that apparently evolved independently. Microbe. 2006;1(9):414-419.
Shah et al., Stabilization of phenylalanine ammonia lyase against organic solvent mediated deactivation. Int J Pharm. Feb. 22, 2007;331(1):107-15.
Kadaba et al., The high-affinity *E. coli* methionine ABC transporter: structure and allosteric regulation. Science. Jul. 1, 20081;321(5886):250-3.
Kwok et al., Nucleotide sequence of a full-length complementary DNA clone and amino acid sequence of human phenylalanine hydroxylase. Biochemistry. Jan. 29, 1985;24(3):556-61.
Kyndt et al., Characterization of a bacterial tyrosine ammonia lyase, a biosynthetic enzyme for the photoactive yellow protein. FEBS Lett. Feb. 1, 20023;512(1-3):240-4.
Lam et al., Retention of phenylalanine ammonia-lyase activity in wheat seedlings during storage and in vitro digestion. J Agric Food Chem. Dec. 10, 2008;56(23):11407-12.
Lamas et al., CARD9 impacts colitis by altering gut microbiota metabolism of tryptophan into aryl hydrocarbon receptor ligands. Nat Med. Jun. 2016;22(6):598-605.
Longo et al., Phase 1 Trial of Subcutaneous rAvPAL-PEG in subjects with Phenylketonuria. Lancet. Jul. 5, 2014;384(9937):37-44.
Merlin et al., The *Escherichia coli* metD locus encodes an ABC transporter which includes Abc (MetN), YaeE (Metl), and YaeC (MetQ). J Bacteriol. Oct. 2002;184(19):5513-7.

TOTAL : 5 PROPHAGE REGIONS HAVE BEEN IDENTIFIED, OF WHICH 3 REGIONS ARE INTACT, 1 REGIONS ARE INCOMPLETE, 1 REGIONS ARE QUESTIONABLE.

| REGION | REGION_LENGTH | COMPLETENESS | SCORE | #CDS | REGION_POSITION | POSSIBLE PHAGE | GC_PERCENTAGE | DETAIL |
|---|---|---|---|---|---|---|---|---|
| 1 | 18.8Kb | INTACT | 110 | 32 | 241563-260441 | PHAGE_Stx2_c_1717_NC_011357, ...... | 50.41% | DETAIL |
| 2 | 52.4Kb | INTACT | 150 | 69 | 1325883-1378287 | PHAGE_Entero_lambda_NC_001416, ...... | 49.66% | DETAIL |
| 3 | 59Kb | INTACT | 150 | 58 | 2023188-2082243 | PHAGE_Entero_c_1_NC_019706, ...... | 51.33% | DETAIL |
| 4 | 13Kb | INCOMPLETE | 10 | 28 | 3405101-3418180 | PHAGE_Cronob_vB_CsaM_GAP32_NC_019401, ...... | 54.22% | DETAIL |
| 5 | 22.4Kb | QUESTIONABLE | 80 | 20 | 5321242-5343732 | PHAGE_Shigel_SfIV_NC_022749, ...... | 42.56% | DETAIL |

FIG. 1B

PROPHAGE REGION: 5
NUMBER OF CDS: 27
LOCATION: FROM 5321242 TO 5343743 (22502 bps)
PREDICTED STATUS: QUESTIONABLE PROPHAGE
GC CONTENT: 42.56%

QUESTIONABLE PHAGE

SCORE 80

Phage 3 Deletion Sequence
49,496 bp

LEFT BAR FOR EACH PEPTIDE: SYN-PKU901

RIGHT BAR FOR EACH PEPTIDE: SYN-PKU2002

LEFT BAR FOR EACH TIME POINT: SYN-PKU2001

RIGHT BAR FOR EACH TIME POINT: SYN-PKU-1037

LEFT BAR FOR EACH TIME POINT: SYN-PKU901
RIGHT BAR FOR EACH TIME POINT: SYN-PKU2001

SEQUENCE LISTING

```
Sequence total quantity: 304
SEQ ID NO: 1            moltype = AA  length = 567
FEATURE                 Location/Qualifiers
source                  1..567
                        mol_type = protein
                        organism = Anabaena variabilis
SEQUENCE: 1
MKTLSQAQSK TSSQQFSFTG NSSANVIIGN QKLTINDVAR VARNGTLVSL TNNTDILQGI  60
QASCDYINNA VESGEPIYGV TSGFGGMANV AISREQASEL QTNLVWFLKT GAGNKLPLAD  120
VRAAMLLRAN SHMRGASGIR LELIKRMEIF LNAGVTPYVY EFGSIGASGD LVPLSYITGS  180
LIGLDPSFKV DFNGKEMDAP TALRQLNLSP LTLLPKEGLA MMNGTSVMTG IAANCVYDTQ  240
ILTAIAMGVH ALDIQALNGT NQSFHPFIHN SKPHPGQLWA ADQMISLLAN SQLVRDELDG  300
KHDYRDHELI QDRYSLRCLP QYLGPIVDGI SQIAKQIEIE INSVTDNPLI DVDNQASYHG  360
GNFLGQYVGM GMDHLRYYIG LLAKHLDVQI ALLASPEFSN GLPPSLLGNR ERKVNMGLKG  420
LQICGNSIMP LLTFYGNSIA DRFPTHAEQF NQNINSQGYT SATLARRSVD IFQNYVAIAL  480
MFGVQAVDLR TYKKTGHYDA RACLSPATER LYSAVRHVVG QKPTSDRPYI WNDNEQGLDE  540
HIARISADIA AGGVIVQAVQ DILPCLH                                      567

SEQ ID NO: 2            moltype = AA  length = 567
FEATURE                 Location/Qualifiers
source                  1..567
                        mol_type = protein
                        organism = Anabaena variabilis
SEQUENCE: 2
MKTLSQAQSK TSSQQFSFTG NSSANVIIGN QKLTINDVAR VARNGTLVSL TNNTDILQGI  60
QASCDYINNA VESGEPIYGV TSGFGGMANV AISREQASEL QTNLVWFLKT GAGNKLPLAD  120
VRAAMLLRAN SHMRGASGIR LELIKRMEIF LNAGVTPYVY EFGSIGASGD LVPLSYITGS  180
LIGLDPSFKV DFNGKEMDAP TALRQLNLSP LTLLPKEGLA MMNGTSVMTG IAANCVYDTQ  240
ILTAIAMGVH ALDIQALNGT NQSFHPFIHN SKPHPGQLWA ADQMISLLAN SQLVRDELDG  300
KHDYRDHELI QDRYSLRCLP QYLGPIVDGI SQIAKQIEIE INSVTDNPLI DVDNQASYHG  360
GNFLGQYVGM GMDHLRYYIG LLAKHLDVQI ALLASPEFSN GLPPSLLGNR ERKVNMGLKG  420
LQICGNSIMP LLTFYGNSIA DRFPTHAEQF NQNINSQGYT SATLARRSVD IFQNYVAIAL  480
MFGVQAVDLR TYKKTGHYDA RACLSPATER LYSAVRHVVG QKPTSDRPYI WNDNEQGLDE  540
HIARISADIA AGGVIVQAVQ DILPCLH                                      567

SEQ ID NO: 3            moltype = AA  length = 532
FEATURE                 Location/Qualifiers
```

```
source                 1..532
                       mol_type = protein
                       organism = Photorhabdus luminescens
SEQUENCE: 3
MKAKDVQPTI IINKNGLISL EDIYDIAIKQ KKVEISTEIT ELLTHGREKL EEKLNSGEVI  60
YGINTGFGGN ANLVVPFEKI AEHQQNLLTF LSAGTGDYMS KPCIKASQFT MLLSVCKGWS  120
ATRPIVAQAI VDHINHDIVP LVPRYGSVGA SGDLIPLSYI ARALCGIGKV YYMGAEIDAA  180
EAIKRAGLTP LSLKAKEGLA LINGTRVMSG ISAITVIKLE KLFKASISAI ALAVEALLAS  240
HEHYDARIQQ VKNHPGQNAV ASALRNLLAG STQVNLLSGV KEQANKACRH QEITQLNDTL  300
QEVYSIRCAP QVLGIVPESL ATARKILERE VISANDNPLI DPENGDVLHG GNFMGQYVAR  360
TMDALKLDIA LIANHLHAIV ALMMDNRFSR GLPNSLSPTP GMYQGFKGVQ LSQTALVAAI  420
RHDCAASGIH TLATEQYNQD IVSLGLHAAQ DVLEMEQKLR NIVSMTILVV CQAIHLRGNI  480
SEIAPETAKF YHAVREISSP LITDRALDED IIRIADAIIN DQLPLPEIML EE          532

SEQ ID NO: 4           moltype = AA  length = 514
FEATURE                Location/Qualifiers
source                 1..514
                       mol_type = protein
                       organism = Photorhabdus luminescens
SEQUENCE: 4
MKQLTIYPGK LTLDELRQVY LQPVKITLDS QIFPAIERSV ECVNAILAEN RTAYGINTGF  60
GLLASTRIEE DNLEKLQRSL VVSHAAGVGK ALDDNMTRLI MVLKINSLSR GYSGIRLAVI  120
QALIALVNAE IYPHIPCKGS VGASGDLAPL AHMSLLLLGE GQARYQGEWL PAKEALAKAN  180
LQPITLAAKE GLALLNGTQV STAFALRGLF EAEDLLAAAI VCGSLSVEAA LGSRKPFDAR  240
VHVVRGQQGQ IDVAALYRHV LEESSELSDS HINCPKVQDP YSLRCQPQVM GACLTQLRHA  300
ADVILTEANA VSDNPLVFAE QGEVISGGNF HAEPVAMASD NLALVLAEIG ALSERRIALL  360
MDSHMSQLPP FLVENGGVNS GFMIAQVTAA ALASENKALA HPASVDSLPT SANQEDHVSM  420
APAAGRRLWE MAENTRGILA IEWLSACQGI DFRNGLKSSP ILEEARVILR AKVDYYDQDR  480
FFAPDIDAAV KLLAEQHLSS LLPSGQILQR KNNR                              514

SEQ ID NO: 5           moltype = AA  length = 471
FEATURE                Location/Qualifiers
source                 1..471
                       mol_type = protein
                       organism = Proteus mirabilis
SEQUENCE: 5
MAISRRKFIL GGTVVAVAAG AGVLTPMLTR EGRFVPGTPR HGFVEGTGGP LPKQDDVVVI  60
GAGILGIMTA INLAERGLSV TIVEKGNIAG EQSSRFYGQA ISYKMPDETF LLHHLGKHRW  120
REMNAKVGID TTYRTQGRVE VPLDEEDLEN VRKWIDAKSK DVGSDIPFRT KMIEGAELKQ  180
RLRGATTDWK IAGFEEDSGS FDPEVATFVM AEYAKKMGIK IFTNCAARGL ETQAGVISDV  240
VTEKGPIKTS RVVVAGGVGS RLFMQNLNVD VPTLPAYQSQ QLISAAPNAP GGNVALPGGI  300
FFRDQADGTY ATSPRVIVAP VVKESFTYGY KYLPLLALPD FPVHISLNEQ LINSFMQSTH  360
WDLNEESPFE KYRDMTALPD LPELNASLEK LKKEFPAFKE STLIDQWSGA MAIAPDENPI  420
ISDVKEYPGL VINTATGWGM TESPVSAEIT ADLLLGKKPV LDAKPFSLYR F            471

SEQ ID NO: 6           moltype = AA  length = 473
FEATURE                Location/Qualifiers
source                 1..473
                       mol_type = protein
                       organism = Proteus mirabilis
SEQUENCE: 6
MNISRRKLLL GVGAAGVLAG GAALVPMVRR DGKFVEAKSR ASFVEGTQGA LPKEADVVII  60
GAGIQGIMTA INLAERGMSV TILEKGQIAG EQSGRAYSQI ISYQTSPEIF PLHHYGKILW  120
RGMNEKIGAD TSYRTQGRVE ALADEKALDK AQAWIKTAKE AAGFDTPLNT RIIKGEELSN  180
RLVGAQTPWT VAAFEEDSGS VDPETGTPAL ARYAKQIGVK IYTNCAVRGI ETAGGKISDV  240
VSEKGAIKTS QVVLAGGIWS RLFMGNMGID IPTLNVYLSQ QRVSGVPGAP RGNVHLPNGI  300
HFREQADGTY AVAPRIFTSS IVKDSFLLGP KFMHLLGGGE LPLEFSIGED LFNSFKMPTS  360
WNLDEKTPFE QFRVATATQN TQHLDAVFQR MKTEFPVFEK SEVVERWGAV VSPTFDELPI  420
ISEVKEYPGL VINTATVWGM TEGPAAGEVT ADIVMGKKPV IDPTPFSLDR FKK          473

SEQ ID NO: 7           moltype = AA  length = 471
FEATURE                Location/Qualifiers
source                 1..471
                       mol_type = protein
                       organism = Proteus vulgaris
SEQUENCE: 7
MAISRRKFII GGTVVAVAAG AGILTPMLTR EGRFVPGTPR HGFVEGTEGA LPKQADVVVV  60
GAGILGIMTA INLVERGLSV VIVEKGNIAG EQSSRFYGQA ISYKMPDETF LLHHLGKHRW  120
REMNAKVGID TTYRTQGRVE VPLDEEDLVN VRKWIDERSK NVGSDIPFKT RIIEGAELNQ  180
RLRGATTDWK IAGFEEDSGS FDPEVATFVM AEYAKKMGVR IYTQCAARGL ETQAGVISDV  240
VTEKGAIKTS QVVVAGGVWS RLFMQNLNVD VPTLPAYQSQ QLISGSPTAP GGNVALPGGI  300
FFREQADGTY ATSPRVIVAP VVKESFTYGY KYLPLLALPD FPVHISLNEQ LINSFMQSTH  360
WNLDEVSPFE QFRNMTALPD LPELNASLEK LKAEFPAFKE SKLIDQWSGA MAIAPDENPI  420
ISEVKEYPGL VINTATGWGM TESPVSAELT ADLLLGKKPV LDPKPFSLYR F            471

SEQ ID NO: 8           moltype = AA  length = 452
FEATURE                Location/Qualifiers
source                 1..452
                       mol_type = protein
```

-continued

```
                         organism = Homo sapiens
SEQUENCE: 8
MSTAVLENPG LGRKLSDFGQ ETSYIEDNCN QNGAISLIFS LKEEVGALAK VLRLFEENDV  60
NLTHIESRPS RLKKDEYEFF THLDKRSLPA LTNIIKILRH DIGATVHELS RDKKKDTVPW  120
FPRTIQELDR FANQILSYGA ELDADHPGFK DPVYRARRKQ FADIAYNYRH GQPIPRVEYM  180
EEGKKTWGTV FKTLKSLYKT HACYEYNHIF PLLEKYCGFH EDNIPQLEDV SQFLQTCTGF  240
RLRPVAGLLS SRDFLGGLAF RVFHCTQYIR HGSKPMYTPE PDICHELLGH VPLFSDRSFA  300
QFSQEIGLAS LGAPDEYIEK LATIYWFTVE FGLCKQGDSI KAYGAGLLSS FGELQYCLSE  360
KPKLLPLELE KTAIQNYTVT EFQPLYYVAE SFNDAKEKVR NFAATIPRPF SVRYDPYTQR  420
IEVLDNTQQL KILADSINSE IGILCSALQK IK                              452

SEQ ID NO: 9             moltype = DNA  length = 433
FEATURE                  Location/Qualifiers
source                   1..433
                         mol_type = genomic DNA
                         organism = Escherichia coli
SEQUENCE: 9
cggcccgatc gttgaacata gcggtccgca ggcggcactg cttacagcaa acggtctgta  60
cgctgtcgtc tttgtgatgt gcttcctgtt aggtttcgtc agccgtcacc gtcagcataa  120
caccctgacc tctcattaat tgctcatgcc ggacggcact atcgtcgtcc ggccttttcc  180
tctcttcccc cgctacgtgc atctatttct ataaacccgc tcattttgtc tattttttgc  240
acaaacatga aatatcagac aattccgtga cttaagaaaa tttatacaaa tcagcaatat  300
acccattaag gagtatataa aggtgaattt gatttacatc aataagcggg gttgctgaat  360
cgttaaggta ggcggtaata gaaaagaaat cgaggcaaaa atgtttgttt aactttaaga  420
aggagatata cat                                                   433

SEQ ID NO: 10            moltype = DNA  length = 290
FEATURE                  Location/Qualifiers
source                   1..290
                         mol_type = genomic DNA
                         organism = Escherichia coli
SEQUENCE: 10
gtcagcataa caccctgacc tctcattaat tgctcatgcc ggacggcact atcgtcgtcc  60
ggccttttcc tctcttcccc cgctacgtgc atctatttct ataaacccgc tcattttgtc  120
tattttttgc acaaacatga aatatcagac aattccgtga cttaagaaaa tttatacaaa  180
tcagcaatat acccattaag gagtatataa aggtgaattt gatttacatc aataagcggg  240
gttgctgaat cgttaaggta ggcggtaata gaaaagaaat cgaggcaaaa            290

SEQ ID NO: 11            moltype = DNA  length = 173
FEATURE                  Location/Qualifiers
source                   1..173
                         mol_type = genomic DNA
                         organism = Escherichia coli
SEQUENCE: 11
atttcctctc atcccatccg ggtgagagt cttttcccc gacttatggc tcatgcatgc  60
atcaaaaaag atgtgagctt gatcaaaaac aaaaaatatt tcactcgaca ggagtattta  120
tattgcgccc gttacgtggg cttcgactgt aaatcagaaa ggagaaaaca cct        173

SEQ ID NO: 12            moltype = DNA  length = 305
FEATURE                  Location/Qualifiers
source                   1..305
                         mol_type = genomic DNA
                         organism = Escherichia coli
SEQUENCE: 12
gtcagcataa caccctgacc tctcattaat tgttcatgcc gggcggcact atcgtcgtcc  60
ggccttttcc tctcttactc tgctacgtac atctatttct ataaatccgt tcaatttgtc  120
tgttttttgc acaaacatga aatatcagac aattccgtga cttaagaaaa tttatacaaa  180
tcagcaatat accccttaag gagtatataa aggtgaattt gatttacatc aataagcggg  240
gttgctgaat cgttaaggat ccctctagaa ataattttgt ttaactttaa gaaggagata  300
tacat                                                            305

SEQ ID NO: 13            moltype = DNA  length = 180
FEATURE                  Location/Qualifiers
source                   1..180
                         mol_type = genomic DNA
                         organism = Escherichia coli
SEQUENCE: 13
catttcctct catcccatcc ggggtgagag tcttttcccc cgacttatgg ctcatgcatg  60
catcaaaaaa gatgtgagct tgatcaaaaa caaaaaatat ttcactcgac aggagtattt  120
atattgcgcc cggatccctc tagaaataat tttgtttaac tttaagaagg agatatacat  180

SEQ ID NO: 14            moltype = DNA  length = 199
FEATURE                  Location/Qualifiers
source                   1..199
                         mol_type = genomic DNA
                         organism = Escherichia coli
SEQUENCE: 14
agttgttctt attggtggtg ttgctttatg gttgcatcgt agtaaatggt tgtaacaaaa  60
gcaatttttc cggctgtctg tatacaaaaa cgccgtaaag tttgagcgaa gtcaataaac  120
```

-continued

```
tctctaccca ttcagggcaa tatctctctt ggatccctct agaaataatt ttgtttaact  180
ttaagaagga gatatacat                                              199

SEQ ID NO: 15          moltype = DNA  length = 207
FEATURE                Location/Qualifiers
source                 1..207
                       mol_type = genomic DNA
                       organism = Escherichia coli
SEQUENCE: 15
agttgttctt attggtggtg ttgctttatg gttgcatcgt agtaaatggt tgtaacaaaa  60
gcaatttttc cggctgtctg tatacaaaaa cgccgcaaag tttgagcgaa gtcaataaac  120
tctctaccca ttcagggcaa tatctctctt ggatccaaag tgaactctag aaataatttt  180
gtttaacttt aagaaggaga tatacat                                     207

SEQ ID NO: 16          moltype = DNA  length = 390
FEATURE                Location/Qualifiers
source                 1..390
                       mol_type = genomic DNA
                       organism = Escherichia coli
SEQUENCE: 16
tcgtctttgt gatgtgcttc ctgttaggtt tcgtcagccg tcaccgtcag cataacaccc  60
tgacctctca ttaattgctc atgccggacg gcactatcgt cgtccggcct tttcctctct  120
tcccccgcta cgtgcatcta tttctataaa cccgctcatt ttgtctattt tttgcacaaa  180
catgaaatat cagacaattc cgtgacttaa gaaaatttat acaaatcagc aatataccca  240
ttaaggagta tataaaggtg aatttgattt acatcaataa gcggggttgc tgaatcgtta  300
aggtagaaat gtgatctagt tcacatttgc ggtaatagaa aagaaatcga ggcaaaaatg  360
tttgtttaac tttaagaagg agatatacat                                  390

SEQ ID NO: 17          moltype = DNA  length = 200
FEATURE                Location/Qualifiers
source                 1..200
                       mol_type = genomic DNA
                       organism = Escherichia coli
SEQUENCE: 17
agttgttctt attggtggtg ttgctttatg gttgcatcgt agtaaatggt tgtaacaaaa  60
gcaatttttc cggctgtctg tatacaaaaa cgccgcaaag tttgagcgaa gtcaataaac  120
tctctaccca ttcagggcaa tatctctcaa atgtgatcta gttcacattt tttgtttaac  180
tttaagaagg agatatacat                                             200

SEQ ID NO: 18          moltype = DNA  length = 355
FEATURE                Location/Qualifiers
misc_feature           1..355
                       note = Synthetic polynucleotide
source                 1..355
                       mol_type = other DNA
                       organism = synthetic construct
SEQUENCE: 18
tgtggctttt atgaaaatca cacagtgatc acaaatttta aacagagcac aaaatgctgc  60
ctcgaaatga gggcgggaaa ataaggttat cagccttgtt ttctccctca ttacttgaag  120
gatatgaagc taaaaccctt ttttataaag catttgtccg aattcggaca taatcaaaaa  180
agcttaatta agatcaattt gatctacatc tctttaacca acaatatgta agatctcaac  240
tatcgcatcc gtggattaat tcaattataa cttctctcta acgctgtgta tcgtaacggt  300
aacactgtag aggggagcac attgatgcga attcattaaa gaggagaaag gtacc       355

SEQ ID NO: 19          moltype = DNA  length = 228
FEATURE                Location/Qualifiers
misc_feature           1..228
                       note = Synthetic polynucleotide
source                 1..228
                       mol_type = other DNA
                       organism = synthetic construct
SEQUENCE: 19
ttccgaaaat tcctggcgag cagataaata agaattgttc ttatcaatat atctaactca  60
ttgaatcttt attagttttg tttttcacgc ttgttaccac tattagtgtg ataggaacag  120
ccagaatagc ggaacacata gccggtgcta tacttaatct cgttaattac tgggacataa  180
catcaagagg atatgaaatt cgaattcatt aaagaggaga aaggtacc               228

SEQ ID NO: 20          moltype = DNA  length = 334
FEATURE                Location/Qualifiers
misc_feature           1..334
                       note = Synthetic polynucleotide
source                 1..334
                       mol_type = other DNA
                       organism = synthetic construct
SEQUENCE: 20
gcttagatca ggtgattgcc ctttgtttat gagggtgttg taatccatgt cgttgttgca  60
tttgtaaggg caacacctca gcctgcaggc aggcactgaa gataccaaag ggtagttcag  120
attacacggt cacctggaaa gggggccatt ttacttttta tcgccgctgg cggtgcaaag  180
ttcacaaagt tgtcttacga aggttgtaag gtaaaactta tcgatttgat aatggaaacg  240
```

```
cattagccga atcggcaaaa attggttacc ttacatctca tcgaaaacac ggaggaagta  300
tagatgcgaa ttcattaaag aggagaaagg tacc                              334

SEQ ID NO: 21          moltype = DNA  length = 134
FEATURE                Location/Qualifiers
misc_feature           1..134
                       note = Synthetic polynucleotide
source                 1..134
                       mol_type = other DNA
                       organism = synthetic construct
SEQUENCE: 21
ctcgagttca ttatccatcc tccatcgcca cgatagttca tggcgatagg tagaatagca  60
atgaacgatt atccctatca agcattctga ctgataattg ctcacacgaa ttcattaaag  120
aggagaaagg tacc                                                    134

SEQ ID NO: 22          moltype = DNA  length = 4428
FEATURE                Location/Qualifiers
misc_feature           1..4428
                       note = Synthetic polynucleotide
source                 1..4428
                       mol_type = other DNA
                       organism = synthetic construct
SEQUENCE: 22
ctcttgatcg ttatcaattc ccacgctgtt tcagagcgtt accttgccct taaacattag  60
caatgtcgat ttatcagagg gccgacaggc tcccacagga gaaaaccgat gaaaacacta  120
tcacaggccc aatctaaaac ttcttcacag caattcagct ttaccgggaa ctcgtctgcg  180
aatgtaatta tcggcaatca aaagctgacc attaatgatg tagctcgcgt tgcccggaat  240
ggcactttgg tgtcactgac gaacaatacc gacattctgc aaggtattca agctagctgc  300
gattatatca ataacgccgt tgaatctggc gagccaatct acggggtaac aagcggtttt  360
ggtgggatgg cgaacgttgc cattagccgt gaacaggcga gcgaacttca gaccaacctc  420
gtttggttcc taaagacagg agctggtaat aagttacctc tggctgacgt aagagccgcg  480
atgctgcttc gcgctaatag tcacatgcgc ggcgccagtg gtatccgtct tgagcttatc  540
aagaggatgg aaatcttcct caacgcgggt gtcacaccat atgtttatga gtttggtagt  600
atcggagcca gtggtgatct tgttcccctg agttatatta cgggttcatt gattggttta  660
gacccgtcct ttaaagtgga ttttaacggg aaagaaatgg acgcccccgac cgctttacga  720
cagcttaatc tgagcccact tactttgctc cctaaagaag gtcttgccat gatgaatggc  780
acctctgtga tgactggaat tgccgcgaat tgtgtgtatg acacgcagat cctaacggcc  840
attgccatgg gtgttcacgc gttggacatt caagccctga atggtacaaa ccagtcgttt  900
catccgttta tccataattc aaaaccccat ccgggacagc tttgggctgc tgatcagatg  960
atctcactcc tggccaatag tcaactggtt cgggacgagc tcgacggcaa acatgattat  1020
cgcgatcatg agctcatcca ggaccggtat tcacttcgtt gtctcccaca atacctgggg  1080
cctatcgttg atggtatatc tcaaattgcg aagcaaattg aaattgagat caatagcgta  1140
accgacaacc cgcttatcga tgttgataat caggcctctt atcacggtgg caattttctg  1200
ggccagtatg ttggtatggg gatggatcac ctgcggtact atattgggct tctggctaaa  1260
catcttgatg tgcagattgc cttattagct tcaccagaat tttcaaatgg actgccgcca  1320
tcattgctcg gtaacagaga aaggaaagta aatatgggcc ttaagggcct tcagatatgt  1380
ggtaactcaa tcatgcccct cctgaccttt tatgggaact caattgctga tcgttttccg  1440
acacatgctg aacagtttaa ccaaaacatt aactcacagg gctatacatc cgcgacgtta  1500
gcgcgtcggt ccgtggatat cttccagaat tatgttgcta tcgctctgat gttcggcgta  1560
caggccgttg atttgcgcac ttataaaaaa accggtcact acgatgctcg ggcttgcctg  1620
tcgcctgcca ccgagcggct ttatagcgcc gtacgtcatg ttgtgggtca gaaaccgacg  1680
tcggaccgcc cctatatttg gaatgataat gaacaagggc tggatgaaca catcgcccgg  1740
atatctgccg atattgccgc cggaggtgtc atcgtccagg cggtacaaga catacttcct  1800
tgcctgcatt aagcttggcg taatcatggt catagctgtt tcctgtgtga aattgttatc  1860
cgctcacaat tccacacaac atacgagccg gaagcataaa gtgtaaagcc tggggtgcct  1920
aatgagtgag ctaactcaca ttaattgcgt tgcgctcact gcccgctttc cagtcgggaa  1980
acctgtcgtg ccagctgcat taatgaatcg gccaacgcgc ggggagaggc ggtttgcgta  2040
ttgggcgctc ttccgcttcc tcgctcactg actcgctgcg ctcggtcgtt cggctgcggc  2100
gagcggtatc agctcactca aaggcggtaa tacggttatc cacagaatca ggggataacg  2160
caggaaagaa catgtgagca aaaggccagc aaaaggccag gaaccgtaaa aaggccgcgt  2220
tgctggcgtt tttccatagg ctccgccccc ctgacgagca tcacaaaaat cgacgctcaa  2280
gtcagaggtg gcgaaacccg acaggactat aaagatacca ggcgtttccc cctggaagct  2340
ccctcgtgcg ctctcctgtt ccgaccctgc cgcttaccgg atacctgtcc gcctttctcc  2400
cttcgggaag cgtggcgctt tctcatagct cacgctgtag gtatctcagt tcggtgtagg  2460
tcgttcgctc caagctgggc tgtgtgcacg aaccccccgt tcagcccgac cgctgcgcct  2520
tatccggtaa ctatcgtctt gagtccaacc cggtaagaca cgacttatcg ccactggcag  2580
cagccactgg taacaggatt agcagagcga ggtatgtagg cggtgctaca gagttcttga  2640
agtggtggcc taactacggc tacactagaa gaacagtatt tggtatctgc gctctgctga  2700
agccagttac cttcggaaaa agagttggta gctcttgatc cggcaaacaa accaccgctg  2760
gtagcggtgg tttttttgtt tgcaagcagc agattacgcg cagaaaaaaa ggatctcaag  2820
aagatccttt gatcttttct acggggtctg acgctcagtg gaacgaaaac tcacgttaag  2880
ggattttggt catgagatta tcaaaaagga tcttcaccta gatcctttta aattaaaaat  2940
gaagttttaa atcaatctaa agtatatatg agtaaacttg gtctgacagt taccaatgct  3000
taatcagtga ggcacctatc tcagcgatct gtctatttcg ttcatccata gttgcctgac  3060
tccccgtcgt gtagataact acgatacggg agggcttacc atctggcccc agtgctgcaa  3120
tgataccgcg agacccacgc tcaccggctc cagatttatc agcaataaac cagccagccg  3180
gaagggccga gcgcagaagt ggtcctgcaa ctttatccgc ctccatccag tctattaatt  3240
gttgccggga agctagagta agtagttcgc cagttaatag tttgcgcaac gttgttgcca  3300
ttgctacagg catcgtggtg tcacgctcgt cgtttggtat ggcttcattc agctccggtt  3360
```

-continued

```
cccaacgatc aaggcgagtt acatgatccc ccatgttgtg caaaaaagcg gttagctcct  3420
tcggtcctcc gatcgttgtc agaagtaagt tggccgcagt gttatcactc atggttatgg  3480
cagcactgca taattctctt actgtcatgc catccgtaag atgcttttct gtgactggtg  3540
agtactcaac caagtcattc tgagaatagt gtatgcggcg accgagttgc tcttgcccgg  3600
cgtcaatacg ggataatacc gcgccacata gcagaacttt aaaagtgctc atcattggaa  3660
aacgttcttc ggggcgaaaa ctctcaagga tcttaccgct gttgagatcc agttcgatgt  3720
aacccactcg tgcacccaac tgatcttcag catcttttac tttcaccagc gtttctgggt  3780
gagcaaaaac aggaaggcaa aatgccgcaa aaaagggaat aagggcgaca cggaaatgtt  3840
gaatactcat actcttcctt tttcaatatt attgaagcat ttatcagggt tattgtctca  3900
tgagcggata catatttgaa tgtatttaga aaaataaaca aataggggtt ccgcgcacat  3960
ttccccgaaa agtgccacct gacgtctaag aaaccattat tatcatgaca ttaacctata  4020
aaaataggcg tatcacgagg ccctttcgtc tcgcgcgttt cggtgatgac ggtgaaaacc  4080
tctgacacat gcagctcccg gagacggtca cagcttgtct gtaagcggat gccgggagca  4140
gacaagcccg tcagggcgcg tcagcgggtg ttggcgggtg tcggggctgg cttaactatg  4200
cggcatcaga gcagattgta ctgagagtgc accatatgcg gtgtgaaata ccgcacagat  4260
gcgtaaggag aaaataccgc atcaggcgcc attcgccatt caggctgcgc aactgttggg  4320
aagggcgatc ggtgcgggcc tcttcgctat tacgccagct ggcgaaaggg ggatgtgctg  4380
caaggcgatt aagttgggta acgccagggt tttcccagtc acgacgtt               4428

SEQ ID NO: 23          moltype = DNA  length = 305
FEATURE                Location/Qualifiers
source                 1..305
                       mol_type = genomic DNA
                       organism = Escherichia coli
SEQUENCE: 23
cagacattgc cgtcactgcg tcttttactg gctcttctcg ctaacccaac cggtaacccc  60
gcttattaaa agcattctgt aacaaagcgg gaccaaagcc atgacaaaaa cgcgtaacaa  120
aagtgtctat aatcacggca gaaaagtcca cattgattat ttgcacggcg tcacactttg  180
ctatgccata gcatttttat ccataagatt agcggatcca gcctgacgct ttttttcgca  240
actctctact gtttctccat acctctagaa ataattttgt ttaactttaa gaaggagata  300
tacat                                                              305

SEQ ID NO: 24          moltype = DNA  length = 897
FEATURE                Location/Qualifiers
source                 1..897
                       mol_type = genomic DNA
                       organism = Escherichia coli
SEQUENCE: 24
ttattcacaa cctgccctaa actcgctcgg actcgccccg gtgcattttt taaatactcg  60
cgagaaatag agttgatcgt caaaaccgac attgcgaccg acggtggcga taggcatccg  120
ggtggtgctc aaaagcagct tcgcctgact gatgcgctgg tcctcgcgcc agcttaatac  180
gctaatccct aactgctggc ggaacaaatg cgacagacgc gacggcgaca ggcagacatg  240
ctgtgcgacg ctggcgatat caaaattact gtctgccagg tgatcgctga tgtactgaca  300
agcctcgcgt acccgattat ccatcggtgg atggagcgac tcgttaatcg cttccatgcg  360
ccgcagtaac aattgctcaa gcagatttat cgccagcaat tccgaatagc gcccttcccc  420
ttgtccggca ttaatgattt gcccaaacag gtcgctgaaa tgcggctggt gcgcttcatc  480
cgggcgaaag aaaccggtat tggcaaatat cgacggccag ttaagccatt catgccagta  540
ggcgcgcgga cgaaagtaaa cccactggtg ataccattcg tgagcctccg gatgacgacc  600
gtagtgatga atctctccag gcgggaacag caaaatatca cccggtcggc agacaaattc  660
tcgtccctga tttttcacca ccccctgacc gcgaatggtg agattgagaa tataaccttt  720
cattcccagc ggtcggtcga taaaaaaatc gagataaccg ttggcctcaa tcggcgttaa  780
acccgccacc agatgggcgt taaacgagta tcccggcagc aggggatcat tttgcgcttc  840
agccatactt ttcatactcc cgccattcag agaagaaacc aattgtccat attgcat     897

SEQ ID NO: 25          moltype = AA  length = 298
FEATURE                Location/Qualifiers
source                 1..298
                       mol_type = protein
                       organism = Escherichia coli
SEQUENCE: 25
MQYGQLVSSL NGGSMKSMAE AQNDPLLPGY SFNAHLVAGL TPIEANGYLD FFIDRPLGMK  60
GYILNLTIRG QGVVKNQGRE FVCRPGDILL FPPGEIHHYG RHPEAHEWYH QWVYFRPRAY  120
WHEWLNWPSI FANTGFFRPD EAHQPHFSDL FGQIINAGQG EGRYSELLAI NLLEQLLLRR  180
MEAINESLHP PMDNRVREAC QYISDHLADS NFDIASVAQH VCLSPSRLSH LFRQQLGISV  240
LSWREDQRIS QAKLLLSTTR MPIATVGRNV GFDDQLYFSR VFKKCTGASP SEFRAGCE    298

SEQ ID NO: 26          moltype = DNA  length = 280
FEATURE                Location/Qualifiers
source                 1..280
                       mol_type = genomic DNA
                       organism = Escherichia coli
SEQUENCE: 26
cggtgagcat cacatcacca caattcagca aattgtgaac atcatcacgt tcatctttcc  60
ctggttgcca atggcccatt ttcctgtcag taacgagaag gtcgcgaatc aggcgctttt  120
tagactggtc gtaatgaaat tcagctgtca ccggatgtgc tttccggtct gatgagtccg  180
tgaggacgaa acagcctcta caaataattt tgtttaaaac aacacccact aagataactc  240
tagaaataat tttgtttaac tttaagaagg agatatacat                        280

SEQ ID NO: 27          moltype = DNA  length = 326
```

```
FEATURE                 Location/Qualifiers
source                  1..326
                        mol_type = genomic DNA
                        organism = Escherichia coli
SEQUENCE: 27
attcaccacc ctgaattgac tctcttccgg gcgctatcat gccataccgc gaaaggtttt  60
gcgccattcg atggcgcgcc gcttcgtcag gccacatagc tttcttgttc tgatcggaac  120
gatcgttggc tgtgttgaca attaatcatc ggctcgtata atgtgtggaa ttgtgagcgc  180
tcacaattag ctgtcaccgg atgtgctttc cggtctgatg agtccgtgag gacgaaacag  240
cctctacaaa taattttgtt taaaacaaca cccactaaga taactctaga aataattttg  300
tttaacttta agaaggagat atacat                                       326

SEQ ID NO: 28           moltype = DNA  length = 1083
FEATURE                 Location/Qualifiers
source                  1..1083
                        mol_type = genomic DNA
                        organism = Escherichia coli
SEQUENCE: 28
tcactgcccg ctttccagtc gggaaacctg tcgtgccagc tgcattaatg aatcggccaa  60
cgcgcgggga gaggcggttt gcgtattggg cgccagggtg gtttttcttt tcaccagtga  120
gactggcaac agctgattgc ccttcaccgc ctggccctga gagagttgca gcaagcggtc  180
cacgctggtt tgccccagca ggcgaaaatc ctgtttgatg gtggttaacg gcgggatata  240
acatgagcta tcttcggtat cgtcgtatcc cactaccgag atatccgcac caacgcgcag  300
cccggactcg gtaatggcgc gcattgcgcc cagcgccatc tgatcgttgg caaccagcat  360
cgcagtggga acgatgccct cattcagcat ttgcatggtt tgttgaaaac cggacatggc  420
actccagtcg ccttcccgtt ccgctatcgg ctgaatttga ttgcgagtga gatatttatg  480
ccagccagcc agacgcagac gcgccgagac agaacttaat gggcccgcta acagcgcgat  540
ttgctggtga cccaatgcga ccagatgctc cacgcccagt cgcgtaccgt cctcatggga  600
gaaaataata ctgttgatgg gtgtctggtc agagacatca agaaataacg ccggaacatt  660
agtgcaggca gcttccacag caatggcatc ctggtcatcc agcggatagt taatgatcag  720
cccactgacg cgttgcgcga gaagattgtg caccgccgct ttacaggctt cgacgccgct  780
tcgttctacc atcgacacca ccacgctggc acccagttga tcggcgcgag atttaatcgc  840
cgcgacaatt tgcgacggcg cgtgcagggc cagactggag gtggcaacgc caatcagcaa  900
cgactgtttg cccgccagtt gttgtgccac gcggttggga atgtaattca gctccgccat  960
cgccgcttcc actttttccc gcgttttcgc agaaacgtgg ctggcctggt tcaccacgcg  1020
ggaaacggtc tgataagaga caccggcata ctctgcgaca tcgtataacg ttactggttt  1080
cat                                                                1083

SEQ ID NO: 29           moltype = AA  length = 360
FEATURE                 Location/Qualifiers
source                  1..360
                        mol_type = protein
                        organism = Escherichia coli
SEQUENCE: 29
MKPVTLYDVA EYAGVSYQTV SRVVNQASHV SAKTREKVEA AMAELNYIPN RVAQQLAGKQ  60
SLLIGVATSS LALHAPSQIV AAIKSRADQL GASVVVSMVE RSGVEACKAA VHNLLAQRVS  120
GLIINYPLDD QDAIAVEAAC TNVPALFLDV SDQTPINSII FSHEDGTRLG VEHLVALGHQ  180
QIALLAGPLS SVSARLRLAG WHKYLTRNQI QPIAEREGDW SAMSGFQQTM QMLNEGIVPT  240
AMLVANDQMA LGAMRAITES GLRVGADISV VGYDDTEDSS CYIPPLTTIK QDFRLLGQTS  300
VDRLLQLSQG QAVKGNQLLP VSLVKRKTTL APNTQTASPR ALADSLMQLA RQVSRLESGQ  360

SEQ ID NO: 30           moltype = DNA  length = 222
FEATURE                 Location/Qualifiers
source                  1..222
                        mol_type = genomic DNA
                        organism = Escherichia coli
SEQUENCE: 30
acgttaaatc tatcaccgca agggataaat atctaacacc gtgcgtgttg actattttac  60
ctctggcggt gataatggtt gcatagctgt caccggatgt gctttccggt ctgatgagtc  120
cgtgaggacg aaacagcctc tacaaataat tttgtttaaa acaacaccca ctaagataac  180
tctagaaata attttgttta actttaagaa ggagatatac at                     222

SEQ ID NO: 31           moltype = DNA  length = 714
FEATURE                 Location/Qualifiers
misc_feature            1..714
                        note = Synthetic polynucleotide
source                  1..714
                        mol_type = other DNA
                        organism = synthetic construct
SEQUENCE: 31
tcagccaaac gtctcttcag gccactgact agcgataact ttccccacaa cggaacaact  60
ctcattgcat gggatcattg ggtactgtgg gtttagtggt tgtaaaaaca cctgaccgct  120
atccctgatc agtttcttga aggtaaactc atcacccccca agtctggcta tgcagaaatc  180
acctggctca acagcctgct cagggtcaac gagaattaac attccgtcag gaaagcttgg  240
cttggagcct gttggtgcgg tcatggaatt accttcaacc tcaagccaga atgcagaatc  300
actggctttt ttggttgtgc ttacccatct ctccgcatca cctttggtaa aggttctaag  360
cttaggtgag aacatccctg cctgaacatg agaaaaaaca gggtactcat actcacttct  420
aagtgacggc tgcatactaa ccgcttcata catctcgtag atttctctgg cgattgaagg  480
gctaaattct tcaacgctaa ctttgagaat ttttgtaagc aatgcggcgt tataagcatt  540
```

```
taatgcattg atgccattaa ataaagcacc aacgcctgac tgccccatcc ccatcttgtc  600
tgcgacagat tcctgggata agccaagttc atttttcttt ttttcataaa ttgctttaag  660
gcgacgtgcg tcctcaagct gctcttgtgt taatggtttc ttttttgtgc tcat        714

SEQ ID NO: 32          moltype = DNA  length = 43
FEATURE                Location/Qualifiers
source                 1..43
                       mol_type = genomic DNA
                       organism = Escherichia coli
SEQUENCE: 32
ctctagaaat aattttgttt aactttaaga aggagatata cat                    43

SEQ ID NO: 33          moltype = AA  length = 237
FEATURE                Location/Qualifiers
REGION                 1..237
                       note = Synthetic polypeptide
source                 1..237
                       mol_type = protein
                       organism = synthetic construct
SEQUENCE: 33
MSTKKKPLTQ EQLEDARRLK AIYEKKKNEL GLSQESVADK MGMGQSGVGA LFNGINALNA  60
YNAALLTKIL KVSVEEFSPS IAREIYEMYE AVSMQPSLRS EYEYPVFSHV QAGMFSPKLR  120
TFTKGDAERW VSTTKKASDS AFWLEVEGNS MTAPTGSKPS FPDGMLILVD PEQAVEPGDF  180
CIARLGGDEF TFKKLIRDSG QVFLQPLNPQ YPMIPCNESC SVVGKVIASQ WPEETFG     237

SEQ ID NO: 34          moltype = DNA  length = 748
FEATURE                Location/Qualifiers
misc_feature           1..748
                       note = Synthetic polynucleotide
source                 1..748
                       mol_type = other DNA
                       organism = synthetic construct
SEQUENCE: 34
ttaagaccca ctttcacatt taagttgttt ttctaatccg catatgatca attcaaggcc  60
gaataagaag gctggctctg caccttggtg atcaaataat tcgatagctt gtcgtaataa  120
tggcggcata ctatcagtag taggtgtttc cctttcttct ttagcgactt gatgctcttg  180
atcttccaat acgcaaccta aagtaaaatg ccccacagcg ctgagtgcat ataatgcatt  240
ctctagtgaa aaaccttgtt ggcataaaaa ggctaattga ttttcgagag tttcatactg  300
tttttctgta ggccgtgtac ctaaatgtac ttttgctcca tcgcgatgac ttagtaaagc  360
acatctaaaa cttttagcgt tattacgtaa aaaatcttgc cagctttccc cttctaaagg  420
gcaaaagtga gtatggtgcc tatctaacat ctcaatggct aaggcgtcga gcaaagcccg  480
cttatttttt acatgccaat acaatgtagg ctgctctaca cctagcttct gggcgagttt  540
acgggttgtt aaaccttcga ttccgacctc attaagcagc tctaatgcgc tgttaatcac  600
tttactttta tctaatctag acatcattaa ttcctaattt ttgttgacac tctatcattg  660
atagagttat tttaccactc cctatcagtg atagagaaaa gtgaactcta gaaataattt  720
tgtttaactt taagaaggag atatacat                                     748

SEQ ID NO: 35          moltype = DNA  length = 225
FEATURE                Location/Qualifiers
source                 1..225
                       mol_type = genomic DNA
                       organism = Escherichia coli
SEQUENCE: 35
tcacctttcc cggattaaac gctttttgc ccggtggcat ggtgctaccg gcgatcacaa  60
acggttaatt atgacacaaa ttgacctgaa tgaatataca gtattggaat gcattacccg  120
gagtgttgtg taacaatgtc tggccaggtt tgtttcccgg aaccgaggtc acaacatagt  180
aaaagcgcta ttggtaatgg tacaatcgcg cgtttacact tattc                  225

SEQ ID NO: 36          moltype =   length =
SEQUENCE: 36
000

SEQ ID NO: 37          moltype =   length =
SEQUENCE: 37
000

SEQ ID NO: 38          moltype =   length =
SEQUENCE: 38
000

SEQ ID NO: 39          moltype =   length =
SEQUENCE: 39
000

SEQ ID NO: 40          moltype =   length =
SEQUENCE: 40
000

SEQ ID NO: 41          moltype =   length =
```

SEQUENCE: 41
000

SEQ ID NO: 42 moltype = length =
SEQUENCE: 42
000

SEQ ID NO: 43 moltype = length =
SEQUENCE: 43
000

SEQ ID NO: 44 moltype = length =
SEQUENCE: 44
000

SEQ ID NO: 45 moltype = length =
SEQUENCE: 45
000

SEQ ID NO: 46 moltype = length =
SEQUENCE: 46
000

SEQ ID NO: 47 moltype = length =
SEQUENCE: 47
000

SEQ ID NO: 48 moltype = length =
SEQUENCE: 48
000

SEQ ID NO: 49 moltype = length =
SEQUENCE: 49
000

SEQ ID NO: 50 moltype = length =
SEQUENCE: 50
000

SEQ ID NO: 51 moltype = length =
SEQUENCE: 51
000

SEQ ID NO: 52 moltype = length =
SEQUENCE: 52
000

SEQ ID NO: 53 moltype = length =
SEQUENCE: 53
000

SEQ ID NO: 54 moltype = length =
SEQUENCE: 54
000

SEQ ID NO: 55 moltype = length =
SEQUENCE: 55
000

SEQ ID NO: 56 moltype = length =
SEQUENCE: 56
000

SEQ ID NO: 57 moltype = length =
SEQUENCE: 57
000

SEQ ID NO: 58 moltype = length =
SEQUENCE: 58
000

SEQ ID NO: 59 moltype = length =
SEQUENCE: 59
000

SEQ ID NO: 60 moltype = length =
SEQUENCE: 60
000

```
SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
000

SEQ ID NO: 64          moltype = DNA  length = 1955
FEATURE                Location/Qualifiers
misc_feature           1..1955
                       note = Synthetic polynucleotide
source                 1..1955
                       mol_type = other DNA
                       organism = synthetic construct
SEQUENCE: 64
ttattcacaa cctgccctaa actcgctcgg actcgccccg gtgcattttt taaatactcg  60
cgagaaatag agttgatcgt caaaaccgac attgcgaccg acggtggcga taggcatccg  120
ggtggtgctc aaaagcagct tcgcctgact gatgcgctgg tcctcgcgcc agcttaatac  180
gctaatccct aactgctggc ggaacaaatg cgacagacgc gacggcgaca ggcagacatg  240
ctgtgcgacg ctggcgatat caaaattact gtctgccagg tgatcgctga tgtactgaca  300
agcctcgcgt acccgattat ccatcggtgg atggagcgac tcgttaatcg cttccatgcg  360
ccgcagtaac aattgctcaa gcagatttat cgccagcaat tccgaatagc gcccttcccc  420
ttgtccggca ttaatgattt gcccaaacag gtcgctgaaa tgcggctggt gcgcttcatc  480
cgggcgaaag aaaccggtat tggcaaatat cgacggccag ttaagccatt catgccagta  540
ggcgcgcgga cgaaagtaaa cccactggtg ataccattcg tgagcctccg gatgacgacc  600
gtagtgatga atctctccag gcgggaacag caaaatatca cccggtcggc agacaaattc  660
tcgtccctga tttttcacca ccccctgacc gcgaatggtg agattgagaa tataaccttt  720
cattcccagc ggtcggtcga taaaaaaatc gagataaccg ttggcctcaa tcggcgttaa  780
acccgccacc agatgggcgt taaacgagta tcccggcagc aggggatcat tttgcgcttc  840
agccatactt ttcatactcc cgccattcag agaagaaacc aattgtccat attgcatcag  900
acattgccgt cactgcgtct tttactggct cttctcgcta acccaaccgg taaccccgct  960
tattaaaagc attctgtaac aaagcgggac caaagccatg acaaaaacgc gtaacaaaag  1020
tgtctataat cacggcagaa aagtccacat tgattatttg cacggcgtca cactttgcta  1080
tgccatagca tttttatcca taagattagc ggatccagcc tgacgctttt tttcgcaact  1140
ctctactgtt tctccatacc tctagaaata attttgttta actttaagaa ggagatatac  1200
atatgatccc ggaaaagcga attatacggc gcattcagtc tggcggttgt gctatccatt  1260
gccaggattg ctatatcagc cagctttgca tcccgttcac actcaacgaa catgagcttg  1320
atcagcttga taatatcatt gagcggaaga agcctattca gaaaggccag acgctgttta  1380
aggctggaga tgaacttaaa tcgctttatg ccatccgctc cggtacgatt aaaagttata  1440
ccatcactga gcaaggcgac gagcaaatca ctggtttcca tttagcaggc gatctggtgg  1500
gatttgatgc catcggcagc ggtcatcacc cgagtttcgc gcaggcgctg gaaacctcga  1560
tggtatgtga aatcccgttc gaaacgctgg acgatttgtc tggtaaaatg ccgaatctgc  1620
gtcagcagat gatgcgtctg atgagcggtg aaatcaaagg cgatcaggac atgatcctgc  1680
tgttgtcgaa gaaaaatgcc gaggaacgtc tggctgcatt catctacaac ctgtcccgtc  1740
gttttgccca acgcggcttc tcccctcgtg aattccgcct gacgatgact cgtggtgata  1800
tcggtaacta tctgggcctg acggttgaaa ccatcagccg tctgctgggt cgcttccaga  1860
aaagcggtat gctggcagtc aaaggtaaat acatcactat cgaaaataac gatgcgctgg  1920
cccagcttgc tggtcatacg cgtaacgttg cctga                            1955

SEQ ID NO: 65          moltype = DNA  length = 753
FEATURE                Location/Qualifiers
misc_feature           1..753
                       note = Synthetic polynucleotide
source                 1..753
                       mol_type = other DNA
                       organism = synthetic construct
SEQUENCE: 65
atgatcccgg aaaagcgaat tatacggcgc attcagtctg gcggttgtgc tatccattgc  60
caggattgct atatcagcca gctttgcatc ccgttcacac tcaacgaaca tgagcttgat  120
cagcttgata atatcattga gcggaagaag cctattcaga aaggccagac gctgtttaag  180
gctggagatg aacttaaatc gctttatgcc atccgctccg gtacgattaa aagttatacc  240
atcactgagc aaggcgacga gcaaatcact ggtttccatt tagcaggcga tctggtggga  300
tttgatgcca tcggcagcgg tcatcacccg agtttcgcgc aggcgctgga aacctcgatg  360
gtatgtgaaa tcccgttcga aacgctggac gatttgtctg gtaaaatgcc gaatctgcgt  420
cagcagatga tgcgtctgat gagcggtgaa atcaaaggcg atcaggacat gatcctgctg  480
ttgtcgaaga aaaatgccga ggaacgtctg gctgcattca tctacaacct gtcccgtcgt  540
tttgcccaac gcggcttctc ccctcgtgaa ttccgcctga cgatgactcg tggtgatatc  600
ggtaactatc tgggcctgac ggttgaaacc atcagccgtc tgctgggtcg cttccagaaa  660
agcggtatgc tggcagtcaa aggtaaatac atcactatcg aaaataacga tgcgctggcc  720
cagcttgctg gtcatacgcg taacgttgcc tga                               753

SEQ ID NO: 66          moltype = DNA  length = 897
FEATURE                Location/Qualifiers
source                 1..897
```

```
                        mol_type = genomic DNA
                        organism = Escherichia coli
SEQUENCE: 66
ttattcacaa cctgccctaa actcgctcgg actcgccccg gtgcattttt taaatactcg  60
cgagaaatag agttgatcgt caaaaccgac attgcgaccg acggtggcga taggcatccg  120
ggtggtgctc aaaagcagct tcgcctgact gatgcgctgg tcctcgcgcc agcttaatac  180
gctaatccct aactgctggc ggaacaaatg cgacagacgc gacggcgaca ggcagacatg  240
ctgtgcgacg ctggcgatat caaaattact gtctgccagg tgatcgctga tgtactgaca  300
agcctcgcgt acccgattat ccatcggtgg atggagcgac tcgttaatcg cttccatgcg  360
ccgcagtaac aattgctcaa gcagatttat cgccagcaat tccgaatagc gcccttcccc  420
ttgtccggca ttaatgattt gcccaaacag gtcgctgaaa tgcggctggt gcgcttcatc  480
cgggcgaaag aaaccggtat tggcaaatat cgacggccag ttaagccatt catgccagta  540
ggcgcgcgga cgaaagtaaa cccactggtg ataccattcg tgagcctccg gatgacgacc  600
gtagtgatga atctctccag gcgggaacag caaaatatca cccggtcggc agacaaattc  660
tcgtccctga tttttcacca ccccctgacc gcgaatggtg agattgagaa tataaccttt  720
cattcccagc ggtcggtcga taaaaaaatc gagataaccg ttggcctcaa tcggcgttaa  780
acccgccacc agatgggcgt taaacgagta tcccggcagc aggggatcat tttgcgcttc  840
agccatactt ttcatactcc cgccattcag agaagaaacc aattgtccat attgcat     897

SEQ ID NO: 67           moltype = DNA  length = 305
FEATURE                 Location/Qualifiers
source                  1..305
                        mol_type = genomic DNA
                        organism = Escherichia coli
SEQUENCE: 67
cagacattgc cgtcactgcg tcttttactg gctcttctcg ctaacccaac cggtaacccc  60
gcttattaaa agcattctgt aacaaagcgg gaccaaagcc atgacaaaaa cgcgtaacaa  120
aagtgtctat aatcacggca gaaaagtcca cattgattat ttgcacggcg tcacactttg  180
ctatgccata gcatttttat ccataagatt agcggatcca gcctgacgct ttttttcgca  240
actctctact gtttctccat acctctagaa ataattttgt ttaactttaa gaaggagata  300
tacat                                                              305

SEQ ID NO: 68           moltype = DNA  length = 43
FEATURE                 Location/Qualifiers
source                  1..43
                        mol_type = genomic DNA
                        organism = Escherichia coli
SEQUENCE: 68
ctctagaaat aattttgttt aactttaaga aggagatata cat                    43

SEQ ID NO: 69           moltype = AA  length = 250
FEATURE                 Location/Qualifiers
REGION                  1..250
                        note = Synthetic polypeptide
source                  1..250
                        mol_type = protein
                        organism = synthetic construct
SEQUENCE: 69
MIPEKRIIRR IQSGGCAIHC QDCYISQLCI PFTLNEHELD QLDNIIERKK PIQKGQTLFK  60
AGDELKSLYA IRSGTIKSYT ITEQGDEQIT GFHLAGDLVG FDAIGSGHHP SFAQALETSM  120
VCEIPFETLD DLSGKMPNLR QQMMRLMSGE IKGDQDMILL LSKKNAEERL AAFIYNLSRR  180
FAQRGFSPRE FRLTMTRGDI GNYLGLTVET ISRLLGRFQK SGMLAVKGKY ITIENNDALA  240
QLAGHTRNVA                                                         250

SEQ ID NO: 70           moltype = AA  length = 298
FEATURE                 Location/Qualifiers
source                  1..298
                        mol_type = protein
                        organism = Escherichia coli
SEQUENCE: 70
MQYGQLVSSL NGGSMKSMAE AQNDPLLPGY SFNAHLVAGL TPIEANGYLD FFIDRPLGMK  60
GYILNLTIRG QGVVKNQGRE FVCRPGDILL FPPGEIHHYG RHPEAHEWYH QWVYFRPRAY  120
WHEWLNWPSI FANTGFFRPD EAHQPHFSDL FGQIINAGQG EGRYSELLAI NLLEQLLLRR  180
MEAINESLHP PMDNRVREAC QYISDHLADS NFDIASVAQH VCLSPSRLSH LFRQQLGISV  240
LSWREDQRIS QAKLLLSTTR MPIATVGRNV GFDDQLYFSR VFKKCTGASP SEFRAGCE    298

SEQ ID NO: 71           moltype = DNA  length = 753
FEATURE                 Location/Qualifiers
source                  1..753
                        mol_type = genomic DNA
                        organism = Escherichia coli
SEQUENCE: 71
atgatcccgg aaaagcgaat tatacggcgc attcagtctg gcggttgtgc tatccattgc  60
caggattgca cgatcagcca gctttgcatc ccgttcacac tcaacgaaca tgagcttgat  120
cagcttgata atatcattga gcggaagaag cctattcaga aaggccagac gctgtttaag  180
gctggagatg aacttaaatc gctttatgcc atccgctccg gtacgattaa aagttatacc  240
atcactgagc aaggcgacga gcaaatcact ggtttccatt tagcaggcga tctggtggga  300
tttgatgcca tcggcagcgg tcatcacccg agtttcgcgc aggcgctgga aacctcgatg  360
gtatgtgaaa tcccgttcga aacgctggac gatttgtctg gtaaaatgcc gaatctgcgt  420
```

```
cagcagatga tgcgtctgat gagcggtgaa atcaaaggcg atcaggacat gatcctgctg  480
ttgtcgaaga aaaatgccga ggaacgtctg gctgcattca tctacaacct gtcccgtcgt  540
tttgcccaac gcggcttctc ccctcgtgaa ttccgcctga cgatgactcg tggtgatatc  600
ggtaactatc tgggcctgac ggttgaaacc atcagccgtc tgctgggtcg cttccagaaa  660
agcggtatgc tggcagtcaa aggtaaatac atcactatcg aaaataacga tgcgctggcc  720
cagcttgctg gtcatacgcg taacgttgcc tga                              753

SEQ ID NO: 72           moltype = AA  length = 250
FEATURE                 Location/Qualifiers
source                  1..250
                        mol_type = protein
                        organism = Escherichia coli
SEQUENCE: 72
MIPEKRIIRR IQSGGCAIHC QDCSISQLCI PFTLNEHELD QLDNIIERKK PIQKGQTLFK  60
AGDELKSLYA IRSGTIKSYT ITEQGDEQIT GFHLAGDLVG FDAIGSGHHP SFAQALETSM  120
VCEIPFETLD DLSGKMPNLR QQMMRLMSGE IKGDQDMILL LSKKNAEERL AAFIYNLSRR  180
FAQRGFSPRE FRLTMTRGDI GNYLGLTVET ISRLLGRFQK SGMLAVKGKY ITIENNDALA  240
QLAGHTRNVA                                                        250

SEQ ID NO: 73           moltype =   length =
SEQUENCE: 73
000

SEQ ID NO: 74           moltype =   length =
SEQUENCE: 74
000

SEQ ID NO: 75           moltype =   length =
SEQUENCE: 75
000

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype =   length =
SEQUENCE: 80
000

SEQ ID NO: 81           moltype = DNA  length = 2555
FEATURE                 Location/Qualifiers
misc_feature            1..2555
                        note = Synthetic polynucleotide
source                  1..2555
                        mol_type = other DNA
                        organism = synthetic construct
SEQUENCE: 81
actcttcctt tttcaatatt attgaagcat ttatcagggt tattgtctca tgagcggata  60
catatttgaa tgtatttaga aaaataaaca aataggggaa ttaaaaaaaa gcccgctcat  120
taggcgggct actacctagg ccgcggccgc gcgaattcga gctcggtacc cggggatcct  180
ctagagtcga cctgcaggca tgcaagcttg cggccgcgtc gtgactggga aaaccctggc  240
gactagtctt ggactcctgt tgatagatcc agtaatgacc tcagaactcc atctggattt  300
gttcagaacg ctcggttgcc gccgggcgtt ttttattggt gagaatccag ggtccccaa  360
taattacgat ttaaatcaca gcaaacacca cgtcggccct atcagctgcg tgctttctat  420
gagtcgttgc tgcataactt gacaattaac atccggctcg tagggtttgt ggagggccca  480
agttcactta aaaaggagat caacaatgaa agcaattttc gtactgaaac atcttaatca  540
tgctggggag ggtttctaat gttcacggga agtattgtcg cgattgttac tccgatggat  600
gaaaaaggta atgtctgtcg ggctagcttg aaaaaactga ttgattatca tgtcgccagc  660
ggtacttcgg cgatcgtttc tgttggcacc actggcgagt ccgctacctt aaatcatgac  720
gaacatgctg atgtggtgat gatgacgctg gatctggctg atgggcgcat tccggtaatt  780
gccgggaccg gcgctaacgc tactgcggaa gccattagcc tgacgcagcg cttcaatgac  840
agtggtatcg tcggctgcct gacggtaacc ccttactaca atcgtccgtc gcaagaaggt  900
ttgtatcagc atttcaaagc catcgctgag catactgacc tgccgcaaat tctgtataat  960
gtgccgtccc gtactggctg cgatctgctc ccggaaacgg tgggccgtct ggcgaaagta  1020
aaaaatatta tcggaatcaa agaggcaaca gggaacttaa cgcgtgtaaa ccagatcaaa  1080
gagctggttt cagatgattt tgttctgctg agcggcgatg atgcgagcgc gctggacttc  1140
atgcaattgg gcggtcatgg ggttatttcc gttacggcta acgtcgcagc gcgtgatatg  1200
```

-continued

```
gcccagatgt gcaaactggc agcagaaggg cattttgccg aggcacgcgt tattaatcag  1260
cgtctgatgc cattacacaa caaactattt gtcgaaccca atccaatccc ggtgaaatgg  1320
gcatgtaagg aactgggtct tgtggcgacc gatacgctgc gcctgccaat gacaccaatc  1380
accgacagtg gccgtgagac ggtcagagcg gcgcttaaac atgccggttt gctgtaagac  1440
ttttgtcagg ttcctactgt gacgactacc accgatagac tggagtgttg ctgcgaaaaa  1500
accccgccga agcggggttt tttgcgagaa gtcaccacga ttgtgcttta cacggagtag  1560
tcggcagttc cttaagtcag aatagtggac aggcggccaa gaacttcgtt catgatagtc  1620
tccggaaccc gttcgagtcg ttttccgccc cgtgctttca tatcaattgt ccggggttga  1680
tcgcaacgta caacacctgt ggtacgtatg ccaacaccat ccaacgacac cgcaaagccg  1740
gcagtgcggg caaaattgcc tccgctggtt acgggcacaa caacaggcag gcgggtcacg  1800
cgattaaagg ccgccggtgt gacaatcagc accggccgcg ttccctgctg ctcatgacct  1860
gcggtaggat caagcgagac aagccagatt tccctcttt ccatctagta taactattgt   1920
ttctctagta acatttattg tacaacacga gcccattttt gtcaaataaa ttttaaatta  1980
tatcaacgtt aataagacgt tgtcaataaa attattttga caaaattggc cggccggcgc  2040
gccgatctga agatcagcag ttcaacctgt tgatagtacg tactaagctc tcatgtttca  2100
cgtactaagc tctcatgttt aacgtactaa gctctcatgt ttaacgaact aaaccctcat  2160
ggctaacgta ctaagctctc atggctaacg tactaagctc tcatgtttca cgtactaagc  2220
tctcatgttt gaacaataaa attaatataa atcagcaact taaatagcct ctaaggtttt  2280
aagttttata agaaaaaaaa gaatatataa ggcttttaaa gcctttaagg tttaacggtt  2340
gtggacaaca agccagggat gtaacgcact gagaagccct tagagcctct caaagcaatt  2400
ttgagtgaca caggaacact taacggctga catggggcgc gcccagctgt ctagggcggc  2460
ggatttgtcc tactcaggag agcgttcacc gacaaacaac agataaaacg aaaggcccag  2520
tctttcgact gagcctttcg ttttatttga tgcct                             2555
```

```
SEQ ID NO: 82          moltype = DNA  length = 2472
FEATURE                Location/Qualifiers
misc_feature           1..2472
                       note = Synthetic polynucleotide
source                 1..2472
                       mol_type = other DNA
                       organism = synthetic construct
SEQUENCE: 82
actcttcctt tttcaatatt attgaagcat ttatcagggt tattgtctca tgagcggata  60
catatttgaa tgtatttaga aaaataaaca aataggggaa ttaaaaaaaa gcccgctcat  120
taggcgggct actacctagg ccgcggccgc gcgaattcga gctcggtacc cggggatcct  180
ctagagtcga cctgcaggca tgcaagcttg cggccgcgtc gtgactggga aaaccctggc  240
gactagtctt ggactcctgt tgatagatcc agtaatgacc tcagaactcc atctggattt  300
gttcagaacg ctcggttgcc gccgggcgtt ttttattggt gagaatccag ggtccccaa   360
taattacgat ttaaatcaca gcaaacacca cgtcggccct atcagctgcg tgctttctat  420
gagtcgttgc tgcataactt gacaattaat catccggctc gtagggtttg tggagggccc  480
aagttcactt aaaaaggaga tcaacaatga aagcaatttt cgtactgaaa catcttaatc  540
atgctgggga gggtttctaa tgaaacagta tttagaactg atgcaaaaag tgctcgacga  600
aggcacacag aaaaacgacc gtaccggaac cggaacgctt tccatttttg gtcatcagat  660
gcgttttaac ctgcaagatg gattcccgct ggtgacaact aaacgttgcc acctgcgttc  720
catcatccat gaactgctgt ggtttcttca gggcgacact aacattgctt atctacacga  780
aaacaatgtc accatctggg acgaatgggc cgatgaaaac ggcgacctcg ggccagtgta  840
tggtaaacag tggcgtgcct ggccaacgcc agatggtcgt catattgacc agatcactac  900
ggtactgaac cagctgaaaa acgacccgga ttcgcgccgc attattgttt cagcgtggaa  960
cgtaggcgaa ctggataaaa tggcgctggc accgtgccat gcattcttcc agttctatgt  1020
ggcagacggc aaactctctt gccagcttta tcagcgctcc tgtgacgtct tcctcggcct  1080
gccgttcaac attgccagct acgcgttatt ggtgcatatg atggcgcagc agtgcgatct  1140
ggaagtgggt gattttgtct ggaccggtgg cgacacgcat ctgtacagca accatatgga  1200
tcaaactcat ctgcaattaa gccgcgaacc gcgtccgctg ccgaagttga ttatcaaacg  1260
taaacccgaa tccatcttcg actaccgttt cgaagacttt gagattgaag gctacgatcc  1320
gcatccgggc attaaagcgc cggtggctat ctaagacttt tgtcaggttc ctactgtgac  1380
gactaccacc gatagactgg agtgttgctg cgaaaaaacc ccgccgaagc ggggtttttt  1440
gcgagaagtc accacgattg tgctttacac ggagtagtcg gcagttcctt aagtcagaat  1500
agtggacagg cggccaagaa cttcgttcat gatagtctcc ggaacccgtt cgagtcgttt  1560
tccgccccgt gctttcatat caattgtccg ggttgatcg caacgtacaa cacctgtggt   1620
acgtatgcca acaccatcca acgacaccgc aaagccggca gtgcgggcaa aattgcctcc  1680
gctggttacg ggcacaacaa caggcaggcg ggtcacgcga ttaaaggccg ccggtgtgac  1740
aatcagcacc ggccgcgttc cctgctgctc atgacctgcg gtaggatcaa gcgagacaag  1800
ccagatttcc ctctttcca tctagtataa ctattgtttc tctagtaaca tttattgtac   1860
aacacgagcc catttttgtc aaataaattt taaattatat caacgttaat aagacgttgt  1920
caataaaatt attttgacaa aattggccgg ccggcgcgcc gatctgaaga tcagcagttc  1980
aacctgttga tagtacgtac taagctctca tgtttcacgt actaagctct catgtttaac  2040
gtactaagct ctcatgttta acgaactaaa ccctcatggc taacgtacta agctctcatg  2100
gctaacgtac taagctctca tgtttcacgt actaagctct catgtttgaa caataaaatt  2160
aatataaatc agcaacttaa atagcctcta aggttttaag ttttataaga aaaaaaagaa  2220
tatataaggc ttttaaagcc tttaaggttt aacggttgtg gacaacaagc cagggatgta  2280
acgcactgag aagcccttag agcctctcaa agcaattttg agtgacacag gaacacttaa  2340
cggctgacat ggggcgcgcc cagctgtcta gggcggcgga tttgtcctac tcaggagagc  2400
gttcaccgac aaacaacaga taaaacgaaa ggcccagtct ttcgactgag cctttcgttt  2460
tatttgatgc ct                                                      2472
```

```
SEQ ID NO: 83          moltype = DNA  length = 333
FEATURE                Location/Qualifiers
misc_feature           1..333
                       note = Synthetic polynucleotide
```

```
source                  1..333
                        mol_type = other DNA
                        organism = synthetic construct
SEQUENCE: 83
ttaagtcaga atagtggaca ggcggccaag aacttcgttc atgatagtct ccggaacccg  60
ttcgagtcgt tttccgcccc gtgctttcat atcaattgtc cggggttgat cgcaacgtac  120
aacacctgtg gtacgtatgc caacaccatc caacgacacc gcaaagccgg cagtgcgggc  180
aaaattgcct ccgctggtta cgggcacaac aacaggcagg cgggtcacgc gattaaaggc  240
cgccggtgtg acaatcagca ccggccgcgt tccctgctgc tcatgacctg cggtaggatc  300
aagcgagaca agccagattt cccctctttc cat                               333

SEQ ID NO: 84           moltype = DNA  length = 879
FEATURE                 Location/Qualifiers
misc_feature            1..879
                        note = Synthetic polynucleotide
source                  1..879
                        mol_type = other DNA
                        organism = synthetic construct
SEQUENCE: 84
atgttcacgg gaagtattgt cgcgattgtt actccgatgg atgaaaaagg taatgtctgt  60
cgggctagct tgaaaaaact gattgattat catgtcgcca gcggtacttc ggcgatcgtt  120
tctgttggca ccactggcga gtccgctacc ttaaatcatg acgaacatgc tgatgtggtg  180
atgatgacgc tggatctggc tgatgggcgc attccggtaa ttgccgggac cggcgctaac  240
gctactgcgg aagccattag cctgacgcag cgcttcaatg acagtggtat cgtcggctgc  300
ctgacggtaa ccccttacta caatcgtccg tcgcaagaag gtttgtatca gcatttcaaa  360
gccatcgctg agcatactga cctgccgcaa attctgtata atgtgccgtc ccgtactggc  420
tgcgatctgc tcccggaaac ggtgggccgt ctggcgaaag taaaaaatat tatcggaatc  480
aaagaggcaa cagggaactt aacgcgtgta aaccagatca aagagctggt ttcagatgat  540
tttgttctgc tgagcggcga tgatgcgagc gcgctggact tcatgcaatt gggcggtcat  600
ggggttattt ccgttacggc taacgtcgca gcgcgtgata tggcccagat gtgcaaactg  660
gcagcagaag ggcattttgc cgaggcacgc gttattaatc agcgtctgat gccattacac  720
aacaaactat ttgtcgaacc caatccaatc ccggtgaaat gggcatgtaa ggaactgggt  780
cttgtggcga ccgatacgct gcgcctgcca atgacaccaa tcaccgacag tggccgtgag  840
acggtcagag cggcgcttaa acatgccggt ttgctgtaa                         879

SEQ ID NO: 85           moltype = DNA  length = 795
FEATURE                 Location/Qualifiers
misc_feature            1..795
                        note = Synthetic polynucleotide
source                  1..795
                        mol_type = other DNA
                        organism = synthetic construct
SEQUENCE: 85
atgaaacagt atttagaact gatgcaaaaa gtgctcgacg aaggcacaca gaaaaacgac  60
cgtaccggaa ccggaacgct ttccattttt ggtcatcaga tgcgttttaa cctgcaagat  120
ggattcccgc tggtgacaac taaacgttgc cacctgcgtt ccatcatcca tgaactgctg  180
tggtttcttc agggcgacac taacattgct tatctacacg aaaacaatgt caccatctgg  240
gacgaatggg ccgatgaaaa cggcgacctc gggccagtgt atggtaaaca gtggcgtgcc  300
tggccaacgc cagatggtcg tcatattgac cagatcacta cggtactgaa ccagctgaaa  360
aacgacccgg attcgcgccg cattattgtt tcagcgtgga acgtaggcga actggataaa  420
atggcgctgg caccgtgcca tgcattcttc cagttctatg tggcagacgg caaactctct  480
tgccagcttt atcagcgctc ctgtgacgtc ttcctcggcc tgccgttcaa cattgccagc  540
tacgcgttat tggtgcatat gatggcgcag cagtgcgatc tggaagtggg tgattttgtc  600
tggaccggtg gcgacacgca tctgtacagc aaccatatgg atcaaactca tctgcaatta  660
agccgcgaac cgcgtccgct gccgaagttg attatcaaac gtaaacccga atccatcttc  720
gactaccgtt tcgaagactt tgagattgaa ggctacgatc cgcatccggg cattaaagcg  780
ccggtggcta tctaa                                                   795

SEQ ID NO: 86           moltype = AA  length = 110
FEATURE                 Location/Qualifiers
REGION                  1..110
                        note = Synthetic polypeptide
source                  1..110
                        mol_type = protein
                        organism = synthetic construct
SEQUENCE: 86
MERGEIWLVS LDPTAGHEQQ GTRPVLIVTP AAFNRVTRLP VVVPVTSGGN FARTAGFAVS  60
LDGVGIRTTG VVRCDQPRTI DMKARGGKRL ERVPETIMNE VLGRLSTILT             110

SEQ ID NO: 87           moltype = AA  length = 292
FEATURE                 Location/Qualifiers
REGION                  1..292
                        note = Synthetic polypeptide
source                  1..292
                        mol_type = protein
                        organism = synthetic construct
SEQUENCE: 87
MFTGSIVAIV TPMDEKGNVC RASLKKLIDY HVASGTSAIV SVGTTGESAT LNHDEHADVV  60
MMTLDLADGR IPVIAGTGAN ATAEAISLTQ RFNDSGIVGC LTVTPYYNRP SQEGLYQHFK  120
```

```
AIAEHTDLPQ ILYNVPSRTG CDLLPETVGR LAKVKNIIGI KEATGNLTRV NQIKELVSDD  180
FVLLSGDDAS ALDFMQLGGH GVISVTANVA ARDMAQMCKL AAEGHFAEAR VINQRLMPLH  240
NKLFVEPNPI PVKWACKELG LVATDTLRLP MTPITDSGRE TVRAALKHAG LL          292

SEQ ID NO: 88          moltype = AA  length = 264
FEATURE                Location/Qualifiers
REGION                 1..264
                       note = Synthetic polypeptide
source                 1..264
                       mol_type = protein
                       organism = synthetic construct
SEQUENCE: 88
MKQYLELMQK VLDEGTQKND RTGTGTLSIF GHQMRFNLQD GFPLVTTKRC HLRSIIHELL  60
WFLQGDTNIA YLHENNVTIW DEWADENGDL GPVYGKQWRA WPTPDGRHID QITTVLNQLK  120
NDPDSRRIIV SAWNVGELDK MALAPCHAFF QFYVADGKLS CQLYQRSCDV FLGLPFNIAS  180
YALLVHMMAQ QCDLEVGDFV WTGGDTHLYS NHMDQTHLQL SREPRPLPKL IIKRKPESIF  240
DYRFEDFEIE GYDPHPGIKA PVAI                                          264

SEQ ID NO: 89          moltype =   length =
SEQUENCE: 89
000

SEQ ID NO: 90          moltype =   length =
SEQUENCE: 90
000

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000

SEQ ID NO: 95          moltype =   length =
SEQUENCE: 95
000

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype =   length =
SEQUENCE: 99
000

SEQ ID NO: 100         moltype =   length =
SEQUENCE: 100
000

SEQ ID NO: 101         moltype =   length =
SEQUENCE: 101
000

SEQ ID NO: 102         moltype =   length =
SEQUENCE: 102
000

SEQ ID NO: 103         moltype =   length =
SEQUENCE: 103
000

SEQ ID NO: 104         moltype =   length =
```

```
SEQUENCE: 104
000

SEQ ID NO: 105         moltype =   length =
SEQUENCE: 105
000

SEQ ID NO: 106         moltype =   length =
SEQUENCE: 106
000

SEQ ID NO: 107         moltype =   length =
SEQUENCE: 107
000

SEQ ID NO: 108         moltype =   length =
SEQUENCE: 108
000

SEQ ID NO: 109         moltype =   length =
SEQUENCE: 109
000

SEQ ID NO: 110         moltype =   length =
SEQUENCE: 110
000

SEQ ID NO: 111         moltype =   length =
SEQUENCE: 111
000

SEQ ID NO: 112         moltype =   length =
SEQUENCE: 112
000

SEQ ID NO: 113         moltype =   length =
SEQUENCE: 113
000

SEQ ID NO: 114         moltype =   length =
SEQUENCE: 114
000

SEQ ID NO: 115         moltype =   length =
SEQUENCE: 115
000

SEQ ID NO: 116         moltype =   length =
SEQUENCE: 116
000

SEQ ID NO: 117         moltype =   length =
SEQUENCE: 117
000

SEQ ID NO: 118         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 118
agtgcctgta ccagacgttc                                              20

SEQ ID NO: 119         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 119
agaaatgaca accagagagc                                              20

SEQ ID NO: 120         moltype = DNA  length = 21
FEATURE                Location/Qualifiers
misc_feature           1..21
                       note = Synthetic primer
```

```
source                  1..21
                        mol_type = other DNA
                        organism = synthetic construct
SEQUENCE: 120
ttgagtttaa tatggcagaa c                                             21

SEQ ID NO: 121          moltype = DNA  length = 19
FEATURE                 Location/Qualifiers
misc_feature            1..19
                        note = Synthetic primer
source                  1..19
                        mol_type = other DNA
                        organism = synthetic construct
SEQUENCE: 121
aaatgatcat cgcgtcatc                                                19

SEQ ID NO: 122          moltype = DNA  length = 19
FEATURE                 Location/Qualifiers
misc_feature            1..19
                        note = Synthetic primer
source                  1..19
                        mol_type = other DNA
                        organism = synthetic construct
SEQUENCE: 122
gcatcaatca gtgattggc                                                19

SEQ ID NO: 123          moltype = DNA  length = 20
FEATURE                 Location/Qualifiers
misc_feature            1..20
                        note = Synthetic primer
source                  1..20
                        mol_type = other DNA
                        organism = synthetic construct
SEQUENCE: 123
acgtctgaat atacgggctg                                               20

SEQ ID NO: 124          moltype = DNA  length = 20
FEATURE                 Location/Qualifiers
misc_feature            1..20
                        note = Synthetic primer
source                  1..20
                        mol_type = other DNA
                        organism = synthetic construct
SEQUENCE: 124
tccagcttga ctcgtttcag                                               20

SEQ ID NO: 125          moltype = DNA  length = 19
FEATURE                 Location/Qualifiers
misc_feature            1..19
                        note = Synthetic primer
source                  1..19
                        mol_type = other DNA
                        organism = synthetic construct
SEQUENCE: 125
agcaccttac ccgaagagt                                                19

SEQ ID NO: 126          moltype = DNA  length = 79
FEATURE                 Location/Qualifiers
misc_feature            1..79
                        note = Synthetic primer
source                  1..79
                        mol_type = other DNA
                        organism = synthetic construct
SEQUENCE: 126
tggaggcttt aagaaatacc tcgatgtgaa caaccgcctg ccacgaatct tcgtcaagcg  60
attacacgtc ttgagcgat                                                79

SEQ ID NO: 127          moltype = DNA  length = 79
FEATURE                 Location/Qualifiers
misc_feature            1..79
                        note = Synthetic primer
source                  1..79
                        mol_type = other DNA
                        organism = synthetic construct
SEQUENCE: 127
gataatggtg agattatccc cggttatacc ggacttatcg cctattcaga atcactggat  60
ctgacatggg aattagcca                                                79

SEQ ID NO: 128          moltype = DNA  length = 20
```

-continued

```
FEATURE                Location/Qualifiers
misc_feature           1..20
                       note = Synthetic primer
source                 1..20
                       mol_type = other DNA
                       organism = synthetic construct
SEQUENCE: 128
tggaggcttt aagaaatacc                                                20

SEQ ID NO: 129         moltype = DNA  length = 20
FEATURE                Location/Qualifiers
misc_feature           1..20
                       note = Synthetic primer
source                 1..20
                       mol_type = other DNA
                       organism = synthetic construct
SEQUENCE: 129
gctggcgatt caggttcatc                                                20

SEQ ID NO: 130         moltype = DNA  length = 9687
FEATURE                Location/Qualifiers
source                 1..9687
                       mol_type = genomic DNA
                       organism = Escherichia coli
SEQUENCE: 130
aatcgccggt gtactccgcg tcagaaaggt atacagccac ggcagggaga tcctgctctt  60
caagaaaaac agggcgcccg tcaaaccagg tgaccgtgtc ggtgatctcg gctttcagtt  120
tggccagaat ggctgcacga attgcgctgt gtctgttcat cgcttcaggt ggatcctcag  180
ttggtttttc agggctgcgg aaagttcttt gggcatatcg ctttcaataa ggcgctttga  240
aatagcggtg aaggccacgg tgagcggtgt ctcaagagga actttgacca catcaatcgg  300
ataacgggcc tgacctacgc gccgcatgac ctgccagcgc ccgttcgcaa gctgttggat  360
aaaagcgtta cgaaaggtat agggcccgat tttaaggacg ctgcccgctc cgtttctggc  420
cccttttta cgcgagagcc tgacgcgcgc cgtgccgagc tttatcgcag gaagattacc  480
gcggttgatt tttatcgacg cgaccgggcg atcgtgacgg gccttgcgca gacgggaacg  540
ctggcggacc agacgaaccg gaagcccctt tttccggtta tcatcaactg ttgcttcttt  600
cgctacagct ttgctcccct ggcttatcgt tcttctggcc accctgttaa gtgcttttgc  660
ggttgcctca ggaacgatta accggctgag gctgttcagg ttctgaatag ccctttccag  720
tcctttcaca gacatagcgc ctcctcattc gagatggatg cggggttttc cgttgaacat  780
gtcatagcgg gtaacgatca ggttcttacc gtcgtagtcg acgctgtcgt ttcggcgtgg  840
ctggtaaagc tcagagaaaa ccaccagcga agtacctgtt cccgacaatg gccccatttc  900
ctcgagttgc tcggcgggaa caacgtcata gctgctgcca ttgatgatcg ctgtctttcc  960
catctttttt atagtggccg cgtccatgcg cgccgccatc cggtcaaagg agttaggcat  1020
tgatcttaac ttcaacaacg gtggtgtttg cccctgcatc ttcccaggcg atgcccgcgg  1080
caacggcgtc cgtttcttcg atcgtgattt tgccgtcctt cagatacacc tgcgcccccgg  1140
cagtaaccgc atctgcggat acttttggca ggaggaaaac accctcagta aaaccgtccc  1200
cggtatcgcc agccgggata tcggtaattg ccaccgcgat aagttttcca acaacaaccg  1260
ggtcgccgct gtgaacatcg gttgcaccac tgtttaccag agggatcgtt ttcccgtcct  1320
gcgcatagtt cttagccata acttctccat tcagcccctt tcgaggctgg tttcaggtat  1380
aaaaaaagcc cttacgggcg tctgtttgtc aggactgttt tttactgacc agaggatttg  1440
gtcatgccgc gatagtccag cggcgccacg ccagcatcaa tacgcacttt cgtggcgata  1500
ccatcagtgg tgaagccttc ctgctgatcg atgtatggcg tgtcgacgcc gttgagataa  1560
gcgacctcaa tggtgtcggt gcccttcgcg gcagccagat accaggcttt cgcatcagct  1620
tcatccagac gtggttcggc aatgacttct gcaaagttct ggatagggtt aacgatcccg  1680
gcattgatgt ctgcaccttt aacactggcc gacttgatgg tctgatttgc cagagtttcc  1740
agggcgacgg gcaccagcat gtaggccgga cggatattca gggttcgctc cccctccttc  1800
tgcagacgca tcagcttgcg cgattcgtcc aggctggcca cagaaattgc acccgagctc  1860
aggttcttgt gatcggcatg gaacagcgcc tttccgtctg agagtttcgg gtttttggtc  1920
agaatggcgt aaaccagatc gccaatcgtt gctttcgccg cgcgccccat cttcatcggt  1980
acgtcggtaa gctggttcag atcgtcgttg atgatcgcct ggcgagttac tgagaagatt  2040
tcaccatacg tggcaagcgc gatggtttcg cctttgtcac tggtagtgat gtacttgtac  2100
tcagcccctt cgcgaacctg tcgcagagaa gggaacccac ccataccgac acgatgcgcc  2160
gttttgaagt ccgacagctg gcctttttttg gtccactgct cgaaggtttc ctgcgcctcg  2220
tcccagccct gaatcagcgc tttgttcgca acatcaagca gaatgttgcc aaagtcagag  2280
gtgctgtggg tcagcgccag gccaaccatc tgcatcgggt tgtagctggc cacgccgata  2340
cctttttctg tcagggccat acgcgcatac tcgcgcagcg tcataccgtt ataaacgtta  2400
tcccgctcct gaccttcgaa cccggcacgc gccatcagtg cctggcgaat accatccgcg  2460
acgaagttac cgttgcccgc atgaatatgc ggctgagtgg ttttattgga cggcgtggcc  2520
gttttaccga gttctgccag cagcaaatct ttcgccttat cgacggagca atcagggtcg  2580
gccacacact gattctgcag ttccatgtgc ttattaccga acatggcaaa gagatcgccg  2640
atagcgttaa cacgggtttt ctgctcagcc aacacctgcg cgcggatcgc attttcatcc  2700
ggtgccgggt ctgtttttgc ctgcggtgcc tgaggctggg taataaccgg gtcacgctgg  2760
gtagtgttgc gcggcggggt gatcatgttg cgaatgcttt ttggcatttt ttcaaattcc  2820
tcaatacgtt ttgaatgaat acaggccata gcctgaaggg atggtgtcac ctggtcggca  2880
aaacccagtt caaggcactc gctgccgttc atccaggttt cgtcctccag cattaccgca  2940
atttcttcgg tggattttcc ggttttctgt gcataagccg ggataagaac ggattcaacc  3000
ttgtcgagaa gatccgcata gtcgcgcata tcgctcgcgt caccaccagc aaaccccccag  3060
ggcttatgga tcatcatcat cgtgttttca ggcatgatga ccggattgcc taccatcgca  3120
atcaccgagg ccatggaggc cgccagaccg tcgatatgta cggtaatcgc cgcgccgtgg  3180
tgcttcagcg cgttataaat agcaattccg tcgaagacat caccaccggg cgagttgata  3240
```

-continued

```
taaaggttga tgtgggtgac gtccccaagt gcccggagat cattgacgaa ctgtttcgcc  3300
gttacgcccc agtacccgat ttcgtcataa ataaaaatgt cggcctcact gttattgctg  3360
gcctgcatgc ggaaccacga attacttttt gcgctggctt tcggacggtg gcgcgcccgg  3420
ttctttggct tcggcactgg tgcctccttt atcattggcg gggtcggtgt caaacaccag  3480
gccctgttca cggttctcgt caacctcagc tttacggcgt gacttaacat catccgggtt  3540
gcgaccgctg gcacgtatcc agtcggattc agtagcagca ccgccgcgga tctgcgtttt  3600
ccaggcattc gcttctttaa cgggatcaat ccacggcata acgggccccg aataaaccgc  3660
gttataaagc gagtccatat caatgcctct cggcagcttg atttctccgg cagcaatagc  3720
catcttgagc caggctcggt acatgggccg ggtcactgaa ccgatgaacc agtcctgaag  3780
aatcagatag ccgtcggttg actcgacaag ctcctgccgc tgggcactgt acgttccgtt  3840
gtagtttctg gatgtgctgg aaaagctgag gcgactgccg gcggacacgg cacgcagctg  3900
tccgttacga aaagattcga ggttagggtt cgggcgatcg gatttaatca tcccgatttc  3960
ttccccggcc tgcagttcgt catagagcat accgggctga atcatcagct cgcggtcatc  4020
gctgcttgaa tcagaatcga agctctgtcc gtcgcctttt ttgatataca tgccgagtgc  4080
cgcagcaatt ctggcagcag taagctccga gtcctcgtat tctttcagcg cgctcagacg  4140
catcagaaca ccagacaaaa gagacgttcc gcgggtctgg tgcaggcgtc gggtgaattt  4200
gagatgcagc atgttctctg catctatctc tttggtatca aactgacgcc cggatactgg  4260
caggctttta tagacctgat attttttcgg gcgtccccag ttatcgacaa aaacgccctg  4320
attgagctgg gtggcagcat cgctgttcat cggcacaaag tccggctcca gcgcttccag  4380
ccagaacggc acgccagcaa ccggctgaag accatttccg gtaccgcgaa ccagctgagc  4440
aaatacctca ccgtcccgga gccacgttcg cagcatcagc cgctccagca ttgggcgggt  4500
aaactgggtt gtgacatctg gccttacgga ccattcgccc cactttcggc ggatatcagt  4560
ggccagcttt ttagcgatct tcccgttact cagcatcgga tgcggttcaa ctatgatgcc  4620
cttcgcaccc accacccttt cttccagctt gtcgaaaacg ccgatcacca gatcgtggtt  4680
gttatccagc cagcgcgcct gctgcctcag cgaaaccgcc cccatctggc tgagctgatc  4740
ggctgaacga ttttccttct gggctttgtg ggtacgcgtt tgctttaccg cctcatacgc  4800
tttaataact gcgcgggcac gcaggcgtga ggctttccag cctggtgaaa acaggccaat  4860
cgcatcatct aaaaaactca tccaaacctc gccagcctgt agccgggtcg cccacggcgt  4920
ttgttattga gcgttgccag tcgtcgctcc cattcctgac ggccttttct gatttccgac  4980
aggttttcga gcgtcatctg ctgcccgttg aaagtgattg atttcccctc cagaacagac  5040
agctcggctg cagcatagcg gtcgatcatg ttttgaatat ctgctggatt cacacccaac  5100
ctcctgacga agaccacgga ttagcctgct cggttacggg cttctcacgt tttggttttg  5160
gtttagattt cggcgcaggc ggcggggatg gcatttcgcc agcttccgtc tgcgtgtcct  5220
cgatccacgt ttcccgccgt gcccactcag gagctgacgg ccatttgatt ttttcgtaac  5280
cactaaggat ggcgagcgcg tcggcataaa cgagcaggtc aaatgcttcg tttgcgcccc  5340
ggccgggctt actccatttc ccttcattcg agcgttcctc atacgtcagt tcgtcataga  5400
accagctgcc cagccaggcg gggaaatgca catagccagg gccgggtgaa tcacgccaca  5460
gcgcattatt cacccggtct ttaagggcat cggtctggag aagataaaga ggcacatcac  5520
cagtcgcctg tgcgcggcgc gttgatctgc ccgtgttgtc gggaaacgtt cgctggataa  5580
gtttgctgcg cctgacgctg tccccttga agagatagat acgcttaccc agcccctcac  5640
ggcgacatct gcgccagaac ttgtaggcat tatccgtcac gccatcttcg cccccctgagt  5700
ccacggccat cgacatcagc cgcatgccct ttgatgggtc agctgcgagc ggccacgttt  5760
tatcaaagac gtcagtgagt aaaagatccc agtcctccgg atagctcgcc ggatccacct  5820
gaatgctttc accgttgccg tcgcagcgca gcgaatgccg gatgttgtaa cggtcaacta  5880
tccagcgctc acccatactt ccataacccg taatctgcac aacaaagcgc cggttgcgcc  5940
cggcctgcac gtccacggtc gcagtgagaa actgcacgcc gttcggtacc gaacgttttg  6000
ggacgtcttc ggcacgctgc tcgagcaatt cacttttacg ctgctccatg ctggctcgcg  6060
gcaaataggg cctgccgaaa tcggtgttga tcaccgtctt cagggtttct tcgctgcgcg  6120
tggattcata ttcctgctcg gcggtcagaa acttataaat aagctgcgcc caggtctggt  6180
aagcagctgc cggaccttcc atccagaagg aggcaatacg ggaacgacgg ccatcaccgc  6240
taaccaggcc tttcctgtcg atggtttgcc cgtcccggag ccagacacat ttcatgttaa  6300
gcgcacgctt catgtccggt gtgatcctgc ctttacaggc agggcactga agaaacgccg  6360
cttcgctggc aagcacagga tcgctgctgt cgcggtatcc ggtcatattg tccatttccg  6420
gctggaaata ttcgccgcaa tgcgggcatg gccagtaaag acgacggcgg tcaccacggt  6480
tatagagcga taaaattccg gtggtcggag gggcttcatg gggcgtggag cgccgccatt  6540
ttgtgtctct gatatccctc ccgggcgagc tctcaaccag cgtcatcccg gaggacatga  6600
atgtcgtggt tcgtttcgat gccagtgaaa aagcatcccc ctccccgtcg atatcttccg  6660
gaaagcggtc ataatccgtc agcgccacac ttttatagtc cgaggacgac atgatattga  6720
cggatggcca gcccagcttc agatagttac cggcgcggaa tgtacggtcg tagacgttgt  6780
tatcgttacg tcttgggctt agccgggttt taacttcagg gctacagcga aaagtacggt  6840
ccaggcgttt tttggaatgc tcgcgcgctt tttcctcaga tacctgaatt acaagcatat  6900
ctgccggatc gcagacaatg ttataaacga tccagccgtc aatcagcccg atggttttac  6960
ccgttcgcgc tgggcccaca aacacaaccg catcgtattc acgcgatgcc agacagttca  7020
tcggctcaat cacatagggt gccagatccg gatcccacgg aactgagttt cccgccccca  7080
ttggcacgcg catataagta ctgaccgcat cggccaccgg catacgacgc ggggctcgta  7140
aaataccgga aacatcgcgg cggatgtccc tggcggatgc ccgctttgcc atcagtcctc  7200
ctcaggctgc tcctcctctt ttccagcgtc ctgcaccttc tccgccatct ggtcgcgcag  7260
atcatcgata acgctttgca cacgaactac cgcagcaggc gttaaagcac agtcgcgctc  7320
gagcacatcc gggagggttt caagtaccat gacgacggct ttcgccatca atgagaattc  7380
tcgcgccact tcatctgcgg gtattaactg ccccgtatcc tgttcgaact tcagcctctc  7440
gttctctgct ttccagtggg acagcctgtc agaagggggc atatcgtcga tgttggccga  7500
aacggtaggg atcatcagtt cggtcagaat gtcggtcacc agatagagct ttaacttgct  7560
attgctgcct ggagcaggtt caacattttt cagtctcgcg gcaaccgtct gacggtgtac  7620
gccggttatc cctgccagct ggttgatatt gagttttaaa gtggcaattt cctggtccat  7680
gatggtgaac actttttgaa cgattcgaca tgttgcgaaa atggcctcta attaaatcaa  7740
agacctgcgc acatgatgat gatgaccctg gatccgaaaa actagccgtt tcccgcgagc  7800
acgccgcccc gtggcagggt ccccctccgg gagtaccttt tgataataat tatcaattgc  7860
acactatcga cggcactgct gccagataac accaccgggg aaacattcca tcatgatggc  7920
cgtgcggaca taggaagcca gttcatccat cgctttcttg tctgctgcca tttgctttgt  7980
```

```
gacatccagc gccgcacatt cagcagcgtt tttcagcgcg ttttcgatca acgtttcaat  8040
gttggtatca acaccaggtt taactttgaa cttatcggca ctgacggtta ccttgttctg  8100
cgctggctca tcacgctgga taccaaggct gatgttgtag atattggtca ccggctgagg  8160
tgtttcgatt gccgctgcgt ggatagcacc atttgcgata gcggcgtcct tgatgaatga  8220
cactccattg cgaataagtt cgaaggagac ggtgtcacga atgcgctggt ccagctcgtc  8280
gattgccttt tgtgcagcag aggtatcaat ctcaacgcca agcgtcatcg aagcgcaata  8340
ttgctgctca ccaaaacgcg tattgaccag gtgttcaacg gcaaatttct gcccttctga  8400
tgtcagaaag gtaaagtgat tttctttctg gtattcagtt gctgtgtgtc tggtttcagc  8460
aaaaccaagc tcgcgcaatt cggctgtgcc agatttagaa ggcagatcac cagacagcaa  8520
cgcgccacgg aaaaacagcg cataaagcac ttcattagca gcgccagata gcgtaatgat  8580
tttgttactc atggaatatt tccttttagg cgtgagcctg tcgcacggca atgccgcccg  8640
agaggtaaac gcaacctaac ggcatcaccc aggctcacta ctgaaagact ctctttgatg  8700
tgcgcgtgcg atgcgcgtag aagactgatt tatcaacctg tctttatatc aggattcatt  8760
acctgactat ttgtgggtaa agttcgtagt gcgctgatcg tgcaaaatga ttttagttgg  8820
gaacagttcg caactctgtc ccataaaaat cagcatattc ccatctatcc catatccagc  8880
gcattgacca tcgggatact gaagggagat tccatcatct cttagaaaga tcaccatctc  8940
ttttgtttca atttgcatat agctacctgg aggatttatg aatgcaagga ttttcatgga  9000
ctattaccat gagattgatt ttccatcttt attcgcgaga gcagtggaaa gcgatgacga  9060
tgtgggtact acattgcgca ttcacctact ttgtgagcgc atggtcgaag catggatatg  9120
cgcatgctgt gactgccaag atctctttgg aagagataaa aacaaacttt taatcgaatg  9180
taatactaaa atatccatgg cgggaaacct gggaatcccc ccggaactta tgaaatcact  9240
taaaaccatc aactcaatgc gtaatgacct tgcacacaat ccatcaatac aaagcattgc  9300
tgattcaagg atccagagcc tgaaggatac tctgactgaa tactttaaac agcatccaac  9360
ggaacccagc atggaagaat caaaactggg tatttttaac gccgagaatc aattaaccga  9420
agaagtttcc ttagatagtg acagttcaaa aaacagactt aagttaatct tgctgttcag  9480
caagttaatg caggcgttaa tgcaattagt tgcagctaat cataatgggc gctgggataa  9540
ccaatttagc caattcgttt accatgtgac catgaacgca acaaagagat aaatccaagc  9600
ccgttttgta cgggctgttg cattatcaca ggcactcagt gaatgcctgc tgtaatgccg  9660
ctagtcgtcg agttgcaaca caccgtg                                      9687
```

SEQ ID NO: 131 moltype = length =
SEQUENCE: 131
000

SEQ ID NO: 132 moltype = DNA length = 19
FEATURE Location/Qualifiers
misc_feature 1..19
note = Synthetic primer
source 1..19
mol_type = other DNA
organism = synthetic construct
SEQUENCE: 132

```
gcatcaatca gtgattggc                                               19
```

SEQ ID NO: 133 moltype = DNA length = 20
FEATURE Location/Qualifiers
misc_feature 1..20
note = Synthetic primer
source 1..20
mol_type = other DNA
organism = synthetic construct
SEQUENCE: 133

```
acgtctgaat atacgggctg                                              20
```

SEQ ID NO: 134 moltype = DNA length = 59056
FEATURE Location/Qualifiers
source 1..59056
mol_type = genomic DNA
organism = Escherichia coli
SEQUENCE: 134

```
aggcctctcc tcgcgagagg cattttttat ttgatgggat aaagatcttt gcgcttatac  60
ggttggattt cgcccggttt gcgagttttc agcaatttta atatccaggt gtattgttct  120
ggtcgcggac caacaaaaat ctcgacttct tcattcatcc gccgcgcaat cgtatgatca  180
tccgcctcta acagatcatc catcggtggg cgcacctgaa tcgtcagacg atgcgtcttg  240
ccatcataaa tcggaaatag cggtacaacg cgcgcacggc acactttcat caaacgacca  300
atcgcgggca acgtcgcttt ataggtggca aagaaatcaa caaattcgct gtgttctggg  360
ccatgatcct gatcgggtaa ataatatccc cagtaaccct gacgtaccga ctggatgaat  420
ggtttaatac catcatttct cgcatgcaga cgaccaccaa agcgacggcg caccgtgttc  480
cagacataat caaaaaccgg gttgccctga ttatggaaca tcgctgccat tttctgccct  540
tgcgaggcca tcagcatggc aggaatatcg acggcccaac cgtgcggcac cagaaaaatc  600
actttctcgt tattacgtcg tatctcttcg atgatctcca gcccttgcca gtcaacgcgc  660
ggctgaattt tctccggccc gcgtattgcc aactcagcca tcattaccat cgcttgcggc  720
gcggtggcaa acatctcatc tacaatcgct tcgcgttcag cttcactacg ttctggaaag  780
cagagcgaca gattgattaa cgcacgacgg cgtgagcttt ttcccagtcg tccggcaaaa  840
cgtcccagcc gtgccagaat gggatcacgg aactttggcg gcgttaaagc gatacccgcc  900
atcgctgcta cgcccagcca tgctccccag tagcgcgggt ggcgaaagga tttatcaaac  960
tcaggaatgt attcgctatt atttttttc gtttccatgc ttttccagtt tcggataagg  1020
caaaaatcaa tctggtgata gtgtagcggc gcaacttgcc ccgcaccaaa taaaaaagcc  1080
ggtactgact gcgtaccggc tgcgaatgga tgttaattaa tcaaaccgta gctgcggcac  1140
```

-continued

```
aatctctttg gcctgtgcca ggaattcgcg acgatcggag ccggtcagcc cttcggtacg  1200
cggcagtttt gccgtcagcg ggtttacggc ctgctggttt atccatactt catagtgcag  1260
atgcggcccg gttgaacgtc cggtattacc ggaaagcgcg atacggtcgc cacgtttcac  1320
cttctgtccc ggtttcacca ggatcttgcg caagtgcata taacgcgtgg tgtagctgcg  1380
accatgacga atagccacat aataacctgc tgcgccacta cgtttggcaa ccaccacttc  1440
accgtcaccc actgaaagca ctggcgtacc ttgtggcatg gcaaaatcaa cacctctgtg  1500
tggcgcaacg cgaccggtca ccggattagt acgacgcggg ttaaagttag atgagatacg  1560
gaactgtttc gccgtcggga atcgcaagaa tcctttcgcc agaccagtac cgttacgatc  1620
gtagaatttg ccatcttcag cgcggattgc gtaataatct ttaccttctg aacgcaaacg  1680
tacgcccagc agctggcttt gctcacgttt accatcaagc atttctcgtg acattaacac  1740
cgcaaattca tcgccttttt tcagtttgcg gaaatccatt tgccactgca tggctttaat  1800
cactgcgctc acttcggcgc tggttaaacc ggcgtttctg gcgctggcaa caaagcttcc  1860
cccgacggta cctttcagca gattgttgac ccactctcct tgctgcattt cgctggtcat  1920
tttaaaaccg ttagcggcag tacggtcata ggttcgggtt tcacgacgag acacttccca  1980
ggtgaggcgc tgcagttcgc cgtccgcggt taatgtccag gagagttgtt gaccgatttt  2040
caggttacgc aattctttgt cggcagcagc cagttgggtg atatcaccca tatcaatacc  2100
atactgattg agaatgctgc ttagcgtatc gccagtggaa acaacatatt catgcacgcc  2160
cgcttcaccg gcgattttgt catccagttc gtcctgggga atggcttcat cttcttgtgc  2220
agcttgatca atcggctcac tggcttcagg taagagcgaa cgaatttcgt tctgttccag  2280
ctcaatggtt ttgacaattg gcgtggcatc gcggtgataa acatagggcc gccagacagc  2340
gacggccaga gtaagaacgg tgagcgaccc caacataacg cggtgtggtc gcggtaaatt  2400
attaaacgcc agggcgacag agcgggctat ctgttgcacg taatcacttc ctcattaatc  2460
tcctttcagg cagctcgcat actggttggc taattgattc aggaattctg aatagcttgt  2520
tttacccagt ttgatattcg tccccagggg atccaacgtt cccatacgaa cggatgtccc  2580
tcgtgcgacg ctctcaacga ccgctggcct gaactgtggc tcagcaaaaa cgcaggttgc  2640
tttttgctca accaactgtg ttcttatttc atgtaaacgc tgcgcgccag gttgaatctc  2700
agggttaacg gtaaaatgac caagcggtgt cagtccgaac tgtttttcga aatagccgta  2760
agcatcgtga aaaacgaaat aacctttccc cttgagcggc gcgagctcgt taccaacctg  2820
cttttcggtt gaggctaatt gtgcctcaaa atccttcagg ttggcgtcaa gtttggctcg  2880
actttgcggc ataagttcca ctaattttcc atggattgca accgctgtag cccgcgctat  2940
ctctggggaa agccaaagat gcatgttgaa atcgccgtga tggtgatctt cgtcactttt  3000
ttccgcgtgg tcgtgatcat catcatcgcc gtgaatactt ttcatcagca gcggtttcac  3060
attctctagc tgcgcaatcg ttacctgttt cgcttcaggt aatttactta ccggtttttg  3120
catgaacgct tccatctccg ggccaaccca aacgactaag tccgcgttct gtaagcgttt  3180
tacatctgat ggacgcagtg aataatcatg ttctgaagcc ccgtcaggta gtaaaacctc  3240
cgtttctgtt accccatcag caatggcaga agcgatgaac ccaacgggtt taagcgaagc  3300
gacaacggca gcatctgcgg cctgtgttgc accgccccag agagcggcgg ataatgctgc  3360
gaaaagaagc gttttttttat gtaacataat gcgaccaatc atcgtaatga atatgagaag  3420
tgtgatatta taacatttca tgactactgc aagactaaaa ttaacatgac aagtctggtt  3480
tccctggaaa atgtctcggt ttcttttggc caacgccgcg tcctctctga tgtgtcgctg  3540
gaacttaaac ctggaaaaat tttgacttta cttgggccaa acggcgcagg taagtcgaca  3600
ctggtacggg tagtgctcgg gctggtaaca cccgatgaag ggttatcaa gcgcaacgga  3660
aaactgcgca tcggctatgt accgcagaag ctgtatctcg acaccacgtt gccactgacc  3720
gtaaaccgtt ttttacgctt acgccctggc acacataaag aagatatttt gcctgcactg  3780
aaacgtgtcc aggccgggca tctgattaac gcaccgatgc aaaagctctc gggtggcgaa  3840
acgcagcgtg tactgttagc gcgagcattg ttaaatcgac cgcaattatt agtgctggat  3900
gaacccactc agggcgtgga tgtgaatggt caggtggcgt tatatgacct tattgaccaa  3960
ctgcgtcgcg aactggattg tggcgtttta atggtatctc acgatctgca tctggtaatg  4020
gcaaaaaccg atgaagtgct ttgcctgaat caccacattt gttgttccgg cacaccggaa  4080
gttgtttccc tgcatccgga gtttatttct atgtttggtc ctcgtggtgc tgaacaactg  4140
ggtatctatc gccatcatca taatcatcgt cacgatttac agggacgaat tgttttgcgt  4200
cggggaaatg atcgctcatg attgaattat tatttcccgg ttggttagcc gggatcatgc  4260
tcgcctgtgc cgcgggtccg ctgggttcgt ttgtagtctg gcgtcgtatg tcttatttcg  4320
gtgatacgct ggctcatgcc tcattacttg gcgtcgcgtt tggtttgttg ctggacgtga  4380
atccattcta tgcggtgatt gccgttacgc tgctgctggc gggcggtctg gtatggctgg  4440
agaagcgtcc acagctggcg atcgacacgt tattagggat tatggcgcac agtgccctgt  4500
cgctgggcct ggtggtcgtt agtctgatgt ctaatattcg tgttgatttg atggcttacc  4560
tgttcggtga tttactggca gtgacgccag aagatctcat ctctattgcg attggcgtgg  4620
tcatcgtggt ggctattttg ttctggcaat ggcgcaattt gctgtcgatg acgattagcc  4680
cggatctggc gtttgttgat ggtgtgaaat tacagcgcgt gaaattgttg ttgatgctgg  4740
tgacggcatt gacgattggt gtagcgatga aattcgtcgg cgcgttgatt attacttcac  4800
tgctgattat tcctgctgct actgcacgtc gctttgcccg cacgccggaa cagatggctg  4860
gtgtcgctgt tttggtgggg atggtggcag tgactggcgg tttaaccttt tccgcatttt  4920
acgatacacc tgcaggcccg tcggtggtgc tatgcgcggc actgttattt attatcagta  4980
tgatgaaaaa gcaggccagc taatctgtcg ctgaacacat ttgtcggatg cggcgcgagc  5040
gccttatccc acctgcggtt cgctatctct ggtaggcctg ataagacgcg aacagcgtcg  5100
catcaggcac actgccagtg tcggatgcgg ctcgagcgac caatccgact tacggcattt  5160
ctggcggcgt gatgccgaag tggttccacg cccgcactgt cgccatacgc ccgcgcggtg  5220
tacgctgcaa aaagccttgc tgaatcaaat aaggttccag tacatcctca atggtttcac  5280
gttcttcgcc aatggctgcc gccaggttat ccagacctac cggcccacca aagaacttat  5340
cgattaccgc cagcaacaat ttgcggtcca tataatcgaa accttcagca tcgacattca  5400
acatatccag cgcctgagca gcgatatctg ccgagatggt gccatcgtgc ttcacttcag  5460
cgaaatcacg cactcgacgc agcagacggt tggcaatacg tggcgtaccg cgcgcacgac  5520
gagcaacttc cagcgcgccg tcatcactca tctcaagccc cataaagcgt gcgctgcgac  5580
tgacgatata ttgcagatcc ggcacctgat aaaactccag acgttgcaca ataccaaaac  5640
gatcgcgcaa cggtgatgtc agcgaacctg cgcgcgtggt tgcaccaatc agggtaaacg  5700
gcggcaaatc aattttaatg gagcgtgccg ccggaccttc accaatcatg atatccagtt  5760
ggtaatcttc cattgccgga tacaacacct cttccaccac tggtgaaaga cggtggatct  5820
catcaataaa cagtacatcg tgtggttcaa ggttagtgag cattgctgcc agatcgcccg  5880
```

```
ccttttccag caccggacca gaagtcgtgc gtaaattaac gcccatttca ttggcgacaa  5940
tattggcaag cgtagtttta cccaaccccg gaggaccaaa aatcaataga tgatcgaggg  6000
catcgccgcg cagtttcgct gctttgatga aaatctccat ctgcgaacga acctgcggct  6060
gaccaacata ctcttccagt aatttagggc gaatggcgcg atctgccaca tcttccggca  6120
aagtggtacc ggcagaaatc agacggtctg cttcaatcat cctttacctc ataacgcggc  6180
gcgtagggct tcgcgaatta atgtttcact gctggcgtca gggcgagcga ttttgctcac  6240
catgcggctt gcttcttgtg gtttatagcc cagtgccacc agcgcagcaa ccgcttcctg  6300
ttcagcatcg tcggtcgccg ggctggcagg agacgtgagt accaggtcgg cggctggcgt  6360
aaagagatcg ccatgcaaac ctttaaatcg gtctttcatt tcgacaatca agcgttcggc  6420
ggtttttttg ccaatacccg gcagtttcac cagtgccccc acttcttcac gctcaacggc  6480
attaacgaac tgctgcgctg acattccgga gaggatcgcc agcgccaact tcgggccgac  6540
gccgttggtt ttgatcaact ctttgaacaa cgtgcgctct tgtttattgt taaaaccgta  6600
cagcagttgc gcgtcttcac gcaccacaaa gtgggtgaaa acgatcgctt cctgacccgc  6660
ttcagggagt tcataaaaac aggtcatcgg catatgcact tcatagccta cgccgcccac  6720
ttcaattaac accagcgggg gttgttttc aatgatgatg cctctgagtc tgcctatcac  6780
atgacgctcc tgcgtaatga atcaaagata atgctgtatg ataaaaaaat gctggataga  6840
tatccagcga aggatgaaga aaacttgcga ggtgtctcga tgatctgaaa aatggcgcag  6900
tataatttat tctacagatt atattggaag caaatattta aatattacat attcagcgaa  6960
gaaatgtgta ataaaaatac acattgcgac ccctgaaaaa aataaatttt ttatgctatt  7020
acgtatattc atatctattt caatggaatg acaacgtgaa tattaattat cctgctgaat  7080
atgaaattgg tgatatcgtc tttacatgta taagtgctgc cttatttggt caaatatcag  7140
ctgcatcaaa ttgctggagt aatcacgtcg ggatcattat cggtcataac ggtgaagact  7200
ttctggttgc agaaagccgt gttcccctct caaccatcac tacgctatcc cgttttatta  7260
aacgctctgc taatcaacgc tatgctataa agcgattaga cgccggacta acagaacaac  7320
aaaatcaacg aattgttgaa caggttcctt cccggctacg caaaatttac cacaccggtt  7380
ttaaatacga atcttcgcgc cagttctgtt caaaatttgt ttttgatatt tataaagagg  7440
cgctatgtat tccggtgggt gaaatagaga cgtttggaga attgttaaat agcaatccaa  7500
atgcaaaact cactttctgg aaattctggt tcttaggttc tattccgtgg gagcgtaaaa  7560
ccgtcacgcc agccagtttg tggcatcatc cgggtttggt gttgattcac gcggtgggag  7620
ttgaaacgcc tcagcctgaa ctgaccgagg cggtataact taacgcagtc gccctctcgc  7680
caggttcagt cgcgattcgc tcatttgcat cgcattctga ctaacgtggc agtgggtgat  7740
ggcaatcgcc agcgcatcgg cggcatccgc ctgtggatta gcgggcagtt tcagcaaggt  7800
gcggaccata tgctgcacct ggctttttc ggcactacca atacctacca ctgtttgctt  7860
tacctgacgt gccgcatatt caaataccgg caattcctga ttcaccgccg ccacaatcgc  7920
cacgccgcgc gcctgcccca gtttcagggc tgagtcagcg ttcttcgcca taaagacctg  7980
ttcaatggcg aaataatcag gctggaattg ggtgatgatt tccgtcacgc ccgcatagat  8040
gagcttcaga cgagacggta aatcatccac tttggtgcgt atgcatccgc tacccaggta  8100
ggacagttgc ctgcctacct ggcggatgac gccatagccg gtcacgcgcg aacccgggtc  8160
aatgccgaga ataatagcca tcacgcgtct ccgttttgct gtttagcagg cctcatcaga  8220
gagtcgctgc aacctcatca gagatttcac cgttatggta aacttcctgc acgtcgtcgc  8280
aatcttccag catatcgatc agacgcatca gtttcggtgc ggtttctgca tccatatcag  8340
ctttggtgga cgggatcatg gaaacttccg cgctgtctgc tttcagacct gccgcttcca  8400
gagcgtcgcg tactttgccc atttcttccc atgcagtgta gacatcaatc gcgccgtcat  8460
cataggtcac aacgtcttca gcaccggctt ccagggctgc ttccatgatg gtgtcttcat  8520
cgcctttctc gaaggagatc acgccttttt tgctgaacaa ataagctacg gaaccatcag  8580
taccgaggtt accgccacat ttgctgaatg catgacgcac ttcagcaacg gtacggttgc  8640
ggttgtcaga cagacattca atcatgattg ccgtgccgcc aggaccgtaa ccttcgtaga  8700
tgatggtttc catgtttgca tcatcatcac cgcccacacc tcgtgcaatt gcgcggttca  8760
gagtgtcacg ggtcatgttg ttagacagtg ctttatcaat tgctgcacgc aaacgcgggt  8820
tagcgtccgg atcaccaccg cccagcttag ccgcggttac cagctcacga atgattttag  8880
tgaagatttt accgcgctta gcatcctgcg cagctttacg atgtctggtg ttggcccatt  8940
tactatgacc tgccataaaa atatctccag atagccctgc ctgttcaggc agcgttaatt  9000
acaaactgtt caatcgcctg ccggttgctc caggacttag tgagcgccgc cgcagcagac  9060
gcatcaagcc acttgtaagc cagatgttca gtgaaaacga tctggcgctc gtgcggaagc  9120
gcaagacaga accatgattc cgtattacgc gtcacgcccg gcgcatagcg atgacgtaaa  9180
tgtgaaaaaa tttcaaactc taccgtgcgc tgacagtcaa ttaaggtcag ttgttcagcg  9240
acaacatcaa tggtgacctc ttcctttact tcgcgcatgg cagcttgcgg cgcggtttca  9300
ccctcttcca cgctgccggt taccgactgc cagaaatcgg gatcgtcacg ccgctgcaac  9360
atcagcaccc gtttcgtatc ttgtgcgtag atgaccacta agatcgaaac gggacgctta  9420
taagccatat cagttattct cagccttctt cacaacctga atgctcagct cagccagtgc  9480
agtcgggtta gcaaagctcg gcgcttcagt catcaaacac gctgccgccg tggttttcgg  9540
gaaggcgata acgtcacgga tattgtcggt gccggtcagc agcatcgtca gacggtcaag  9600
accgaatgcc aaacctgcgt gcggcggagt accgtatttc agggcgtcga gcaggaagcc  9660
gaatttctcg cgctgttcct cttcgttgat acccagaata ccaaacaccg tctgctgcat  9720
atcaccatta tggatacgca cagaaccacc gcccacttcg taaccattga tgaccatatc  9780
gtaagcgtta gccaccgcat tttccggtgc agctttcagt tctgctgccg tcatgtcttt  9840
cggtgaggtg aacggatggt gcattgctgt caggccgcct tcaccgtcgt cttcaaacat  9900
cgggaagtcg ataacccaca gcggtgccca tttgctttcg tcggtcagac caaggtcttt  9960
acccactttc aggcgcagtg cgcccatcgc gtcggcaaca attttcttgt tgtcggcacc  10020
gaagaaaatc atatcgccat cttgcgcgcc agtacgctcc aggatggctt cgatgatttc  10080
tgcattaagg aacttcgcta ccgggctatt gataccttcc agacctttcg cgcgttcgtt  10140
aactttgatg taagccagac ctttcgcgcc gtagatttta acgaagttac cgtattcgtc  10200
gatctgctta cgggtcaacg atgcgccgcc cggaacacgc agagcggcaa cacggccttt  10260
cggatcgttc gccggacctg caaatactgc aaactcaaca gatttcagca gatcggcaac  10320
gtcggtcagt tccatcgggt tacgcagatc cggtttatca gaaccataac ggcgttctgc  10380
ttctgcaaag gtcattaccg ggaaatcgcc cagatccacg cccttcactt ccagccacag  10440
atgacgcacc agcgcttcca tcacttcacg cacttgcggc gcggtcatga aagaagtttc  10500
cacatcgatc tgagtaaatt caggctgacg gtcagcacgc aggtcttcgt cacggaagca  10560
tttaacgatc tgatagtagc ggtcaaagcc ggacatcatc agtagctgtt tgaacaactg  10620
```

-continued

```
cggggattgc ggcagcgcgt agaatttacc tttgtgcaca cgagaaggca ccaggtagtc  10680
acgcgcgcct tcaggcgtgg ctttggtcag catcggagtt tcgatgtcga ggaagccgtg  10740
gtcatccata aaacggcgca ccaggctggt gattttagcg cgggttttca ggcgctgagc  10800
catttccggg cgacgcaggt cgaggtagcg gtatttcaga cgcgcttctt cggtgttgac  10860
gtggttagag tcaagcggca gaacatctgc acggttgatg atagtcagcg aggacgccag  10920
tacttcgatt tcgccagtcg ccatatcgcg gttaatattt ttttcgtcac gcgcacgtac  10980
ggtgcccgtg acctgaatgc agaactcatt acgcagttca gaggccagct ttaacgcgtc  11040
cgcacgatcc ggatcgaaaa atacctgcac gataccttcg cggtcgcgca tatcgatgaa  11100
gatcaggcta ccaagatcac gacgacggtt gacccaacca cacagagtca cctgctgccc  11160
cacgtgggac aaacggagct gtccacaata ttctgtacgc atgagatatc ccttaactta  11220
gctgccggcg gatgcccccct gctgcgcagg tgaccaagtc gcagcgttag ctgtatgtca  11280
caactgaatg aaaaaaggcg gctattatac tggaaattct gccgcaccgt aagagcctgg  11340
cccgcgctgg aacgcctcgt taccacttta tatcggcct gaaatcagac tctacgccag  11400
tttgctataa aggtgttgcc cgaactcata aaaattaaca aaatttgtcg ttccgccatc  11460
ggctaatcgc attaaggtga gaggcacgat tttgttttgt caggagtcat catgcttgaa  11520
cttaatgcta aaaccaccgc gctggtggtg attgatttac aagaaggcat cttgcctttt  11580
gccggaggtc cacatactgc cgatgaggtg gttaatcgcg ccgggaagct ggcggcgaaa  11640
tttcgcgcca gcggtcagcc cgtgtttctg gtgcgcgttg gctggtctgc cgattacgcc  11700
gaagcattaa aacagccggt tgatgccccc tcccccgcaa aagtgttgcc cgaaaactgg  11760
tggcaacatc ctgctgcatt aggtgcaacc gacagcgata tcgaaatcat caaacgtcaa  11820
tggggtgcgt tttacggtac ggatctggag ttgcaattac gccgccgggg tatcgataca  11880
atagtgttat gtgggatctc gaccaatatc ggtgttgaat ccaccgcccg caatgcctgg  11940
gaactcggtt ttaatctggt gattgccgaa gatgcctgta gcgccgctag cgccgagcag  12000
cacaataaca gcattaatca tatctacccg cgcatcgccc gtgtgcgtag cgttgaagag  12060
atcctcaacg cgttatgatt tacatcggtt tgccacaatg gtcgcatcct aaatgggtgc  12120
ggttggggat caccagcctt gaagagtatg cccgccactt taactgcgtg acgcgggcat  12180
tttaaaaatc actaaagaac gcccaagagc atgtgttttc tttagtttat tcaatgcatt  12240
aaaaaatagt ttcgcatgaa attcggtaaa cttcatgtgt gcaataatgt cccattcatg  12300
ccccaaaatg ccccaaagca gacatttttg ccccaagtat gccccacaag tcacgtcttc  12360
aagtcgtcta tatccatagc acaccgagtt acattcttgc atccggggtg tcgacaatac  12420
ctactttatt gagtgtgcga gaattaccag gaacctttcc acaatgtagt agtctaatag  12480
tcgaatccat ctaacattaa gaagcgttat gatcactagc ctctcattga tatcttctgt  12540
aatagtcact ctatgtatca tggtgttcgc tacagtaaag gtagggattg gtttgtctaa  12600
caatccagac agaaatgata attaacctca accacgtaac cacacttcat acttcatact  12660
tcacttaaca gtgaagtgct cacatcaccg ggcagtcatc aaactccgca ttcctggcat  12720
cattaatgat gtacgtgatc actccaaata tagcgggtgc agaactgtaa ccatcatcat  12780
ctgctggcag cgcttccctt ctcccgttat ccagattaac caggtgcggc tgaggatgag  12840
tccgatatcg cttgatcctg aattccccgt cgattgcaca tatcagcagt gaaccatcgc  12900
aggcagtaag tgacgcatcc acaacaagca acgctccctg gattatccct tccctgaaat  12960
gtgaacgcga tgcccgcatg aaataagtcg ctgcgggctg actgattagc tgctgatcga  13020
gggagattcg tgtttcaaca taatctgccg caggtgaagg aaatcccatg tttacgccct  13080
ctcttgaata ccggataaaa acacagtata aatactgtat atccatccag caaagaggca  13140
atgagcaatg ttcgtggaac tcgtttatga caaaaggaat tttgatggtc tgcccggtgc  13200
aaaagatatc attctgggcg agttaactaa gagagttcac cggatcttcc ccgatgctga  13260
tgttcgggtt aaaccgatga tgacactgcc ggcgatcaac actgacgcca gcaagcatga  13320
gaaggaacag ataagccgta ctgttcagga aatgtttgaa gaggctgaat tctggttagt  13380
gagtgagtaa agattttcaa tgcccgccac agttacgtat tgattatgct gtggaggata  13440
ttcattttcg taaacgttgg tttgggagaa gcggcaaaac ggaatgtggg aacaggggaa  13500
aatcagatac cagatatgtc tgcatttcca tctggcaata actggtttca gttaccaagt  13560
ggacatatcg ttcagatatt ttccatgaac gttcttggtg cagatgctaa tggcacgtca  13620
gctaattacc ccattgcttt tccaacaacg atgattgctg tcagtgctct atggtctgat  13680
gggactgtag caaatgcacc gacatacaag atgatgggga acacgactaa cagaacaact  13740
ttgacgataa aagtatcagc cagctcaggt acttacggga caatgattat tgcggtggga  13800
cgataatatg aataaataca gttactctcc ttcagaaaat gccttttatg ctgttgcgtt  13860
aaaaaatacc tatgaattga gtggcacatg gccagctgat gcattagata ttcctgatga  13920
catttctgta aaatatatgg cggaaccgcc acaagggaaa atccgagttg caggggaaaa  13980
tggttttccc acatgggctg aaatacctcc accatcacat gaggaactta ttgaacaggc  14040
cgaatcagag aggcaattat tgattaacca ggccaacgaa tacatgaaca gtaaacaatg  14100
gcccggtaaa gccgctattg gtcgtctgaa aggcgaggaa ctggcacaat ataattcgtg  14160
gctggattat ctggacgcac tggaactggt cgatacttcc ggtacgcccg atattgaatg  14220
gcctacgcct ccggcagttc aggccagatg acatccggcg cggtgctggt atctgttgca  14280
gtcaccgcgt caatgtaatc cagcacggcg ttaagtcggg ttgtttctgc ctgagtcagt  14340
ttccgtccgg cctgtaattt cagctgaatc agactaatgg aagccattgc tgcatcaatc  14400
agtgattggc gctgtgcttc tgccgcttct actgaggcac cgtgttgtgc ctcagtatct  14460
gtcacccatt tctcaccatc ccatttatca tatggcgtta acggtgaaag cgtgacataa  14520
ccgtttttga tggcaccgat ataatccact gtaacagctg cgccatttc gattgagtaa  14580
acagtctcat tgcgatggtc ttcctcatgg ctccatccct tacctgtaaa tactgccact  14640
cttcccggaa tgttttcgtc cgggtcaata ccagtggaac aggcgggcat acttacgcca  14700
gtattaatat attcatcaga ccagcccgta tattcagacg ttactgcatc ataataaaaa  14760
caacgcatat cacccggcac tgcagccagc ccattttcat caaaaacagg tttcattatt  14820
tagccctcac cagaaagtta aatgcaatat ttcgcggtct gacagcaaca aaattcacac  14880
catcacccac agagttactg ttgaaattaa atcgtgaaaa tcctggctga tttccggcga  14940
tgccatcatg aaagttaatt gcgtgtccag cacctccgcc tatattcccg gcaaactgag  15000
aaaagtttgt agcttcctgc cagcttaata attcgcgacc accatctgca cctcgcccgt  15060
catcccagac acgaatgaaa tcaccgcggg cttcaggtaa taccagcgaa ggaaacactt  15120
tcgccagcac aggataatca gtggcagaga atttcgcgcc gttgaacttc aaaaacacca  15180
tactggacca gctgtcgatt acagtatttg gcattgcagc ggacggccag aagaacggaa  15240
cgccaatagc tggagaacct tctcccaaac caaggtttgt gcgagcgtct gcggcattcg  15300
ttgcgccggt tccgccgtct gcgacagtaa ccgcaccgtt gctccctttc tgcgcaagtt  15360
```

-continued

```
taccgatgcc tgggatggtt acggcggtgc cgttgatggt aactgtgatg ctttggtttg  15420
ctgaggtggt ggcgaacgtc tcccacgcgc caatattctc gtcgtactct ttgatgagct  15480
gtgacatggc ctgcgccagg ccgtcgactg agatattgtc cgacacaagg attccatact  15540
tctggccgct cagcgccggg gaaactgctg gcgtaaccgt cattgacgtg gcgctgttca  15600
cggatgaaat ctgaaacagc tgcaccgggt tagacatcac gataatcgtc tggccagcgc  15660
ggacctggct ggcgggagct gtccagtttg tgccggagcc ggttgcggta tttccgttaa  15720
tagagatagt tccggtgcta taaatcataa caactcctaa atttagacaa catgaagccc  15780
ggagaggtat ataaccctca ccagaaataa tttctgaatt ggtttttaat acatgttggg  15840
caacgccagt gttggcatag ctatagttgt atcaaatgcc attgaccacc cacccaaata  15900
ataattgccg actactttat tcctttctgc tctgacattc ccacctgtca ttacaattcc  15960
tttataccta atatttccgt aaccaccaac gtgtcgacag ttagccccgg tataaacaat  16020
ctggcaaaat tcatcaccaa tattcaggtt cgcattggcg atatttattg tcccatcaaa  16080
aatgaatggc ttcgtgcaag taagaagacg tttgcgttga cgattggttt attcaatcca  16140
tcaactaaaa tatcatgtaa acgaattgcc ataacatttc ccactttatt ttacttactc  16200
aacacaacaa gtatattaaa attgaacctt gtcaacaaca caaaggagtc ccaatgaaac  16260
tcgctctaat tatgctgcca ttatgtctgt ccctcactgc atgtggtaat ggtttaaata  16320
ccggtaaacc aaattccggt gtcattccaa aacctttgga tcgagatggt aacggttctt  16380
taatttatga taccgaaaac cttccaatga cggggcagtg gtgtcacgag attgatcacg  16440
aataccgacg aatcggtagc ccttctaact gtgttataga ctactaaata ttaacccctc  16500
aaaagagggg ttaatatttt aacctgtgaa tgaaccagat ccgtgtgata ctatgatagt  16560
aggcgaagaa attgacgcac ccctgttatt ttgagcggac actttaatac gcactgttac  16620
gtttggacct gttacaaccg cagaatgcat gataagtctc tccatgtctt gcacggatga  16680
accactctca ttgccgttaa tgtcgattgt tcctgcacca ttacctttaa cgtttgctat  16740
aacacagacg tgtcttgcgt gcccagaact ggatgaatca ttataagtca ttaccttttc  16800
taaatatccg tcactagacc gactcacatt cgtccctgtg tgcatatttg caatgtcccc  16860
gataaaactt tgggcttcca cagtcccttt gaatttaccg cttgttgctt ggatctcacc  16920
agtaaagcta ccgccactag catatactac acctctgacg gtcacattgt tgaattcagc  16980
atctccagct ttattcaact tccaaccagc agaaccagct gcatagttgt tggactggat  17040
atagttaccg atttttgcgt tctcaatggt gccgtcctgg atgaagctgg cccggatgaa  17100
tgtctgcccg ttctggatca cgaacggcaa agctacgcta tttccggctg ccgtggtgac  17160
ggcgaagcgg tcagccagga agataacctg cgactgcatg ccggatggcg tattctccac  17220
gccgataccc atccccgcgg cgtaatactg cccgttgctg gagacaccaa ccttgatgtt  17280
gtacatcgcg ctgagttcgc cattaacgtt ggctatagcc tgagcgttag tggtgatggc  17340
ggaggtatgc ccgttcacgg tcgccgtgat gccgtttatc tgcgtggcgg tggcctgctg  17400
atagtcggag agcgtctgat tcaggctgtt gatggatgcc ttgttgccgt tgacgtccgt  17460
ctgcaggctc agcaatgaac gtgctgtggc ttccttctca ctgacgatca cctcgtcgag  17520
acggtccaga ttcgcgctgt tgccggcgac cgatgcagaa agggttttac gcgtggccac  17580
ctgagcgagg ttggcctgga ttatcgcaat tgcagagttc ttcaccccgc ccgtcatgcc  17640
gtccatagaa acgctgatgt tgtcgattcg ctggcccagg gcggtatcag ccgtcgcaac  17700
ggtctgctca agctgactga gtgaagacga aacattcccg accgtgctgg aaagctcatt  17760
aacgctggtc tgaaccttcc cgacgtcctg ggcatttttg gcgatatctt tcgcttgctg  17820
ctccagttcg tcgttggcct gtttgatatc gttagccatg ccagcaattt tttcgttgct  17880
gtccaccgcg ttctcgatca ggtctttgaa cgtttccgac tctttcatat cctccagaat  17940
gtcattagtt atttcgctga catctatcga ggacgtgccc atgatccagt cggtccagtc  18000
cccggcgtta ccgatacggt caatcaggcg cgcgcggtac cactggcgaa cgccggcagg  18060
catggggcca tgctgataat ctgcagccgg gtacggcacc aggaccagca gttcaggatt  18120
ggcgtagtcg gcagttgtgg cgcgctgaat ctctgtatag gccgtgtcgc ctgagccatc  18180
cggaaatttc caggtcaggt cgatatgcca gaccacatct tcggtcgcca ggaagttgag  18240
cggagtaccc ggttttcccg ttttaccgga gagataagtt gtttcaccgt atccccatgg  18300
tgacgacgta tcctgcgcat tcagcgcccg tacgcgcacg tcatagctgc ccgaataaat  18360
gccctgaacc gagaaaccct gcgcgctggt aaccggaacg tttatccagt ccccgttgtc  18420
cttacgccac tgggcaacat accggattgc gccctctacc ttatcccatg acacgtccag  18480
gcttgctaca gtcagcccct gagacacatg atcgctctca gtcaccacga tattcttcgg  18540
agcagacagg acgcttatcg gcgtgacggt gatcggggga gactcgaccc gaacgccgtc  18600
atcgatgtaa cgatatttgt ttggatcgtg ctgaacggcc gtaatagtga aaccgcctgt  18660
actgtcgtcg ttagccgcga ttgaggtgac cctgaagtac tgtattgcga ggttatcact  18720
gtctatcgcc caaacagcgc ccgccacagg aacctgactg aatgccgtag ccaccgtcac  18780
cgttttttta tcggcgctca ccgcgctgat tgtccgcgtc tgggcttttc cgtcgggaag  18840
gttaaccacc agccggtctt tcgccgcgta gtctatttct cgatcgaggg taatttggcg  18900
gccgttggcc gcgcttatac ggccccccgtt ctccttacca gagcggaaag gatcggcgac  18960
accgataatt tcagcgggca aagggatata accgtccagc cccacgccaa acgatacggt  19020
cccgtctttg gcattggaga gcaataccca gcgaccgcgt cggtgcgctt cactttgcga  19080
ggtgcagccg attgcggtca gggacgtctg ccggacgtcg taacgttcta caagcgccga  19140
atcgtaaacc ccctcaacgg tatcgctgta atggttctgc ggatcggacc aggacaccag  19200
gcaggagctg tagcgattct tgtatgagcc gcccgcataa gtaaacagcc catcgataac  19260
gtttgagacg ttataaaccc agtcaacatc gtcctgcggg acgtctgcct ggacataaat  19320
ctgatcgttt ccccagaacg ttattccacg aaataccgcg gcgagatcgt taagtacctg  19380
ccaggcgtcc tcctggctct gaatgaaaac gttgcaggtg aaacgcggtt cggtgccacc  19440
ggccccgtcg gaaaccattt cgtcacagta ctgggcgatt gaatacagcg cccacttatc  19500
caccatggac gcatccacgc gcgtgcccat gccgtaaatt tcatccagaa ccagatcgta  19560
aaagatccag gcagggttat tggaccatgc catttttgaac ccgccggacc atgaaccaga  19620
ataggttcgg gttttcggat cgtaattatc cggaacctta atcagcttgc cttttatctt  19680
acaggtcact ttcggcgcgc tgccgttgaa ttggctgctg tccacttcga catacaggag  19740
cgctgttaaa ggataacgaa gcttgctgtc gatgacttcc gcatacgaaa acaccttgaa  19800
ggcgttaacc agtttcgaat ttgatccgct ggcatcagcc gtaatacgcc tgaccctgac  19860
agaccagccg gacgtggatt ttggcagatc gatacggtgg tcacgctgat attccgtcgt  19920
ggtctttccg tcaaacttgc cgtttacaac cgttttccag gcgccgccgt ccgttgataa  19980
atcgatcgca tactcggtga ccgtgcccac catatcgcca ttatctttat agagatactg  20040
gaccggaagg ctgagcttga tacggatggc atccagggaa aggtttgtaa actggcgcgt  20100
```

-continued

```
ccagggcgcg gtggtggtga cagttgtgcc cacggccagc tcgttgtcga cctggggcat  20160
cccggcaata taggtctggt cctgtgtgcc cttgcggaac tcccatttca cgccgctgaa  20220
gttgtattcc ccgctgtcgt ttgccagcgg cgtatcgttg agaaaaatgt tctgagcggt  20280
caggtcgccc tgtatttccc cctcagaaac ggcaatgagc atttttaatt ttgcgaccga  20340
cagcagatcg tcaggctgct caaccggagt atgtgaactg ccacctcccc ctttggcacc  20400
ctgcaggatg gtttcttgtt taagaagctg catttttca cccataaaaa aaggtgccga  20460
agcacctta agttagtggc cgctggccta ctgctgatcg ctcgagtaca taccggcgct  20520
gactatcgct cccctgcct cagtcagacc gtaggccagg gggacaggat gccccatagc  20580
gacggtattg accggcgccc cgaaggcgta gttaggcgtg ttgtccgtgc tggaggattt  20640
acccgcgccg aaggatggct ggggcgtgag catctggaca acgcccccca gcatcatcga  20700
cactccgacc cctgtcagaa ttgacgtggc gctgatagct gttgcactca tcgccgcgcc  20760
ccaggctgcc atgctcgcac cagcggtaaa gaatgcagcg accagcgcaa cagccccgac  20820
aactatctgc aggacgcccg aacttttggc cccctcataa acgggcacga tccggtacac  20880
gcttccaccg cgggtcatat caaactcttc cagcccgata ttgttgccac cgttaaaaaa  20940
ggcgaaacgg atccccttca tatgagcttc agacatatat tttttgaatc cgggaacctg  21000
tgaacacatg gccctgagca tctcgcgcag gtcggcaaca tcaaactgaa cgcgtttacc  21060
gaattttttt gccattttac cttcgagaat aagcgtctta accatgcatt ctgtccttat  21120
gcctgaccac ccggaccgtt ctgtcgcgat aatatttcc ataaggcgtt cgcgaagaaa  21180
ggtgcccgaa aagatgatgg agaatgatgt tatcacccac atataccgcg gcgtgattag  21240
tcaccgatgc ctgcacactc atcatgatga tatctccggg ctgcattgca ccggcggcaa  21300
tctcaacgaa tccctcacgc tcccagttgt cgtcgtagag acgctccttg ccgctctccc  21360
accattcgta aggtactgaa taattgccga gaacaatgcc gtattcgcgc agataaaatt  21420
cacggataag cgaccagcag tcggcgtaac ccagcaccca ctgccgcccg gcataatccc  21480
ggtcttcacg cggggaaatc gtacaaaaat ccccgtccgg ccaggacatg atccccccact  21540
caatccccga ccagtcgcac tggatccggt ccagctctga gggcaccagc cgaaccacat  21600
ccggatggga atgaatgagc atgatgatct caccgcgcgc gcgggcagcg agctggtctt  21660
ccggggagag cgtgaatgtc tcctcgggtt tatcggcaat gttgcggcag ggaataaaga  21720
tttgttgctg gcctgactga acaatcaggc cgcaggcttc tttggggtat tcagcagcga  21780
cgtgctgacg gatagcatcc agcaattttt cacgcatttt tatttcccct gcaggtttgc  21840
agccggaaaa ccgccgaacg gcagcggcgc atccgggccg tgacgatcct gacaatcctg  21900
ccggcggccg ccacaaacat ctttcgacgg gtcatcggtc ggtgtaccgt ctttggtaaa  21960
gtatttcgtg ccgttgtaat cgcatccggt cccgcttcgg taccagcccc gcatacacca  22020
ggtgcagaca ggcgtaatct gccgtgtcgg cagctgcagg ctctgaatat cgaaaggaga  22080
acacagctcg aaatcaacct gtacccgcgt ctctgcggtt ttagcattga cgtaaaagag  22140
ctgtaagcgc tcatcggccg ggctggcacc cggattaccg tttttccagt tggcggcatc  22200
gagatacttc gaaagcgtgg tatggatttt gaccttagcc ctgaccatat cgtcatattc  22260
aagacacagc gcggtgacat agtttccgac gttcccgacg gacagcgtgg gcgttggctg  22320
ggaacctgta ctcgataact ccatcccctt aagttcgtag ggatggggat cgtactggtt  22380
tccctgccag ataatggcgg gcagattttc tgcggcgaag gctgcccacc cctcttcctg  22440
aatattgtgc gcatgaaaac gcagcacctg atccataccg aattcagtgc cgtcgatctc  22500
aatcagctga ataacgctgc cgggctcaag ctgttgtatg tctgccgtaa aactcatact  22560
ccccccataa aaaaaagccg cccggaggca gctttcagtg tttttcgaga aaatcagggc  22620
gcgaacgcct gttcaaaagt gaaggccaca gtggcttttt tcccggtagg gaaagaaacg  22680
ctgaacgaat cggccttcat tctgaacagc ttttttttcac cccatggagt ggtccaccag  22740
aacgatttag taacgtgaga catcaggaaa gcgcgcagcg cagccgcctc ctgtctggtg  22800
cccgtccagt ccaggttcca cgtttcctgt ttgtcgttga tccccatccc cgctatctgt  22860
ttgtagccat ccccgaactg ggcctgcagc gttcgggctg tttcagtgcc ctgcgctgtt  22920
tttcgcgtgc gccaggtaaa cgtgtccgtc actgtgtcct cctcgaataa agcacgccgc  22980
ccgcggacat ttcttttttc agtcgctcgg tgattgtctg ctgaacaatc gcctgcagct  23040
gtttcgccgt ccccgtggcg ttcgcctgat ttatgcttcc gtcactcccc tgctggctga  23100
tgctgactgg ggcataaaca ctgatcccgc ccatgccagc accggctgcg ttcccgccgc  23160
cgaccagacc acccgaggca tacccgcgca tcaggcgata gagattagcc acgccgatgc  23220
ggctggttga ttctttggtg aagacgaatt ccccgcggtg aacgataccg gctggctcgt  23280
acttgccgcc gtgcccggta aaaccgccca cgtcaaaacc ctgtggccgg tatgacggga  23340
ccgcgaatga ctgaccggca gaggaggttt tcgccccgcc gctaacccag cccattgcac  23400
tctggatggt gtaagccacc agcagctggt tgataacgga cacaatcatt ttaaggatcg  23460
agctggtgaa ttccctgaag ctcgccttcc cggttgtcgt caggctggta agctggcccg  23520
ccaacccgct gaacgtagcc tgagaaatct gctgaacgga gctgaaaacg tttgtcgctg  23580
aatcctgata ttcggcccaa ccctgtttcg caccggccag ccagtttgca cgcagggcat  23640
cttcagcttc gaacgtcgcc ctttgctctt ccagaacctt ttgctgcgcc tgagggttgt  23700
acgaatagct ttcgctgaga cgctgcagcg tagtttgtcg cccggcttcc cgggtggata  23760
acccctcaga ctgagcctgc aggcccgccc tggcggcttt ttgctgctgc tcaaacttca  23820
cggcctgatc ggccagctgg ttgagctttt gctggctggc aaccttatcg cccaggtcgg  23880
ccagctgccg cttgtactcg agcgtttctt ctttgtgcgc cagcagggat ttttcctgcg  23940
ccgtaagctg acgacgccca gcggcctcct gcagaacggt gaactgattt tcagtttgcc  24000
agagatcctg acgctgttta cttatgacgt cgttcacgct ggtatgctgc tcaagcgttt  24060
taagctgggc ctgaagggtg agaagttcgg cctgcgcctt ttcctcggct ttgtccccgg  24120
cgggcgttga gtagcttttg cctttcggtg tttttggatc cttccactgc ttttcaatcc  24180
cggcgcgggc cgcggcaatg tccttttcag tccacagcgt ggcgacaccg tctttcgcat  24240
cctggcggtt tttctcaata agctgactga gcttttctc tgctgaagcc cgcttttctg  24300
ccgccgtcgc gccggactcc accagctggt taaactgctg ctggctgcgg attgcctgag  24360
cctgctggtc cgttcgcatt ttttcccgcg cggctgccag cccttcctgg gcgtattgct  24420
gatcggcaag atcgtaagcc tgctttttca gctccacctg ctggcgcgcg tttctcagcc  24480
tttccgcatc cgctttctgc agaacgttgt taccggcata atccgggtcg accttaagat  24540
tgctggacag cgcgcggtac tctttctctg ctgcctgcca ctcagcaaaa gagtcctggc  24600
gcttcatcgc ggtgtcagga ttacgcccga cgcccagcat cgcatcccac gcaccggagg  24660
cggcattctt cacccagttc caggcttttt cgagggatcc gagattatcc tcgaccgcac  24720
cggcgcgctg aatgaccgcg tcggaatatg cccgcatggc cagctcggca gccttctgag  24780
aatcccccag cgcctgagca gaagctatct gttcatactg ggtggctgtc agaaaatgaa  24840
```

```
gggaatcgtt gagcgtcgcg accgcgttaa ccggatcatc cttcaggcgt ttaaactgat  24900
ttatggtttc gtcaacggcc tgcccggtag cctgctgcag cctggcggca acattgctga  24960
ccatgctgac gtcattaccg ctgaacgcgc cgctgccaac gacctgcgcc agcacgcctg  25020
cagcggcatg ctgagtgatg ccattacctg ccagcgagcg cgccagcgcc tgcagctgcc  25080
ctgacgtttt ccccgcgtag ttcccggtca ggatcagctg cctgttaaat tcctcagact  25140
ctttgctgcc gtcgtaccag gccttaccca acccgaatac cgccgcggca atccctccga  25200
ccatgctggc gatcccaaga ccgcgcagtg acagaagctg gtctatccac cctgcccggt  25260
tagccagcgt gatcccggag ccgcgcagcg cgccgaagtt accgcgcatg acctcgccga  25320
tcagtattcc cagttcctgc cgggcggcgg cactttgcag ccccagaccg tgcgtggcga  25380
ctttggcagc ttcgagcttg cggatataga cttcagccgc atcgctggca ccgacctgcg  25440
ccgccttcat gcgcagtagc tcggtaccgg agagcttttg ctctgcaacc tgttgcttca  25500
gctggctgag gaatcgcgtg cgcgctgcgg ccgatttttc ctccacgatc tgcagttctt  25560
tttgacgggc cgtggtgcgg gaaataaggg cgagataatc ctgctgggtt atgttgccct  25620
gtgccctcgc tgcgcgaaag cgcgcctgca cgttcgcaag cgactgtgtt tcaccattga  25680
gctggcgtac gccgtcgatc tggcggaaaa atgatgccgc aagttcatcc tgtcgacggg  25740
caagcgcagc ggcctgcccg tcattctcac gcatgcgctg attaagctcg gtcacgcggc  25800
ggtgagtttc atcaacggac tttgaaacgt tctgccagtc tttggtaagc ccttccgttg  25860
cggccgactg gcgggatttc atatctgcgg cagccgccgc gccagcgtca cccacggttt  25920
taaacgcagc cgcctgccgc tctgaagcgc gctgcattcg cgtctggact ttttcagagt  25980
cctcagccat cccggttagc tggcccttta tgcgggcaac ctgctcacta aacgtggcgc  26040
tgtcgacgtc aaggttgatg accagatcgc taatctgctg ggccatatcg gatacctcct  26100
gttatcccct cagctgcggc catcagcgca tcatcatccg gctcgtcatc gctgatgacg  26160
ataccggaag gagaaagcag gctgaaatgt gcgggggtaa gttccgggtc gcggaagaaa  26220
agagtggaga tggaataaag cagctctgag aaatgcgcat cgagctgagc gtcctgaaaa  26280
taatgctccc ggtagaactg gtgccagtcg cccagctcag tggaagtcat tccagccagc  26340
atggcgcgcc agtcgggtcg cccgaactcg cgcgccagat tcaggacaaa cttcagctcg  26400
ctggcaaggg cttttccgcc gcaacgggtt ctgcgctttc ggcctccgct ggggcatccg  26460
gatcggcagc tttgtcatcc tcaaccggaa cgagcatgcc ggagagcagc tttatttcca  26520
tttctgcttt accgatcgcc tccggcggcc agccgctaag cacctgctgg taaagcgtct  26580
ccacatccgt gccagccgga tcgttatgcc acaaagacat cgcaatcaaa cgcgcaccgc  26640
agcgaatatt tgagccaatc agcctggccg tcatttcctg atcgctgatg ccgtcgctgt  26700
cagcgctgac ggcctttttcc tctgcggcca taaacgtgat gtactcaata cgctgaagcg  26760
ccgacagctc gaagatggtc agtgattctt tttgccaggt gaacttctct tttttcagaa  26820
acatgcgtcc ttccttacgc tgcagttacg gtaactttgc agaccgcaac gaaattaccg  26880
tcgctggtca taacaataac gtcagcggtg cctgccgcca cgccggtgac ggtgatcgca  26940
ttaccgctaa cggtgaccgt tgcttttgcc ccgtctgagg ttgccacacg gaacgaggta  27000
tctgaggcac tggctgggtt aaccgtcaca ttgagcgttg tggttgcgcc gacggccacg  27060
cttgccgtgg ctttatcgag cgtaacgcct gtcacgggga tattcggggt cccgctttct  27120
tctgccagtt ccggcttgcc ggtattggta attttcgctg tacgggttat gacctctttt  27180
gccggaatgg ctttacccag gctgctgcac cagccgcgga aaacgtcgac ggtaccgttc  27240
gggtatttga ttttgtaata gcgtactgag ccatcaataa accatgcgac aaggtctttt  27300
tgcccttctt cgcccggctt ccaggcgagg gtgaacgagg tatcgccagc agattttgcc  27360
ccctgggccg tcgcgttcca gtcggcatcc tcgtcgtcga ggtaagtgtc gtcatacgat  27420
tcggcggtca tttcgcccgg cgtcagctct ttaattttcg ccaggcggtt ccagtcgata  27480
tccgagagtg ggttagcgaa agcgttgccc gttccggtgt aaagccagag ggtggtaccg  27540
gcacctttca caggggccag cgggtttgga gtaggcataa gtacctctta aattgaatag  27600
gtgattaagt acgtgaaatc gactgaaccc caggtggcca tttcatcatc ccgctgatag  27660
tcataaccct gcggggtgaa cgtctcgacc agttcggtca gacctgggat gaaggccatt  27720
gccggataca ctttctcttc catccaggaa tcaagcgcgc tgtcggggct ggaggcttta  27780
agaaatacct cgatgtgaac aaccgcctgc cacgaatctt cgtcaagcga atcgccggtg  27840
tactccgcgt cagaaaggta tacagccacg gcagggagat cctgctcttc aagaaaaaca  27900
gggcgcccgt caaaccaggt gaccgtgtcg gtgatctcgg ctttcagttt ggccagaatg  27960
gctgcacgaa ttgcgctgtg tctgttcatc gcttcaggtg gatcctcagt tggtttttca  28020
gggctgcgga aagttctttg ggcatatcgc tttcaataag gcgctttgaa atagcggtga  28080
aggccacggt gagcggtgtc tcaagaggaa ctttgaccac atcaatcgga taacgggcct  28140
gacctacgcg ccgcatgacc tgccagcgcc cgttcgcaag ctgttggata aaagcgttac  28200
gaaaggtata gggcccgatt ttaaggacgc tgcccgctcc gtttctggcc cctttttttac  28260
gcgagagcct gacgcgcgcc gtgccgagct ttatcgcagg aagattaccg cggttgattt  28320
ttatcgacgc gaccgggcga tcgtgacggc ccttgcgcag acgggaacgc tggcggacca  28380
gacgaaccgg aagccccttt ttccggttat catcaactgt tgcttctttc gctacagctt  28440
tgctcccctg gcttatcgtt cttctggcca ccctgttaag tgcttttgcg gttgcctcag  28500
gaacgattaa ccggctgagg ctgttcaggt tctgaatagc cctttccagt cctttcacag  28560
acatagcgcc tcctcattcg agatggatgc ggggttttcc gttgaacatg tcatagcggg  28620
taacgatcag gttcttaccg tcgtagtcga cgctgtcgtt tcggcgtggc tggtaaagct  28680
cagagaaaac caccagcgaa gtacctgttc ccgacaatgg ccccatttcc tcgagttgct  28740
cggcgggaac aacgtcatag ctgctgccat tgatgatcgc tgtctttccc atctttttta  28800
tagtggccgc gtccatgcgc gccgccatcc ggtcaaagga gttaggcatt gatcttaact  28860
tcaacaacgg tggtgtttgc ccctgcatct tcccaggcga tgcccgcggc aacggcgtcc  28920
gtttcttcga tcgtgatttt gccgtccttc agatacacct gcgcccggc agtaaccgca  28980
tctgcggata cttttggcag gaggaaaaca ccctcagtaa aaccgtcccc ggtatcgcca  29040
gccgggatat cggtaattgc caccgcgata agttttccaa caacaaccgg gtcgccgctg  29100
tgaacatcgg ttgcaccact gtttaccaga gggatcgttt tcccgtcctg cgcatagttc  29160
ttagccataa cttctccatt cagccccttt cgaggctggt ttcaggtata aaaaaagccc  29220
ttacgggcgt ctgtttgtca ggactgtttt ttactgacca gaggatttgg tcatgccgcg  29280
atagtccagc ggcgccacgc cagcatcaat acgcactttc gtggcgatac catcagtggt  29340
gaagccttcc tgctgatcga tgtatggcgt gtcgacgccg ttgagataag cgacctcaat  29400
ggtgtcggtg cccttcgcgg cagccagata ccaggctttc gcatcagctt catccagacg  29460
tggttcggca atgacttctg caaagttctg gatagggtta acgatcccgg cattgatgtc  29520
tgcaccttta acactggccg acttgatggt ctgatttgcc agagtttcca gggcgacggg  29580
```

-continued

```
caccagcatg taggccggac ggatattcag ggttcgctcc ccctccttct gcagacgcat  29640
cagcttgcgc gattcgtcca ggctggccac agaaattgca cccgagctca ggttcttgtg  29700
atcggcatgg aacagcgcct ttccgtctga gagtttcggg tttttggtca gaatggcgta  29760
aaccagatcg ccaatcgttg ctttcgccgc gcgccccatc ttcatcggta cgtcggtaag  29820
ctggttcaga tcgtcgttga tgatcgcctg gcgagttact gagaagattt caccatacgt  29880
ggcaagcgcg atggtttcgc ctttgtcact ggtagtgatg tacttgtact cagccccttc  29940
gcgaacctgt cgcagagaag ggaacccacc cataccgaca cgatgcgccg ttttgaagtc  30000
cgacagctgg cctttttgg tccactgctc gaaggtttcc tgcgcctcgt cccagccctg  30060
aatcagcgct ttgttcgcaa catcaagcag aatgttgcca aagtcagagg tgctgtgggt  30120
cagcgccagg ccaaccatct gcatcgggtt gtagctggcc acgccgatac ctttttctgt  30180
cagggccata cgcgcatact cgcgcagcgt cataccgtta taaacgttat cccgctcctg  30240
accttcgaac ccggcacgcg ccatcagtgc ctggcgaata ccatccgcga cgaagttacc  30300
gttgcccgca tgaatatgcg gctgagtggt tttattggac ggcgtggccg ttttaccgag  30360
ttctgccagc agcaaatctt tcgccttatc gacggagcaa tcagggtcgg ccacacactg  30420
attctgcagt tccatgtgct tattaccgaa catggcaaag agatcgccga tagcgttaac  30480
acgggttttc tgctcagcca acacctgcgc gcggatcgca ttttcatccg gtgccgggtc  30540
tgtttttgcc tgcggtgcct gaggctgggt aataaccggg tcacgctggg tagtgttgcg  30600
cggcggggtg atcatgttgc gaatgctttt tggcattttt tcaaattcct caatacgttt  30660
tgaatgaata caggccatag cctgaaggga tggtgtcacc tggtcggcaa aacccagttc  30720
aaggcactcg ctgccgttca tccaggtttc gtcctccagc attaccgcaa tttcttcggt  30780
ggattttccg gttttctgtg cataagccgg gataagaacg gattcaacct tgtcgagaag  30840
atccgcatag tcgcgcatat cgctcgcgtc accaccagca aacccccagg gcttatggat  30900
catcatcatc gtgttttcag gcatgatgac cggattgcct accatcgcaa tcaccgaggc  30960
catggaggcc gccagaccgt cgatatgtac ggtaatcgcc gcgccgtggt gcttcagcgc  31020
gttataaata gcaattccgt cgaagacatc accaccgggc gagttgatat aaaggttgat  31080
gtgggtgacg tccccaagtg cccggagatc attgacgaac tgtttcgccg ttacgcccca  31140
gtacccgatt tcgtcataaa taaaaatgtc ggcctcactg ttattgctgg cctgcatgcg  31200
gaaccacgaa ttacttttg cgctggcttt cggacggtgg cgcgcccggt tctttggctt  31260
cggcactggt gcctccttta tcattggcgg ggtcggtgtc aaacaccagg ccctgttcac  31320
ggttctcgtc aacctcagct ttacggcgtg acttaacatc atccgggttg cgaccgctgg  31380
cacgtatcca gtcggattca gtagcagcac cgccgcggat ctgcgttttc caggcattcg  31440
cttctttaac gggatcaatc cacggcataa cgggccccga ataaaccgcg ttataaagcg  31500
agtccatatc aatgcctctc ggcagcttga tttctccggc agcaatagcc atcttgagcc  31560
aggctcggta catgggccgg gtcactgaac cgatgaacca gtcctgaaga atcagatagc  31620
cgtcggttga ctcgacaagc tcctgccgct gggcactgta cgttccgttg tagtttctgg  31680
atgtgctgga aaagctgagg cgactgccgg cggacacggc acgcagctgt ccgttacgaa  31740
aagattcgag gttagggttc gggcgatcgg atttaatcat cccgatttct tccccggcct  31800
gcagttcgtc atagagcata ccgggctgaa tcatcagctc gcggtcatcg ctgcttgaat  31860
cagaatcgaa gctctgtccg tcgccttttt tgatatacat gccgagtgcc gcagcaattc  31920
tggcagcagt aagctccgag tcctcgtatt ctttcagcgc gctcagacgc atcagaacac  31980
cagacaaaag agacgttccg cgggtctggt gcaggcgtcg ggtgaatttg agatgcagca  32040
tgttctctgc atctatctct ttggtatcaa actgacgccc ggatactggc aggcttttat  32100
agacctgata tttttcggg cgtccccagt tatcgacaaa aacgccctga ttgagctggg  32160
tggcagcatc gctgttcatc ggcacaaagt ccggctccag cgcttccagc cagaacggca  32220
cgccagcaac cggctgaaga ccatttccgg taccgcgaac cagctgagca aatacctcac  32280
cgtcccggag ccacgttcgc agcatcagcc gctccagcat tgggcgggta aactgggttg  32340
tgacatctgg ccttacggac cattcgcccc actttcggcg gatatcagtg gccagctttt  32400
tagcgatctt cccgttactc agcatcggat gcggttcaac tatgatgccc ttcgcaccca  32460
ccaccctttc ttccagcttg tcgaaaacgc cgatcaccag atcgtggttg ttatccagcc  32520
agcgcgcctg ctgcctcagc gaaaccgccc ccatctggct gagctgatcg gctgaacgat  32580
tttccttctg ggctttgtgg gtacgcgttt gctttaccgc ctcatacgct ttaataactg  32640
cgcgggcacg caggcgtgag gctttccagc ctggtgaaaa caggccaatc gcatcatcta  32700
aaaaactcat ccaaacctcg ccagcctgta gccgggtcgc ccacggcgtt tgttattgag  32760
cgttgccagt cgtcgctccc attcctgacg gccttttctg atttccgaca ggttttcgag  32820
cgtcatctgc tgcccgttga aagtgattga tttcccctcc agaacagaca gctcggctgc  32880
agcatagcgg tcgatcatgt tttgaatatc tgctggattc acacccaacc tcctgacgaa  32940
gaccacggat tagcctgctc ggttacgggc ttctcacgtt ttggttttgg tttagatttc  33000
ggcgcaggcg gcggggatgg catttcgcca gcttccgtct gcgtgtcctc gatccacgtt  33060
tcccgccgtg cccactcagg agctgacggc catttgattt tttcgtaacc actaaggatg  33120
gcgagcgcgt cggcataaac gagcaggtca aatgcttcgt ttgcgccccg gccgggctta  33180
ctccatttcc cttcattcga gcgttcctca tacgtcagtt cgtcatagaa ccagctgccc  33240
agccaggcgg ggaaatgcac atagccaggg ccgggtgaat cacgccacag cgcattattc  33300
acccggtctt taagggcatc ggtctggaga agataaagag gcacatcacc agtcgcctgt  33360
gcgcggcgcg ttgatctgcc cgtgttgtcg ggaaacgttc gctggataag tttgctgcgc  33420
ctgacgctgt cccctttgaa gagatagata cgcttaccca gcccctcacg gcgacatctg  33480
cgccagaact tgtaggcatt atccgtcacg ccatcttcgc cccctgagtc cacggccatc  33540
gacatcagcc gcatgccctt tgatgggtca gctgcgagcg gccacgtttt atcaaagacg  33600
tcagtgagta aaagatccca gtcctccgga tagctcgccg gatccacctg aatgctttca  33660
ccgttgccgt cgcagcgcag cgaatgccgg atgttgtaac ggtcaactat ccagcgctca  33720
cccatacttc cataacccgt aatctgcaca acaaagcgcc ggttgcgccc ggcctgcacg  33780
tccacggtcg cagtgagaaa ctgcacgccg ttcggtaccg aacgttttgg gacgtcttcg  33840
gcacgctgct cgagcaattc acttttacgc tgctccatgc tggctcgcgg caaatagggc  33900
ctgccgaaat cggtgttgat caccgtcttc agggtttctt cgctgcgcgt ggattcatat  33960
tcctgctcgg cggtcagaaa cttataaata agctgcgccc aggtctggta agcagctgcc  34020
ggaccttcca tccagaagga ggcaatacgg gaacgacggc catcaccgct aaccaggcct  34080
ttcctgtcga tggtttgccc gtcccggagc cagacacatt tcatgttaag cgcacgcttc  34140
atgtccggtg tgatcctgcc tttacaggca gggcactgaa gaaacgccgc ttcgctggca  34200
agcacaggat cgctgctgtc gcggtatccg gtcatattgt ccatttccgg ctggaaatat  34260
tcgccgcaat gcgggcatgg ccagtaaaga cgacggcggt caccacggtt atagagcgat  34320
```

-continued

```
aaaattccgg tggtcggagg ggcttcatgg ggcgtggagc gccgccattt tgtgtctctg  34380
atatccctcc cgggcgagct ctcaaccagc gtcatcccgg aggacatgaa tgtcgtggtt  34440
cgtttcgatg ccagtgaaaa agcatccccc tccccgtcga tatcttccgg aaagcggtca  34500
taatccgtca gcgccacact tttatagtcc gaggacgaca tgatattgac ggatggccag  34560
cccagcttca gatagttacc ggcgcggaat gtacggtcgt agacgttgtt atcgttacgt  34620
cttgggctta gccgggtttt aacttcaggg ctacagcgaa aagtacggtc caggcgtttt  34680
ttggaatgct cgcgcgcttt ttcctcagat acctgaatta caagcatatc tgccggatcg  34740
cagacaatgt tataaacgat ccagccgtca atcagcccga tggttttacc cgttcgcgct  34800
gggcccacaa acacaaccgc atcgtattca cgcgatgcca gacagttcat cggctcaatc  34860
acatagggtg ccagatccgg atcccacgga actgagtttc ccgcccccat tggcacgcgc  34920
atataagtac tgaccgcatc ggccaccggc atacgacgcg gggctcgtaa aataccggaa  34980
acatcgcggc ggatgtccct ggcggatgcc cgctttgcca tcagtcctcc tcaggctgct  35040
cctcctcttt tccagcgtcc tgcaccttct ccgccatctg gtcgcgcaga tcatcgataa  35100
cgctttgcac acgaactacc gcagcaggcg ttaaagcaca gtcgcgctcg agcacatccg  35160
ggagggtttc aagtaccatg acgacggctt tcgccatcaa tgagaattct cgcgccactt  35220
catctgcggg tattaactgc cccgtatcct gttcgaactt cagcctctcg ttctctgctt  35280
tccagtggga cagcctgtca gaagggggca tatcgtcgat gttggccgaa acggtaggga  35340
tcatcagttc ggtcagaatg tcggtcacca gatagagctt taacttgcta ttgctgcctg  35400
gagcaggttc aacatttttc agtctcgcgg caaccgtctg acggtgtacg ccggttatcc  35460
ctgccagctg gttgatattg agttttaaag tggcaatttc ctggtccatg atggtgaaca  35520
ctttttgaac gattcgacat gttgcgaaaa tggcctctaa ttaaatcaaa gacctgcgca  35580
catgatgatg atgaccctgg atccgaaaaa ctagccgttt cccgcgagca cgccgccccg  35640
tggcagggtc cccctccggg agtacctttt gataataatt atcaattgca cactatcgac  35700
ggcactgctg ccagataaca ccaccgggga aacattccat catgatggcc gtgcggacat  35760
aggaagccag ttcatccatc gctttcttgt ctgctgccat ttgctttgtg acatccagcg  35820
ccgcacattc agcagcgttt ttcagcgcgt tttcgatcaa cgtttcaatg ttggtatcaa  35880
caccaggttt aactttgaac ttatcggcac tgacggttac cttgttctgc gctggctcat  35940
cacgctggat accaaggctg atgttgtaga tattggtcac cggctgaggt gtttcgattg  36000
ccgctgcgtg gatagcacca tttgcgatag cggcgtcctt gatgaatgac actccattgc  36060
gaataagttc gaaggagacg gtgtcacgaa tgcgctggtc cagctcgtcg attgcctttt  36120
gtgcagcaga ggtatcaatc tcaacgccaa gcgtcatcga agcgcaatat tgctgctcac  36180
caaaacgcgt attgaccagg tgttcaacgg caaatttctg cccttctgat gtcagaaagg  36240
taaagtgatt ttctttctgg tattcagttg ctgtgtgtct ggtttcagca aaaccaagct  36300
cgcgcaattc ggctgtgcca gatttagaag gcagatcacc agacagcaac gcgccacgga  36360
aaaacagcgc ataaagcact tcattagcag cgccagatag cgtaatgatt ttgttactca  36420
tggaatattt ccttttaggc gtgagcctgt cgcacggcaa tgccgcccga gaggtaaacg  36480
caacctaacg gcatcaccca ggctcactac tgaaagactc tctttgatgt gcgcgtgcga  36540
tgcgcgtaga agactgattt atcaacctgt ctttatatca ggattcatta cctgactatt  36600
tgtgggtaaa gttcgtagtg cgctgatcgt gcaaaatgat tttagttggg aacagttcgc  36660
aactctgtcc cataaaaatc agcatattcc catctatccc atatccagcg cattgaccat  36720
cgggatactg aagggagatt ccatcatctc ttagaaagat caccatctct tttgtttcaa  36780
tttgcatata gctacctgga ggatttatga atgcaaggat tttcatggac tattaccatg  36840
agattgattt tccatcttta ttcgcgagag cagtggaaag cgatgacgat gtgggtacta  36900
cattgcgcat tcacctactt tgtgagcgca tggtcgaagc atggatatgc gcatgctgtg  36960
actgccaaga tctctttgga agagataaaa acaaactttt aatcgaatgt aatactaaaa  37020
tatccatggc gggaaacctg ggaatccccc cggaacttat gaaatcactt aaaaccatca  37080
actcaatgcg taatgacctt gcacacaatc catcaataca aagcattgct gattcaagga  37140
tccagagcct gaaggatact ctgactgaat actttaaaca gcatccaacg gaacccagca  37200
tggaagaatc aaaactgggt atttttaacg ccgagaatca attaaccgaa gaagtttcct  37260
tagatagtga cagttcaaaa aacagactta agttaatctt gctgttcagc aagttaatgc  37320
aggcgttaat gcaattagtt gcagctaatc ataatgggcg ctgggataac caatttagcc  37380
aattcgttta ccatgtgacc atgaacgcaa caaagagata aatccaagcc cgttttgtac  37440
gggctgttgc attatcacag gcactcagtg aatgcctgct gtaatgccgc tagtcgtcga  37500
gttgcaacac accgtgatcc agtgattctg aataggcgat aagtccggta taaccgggga  37560
taatctcacc attatcagct tcaaattcag gaattgtgcc ggtggtgatg gtgtattgag  37620
gctggccatc ttccttcgcg aaggctgcca ggtcttcaat ctgcttagct gtaagaacta  37680
ctgtcatgct cattcctcag ttgtaaaaaa gccccgcgag tgcgaggcga tttgattgaa  37740
ttctcggctc ttatctcagc gcagcccctt actgcgtgcc ggttgctcgg tgatgagcat  37800
cagcgatgag acattaaagc cgaccgaagg ccagcggcgt tcctcatgtt gccgacagag  37860
ccatatcgac aagaggacga aaactagcag catgaatcgc ctattggtta ttcgacagtc  37920
gcactgattc gtaaatccgc tcacacgtca ttcctgcccg gtagctttcg tcagatcgtc  37980
cagcataata tcgagctgct tctgcaaggc ttccgagcat gtcggcaagc attgctgcgt  38040
tggctccggc tgttttgctt ctgacggaag tggcgagatc tgcggtgtgc tttgcggcgt  38100
ccatgtgggt agcgagtttt gttgcttcgg cgcgcagctg cttaacagtg gtagccaggc  38160
cagcagaagt aacggcagcg ctcgctgctt gagcttgagc atctttaacg gcctcatccc  38220
gggcgattgt tcgcccttgt tcaatcatac gagctgcggt ctgtgcattc gcttcctgtg  38280
aagattccgc gctatcccgg tcagcccact ttattttcca gctgcggttc gtccactcac  38340
tgccagcgag aaacgaacct accaacgcaa caatcacaat gatgcagatg ccacccggct  38400
tcactggtct atcccccagc acgtcagtgc gctttcctgg tcccgccgtt ctacctgccc  38460
ataacatcca tccttctggc ccttggtcag gcggcaatcg cggccaccgt ctttaatcca  38520
ccagcggata gcttcacagg ctcctttcgt atcgccagca ttaattcgct tatagaacgt  38580
agacgggaaa cattttccgg ggccgatgtt atatgggcag aaagaagcga tacccgcttt  38640
ctgtggttcg gtcagtggta ctttgatatt tcggtcaacc cacgccagcg ccttgtcgcg  38700
ttcaatggcg tttacctggg cgcatttctc agctgacagc ttcatgccct gtactactgg  38760
cttgccatca accattgttg caccacggca aatggtccag agtccgccgc cgtcgcgata  38820
tgctgtcaag ctgttaccct ctttctcatc cagaaactga tcgagaatca cgggtgcgga  38880
agccccggca agaatcaaac caacgaccgc tgcgctcaat ttattcttca gctttagaga  38940
catagccatt gcgccgatcc tcccgttctt tccagcggaa ataccagttc actgcacagg  39000
tgattaccgt gcatgcgata ccgacaataa ttgcccagtc gctcaggctt aaccctgcaa  39060
```

-continued

```
ttctgtcggc caacatccag gacacctctt ttgctgtttt agctgtttcg gcatatgcct  39120
tcgctgatac accgcagccg gcaagcgtgg ttcctgatcc atatgaaagt ctgctgtaaa  39180
tggtgctcat tctggtcata gcctcacctc cgatagttcg gatggcgctg tgtgtgattg  39240
aaggggatca ggcaaccggg ctcttatgtt caagtaaaaa ttaaggatga ttcccggtgc  39300
ctgaagatgg tgatcaccac agcaacgggg gagcgtggtg atcgttatga tttttttcagt  39360
ttttccacct cttcggtggt ctgtataaac ctgtctgcct ccagttctac gccgatcgcc  39420
cgacggccaa gttctattgc agctttcaca gttgaaccag agcccataaa gaaatcggca  39480
acgatatccc ccggtctgct gctggcgcta atgatctgtt tcagcatgtc ggcaggtttt  39540
tcgcatggat gtttgcctgg ataaaactga acaggcttat gtgtccatac gtcggtataa  39600
ggaacaagag cggaaacaga gaagcagcgc cgaaggattt tgtattcctc cagcaattct  39660
gaatacttgc ggtttaatga ctggtaggta gccaccagct ggtggtgagg atgttcaagc  39720
ttttgctgaa tatgtttatc gatggcgatc cgcgtgaaca gttcctgcaa ttttcgatag  39780
tccacttcat tcggtagttg ccattggctt gcaccaaacc agtgtgacgc catgtttttc  39840
tttccggttg cctcagctat ttctttcgag ctgacaccca gtgattcacg ggcattacgg  39900
aagtaatcaa tcagcggcgt cataatgtgc tgctttagct ctgtgctttt cctttcgtaa  39960
acatcctctt tacctgtata cggtccaaga tagtgctcag caaacaaaat ccgttccgta  40020
gatggaaagt acgcacgcag gctttcttta ttacatccat tccagcggcc cgatggtttt  40080
gcccaaatga tgtgattcaa aacgttgaat cgggcgcgca tcataatctc tatatctgag  40140
gccagtcggt gaccgcaaaa caggtagatg ctgccagcag gtttaagaac gcgagcatac  40200
tcagccaggc agctatcaag ccagcgtaag tagtcctcgt ccccccttcca ttggttgtcc  40260
cagccgttgg gcttcacttt gaagtacgga ggatccgtaa ctataagatc aatagagtta  40320
tccgggaggg tggcgacgta atgcagacta tcagcgttga ttaactcaac actgtttatt  40380
tttacagtat ttttcataga tcagtaagcg taactctgat aggctcacgt tgcttttgcg  40440
ctaaagcagt gggccttggt tagcttgtga cctgaaagca tgagctgatg gctggccggg  40500
tgcgctaaca cccaccagcc gcccatttcc acagcagaaa accccccatta ctggaggcgt  40560
ttataacatc cgaactggta atcagataac cccgccatca ccagctgcgt aagtatgagc  40620
tggcaacgtt cgtggctgag gtgggtattc tgtgcaatct ccccagccgt tgctggttta  40680
tcgcttaatt cattgaaaac agcctttgcc gtttctgtca tatcttcctg atttagcatg  40740
tcttttacct aaaattagtt gcgtgacata cagataactc tggttggtga taccagcaag  40800
agaagaattt gattctgcaa ccaacaaggc ctttaggcat caggcaggaa tgagatgcaa  40860
taaaaaaaacc acccgaaggt ggtcttatat gaatctttaa cgcggactta gcaaatattc  40920
cacatcatcg tactaccgtt atggttttcg ataatttttg cggctgggct agtaccaaaa  40980
gagtgcatat agcaatgatg aatagtaagg accagatcct gcaacgtttg gtcactctct  41040
agctccatga tatttaaacc aatattttga gctttgtcca aatgaatatg tctggcatgt  41100
gcatacgttg cttggtggtt gtttaactca tcacatatac gcttagcctt agcttcagcg  41160
tcagcctgac ctgcgaacat accagtacaa agccatttct ggacaatttc gttcgcccag  41220
agaattgctt tttcacactc gccaatcaac gttggattta gtttttggaa cgtaaattgc  41280
caccattgca gtgcagcagg gttggcaaaa atttccgctt ttgctctctc atactcctca  41340
ataattgcat gagatgataa cccattaaac tgtggatcaa ttggccccaa gttcgactgt  41400
ttacctaaaa cgatctgctc agcacaacaa gcaagcattg tgccacaact cattgaaatc  41460
ataggtacaa tcgctcggat attggttccg aactttgaac gaagataatg accaattgat  41520
tctagagctg cgatatcgcc tccaggagta tggagtaaga tatccaatcc cagactcgta  41580
tctaacccat tgatagcaga cataagacca tttttatcat catctgacat ctggatcaga  41640
tgttgaaacc caggcccccc tttttgaagg aagcctgagt aataagaaat tacatttcgg  41700
ccagtatgtt tcgataaatc acgtaagtac ttgtggcgaa cctcatccgc tggtgtacgt  41760
tgagcgatag tacccatctc acccaatacg tctatccaat ttggcatgtt atcaatttat  41820
cagtatgagt acagttggtg agattgctga ccgttctgct cagtagtatt tggtgttact  41880
gtgctgtatg aatagagcac accacttctc acattcagat cgttttgctg agcgagaaca  41940
cgcatagcaa aatgctgtac ggattcgcct ttttgaaact cttggggttg tatgcccatt  42000
ttttcgtaaa attcagcagc gctcatgata tgtccctcgt ttttttctac atctatgcaa  42060
ttccaggagc catcaacaca agatgtagta gttagcagtc gtcaaataca cgaaaagcct  42120
caagatgagg cttaaaaaga ttctttttga taaagattta gccaaactat agcggtcaaa  42180
atgcagattt gacaagtata aaaagcactt aaagcctata aataggcagt ttttgagaat  42240
taaagcatct ttaatgaggt tgaacaaaat gcagtcttga cgctgaacag gactttactg  42300
gaacgtagag ctaaatggtt cgatttcatg aaccagttac aaaaaaaaccc gctcatcggc  42360
gggtttataa aactttggca acatatcaaa tatgcttcaa atatggctta ttttgttgca  42420
ttttgcaagc gtgtttgaag gagatggtga aatttacttc acatttctgc cactttgagg  42480
gcttcttctt cctcatagta ttcaagagcc atggccaacg cagattcatc aagctgggta  42540
aaagcggcct ttaacccagc ccagtgccct gaatagacac gcaaccatgt cgaacggtca  42600
acgctaacca tgcgggccaa cgctgcacca gcatagtctt tataggtttc attatttctg  42660
gttgcggcaa tttcctgccc tgccagccat accaggccta tcagtttctt tactacgcgc  42720
tcctgaaggg agttatcacc caggcatttc tgataagttt tccagacgta ttcacacatc  42780
atcacctggt gcttatagct aaggtcaaaa ccgtagcagt accgcaacca ggcctgctgg  42840
tatccactaa gcgcggacac tgccctacgc cacggcgcgg actcaaattc cgcatctttt  42900
atcggcggca ttggcctgcg gcggctgcgt gtttccagca catacagtgg cgcggaaagt  42960
gagttaacaa agcgtggccc cttctctcct tcgagttcga cgagatgaat tccacggcga  43020
ggggtggcat ttttgtctgc tggtgggtgt tcactgaaag cctcaagctg cccttttgtt  43080
cccccagaca ggtcaggtag cgcgcggcgc aattctattc ttacaaaatt caggtcttgt  43140
tgattcatgc ttctttgcgc tccatacact taagctttcg caattacgcc gatcgccagc  43200
gcccgatcca taaaacgcag tagcagctca agctgcgtac catgcttctg ctcgaatgcc  43260
ggtacatcgg cgtgtaactc gtcgtggcac tctctgcaca gagggatcac gaagagatca  43320
tgggcttttg ttgctgtccc ccccataccg tgccctacga tatggtgcgg atcatctgct  43380
ggccgtcggc aacactcaca gggttgtgtt ttaacccagc gggtgtacgt ctcatttatc  43440
cagcggcgtc gctttggcct gagcatgaaa gattctggag actccggatc aacagagagc  43500
gtgaggatct tcttcgcctt ctcctgcacg aggctggttg cagaagcgga aggcacaatg  43560
tcgctttccc tcatgaccga gcggatctta tcatccggaa ggcgtagccc cttgtgcgca  43620
acgctttccg gaataacatc agccaggtcg tttctgacca tccaccagca cagttccgga  43680
agcgtcagga tatgcgactc gggaaaacca gaatcacgcc gaatgacttc cagaatccag  43740
gataccaggt ttcctgccgc tatacctgca agctgttcgg tatgctgccc cgacaaagtg  43800
```

tgatcgcaat gccagcacag gcgaatactt cctggtgggt gccgcattgt tgtgaagttc 43860
ttgtcgtgcc acgatgaatg tggccactgg cattcaaacc gattactcaa ccattgctca 43920
agggaaggaa gcccaccagc acgctgaata acccgatcat tctcgaagac ctgccgcatt 43980
accggatcat cagccagcgg ctgaatggcg gcgggaacag ctcctgtact gaatgacgcc 44040
atttcttctg gttcaggctc aagcagaacg cgaccgcgca taaagaggtg catcagttcc 44100
gcgccgggac gaaacaacac aatccccata cgatgggcga tctcgggggt aagcagagct 44160
ctcacgcgac ctgccccctg gcaatgtgtt ctgcccacag tccaccaatc cagcgcacgc 44220
ctttcgccgt gaaacgtgcc tggctgaatg catgatttga ggttacggat gtgccggttt 44280
tcacttcaaa acggcccgca tcaatatgct gatgccgtgg ggtcatcgtt ccgccaagac 44340
gatacatgat gtcgttctca aggaggaata accgcagatc gggctctttg gccttaagca 44400
gttttgccac ctggcggaat gacattgacc cactggctgt acagtaccga tcaacaaacg 44460
ctaccttcgg cgccgcggca gccagttcgt tagtcaactg ctgtttttgt tctgcaaggt 44520
cagctgcaag acgtagggct tcagagaatg attgaggaat cgtctgctgc tgtgcctgct 44580
caagctcctg ccagcgatca accagacgcg cggtaaactc cggcgacagc tgcgcgacaa 44640
cgatataact gtcccgcttc cctatcagat aaaccgatac cgactgattg aggtgatttt 44700
taacttcccc cattgggggg agttcaataa caccgcgctc tgccaggcgt tcaatggacc 44760
gtttaacatg gtcatgtctt gattccacca gctcagcaat atcgctgctg gacatggtta 44820
acgctgttgt tgctaactgg ctcatacttt tctccatatc aggcggctgc acccgccggt 44880
tcatatctgc tgattgttat ctctacccga cctttcggca caacgggtcc ccattccacc 44940
agcatgcgct taatctggct gtcgtcttcc cagacacccg catgcgtcag cgcgtcaaac 45000
agggctttgt tgtaattatc gatatcccgg cggcgcgcat ccggcgggta cagagtgatt 45060
tctaccgctg ccagttcagt cgatggcttc gggagacgtc gtaattgctc aatgatcgcc 45120
acgcaggcag cgctctggta tttacggcca gcggcgctaa tgaggtgacg accggccagc 45180
ggccccttgt taggggcgcg ccagtaagtg ttcacgctcg gaggaaaagg caggatcagt 45240
ttcacgcggc ctctccccgc atattgcgaa caagttcaga agcagcagta atgatttcgc 45300
tggtggcagt ccgctccagc cagagttgat tgatattggc tttcagcttg tgttgcagtg 45360
actcatccag catgtcagca ccatccacct ggtcgaatac aattctaacc tccagcggcc 45420
agatacggga ctcgggaagc ggatccgata ctggtttagc tttctcacga atgtgcatgc 45480
ggatctggcg aatattggac caactggaaa catccaggct tcccatggct gcaatgaagt 45540
cagtgctgtt catgccatat tcaccggatg cttcaagggc aacagtgcga atacgttccg 45600
acatatccag gcgcacagca gcgtcatcga attcaatcga caacagccac tcatccacac 45660
cgaacaaaat actctcacga ataagcagct tcgctttgtc gatcgttaaa ggtgatacct 45720
gagtgaattc cggtgcttcg acagaatccg ccgcccaggt atgcccaaac ttcgattcac 45780
tgaatgtgta ttcttcttta tcgccaaacg cagctctaac gcatgcccac gcctcgacac 45840
cgctgatagc aaaaatatct ttctgggtga gtggcaactc tgcttctggc ttatcagctg 45900
caggaggtgt ggcagttaca ggttgagact tgctggcagc aaattgtgcc aaagccataa 45960
acgcccgccc ttttgcctcc agttctgtgc ggttgatata gctgaaccgc tcgccacgcc 46020
atgacttatc gaatacagct atggcaccgg caaaaaacgc gctggtgggt ttctgttttt 46080
cgtcagcagg tacaaaccac acaggcagat cgaacccaat gcgcccgcga atgaatacaa 46140
tgtgatcggc atcttccggc caccacgttt cactcggcgc ggcttttatc aggaatacat 46200
agcgaccgcc cttctcgcgc tgggctgctg cgtagttcat gatgtgcgtc atgccggtga 46260
tcgcctgctt ctcgtggtac tgcgaacggc tatacggtgg gttgccatag ccagcgccac 46320
ccagttcagc cagacgttca gaccagtcct gcgtcagcgc gttatcttcg gcggtgtacc 46380
atgccgggca tttcgcgttg tcgtcgtcag caaacaaatc cagaactaat ggaccaaata 46440
gcgcgttgat cccccaaaaa agcagatccg gtgtccgcca ctgatcgcca acctctttca 46500
attcgtgagc tggtttgcta cgcagtgccg ccagcgcctg gcaatattta ttggtcatca 46560
tgaacggaac cccgaatttt ctggcagtga gtaatcaaca ctctggaagt ttgcgcggct 46620
ggctgagtta gtctcccatt tgccgttaac gcgttcaggc cggccagcac tggaccattt 46680
ggtcgcgctt tgcaggtaac cagggaagtt ttttggaatg aacagagttg ccgggcggag 46740
gtattgcgcc tgctcgctat cacgccaatc ggcatttttg taatccacta ccaagcacag 46800
gtcatcaaca gtgaattgtt cccgaagacg ggcgcgaata ttctccagcg acgtgctgca 46860
tacctggtag cgtgagccag tagtctgatt caggtaagac aaaacctgtc tggcctgatc 46920
agtaatcaca acctcagggt cgggttgcgc cgcaaccgga caagagggtt ttgaagttac 46980
ttgtggttct tgttttgatt ttactgacgg atccccacca gattctgacg ggtcaaaacc 47040
gcctttttttg ctggatttcg acgcctcaaa ttttgacggg tcggattttg atgcatcaga 47100
ttttgatggg tcagatttttg atgcgtcaga ttctgacagg tgagaaaaag cagcctctcg 47160
caacttaacg acgttaagct gatatacgtt cgatgcgtta cggttcccat tacggcgctg 47220
cttacgggaa agccagccat ccttctcaag ctgagcaagg gccgtcctta ccgtactttc 47280
tccagcaccg atttgacgtg cgatcgtgcc aatagacggc cagctaacac cctcatcact 47340
actgaagtcg gccagacgcg ccatgatggc aacgctggat aacttcatgc ctgacgaagc 47400
gcatgcatcc catacgtaac cggttaattt agtgctcatg gtcgtccttt aattctgtaa 47460
atttacgctg gaattgttca agagggctga agcactcatg atcgtaccct tcgcgaaggt 47520
atataacgcg ctgtgtatct ggctcccagc ggacaactct gacgggaact ccgtagtgat 47580
ctctgaaccg ccggttaact tcagccattc ctcgcgcccc ttctcgttca tctgaacaaa 47640
tgcttctacc atcaagtctg ctggctggta gttgcctcca tcagccgcgt tatttatgat 47700
ttccacatag ccgaactggg catctttacc caccagcggc aaacatctga attgcttagc 47760
tggtctgaat cggtttacac tgttcatgcg ttagtttctc cactgatacg acacgccaag 47820
gcgcccggag ctgcacactc gcgggcgtca ccttttctgc ctgttgaaac gaatacgtca 47880
atcgcctgat ctgaaacacc aaccccataa agcgccataa atcccaggaa cccgtgaatc 47940
tggtggcgga gcttcttact gaataattct gaaagcattt tgcgctctga tgaatcaatt 48000
accccatcag ccgctgctgc catcttggca ttagccagct caccagatgc tgctgccgct 48060
ttcatctcaa tgctgtacag ctcaacgtta tccaggctct cagcagttgg aacatccacc 48120
agccatttcc cttttcggtt cgcctggtac tcggccaagt aacaagaacc agacaggtcc 48180
tccatccgtt ccagttctgc caaggtaaag aaccgactgc cacacttctg gtacaggtgg 48240
ttgtggaact ggtcgatagt catccctaaa tcggaagcca tacctaagcg accatgcttg 48300
tgtgccttac acatcaggcg gattgctgta tttatgctgt ctaccatgtt gatttccctc 48360
tggtagttaa taatcaactt aaagttgact attgttgtta gcggaaggta tgccgtcatt 48420
tttgttcgga taaatatcag gtcgtaattg atggggagtt actacccatc cgccccattg 48480
gcagagttga ataactcttt cagaaggtac tcggttcttt gcaatccagt tcgcaacaga 48540

-continued

```
ttgaactgat tggaattcaa accgccttga tacctctgaa atcgacccga tcgccttcac  48600
agctttagct gttacattct tgtgttgaga tgacatgtgt tctcctatga ctaagcctgc  48660
atcaatacta cttatagtag caattattag caacttaaaa tagaaatgac aactatgcct  48720
tgtgcgctta atcttctact tatggtggaa aatgctaaat acaaagactt tgccgaaagg  48780
ctaaacaggt ctctccaaga gcaatctatt ggagttaaag aattgtcaga gttcagtggt  48840
gtctcgtatg agatggcgcg gcgctacact cttggtactg caaagccgag agatgagaag  48900
atgattcgaa ttgcagaaag acttgccgtc tcaccggctt atcttgatta tggtgtgcct  48960
gttaatggtg gcgacgcgcc agccaaaggc acggtcagaa tagagcaatt ggatgttcat  49020
gcttcagccg gttccggata tataaaccaa ccattcccta caatagtgag ctcaatagag  49080
attccagaag agaggatctt cgagttgttt ggtcgtagaa gccttgatgg catcgtcatg  49140
ataaatgttg atggcgatag catgatgccc acgctttgcc caaaggacct gcttttcata  49200
gacagcaagg ttgaacaatt cagcggcgac ggcgtttatg tgttcaattt tgaagacagt  49260
acgttcgtta aacgtttgca gaaggtaaaa gggcgccgac tggcagttct ttcagacaat  49320
gaacattacc cgcccttctt catagaggag catgaaatga atgaactata catattcggc  49380
aagctaatca gatgcttacc tctaaaaatg atagagtttg gctaataatt aattcatcaa  49440
gaaaccggcg aaagccggtt ttttttacgc ctccaattcc tcacctcata acactacact  49500
actaaaaatt tcatttcta cttttttgttg ttgcaattat ctacttaaag tagctatagt  49560
cattgcatcg aaagcgaaca ggcaggacgc ccacgaagta gccgccggtg gcatatgaat  49620
aaccggatga ttcgctgaca gaaaacttag gttgggggta gaggtttaca tgaatcattt  49680
attcacatgc tcattttgcg gagcaaccga actgggagcg ataaagatcg tcgcaaaagg  49740
tggtaaggac gaacctgcca tctgttcgga atgcgtagtc acatgtgtag aaaaaatgat  49800
cctgactaaa aaatcagagg ctgaaaaacc aacctctgat aacgaaataa tatcagtcga  49860
taaaaaacta tttaaagagc ttcttcagct tgtcctcaac cttcctgatt tcggaagtaa  49920
gctggctgct gttgacattg atagtagctc cacatcgaca agtgaaactt ttgttcgact  49980
tgagccaagc gattttcttc ttcgtcttag tgccgcactt agggcatgcg ggtaacgtaa  50040
tttcctggtt atcaaaagcg cccataaaca tccctcttgg ttgtgtgaga acaccaagat  50100
accaccgcgc ctgatgtggt taaaagcagg ctaaagcaat aacaagtaac tccctgttct  50160
ggcggcccgg tgttttcccg tgtatttccg gtaaccgcca gccttttca gggcacaaca  50220
gaaaagggca tcaccgggcg acgggctcat aacccaatcc acccgggcaa aaagaaagcg  50280
gtctctgcaa gccgccgacc aatgcaggtg cccttctctg ttgtgtatgg agaaactaac  50340
tttttagcgt ctgtgcagat gcgctgagga accgagaatg aataatccgt ttttcaaaaa  50400
tatgttggtg tatcgcatta gtcgcgattt caccatcaac caggaagagc tggaacagca  50460
gcttgaacta tttcgcttca ctccatgcgg tagccaggat atggcaaaaa ccggttgggt  50520
atcaccactt ggtcagctgt cagatcgctt gcatcacact gtcaataatc aagtgttgtt  50580
ggttattcgc cgggaagaaa aaatactgcc atctcctgtc attactgaag aactgcgcaa  50640
gcgtgtgtcg cgtctagaat ccgatcaggg gcgtcgcctc aaaaaaactg agaaagattc  50700
gctgcgtgat gaagtgttgc actccctgct tcctcgggcg ttctccaaaa actcgactgt  50760
tggtttgtgg atcaacgtca ccgacggtct gatcatggtt gatgcagcca gcgctaaacg  50820
tgccgaagac tcactggccc tgcttcgtaa aactctcggt tctctcccgg tggtaccgct  50880
gactatggaa acgccgatcg aactaactat gaccgactgg gttcgttccg gtagtgcgcc  50940
tgctggcttt ggcctgggtg atgaagccga actgaaagct attcttgaag atggcggtat  51000
tggacgcttt aaaaaacaga ctctggtcag tgacgaaatt catgtgcatc tggaagctgg  51060
caaagtagtt acaaagctgt ctatcgactg gcaacagcgc attcagttcg ttctttgcga  51120
tgacggcagc atcaaacgcc ttaagttctc taatgagatt acagaacaaa acgacgatat  51180
cgaccgtgag gatgcggctc agcggttcga cgctgacttt gttctgatga ccggcgagct  51240
tatctctctc attaacggat taacaacctc tctcggcggc gaagccaagc gataaacacc  51300
aggcaacaat tacccccata agcatgggtt gggttgctgc acgctaaatt cagcaattca  51360
ttaatttaat ggcgcggtgc agcgcgccaa tatggagaaa accatgagct acattcagac  51420
attatccggc aaacatttta attacctcga tatccaacag gacgatatcg tgatcgagga  51480
tattgctacc gcgttgtctc atatctgccg ctttgcaggg catcttcctg agttttacag  51540
tgtcggccag catagcgttt taaccagcca cctcgttccg caggagtttg cattagaagc  51600
actgcttcat gatgctgctg aagcctacct gcaggacatc ccctccccac ttaagcgcct  51660
gcttccggat taccaggcaa tcgaagctcg tgtggacgca gccattcggc agaagttcgg  51720
tctaccaact gagcaacacc caaccgtgaa atatgccgac ctggtgatgc tcgccagcga  51780
acgccgcgat tttgagattg acgaaggttc catttggcca tgcctcgagg gagttgtccc  51840
aacggattta ttcattatca acccagttcg tcctggccag tcatacggca tgttcatcaa  51900
tcgctttaac gagttgatgg agcagcgcca atgcgccgca tgaaggtaaa agaactcgta  51960
gcggaggcgt ttgcctccgt tgctgaattg ccaccaaagc atgcgccgct tatgcgcgaa  52020
gtcgccacca gactggacgc tacgttcgca gcattaaaag agtctctggt gcaactggaa  52080
caggaacgta aagataaaac gccatgaccg tatttgaata tctccaggct catccgaata  52140
ccaccagcgg tgaaatcgcc aaaggtatga acaaaaagac cccagcggtc gccggagcat  52200
tatctcagct ctatggcacc ggtcggatcg tgaagtctgg tgttcgcaag ggtattccaa  52260
cataccgcat taacgatatg ccgtttggtt gcagtaacag cctaaccatg atgtttaacc  52320
agctcttgag cagagccaga caaggagcag cccaatgaca gcactcaaca aacaggcgct  52380
gcgtgaagaa ttccagttca tgcaggacaa cctatagcgac ccggcagacc acgatcggca  52440
ggtgatttac atcgaggcgg aggcgctgct ggatgagttg gaagccaaag actcaacgat  52500
agcagcacaa caacatgaga tccgtatgtt gctgaatgcg cttgaggaaa aaccatgccc  52560
gaaatgcaac gacacaggaa tgactgatag tggcggcacg cagccatggg gcgagccgat  52620
tgagattgaa tgcgactgcc gacagcagga tgccaacacc gcagaacttg tagccgctgg  52680
cattggcgtg aagggggagt gagatggata aattaatcaa acctaccgcc aaaggtaaat  52740
atgacggttc atgtgattat ctttgctcgg aagatgcgcg attcatcgtt atgcgcggcg  52800
attatacgga agcggaaata attcaggctt ctgtgtctca agatgtaatc gactcggatg  52860
gtgcggctga ttttgcaagt agcgcccgct attatcagtg ctggtacaaa gttagcccaa  52920
taggtggtca ggatggctat tcaggctggc atcatcctcg tgattcgccg tgtcgcggtg  52980
catatttcgc atcagttttg caatgggatt aaggaggact aacccatgac aactaacaac  53040
cacccggcgc acggtcctgt atcactcgat cgcctgcacc agatacgcga acacctgctg  53100
catgataccc aatactcaaa cggcgggaac agagcctaca ttctcgctga tgtattgaag  53160
gtgattgatg gggctattgc ccgcgagctg gtacgccgtg agcatgcagc gtggtcacag  53220
gctactttcg gcgatgtcgg tccagttggt ccgctgaagc acctttccaa agaagcgctc  53280
```

```
gaggctgctg ctgaaccagg cgaccttagc gaatgggctg acatgcaatt cctgttatgg  53340
gatgcgcaac gtcgtgccgg tatcagtgat gagcagatta cccaggcaat gataaaaaag  53400
ctggctataa ataaggttcg ccaatggcct gagccgaaag acggggaacc tcgattgcat  53460
atcaaagaac agtcagagca ggagaaaaaa taagaatgtt tagcctgatt cggcgcggtc  53520
aaatctacac ggacagtagc aactggcccg taattatcca tagctgtagt gatcactcgg  53580
tccgaattaa acgcaatgat ggcgagctga gaacgattag catcaaacgc tttaacgaag  53640
attttgaacg agtggagcat gatgagtatc gcaaaatatg tgccgaaata gagcaggaaa  53700
caaacctgaa aaacctacgt gcgatgcgtc gcggcaagat tactgaatag ccaaacagga  53760
gaatatttaa cgtgaacaac ttaatgatcg accttgagtc catgggcaaa aaaccgaatg  53820
cccctattgt ctccattggt gccgtattct tcgatccgca aagcggtgaa ctgggtcagg  53880
agttttacac cgctgttaat cttgaaagcg ctatggagca gggagcggtg ccggatggtg  53940
acactattct gtggtggtta agacaaagct cagaagcacg atcagcaatc tgtgttgatg  54000
atgcgatgcc gatatcatct gccctatctg aactgagcca tttcattaat cggcattctg  54060
ataaccctaa atatttaaaa gtttggggca atggagctac tttcgacaac gttatattgc  54120
gcggcgcata tgagcgtgcc ggccaggttt gcccgtggca attttggaat gatcacgacg  54180
tcagaaccat cgtcacatta ggcagatctg taggtttcga tcctaagcgt gatatgccat  54240
ttgatggggt tgcacataac gcactggctg atgcccgcca ccaggcgaaa tatgtttcag  54300
cgatttggca gaaactaatc ccaaccacca gcaacagcta aagttttccc cgggtgcagc  54360
cgggataatg gagaaataac tatgagcaat attttccagt tagctcccaa cgattgggtt  54420
tgtgaaagcg ttttgatcgc ggttactggg ctcaaacccg gaaccatcct ccgtgccaga  54480
aaagaatgct ggatgattgg gagggagtat atccacgtat cgcctgacgg aaatcctaaa  54540
ccttccagtg agtgcatgta taacagaaag gctgtagatg cctgggtcgc ttcaatgaaa  54600
agcaagcaac cagggtgatt tgatgccatg aaaaaggtaa gctcgtatcg ctcttgggcg  54660
tctggaggta acaccaatgg ataaagtcac atatccaaca ggcgtcgaaa accacggtgg  54720
cacattacgc atctggttta attttaaagg taagcgtgtc agggaaagtc tcggtgtccc  54780
tgacaccgct aagaacagga agatagccgg ggaactgcgg acatcagtat gttttgccat  54840
ccgcacagga acctttgatt atgcaaccca gtttcctgac tcccctaacc tcaaggcttt  54900
tggtgtaagt aaaaaagaca ttacagtgaa agaacttgaa gaaaaatggc tggatctgaa  54960
acggatggaa atctgcgcga acgcatttaa tcgctatgaa tctgtcgcaa ggaatatggt  55020
gccgaggatc ggaggtaatc gcctggtgtc agcagtaacc aaagaggaat tgctgtatct  55080
gaggaaatat ttgctaactg gttatcagaa tccgacgaaa aacaaagccc cggcaaaagg  55140
gcgaagcgtt gttactgtga actattacat gacgacaatg gccggaatgt ttcagtttgc  55200
tgcggatcac ggttacttag aggtgaaccc attcgaggga attaagcctc tgaaaaaagc  55260
cagggcagaa ccagatcctc tgtctcgtga tgaatttatt cgcctgatag atgcatgccg  55320
gcatcagcag acgaaaaacc tgtggtcatt agcagtgtac acaggaatgc gtcacgggga  55380
actggtctcc ctggcctggg aagatatcga cctgaaggct ggaacaatta ccgtcagacg  55440
taattatacg aaacttggtg agttcactct accgaaaacc gaggcaagca cagatcgagt  55500
ggtgcatctt atccagcccg caatcagtat cctgaaaaat caggctgaaa tgacaaggct  55560
gggcaggcaa tatcacattg aagtgcagtt acgtgagtac ggccgttcgg tgaaccatga  55620
gtgtacattc gtctttaatc cgcatgtggt cagacgcagt aagcaggtcg gatttatcta  55680
ccgggtcgat tcagtaggcg actcatggga agcggcactt aagcgtgcgg ggatcagaca  55740
cagaaaggcg taccagtcac gacacaccta tgcgtgctgg tcattatcag ctggtgcaaa  55800
ccctagtttt attgccagtc agatggggca tgcgagcgcg cagatggtgt tcaatgttta  55860
cggtgcatgg atggctgaca gcagcgcaga gcagatcgca atgctgaatc agaagctggc  55920
agattttgcc ccattgatgc cccatagcca cgagaacagt acgggaggat tattaaaatc  55980
agtaagttaa cccctaacgc ccgtcatgtt aactgtgtgg agggtaacac cacgctttat  56040
gccctgccga aacccgaggt tgtcctgcgc tggcgtgagc agaccacaga tgacttccgc  56100
ttctgtttta agtttccggc gaccatttcg catcaggcag cattacggca ttgcgatgat  56160
ttagtgactg aatttttgac ccgcatgtca ccgttggctc cgcgcattgg acaatactgg  56220
ctgcaactgc ctgccacatt cggcccacgg gagctgcctg cgctttggca ttttctcgat  56280
tctcttcccg gtgaatttaa ttatggggtg gaagtccgcc atccacagtt tttcgccaaa  56340
ggggaagagg aacaaacgct taatcgcggt ttacatcagc gcggcgttaa tcgggtgatt  56400
ttagacagcc gcccggttca tgcagcacgt ccatacagtg aagctattcg cgacgctcaa  56460
cgaaaaaaac ctaaagttcc ggtacatgct gtactgacgg cgaaaaatcc actgatccgt  56520
tttatcggta gtgatgatat gacgcaaaac cgggaattat ttcaggtctg gttacaaaaa  56580
ttagcgcagt ggcatcagac cactacgcct tatcttttt tacatacgcc agatattgcc  56640
caggccccgg aactggtaca taccctgtgg gaagacttac gtaaaacgct tccagagatc  56700
ggagcagttc cggctattcc acagcaatct tctcttttct gaatttgcca cctatcatag  56760
acaggtgcca tcggccattt taaagggagt ttgtatggta agcgcgctgt atgccgtttt  56820
aagtgcgttg ttattaatga agttctcttt tgatgtcgtt cgcctgcgaa tgcagtaccg  56880
cgttgcctat ggcgacggcg gttttagcga actgcaaagc gctattcgca ttcatggtaa  56940
cgcggtggaa tatattccta tcgcgattgt gttgatgctg tttatggaaa tgaatggcgc  57000
agaaacctgg atggtgcata tttgcggcat cgttttgctt gctggtcgtc tgatgcatta  57060
ttacggtttt catcaccgtc tgttccgctg gcgacgttct ggcatgagcg ccacctggtg  57120
tgcgctgttg ctgatggtgc tggcgaatct ttggtatatg ccctgggagt tggttttctc  57180
cctgcgttag cgcacaatac gccactttct ttttcccgga tttttacgtt atgtctcacc  57240
gcgacacgct attttctgcc cctatcgcca gactgggcga ctggaccttt gatgaacggg  57300
tagctgaagt cttcccggat atgatccagc gttccgttcc cggctattcc aatattattt  57360
ccatgattgg tatgttagcc gagcgcttcg ttcaacctgg tacgcaggtt tacgatctgg  57420
gttgttctct gggcgcggcg acgctctcgg tgcgtcgcaa cattcatcat gataattgca  57480
aaattattgc catcgacaac tccccggcga tgattgaacg ctgccgtcgt catattgacg  57540
cctataaagc ccctacgcca gtagacgtta ttgaaggtga tattcgcgat atcgccattg  57600
aaaacgcatc gatggtggtg ctgaatttta ccctgcaatt cctggaacct tccgagcgcc  57660
aggcgttact ggataaaatt tatcaagggc tgaacccggg cggtgcgctg gtgctttcgg  57720
aaaaattcag tttcgaagat gccaaagttg gtgaactgct gttcaacatg caccacgact  57780
ttaaacgtgc caacggttac agcgaactgg agatcagcca gaaacgcagc atgctggaaa  57840
acgtgatgct gaccgattcc gtggaaaccc ataaagcacg cctgcataaa gccggttttg  57900
agcatagcga gctgtggttc cagtgcttta actttggttc actggtggca ttaaaagcag  57960
aggacgctgc atgatcgact ttggtaactt ttattctctg attgccaaaa atcatctttc  58020
```

```
acactggctc gaaacgctgc ccgcgcagat tgctaactgg cagcgcgagc agcagcacgg  58080
gctgtttaag cagtggtcca acgcggtgga atttctgcct gaaattaaac cgtatcgtct  58140
ggatttattg catagcgtaa ccgccgaaag cgaagagcca ctgagcgccg ggcaaattaa  58200
gcgcattgaa acgctgatgc gcaacctgat gccgtggcgc aaagggccgt tctcactgta  58260
tggcgtcaac atcgataccg aatggcgttc cgactggaaa tgggatcgcg ttatgcccca  58320
tctttctgat ttaaccgggc gcaccattct tgatgtcggc tgtggcagcg gttatcacat  58380
gtggcgcatg attggcgcag gggcgcatct ggcggtgggt atcgatccca cgcagctatt  58440
cctctgccag tttgaagcag tgcgtaaact gctgggtaac gatcagcgcg cacatttgtt  58500
accgttaggt attgaacaac ttccggcact gaaagccttt gataccgtct tttcgatggg  58560
cgtgctttat catcgtcgtt caccgctgga gcatctctgg cagttaaaag accaactggt  58620
gaatgaaggc gaactggtgc tggaaacgct ggttattgat ggcgacgaaa acacggtgct  58680
ggtgccgggc gatcgttacg ctcaaatgcg taatgtctat ttcattcctt ccgcgctggc  58740
gctgaaaaac tggctgaaga agtgtggttt tgttgatatt cgcattgcag atgtgagcgt  58800
taccaccaca gaagagcagc gacgcaccga atggatggtc accgagtctc tggccgattt  58860
tctcgacccg catgatccgg gtaaaacggt ggaaggttat cctgcgccta aacgcgcggt  58920
gctgattgcg cgcaagccgt aaaggtctgg taatactgcc ggatgcggcg tgaacgcctt  58980
atccggccta caaagtcttg ctaattcaat atattgcagg ggctatgtag gcctgataag  59040
catagcgcat caggca                                                  59056
```

```
SEQ ID NO: 135          moltype = DNA  length = 972
FEATURE                 Location/Qualifiers
source                  1..972
                        mol_type = genomic DNA
                        organism = Escherichia coli
SEQUENCE: 135
ttatttgatg ggataaagat ctttgcgctt atacggttgg atttcgcccg gtttgcgagt  60
tttcagcaat tttaatatcc aggtgtattg ttctggtcgc ggaccaacaa aaatctcgac  120
ttcttcattc atccgccgcg caatcgtatg atcatccgcc tctaacagat catccatcgg  180
tgggcgcacc tgaatcgtca gacgatgcgt cttgccatca taaatcggaa atagcggtac  240
aacgcgcgca cggcacactt tcatcaaacg accaatcgcg ggcaacgtcg ctttataggt  300
ggcaaagaaa tcaacaaatt cgctgtgttc tgggccatga tcctgatcgg gtaaataata  360
tccccagtaa ccctgacgta ccgactggat gaatggttta ataccatcat ttctcgcatg  420
cagacgacca ccaaagcgac ggcgcaccgt gttccagaca taatcaaaaa ccgggttgcc  480
ctgattatgg aacatcgctg ccatttttctg cccttgcgag gccatcagca tggcaggaat  540
atcgacggcc caaccgtgcg gcaccagaaa aatcactttc tcgttattac gtcgtatctc  600
ttcgatgatc tccagccctt gccagtcaac gcgcggctga attttctccg gcccgcgtat  660
tgccaactca gccatcatta ccatcgcttg cggcgcggtg gcaaacatct catctacaat  720
cgcttcgcgt tcagcttcac tacgttctgg aaagcagagc gacagattga ttaacgcacg  780
acggcgtgag ctttttccca gtcgtccggc aaaacgtccc agccgtgcca gaatgggatc  840
acggaacttt ggcggcgtta aagcgatacc cgccatcgct gctacgccca gccatgctcc  900
ccagtagcgc gggtggcgaa aggatttatc aaactcagga atgtattcgc tattattttt  960
tttcgtttcc at                                                      972
```

```
SEQ ID NO: 136          moltype = DNA  length = 1323
FEATURE                 Location/Qualifiers
source                  1..1323
                        mol_type = genomic DNA
                        organism = Escherichia coli
SEQUENCE: 136
ttaatcaaac cgtagctgcg gcacaatctc tttggcctgt gccaggaatt cgcgacgatc  60
ggagccggtc agcccttcgg tacgcggcag ttttgccgtc agcgggttta cggcctgctg  120
gtttatccat acttcatagt gcagatgcgg cccggttgaa cgtccggtat taccggaaag  180
cgcgatacgg tcgccacgtt tcaccttctg tcccggtttc accaggatct tgcgcaagtg  240
catataacgc gtggtgtagc tgcgaccatg acgaatagcc acataataac ctgctgcgcc  300
actacgtttg gcaaccacca cttcaccgtc acccactgaa agcactggcg taccttgtgg  360
catggcaaaa tcaacacctc tgtgtggcgc aacgcgaccg gtcaccggat tagtacgacg  420
cgggttaaag ttagatgaga tacggaactg tttcgccgtc gggaatcgca agaatccttt  480
cgccagacca gtaccgttac gatcgtagaa tttgccatct tcagcgcgga ttgcgtaata  540
atctttacct tctgaacgca aacgtacgcc cagcagctgg ctttgctcac gtttaccatc  600
aagcatttct cgtgacatta acaccgcaaa ttcatcgcct tttttcagtt tgcggaaatc  660
catttgccac tgcatggctt taatcactgc gctcacttcg gcgctggtta aaccggcgtt  720
tctggcgctg gcaacaaagc ttcccccgac ggtacctttc agcagattgt tgacccactc  780
tccttgctgc atttcgctgg tcattttaaa accgttagcg gcagtacggt cataggttcg  840
ggtttcacga cgagacactt cccaggtgag gcgctgcagt tcgccgtccg cggttaatgt  900
ccaggagagt tgttgaccga ttttcaggtt acgcaattct ttgtcggcag cagccagttg  960
ggtgatatca cccatatcaa taccatactg attgagaatg ctgcttagcg tatcgccagt  1020
ggaaacaaca tattcatgca cgcccgcttc accggcgatt ttgtcatcca gttcgtcctg  1080
gggaatggct tcatcttctt gtgcagcttg atcaatcggc tcactggctt caggtaagag  1140
cgaacgaatt tcgttctgtt ccagctcaat ggttttgaca attggcgtgg catcgcggtg  1200
ataaacatag ggccgccaga cagcgacggc cagagtaaga acggtgagcg accccaacat  1260
aacgcggtgt ggtcgcggta aattattaaa cgccagggcg acagagcggg ctatctgttg  1320
cac                                                                1323
```

```
SEQ ID NO: 137          moltype = DNA  length = 933
FEATURE                 Location/Qualifiers
source                  1..933
                        mol_type = genomic DNA
                        organism = Escherichia coli
SEQUENCE: 137
```

-continued

```
ttaatctcct ttcaggcagc tcgcatactg gttggctaat tgattcagga attctgaata  60
gcttgtttta cccagtttga tattcgtccc caggggatcc aacgttccca tacgaacgga  120
tgtccctcgt gcgacgctct caacgaccgc tggcctgaac tgtggctcag caaaaacgca  180
ggttgctttt tgctcaacca actgtgttct tatttcatgt aaacgctgcg cgccaggttg  240
aatctcaggg ttaacggtaa aatgaccaag cggtgtcagt ccgaactgtt tttcgaaata  300
gccgtaagca tcgtgaaaaa cgaaataacc tttccccttg agcggcgcga gctcgttacc  360
aacctgcttt tcggttgagg ctaattgtgc ctcaaaatcc ttcaggttgg cgtcaagttt  420
ggctcgactt tgcggcataa gttccactaa ttttccatgg attgcaaccg ctgtagcccg  480
cgctatctct ggggaaagcc aaagatgcat gttgaaatcg ccgtgatggt gatcttcgtc  540
actttttcc gcgtggtcgt gatcatcatc atcgccgtga atacttttca tcagcagcgg  600
tttcacattc tctagctgcg caatcgttac ctgtttcgct tcaggtaatt tacttaccgg  660
tttttgcatg aacgcttcca tctccgggcc aacccaaacg actaagtccg cgttctgtaa  720
gcgttttaca tctgatggac gcagtgaata atcatgttct gaagccccgt caggtagtaa  780
aacctccgtt tctgttaccc catcagcaat ggcagaagcg atgaacccaa cgggtttaag  840
cgaagcgaca acggcagcat ctgcggcctg tgttgcaccg ccccagagag cggcggataa  900
tgctgcgaaa agaagcgttt ttttatgtaa cat                               933
```

```
SEQ ID NO: 138         moltype = DNA  length = 756
FEATURE                Location/Qualifiers
source                 1..756
                       mol_type = genomic DNA
                       organism = Escherichia coli
SEQUENCE: 138
atgacaagtc tggtttccct ggaaaatgtc tcggtttctt ttggccaacg ccgcgtcctc  60
tctgatgtgt cgctggaact taaacctgga aaaattttga ctttacttgg gccaaacggc  120
gcaggtaagt cgacactggt acgggtagtg ctcgggctgg taacacccga tgaaggggtt  180
atcaagcgca acggaaaact gcgcatcggc tatgtaccgc agaagctgta tctcgacacc  240
acgttgccac tgaccgtaaa ccgttttta cgcttacgcc ctggcacaca taaagaagat  300
attttgcctg cactgaaacg tgtccaggcc gggcatctga ttaacgcacc gatgcaaaag  360
ctctcgggtg gcgaaacgca gcgtgtactg ttagcgcgag cattgttaaa tcgaccgcaa  420
ttattagtgc tggatgaacc cactcagggc gtggatgtga atggtcaggt ggcgttatat  480
gaccttattg accaactgcg tcgcgaactg gattgtggcg ttttaatggt atctcacgat  540
ctgcatctgg taatggcaaa aaccgatgaa gtgctttgcc tgaatcacca catttgttgt  600
tccggcacac cggaagttgt ttccctgcat ccggagttta tttctatgtt tggtcctcgt  660
ggtgctgaac aactgggtat ctatcgccat catcataatc atcgtcacga tttacaggga  720
cgaattgttt tgcgtcgggg aaatgatcgc tcatga                            756
```

```
SEQ ID NO: 139         moltype = DNA  length = 786
FEATURE                Location/Qualifiers
source                 1..786
                       mol_type = genomic DNA
                       organism = Escherichia coli
SEQUENCE: 139
atgattgaat tattatttcc cggttggtta gccgggatca tgctcgcctg tgccgcgggt  60
ccgctgggtt cgtttgtagt ctggcgtcgt atgtcttatt tcggtgatac gctggctcat  120
gcctcattac ttggcgtcgc gtttggtttg ttgctggacg tgaatccatt ctatgcggtg  180
attgccgtta cgctgctgct ggcgggcggt ctggtatggc tggagaagcg tccacagctg  240
gcgatcgaca cgttattagg gattatggcg cacagtgccc tgtcgctggg cctggtggtc  300
gttagtctga tgtctaatat tcgtgttgat ttgatggctt acctgttcgg tgatttactg  360
gcagtgacgc cagaagatct catctctatt gcgattggcg tggtcatcgt ggtggctatt  420
ttgttctggc aatggcgcaa tttgctgtcg atgacgatta gcccggatct ggcgtttgtt  480
gatggtgtga aattacagcg cgtgaaattg ttgttgatgc tggtgacggc attgacgatt  540
ggtgtagcga tgaaattcgt cggcgcgttg attattactt cactgctgat tattcctgct  600
gctactgcac gtcgctttgc ccgcacgccg gaacagatgg ctggtgtcgc tgttttggtg  660
gggatggtgg cagtgactgg cggtttaacc ttttccgcat tttacgatac acctgcaggc  720
ccgtcggtgg tgctatgcgc ggcactgtta tttattatca gtatgatgaa aaagcaggcc  780
agctaa                                                             786
```

```
SEQ ID NO: 140         moltype = DNA  length = 1011
FEATURE                Location/Qualifiers
source                 1..1011
                       mol_type = genomic DNA
                       organism = Escherichia coli
SEQUENCE: 140
ttacggcatt tctggcggcg tgatgccgaa gtggttccac gcccgcactg tcgccatacg  60
cccgcgcggt gtacgctgca aaaagccttg ctgaatcaaa taaggttcca gtacatcctc  120
aatggtttca cgttcttcgc caatggctgc cgccaggtta tccagaccta ccggcccacc  180
aaagaactta tcgattaccg ccagcaacaa tttgcggtcc atataatcga aaccttcagc  240
atcgacattc aacatatcca gcgcctgagc agcgatatct gccgagatgg tgccatcgtg  300
cttcacttca gcgaaatcac gcactcgacg cagcagacgg ttggcaatac gtggcgtacc  360
gcgcgcacga cgagcaactt ccagcgcgcc gtcatcactc atctcaagcc ccataaagcg  420
tgcgctgcga ctgacgatat attgcagatc cggcacctga taaaactcca gacgttgcac  480
aataccaaaa cgatcgcgca acggtgatgt cagcgaacct gcgcgcgtgg ttgcaccaat  540
cagggtaaac ggcggcaaat caattttaat ggagcgtgcc gccggacctt caccaatcat  600
gatatccagt tggtaatctt ccattgccgg atacaacacc tcttccacca ctggtgaaag  660
acggtggatc tcatcaataa acagtacatc gtgtggttca aggttagtga gcattgctgc  720
cagatcgccc gccttttcca gcaccggacc agaagtcgtg cgtaaattaa cgcccatttc  780
attggcgaca atattggcaa gcgtagtttt acccaacccc ggaggaccaa aaatcaatag  840
atgatcgagg gcatcgccgc gcagtttcgc tgctttgatg aaaatctcca tctgcgaacg  900
```

-continued

```
aacctgcggc tgaccaacat actcttccag taatttaggg cgaatggcgc gatctgccac  960
atcttccggc aaagtggtac cggcagaaat cagacggtct gcttcaatca t           1011

SEQ ID NO: 141          moltype = DNA  length = 612
FEATURE                 Location/Qualifiers
source                  1..612
                        mol_type = genomic DNA
                        organism = Escherichia coli
SEQUENCE: 141
tcataacgcg gcgcgtaggg cttcgcgaat taatgtttca ctgctggcgt cagggcgagc  60
gattttgctc accatgcggc ttgcttcttg tggtttatag cccagtgcca ccagcgcagc  120
aaccgcttcc tgttcagcat cgtcggtcgc cgggctggca ggagacgtga gtaccaggtc  180
ggcggctggc gtaaagagat cgccatgcaa acctttaaat cggtctttca tttcgacaat  240
caagcgttcg gcggtttttt tgccaatacc cggcagtttc accagtgccc ccacttcttc  300
acgctcaacg gcattaacga actgctgcgc tgacattccg gagaggatcg ccagcgccaa  360
cttcgggccg acgccgttgg ttttgatcaa ctctttgaac aacgtgcgct cttgtttatt  420
gttaaaaccg tacagcagtt gcgcgtcttc acgcaccaca aagtgggtga aaacgatcgc  480
ttcctgaccc gcttcaggga gttcataaaa acaggtcatc ggcatatgca cttcatagcc  540
tacgccgccc acttcaatta acaccagcgg gggttgtttt tcaatgatga tgcctctgag  600
tctgcctatc ac                                                      612

SEQ ID NO: 142          moltype = DNA  length = 603
FEATURE                 Location/Qualifiers
source                  1..603
                        mol_type = genomic DNA
                        organism = Escherichia coli
SEQUENCE: 142
gtgaatatta attatcctgc tgaatatgaa attggtgata tcgtctttac atgtataagt  60
gctgccttat ttggtcaaat atcagctgca tcaaattgct ggagtaatca cgtcgggatc  120
attatcggtc ataacggtga agactttctg gttgcagaaa gccgtgttcc cctctcaacc  180
atcactacgc tatcccgttt tattaaacgc tctgctaatc aacgctatgc tataaagcga  240
ttagacgccg gactaacaga acaacaaaat caacgaattg ttgaacaggt tccttcccgg  300
ctacgcaaaa tttaccacac cggttttaaa tacgaatctt cgcgccagtt ctgttcaaaa  360
tttgtttttg atatttataa agaggcgcta tgtattccgg tgggtgaaat agagacgttt  420
ggagaattgt taaatagcaa tccaaatgca aaactcactt tctggaaatt ctggttctta  480
ggttctattc cgtgggagcg taaaaccgtc acgccagcca gtttgtggca tcatccgggt  540
ttggtgttga ttcacgcggt gggagttgaa acgcctcagc ctgaactgac cgaggcggta  600
taa                                                                603

SEQ ID NO: 143          moltype = DNA  length = 522
FEATURE                 Location/Qualifiers
source                  1..522
                        mol_type = genomic DNA
                        organism = Escherichia coli
SEQUENCE: 143
ttaacgcagt cgccctctcg ccaggttcag tcgcgattcg ctcatttgca tcgcattctg  60
actaacgtgg cagtgggtga tggcaatcgc cagcgcatcg gcggcatccg cctgtggatt  120
agcgggcagt ttcagcaagg tgcggaccat atgctgcacc tggctttttt cggcactacc  180
aatacctacc actgtttgct ttacctgacg tgccgcatat tcaaataccg gcaattcctg  240
attcaccgcc gccacaatcg ccacgccgcg cgcctgcccc agtttcaggg ctgagtcagc  300
gttcttcgcc ataaagacct gttcaatggc gaaataatca ggctggaatt gggtgatgat  360
ttccgtcacg cccgcataga tgagcttcag acgagacggt aaatcatcca ctttggtgcg  420
tatgcatccg ctacccaggt aggacagttg cctgcctacc tggcggatga cgccatagcc  480
ggtcacgcgc gaacccgggt caatgccgag aataatagcc at                     522

SEQ ID NO: 144          moltype = DNA  length = 741
FEATURE                 Location/Qualifiers
source                  1..741
                        mol_type = genomic DNA
                        organism = Escherichia coli
SEQUENCE: 144
tcagagagtc gctgcaacct catcagagat ttcaccgtta tggtaaactt cctgcacgtc  60
gtcgcaatct tccagcatat cgatcagacg catcagtttc ggtgcggttt ctgcatccat  120
atcagctttg gtggacggga tcatggaaac ttccgcgctg tctgctttca gacctgccgc  180
ttccagagcg tcgcgtactt tgcccatttc ttcccatgca gtgtagacat caatcgcgcc  240
gtcatcatag gtcacaacgt cttcagcacc ggcttccagg gctgcttcca tgatggtgtc  300
ttcatcgcct ttctcgaagg agatcacgcc ttttttgctg aacaaataag ctacggaacc  360
atcagtaccg aggttaccgc cacatttgct gaatgcatga cgcacttcag caacggtacg  420
gttgcggttg tcagacagac attcaatcat gattgccgtg ccgccaggac cgtaaccttc  480
gtagatgatg gtttccatgt ttgcatcatc atcaccgccc acacctcgtg caattgcgcg  540
gttcagagtg tcacgggtca tgttgttaga cagtgcttta tcaattgctg cacgcaaacg  600
cgggttagcg tccggatcac caccgcccag cttagccgcg gttaccagct cacgaatgat  660
tttagtgaag attttaccgc gcttagcatc ctgcgcagct ttacgatgtc tggtgttggc  720
ccatttacta tgacctgcca t                                            741

SEQ ID NO: 145          moltype = DNA  length = 444
FEATURE                 Location/Qualifiers
source                  1..444
                        mol_type = genomic DNA
```

```
                         organism = Escherichia coli
SEQUENCE: 145
tcaggcagcg ttaattacaa actgttcaat cgcctgccgg ttgctccagg acttagtgag  60
cgccgccgca gcagacgcat caagccactt gtaagccaga tgttcagtga aaacgatctg  120
gcgctcgtgc ggaagcgcaa gacagaacca tgattccgta ttacgcgtca cgcccggcgc  180
atagcgatga cgtaaatgtg aaaaaatttc aaactctacc gtgcgctgac agtcaattaa  240
ggtcagttgt tcagcgacaa catcaatggt gacctcttcc tttacttcgc gcatggcagc  300
ttgcggcgcg gtttcaccct cttccacgct gccggttacc gactgccaga aatcgggatc  360
gtcacgccgc tgcaacatca gcacccgttt cgtatcttgt gcgtagatga ccactaagat  420
cgaaacggga cgcttataag ccat                                        444

SEQ ID NO: 146           moltype = DNA  length = 1773
FEATURE                  Location/Qualifiers
source                   1..1773
                         mol_type = genomic DNA
                         organism = Escherichia coli
SEQUENCE: 146
tcagttattc tcagccttct tcacaacctg aatgctcagc tcagccagtg cagtcgggtt  60
agcaaagctc ggcgcttcag tcatcaaaca cgctgccgcc gtggttttcg ggaaggcgat  120
aacgtcacgg atattgtcgg tgccggtcag cagcatcgtc agacggtcaa gaccgaatgc  180
caaacctgcg tgcggcggag taccgtattt cagggcgtcg agcaggaagc cgaatttctc  240
gcgctgttcc tcttcgttga tacccagaat accaaacacc gtctgctgca tatcaccatt  300
atggatacgc acagaaccac cgcccacttc gtaaccattg atgaccatat cgtaagcgtt  360
agccaccgca ttttccggtg cagctttcag ttctgctgcc gtcatgtctt tcggtgaggt  420
gaacggatgg tgcattgctg tcaggccgcc ttcaccgtcg tcttcaaaca tcgggaagtc  480
gataacccac agcggtgccc atttgctttc gtcggtcaga ccaaggtctt tacccacttt  540
caggcgcagt gcgcccatcg cgtcggcaac aatttttcttg ttgtcggcac cgaagaaaat  600
catatcgcca tcttgcgcgc cagtacgctc caggatggct tcgatgattt ctgcattaag  660
gaacttcgct accgggctat tgataccttc cagacctttc gcgcgttcgt taactttgat  720
gtaagccaga cctttcgcgc cgtagatttt aacgaagtta ccgtattcgt cgatctgctt  780
acgggtcaac gatgcgccgc ccggaacacg cagagcggca acacggcctt tcggatcgtt  840
cgccggacct gcaaatactg caaactcaac agatttcagc agatcggcaa cgtcggtcag  900
ttccatcggg ttacgcagat ccggtttatc agaaccataa cggcgttctg cttctgcaaa  960
ggtcattacc gggaaatcgc ccagatccac gcccttcact tccagccaca gatgacgcac  1020
cagcgcttcc atcacttcac gcacttgcgg cgcggtcatg aaagaagttt ccacatcgat  1080
ctgagtaaat tcaggctgac ggtcagcacg caggtcttcg tcacggaagc atttaacgat  1140
ctgatagtag cggtcaaagc cggacatcat cagtagctgt ttgaacaact gcggggattg  1200
cggcagcgcg tagaatttac ctttgtgcac acgagaaggc accaggtagt cacgcgcgcc  1260
ttcaggcgtg gctttggtca gcatcggagt ttcgatgtcg aggaagccgt ggtcatccat  1320
aaaacggcgc accaggctgg tgattttagc gcgggtttc aggcgctgag ccatttccgg  1380
gcgacgcagg tcgaggtagc ggtatttcag acgcgcttct tcggtgttga cgtggttaga  1440
gtcaagcggc agaacatctg cacggttgat gatagtcagc gaggacgcca gtacttcgat  1500
ttcgccagtc gccatatcgc ggttaatatt tttttcgtca cgcgcacgta cggtgcccgt  1560
gacctgaatg cagaactcat tacgcagttc agaggccagc tttaacgcgt ccgcacgatc  1620
cggatcgaaa aatacctgca cgataccttc gcggtcgcgc atatcgatga agatcaggct  1680
accaagatca cgacgacggt tgacccaacc acacagagtc acctgctgcc ccacgtggga  1740
caaacggagc tgtccacaat attctgtacg cat                              1773

SEQ ID NO: 147           moltype = DNA  length = 567
FEATURE                  Location/Qualifiers
source                   1..567
                         mol_type = genomic DNA
                         organism = Escherichia coli
SEQUENCE: 147
atgcttgaac ttaatgctaa aaccaccgcg ctggtggtga ttgatttaca agaaggcatc  60
ttgccttttg ccggaggtcc acatactgcc gatgaggtgg ttaatcgcgc cgggaagctg  120
gcggcgaaat ttcgcgccag cggtcagccc gtgtttctgg tgcgcgttgg ctggtctgcc  180
gattacgccg aagcattaaa acagccggtt gatgcccccct cccccgcaaa agtgttgccc  240
gaaaactggt ggcaacatcc tgctgcatta ggtgcaaccg acagcgatat cgaaatcatc  300
aaacgtcaat ggggtgcgtt ttacggtacg gatctggagt tgcaattacg ccgccggggt  360
atcgatacaa tagtgttatg tgggatctcg accaatatcg gtgttgaatc caccgcccgc  420
aatgcctggg aactcggttt taatctggtg attgccgaag atgcctgtag cgccgctagc  480
gccgagcagc acaataacag cattaatcat atctacccgc gcatcgcccg tgtgcgtagc  540
gttgaagaga tcctcaacgc gttatga                                     567

SEQ ID NO: 148           moltype = DNA  length = 390
FEATURE                  Location/Qualifiers
source                   1..390
                         mol_type = genomic DNA
                         organism = Escherichia coli
SEQUENCE: 148
tcacatcacc gggcagtcat caaactccgc attcctggca tcattaatga tgtacgtgat  60
cactccaaat atagcgggtg cagaactgta accatcatca tctgctggca gcgcttccct  120
tctcccgtta tccagattaa ccaggtgcgg ctgaggatga gtccgatatc gcttgatcct  180
gaattccccg tcgattgcac atatcagcag tgaaccatcg caggcagtaa gtgacgcatc  240
cacaacaagc aacgctccct ggattatccc ttccctgaaa tgtgaacgcg atgcccgcat  300
gaaataagtc gctgcgggct gactgattag ctgctgatcg agggagattc gtgtttcaac  360
ataatctgcc gcaggtgaag gaaatcccat                                  390
```

```
SEQ ID NO: 149          moltype = DNA  length = 243
FEATURE                 Location/Qualifiers
source                  1..243
                        mol_type = genomic DNA
                        organism = Escherichia coli
SEQUENCE: 149
atgttcgtgg aactcgttta tgacaaaagg aattttgatg gtctgcccgg tgcaaaagat  60
atcattctgg gcgagttaac taagagagtt caccggatct tccccgatgc tgatgttcgg  120
gttaaaccga tgatgacact gccggcgatc aacactgacg ccagcaagca tgagaaggaa  180
cagataagcc gtactgttca ggaaatgttt gaagaggctg aattctggtt agtgagtgag  240
taa                                                                243

SEQ ID NO: 150          moltype = DNA  length = 381
FEATURE                 Location/Qualifiers
source                  1..381
                        mol_type = genomic DNA
                        organism = Escherichia coli
SEQUENCE: 150
atgctgtgga ggatattcat tttcgtaaac gttggtttgg gagaagcggc aaaacggaat  60
gtgggaacag gggaaaatca gataccagat atgtctgcat ttccatctgg caataactgg  120
tttcagttac caagtggaca tatcgttcag atattttcca tgaacgttct tggtgcagat  180
gctaatggca cgtcagctaa ttaccccatt gcttttccaa caacgatgat tgctgtcagt  240
gctctatggt ctgatgggac tgtagcaaat gcaccgacat acaagatgat ggggaacacg  300
actaacagaa caactttgac gataaaagta tcagccagct caggtactta cgggacaatg  360
attattgcgg tgggacgata a                                            381

SEQ ID NO: 151          moltype = DNA  length = 444
FEATURE                 Location/Qualifiers
source                  1..444
                        mol_type = genomic DNA
                        organism = Escherichia coli
SEQUENCE: 151
atgaataaat acagttactc tccttcagaa aatgcctttt atgctgttgc gttaaaaaat  60
acctatgaat tgagtggcac atggccagct gatgcattag atattcctga tgacatttct  120
gtaaaatata tggcggaacc gccacaaggg aaaatccgag ttgcagggga aaatggtttt  180
cccacatggg ctgaaatacc tccaccatca catgaggaac ttattgaaca ggccgaatca  240
gagaggcaat tattgattaa ccaggccaac gaatacatga acagtaaaca atggcccggt  300
aaagccgcta ttggtcgtct gaaaggcgag gaactggcac aatataattc gtggctggat  360
tatctggacg cactggaact ggtcgatact tccggtacgc ccgatattga atggcctacg  420
cctccggcag ttcaggccag atga                                         444

SEQ ID NO: 152          moltype = DNA  length = 594
FEATURE                 Location/Qualifiers
source                  1..594
                        mol_type = genomic DNA
                        organism = Escherichia coli
SEQUENCE: 152
ctacgcctcc ggcagttcag gccagatgac atccggcgcg gtgctggtat ctgttgcagt  60
caccgcgtca atgtaatcca gcacggcgtt aagtcgggtt gtttctgcct gagtcagttt  120
ccgtccggcc tgtaatttca gctgaatcag actaatggaa gccattgctg catcaatcag  180
tgattggcgc tgtgcttctg ccgcttctac tgaggcaccg tgttgtgcct cagtatctgt  240
cacccatttc tcaccatccc atttatcata tggcgttaac ggtgaaagcg tgacataacc  300
gtttttgatg gcaccgatat aatccactgt aacagctgcg ccatttttcga ttgagtaaac  360
agtctcattg cgatggtctt cctcatggct ccatccctta cctgtaaata ctgccactct  420
tcccggaatg ttttcgtccg ggtcaatacc agtggaacag gcgggcatac ttacgccagt  480
attaatatat tcatcagacc agcccgtata ttcagacgtt actgcatcat aataaaaaca  540
acgcatatca cccggcactg cagccagccc attttcatca aaaacaggtt tcat        594

SEQ ID NO: 153          moltype = DNA  length = 933
FEATURE                 Location/Qualifiers
source                  1..933
                        mol_type = genomic DNA
                        organism = Escherichia coli
SEQUENCE: 153
ttatttagcc ctcaccagaa agttaaatgc aatatttcgc ggtctgacag caacaaaatt  60
cacaccatca cccacagagt tactgttgaa attaaatcgt gaaaatcctg gctgatttcc  120
ggcgatgcca tcatgaaagt taattgcgtg tccagcacct ccgcctatat tcccggcaaa  180
ctgagaaaag tttgtagctt cctgccagct taataattcg cgaccaccat ctgcacctcg  240
cccgtcatcc cagacacgaa tgaaatcacc gcgggcttca ggtaatacca gcgaaggaaa  300
cactttcgcc agcacaggat aatcagtggc agagaatttc gcgccgttga acttcaaaaa  360
caccatactg gaccagctgt cgattacagt atttggcatt gcagcggacg gccagaagaa  420
cggaacgcca atagctggag aaccttctcc caaaccaagg tttgtgcgag cgtctgcggc  480
attcgttgcg ccggttccgc cgtctgcgac agtaaccgca ccgttgctcc ctttctgcgc  540
aagtttaccg atgcctggga tggttacggc ggtgccgttg atggtaactg tgatgctttg  600
gtttgctgag gtggtggcga acgtctccca cgcgccaata ttctcgtcgt actctttgat  660
gagctgtgac atggcctgcg ccaggccgtc gactgagata ttgtccgaca caaggattcc  720
atacttctgg ccgctcagcg ccggggaaac tgctggcgta accgtcattg acgtggcgct  780
gttcacggat gaaatctgaa acagctgcac cgggttagac atcacgataa tcgtctggcc  840
agcgcggacc tggctggcgg gagctgtcca gtttgtgccg gagccggttg cggtatttcc  900
```

```
gttaatagag atagttccgg tgctataaat cat                            933

SEQ ID NO: 154          moltype = DNA  length = 3927
FEATURE                 Location/Qualifiers
source                  1..3927
                        mol_type = genomic DNA
                        organism = Escherichia coli
SEQUENCE: 154
ttaacctgtg aatgaaccag atccgtgtga tactatgata gtaggcgaag aaattgacgc  60
acccctgtta ttttgagcgg acactttaat acgcactgtt acgtttggac ctgttacaac  120
cgcagaatgc atgataagtc tctccatgtc ttgcacggat gaaccactct cattgccgtt  180
aatgtcgatt gttcctgcac cattaccttt aacgtttgct ataacacaga cgtgtcttgc  240
gtgcccagaa ctggatgaat cattataagt cattaccttt tctaaatatc cgtcactaga  300
ccgactcaca ttcgtccctg tgtgcatatt tgcaatgtcc ccgataaaac tttgggcttc  360
cacagtccct ttgaatttac cgcttgttgc ttggatctca ccagtaaagc taccgccact  420
agcatatact acacctctga cggtcacatt gttgaattca gcatctccag ctttattcaa  480
cttccaacca gcagaaccag ctgcatagtt gttggactgg atatagttac cgatttttgc  540
gttctcaatg gtgccgtcct ggatgaagct ggcccggatg aatgtctgcc cgttctggat  600
cacgaacggc aaagctacgc tatttccggc tgccgtggtg acggcgaagc ggtcagccag  660
gaagataacc tgcgactgca tgccggatgg cgtattctcc acgccgatac ccatccccgc  720
ggcgtaatac tgcccgttgc tggagacacc aaccttgatg ttgtacatcg cgctgagttc  780
gccattaacg ttggctatag cctgagcgtt agtggtgatg gcggaggtat gcccgttcac  840
ggtcgccgtg atgccgttta tctgcgtggc ggtggcctgc tgatagtcgg agagcgtctg  900
attcaggctg ttgatggatg ccttgttgcc gttgacgtcc gtctgcaggc tcagcaatga  960
acgtgctgtg gcttccttct cactgacgat cacctcgtcg agacggtcca gattcgcgct  1020
gttgccggcg accgatgcag aaagggtttt acgcgtggcc acctgagcga ggttggcctg  1080
gattatcgca attgcagagt tcttcacccc gcccgtcatg ccgtccatag aaacgctgat  1140
gttgtcgatt cgctggccca gggcggtatc agccgtcgca acggtctgct caagctgact  1200
gagtgaagac gaaacattcc cgaccgtgct ggaaagctca ttaacgctgg tctgaacctt  1260
cccgacgtcc tgggcatttt tggcgatatc tttcgcttgc tgctccagtt cgtcgttggc  1320
ctgtttgata tcgttagcca tgccagcaat tttttcgttg ctgtccaccg cgttctcgat  1380
caggtctttg aacgtttccg actctttcat atcctccaga atgtcattag ttatttcgct  1440
gacatctatc gaggacgtgc ccatgatcca gtcggtccag tccccggcgt taccgatacg  1500
gtcaatcagg cgcgcgcggt accactggcg aacgccggca ggcatggggc catgctgata  1560
atctgcagcc gggtacggca ccaggaccag cagttcagga ttggcgtagt cggcagttgt  1620
ggcgcgctga atctctgtat aggccgtgtc gcctgagcca tccggaaatt tccaggtcag  1680
gtcgatatgc cagaccacat cttcggtcgc caggaagttg agcggagtac ccggttttcc  1740
cgttttaccg gagagataag ttgtttcacc gtatccccat ggtgacgacg tatcctgcgc  1800
attcagcgcc cgtacgcgca cgtcatagct gcccgaataa atgccctgaa ccgagaaacc  1860
ctgcgcgctg gtaaccggaa cgtttatcca gtccccgttg tccttacgcc actgggcaac  1920
ataccggatt gcgccctcta ccttatccca tgacacgtcc aggcttgcta cagtcagccc  1980
ctgagacaca tgatcgctct cagtcaccac gatattcttc ggagcagaca ggacgcttat  2040
cggcgtgacg gtgatcgggg gagactcgac ccgaacgccg tcatcgatgt aacgatattt  2100
gtttggatcg tgctgaacgg ccgtaatagt gaaaccgcct gtactgtcgt cgttagccgc  2160
gattgaggtg accctgaagt actgtattgc gaggttatca ctgtctatcg cccaaacagc  2220
gcccgccaca ggaacctgac tgaatgccgt agccaccgtc accgtttttt tatcggcgct  2280
caccgcgctg attgtccgcg tctgggcttt tccgtcggga aggttaacca ccagccggtc  2340
tttcgccgcg tagtctattt ctcgatcgag ggtaatttgg cggccgttgg ccgcgcttat  2400
acggcccccg ttctccttac cagagcggaa aggatcggcg acaccgataa tttcagcggg  2460
caaagggata taaccgtcca gccccacgcc aaacgatacg gtcccgtctt tggcattgga  2520
gagcaatacc cagcgaccgc gtcggtgcgc ttcactttgc gaggtgcagc cgattgcggt  2580
cagggacgtc tgccggacgt cgtaacgttc tacaagcgcc gaatcgtaaa ccccctcaac  2640
ggtatcgctg taatggttct gcggatcgga ccaggacacc aggcaggagc tgtagcgatt  2700
cttgtatgag ccgcccgcat aagtaaacag cccatcgata acgtttgaga cgttataaac  2760
ccagtcaaca tcgtcctgcg ggacgtctgc ctggacataa atctgatcgt ttccccagaa  2820
cgttattcca cgaaataccg cggcgagatc gttaagtacc tgccaggcgt cctcctggct  2880
ctgaatgaaa acgttgcagg tgaaacgcgg ttcggtgcca ccggccccgt cggaaaccat  2940
ttcgtcacag tactgggcga ttgaatacag cgcccactta tccaccatgg acgcatccac  3000
gcgcgtgccc atgccgtaaa tttcatccag aaccagatcg taaaagatcc aggcagggtt  3060
attggaccat gccattttga acccgccgga ccatgaacca gaataggttc gggttttcgg  3120
atcgtaatta tccggaacct taatcagctt gccttttatc ttacaggtca ctttcggcgc  3180
gctgccgttg aattggctgc tgtccacttc gacatacagg agcgctgtta aaggataacg  3240
aagcttgctg tcgatgactt ccgcatacga aaacaccttg aaggcgttaa ccagtttcga  3300
atttgatccg ctggcatcag ccgtaatacg cctgaccctg acagaccagc cggacgtgga  3360
ttttggcaga tcgatacggt ggtcacgctg atattccgtc gtggtctttc cgtcaaactt  3420
gccgtttaca accgttttcc aggcgccgcc gtccgttgat aaatcgatcg catactcggt  3480
gaccgtgccc accatatcgc cattatcttt atagagatac tggaccggaa ggctgagctt  3540
gatacggatg gcatccaggg aaaggtttgt aaactggcgc gtccagggcg cggtggtggt  3600
gacagttgtg cccacggcca gctcgttgtc gacctggggc atcccggcaa tataggtctg  3660
gtcctgtgtg cccttgcgga actcccattt cacgccgctg aagttgtatt ccccgctgtc  3720
gtttgccagc ggcgtatcgt tgagaaaaat gttctgagcg gtcaggtcgc cctgtatttc  3780
cccctcagaa acggcaatga gcatttttaa ttttgcgacc gacagcagat cgtcaggctg  3840
ctcaaccgga gtatgtgaac tgccacctcc ccctttggca ccctgcagga tggtttcttg  3900
tttaagaagc tgcatttttt cacccat                                   3927

SEQ ID NO: 155          moltype = DNA  length = 618
FEATURE                 Location/Qualifiers
source                  1..618
                        mol_type = genomic DNA
```

```
                         organism = Escherichia coli
SEQUENCE: 155
ctactgctga tcgctcgagt acataccggc gctgactatc gctccccctg cctcagtcag  60
accgtaggcc agggggacag gatgccccat agcgacggta ttgaccggcg ccccgaaggc  120
gtagttaggc gtgttgtccg tgctggagga tttacccgcg ccgaaggatg gctggggcgt  180
gagcatctgg acaacgcccc ccagcatcat cgacactccg acccctgtca gaattgacgt  240
ggcgctgata gctgttgcac tcatcgccgc gccccaggct gccatgctcg caccagcggt  300
aaagaatgca gcgaccagcg caacagcccc gacaactatc tgcaggacgc ccgaactttt  360
ggccccctca taaacgggca cgatccggta cacgcttcca ccgcgggtca tatcaaactc  420
ttccagcccg atattgttgc caccgttaaa aaggcgaaa cggatcccct tcatatgagc  480
ttcagacata tattttttga atccgggaac ctgtgaacac atggccctga gcatctcgcg  540
caggtcggca acatcaaact gaacgcgttt accgaatttt tttgccattt taccttcgag  600
aataagcgtc ttaaccat                                                618

SEQ ID NO: 156           moltype = DNA  length = 720
FEATURE                  Location/Qualifiers
source                   1..720
                         mol_type = genomic DNA
                         organism = Escherichia coli
SEQUENCE: 156
ttaaccatgc attctgtcct tatgcctgac cacccggacc gttctgtcgc gataatattt  60
tccataaggc gttcgcgaag aaaggtgccc gaaaagatga tggagaatga tgttatcacc  120
cacatatacc gcggcgtgat tagtcaccga tgcctgcaca ctcatcatga tgatatctcc  180
gggctgcatt gcaccggcgg caatctcaac gaatccctca cgctcccagt tgtcgtcgta  240
gagacgctcc ttgccgctct cccaccattc gtaaggtact gaataattgc cgagaacaat  300
gccgtattcg cgcagataaa attcacggat aagcgaccag cagtcggcgt aacccagcac  360
ccactgccgc ccggcataat cccggtcttc acgcggggaa atcgtacaaa aatccccgtc  420
cggccaggac atgatccccc actcaatccc cgaccagtcg cactggatcc ggtccagctc  480
tgagggcacc agccgaacca catccggatg ggaatgaatg agcatgatga tctcaccgcg  540
cgcgcgggca gcgagctggt cttccgggga gagcgtgaat gtctcctcgg gtttatcggc  600
aatgttgcgg cagggaataa agatttgttg ctggcctgac tgaacaatca ggccgcaggc  660
ttctttgggg tattcagcag cgacgtgctg acggatagca tccagcaatt tttcacgcat  720

SEQ ID NO: 157           moltype = DNA  length = 738
FEATURE                  Location/Qualifiers
source                   1..738
                         mol_type = genomic DNA
                         organism = Escherichia coli
SEQUENCE: 157
ttatttcccc tgcaggtttg cagccggaaa accgccgaac ggcagcggcg catccgggcc  60
gtgacgatcc tgacaatcct gccggcggcc gccacaaaca tctttcgacg ggtcatcggt  120
cggtgtaccg tctttggtaa agtatttcgt gccgttgtaa tcgcatccgg tcccgcttcg  180
gtaccagccc cgcatacacc aggtgcagac aggcgtaatc tgccgtgtcg gcagctgcag  240
gctctgaata tcgaaaggag aacacagctc gaaatcaacc tgtacccgcg tctctgcggt  300
tttagcattg acgtaaaaga gctgtaagcg ctcatcggcc gggctggcac ccggattacc  360
gtttttccag ttggcggcat cgagatactt cgaaagcgtg gtatggattt tgaccttagc  420
cctgaccata tcgtcatatt caagacacag cgcggtgaca tagtttccga cgttcccgac  480
ggacagcgtg ggcgttggct gggaacctgt actcgataac tccatcccct taagttcgta  540
gggatgggga tcgtactggt ttccctgcca gataatggcg ggcagatttt ctgcggcgaa  600
ggctgcccac ccctcttcct gaatattgtg cgcatgaaaa cgcagcacct gatccatacc  660
gaattcagtg ccgtcgatct caatcagctg aataacgctg ccgggctcaa gctgttgtat  720
gtctgccgta aaactcat                                                738

SEQ ID NO: 158           moltype = DNA  length = 339
FEATURE                  Location/Qualifiers
source                   1..339
                         mol_type = genomic DNA
                         organism = Escherichia coli
SEQUENCE: 158
tcagggcgcg aacgcctgtt caaaagtgaa ggccacagtg gctttttttcc cggtagggaa  60
agaaacgctg aacgaatcgg ccttcattct gaacagcttt ttttcacccc atggagtggt  120
ccaccagaac gatttagtaa cgtgagacat caggaaagcg cgcagcgcag ccgcctcctg  180
tctggtgccc gtccagtcca ggttccacgt ttcctgtttg tcgttgatcc ccatccccgc  240
tatctgtttg tagccatccc cgaactgggc ctgcagcgtt cgggctgttt cagtgccctg  300
cgctgttttt cgcgtgcgcc aggtaaacgt gtccgtcac                         339

SEQ ID NO: 159           moltype = DNA  length = 3138
FEATURE                  Location/Qualifiers
source                   1..3138
                         mol_type = genomic DNA
                         organism = Escherichia coli
SEQUENCE: 159
tcactgtgtc ctcctcgaat aaagcacgcc gcccgcggac atttcttttt tcagtcgctc  60
ggtgattgtc tgctgaacaa tcgcctgcag ctgtttcgcc gtccccgtgg cgttcgcctg  120
atttatgctt ccgtcactcc cctgctggct gatgctgact ggggcataaa cactgatccc  180
gcccatgcca gcaccggctg cgttcccgcc gccgaccaga ccacccgagg catacccgcg  240
catcaggcga tagagattag ccacgccgat gcggctggtt gattctttgg tgaagacgaa  300
ttccccgcgg tgaacgatac cggctggctc gtacttgccg ccgtgcccgg taaaaccgcc  360
cacgtcaaaa ccctgtggcc ggtatgacgg gaccgcgaat gactgaccgg cagaggaggt  420
```

```
tttcgccccg ccgctaaccc agcccattgc actctggatg gtgtaagcca ccagcagctg  480
gttgataacg gacacaatca ttttaaggat cgagctggtg aattccctga agctcgcctt  540
cccggttgtc gtcaggctgg taagctggcc cgccaacccg ctgaacgtag cctgagaaat  600
ctgctgaacg gagctgaaaa cgtttgtcgc tgaatcctga tattcggccc aaccctgttt  660
cgcaccggcc agccagtttg cacgcagggc atcttcagct tcgaacgtcg ccctttgctc  720
ttccagaacc ttttgctgcg cctgagggtt gtacgaatag ctttcgctga gacgctgcag  780
cgtagtttgt cgcccggctt cccgggtgga taacccctca gactgagcct gcaggcccgc  840
cctggcggct ttttgctgct gctcaaactt cacggcctga tcggccagct ggttgagctt  900
ttgctggctg gcaaccttat cgcccaggtc ggccagctgc cgcttgtact cgagcgtttc  960
ttctttgtgc gccagcaggg atttttcctg cgccgtaagc tgacgacgcc cagcggcctc  1020
ctgcagaacg gtgaactgat tttcagtttg ccagagatcc tgacgctgtt tacttatgac  1080
gtcgttcacg ctggtatgct gctcaagcgt tttaagctgg gcctgaaggg tgagaagttc  1140
ggcctgcgcc ttttcctcgg ctttgtcccc ggcgggcgtt gagtagcttt tgcctttcgg  1200
tgtttttgga tccttccact gcttttcaat cccggcgcgg gccgcggcaa tgtccttttc  1260
agtccacagc gtggcgacac cgtctttcgc atcctggcgg tttttctcaa taagctgact  1320
gagctttttc tctgctgaag cccgcttttc tgccgccgtc gcgccggact ccaccagctg  1380
gttaaactgc tgctggctgc ggattgcctg agcctgctgg tccgttcgca ttttttcccg  1440
cgcggctgcc agcccttcct gggcgtattg ctgatcggca agatcgtaag cctgcttttt  1500
cagctccacc tgctggcgcg cgtttctcag cctttccgca tccgctttct gcagaacgtt  1560
gttaccggca taatccgggt cgaccttaag attgctggac agcgcgcggt actctttctc  1620
tgctgcctgc cactcagcaa aagagtcctg gcgcttcatc gcggtgtcag gattacgccc  1680
gacgcccagc atcgcatccc acgcaccgga ggcggcattc ttcacccagt tccaggcttt  1740
ttcgagggat ccgagattat cctcgaccgc accggcgcgc tgaatgaccg cgtcggaata  1800
tgcccgcatg gccagctcgg cagccttctg agaatccccc agcgcctgag cagaagctat  1860
ctgttcatac tgggtggctg tcagaaaatg aagggaatcg ttgagcgtcg cgaccgcgtt  1920
aaccggatca tccttcaggc gtttaaactg atttatggtt tcgtcaacgg cctgcccggt  1980
agcctgctgc agcctggcgg caacattgct gaccatgctg acgtcattac cgctgaacgc  2040
gccgctgcca acgacctgcg ccagcacgcc tgcagcggca tgctgagtga tgccattacc  2100
tgccagcgag cgcgccagcg cctgcagctg ccctgacgtt ttccccgcgt agttcccggt  2160
caggatcagc tgcctgttaa attcctcaga ctctttgctg ccgtcgtacc aggccttacc  2220
caacccgaat accgccgcgg caatccctcc gaccatgctg gcgatcccaa gaccgcgcag  2280
tgacagaagc tggtctatcc accctgcccg gttagccagc gtgatcccgg agccgcgcag  2340
cgcgccgaag ttaccgcgca tgacctcgcc gatcagtatt cccagttcct gccgggcggc  2400
ggcactttgc agccccagac cgtgcgtggc gactttggca gcttcgagct tgcggatata  2460
gacttcagcc gcatcgctgg caccgacctg cgccgccttc atgcgcagta gctcggtacc  2520
ggagagcttt tgctctgcaa cctgttgctt cagctggctg aggaatcgcg tgcgcgctgc  2580
ggccgatttt tcctccacga tctgcagttc tttttgacgg gccgtggtgc gggaaataag  2640
ggcgagataa tcctgctggg ttatgttgcc ctgtgccctc gctgcgcgaa agcgcgcctg  2700
cacgttcgca agcgactgtg tttcaccatt gagctggcgt acgccgtcga tctggcggaa  2760
aaatgatgcc gcaagttcat cctgtcgacg ggcaagcgca gcggcctgcc cgtcattctc  2820
acgcatgcgc tgattaagct cggtcacgcg gcggtgagtt tcatcaacgg actttgaaac  2880
gttctgccag tctttggtaa gcccttccgt tgcggccgac tggcgggatt tcatatctgc  2940
ggcagccgcc gcgccagcgt cacccacggt tttaaacgca gccgcctgcc gctctgaagc  3000
gcgctgcatt cgcgtctgga ctttttcaga gtcctcagcc atcccggtta gctggccctt  3060
tatgcgggca acctgctcac taaacgtggc gctgtcgacg tcaaggttga tgaccagatc  3120
gctaatctgc tgggccat                                                3138

SEQ ID NO: 160          moltype = DNA  length = 273
FEATURE                 Location/Qualifiers
source                  1..273
                        mol_type = genomic DNA
                        organism = Escherichia coli
SEQUENCE: 160
ctaatctgct gggccatatc ggatacctcc tgttatcccc tcagctgcgg ccatcagcgc  60
atcatcatcc ggctcgtcat cgctgatgac gataccggaa ggagaaagca ggctgaaatg  120
tgcgggggta agttccgggt cgcggaagaa aagagtggag atggaataaa gcagctctga  180
gaaatgcgca tcgagctgag cgtcctgaaa ataatgctcc cggtagaact ggtgccagtc  240
gcccagctca gtggaagtca ttccagccag cat                               273

SEQ ID NO: 161          moltype = DNA  length = 432
FEATURE                 Location/Qualifiers
source                  1..432
                        mol_type = genomic DNA
                        organism = Escherichia coli
SEQUENCE: 161
tcagctcgct ggcaagggct tttccgccgc aacgggttct gcgctttcgg cctccgctgg  60
ggcatccgga tcggcagctt tgtcatcctc aaccggaacg agcatgccgg agagcagctt  120
tatttccatt tctgctttac cgatcgcctc cggcggccag ccgctaagca cctgctggta  180
aagcgtctcc acatccgtgc cagccggatc gttatgccac aaagacatcg caatcaaacg  240
cgcaccgcag cgaatatttg agccaatcag cctggccgtc atttcctgat cgctgatgcc  300
gtcgctgtca gcgctgacgg ccttttcctc tgcggccata aacgtgatgt actcaatacg  360
ctgaagcgcc gacagctcga agatggtcag tgattctttt tgccaggtga acttctcttt  420
tttcagaaac at                                                      432

SEQ ID NO: 162          moltype = DNA  length = 744
FEATURE                 Location/Qualifiers
source                  1..744
                        mol_type = genomic DNA
                        organism = Escherichia coli
```

```
SEQUENCE: 162
ttacgctgca gttacggtaa ctttgcagac cgcaacgaaa ttaccgtcgc tggtcataac  60
aataacgtca gcggtgcctg ccgccacgcc ggtgacggtg atcgcattac cgctaacggt  120
gaccgttgct tttgccccgt ctgaggttgc cacacggaac gaggtatctg aggcactggc  180
tgggttaacc gtcacattga gcgttgtggt tgcgccgacg gccacgcttg ccgtggcttt  240
atcgagcgta acgcctgtca cggggatatt cggggtcccg ctttcttctg ccagttccgg  300
cttgccggta ttggtaattt tcgctgtacg ggttatgacc tcttttgccg gaatggcttt  360
acccaggctg ctgcaccagc cgcggaaaac gtcgacggta ccgttcgggt atttgatttt  420
gtaatagcgt actgagccat caataaacca tgcgacaagg tctttttgcc cttcttcgcc  480
cggcttccag gcgagggtga acgaggtatc gccagcagat tttgcccccct gggccgtcgc  540
gttccagtcg gcatcctcgt cgtcgaggta agtgtcgtca tacgattcgg cggtcatttc  600
gcccggcgtc agctctttaa ttttcgccag gcggttccag tcgatatccg agagtgggtt  660
agcgaaagcg ttgcccgttc cggtgtaaag ccagagggtg gtaccggcac ctttcacagg  720
ggccagcggg tttggagtag gcat                                          744

SEQ ID NO: 163          moltype = DNA  length = 402
FEATURE                 Location/Qualifiers
source                  1..402
                        mol_type = genomic DNA
                        organism = Escherichia coli
SEQUENCE: 163
ttaaattgaa taggtgatta agtacgtgaa atcgactgaa ccccaggtgg ccatttcatc  60
atcccgctga tagtcataac cctgcggggt gaacgtctcg accagttcgg tcagacctgg  120
gatgaaggcc attgccggat acactttctc ttccatccag gaatcaagcg cgctgtcggg  180
gctggaggct ttaagaaata cctcgatgtg aacaaccgcc tgccacgaat cttcgtcaag  240
cgaatcgccg gtgtactccg cgtcagaaag gtatacagcc acggcaggga gatcctgctc  300
ttcaagaaaa acagggcgcc cgtcaaacca ggtgaccgtg tcggtgatct cggctttcag  360
tttggccaga atggctgcac gaattgcgct gtgtctgttc at                      402

SEQ ID NO: 164          moltype = DNA  length = 573
FEATURE                 Location/Qualifiers
source                  1..573
                        mol_type = genomic DNA
                        organism = Escherichia coli
SEQUENCE: 164
tcatcgcttc aggtggatcc tcagttggtt tttcagggct gcggaaagtt ctttgggcat  60
atcgctttca ataaggcgct ttgaaatagc ggtgaaggcc acggtgagcg gtgtctcaag  120
aggaactttg accacatcaa tcggataacg ggcctgacct acgcgccgca tgacctgcca  180
gcgcccgttc gcaagctgtt ggataaaagc gttacgaaag gtatagggcc cgattttaag  240
gacgctgccc gctccgtttc tggccccttt tttacgcgag agcctgacgc gcgccgtgcc  300
gagctttatc gcaggaagat taccgcggtt gatttttatc gacgcgaccg ggcgatcgtg  360
acgggccttg cgcagacggg aacgctggcg gaccagacga accggaagcc cctttttccg  420
gttatcatca actgttgctt ctttcgctac agctttgctc ccctggctta tcgttcttct  480
ggccaccctg ttaagtgctt ttgcggttgc ctcaggaacg attaaccggc tgaggctgtt  540
caggttctga atagcccttt ccagtccttt cac                                573

SEQ ID NO: 165          moltype = DNA  length = 243
FEATURE                 Location/Qualifiers
source                  1..243
                        mol_type = genomic DNA
                        organism = Escherichia coli
SEQUENCE: 165
tcattcgaga tggatgcggg gttttccgtt gaacatgtca tagcgggtaa cgatcaggtt  60
cttaccgtcg tagtcgacgc tgtcgtttcg gcgtggctgg taaagctcag agaaaaccac  120
cagcgaagta cctgttcccg acaatggccc catttcctcg agttgctcgg cgggaacaac  180
gtcatagctg ctgccattga tgatcgctgt ctttcccatc ttttttatag tggccgcgtc  240
cat                                                                 243

SEQ ID NO: 166          moltype = DNA  length = 327
FEATURE                 Location/Qualifiers
source                  1..327
                        mol_type = genomic DNA
                        organism = Escherichia coli
SEQUENCE: 166
ttaggcattg atcttaactt caacaacggt ggtgtttgcc cctgcatctt cccaggcgat  60
gcccgcggca acggcgtccg tttcttcgat cgtgattttg ccgtccttca gatacacctg  120
cgccccggca gtaaccgcat ctgcggatac ttttggcagg aggaaaacac cctcagtaaa  180
accgtccccg gtatcgccag ccgggatatc ggtaattgcc accgcgataa gttttccaac  240
aacaaccggg tcgccgctgt gaacatcggt tgcaccactg tttaccagag ggatcgtttt  300
cccgtcctgc gcatagttct tagccat                                       327

SEQ ID NO: 167          moltype = DNA  length = 1947
FEATURE                 Location/Qualifiers
source                  1..1947
                        mol_type = genomic DNA
                        organism = Escherichia coli
SEQUENCE: 167
ttactgacca gaggatttgg tcatgccgcg atagtccagc ggcgccacgc cagcatcaat  60
acgcactttc gtggcgatac catcagtggt gaagccttcc tgctgatcga tgtatggcgt  120
```

-continued

```
gtcgacgccg ttgagataag cgacctcaat ggtgtcggtg cccttcgcgg cagccagata  180
ccaggctttc gcatcagctt catccagacg tggttcggca atgacttctg caaagttctg  240
gatagggtta acgatcccgg cattgatgtc tgcaccttta acactggccg acttgatggt  300
ctgatttgcc agagtttcca gggcgacggg caccagcatg taggccggac ggatattcag  360
ggttcgctcc ccctccttct gcagacgcat cagcttgcgc gattcgtcca ggctggccac  420
agaaattgca cccgagctca ggttcttgtg atcggcatgg aacagcgcct ttccgtctga  480
gagtttcggg tttttggtca gaatggcgta aaccagatcg ccaatcgttg ctttcgccgc  540
gcgccccatc ttcatcggta cgtcggtaag ctggttcaga tcgtcgttga tgatcgcctg  600
gcgagttact gagaagattt caccatacgt ggcaagcgcg atggtttcgc ctttgtcact  660
ggtagtgatg tacttgtact cagccccttc gcgaacctgt cgcagagaag ggaacccacc  720
cataccgaca cgatgcgccg ttttgaagtc cgacagctgg cctttttttgg tccactgctc  780
gaaggtttcc tgcgcctcgt cccagccctg aatcagcgct ttgttcgcaa catcaagcag  840
aatgttgcca aagtcagagg tgctgtgggt cagcgccagg ccaaccatct gcatcgggtt  900
gtagctggcc acgccgatac ctttttctgt cagggccata cgcgcatact cgcgcagcgt  960
cataccgtta taaacgttat cccgctcctg accttcgaac ccggcacgcg ccatcagtgc  1020
ctggcgaata ccatccgcga cgaagttacc gttgcccgca tgaatatgcg gctgagtggt  1080
tttattggac ggcgtggccg ttttaccgag ttctgccagc agcaaatctt tcgccttatc  1140
gacggagcaa tcagggtcgg ccacacactg attctgcagt tccatgtgct tattaccgaa  1200
catggcaaag agatcgccga tagcgttaac acgggttttc tgctcagcca acacctgcgc  1260
gcggatcgca ttttcatccg gtgccgggtc tgtttttgcc tgcggtgcct gaggctgggt  1320
aataaccggg tcacgctggg tagtgttgcg cggcggggtg atcatgttgc gaatgctttt  1380
tggcattttt tcaaattcct caatacgttt tgaatgaata caggccatag cctgaaggga  1440
tggtgtcacc tggtcggcaa aacccagttc aaggcactcg ctgccgttca tccaggtttc  1500
gtcctccagc attaccgcaa tttcttcggt ggattttccg gtttctgtg cataagccgg  1560
gataagaacg gattcaacct tgtcgagaag atccgcatag tcgcgcatat cgctcgcgtc  1620
accaccagca aacccccagg gcttatggat catcatcatc gtgttttcag gcatgatgac  1680
cggattgcct accatcgcaa tcaccgaggc catggaggcc gccagaccgt cgatatgtac  1740
ggtaatcgcc gcgccgtggt gcttcagcgc gttataaata gcaattccgt cgaagacatc  1800
accaccgggc gagttgatat aaaggttgat gtgggtgacg tccccaagtg cccggagatc  1860
attgacgaac tgtttcgccg ttacgcccca gtacccgatt tcgtcataaa taaaaatgtc  1920
ggcctcactg ttattgctgg cctgcat                                     1947
```

```
SEQ ID NO: 168          moltype = DNA  length = 1500
FEATURE                 Location/Qualifiers
source                  1..1500
                        mol_type = genomic DNA
                        organism = Escherichia coli
SEQUENCE: 168
ttactttttg cgctggcttt cggacggtgg cgcgcccggt tctttggctt cggcactggt  60
gcctccttta tcattggcgg ggtcggtgtc aaacaccagg ccctgttcac ggttctcgtc  120
aacctcagct ttacggcgtg acttaacatc atccgggttg cgaccgctgg cacgtatcca  180
gtcggattca gtagcagcac cgccgcggat ctgcgttttc caggcattcg cttctttaac  240
gggatcaatc cacggcataa cgggccccga ataaaccgcg ttataaagcg agtccatatc  300
aatgcctctc ggcagcttga tttctccggc agcaatagcc atcttgagcc aggctcggta  360
catgggccgg gtcactgaac cgatgaacca gtcctgaaga atcagatagc cgtcggttga  420
ctcgacaagc tcctgccgct gggcactgta cgttccgttg tagtttctgg atgtgctgga  480
aaagctgagg cgactgccgg cggacacggc acgcagctgt ccgttacgaa aagattcgag  540
gttagggttc gggcgatcgg atttaatcat cccgatttct tccccggcct gcagttcgtc  600
atagagcata ccgggctgaa tcatcagctc gcggtcatcg ctgcttgaat cagaatcgaa  660
gctctgtccg tcgccttttt tgatatacat gccgagtgcc gcagcaattc tggcagcagt  720
aagctccgag tcctcgtatt ctttcagcgc gctcagacgc atcagaacac cagacaaaag  780
agacgttccg cgggtctggt gcaggcgtcg ggtgaatttg agatgcagca tgttctctgc  840
atctatctct ttggtatcaa actgacgccc ggatactggc aggcttttat agacctgata  900
ttttttcggg cgtccccagt tatcgacaaa aacgccctga ttgagctggg tggcagcatc  960
gctgttcatc ggcacaaagt ccggctccag cgcttccagc cagaacggca cgccagcaac  1020
cggctgaaga ccatttccgg taccgcgaac cagctgagca aatacctcac cgtcccggag  1080
ccacgttcgc agcatcagcc gctccagcat tgggcgggta aactgggttg tgacatctgg  1140
ccttacggac cattcgcccc actttcggcg gatatcagtg gccagctttt tagcgatctt  1200
cccgttactc agcatcggat gcggttcaac tatgatgccc ttcgcaccca ccaccctttc  1260
ttccagcttg tcgaaaacgc cgatcaccag atcgtggttg ttatccagcc agcgcgcctg  1320
ctgcctcagc gaaaccgccc ccatctggct gagctgatcg gctgaacgat tttccttctg  1380
ggctttgtgg gtacgcgttt gctttaccgc ctcatacgct ttaataactg cgcgggcacg  1440
caggcgtgag gctttccagc ctggtgaaaa caggccaatc gcatcatcta aaaaactcat  1500
```

```
SEQ ID NO: 169          moltype = DNA  length = 216
FEATURE                 Location/Qualifiers
source                  1..216
                        mol_type = genomic DNA
                        organism = Escherichia coli
SEQUENCE: 169
tcatccaaac ctcgccagcc tgtagccggg tcgcccacgg cgtttgttat tgagcgttgc  60
cagtcgtcgc tcccattcct gacggccttt tctgatttcc gacaggtttt cgagcgtcat  120
ctgctgcccg ttgaaagtga ttgatttccc ctccagaaca gacagctcgg ctgcagcata  180
gcggtcgatc atgttttgaa tatctgctgg attcac                             216
```

```
SEQ ID NO: 170          moltype = DNA  length = 2103
FEATURE                 Location/Qualifiers
source                  1..2103
                        mol_type = genomic DNA
```

```
                         organism = Escherichia coli
SEQUENCE: 170
tcacacccaa cctcctgacg aagaccacgg attagcctgc tcggttacgg gcttctcacg  60
ttttggtttt ggtttagatt tcggcgcagg cggcggggat ggcatttcgc cagcttccgt  120
ctgcgtgtcc tcgatccacg tttcccgccg tgcccactca ggagctgacg gccatttgat  180
tttttcgtaa ccactaagga tggcgagcgc gtcggcataa acgagcaggt caaatgcttc  240
gtttgcgccc cggccgggct tactccattt cccttcattc gagcgttcct catacgtcag  300
ttcgtcatag aaccagctgc ccagccaggc ggggaaatgc acatagccag ggccgggtga  360
atcacgccac agcgcattat tcacccggtc tttaagggca tcggtctgga gaagataaag  420
aggcacatca ccagtcgcct gtgcgcggcg cgttgatctg cccgtgttgt cgggaaacgt  480
tcgctggata agtttgctgc gcctgacgct gtccccttg aagagataga tacgcttacc  540
cagcccctca cggcgacatc tgcgccagaa cttgtaggca ttatccgtca cgccatcttc  600
gccccctgag tccacggcca tcgacatcag ccgcatgccc tttgatgggt cagctgcgag  660
cggccacgtt ttatcaaaga cgtcagtgag taaaagatcc cagtcctccg gatagctcgc  720
cggatccacc tgaatgcttt caccgttgcc gtcgcagcgc agcgaatgcc ggatgttgta  780
acggtcaact atccagcgct cacccatact tccataaccc gtaatctgca caacaaagcg  840
ccggttgcgc ccggcctgca cgtccacggt cgcagtgaga aactgcacgc cgttcggtac  900
cgaacgtttt gggacgtctt cggcacgctg ctcgagcaat tcacttttac gctgctccat  960
gctggctcgc ggcaaatagg gcctgccgaa atcggtgttg atcaccgtct tcagggtttc  1020
ttcgctgcgc gtggattcat attcctgctc ggcggtcaga aacttataaa taagctgcgc  1080
ccaggtctgg taagcagctg ccggaccttc catccagaag gaggcaatac gggaacgacg  1140
gccatcaccg ctaaccaggc ctttcctgtc gatggtttgc ccgtcccgga gccagacaca  1200
tttcatgtta agcgcacgct tcatgtccgg tgtgatcctg cctttacagg cagggcactg  1260
aagaaacgcc gcttcgctgg caagcacagg atcgctgctg tcgcggtatc cggtcatatt  1320
gtccatttcc ggctggaaat attcgccgca atgcgggcat ggccagtaaa gacgacggcg  1380
gtcaccacgg ttatagagcg ataaaattcc ggtggtcgga ggggcttcat ggggcgtgga  1440
gcgccgccat tttgtgtctc tgatatccct cccgggcgag ctctcaacca gcgtcatccc  1500
ggaggacatg aatgtcgtgg ttcgtttcga tgccagtgaa aaagcatccc cctccccgtc  1560
gatatcttcc ggaaagcggt cataatccgt cagcgccaca cttttatagt ccgaggacga  1620
catgatattg acggatggcc agcccagctt cagatagtta ccggcgcgga atgtacggtc  1680
gtagacgttg ttatcgttac gtcttgggct tagccgggtt ttaacttcag ggctacagcg  1740
aaaagtacgg tccaggcgtt ttttggaatg ctcgcgcgct ttttcctcag atacctgaat  1800
tacaagcata tctgccggat cgcagacaat gttataaacg atccagccgt caatcagccc  1860
gatggtttta cccgttcgcg ctgggcccac aaacacaacc gcatcgtatt cacgcgatgc  1920
cagacagttc atcggctcaa tcacataggg tgccagatcc ggatcccacg gaactgagtt  1980
tcccgccccc attggcacgc gcatataagt actgaccgca tcggccaccg gcatacgacg  2040
cggggctcgt aaaataccgg aaacatcgcg gcggatgtcc ctggcggatg cccgctttgc  2100
cat                                                                2103

SEQ ID NO: 171          moltype = DNA  length = 489
FEATURE                 Location/Qualifiers
source                  1..489
                        mol_type = genomic DNA
                        organism = Escherichia coli
SEQUENCE: 171
tcagtcctcc tcaggctgct cctcctcttt tccagcgtcc tgcaccttct ccgccatctg  60
gtcgcgcaga tcatcgataa cgctttgcac acgaactacc gcagcaggcg ttaaagcaca  120
gtcgcgctcg agcacatccg ggagggtttc aagtaccatg acgacggctt tcgccatcaa  180
tgagaattct cgcgccactt catctgcggg tattaactgc cccgtatcct gttcgaactt  240
cagcctctcg ttctctgctt tccagtggga cagcctgtca gaagggggca tatcgtcgat  300
gttggccgaa acggtaggga tcatcagttc ggtcagaatg tcggtcacca gatagagctt  360
taacttgcta ttgctgcctg gagcaggttc aacatttttc agtctcgcgg caaccgtctg  420
acggtgtacg ccggttatcc ctgccagctg gttgatattg agttttaaag tggcaatttc  480
ctggtccat                                                          489

SEQ ID NO: 172          moltype = DNA  length = 729
FEATURE                 Location/Qualifiers
source                  1..729
                        mol_type = genomic DNA
                        organism = Escherichia coli
SEQUENCE: 172
ctatcgacgg cactgctgcc agataacacc accggggaaa cattccatca tgatggccgt  60
gcggacatag gaagccagtt catccatcgc tttcttgtct gctgccattt gctttgtgac  120
atccagcgcc gcacattcag cagcgttttt cagcgcgttt tcgatcaacg tttcaatgtt  180
ggtatcaaca ccaggtttaa ctttgaactt atcggcactg acggttacct tgttctgcgc  240
tggctcatca cgctggatac caaggctgat gttgtagata ttggtcaccg gctgaggtgt  300
ttcgattgcc gctgcgtgga tagcaccatt tgcgatagcg gcgtccttga tgaatgacac  360
tccattgcga ataagttcga aggagacggt gtcacgaatg cgctggtcca gctcgtcgat  420
tgccttttgt gcagcagagg tatcaatctc aacgccaagc gtcatcgaag cgcaatattg  480
ctgctcacca aaacgcgtat tgaccaggtg ttcaacggca aatttctgcc cttctgatgt  540
cagaaaggta aagtgatttt ctttctggta ttcagttgct gtgtgtctgg tttcagcaaa  600
accaagctcg cgcaattcgg ctgtgccaga tttagaaggc agatcaccag acagcaacgc  660
gccacggaaa aacagcgcat aaagcacttc attagcagcg ccagatagcg taatgatttt  720
gttactcat                                                          729

SEQ ID NO: 173          moltype = DNA  length = 231
FEATURE                 Location/Qualifiers
source                  1..231
                        mol_type = genomic DNA
```

```
                         organism = Escherichia coli
SEQUENCE: 173
ctatttgtgg gtaaagttcg tagtgcgctg atcgtgcaaa atgattttag ttgggaacag  60
ttcgcaactc tgtcccataa aaatcagcat attcccatct atcccatatc cagcgcattg  120
accatcggga tactgaaggg agattccatc atctcttaga aagatcacca tctcttttgt  180
ttcaatttgc atatagctac ctggaggatt tatgaatgca aggattttca t           231

SEQ ID NO: 174           moltype = DNA  length = 597
FEATURE                  Location/Qualifiers
source                   1..597
                         mol_type = genomic DNA
                         organism = Escherichia coli
SEQUENCE: 174
atggactatt accatgagat tgattttcca tctttattcg cgagagcagt ggaaagcgat  60
gacgatgtgg gtactacatt gcgcattcac ctactttgtg agcgcatggt cgaagcatgg  120
atatgcgcat gctgtgactg ccaagatctc tttggaagag ataaaaacaa acttttaatc  180
gaatgtaata ctaaaatatc catggcggga aacctgggaa tccccccgga acttatgaaa  240
tcacttaaaa ccatcaactc aatgcgtaat gaccttgcac acaatccatc aatacaaagc  300
attgctgatt caaggatcca gagcctgaag gatactctga ctgaatactt taaacagcat  360
ccaacggaac ccagcatgga agaatcaaaa ctgggtattt ttaacgccga gaatcaatta  420
accgaagaag tttccttaga tagtgacagt tcaaaaaaca gacttaagtt aatcttgctg  480
ttcagcaagt taatgcaggc gttaatgcaa ttagttgcag ctaatcataa tgggcgctgg  540
gataaccaat ttagccaatt cgtttaccat gtgaccatga acgcaacaaa gagataa     597

SEQ ID NO: 175           moltype = DNA  length = 198
FEATURE                  Location/Qualifiers
source                   1..198
                         mol_type = genomic DNA
                         organism = Escherichia coli
SEQUENCE: 175
ctagtcgtcg agttgcaaca caccgtgatc cagtgattct gaataggcga taagtccggt  60
ataaccgggg ataatctcac cattatcagc ttcaaattca ggaattgtgc cggtggtgat  120
ggtgtattga ggctggccat cttccttcgc gaaggctgcc aggtcttcaa tctgcttagc  180
tgtaagaact actgtcat                                                198

SEQ ID NO: 176           moltype = DNA  length = 480
FEATURE                  Location/Qualifiers
source                   1..480
                         mol_type = genomic DNA
                         organism = Escherichia coli
SEQUENCE: 176
ctattggtta ttcgacagtc gcactgattc gtaaatccgc tcacacgtca ttcctgcccg  60
gtagctttcg tcagatcgtc cagcataata tcgagctgct tctgcaaggc ttccgagcat  120
gtcggcaagc attgctgcgt tggctccggc tgttttgctt ctgacggaag tggcgagatc  180
tgcggtgtgc tttgcggcgt ccatgtgggt agcgagtttt gttgcttcgg cgcgcagctg  240
cttaacagtg gtagccaggc cagcagaagt aacggcagcg ctcgctgctt gagcttgagc  300
atctttaacg gcctcatccc gggcgattgt tcgcccttgt tcaatcatac gagctgcggt  360
ctgtgcattc gcttcctgtg aagattccgc gctatcccgg tcagcccact ttattttcca  420
gctgcggttc gtccactcac tgccagcgag aaacgaacct accaacgcaa caatcacaat  480

SEQ ID NO: 177           moltype = DNA  length = 549
FEATURE                  Location/Qualifiers
source                   1..549
                         mol_type = genomic DNA
                         organism = Escherichia coli
SEQUENCE: 177
tcactggtct atcccccagc acgtcagtgc gctttcctgg tcccgccgtt ctacctgccc  60
ataacatcca tccttctggc ccttggtcag gcggcaatcg cggccaccgt ctttaatcca  120
ccagcggata gcttcacagg ctcctttcgt atcgccagca ttaattcgct tatagaacgt  180
agacgggaaa cattttccgg ggccgatgtt atatgggcag aaagaagcga tacccgcttt  240
ctgtggttcg gtcagtggta ctttgatatt tcggtcaacc cacgccagcg ccttgtcgcg  300
ttcaatggcg tttacctggg cgcatttctc agctgacagc ttcatgccct gtactactgg  360
cttgccatca accattgttg caccacggca aatggtccag agtccgccgc cgtcgcgata  420
tgctgtcaag ctgttaccct ctttctcatc cagaaactga tcgagaatca cgggtgcgga  480
agccccggca agaatcaaac caacgaccgc tgcgctcaat ttattcttca gctttagaga  540
catagccat                                                          549

SEQ ID NO: 178           moltype = DNA  length = 279
FEATURE                  Location/Qualifiers
source                   1..279
                         mol_type = genomic DNA
                         organism = Escherichia coli
SEQUENCE: 178
ttattcttca gctttagaga catagccatt gcgccgatcc tcccgttctt tccagcggaa  60
ataccagttc actgcacagg tgattaccgt gcatgcgata ccgacaataa ttgcccagtc  120
gctcaggctt aaccctgcaa ttctgtcggc caacatccag gacacctctt ttgctgtttt  180
agctgtttcg gcatatgcct tcgctgatac accgcagccg gcaagcgtgg ttcctgatcc  240
atatgaaagt ctgctgtaaa tggtgctcat tctggtcat                         279
```

```
SEQ ID NO: 179          moltype = DNA  length = 1053
FEATURE                 Location/Qualifiers
source                  1..1053
                        mol_type = genomic DNA
                        organism = Escherichia coli
SEQUENCE: 179
ttatgatttt ttcagttttt ccacctcttc ggtggtctgt ataaacctgt ctgcctccag  60
ttctacgccg atcgcccgac ggccaagttc tattgcagct ttcacagttg aaccagagcc  120
cataaagaaa tcggcaacga tatcccccgg tctgctgctg gcgctaatga tctgtttcag  180
catgtcggca ggtttttcgc atggatgttt gcctggataa aactgaacag gcttatgtgt  240
ccatacgtcg gtataaggaa caagagcgga aacagagaag cagcgccgaa ggattttgta  300
ttcctccagc aattctgaat acttgcggtt taatgactgg taggtagcca ccagctggtg  360
gtgaggatgt tcaagctttt gctgaatatg tttatcgatg gcgatccgcg tgaacagttc  420
ctgcaatttt cgatagtcca cttcattcgg tagttgccat tggcttgcac caaaccagtg  480
tgacgccatg tttttctttc cggttgcctc agctatttct ttcgagctga cacccagtga  540
ttcacgggca ttacggaagt aatcaatcag cggcgtcata atgtgctgct ttagctctgt  600
gcttttcctt tcgtaaacat cctctttacc tgtatacggt ccaagatagt gctcagcaaa  660
caaaatccgt tccgtagatg gaaagtacgc acgcaggctt tctttattac atccattcca  720
gcggcccgat ggttttgccc aaatgatgtg attcaaaacg ttgaatcggg cgcgcatcat  780
aatctctata tctgaggcca gtcggtgacc gcaaaacagg tagatgctgc cagcaggttt  840
aagaacgcga gcatactcag ccaggcagct atcaagccag cgtaagtagt cctcgtcccc  900
cttccattgg ttgtcccagc cgttgggctt cactttgaag tacggaggat ccgtaactat  960
aagatcaata gagttatccg ggagggtggc gacgtaatgc agactatcag cgttgattaa  1020
ctcaacactg tttattttta cagtattttt cat                                1053

SEQ ID NO: 180          moltype = DNA  length = 192
FEATURE                 Location/Qualifiers
source                  1..192
                        mol_type = genomic DNA
                        organism = Escherichia coli
SEQUENCE: 180
ttactggagg cgtttataac atccgaactg gtaatcagat aaccccgcca tcaccagctg  60
cgtaagtatg agctggcaac gttcgtggct gaggtgggta ttctgtgcaa tctccccagc  120
cgttgctggt ttatcgctta attcattgaa aacagccttt gccgtttctg tcatatcttc  180
ctgatttagc at                                                       192

SEQ ID NO: 181          moltype = DNA  length = 900
FEATURE                 Location/Qualifiers
source                  1..900
                        mol_type = genomic DNA
                        organism = Escherichia coli
SEQUENCE: 181
ttagcaaata ttccacatca tcgtactacc gttatggttt tcgataattt ttgcggctgg  60
gctagtacca aaagagtgca tatagcaatg atgaatagta aggaccagat cctgcaacgt  120
ttggtcactc tctagctcca tgatatttaa accaatattt tgagctttgt ccaaatgaat  180
atgtctggca tgtgcatacg ttgcttggtg gttgtttaac tcatcacata tacgcttagc  240
cttagcttca gcgtcagcct gacctgcgaa cataccagta caaagccatt tctggacaat  300
ttcgttcgcc cagagaattg ctttttcaca ctcgccaatc aacgttggat ttagtttttg  360
gaacgtaaat tgccaccatt gcagtgcagc agggttggca aaaatttccg cttttgctct  420
ctcatactcc tcaataattg catgagatga taacccatta aactgtggat caattggccc  480
caagttcgac tgtttaccta aaacgatctg ctcagcacaa caagcaagca ttgtgccaca  540
actcattgaa atcataggta caatcgctcg gatattggtt ccgaactttg aacgaagata  600
atgaccaatt gattctagag ctgcgatatc gcctccagga gtatggagta agatatccaa  660
tcccagactc gtatctaacc cattgatagc agacataaga ccatttttat catcatctga  720
catctggatc agatgttgaa acccaggccc cccttttga aggaagcctg agtaataaga  780
aattacattt cggccagtat gtttcgataa atcacgtaag tacttgtggc gaacctcatc  840
cgctggtgta cgttgagcga tagtacccat ctcacccaat acgtctatcc aatttggcat  900

SEQ ID NO: 182          moltype = DNA  length = 207
FEATURE                 Location/Qualifiers
source                  1..207
                        mol_type = genomic DNA
                        organism = Escherichia coli
SEQUENCE: 182
tcagtatgag tacagttggt gagattgctg accgttctgc tcagtagtat ttggtgttac  60
tgtgctgtat gaatagagca caccacttct cacattcaga tcgttttgct gagcgagaac  120
acgcatagca aaatgctgta cggattcgcc tttttgaaac tcttggggtt gtatgcccat  180
tttttcgtaa aattcagcag cgctcat                                       207

SEQ ID NO: 183          moltype = DNA  length = 690
FEATURE                 Location/Qualifiers
source                  1..690
                        mol_type = genomic DNA
                        organism = Escherichia coli
SEQUENCE: 183
tcacatttct gccactttga gggcttcttc ttcctcatag tattcaagag ccatggccaa  60
cgcagattca tcaagctggg taaaagcggc ctttaaccca gcccagtgcc ctgaatagac  120
acgcaaccat gtcgaacggt caacgctaac catgcgggcc aacgctgcac cagcatagtc  180
tttataggtt tcattatttc tggttgcggc aatttcctgc cctgccagcc ataccaggcc  240
```

```
tatcagtttc tttactacgc gctcctgaag ggagttatca cccaggcatt tctgataagt  300
tttccagacg tattcacaca tcatcacctg gtgcttatag ctaaggtcaa aaccgtagca  360
gtaccgcaac caggcctgct ggtatccact aagcgcggac actgccctac gccacggcgc  420
ggactcaaat tccgcatctt ttatcggcgg cattggcctg cggcggctgc gtgtttccag  480
cacatacagt ggcgcggaaa gtgagttaac aaagcgtggc cccttctctc cttcgagttc  540
gacgagatga attccacggc gaggggtggc atttttgtct gctggtgggt gttcactgaa  600
agcctcaagc tgccctttg ttcccccaga caggtcaggt agcgcgcggc gcaattctat  660
tcttacaaaa ttcaggtctt gttgattcat                                  690

SEQ ID NO: 184         moltype = DNA  length = 996
FEATURE                Location/Qualifiers
source                 1..996
                       mol_type = genomic DNA
                       organism = Escherichia coli
SEQUENCE: 184
ttaagctttc gcaattacgc cgatcgccag cgcccgatcc ataaaacgca gtagcagctc  60
aagctgcgta ccatgcttct gctcgaatgc cggtacatcg gcgtgtaact cgtcgtggca  120
ctctctgcac agagggatca cgaagagatc atgggctttt gttgctgtcc cccccatacc  180
gtgccctacg atatggtgcg gatcatctgc tggccgtcgg caacactcac agggttgtgt  240
tttaacccag cgggtgtacg tctcatttat ccagcggcgt cgctttggcc tgagcatgaa  300
agattctgga gactccggat caacagagag cgtgaggatc ttcttcgcct tctcctgcac  360
gaggctggtt gcagaagcgg aaggcacaat gtcgctttcc ctcatgaccg agcggatctt  420
atcatccgga aggcgtagcc ccttgtgcgc aacgctttcc ggaataacat cagccaggtc  480
gtttctgacc atccaccagc acagttccgg aagcgtcagg atatgcgact cgggaaaacc  540
agaatcacgc cgaatgactt ccagaatcca ggataccagg tttcctgccg ctatacctgc  600
aagctgttcg gtatgctgcc ccgacaaagt gtgatcgcaa tgccagcaca ggcgaatact  660
tcctggtggg tgccgcattg ttgtgaagtt cttgtcgtgc cacgatgaat gtggccactg  720
gcattcaaac cgattactca accattgctc aagggaagga agcccaccag cacgctgaat  780
aacccgatca ttctcgaaga cctgccgcat taccggatca tcagccagcg gctgaatggc  840
ggcgggaaca gctcctgtac tgaatgacgc catttcttct ggttcaggct caagcagaac  900
gcgaccgcgc ataaagaggt gcatcagttc cgcgccggga cgaaacaaca caatccccat  960
acgatgggcg atctcggggg taagcagagc tctcac                           996

SEQ ID NO: 185         moltype = DNA  length = 684
FEATURE                Location/Qualifiers
source                 1..684
                       mol_type = genomic DNA
                       organism = Escherichia coli
SEQUENCE: 185
tcacgcgacc tgcccctgg caatgtgttc tgcccacagt ccaccaatcc agcgcacgcc  60
tttcgccgtg aaacgtgcct ggctgaatgc atgatttgag gttacggatg tgccggtttt  120
cacttcaaaa cggcccgcat caatatgctg atgccgtggg gtcatcgttc cgccaagacg  180
atacatgatg tcgttctcaa ggaggaataa ccgcagatcg ggctctttgg ccttaagcag  240
ttttgccacc tggcggaatg acattgaccc actggctgta cagtaccgat caacaaacgc  300
taccttcggc gccgcggcag ccagttcgtt agtcaactgc tgtttttgtt ctgcaaggtc  360
agctgcaaga cgtagggctt cagagaatga ttgaggaatc gtctgctgct gtgcctgctc  420
aagctcctgc cagcgatcaa ccagacgcgc ggtaaactcc ggcgacagct gcgcgacaac  480
gatataactg tcccgcttcc ctatcagata aaccgatacc gactgattga ggtgattttt  540
aacttcccc attgggggga gttcaataac accgcgctct gccaggcgtt caatggaccg  600
tttaacatgg tcatgtcttg attccaccag ctcagcaata tcgctgctgg acatggttaa  660
cgctgttgtt gctaactggc tcat                                        684

SEQ ID NO: 186         moltype = DNA  length = 387
FEATURE                Location/Qualifiers
source                 1..387
                       mol_type = genomic DNA
                       organism = Escherichia coli
SEQUENCE: 186
tcaggcggct gcacccgccg gttcatatct gctgattgtt atctctaccc gacctttcgg  60
cacaacgggt ccccattcca ccagcatgcg cttaatctgg ctgtcgtctt cccagacacc  120
cgcatgcgtc agcgcgtcaa acagggcttt gttgtaatta tcgatatccc ggcggcgcgc  180
atccggcggg tacagagtga tttctaccgc tgccagttca gtcgatggct tcgggagacg  240
tcgtaattgc tcaatgatcg ccacgcaggc agcgctctgg tatttacggc cagcggcgct  300
aatgaggtga cgaccggcca gcggcccctt gttaggggcg cgccagtaag tgttcacgct  360
cggaggaaaa ggcaggatca gtttcac                                     387

SEQ ID NO: 187         moltype = DNA  length = 1320
FEATURE                Location/Qualifiers
source                 1..1320
                       mol_type = genomic DNA
                       organism = Escherichia coli
SEQUENCE: 187
tcacgcggcc tctccccgca tattgcgaac aagttcagaa gcagcagtaa tgatttcgct  60
ggtggcagtc cgctccagcc agagttgatt gatattggct ttcagcttgt gttgcagtga  120
ctcatccagc atgtcagcac catccacctg gtcgaataca attctaacct ccagcggcca  180
gatacgggac tcgggaagcg gatccgatac tggtttagct ttctcacgaa tgtgcatgcg  240
gatctggcga atattggacc aactggaaac atccaggctt cccatggctg caatgaagtc  300
agtgctgttc atgccatatt caccggatgc ttcaagggca acagtgcgaa tacgttccga  360
catatccagg cgcacagcag cgtcatcgaa ttcaatcgac aacagccact catccacacc  420
```

```
gaacaaaata ctctcacgaa taagcagctt cgctttgtcg atcgttaaag gtgatacctg  480
agtgaattcc ggtgcttcga cagaatccgc cgcccaggta tgcccaaact tcgattcact  540
gaatgtgtat tcttctttat cgccaaacgc agctctaacg catgcccacg cctcgacacc  600
gctgatagca aaaatatctt tctgggtgag tggcaactct gcttctggct tatcagctgc  660
aggaggtgtg gcagttacag gttgagactt gctggcagca aattgtgcca aagccataaa  720
cgcccgccct tttgcctcca gttctgtgcg gttgatatag ctgaaccgct cgccacgcca  780
tgacttatcg aatacagcta tggcaccggc aaaaaacgcg ctggtgggtt tctgtttttc  840
gtcagcaggt acaaaccaca caggcagatc gaacccaatg cgcccgcgaa tgaatacaat  900
gtgatcggca tcttccggcc accacgtttc actcggcgcg gcttttatca ggaatacata  960
gcgaccgccc ttctcgcgct gggctgctgc gtagttcatg atgtgcgtca tgccggtgat  1020
cgcctgcttc tcgtggtact gcgaacggct atacggtggg ttgccatagc cagcgccacc  1080
cagttcagcc agacgttcag accagtcctg cgtcagcgcg ttatcttcgg cggtgtacca  1140
tgccgggcat ttcgcgttgt cgtcgtcagc aaacaaatcc agaactaatg gaccaaatag  1200
cgcgttgatc ccccaaaaaa gcagatccgg tgtccgccac tgatcgccaa cctctttcaa  1260
ttcgtgagct ggtttgctac gcagtgccgc cagcgcctgg caatatttat tggtcatcat  1320

SEQ ID NO: 188          moltype = DNA  length = 882
FEATURE                 Location/Qualifiers
source                  1..882
                        mol_type = genomic DNA
                        organism = Escherichia coli
SEQUENCE: 188
tcatgaacgg aaccccgaat tttctggcag tgagtaatca acactctgga agtttgcgcg  60
gctggctgag ttagtctccc atttgccgtt aacgcgttca ggccggccag cactggacca  120
tttggtcgcg ctttgcaggt aaccagggaa gtttttttgga atgaacagag ttgccgggcg  180
gaggtattgc gcctgctcgc tatcacgcca atcggcattt ttgtaatcca ctaccaagca  240
caggtcatca acagtgaatt gttcccgaag acgggcgcga atattctcca gcgacgtgct  300
gcatacctgg tagcgtgagc cagtagtctg attcaggtaa gacaaaacct gtctggcctg  360
atcagtaatc acaacctcag ggtcgggttg cgccgcaacc ggacaagagg gttttgaagt  420
tacttgtggt tcttgttttg attttactga cggatcccca ccagattctg acgggtcaaa  480
accgcctttt ttgctggatt tcgacgcctc aaattttgac gggtcggatt ttgatgcatc  540
agattttgat gggtcagatt ttgatgcgtc agattctgac aggtgagaaa aagcagcctc  600
tcgcaactta acgacgttaa gctgatatac gttcgatgcg ttacggttcc cattacggcg  660
ctgcttacgg gaaagccagc catccttctc aagctgagca agggccgtcc ttaccgtact  720
ttctccagca ccgatttgac gtgcgatcgt gccaatagac ggccagctaa caccctcatc  780
actactgaag tcggccagac gcgccatgat ggcaacgctg gataacttca tgcctgacga  840
agcgcatgca tcccatacgt aaccggttaa tttagtgctc at                    882

SEQ ID NO: 189          moltype = DNA  length = 339
FEATURE                 Location/Qualifiers
source                  1..339
                        mol_type = genomic DNA
                        organism = Escherichia coli
SEQUENCE: 189
ttaattctgt aaatttacgc tggaattgtt caagagggct gaagcactca tgatcgtacc  60
cttcgcgaag gtatataacg cgctgtgtat ctggctccca gcggacaact ctgacgggaa  120
ctccgtagtg atctctgaac cgccggttaa cttcagccat tcctcgcgcc ccttctcgtt  180
catctgaaca aatgcttcta ccatcaagtc tgctggctgg tagttgcctc catcagccgc  240
gttatttatg atttccacat agccgaactg ggcatcttta cccaccagcg gcaaacatct  300
gaattgctta gctggtctga atcggtttac actgttcat                        339

SEQ ID NO: 190          moltype = DNA  length = 564
FEATURE                 Location/Qualifiers
source                  1..564
                        mol_type = genomic DNA
                        organism = Escherichia coli
SEQUENCE: 190
tcatgcgtta gtttctccac tgatacgaca cgccaaggcg cccggagctg cacactcgcg  60
ggcgtcacct tttctgcctg ttgaaacgaa tacgtcaatc gcctgatctg aaacaccaac  120
cccataaagc gccataaatc ccaggaaccc gtgaatctgg tggcggagct tcttactgaa  180
taattctgaa agcattttgc gctctgatga atcaattacc ccatcagccg ctgctgccat  240
cttggcatta gccagctcac cagatgctgc tgccgctttc atctcaatgc tgtacagctc  300
aacgttatcc aggctctcag cagttggaac atccaccagc catttccctt ttcggttcgc  360
ctggtactcg gccaagtaac aagaaccaga caggtcctcc atccgttcca gttctgccaa  420
ggtaaagaac cgactgccac acttctggta caggtggttg tggaactggt cgatagtcat  480
ccctaaatcg gaagccatac ctaagcgacc atgcttgtgt gccttacaca tcaggcggat  540
tgctgtattt atgctgtcta ccat                                         564

SEQ ID NO: 191          moltype = DNA  length = 258
FEATURE                 Location/Qualifiers
source                  1..258
                        mol_type = genomic DNA
                        organism = Escherichia coli
SEQUENCE: 191
ttaaagttga ctattgttgt tagcggaagg tatgccgtca tttttgttcg gataaatatc  60
aggtcgtaat tgatggggag ttactaccca tccgccccat tggcagagtt gaataactct  120
ttcagaaggt actcggttct ttgcaatcca gttcgcaaca gattgaactg attggaattc  180
aaaccgcctt gatacctctg aaatcgaccc gatcgccttc acagctttag ctgttacatt  240
cttgtgttga gatgacat                                                258
```

```
SEQ ID NO: 192          moltype = DNA  length = 711
FEATURE                 Location/Qualifiers
source                  1..711
                        mol_type = genomic DNA
                        organism = Escherichia coli
SEQUENCE: 192
atgccttgtg cgcttaatct tctacttatg gtggaaaatg ctaaatacaa agactttgcc  60
gaaaggctaa acaggtctct ccaagagcaa tctattggag ttaaagaatt gtcagagttc  120
agtggtgtct cgtatgagat ggcgcggcgc tacactcttg gtactgcaaa gccgagagat  180
gagaagatga ttcgaattgc agaaagactt gccgtctcac cggcttatct tgattatggt  240
gtgcctgtta atggtggcga cgcgccagcc aaaggcacgg tcagaataga gcaattggat  300
gttcatgctt cagccggttc cggatatata aaccaaccat tccctacaat agtgagctca  360
atagagattc cagaagagag gatcttcgag ttgtttggtc gtagaagcct tgatggcatc  420
gtcatgataa atgttgatgg cgatagcatg atgcccacgc tttgcccaaa ggacctgctt  480
ttcatagaca gcaaggttga acaattcagc ggcgacggcg tttatgtgtt caattttgaa  540
gacagtacgt tcgttaaacg tttgcagaag gtaaaagggc gccgactggc agttctttca  600
gacaatgaac attacccgcc cttcttcata gaggagcatg aaatgaatga actatacata  660
ttcggcaagc taatcagatg cttacctcta aaaatgatag agtttggcta a           711

SEQ ID NO: 193          moltype = DNA  length = 198
FEATURE                 Location/Qualifiers
source                  1..198
                        mol_type = genomic DNA
                        organism = Escherichia coli
SEQUENCE: 193
ctatttaaag agcttcttca gcttgtcctc aaccttcctg atttcggaag taagctggct  60
gctgttgaca ttgatagtag ctccacatcg acaagtgaaa cttttgttcg acttgagcca  120
agcgattttc ttcttcgtct tagtgccgca cttagggcat gcgggtaacg taatttcctg  180
gttatcaaaa gcgcccat                                                198

SEQ ID NO: 194          moltype = DNA  length = 918
FEATURE                 Location/Qualifiers
source                  1..918
                        mol_type = genomic DNA
                        organism = Escherichia coli
SEQUENCE: 194
atgaataatc cgtttttcaa aaatatgttg gtgtatcgca ttagtcgcga tttcaccatc  60
aaccaggaag agctggaaca gcagcttgaa ctatttcgct tcactccatg cggtagccag  120
gatatggcaa aaaccggttg ggtatcacca cttggtcagc tgtcagatcg cttgcatcac  180
actgtcaata atcaagtgtt gttggttatt cgccgggaag aaaaaatact gccatctcct  240
gtcattactg aagaactgcg caagcgtgtg tcgcgtctag aatccgatca ggggcgtcgc  300
ctcaaaaaaa ctgagaaaga ttcgctgcgt gatgaagtgt tgcactccct gcttcctcgg  360
gcgttctcca aaaactcgac tgttggtttg tggatcaacg tcaccgacgg tctgatcatg  420
gttgatgcag ccagcgctaa acgtgccgaa gactcactgg ccctgcttcg taaaactctc  480
ggttctctcc cggtggtacc gctgactatg gaaacgccga tcgaactaac tatgaccgac  540
tgggttcgtt ccggtagtgc gcctgctggc tttggcctgg gtgatgaagc cgaactgaaa  600
gctattcttg aagatggcgg tattggacgc tttaaaaaac agactctggt cagtgacgaa  660
attcatgtgc atctggaagc tggcaaagta gttacaaagc tgtctatcga ctggcaacag  720
cgcattcagt tcgttctttg cgatgacggc agcatcaaac gccttaagtt ctctaatgag  780
attacagaac aaaacgacga tatcgaccgt gaggatgcgg ctcagcggtt cgacgctgac  840
tttgttctga tgaccggcga gcttatctct ctcattaacg gattaacaac ctctctcggc  900
ggcgaagcca agcgataa                                                918

SEQ ID NO: 195          moltype = DNA  length = 540
FEATURE                 Location/Qualifiers
source                  1..540
                        mol_type = genomic DNA
                        organism = Escherichia coli
SEQUENCE: 195
atgagctaca ttcagacatt atccggcaaa cattttaatt acctcgatat ccaacaggac  60
gatatcgtga tcgaggatat tgctaccgcg ttgtctcata tctgccgctt tgcagggcat  120
cttcctgagt tttacagtgt cggccagcat agcgttttaa ccagccacct cgttccgcag  180
gagtttgcat tagaagcact gcttcatgat gctgctgaag cctacctgca ggacatcccc  240
tccccactta agcgcctgct tccggattac caggcaatcg aagctcgtgt ggacgcagcc  300
attcggcaga agttcggtct accaactgag caacacccaa ccgtgaaata tgccgacctg  360
gtgatgctcg ccagcgaacg ccgcgatttt gagattgacg aaggttccat ttggccatgc  420
ctcgagggag ttgtcccaac ggatttattc attatcaacc cagttcgtcc tggccagtca  480
tacggcatgt tcatcaatcg ctttaacgag ttgatggagc agcgccaatg cgccgcatga  540

SEQ ID NO: 196          moltype = DNA  length = 255
FEATURE                 Location/Qualifiers
source                  1..255
                        mol_type = genomic DNA
                        organism = Escherichia coli
SEQUENCE: 196
atgaccgtat ttgaatatct ccaggctcat ccgaatacca ccagcggtga aatcgccaaa  60
ggtatgaaca aaaagacccc agcggtcgcc ggagcattat ctcagctcta tggcaccggt  120
cggatcgtga agtctggtgt tcgcaagggt attccaacat accgcattaa cgatatgccg  180
```

-continued

```
tttggttgca gtaacagcct aaccatgatg tttaaccagc tcttgagcag agccagacaa  240
ggagcagccc aatga                                                    255

SEQ ID NO: 197          moltype = DNA  length = 348
FEATURE                 Location/Qualifiers
source                  1..348
                        mol_type = genomic DNA
                        organism = Escherichia coli
SEQUENCE: 197
atgacagcac tcaacaaaca ggcgctgcgt gaagaattcc agttcatgca ggacaactat  60
agcgacccgg cagaccacga tcggcaggtg atttacatcg aggcggaggc gctgctggat  120
gagttggaag ccaaagactc aacgatagca gcacaacaac atgagatccg tatgttgctg  180
aatgcgcttg aggaaaaacc atgcccgaaa tgcaacgaca caggaatgac tgatagtggc  240
ggcacgcagc catggggcga gccgattgag attgaatgcg actgccgaca gcaggatgcc  300
aacaccgcag aacttgtagc cgctggcatt ggcgtgaagg gggagtga                348

SEQ ID NO: 198          moltype = DNA  length = 309
FEATURE                 Location/Qualifiers
source                  1..309
                        mol_type = genomic DNA
                        organism = Escherichia coli
SEQUENCE: 198
atggataaat taatcaaacc taccgccaaa ggtaaatatg acggttcatg tgattatctt  60
tgctcggaag atgcgcgatt catcgttatg cgcggcgatt atacggaagc ggaaataatt  120
caggcttctg tgtctcaaga tgtaatcgac tcggatggtg cggctgattt tgcaagtagc  180
gcccgctatt atcagtgctg gtacaaagtt agcccaatag gtggtcagga tggctattca  240
ggctggcatc atcctcgtga ttcgccgtgt cgcggtgcat atttcgcatc agttttgcaa  300
tgggattaa                                                           309

SEQ ID NO: 199          moltype = DNA  length = 468
FEATURE                 Location/Qualifiers
source                  1..468
                        mol_type = genomic DNA
                        organism = Escherichia coli
SEQUENCE: 199
atgacaacta acaaccaccc ggcgcacggt cctgtatcac tcgatcgcct gcaccagata  60
cgcgaacacc tgctgcatga tacccaatac tcaaacggcg ggaacagagc ctacattctc  120
gctgatgtat tgaaggtgat tgatggggct attgcccgcg agctggtacg ccgtgagcat  180
gcagcgtggt cacaggctac tttcggcgat gtcggtccag ttggtccgct gaagcacctt  240
tccaaagaag cgctcgaggc tgctgctgaa ccaggcgacc ttagcgaatg ggctgacatg  300
caattcctgt tatgggatgc gcaacgtcgt gccggtatca gtgatgagca gattacccag  360
gcaatgataa aaaagctggc tataaataag gttcgccaat ggcctgagcc gaaagacggg  420
gaacctcgat tgcatatcaa agaacagtca gagcaggaga aaaaataa                468

SEQ ID NO: 200          moltype = DNA  length = 255
FEATURE                 Location/Qualifiers
source                  1..255
                        mol_type = genomic DNA
                        organism = Escherichia coli
SEQUENCE: 200
atgtttagcc tgattcggcg cggtcaaatc tacacggaca gtagcaactg gcccgtaatt  60
atccatagct gtagtgatca ctcggtccga attaaacgca atgatggcga gctgagaacg  120
attagcatca aacgctttaa cgaagatttt gaacgagtgg agcatgatga gtatcgcaaa  180
atatgtgccg aaatagagca ggaaacaaac ctgaaaaacc tacgtgcgat gcgtcgcggc  240
aagattactg aatag                                                    255

SEQ ID NO: 201          moltype = DNA  length = 570
FEATURE                 Location/Qualifiers
source                  1..570
                        mol_type = genomic DNA
                        organism = Escherichia coli
SEQUENCE: 201
gtgaacaact taatgatcga ccttgagtcc atgggcaaaa aaccgaatgc ccctattgtc  60
tccattggtg ccgtattctt cgatccgcaa agcggtgaac tgggtcagga gttttacacc  120
gctgttaatc ttgaaagcgc tatggagcag ggagcggtgc cggatggtga cactattctg  180
tggtggttaa gacaaagctc agaagcacga tcagcaatct gtgttgatga tgcgatgccg  240
atatcatctg ccctatctga actgagccat ttcattaatc ggcattctga taaccctaaa  300
tatttaaaag tttggggcaa tggagctact ttcgacaacg ttatattgcg cggcgcatat  360
gagcgtgccg gccaggtttg cccgtggcaa ttttggaatg atcacgacgt cagaaccatc  420
gtcacattag gcagatctgt aggtttcgat cctaagcgtg atatgccatt tgatggggtt  480
gcacataacg cactggctga tgcccgccac caggcgaaat atgtttcagc gatttggcag  540
aaactaatcc caaccaccag caacagctaa                                    570

SEQ ID NO: 202          moltype = DNA  length = 237
FEATURE                 Location/Qualifiers
source                  1..237
                        mol_type = genomic DNA
                        organism = Escherichia coli
SEQUENCE: 202
```

-continued

```
atgagcaata ttttccagtt agctcccaac gattgggttt gtgaaagcgt tttgatcgcg  60
gttactgggc tcaaacccgg aaccatcctc cgtgccagaa aagaatgctg gatgattggg  120
agggagtata tccacgtatc gcctgacgga aatcctaaac cttccagtga gtgcatgtat  180
aacagaaagg ctgtagatgc ctgggtcgct tcaatgaaaa gcaagcaacc agggtga     237

SEQ ID NO: 203          moltype = DNA  length = 1314
FEATURE                 Location/Qualifiers
source                  1..1314
                        mol_type = genomic DNA
                        organism = Escherichia coli
SEQUENCE: 203
atggataaag tcacatatcc aacaggcgtc gaaaaccacg gtggcacatt acgcatctgg  60
tttaatttta aaggtaagcg tgtcagggaa agtctcggtg tccctgacac cgctaagaac  120
aggaagatag ccggggaact gcggacatca gtatgttttg ccatccgcac aggaaccttt  180
gattatgcaa cccagtttcc tgactcccct aacctcaagg cttttggtgt aagtaaaaaa  240
gacattacag tgaaagaact tgaagaaaaa tggctggatc tgaaacggat ggaaatctgc  300
gcgaacgcat ttaatcgcta tgaatctgtc gcaaggaata tggtgccgag gatcggaggt  360
aatcgcctgg tgtcagcagt aaccaaagag gaattgctgt atctgaggaa atatttgcta  420
actggttatc agaatccgac gaaaaacaaa gccccggcaa aagggcgaag cgttgttact  480
gtgaactatt acatgacgac aatggccgga atgtttcagt ttgctgcgga tcacggttac  540
ttagaggtga acccattcga gggaattaag cctctgaaaa aagccagggc agaaccagat  600
cctctgtctc gtgatgaatt tattcgcctg atagatgcat gccggcatca gcagacgaaa  660
aacctgtggt cattagcagt gtacacagga atgcgtcacg ggaactggt ctccctggcc  720
tgggaagata tcgacctgaa ggctggaaca attaccgtca gacgtaatta tacgaaactt  780
ggtgagttca ctctaccgaa aaccgaggca agcacagatc gagtggtgca tcttatccag  840
cccgcaatca gtatcctgaa aaatcaggct gaaatgacaa ggctgggcag gcaatatcac  900
attgaagtgc agttacgtga gtacggccgt tcggtgaacc atgagtgtac attcgtcttt  960
aatccgcatg tggtcagacg cagtaagcag gtcggattta tctaccgggt cgattcagta  1020
ggcgactcat gggaagcggc acttaagcgt gcggggatca gacacagaaa ggcgtaccag  1080
tcacgacaca cctatgcgtg ctggtcatta tcagctggtg caaaccctag ttttattgcc  1140
agtcagatgg ggcatgcgag cgcgcagatg gtgttcaatg tttacggtgc atggatggct  1200
gacagcagcg cagagcagat cgcaatgctg aatcagaagc tggcagattt tgccccattg  1260
atgccccata gccacgagaa cagtacggga ggattattaa aatcagtaag ttaa        1314

SEQ ID NO: 204          moltype = DNA  length = 726
FEATURE                 Location/Qualifiers
source                  1..726
                        mol_type = genomic DNA
                        organism = Escherichia coli
SEQUENCE: 204
gtggagggta acaccacgct ttatgccctg ccgaaacccg aggttgtcct gcgctggcgt  60
gagcagacca cagatgactt ccgcttctgt tttaagtttc cggcgaccat ttcgcatcag  120
gcagcattac ggcattgcga tgatttagtg actgaatttt tgacccgcat gtcaccgttg  180
gctccgcgca ttggacaata ctggctgcaa ctgcctgcca cattcggccc acgggagctg  240
cctgcgcttt ggcattttct cgattctctt cccggtgaat ttaattatgg ggtggaagtc  300
cgccatccac agtttttcgc caaaggggaa gaggaacaaa cgcttaatcg cggtttacat  360
cagcgcggcg ttaatcgggt gattttagac agccgcccgg ttcatgcagc acgtccatac  420
agtgaagcta ttcgcgacgc tcaacgaaaa aaacctaaag ttccggtaca tgctgtactg  480
acggcgaaaa atccactgat ccgttttatc ggtagtgatg atatgacgca aaaccgggaa  540
ttatttcagg tctggttaca aaaattagcg cagtggcatc agaccactac gccttatctt  600
tttttacata cgccagatat tgcccaggcc ccggaactgg tacataccct gtgggaagac  660
ttacgtaaaa cgcttccaga gatcggagca gttccggcta ttccacagca atcttctctt  720
ttctga                                                             726

SEQ ID NO: 205          moltype = DNA  length = 396
FEATURE                 Location/Qualifiers
source                  1..396
                        mol_type = genomic DNA
                        organism = Escherichia coli
SEQUENCE: 205
atggtaagcg cgctgtatgc cgttttaagt gcgttgttat taatgaagtt ctcttttgat  60
gtcgttcgcc tgcgaatgca gtaccgcgtt gcctatggcg acggcggttt tagcgaactg  120
caaagcgcta ttcgcattca tggtaacgcg gtggaatata ttcctatcgc gattgtgttg  180
atgctgttta tggaaatgaa tggcgcagaa acctggatgg tgcatatttg cggcatcgtt  240
ttgcttgctg gtcgtctgat gcattattac ggttttcatc accgtctgtt ccgctggcga  300
cgttctggca tgagcgccac ctggtgtgcg ctgttgctga tggtgctggc gaatctttgg  360
tatatgccct gggagttggt tttctccctg cgttag                            396

SEQ ID NO: 206          moltype = DNA  length = 744
FEATURE                 Location/Qualifiers
source                  1..744
                        mol_type = genomic DNA
                        organism = Escherichia coli
SEQUENCE: 206
atgtctcacc gcgacacgct atttctgcc cctatcgcca gactgggcga ctggaccttt  60
gatgaacggg tagctgaagt cttcccggat atgatccagc gttccgttcc cggctattcc  120
aatattattt ccatgattgg tatgttagcc gagcgcttcg ttcaacctgg tacgcaggtt  180
tacgatctgg gttgttctct gggcgcggcg acgctctcgg tgcgtcgcaa cattcatcat  240
gataattgca aaattattgc catcgacaac tccccggcga tgattgaacg ctgccgtcgt  300
```

-continued

```
catattgacg cctataaagc ccctacgcca gtagacgtta ttgaaggtga tattcgcgat  360
atcgccattg aaaacgcatc gatggtggtg ctgaatttta ccctgcaatt cctggaacct  420
tccgagcgcc aggcgttact ggataaaatt tatcaagggc tgaacccggg cggtgcgctg  480
gtgctttcgg aaaaattcag tttcgaagat gccaaagttg gtgaactgct gttcaacatg  540
caccacgact ttaaacgtgc caacggttac agcgaactgg agatcagcca gaaacgcagc  600
atgctggaaa acgtgatgct gaccgattcc gtggaaaccc ataaagcacg cctgcataaa  660
gccggttttg agcatagcga gctgtggttc cagtgcttta actttggttc actggtggca  720
ttaaaagcag aggacgctgc atga                                          744

SEQ ID NO: 207         moltype = DNA  length = 972
FEATURE                Location/Qualifiers
source                 1..972
                       mol_type = genomic DNA
                       organism = Escherichia coli
SEQUENCE: 207
atgatcgact ttggtaactt ttattctctg attgccaaaa atcatctttc acactggctc  60
gaaacgctgc ccgcgcagat tgctaactgg cagcgcgagc agcagcacgg gctgtttaag  120
cagtggtcca acgcggtgga atttctgcct gaaattaaac cgtatcgtct ggatttattg  180
catagcgtaa ccgccgaaag cgaagagcca ctgagcgccg ggcaaattaa gcgcattgaa  240
acgctgatgc gcaacctgat gccgtggcgc aaagggccgt tctcactgta tggcgtcaac  300
atcgataccg aatggcgttc cgactggaaa tgggatcgcg ttatgcccca tctttctgat  360
ttaaccgggc gcaccattct tgatgtcggc tgtggcagcg gttatcacat gtggcgcatg  420
attggcgcag gggcgcatct ggcggtgggt atcgatccca cgcagctatt cctctgccag  480
tttgaagcag tgcgtaaact gctgggtaac gatcagcgcg cacatttgtt accgttaggt  540
attgaacaac ttccggcact gaaagccttt gataccgtct tttcgatggg cgtgctttat  600
catcgtcgtt caccgctgga gcatctctgg cagttaaaag accaactggt gaatgaaggc  660
gaactggtgc tggaaacgct ggttattgat ggcgacgaaa acacggtgct ggtgccgggc  720
gatcgttacg ctcaaatgcg taatgtctat ttcattcctt ccgcgctggc gctgaaaaac  780
tggctgaaga agtgtggttt tgttgatatt cgcattgcag atgtgagcgt taccaccaca  840
gaagagcagc gacgcaccga atggatggtc accgagtctc tggccgattt tctcgacccg  900
catgatccgg gtaaaacggt ggaaggttat cctgcgccta aacgcgcggt gctgattgcg  960
cgcaagccgt aa                                                       972

SEQ ID NO: 208         moltype = AA  length = 323
FEATURE                Location/Qualifiers
source                 1..323
                       mol_type = protein
                       organism = Escherichia coli
SEQUENCE: 208
METKKNNSEY IPEFDKSFRH PRYWGAWLGV AAMAGIALTP PKFRDPILAR LGRFAGRLGK  60
SSRRRALINL SLCFPERSEA EREAIVDEMF ATAPQAMVMM AELAIRGPEK IQPRVDWQGL  120
EIIEEIRRNN EKVIFLVPHG WAVDIPAMLM ASQGQKMAAM FHNQGNPVFD YVWNTVRRRF  180
GGRLHARNDG IKPFIQSVRQ GYWGYYLPDQ DHGPEHSEFV DFFATYKATL PAIGRLMKVC  240
RARVVPLFPI YDGKTHRLTI QVRPPMDDLL EADDHTIARR MNEEVEIFVG PRPEQYTWIL  300
KLLKTRKPGE IQPYKRKDLY PIK                                           323

SEQ ID NO: 209         moltype = AA  length = 440
FEATURE                Location/Qualifiers
source                 1..440
                       mol_type = protein
                       organism = Escherichia coli
SEQUENCE: 209
MQQIARSVAL AFNNLPRPHR VMLGSLTVLT LAVAVWRPYV YHRDATPIVK TIELEQNEIR  60
SLLPEASEPI DQAAQEDEAI PQDELDDKIA GEAGVHEYVV STGDTLSSIL NQYGIDMGDI  120
TQLAAADKEL RNLKIGQQLS WTLTADGELQ RLTWEVSRRE TRTYDRTAAN GFKMTSEMQQ  180
GEWVNNLLKG TVGGSFVASA RNAGLTSAEV SAVIKAMQWQ MDFRKLKKGD EFAVLMSREM  240
LDGKREQSQL LGVRLRSEGK DYYAIRAEDG KFYDRNGTGL AKGFLRFPTA KQFRISSNFN  300
PRRTNPVTGR VAPHRGVDFA MPQGTPVLSV GDGEVVVAKR SGAAGYYVAI RHGRSYTTRY  360
MHLRKILVKP GQKVKRGDRI ALSGNTGRST GPHLHYEVWI NQQAVNPLTA KLPRTEGLTG  420
SDRREFLAQA KEIVPQLRFD                                               440

SEQ ID NO: 210         moltype = AA  length = 310
FEATURE                Location/Qualifiers
source                 1..310
                       mol_type = protein
                       organism = Escherichia coli
SEQUENCE: 210
MLHKKTLLFA ALSAALWGGA TQAADAAVVA SLKPVGFIAS AIADGVTETE VLLPDGASEH  60
DYSLRPSDVK RLQNADLVVW VGPEMEAFMQ KPVSKLPEAK QVTIAQLENV KPLLMKSIHG  120
DDDDHDHAEK SDEDHHHGDF NMHLWLSPEI ARATAVAIHG KLVELMPQSR AKLDANLKDF  180
EAQLASTEKQ VGNELAPLKG KGYFVFHDAY GYFEKQFGLT PLGHFTVNPE IQPGAQRLHE  240
IRTQLVEQKA TCVFAEPQFR PAVVESVARG TSVRMGTLDP LGTNIKLGKT SYSEFLNQLA  300
NQYASCLKGD                                                          310

SEQ ID NO: 211         moltype = AA  length = 251
FEATURE                Location/Qualifiers
source                 1..251
                       mol_type = protein
                       organism = Escherichia coli
```

```
SEQUENCE: 211
MTSLVSLENV SVSFGQRRVL SDVSLELKPG KILTLLGPNG AGKSTLVRVV LGLVTPDEGV  60
IKRNGKLRIG YVPQKLYLDT TLPLTVNRFL RLRPGTHKED ILPALKRVQA GHLINAPMQK  120
LSGGETQRVL LARALLNRPQ LLVLDEPTQG VDVNGQVALY DLIDQLRREL DCGVLMVSHD  180
LHLVMAKTDE VLCLNHHICC SGTPEVVSLH PEFISMFGPR GAEQLGIYRH HHNHRHDLQG  240
RIVLRRGNDR S                                                       251

SEQ ID NO: 212         moltype = AA  length = 261
FEATURE                Location/Qualifiers
source                 1..261
                       mol_type = protein
                       organism = Escherichia coli
SEQUENCE: 212
MIELLFPGWL AGIMLACAAG PLGSFVVWRR MSYFGDTLAH ASLLGVAFGL LLDVNPFYAV  60
IAVTLLLAGG LVWLEKRPQL AIDTLLGIMA HSALSLGLVV VSLMSNIRVD LMAYLFGDLL  120
AVTPEDLISI AIGVVIVVAI LFWQWRNLLS MTISPDLAFV DGVKLQRVKL LLMLVTALTI  180
GVAMKFVGAL IITSLLIIPA ATARRFARTP EQMAGVAVLV GMVAVTGGLT FSAFYDTPAG  240
PSVVLCAALL FIISMMKKQA S                                            261

SEQ ID NO: 213         moltype = AA  length = 336
FEATURE                Location/Qualifiers
source                 1..336
                       mol_type = protein
                       organism = Escherichia coli
SEQUENCE: 213
MIEADRLISA GTTLPEDVAD RAIRPKLLEE YVGQPQVRSQ MEIFIKAAKL RGDALDHLLI  60
FGPPGLGKTT LANIVANEMG VNLRTTSGPV LEKAGDLAAM LTNLEPHDVL FIDEIHRLSP  120
VVEEVLYPAM EDYQLDIMIG EGPAARSIKI DLPPFTLIGA TTRAGSLTSP LRDRFGIVQR  180
LEFYQVPDLQ YIVSRSARFM GLEMSDDGAL EVARRARGTP RIANRLLRRV RDFAEVKHDG  240
TISADIAAQA LDMLNVDAEG FDYMDRKLLL AVIDKFFGGP VGLDNLAAAI GEERETIEDV  300
LEPYLIQQGF LQRTPRGRMA TVRAWNHFGI TPPEMP                            336

SEQ ID NO: 214         moltype = AA  length = 203
FEATURE                Location/Qualifiers
source                 1..203
                       mol_type = protein
                       organism = Escherichia coli
SEQUENCE: 214
MIGRLRGIII EKQPPLVLIE VGGVGYEVHM PMTCFYELPE AGQEAIVFTH FVVREDAQLL  60
YGFNNKQERT LFKELIKTNG VGPKLALAIL SGMSAQQFVN AVEREEVGAL VKLPGIGKKT  120
AERLIVEMKD RFKGLHGDLF TPAADLVLTS PASPATDDAE QEAVAALVAL GYKPQEASRM  180
VSKIARPDAS SETLIREALR AAL                                          203

SEQ ID NO: 215         moltype = AA  length = 200
FEATURE                Location/Qualifiers
source                 1..200
                       mol_type = protein
                       organism = Escherichia coli
SEQUENCE: 215
MNINYPAEYE IGDIVFTCIS AALFGQISAA SNCWSNHVGI IIGHNGEDFL VAESRVPLST  60
ITTLSRFIKR SANQRYAIKR LDAGLTEQQN QRIVEQVPSR LRKIYHTGFK YESSRQFCSK  120
FVFDIYKEAL CIPVGEIETF GELLNSNPNA KLTFWKFWFL GSIPWERKTV TPASLWHHPG  180
LVLIHAVGVE TPQPELTEAV                                              200

SEQ ID NO: 216         moltype = AA  length = 173
FEATURE                Location/Qualifiers
source                 1..173
                       mol_type = protein
                       organism = Escherichia coli
SEQUENCE: 216
MAIILGIDPG SRVTGYGVIR QVGRQLSYLG SGCIRTKVDD LPSRLKLIYA GVTEIITQFQ  60
PDYFAIEQVF MAKNADSALK LGQARGVAIV AAVNQELPVF EYAARQVKQT VVGIGSAEKS  120
QVQHMVRTLL KLPANPQADA ADALAIAITH CHVSQNAMQM SESRLNLARG RLR         173

SEQ ID NO: 217         moltype = AA  length = 246
FEATURE                Location/Qualifiers
source                 1..246
                       mol_type = protein
                       organism = Escherichia coli
SEQUENCE: 217
MAGHSKWANT RHRKAAQDAK RGKIFTKIIR ELVTAAKLGG GDPDANPRLR AAIDKALSNN  60
MTRDTLNRAI ARGVGGDDDA NMETIIYEGY GPGGTAIMIE CLSDNRNRTV AEVRHAFSKC  120
GGNLGTDGSV AYLFSKKGVI SFEKGDEDTI MEAALEAGAE DVVTYDDGAI DVYTAWEEMG  180
KVRDALEAAG LKADSAEVSM IPSTKADMDA ETAPKLMRLI DMLEDCDDVQ EVYHNGEISD  240
EVAATL                                                             246

SEQ ID NO: 218         moltype = AA  length = 147
FEATURE                Location/Qualifiers
source                 1..147
```

```
                         mol_type = protein
                         organism = Escherichia coli
SEQUENCE: 218
MAYKRPVSIL VVIYAQDTKR VLMLQRRDDP DFWQSVTGSV EEGETAPQAA MREVKEEVTI  60
DVVAEQLTLI DCQRTVEFEI FSHLRHRYAP GVTRNTESWF CLALPHERQI VFTEHLAYKW  120
LDASAAAALT KSWSNRQAIE QFVINAA                                     147

SEQ ID NO: 219           moltype = AA  length = 590
FEATURE                  Location/Qualifiers
source                   1..590
                         mol_type = protein
                         organism = Escherichia coli
SEQUENCE: 219
MRTEYCGQLR LSHVGQQVTL CGWVNRRRDL GSLIFIDMRD REGIVQVFFD PDRADALKLA  60
SELRNEFCIQ VTGTVRARDE KNINRDMATG EIEVLASSLT IINRADVLPL DSNHVNTEEA  120
RLKYRYLDLR RPEMAQRLKT RAKITSLVRR FMDDHGFLDI ETPMLTKATP EGARDYLVPS  180
RVHKGKFYAL PQSPQLFKQL LMMSGFDRYY QIVKCFRDED LRADRQPEFT QIDVETSFMT  240
APQVREVMEA LVRHLWLEVK GVDLGDFPVM TFAEAERRYG SDKPDLRNPM ELTDVADLLK  300
SVEFAVFAGP ANDPKGRVAA LRVPGGASLT RKQIDEYGNF VKIYGAKGLA YIKVNERAKG  360
LEGINSPVAK FLNAEIIEAI LERTGAQDGD MIFFGADNKK IVADAMGALR LKVGKDLGLT  420
DESKWAPLWV IDFPMFEDDG EGGLTAMHHP FTSPKDMTAA ELKAAPENAV ANAYDMVING  480
YEVGGGSVRI HNGDMQQTVF GILGINEEEQ REKFGFLLDA LKYGTPPHAG LAFGLDRLTM  540
LLTGTDNIRD VIAFPKTTAA ACLMTEAPSF ANPTALAELS IQVVKKAENN             590

SEQ ID NO: 220           moltype = AA  length = 188
FEATURE                  Location/Qualifiers
source                   1..188
                         mol_type = protein
                         organism = Escherichia coli
SEQUENCE: 220
MLELNAKTTA LVVIDLQEGI LPFAGGPHTA DEVVNRAGKL AAKFRASGQP VFLVRVGWSA  60
DYAEALKQPV DAPSPAKVLP ENWWQHPAAL GATDSDIEII KRQWGAFYGT DLELQLRRRG  120
IDTIVLCGIS TNIGVESTAR NAWELGFNLV IAEDACSAAS AEQHNNSINH IYPRIARVRS  180
VEEILNAL                                                          188

SEQ ID NO: 221           moltype = AA  length = 129
FEATURE                  Location/Qualifiers
source                   1..129
                         mol_type = protein
                         organism = Escherichia coli
SEQUENCE: 221
MGFPSPAADY VETRISLDQQ LISQPAATYF MRASRSHFRE GIIQGALLVV DASLTACDGS  60
LLICAIDGEF RIKRYRTHPQ PHLVNLDNGR REALPADDDG YSSAPAIFGV ITYIINDARN  120
AEFDDCPVM                                                         129

SEQ ID NO: 222           moltype = AA  length = 80
FEATURE                  Location/Qualifiers
source                   1..80
                         mol_type = protein
                         organism = Escherichia coli
SEQUENCE: 222
MFVELVYDKR NFDGLPGAKD IILGELTKRV HRIFPDADVR VKPMMTLPAI NTDASKHEKE  60
QISRTVQEMF EEAEFWLVSE                                             80

SEQ ID NO: 223           moltype = AA  length = 126
FEATURE                  Location/Qualifiers
source                   1..126
                         mol_type = protein
                         organism = Escherichia coli
SEQUENCE: 223
MLWRIFIFVN VGLGEAAKRN VGTGENQIPD MSAFPSGNNW FQLPSGHIVQ IFSMNVLGAD  60
ANGTSANYPI AFPTTMIAVS ALWSDGTVAN APTYKMMGNT TNRTTLTIKV SASSGTYGTM  120
IIAVGR                                                            126

SEQ ID NO: 224           moltype = AA  length = 147
FEATURE                  Location/Qualifiers
source                   1..147
                         mol_type = protein
                         organism = Escherichia coli
SEQUENCE: 224
MNKYSYSPSE NAFYAVALKN TYELSGTWPA DALDIPDDIS VKYMAEPPQG KIRVAGENGF  60
PTWAEIPPPS HEELIEQAES ERQLLINQAN EYMNSKQWPG KAAIGRLKGE ELAQYNSWLD  120
YLDALELVDT SGTPDIEWPT PPAVQAR                                     147

SEQ ID NO: 225           moltype = AA  length = 197
FEATURE                  Location/Qualifiers
source                   1..197
                         mol_type = protein
                         organism = Escherichia coli
```

SEQUENCE: 225
MKPVFDENGL AAVPGDMRCF YYDAVTSEYT GWSDEYINTG VSMPACSTGI DPDENIPGRV 60
AVFTGKGWSH EEDHRNETVY SIENGAAVTV DYIGAIKNGY VTLSPLTPYD KWDGEKWVTD 120
TEAQHGASVE AAEAQRQSLI DAAMASISLI QLKLQAGRKL TQAETTRLNA VLDYIDAVTA 180
TDTSTAPDVI WPELPEA 197

SEQ ID NO: 226 moltype = AA length = 310
FEATURE Location/Qualifiers
source 1..310
mol_type = protein
organism = Escherichia coli
SEQUENCE: 226
MIYSTGTISI NGNTATGSGT NWTAPASQVR AGQTIIVMSN PVQLFQISSV NSATSMTVTP 60
AVSPALSGQK YGILVSDNIS VDGLAQAMSQ LIKEYDENIG AWETFATTSA NQSITVTING 120
TAVTIPGIGK LAQKGSNGAV TVADGGTGAT NAADARTNLG LGEGSPAIGV PFFWPSAAMP 180
NTVIDSWSSM VFLKFNGAKF SATDYPVLAK VFPSLVLPEA RGDFIRVWDD GRGADGGREL 240
LSWQEATNFS QFAGNIGGGA GHAINFHDGI AGNQPGFSRF NFNSNSVGDG VNFVAVRPRN 300
IAFNFLVRAK 310

SEQ ID NO: 227 moltype = AA length = 1308
FEATURE Location/Qualifiers
source 1..1308
mol_type = protein
organism = Escherichia coli
SEQUENCE: 227
MGEKMQLLKQ ETILQGAKGG GGSSHTPVEQ PDDLLSVAKL KMLIAVSEGE IQGDLTAQNI 60
FLNDTPLAND SGEYNFSGVK WEFRKGTQDQ TYIAGMPQVD NELAVGTTVT TTAPWTRQFT 120
NLSLDAIRIK LSLPVQYLYK DNGDMVGTVT EYAIDLSTDG GAWKTVVNGK FDGKTTTEYQ 180
RDHRIDLPKS TSGWSVRVRR ITADASGSNS KLVNAFKVFS YAEVIDSKLR YPLTALLYVE 240
VDSSQFNGSA PKVTCKIKGK LIKVPDNYDP KTRTYSGSWS GGFKMAWSNN PAWIFYDLVL 300
DEIYGMGTRV DASMVDKWAL YSIAQYCDEM VSDGAGGTEP RFTCNVFIQS QEDAWQVLND 360
LAAVFRGITF WGNDQIYVQA DVPQDDVDWV YNVSNVIDGL FTYAGGSYKN RYSSCLVSWS 420
DPQNHYSDTV EGVYDSALVE RYDVRQTSLT AIGCTSQSEA HRRGRWVLLS NAKDGTVSFG 480
VGLDGYIPLP AEIIGVADPF RSGKENGGRI SAANGRQITL DREIDYAAKD RLVVNLPDGK 540
AQTRTISAVS ADKKTVTVAT AFSQVPVAGA VWAIDSDNLA IQYFRVTSIA ANDDSTGGFT 600
ITAVQHDPNK YRYIDDGVRV ESPPITVTPI SVLSAPKNIV VTESDHVSQG LTVASLDVSW 660
DKVEGAIRYV AQWRKDNGDW INVPVTSAQG FSVQGIYSGS YDVRVRALNA QDTSSPWGYG 720
ETTYLSGKTG KPGTPLNFLA TEDVVWHIDL TWKFPDGSGD TAYTEIQRAT TADYANPELL 780
VLVPYPAADY QHGPMPAGVR QWYRARLIDR IGNAGDWTDW IMGTSSIDVS EITNDILEDM 840
KESETFKDLI ENAVDSNEKI AGMANDIKQA NDELEQQAKD IAKNAQDVGK VQTSVNELSS 900
TVGNVSSSLS QLEQTVATAD TALGQRIDNI SVSMDGMTGG VKNSAIAIIQ ANLAQVATRK 960
TLSASVAGNS ANLDRLDEVI VSEKEATARS LLSLQTDVNG NKASINSLNQ TLSDYQQATA 1020
TQINGITATV NGHTSAITTN AQAIANVNGE LSAMYNIKVG VSSNGQYYAA GMGIGVENTP 1080
SGMQSQVIFL ADRFAVTTAA GNSVALPFVI QNGQTFIRAS FIQDGTIENA KIGNYIQSNN 1140
YAAGSAGWKL NKAGDAEFNN VTVRGVVYAS GGSFTGEIQA TSGKFKGTVE AQSFIGDIAN 1200
MHTGTNVSRS SDGYLEKVMT YNDSSSSGHA RHVCVIANVK GNGAGTIDIN GNESGSSVQD 1260
MERLIMHSAV VTGPNVTVRI KVSAQNNRGA SISSPTIIVS HGSGSFTG 1308

SEQ ID NO: 228 moltype = AA length = 205
FEATURE Location/Qualifiers
source 1..205
mol_type = protein
organism = Escherichia coli
SEQUENCE: 228
MVKTLILEGK MAKKFGKRVQ FDVADLREML RAMCSQVPGF KKYMSEAHMK GIRFAFFNGG 60
NNIGLEEFDM TRGGSVYRIV PVYEGAKSSG VLQIVVGAVA LVAAFFTAGA SMAAWGAAMS 120
ATAISATSIL TGVGVSMMLG GVVQMLTPQP SFGAGKSSST DNTPNYAFGA PVNTVAMGHP 180
VPLAYGLTEA GGAIVSAGMY SSDQQ 205

SEQ ID NO: 229 moltype = AA length = 239
FEATURE Location/Qualifiers
source 1..239
mol_type = protein
organism = Escherichia coli
SEQUENCE: 229
MREKLLDAIR QHVAAEYPKE ACGLIVQSGQ QQIFIPCRNI ADKPEETFTL SPEDQLAARA 60
RGEIIMLIHS HPDVVRLVPS ELDRIQCDWS GIEWGIMSWP DGDFCTISPR EDRDYAGRQW 120
VLGYADCWSL IREFYLREYG IVLGNYSVPY EWWESGKERL YDDNWEREGF VEIAAGAMQP 180
GDIIMMSVQA SVTNHAAVYV GDNIILHHLF GHLSSRTPYG KYYRDRTVRV VRHKDRMHG 239

SEQ ID NO: 230 moltype = AA length = 245
FEATURE Location/Qualifiers
source 1..245
mol_type = protein
organism = Escherichia coli
SEQUENCE: 230
MSFTADIQQL EPGSVIQLIE IDGTEFGMDQ VLRFHAHNIQ EEGWAAFAAE NLPAIIWQGN 60
QYDPHPYELK GMELSSTGSQ PTPTLSVGNV GNYVTALCLE YDDMVRAKVK IHTTLSKYLD 120
AANWKNGNPG ASPADERLQL FYVNAKTAET RVQVDFELCS PFDIQSLQLP TRQITPVCTW 180

```
CMRGWYRSGT GCDYNGTKYF TKDGTPTDDP SKDVCGGRRQ DCQDRHGPDA PLPFGGFPAA  240
NLQGK                                                              245

SEQ ID NO: 231          moltype = AA  length = 112
FEATURE                 Location/Qualifiers
source                  1..112
                        mol_type = protein
                        organism = Escherichia coli
SEQUENCE: 231
MTDTFTWRTR KTAQGTETAR TLQAQFGDGY KQIAGMGIND KQETWNLDWT GTRQEAAALR  60
AFLMSHVTKS FWWTTPWGEK KLFRMKADSF SVSFPTGKKA TVAFTFEQAF AP          112

SEQ ID NO: 232          moltype = AA  length = 1045
FEATURE                 Location/Qualifiers
source                  1..1045
                        mol_type = protein
                        organism = Escherichia coli
SEQUENCE: 232
MAQQISDLVI NLDVDSATFS EQVARIKGQL TGMAEDSEKV QTRMQRASER QAAAFKTVGD  60
AGAAAAADMK SRQSAATEGL TKDWQNVSKS VDETHRRVTE LNQRMRENDG QAAALARRQD  120
ELAASFFRQI DGVRQLNGET QSLANVQARF RAARAQGNIT QQDYLALISR TTARQKELQI  180
VEEKSAAART RFLSQLKQQV AEQKLSGTEL LRMKAAQVGA SDAAEVYIRK LEAAKVATHG  240
LGLQSAAARQ ELGILIGEVM RGNFGALRGS GITLANRAGW IDQLLSLRGL GIASMVGGIA  300
AAVFGLGKAW YDGSKESEEF NRQLILTGNY AGKTSGQLQA LARSLAGNGI TQHAAAGVLA  360
QVVGSGAFSG NDVSMVSNVA ARLQQATGQA VDETINQFKR LKDDPVNAVA TLNDSLHFLT  420
ATQYEQIASA QALGDSQKAA ELAMRAYSDA VIQRAGAVED NLGSLEKAWN WVKNAASGAW  480
DAMLGVGRNP DTAMKRQDSF AEWQAAEKEY RALSSNLKVD PDYAGNNVLQ KADAERLRNA  540
RQQVELKKQA YDLADQQYAQ EGLAAAREKM RTDQQAQAIR SQQQFNQLVE SGATAAEKRA  600
SAEKKLSQLI EKNRQDAKDG VATLWTEKDI AAARAGIEKQ WKDPKTPKGK SYSTPAGDKA  660
EEKAQAELLT LQAQLKTLEQ HTSVNDVISK QRQDLWQTEN QFTVLQEAAG RRQLTAQEKS  720
LLAHKEETLE YKRQLADLGD KVASQQKLNQ LADQAVKFEQ QQKAARAGLQ AQSEGLSTRE  780
AGRQTTLQRL SESYSYNPQA QQKVLEEQRA TFEAEDALRA NWLAGAKQGW AEYQDSATNV  840
FSSVQQISQA TFSGLAGQLT SLTTTGKASF REFTSSILKM IVSVINQLLV AYTIQSAMGW  900
VSGGAKTSSA GQSFAVPSYR PQGFDVGGFT GHGGKYEPAG IVHRGEFVFT KESTSRIGVA  960
NLYRLMRGYA SGGLVGGGNA AGAGMGGISV YAPVSISQQG SDGSINQANA TGTAKQLQAI  1020
VQQTITERLK KEMSAGGVLY SRRTQ                                        1045

SEQ ID NO: 233          moltype = AA  length = 90
FEATURE                 Location/Qualifiers
source                  1..90
                        mol_type = protein
                        organism = Escherichia coli
SEQUENCE: 233
MLAGMTSTEL GDWHQFYREH YFQDAQLDAH FSELLYSIST LFFRDPELTP AHFSLLSPSG  60
IVISDDEPDD DALMAAAEGI TGGIRYGPAD                                   90

SEQ ID NO: 234          moltype = AA  length = 143
FEATURE                 Location/Qualifiers
source                  1..143
                        mol_type = protein
                        organism = Escherichia coli
SEQUENCE: 234
MFLKKEKFTW QKESLTIFEL SALQRIEYIT FMAAEEKAVS ADSDGISDQE MTARLIGSNI  60
RCGARLIAMS LWHNDPAGTD VETLYQQVLS GWPPEAIGKA EMEIKLLSGM LVPVEDDKAA  120
DPDAPAEAES AEPVAAEKPL PAS                                          143

SEQ ID NO: 235          moltype = AA  length = 247
FEATURE                 Location/Qualifiers
source                  1..247
                        mol_type = protein
                        organism = Escherichia coli
SEQUENCE: 235
MPTPNPLAPV KGAGTTLWLY TGTGNAFANP LSDIDWNRLA KIKELTPGEM TAESYDDTYL  60
DDEDADWNAT AQGAKSAGDT SFTLAWKPGE EGQKDLVAWF IDGSVRYYKI KYPNGTVDVF  120
RGWCSSLGKA IPAKEVITRT AKITNTGKPE LAEESGTPNI PVTGVTLDKA TASVAVGATT  180
TLNVTVNPAS ASDTSFRVAT SDGAKATVTV SGNAITVTGV AAGTADVIVM TSDGNFVAVC  240
KVTVTAA                                                            247

SEQ ID NO: 236          moltype = AA  length = 133
FEATURE                 Location/Qualifiers
source                  1..133
                        mol_type = protein
                        organism = Escherichia coli
SEQUENCE: 236
MNRHSAIRAA ILAKLKAEIT DTVTWFDGRP VFLEEQDLPA VAVYLSDAEY TGDSLDEDSW  60
QAVVHIEVFL KASSPDSALD SWMEEKVYPA MAFIPGLTEL VETFTPQGYD YQRDDEMATW  120
GSVDFTYLIT YSI                                                     133

SEQ ID NO: 237          moltype = AA  length = 190
```

```
FEATURE                Location/Qualifiers
source                 1..190
                       mol_type = protein
                       organism = Escherichia coli
SEQUENCE: 237
MKGLERAIQN LNSLSRLIVP EATAKALNRV ARRTISQGSK AVAKEATVDD NRKKGLPVRL  60
VRQRSRLRKA RHDRPVASIK INRGNLPAIK LGTARVRLSR KKGARNGAGS VLKIGPYTFR  120
NAFIQQLANG RWQVMRRVGQ ARYPIDVVKV PLETPLTVAF TAISKRLIES DMPKELSAAL  180
KNQLRIHLKR                                                         190

SEQ ID NO: 238         moltype = AA  length = 80
FEATURE                Location/Qualifiers
source                 1..80
                       mol_type = protein
                       organism = Escherichia coli
SEQUENCE: 238
MDAATIKKMG KTAIINGSSY DVVPAEQLEE MGPLSGTGTS LVVFSELYQP RRNDSVDYDG  60
KNLIVTRYDM FNGKPRIHLE                                              80

SEQ ID NO: 239         moltype = AA  length = 108
FEATURE                Location/Qualifiers
source                 1..108
                       mol_type = protein
                       organism = Escherichia coli
SEQUENCE: 239
MAKNYAQDGK TIPLVNSGAT DVHSGDPVVV GKLIAVAITD IPAGDTGDGF TEGVFLLPKV  60
SADAVTAGAQ VYLKDGKITI EETDAVAAGI AWEDAGANTT VVEVKINA                108

SEQ ID NO: 240         moltype = AA  length = 648
FEATURE                Location/Qualifiers
source                 1..648
                       mol_type = protein
                       organism = Escherichia coli
SEQUENCE: 240
MQASNNSEAD IFIYDEIGYW GVTAKQFVND LRALGDVTHI NLYINSPGGD VFDGIAIYNA  60
LKHHGAAITV HIDGLAASMA SVIAMVGNPV IMPENTMMMI HKPWGFAGGD ASDMRDYADL  120
LDKVESVLIP AYAQKTGKST EEIAVMLEDE TWMNGSECLE LGFADQVTPS LQAMACIHSK  180
RIEEFEKMPK SIRNMITPPR NTTQRDPVIT QPQAPQAKTD PAPDENAIRA QVLAEQKTRV  240
NAIGDLFAMF GNKHMELQNQ CVADPDCSVD KAKDLLLAEL GKTATPSNKT TQPHIHAGNG  300
NFVADGIRQA LMARAGFEGQ ERDNVYNGMT LREYARMALT EKGIGVASYN PMQMVGLALT  360
HSTSDFGNIL LDVANKALIQ GWDEAQETFE QWTKKGQLSD FKTAHRVGMG GFPSLRQVRE  420
GAEYKYITTS DKGETIALAT YGEIFSVTRQ AIINDDLNQL TDVPMKMGRA AKATIGDLVY  480
AILTKNPKLS DGKALFHADH KNLSSGAISV ASLDESRKLM RLQKEGERTL NIRPAYMLVP  540
VALETLANQT IKSASVKGAD INAGIVNPIQ NFAEVIAEPR LDEADAKAWY LAAAKGTDTI  600
EVAYLNGVDT PYIDQQEGFT TDGIATKVRI DAGVAPLDYR GMTKSSGQ                648

SEQ ID NO: 241         moltype = AA  length = 499
FEATURE                Location/Qualifiers
source                 1..499
                       mol_type = protein
                       organism = Escherichia coli
SEQUENCE: 241
MSFLDDAIGL FSPGWKASRL RARAVIKAYE AVKQTRTHKA QKENRSADQL SQMGAVSLRQ  60
QARWLDNNHD LVIGVFDKLE ERVVGAKGII VEPHPMLSNG KIAKKLATDI RRKWGEWSVR  120
PDVTTQFTRP MLERLMLRTW LRDGEVFAQL VRGTGNGLQP VAGVPFWLEA LEPDFVPMNS  180
DAATQLNQGV FVDNWGRPKK YQVYKSLPVS GRQFDTKEID AENMLHLKFT RRLHQTRGTS  240
LLSGVLMRLS ALKEYEDSEL TAARIAAALG MYIKKGDGQS FDSDSSSDDR ELMIQPGMLY  300
DELQAGEEIG MIKSDRPNPN LESFRNGQLR AVSAGSRLSF SSTSRNYNGT YSAQRQELVE  360
STDGYLILQD WFIGSVTRPM YRAWLKMAIA AGEIKLPRGI DMDSLYNAVY SGPVMPWIDP  420
VKEANAWKTQ IRGGAATESD WIRASGRNPD DVKSRRKAEV DENREQGLVF DTDPANDKGG  480
TSAEAKEPGA PPSESQRKK                                               499

SEQ ID NO: 242         moltype = AA  length = 71
FEATURE                Location/Qualifiers
source                 1..71
                       mol_type = protein
                       organism = Escherichia coli
SEQUENCE: 242
MNPADIQNMI DRYAAAELSV LEGKSITFNG QQMTLENLSE IRKGRQEWER RLATLNNKRR  60
GRPGYRLARF G                                                       71

SEQ ID NO: 243         moltype = AA  length = 700
FEATURE                Location/Qualifiers
source                 1..700
                       mol_type = protein
                       organism = Escherichia coli
SEQUENCE: 243
MAKRASARDI RRDVSGILRA PRRMPVADAV STYMRVPMGA GNSVPWDPDL APYVIEPMNC  60
LASREYDAVV FVGPARTGKT IGLIDGWIVY NIVCDPADML VIQVSEEKAR EHSKKRLDRT  120
```

```
FRCSPEVKTR LSPRRNDNNV YDRTFRAGNY LKLGWPSVNI MSSSDYKSVA LTDYDRFPED  180
IDGEGDAFSL ASKRTTTFMS SGMTLVESSP GRDIRDTKWR RSTPHEAPPT TGILSLYNRG  240
DRRRLYWPCP HCGEYFQPEM DNMTGYRDSS DPVLASEAAF LQCPACKGRI TPDMKRALNM  300
KCVWLRDGQT IDRKGLVSGD GRRSRIASFW MEGPAAAYQT WAQLIYKFLT AEQEYESTRS  360
EETLKTVINT DFGRPYLPRA SMEQRKSELL EQRAEDVPKR SVPNGVQFLT ATVDVQAGRN  420
RRFVVQITGY GSMGERWIVD RYNIRHSLRC DGNGESIQVD PASYPEDWDL LLTDVFDKTW  480
PLAADPSKGM RLMSMAVDSG GEDGVTDNAY KFWRRCRREG LGKRIYLFKG DSVRRSKLIQ  540
RTFPDNTGRS TRRAQATGDV PLYLLQTDAL KDRVNNALWR DSPGPGYVHF PAWLGSWFYD  600
ELTYEERSNE GKWSKPGRGA NEAFDLLVYA DALAILSGYE KIKWPSAPEW ARRETWIEDT  660
QTEAGEMPSP PPAPKSKPKP KREKPVTEQA NPWSSSGGWV                         700

SEQ ID NO: 244          moltype = AA  length = 162
FEATURE                 Location/Qualifiers
source                  1..162
                        mol_type = protein
                        organism = Escherichia coli
SEQUENCE: 244
MDQEIATLKL NINQLAGITG VHRQTVAARL KNVEPAPGSN SKLKLYLVTD ILTELMIPTV  60
SANIDDMPPS DRLSHWKAEN ERLKFEQDTG QLIPADEVAR EFSLMAKAVV MVLETLPDVL  120
ERDCALTPAA VVRVQSVIDD LRDQMAEKVQ DAGKEEEQPE ED                    162

SEQ ID NO: 245          moltype = AA  length = 242
FEATURE                 Location/Qualifiers
source                  1..242
                        mol_type = protein
                        organism = Escherichia coli
SEQUENCE: 245
MSNKIITLSG AANEVLYALF FRGALLSGDL PSKSGTAELR ELGFAETRHT ATEYQKENHF  60
TFLTSEGQKF AVEHLVNTRF GEQQYCASMT LGVEIDTSAA QKAIDELDQR IRDTVSFELI  120
RNGVSFIKDA AIANGAIHAA AIETPQPVTN IYNISLGIQR DEPAQNKVTV SADKFKVKPG  180
VDTNIETLIE NALKNAAECA ALDVTKQMAA DKKAMDELAS YVRTAIMMEC FPGGVIWQQC  240
RR                                                                242

SEQ ID NO: 246          moltype = AA  length = 76
FEATURE                 Location/Qualifiers
source                  1..76
                        mol_type = protein
                        organism = Escherichia coli
SEQUENCE: 246
MKILAFINPP GSYMQIETKE MVIFLRDDGI SLQYPDGQCA GYGIDGNMLI FMGQSCELFP  60
TKIILHDQRT TNFTHK                                                 76

SEQ ID NO: 247          moltype = AA  length = 198
FEATURE                 Location/Qualifiers
source                  1..198
                        mol_type = protein
                        organism = Escherichia coli
SEQUENCE: 247
MDYYHEIDFP SLFARAVESD DDVGTTLRIH LLCERMVEAW ICACCDCQDL FGRDKNKLLI  60
ECNTKISMAG NLGIPPELMK SLKTINSMRN DLAHNPSIQS IADSRIQSLK DTLTEYFKQH  120
PTEPSMEESK LGIFNAENQL TEEVSLDSDS SKNRLKLILL FSKLMQALMQ LVAANHNGRW  180
DNQFSQFVYH VTMNATKR                                               198

SEQ ID NO: 248          moltype = AA  length = 65
FEATURE                 Location/Qualifiers
source                  1..65
                        mol_type = protein
                        organism = Escherichia coli
SEQUENCE: 248
MTVVLTAKQI EDLAAFAKED GQPQYTITTG TIPEFEADNG EIIPGYTGLI AYSESLDHGV  60
LQLDD                                                             65

SEQ ID NO: 249          moltype = AA  length = 159
FEATURE                 Location/Qualifiers
source                  1..159
                        mol_type = protein
                        organism = Escherichia coli
SEQUENCE: 249
MVIVALVGSF LAGSEWTNRS WKIKWADRDS AESSQEANAQ TAARMIEQGR TIARDEAVKD  60
AQAQAASAAV TSAGLATTVK QLRAEATKLA THMDAAKHTA DLATSVRSKT AGANAAMLAD  120
MLGSLAEAAR YYAGRSDESY RAGMTCERIY ESVRLSNNQ                        159

SEQ ID NO: 250          moltype = AA  length = 182
FEATURE                 Location/Qualifiers
source                  1..182
                        mol_type = protein
                        organism = Escherichia coli
SEQUENCE: 250
MAMSLKLKNK LSAAVVGLIL AGASAPVILD QFLDEKEGNS LTAYRDGGGL WTICRGATMV  60
```

-continued

```
DGKPVVQGMK LSAEKCAQVN AIERDKALAW VDRNIKVPLT EPQKAGIASF CPYNIGPGKC  120
FPSTFYKRIN AGDTKGACEA IRWWIKDGGR DCRLTKGQKD GCYGQVERRD QESALTCWGI  180
DQ                                                                182

SEQ ID NO: 251         moltype = AA  length = 92
FEATURE                Location/Qualifiers
source                 1..92
                       mol_type = protein
                       organism = Escherichia coli
SEQUENCE: 251
MTRMSTIYSR LSYGSGTTLA GCGVSAKAYA ETAKTAKEVS WMLADRIAGL SLSDWAIIVG  60
IACTVITCAV NWYFRWKERE DRRNGYVSKA EE                               92

SEQ ID NO: 252         moltype = AA  length = 350
FEATURE                Location/Qualifiers
source                 1..350
                       mol_type = protein
                       organism = Escherichia coli
SEQUENCE: 252
MKNTVKINSV ELINADSLHY VATLPDNSID LIVTDPPYFK VKPNGWDNQW KGDEDYLRWL  60
DSCLAEYARV LKPAGSIYLF CGHRLASDIE IMMRARFNVL NHIIWAKPSG RWNGCNKESL  120
RAYFPSTERI LFAEHYLGPY TGKEDVYERK STELKQHIMT PLIDYFRNAR ESLGVSSKEI  180
AEATGKKNMA SHWFGASQWQ LPNEVDYRKL QELFTRIAID KHIQQKLEHP HHQLVATYQS  240
LNRKYSELLE EYKILRRCFS VSALVPYTDV WTHKPVQFYP GKHPCEKPAD MLKQIISASS  300
RPGDIVADFF MGSGSTVKAA IELGRRAIGV ELEADRFIQT TEEVEKLKKS            350

SEQ ID NO: 253         moltype = AA  length = 63
FEATURE                Location/Qualifiers
source                 1..63
                       mol_type = protein
                       organism = Escherichia coli
SEQUENCE: 253
MLNQEDMTET AKAVFNELSD KPATAGEIAQ NTHLSHERCQ LILTQLVMAG LSDYQFGCYK  60
RLQ                                                               63

SEQ ID NO: 254         moltype = AA  length = 299
FEATURE                Location/Qualifiers
source                 1..299
                       mol_type = protein
                       organism = Escherichia coli
SEQUENCE: 254
MPNWIDVLGE MGTIAQRTPA DEVRHKYLRD LSKHTGRNVI SYYSGFLQKG GPGFQHLIQM  60
SDDDKNGLMS AINGLDTSLG LDILLHTPGG DIAALESIGH YLRSKFGTNI RAIVPMISMS  120
CGTMLACCAE QIVLGKQSNL GPIDPQFNGL SSHAIIEEYE RAKAEIFANP AALQWWQFTF  180
QKLNPTLIGE CEKAILWANE IVQKWLCTGM FAGQADAEAK AKRICDELNN HQATYAHARH  240
IHLDKAQNIG LNIMELESDQ TLQDLVLTIH HCYMHSFGTS PAAKIIENHN GSTMMWNIC   299

SEQ ID NO: 255         moltype = AA  length = 68
FEATURE                Location/Qualifiers
source                 1..68
                       mol_type = protein
                       organism = Escherichia coli
SEQUENCE: 255
MSAAEFYEKM GIQPQEFQKG ESVQHFAMRV LAQQNDLNVR SGVLYSYSTV TPNTTEQNGQ  60
QSHQLYSY                                                          68

SEQ ID NO: 256         moltype = AA  length = 229
FEATURE                Location/Qualifiers
source                 1..229
                       mol_type = protein
                       organism = Escherichia coli
SEQUENCE: 256
MNQQDLNFVR IELRRALPDL SGGTKGQLEA FSEHPPADKN ATPRRGIHLV ELEGEKGPRF  60
VNSLSAPLYV LETRSRRRPM PPIKDAEFES APWRRAVSAL SGYQQAWLRY CYGFDLSYKH  120
QVMMCEYVWK TYQKCLGDNS LQERVVKKLI GLVWLAGQEI AATRNNETYK DYAGAALARM  180
VSVDRSTWLR VYSGHWAGLK AAFTQLDESA LAMALEYYEE EEALKVAEM             229

SEQ ID NO: 257         moltype = AA  length = 331
FEATURE                Location/Qualifiers
source                 1..331
                       mol_type = protein
                       organism = Escherichia coli
SEQUENCE: 257
MRALLTPEIA HRMGIVLFRP GAELMHLFMR GRVLLEPEPE EMASFSTGAV PAAIQPLADD  60
PVMRQVFEND RVIQRAGGLP SLEQWLSNRF ECQWPHSSWH DKNFTTMRHP PGSIRLCWHC  120
DHTLSGQHTE QLAGIAAGNL VSWILEVIRR DSGFPESHIL TLPELCWWMV RNDLADVIPE  180
SVAHKGLRLP DDKIRSVMRE SDIVPSASAT SLVQEKAKKI LTLSVDPESP ESFMLRPKRR  240
RWINETYTRW VKTQPCECCR RPADDPHHIV GHGMGGTATK AHDLFVIPLC RECHDELHAD  300
VPAFEQKHGT QLELLLRFMD RALAIGVIAK A                                331
```

```
SEQ ID NO: 258         moltype = AA  length = 227
FEATURE                Location/Qualifiers
source                 1..227
                       mol_type = protein
                       organism = Escherichia coli
SEQUENCE: 258
MSQLATTALT MSSSDIAELV ESRHDHVKRS IERLAERGVI ELPPMGEVKN HLNQSVSVYL  60
IGKRDSYIVV AQLSPEFTAR LVDRWQELEQ AQQQTIPQSF SEALRLAADL AEQKQQLTNE  120
LAAAAPKVAF VDRYCTASGS MSFRQVAKLL KAKEPDLRLF LLENDIMYRL GGTMTPRHQH  180
IDAGRFEVKT GTSVTSNHAF SQARFTAKGV RWIGGLWAEH IARGQVA               227

SEQ ID NO: 259         moltype = AA  length = 128
FEATURE                Location/Qualifiers
source                 1..128
                       mol_type = protein
                       organism = Escherichia coli
SEQUENCE: 259
MKLILPFPPS VNTYWRAPNK GPLAGRHLIS AAGRKYQSAA CVAIIEQLRR LPKPSTELAA  60
VEITLYPPDA RRRDIDNYNK ALFDALTHAG VWEDDSQIKR MLVEWGPVVP KGRVEITISR  120
YEPAGAAA                                                          128

SEQ ID NO: 260         moltype = AA  length = 439
FEATURE                Location/Qualifiers
source                 1..439
                       mol_type = protein
                       organism = Escherichia coli
SEQUENCE: 260
MMTNKYCQAL AALRSKPAHE LKEVGDQWRT PDLLFWGINA LFGPLVLDLF ADDDNAKCPA  60
WYTAEDNALT QDWSERLAEL GGAGYGNPPY SRSQYHEKQA ITGMTHIMNY AAAQREKGGR  120
YVFLIKAAPS ETWWPEDADH IVFIRGRIGF DLPVWFVPAD EKQKPTSAFF AGAIAVFDKS  180
WRGERFSYIN RTELEAKGRA FMALAQFAAS KSQPVTATPP AADKPEAELP LTQKDIFAIS  240
GVEAWACVRA AFGDKEEYTF SESKFGHTWA ADSVEAPEFT QVSPLTIDKA KLLIRESILF  300
GVDEWLLSIE FDDAAVRLDM SERIRTVALE ASGEYGMNST DFIAAMGSLD VSSWSNIRQI  360
RMHIREKAKP VSDPLPESRI WPLEVRIVFD QVDGADMLDE SLQHKLKANI NQLWLERTAT  420
SEIITAASEL VRNMRGEAA                                              439

SEQ ID NO: 261         moltype = AA  length = 293
FEATURE                Location/Qualifiers
source                 1..293
                       mol_type = protein
                       organism = Escherichia coli
SEQUENCE: 261
MSTKLTGYVW DACASSGMKL SSVAIMARLA DFSSDEGVSW PSIGTIARQI GAGESTVRTA  60
LAQLEKDGWL SRKQRRNGNR NASNVYQLNV VKLREAAFSH LSESDASKSD PSKSDASKSD  120
PSKFEASKSS KKGGFDPSES GGDPSVKSKQ EPQVTSKPSC PVAAQPDPEV VITDQARQVL  180
SYLNQTTGSR YQVCSTSLEN IRARLREQFT VDDLCLVVDY KNADWRDSEQ AQYLRPATLF  240
IPKNFPGYLQ SATKWSSAGR PERVNGKWET NSASRANFQS VDYSLPENSG FRS        293

SEQ ID NO: 262         moltype = AA  length = 112
FEATURE                Location/Qualifiers
source                 1..112
                       mol_type = protein
                       organism = Escherichia coli
SEQUENCE: 262
MNSVNRFRPA KQFRCLPLVG KDAQFGYVEI INNAADGGNY QPADLMVEAF VQMNEKGREE  60
WLKLTGGSEI TTEFPSELSA GSQIHSALYT FAKGTIMSAS ALLNNSSVNL QN         112

SEQ ID NO: 263         moltype = AA  length = 187
FEATURE                Location/Qualifiers
source                 1..187
                       mol_type = protein
                       organism = Escherichia coli
SEQUENCE: 263
MVDSINTAIR LMCKAHKHGR LGMASDLGMT IDQFHNHLYQ KCGSRFFTLA ELERMEDLSG  60
SCYLAEYQAN RKGKWLVDVP TAESLDNVEL YSIEMKAAAA SGELANAKMA AAADGVIDSS  120
ERKMLSELFS KKLRHQIHGF LGFMALYGVG VSDQAIDVFV STGRKGDARE CAAPGALACR  180
ISGETNA                                                           187

SEQ ID NO: 264         moltype = AA  length = 85
FEATURE                Location/Qualifiers
source                 1..85
                       mol_type = protein
                       organism = Escherichia coli
SEQUENCE: 264
MSSQHKNVTA KAVKAIGSIS EVSRRFEFQS VQSVANWIAK NRVPSERVIQ LCQWGGWVVT  60
PHQLRPDIYP NKNDGIPSAN NNSQL                                       85

SEQ ID NO: 265         moltype = AA  length = 236
```

-continued

```
FEATURE               Location/Qualifiers
source                1..236
                      mol_type = protein
                      organism = Escherichia coli
SEQUENCE: 265
MPCALNLLLM VENAKYKDFA ERLNRSLQEQ SIGVKELSEF SGVSYEMARR YTLGTAKPRD  60
EKMIRIAERL AVSPAYLDYG VPVNGGDAPA KGTVRIEQLD VHASAGSGYI NQPFPTIVSS  120
IEIPEERIFE LFGRRSLDGI VMINVDGDSM MPTLCPKDLL FIDSKVEQFS GDGVYVFNFE  180
DSTFVKRLQK VKGRRLAVLS DNEHYPPFFI EEHEMNELYI FGKLIRCLPL KMIEFG      236

SEQ ID NO: 266        moltype = AA  length = 65
FEATURE               Location/Qualifiers
source                1..65
                      mol_type = protein
                      organism = Escherichia coli
SEQUENCE: 266
MGAFDNQEIT LPACPKCGTK TKKKIAWLKS NKSFTCRCGA TINVNSSQLT SEIRKVEDKL  60
KKLFK                                                             65

SEQ ID NO: 267        moltype = AA  length = 305
FEATURE               Location/Qualifiers
source                1..305
                      mol_type = protein
                      organism = Escherichia coli
SEQUENCE: 267
MNNPFFKNML VYRISRDFTI NQEELEQQLE LFRFTPCGSQ DMAKTGWVSP LGQLSDRLHH  60
TVNNQVLLVI RREEKILPSP VITEELRKRV SRLESDQGRR LKKTEKDSLR DEVLHSLLPR  120
AFSKNSTVGL WINVTDGLIM VDAASAKRAE DSLALLRKTL GSLPVVPLTM ETPIELTMTD  180
WVRSGSAPAG FGLGDEAELK AILEDGGIGR FKKQTLVSDE IHVHLEAGKV VTKLSIDWQQ  240
RIQFVLCDDG SIKRLKFSNE ITEQNDDIDR EDAAQRFDAD FVLMTGELIS LINGLTTSLG  300
GEAKR                                                             305

SEQ ID NO: 268        moltype = AA  length = 179
FEATURE               Location/Qualifiers
source                1..179
                      mol_type = protein
                      organism = Escherichia coli
SEQUENCE: 268
MSYIQTLSGK HFNYLDIQQD DIVIEDIATA LSHICRFAGH LPEFYSVGQH SVLTSHLVPQ  60
EFALEALLHD AAEAYLQDIP SPLKRLLPDY QAIEARVDAA IRQKFGLPTE QHPTVKYADL  120
VMLASERRDF EIDEGSIWPC LEGVVPTDLF IINPVRPGQS YGMFINRFNE LMEQRQCAA   179

SEQ ID NO: 269        moltype = AA  length = 84
FEATURE               Location/Qualifiers
source                1..84
                      mol_type = protein
                      organism = Escherichia coli
SEQUENCE: 269
MTVFEYLQAH PNTTSGEIAK GMNKKTPAVA GALSQLYGTG RIVKSGVRKG IPTYRINDMP  60
FGCSNSLTMM FNQLLSRARQ GAAQ                                        84

SEQ ID NO: 270        moltype = AA  length = 115
FEATURE               Location/Qualifiers
source                1..115
                      mol_type = protein
                      organism = Escherichia coli
SEQUENCE: 270
MTALNKQALR EEFQFMQDNY SDPADHDRQV IYIEAEALLD ELEAKDSTIA AQQHEIRMLL  60
NALEEKPCPK CNDTGMTDSG GTQPWGEPIE IECDCRQQDA NTAELVAAGI GVKGE      115

SEQ ID NO: 271        moltype = AA  length = 102
FEATURE               Location/Qualifiers
source                1..102
                      mol_type = protein
                      organism = Escherichia coli
SEQUENCE: 271
MDKLIKPTAK GKYDGSCDYL CSEDARFIVM RGDYTEAEII QASVSQDVID SDGAADFASS  60
ARYYQCWYKV SPIGGQDGYS GWHHPRDSPC RGAYFASVLQ WD                    102

SEQ ID NO: 272        moltype = AA  length = 155
FEATURE               Location/Qualifiers
source                1..155
                      mol_type = protein
                      organism = Escherichia coli
SEQUENCE: 272
MTTNNHPAHG PVSLDRLHQI REHLLHDTQY SNGGNRAYIL ADVLKVIDGA IARELVRREH  60
AAWSQATFGD VGPVGPLKHL SKEALEAAAE PGDLSEWADM QFLLWDAQRR AGISDEQITQ  120
AMIKKLAINK VRQWPEPKDG EPRLHIKEQS EQEKK                            155
```

-continued

```
SEQ ID NO: 273         moltype = AA  length = 84
FEATURE                Location/Qualifiers
source                 1..84
                       mol_type = protein
                       organism = Escherichia coli
SEQUENCE: 273
MFSLIRRGQI YTDSSNWPVI IHSCSDHSVR IKRNDGELRT ISIKRFNEDF ERVEHDEYRK  60
ICAEIEQETN LKNLRAMRRG KITE                                         84

SEQ ID NO: 274         moltype = AA  length = 189
FEATURE                Location/Qualifiers
source                 1..189
                       mol_type = protein
                       organism = Escherichia coli
SEQUENCE: 274
MNNLMIDLES MGKKPNAPIV SIGAVFFDPQ SGELGQEFYT AVNLESAMEQ GAVPDGDTIL  60
WWLRQSSEAR SAICVDDAMP ISSALSELSH FINRHSDNPK YLKVWGNGAT FDNVILRGAY  120
ERAGQVCPWQ FWNDHDVRTI VTLGRSVGFD PKRDMPFDGV AHNALADARH QAKYVSAIWQ  180
KLIPTTSNS                                                          189

SEQ ID NO: 275         moltype = AA  length = 78
FEATURE                Location/Qualifiers
source                 1..78
                       mol_type = protein
                       organism = Escherichia coli
SEQUENCE: 275
MSNIFQLAPN DWVCESVLIA VTGLKPGTIL RARKECWMIG REYIHVSPDG NPKPSSECMY  60
NRKAVDAWVA SMKSKQPG                                                78

SEQ ID NO: 276         moltype = AA  length = 437
FEATURE                Location/Qualifiers
source                 1..437
                       mol_type = protein
                       organism = Escherichia coli
SEQUENCE: 276
MDKVTYPTGV ENHGGTLRIW FNFKGKRVRE SLGVPDTAKN RKIAGELRTS VCFAIRTGTF  60
DYATQFPDSP NLKAFGVSKK DITVKELEEK WLDLKRMEIC ANAFNRYESV ARNMVPRIGG  120
NRLVSAVTKE ELLYLRKYLL TGYQNPTKNK APAKGRSVVT VNYYMTTMAG MFQFAADHGY  180
LEVNPFEGIK PLKKARAEPD PLSRDEFIRL IDACRHQQTK NLWSLAVYTG MRHGELVSLA  240
WEDIDLKAGT ITVRRNYTKL GEFTLPKTEA STDRVVHLIQ PAISILKNQA EMTRLGRQYH  300
IEVQLREYGR SVNHECTFVF NPHVVRRSKQ VGFIYRVDSV GDSWEAALKR AGIRHRKAYQ  360
SRHTYACWSL SAGANPSFIA SQMGHASAQM VFNVYGAWMA DSSAEQIAML NQKLADFAPL  420
MPHSHENSTG GLLKSVS                                                 437

SEQ ID NO: 277         moltype = AA  length = 241
FEATURE                Location/Qualifiers
source                 1..241
                       mol_type = protein
                       organism = Escherichia coli
SEQUENCE: 277
MEGNTTLYAL PKPEVVLRWR EQTTDDFRFC FKFPATISHQ AALRHCDDLV TEFLTRMSPL  60
APRIGQYWLQ LPATFGPREL PALWHFLDSL PGEFNYGVEV RHPQFFAKGE EEQTLNRGLH  120
QRGVNRVILD SRPVHAARPY SEAIRDAQRK KPKVPVHAVL TAKNPLIRFI GSDDMTQNRE  180
LFQVWLQKLA QWHQTTTPYL FLHTPDIAQA PELVHTLWED LRKTLPEIGA VPAIPQQSSL  240
F                                                                  241

SEQ ID NO: 278         moltype = AA  length = 131
FEATURE                Location/Qualifiers
source                 1..131
                       mol_type = protein
                       organism = Escherichia coli
SEQUENCE: 278
MVSALYAVLS ALLLMKFSFD VVRLRMQYRV AYGDGGFSEL QSAIRIHGNA VEYIPIAIVL  60
MLFMEMNGAE TWMVHICGIV LLAGRLMHYY GFHHRLFRWR RSGMSATWCA LLLMVLANLW  120
YMPWELVFSL R                                                       131

SEQ ID NO: 279         moltype = AA  length = 247
FEATURE                Location/Qualifiers
source                 1..247
                       mol_type = protein
                       organism = Escherichia coli
SEQUENCE: 279
MSHRDTLFSA PIARLGDWTF DERVAEVFPD MIQRSVPGYS NIISMIGMLA ERFVQPGTQV  60
YDLGCSLGAA TLSVRRNIHH DNCKIIAIDN SPAMIERCRR HIDAYKAPTP VDVIEGDIRD  120
IAIENASMVV LNFTLQFLEP SERQALLDKI YQGLNPGGAL VLSEKFSFED AKVGELLFNM  180
HHDFKRANGY SELEISQKRS MLENVMLTDS VETHKARLHK AGFEHSELWF QCFNFGSLVA  240
LKAEDAA                                                            247

SEQ ID NO: 280         moltype = AA  length = 323
```

-continued

```
FEATURE                 Location/Qualifiers
source                  1..323
                        mol_type = protein
                        organism = Escherichia coli
SEQUENCE: 280
MIDFGNFYSL IAKNHLSHWL ETLPAQIANW QREQQHGLFK QWSNAVEFLP EIKPYRLDLL  60
HSVTAESEEP LSAGQIKRIE TLMRNLMPWR KGPFSLYGVN IDTEWRSDWK WDRVMPHLSD  120
LTGRTILDVG CGSGYHMWRM IGAGAHLAVG IDPTQLFLCQ FEAVRKLLGN DQRAHLLPLG  180
IEQLPALKAF DTVFSMGVLY HRRSPLEHLW QLKDQLVNEG ELVLETLVID GDENTVLVPG  240
DRYAQMRNVY FIPSALALKN WLKKCGFVDI RIADVSVTTT EEQRRTEWMV TESLADFLDP  300
HDPGKTVEGY PAPKRAVLIA RKP                                         323

SEQ ID NO: 281          moltype = DNA  length = 49496
FEATURE                 Location/Qualifiers
misc_feature            1..49496
                        note = Synthetic polynucleotide
source                  1..49496
                        mol_type = other DNA
                        organism = synthetic construct
SEQUENCE: 281
aggcctctcc tcgcgagagg catttttat ttgatgggat aaagatcttt gcgcttatac  60
ggttggattt cgcccggttt gcgagttttc agcaatttta atatccaggt gtattgttct  120
ggtcgcggac caacaaaaat ctcgacttct tcattcatcc gccgcgcaat cgtatgatca  180
tccgcctcta acagatcatc catcggtggg cgcacctgaa tcgtcagacg atgcgtcttg  240
ccatcataaa tcggaaatag cggtacaacg cgcgcacggc acactttcat caaacgacca  300
atcgcgggca acgtcgcttt ataggtggca aagaaatcaa caaattcgct gtgttctggg  360
ccatgatcct gatcgggtaa ataatatccc cagtaaccct gacgtaccga ctggatgaat  420
ggtttaatac catcatttct cgcatgcaga cgaccaccaa agcgacggcg caccgtgttc  480
cagacataat caaaaaccgg gttgccctga ttatggaaca tcgctgccat tttctgccct  540
tgcgaggcca tcagcatggc aggaatatcg acggcccaac cgtgcggcac cagaaaaatc  600
actttctcgt tattacgtcg tatctcttcg atgatctcca gcccttgcca gtcaacgcgc  660
ggctgaattt tctccggccc gcgtattgcc aactcagcca tcattaccat cgcttgcggc  720
gcggtggcaa acatctcatc tacaatcgct tcgcgttcag cttcactacg ttctggaaag  780
cagagcgaca gattgattaa cgcacgacgg cgtgagcttt ttcccagtcg tccggcaaaa  840
cgtcccagcc gtgccagaat gggatcacgg aactttggcg gcgttaaagc gatacccgcc  900
atcgctgcta cgcccagcca tgctccccag tagcgcgggt ggcgaaagga tttatcaaac  960
tcaggaatgt attcgctatt attttttttc gtttccatgc ttttccagtt tcggataagg  1020
caaaaatcaa tctggtgata gtgtagcggc gcaacttgcc ccgcaccaaa taaaaaagcc  1080
ggtactgact gcgtaccggc tgcgaatgga tgttaattaa tcaaaccgta gctgcggcac  1140
aatctctttg gcctgtgcca ggaattcgcg acgatcggag ccggtcagcc cttcggtacg  1200
cggcagtttt gccgtcagcg ggtttacggc ctgctggttt atccatactt catagtgcag  1260
atgcggcccg gttgaacgtc cggtattacc ggaaagcgcg atacggtcgc cacgtttcac  1320
cttctgtccc ggtttcacca ggatcttgcg caagtgcata taacgcgtgg tgtagctgcg  1380
accatgacga atagccacat aataacctgc tgcgccacta cgtttggcaa ccaccacttc  1440
accgtcaccc actgaaagca ctggcgtacc ttgtggcatg gcaaaatcaa cacctctgtg  1500
tggcgcaacg cgaccggtca ccggattagt acgacgcggg ttaaagttag atgagatacg  1560
gaactgtttc gccgtcggga atcgcaagaa tcctttcgcc agaccagtac cgttacgatc  1620
gtagaatttg ccatcttcag cgcggattgc gtaataatct ttaccttctg aacgcaaacg  1680
tacgcccagc agctggcttt gctcacgttt accatcaagc atttctcgtg acattaacac  1740
cgcaaattca tcgccttttt tcagtttgcg gaaatccatt tgccactgca tggctttaat  1800
cactgcgctc acttcggcgc tggttaaacc ggcgtttctg gcgctggcaa caaagcttcc  1860
cccgacggta cctttcagca gattgttgac ccactctcct tgctgcattt cgctggtcat  1920
tttaaaaccg ttagcggcag tacggtcata ggttcgggtt tcacgacgag acacttccca  1980
ggtgaggcgc tgcagttcgc cgtccgcggt taatgtccag gagagttgtt gaccgatttt  2040
caggttacgc aattctttgt cggcagcagc cagttgggtg atatcaccca tatcaatacc  2100
atactgattg agaatgctgc ttagcgtatc gccagtggaa acaacatatt catgcacgcc  2160
cgcttcaccg gcgattttgt catccagttc gtcctgggga atggcttcat cttcttgtgc  2220
agcttgatca atcggctcac tggcttcagg taagagcgaa cgaatttcgt tctgttccag  2280
ctcaatggtt ttgacaattg gcgtggcatc gcggtgataa acatagggcc gccagacagc  2340
gacggccaga gtaagaacgg tgagcgaccc caacataacg cggtgtggtc gcggtaaatt  2400
attaaacgcc agggcgacag agcgggctat ctgttgcacg taatcacttc ctcattaatc  2460
tcctttcagg cagctcgcat actggttggc taattgattc aggaattctg aatagcttgt  2520
tttacccagt ttgatattcg tccccagggg atccaacgtt cccatacgaa cggatgtccc  2580
tcgtgcgacg ctctcaacga ccgctggcct gaactgtggc tcagcaaaaa cgcaggttgc  2640
tttttgctca accaactgtg ttcttatttc atgtaaacgc tgcgcgccag gttgaatctc  2700
agggttaacg gtaaaatgac caagcggtgt cagtccgaac tgtttttcga aatagccgta  2760
agcatcgtga aaaacgaaat aacctttccc cttgagcggc gcgagctcgt taccaacctg  2820
cttttcggtt gaggctaatt gtgcctcaaa atccttcagg ttggcgtcaa gtttggctcg  2880
actttgcggc ataagttcca ctaattttcc atggattgca accgctgtag cccgcgctat  2940
ctctggggaa agccaaagat gcatgttgaa atcgccgtga tggtgatctt cgtcactttt  3000
ttccgcgtgg tcgtgatcat catcatcgcc gtgaatactt ttcatcagca gcggtttcac  3060
attctctagc tgcgcaatcg ttacctgttt cgcttcaggt aatttactta ccggtttttg  3120
catgaacgct tccatctccg ggccaaccca aacgactaag tccgcgttct gtaagcgttt  3180
tacatctgat ggacgcagtg aataatcatg ttctgaagcc ccgtcaggta gtaaaacctc  3240
cgtttctgtt accccatcag caatggcaga agcgatgaac ccaacgggtt taagcgaagc  3300
gacaacggca gcatctgcgg cctgtgttgc accgccccag agagcggcgg ataatgctgc  3360
gaaaagaagc gttttttat gtaacataat gcgaccaatc atcgtaatga atatgagaag  3420
tgtgatatta taacatttca tgactactgc aagactaaaa ttaacatgac aagtctggtt  3480
tccctggaaa atgtctcggt ttcttttggc caacgccgcg tcctctctga tgtgtcgctg  3540
```

-continued gaacttaaac ctggaaaaat tttgacttta cttgggccaa acggcgcagg taagtcgaca 3600
ctggtacggg tagtgctcgg gctggtaaca cccgatgaag gggttatcaa gcgcaacgga 3660
aaactgcgca tcggctatgt accgcagaag ctgtatctcg acaccacgtt gccactgacc 3720
gtaaaccgtt ttttacgctt acgccctggc acacataaag aagatatttt gcctgcactg 3780
aaacgtgtcc aggccgggca tctgattaac gcaccgatgc aaaagctctc gggtggcgaa 3840
acgcagcgtg tactgttagc gcgagcattg ttaaatcgac cgcaattatt agtgctggat 3900
gaacccactc agggcgtgga tgtgaatggt caggtggcgt tatatgacct tattgaccaa 3960
ctgcgtcgcg aactggattg tggcgtttta atggtatctc acgatctgca tctggtaatg 4020
gcaaaaaccg atgaagtgct ttgcctgaat caccacattt gttgttccgg cacaccggaa 4080
gttgtttccc tgcatccgga gtttatttct atgtttggtc ctcgtggtgc tgaacaactg 4140
ggtatctatc gccatcatca taatcatcgt cacgatttac agggacgaat tgttttgcgt 4200
cggggaaatg atcgctcatg attgaattat tatttcccgg ttggttagcc gggatcatgc 4260
tcgcctgtgc cgcgggtccg ctgggttcgt ttgtagtctg gcgtcgtatg tcttatttcg 4320
gtgatacgct ggctcatgcc tcattacttg gcgtcgcgtt tggtttgttg ctggacgtga 4380
atccattcta tgcggtgatt gccgttacgc tgctgctggc gggcggtctg gtatggctgg 4440
agaagcgtcc acagctggcg atcgacacgt tattagggat tatggcgcac agtgccctgt 4500
cgctgggcct ggtggtcgtt agtctgatgt ctaatattcg tgttgatttg atggcttacc 4560
tgttcggtga tttactggca gtgacgccag aagatctcat ctctattgcg attggcgtgg 4620
tcatcgtggt ggctattttg ttctggcaat ggcgcaattt gctgtcgatg acgattagcc 4680
cggatctggc gtttgttgat ggtgtgaaat tacagcgcgt gaaattgttg ttgatgctgg 4740
tgacggcatt gacgattggt gtagcgatga aattcgtcgg cgcgttgatt attacttcac 4800
tgctgattat tcctgctgct actgcacgtc gctttgcccg cacgccggaa cagatggctg 4860
gtgtcgctgt tttggtgggg atggtggcag tgactggcgg tttaaccttt tccgcatttt 4920
acgatacacc tgcaggcccg tcggtggtgc tatgcgcggc actgttattt attatcagta 4980
tgatgaaaaa gcaggccagc taatctgtcg ctgaacacat ttgtcggatg cggcgcgagc 5040
gccttatccc acctgcggtt cgctatctct ggtaggcctg ataagacgcg aacagcgtcg 5100
catcaggcac actgccagtg tcggatgcgg ctcgagcgac caatccgact tacggcattt 5160
ctggcggcgt gatgccgaag tggttccacg cccgcactgt cgccatacgc ccgcgcggtg 5220
tacgctgcaa aaagccttgc tgaatcaaat aaggttccag tacatcctca atggtttcac 5280
gttcttcgcc aatggctgcc gccaggttat ccagacctac cggcccacca aagaacttat 5340
cgattaccgc cagcaacaat ttgcggtcca tataatcgaa accttcagca tcgacattca 5400
acatatccag cgcctgagca gcgatatctg ccgagatggt gccatcgtgc ttcacttcag 5460
cgaaatcacg cactcgacgc agcagacggt tggcaatacg tggcgtaccg cgcgcacgac 5520
gagcaacttc cagcgcgccg tcatcactca tctcaagccc cataaagcgt gcgctgcgac 5580
tgacgatata ttgcagatcc ggcacctgat aaaactccag acgttgcaca ataccaaaac 5640
gatcgcgcaa cggtgatgtc agcgaacctg cgcgcgtggt tgcaccaatc agggtaaacg 5700
gcggcaaatc aattttaatg gagcgtgccg ccggaccttc accaatcatg atatccagtt 5760
ggtaatcttc cattgccgga tacaacacct cttccaccac tggtgaaaga cggtggatct 5820
catcaataaa cagtacatcg tgtggttcaa ggttagtgag cattgctgcc agatcgcccg 5880
ccttttccag caccggacca gaagtcgtgc gtaaattaac gcccatttca ttggcgacaa 5940
tattggcaag cgtagtttta cccaaccccg gaggaccaaa aatcaataga tgatcgaggg 6000
catcgccgcg cagtttcgct gctttgatga aaatctccat ctgcgaacga acctgcggct 6060
gaccaacata ctcttccagt aatttagggc gaatggcgcg atctgccaca tcttccggca 6120
aagtggtacc ggcagaaatc agacggtctg cttcaatcat cctttacctc ataacgcggc 6180
gcgtagggct tcgcgaatta atgtttcact gctggcgtca gggcgagcga ttttgctcac 6240
catgcggctt gcttcttgtg gtttatagcc cagtgccacc agcgcagcaa ccgcttcctg 6300
ttcagcatcg tcggtcgccg ggctggcagg agacgtgagt accaggtcgg cggctggcgt 6360
aaagagatcg ccatgcaaac ctttaaatcg gtctttcatt tcgacaatca agcgttcggc 6420
ggtttttttg ccaatacccg gcagtttcac cagtgccccc acttcttcac gctcaacggc 6480
attaacgaac tgctgcgctg acattccgga gaggatcgcc agcgccaact tcgggccgac 6540
gccgttggtt ttgatcaact ctttgaacaa cgtgcgctct tgtttattgt taaaaccgta 6600
cagcagttgc gcgtcttcac gcaccacaaa gtgggtgaaa acgatcgctt cctgacccgc 6660
ttcagggagt tcataaaaac aggtcatcgg catatgcact tcatagccta cgccgcccac 6720
ttcaattaac accagcgggg gttgtttttc aatgatgatg cctctgagtc tgcctatcac 6780
atgacgctcc tgcgtaatga atcaaagata atgctgtatg ataaaaaaat gctggataga 6840
tatccagcga aggatgaaga aaacttgcga ggtgtctcga tgatctgaaa aatggcgcag 6900
tataatttat tctacagatt atattggaag caaatattta aatattacat attcagcgaa 6960
gaaatgtgta ataaaaatac acattgcgac ccctgaaaaa aataaatttt ttatgctatt 7020
acgtatattc atatctattt caatggaatg acaacgtgaa tattaattat cctgctgaat 7080
atgaaattgg tgatatcgtc tttacatgta taagtgctgc cttatttggt caaatatcag 7140
ctgcatcaaa ttgctggagt aatcacgtcg ggatcattat cggtcataac ggtgaagact 7200
ttctggttgc agaaagccgt gttcccctct caaccatcac tacgctatcc cgttttatta 7260
aacgctctgc taatcaacgc tatgctataa agcgattaga cgccggacta acagaacaac 7320
aaaatcaacg aattgttgaa caggttcctt cccggctacg caaaatttac cacaccggtt 7380
ttaaatacga atcttcgcgc cagttctgtt caaaatttgt ttttgatatt tataaagagg 7440
cgctatgtat tccggtgggt gaaatagaga cgtttggaga attgttaaat agcaatccaa 7500
atgcaaaact cactttctgg aaattctggt tcttaggttc tattccgtgg gagcgtaaaa 7560
ccgtcacgcc agccagtttg tggcatcatc cgggtttggt gttgattcac gcggtgggag 7620
ttgaaacgcc tcagcctgaa ctgaccgagg cggtataact taacgcagtc gccctctcgc 7680
caggttcagt cgcgattcgc tcatttgcat cgcattctga ctaacgtggc agtgggtgat 7740
ggcaatcgcc agcgcatcgg cggcatccgc ctgtggatta gcgggcagtt tcagcaaggt 7800
gcggaccata tgctgcacct ggcttttttc ggcactacca atacctacca ctgtttgctt 7860
tacctgacgt gccgcatatt caaataccgg caattcctga ttcaccgccg ccacaatcgc 7920
cacgccgcgc gcctgcccca gtttcagggc tgagtcagcg ttcttcgcca taaagacctg 7980
ttcaatggcg aaataatcag gctggaattg ggtgatgatt tccgtcacgc ccgcatagat 8040
gagcttcaga cgagacggta aatcatccac tttggtgcgt atgcatccgc tacccaggta 8100
ggacagttgc ctgcctacct ggcggatgac gccatagccg gtcacgcgcg aacccgggtc 8160
aatgccgaga ataatagcca tcacgcgtct ccgttttgct gtttagcagg cctcatcaga 8220
gagtcgctgc aacctcatca gagatttcac cgttatggta aacttcctgc acgtcgtcgc 8280

-continued

```
aatcttccag catatcgatc agacgcatca gtttcggtgc ggtttctgca tccatatcag  8340
ctttggtgga cgggatcatg gaaacttccg cgctgtctgc tttcagacct gccgcttcca  8400
gagcgtcgcg tactttgccc atttcttccc atgcagtgta gacatcaatc gcgccgtcat  8460
cataggtcac aacgtcttca gcaccggctt ccagggctgc ttccatgatg gtgtcttcat  8520
cgcctttctc gaaggagatc acgccttttt tgctgaacaa ataagctacg gaaccatcag  8580
taccgaggtt accgccacat ttgctgaatg catgacgcac ttcagcaacg gtacggttgc  8640
ggttgtcaga cagacattca atcatgattg ccgtgccgcc aggaccgtaa ccttcgtaga  8700
tgatggtttc catgtttgca tcatcatcac cgcccacacc tcgtgcaatt gcgcggttca  8760
gagtgtcacg ggtcatgttg ttagacagtg ctttatcaat tgctgcacgc aaacgcgggt  8820
tagcgtccgg atcaccaccg cccagcttag ccgcggttac cagctcacga atgattttag  8880
tgaagatttt accgcgctta gcatcctgcg cagctttacg atgtctggtg ttggcccatt  8940
tactatgacc tgccataaaa atatctccag atagccctgc ctgttcaggc agcgttaatt  9000
acaaactgtt caatcgcctg ccggttgctc caggacttag tgagcgccgc cgcagcagac  9060
gcatcaagcc acttgtaagc cagatgttca gtgaaaacga tctggcgctc gtgcggaagc  9120
gcaagacaga accatgattc cgtattacgc gtcacgcccg gcgcatagcg atgacgtaaa  9180
tgtgaaaaaa tttcaaactc taccgtgcgc tgacagtcaa ttaaggtcag ttgttcagcg  9240
acaacatcaa tggtgacctc ttcctttact tcgcgcatgg cagcttgcgg cgcggtttca  9300
ccctcttcca cgctgccggt taccgactgc cagaaatcgg gatcgtcacg ccgctgcaac  9360
atcagcaccc gtttcgtatc ttgtgcgtag atgaccacta agatcgaaac gggacgctta  9420
taagccatat cagttattct cagccttctt cacaacctga atgctcagct cagccagtgc  9480
agtcgggtta gcaaagctcg gcgcttcagt catcaaacac gctgccgccg tggttttcgg  9540
gaaggcgata acgtcacgga tattgtcggt gccggtcagc agcatcgtca gacggtcaag  9600
accgaatgcc aaacctgcgt gcggcggagt accgtatttc agggcgtcga gcaggaagcc  9660
gaatttctcg cgctgttcct cttcgttgat acccagaata ccaaacaccg tctgctgcat  9720
atcaccatta tggatacgca cagaaccacc gcccacttcg taaccattga tgaccatatc  9780
gtaagcgtta gccaccgcat tttccggtgc agctttcagt tctgctgccg tcatgtcttt  9840
cggtgaggtg aacggatggt gcattgctgt caggccgcct tcaccgtcgt cttcaaacat  9900
cgggaagtcg ataacccaca gcggtgccca tttgctttcg tcggtcagac caaggtcttt  9960
acccactttc aggcgcagtg cgcccatcgc gtcggcaaca attttcttgt tgtcggcacc  10020
gaagaaaatc atatcgccat cttgcgcgcc agtacgctcc aggatggctt cgatgatttc  10080
tgcattaagg aacttcgcta ccgggctatt gataccttcc agacctttcg cgcgttcgtt  10140
aactttgatg taagccagac ctttcgcgcc gtagatttta acgaagttac cgtattcgtc  10200
gatctgctta cgggtcaacg atgcgccgcc cggaacacgc agagcggcaa cacggccttt  10260
cggatcgttc gccggacctg caaatactgc aaactcaaca gatttcagca gatcggcaac  10320
gtcggtcagt tccatcgggt tacgcagatc cggtttatca gaaccataac ggcgttctgc  10380
ttctgcaaag gtcattaccg ggaaatcgcc cagatccacg cccttcactt ccagccacag  10440
atgacgcacc agcgcttcca tcacttcacg cacttgcggc gcggtcatga aagaagtttc  10500
cacatcgatc tgagtaaatt caggctgacg gtcagcacgc aggtcttcgt cacggaagca  10560
tttaacgatc tgatagtagc ggtcaaagcc ggacatcatc agtagctgtt tgaacaactg  10620
cggggattgc ggcagcgcgt agaatttacc tttgtgcaca cgagaaggca ccaggtagtc  10680
acgcgcgcct tcaggcgtgg ctttggtcag catcggagtt tcgatgtcga ggaagccgtg  10740
gtcatccata aaacggcgca ccaggctggt gattttagcg cgggttttca ggcgctgagc  10800
catttccggg cgacgcaggt cgaggtagcg gtatttcaga cgcgcttctt cggtgttgac  10860
gtggttagag tcaagcggca gaacatctgc acggttgatg atagtcagcg aggacgccag  10920
tacttcgatt tcgccagtcg ccatatcgcg gttaatattt ttttcgtcac gcgcacgtac  10980
ggtgcccgtg acctgaatgc agaactcatt acgcagttca gaggccagct ttaacgcgtc  11040
cgcacgatcc ggatcgaaaa atacctgcac gataccttcg cggtcgcgca tatcgatgaa  11100
gatcaggcta ccaagatcac gacgacggtt gacccaacca cacagagtca cctgctgccc  11160
cacgtgggac aaacggagct gtccacaata ttctgtacgc atgagatatc ccttaactta  11220
gctgccggcg gatgccccct gctgcgcagg tgaccaagtc gcagcgttag ctgtatgtca  11280
caactgaatg aaaaaaggcg gctattatac tggaaattct gccgcaccgt aagagcctgg  11340
cccgcgctgg aacgcctcgt taccacttta tatcgggcct gaaatcagac tctacgccag  11400
tttgctataa aggtgttgcc cgaactcata aaaattaaca aaatttgtcg ttccgccatc  11460
ggctaatcgc attaaggtga gaggcacgat tttgttttgt caggagtcat catgcttgaa  11520
cttaatgcta aaaccaccgc gctggtggtg attgatttac aagaaggcat cttgcctttt  11580
gccggaggtc cacatactgc cgatgaggtg gttaatcgcg ccgggaagct ggcggcgaaa  11640
tttcgcgcca gcggtcagcc cgtgtttctg gtgcgcgttg gctggtctgc cgattacgcc  11700
gaagcattaa aacagccggt tgatgccccc tcccccgcaa aagtgttgcc cgaaaactgg  11760
tggcaacatc ctgctgcatt aggtgcaacc gacagcgata tcgaaatcat caaacgtcaa  11820
tggggtgcgt tttacggtac ggatctggag ttgcaattac gccgccgggg tatcgataca  11880
atagtgttat gtgggatctc gaccaatatc ggtgttgaat ccaccgcccg caatgcctgg  11940
gaactcggtt ttaatctggt gattgccgaa gatgcctgta gcgccgctag cgccgagcag  12000
cacaataaca gcattaatca tatctacccg cgcatcgccc gtgtgcgtag cgttgaagag  12060
atcctcaacg cgttatgatt tacatcggtt tgccacaatg gtcgcatcct aaatgggtgc  12120
ggttggggat caccagcctt gaagagtatg cccgccactt taactgcgtg acgcgggcat  12180
tttaaaaatc actaaagaac gcccaagagc atgtgtttc tttagtttat tcaatgcatt  12240
aaaaaatagt ttcgcatgaa attcggtaaa cttcatgtgt gcaataatgt cccattcatg  12300
ccccaaaatg ccccaaagca gacatttttg ccccaagtat gccccacaag tcacgtcttc  12360
aagtcgtcta tatccatagc acaccgagtt acattcttgc atccggggtg tcgacaatac  12420
ctactttatt gagtgtgcga gaattaccag gaacctttcc acaatgtagt agtctaatag  12480
tcgaatccat ctaacattaa gaagcgttat gatcactagc ctctcattga tatcttctgt  12540
aatagtcact ctatgtatca tggtgttcgc tacagtaaag gtagggattg gtttgtctaa  12600
caatccagac agaaatgata attaacctca accacgtaac cacacttcat acttcatact  12660
tcacttaaca gtgaagtgct cacatcaccg ggcagtcatc aaactccgca ttcctggcat  12720
cattaatgat gtacgtgatc actccaaata tagcgggtgc agaactgtaa ccatcatcat  12780
ctgctggcag cgcttccctt ctcccgttat ccagattaac caggtgcggc tgaggatgag  12840
tccgatatcg cttgatcctg aattccccgt cgattgcaca tatcagcagt gaaccatcgc  12900
aggcagtaag tgacgcatcc acaacaagca acgctccctg gattatccct tccctgaaat  12960
gtgaacgcga tgcccgcatg aaataagtcg ctgcgggctg actgattagc tgctgatcga  13020
```

-continued

```
gggagattcg tgtttcaaca taatctgccg caggtgaagg aaatcccatg tttacgccct  13080
ctcttgaata ccggataaaa acacagtata aatactgtat atccatccag caaagaggca  13140
atgagcaatg ttcgtggaac tcgtttatga caaaaggaat tttgatggtc tgcccggtgc  13200
aaaagatatc attctgggcg agttaactaa gagagttcac cggatcttcc ccgatgctga  13260
tgttcgggtt aaaccgatga tgacactgcc ggcgatcaac actgacgcca gcaagcatga  13320
gaaggaacag ataagccgta ctgttcagga aatgtttgaa gaggctgaat tctggttagt  13380
gagtgagtaa agattttcaa tgcccgccac agttacgtat tgattatgct gtggaggata  13440
ttcattttcg taaacgttgg tttgggagaa gcggcaaaac ggaatgtggg aacaggggaa  13500
aatcagatac cagatatgtc tgcatttcca tctggcaata actggtttca gttaccaagt  13560
ggacatatcg ttcagatatt ttccatgaac gttcttggtg cagatgctaa tggcacgtca  13620
gctaattacc ccattgcttt tccaacaacg atgattgctg tcagtgctct atggtctgat  13680
gggactgtag caaatgcacc gacatacaag atgatgggga acacgactaa cagaacaact  13740
ttgacgataa aagtatcagc cagctcaggt acttacggga caatgattat tgcggtggga  13800
cgataaatatg aataaataca gttactctcc ttcagaaaat gccttttatg ctgttgcgtt  13860
aaaaaatacc tatgaattga gtggcacatg gccagctgat gcattagata ttcctgatga  13920
catttctgta aaatatatgg cggaaccgcc acaagggaaa atccgagttg caggggaaaa  13980
tggttttccc acatgggctg aaatacctcc accatcacat gaggaactta ttgaacaggc  14040
cgaatcagag aggcaattat tgattaacca ggccaacgaa tacatgaaca gtaaacaatg  14100
gcccggtaaa gccgctattg gtcgtctgaa aggcgaggaa ctggcacaat ataattcgtg  14160
gctggattat ctggacgcac tggaactggt cgatacttcc ggtacgcccg atattgaatg  14220
gcctacgcct ccggcagttc aggccagatg acatccggcg cggtgctggt atctgttgca  14280
gtcaccgcgt caatgtaatc cagcacggcg ttaagtcggg ttgtttctgc ctgagtcagt  14340
ttccgtccgg cctgtaattt cagctgaatc agactaatgg aagccattgc tgcatcaatc  14400
agtgattggc gctgtgcttc tgccgcttct actgaggcac cgtgttgtgc ctcagtatct  14460
gtcacccatt tctcaccatc ccatttatca tatggcgtta acggtgaaag cgtgacataa  14520
ccgtttttga tggcaccgat ataatccact gtaacagctg cgccattttc gattgagtaa  14580
acagtctcat tgcgatggtc ttcctcatgg ctccatccct tacctgtaaa tactgccact  14640
cttccccggaa tgttttcgtc cgggtcaata ccagtggaac aggcgggcat acttacgcca  14700
gtattaatat attcatcaga ccagcccgta tattcagacg ttactgcatc ataataaaaa  14760
caacgcatat cacccggcac tgcagccagc ccattttcat caaaaacagg tttcattatt  14820
tagccctcac cagaaagtta aatgcaatat ttcgcggtct gacagcaaca aaattcacac  14880
catcacccac agagttactg ttgaaattaa atcgtgaaaa tcctggctga tttccggcga  14940
tgccatcatg aaagttaatt gcgtgtccag cacctccgcc tatattcccg gcaaactgag  15000
aaaagtttgt agcttcctgc cagcttaata attcgcgacc accatctgca cctcgcccgt  15060
catcccagac acgaatgaaa tcaccgcggg cttcaggtaa taccagcgaa ggaaacactt  15120
tcgccagcac aggataatca gtggcagaga atttcgcgcc gttgaacttc aaaaacacca  15180
tactggacca gctgtcgatt acagtatttg gcattgcagc ggacggccag aagaacggaa  15240
cgccaatagc tggagaacct tctcccaaac caaggtttgt gcgagcgtct gcggcattcg  15300
ttgcgccggt tccgccgtct gcgacagtaa ccgcaccgtt gctccctttc tgcgcaagtt  15360
taccgatgcc tgggatggtt acggcggtgc cgttgatggt aactgtggtg ctttggtttg  15420
ctgaggtggt ggcgaacgtc tcccacgcgc caatattctc gtcgtactct ttgatgagct  15480
gtgacatggc ctgcgccagg ccgtcgactg agatattgtc cgacacaagg attccatact  15540
tctggccgct cagcgccggg gaaactgctg gcgtaaccgt cattgacgtg gcgctgttca  15600
cggatgaaat ctgaaacagc tgcaccgggt tagacatcac gataatcgtc tggccagcgc  15660
ggacctggct ggcgggagct gtccagtttg tgccggagcc ggttgcggta tttccgttaa  15720
tagagatagt tccggtgcta taaatcataa caactcctaa atttagacaa catgaagccc  15780
ggagaggtat ataaccctca ccagaaataa tttctgaatt ggtttttaat acatgttggg  15840
caacgccagt gttggcatag ctatagttgt atcaaatgcc attgaccacc cacccaaata  15900
ataattgccg actactttat tcctttctgc tctgacattc ccacctgtca ttacaattcc  15960
tttataccta atatttccgt aaccaccaac gtgtcgacag ttagccccgg tataaacaat  16020
ctggcaaaat tcatcaccaa tattcaggtt cgcattggcg atatttattg tcccatcaaa  16080
aatgaatggc ttcgtgcaag taagaagacg tttgcgttga cgattggttt attcaatcca  16140
tcaactaaaa tatcatgtaa acgaattgcc ataacatttc ccactttatt ttacttactc  16200
aacacaacaa gtatattaaa attgaacctt gtcaacaaca caaaggagtc ccaatgaaac  16260
tcgctctaat tatgctgcca ttatgtctgt ccctcactgc atgtggtaat ggtttaaata  16320
ccggtaaacc aaattccggt gtcattccaa aacctttgga tcgagatggt aacggttctt  16380
taatttatga taccgaaaac cttccaatga cggggcagtg gtgtcacgag attgatcacg  16440
aataccgacg aatcggtagc ccttctaact gtgttataga ctactaaata ttaacccctc  16500
aaaagagggg ttaatatttt aacctgtgaa tgaaccagat ccgtgtgata ctatgatagt  16560
aggcgaagaa attgacgcac ccctgttatt ttgagcggac actttaatac gcactgttac  16620
gtttggacct gttacaaccg cagaatgcat gataagtctc tccatgtctt gcacggatga  16680
accactctca ttgccgttaa tgtcgattgt tcctgcacca ttacctttaa cgtttgctat  16740
aacacagacg tgtcttgcgt gcccagaact ggatgaatca ttataagtca ttaccttttc  16800
taaatatccg tcactagacc gactcacatt cgtccctgtg tgcatatttg caatgtcccc  16860
gataaaactt tgggcttcca cagtcccttt gaatttaccg cttgttgctt ggatctcacc  16920
agtaaagcta ccgccactag catatactac acctctgacg gtcacattgt tgaattcagc  16980
atctccagct ttattcaact tccaaccagc agaaccagct gcatagttgt tggactggat  17040
atagttaccg atttttgcgt tctcaatggt gccgtcctgg atgaagctgg cccggatgaa  17100
tgtctgcccg ttctggatca cgaacggcaa agctacgcta tttccggctg ccgtggtgac  17160
ggcgaagcgg tcagccagga agataacctg cgactgcatg ccggatggcg tattctccac  17220
gccgataccc atccccgcgg cgtaatactg cccgttgctg gagacaccaa ccttgatgtt  17280
gtacatcgcg ctgagttcgc cattaacgtt ggctatagcc tgagcgttag tggtgatggc  17340
ggaggtatgc ccgttcacgg tcgccgtgat gccgtttatc tgcgtggcgg tggcctgctg  17400
atagtcggag agcgtctgat tcaggctgtt gatggatgcc ttgttgccgt tgacgtccgt  17460
ctgcaggctc agcaatgaac gtgctgtggc ttccttctca ctgacgatca cctcgtcgag  17520
acggtccaga ttcgcgctgt tgccggcgac cgatgcagaa agggttttac gcgtggccac  17580
ctgagcgagg ttggcctgga ttatcgcaat tgcagagttc ttcaccccgc ccgtcatgcc  17640
gtccatagaa acgctgatgt tgtcgattcg ctggcccagg gcggtatcag ccgtcgcaac  17700
ggtctgctca agctgactga gtgaagacga aacattcccg accgtgctgg aaagctcatt  17760
```

```
aacgctggtc tgaaccttcc cgacgtcctg ggcatttttg gcgatatctt tcgcttgctg  17820
ctccagttcg tcgttggcct gtttgatatc gttagccatg ccagcaattt tttcgttgct  17880
gtccaccgcg ttctcgatca ggtctttgaa cgtttccgac tctttcatat cctccagaat  17940
gtcattagtt atttcgctga catctatcga ggacgtgccc atgatccagt cggtccagtc  18000
cccggcgtta ccgatacggt caatcaggcg cgcgcggtac cactggcgaa cgccggcagg  18060
catggggcca tgctgataat ctgcagccgg gtacggcacc aggaccagca gttcaggatt  18120
ggcgtagtcg gcagttgtgg cgcgctgaat ctctgtatag gccgtgtcgc ctgagccatc  18180
cggaaatttc caggtcaggt cgatatgcca gaccacatct tcggtcgcca ggaagttgag  18240
cggagtaccc ggttttcccg ttttaccgga gagataagtt gtttcaccgt atccccatgg  18300
tgacgacgta tcctgcgcat tcagcgcccg tacgcgcacg tcatagctgc ccgaataaat  18360
gccctgaacc gagaaaccct gcgcgctggt aaccggaacg tttatccagt ccccgttgtc  18420
cttacgccac tgggcaacat accggattgc gccctctacc ttatcccatg acacgtccag  18480
gcttgctaca gtcagcccct gagacacatg atcgctctca gtcaccacga tattcttcgg  18540
agcagacagg acgcttatcg gcgtgacggt gatcggggga gactcgaccc gaacgccgtc  18600
atcgatgtaa cgatatttgt ttggatcgtg ctgaacggcc gtaatagtga aaccgcctgt  18660
actgtcgtcg ttagccgcga ttgaggtgac cctgaagtac tgtattgcga ggttatcact  18720
gtctatcgcc caaacagcgc ccgccacagg aacctgactg aatgccgtag ccaccgtcac  18780
cgttttttta tcggcgctca ccgcgctgat tgtccgcgtc tgggcttttc cgtcgggaag  18840
gttaaccacc agccggtctt tcgccgcgta gtctatttct cgatcgaggg taatttggcg  18900
gccgttggcc gcgcttatac ggcccccgtt ctccttacca gagcggaaag gatcggcgac  18960
accgataatt tcagcgggca aagggatata accgtccagc cccacgccaa acgatacggt  19020
cccgtctttg gcattggaga gcaataccca gcgaccgcgt cggtgcgctt cactttgcga  19080
ggtgcagccg attgcggtca gggacgtctg ccggacgtcg taacgttcta caagcgccga  19140
atcgtaaacc ccctcaacgg tatcgctgta atggttctgc ggatcggacc aggacaccag  19200
gcaggagctg tagcgattct tgtatgagcc gcccgcataa gtaaacagcc catcgataac  19260
gtttgagacg ttataaaccc agtcaacatc gtcctgcggg acgtctgcct ggacataaat  19320
ctgatcgttt ccccagaacg ttattccacg aaataccgcg gcgagatcgt taagtacctg  19380
ccaggcgtcc tcctggctct gaatgaaaac gttgcaggtg aaacgcggtt cggtgccacc  19440
ggccccgtcg gaaaccattt cgtcacagta ctgggcgatt gaatacagcg cccacttatc  19500
caccatggac gcatccacgc gcgtgcccat gccgtaaatt tcatccagaa ccagatcgta  19560
aaagatccag gcagggttat tggaccatgc cattttgaac ccgccggacc atgaaccaga  19620
ataggttcgg gttttcggat cgtaattatc cggaacctta atcagcttgc cttttatctt  19680
acaggtcact ttcggcgcgc tgccgttgaa ttggctgctg tccacttcga catacaggag  19740
cgctgttaaa ggataacgaa gcttgctgtc gatgacttcc gcatacgaaa acaccttgaa  19800
ggcgttaacc agtttcgaat ttgatccgct ggcatcagcc gtaatacgcc tgaccctgac  19860
agaccagccg gacgtggatt ttggcagatc gatacggtgg tcacgctgat attccgtcgt  19920
ggtctttccg tcaaacttgc cgtttacaac cgttttccag gcgccgccgt ccgttgataa  19980
atcgatcgca tactcggtga ccgtgcccac catatcgcca ttatctttat agagatactg  20040
gaccggaagg ctgagcttga tacggatggc atccagggaa aggtttgtaa actggcgcgt  20100
ccagggcgcg gtggtggtga cagttgtgcc cacggccagc tcgttgtcga cctggggcat  20160
cccggcaata taggtctggt cctgtgtgcc cttgcggaac tcccatttca cgccgctgaa  20220
gttgtattcc ccgctgtcgt ttgccagcgg cgtatcgttg agaaaaatgt tctgagcggt  20280
caggtcgccc tgtatttccc cctcagaaac ggcaatgagc atttttaatt ttgcgaccga  20340
cagcagatcg tcaggctgct caaccggagt atgtgaactg ccacctcccc ctttggcacc  20400
ctgcaggatg gtttcttgtt taagaagctg catttttcca cccataaaaa aaggtgccga  20460
agcaccttta agttagtggc cgctggccta ctgctgatcg ctcgagtaca taccggcgct  20520
gactatcgct ccccctgcct cagtcagacc gtaggccagg gggacaggat gccccatagc  20580
gacggtattg accggcgccc cgaaggcgta gttaggcgtg ttgtccgtgc tggaggattt  20640
acccgcgccg aaggatggct ggggcgtgag catctggaca acgcccccca gcatcatcga  20700
cactccgacc cctgtcagaa ttgacgtggc gctgatagct gttgcactca tcgccgcgcc  20760
ccaggctgcc atgctcgcac cagcggtaaa gaatgcagcg accagcgcaa cagccccgac  20820
aactatctgc aggacgcccg aacttttggc cccctcataa acgggcacga tccggtacac  20880
gcttccaccg cgggtcatat caaactcttc cagcccgata ttgttgccac cgttaaaaaa  20940
ggcgaaacgg atccccttca tatgagcttc agacatatat tttttgaatc cgggaacctg  21000
tgaacacatg gccctgagca tctcgcgcag gtcggcaaca tcaaactgaa cgcgtttacc  21060
gaattttttt gccattttac cttcgagaat aagcgtctta accatgcatt ctgtccttat  21120
gcctgaccac ccggaccgtt ctgtcgcgat aatattttcc ataaggcgtt cgcgaagaaa  21180
ggtgcccgaa aagatgatgg agaatgatgt tatcacccac atataccgcg gcgtgattag  21240
tcaccgatgc ctgcacactc atcatgatga tatctccggg ctgcattgca ccggcggcaa  21300
tctcaacgaa tccctcacgc tcccagttgt cgtcgtagag acgctccttg ccgctctccc  21360
accattcgta aggtactgaa taattgccga gaacaatgcc gtattcgcgc agataaaatt  21420
cacggataag cgaccagcag tcggcgtaac ccagcaccca ctgccgcccg gcataatccc  21480
ggtcttcacg cggggaaatc gtacaaaaat ccccgtccgg ccaggacatg atccccccact  21540
caatccccga ccagtcgcac tggatccggt ccagctctga gggcaccagc cgaaccacat  21600
ccggatggga atgaatgagc atgatgatct caccgcgcgc gcgggcagcg agctggtctt  21660
ccggggagag cgtgaatgtc tcctcgggtt tatcggcaat gttgcggcag ggaataaaga  21720
tttgttgctg gcctgactga acaatcaggc cgcaggcttc tttggggtat tcagcagcga  21780
cgtgctgacg gatagcatcc agcaattttt cacgcatttt tatttcccct gcaggtttgc  21840
agccggaaaa ccgccgaacg gcagcggcgc atccgggccg tgacgatcct gacaatcctg  21900
ccggcggccg ccacaaacat ctttcgacgg gtcatcggtc ggtgtaccgt ctttggtaaa  21960
gtatttcgtg ccgttgtaat cgcatccggt cccgcttcgg taccagcccc gcatacacca  22020
ggtgcagaca ggcgtaatct gccgtgtcgg cagctgcagg ctctgaatat cgaaaggaga  22080
acacagctcg aaatcaacct gtacccgcgt ctctgcggtt ttagcattga cgtaaaagag  22140
ctgtaagcgc tcatcggccg ggctggcacc cggattaccg tttttccagt tggcggcatc  22200
gagatacttc gaaagcgtgg tatggatttt gaccttagcc ctgaccatat cgtcatattc  22260
aagacacagc gcggtgacat agtttccgac gttcccgacg gacagcgtgg gcgttggctg  22320
ggaacctgta ctcgataact ccatcccctt aagttcgtag ggatggggat cgtactggtt  22380
tccctgccag ataatggcgg gcagattttc tgcggcgaag gctgcccacc cctcttcctg  22440
aatattgtgc gcatgaaaac gcagcacctg atccataccg aattcagtgc cgtcgatctc  22500
```

-continued

```
aatcagctga ataacgctgc cgggctcaag ctgttgtatg tctgccgtaa aactcatact  22560
ccccccataa aaaaaagccg cccggaggca gctttcagtg tttttcgaga aaatcagggc  22620
gcgaacgcct gttcaaaagt gaaggccaca gtggcttttt tcccggtagg gaaagaaacg  22680
ctgaacgaat cggccttcat tctgaacagc tttttttcac cccatggagt ggtccaccag  22740
aacgatttag taacgtgaga catcaggaaa gcgcgcagcg cagccgcctc ctgtctggtg  22800
cccgtccagt ccaggttcca cgtttcctgt ttgtcgttga tccccatccc cgctatctgt  22860
ttgtagccat ccccgaactg ggcctgcagc gttcgggctg tttcagtgcc ctgcgctgtt  22920
tttcgcgtgc gccaggtaaa cgtgtccgtc actgtgtcct cctcgaataa agcacgccgc  22980
ccgcggacat ttcttttttc agtcgctcgg tgattgtctg ctgaacaatc gcctgcagct  23040
gtttcgccgt ccccgtggcg ttcgcctgat ttatgcttcc gtcactcccc tgctggctga  23100
tgctgactgg ggcataaaca ctgatcccgc ccatgccagc accggctgcg ttcccgccgc  23160
cgaccagacc acccgaggca tacccgcgca tcaggcgata gagattagcc acgccgatgc  23220
ggctggttga ttctttggtg aagacgaatt ccccgcggtg aacgataccg gctggctcgt  23280
acttgccgcc gtgcccggta aaaccgccca cgtcaaaacc ctgtggccgg tatgacggga  23340
ccgcgaatga ctgaccggca gaggaggttt tcgccccgcc gctaacccag cccattgcac  23400
tctggatggt gtaagccacc agcagctggt tgataacgga cacaatcatt ttaaggatcg  23460
agctggtgaa ttccctgaag ctcgccttcc cggttgtcgt caggctggta agctggcccg  23520
ccaacccgct gaacgtagcc tgagaaatct gctgaacgga gctgaaaacg tttgtcgctg  23580
aatcctgata ttcggcccaa ccctgtttcg caccggccag ccagtttgca cgcagggcat  23640
cttcagcttc gaacgtcgcc ctttgctctt ccagaacctt ttgctgcgcc tgagggttgt  23700
acgaatagct ttcgctgaga cgctgcagcg tagtttgtcg cccggcttcc cgggtggata  23760
acccctcaga ctgagcctgc aggcccgccc tggcggcttt ttgctgctgc tcaaacttca  23820
cggcctgatc ggccagctgg ttgagctttt gctggctggc aaccttatcg cccaggtcgg  23880
ccagctgccg cttgtactcg agcgtttctt ctttgtgcgc cagcagggat ttttcctgcg  23940
ccgtaagctg acgacgccca gcggcctcct gcagaacggt gaactgattt tcagtttgcc  24000
agagatcctg acgctgttta cttatgacgt cgttcacgct ggtatgctgc tcaagcgttt  24060
taagctgggc ctgaagggtg agaagttcgg cctgcgcctt ttcctcggct ttgtccccgg  24120
cgggcgttga gtagcttttg cctttcggtg tttttggatc cttccactgc ttttcaatcc  24180
cggcgcgggc cgcggcaatg tccttttcag tccacagcgt ggcgacaccg tctttcgcat  24240
cctggcggtt tttctcaata agctgactga gctttttctc tgctgaagcc cgcttttctg  24300
ccgccgtcgc gccggactcc accagctggt taaactgctg ctggctgcgg attgcctgag  24360
cctgctggtc cgttcgcatt ttttcccgcg cggctgccag cccttcctgg gcgtattgct  24420
gatcggcaag atcgtaagcc tgctttttca gctccacctg ctggcgcgcg tttctcagcc  24480
tttccgcatc cgctttctgc agaacgttgt taccggcata atccgggtcg accttaagat  24540
tgctggacag cgcgcggtac tctttctctg ctgcctgcca ctcagcaaaa gagtcctggc  24600
gcttcatcgc ggtgtcagga ttacgcccga cgcccagcat cgcatcccac gcaccggagg  24660
cggcattctt cacccagttc caggcttttt cgagggatcc gagattatcc tcgaccgcac  24720
cggcgcgctg aatgaccgcg tcggaatatg cccgcatggc cagctcggca gccttctgag  24780
aatcccccag cgcctgagca gaagctatct gttcatactg ggtggctgtc agaaaatgaa  24840
gggaatcgtt gagcgtcgcg accgcgttaa ccggatcatc cttcaggcgt ttaaactgat  24900
ttatggtttc gtcaacggcc tgcccggtag cctgctgcag cctggcggca acattgctga  24960
ccatgctgac gtcattaccg ctgaacgcgc cgctgccaac gacctgcgcc agcacgcctg  25020
cagcggcatg ctgagtgatg ccattacctg ccagcgagcg cgccagcgcc tgcagctgcc  25080
ctgacgtttt ccccgcgtag ttcccggtca ggatcagctg cctgttaaat tcctcagact  25140
ctttgctgcc gtcgtaccag gccttaccca acccgaatac cgccgcggca atccctccga  25200
ccatgctggc gatcccaaga ccgcgcagtg acagaagctg gtctatccac cctgcccggt  25260
tagccagcgt gatcccggag ccgcgcagcg cgccgaagtt accgcgcatg acctcgccga  25320
tcagtattcc cagttcctgc cgggcggcgg cactttgcag ccccagaccg tgcgtggcga  25380
ctttggcagc ttcgagcttg cggatataga cttcagccgc atcgctggca ccgacctgcg  25440
ccgccttcat gcgcagtagc tcggtaccgg agagcttttg ctctgcaacc tgttgcttca  25500
gctggctgag gaatcgcgtg cgcgctgcgg ccgatttttc ctccacgatc tgcagttctt  25560
tttgacgggc cgtggtgcgg gaaataaggg cgagataatc ctgctgggtt atgttgccct  25620
gtgccctcgc tgcgcgaaag cgcgcctgca cgttcgcaag cgactgtgtt tcaccattga  25680
gctggcgtac gccgtcgatc tggcggaaaa atgatgccgc aagttcatcc tgtcgacggg  25740
caagcgcagc ggcctgcccg tcattctcac gcatgcgctg attaagctcg gtcacgcggc  25800
ggtgagtttc atcaacggac tttgaaacgt tctgccagtc tttggtaagc ccttccgttg  25860
cggccgactg gcgggatttc atatctgcgg cagccgccgc gccagcgtca cccacggttt  25920
taaacgcagc cgcctgccgc tctgaagcgc gctgcattcg cgtctggact ttttcagagt  25980
cctcagccat cccggttagc tggccctttta tgcgggcaac ctgctcacta aacgtggcgc  26040
tgtcgacgtc aaggttgatg accagatcgc taatctgctg ggccatatcg gatacctcct  26100
gttatcccct cagctgcggc catcagcgca tcatcatccg gctcgtcatc gctgatgacg  26160
ataccggaag gagaaagcag gctgaaatgt gcgggggtaa gttccgggtc gcggaagaaa  26220
agagtggaga tggaataaag cagctctgag aaatgcgcat cgagctgagc gtcctgaaaa  26280
taatgctccc ggtagaactg gtgccagtcg cccagctcag tggaagtcat tccagccagc  26340
atggcgcgcc agtcgggtcg cccgaactcg cgcgccagat tcaggacaaa cttcagctcg  26400
ctggcaaggg cttttccgcc gcaacgggtt ctgcgctttc ggcctccgct ggggcatccg  26460
gatcggcagc tttgtcatcc tcaaccggaa cgagcatgcc ggagagcagc tttatttcca  26520
tttctgcttt accgatcgcc tccggcggcc agccgctaag cacctgctgg taaagcgtct  26580
ccacatccgt gccagccgga tcgttatgcc acaaagacat cgcaatcaaa cgcgcaccgc  26640
agcgaatatt tgagccaatc agcctggccg tcatttcctg atcgctgatg ccgtcgctgt  26700
cagcgctgac ggccttttcc tctgcggcca taaacgtgat gtactcaata cgctgaagcg  26760
ccgacagctc gaagatggtc agtgattctt tttgccaggt gaacttctct tttttcagaa  26820
acatgcgtcc ttccttacgc tgcagttacg gtaactttgc agaccgcaac gaaattaccg  26880
tcgctggtca taacaataac gtcagcggtg cctgccgcca cgccggtgac ggtgatcgca  26940
ttaccgctaa cggtgaccgt tgcttttgcc ccgtctgagg ttgccacacg gaacgaggta  27000
tctgaggcac tggctgggtt aaccgtcaca ttgagcgttg tggttgcgcc gacggccacg  27060
cttgccgtgg ctttatcgag cgtaacgcct gtcacgggga tattcggggt cccgctttct  27120
tctgccagtt ccggcttgcc ggtattggta attttcgctg tacgggttat gacctctttt  27180
gccggaatgg ctttacccag gctgctgcac cagccgcgga aaacgtcgac ggtaccgttc  27240
```

-continued

```
gggtatttga ttttgtaata gcgtactgag ccatcaataa accatgcgac aaggtctttt 27300
tgcccttctt cgcccggctt ccaggcgagg gtgaacgagg tatcgccagc agattttgcc 27360
ccctgggccg tcgcgttcca gtcggcatcc tcgtcgtcga ggtaagtgtc gtcatacgat 27420
tcggcggtca tttcgcccgg cgtcagctct ttaattttcg ccaggcggtt ccagtcgata 27480
tccgagagtg ggttagcgaa agcgttgccc gttccggtgt aaagccagag ggtggtaccg 27540
gcacctttca caggggccag cgggtttgga gtaggcataa gtacctctta aattgaatag 27600
gtgattaagt acgtgaaatc gactgaaccc caggtggcca tttcatcatc ccgctgatag 27660
tcataaccct gcggggtgaa cgtctcgacc agttcggtca gacctgggat gaaggccatt 27720
gccggataca ctttctcttc catccaggaa tcaagcgcgc tgtcggggct ggaggcttta 27780
agaaatacct cgatgtgaac aaccgcctgc cacgaatctt cgtcaagcga ttacacgtct 27840
tgagcgattg tgtaggctgg agctgcttcg aagttcctat actttctaga gaataggaac 27900
ttcggaatag gaactaagga ggatattcat atggaccatg gctaattccc atgtcagtcc 27960
agtgattctg aataggcgat aagtccggta taaccgggga taatctcacc attatcagct 28020
tcaaattcag gaattgtgcc ggtggtgatg gtgtattgag gctggccatc ttccttcgcg 28080
aaggctgcca ggtcttcaat ctgcttagct gtaagaacta ctgtcatgct cattcctcag 28140
ttgtaaaaaa gccccgcgag tgcgaggcga tttgattgaa ttctcggctc ttatctcagc 28200
gcagcccctt actgcgtgcc ggttgctcgg tgatgagcat cagcgatgag acattaaagc 28260
cgaccgaagg ccagcggcgt tcctcatgtt gccgacagag ccatatcgac aagaggacga 28320
aaactagcag catgaatcgc ctattggtta ttcgacagtc gcactgattc gtaaatccgc 28380
tcacacgtca ttcctgcccg gtagctttcg tcagatcgtc cagcataata tcgagctgct 28440
tctgcaaggc ttccgagcat gtcggcaagc attgctgcgt tggctccggc tgttttgctt 28500
ctgacggaag tggcgagatc tgcggtgtgc tttgcggcgt ccatgtgggt agcgagtttt 28560
gttgcttcgg cgcgcagctg cttaacagtg gtagccaggc cagcagaagt aacggcagcg 28620
ctcgctgctt gagcttgagc atctttaacg gcctcatccc gggcgattgt tcgcccttgt 28680
tcaatcatac gagctgcggt ctgtgcattc gcttcctgtg aagattccgc gctatcccgg 28740
tcagcccact ttattttcca gctgcggttc gtccactcac tgccagcgag aaacgaacct 28800
accaacgcaa caatcacaat gatgcagatg ccacccggct tcactggtct atcccccagc 28860
acgtcagtgc gctttcctgg tcccgccgtt ctacctgccc ataacatcca tccttctggc 28920
ccttggtcag gcggcaatcg cggccaccgt ctttaatcca ccagcggata gcttcacagg 28980
ctcctttcgt atcgccagca ttaattcgct tatagaacgt agacgggaaa catttccgg 29040
ggccgatgtt atatgggcag aaagaagcga tacccgcttt ctgtggttcg gtcagtggta 29100
ctttgatatt tcggtcaacc cacgccagcg ccttgtcgcg ttcaatggcg tttacctggg 29160
cgcatttctc agctgacagc ttcatgccct gtactactgg cttgccatca accattgttg 29220
caccacggca aatggtccag agtccgccgc cgtcgcgata tgctgtcaag ctgttaccct 29280
ctttctcatc cagaaactga tcgagaatca cgggtgcgga agccccggca agaatcaaac 29340
caacgaccgc tgcgctcaat ttattcttca gctttagaga catagccatt gcgccgatcc 29400
tcccgttctt tccagcggaa ataccagttc actgcacagg tgattaccgt gcatgcgata 29460
ccgacaataa ttgcccagtc gctcaggctt aaccctgcaa ttctgtcggc caacatccag 29520
gacacctctt ttgctgtttt agctgtttcg gcatatgcct tcgctgatac accgcagccg 29580
gcaagcgtgg ttcctgatcc atatgaaagt ctgctgtaaa tggtgctcat tctggtcata 29640
gcctcacctc cgatagttcg gatggcgctg tgtgtgattg aaggggatca ggcaaccggg 29700
ctcttatgtt caagtaaaaa ttaaggatga ttcccggtgc ctgaagatgg tgatcaccac 29760
agcaacgggg gagcgtggtg atcgttatga ttttttcagt ttttccacct cttcggtggt 29820
ctgtataaac ctgtctgcct ccagttctac gccgatcgcc cgacggccaa gttctattgc 29880
agctttcaca gttgaaccag agcccataaa gaaatcggca acgatatccc ccggtctgct 29940
gctggcgcta atgatctgtt tcagcatgtc ggcaggtttt tcgcatggat gtttgcctgg 30000
ataaaactga acaggcttat gtgtccatac gtcggtataa ggaacaagag cggaaacaga 30060
gaagcagcgc cgaaggattt tgtattcctc cagcaattct gaatacttgc ggtttaatga 30120
ctggtaggta gccaccagct ggtggtgagg atgttcaagc ttttgctgaa tatgtttatc 30180
gatggcgatc cgcgtgaaca gttcctgcaa ttttcgatag tccacttcat tcggtagttg 30240
ccattggctt gcaccaaacc agtgtgacgc catgtttttc tttccggttg cctcagctat 30300
ttctttcgag ctgacaccca gtgattcacg ggcattacgg aagtaatcaa tcagcggcgt 30360
cataatgtgc tgctttagct ctgtgctttt cctttcgtaa acatcctctt tacctgtata 30420
cggtccaaga tagtgctcag caaacaaaat ccgttccgta gatggaaagt acgcacgcag 30480
gctttcttta ttacatccat tccagcggcc cgatggtttt gcccaaatga tgtgattcaa 30540
aacgttgaat cgggcgcgca tcataatctc tatatctgag gccagtcggt gaccgcaaaa 30600
caggtagatg ctgccagcag gtttaagaac gcgagcatac tcagccaggc agctatcaag 30660
ccagcgtaag tagtcctcgt cccccttcca ttggttgtcc cagccgttgg gcttcacttt 30720
gaagtacgga ggatccgtaa ctataagatc aatagagtta tccgggaggg tggcgacgta 30780
atgcagacta tcagcgttga ttaactcaac actgtttatt tttacagtat ttttcataga 30840
tcagtaagcg taactctgat aggctcacgt tgcttttgcg ctaaagcagt gggccttggt 30900
tagcttgtga cctgaaagca tgagctgatg gctggccggg tgcgctaaca cccaccagcc 30960
gcccatttcc acagcagaaa acccccatta ctggaggcgt ttataacatc cgaactggta 31020
atcagataac cccgccatca ccagctgcgt aagtatgagc tggcaacgtt cgtggctgag 31080
gtgggtattc tgtgcaatct ccccagccgt tgctggttta tcgcttaatt cattgaaaac 31140
agcctttgcc gtttctgtca tatcttcctg atttagcatg tcttttacct aaaattagtt 31200
gcgtgacata cagataactc tggttggtga taccagcaag agaagaattt gattctgcaa 31260
ccaacaaggc ctttaggcat caggcaggaa tgagatgcaa taaaaaaacc acccgaaggt 31320
ggtcttatat gaatctttaa cgcggactta gcaaatattc cacatcatcg tactaccgtt 31380
atggttttcg ataatttttg cggctgggct agtaccaaaa gagtgcatat agcaatgatg 31440
aatagtaagg accagatcct gcaacgtttg gtcactctct agctccatga tatttaaacc 31500
aatattttga gctttgtcca aatgaatatg tctggcatgt gcatacgttg cttggtggtt 31560
gtttaactca tcacatatac gcttagcctt agcttcagcg tcagcctgac ctgcgaacat 31620
accagtacaa agccatttct ggacaatttc gttcgcccag agaattgctt tttcacactc 31680
gccaatcaac gttggattta gtttttggaa cgtaaattgc caccattgca gtgcagcagg 31740
gttggcaaaa atttccgctt ttgctctctc atactcctca ataattgcat gagatgataa 31800
cccattaaac tgtggatcaa ttggccccaa gttcgactgt ttacctaaaa cgatctgctc 31860
agcacaacaa gcaagcattg tgccacaact cattgaaatc ataggtacaa tcgctcggat 31920
attggttccg aactttgaac gaagataatg accaattgat tctagagctg cgatatcgcc 31980
```

-continued

```
tccaggagta tggagtaaga tatccaatcc cagactcgta tctaacccat tgatagcaga  32040
cataagacca tttttatcat catctgacat ctggatcaga tgttgaaacc caggcccccc  32100
tttttgaagg aagcctgagt aataagaaat tacatttcgg ccagtatgtt tcgataaatc  32160
acgtaagtac ttgtggcgaa cctcatccgc tggtgtacgt tgagcgatag tacccatctc  32220
acccaatacg tctatccaat ttggcatgtt atcaatttat cagtatgagt acagttggtg  32280
agattgctga ccgttctgct cagtagtatt tggtgttact gtgctgtatg aatagagcac  32340
accacttctc acattcagat cgttttgctg agcgagaaca cgcatagcaa aatgctgtac  32400
ggattcgcct ttttgaaact cttggggttg tatgcccatt ttttcgtaaa attcagcagc  32460
gctcatgata tgtccctcgt ttttttctac atctatgcaa ttccaggagc catcaacaca  32520
agatgtagta gttagcagtc gtcaaataca cgaaaagcct caagatgagg cttaaaaaga  32580
ttctttttga taaagattta gccaaactat agcggtcaaa atgcagattt gacaagtata  32640
aaaagcactt aaagcctata aataggcagt ttttgagaat taaagcatct ttaatgaggt  32700
tgaacaaaat gcagtcttga cgctgaacag gactttactg gaacgtagag ctaaatggtt  32760
cgatttcatg aaccagttac aaaaaaaccc gctcatcggc gggtttataa aactttggca  32820
acatatcaaa tatgcttcaa atatggctta ttttgttgca ttttgcaagc gtgtttgaag  32880
gagatggtga aatttacttc acatttctgc cactttgagg gcttcttctt cctcatagta  32940
ttcaagagcc atggccaacg cagattcatc aagctgggta aaagcggcct ttaacccagc  33000
ccagtgccct gaatagacac gcaaccatgt cgaacggtca acgctaacca tgcgggccaa  33060
cgctgcacca gcatagtctt tataggtttc attatttctg gttgcggcaa tttcctgccc  33120
tgccagccat accaggccta tcagtttctt tactacgcgc tcctgaaggg agttatcacc  33180
caggcatttc tgataagttt tccagacgta ttcacacatc atcacctggt gcttatagct  33240
aaggtcaaaa ccgtagcagt accgcaacca ggcctgctgg tatccactaa gcgcggacac  33300
tgccctacgc cacggcgcgg actcaaattc cgcatctttt atcggcggca ttggcctgcg  33360
gcggctgcgt gtttccagca catacagtgg cgcggaaagt gagttaacaa agcgtggccc  33420
cttctctcct tcgagttcga cgagatgaat tccacggcga ggggtggcat ttttgtctgc  33480
tggtgggtgt tcactgaaag cctcaagctg cccttttgtt cccccagaca ggtcaggtag  33540
cgcgcggcgc aattctattc ttacaaaatt caggtcttgt tgattcatgc ttctttgcgc  33600
tccatacact taagctttcg caattacgcc gatcgccagc gcccgatcca taaaacgcag  33660
tagcagctca agctgcgtac catgcttctg ctcgaatgcc ggtacatcgg cgtgtaactc  33720
gtcgtggcac tctctgcaca gagggatcac gaagagatca tgggcttttg ttgctgtccc  33780
ccccataccg tgccctacga tatggtgcgg atcatctgct ggccgtcggc aacactcaca  33840
gggttgtgtt ttaacccagc gggtgtacgt ctcatttatc cagcggcgtc gctttggcct  33900
gagcatgaaa gattctggag actccggatc aacagagagc gtgaggatct tcttcgcctt  33960
ctcctgcacg aggctggttg cagaagcgga aggcacaatg tcgctttccc tcatgaccga  34020
gcggatctta tcatccggaa ggcgtagccc cttgtgcgca acgctttccg gaataacatc  34080
agccaggtcg tttctgacca tccaccagca cagttccgga agcgtcagga tatgcgactc  34140
gggaaaacca gaatcacgcc gaatgacttc cagaatccag gataccaggt ttcctgccgc  34200
tatacctgca agctgttcgg tatgctgccc cgacaaagtg tgatcgcaat gccagcacag  34260
gcgaatactt cctggtgggt gccgcattgt tgtgaagttc ttgtcgtgcc acgatgaatg  34320
tggccactgg cattcaaacc gattactcaa ccattgctca agggaaggaa gcccaccagc  34380
acgctgaata acccgatcat tctcgaagac ctgccgcatt accggatcat cagccagcgg  34440
ctgaatggcg gcgggaacag ctcctgtact gaatgacgcc atttcttctg gttcaggctc  34500
aagcagaacg cgaccgcgca taaagaggtg catcagttcc gcgccgggac gaaacaacac  34560
aatccccata cgatgggcga tctcgggggt aagcagagct ctcacgcgac ctgccccctg  34620
gcaatgtgtt ctgcccacag tccaccaatc cagcgcacgc ctttcgccgt gaaacgtgcc  34680
tggctgaatg catgatttga ggttacggat gtgccggttt tcacttcaaa acggcccgca  34740
tcaatatgct gatgccgtgg ggtcatcgtt ccgccaagac gatacatgat gtcgttctca  34800
aggaggaata accgcagatc gggctctttg gccttaagca gttttgccac ctggcggaat  34860
gacattgacc cactggctgt acagtaccga tcaacaaacg ctaccttcgg cgccgcggca  34920
gccagttcgt tagtcaactg ctgtttttgt tctgcaaggt cagctgcaag acgtagggct  34980
tcagagaatg attgaggaat cgtctgctgc tgtgcctgct caagctcctg ccagcgatca  35040
accagacgcg cggtaaactc cggcgacagc tgcgcgacaa cgatataact gtcccgcttc  35100
cctatcagat aaaccgatac cgactgattg aggtgatttt taacttcccc cattgggggg  35160
agttcaataa caccgcgctc tgccaggcgt tcaatggacc gtttaacatg gtcatgtctt  35220
gattccacca gctcagcaat atcgctgctg gacatggtta acgctgttgt tgctaactgg  35280
ctcatacttt tctccatatc aggcggctgc acccgccggt tcatatctgc tgattgttat  35340
ctctacccga cctttcggca caacgggtcc ccattccacc agcatgcgct taatctggct  35400
gtcgtcttcc cagacacccg catgcgtcag cgcgtcaaac agggctttgt tgtaattatc  35460
gatatcccgg cggcgcgcat ccggcgggta cagagtgatt tctaccgctg ccagttcagt  35520
cgatggcttc gggagacgtc gtaattgctc aatgatcgcc acgcaggcag cgctctggta  35580
tttacggcca gcggcgctaa tgaggtgacg accggccagc ggccccttgt tagggggcgcg  35640
ccagtaagtg ttcacgctcg gaggaaaagg caggatcagt ttcacgcggc ctctccccgc  35700
atattgcgaa caagttcaga agcagcagta atgatttcgc tggtggcagt ccgctccagc  35760
cagagttgat tgatattggc tttcagcttg tgttgcagtg actcatccag catgtcagca  35820
ccatccacct ggtcgaatac aattctaacc tccagcggcc agatacggga ctcgggaagc  35880
ggatccgata ctggtttagc tttctcacga atgtgcatgc ggatctggcg aatattggac  35940
caactggaaa catccaggct tcccatggct gcaatgaagt cagtgctgtt catgccatat  36000
tcaccggatg cttcaagggc aacagtgcga atacgttccg acatatccag gcgcacagca  36060
gcgtcatcga attcaatcga caacagccac tcatccacac cgaacaaaat actctcacga  36120
ataagcagct tcgctttgtc gatcgttaaa ggtgatacct gagtgaattc cggtgcttcg  36180
acagaatccg ccgcccaggt atgcccaaac ttcgattcac tgaatgtgta ttcttcttta  36240
tcgccaaacg cagctctaac gcatgcccac gcctcgacac cgctgatagc aaaaatatct  36300
ttctgggtga gtggcaactc tgcttctggc ttatcagctg caggaggtgt ggcagttaca  36360
ggttgagact tgctggcagc aaattgtgcc aaagccataa acgcccgccc ttttgcctcc  36420
agttctgtgc ggttgatata gctgaaccgc tcgccacgcc atgacttatc gaatacagct  36480
atggcaccgg caaaaaacgc gctggtgggt ttctgttttt cgtcagcagg tacaaaccac  36540
acaggcagat cgaacccaat gcgcccgcga atgaatacaa tgtgatcggc atcttccggc  36600
caccacgttt cactcggcgc ggcttttatc aggaatacat agcgaccgcc cttctcgcgc  36660
tgggctgctg cgtagttcat gatgtgcgtc atgccggtga tcgcctgctt ctcgtggtac  36720
```

-continued

```
tgcgaacggc tatacggtgg gttgccatag ccagcgccac ccagttcagc cagacgttca  36780
gaccagtcct gcgtcagcgc gttatcttcg gcggtgtacc atgccgggca tttcgcgttg  36840
tcgtcgtcag caaacaaatc cagaactaat ggaccaaata gcgcgttgat cccccaaaaa  36900
agcagatccg gtgtccgcca ctgatcgcca acctctttca attcgtgagc tggtttgcta  36960
cgcagtgccg ccagcgcctg gcaatattta ttggtcatca tgaacggaac cccgaatttt  37020
ctggcagtga gtaatcaaca ctctggaagt ttgcgcggct ggctgagtta gtctcccatt  37080
tgccgttaac gcgttcaggc cggccagcac tggaccattt ggtcgcgctt tgcaggtaac  37140
cagggaagtt ttttggaatg aacagagttg ccgggcggag gtattgcgcc tgctcgctat  37200
cacgccaatc ggcatttttg taatccacta ccaagcacag gtcatcaaca gtgaattgtt  37260
cccgaagacg ggcgcgaata ttctccagcg acgtgctgca tacctggtag cgtgagccag  37320
tagtctgatt caggtaagac aaaacctgtc tggcctgatc agtaatcaca acctcagggt  37380
cgggttgcgc cgcaaccgga caagagggtt ttgaagttac ttgtggttct tgttttgatt  37440
ttactgacgg atccccacca gattctgacg ggtcaaaacc gccttttttg ctggatttcg  37500
acgcctcaaa ttttgacggg tcggattttg atgcatcaga ttttgatggg tcagattttg  37560
atgcgtcaga ttctgacagg tgagaaaaag cagcctctcg caacttaacg acgttaagct  37620
gatatacgtt cgatgcgtta cggttcccat tacggcgctg cttacgggaa agccagccat  37680
ccttctcaag ctgagcaagg gccgtcctta ccgtactttc tccagcaccg atttgacgtg  37740
cgatcgtgcc aatagacggc cagctaacac cctcatcact actgaagtcg gccagacgcg  37800
ccatgatggc aacgctggat aacttcatgc ctgacgaagc gcatgcatcc catacgtaac  37860
cggttaattt agtgctcatg gtcgtccttt aattctgtaa atttacgctg gaattgttca  37920
agagggctga agcactcatg atcgtaccct tcgcgaaggt atataacgcg ctgtgtatct  37980
ggctcccagc ggacaactct gacgggaact ccgtagtgat ctctgaaccg ccggttaact  38040
tcagccattc ctcgcgcccc ttctcgttca tctgaacaaa tgcttctacc atcaagtctg  38100
ctggctggta gttgcctcca tcagccgcgt tatttatgat ttccacatag ccgaactggg  38160
catctttacc caccagcggc aaacatctga attgcttagc tggtctgaat cggtttacac  38220
tgttcatgcg ttagtttctc cactgatacg acacgccaag gcgcccggag ctgcacactc  38280
gcgggcgtca ccttttctgc ctgttgaaac gaatacgtca atcgcctgat ctgaaacacc  38340
aaccccataa agcgccataa atcccaggaa cccgtgaatc tggtggcgga gcttcttact  38400
gaataattct gaaagcattt tgcgctctga tgaatcaatt accccatcag ccgctgctgc  38460
catcttggca ttagccagct caccagatgc tgctgccgct ttcatctcaa tgctgtacag  38520
ctcaacgtta tccaggctct cagcagttgg aacatccacc agccatttcc cttttcggtt  38580
cgcctggtac tcggccaagt aacaagaacc agacaggtcc tccatccgtt ccagttctgc  38640
caaggtaaag aaccgactgc cacacttctg gtacaggtgg ttgtggaact ggtcgatagt  38700
catccctaaa tcggaagcca tacctaagcg accatgcttg tgtgccttac acatcaggcg  38760
gattgctgta tttatgctgt ctaccatgtt gatttccctc tggtagttaa taatcaactt  38820
aaagttgact attgttgtta gcggaaggta tgccgtcatt tttgttcgga taaatatcag  38880
gtcgtaattg atggggagtt actacccatc cgccccattg gcagagttga ataactcttt  38940
cagaaggtac tcggttcttt gcaatccagt tcgcaacaga ttgaactgat tggaattcaa  39000
accgccttga tacctctgaa atcgacccga tcgccttcac agctttagct gttacattct  39060
tgtgttgaga tgacatgtgt tctcctatga ctaagcctgc atcaatacta cttatagtag  39120
caattattag caacttaaaa tagaaatgac aactatgcct tgtgcgctta atcttctact  39180
tatggtggaa aatgctaaat acaaagactt tgccgaaagg ctaaacaggt ctctccaaga  39240
gcaatctatt ggagttaaag aattgtcaga gttcagtggt gtctcgtatg agatggcgcg  39300
gcgctacact cttggtactg caaagccgag agatgagaag atgattcgaa ttgcagaaag  39360
acttgccgtc tcaccggctt atcttgatta tggtgtgcct gttaatggtg gcgacgcgcc  39420
agccaaaggc acggtcagaa tagagcaatt ggatgttcat gcttcagccg gttccggata  39480
tataaaccaa ccattcccta caatagtgag ctcaatagag attccagaag agaggatctt  39540
cgagttgttt ggtcgtagaa gccttgatgg catcgtcatg ataaatgttg atggcgatag  39600
catgatgccc acgctttgcc caaaggacct gcttttcata gacagcaagg ttgaacaatt  39660
cagcggcgac ggcgtttatg tgttcaattt tgaagacagt acgttcgtta aacgtttgca  39720
gaaggtaaaa gggcgccgac tggcagttct ttcagacaat gaacattacc cgcccttctt  39780
catagaggag catgaaatga atgaactata catattcggc aagctaatca gatgcttacc  39840
tctaaaaatg atagagtttg gctaataatt aattcatcaa gaaaccggcg aaagccggtt  39900
ttttttacgc ctccaattcc tcacctcata acactacact actaaaaatt tcatttccta  39960
ctttttgttg ttgcaattat ctacttaaag tagctatagt cattgcatcg aaagcgaaca  40020
ggcaggacgc ccacgaagta gccgccggtg gcatatgaat aaccggatga ttcgctgaca  40080
gaaaacttag gttggggta gaggtttaca tgaatcattt attcacatgc tcattttgcg  40140
gagcaaccga actgggagcg ataaagatcg tcgcaaaagg tggtaaggac gaacctgcca  40200
tctgttcgga atgcgtagtc acatgtgtag aaaaaatgat cctgactaaa aaatcagagg  40260
ctgaaaaacc aacctctgat aacgaaataa tatcagtcga taaaaaacta tttaaagagc  40320
ttcttcagct tgtcctcaac cttcctgatt tcggaagtaa gctggctgct gttgacattg  40380
atagtagctc cacatcgaca agtgaaactt ttgttcgact tgagccaagc gatttcttc  40440
ttcgtcttag tgccgcactt agggcatgcg ggtaacgtaa tttcctggtt atcaaaagcg  40500
cccataaaca tccctcttgg ttgtgtgaga acaccaagat accaccgcgc ctgatgtggt  40560
taaaagcagg ctaaagcaat aacaagtaac tccctgttct ggcggcccgg tgttttcccg  40620
tgtatttccg gtaaccgcca gccttttca gggcacaaca gaaaagggca tcaccgggcg  40680
acgggctcat aacccaatcc acccgggcaa aaagaaagcg gtctctgcaa gccgccgacc  40740
aatgcaggtg cccttctctg ttgtgtatgg agaaactaac tttttagcgt ctgtgcagat  40800
gcgctgagga accgagaatg aataatccgt ttttcaaaaa tatgttggtg tatcgcatta  40860
gtcgcgattt caccatcaac caggaagagc tggaacagca gcttgaacta tttcgcttca  40920
ctccatgcgg tagccaggat atggcaaaaa ccggttgggt atcaccactt ggtcagctgt  40980
cagatcgctt gcatcacact gtcaataatc aagtgttgtt ggttattcgc cgggaagaaa  41040
aaatactgcc atctcctgtc attactgaag aactgcgcaa gcgtgtgtcg cgtctagaat  41100
ccgatcaggg gcgtcgcctc aaaaaaactg agaaagattc gctgcgtgat gaagtgttgc  41160
actccctgct tcctcgggcg ttctccaaaa actcgactgt tggtttgtgg atcaacgtca  41220
ccgacggtct gatcatggtt gatgcagcca gcgctaaacg tgccgaagac tcactggccc  41280
tgcttcgtaa aactctcggt tctctcccgg tggtaccgct gactatggaa acgccgatcg  41340
aactaactat gaccgactgg gttcgttccg gtagtgcgcc tgctggcttt ggcctgggtg  41400
atgaagccga actgaaagct attcttgaag atggcggtat tggacgcttt aaaaaacaga  41460
```

-continued

```
ctctggtcag tgacgaaatt catgtgcatc tggaagctgg caaagtagtt acaaagctgt  41520
ctatcgactg gcaacagcgc attcagttcg ttctttgcga tgacggcagc atcaaacgcc  41580
ttaagttctc taatgagatt acagaacaaa acgacgatat cgaccgtgag gatgcggctc  41640
agcggttcga cgctgacttt gttctgatga ccggcgagct tatctctctc attaacggat  41700
taacaacctc tctcggcggc gaagccaagc gataaacacc aggcaacaat taccccccata  41760
agcatgggtt gggttgctgc acgctaaatt cagcaattca ttaatttaat ggcgcggtgc  41820
agcgcgccaa tatggagaaa accatgagct acattcagac attatccggc aaacatttta  41880
attacctcga tatccaacag gacgatatcg tgatcgagga tattgctacc gcgttgtctc  41940
atatctgccg ctttgcaggg catcttcctg agttttacag tgtcggccag catagcgttt  42000
taaccagcca cctcgttccg caggagtttg cattagaagc actgcttcat gatgctgctg  42060
aagcctacct gcaggacatc ccctccccac ttaagcgcct gcttccggat taccaggcaa  42120
tcgaagctcg tgtggacgca gccattcggc agaagttcgg tctaccaact gagcaacacc  42180
caaccgtgaa atatgccgac ctggtgatgc tcgccagcga acgccgcgat tttgagattg  42240
acgaaggttc catttggcca tgcctcgagg gagttgtccc aacggattta ttcattatca  42300
acccagttcg tcctggccag tcatacggca tgttcatcaa tcgctttaac gagttgatgg  42360
agcagcgcca atgcgccgca tgaaggtaaa agaactcgta gcggaggcgt ttgcctccgt  42420
tgctgaattg ccaccaaagc atgcgccgct tatgcgcgaa gtcgccacca gactggacgc  42480
tacgttcgca gcattaaaag agtctctggt gcaactggaa caggaacgta aagataaaac  42540
gccatgaccg tatttgaata tctccaggct catccgaata ccaccagcgg tgaaatcgcc  42600
aaaggtatga acaaaaagac cccagcggtc gccggagcat tatctcagct ctatggcacc  42660
ggtcggatcg tgaagtctgg tgttcgcaag ggtattccaa cataccgcat taacgatatg  42720
ccgtttggtt gcagtaacag cctaaccatg atgtttaacc agctcttgag cagagccaga  42780
caaggagcag cccaatgaca gcactcaaca aacaggcgct gcgtgaagaa ttccagttca  42840
tgcaggacaa ctatagcgac ccggcagacc acgatcggca ggtgatttac atcgaggcgg  42900
aggcgctgct ggatgagttg gaagccaaag actcaacgat agcagcacaa caacatgaga  42960
tccgtatgtt gctgaatgcg cttgaggaaa aaccatgccc gaaatgcaac gacacaggaa  43020
tgactgatag tggcggcacg cagccatggg gcgagccgat tgagattgaa tgcgactgcc  43080
gacagcagga tgccaacacc gcagaacttg tagccgctgg cattggcgtg aagggggagt  43140
gagatggata aattaatcaa acctaccgcc aaaggtaaat atgacggttc atgtgattat  43200
ctttgctcgg aagatgcgcg attcatcgtt atgcgcggcg attatacgga agcggaaata  43260
attcaggctt ctgtgtctca agatgtaatc gactcggatg gtgcggctga ttttgcaagt  43320
agcgcccgct attatcagtg ctggtacaaa gttagcccaa taggtggtca ggatggctat  43380
tcaggctggc atcatcctcg tgattcgccg tgtcgcggtg catatttcgc atcagttttg  43440
caatgggatt aaggaggact aacccatgac aactaacaac cacccggcgc acggtcctgt  43500
atcactcgat cgcctgcacc agatacgcga acacctgctg catgataccc aatactcaaa  43560
cggcgggaac agagcctaca ttctcgctga tgtattgaag gtgattgatg gggctattgc  43620
ccgcgagctg gtacgccgtg agcatgcagc gtggtcacag gctactttcg gcgatgtcgg  43680
tccagttggt ccgctgaagc acctttccaa agaagcgctc gaggctgctg ctgaaccagg  43740
cgaccttagc gaatgggctg acatgcaatt cctgttatgg gatgcgcaac gtcgtgccgg  43800
tatcagtgat gagcagatta cccaggcaat gataaaaaag ctggctataa ataaggttcg  43860
ccaatggcct gagccgaaag acggggaacc tcgattgcat atcaaagaac agtcagagca  43920
ggagaaaaaa taagaatgtt tagcctgatt cggcgcggtc aaatctacac ggacagtagc  43980
aactggcccg taattatcca tagctgtagt gatcactcgg tccgaattaa acgcaatgat  44040
ggcgagctga gaacgattag catcaaacgc tttaacgaag attttgaacg agtggagcat  44100
gatgagtatc gcaaaatatg tgccgaaata gagcaggaaa caaacctgaa aaacctacgt  44160
gcgatgcgtc gcggcaagat tactgaatag ccaaacagga gaatatttaa cgtgaacaac  44220
ttaatgatcg accttgagtc catgggcaaa aaaccgaatg cccctattgt ctccattggt  44280
gccgtattct tcgatccgca aagcggtgaa ctgggtcagg agttttacac cgctgttaat  44340
cttgaaagcg ctatggagca gggagcggtg ccggatggtg acactattct gtggtggtta  44400
agacaaagct cagaagcacg atcagcaatc tgtgttgatg atgcgatgcc gatatcatct  44460
gccctatctg aactgagcca tttcattaat cggcattctg ataaccctaa atatttaaaa  44520
gtttggggca atggagctac tttcgacaac gttatattgc gcggcgcata tgagcgtgcc  44580
ggccaggttt gcccgtggca attttggaat gatcacgacg tcagaaccat cgtcacatta  44640
ggcagatctg taggtttcga tcctaagcgt gatatgccat ttgatggggt tgcacataac  44700
gcactggctg atgcccgcca ccaggcgaaa tatgtttcag cgatttggca gaaactaatc  44760
ccaaccacca gcaacagcta aagttttccc cgggtgcagc cgggataatg gagaaataac  44820
tatgagcaat attttccagt tagctcccaa cgattgggtt tgtgaaagcg ttttgatcgc  44880
ggttactggg ctcaaacccg gaaccatcct ccgtgccaga aaagaatgct ggatgattgg  44940
gagggagtat atccacgtat cgcctgacgg aaatcctaaa ccttccagtg agtgcatgta  45000
taacagaaag gctgtagatg cctgggtcgc ttcaatgaaa agcaagcaac cagggtgatt  45060
tgatgccatg aaaaaggtaa gctcgtatcg ctcttgggcg tctggaggta acaccaatgg  45120
ataaagtcac atatccaaca ggcgtcgaaa accacggtgg cacattacgc atctggttta  45180
attttaaagg taagcgtgtc agggaaagtc tcggtgtccc tgacaccgct aagaacagga  45240
agatagccgg ggaactgcgg acatcagtat gttttgccat ccgcacagga acctttgatt  45300
atgcaaccca gtttcctgac tcccctaacc tcaaggcttt tggtgtaagt aaaaaagaca  45360
ttacagtgaa agaacttgaa gaaaaatggc tggatctgaa acggatggaa atctgcgcga  45420
acgcatttaa tcgctatgaa tctgtcgcaa ggaatatggt gccgaggatc ggaggtaatc  45480
gcctggtgtc agcagtaacc aaagaggaat tgctgtatct gaggaaatat ttgctaactg  45540
gttatcagaa tccgacgaaa aacaaagccc cggcaaaagg gcgaagcgtt gttactgtga  45600
actattacat gacgacaatg gccggaatgt ttcagtttgc tgcggatcac ggttacttag  45660
aggtgaaccc attcgaggga attaagcctc tgaaaaaagc cagggcagaa ccagatcctc  45720
tgtctcgtga tgaatttatt cgcctgatag atgcatgccg gcatcagcag acgaaaaacc  45780
tgtggtcatt agcagtgtac acaggaatgc gtcacgggga actggtctcc ctggcctggg  45840
aagatatcga cctgaaggct ggaacaatta ccgtcagacg taattatacg aaacttggtg  45900
agttcactct accgaaaacc gaggcaagca cagatcgagt ggtgcatctt atccagcccg  45960
caatcagtat cctgaaaaat caggctgaaa tgacaaggct gggcaggcaa tatcacattg  46020
aagtgcagtt acgtgagtac ggccgttcgg tgaaccatga gtgtacattc gtctttaatc  46080
cgcatgtggt cagacgcagt aagcaggtcg gatttatcta ccgggtcgat tcagtaggcg  46140
actcatggga agcggcactt aagcgtgcgg ggatcagaca cagaaaggcg taccagtcac  46200
```

```
gacacaccta tgcgtgctgg tcattatcag ctggtgcaaa ccctagtttt attgccagtc  46260
agatggggca tgcgagcgcg cagatggtgt tcaatgttta cggtgcatgg atggctgaca  46320
gcagcgcaga gcagatcgca atgctgaatc agaagctggc agattttgcc ccattgatgc  46380
cccatagcca cgagaacagt acgggaggat tattaaaatc agtaagttaa cccctaacgc  46440
ccgtcatgtt aactgtgtgg agggtaacac cacgctttat gccctgccga aacccgaggt  46500
tgtcctgcgc tggcgtgagc agaccacaga tgacttccgc ttctgtttta agtttccggc  46560
gaccatttcg catcaggcag cattacggca ttgcgatgat ttagtgactg aatttttgac  46620
ccgcatgtca ccgttggctc cgcgcattgg acaatactgg ctgcaactgc ctgccacatt  46680
cggcccacgg gagctgcctg cgctttggca ttttctcgat tctcttcccg gtgaatttaa  46740
ttatggggtg gaagtccgcc atccacagtt tttcgccaaa ggggaagagg aacaaacgct  46800
taatcgcggt ttacatcagc gcggcgttaa tcgggtgatt ttagacagcc gcccggttca  46860
tgcagcacgt ccatacagtg aagctattcg cgacgctcaa cgaaaaaaac ctaaagttcc  46920
ggtacatgct gtactgacgg cgaaaaaatcc actgatccgt tttatcggta gtgatgatat  46980
gacgcaaaac cgggaattat ttcaggtctg gttacaaaaa ttagcgcagt ggcatcagac  47040
cactacgcct tatcttttt tacatacgcc agatattgcc caggccccgg aactggtaca  47100
taccctgtgg gaagacttac gtaaaacgct tccagagatc ggagcagttc cggctattcc  47160
acagcaatct tctcttttct gaatttgcca cctatcatag acaggtgcca tcggccattt  47220
taaagggagt ttgtatggta agcgcgctgt atgccgtttt aagtgcgttg ttattaatga  47280
agttctcttt tgatgtcgtt cgcctgcgaa tgcagtaccg cgttgcctat ggcgacggcg  47340
gttttagcga actgcaaagc gctattcgca ttcatggtaa cgcggtggaa tatattccta  47400
tcgcgattgt gttgatgctg tttatggaaa tgaatggcgc agaaacctgg atggtgcata  47460
tttgcggcat cgttttgctt gctggtcgtc tgatgcatta ttacggtttt catcaccgtc  47520
tgttccgctg gcgacgttct ggcatgagcg ccacctggtg tgcgctgttg ctgatggtgc  47580
tggcgaatct ttggtatatg ccctgggagt tggttttctc cctgcgttag cgcacaatac  47640
gccactttct ttttcccgga tttttacgtt atgtctcacc gcgacacgct attttctgcc  47700
cctatcgcca gactgggcga ctggaccttt gatgaacggg tagctgaagt cttcccggat  47760
atgatccagc gttccgttcc cggctattcc aatattattt ccatgattgg tatgttagcc  47820
gagcgcttcg ttcaacctgg tacgcaggtt tacgatctgg gttgttctct gggcgcggcg  47880
acgctctcgg tgcgtcgcaa cattcatcat gataattgca aaattattgc catcgacaac  47940
tccccggcga tgattgaacg ctgccgtcgt catattgacg cctataaagc ccctacgcca  48000
gtagacgtta ttgaaggtga tattcgcgat atcgccattg aaaacgcatc gatggtggtg  48060
ctgaatttta ccctgcaatt cctggaacct tccgagcgcc aggcgttact ggataaaatt  48120
tatcaagggc tgaacccggg cggtgcgctg gtgctttcgg aaaaattcag tttcgaagat  48180
gccaaagttg gtgaactgct gttcaacatg caccacgact ttaaacgtgc caacggttac  48240
agcgaactgg agatcagcca gaaacgcagc atgctggaaa acgtgatgct gaccgattcc  48300
gtggaaaccc ataaagcacg cctgcataaa gccggttttg agcatagcga gctgtggttc  48360
cagtgcttta actttggttc actggtggca ttaaaagcag aggacgctgc atgatcgact  48420
ttggtaactt ttattctctg attgccaaaa atcatctttc acactggctc gaaacgctgc  48480
ccgcgcagat tgctaactgg cagcgcgagc agcagcacgg gctgtttaag cagtggtcca  48540
acgcggtgga atttctgcct gaaattaaac cgtatcgtct ggatttattg catagcgtaa  48600
ccgccgaaag cgaagagcca ctgagcgccg ggcaaattaa gcgcattgaa acgctgatgc  48660
gcaacctgat gccgtggcgc aaagggccgt tctcactgta tggcgtcaac atcgataccg  48720
aatggcgttc cgactggaaa tgggatcgcg ttatgcccca tctttctgat ttaaccgggc  48780
gcaccattct tgatgtcggc tgtggcagcg gttatcacat gtggcgcatg attggcgcag  48840
gggcgcatct ggcggtgggt atcgatccca cgcagctatt cctctgccag tttgaagcag  48900
tgcgtaaact gctgggtaac gatcagcgcg cacatttgtt accgttaggt attgaacaac  48960
ttccggcact gaaagccttt gataccgtct tttcgatggg cgtgctttat catcgtcgtt  49020
caccgctgga gcatctctgg cagttaaaag accaactggt gaatgaaggc gaactggtgc  49080
tggaaacgct ggttattgat ggcgacgaaa acacggtgct ggtgccgggc gatcgttacg  49140
ctcaaatgcg taatgtctat ttcattcctt ccgcgctggc gctgaaaaac tggctgaaga  49200
agtgtggttt tgttgatatt cgcattgcag atgtgagcgt taccaccaca gaagagcagc  49260
gacgcaccga atggatggtc accgagtctc tggccgattt tctcgacccg catgatccgg  49320
gtaaaacggt ggaaggttat cctgcgccta aacgcgcggt gctgattgcg cgcaagccgt  49380
aaaggtctgg taatactgcc ggatgcggcg tgaacgcctt atccggccta caaagtcttg  49440
ctaattcaat atattgcagg ggctatgtag gcctgataag catagcgcat caggca      49496
```

```
SEQ ID NO: 282         moltype = DNA  length = 290
FEATURE                Location/Qualifiers
source                 1..290
                       mol_type = genomic DNA
                       organism = Escherichia coli
SEQUENCE: 282
gtcagcataa caccctgacc tctcattaat tgttcatgcc gggcggcact atcgtcgtcc  60
ggccttttcc tctcttactc tgctacgtac atctatttct ataaatccgt tcaatttgtc  120
tgttttttgc acaaacatga aatatcagac aattccgtga cttaagaaaa tttatacaaa  180
tcagcaatat accccttaag gagtatataa aggtgaattt gatttacatc aataagcggg  240
gttgctgaat cgttaaggta ggcggtaata gaaaagaaat cgaggcaaaa             290
```

```
SEQ ID NO: 283         moltype = DNA  length = 173
FEATURE                Location/Qualifiers
source                 1..173
                       mol_type = genomic DNA
                       organism = Escherichia coli
SEQUENCE: 283
atttcctctc atcccatccg gggtgagagt cttttccccc gacttatggc tcatgcatgc  60
atcaaaaaag atgtgagctt gatcaaaaac aaaaaatatt tcactcgaca ggagtattta  120
tattgcgccc gttacgtggg cttcgactgt aaatcagaaa ggagaaaaca cct         173
```

```
SEQ ID NO: 284         moltype = DNA  length = 305
```

-continued

```
FEATURE                Location/Qualifiers
source                 1..305
                       mol_type = genomic DNA
                       organism = Escherichia coli
SEQUENCE: 284
gtcagcataa caccctgacc tctcattaat tgttcatgcc gggcggcact atcgtcgtcc  60
ggcctttcc tctcttactc tgctacgtac atctatttct ataaatccgt tcaatttgtc  120
tgtttttgc acaaacatga aatatcagac aattccgtga cttaagaaaa tttatacaaa  180
tcagcaatat acccctaag gagtatataa aggtgaattt gatttacatc aataagcggg  240
gttgctgaat cgttaaggat ccctctagaa ataattttgt ttaactttaa gaaggagata  300
tacat                                                             305

SEQ ID NO: 285         moltype = DNA  length = 180
FEATURE                Location/Qualifiers
source                 1..180
                       mol_type = genomic DNA
                       organism = Escherichia coli
SEQUENCE: 285
catttcctct catcccatcc ggggtgagag tcttttcccc cgacttatgg ctcatgcatg  60
catcaaaaaa gatgtgagct tgatcaaaaa caaaaaatat ttcactcgac aggagtattt  120
atattgcgcc cggatccctc tagaaataat tttgtttaac tttaagaagg agatatacat  180

SEQ ID NO: 286         moltype = DNA  length = 199
FEATURE                Location/Qualifiers
source                 1..199
                       mol_type = genomic DNA
                       organism = Escherichia coli
SEQUENCE: 286
agttgttctt attggtggtg ttgctttatg gttgcatcgt agtaaatggt tgtaacaaaa  60
gcaatttttc cggctgtctg tatacaaaaa cgccgtaaag tttgagcgaa gtcaataaac  120
tctctaccca ttcagggcaa tatctctctt ggatccctct agaaataatt ttgtttaact  180
ttaagaagga gatatacat                                              199

SEQ ID NO: 287         moltype = DNA  length = 117
FEATURE                Location/Qualifiers
source                 1..117
                       mol_type = genomic DNA
                       organism = Escherichia coli
SEQUENCE: 287
atccccatca ctcttgatgg agatcaattc cccaagctgc tagagcgtta ccttgccctt  60
aaacattagc aatgtcgatt tatcagaggg ccgacaggct cccacaggag aaaaccg     117

SEQ ID NO: 288         moltype = DNA  length = 108
FEATURE                Location/Qualifiers
source                 1..108
                       mol_type = genomic DNA
                       organism = Escherichia coli
SEQUENCE: 288
ctcttgatcg ttatcaattc ccacgctgtt tcagagcgtt accttgccct taaacattag  60
caatgtcgat ttatcagagg gccgacaggc tcccacagga gaaaaccg              108

SEQ ID NO: 289         moltype = DNA  length = 290
FEATURE                Location/Qualifiers
source                 1..290
                       mol_type = genomic DNA
                       organism = Escherichia coli
SEQUENCE: 289
gtcagcataa caccctgacc tctcattaat tgttcatgcc gggcggcact atcgtcgtcc  60
ggcctttcc tctcttactc tgctacgtac atctatttct ataaatccgt tcaatttgtc  120
tgtttttgc acaaacatga aatatcagac aattccgtga cttaagaaaa tttatacaaa  180
tcagcaatat acccctaag gagtatataa aggtgaattt gatttacatc aataagcggg  240
gttgctgaat cgttaaggta ggcggtaata gaaaagaaat cgaggcaaaa            290

SEQ ID NO: 290         moltype = DNA  length = 1485
FEATURE                Location/Qualifiers
misc_feature           1..1485
                       note = Synthetic polynucleotide
source                 1..1485
                       mol_type = other DNA
                       organism = synthetic construct
SEQUENCE: 290
ctcttgatcg ttatcaattc ccacgctgtt tcagagcgtt accttgccct taaacattag  60
caatgtcgat ttatcagagg gccgacaggc tcccacagga gaaaaccgat gaaaaacgcg  120
tcaaccgtat cggaagatac tgcgtcgaat caagagccga cgcttcatcg cggattacat  180
aaccgtcata ttcaactgat tgcgttgggt ggcgcaattg gtactggtct gtttcttggc  240
attggcccgg cgattcagat ggcgggtccg gctgtattgc tgggctacgg cgtcgccggg  300
atcatcgctt tcctgattat gcgccagctt ggcgaaatgg tggttgagga gccggtatcc  360
ggttcatttg cccactttgc ctataaatac tggggaccgt ttgcgggctt cctctctggc  420
tggaactact gggtaatgtt cgtgctggtg ggaatggcag agctgaccgc tgcgggcatc  480
```

-continued

```
tatatgcagt actggttccc ggatgttcca acgtggattt gggctgccgc cttctttatt  540
atcatcaacg ccgttaacct ggtgaacgtg cgcttatatg gcgaaaccga gttctggttt  600
gcgttgatta aagtgctggc aatcatcggt atgatcggct ttggcctgtg gctgctgttt  660
tctggtcacg gcggcgagaa agccagtatc gacaacctct ggcgctacgg tggtttcttc  720
gccaccggct ggaatgggct gattttgtcg ctggcggtaa ttatgttctc cttcggcggt  780
ctggagctga ttgggattac tgccgctgaa gcgcgcgatc cggaaaaaag cattccaaaa  840
gcggtaaatc aggtggtgta tcgcatcctg ctgttttaca tcggttcact ggtggtttta  900
ctggcgctct atccgtgggt ggaagtgaaa tccaacagta gcccgtttgt gatgattttc  960
cataatctcg acagcaacgt ggtagcttct gcgctgaact tcgtcattct ggtagcatcg  1020
ctgtcagtgt ataacagcgg ggtttactct aacagccgca tgctgtttgg cctttctgtg  1080
cagggtaatg cgccgaagtt tttgactcgc gtcagccgtc gcggtgtgcc gattaactcg  1140
ctgatgcttt ccggagcgat cacttcgctg gtggtgttaa tcaactatct gctgccgcaa  1200
aaagcgtttg gtctgctgat ggcgctggtg gtagcaacgc tgctgttgaa ctggattatg  1260
atctgtctgg cgcatctgcg ttttcgtgca gcgatgcgac gtcaggggcg tgaaacacag  1320
tttaaggcgc tgctctatcc gttcggcaac tatctctgca ttgccttcct cggcatgatt  1380
ttgctgctga tgtgcacgat ggatgatatg cgcttgtcag cgatcctgct gccggtgtgg  1440
attgtattcc tgtttatggc atttaaaacg ctgcgtcgga aataa                  1485

SEQ ID NO: 291         moltype = DNA  length = 4323
FEATURE                Location/Qualifiers
misc_feature           1..4323
                       note = Synthetic polynucleotide
source                 1..4323
                       mol_type = other DNA
                       organism = synthetic construct
SEQUENCE: 291
ctcttgatcg ttatcaattc ccacgctgtt tcagagcgtt accttgccct taaacattag  60
caatgtcgat ttatcagagg gccgacaggc tcccacagga gaaaaccgat gaaagctaaa  120
gatgttcagc caaccattat tattaataaa aatggcctta tctctttgga agatatctat  180
gacattgcga taaaacaaaa aaaagtagaa atatcaacgg agatcactga acttttgacg  240
catggtcgtg aaaaattaga ggaaaaatta aattcaggag aggttatata tggaatcaat  300
acaggatttg gagggaatgc caatttagtt gtgccatttg agaaaatcgc agagcatcag  360
caaaatctgt taactttttct ttctgctggt actggggact atatgtccaa accttgtatt  420
aaagcgtcac aatttactat gttactttct gtttgcaaag gttggtctgc aaccagacca  480
attgtcgctc aagcaattgt tgatcatatt aatcatgaca ttgttcctct ggttcctcgc  540
tatggctcag tgggtgcaag cggtgattta attcctttat cttatattgc acgagcatta  600
tgtggtatcg gcaaagttta ttatatgggc gcagaaattg acgctgctga agcaattaaa  660
cgtgcagggt tgacaccatt atcgttaaaa gccaaagaag gtcttgctct gattaacggc  720
acccgggtaa tgtcaggaat cagtgcaatc accgtcatta aactggaaaa actatttaaa  780
gcctcaattt ctgcgattgc ccttgctgtt gaagcattac ttgcatctca tgaacattat  840
gatgcccgga ttcaacaagt aaaaaatcat cctggtcaaa acgcggtggc aagtgcattg  900
cgtaatttat tggcaggttc aacgcaggtt aatctattat ctggggttaa agaacaagcc  960
aataaagctt gtcgtcatca agaaattacc caactaaatg ataccttaca ggaagtttat  1020
tcaattcgct gtgcaccaca agtattaggt atagtgccag aatctttagc taccgctcgg  1080
aaaatattgg aacgggaagt tatctcagct aatgataatc cattgataga tccagaaaat  1140
ggcgatgttc tacacggtgg aaattttatg gggcaatatg tcgcccgaac aatggatgca  1200
ttaaaactgg atattgcttt aattgccaat catcttcacg ccattgtggc tcttatgatg  1260
gataaccgtt tctctcgtgg attacctaat tcactgagtc cgacacccgg catgtatcaa  1320
ggttttaaag gcgtccaact ttctcaaacc gctttagttg ctgcaattcg ccatgattgt  1380
gctgcatcag gtattcatac cctcgccaca gaacaataca atcaagatat tgtcagttta  1440
ggtctgcatg ccgctcaaga tgttttagag atggagcaga aattacgcaa tattgtttca  1500
atgacaattc tggtagtttg tcaggccatt catcttcgcg gcaatattag tgaaattgcg  1560
cctgaaactg ctaaatttta ccatgcagta cgcgaaatca gttctccttt gatcactgat  1620
cgtgcgttgg atgaagatat aatccgcatt gcggatgcaa ttattaatga tcaacttcct  1680
ctgccagaaa tcatgctgga agaataagct tggcgtaatc atggtcatag ctgtttcctg  1740
tgtgaaattg ttatccgctc acaattccac acaacatacg agccggaagc ataaagtgta  1800
aagcctgggg tgcctaatga gtgagctaac tcacattaat tgcgttgcgc tcactgcccg  1860
ctttccagtc gggaaacctg tcgtgccagc tgcattaatg aatcggccaa cgcgcgggga  1920
gaggcggttt gcgtattggg cgctcttccg cttcctcgct cactgactcg ctgcgctcgg  1980
tcgttcggct gcggcgagcg gtatcagctc actcaaaggc ggtaatacgg ttatccacag  2040
aatcagggga taacgcagga aagaacatgt gagcaaaagg ccagcaaaag gccaggaacc  2100
gtaaaaaggc cgcgttgctg gcgtttttcc ataggctccg cccccctgac gagcatcaca  2160
aaaatcgacg ctcaagtcag aggtggcgaa acccgacagg actataaaga taccaggcgt  2220
ttccccctgg aagctccctc gtgcgctctc ctgttccgac cctgccgctt accggatacc  2280
tgtccgcctt tctcccttcg ggaagcgtgg cgctttctca tagctcacgc tgtaggtatc  2340
tcagttcggt gtaggtcgtt cgctccaagc tgggctgtgt gcacgaaccc cccgttcagc  2400
ccgaccgctg cgccttatcc ggtaactatc gtcttgagtc caacccggta agacacgact  2460
tatcgccact ggcagcagcc actggtaaca ggattagcag agcgaggtat gtaggcggtg  2520
ctacagagtt cttgaagtgg tggcctaact acggctacac tagaagaaca gtatttggta  2580
tctgcgctct gctgaagcca gttaccttcg gaaaaagagt tggtagctct tgatccggca  2640
aacaaaccac cgctggtagc ggtggttttt ttgtttgcaa gcagcagatt acgcgcagaa  2700
aaaaaggatc tcaagaagat cctttgatct tttctacggg gtctgacgct cagtggaacg  2760
aaaactcacg ttaagggatt ttggtcatga gattatcaaa aaggatcttc acctagatcc  2820
ttttaaatta aaaatgaagt tttaaatcaa tctaaagtat atatgagtaa acttggtctg  2880
acagttacca atgcttaatc agtgaggcac ctatctcagc gatctgtcta tttcgttcat  2940
ccatagttgc ctgactcccc gtcgtgtaga taactacgat acgggagggc ttaccatctg  3000
gccccagtgc tgcaatgata ccgcgagacc cacgctcacc ggctccagat ttatcagcaa  3060
taaaccagcc agccggaagg gccgagcgca gaagtggtcc tgcaacttta tccgcctcca  3120
tccagtctat taattgttgc cgggaagcta gagtaagtag ttcgccagtt aatagtttgc  3180
```

```
gcaacgttgt tgccattgct acaggcatcg tggtgtcacg ctcgtcgttt ggtatggctt  3240
cattcagctc cggttcccaa cgatcaaggc gagttacatg atcccccatg ttgtgcaaaa  3300
aagcggttag ctccttcggt cctccgatcg ttgtcagaag taagttggcc gcagtgttat  3360
cactcatggt tatggcagca ctgcataatt ctcttactgt catgccatcc gtaagatgct  3420
tttctgtgac tggtgagtac tcaaccaagt cattctgaga atagtgtatg cggcgaccga  3480
gttgctcttg cccggcgtca atacgggata ataccgcgcc acatagcaga actttaaaag  3540
tgctcatcat tggaaaacgt tcttcggggc gaaaactctc aaggatctta ccgctgttga  3600
gatccagttc gatgtaaccc actcgtgcac ccaactgatc ttcagcatct tttactttca  3660
ccagcgtttc tgggtgagca aaaacaggaa ggcaaaatgc cgcaaaaaag ggaataaggg  3720
cgacacggaa atgttgaata ctcatactct tcctttttca atattattga agcatttatc  3780
agggttattg tctcatgagc ggatacatat ttgaatgtat ttagaaaaat aaacaaatag  3840
gggttccgcg cacatttccc cgaaaagtgc cacctgacgt ctaagaaacc attattatca  3900
tgacattaac ctataaaaat aggcgtatca cgaggccctt tcgtctcgcg cgtttcggtg  3960
atgacggtga aaacctctga cacatgcagc tcccggagac ggtcacagct tgtctgtaag  4020
cggatgccgg gagcagacaa gcccgtcagg gcgcgtcagc gggtgttggc gggtgtcggg  4080
gctggcttaa ctatgcggca tcagagcaga ttgtactgag agtgcaccat atgcggtgtg  4140
aaataccgca cagatgcgta aggagaaaat accgcatcag gcgccattcg ccattcaggc  4200
tgcgcaactg ttgggaaggg cgatcggtgc gggcctcttc gctattacgc cagctggcga  4260
aagggggatg tgctgcaagg cgattaagtt gggtaacgcc agggttttcc cagtcacgac  4320
gtt                                                                4323

SEQ ID NO: 292         moltype = DNA  length = 5092
FEATURE                Location/Qualifiers
misc_feature           1..5092
                       note = Synthetic polynucleotide
source                 1..5092
                       mol_type = other DNA
                       organism = synthetic construct
SEQUENCE: 292
ctctagaaat aattttgttt aactttaaga aggagatata catatgaaaa cactatcaca  60
ggcccaatct aaaacttctt cacagcaatt cagctttacc gggaactcgt ctgcgaatgt  120
aattatcggc aatcaaaagc tgaccattaa tgatgtagct cgcgttgccc ggaatggcac  180
tttggtgtca ctgacgaaca ataccgacat tctgcaaggt attcaagcta gctgcgatta  240
tatcaataac gccgttgaat ctggcgagcc aatctacggg gtaacaagcg gttttggtgg  300
gatggcgaac gttgccatta gccgtgaaca ggcgagcgaa cttcagacca acctcgtttg  360
gttcctaaag acaggagctg gtaataagtt acctctggct gacgtaagag ccgcgatgct  420
gcttcgcgct aatagtcaca tgcgcggcgc cagtggtatc cgtcttgagc ttatcaagag  480
gatggaaatc ttcctcaacg cgggtgtcac accatatgtt tatgagtttg gtagtatcgg  540
agccagtggt gatcttgttc ccctgagtta tattacgggt tcattgattg gtttagaccc  600
gtcctttaaa gtggatttta acgggaaaga aatggacgcc ccgaccgctt tacgacagct  660
taatctgagc ccacttactt tgctccctaa agaaggtctt gccatgatga atggcacctc  720
tgtgatgact ggaattgccg cgaattgtgt gtatgacacg cagatcctaa cggccattgc  780
catgggtgtt cacgcgttgg acattcaagc cctgaatggt acaaaccagt cgtttcatcc  840
gtttatccat aattcaaaac cccatccggg acagctttgg gctgctgatc agatgatctc  900
actcctggcc aatagtcaac tggttcggga cgagctcgac ggcaaacatg attatcgcga  960
tcatgagctc atccaggacc ggtattcact tcgttgtctc ccacaatacc tggggcctat  1020
cgttgatggt atatctcaaa ttgcgaagca aattgaaatt gagatcaata gcgtaaccga  1080
caacccgctt atcgatgttg ataatcaggc ctcttatcac ggtggcaatt ttctgggcca  1140
gtatgttggt atggggatgg atcacctgcg gtactatatt gggcttctgg ctaaacatct  1200
tgatgtgcag attgccttat tagcttcacc agaattttca aatggactgc cgccatcatt  1260
gctcggtaac agagaaagga aagtaaatat gggccttaag ggccttcaga tatgtggtaa  1320
ctcaatcatg cccctcctga ccttttatgg gaactcaatt gctgatcgtt ttccgacaca  1380
tgctgaacag tttaaccaaa acattaactc acagggctat acatccgcga cgttagcgcg  1440
tcggtccgtg gatatcttcc agaattatgt tgctatcgct ctgatgttcg gcgtacaggc  1500
cgttgatttg cgcacttata aaaaaaccgg tcactacgat gctcgggctt gcctgtcgcc  1560
tgccaccgag cggctttata gcgccgtacg tcatgttgtg ggtcagaaac cgacgtcgga  1620
ccgcccctat atttggaatg ataatgaaca agggctggat gaacacatcg cccggatatc  1680
tgccgatatt gccgccggag gtgtcatcgt ccaggcggta caagacatac ttccttgcct  1740
gcattaagct tggcgtaatc atggtcatag ctgtttcctg tgtgaaattg ttatccgctc  1800
acaattccac acaacatacg agccggaagc ataaagtgta aagcctgggg tgcctaatga  1860
gtgagctaac tcacattaat tgcgttgcgc tcactgcccg ctttccagtc gggaaacctg  1920
tcgtgccagc tgcattaatg aatcggccaa cgcgcgggga gaggcggttt gcgtattggg  1980
cgctcttccg cttcctcgct cactgactcg ctgcgctcgg tcgttcggct gcggcgagcg  2040
gtatcagctc actcaaaggc ggtaatacgg ttatccacag aatcagggga taacgcagga  2100
aagaacatgt gagcaaaagg ccagcaaaag gccaggaacc gtaaaaaggc cgcgttgctg  2160
gcgtttttcc ataggctccg cccccctgac gagcatcaca aaaatcgacg ctcaagtcag  2220
aggtggcgaa acccgacagg actataaaga taccaggcgt ttccccctgg aagctccctc  2280
gtgcgctctc ctgttccgac cctgccgctt accggatacc tgtccgcctt tctcccttcg  2340
ggaagcgtgg cgctttctca tagctcacgc tgtaggtatc tcagttcggt gtaggtcgtt  2400
cgctccaagc tgggctgtgt gcacgaaccc cccgttcagc ccgaccgctg cgccttatcc  2460
ggtaactatc gtcttgagtc caacccggta agacacgact tatcgccact ggcagcagcc  2520
actggtaaca ggattagcag agcgaggtat gtaggcggtg ctacagagtt cttgaagtgg  2580
tggcctaact acggctacac tagaagaaca gtatttggta tctgcgctct gctgaagcca  2640
gttaccttcg gaaaaagagt tggtagctct tgatccggca aacaaaccac cgctggtagc  2700
ggtggttttt ttgtttgcaa gcagcagatt acgcgcagaa aaaaaggatc tcaagaagat  2760
cctttgatct tttctacggg gtctgacgct cagtggaacg aaaactcacg ttaagggatt  2820
ttggtcatga gattatcaaa aaggatcttc acctagatcc ttttaaatta aaaatgaagt  2880
tttaaatcaa tctaaagtat atatgagtaa acttggtctg acagttacca atgcttaatc  2940
agtgaggcac ctatctcagc gatctgtcta tttcgttcat ccatagttgc ctgactcccc  3000
```

```
gtcgtgtaga taactacgat acgggagggc ttaccatctg gccccagtgc tgcaatgata  3060
ccgcgagacc cacgctcacc ggctccagat ttatcagcaa taaaccagcc agccggaagg  3120
gccgagcgca gaagtggtcc tgcaacttta tccgcctcca tccagtctat taattgttgc  3180
cgggaagcta gagtaagtag ttcgccagtt aatagtttgc gcaacgttgt tgccattgct  3240
acaggcatcg tggtgtcacg ctcgtcgttt ggtatggctt cattcagctc cggttcccaa  3300
cgatcaaggc gagttacatg atcccccatg ttgtgcaaaa aagcggttag ctccttcggt  3360
cctccgatcg ttgtcagaag taagttggcc gcagtgttat cactcatggt tatggcagca  3420
ctgcataatt ctcttactgt catgccatcc gtaagatgct tttctgtgac tggtgagtac  3480
tcaaccaagt cattctgaga atagtgtatg cggcgaccga gttgctcttg cccggcgtca  3540
atacgggata ataccgcgcc acatagcaga actttaaaag tgctcatcat tggaaaacgt  3600
tcttcggggc gaaaactctc aaggatctta ccgctgttga gatccagttc gatgtaaccc  3660
actcgtgcac ccaactgatc ttcagcatct tttactttca ccagcgtttc tgggtgagca  3720
aaaacaggaa ggcaaaatgc cgcaaaaaag ggaataaggg cgacacggaa atgttgaata  3780
ctcatactct tcctttttca atattattga agcatttatc agggttattg tctcatgagc  3840
ggatacatat ttgaatgtat ttagaaaaat aaacaaatag gggttccgcg cacatttccc  3900
cgaaaagtgc cacctgacgt ctaagaaacc attattatca tgacattaac ctataaaaat  3960
aggcgtatca cgaggccctt tcgtctcgcg cgtttcggtg atgacggtga aaacctctga  4020
cacatgcagc tcccggagac ggtcacagct tgtctgtaag cggatgccgg gagcagacaa  4080
gcccgtcagg gcgcgtcagc gggtgttggc gggtgtcggg gctggcttaa ctatgcggca  4140
tcagagcaga ttgtactgag agtgcaccat atgcggtgtg aaataccgca cagatgcgta  4200
aggagaaaat accgcatcag gcgccattcg ccattcaggc tgcgcaactg ttgggaaggg  4260
cgatcggtgc gggcctcttc gctattacgc cagctggcga aagggggatg tgctgcaagg  4320
cgattaagtt gggtaacgcc agggttttcc cagtcacgac gttgtaaaac gacggccagt  4380
gaattcgtta agacccactt tcacatttaa gttgtttttc taatccgcat atgatcaatt  4440
caaggccgaa taagaaggct ggctctgcac cttggtgatc aaataattcg atagcttgtc  4500
gtaataatgg cggcatacta tcagtagtag gtgtttccct ttcttcttta gcgacttgat  4560
gctcttgatc ttccaatacg caacctaaag taaaatgccc cacagcgctg agtgcatata  4620
atgcattctc tagtgaaaaa ccttgttggc ataaaaaggc taattgattt tcgagagttt  4680
catactgttt ttctgtaggc cgtgtaccta aatgtacttt tgctccatcg cgatgactta  4740
gtaaagcaca tctaaaactt ttagcgttat tacgtaaaaa atcttgccag ctttcccctt  4800
ctaaagggca aaagtgagta tggtgcctat ctaacatctc aatggctaag gcgtcgagca  4860
aagcccgctt atttttttaca tgccaataca atgtaggctg ctctacacct agcttctggg  4920
cgagtttacg ggttgttaaa ccttcgattc cgacctcatt aagcagctct aatgcgctgt  4980
taatcacttt actttatct aatctagaca tcattaattc ctaatttttg ttgacactct  5040
atcattgata gagttatttt accactccct atcagtgata gagaaaagtg aa          5092

SEQ ID NO: 293          moltype = DNA  length = 4987
FEATURE                 Location/Qualifiers
misc_feature            1..4987
                        note = Synthetic polynucleotide
source                  1..4987
                        mol_type = other DNA
                        organism = synthetic construct
SEQUENCE: 293
ctctagaaat aattttgttt aactttaaga aggagatata catatgaaag ctaaagatgt  60
tcagccaacc attattatta ataaaaatgg ccttatctct ttggaagata tctatgacat  120
tgcgataaaa caaaaaaaag tagaaatatc aacggagatc actgaacttt tgacgcatgg  180
tcgtgaaaaa ttagaggaaa aattaaattc aggagaggtt atatatggaa tcaatacagg  240
atttggaggg aatgccaatt tagttgtgcc atttgagaaa atcgcagagc atcagcaaaa  300
tctgttaact tttctttctg ctggtactgg ggactatatg tccaaacctt gtattaaagc  360
gtcacaattt actatgttac tttctgtttg caaaggttgg tctgcaacca gaccaattgt  420
cgctcaagca attgttgatc atattaatca tgacattgtt cctctggttc ctcgctatgg  480
ctcagtgggt gcaagcggtg atttaattcc tttatcttat attgcacgag cattatgtgg  540
tatcggcaaa gtttattata tgggcgcaga aattgacgct gctgaagcaa ttaaacgtgc  600
agggttgaca ccattatcgt taaaagccaa agaaggtctt gctctgatta acggcacccg  660
ggtaatgtca ggaatcagtg caatcaccgt cattaaactg gaaaaactat ttaaagcctc  720
aatttctgcg attgcccttg ctgttgaagc attacttgca tctcatgaac attatgatgc  780
ccggattcaa caagtaaaaa atcatcctgg tcaaaacgcg gtggcaagtg cattgcgtaa  840
tttattggca ggttcaacgc aggttaatct attatctggg gttaaagaac aagccaataa  900
agcttgtcgt catcaagaaa ttacccaact aaatgatacc ttacaggaag tttattcaat  960
tcgctgtgca ccacaagtat taggtatagt gccagaatct ttagctaccg ctcggaaaat  1020
attggaacgg gaagttatct cagctaatga taatccattg atagatccag aaaatggcga  1080
tgttctacac ggtggaaatt ttatggggca atatgtcgcc cgaacaatgg atgcattaaa  1140
actggatatt gctttaattg ccaatcatct tcacgccatt gtggctctta tgatggataa  1200
ccgtttctct cgtggattac ctaattcact gagtccgaca cccggcatgt atcaaggttt  1260
taaaggcgtc caactttctc aaaccgcttt agttgctgca attcgccatg attgtgctgc  1320
atcaggtatt catacccctcg ccacagaaca atacaatcaa gatattgtca gtttaggtct  1380
gcatgccgct caagatgttt tagagatgga gcagaaatta cgcaatattg tttcaatgac  1440
aattctggta gtttgtcagg ccattcatct tcgcggcaat attagtgaaa ttgcgcctga  1500
aactgctaaa ttttaccatg cagtacgcga aatcagttct cctttgatca ctgatcgtgc  1560
gttggatgaa gatataatcc gcattgcgga tgcaattatt aatgatcaac ttcctctgcc  1620
agaaatcatg ctggaagaat aagcttggcg taatcatggt catagctgtt tcctgtgtga  1680
aattgttatc cgctcacaat tccacacaac atacgagccg gaagcataaa gtgtaaagcc  1740
tggggtgcct aatgagtgag ctaactcaca ttaattgcgt tgcgctcact gcccgctttc  1800
cagtcgggaa acctgtcgtg ccagctgcat taatgaatcg gccaacgcgc ggggagaggc  1860
ggtttgcgta ttgggcgctc ttccgcttcc tcgctcactg actcgctgcg ctcggtcgtt  1920
cggctgcggc gagcggtatc agctcactca aaggcggtaa tacggttatc cacagaatca  1980
ggggataacg caggaaagaa catgtgagca aaaggccagc aaaaggccag gaaccgtaaa  2040
aaggccgcgt tgctggcgtt tttccatagg ctccgccccc ctgacgagca tcacaaaaat  2100
```

```
cgacgctcaa gtcagaggtg gcgaaacccg acaggactat aaagatacca ggcgtttccc  2160
cctggaagct ccctcgtgcg ctctcctgtt ccgaccctgc cgcttaccgg atacctgtcc  2220
gcctttctcc cttcgggaag cgtggcgctt tctcatagct cacgctgtag gtatctcagt  2280
tcggtgtagg tcgttcgctc caagctgggc tgtgtgcacg aaccccccgt tcagcccgac  2340
cgctgcgcct tatccggtaa ctatcgtctt gagtccaacc cggtaagaca cgacttatcg  2400
ccactggcag cagccactgg taacaggatt agcagagcga ggtatgtagg cggtgctaca  2460
gagttcttga agtggtggcc taactacggc tacactagaa gaacagtatt tggtatctgc  2520
gctctgctga agccagttac cttcggaaaa agagttggta gctcttgatc cggcaaacaa  2580
accaccgctg gtagcggtgg tttttttgtt tgcaagcagc agattacgcg cagaaaaaaa  2640
ggatctcaag aagatccttt gatcttttct acggggtctg acgctcagtg gaacgaaaac  2700
tcacgttaag ggattttggt catgagatta tcaaaaagga tcttcaccta gatcctttta  2760
aattaaaaat gaagttttaa atcaatctaa agtatatatg agtaaacttg gtctgacagt  2820
taccaatgct taatcagtga ggcacctatc tcagcgatct gtctatttcg ttcatccata  2880
gttgcctgac tccccgtcgt gtagataact acgatacggg agggcttacc atctggcccc  2940
agtgctgcaa tgataccgcg agacccacgc tcaccggctc cagatttatc agcaataaac  3000
cagccagccg gaagggccga gcgcagaagt ggtcctgcaa ctttatccgc ctccatccag  3060
tctattaatt gttgccggga agctagagta agtagttcgc cagttaatag tttgcgcaac  3120
gttgttgcca ttgctacagg catcgtggtg tcacgctcgt cgtttggtat ggcttcattc  3180
agctccggtt cccaacgatc aaggcgagtt acatgatccc ccatgttgtg caaaaaagcg  3240
gttagctcct tcggtcctcc gatcgttgtc agaagtaagt tggccgcagt gttatcactc  3300
atggttatgg cagcactgca taattctctt actgtcatgc catccgtaag atgcttttct  3360
gtgactggtg agtactcaac caagtcattc tgagaatagt gtatgcggcg accgagttgc  3420
tcttgcccgg cgtcaatacg ggataatacc gcgccacata gcagaacttt aaaagtgctc  3480
atcattggaa aacgttcttc ggggcgaaaa ctctcaagga tcttaccgct gttgagatcc  3540
agttcgatgt aacccactcg tgcacccaac tgatcttcag catcttttac tttcaccagc  3600
gtttctgggt gagcaaaaac aggaaggcaa aatgccgcaa aaaagggaat aagggcgaca  3660
cggaaatgtt gaatactcat actcttcctt tttcaatatt attgaagcat ttatcagggt  3720
tattgtctca tgagcggata catatttgaa tgtatttaga aaaataaaca aataggggtt  3780
ccgcgcacat ttccccgaaa agtgccacct gacgtctaag aaaccattat tatcatgaca  3840
ttaacctata aaaataggcg tatcacgagg ccctttcgtc tcgcgcgttt cggtgatgac  3900
ggtgaaaacc tctgacacat gcagctcccg gagacggtca cagcttgtct gtaagcggat  3960
gccgggagca gacaagcccg tcagggcgcg tcagcgggtg ttggcgggtg tcggggctgg  4020
cttaactatg cggcatcaga gcagattgta ctgagagtgc accatatgcg gtgtgaaata  4080
ccgcacagat gcgtaaggag aaaataccgc atcaggcgcc attcgccatt caggctgcgc  4140
aactgttggg aagggcgatc ggtgcgggcc tcttcgctat tacgccagct ggcgaaaggg  4200
ggatgtgctg caaggcgatt aagttgggta acgccagggt tttcccagtc acgacgttgt  4260
aaaacgacgg ccagtgaatt cgttaagacc cactttcaca tttaagttgt ttttctaatc  4320
cgcatatgat caattcaagg ccgaataaga aggctggctc tgcaccttgg tgatcaaata  4380
attcgatagc ttgtcgtaat aatggcggca tactatcagt agtaggtgtt tccctttctt  4440
ctttagcgac ttgatgctct tgatcttcca atacgcaacc taaagtaaaa tgccccacag  4500
cgctgagtgc atataatgca ttctctagtg aaaaaccttg ttggcataaa aaggctaatt  4560
gattttcgag agtttcatac tgtttttctg taggccgtgt acctaaatgt actttttgctc 4620
catcgcgatg acttagtaaa gcacatctaa aacttttagc gttattacgt aaaaaatctt  4680
gccagctttc cccttctaaa gggcaaaagt gagtatggtg cctatctaac atctcaatgg  4740
ctaaggcgtc gagcaaagcc cgcttatttt ttacatgcca atacaatgta ggctgctcta  4800
cacctagctt ctgggcgagt ttacgggttg ttaaaccttc gattccgacc tcattaagca  4860
gctctaatgc gctgttaatc actttacttt tatctaatct agacatcatt aattcctaat  4920
ttttgttgac actctatcat tgatagagtt attttaccac tccctatcag tgatagagaa  4980
aagtgaa                                                            4987
```

```
SEQ ID NO: 294          moltype = DNA  length = 5962
FEATURE                 Location/Qualifiers
misc_feature            1..5962
                        note = Synthetic polynucleotide
source                  1..5962
                        mol_type = other DNA
                        organism = synthetic construct
SEQUENCE: 294
ctcttgatcg ttatcaattc ccacgctgtt tcagagcgtt accttgccct taaacattag  60
caatgtcgat ttatcagagg gccgacaggc tcccacagga gaaaaccgat gaaaacacta  120
tcacaggccc aatctaaaac ttcttcacag caattcagct ttaccgggaa ctcgtctgcg  180
aatgtaatta tcggcaatca aaagctgacc attaatgatg tagctcgcgt tgcccggaat  240
ggcactttgg tgtcactgac gaacaatacc gacattctgc aaggtattca agctagctgc  300
gattatatca ataacgccgt tgaatctggc gagccaatct acggggtaac aagcggtttt  360
ggtgggatgg cgaacgttgc cattagccgt gaacaggcga gcgaacttca gaccaacctc  420
gtttggttcc taaagacagg agctggtaat aagttacctc tggctgacgt aagagccgcg  480
atgctgcttc gcgctaatag tcacatgcgc ggcgccagtg gtatccgtct tgagcttatc  540
aagaggatgg aaatcttcct caacgcgggt gtcacaccat atgtttatga gtttggtagt  600
atcggagcca gtggtgatct tgttcccctg agttatatta cgggttcatt gattggttta  660
gacccgtcct ttaaagtgga ttttaacggg aaagaaatgg acgccccgac cgctttacga  720
cagcttaatc tgagcccact tactttgctc cctaaagaag gtcttgccat gatgaatggc  780
acctctgtga tgactggaat tgccgcgaat tgtgtgtatg acacgcagat cctaacggcc  840
attgccatgg gtgttcacgc gttggacatt caagccctga atggtacaaa ccagtcgttt  900
catccgttta tccataattc aaaaccccat ccgggacagc tttgggctgc tgatcagatg  960
atctcactcc tggccaatag tcaactggtt cgggacgagc tcgacggcaa acatgattat  1020
cgcgatcatg agctcatcca ggaccggtat tcacttcgtt gtctcccaca atacctgggg  1080
cctatcgttg atggtatatc tcaaattgcg aagcaaattg aaattgagat caatagcgta  1140
accgacaacc cgcttatcga tgttgataat caggcctctt atcacggtgg caattttctg  1200
ggccagtatg ttggtatggg gatggatcac ctgcggtact atattgggct tctggctaaa  1260
```

```
catcttgatg tgcagattgc cttattagct tcaccagaat tttcaaatgg actgccgcca  1320
tcattgctcg gtaacagaga aaggaaagta aatatgggcc ttaagggcct tcagatatgt  1380
ggtaactcaa tcatgcccct cctgaccttt tatgggaact caattgctga tcgttttccg  1440
acacatgctg aacagtttaa ccaaaacatt aactcacagg gctatacatc cgcgacgtta  1500
gcgcgtcggt ccgtggatat cttccagaat tatgttgcta tcgctctgat gttcggcgta  1560
caggccgttg atttgcgcac ttataaaaaa accggtcact acgatgctcg ggcttgcctg  1620
tcgcctgcca ccgagcggct ttatagcgcc gtacgtcatg ttgtgggtca gaaaccgacg  1680
tcggaccgcc cctatatttg gaatgataat gaacaagggc tggatgaaca catcgcccgg  1740
atatctgccg atattgccgc cggaggtgtc atcgtccagg cggtacaaga catacttcct  1800
tgcctgcatt aagcttggcg taatcatggt catagctgtt tcctgtgtga aattgttatc  1860
cgctcacaat tccacacaac atacgagccg gaagcataaa gtgtaaagcc tggggtgcct  1920
aatgagtgag ctaactcaca ttaattgcgt tgcgctcact gcccgctttc cagtcgggaa  1980
acctgtcgtg ccagctgcat taatgaatcg gccaacgcgc ggggagaggc ggtttgcgta  2040
ttgggcgctc ttccgcttcc tcgctcactg actcgctgcg ctcggtcgtt cggctgcggc  2100
gagcggtatc agctcactca aaggcggtag tacgggtttt gctgcccgca aacgggctgt  2160
tctggtgttg ctagtttgtt atcagaatcg cagatccggc ttcaggtttg ccggctgaaa  2220
gcgctatttc ttccagaatt gccatgattt tttccccacg ggaggcgtca ctggctcccg  2280
tgttgtcggc agctttgatt cgataagcag catcgcctgt ttcaggctgt ctatgtgtga  2340
ctgttgagct gtaacaagtt gtctcaggtg ttcaatttca tgttctagtt gctttgtttt  2400
actggtttca cctgttctat taggtgttac atgctgttca tctgttacat tgtcgatctg  2460
ttcatggtga acagctttaa atgcaccaaa aactcgtaaa agctctgatg tatctatctt  2520
ttttacaccg ttttcatctg tgcatatgga cagttttccc tttgatatct aacggtgaac  2580
agttgttcta cttttgtttg ttagtcttga tgcttcactg atagatacaa gagccataag  2640
aacctcagat ccttccgtat ttagccagta tgttctctag tgtggttcgt tgtttttgcg  2700
tgagccatga gaacgaacca ttgagatcat gcttactttg catgtcactc aaaaattttg  2760
cctcaaaact ggtgagctga atttttgcag ttaaagcatc gtgtagtgtt tttcttagtc  2820
cgttacgtag gtaggaatct gatgtaatgg ttgttggtat tttgtcacca ttcattttta  2880
tctggttgtt ctcaagttcg gttacgagat ccatttgtct atctagttca acttggaaaa  2940
tcaacgtatc agtcgggcgg cctcgcttat caaccaccaa tttcatattg ctgtaagtgt  3000
ttaaatcttt acttattggt ttcaaaaccc attggttaag ccttttaaac tcatggtagt  3060
tattttcaag cattaacatg aacttaaatt catcaaggct aatctctata tttgccttgt  3120
gagttttctt ttgtgttagt tcttttaata accactcata aatcctcata gagtatttgt  3180
tttcaaaaga cttaacatgt tccagattat attttatgaa ttttttttaac tggaaaagat  3240
aaggcaatat ctcttcacta aaaactaatt ctaatttttc gcttgagaac ttggcatagt  3300
ttgtccactg gaaaatctca aagcctttaa ccaaaggatt cctgatttcc acagttctcg  3360
tcatcagctc tctggttgct ttagctaata caccataagc attttcccta ctgatgttca  3420
tcatctgagc gtattggtta taagtgaacg ataccgtccg ttctttcctt gtagggtttt  3480
caatcgtggg gttgagtagt gccacacagc ataaaattag cttggtttca tgctccgtta  3540
agtcatagcg actaatcgct agttcatttg ctttgaaaac aactaattca gacatacatc  3600
tcaattggtc taggtgattt taatcactat accaattgag atgggctagt caatgataat  3660
tactagtcct tttcctttga gttgtgggta tctgtaaatt ctgctagacc tttgctggaa  3720
aacttgtaaa ttctgctaga ccctctgtaa attccgctag acctttgtgt gttttttttg  3780
tttatattca agtggttata atttatagaa taaagaaaga ataaaaaaag ataaaaagaa  3840
tagatcccag ccctgtgtat aactcactac tttagtcagt tccgcagtat tacaaaagga  3900
tgtcgcaaac gctgtttgct cctctacaaa acagacctta aaaccctaaa ggcttaagta  3960
gcaccctcgc aagctcgggc aaatcgctga atattccttt tgtctccgac catcaggcac  4020
ctgagtcgct gtctttttcg tgacattcag ttcgctgcgc tcacggctct ggcagtgaat  4080
gggggtaaat ggcactacag gcgcctttta tggattcatg caaggaaact acccataata  4140
caagaaaagc ccgtcacggg cttctcaggg cgttttatgg cgggtctgct atgtggtgct  4200
atctgacttt ttgctgttca gcagttcctg ccctctgatt ttccagtctg accacttcgg  4260
attatcccgt gacaggtcat tcagactggc taatgcaccc agtaaggcag cggtatcatc  4320
aacaggctta cccgtcttac tgtcttttct acggggtctg acgctcagtg gaacgaaaac  4380
tcacgttaag ggattttggt catgagatta tcaaaaagga tcttcaccta gatcctttta  4440
aattaaaaat gaagttttaa atcaatctaa agtatatatg agtaaacttg gtctgacagt  4500
taccaatgct taatcagtga ggcacctatc tcagcgatct gtctatttcg ttcatccata  4560
gttgcctgac tccccgtcgt gtagataact acgatacggg agggcttacc atctggcccc  4620
agtgctgcaa tgataccgcg agacccacgc tcaccggctc cagatttatc agcaataaac  4680
cagccagccg gaagggccga gcgcagaagt ggtcctgcaa ctttatccgc ctccatccag  4740
tctattaatt gttgccggga agctagagta agtagttcgc cagttaatag tttgcgcaac  4800
gttgttgcca ttgctacagg catcgtggtg tcacgctcgt cgtttggtat ggcttcattc  4860
agctccggtt cccaacgatc aaggcgagtt acatgatccc ccatgttgtg caaaaaagcg  4920
gttagctcct tcggtcctcc gatcgttgtc agaagtaagt tggccgcagt gttatcactc  4980
atggttatgg cagcactgca taattctctt actgtcatgc catccgtaag atgcttttct  5040
gtgactggtg agtactcaac caagtcattc tgagaatagt gtatgcggcg accgagttgc  5100
tcttgcccgg cgtcaatacg ggataatacc gcgccacata gcagaacttt aaaagtgctc  5160
atcattggaa aacgttcttc ggggcgaaaa ctctcaagga tcttaccgct gttgagatcc  5220
agttcgatgt aacccactcg tgcacccaac tgatcttcag catcttttac tttcaccagc  5280
gtttctgggt gagcaaaaac aggaaggcaa aatgccgcaa aaaagggaat aagggcgaca  5340
cggaaatgtt gaatactcat actcttcctt tttcaatatt attgaagcat ttatcagggt  5400
tattgtctca tgagcggata catatttgaa tgtatttaga aaaataaaca aataggggtt  5460
ccgcgcacat ttccccgaaa agtgccacct gacgtctaag aaaccattat tatcatgaca  5520
ttaacctata aaaataggcg tatcacgagg ccctttcgtc tcgcgcgttt cggtgatgac  5580
ggtgaaaacc tctgacacat gcagctcccg gagacggtca cagcttgtct gtaagcggat  5640
gccgggagca gacaagcccg tcagggcgcg tcagcgggtg ttggcgggtg tcggggctgg  5700
cttaactatg cggcatcaga gcagattgta ctgagagtgc accatatgcg gtgtgaaata  5760
ccgcacagat gcgtaaggag aaaataccgc atcaggcgcc attcgccatt caggctgcgc  5820
aactgttggg aagggcgatc ggtgcgggcc tcttcgctat tacgccagct ggcgaaaggg  5880
ggatgtgctg caaggcgatt aagttgggta acgccagggt tttcccagtc acgacgttgt  5940
aaaacgacgg ccagtgaatt cg                                          5962
```

```
SEQ ID NO: 295          moltype = DNA  length = 5857
FEATURE                 Location/Qualifiers
misc_feature            1..5857
                        note = Synthetic polynucleotide
source                  1..5857
                        mol_type = other DNA
                        organism = synthetic construct
SEQUENCE: 295
ctcttgatcg ttatcaattc ccacgctgtt tcagagcgtt accttgccct taaacattag  60
caatgtcgat ttatcagagg gccgacaggc tcccacagga gaaaaccgat gaaagctaaa  120
gatgttcagc caaccattat tattaataaa aatggcctta tctctttgga agatatctat  180
gacattgcga taaaacaaaa aaaagtagaa atatcaacgg agatcactga acttttgacg  240
catggtcgtg aaaaattaga ggaaaaatta aattcaggag aggttatata tggaatcaat  300
acaggatttg gagggaatgc caatttagtt gtgccatttg agaaaatcgc agagcatcag  360
caaaatctgt taacttttct ttctgctggt actggggact atatgtccaa accttgtatt  420
aaagcgtcac aatttactat gttactttct gtttgcaaag gttggtctgc aaccagacca  480
attgtcgctc aagcaattgt tgatcatatt aatcatgaca ttgttcctct ggttcctcgc  540
tatggctcag tgggtgcaag cggtgattta attcctttat cttatattgc acgagcatta  600
tgtggtatcg gcaaagttta ttatatgggc gcagaaattg acgctgctga agcaattaaa  660
cgtgcagggt tgacaccatt atcgttaaaa gccaaagaag gtcttgctct gattaacggc  720
acccgggtaa tgtcaggaat cagtgcaatc accgtcatta aactggaaaa actatttaaa  780
gcctcaattt ctgcgattgc ccttgctgtt gaagcattac ttgcatctca tgaacattat  840
gatgcccgga ttcaacaagt aaaaaatcat cctggtcaaa acgcggtggc aagtgcattg  900
cgtaatttat tggcaggttc aacgcaggtt aatctattat ctggggttaa agaacaagcc  960
aataaagctt gtcgtcatca agaaattacc caactaaatg ataccttaca ggaagtttat  1020
tcaattcgct gtgcaccaca agtattaggt atagtgccag aatctttagc taccgctcgg  1080
aaaatattgg aacgggaagt tatctcagct aatgataatc cattgataga tccagaaaat  1140
ggcgatgttc tacacggtgg aaattttatg ggcaatatg tcgcccgaac aatggatgca  1200
ttaaaactgg atattgcttt aattgccaat catcttcacg ccattgtggc tcttatgatg  1260
gataaccgtt tctctcgtgg attacctaat tcactgagtc cgacacccgg catgtatcaa  1320
ggttttaaag gcgtccaact ttctcaaacc gctttagttg ctgcaattcg ccatgattgt  1380
gctgcatcag gtattcatac cctcgccaca gaacaataca atcaagatat tgtcagttta  1440
ggtctgcatg ccgctcaaga tgttttagag atggagcaga aattacgcaa tattgtttca  1500
atgacaattc tggtagtttg tcaggccatt catcttcgcg gcaatattag tgaaattgcg  1560
cctgaaactg ctaaatttta ccatgcagta cgcgaaatca gttctccttt gatcactgat  1620
cgtgcgttgg atgaagatat aatccgcatt gcggatgcaa ttattaatga tcaacttcct  1680
ctgccagaaa tcatgctgga agaataagct tggcgtaatc atggtcatag ctgtttcctg  1740
tgtgaaattg ttatccgctc acaattccac acaacatacg agccggaagc ataaagtgta  1800
aagcctgggg tgcctaatga gtgagctaac tcacattaat tgcgttgcgc tcactgcccg  1860
ctttccagtc gggaaacctg tcgtgccagc tgcattaatg aatcggccaa cgcgcgggga  1920
gaggcggttt gcgtattggg cgctcttccg cttcctcgct cactgactcg ctgcgctcgg  1980
tcgttcggct gcggcgagcg gtatcagctc actcaaaggc ggtagtacgg gttttgctgc  2040
ccgcaaacgg gctgttctgg tgttgctagt ttgttatcag aatcgcagat ccggcttcag  2100
gtttgccggc tgaaagcgct atttcttcca gaattgccat gatttttcc ccacgggagg  2160
cgtcactggc tcccgtgttg tcggcagctt tgattcgata agcagcatcg cctgtttcag  2220
gctgtctatg tgtgactgtt gagctgtaac aagttgtctc aggtgttcaa tttcatgttc  2280
tagttgcttt gttttactgg tttcacctgt tctattaggt gttacatgct gttcatctgt  2340
tacattgtcg atctgttcat ggtgaacagc tttaaatgca ccaaaaactc gtaaaagctc  2400
tgatgtatct atcttttta caccgtttc atctgtgcat atggacagtt ttccctttga  2460
tatctaacgg tgaacagttg ttctactttt gtttgttagt cttgatgctt cactgataga  2520
tacaagagcc ataagaacct cagatccttc cgtatttagc cagtatgttc tctagtgtgg  2580
ttcgttgttt ttgcgtgagc catgagaacg aaccattgag atcatgctta ctttgcatgt  2640
cactcaaaaa ttttgcctca aaactggtga gctgaatttt tgcagttaaa gcatcgtgta  2700
gtgtttttct tagtccgtta cgtaggtagg aatctgatgt aatggttgtt ggtattttgt  2760
caccattcat ttttatctgg ttgttctcaa gttcggttac gagatccatt tgtctatcta  2820
gttcaacttg gaaaatcaac gtatcagtcg ggcggcctcg cttatcaacc accaatttca  2880
tattgctgta agtgtttaaa tctttactta ttggtttcaa aacccattgg ttaagccttt  2940
taaactcatg gtagttattt tcaagcatta acatgaactt aaattcatca aggctaatct  3000
ctatatttgc cttgtgagtt ttcttttgtg ttagttcttt taataaccac tcataaatcc  3060
tcatagagta tttgttttca aaagacttaa catgttccag attatatttt atgaattttt  3120
ttaactggaa aagataaggc aatatctctt cactaaaaac taattctaat tttcgcttg  3180
agaacttggc atagtttgtc cactggaaaa tctcaaagcc tttaaccaaa ggattcctga  3240
tttccacagt tctcgtcatc agctctctgg ttgctttagc taatacacca taagcatttt  3300
ccctactgat gttcatcatc tgagcgtatt ggttataagt gaacgatacc gtccgttctt  3360
tccttgtagg gttttcaatc gtggggttga gtagtgccac acagcataaa attagcttgg  3420
tttcatgctc cgttaagtca tagcgactaa tcgctagttc atttgctttg aaaacaacta  3480
attcagacat acatctcaat tggtctaggt gattttaatc actataccaa ttgagatggg  3540
ctagtcaatg ataattacta gtcctttcc tttgagttgt gggtatctgt aaattctgct  3600
agacctttgc tggaaaactt gtaaattctg ctagaccctc tgtaaattcc gctagacctt  3660
tgtgtgtttt ttttgtttat attcaagtgg ttataattta tagaataaag aaagaataaa  3720
aaaagataaa aagaatagat cccagccctg tgtataactc actactttag tcagttccgc  3780
agtattacaa aaggatgtcg caaacgctgt ttgctcctct acaaaacaga ccttaaaacc  3840
ctaaaggctt aagtagcacc ctcgcaagct cgggcaaatc gctgaatatt ccttttgtct  3900
ccgaccatca ggcacctgag tcgctgtctt tttcgtgaca ttcagttcgc tgcgctcacg  3960
gctctggcag tgaatggggg taaatggcac tacaggcgcc ttttatggat tcatgcaagg  4020
aaactaccca taatacaaga aaagcccgtc acgggcttct cagggcgttt tatggcgggt  4080
ctgctatgtg gtgctatctg acttttgct gttcagcagt tcctgccctc tgattttcca  4140
gtctgaccac ttcggattat cccgtgacag gtcattcaga ctggctaatg cacccagtaa  4200
```

```
ggcagcggta tcatcaacag gcttacccgt cttactgtct tttctacggg gtctgacgct  4260
cagtggaacg aaaactcacg ttaagggatt ttggtcatga gattatcaaa aaggatcttc  4320
acctagatcc ttttaaatta aaaatgaagt tttaaatcaa tctaaagtat atatgagtaa  4380
acttggtctg acagttacca atgcttaatc agtgaggcac ctatctcagc gatctgtcta  4440
tttcgttcat ccatagttgc ctgactcccc gtcgtgtaga taactacgat acgggagggc  4500
ttaccatctg gccccagtgc tgcaatgata ccgcgagacc cacgctcacc ggctccagat  4560
ttatcagcaa taaaccagcc agccggaagg gccgagcgca gaagtggtcc tgcaacttta  4620
tccgcctcca tccagtctat taattgttgc cgggaagcta gagtaagtag ttcgccagtt  4680
aatagtttgc gcaacgttgt tgccattgct acaggcatcg tggtgtcacg ctcgtcgttt  4740
ggtatggctt cattcagctc cggttcccaa cgatcaaggc gagttacatg atcccccatg  4800
ttgtgcaaaa aagcggttag ctccttcggt cctccgatcg ttgtcagaag taagttggcc  4860
gcagtgttat cactcatggt tatggcagca ctgcataatt ctcttactgt catgccatcc  4920
gtaagatgct tttctgtgac tggtgagtac tcaaccaagt cattctgaga atagtgtatg  4980
cggcgaccga gttgctcttg cccggcgtca atacgggata ataccgcgcc acatagcaga  5040
actttaaaag tgctcatcat tggaaaacgt tcttcggggc gaaaactctc aaggatctta  5100
ccgctgttga gatccagttc gatgtaaccc actcgtgcac ccaactgatc ttcagcatct  5160
tttactttca ccagcgtttc tgggtgagca aaaacaggaa ggcaaaatgc cgcaaaaaag  5220
ggaataaggg cgacacggaa atgttgaata ctcatactct tcctttttca atattattga  5280
agcatttatc agggttattg tctcatgagc ggatacatat ttgaatgtat ttagaaaaat  5340
aaacaaatag gggttccgcg cacatttccc cgaaaagtgc cacctgacgt ctaagaaacc  5400
attattatca tgacattaac ctataaaaat aggcgtatca cgaggccctt tcgtctcgcg  5460
cgtttcggtg atgacggtga aaacctctga cacatgcagc tcccggagac ggtcacagct  5520
tgtctgtaag cggatgccgg gagcagacaa gcccgtcagg gcgcgtcagc gggtgttggc  5580
gggtgtcggg gctggcttaa ctatgcggca tcagagcaga ttgtactgag agtgcaccat  5640
atgcggtgtg aaataccgca cagatgcgta aggagaaaat accgcatcag gcgccattcg  5700
ccattcaggc tgcgcaactg ttgggaaggg cgatcggtgc gggcctcttc gctattacgc  5760
cagctggcga aagggggatg tgctgcaagg cgattaagtt gggtaacgcc agggttttcc  5820
cagtcacgac gttgtaaaac gacggccagt gaattcg                          5857

SEQ ID NO: 296          moltype = DNA  length = 6602
FEATURE                 Location/Qualifiers
misc_feature            1..6602
                        note = Synthetic polynucleotide
source                  1..6602
                        mol_type = other DNA
                        organism = synthetic construct
SEQUENCE: 296
accactccct atcagtgata gagaaaagtg aactctagaa ataattttgt ttaactttaa  60
gaaggagata tacatatgaa aacactatca caggcccaat ctaaaacttc ttcacagcaa  120
ttcagcttta ccgggaactc gtctgcgaat gtaattatcg gcaatcaaaa gctgaccatt  180
aatgatgtag ctcgcgttgc ccggaatggc actttggtgt cactgacgaa caataccgac  240
attctgcaag gtattcaagc tagctgcgat tatatcaata acgccgttga atctggcgag  300
ccaatctacg gggtaacaag cggttttggt gggatggcga acgttgccat tagccgtgaa  360
caggcgagcg aacttcagac caacctcgtt tggttcctaa agacaggagc tggtaataag  420
ttacctctgg ctgacgtaag agccgcgatg ctgcttcgcg ctaatagtca catgcgcggc  480
gccagtggta tccgtcttga gcttatcaag aggatggaaa tcttcctcaa cgcgggtgtc  540
acaccatatg tttatgagtt tggtagtatc ggagccagtg gtgatcttgt tcccctgagt  600
tatattacgg gttcattgat tggtttagac ccgtccttta aagtggattt taacgggaaa  660
gaaatggacg ccccgaccgc tttacgacag cttaatctga gcccacttac tttgctccct  720
aaagaaggtc ttgccatgat gaatggcacc tctgtgatga ctggaattgc cgcgaattgt  780
gtgtatgaca cgcagatcct aacggccatt gccatgggtg ttcacgcgtt ggacattcaa  840
gccctgaatg gtacaaacca gtcgtttcat ccgtttatcc ataattcaaa accccatccg  900
ggacagcttt gggctgctga tcagatgatc tcactcctgg ccaatagtca actggttcgg  960
gacgagctcg acggcaaaca tgattatcgc gatcatgagc tcatccagga ccggtattca  1020
cttcgttgtc tcccacaata cctggggcct atcgttgatg gtatatctca aattgcgaag  1080
caaattgaaa ttgagatcaa tagcgtaacc gacaacccgc ttatcgatgt tgataatcag  1140
gcctcttatc acggtggcaa ttttctgggc cagtatgttg gtatggggat ggatcacctg  1200
cggtactata ttgggcttct ggctaaacat cttgatgtgc agattgcctt attagcttca  1260
ccagaatttt caaatggact gccgccatca ttgctcggta acagagaaag gaaagtaaat  1320
atgggcctta agggccttca gatatgtggt aactcaatca tgcccctcct gacctttat  1380
gggaactcaa ttgctgatcg ttttccgaca catgctgaac agtttaacca aaacattaac  1440
tcacagggct atacatccgc gacgttagcg cgtcggtccg tggatatctt ccagaattat  1500
gttgctatcg ctctgatgtt cggcgtacag gccgttgatt tgcgcactta taaaaaaacc  1560
ggtcactacg atgctcgggc ttgcctgtcg cctgccaccg agcggcttta tagcgccgta  1620
cgtcatgttg tgggtcagaa accgacgtcg gaccgcccct atatttggaa tgataatgaa  1680
caagggctgg atgaacacat cgcccggata tctgccgata ttgccgccgg aggtgtcatc  1740
gtccaggcgg tacaagacat acttccttgc ctgcattaag cttggcgtaa tcatggtcat  1800
agctgtttcc tgtgtgaaat tgttatccgc tcacaattcc acacaacata cgagccggaa  1860
gcataaagtg taaagcctgg ggtgcctaat gagtgagcta actcacatta attgcgttgc  1920
gctcactgcc cgctttccag tcgggaaacc tgtcgtgcca gctgcattaa tgaatcggcc  1980
aacgcgcggg gagaggcggt ttgcgtattg ggcgctcttc cgcttcctcg ctcactgact  2040
cgctgcgctc ggtcgttcgg ctgcggcgag cggtatcagc tcactcaaag gcggtagtac  2100
gggttttgct gcccgcaaac gggctgttct ggtgttgcta gtttgttatc agaatcgcag  2160
atccggcttc aggtttgccg gctgaaagcg ctatttcttc cagaattgcc atgatttttt  2220
ccccacggga ggcgtcactg gctcccgtgt tgtcggcagc tttgattcga taagcagcat  2280
cgcctgtttc aggctgtcta tgtgtgactg ttgagctgta acaagttgtc tcaggtgttc  2340
aatttcatgt tctagttgct ttgttttact ggtttcacct gttctattag gtgttacatg  2400
ctgttcatct gttacattgt cgatctgttc atggtgaaca gctttaaatg caccaaaaac  2460
tcgtaaaagc tctgatgtat ctatcttttt tacaccgttt tcatctgtgc atatggacag  2520
```

```
ttttcccttt gatatctaac ggtgaacagt tgttctactt ttgtttgtta gtcttgatgc  2580
ttcactgata gatacaagag ccataagaac ctcagatcct tccgtattta gccagtatgt  2640
tctctagtgt ggttcgttgt ttttgcgtga gccatgagaa cgaaccattg agatcatgct  2700
tactttgcat gtcactcaaa aattttgcct caaaactggt gagctgaatt tttgcagtta  2760
aagcatcgtg tagtgttttt cttagtccgt tacgtaggta ggaatctgat gtaatggttg  2820
ttggtatttt gtcaccattc atttttatct ggttgttctc aagttcggtt acgagatcca  2880
tttgtctatc tagttcaact tggaaaatca acgtatcagt cgggcggcct cgcttatcaa  2940
ccaccaattt catattgctg taagtgttta aatctttact tattggtttc aaaacccatt  3000
ggttaagcct tttaaactca tggtagttat tttcaagcat taacatgaac ttaaattcat  3060
caaggctaat ctctatattt gccttgtgag ttttcttttg tgttagttct tttaataacc  3120
actcataaat cctcatagag tatttgtttt caaaagactt aacatgttcc agattatatt  3180
ttatgaattt ttttaactgg aaaagataag gcaatatctc ttcactaaaa actaattcta  3240
atttttcgct tgagaacttg gcatagtttg tccactggaa aatctcaaag cctttaacca  3300
aaggattcct gatttccaca gttctcgtca tcagctctct ggttgcttta gctaatacac  3360
cataagcatt ttccctactg atgttcatca tctgagcgta ttggttataa gtgaacgata  3420
ccgtccgttc tttccttgta gggttttcaa tcgtggggtt gagtagtgcc acacagcata  3480
aaattagctt ggtttcatgc tccgttaagt catagcgact aatcgctagt tcatttgctt  3540
tgaaaacaac taattcagac atacatctca attggtctag gtgattttaa tcactatacc  3600
aattgagatg ggctagtcaa tgataattac tagtcctttt cctttgagtt gtgggtatct  3660
gtaaattctg ctagaccttt gctggaaaac ttgtaaattc tgctagaccc tctgtaaatt  3720
ccgctagacc tttgtgtgtt ttttttgttt atattcaagt ggttataatt tatagaataa  3780
agaaagaata aaaaaagata aaaagaatag atcccagccc tgtgtataac tcactacttt  3840
agtcagttcc gcagtattac aaaaggatgt cgcaaacgct gtttgctcct ctacaaaaca  3900
gaccttaaaa ccctaaaggc ttaagtagca ccctcgcaag ctcgggcaaa tcgctgaata  3960
ttccttttgt ctccgaccat caggcacctg agtcgctgtc tttttcgtga cattcagttc  4020
gctgcgctca cggctctggc agtgaatggg ggtaaatggc actacaggcg ccttttatgg  4080
attcatgcaa ggaaactacc cataatacaa gaaaagcccg tcacgggctt ctcagggcgt  4140
tttatggcgg gtctgctatg tggtgctatc tgactttttg ctgttcagca gttcctgccc  4200
tctgattttc cagtctgacc acttcggatt atcccgtgac aggtcattca gactggctaa  4260
tgcacccagt aaggcagcgg tatcatcaac aggcttaccc gtcttactgt cttttctacg  4320
gggtctgacg ctcagtggaa cgaaaactca cgttaaggga ttttggtcat gagattatca  4380
aaaaggatct tcacctagat ccttttaaat taaaaatgaa gttttaaatc aatctaaagt  4440
atatatgagt aaacttggtc tgacagttac caatgcttaa tcagtgaggc acctatctca  4500
gcgatctgtc tatttcgttc atccatagtt gcctgactcc ccgtcgtgta gataactacg  4560
atacgggagg gcttaccatc tggccccagt gctgcaatga taccgcgaga cccacgctca  4620
ccggctccag atttatcagc aataaaccag ccagccggaa gggccgagcg cagaagtggt  4680
cctgcaactt tatccgcctc catccagtct attaattgtt gccgggaagc tagagtaagt  4740
agttcgccag ttaatagttt gcgcaacgtt gttgccattg ctacaggcat cgtggtgtca  4800
cgctcgtcgt ttggtatggc ttcattcagc tccggttccc aacgatcaag gcgagttaca  4860
tgatccccca tgttgtgcaa aaaagcggtt agctccttcg gtcctccgat cgttgtcaga  4920
agtaagttgg ccgcagtgtt atcactcatg gttatggcag cactgcataa ttctcttact  4980
gtcatgccat ccgtaagatg cttttctgtg actggtgagt actcaaccaa gtcattctga  5040
gaatagtgta tgcggcgacc gagttgctct tgcccggcgt caatacggga taataccgcg  5100
ccacatagca gaactttaaa agtgctcatc attggaaaac gttcttcggg gcgaaaactc  5160
tcaaggatct taccgctgtt gagatccagt tcgatgtaac ccactcgtgc acccaactga  5220
tcttcagcat cttttacttt caccagcgtt tctgggtgag caaaaacagg aaggcaaaat  5280
gccgcaaaaa agggaataag ggcgacacgg aaatgttgaa tactcatact cttccttttt  5340
caatattatt gaagcattta tcagggttat tgtctcatga gcggatacat atttgaatgt  5400
atttagaaaa ataaacaaat aggggttccg cgcacatttc cccgaaaagt gccacctgac  5460
gtctaagaaa ccattattat catgacatta acctataaaa ataggcgtat cacgaggccc  5520
tttcgtctcg cgcgtttcgg tgatgacggt gaaaacctct gacacatgca gctcccggag  5580
acggtcacag cttgtctgta agcggatgcc gggagcagac aagcccgtca gggcgcgtca  5640
gcgggtgttg gcgggtgtcg gggctggctt aactatgcgg catcagagca gattgtactg  5700
agagtgcacc atatgcggtg tgaaataccg cacagatgcg taaggagaaa ataccgcatc  5760
aggcgccatt cgccattcag gctgcgcaac tgttgggaag ggcgatcggt gcgggcctct  5820
tcgctattac gccagctggc gaaaggggga tgtgctgcaa ggcgattaag ttgggtaacg  5880
ccagggtttt cccagtcacg acgttgtaaa acgacggcca gtgaattcgt taagacccac  5940
tttcacattt aagttgtttt tctaatccgc atatgatcaa ttcaaggccg aataagaagg  6000
ctggctctgc accttggtga tcaaataatt cgatagcttg tcgtaataat ggcggcatac  6060
tatcagtagt aggtgtttcc ctttcttctt tagcgacttg atgctcttga tcttccaata  6120
cgcaacctaa agtaaaatgc cccacagcgc tgagtgcata taatgcattc tctagtgaaa  6180
aaccttgttg gcataaaaag gctaattgat tttcgagagt ttcatactgt ttttctgtag  6240
gccgtgtacc taaatgtact tttgctccat cgcgatgact tagtaaagca catctaaaac  6300
ttttagcgtt attacgtaaa aaatcttgcc agctttcccc ttctaaaggg caaaagtgag  6360
tatggtgcct atctaacatc tcaatggcta aggcgtcgag caaagcccgc ttattttttta  6420
catgccaata caatgtaggc tgctctacac ctagcttctg ggcgagttta cgggttgtta  6480
aaccttcgat tccgacctca ttaagcagct ctaatgcgct gttaatcact ttacttttat  6540
ctaatctaga catcattaat tcctaatttt tgttgacact ctatcattga tagagttatt  6600
tt                                                                 6602
```

```
SEQ ID NO: 297          moltype = DNA  length = 6497
FEATURE                 Location/Qualifiers
misc_feature            1..6497
                        note = Synthetic polynucleotide
source                  1..6497
                        mol_type = other DNA
                        organism = synthetic construct
SEQUENCE: 297
accactccct atcagtgata gagaaaagtg aactctagaa ataattttgt ttaactttaa  60
```

-continued

```
gaaggagata tacatatgaa agctaaagat gttcagccaa ccattattat taataaaaat  120
ggccttatct ctttggaaga tatctatgac attgcgataa aacaaaaaaa agtagaaata  180
tcaacggaga tcactgaact tttgacgcat ggtcgtgaaa aattagagga aaaattaaat  240
tcaggagagg ttatatatgg aatcaataca ggatttggag ggaatgccaa tttagttgtg  300
ccatttgaga aaatcgcaga gcatcagcaa aatctgttaa cttttctttc tgctggtact  360
ggggactata tgtccaaacc ttgtattaaa gcgtcacaat ttactatgtt actttctgtt  420
tgcaaaggtt ggtctgcaac cagaccaatt gtcgctcaag caattgttga tcatattaat  480
catgacattg ttcctctggt tcctcgctat ggctcagtgg gtgcaagcgg tgatttaatt  540
cctttatctt atattgcacg agcattatgt ggtatcggca aagtttatta tatgggcgca  600
gaaattgacg ctgctgaagc aattaaacgt gcagggttga caccattatc gttaaaagcc  660
aaagaaggtc ttgctctgat taacggcacc cgggtaatgt caggaatcag tgcaatcacc  720
gtcattaaac tggaaaaact atttaaagcc tcaatttctg cgattgccct tgctgttgaa  780
gcattacttg catctcatga acattatgat gcccggattc aacaagtaaa aaatcatcct  840
ggtcaaaacg cggtggcaag tgcattgcgt aatttattgg caggttcaac gcaggttaat  900
ctattatctg gggttaaaga acaagccaat aaagcttgtc gtcatcaaga aattacccaa  960
ctaaatgata ccttacagga agtttattca attcgctgtg caccacaagt attaggtata  1020
gtgccagaat ctttagctac cgctcggaaa atattggaac gggaagttat ctcagctaat  1080
gataatccat tgatagatcc agaaaatggc gatgttctac acggtggaaa ttttatgggg  1140
caatatgtcg cccgaacaat ggatgcatta aaactggata ttgctttaat tgccaatcat  1200
cttcacgcca ttgtggctct tatgatggat aaccgtttct ctcgtggatt acctaattca  1260
ctgagtccga cacccggcat gtatcaaggt tttaaaggcg tccaactttc tcaaaccgct  1320
ttagttgctg caattcgcca tgattgtgct gcatcaggta ttcataccct cgccacagaa  1380
caatacaatc aagatattgt cagtttaggt ctgcatgccg ctcaagatgt tttagagatg  1440
gagcagaaat tacgcaatat tgtttcaatg acaattctgg tagtttgtca ggccattcat  1500
cttcgcggca atattagtga aattgcgcct gaaactgcta aattttacca tgcagtacgc  1560
gaaatcagtt ctcctttgat cactgatcgt gcgttggatg aagatataat ccgcattgcg  1620
gatgcaatta ttaatgatca acttcctctg ccagaaatca tgctggaaga ataagcttgg  1680
cgtaatcatg gtcatagctg tttcctgtgt gaaattgtta tccgctcaca attccacaca  1740
acatacgagc cggaagcata aagtgtaaag cctggggtgc ctaatgagtg agctaactca  1800
cattaattgc gttgcgctca ctgcccgctt tccagtcggg aaacctgtcg tgccagctgc  1860
attaatgaat cggccaacgc gcggggagag gcggtttgcg tattgggcgc tcttccgctt  1920
cctcgctcac tgactcgctg cgctcggtcg ttcggctgcg gcgagcggta tcagctcact  1980
caaaggcggt agtacgggtt ttgctgcccg caaacgggct gttctggtgt tgctagtttg  2040
ttatcagaat cgcagatccg gcttcaggtt tgccggctga aagcgctatt tcttccagaa  2100
ttgccatgat tttttcccca cgggaggcgt cactggctcc cgtgttgtcg gcagctttga  2160
ttcgataagc agcatcgcct gtttcaggct gtctatgtgt gactgttgag ctgtaacaag  2220
ttgtctcagg tgttcaattt catgttctag ttgctttgtt ttactggttt cacctgttct  2280
attaggtgtt acatgctgtt catctgttac attgtcgatc tgttcatggt gaacagcttt  2340
aaatgcacca aaaactcgta aaagctctga tgtatctatc ttttttacac cgttttcatc  2400
tgtgcatatg gacagttttc cctttgatat ctaacggtga acagttgttc tacttttgtt  2460
tgttagtctt gatgcttcac tgatagatac aagagccata agaacctcag atccttccgt  2520
atttagccag tatgttctct agtgtggttc gttgttttttg cgtgagccat gagaacgaac  2580
cattgagatc atgcttactt tgcatgtcac tcaaaaattt tgcctcaaaa ctggtgagct  2640
gaatttttgc agttaaagca tcgtgtagtg tttttcttag tccgttacgt aggtaggaat  2700
ctgatgtaat ggttgttggt attttgtcac cattcatttt tatctggttg ttctcaagtt  2760
cggttacgag atccatttgt ctatctagtt caacttggaa aatcaacgta tcagtcgggc  2820
ggcctcgctt atcaaccacc aatttcatat tgctgtaagt gtttaaatct ttacttattg  2880
gtttcaaaac ccattggtta agccttttaa actcatggta gttattttca agcattaaca  2940
tgaacttaaa ttcatcaagg ctaatctcta tatttgcctt gtgagttttc ttttgtgtta  3000
gttcttttaa taaccactca taaatcctca tagagtattt gttttcaaaa gacttaacat  3060
gttccagatt atattttatg aatttttttta actggaaaag ataaggcaat atctcttcac  3120
taaaaactaa ttctaatttt tcgcttgaga acttggcata gtttgtccac tggaaaatct  3180
caaagccttt aaccaaagga ttcctgattt ccacagttct cgtcatcagc tctctggttg  3240
ctttagctaa tacaccataa gcattttccc tactgatgtt catcatctga gcgtattggt  3300
tataagtgaa cgataccgtc cgttctttcc ttgtagggtt ttcaatcgtg gggttgagta  3360
gtgccacaca gcataaaatt agcttggttt catgctccgt taagtcatag cgactaatcg  3420
ctagttcatt tgctttgaaa acaactaatt cagacataca tctcaattgg tctaggtgat  3480
tttaatcact ataccaattg agatgggcta gtcaatgata attactagtc cttttccttt  3540
gagttgtggg tatctgtaaa ttctgctaga cctttgctgg aaaacttgta aattctgcta  3600
gaccctctgt aaattccgct agacctttgt gtgtttttttt tgtttatatt caagtggtta  3660
taatttatag aataaagaaa gaataaaaaa agataaaaag aatagatccc agccctgtgt  3720
ataactcact actttagtca gttccgcagt attacaaaag gatgtcgcaa acgctgtttg  3780
ctcctctaca aaacagacct taaaacccta aaggcttaag tagcaccctc gcaagctcgg  3840
gcaaatcgct gaatattcct tttgtctccg accatcaggc acctgagtcg ctgtcttttt  3900
cgtgacattc agttcgctgc gctcacggct ctggcagtga atgggggtaa atggcactac  3960
aggcgccttt tatggattca tgcaaggaaa ctacccataa tacaagaaaa gcccgtcacg  4020
ggcttctcag ggcgttttat ggcgggtctg ctatgtggtg ctatctgact ttttgctgtt  4080
cagcagttcc tgccctctga ttttccagtc tgaccacttc ggattatccc gtgacaggtc  4140
attcagactg gctaatgcac ccagtaaggc agcggtatca tcaacaggct tacccgtctt  4200
actgtctttt ctacggggtc tgacgctcag tggaacgaaa actcacgtta agggattttg  4260
gtcatgagat tatcaaaaag gatcttcacc tagatccttt taaattaaaa atgaagtttt  4320
aaatcaatct aaagtatata tgagtaaact tggtctgaca gttaccaatg cttaatcagt  4380
gaggcaccta tctcagcgat ctgtctattt cgttcatcca tagttgcctg actccccgtc  4440
gtgtagataa ctacgatacg ggagggctta ccatctggcc ccagtgctgc aatgataccg  4500
cgagacccac gctcaccggc tccagattta tcagcaataa accagccagc cggaagggcc  4560
gagcgcagaa gtggtcctgc aactttatcc gcctccatcc agtctattaa ttgttgccgg  4620
gaagctagag taagtagttc gccagttaat agtttgcgca acgttgttgc cattgctaca  4680
ggcatcgtgg tgtcacgctc gtcgtttggt atggcttcat tcagctccgg ttcccaacga  4740
tcaaggcgag ttacatgatc ccccatgttg tgcaaaaaag cggttagctc cttcggtcct  4800
```

-continued

```
ccgatcgttg tcagaagtaa gttggccgca gtgttatcac tcatggttat ggcagcactg  4860
cataattctc ttactgtcat gccatccgta agatgctttt ctgtgactgg tgagtactca  4920
accaagtcat tctgagaata gtgtatgcgg cgaccgagtt gctcttgccc ggcgtcaata  4980
cgggataata ccgcgccaca tagcagaact ttaaaagtgc tcatcattgg aaaacgttct  5040
tcggggcgaa aactctcaag gatcttaccg ctgttgagat ccagttcgat gtaacccact  5100
cgtgcaccca actgatcttc agcatctttt actttcacca gcgtttctgg gtgagcaaaa  5160
acaggaaggc aaaatgccgc aaaaaaggga ataagggcga cacggaaatg ttgaatactc  5220
atactcttcc tttttcaata ttattgaagc atttatcagg gttattgtct catgagcgga  5280
tacatatttg aatgtattta gaaaaataaa caaatagggg ttccgcgcac atttccccga  5340
aaagtgccac ctgacgtcta agaaaccatt attatcatga cattaaccta taaaaatagg  5400
cgtatcacga ggccctttcg tctcgcgcgt ttcggtgatg acggtgaaaa cctctgacac  5460
atgcagctcc cggagacggt cacagcttgt ctgtaagcgg atgccgggag cagacaagcc  5520
cgtcagggcg cgtcagcggg tgttggcggg tgtcggggct ggcttaacta tgcggcatca  5580
gagcagattg tactgagagt gcaccatatg cggtgtgaaa taccgcacag atgcgtaagg  5640
agaaaatacc gcatcaggcg ccattcgcca ttcaggctgc gcaactgttg ggaagggcga  5700
tcggtgcggg cctcttcgct attacgccag ctggcgaaag ggggatgtgc tgcaaggcga  5760
ttaagttggg taacgccagg gttttcccag tcacgacgtt gtaaaacgac ggccagtgaa  5820
ttcgttaaga cccactttca catttaagtt gtttttctaa tccgcatatg atcaattcaa  5880
ggccgaataa gaaggctggc tctgcacctt ggtgatcaaa taattcgata gcttgtcgta  5940
ataatggcgg catactatca gtagtaggtg tttccctttc ttctttagcg acttgatgct  6000
cttgatcttc caatacgcaa cctaaagtaa aatgccccac agcgctgagt gcatataatg  6060
cattctctag tgaaaaacct tgttggcata aaaaggctaa ttgattttcg agagtttcat  6120
actgtttttc tgtaggccgt gtacctaaat gtacttttgc tccatcgcga tgacttagta  6180
aagcacatct aaaactttta gcgttattac gtaaaaaatc ttgccagctt tccccttcta  6240
aagggcaaaa gtgagtatgg tgcctatcta acatctcaat ggctaaggcg tcgagcaaag  6300
cccgcttatt ttttacatgc caatacaatg taggctgctc tacacctagc ttctgggcga  6360
gtttacgggt tgttaaacct tcgattccga cctcattaag cagctctaat gcgctgttaa  6420
tcactttact tttatctaat ctagacatca ttaattccta atttttgttg acactctatc  6480
attgatagag ttatttt                                                 6497
```

```
SEQ ID NO: 298          moltype = DNA  length = 2137
FEATURE                 Location/Qualifiers
misc_feature            1..2137
                        note = Synthetic polynucleotide
source                  1..2137
                        mol_type = other DNA
                        organism = synthetic construct
SEQUENCE: 298
ccagtgaatt cgttaagacc cactttcaca tttaagttgt ttttctaatc cgcatatgat  60
caattcaagg ccgaataaga aggctggctc tgcaccttgg tgatcaaata attcgatagc  120
ttgtcgtaat aatggcggca tactatcagt agtaggtgtt tccctttctt ctttagcgac  180
ttgatgctct tgatcttcca atacgcaacc taaagtaaaa tgccccacag cgctgagtgc  240
atataatgca ttctctagtg aaaaaccttg ttggcataaa aaggctaatt gattttcgag  300
agtttcatac tgtttttctg taggccgtgt acctaaatgt acttttgctc catcgcgatg  360
acttagtaaa gcacatctaa aacttttagc gttattacgt aaaaaatctt gccagctttc  420
cccttctaaa gggcaaaagt gagtatggtg cctatctaac atctcaatgg ctaaggcgtc  480
gagcaaagcc cgcttatttt ttacatgcca atacaatgta ggctgctcta cacctagctt  540
ctgggcgagt ttacgggttg ttaaaccttc gattccgacc tcattaagca gctctaatgc  600
gctgttaatc actttacttt tatctaatct agacatcatt aattcctaat ttttgttgac  660
actctatcat tgatagagtt attttaccac tccctatcag tgatagagaa aagtgaactc  720
tagaaataat tttgtttaac tttaagaagg agatatacat atgaaaaacg cgtcaaccgt  780
atcggaagat actgcgtcga atcaagagcc gacgcttcat cgcggattac ataaccgtca  840
tattcaactg attgcgttgg gtggcgcaat tggtactggt ctgtttcttg gcattggccc  900
ggcgattcag atggcgggtc cggctgtatt gctgggctac ggcgtcgccg ggatcatcgc  960
tttcctgatt atgcgccagc ttggcgaaat ggtggttgag gagccggtat ccggttcatt  1020
tgcccacttt gcctataaat actggggacc gtttgcgggc ttcctctctg gctggaacta  1080
ctgggtaatg ttcgtgctgg tgggaatggc agagctgacc gctgcgggca tctatatgca  1140
gtactggttc ccggatgttc caacgtggat ttgggctgcc gccttcttta ttatcatcaa  1200
cgccgttaac ctggtgaacg tgcgcttata tggcgaaacc gagttctggt ttgcgttgat  1260
taaagtgctg gcaatcatcg gtatgatcgg ctttggcctg tggctgctgt tttctggtca  1320
cggcggcgag aaagccagta tcgacaacct ctggcgctac ggtggtttct tcgccaccgg  1380
ctggaatggg ctgattttgt cgctggcggt aattatgttc tccttcggcg gtctggagct  1440
gattgggatt actgccgctg aagcgcgcga tccggaaaaa agcattccaa aagcggtaaa  1500
tcaggtggtg tatcgcatcc tgctgtttta catcggttca ctggtggttt tactggcgct  1560
ctatccgtgg gtggaagtga aatccaacag tagcccgttt gtgatgattt tccataatct  1620
cgacagcaac gtggtagctt ctgcgctgaa cttcgtcatt ctggtagcat cgctgtcagt  1680
gtataacagc ggggtttact ctaacagccg catgctgttt ggcctttctg tgcagggtaa  1740
tgcgccgaag tttttgactc gcgtcagccg tcgcggtgtg ccgattaact cgctgatgct  1800
ttccggagcg atcacttcgc tggtggtgtt aatcaactat ctgctgccgc aaaaagcgtt  1860
tggtctgctg atggcgctgg tggtagcaac gctgctgttg aactggatta tgatctgtct  1920
ggcgcatctg cgttttcgtg cagcgatgcg acgtcagggg cgtgaaacac agtttaaggc  1980
gctgctctat ccgttcggca actatctctg cattgccttc ctcggcatga ttttgctgct  2040
gatgtgcacg atggatgata tgcgcttgtc agcgatcctg ctgccggtgt ggattgtatt  2100
cctgtttatg gcatttaaaa cgctgcgtcg gaaataa                           2137
```

```
SEQ ID NO: 299          moltype = AA  length = 5
FEATURE                 Location/Qualifiers
REGION                  1..5
                        note = Synthetic peptide
```

-continued

```
source                  1..5
                        mol_type = protein
                        organism = synthetic construct
SEQUENCE: 299
GGGGS                                                                     5

SEQ ID NO: 300          moltype = AA  length = 18
FEATURE                 Location/Qualifiers
REGION                  1..18
                        note = Synthetic peptide
source                  1..18
                        mol_type = protein
                        organism = synthetic construct
SEQUENCE: 300
KESGSVSSEQ LAQFRSLD                                                       18

SEQ ID NO: 301          moltype = AA  length = 14
FEATURE                 Location/Qualifiers
REGION                  1..14
                        note = Synthetic peptide
source                  1..14
                        mol_type = protein
                        organism = synthetic construct
SEQUENCE: 301
EGKSSGSGSE SKST                                                           14

SEQ ID NO: 302          moltype = AA  length = 8
FEATURE                 Location/Qualifiers
REGION                  1..8
                        note = Synthetic peptide
source                  1..8
                        mol_type = protein
                        organism = synthetic construct
SEQUENCE: 302
GGGGGGGG                                                                  8

SEQ ID NO: 303          moltype = AA  length = 12
FEATURE                 Location/Qualifiers
REGION                  1..12
                        note = Synthetic peptide
source                  1..12
                        mol_type = protein
                        organism = synthetic construct
SEQUENCE: 303
GSAGSAAGSG EF                                                             12

SEQ ID NO: 304          moltype = DNA  length = 22
FEATURE                 Location/Qualifiers
source                  1..22
                        mol_type = genomic DNA
                        organism = Escherichia coli
SEQUENCE: 304
ggaattgtga gcgctcacaa tt                                                  22
```

BACTERIA FOR THE TREATMENT OF DISORDERS

RELATED APPLICATIONS

The instant application is a continuation application based upon U.S. patent application Ser. No. 16/621,792, filed Dec. 12, 2019, which is a national stage application under 35 U.S.C. § 371 of international application number PCT/US2018/038840, filed Jun. 21, 2018, which further claims priority to U.S. Provisional Application No. 62/523,225, filed Jun. 21, 2017; U.S. Provisional Application No. 62/552,785, filed Aug. 31, 2017; U.S. Provisional Application No. 62/552,829, filed Aug. 31, 2017; U.S. Provisional Application No. 62/614,213, filed Jan. 5, 2018; U.S. Provisional Application No. 62/624,299, filed Jan. 31, 2018, and U.S. Provisional Application No. 62/523,202, filed Jun. 21, 2017. The entire contents of each of the foregoing applications are hereby expressly incorporated herein by reference in their respective entireties.

SEQUENCE LISTING

The application contains a Sequence Listing which has been submitted electronically in .XML format and is hereby incorporated by reference in its entirety. Said .XML copy, created on Nov. 6, 2023, is named "126046-09402.xml" and is 502,239 bytes in size. The sequence listing contained in this .XML file is part of the specification and is hereby incorporated by reference herein in its entirety.

BACKGROUND

A growing body of scientific evidence suggests that probiotic bacteria are beneficial in the treatment or prevention of various diseases or disorders associated with the gut, including, for example, gastrointestinal disorders such as Crohn's disease and inflammatory bowel syndrome. More recently, genetically engineered bacteria have emerged as a potential new therapeutic treatment modality for gastrointestinal diseases and have also opened the field of bacterial therapies to a large number of other indications, including metabolic diseases, inflammatory diseases, and cancer. One benefit of genetically engineered bacteria is the ability to specifically target one or more disease mechanisms. For example, for gastrointestinal disorders, bacteria can be engineered to contain genes for the expression of anti-inflammatory agents or agents that aid in the healing of a disrupted gut-barrier, such as the short chain fatty acid butyrate, e.g., as described in International Patent Publication WO2016141108. Genetically engineered bacteria may also be considered as a treatment modality for various metabolic disorders, including but not limited to rare metabolic disorders arising from inborn errors in metabolism or IEMs. For example, as described in International Patent Publication WO2016090343, bacteria have been genetically modified to treat phenylketonuria (PKU) by expressing one or more enzymes which metabolize phenylalanine and thereby consuming excess phenylalanine within the gastrointestinal tract.

Bacteriophage are the most common biological entity in the world, and it is well documented that a majority of bacterial species, both gram positive and gram negative, contain one or more DNA bacteriophages which are integrated as so-called prophages in the bacterial chromosome (Clokie et al, Phages in Nature, Bacteriophage. 2011 January-February; 1(1): 31-45).

DNA phages can be lytic or temperate. Lytic phages infect bacterial cells and then program the synthesis of progeny phages, which are then released from the lysed cell. Conversely, temperate DNA phages establish a stable relationship with their host bacteria in which the integrated phage DNA, i.e., the prophage, is replicated in concert with the host's genome, and any host-damaging phage genes are not expressed. However, bacteriophage particles can be released from cells containing an intact prophage by a process called induction, during which prophage genes required for lytic growth are turned on and progeny phage particles are produced and released from the cell through lysis of the cell (reviewed in Casjens, Prophages and bacterial genomics: what have we learned so far?; Mol Microbiol. 2003 July; 49(2):277-300). In some cases, induction can occur spontaneously and randomly in a small or large fraction of the bacteria that harbor the prophage. In other cases, specific, often undefined, environmental signals can cause simultaneous induction of a particular prophage in many cells, causing death of the bacterial cells.

Not all prophages have the ability to undergo a lytic cycle. Non-functional, i.e., defective or cryptic prophages can accrue to a high level of abundancy in many bacteria as a result of mutational decay and/or the loss of one or more genes essential to the lytic cycle over thousands of bacterial replication cycles (Bobay et al., Pervasive domestication of defective prophages by bacteria, Proc Natl Acad Sci USA. 2014 Aug. 19; 111(33): 12127-12132, and references therein).

SUMMARY

In some embodiments, the disclosure provides a bacterium comprising one or more phage genome(s), wherein one or more of the phage genomes are defective. In some embodiments, the disclosure provides a bacterium comprising one or more phage genome(s), wherein one or more of the phage genomes are defective such that lytic phage is not produced. In some embodiments, the disclosure provides a bacterium comprising one or more phage genome(s), wherein one or more of the phage genomes are defective in that one or more phage genes are not expressed. In some embodiments, the disclosure provides a bacterium comprising one or more phage genome(s), wherein one or more phage genes in the one or more phage genome(s) comprise one or more mutations. In some embodiments, the one or more phage genome(s) are present in the natural state of the probiotic bacterium. In some embodiments, the bacteria encode one or more lysogenic phage(s). In some embodiments, the bacteria encode one or more defective or cryptic phage(s) or satellite phage(s). In some embodiments, the bacteria encode one or more tailiocins or gene transfer agents.

In some of the embodiments of the disclosure, one or more of the phage genomes are mutated. Such mutations may include one or more deletion(s) of a part of or the complete sequence of one or more phage genes. Alternatively, the mutations may include one or more insertion(s) of one or more nucleotides into one or more phage genes. In another example, the mutations may include one or more substitution(s) of a part of or the complete sequence of one or more phage genes. In another example, the mutations include one or more inversion(s) of a part of or the complete sequence of one or more phage genes in the phage genome. Additionally, the mutations may include any combination of one or more deletions, insertions, substitutions or inversions. In certain embodiments, the one or more mutations reduce or prevent the production and release of phage particles from the bacterium relative to the same bacterium not having the one or more targeted mutations in the one or more phage genomes. In some embodiments, the bacterium is a probiotic bacterium. Non-limiting examples of such probiotic bacteria include *Bacteroides, Bifidobacterium, Clostridium, Escherichia, Lactobacillus*, and *Lactococcus*. In some embodiments, the bacterium is *Escherichia coli* strain Nissle. In some embodiments, the phage genome which is mutated is *E. coli* Nissle Phage 1 genome, the *E. coli* Nissle Phage 2 genome and/or the *E. coli* Nissle Phage 3 genome. In one embodiment, the mutated phage genome is the *E. coli* Nissle Phage 3 genome. In one embodiment, the mutations are located in or comprise one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the mutations, e.g., one or more deletions, are located in or comprise one or more genes selected from ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. pharmaceutically acceptable composition comprising the bacterium disclosed herein and a pharmaceutically acceptable carrier.

In some embodiments, the bacteria further comprise one or more circuits for the expression of one or more effector molecules.

In some embodiments, the disclosure relates to compositions and therapeutic methods for reducing hyperphenylalaninemia. In some embodiments, the compositions comprise a genetically engineered bacterium that is capable of expressing a phenylalanine metabolizing enzyme (PME). See, e.g., WO2017087580 A1, the contents of which are herein incorporated by reference in entirety. Phenylalanine is an essential amino acid primarily found in dietary protein. Typically, a small amount is utilized for protein synthesis, and the remainder is hydroxylated to tyrosine in an enzymatic pathway that requires phenylalanine hydroxylase (PAH) and the cofactor tetrahydrobiopterin. Hyperphenylalaninemia is a group of diseases associated with excess levels of phenylalanine, which can be toxic and cause brain damage. Primary hyperphenylalaninemia is caused by deficiencies in PAH activity that result from mutations in the PAH gene and/or a block in cofactor metabolism.

PKU is a severe form of hyperphenylalaninemia caused by mutations in the PAH gene. PKU is an autosomal recessive genetic disease that ranks as the most common inborn error of metabolism worldwide (1 in 3,000 births), and affects approximately 13,000 patients in the United States. More than 400 different PAH gene mutations have been identified (Hoeks et al., 2009). A buildup of phenylalanine (phe) in the blood can cause profound damage to the central nervous system in children and adults. If untreated in newborns, PKU can cause irreversible brain damage. Treatment for PKU currently involves complete exclusion of phenylalanine from the diet. Most natural sources of protein contain phenylalanine which is an essential amino acid and necessary for growth. In patients with PKU, this means that they rely on medical foods and phe-free protein supplements together with amino acid supplements to provide just enough phenylalanine for growth. This diet is difficult for patients and has an impact on quality of life.

Current PKU therapies require substantially modified diets consisting of protein restriction. Treatment from birth generally reduces brain damage and mental retardation (Hoeks et al., 2009; Sarkissian et al., 1999). However, the protein-restricted diet must be carefully monitored, and essential amino acids as well as vitamins must be supplemented in the diet. Furthermore, access to low protein foods is a challenge as they are more costly than their higher protein, nonmodified counterparts (Vockley et al., 2014). In children with PKU, growth retardation is common on a low-phenylalanine diet (Dobbelaere et al., 2003). In adulthood, new problems such as osteoporosis, maternal PKU, and vitamin deficiencies may occur (Hoeks et al., 2009). Excess levels of phenylalanine in the blood, which can freely penetrate the blood-brain barrier, can also lead to neurological impairment, behavioral problems (e.g., irritability, fatigue), and/or physical symptoms (e.g., convulsions, skin rashes, musty body odor). International guidelines recommend lifelong dietary phenylalanine restriction, which is widely regarded as difficult and unrealistic (Sarkissian et al., 1999), and "continued efforts are needed to overcome the biggest challenge to living with PKU—lifelong adherence to the low-phe diet" (Macleod et al., 2010).

In a subset of patients with residual PAH activity, oral administration of the cofactor tetrahydrobiopterin (also referred to as THB, BH4, Kuvan, or sapropterin) may be used together with dietary restriction to lower blood phenylalanine levels. However, cofactor therapy is costly and only suitable for mild forms of phenylketonuria. The annual cost of Kuvan, for example, may be as much as $57,000 per patient. Additionally, the side effects of Kuvan can include gastritis and severe allergic reactions (e.g., wheezing, lightheadedness, nausea, flushing of the skin).

The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. Studies of oral enzyme therapy using PAL have been conducted, but "human and even the animal studies were not continued because PAL was not available in sufficient amounts at reasonable cost" (Sarkissian et al., 1999). A pegylated form of recombinant PAL (PEG-PAL) is also in development as an injectable form of treatment. However, most subjects dosed with PEG-PAL have suffered from injection site reactions and/or developed antibodies to this therapeutic enzyme (Longo et al., 2014). Thus, there is significant unmet need for effective, reliable, and/or long-term treatment for diseases associated with hyperphenylalaninemia, including PKU. There is an unmet need for a treatment that will control blood Phe levels in patients while allowing consumption of more natural protein.

In some embodiments, the disclosure provides genetically engineered bacteria that encode and express phenylalanine ammonia lyase and/or phenylalanine hydroxylase and/or L-aminoacid deaminase and are capable of reducing hyperphenylalaninemia. The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. L-amino acid deaminase (LAAD) catalyzes oxidative deamination of phenylalanine to generate phenylpyruvate, and trace amounts of ammonia and hydrogen peroxide. Phenylpyruvic acid (PPA) is widely used in the pharmaceutical, food, and chemical industries, and PPA is the starting material for the synthesis of D-phenylalanine, a raw intermediate in the production of many chiral drugs and food additives. LAAD has therefore been studied in the context of industrial PPA production (Hou et al. 2015, Appl Microbiol Biotechnol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Phenylpyruvate is unable to cross the blood brain barrier (Steele, Fed Proc. 1986 June; 45(7): 2060-4; "Blood-brain barrier transport of the alpha-keto acid analogs of amino acids." indicating that this conversion is useful in controlling the neurological phenotypes of PKU.

In certain aspects, the disclosure relates to genetically engineered bacteria that are capable of reducing hyperphenylalaninemia in a mammal. In certain aspects, the compositions and methods disclosed herein may be used for treating diseases associated with hyperphenylalaninemia, e.g., phenylketonuria. In certain embodiments, the genetically engineered bacteria are non-pathogenic and may be introduced into the gut in order to reduce toxic levels of phenylalanine. In certain embodiments, the phenylalanine ammonia lyase and/or phenylalanine hydroxylase and/or L-aminoacid deaminase is stably produced by the genetically engineered bacteria, and/or the genetically engineered bacteria are stably maintained in vivo and/or in vitro. In certain embodiments, the genetically engineered bacteria further comprise a phenylalanine transporter gene to increase their uptake of phenylalanine. The invention also provides pharmaceutical compositions comprising the genetically engineered bacteria, and methods of modulating and treating disorders associated with hyperphenylalaninemia.

The engineered bacteria may also contain one or more gene sequences relating to bio-safety and/or bio-containment, e.g., a kill-switch, gene guard system, and/or auxotrophy. In some embodiments, the engineered bacteria may contain an antibiotic resistance gene. The expression of any these gene sequence(s) may be regulated using a variety of promoter systems, such as any of the promoter systems disclosed herein, which promoter system may involve use of the same promoter to regulate one or more different genes, may involve use of a different copy of the same promoter to regulate different genes, and/or may involve the use of different promoters used in combination to regulate the expression of different genes. The use of different regulatory or promoter systems to control gene expression provides flexibility (e.g., the ability to differentially control gene expression under different environmental conditions and/or the ability to differentially control gene expression temporally) and also provides the ability to "fine-tune" gene expression, any or all of which regulation may serve to optimize gene expression and/or growth of the bacteria.

In some embodiments, the bacteria are capable of expressing any one or more effector molecules in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the circuits are present on one or more plasmids (e.g., high copy or low copy) or are integrated into one or more sites in the bacterial chromosome. Also, in some embodiments, the genetically engineered bacteria further comprise one or more of the following: (1) one or more auxotrophies, such as any auxotrophies known in the art and provided herein, e.g., thyA or dapB auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits. Compositions of the bacteria and methods for the treatment, prevention, or management of one or more diseases or disorders are also provided.

BRIEF DESCRIPTION OF THE FIGURES

FIG. 1B depicts a table describing 5 putative prophage in the Nissle genome (3 intact, 1 incomplete, and 1 questionable) according to PHASTER scoring.

In FIG. 22A, fasted NHPs (n=6) were administered a 5 g peptide (left) or mock challenge (right) alone (black bars) or with $5\times10^{11}$ cells of SYN-PKU-2002 (striped bars) and urine was collected for 6 h. Normalized HA recovery is shown as the average±standard deviation. Animals receiving SYN-PKU during the studies performed in FIG. 22A were also administered a dose of $^{13}$C-phenylalanine intravenously (IV) 1 h after peptide or mock challenge (FIG. 22B). Normalized urinary $^{13}$C-HA, which could only be derived from the IV administered $^{13}$C-Phe, was found in animals that received a peptide challenge and is displayed as black bars. No urinary $^{13}$C-HA was recovered in animals that remained fasting. In FIG. 22C, fasted NHPs were administered an oral dose of $d_5$-phenylalanine ($d_5$-Phe) with or without administration of SYN-PKU-2002. The dashed line represents the quantity of $d_5$-Phe administered. $d_5$-hippurate ($d_5$-HA) was only found in animals that received SYN-PKU-2002 (striped bar). Data is representative of the average normalized $d_5$-HA recovery±standard deviation (n=6). Serum $d_5$-Phe was measured in NHPs that received SYN-PKU-2002 (light grey line) or mock administration (dark gray line) (FIG. 22D). Data represent the average $d_5$-Phe concentration±standard deviation (n=6) In FIG. 22E, NHPs received a $d_5$-Phe alone or with $5\times10^{11}$ cells of SYN-PKU-2002. Blood was collected over 6 h and areas under the curve for serum $d_5$-Phe were calculated. Data show AUCs plus and minus the upper and lower bounds of the 90% credible level respectively.

FIG. 26A depicts a graph showing normalized urinary HA recovery from dose groups shown as the average±standard deviation. FIG. 26B and FIG. 26C depict graphs showing the calculated AUCs for the concentrations of serum HA and. White bars represent the average AUC±standard deviation. FIG. 26D depicts a graph showing serum Phe concentration as determined at the indicated time points. The 3 highest doses administered in the dose response are shown compared to the No Cells control, as these 3 doses showed a significant reduction in serum Phe AUC ($p<0.05$).

FIG. 35A shows the effect of DAP auxotrophy on fecal clearance in group 1 mice (SYN-PKU901/SYN766). FIG. 35B depicts the effect of genetic engineering for Phe-degradation on fecal clearance in group 2 mice (SYN-PKU901/SYN3282). FIG. 35C depicts the effect of genetic engineering for Phe-degradation and DAP auxotrophy on fecal clearance in group 3 mice (SYN-PKU-2001/SYN3282). Mixed doses of bacteria were administered orally to C57BL/6 mice (n=5). Doses were plated for CFU counts in quadruplicate to determine the number of bacteria administered. At each time point, feces were collected, homogenized, and plated for bacterial CFU determination on antibiotic selective media. For each time point, data represent the average CFU/mg counts of 5 fecal samples±standard deviation, normalized for each strain as a fraction of the initial CFU dosed unless otherwise denoted in the appendix. This normalization allows direct comparison of survival/clearance between the 2 strains within a group, even with variation in the actual CFU of each strain administered at T=0.

DESCRIPTION OF EMBODIMENTS

Figure 1A:
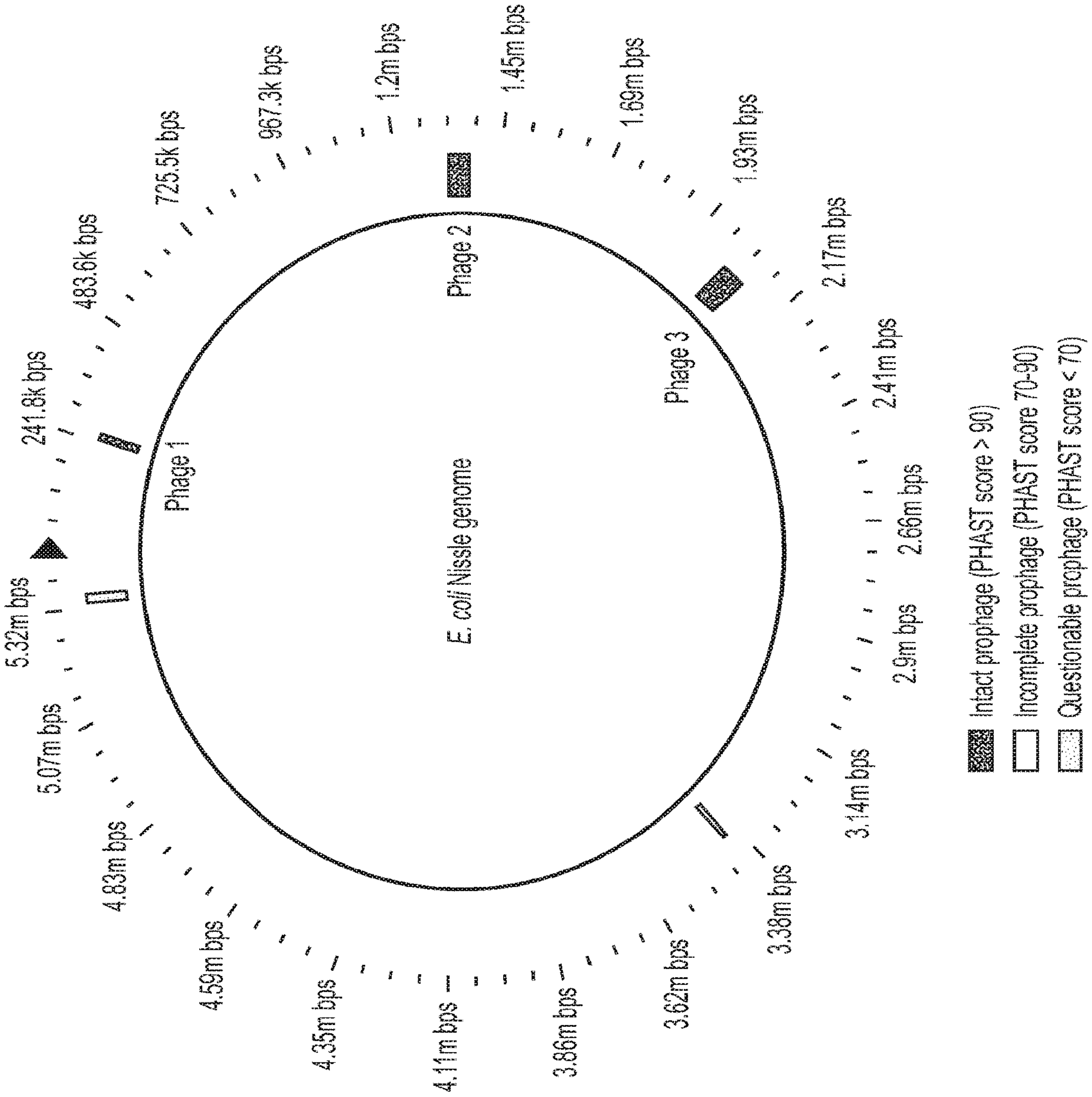
FIG. 1A depicts a schematic of locations of predicted phage on the EcN Genome (CP007799.1) from PHAST Analysis. The three high-scoring, intact phages are labeled as Phages 1-3. Phage 1 (PHAST score 110) is 18.8 kb long and stretches from coordinates 241,563-260,441 within the EcN genome. Phage 2 (PHAST score 150) is 52.4 kb long and stretches from 1,325,883-1,378,287. Phage 3 (PHAST score 150) is 59 kb long and stretches from 3,405,101-3,418,180. Also identified were several low-scoring phage, designated as "incomplete" or "questionable" by the PHAST algorithm, which do not contain all the major components of a phage and could therefore represent partial phage, or false positive predictions. Abbreviations: EcN=*Escherichia coli* Nissle 1917; PHAST=Phage Search Tool software; kb=kilobases.

In one aspect, the disclosure provides bacteria which contain an endogenous phage and comprise one or more modifications to the phage sequence. In some embodiments, the modifications alter the properties of the prophage sequence. Such mutations include one or more partial or complete deletion(s) of one or more phage genes, one or more insertion(s) of one or more nucleotides into one or more phage genes, one or more partial or complete substitution(s) of one or more phage genes in the phage genome; one or more inversion(s) of one or more phage genes or combinations thereof.

This disclosure provides compositions comprising novel bacteria for the treatment of a disorder, which comprise one or more bacteriophages or prophages in their natural state. In some embodiments, the bacteria comprise one or more modifications to the genomes of the one or more phages. In some embodiments, the one or more modifications render the phage or prophage inactive. In some embodiments, these bacteria are further genetically modified to comprise one or more genes for the expression or production of one or more effector molecules. Methods for the production and use of these genetically engineered bacteria in novel therapies for the treatment of disorders are provided.

In one embodiment, *E. coli* Nissle is used as a starting point, parental strain or "chassis" for the genetically engineered bacteria. In one embodiment, the bacteriophage which is modified is a phage which is endogenous to *E. coli* Nissle in its phage is present in the bacteria in their natural state.

In some embodiments, the genetically engineered bacteria comprise one or more genes encoding one or more effectors, e.g., PME(s). In some embodiments, the genetically engineered bacteria comprise one or more genes encoding PAL. In some embodiments, the genetically engineered bacteria comprise one or more genes encoding LAAD. In some embodiments, the genetically engineered bacteria comprise one or more genes encoding PAL and one or more genes encoding LAAD. In some embodiments, the genetically engineered bacteria comprise one or more genes encoding a transporter, e.g., PheP. In some embodiments, the genetically engineered bacteria comprise one or more genes encoding a transporter, e.g., PheP and one or more genes encoding PAL. In some embodiments, the genetically engineered bacteria comprise one or more genes encoding a transporter, e.g., PheP and one or more genes encoding LAAD. In some embodiments, the genetically engineered bacteria comprise one or more genes encoding a transporter, e.g., PheP, one or more genes encoding LAAD, and one or more genes encoding PAL. In any of the preceding embodiments, the genetically engineered bacteria for the consumption of phenylalanine further comprise one or more relative to its original state. In some embodiments, the endogenous bacteriophage genomes. In some embodiments, the bacteriophage(s) have been mutated in one or more genes within the bacteriophage genome. Such mutations include deletions, insertions, substitutions and inversions and are located in or encompass one or more bacteriophage genes.

Bacteriophage are the most common biological entity in the world, and it is well documented that a majority of bacterial species, both gram positive and gram negative, contain one or more DNA bacteriophages which are integrated as so-called prophages in the bacterial chromosome (Clokie et al, Phages in Nature, Bacteriophage. 2011 January-February; 1(1): 31-45). For example, two separate studies on *E. coli* strains studies showed that 51 different functional phages were released from 27 *E. coli* strains analyzed, and 83 of 107 *E. coli* strains tested released at least one functional phage type (Casjens, Prophages and bacterial genomics: what have we learned so far?; Mol Microbiol. 2003 July; 49(2):277-300; Osawa et al., Genotypic variations of Shiga toxin-converting phages from enterohaemorrhagic *Escherichia coli* O157:H7 isolates; J Med Microbiol (2001) 49: 565-574, and Schicklmaier et al., A comparative study on the frequency of prophages among natural isolates of *Salmonella* and *Escherichia coli* with emphasis on generalized transducers. Antonie Van Leeuwenhoek (1998) 73: 49-54).

Figure 12:
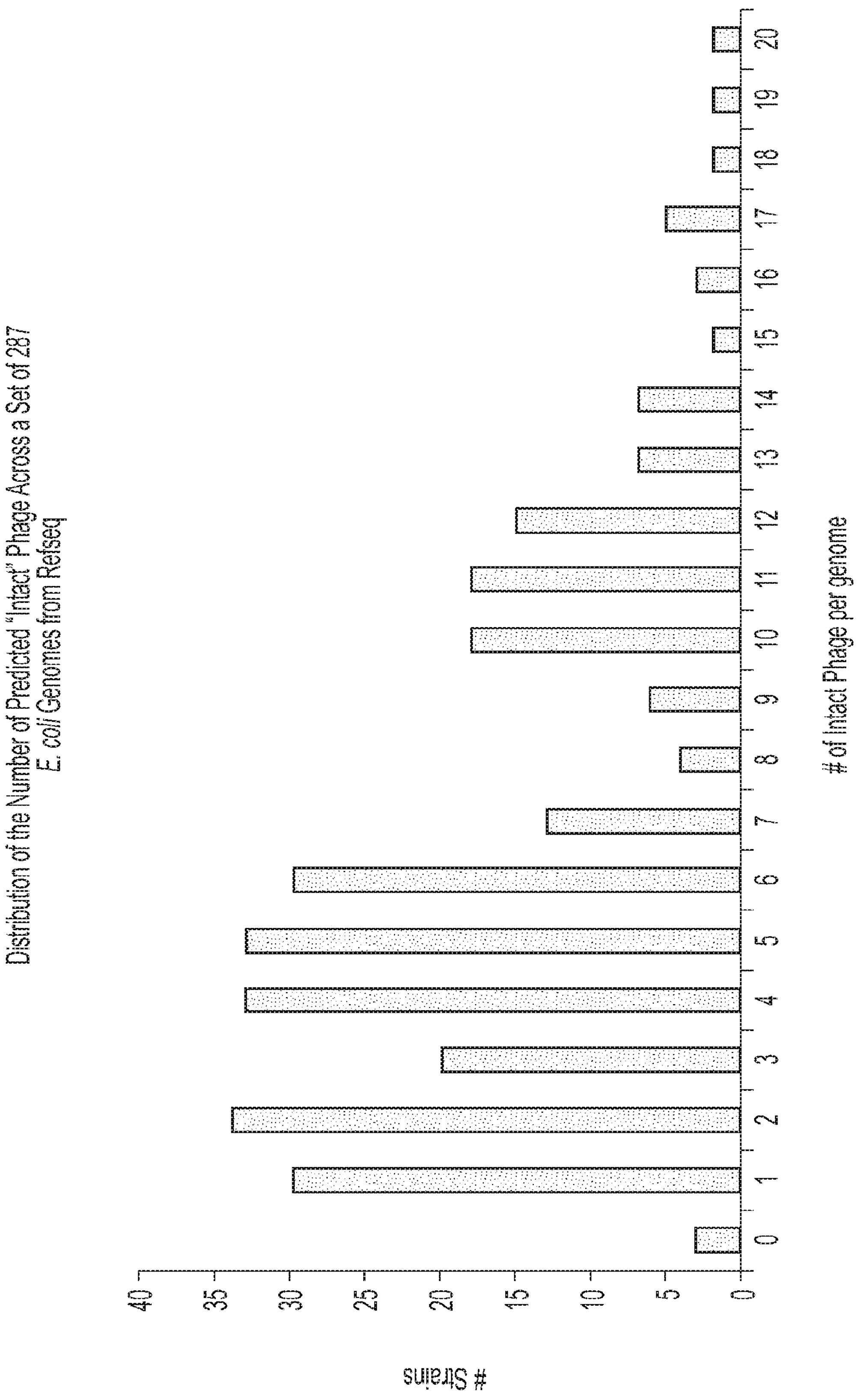
FIG. 12 depicts a bar graph showing the distribution of the number of predicted "intact" phage across a set of 287 *E. coli* genomes from Refseq. The Refseq database was analyzed for the number of intact phage that were present in published, complete *E. coli* genomes. The histogram displays a non-normal distribution, but it is clear that nearly all *E. coli* genomes contain intact prophage, and the majority of published, complete *E. coli* genomes contain more intact prophage than EcN. Abbreviations: *E. coli=Escherichia coli*; EcN=*Escherichia coli* Nissle 1917; Refseq=reference sequence.

As shown in FIG. 12, nearly all *E. coli* genomes contain intact prophage, and the majority of published, complete *E. coli* genomes contain more intact prophage than EcN. Abbreviations: *E. coli*=*Escherichia coli*; EcN=*Escherichia coli* Nissle 1917; Refseq=reference sequence.

Among Gram-positive bacteria, the genomes of *B. subtilis, Clostridium acetobutylicum, Lactococcus lactis*, and many others have been shown to include largely intact prophages (Kunst et al., 1997; Bolotin et al., The complete genome sequence of the gram-positive bacterium *Bacillus subtilis*. Nature (2001) 390: 249-256, Nolling et al., Genome sequence and comparative analysis of the solvent-producing bacterium *Clostridium acetobutylicum*. J Bacteriol (2001) 183: 4823-4838; Bolotin et al., The complete genome sequence of the lactic acid bacterium *Lactococcus lactis* ssp. *lactis* IL1403. Genome Res (2001) 11: 731-753).

DNA phages can be lytic or temperate. Lytic phages infect bacterial cells and then program the synthesis of progeny phages, which are then released from the lysed cell. Conversely, temperate DNA phages establish a stable relationship with their host bacteria in which the integrated phage DNA, i.e., the prophage, is replicated in concert with the host's genome, and any host-damaging phage genes are not expressed. However, bacteriophage particles can be released from cells containing an intact prophage by a process called induction, during which prophage genes required for lytic growth are turned on and progeny phage particles are produced and released from the cell through lysis of the cell (reviewed in Casjens, Prophages and bacterial genomics: what have we learned so far?; Mol Microbiol. 2003 July; 49(2):277-300). Induction can occur in some cases spontaneously and randomly in a small or large fraction of the bacteria that harbor the prophage, or specific, often undefined, environmental signals can cause simultaneous induction of a particular prophage in many cells, causing death of the bacterial cells. In some cases, presence of prophage sequences may also allow some bacteria to have properties they would not have without the phage, such as antibiotic resistance, the ability to exist in different environmental conditions, improved adhesion, pathogenicity or facilitated horizontal gene transfer (Casjens et al., 2001).

Not all prophage have the ability to undergo a lytic cycle. Non-functional, i.e., defective or cryptic prophages can accrue to a high level of abundancy in many bacteria as a result of mutational decay and/or the loss of one or more genes essential to the lytic cycle over thousands of bacterial replication cycles (Bobay et al., Pervasive domestication of defective prophages by bacteria, Proc Natl Acad Sci USA. 2014 Aug. 19; 111(33): 12127-12132, and references therein). Of note, defective prophages often also contain a number of genes that can provide advantageous functionality to the host, including genes encoding proteins with homologous recombination functions, prevention of further infection, or bacteriocins, which may be helpful in competition for nutrients, e.g., through growth inhibition of other neighboring bacterial species.

Phages can positively affect gene expression and fitness in *E. coli* in numerous ways. Cryptic, lysogenic, and lytic phages have been shown to provide multiple benefits to the host promoting survival in adverse environmental conditions. For example, gene sequences transferred to the bacterium by phages have been linked to adaptation to different nutrients or a different niche, or to increased ability to eliminate competing strains. Dormant prophage has also been shown to prevent superinfection with another, e.g., lytic, phage.

Several studies have shown that endogenous phages affect the ability of bacteria to grow in certain carbon sources. Along with lambda, active Mu, P1 and P2 prophages and cryptic prophage CP4-57 increase growth under glucose-limited and other growing conditions (Edlin, G., Lin, L. & Bitner, R. Reproductive fitness of P1, P2, and Mu lysogens of *Escherichia coli. J. Virol.* 21, 560-564 (1977); Edlin, G., Lin, L. & Kudmar, R. λ Lysogens of *E. coli* reproduce more rapidly than non-lysogens. Nature 255, 735-737 (1975); Wang, X., Kim, Y. & Wood, T. K. Control and benefits of CP4-57 prophage excision in *Escherichia coli* biofilms. ISME J. 3, 1164-1179 (2009). In another study, it was shown that when λ integrates into the *E. coli* genome, ability of the cell to grow on poor carbon sources is shut down. IN this case, limitation of metabolism may confer a survival benefit to the bacterium. Slowing bacterial growth in glucose-poor environments might help the bacterium, elude detection by the immune system, increasing the chances of survival.

Other survival properties may be affected as well. Wang et al created a single *E. coli* strain lacks all nine cryptic prophages. In this study, it was shown that these prophages are beneficial for withstanding osmotic, oxidative and acid stresses, for increasing growth under various conditions, enhancing phosphorus and nitrogen utilization, and for influencing biofilm formation (Wang et al., Cryptic prophages help bacteria cope with adverse environments; DOI: 10.1038/ncomms1146). In pathogenic bacteria prophage, several studies suggest that acquisition is associated with changes in pathogen virulence.

Accordingly, a skilled artisan might expect that modification, e.g., mutation or deletion of portions or entirety of an endogenous prophage may alter, e.g., negatively affect, bacterial fitness. Additionally, one might assume that endogenous prophage may alter, e.g., negatively affect, effector activity in a genetically engineered bacterium capable of producing this effector. This may be especially the case if the endogenous prophage is present in all specimen of a particular strain subtype—this would indicate that the bacterium comprising the prophage sequences evolutionarily was able to out compete a form of the bacterium that lacks the prophage.

As described further in this disclosure, a prophage in *E. coli* Nissle was identified, which is capable of undergoing lysis under certain conditions, and which is present in all specimens of *E. coli* Nissle. Surprisingly, testing of bacterial fitness, residence time, and activity showed that the bacterium comprising the mutation or deletion in the endogenous phage was essentially the same, e.g., at least the same order of magnitude.

Under similar assay conditions, there was no discernable difference in Phe degradation activity (in vitro or in vivo) between the strains. For example, under similar assay conditions, Phe consumption is within the same magnitude between the two strains (see, e.g., FIG. 15 and FIG. 17A). In vivo competition studies between phage containing and phage free strains indicate that there is no discernable difference in transit or colonization between the phage-free PKU strain of Nissle (see, e.g. FIG. 19).

Accordingly, in some embodiments, one or more modification(s), e.g., mutation(s) or deletion(s) or other modifications described herein, in the genome of a phage does not alter the bacterial fitness of the modified or genetically engineered bacterium. In some embodiments, the engineered bacteria comprising one or more phage modifications, e.g., mutation(s) or deletion(s) or other modifications described herein, have essentially the same or at least similar bacterial fitness as the corresponding isogenic strain in the absence of the phage mutation. In further embodiments, one or more modification(s), e.g., mutation(s) or deletion(s) or other modifications described herein in the genome of a phage does not alter the strain activity (e.g., effector activity or metabolic activity) of the engineered bacterium capable of producing the effector as compared to the corresponding isogenic strain without the phage mutation. In some embodiments, the unmodified or genetically engineered bacteria comprising one or more phage modifications, e.g., mutation(s) or deletion(s) or other modifications described herein, have essentially the same or at least similar bacterial strain activity (e.g., effector activity or metabolic activity) when compared to the corresponding isogenic strain without the phage mutation.

Additionally, in some embodiments, one or more modification(s), e.g., mutation(s) or deletion(s) or other modifications described herein, in the genome of a phage alters, e.g., increases or reduces, the bacterial fitness of the engineered bacterium. In some embodiments, the engineered bacteria comprising one or more phage modifications, e.g., mutation(s) or deletion(s) or other modifications described herein, have altered, e.g., reduced or increased, bacterial fitness as compared to the corresponding isogenic strain without the phage mutation. In some embodiments, the one or more modification(s), e.g., mutation(s) or deletion(s) or other modifications described herein in the genome of a phage alters, e.g., reduces or increases, strain activity (e.g., effector activity or metabolic activity) of the bacterium capable of producing the effector as compared to the corresponding isogenic strain without the phage mutation. In some embodiments, unmodified or genetically engineered bacteria comprising one or more phage modifications, e.g., mutation(s) or deletion(s) or other modifications described herein, have altered, e.g., reduced or increased, bacterial strain activity (e.g., effector activity or metabolic activity) as the corresponding isogenic strain without the phage mutation.

In some embodiments, the genetically engineered bacteria comprise one or more *E. coli* Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the one or more insertions comprise an antibiotic cassette. In some embodiments, the mutation is a deletion. In some embodiments, the genetically engineered bacteria comprise one or more deletions, which are located in or comprise one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise a modified phage genome sequence consisting of SEQ ID NO: 281.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperphenylalaninemia," "hyperphenylalaninemic," and "excess phenylalanine" are used interchangeably herein to refer to increased or abnormally high concentrations of phenylalanine in the body. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL. As used herein, diseases associated with hyperphenylalaninemia include, but are not limited to, phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. Affected individuals can suffer progressive and irreversible neurological deficits, mental retardation, encephalopathy, epilepsy, eczema, reduced growth, microcephaly, tremor, limb spasticity, and/or hypopigmentation (Leonard 2006). Hyperphenylalaninemia can also be secondary to other conditions, e.g., liver diseases.

"Phenylalanine ammonia lyase" and "PAL" are used to refer to a phenylalanine metabolizing enzyme (PME) that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene derived from a prokaryotic species. In alternate embodiments, PAL is encoded by a PAL gene derived from a eukaryotic species. In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, PAL is encoded by a PAL gene derived from *Anabaena variabilis* and referred to as "PAL1" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., *Rhodosporidium toruloides* (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

"Phenylalanine hydroxylase" and "PAH" are used to refer to an enzyme that catalyzes the hydroxylation of the aromatic side chain of phenylalanine to create tyrosine in the human body in conjunction with the cofactor tetrahydrobiopterin. The human gene encoding PAH is located on the long (q) arm of chromosome 12 between positions 22 and 24.2. The amino acid sequence of PAH is highly conserved among mammals. Nucleic acid sequences for human and mammalian PAH are well known and widely available. The full-length human cDNA sequence for PAH was reported in 1985 (Kwok et al. 1985). Active fragments of PAH are also well known (e.g., Kobe et al. 1997).

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia*, and *Morganella*, or venom. LAAD is characterized by fast reaction rate of phenylalanine degradation (Hou et al., Appl Microbiol Technol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability.

In some embodiments, the genetically engineered bacteria comprise a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the LAAD encoded by the genetically engineered bacteria is localized to the plasma membrane, facing into the periplasmic space and with the catalytic activity occurring in the periplasmic space.

"Phenylalanine metabolizing enzyme" or "PME" are used to refer to an enzyme which is able to degrade phenylalanine. Any phenylalanine metabolizing enzyme known in the art may be encoded by the genetically engineered bacteria. PMEs include, but are not limited to, phenylalanine hydroxylase (PAH), phenylalanine ammonia lyase (PAL), aminotransferase, L-amino acid deaminase (LAAD), and phenylalanine dehydrogenases.

Reactions with phenylalanine hydroxylases, phenylalanine dehydrogenases or aminotransferases require cofactors, while LAAD and PAL do not require any additional cofactors. In some embodiments, the PME encoded by the genetically engineered bacteria requires a cofactor. In some embodiments, this cofactor is provided concurrently or sequentially with the administration of the genetically engineered bacteria. In other embodiments, the genetically engineered bacteria can produce the cofactor. In some embodiments, the genetically engineered bacteria encode a phenylalanine hydroxylase. In some embodiments, the genetically engineered bacteria encode a phenylalanine dehydrogenase. In some embodiments, the genetically engineered bacteria encode an aminotransferase. In some embodiments, the PME encoded by the genetically engineered bacteria does not require a cofactor. Without wishing to be bound by theory, the lack of need for a cofactor means that the rate of phenylalanine degradation by the enzyme is dependent on the availability of the substrate and is not limited by the availability of the cofactor. In some embodiments, the PME produced by the genetically engineered bacteria is PAL. In some embodiments, the PME produced by the genetically engineered bacteria is LAAD. In some embodiments, the genetically engineered bacteria encode combinations of PMEs.

In some embodiments, the catalytic activity of the PME is dependent on oxygen levels. In some embodiments, the PME is catalytically active under microaerobic conditions. As a non-limiting example, LAAD catalytic activity is dependent on oxygen. In some embodiments, LAAD is active under low oxygen conditions, such as microaerobic conditions. In some embodiments, of the invention, the PME functions at very low levels of oxygen or in the absence of oxygen, e.g. as found in the colon. As a non-limiting example, PAL activity is not dependent on the presence of oxygen.

As used herein, "effector" or "effector molecule" can refers to a molecule, such as a metabolite or a polypeptide, which exerts a desired function. An effector may be encoded by a single gene. For example, a single gene can encode a polypeptide which is secreted or displayed. Alternatively, an effector may be synthesized by a biosynthetic pathway requiring multiple genes, e.g., butyrate. The polypeptides encoded by multiple genes within a biosynthetic pathway, e.g., which synthesizes a metabolite with desirable properties, may also be referred to as effectors. Similarly, polypeptides encoded by multiple genes within a catabolic pathway, e.g., for the breakdown of a toxic metabolite, may also be referred to as effectors. These effector molecules may also be referred to as "therapeutic metabolites", "therapeutic molecules" or "therapeutic polypeptides". Other terms that are used interchangeably herein with effector are "polypeptide of interest" or "polypeptides of interest", "protein of interest", "proteins of interest".

As used herein, "payload" refers to one or more polynucleotides and/or polypeptides of interest to be produced by a genetically engineered microorganism, such as a bacterium. In some embodiments, the payload is encoded by a gene or multiple genes or an operon. In some embodiments, the one or more genes and/or operon(s) comprising the payload are endogenous to the microorganism. In some embodiments, the one or more elements of the payload is derived from a different microorganism and/or organism. In some embodiments, the payload is a therapeutic payload. In some embodiments, the payload is encoded by genes for the biosynthesis of a molecule. In some embodiments, the payload is encoded by genes for the metabolism, catabolism, or degradation of a molecule. In some embodiments, the payload is encoded by genes for the importation of a molecule. In some embodiments, the payload is encoded by genes for the exportation of a molecule. In some embodiments, the payload is a regulatory molecule(s), e.g., a transcriptional regulator such as FNR. In some embodiments, the payload comprises a regulatory element, such as a promoter or a repressor. In some embodiments, the payload expression is driven from an inducible promoter, such as from FNRS. In some embodiments, payload expression is driven from a constitutive promoter. In some embodiments, the payload comprises a repressor element, such as a kill switch. In alternate embodiments, the payload is produced by a biosynthetic or biochemical pathway, wherein the biosynthetic or biochemical pathway may optionally be endogenous to the microorganism. In some embodiments, the genetically engineered microorganism comprises two or more payloads.

The present disclosure includes, inter alia, genetically engineered bacteria, pharmaceutical compositions thereof, and methods of modulating and treating disorders associated with hyperphenylalaninemia. In some embodiments, the genetically engineered bacteria comprise a gene encoding non-native phenylalanine ammonia lyase (PAL) and are capable of processing and reducing phenylalanine in a mammal. In some embodiments, the engineered bacteria further comprise a gene encoding a phenylalanine transporter. In some embodiments, the engineered bacteria may also comprise a gene encoding LAAD. The engineered bacteria may also contain one or more gene sequences relating to bio-safety and/or bio-containment, e.g., a kill-switch, gene guard system, and/or auxotrophy. The expression of these gene sequence(s) may be regulated using a variety of promoter systems, such as any of the promoter systems disclosed herein, which promoter may be the same promoter to regulate one or more different genes, may be a different copy of the same promoter to regulate different genes, or may involve the use of different promoters used in combination to regulate the expression of different genes. The use of different regulatory or promoter systems to control gene expression provides flexibility (e.g., the ability to differentially control gene expression under different environmental conditions and/or the ability to differentially control gene expression temporally) and also provides the ability to "fine-tune" gene expression, any or all of which regulation may serve to optimize gene expression and/or growth of the bacteria. The genetically engineered bacteria and pharmaceutical compositions comprising those bacteria may be used to metabolize phenylalanine in the body into non-toxic molecules in order to treat and/or prevent conditions associated with hyperphenylalaninemia, including PKU. In certain aspects, the compositions comprising the genetically engineered bacteria may be used in the methods of the disclosure to treat and/or prevent disorders associated with hyperphenylalaninemia.

Effector molecules also include anti-cancer molecules. "anti-cancer molecule" refers to one or more therapeutic substances or drugs of interest to be produced by a genetically engineered microorganism, e.g., engineered bacteria or engineered oncolytic virus, which are capable of reducing and/or inhibiting cell growth or replication. In some embodiments, the anti-cancer molecule is a therapeutic molecule that is useful for modulating or treating a cancer. In some embodiments, the anti-cancer molecule is a therapeutic molecule encoded by a gene. In alternate embodiments, the anti-cancer molecule is a therapeutic molecule produced by a biochemical or biosynthetic pathway, wherein the biosynthetic or biochemical pathway may optionally be endogenous to the microorganism. In some embodiments, the genetically engineered microorganism is capable of producing two or more anti-cancer molecules. Non-limiting examples of anti-cancer molecules include immune checkpoint inhibitors (e.g., CTLA-4 antibodies, PD-1 antibodies, PDL-1 antibodies), cytotoxic agents (e.g., Cly A, FASL, TRAIL, TNF-alpha), immunostimulatory cytokines and co-stimulatory molecules (e.g., OX40, CD28, ICOS, CCL21, IL-2, IL-18, IL-15, IL-12, IFN-gamma, IL-21, TNFs, GM-CSF), antigens and antibodies (e.g., tumor antigens, neoantigens, CtxB-PSA fusion protein, CPV-OmpA fusion protein, NY-ESO-1 tumor antigen, RAFI, antibodies against immune suppressor molecules, anti-VEGF, Anti-CXR4/CXCL12, anti-GLP1, anti-GLP2, anti-galectin1, anti-galectin3, anti-Tie2, anti-CD47, antibodies against immune checkpoints, antibodies against immunosuppressive cytokines and chemokines), DNA transfer vectors (e.g., endostatin, thrombospondin-1, TRAIL, SMAC, Stat3, Bcl2, FLT3L, GM-CSF, IL-12, AFP, VEGFR2), and enzymes (e.g., *E. coli* CD, HSV-TK). In some embodiments, the anti-cancer molecule includes nucleic acid molecules that mediate RNA interference, microRNA response or inhibition, TLR response, antisense gene regulation, target protein binding (aptamer or decoy oligos), gene editing, such as CRISPR interference. In some embodiments, bacteria or virus can be used as vectors to transfer DNA into mammalian cells, e.g., by bactofection (Bernardes et al., 2013).

Non-limiting examples of effector molecules include "anti-inflammation molecules" and/or "gut barrier function enhancer molecules". Anti-inflammation molecules and/or gut barrier function enhancer molecules include, but are not limited to, short-chain fatty acids, butyrate, propionate, acetate, IL-2, IL-22, superoxide dismutase (SOD), GLP-2 and analogs, GLP-1, IL-10, IL-27, TGF-β1, TGF-β2, N-acylphosphatidylethanolamines (NAPEs), elafin (also called peptidase inhibitor 3 and SKALP), trefoil factor, melatonin, tryptophan, $PGD_2$, and kynurenic acid, indole metabolites, and other tryptophan metabolites, as well as other molecules disclosed herein. Such molecules may also include compounds that inhibit pro-inflammatory molecules, e.g., a single-chain variable fragment (scFv), antisense RNA, siRNA, or shRNA that neutralizes TNF-α, IFN-γ, IL-1β, IL-6, IL-8, IL-17, and/or chemokines, e.g., CXCL-8 and CCL2. Such molecules also include AHR agonists (e.g., which result in IL-22 production, e.g., indole acetic acid, indole-3-aldehyde, and indole) and PXR agonists (e.g., IPA), as described herein. Such molecules also include HDAC inhibitors (e.g., butyrate), activators of GPR41 and/or GPR43 (e.g., butyrate and/or propionate and/or acetate), activators of GPR109A (e.g., butyrate), inhibitors of NF-kappaB signaling (e.g., butyrate), and modulators of PPARgamma (e.g., butyrate), activators of AMPK signaling (e.g., acetate), and modulators of GLP-1 secretion. Such molecules also include hydroxyl radical scavengers and antioxidants (e.g., IPA). A molecule may be primarily anti-inflammatory, e.g., IL-10, or primarily gut barrier function enhancing, e.g., GLP-2. A molecule may be both anti-inflammatory and gut barrier function enhancing. An anti-inflammation and/or gut barrier function enhancer molecule may be encoded by a single gene, e.g., elafin is encoded by the PI3 gene. Alternatively, an anti-inflammation and/or gut barrier function enhancer molecule may be synthesized by a biosynthetic pathway requiring multiple genes, e.g., butyrate.

Effector molecules also include metabolic effector molecules. "Metabolic effector molecules" and/or "satiety effector molecules" include, but are not limited to, n-acyl-phophatidylethanolamines (NAPEs), n-acyl-ethanolamines (NAEs), ghrelin receptor antagonists, peptide YY3-36, cholecystokinin (CCK) family molecules, CCK58, CCK33, CCK22, CCK8, bombesin family molecules, bombesin, gastrin releasing peptide (GRP), neuromedin B (P), glucagon, GLP-1, GLP-2, apolipoprotein A-IV, amylin, somatostatin, enterostatin, oxyntomodulin, pancreatic peptide, short-chain fatty acids, butyrate, propionate, acetate, serotonin receptor agonists, nicotinamide adenine dinucleotide (NAD), nicotinamide mononucleotide (NMN), nucleotide riboside (NR), nicotinamide, and nicotinic acid (NA). Such molecules may also include compounds that inhibit a molecule that promotes metabolic disease, e.g., a single-chain variable fragment (scFv), antisense RNA, siRNA, or shRNA that inhibits dipeptidyl peptidase-4 (DPP4) or ghrelin receptor. A metabolic and/or satiety effector molecule may be encoded by a single gene, e.g., glucagon-like peptide 1 is encoded by the GLP-1 gene. In some embodiments, the genetically engineered bacteria comprising gene sequences comprising one or more circuits for the production or catabolism of tryptophan and/or one of its metabolites further comprise gene sequences for the expression of one or more metabolic effector molecule and/or satiety effector molecules.

Other non-limiting examples of effector molecules are described in in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

In certain embodiments, new or improved effectors (e.g., PMEs) can be identified according to methods known in the art or described herein, and are encoded by the genetically engineered bacteria. In some embodiments, the enzyme encoded by the genetically engineered bacteria is a wild type enzyme isolated from a viral, prokaryotic or eukaryotic organism. In some embodiments, the enzyme sequence has been further modified or mutated to increase one or more specific properties of the enzyme, such as stability or catalytic activity.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the genetically engineered bacteria encoding a PME.

In some embodiments, the phenylalanine metabolite results directly or indirectly from PAH activity, e.g., from PAH produced by the genetically engineered bacteria. In some embodiments, the metabolite is tyrosine. In some embodiments, the phenylalanine metabolite accumulates in the blood or the urine of a PKU patient, due to defective PAH activity. Non-limiting examples of such PKU metabolites are phenylpyruvic acid and phenyl-lactic acid. Other examples include phenylacetate, phenylethylamine, and phenylacetyl glutamine.

In some embodiments, the phenylalanine metabolite results directly or indirectly from PAL action, e.g., from PAL produced by the genetically engineered bacteria. Non-limiting examples of such PAL metabolites are trans-cinnamic acid and hippuric acid. In some embodiments, the phenylalanine metabolite results directly or indirectly from LAAD action, e.g., from LAAD produced by the genetically engineered bacteria. Examples of such LAAD metabolites are phenylpyruvate and phenyllactic acid.

"Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica*, and *Escherichia coli*. Other phenylalanine transporters include a general amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the genetically engineered bacteria comprise more than one type of phenylalanine transporter, selected from pheP, aroP, and the LIV-I/LS system.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

As used herein, the term "transporter" is meant to refer to a mechanism, e.g., protein, proteins, or protein complex, for importing a molecule, e.g., amino acid, peptide (di-peptide, tri-peptide, polypeptide, etc.), toxin, metabolite, substrate, as well as other biomolecules into the microorganism from the extracellular milieu.

"Operably linked" refers a nucleic acid sequence, e.g., a gene encoding PAL, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region.

A "directly inducible promoter" refers to a regulatory region, wherein the regulatory region is operably linked to a gene encoding an effector molecule (e.g. a phenylalanine metabolizing enzyme, e.g. PAL) in the presence of an inducer of said regulatory region, the effector molecule is expressed. An "indirectly inducible promoter" refers to a regulatory system comprising two or more regulatory regions, for example, a first regulatory region that is operably linked to a gene encoding a first molecule, e.g., a transcriptional regulator, which is capable of regulating a second regulatory region that is operably linked to a gene encoding an effector molecule. In the presence of an inducer of the first regulatory region, the second regulatory region may be activated or repressed, thereby activating or repressing expression of the effector molecule. Both a directly inducible promoter and an indirectly inducible promoter are encompassed by "inducible promoter."

"Exogenous environmental condition(s)" or "environmental conditions" refer to settings or circumstances under which the promoter described herein is directly or indirectly induced. The phrase is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions refer to the presence of molecules or metabolites that are specific to the mammalian gut in a healthy or disease-state, e.g., propionate. In some embodiments, the exogenous environmental conditions are specific to the tumor microenvironment. In some embodiments, exogenous environmental conditions are molecules or metabolites that are specific to the tumor microenvironment. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprises an oxygen level-dependent promoter. In some aspects, bacteria have evolved transcription factors that are capable of sensing oxygen levels. Different signaling pathways may be triggered by different oxygen levels and occur with different kinetics.

As used herein, "exogenous environmental conditions" or "environmental conditions" also refers to settings or circumstances or environmental conditions external to the engineered microorganism, which relate to in vitro culture conditions of the microorganism. "Exogenous environmental conditions" may also refer to the conditions during growth, production, and manufacture of the organism. Such conditions include aerobic culture conditions, anaerobic culture conditions, low oxygen culture conditions and other conditions under set oxygen concentrations. Such conditions also include the presence of a chemical and/or nutritional inducer, such as tetracycline, arabinose, IPTG, rhamnose, and the like in the culture medium. Such conditions also include the temperatures at which the microorganisms are grown prior to in vivo administration. For example, using certain promoter systems, certain temperatures are permissive to expression of a payload, while other temperatures are non-permissive. Oxygen levels, temperature and media composition influence such exogenous environmental conditions. Such conditions affect proliferation rate, rate of induction of the payload (e.g. PME, e.g. PAL or LAAD) or rate of induction of the transporter (e.g. PheP), and overall viability and metabolic activity of the strain during strain production.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003). Non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic and/or low oxygen conditions by the global transcriptional regulator FNR that is naturally found in Nissle. Under anaerobic and/or low oxygen conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrS, FNR, P-FNRS promoter and other such related designations to indicate the promoter PfnrS.

TABLE 1

| Examples of transcription factors and responsive genes and regulatory regions | |
|---|---|
| Transcription factor | Examples of responsive genes, promoters, and/or regulatory regions: |
| FNR | nirB, ydfZ, pdhR, focA, ndH, hlyE, narK, narX, narG, yfiD, tdcD |
| ANR | arcDABC |
| DNR | norb, norC |

As used herein, a "tunable regulatory region" refers to a nucleic acid sequence under direct or indirect control of a transcription factor and which is capable of activating, repressing, derepressing, or otherwise controlling gene expression relative to levels of an inducer. In some embodiments, the tunable regulatory region comprises a promoter sequence. The inducer may be RNS, or other inducer described herein, and the tunable regulatory region may be a RNS-responsive regulatory region or other responsive regulatory region described herein. The tunable regulatory region may be operatively linked to a gene sequence(s) or gene cassette for the production of one or more payloads, e.g., a butyrogenic or other gene cassette or gene sequence(s). For example, in one specific embodiment, the tunable regulatory region is a RNS-derepressible regulatory region, and when RNS is present, a RNS-sensing transcription factor no longer binds to and/or represses the regulatory region, thereby permitting expression of the operatively linked gene or gene cassette. In this instance, the tunable regulatory region derepresses gene or gene cassette expression relative to RNS levels. Each gene or gene cassette may be operatively linked to a tunable regulatory region that is directly or indirectly controlled by a transcription factor that is capable of sensing at least one RNS.

In some embodiments, the exogenous environmental conditions are the presence or absence of reactive oxygen species (ROS). In other embodiments, the exogenous environmental conditions are the presence or absence of reactive nitrogen species (RNS). In some embodiments, exogenous environmental conditions are biological molecules that are involved in the inflammatory response, for example, molecules present in an inflammatory disorder of the gut. In some embodiments, the exogenous environmental conditions or signals exist naturally or are naturally absent in the environment in which the recombinant bacterial cell resides. In some embodiments, the exogenous environmental conditions or signals are artificially created, for example, by the creation or removal of biological conditions and/or the administration or removal of biological molecules.

In some embodiments, the exogenous environmental condition(s) and/or signal(s) stimulates the activity of an inducible promoter. In some embodiments, the exogenous environmental condition(s) and/or signal(s) that serves to activate the inducible promoter is not naturally present within the gut of a mammal. In some embodiments, the inducible promoter is stimulated by a molecule or metabolite that is administered in combination with the pharmaceutical composition of the disclosure, for example, tetracycline, arabinose, or any biological molecule that serves to activate an inducible promoter. In some embodiments, the exogenous environmental condition(s) and/or signal(s) is added to culture media comprising a recombinant bacterial cell of the disclosure. In some embodiments, the exogenous environmental condition that serves to activate the inducible promoter is naturally present within the gut of a mammal (for example, low oxygen or anaerobic conditions, or biological molecules involved in an inflammatory response). In some embodiments, the loss of exposure to an exogenous environmental condition (for example, in vivo) inhibits the activity of an inducible promoter, as the exogenous environmental condition is not present to induce the promoter (for example, an aerobic environment outside the gut). As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions. In some embodiments, the genetically engineered bacteria of the invention comprise a gene encoding a effector molecule (e.g. PME) that is operably linked to a directly or indirectly inducible promoter that is not associated with said gene in nature, e.g., an FNR promoter operably linked to a gene encoding an effector molecule or a ParaBAD promoter operably linked to a second effector molecule.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^s$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_1712074; BBa_1719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998)), and functional fragments thereof.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

In some embodiments, the genetically engineered bacteria are active (e.g., express one or more payloads (e.g. PME(s)) in the gut. In some embodiments, the genetically engineered bacteria are active (e.g., express one or more payloads) in the large intestine. In some embodiments, the genetically engineered bacteria are active (e.g., express one or more payloads) in the small intestine. In some embodiments, the genetically engineered bacteria are active in the small intestine and in the large intestine. Without wishing to be bound by theory, phenylalanine degradation may be every effective in the small intestine, because amino acid absorption, e.g., phenylalanine absorption, occurs in the small intestine. Through the prevention or reduction of phenylalanine uptake into the blood, increased levels and resulting Phe toxicity can be avoided. Additionally, extensive enterorecirculation of amino acids between the intestine and the body may allow the removal of systemic phenylalanine in PKU (e.g., described by Chang et al., in a rat model of PKU (Chang et al., A new theory of enterorecirculation of amino acids and its use for depleting unwanted amino acids using oral enzyme-artificial cells, as in removing phenylalanine in phenylketonuria; Artif Cells Blood Substit Immobil Biotechnol. 1995; 23(1):1-21)). Phenylalanine from the blood circulates into the small intestine (see, e.g., FIG. 15) and can be cleared by bacteria which are active at this location. In some embodiments, the genetically engineered bacteria transit through the small intestine. In some embodiments, the genetically engineered bacteria have increased residence time in the gut. In some embodiments, the genetically engineered bacteria colonize the small or large intestine. In some embodiments, the genetically engineered bacteria colonize the colon. In some embodiments, the genetically engineered bacteria have increased residence time in the gut. In some embodiments, the genetically engineered bacteria do not colonize the gut.

As used herein, the term "low oxygen" is meant to refer to a level, amount, or concentration of oxygen ($O_2$) that is lower than the level, amount, or concentration of oxygen that is present in the atmosphere (e.g., <21% $O_2$; <160 torr $O_2$). Thus, the term "low oxygen condition or conditions" or "low oxygen environment" refers to conditions or environments containing lower levels of oxygen than are present in the atmosphere. In some embodiments, the term "low oxygen" is meant to refer to the level, amount, or concentration of oxygen ($O_2$) found in a mammalian gut, e.g., lumen, stomach, small intestine, duodenum, jejunum, ileum, large intestine, cecum, colon, distal sigmoid colon, rectum, and anal canal. In some embodiments, the term "low oxygen" is meant to refer to a level, amount, or concentration of $O_2$ that is 0-60 mmHg $O_2$ (0-60 torr $O_2$) (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 mmHg $O_2$), including any and all incremental fraction(s) thereof (e.g., 0.2 mmHg, 0.5 mmHg $O_2$, 0.75 mmHg $O_2$, 1.25 mmHg $O_2$, 2.175 mmHg $O_2$, 3.45 mmHg $O_2$, 3.75 mmHg $O_2$, 4.5 mmHg $O_2$, 6.8 mmHg $O_2$, 11.35 mmHg $O_2$, 46.3 mmHg $O_2$, 58.75 mmHg, etc., which exemplary fractions are listed here for illustrative purposes and not meant to be limiting in any way). In some embodiments, "low oxygen" refers to about 60 mmHg $O_2$ or less (e.g., 0 to about 60 mmHg $O_2$). The term "low oxygen" may also refer to a range of $O_2$ levels, amounts, or concentrations between 0-60 mmHg $O_2$ (inclusive), e.g., 0-5 mmHg $O_2$, <1.5 mmHg $O_2$, 6-10 mmHg, <8 mmHg, 47-60 mmHg, etc. which listed exemplary ranges are listed here for illustrative purposes and not meant to be limiting in any way. See, for example, Albenberg et al., Gastroenterology, 147(5): 1055-1063 (2014); Bergofsky et al., J Clin. Invest., 41(11): 1971-1980 (1962); Crompton et al., J Exp. Biol., 43: 473-478 (1965); He et al., PNAS (USA), 96: 4586-4591 (1999); McKeown, Br. J. Radiol., 87:20130676 (2014) (doi: 10.1259/brj.20130676), each of which discusses the oxygen levels found in the mammalian gut of various species and each of which are incorporated by reference herewith in their entireties. In some embodiments, the term "low oxygen" is meant to refer to the level, amount, or concentration of oxygen ($O_2$) found in a mammalian organ or tissue other than the gut, e.g., urogenital tract, tumor tissue, etc. in which oxygen is present at a reduced level, e.g., at a hypoxic or anoxic level. In some embodiments, "low oxygen" is meant to refer to the level, amount, or concentration of oxygen ($O_2$) present in partially aerobic, semi aerobic, microaerobic, nanoaerobic, microoxic, hypoxic, anoxic, and/or anaerobic conditions. For example, Table A summarizes the amount of oxygen present in various organs and tissues. In some embodiments, the level, amount, or concentration of oxygen ($O_2$) is expressed as the amount of dissolved oxygen ("DO") which refers to the level of free, non-compound oxygen ($O_2$) present in liquids and is typically reported in milligrams per liter (mg/L), parts per million (ppm; lmg/L=1 ppm), or in micromoles (umole) (1 umole $O_2$=0.022391 mg/L $O_2$). Fondriest Environmental, Inc., "Dissolved Oxygen", Fundamentals of Environmental Measurements, 19 Nov. 2013, www.fondriest.com/environmental-measurements/parameters/water-quality/dissolved-oxygen/>. In some embodiments, the term "low oxygen" is meant to refer to a level, amount, or concentration of oxygen ($O_2$) that is about 6.0 mg/L DO or less, e.g., 6.0 mg/L, 5.0 mg/L, 4.0 mg/L, 3.0 mg/L, 2.0 mg/L, 1.0 mg/L, or 0 mg/L, and any fraction therein, e.g., 3.25 mg/L, 2.5 mg/L, 1.75 mg/L, 1.5 mg/L, 1.25 mg/L, 0.9 mg/L, 0.8 mg/L, 0.7 mg/L, 0.6 mg/L, 0.5 mg/L, 0.4 mg/L, 0.3 mg/L, 0.2 mg/L and 0.1 mg/L DO, which exemplary fractions are listed here for illustrative purposes and not meant to be limiting in any way. The level of oxygen in a liquid or solution may also be reported as a percentage of air saturation or as a percentage of oxygen saturation (the ratio of the concentration of dissolved oxygen ($O_2$) in the solution to the maximum amount of oxygen that will dissolve in the solution at a certain temperature, pressure, and salinity under stable equilibrium). Well-aerated solutions (e.g., solutions subjected to mixing and/or stirring) without oxygen producers or consumers are 100% air saturated. In some embodiments, the term "low oxygen" is meant to refer to 40% air saturation or less, e.g., 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, and 0% air saturation, including any and all incremental fraction(s) thereof (e.g., 30.25%, 22.70%, 15.5%, 7.7%, 5.0%, 2.8%, 2.0%, 1.65%, 1.0%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of air saturation levels between 0-40%, inclusive (e.g., 0-5%, 0.05-0.1%, 0.1-0.2%, 0.1-0.5%, 0.5-2.0%, 0-10%, 5-10%, 10-15%, 15-20%, 20-25%, 25-30%, etc.). The exemplary fractions and ranges listed here are for illustrative purposes and not meant to be limiting in any way. In some embodiments, the term "low oxygen" is meant to refer to 9% 02 saturation or less, e.g., 9%, 8%, 7%, 6%, 5%, 4%, 3%, 2%, 1%, 0%, 02 saturation, including any and all incremental fraction(s) thereof (e.g., 6.5%, 5.0%, 2.2%, 1.7%, 1.4%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of 02 saturation levels between 0-9%, inclusive (e.g., 0-5%, 0.05-0.1%, 0.1-0.2%, 0.1-0.5%, 0.5-2.0%, 0-8%, 5-7%, 0.3-4.2% 02, etc.). The exemplary fractions and ranges listed here are for illustrative purposes and not meant to be limiting in any way.

TABLE A

Intestinal Oxygen Tension

| Compartment | Oxygen Tension |
|---|---|
| stomach | ~60 torr (e.g., 58 +/− 15 torr) |
| duodenum and first | ~30 torr (e.g., 32 +/− 8 torr); |
| part of jejunum | ~20% oxygen in ambient air |
| Ileum (mid- small | ~10 torr; ~6% oxygen in ambient air |
| intestine) | (e.g., 11 +/− 3 torr) |
| Distal sigmoid colon | ~3 torr (e.g., 3 +/− 1 torr) |
| colon | <2 torr |
| Lumen of cecum | <1 torr |
| tumor | <32 torr (most tumors are <15 torr) |

In some embodiments, a promoter described herein is directly or indirectly induced by conditions in a culture vessel (e.g., a flask or a fermenter or other appropriate culture vessel), in which the strain is grown or maintained prior to in vivo administration. Non-limiting examples of such conditions which are provided during culture of the strain prior to in vivo administration include low oxygen, anaerobic, microaerobic, or aerobic conditions, other defined oxygen levels (such as those exemplified below), presence of arabinose, presence of IPTG, rhamnose or other chemical and/or nutritional inducers described herein or known in the art. In some embodiments, the conditions in a culture vessel are set at certain oxygen levels, e.g., between 1% and 10% oxygen, between 10% and 20% oxygen, between 20% and 30% oxygen, between 30% and 40% oxygen, between 40% and 50% oxygen, between 60% and 70% oxygen, between 70% and 80% oxygen, between 80% and 90% oxygen, between 90% and 100% oxygen, and other levels of oxygen as described herein, at which point the promoter is directly or indirectly induced.

As used herein, the term "gene" or "gene sequence" is meant to refer to a genetic sequence, e.g., a nucleic acid sequence. The gene, gene sequence or genetic sequence is meant to include a complete gene sequence or a partial gene sequence. The gene, gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, Bifidobacteria, *Escherichia, Lactobacillus*, and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum*, and *Sac-*

*charomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained" or "stable" bacterium is used to refer to a bacterial host cell carrying non-native genetic material, e.g., a gene encoding an effector molecule, which is incorporated into the host genome or propagated on a self-replicating extra-chromosomal plasmid, such that the non-native genetic material is retained, expressed, and/or propagated. The stable bacterium is capable of survival and/or growth in vitro, e.g., in medium, and/or in vivo, e.g., in the gut. For example, the stable bacterium may be a genetically modified bacterium comprising a gene encoding an effector molecule (e.g., a PAL), in which the plasmid or chromosome carrying the effector gene is stably maintained in the host cell, such that the effector can be expressed in the host cell, and the host cell is capable of survival and/or growth in vitro and/or in vivo. In some embodiments, copy number affects the stability of expression of the non-native genetic material, e.g. a PAL gene. In some embodiments, copy number affects the level of expression of the non-native genetic material, e.g. a PAL gene or a PAH gene.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. Treating a disease, disorder, or condition may encompass reducing or eliminating an associated symptom without necessarily encompassing the elimination of the underlying disease. For example, primary hyperphenylalaninemia is caused by inborn genetic mutations for which there are no known cures. Hyperphenylalaninemia can also be secondary to other conditions, e.g., liver diseases. Treating hyperphenylalaninemia may encompass reducing or eliminating excess phenylalanine and/or associated symptoms, and does not necessarily encompass the elimination of the underlying disease. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition. A therapeutically effective amount may, for example, be sufficient to treat, prevent, reduce the severity, delay the onset, and/or reduce the risk of occurrence of one or more symptoms of a disease or condition. A therapeutically effective amount, as well as a therapeutically effective frequency of administration, can be determined by methods known in the art and discussed below.

As used herein, the term "antibody" or "antibodies" is meant to encompasses all variations of antibody and fragments thereof that possess one or more particular binding specificities. Thus, the term "antibody" or "antibodies" is meant to include full length antibodies, chimeric antibodies, humanized antibodies, single chain antibodies (ScFv, camelids), Fab, Fab', multimeric versions of these fragments (e.g., F(ab')2), single domain antibodies (sdAB, VHH fragments), heavy chain antibodies (HCAb), nanobodies, diabodies, and minibodies. Antibodies can have more than one binding specificity, e.g. be bispecific. The term "antibody" is also meant to include so-called antibody mimetics. Antibody mimetics refers to small molecules, e.g., 3-30 kDa, which can be single amino acid chain molecules, which can specifically bind antigens but do not have an antibody-related structure. Antibody mimetics, include, but are not limited to, Affibody molecules (Z domain of Protein A), Affilins (Gamma-B crystalline), Ubiquitin, Affimers (Cystatin), Affitins (Sac7d (from *Sulfolobus acidocaldarius*), Alphabodies (Triple helix coiled coil), Anticalins (Lipocalins), Avimers (domains of various membrane receptors), DARPins (Ankyrin repeat motif), Fynomers (SH3 domain of Fyn), Kunitz domain peptides Kunitz domains of various protease inhibitors), Ecallantide (Kalbitor), and Monobodies. In certain aspects, the term "antibody" or "antibodies" is meant to refer to a single chain antibody(ies), single domain antibody(ies), and camelid antibody(ies). Utility of antibodies in the treatment of cancer and additional anti cancer antibodies can for example be found in Scott et al., Antibody Therapy for Cancer, Nature Reviews Cancer April 2012 Volume 12, incorporated by reference in its entirety.

A "single-chain antibody" or "single-chain antibodies" typically refers to a peptide comprising a heavy chain of an immunoglobulin, a light chain of an immunoglobulin, and optionally a linker or bond, such as a disulfide bond. The single-chain antibody lacks the constant Fc region found in traditional antibodies. In some embodiments, the single-chain antibody is a naturally occurring single-chain antibody, e.g., a camelid antibody. In some embodiments, the single-chain antibody is a synthetic, engineered, or modified single-chain antibody. In some embodiments, the single-chain antibody is capable of retaining substantially the same antigen specificity as compared to the original immunoglobulin despite the addition of a linker and the removal of the constant regions. In some aspects, the single chain antibody can be a "scFv antibody", which refers to a fusion protein of the variable regions of the heavy (VH) and light chains (VL) of immunoglobulins (without any constant regions), optionally connected with a short linker peptide of ten to about 25 amino acids, as described, for example, in U.S. Pat. No. 4,946,778, the contents of which is herein incorporated by reference in its entirety. The Fv fragment is the smallest fragment that holds a binding site of an antibody, which binding site may, in some aspects, maintain the specificity of the original antibody. Techniques for the production of single chain antibodies are described in U.S. Pat. No. 4,946,778. The Vh and VL sequences of the scFv can be connected via the N-terminus of the VH connecting to the C-terminus of the VL or via the C-terminus of the VH connecting to the N-terminus of the VL. ScFv fragments are independent folding entities that can be fused indistinctively on either end to other epitope tags or protein domains. Linkers of varying length can be used to link the Vh and VL sequences, which the linkers can be glycine rich (provides flexibility) and serine or threonine rich (increases solubility). Short linkers may prevent association of the two domains and can result in multimers (diabodies, tribodies, etc.). Long linkers may result in proteolysis or weak domain association (described in Voelkel et al el., 2011). Linkers of length between 15 and 20 amino acids or 18 and 20 amino acids are most often used. Additional non-limiting examples of linkers, including other flexible linkers are described in Chen et al., 2013 (Adv Drug Deliv Rev. 2013 Oct. 15; 65(10): 1357-1369. Fusion Protein Linkers: Property, Design and Functionality), the contents of which is herein incorporated by reference in its entirety. Flexible linkers are also rich in small or polar amino acids such as Glycine and Serine, but can contain additional amino acids such as Threonine and Alanine to maintain flexibility, as well as polar amino acids such as Lysine and Glutamate to improve solubility. Exemplary linkers include, but are not limited to, (Gly-Gly-Gly-Gly-Ser)n, KESGSVSSEQLAQFRSLD and EGKSSGSGS-ESKST, (Gly)8, and Gly and Ser rich flexible linker, GSAGSAAGSGEF. "Single chain antibodies" as used herein also include single-domain antibodies, which include camelid antibodies and other heavy chain antibodies, light chain antibodies, including nanobodies and single domains VH or VL domains derived from human, mouse or other species. Single domain antibodies may be derived from any species including, but not limited to mouse, human, camel, llama, fish, shark, goat, rabbit, and bovine. Single domain antibodies include domain antigen-binding units which have a camelid scaffold, derived from camels, llamas, or alpacas. Camelids produce functional antibodies devoid of light chains. The heavy chain variable (VH) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies. Camelid scaffold-based antibodies can be produced using methods well known in the art. Cartilaginous fishes also have heavy-chain antibodies (IgNAR, 'immunoglobulin new antigen receptor'), from which single-domain antibodies called VNAR fragments can be obtained. Alternatively, the dimeric variable domains from IgG from humans or mice can be split into monomers. Nanobodies are single chain antibodies derived from light chains. The term "single chain antibody" also refers to antibody mimetics.

In some embodiments, the antibodies expressed by the engineered microorganisms are bispecific. In certain embodiments, a bispecific antibody molecule comprises a scFv, or fragment thereof, have binding specificity for a first epitope and a scFv, or fragment thereof, have binding specificity for a second epitope. Antigen-binding fragments or antibody portions include bivalent scFv (diabody), bispecific scFv antibodies where the antibody molecule recognizes two different epitopes, single binding domains (dAbs), and minibodies. Monomeric single-chain diabodies (scDb) are readily assembled in bacterial and mammalian cells and show improved stability under physiological conditions (Voelkel et al., 2001 and references therein; Protein Eng. (2001) 14 (10): 815-823 (describes optimized linker sequences for the expression of monomeric and dimeric bispecific single-chain diabodies).

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cysm Ser, Tyr, Thr; -Val, Ile, Len, Met, Ala, Phe; -Lys, Arg, His; -Phe, Tyr, Trp, His; and -Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. The term "codon-optimized" refers to the modification of codons in the gene or coding regions of a nucleic acid molecule to reflect the typical codon usage of the host organism without altering the polypeptide encoded by the nucleic acid molecule. Such optimization includes replacing at least one, or more than one, or a significant number, of codons with one or more codons that are more frequently used in the genes of the host organism. A "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. In some embodiments, the improvement of transcription and/or translation involves increasing the level of transcription and/or translation. In some embodiments, the improvement of transcription and/or translation involves decreasing the level of transcription and/or translation. In some embodiments, codon optimization is used to fine-tune the levels of expression from a construct of interest. Codon optimization includes, but is not limited to, processes including selecting codons for the coding sequence to suit the codon preference of the expression host organism. Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent, inter alia, on the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting the protein(s) of interest or therapeutic protein(s) from the microbial, e.g., bacterial cytoplasm. The secretion system may comprise a single protein or may comprise two or more proteins assembled in a complex e.g., HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RND) multi-drug efflux pumps, various single membrane secretion systems. Non-liming examples of secretion systems for gram positive bacteria include Sec and TAT secretion systems. In some embodiments, the proteins of interest include a "secretion tag" of either RNA or peptide origin to direct the protein(s) of interest or therapeutic protein(s) to specific secretion systems. In some embodiments, the secretion system is able to remove this tag before secreting the protein(s) of interest from the engineered bacteria. For example, in Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the protein(s) of interest into the extracellular milieu.]]

As used herein, the term "transporter" is meant to refer to a mechanism, e.g., protein or proteins, for importing a molecule, e.g., amino acid, toxin, metabolite, substrate, etc. into the microorganism from the extracellular milieu. For example, a phenylalanine transporter such as PheP imports phenylalanine into the microorganism.

Effectors also include immune checkpoint inhibitors. An "immune checkpoint inhibitor" or "immune checkpoint" refers to a molecule that completely or partially reduces, inhibits, interferes with, or modulates one or more immune checkpoint proteins. Immune checkpoint proteins regulate T-cell activation or function, and are known in the art. Non-limiting examples include CTLA-4 and its ligands CD 80 and CD86, and PD-1 and its ligands PD-L1 and PD-L2. Immune checkpoint proteins are responsible for co-stimulatory or inhibitory interactions of T-cell responses, and regulate and maintain self-tolerance and physiological immune responses. Systemic immunotherapy, e.g., using CTLA-4 inhibitors, may alter immunoregulation, provoke immune dysfunction, and result in opportunistic autoimmune disorders (see, e.g., Kong et al., 2014).

As used herein, a genetically engineered microorganism, e.g., engineered bacterium or phage, or molecule that "inhibits" a biological molecule refers to a bacterium or virus or molecule that is capable of reducing, decreasing, or eliminating the biological activity, biological function, and/or number of that biological molecule, as compared to control, e.g., an untreated control or an unmodified microorganism of the same subtype under the same conditions.

As used herein, a genetically engineered microorganism, e.g., engineered bacterium or phage molecule that "activates" or "stimulates" a biological molecule, refers to a bacterium or phage molecule that is capable of activating, increasing, enhancing, or promoting the biological activity, biological function, and/or number of that biological molecule, as compared to control, e.g., an untreated control or an unmodified microorganism of the same subtype under the same conditions.

The terms "phage" and "bacteriophage" are used interchangeably herein. Both terms refer to a virus that infects and replicates within a bacterium. As used herein "phage" or bacteriophage" collectively refers to prophage, lysogenic, dormant, temperate, intact, defective, cryptic, and satellite phage, phage tail bacteriocins, tailiocins, and gene transfer agents.

As used therein the term "prophage" refers to the genomic material of a bacteriophage, which is integrated into a replicon of the host cell and replicates along with the host. The prophage may be able to produce phages if specifically activated. In some cases, the prophage is not able to produce phages or has never done so (i.e., defective or cryptic prophages). In some cases, prophage also refers to satellite phages. The terms "prophage" and "endogenous phage" are used interchangeably herein.

As used herein, the term "temperate phage" or "temperate bacteriophage" or "prophage" are used interchangeably to refer to a phage which exists within the DNA of the bacterial host and replicate along with the host during the bacterial replication cycle and cell division.

As used herein the term "natural state" of a bacterium or organism or "native state" of a bacterium or refers to an organism which has not been modified by genetic engineering. In some cases, the term "natural state" of a bacterium or organism or "native state" of a bacterium refers to an organism which has not been modified by genetic engineering as compared to an isogenic strain that has been modified with respect to a defined element. As such, the bacterium may be in its natural state with respect to one defined element, but not in its natural state with respect to another defined element. In some embodiments, a bacterium may comprise one or more of the same or different phage(s) or prophage(s) in its natural or native state. In some embodiments, a bacterium, which in its native or natural state comprises one or more of the same or different types of phages or prophages, serves a progenitor strain for an engineered strain. Consequently, the same one or more endogenous phage(s) or prophage(s) may also be present in a genetically engineered bacterium, e.g., if the progenitor or parental strain contained such an endogenous phage or prophage in its native state. As such the genetically engineered bacterium also contains the prophage in its natural state (wherein the phage is the defined element that is in its natural state).

"Endogenous phage" or "endogenous prophage" also refers to a phage that is present in the natural state of a bacterium (and its parental strain).

As used herein the term "phage knockout" or "inactivated phage" refers to a phage which has been modified so that it can either no longer produce and/or package phage particles or it produces fewer phage particles than the wild type phage sequence. In some embodiments, the inactivated phage or phage knockout refers to the inactivation of a temperate phage in its lysogenic state, i.e., to a prophage. Such a modification refers to a mutation in the phage; such mutations include insertions, deletions (partial or complete deletion of phage genome), substitutions, inversions, at one or more positions within the phage genome, e.g., within one or more genes within the phage genome.

As used herein the term "isogenic" bacterial strains refers to bacterial strains that are genetically identical or that contain defined changes but are otherwise identical. For example, isogenic mutants typically refers to two strains that are identical except that one contains a defined mutation in one or more known genes or proteins. As such, a phage free or phage less strain has a corresponding isogenic strain which contains prophage which can be induced and release phage particles from the bacterial cell.

As used herein the adjectives "phage-free", "phage free" and "phageless" are used interchangeably to characterize a bacterium or strain which contains one or more prophages, one or more of which have been modified. The modification can result in a loss of the ability of the prophage to be induced or release phage particles. Alternatively, the modification can result in less efficient or less frequent induction or less efficient or less frequent phage release as compared to the isogenic strain without the modification. Ability to induce and release phage can be measured using a plaque assay as described herein.

As used herein, the term "lysogen" refers to a bacterium containing a prophage, which is in the lysogenic cycle, in which the phage genes required for lysis are not expressed.

As used herein phage induction refers to the part of the life cycle of a lysogenic prophage, in which the lytic phage genes are activated, phage particles are produced and lysis occurs.

As used herein, the term induction refers to the conversion of a lysogenic infection into a productive infection, i.e., the induced prophage initiates the production and release of phage particles. Induction often is stimulated by damage to bacterial DNA, and may or may not involve excision of the prophage from the bacterial chromosome.

In some embodiments, the genetically engineered bacteria are useful for the treatment, prevention, management, reduction in severity of, amelioration, cure a disorder, disease or condition. In some embodiments, the disorder is an autoimmune disorder. As used herein, "autoimmune disorders" include, but are not limited to, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, asthma, ulcerative colitis, undifferentiated connective tissue disease (UCTD), uveitis, vasculitis, vesiculobullous dermatosis, vitiligo, and Wegener's granulomatosis. In some embodiments, the disorder is graft vs host disease.

In some embodiments, the disease is a metabolic disease. As used herein, "metabolic diseases" include, but are not limited to, type 1 diabetes; type 2 diabetes; metabolic syndrome; Bardet-Biedel syndrome; Prader-Willi syndrome; non-alcoholic fatty liver disease; tuberous sclerosis; Albright hereditary osteodystrophy; brain-derived neurotrophic factor (BDNF) deficiency; Single-minded 1 (SIM1) deficiency; leptin deficiency; leptin receptor deficiency; proopiomelanocortin (POMC) defects; proprotein convertase subtilisin/kexin type 1 (PCSK1) deficiency; Src homology 2B1 (SH2B1) deficiency; pro-hormone convertase 1/3 deficiency; melanocortin-4-receptor (MC4R) deficiency; Wilms tumor, aniridia, genitourinary anomalies, and mental retardation (WAGR) syndrome; pseudohypoparathyroidism type 1A; Fragile X syndrome; Borjeson-Forsmann-Lehmann syndrome; Alstrom syndrome; Cohen syndrome; and ulnar-mammary syndrome.

In some embodiments, the disorder is cancer. "Cancer" or "cancerous" is used to refer to a physiological condition that is characterized by unregulated cell growth. In some embodiments, cancer refers to a tumor. "Tumor" is used to refer to any neoplastic cell growth or proliferation or any pre-cancerous or cancerous cell or tissue. A tumor may be malignant or benign. Types of cancer include, but are not limited to, adrenal cancer, adrenocortical carcinoma, anal cancer, appendix cancer, bile duct cancer, bladder cancer, bone cancer (e.g., Ewing sarcoma tumors, osteosarcoma, malignant fibrous histiocytoma), brain cancer (e.g., astrocytomas, brain stem glioma, craniopharyngioma, ependymoma), bronchial tumors, central nervous system tumors, breast cancer, Castleman disease, cervical cancer, colon cancer, rectal cancer, colorectal cancer, endometrial cancer, esophageal cancer, eye cancer, gallbladder cancer, gastrointestinal cancer, gastrointestinal carcinoid tumors, gastrointestinal stromal tumors, gestational trophoblastic disease, heart cancer, Kaposi sarcoma, kidney cancer, largyngeal cancer, hypopharyngeal cancer, leukemia (e.g., acute lymphoblastic leukemia, acute myeloid leukemia, chronic lymphocytic leukemia, chronic myelogenous leukemia), liver cancer, lung cancer, lymphoma (e.g., AIDS-related lymphoma, Burkitt lymphoma, cutaneous T cell lymphoma, Hodgkin lymphoma, Non-Hodgkin lymphoma, primary central nervous system lymphoma), malignant mesothelioma, multiple myeloma, myelodysplastic syndrome, nasal cavity cancer, paranasal sinus cancer, nasopharyngeal cancer, neuroblastoma, oral cavity cancer, oropharyngeal cancer, osteosarcoma, ovarian cancer, pancreatic cancer, penile cancer, pituitary tumors, prostate cancer, retinoblastoma, rhabdomyosarcoma, rhabdoid tumor, salivary gland cancer, sarcoma, skin cancer (e.g., basal cell carcinoma, melanoma), small intestine cancer, stomach cancer, teratoid tumor, testicular cancer, throat cancer, thymus cancer, thyroid cancer, unusual childhood cancers, urethral cancer, uterine cancer, uterine sarcoma, vaginal cancer, vulvar cancer, Waldenström macrogloblulinemia, and Wilms tumor. Side effects of cancer treatment may include, but are not limited to, opportunistic autoimmune disorder(s), systemic toxicity, anemia, loss of appetite, irritation of bladder lining, bleeding and bruising (thrombocytopenia), changes in taste or smell, constipation, diarrhea, dry mouth, dysphagia, edema, fatigue, hair loss (alopecia), infection, infertility, lymphedema, mouth sores, nausea, pain, peripheral neuropathy, tooth decay, urinary tract infections, and/or problems with memory and concentration (National Cancer Institute). In some embodiments, the disorder is a hyperammonemia disorder.

In some embodiments, the disorders are rare diseases, including but not limited to, hyperammonemia, ureacycle disorders, propionic acidemia, methylmalonic acidemia, maple syrup urine disease, isovaleric acidemia, hyperoxaluria, phenylketonurea.

Exemplary circuitry for the treatment, prevention, reduction in severity, management, amelioration, cure of one or more of the disorders described above are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

In some embodiments, the bacteria disclosed herein contain one or more mutations or modifications to an endogenous phage genome. In some embodiments, the bacterium comprises the bacteriophage in its natural or native state. In some embodiments, the phage is present in all isolates of a particular bacterium. In some embodiments, the phage is present in bacteria of the same species, strain, or substrain. In some embodiments, the phage is an intact prophage. In some embodiments, the phage is a defective prophage. In some embodiments, the one or more mutations renders the phage unable to enter the lytic cycle. In some embodiments, the one or more mutations affect the ability of the phage to undergo the lytic cycle, e.g., reduce the frequency or reduce the number of bacteria in a given population that can undergo the lytic stage. In some embodiments, the one or more mutations prevent the phage from infecting other bacteria. In some embodiments, the one or more mutations alters, e.g., increases or reduces, bacterial fitness. In some embodiments, the one or more mutations alters e.g., increases or reduces, effector function. In some embodiments, the one or more mutations do not alter bacterial fitness. In some embodiments, the one or more mutations do not alter effector function. In some embodiments, the one or more mutations improve the process by which the bacteria is manufactured or produced, including large-scale manufacturing. In any of these embodiments, the bacterium may otherwise be in its natural state. Alternatively, in any of these embodiments, the bacteria may be further genetically engineered to include gene sequence encoding one or more effector molecules.

In some embodiments, a bacterium comprising one or more mutated phages can be used as a bacterial chassis, to which genetic circuitry is added or modified.

In some embodiments, the bacteria are non-pathogenic bacteria. In some embodiments, the bacteria are commensal bacteria. In some embodiments, the bacteria are probiotic bacteria. In some embodiments, the bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*. In certain embodiments, the bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*.

In some embodiments, the bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and is not uropathogenic (Sonnenborn et al., 2009). As early as in 1917, *E. coli* Nissle was packaged into medicinal capsules, called Mutaflor, for therapeutic use. It is commonly accepted that *E. coli* Nissle's therapeutic efficacy and safety have convincingly been proven (Ukena et al., 2007).

In some embodiments, the bacteria of the disclosure or tumor-targeting bacteria. Tumor-targeting bacteria are described are described in International Patent Application PCT/US2017/013072, filed Jan. 11, 2017, published as WO2017/123675, the contents of which is herein incorporated by reference in its entirety.

One of ordinary skill in the art would appreciate that the genetic modifications disclosed herein may be adapted for other species, strains, and subtypes of bacteria. Furthermore, genes from one or more different species can be introduced into one another, e.g., the PAL gene from *Rhodosporidium toruloides* can be expressed in *Escherichia coli* (Sarkissian et al., 1999).

In any of these embodiments, any of the bacterial species disclosed herein or known in the art, and which may be used according to the disclosure, contain one or more mutations or modifications to one or more endogenous phage genomes. In some embodiments, the modifications to the endogenous phage genomes comprise one or more deletion(s), insertion(s), substitution(s) or inversions(s) or combinations thereof within the phage genomes. In some embodiments, the modification(s) is one or more deletions in the phage genome(s). In some embodiments, one or more phage genes are deleted. In some embodiments, one or more phage genes are partially deleted. In some embodiments, the modification(s) is one or more insertions in the phage genome(s). In some embodiments, the insertion comprises gene sequence encoding an antibiotic cassette as described herein. In some embodiments, one or more genes in the phage genome(s) are substituted with alternate gene sequence(s). In some embodiments, the substitution comprises gene sequence encoding an antibiotic cassette. In some embodiments, the entire sequence(s) of one or more phage genes is inverted. In some embodiments a partial sequence of one or more phage genes are inverted.

Unmodified *E. coli* Nissle and the genetically engineered bacteria of the invention may be destroyed, e.g., by defense factors in the gut or blood serum (Sonnenborn et al., 2009) or by activation of a kill switch, several hours or days after administration. Thus, the genetically engineered bacteria may require continued administration. In some embodiments, the residence time is calculated for a human subject. Residence time in vivo may be calculated for the genetically engineered bacteria of the invention (see, e.g., FIG. 68 of WO2017087580, the contents of which are herein incorporated by reference in their entirety).

In some embodiments, the genetically engineered bacteria comprise a gene encoding PAL, wherein the PAL gene is operably linked to a directly or indirectly inducible promoter. In some embodiments, the bacteria comprise a non-native PAL gene. In some embodiments, the bacteria comprise additional copies of a native PAL gene. In some embodiments, the promoter is not associated with the PAL gene in nature. In some embodiments, the promoter is any one or more of the promoters disclosed herein.

In some embodiments, the genetically engineered bacteria comprise a gene encoding PAH, wherein the PAH gene is operably linked to a directly or indirectly inducible promoter. In some embodiments, the bacteria comprise a non-native PAH gene. In some embodiments, the bacteria comprise additional copies of a native PAH gene. In some embodiments, the promoter is not associated with the PAH gene in nature. In some embodiments, the promoter is any one or more of the promoters disclosed herein.

In some embodiments, the genetically engineered bacteria comprise a gene encoding LAAD, wherein the LAAD gene is operably linked to a directly or indirectly inducible promoter. In some embodiments, the bacteria comprise a non-native LAAD gene. In some embodiments, the bacteria comprise additional copies of a native LAAD gene. In some embodiments, the promoter is not associated with the LAAD gene in nature. In some embodiments, the promoter is any one or more of the promoters disclosed herein.

In some embodiments, the genetically engineered bacteria further comprise a gene encoding a phenylalanine transporter (PheP). In certain embodiments, the bacteria comprise additional copies of a native gene encoding a phenylalanine transporter, wherein the phenylalanine transporter gene is operably linked to a directly or indirectly inducible promoter. In alternate embodiments, the bacteria comprise a gene encoding a non-native phenylalanine transporter, wherein the phenylalanine transporter gene is operably linked to a directly or indirectly inducible promoter. Both embodiments are encompassed by the term "non-native" phenylalanine transporter. In some embodiments, the promoter is not associated with the pheP gene in nature. In some embodiments, the same promoter controls expression of PheP and PAL and/or PAH and/or LAAD. In some embodiments, the promoter that controls expression of PheP differs from the promoter that controls expression of PAL and/or PAH and/or LAAD. In some embodiments, the promoter that controls the expression of PheP is any one or more of the promoters disclosed herein.

In some embodiments, the promoter that is operably linked to PAL, PAH, LAAD, and/or pheP is directly or indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by exogenous environmental conditions specific to the large intestine of a mammal. In some embodiments, the promoter is directly or indirectly induced by low-oxygen or anaerobic and/or low oxygen conditions such as the environment of the mammalian gut. In some embodiments, the promoter is directly or indirectly induced by the presence of molecules or metabolites that are specific to the gut of a mammal, e.g., propionate. In some embodiments, the promoter is directly or indirectly induced by exposure to tetracycline. In some embodiments, the promoter is directly or indirectly induced by exposure to arabinose. In some embodiments, the promoter is directly or indirectly induced by exposure to IPTG. In some embodiments, the promoter is directly or indirectly induced by exposure to rhamnose or other chemical and/or nutritional inducer known in the art. In some embodiments, the promoter is directly or indirectly regulated by the exogenous environmental temperature. In some embodiments, the promoter is directly or indirectly induced by exposure to IPTG or other lacI binding compound. In some embodiments, the promoter is directly or indirectly induced by exposure to rhamnose. In some embodiments, the promoter is directly or indirectly induced by increase in temperature. In some embodiments, the promoter is directly or indirectly induced by decrease in temperature. In some embodiments, the promoter is directly or indirectly induced by a molecule that is co-administered with the genetically engineered bacteria of the invention. Such a molecule may be tetracycline or IPTG or arabinose or other chemical and/or nutritional inducer known in the art.

In some embodiments, the promoter is directly or indirectly induced prior to in vivo administration. Non-limiting examples of such conditions which are provided during culture of the strain prior to in vivo administration include low oxygen, anaerobic, microaerobic, or aerobic conditions, other defined oxygen levels (such as those exemplified below), presence of arabinose, presence of IPTG, rhamnose or other chemical and/or nutritional inducers described herein or known in the art. In some embodiments, the conditions in a culture vessel are set at certain oxygen levels, e.g between 1% and 10% oxygen, between 10% and 20% oxygen, between 20% and 30% oxygen, between 30% and 40% oxygen, between 40% and 50% oxygen, between 60% and 70% oxygen, between 70% and 80% oxygen, between 80% and 90% oxygen, between 90% and 100% oxygen, and other levels of oxygen as described herein, at which point the promoter is directly or indirectly induced.

Bacteriophages

In some embodiments, the bacteria of the disclosure comprise one or more lysogenic, dormant, temperate, intact, defective, cryptic, or satellite phage or bacteriocins/phage tail or gene transfer agents in their natural state. In some embodiments, the prophage or bacteriophage exists in all isolates of a particular bacterium of interest. In some embodiments, the bacteria are probiotic bacteria. In some embodiments, the bacteria are genetically engineered derivatives of a parental strain comprising one or more of such bacteriophage. Accordingly, such bacteria of the disclosure may be in their natural state or be further genetically modified to contain circuitry for the expression or production of one or more effector molecules. In any of the embodiments described herein, the bacteria comprise one or more modifications or mutations within a prophage or bacteriophage genome which alters the properties or behavior of the bacteriophage. In some embodiments, the modifications or mutations prevent the prophage from entering or completing the lytic process. In some embodiments, the modifications or mutations prevent the phage from infecting other bacteria of the same or a different type.

In some embodiments, the modifications or mutations alter, e.g., reduce or increase, the fitness of the bacterial host. In some embodiments, the modifications or mutations alter, e.g., reduce or increase, desired effector function, e.g., of a genetically engineered bacterium. In some embodiments, the modifications or mutations do not alter, e.g., reduce or increase, the fitness of the bacterial host. In some embodiments, the modifications or mutations do not alter, e.g., reduce or increase, desired effector function, e.g., of a genetically engineered bacterium.

Phage genome size varies enormously, ranging from the smallest *Leuconostoc* phage L5 (2,435 bp), ~11.5 kbp (e.g. *Mycoplasma* phage P1), ~21 kbp (e.g. *Lactococcus* phage c2), and ~30 kbp (e.g. *Pasteurella* phage F108) to the almost 500 kbp genome of *Bacillus megaterium* phage G (Hatfull and Hendrix; Bacteriophages and their Genomes, Curr Opin Virol. 2011 Oct. 1; 1(4): 298-303, and references therein). Phage genomes may encode less than 10 genes up to several hundreds of genes. Temperate phages or prophages are typically integrated into the chromosome(s) of the bacterial host, although some examples of phages that are integrated into bacterial plasmids also exist (Little, Loysogeny, Prophage Induction, and Lysogenic Conversion. In: Waldor M K, Friedman D I, Adhya S, editors. Phages Their Role in Bacterial Pathogenesis and Biotechnology. Washington DC: ASM Press; 2005. pp. 37-54). In some cases, the phages are always located at the same position within the bacterial host chromosome(s), and this position is specific to each phage, i.e., different phages are located at different positions. Other phages are more permissive in that they can integrate at numerous different locations.

Accordingly, the bacteria of the disclosure comprise one or more phages genomes which may vary in length. In one embodiment, the genetically engineered bacteria comprise a bacteriophage genome ranging in length from at least about 1 bp to 10 kb. In one embodiment, the bacteria comprise a bacteriophage genome ranging in length from at least about 1 bp to 10 kb. In one embodiment, the genetically engineered bacteria comprise a bacteriophage genome ranging in length from at least about 10 kb to 20 kb. In one embodiment, the genetically engineered bacteria comprise a bacteriophage genome ranging in length from at least about 20 kb to 30 kb. In one embodiment, the genetically engineered bacteria comprise a bacteriophage genome ranging in length from at least about 30 kb to 40 kb. In one embodiment, the genetically engineered bacteria comprise a bacteriophage genome ranging in length from at least about 30 kb to 40 kb. In one embodiment, the genetically engineered bacteria comprise a bacteriophage genome ranging in length from at least about 40 kb to 50 kb. In one embodiment, the genetically engineered bacteria comprise a bacteriophage genome ranging in length from at least about 50 kb to 60 kb. In one embodiment, the genetically engineered bacteria comprise a bacteriophage genome ranging in length from at least about 60 kb to 70 kb. In one embodiment, the genetically engineered bacteria comprise a bacteriophage genome ranging in length from at least about 70 kb to 80 kb. In one embodiment, the genetically engineered bacteria comprise a bacteriophage genome ranging in length from at least about 80 kb to 90 kb. In one embodiment, the genetically engineered bacteria comprise a bacteriophage genome ranging in length from at least about 90 kb to 100 kb. In one embodiment, the genetically engineered bacteria comprise a bacteriophage genome ranging in length from at least about 100 kb to 120 kb. In one embodiment, the genetically engineered bacteria comprise a bacteriophage genome ranging in length from at least about 120 kb to 140 kb. In one embodiment, the genetically engineered bacteria comprise a bacteriophage genome ranging in length from at least about 140 kb to 160 kb. In one embodiment, the genetically engineered bacteria comprise a bacteriophage genome ranging in length from at least about 160 kb to 180 kb. In one embodiment, the genetically engineered bacteria comprise a bacteriophage genome ranging in length from at least about 180 kb to 200 kb. In one embodiment, the genetically engineered bacteria comprise a bacteriophage genome ranging in length from at least about 200 kb to 180 kb. In one embodiment, the genetically engineered bacteria comprise a bacteriophage genome ranging in length from at least about 160 kb to 250 kb. In one embodiment, the genetically engineered bacteria comprise a bacteriophage genome ranging in length from at least about 250 kb to 300 kb. In one embodiment, the genetically engineered bacteria comprise a bacteriophage genome ranging in length from at least about 300 kb to 350 kb. In one embodiment, the genetically engineered bacteria comprise a bacteriophage genome ranging in length from at least about 350 kb to 400 kb. In one embodiment, the genetically engineered bacteria comprise a bacteriophage genome ranging in length from at least about 400 kb to 500 kb. In one embodiment, the genetically engineered bacteria comprise a bacteriophage genome ranging in length from at least about 500 kb to 1000 kb. In one embodiment, the genetically engineered bacteria comprise a bacteriophage genome greater than 1000 kb in length.

In some embodiments, the bacteria of the disclosure comprise one or more phages genomes, which comprise one or more genes encoding one or more polypeptides. In one embodiment, the genetically engineered bacteria comprise a bacteriophage genome comprising at least about 1 to 5 genes. In one embodiment, the genetically engineered bacteria comprise a bacteriophage genome comprising at least about 5 to 10 genes. In one embodiment, the genetically engineered bacteria comprise a bacteriophage genome comprising at least about 10 to 15 genes. In one embodiment, the genetically engineered bacteria comprise a bacteriophage genome comprising at least about 15 to 20 genes. In one embodiment, the genetically engineered bacteria comprise a bacteriophage genome comprising at least about 20 to 25 genes. In one embodiment, the genetically engineered bacteria comprise a bacteriophage genome comprising at least about 25 to 30 genes. In one embodiment, the genetically engineered bacteria comprise a bacteriophage genome comprising at least about 30 to 35 genes. In one embodiment, the genetically engineered bacteria comprise a bacteriophage genome comprising at least about 35 to 40 genes. In one embodiment, the genetically engineered bacteria comprise a bacteriophage genome comprising at least about 40 to 45 genes. In one embodiment, the genetically engineered bacteria comprise a bacteriophage genome comprising at least about 45 to 50 genes. In one embodiment, the genetically engineered bacteria comprise a bacteriophage genome comprising at least about 50 to 55 genes. In one embodiment, the genetically engineered bacteria comprise a bacteriophage genome comprising at least about 55 to 60 genes. In one embodiment, the genetically engineered bacteria comprise a bacteriophage genome comprising at least about 60 to 65 genes. In one embodiment, the genetically engineered bacteria comprise a bacteriophage genome comprising at least about 65 to 70 genes. In one embodiment, the genetically engineered bacteria comprise a bacteriophage genome comprising at least about 70 to 75 genes. In one embodiment, the genetically engineered bacteria comprise a bacteriophage genome comprising at least about 75 to 80 genes. In one embodiment, the genetically engineered bacteria comprise a bacteriophage genome comprising at least about 80 to 85 genes. In one embodiment, the genetically engineered bacteria comprise a bacteriophage genome comprising at least about 85 to 90 genes. In one embodiment, the genetically engineered bacteria comprise a bacteriophage genome comprising at least about 90 to 95 genes. In one embodiment, the genetically engineered bacteria comprise a bacteriophage genome comprising at least about 95 to 100 genes. In one embodiment, the genetically engineered bacteria comprise a bacteriophage genome comprising at least about 100 to 115 genes. In one embodiment, the genetically engineered bacteria comprise a bacteriophage genome comprising at least about 115 to 120 genes. In one embodiment, the genetically engineered bacteria comprise a bacteriophage genome comprising at least about 120 to 125 genes. In one embodiment, the genetically engineered bacteria comprise a bacteriophage genome comprising at least about 125 to 130 genes. In one embodiment, the genetically engineered bacteria comprise a bacteriophage genome comprising at least about 130 to 135 genes. In one embodiment, the genetically engineered bacteria comprise a bacteriophage genome comprising at least about 135 to 140 genes. In one embodiment, the genetically engineered bacteria comprise a bacteriophage genome comprising at least about 140 to 145 genes. In one embodiment, the genetically engineered bacteria comprise a bacteriophage genome comprising at least about 145 to 150 genes. In one embodiment, the genetically engineered bacteria comprise a bacteriophage genome comprising at least about 150 to 160 genes. In one embodiment, the genetically engineered bacteria comprise a bacteriophage genome comprising at least about 160 to 170 genes. In one embodiment, the genetically engineered bacteria comprise a bacteriophage genome comprising at least about 170 to 180 genes. In one embodiment, the genetically engineered bacteria comprise a bacteriophage genome comprising at least about 180 to 190 genes. In one embodiment, the genetically engineered bacteria comprise a bacteriophage genome comprising at least about 190 to 200 genes. In one embodiment, the genetically engineered bacteria comprise a bacteriophage genome comprising at least about 200 to 300 genes. In one embodiment, the genetically engineered bacteria comprise a bacteriophage genome comprising more than about 300 genes.

In some embodiments, the phage is always or almost always located at the same location or position within the bacterial host chromosome(s) in a particular species. In some embodiments, the phages are found integrated at different locations within the host chromosome in a particular species. In some embodiments, the phage is located on a plasmid.

The presence of prophage sequences may also confer certain properties to the bacteria which are not present in an isogenic strain without the phage. For example, the prophage may in some cases allow bacteria to acquire antibiotic resistance, to exist in new environmental niches, to improve adhesion or to become pathogenic. Additionally, through the lytic process, DNA from one bacterium can be picked up and released in another bacterium, and phages therefore function as a vehicle for gene transfer.

Accordingly, in some embodiments, the bacteria comprise a phage which bestows antibiotic resistance to the bacterium. In some embodiments, the bacteria comprise a phage which bestows additional fitness to the bacterium. In some embodiments, the bacteria comprise a phage which bestows ability to grow in new environments to the bacterium. In some embodiments, the bacteria comprise a phage which bestows the ability to transfer host genetic material to another bacterium of the same or different species.

In some embodiments, the prophage may be a defective or a cryptic prophage. Defective prophages can no longer undergo a lytic cycle. Cryptic prophages may not be able to undergo a lytic cycle or never have undergone a lytic cycle. Functional studies of the full repertoire of prophages of bacterial genomes suggest that the majority of prophages are defective at some level: excision, virion formation, lysis, or infective ability (Bobay et al., 2014). Defective or cryptic prophages accrue to a high level of abundancy in many bacteria as a result of mutational decay and/or the loss of one or more genes essential to the lytic cycle over thousands of bacterial replication cycles. (Bobay et al., Pervasive domestication of defective prohages by bacteria, Proc Natl Acad Sci USA). Of note, defective prophages often also contain a number of genes that can provide adaptive or advantageous functionality to the host, including genes encoding proteins with homologous recombination functions, mechanisms for prevention of further infection, or bacteriocins, which may be helpful in competition for nutrients, e.g., through growth inhibition of other neighboring bacterial species. For example, several defective prophages have been characterized in *E. coli* K-12 (e.g., Rac, e14, DLP12, and QIN) and in *Bacillus subtilis* (e.g., 186 and SKIN) (Casjens, 2001, and references therein). Each of these phage harbors some functional genes. For example, Rac encodes the RecE homologous recombination system.

Accordingly, in some embodiments, the bacteria comprise one or more defective or cryptic prophages. In some embodiments, the prophage genes confer homologous recombination functions. In some embodiments, the prophage genes confer the ability to prevent further infection. In some embodiments, the prophage genes confer bacteriocins. IN some embodiments, the phage genes promote growth under adverse conditions by increasing carbon utilization, improving resistance to osmotic, oxidative and acid stresses, for increasing growth under various conditions, enhancing phosphorus and nitrogen utilization, or influencing biofilm formation.

In some embodiments, the bacteria comprise one or more satellite phage genomes. Satellite phages are otherwise functional phages that do not carry their own structural protein genes, and have genomes that are configures for encapsulation by the structural proteins of other specific phages (Six and Klug Bacteriophage P4: a satellite virus depending on a helper such as prophage P2, Virology, Volume 51, Issue 2, February 1973, Pages 327-344). Accordingly, in some embodiments, the bacteria comprise phage genomes which do not carry their own structural genes.

In some embodiments, the bacteria comprise one or more tailiocins. Many bacteria, both gram positive and gram negative, produce a variety of particles resembling phage tails that are functional without an associated phage head (termed tailiocins), and many of which have been shown to have bacteriocin properties (reviewed in Ghequire and Mot, The Tailocin Tale: Peeling off Phage; Trends in Microbiology, October 2015, Vol. 23, No. 10). Phage tail-like bacteriocins are classified two different families: contractile phage tail-like (R-type) and noncontractile but flexible ones (F-type). Accordingly, in some embodiments, bacteria comprise one or more tailiocins which confer bacteriocin or other beneficial properties.

In some embodiments, the bacteria comprise one or more gene transfer agents. Gene transfer agents (GTAs) are phage-like elements that are encoded by some bacterial genomes. Although GTAs resemble phages, they lack the hallmark capabilities that define typical phages, and they package random fragments of the host cell DNA and then transfer them horizontally to other bacteria of the same species (reviewed in Lang et al., Gene transfer agents: phage-like elements of genetic exchange, Nat Rev Microbiol. 2012 Jun. 11; 10(7): 472-482). There, the DNA can replace the resident cognate chromosomal region by homologous recombination. However, these particles cannot propagate as viruses, as the vast majority of the particles do not carry the genes that encode the GTA.

In some embodiments, the bacteria comprise one or more filamentous virions. Filamentous virions integrate as dsDNA prophages (reviewed in Marvin D A, et al, Structure and assembly of filamentous bacteriophages, Prog Biophys Mol Biol. 2014 April; 114(2):80-122).

In any of the embodiments described herein, the genetically engineered bacteria described herein which express one or more enzymes and transporters (e.g. for the consumption of phenylalanine), comprise one or more modifications or mutations within an endogenous prophage or bacteriophage genome. These modifications may alter the properties or behavior of the prophage. In some embodiments, the modifications or mutations essentially have no effect on bacterial fitness, and the bacterial fitness is essentially the same as the fitness of the isogenic strain without the modifications or mutations. Prophages can be either identified experimentally or computationally. The experimental approach involves inducing the host bacteria to release phage particles by exposing them to UV light or other DNA-damaging conditions. However, in some cases, the conditions under which a prophage is induced is unknown, and therefore the absence of plaques in a plaque assay does not necessarily prove the absence of a prophage. Additionally, this approach can show only the existence of viable phages, but will not reveal defective prophages. As such, computational identification of prophages from genomic sequence data has become the most preferred route.

In some embodiments, the modifications or mutations essentially have no effect on effector function, and the effector function is essentially the same as the effector function of the isogenic strain without the modifications or mutations. Table H provides a list of non-limiting examples of probiotic bacteria and the number of potential bacteriophages contained in the bacterial genome as determined by Phaster scoring. Table I provides a list of Clostridial strains and potential phage genomes. Phaster is a web server for bioinformatically identifying Phage sequences in organisms (http://phaster.ca/). Phaster scoring is described in detail at phaster.ca and in Zhou, et al. ("PHAST: A Fast Phage Search Tool" Nucl. Acids Res. (2011) 39(suppl 2): W347-W352) and Arndt et al. (Arndt, et al. (2016) PHASTER: a better, faster version of the PHAST phage search tool. Nucleic Acids Res., 2016 May 3). In brief, three methods are applied with different criteria to score for prophage regions (as intact, questionable, or incomplete) within a provided bacterial genome sequence. In the first method, if the number of certain phage organism identified by Phaster is more than or equal to 100% of the total number of CDS of the region, the region is marked with total score 150. If less than 100%, method 2 and 3 is used. In method 2, if the number of certain phage organism identified by Phaster in the bacterial genome sequence provided is more than 50% of the total number of CDS of the region, that phage organism is considered as the major potential phage for that region; the percentage of the total number of that phage organism in this table in the total number of proteins of the region is calculated and then multiplied by 100; the percentage of the length of that phage organism in the length of the region is calculated and then multiplied by 50 (phage head's encapsulation capability is considered). In method 3, if any of the specific phage-related keywords (such as 'capsid', 'head', 'integrase', 'plate', 'tail', 'fiber', 'coat', 'transposase', 'portal', 'terminase', 'protease' or 'lysin') are present, the score is increased by 10 for each keyword found. If the size of the region is greater than 30 Kb, the score is increased by 10. If there are at least 40 proteins in the region, the score is increased by 10. If all of the phage-related proteins and hypothetical proteins constitute more than 70% of the total number of proteins in the region, the score is increased by 10. The total score of method 2 is compared with the total score of method 3, and the bigger one is chosen as the total score of the region. If the region's total score is less than 70, it is marked as incomplete; if between 70 to 90, it is marked as questionable; if greater than 90, it is marked as intact.

TABLE H

| Matched Strains for Common Probiotics | | | |
|---|---|---|---|
| Organism | PHASTER Prophage (Intact) | PHASTER questionable/ incomplete (scores) | ACLAME Prediction |
| *Bacillus coagulans* | | | |
| *Bacillus subtilis* | | | |
| *Bacillus cereus* | | | |
| *Bifidobacterium animalis* | 0 | 0 | |
| *Bifidobacterium bifidum* | 0 | 2 (90, 30) | |
| *Bifidobacterium breve* | 1 | 0 | |
| *Bifidobacterium infantis* | | | |
| *Bifidobacterium longum* | 0 | 1 (70) | |
| *Enterococcus faecium* | | | |
| *Enterococcus durans* | | | |
| *Lactobacillus caucasicus* | | | |
| *Lactobacillus acidophilus* | 0 | 1 (20) | |
| *Lactobacillus brevis* | 1 | 1 (20) | 2 |
| *Lactobacillus casei* | | | 2 |
| *Lactobacillus delbrueckii* | 0 | 0 | |
| *Lactobacillus fermentum* | 1 | 1 (40) | |
| *Lactobacillus gasseri* | 1 | 2 (60, 40) | |
| *Lactobacillus helveticus* | | | |
| *Lactobacillus paracasei* | 2 | 1 (30) | |
| *Lactobacillus plantarum* | 2 | 0 | 3 |
| *Lactobacillus reuteri* | 3 | 4 (70, 60, 40, 30) | 4 |
| *Lactobacillus rhamnosus* | 2 | 3 (70, 60, 40) | |
| *Lactobacillus salivarius* | 2 | 2 (50, 20) | 3 |
| *Lactobacillus thermophilus* | | | |
| *Lactococcus lactis* | 6 | 0 | 5 |
| *Leuconostoc mesenteroides* | | | |
| *Pediococcus acidilactici* | | | |
| *Streptococcus thermophilus* | | | |

TABLE I

| Clostridial Strains | | | |
|---|---|---|---|
| | Intact (phaster score) | Incomplete (phaster score) | Questionable (phaster score) |
| *Clostridium butyricum* 5521 | 1 (110) | 3 (40, 40, 20) | 2 (90, 70) |
| *Clostridium butyricum* E4 str. BoNT E BL5262 | 4 (150, 110, 130, 130) | 2 (50, 10) | 1 (70) |
| *Clostridium tyrobutyricum* UC7086 | | | |
| *Clostridium butyricum* strain KNU-L09 chromosome 1 | 2 | | |
| *Clostridium butyricum* strain CDC_51208 | 2 | | |
| *Clostridium butyricum* strain JKY6D1 chromosome 1 | 2 | | |
| *Clostridium butyricum* strain JKY6D1 chromosome 2 | 1 | | |
| *Clostridium tyrobutyricum* strain KCTC 5387 | 5 | | |
| *Clostridium butyricum* strain TOA chromosome 1 | 2 | | |
| *Clostridium butyricum* strain TOA chromosome 2 | 1 | | |

In any of these embodiments, the bacteria described herein comprise one or more modifications or mutations within an existing prophage or bacteriophage genome. These modifications alter the properties or behavior of the prophage. In some embodiments, the modifications or mutations prevent the prophage from entering or completing the lytic process. In some embodiments, the modifications or mutations prevent the phage from infecting other bacteria of the same or a different type.

In some embodiments, the modifications or mutations alter, e.g., reduce or increase, the fitness of the bacterial host. In some embodiments, the modifications or mutations alter, e.g., reduce or increase, desired effector function, e.g., of a genetically engineered bacterium. In some embodiments, the modifications or mutations do not alter, e.g., reduce or increase, the fitness of the bacterial host. In some embodiments, the modifications or mutations do not alter, e.g., reduce or increase, desired effector function, e.g., of a genetically engineered bacterium.

In some embodiments, the modifications or mutations improve phenylalanine consumption. In some embodiments, phenylalanine consumption remains similar to the levels observed in the isogenic strain comprising the unmodified phage. In some embodiments, the modifications or mutations essentially have no effect on bacterial fitness, and the bacterial fitness is essentially the same as the fitness of the isogenic strain without the modifications or mutations.

In some embodiments, the bacteria comprise at least about 1 to 2, at least about 2 to 3, at least about 3 to 4, at least about 4 to 5, at least about 5 to 6, at least about 6 to 7, at least about 7 to 8, at least about 8 to 9, at least about 9 to 10, at least about 10 to 11, at least about 11 to 12, at least about 12 to 13, at least about 13 to 14, at least about 14 to 15, at least about 15 to 16, at least about 16 to 17, at least about 17 to 18, at least about 18 to 19, at least about 19 to 20, at least about 20 to 21, at least about 21 to 22, at least about 22 to 23, at least about 23 to 24, at least about 24 to 25, at least about 25 to 26, at least about 26 to 27, at least about 27 to 28, at least about 28 to 29, at least about 29 to 30, at least about 30 to 31, at least about 31 to 32, at least about 32 to 33, at least about 33 to 34, at least about 34 to 35, at least about 35 to 36, at least about 36 to 37, at least about 37 to 38, at least about 38 to 39, at least about 39 to 40, at least about 40 to 41, at least about 41 to 42, at least about 42 to 43, at least about 43 to 44, at least about 44 to 45, at least about 45 to 46, at least about 46 to 47, at least about 47 to 48, at least about 48 to 49, at least about 49 to 50, at least about 50 to 51, at least about 51 to 52, at least about 52 to 53, at least about 53 to 54, at least about 54 to 55, at least about 55 to 56, at least about 56 to 57, at least about 57 to 58, at least about 58 to 59, at least about 59 to 60, at least about 60 to 61, at least about 61 to 62, at least about 62 to 63, at least about 63 to 64, at least about 64 to 65, at least about 65 to 66, at least about 66 to 67, at least about 67 to 68, at least about 68 to 69, at least about 69 to 70, at least about 70 to 71, at least about 71 to 72, at least about 72 to 73, at least about 73 to 74, at least about 74 to 75, at least about 75 to 76, at least about 76 to 77, at least about 77 to 78, at least about 78 to 79, at least about 79 to 80, at least about 80 to 81, at least about 81 to 82, at least about 82 to 83, at least about 83 to 84, at least about 84 to 85, at least about 85 to 86, at least about 86 to 87, at least about 87 to 88, at least about 88 to 89, at least about 89 to 90, at least about 90 to 91, at least about 91 to 92, at least about 92 to 93, at least about 93 to 94, at least about 94 to 95, at least about 95 to 96, at least about 96 to 97, at least about 97 to 98, at least about 98 to 99, at least about 99 to 100, or at least about 100 or more modifications or mutations to an existing prophage or bacteriophage genome.

In some embodiments, the modifications or mutations improve effector function, e.g., phenylalanine consumption.

In some embodiments, effector function, e.g., phenylalanine consumption, remains similar to that observed in the isogenic strain comprising the unmodified phage. In some embodiments, the modifications or mutations essentially have no effect on bacterial fitness, and the bacterial fitness is essentially the same as the fitness of the isogenic strain without the modifications or mutations.

In some embodiments, the modifications or mutations reduce entry or completion of prophage lytic process at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold relative to the isogenic strain without the phage modification. In some embodiments, the modifications or mutations completely prevent entry or completion of prophage lytic process.

In some embodiments, the modifications or mutations reduce entry or completion of prophage lytic process by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% relative to the isogenic strain without the phage modification.

In some embodiments, the modifications or mutations prevent the phage from infecting other bacteria of the same or a different type by at least about 1- to 2-fold, at least about 2- to 3-fold, at least about 3- to 4-fold, at least about 4- to 5-fold, at least about 5- to 10-fold, at least about 10- to 100-fold, at least about 10- to 20-fold, at least about 20- to 30-fold, at least about 30- to 40-fold, at least about 40- to 50-fold, at least about 50- to 60-fold, at least about 60- to 70-fold, at least about 70- to 80-fold, at least about 80- to 90-fold, at least about 90- to 100-fold, or at least about 100- to 1000-fold relative to the isogenic strain without the phage modification. In some embodiments, the modifications or mutations completely prevent the phage from infecting other bacteria of the same or a different type. In some embodiments, the modifications or mutations prevent the phage from infecting other bacteria of the same or a different type by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100%.

In some embodiments, the modifications or mutations alters or alters, e.g., reduces or increases, the fitness of the bacterial host by at least about 1- to 2-fold, at least about 2- to 3-fold, at least about 3- to 4-fold, at least about 4- to 5-fold, at least about 5- to 10-fold, at least about 10- to 100-fold, or at least about 100- to 1000-fold relative to the isogenic strain without the phage modification. In some embodiments, the modifications or mutations alters, e.g., reduces or increases, the fitness of the bacterial host by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% relative to the isogenic strain without the phage modification as compared to the isogenic strain without the phage modification.

In some embodiments, the modifications or mutations alter, e.g., reduce or increase, the desired effector function, e.g., of a genetically engineered bacterium by at least about 1- to 2-fold, at least about 2- to 3-fold, at least about 3- to 4-fold, at least about 4- to 5-fold, at least about 5- to 10-fold, at least about 10- to 100-fold, or at least about 100- to 1000-fold. In some embodiments, the modifications or mutations alter, e.g., reduce or increase, the desired effector function, e.g., of a genetically engineered bacterium by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% relative to the isogenic strain without the phage modification.

In some embodiments, the mutations include one or more deletions within the phage genome sequence. As used herein, "deletion" refers to the removal of one or more nucleotides from a polynucleotide sequence. In some embodiments, the mutations include one or more insertions into the phage genome sequence. As used herein, "insertion" refers to the addition of one or more nucleotides to a polynucleotide sequence. In some embodiments, an antibiotic cassette can be inserted into one or more positions within the phage genome sequence. In some embodiments, the mutations include one or more substitutions within the phage genome sequence. As used herein, "substitution" refers to the replacement of one or more nucleotides with the same number of nucleotides within a polynucleotide sequence. In some embodiments, the mutations include one or more inversions within the phage genome sequence. As used herein, "inversion" refers to when a segment comprising 2 or more nucleotides is reversed end to end within a polynucleotide sequence. In some embodiments, the inversion may be governed by a specific flippase. Exemplary circuitry comprising multiple levels of control are exemplified herein and are also described in co-owned pending PCT Application PCT/US2016/039434, the contents of which is herein incorporated by reference in its entirety.

In some embodiments, the modifications within the phage genome are combinations of two or more of insertions, deletions, substitutions, or inversions within one or more phage genome genes.

In any of the embodiments described herein, the modifications may result in one or more frameshift mutations in one or more genes within the phage genome. As used herein, a frameshift mutation (also called a framing error or a reading frame shift) refers to a genetic mutation caused by indels (insertions or deletions) of a number of nucleotides in a DNA sequence that is not divisible by three. The earlier in the sequence the deletion or insertion occurs, the more altered the protein. In any of the embodiments described herein, the modifications may result in one or more missense mutation in one or more genes within the phage genome. As used herein, a missense mutation refers to when the change of a single base pair causes the substitution of a different amino acid in the resulting protein. This amino acid substitution may have no effect, or it may render the protein nonfunctional. In any of the embodiments described herein, the modifications may result in one or more nonsense mutations in one or more genes within the phage genome. As used herein, a nonsense mutation refers to a mutation in which a sense codon that corresponds to one of the twenty amino acids specified by the genetic code is changed to a chain-terminating codon and the polypeptide of interest is thereby truncated.

In some embodiments, the modifications within the phage genome are combinations of two or more frameshift, nonsense or missense mutations within one or more phage genome genes. In some embodiments, the bacteriophage that is modified is located on a bacterial chromosome. In some embodiments, the bacteriophage that is modified is located on a bacterial plasmid. In some embodiments, the plasmid is modified. In some embodiments, the plasmid is removed entirely. In some embodiments, the phage or prophage exists in all isolates of a particular species. In some embodiments, the prophage exists in all isolates of a particular phylum, order, sub order, family, class, subclass genus, species, sub species, or clade.

Mutations

In some embodiments, the one or more mutations comprise at least about 1-500 bp of the phage genome. In some embodiments, the one or more mutations comprise at least about 500-1000 bp of the phage genome. In some embodiments, the one or more mutations comprise at least about 1000-2000 bp of the phage genome. In some embodiments, the one or more mutations comprise at least about 1000-2000 bp of the phage genome. In some embodiments, the one or more mutations comprise at least about 2000-3000 bp of the phage genome. In some embodiments, the one or more mutations comprise at least about 3000-4000 bp of the phage genome. In some embodiments, the one or more mutations comprise at least about 4000-5000 bp of the phage genome. In some embodiments, the one or more mutations comprise at least about 5,000-6,000 bp of the phage genome. In some embodiments, the one or more mutations comprise at least about 6,000-7,000 bp of the phage genome. In some embodiments, the one or more mutations comprise at least about 7,000-8,000 bp of the phage genome. In some embodiments, the one or more mutations comprise at least about 8,000-9,000 bp of the phage genome. In some embodiments, the one or more mutations comprise at least about 9,000-10,000 bp of the phage genome. In some embodiments, the one or more mutations comprise at least about 10,000-15,000 bp of the phage genome. In some embodiments, the one or more mutations comprise at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are mutated. In some embodiments, the mutated nucleotides are interspersed. In some embodiments, the mutated nucleotides are consecutive. In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome is mutated. In some embodiments, at least about 30-40% of the phage genome is mutated. In some embodiments, at least about 40-50% of the phage genome is mutated. In some embodiments, at least about 50-60% of the phage genome is mutated. In some embodiments, at least about 60-70% of the phage genome is mutated. In some embodiments, at least about 70-80% of the phage genome is mutated. In some embodiments, at least about 80-90% of the phage genome is mutated. In some embodiments, at least about 90-100% of the phage genome is mutated.

In some embodiments, at least about 1, 2, 3, 4, 5, 6, 7, 8, 9, 10, 11, 12, 13, 14, 15, 16, 17, 18, 19, or 20 genes are mutated. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are mutated. In some embodiments, 13 genes are completely or partially mutated. In one embodiment, 74 genes are completely or partially mutated.

In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the phage genome are completely or partially mutated.

In some embodiments, the one or more mutations are located at the beginning or 5' end of the phage genome. In some embodiments, the one or more mutations are located at the end or 3' end of the phage genome. In some embodiments, the one or more mutations are located in the middle of the phage genome. In some embodiments, the phage genes are interspersed within the bacterial genome and the mutation are located in one or more of the interspersed positions.

In some embodiments, the region for an optimal mutation, i.e., to achieve a desired effect, can be determined through analysis of homology with other phages in other bacteria. Homologous conserved regions in phages may be suitable for mutation, as these are conserved and may comprise one or more essential genes. In some embodiments, regulatory elements, such as promoters, are mutated. In some embodiments, coding sequences are mutated. In some embodiments, the one or more mutated regions contain one or more genes essential for the lytic cycle.

In some embodiments, the mutations are located within or encompass one or more genes encoding lytic genes. In some embodiments, the mutations are located within or encompass one or more genes encoding one or more proteases or lysins. In some embodiments, the mutations are located within or encompass one or more genes encoding one or more toxins. In some embodiments, the mutations are located within or encompass one or more genes encoding one or more antibiotic resistance related proteins. In some embodiments, the mutations are located within or encompass one or more genes encoding one or phage translation related proteins. In some embodiments, the one or more mutations are located within or encompass one or more genes encoding structural proteins. Such structural genes include genes encoding polypeptides of the head, tail, collar, or coat. In some embodiments, the one or more mutations are located within or encompass one or more genes encoding polypeptides of the head structure. In some embodiments, the one or more mutations are located within or encompass one or more genes encoding polypeptides of the tail structure. In some embodiments, the one or more mutations are located within or encompass one or more genes encoding polypeptides of the collar structure. In some embodiments, the one or more mutations are located within or encompass one or more genes encoding tail proteins. In some embodiments, the one or more mutations are located within or encompass one or more genes encoding polypeptides of the coat structure. In some embodiments, the mutations are located within or encompass one or more genes encoding one or more plate proteins. In some embodiments, the mutations are located within or encompass one or more genes encoding one or more proteins require for assembly of the bacteriophage. In some embodiments, the mutations are located within or encompass one or more genes encoding one or more portal proteins. In some embodiments, the mutations are located within or encompass one or more genes encoding one or more polypeptides involved in recombination. In some embodiments, the mutations are located within or encompass one or more genes encoding one or more integrases. In some embodiments, the mutations are located within or encompass one or more genes encoding one or more invertases. In some embodiments, the mutations are located within or encompass one or more genes encoding one or more transposases. In some embodiments, the mutations are located with within or encompass one or more genes encoding one or more polypeptides involved in replication or translation. In some embodiments, the mutations are located within or encompass one or more genes encoding one or more primases. In some embodiments, the mutations are located within or encompass one or more genes encoding one or more tRNA related proteins. In some embodiments, the mutations are located within or encompass one or more genes encoding one or more polypeptides involved in phage insertion. In some embodiments, the mutations are located within or encompass one or more genes encoding an attachment site. In some embodiments, the mutations are located within or encompass one or more genes encoding one or more polypeptides involved in packaging. In some embodiments, the mutations are located within or encompass one or more genes encoding one or more terminases. In some embodiments, the mutations are located within or encompass one or more genes encoding one or more host genes.

In some embodiments, the mutations are located within or encompass genes encoding one or more polypeptides involved in one or more of cell lysis, phage structure, phage assembly, phage packaging recombination, replication or translation, phage insertion, or are host proteins, and combinations thereof.

In some embodiments, the mutations are located within or encompass genes encoding one or more polypeptides involved in one or more of cell lysis, phage structure, phage assembly, phage packaging recombination, replication or translation, phage insertion, and combinations thereof.

In some embodiments, the mutations are located within or encompass 1 genes encoding polypeptides involved in cell lysis, phage structure, phage assembly, phage packaging recombination, replication or translation, phage insertion, and combinations thereof. In some embodiments, the mutations are located within or encompass 2 genes encoding polypeptides involved in cell lysis, phage structure, phage assembly, phage packaging recombination, replication or translation, phage insertion, and combinations thereof. In some embodiments, the mutations are located within or encompass 3 genes encoding polypeptides involved in cell lysis, phage structure, phage assembly, phage packaging recombination, replication or translation, phage insertion, and combinations thereof. In some embodiments, the mutations are located within or encompass 4 genes encoding polypeptides involved in cell lysis, phage structure, phage assembly, phage packaging recombination, replication or translation, phage insertion, and combinations thereof. In some embodiments, the mutations are located within or encompass 2 genes encoding polypeptides involved in cell lysis, phage structure, phage assembly, phage packaging recombination, replication or translation, phage insertion, and combinations thereof. In some embodiments, the mutations are located within or encompass 5 genes encoding polypeptides involved in cell lysis, phage structure, phage assembly, phage packaging recombination, replication or translation, phage insertion, and combinations thereof. In some embodiments, the mutations are located within or encompass 6 genes encoding polypeptides involved in cell lysis, phage structure, phage assembly, phage packaging recombination, replication or translation, phage insertion, and combinations thereof. In some embodiments, the mutations are located within or encompass 7 genes encoding polypeptides involved in cell lysis, phage structure, phage assembly, phage packaging recombination, replication or translation, phage insertion, and combinations thereof. In some embodiments, the mutations are located within or encompass 8 genes encoding polypeptides involved in cell lysis, phage structure, phage assembly, phage packaging recombination, replication or translation, phage insertion, and combinations thereof. In some embodiments, the mutations are located within or encompass 9 genes encoding polypeptides involved in cell lysis, phage structure, phage assembly, phage packaging recombination, replication or translation, phage insertion, and combinations thereof. In some embodiments, the mutations are located within or encompass 10 genes encoding polypeptides involved in cell lysis, phage structure, phage assembly, phage packaging recombination, replication or translation, phage insertion, and combinations thereof. In some embodiments, the mutations are located within or encompass 11 genes encoding polypeptides involved in cell lysis, phage structure, phage assembly, phage packaging recombination, replication or translation, phage insertion, and combinations thereof. In some embodiments, the mutations are located within or encompass 12 genes encoding polypeptides involved in cell lysis, phage structure, phage assembly, phage packaging recombination, replication or translation, phage insertion, and combinations thereof. In some embodiments, the mutations are located within or encompass 13 genes encoding polypeptides involved in cell lysis, phage structure, phage assembly, phage packaging recombination, replication or translation, phage insertion, and combinations thereof. In some embodiments, the mutations are located within or encompass 14 genes encoding polypeptides involved in cell lysis, phage structure, phage assembly, phage packaging recombination, replication or translation, phage insertion, and combinations thereof. In some embodiments, the mutations are located within or encompass 15 genes encoding polypeptides involved in cell lysis, phage structure, phage assembly, phage packaging recombination, replication or translation, phage insertion, and combinations thereof. In some embodiments, the mutations are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the mutations are located within or encompass one or more host proteins within the phage genome.

Deletions

In some embodiments, the one or more deletions comprise at least about 1-500 bp of the phage genome. In some embodiments, the one or more deletions comprise at least about 500-1000 bp of the phage genome. In some embodiments, the one or more deletions comprise at least about 1000-2000 bp of the phage genome. In some embodiments, the one or more deletions comprise at least about 1000-2000 bp of the phage genome. In some embodiments, the one or more deletions comprise at least about 2000-3000 bp of the phage genome. In some embodiments, the one or more deletions comprise at least about 3000-4000 bp of the phage genome. In some embodiments, the one or more deletions comprise at least about 4000-5000 bp of the phage genome. In some embodiments, the one or more deletions comprise at least about 5,000-6,000 bp of the phage genome. In some embodiments, the one or more deletions comprise at least about 6,000-7,000 bp of the phage genome. In some embodiments, the one or more deletions comprise at least about 7,000-8,000 bp of the phage genome. In some embodiments, the one or more deletions comprise at least about 8,000-9,000 bp of the phage genome. In some embodiments, the one or more deletions comprise at least about 9,000-10,000 bp of the phage genome. In some embodiments, the one or more deletions comprise at least about 10,000-15,000 bp of the phage genome. In some embodiments, the one or more deletions comprise at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than 200,000 bp of the phage genome. In one specific embodiment, 9687 bp of the phage genome are deleted. In some embodiments, the deleted nucleotides are interspersed. In some embodiments, the deleted nucleotides are consecutive.

In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome is deleted. In some embodiments, at least about 30-40% of the phage genome is deleted. In some embodiments, at least about 40-50% of the phage genome is deleted. In some embodiments, at least about 50-60% of the phage genome is deleted. In some embodiments, at least about 60-70% of the phage genome is deleted. In some embodiments, at least about 70-80% of the phage genome is deleted. In some embodiments, at least about 80-90% of the phage genome is deleted. In some embodiments, at least about 90-100% of the phage genome is deleted.

In some embodiments, one or more genes are partially or completely deleted within the phage genome. In some embodiments, one or more genes are completely deleted and one or more genes are partially deleted. In one embodiment, there is one deletion within the phage genome and one or two genes at the ends of the deletion are partially deleted and the rest of the genes are completely deleted. In some embodiments, the deleted genes are adjacent to each other. In some embodiments, the deleted genes are not adjacent to each other.

In some embodiments, at least about 1, 2, 3, 4, 5, 6, 7, 8, 9, 10, 11, 12, 13, 14, 15, 16, 17, 18, 19, or 20 genes are deleted. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are deleted. In some embodiments, 13 genes are completely or partially deleted. In one embodiment, 74 genes are completely or partially deleted. In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the phage genome are completely or partially deleted.

In some embodiments, the one or more deletions are located at the beginning or 5' end of the phage genome. In some embodiments, the one or more deletions are located at the end or 3' end of the phage genome. In some embodiments, the one or more deletions are located in the middle of the phage genome. In some embodiments, the phage genes are interspersed within the bacterial genome and the deletion are located in one or more of the interspersed positions.

In some embodiments, the region for an optimal deletion, i.e., to achieve a desired effect, can be determined through analysis of homology with other phages is other bacteria. Homologous conserved regions in phages may be suitable for deletion, as these are conserved and may comprise one or more essential genes. In some embodiments, regulatory elements, such as promoters, are deleted. In some embodiments, coding sequences are deleted. In some embodiments, the one or more deleted regions contain one or more genes essential for the lytic cycle.

In some embodiments, the deletions are located within or encompass one or more genes encoding lytic genes. In some embodiments, the deletions are located within or encompass one or more genes encoding one or more proteases or lysins. In some embodiments, the deletions are located within or encompass one or more genes encoding one or more toxins. In some embodiments, the deletions are located within or encompass one or more genes encoding one or more antibiotic resistance related proteins. In some embodiments, the deletions are located within or encompass one or more genes encoding one or phage translation related proteins. In some embodiments, the one or more deletions are located within or encompass one or more genes encoding structural proteins. Such structural genes include genes encoding polypeptides of the head, tail, collar, or coat. In some embodiments, the one or more deletions are located within or encompass one or more genes encoding polypeptides of the head structure. In some embodiments, the one or more deletions are located within or encompass one or more genes encoding polypeptides of the tail structure. In some embodiments, the one or more deletions are located within or encompass one or more genes encoding polypeptides of the collar structure. In some embodiments, the one or more deletions are located within or encompass one or more genes encoding polypeptides of the coat structure. In some embodiments, the deletions are located within or encompass one or more genes encoding one or more plate proteins. In some embodiments, the deletions are located within or encompass one or more genes encoding one or more proteins require for assembly of the bacteriophage. In some embodiments, the deletions are located within or encompass one or more genes encoding one or more portal proteins. In some embodiments, the deletions are located within or encompass one or more genes encoding one or more polypeptides involved in recombination. In some embodiments, the deletions are located within or encompass one or more genes encoding one or more integrases. In some embodiments, the deletions are located within or encompass one or more genes encoding one or more invertases. In some embodiments, the deletions are located within or encompass one or more genes encoding one or more transposases. In some embodiments, the deletions are located with within or encompass one or more genes encoding one or more polypeptides involved in replication or translation. In some embodiments, the deletions are located within or encompass one or more genes encoding one or more primases. In some embodiments, the deletions are located within or encompass one or more genes encoding one or more tRNA related proteins. In some embodiments, the deletions are located within or encompass one or more genes encoding one or more polypeptides involved in phage insertion. In some embodiments, the deletions are located within or encompass one or more genes encoding an attachment site. In some embodiments, the deletions are located within or encompass one or more genes encoding one or more polypeptides involved in packaging. In some embodiments, the deletions are located within or encompass one or more genes encoding one or more terminases. In some embodiments, the deletions are located within or encompass one or more genes encoding one or more host genes.

In some embodiments, the deletions are located within or encompass genes encoding one or more polypeptides involved in one or more of cell lysis, phage structure, phage assembly, phage packaging recombination, replication or translation, phage insertion, or are host proteins, and combinations thereof.

In some embodiments, the deletions are located within or encompass genes encoding one or more polypeptides involved in one or more of cell lysis, phage structure, phage assembly, phage packaging recombination, replication or translation, phage insertion, and combinations thereof.

In some embodiments, the deletions are located within or encompass 1 genes encoding polypeptides involved in cell lysis, phage structure, phage assembly, phage packaging recombination, replication or translation, phage insertion, and combinations thereof. In some embodiments, the deletions are located within or encompass 2 genes encoding polypeptides involved in cell lysis, phage structure, phage assembly, phage packaging recombination, replication or translation, phage insertion, and combinations thereof. In some embodiments, the deletions are located within or encompass 3 genes encoding polypeptides involved in cell lysis, phage structure, phage assembly, phage packaging recombination, replication or translation, phage insertion, and combinations thereof. In some embodiments, the deletions are located within or encompass 4 genes encoding polypeptides involved in cell lysis, phage structure, phage assembly, phage packaging recombination, replication or translation, phage insertion, and combinations thereof. In some embodiments, the deletions are located within or encompass 2 genes encoding polypeptides involved in cell lysis, phage structure, phage assembly, phage packaging recombination, replication or translation, phage insertion, and combinations thereof. In some embodiments, the deletions are located within or encompass 5 genes encoding polypeptides involved in cell lysis, phage structure, phage assembly, phage packaging recombination, replication or translation, phage insertion, and combinations thereof. In some embodiments, the deletions are located within or encompass 6 genes encoding polypeptides involved in cell lysis, phage structure, phage assembly, phage packaging recombination, replication or translation, phage insertion, and combinations thereof. In some embodiments, the deletions are located within or encompass 7 genes encoding polypeptides involved in cell lysis, phage structure, phage assembly, phage packaging recombination, replication or translation, phage insertion, and combinations thereof. In some embodiments, the deletions are located within or encompass 8 genes encoding polypeptides involved in cell lysis, phage structure, phage assembly, phage packaging recombination, replication or translation, phage insertion, and combinations thereof. In some embodiments, the deletions are located within or encompass 9 genes encoding polypeptides involved in cell lysis, phage structure, phage assembly, phage packaging recombination, replication or translation, phage insertion, and combinations thereof. In some embodiments, the deletions are located within or encompass 10 genes encoding polypeptides involved in cell lysis, phage structure, phage assembly, phage packaging recombination, replication or translation, phage insertion, and combinations thereof. In some embodiments, the deletions are located within or encompass 11 genes encoding polypeptides involved in cell lysis, phage structure, phage assembly, phage packaging recombination, replication or translation, phage insertion, and combinations thereof. In some embodiments, the deletions are located within or encompass 12 genes encoding polypeptides involved in cell lysis, phage structure, phage assembly, phage packaging recombination, replication or translation, phage insertion, and combinations thereof. In some embodiments, the deletions are located within or encompass 13 genes encoding polypeptides involved in cell lysis, phage structure, phage assembly, phage packaging recombination, replication or translation, phage insertion, and combinations thereof. In some embodiments, the deletions are located within or encompass 14 genes encoding polypeptides involved in cell lysis, phage structure, phage assembly, phage packaging recombination, replication or translation, phage insertion, and combinations thereof. In some embodiments, the deletions are located within or encompass 15 genes encoding polypeptides involved in cell lysis, phage structure, phage assembly, phage packaging recombination, replication or translation, phage insertion, and combinations thereof. In some embodiments, the deletions are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the deletions are located within or encompass one or more host proteins within the phage genome.

Insertions

In some embodiments, the insertion is in a coding region of the phage genome. In some embodiments, the insertion is inserted into a regulatory region of the phage genome. In some embodiments, the insertions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more insertions comprise at least about 1-500 bp in length. In some embodiments, the one or more insertions comprise at least about 500-1000 bp in length. In some embodiments, the one or more insertions comprise at least about 1000-2000 bp in length. In some embodiments, the one or more insertions comprise at least about 1000-2000 bp in length. In some embodiments, the one or more insertions comprise at least about 2000-3000 bp in length. In some embodiments, the one or more insertions comprise at least about 3000-4000 bp in length. In some embodiments, the one or more insertions comprise at least about 4000-5000 bp in length. In some embodiments, the one or more insertions comprise at least about 5,000-6,000 bp in length. In some embodiments, the one or more insertions comprise at least about 6,000-7,000 bp in length. In some embodiments, the one or more insertions comprise at least about 7,000-8,000 bp in length. In some embodiments, the one or more insertions comprise at least about 8,000-9,000 bp in length. In some embodiments, the one or more insertions comprise at least about 9,000-10,000 bp in length. In some embodiments, the one or more insertions comprise at least about 10,000-15,000 bp in length. In some embodiments, the one or more insertions comprise at least about 10,000-15,000 bp in length, at least about 15,000-20,000 bp in length, at least about 20,000-25,000 bp in length, at least about 25,000-30,000 bp in length, at least about 30,000-35,000 bp in length, at least about 35,000-40,000 bp in length, at least about 40,000-45,000 bp in length, at least about 45,000-50,000 bp in length, at least about 50,000-55,000 bp in length, at least about 55,000-60,000 bp in length, at least about 60,000-65,000 bp in length, at least about 65,000-70,000 bp in length, at least about 70,000-75,000 bp in length, at least about 75,000-80,000 bp in length, at least about 80,000-85,000 bp in length, at least about 85,000-90,000 bp in length, at least about 90,000-95,000 bp in length, at least about 95,000-100,000 bp in length, at least about 100,000-110,000 bp in length, at least about 110,000-120,000 bp in length, at least about 120,000-130,000 bp in length, at least about 130,000-140,000 bp in length, at least about 140,000-150,000 bp in length, at least about 150,000-200,000 bp in length, or more than at least about 200,000 bp in length. In one specific embodiment, 9687 bp in length are inserted. In some embodiments, the inserted nucleotides are interspersed. In some embodiments, the inserted nucleotides are consecutive.

In some embodiments, the one or more insertions are located within 1-500 bp of the phage genome. In some embodiments, the one or more insertions are located within at least about 500-1000 bp of the phage genome. In some embodiments, the one or more insertions are located within at least about 1000-2000 bp of the phage genome. In some embodiments, the one or more insertions are located within at least about 1000-2000 bp of the phage genome. In some embodiments, the one or more insertions are located within at least about 2000-3000 bp of the phage genome. In some embodiments, the one or more insertions are located within at least about 3000-4000 bp of the phage genome. In some embodiments, the one or more insertions are located within at least about 4000-5000 bp of the phage genome. In some embodiments, the one or more insertions are located within at least about 5,000-6,000 bp of the phage genome. In some embodiments, the one or more insertions are located within at least about 6,000-7,000 bp of the phage genome. In some embodiments, the one or more insertions are located within at least about 7,000-8,000 bp of the phage genome. In some embodiments, the one or more insertions are located within at least about 8,000-9,000 bp of the phage genome. In some embodiments, the one or more insertions are located within at least about 9,000-10,000 bp of the phage genome. In some embodiments, the one or more insertions are located within at least about 10,000-15,000 bp of the phage genome. In some embodiments, the one or more insertions are located within at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are inserted. In some embodiments, the inserted nucleotides are interspersed. In some embodiments, the inserted nucleotides are consecutive.

In some embodiments, the insertions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome. In some embodiments, at least about 30-40% of the phage genome is inserted. In some embodiments, the insertions are located within at least about 40-50% of the phage genome. In some embodiments, the insertions are located within at least about 50-60% of the phage genome. In some embodiments, the insertions are located within at least about 60-70% of the phage genome. In some embodiments, the insertions are located within at least about 70-80% of the phage genome. In some embodiments, the insertions are located within at least about 80-90% of the phage genome. In some embodiments, the insertions are located within at least about 90-100% of the phage genome.

In some embodiments, at least about 1, 2, 3, 4, 5, 6, 7, 8, 9, 10, 11, 12, 13, 14, 15, 16, 17, 18, 19, or 20 genes comprise insertions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise insertions. In some embodiments, 13 genes comprise insertions. In one embodiment, 74 genes comprise insertions.

In some embodiments, the one or more insertions are located at the beginning or 5' end of the phage genome. In some embodiments, the one or more insertions are located at the end or 3' end of the phage genome. In some embodiments, the one or more insertions are located in the middle of the phage genome. In some embodiments, the phage genes are interspersed within the bacterial genome and the insertion are located in one or more of the interspersed positions.

In some embodiments, the region for an optimal insertion, i.e., to achieve a desired effect, can be determined through analysis of homology with other phages is other bacteria. Homologous conserved regions in phages may be suitable for insertion, as these are conserved and may comprise one or more essential genes. In some embodiments, regulatory elements, such as promoters, are inserted. In some embodiments, coding sequences are inserted. In some embodiments, the one or more inserted regions contain one or more genes essential for the lytic cycle.

In some embodiments, the insertions are located within one or more genes encoding lytic genes. In some embodiments, the insertions are located within one or more genes encoding one or more proteases or lysins. In some embodiments, the insertions are located within one or more genes encoding one or more toxins. In some embodiments, the insertions are located within one or more genes encoding one or more antibiotic resistance related proteins. In some embodiments, the insertions are located within one or more genes encoding one or phage translation related proteins. In some embodiments, the one or more insertions are located within one or more genes encoding structural proteins. Such structural genes include genes encoding polypeptides of the head, tail, collar, or coat. In some embodiments, the one or more insertions are located within one or more genes encoding polypeptides of the head structure. In some embodiments, the one or more insertions are located within one or more genes encoding polypeptides of the tail structure. In some embodiments, the one or more insertions are located within one or more genes encoding polypeptides of the collar structure. In some embodiments, the one or more insertions are located within one or more genes encoding polypeptides of the coat structure. In some embodiments, the insertions are located within one or more genes encoding one or more plate proteins. In some embodiments, the insertions are located within one or more genes encoding one or more proteins require for assembly of the bacteriophage. In some embodiments, the insertions are located within one or more genes encoding one or more portal proteins. In some embodiments, the insertions are located within one or more genes encoding one or more polypeptides involved in recombination. In some embodiments, the insertions are located within one or more genes encoding one or more integrases. In some embodiments, the insertions are located within one or more genes encoding one or more invertases. In some embodiments, the insertions are located within one or more genes encoding one or more transposases. In some embodiments, the insertions are located with within one or more genes encoding one or more polypeptides involved in replication or translation. In some embodiments, the insertions are located within one or more genes encoding one or more primases. In some embodiments, the insertions are located within one or more genes encoding one or more tRNA related proteins. In some embodiments, the insertions are located within one or more genes encoding one or more polypeptides involved in phage insertion. In some embodiments, the insertions are located within one or more genes encoding an attachment site. In some embodiments, the insertions are located within one or more genes encoding one or more polypeptides involved in packaging. In some embodiments, the insertions are located within one or more genes encoding one or more terminases. In some embodiments, the insertions are located within one or more genes encoding one or more host genes.

In some embodiments, the insertions are located within genes encoding one or more polypeptides involved in one or more of cell lysis, phage structure, phage assembly, phage packaging recombination, replication or translation, phage insertion, or are host proteins, and combinations thereof.

In some embodiments, the insertions are located within genes encoding one or more polypeptides involved in one or more of cell lysis, phage structure, phage assembly, phage packaging recombination, replication or translation, phage insertion, and combinations thereof.

In some embodiments, the insertions are located within 1 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 3 genes encoding polypeptides involved in cell lysis, phage structure, phage assembly, phage packaging recombination, replication or translation, phage insertion, and combinations thereof. In some embodiments, the insertions are located within 4 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 5 genes encoding polypeptides involved in cell lysis, phage structure, phage assembly, phage packaging recombination, replication or translation, phage insertion, and combinations thereof. In some embodiments, the insertions are located within 6 genes encoding polypeptides involved in cell lysis, phage structure, phage assembly, phage packaging recombination, replication or translation, phage insertion, and combinations thereof. In some embodiments, the insertions are located within 7 genes encoding polypeptides involved in cell lysis, phage structure, phage assembly, phage packaging recombination, replication or translation, phage insertion, and combinations thereof. In some embodiments, the insertions are located within 8 genes encoding polypeptides involved in cell lysis, phage structure, phage assembly, phage packaging recombination, replication or translation, phage insertion, and combinations thereof. In some embodiments, the insertions are located within 9 genes encoding polypeptides involved in cell lysis, phage structure, phage assembly, phage packaging recombination, replication or translation, phage insertion, and combinations thereof. In some embodiments, the insertions are located within 10 genes encoding polypeptides involved in cell lysis, phage structure, phage assembly, phage packaging recombination, replication or translation, phage insertion, and combinations thereof. In some embodiments, the insertions are located within 11 genes encoding polypeptides involved in cell lysis, phage structure, phage assembly, phage packaging recombination, replication or translation, phage insertion, and combinations thereof. In some embodiments, the insertions are located within 12 genes encoding polypeptides involved in cell lysis, phage structure, phage assembly, phage packaging recombination, replication or translation, phage insertion, and combinations thereof. In some embodiments, the insertions are located within 13 genes encoding polypeptides involved in cell lysis, phage structure, phage assembly, phage packaging recombination, replication or translation, phage insertion, and combinations thereof. In some embodiments, the insertions are located within 14 genes encoding polypeptides involved in cell lysis, phage structure, phage assembly, phage packaging recombination, replication or translation, phage insertion, and combinations thereof. In some embodiments, the insertions are located within 15 genes encoding polypeptides involved in cell lysis, phage structure, phage assembly, phage packaging recombination, replication or translation, phage insertion, and combinations thereof. In some embodiments, the insertions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the insertions are located within one or more host proteins within the phage genome.

Inversions

In some embodiments, the inversion is in a coding region of the phage genome. In some embodiments, the inversion is inverted into a regulatory region of the phage genome. In some embodiments, the inversions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more inversions comprise at least about 1-500 bp. In some embodiments, the one or more inversions comprise at least about 500-1000 bp. In some embodiments, the one or more inversions comprise at least about 1000-2000 bp. In some embodiments, the one or more inversions comprise at least about 1000-2000 bp. In some embodiments, the one or more inversions comprise at least about 2000-3000 bp. In some embodiments, the one or more inversions comprise at least about 3000-4000 bp. In some embodiments, the one or more inversions comprise at least about 4000-5000 bp. In some embodiments, the one or more inversions comprise at least about 5,000-6,000 bp. In some embodiments, the one or more inversions comprise at least about 6,000-7,000 bp. In some embodiments, the one or more inversions comprise at least about 7,000-8,000 bp. In some embodiments, the one or more inversions comprise at least about 8,000-9,000 bp. In some embodiments, the one or more inversions comprise at least about 9,000-10,000 bp. In some embodiments, the one or more inversions comprise at least about 10,000-15,000 bp. In some embodiments, the one or more inversions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, at least about 55,000-60,000 bp, at least about 60,000-65,000 bp, at least about 65,000-70,000 bp, at least about 70,000-75,000 bp, at least about 75,000-80,000 bp, at least about 80,000-85,000 bp, at least about 85,000-90,000 bp, at least about 90,000-95,000 bp, at least about 95,000-100,000 bp, at least about 100,000-110,000 bp, at least about 110,000-120,000 bp, at least about 120,000-130,000 bp, at least about 130,000-140,000 bp, at least about 140,000-150,000 bp, at least about 150,000-200,000 bp, or more than at least about 200,000 bp. In one specific embodiment, 9687 bp are inverted. In some embodiments, the inverted nucleotides are interspersed. In some embodiments, the inverted nucleotides are consecutive.

In some embodiments, the one or more inversions are located within at least about 1-500 bp of the phage genome. In some embodiments, the one or more inversions are located within at least about 500-1000 bp of the phage genome. In some embodiments, the one or more inversions are located within at least about 1000-2000 bp of the phage genome. In some embodiments, the one or more inversions are located within at least about 1000-2000 bp of the phage genome. In some embodiments, the one or more inversions are located within at least about 2000-3000 bp of the phage genome. In some embodiments, the one or more inversions are located within at least about 3000-4000 bp of the phage genome. In some embodiments, the one or more inversions are located within at least about 4000-5000 bp of the phage genome. In some embodiments, the one or more inversions are located within at least about 5,000-6,000 bp of the phage genome. In some embodiments, the one or more inversions are located within at least about 6,000-7,000 bp of the phage genome. In some embodiments, the one or more inversions are located within at least about 7,000-8,000 bp of the phage genome. In some embodiments, the one or more inversions are located within at least about 8,000-9,000 bp of the phage genome. In some embodiments, the one or more inversions are located within at least about 9,000-10,000 bp of the phage genome. In some embodiments, the one or more inversions are located within at least about 10,000-15,000 bp of the phage genome. In some embodiments, the one or more inversions are located within at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, at least about 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are inverted. In some embodiments, the inverted nucleotides are interspersed. In some embodiments, the inverted nucleotides are consecutive.

In some embodiments, the inversions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome. In some embodiments, at least about 30-40% of the phage genome is inverted. In some embodiments, the inversions are located within at least about 40-50% of the phage genome. In some embodiments, the inversions are located within at least about 50-60% of the phage genome. In some embodiments, the inversions are located within at least about 60-70% of the phage genome. In some embodiments, the inversions are located within at least about 70-80% of the phage genome. In some embodiments, the inversions are located within at least about 80-90% of the phage genome. In some embodiments, the inversions are located within at least about 90-100% of the phage genome.

In some embodiments, at least about 1, 2, 3, 4, 5, 6, 7, 8, 9, 10, 11, 12, 13, 14, 15, 16, 17, 18, 19, or 20 genes comprise inversions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise inversions. In some embodiments, 13 genes comprise inversions. In one embodiment, 74 genes comprise inversions.

In some embodiments, the one or more inversions are located at the beginning or 5' end of the phage genome. In some embodiments, the one or more inversions are located at the end or 3' end of the phage genome. In some embodiments, the one or more inversions are located in the middle of the phage genome. In some embodiments, the phage genes are interspersed within the bacterial genome and the inversion are located in one or more of the interspersed positions.

In some embodiments, the region for an optimal inversion, i.e., to achieve a desired effect, can be determined through analysis of homology with other phages is other bacteria. Homologous conserved regions in phages may be suitable for inversion, as these are conserved and may comprise one or more essential genes. In some embodiments, regulatory elements, such as promoters, are inverted. In some embodiments, coding sequences are inverted. In some embodiments, the one or more inverted regions contain one or more genes essential for the lytic cycle.

In some embodiments, the inversions are located within one or more genes encoding lytic genes. In some embodiments, the inversions are located within one or more genes encoding one or more proteases or lysins. In some embodiments, the inversions are located within one or more genes encoding one or more toxins. In some embodiments, the inversions are located within one or more genes encoding one or more antibiotic resistance related proteins. In some embodiments, the inversions are located within one or more genes encoding one or phage translation related proteins. In some embodiments, the one or more inversions are located within one or more genes encoding structural proteins. Such structural genes include genes encoding polypeptides of the head, tail, collar, or coat. In some embodiments, the inversions are located within one or more genes encoding one or more plate proteins. In some embodiments, the inversions are located within one or more genes encoding one or more proteins require for assembly of the bacteriophage. In some embodiments, the inversions are located within one or more genes encoding one or more portal proteins. In some embodiments, the inversions are located within one or more genes encoding one or more polypeptides involved in recombination. In some embodiments, the inversions are located within one or more genes encoding one or more integrases. In some embodiments, the inversions are located within one or more genes encoding one or more invertases. In some embodiments, the inversions are located within one or more genes encoding one or more transposases. In some embodiments, the inversions are located with within one or more genes encoding one or more polypeptides involved in replication or translation. In some embodiments, the inversions are located within one or more genes encoding one or more primases. In some embodiments, the inversions are located within one or more genes encoding one or more tRNA related proteins. In some embodiments, the inversions are located within one or more genes encoding one or more polypeptides involved in phage inversion. In some embodiments, the inversions are located within one or more genes encoding an attachment site. In some embodiments, the inversions are located within one or more genes encoding one or more polypeptides involved in packaging. In some embodiments, the inversions are located within one or more genes encoding one or more terminases. In some embodiments, the inversions are located within one or more genes encoding one or more host genes.

In some embodiments, the inversions are located within genes encoding one or more polypeptides involved in one or more of cell lysis, phage structure, phage assembly, phage packaging recombination, replication or translation, phage inversion, or are host proteins, and combinations thereof.

In some embodiments, the inversions are located within genes encoding one or more polypeptides involved in one or more of cell lysis, phage structure, phage assembly, phage packaging recombination, replication or translation, phage inversion, and combinations thereof.

In some embodiments, the inversions are located within 1 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 3 genes encoding polypeptides involved in cell lysis, phage structure, phage assembly, phage packaging recombination, replication or translation, phage inversion, and combinations thereof. In some embodiments, the inversions are located within 4 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 5 genes encoding polypeptides involved in cell lysis, phage structure, phage assembly, phage packaging recombination, replication or translation, phage inversion, and combinations thereof. In some embodiments, the inversions are located within 6 genes encoding polypeptides involved in cell lysis, phage structure, phage assembly, phage packaging recombination, replication or translation, phage inversion, and combinations thereof. In some embodiments, the inversions are located within 7 genes encoding polypeptides involved in cell lysis, phage structure, phage assembly, phage packaging recombination, replication or translation, phage inversion, and combinations thereof. In some embodiments, the inversions are located within 8 genes encoding polypeptides involved in cell lysis, phage structure, phage assembly, phage packaging recombination, replication or translation, phage inversion, and combinations thereof. In some embodiments, the inversions are located within 9 genes encoding polypeptides involved in cell lysis, phage structure, phage assembly, phage packaging recombination, replication or translation, phage inversion, and combinations thereof. In some embodiments, the inversions are located within 10 genes encoding polypeptides involved in cell lysis, phage structure, phage assembly, phage packaging recombination, replication or translation, phage inversion, and combinations thereof. In some embodiments, the inversions are located within 11 genes encoding polypeptides involved in cell lysis, phage structure, phage assembly, phage packaging recombination, replication or translation, phage inversion, and combinations thereof. In some embodiments, the inversions are located within 12 genes encoding polypeptides involved in cell lysis, phage structure, phage assembly, phage packaging recombination, replication or translation, phage inversion, and combinations thereof. In some embodiments, the inversions are located within 13 genes encoding polypeptides involved in cell lysis, phage structure, phage assembly, phage packaging recombination, replication or translation, phage inversion, and combinations thereof. In some embodiments, the inversions are located within 14 genes encoding polypeptides involved in cell lysis, phage structure, phage assembly, phage packaging recombination, replication or translation, phage inversion, and combinations thereof. In some embodiments, the inversions are located within 15 genes encoding polypeptides involved in cell lysis, phage structure, phage assembly, phage packaging recombination, replication or translation, phage inversion, and combinations thereof. In some embodiments, the inversions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage inversion, and combinations thereof. In some embodiments, the inversions are located within one or more host proteins within the phage genome.

Substitutions

In some embodiments, the substitution is in a coding region of the phage genome. In some embodiments, the substitution is substituted into a regulatory region of the phage genome. In some embodiments, the substitutions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more substitutions comprise at least about 1-500 bp. In some embodiments, the one or more substitutions comprise at least about 500-1000 bp. In some embodiments, the one or more substitutions comprise at least about 1000-2000 bp. In some embodiments, the one or more substitutions comprise at least about 1000-2000 bp. In some embodiments, the one or more substitutions comprise at least about 2000-3000 bp. In some embodiments, the one or more substitutions comprise at least about 3000-4000 bp. In some embodiments, the one or more substitutions comprise at least about 4000-5000 bp. In some embodiments, the one or more substitutions comprise at least about 5,000-6,000 bp. In some embodiments, the one or more substitutions comprise at least about 6,000-7,000 bp. In some embodiments, the one or more substitutions comprise at least about 7,000-8,000 bp. In some embodiments, the one or more substitutions comprise at least about 8,000-9,000 bp. In some embodiments, the one or more substitutions comprise at least about 9,000-10,000 bp. In some embodiments, the one or more substitutions comprise at least about 10,000-15,000 bp. In some embodiments, the one or more substitutions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, at least about 55,000-60,000 bp, at least about 60,000-65,000 bp, at least about 65,000-70,000 bp, at least about 70,000-75,000 bp, at least about 75,000-80,000 bp, at least about 80,000-85,000 bp, at least about 85,000-90,000 bp, at least about 90,000-95,000 bp, at least about 95,000-100,000 bp, at least about 100,000-110,000 bp, at least about 110,000-120,000 bp, at least about 120,000-130,000 bp, at least about 130,000-140,000 bp, at least about 140,000-150,000 bp, at least about 150,000-200,000 bp, or more than at least about 200,000 bp. In one specific embodiment, 9687 bp are substituted. In some embodiments, the substituted nucleotides are interspersed. In some embodiments, the substituted nucleotides are consecutive.

In some embodiments, the one or more substitutions are located within 1-500 bp of the phage genome. In some embodiments, the one or more substitutions are located within at least about 500-1000 bp of the phage genome. In some embodiments, the one or more substitutions are located within at least about 1000-2000 bp of the phage genome. In some embodiments, the one or more substitutions are located within at least about 1000-2000 bp of the phage genome. In some embodiments, the one or more substitutions are located within at least about 2000-3000 bp of the phage genome. In some embodiments, the one or more substitutions are located within at least about 3000-4000 bp of the phage genome. In some embodiments, the one or more substitutions are located within at least about 4000-5000 bp of the phage genome. In some embodiments, the one or more substitutions are located within at least about 5,000-6,000 bp of the phage genome. In some embodiments, the one or more substitutions are located within at least about 6,000-7,000 bp of the phage genome. In some embodiments, the one or more substitutions are located within at least about 7,000-8,000 bp of the phage genome. In some embodiments, the one or more substitutions are located within at least about 8,000-9,000 bp of the phage genome. In some embodiments, the one or more substitutions are located within at least about 9,000-10,000 bp of the phage genome. In some embodiments, the one or more substitutions are located within at least about 10,000-15,000 bp of the phage genome. In some embodiments, the one or more substitutions are located within at least about 10,000-15,000 bp of the phage genome, at least about 15,000-20,000 bp of the phage genome, at least about 20,000-25,000 bp of the phage genome, at least about 25,000-30,000 bp of the phage genome, at least about 30,000-35,000 bp of the phage genome, at least about 35,000-40,000 bp of the phage genome, at least about 40,000-45,000 bp of the phage genome, at least about 45,000-50,000 bp of the phage genome, at least about 50,000-55,000 bp of the phage genome, at least about 55,000-60,000 bp of the phage genome, at least about 60,000-65,000 bp of the phage genome, at least about 65,000-70,000 bp of the phage genome, at least about 70,000-75,000 bp of the phage genome, at least about 75,000-80,000 bp of the phage genome, 80,000-85,000 bp of the phage genome, at least about 85,000-90,000 bp of the phage genome, at least about 90,000-95,000 bp of the phage genome, at least about 95,000-100,000 bp of the phage genome, at least about 100,000-110,000 bp of the phage genome, at least about 110,000-120,000 bp of the phage genome, at least about 120,000-130,000 bp of the phage genome, at least about 130,000-140,000 bp of the phage genome, at least about 140,000-150,000 bp of the phage genome, at least about 150,000-200,000 bp of the phage genome, or more than at least about 200,000 bp of the phage genome. In one specific embodiment, 9687 bp of the phage genome are substituted. In some embodiments, the substituted nucleotides are interspersed. In some embodiments, the substituted nucleotides are consecutive.

In some embodiments, the substitutions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the phage genome. In some embodiments, at least about 30-40% of the phage genome is substituted. In some embodiments, the substitutions are located within at least about 40-50% of the phage genome. In some embodiments, the substitutions are located within at least about 50-60% of the phage genome. In some embodiments, the substitutions are located within at least about 60-70% of the phage genome. In some embodiments, the substitutions are located within at least about 70-80% of the phage genome. In some embodiments, the substitutions are located within at least about 80-90% of the phage genome. In some embodiments, the substitutions are located within at least about 90-100% of the phage genome.

In some embodiments, at least about 1, 2, 3, 4, 5, 6, 7, 8, 9, 10, 11, 12, 13, 14, 15, 16, 17, 18, 19, or 20 genes comprise substitutions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise substitutions. In some embodiments, 13 genes comprise substitutions. In one embodiment, 74 genes comprise substitutions.

In some embodiments, the one or more substitutions are located at the beginning or 5' end of the phage genome. In some embodiments, the one or more substitutions are located at the end or 3' end of the phage genome. In some embodiments, the one or more substitutions are located in the middle of the phage genome. In some embodiments, the phage genes are interspersed within the bacterial genome and the substitution are located in one or more of the interspersed positions.

In some embodiments, the region for an optimal substitution, i.e., to achieve a desired effect, can be determined through analysis of homology with other phages is other bacteria. Homologous conserved regions in phages may be suitable for substitution, as these are conserved and may comprise one or more essential genes. In some embodiments, regulatory elements, such as promoters, are substituted. In some embodiments, coding sequences are substituted. In some embodiments, the one or more substituted regions contain one or more genes essential for the lytic cycle.

In some embodiments, the substitutions are located within one or more genes encoding lytic genes. In some embodiments, the substitutions are located within one or more genes encoding one or more proteases or lysins. In some embodiments, the substitutions are located within one or more genes encoding one or more toxins. In some embodiments, the substitutions are located within one or more genes encoding one or more antibiotic resistance related proteins. In some embodiments, the substitutions are located within one or more genes encoding one or phage translation related proteins. In some embodiments, the one or more substitutions are located within one or more genes encoding structural proteins. Such structural genes include genes encoding polypeptides of the head, tail, collar, or coat. In some embodiments, the substitutions are located within one or more genes encoding one or more plate proteins. In some embodiments, the substitutions are located within one or more genes encoding one or more proteins require for assembly of the bacteriophage. In some embodiments, the substitutions are located within one or more genes encoding one or more portal proteins. In some embodiments, the substitutions are located within one or more genes encoding one or more polypeptides involved in recombination. In some embodiments, the substitutions are located within one or more genes encoding one or more integrases. In some embodiments, the substitutions are located within one or more genes encoding one or more invertases. In some embodiments, the substitutions are located within one or more genes encoding one or more transposases. In some embodiments, the substitutions are located with within one or more genes encoding one or more polypeptides involved in replication or translation. In some embodiments, the substitutions are located within one or more genes encoding one or more primases. In some embodiments, the substitutions are located within one or more genes encoding one or more tRNA related proteins. In some embodiments, the substitutions are located within one or more genes encoding one or more polypeptides involved in phage substitution. In some embodiments, the substitutions are located within one or more genes encoding an attachment site. In some embodiments, the substitutions are located within one or more genes encoding one or more polypeptides involved in packaging. In some embodiments, the substitutions are located within one or more genes encoding one or more terminases. In some embodiments, the substitutions are located within one or more genes encoding one or more host genes.

In some embodiments, the substitutions are located within genes encoding one or more polypeptides involved in one or more of cell lysis, phage structure, phage assembly, phage packaging recombination, replication or translation, phage substitution, or are host proteins, and combinations thereof.

In some embodiments, the substitutions are located within genes encoding one or more polypeptides involved in one or more of cell lysis, phage structure, phage assembly, phage packaging recombination, replication or translation, phage substitution, and combinations thereof.

In some embodiments, the substitutions are located within 1 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 3 genes encoding polypeptides involved in cell lysis, phage structure, phage assembly, phage packaging recombination, replication or translation, phage substitution, and combinations thereof. In some embodiments, the substitutions are located within 4 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 5 genes encoding polypeptides involved in cell lysis, phage structure, phage assembly, phage packaging recombination, replication or translation, phage substitution, and combinations thereof. In some embodiments, the substitutions are located within 6 genes encoding polypeptides involved in cell lysis, phage structure, phage assembly, phage packaging recombination, replication or translation, phage substitution, and combinations thereof. In some embodiments, the substitutions are located within 7 genes encoding polypeptides involved in cell lysis, phage structure, phage assembly, phage packaging recombination, replication or translation, phage substitution, and combinations thereof. In some embodiments, the substitutions are located within 8 genes encoding polypeptides involved in cell lysis, phage structure, phage assembly, phage packaging recombination, replication or translation, phage substitution, and combinations thereof. In some embodiments, the substitutions are located within 9 genes encoding polypeptides involved in cell lysis, phage structure, phage assembly, phage packaging recombination, replication or translation, phage substitution, and combinations thereof. In some embodiments, the substitutions are located within 10 genes encoding polypeptides involved in cell lysis, phage structure, phage assembly, phage packaging recombination, replication or translation, phage substitution, and combinations thereof. In some embodiments, the substitutions are located within 11 genes encoding polypeptides involved in cell lysis, phage structure, phage assembly, phage packaging recombination, replication or translation, phage substitution, and combinations thereof. In some embodiments, the substitutions are located within 12 genes encoding polypeptides involved in cell lysis, phage structure, phage assembly, phage packaging recombination, replication or translation, phage substitution, and combinations thereof. In some embodiments, the substitutions are located within 13 genes encoding polypeptides involved in cell lysis, phage structure, phage assembly, phage packaging recombination, replication or translation, phage substitution, and combinations thereof. In some embodiments, the substitutions are located within 14 genes encoding polypeptides involved in cell lysis, phage structure, phage assembly, phage packaging recombination, replication or translation, phage substitution, and combinations thereof. In some embodiments, the substitutions are located within 15 genes encoding polypeptides involved in cell lysis, phage structure, phage assembly, phage packaging recombination, replication or translation, phage substitution, and combinations thereof. In some embodiments, the substitutions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage substitution, and combinations thereof. In some embodiments, the substitutions are located within one or more host proteins within the phage genome.

Phage in *E. coli* Nissle

Figure 2:
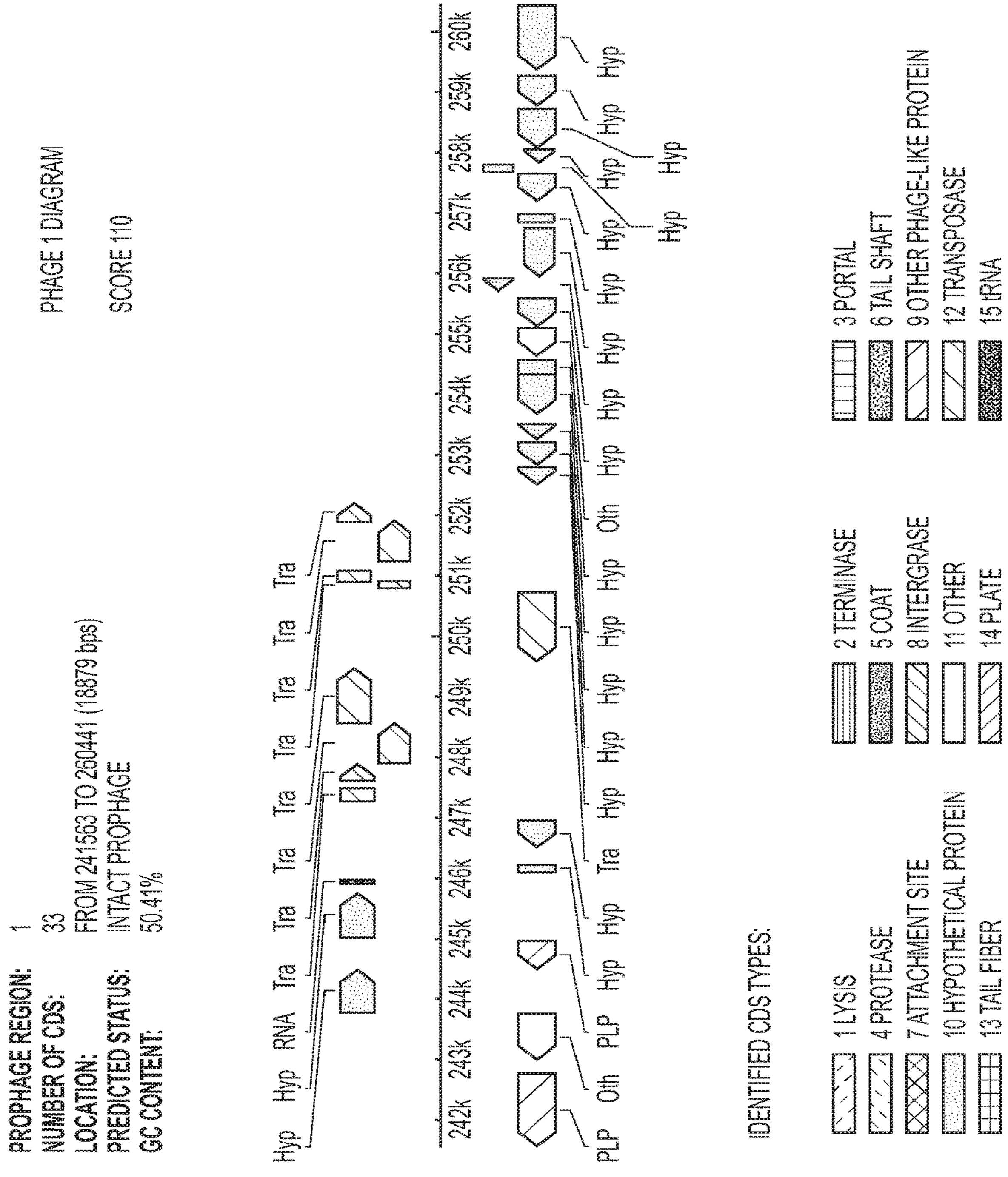
FIG. 2 depicts a schematic showing 1 of 3 high-scoring phage in Nissle using the Phast tool, referred to herein as "Phage 1", and which contains all major components of a phage. Putative genes are labeled Hyp=Hypothetical, PLP=other phage like protein, Oth=Other, RNA=tRNA, TRA=transposase.
Figure 3:
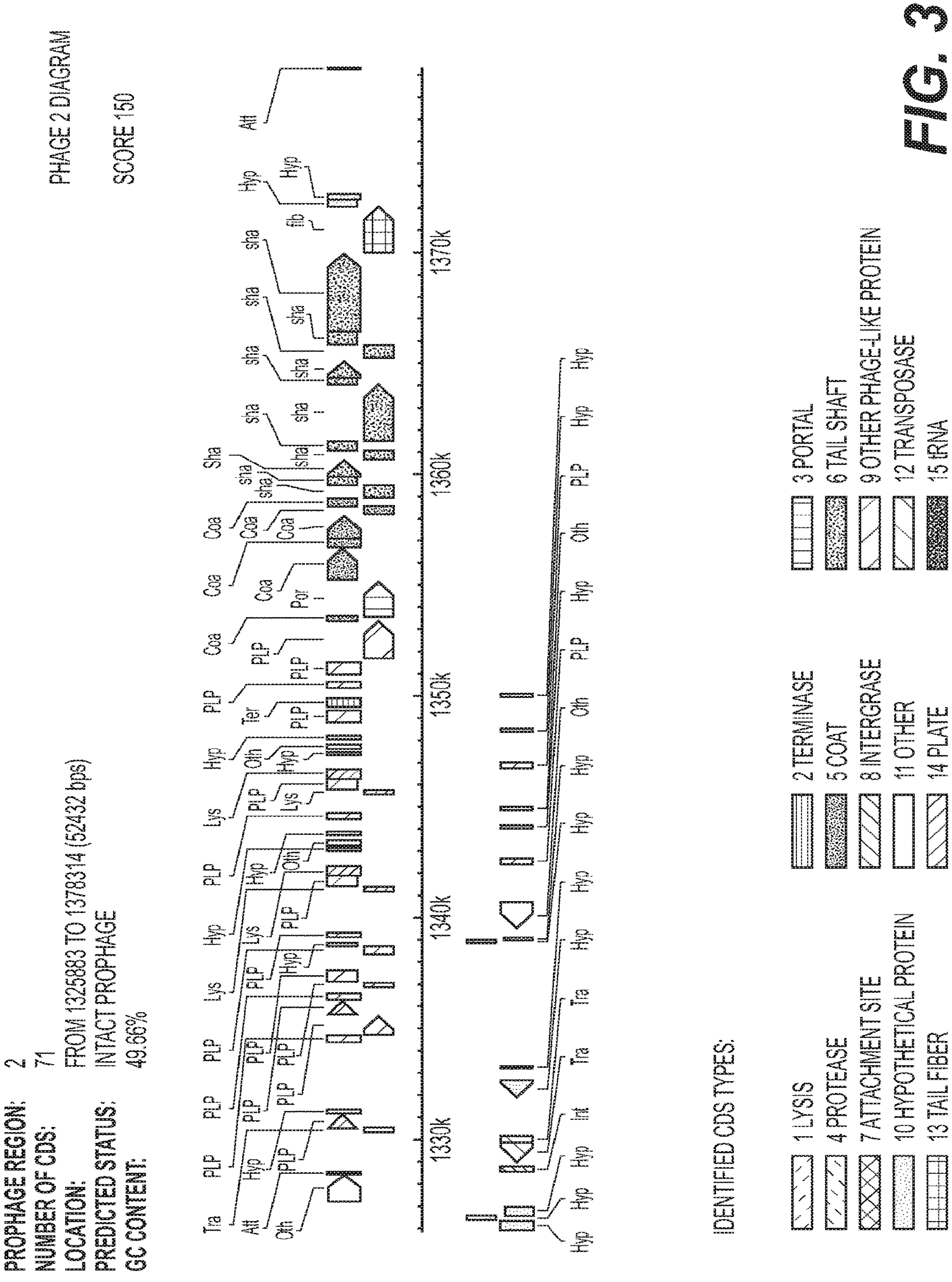
FIG. 3 depicts a schematic showing 1 of 3 high-scoring phage in Nissle using the Phast tool, referred to herein as "Phage 2", and which contains all major components of a phage. Putative genes are labeled Hyp=Hypothetical, PLP=other phage like protein, Oth=Other, RNA=tRNA, TRA=transposase, Lys=Lysis, Ter=Terminase, Coa=Coat, Sha=Tail shaft, Fib=Tail fiber.
Figure 4:
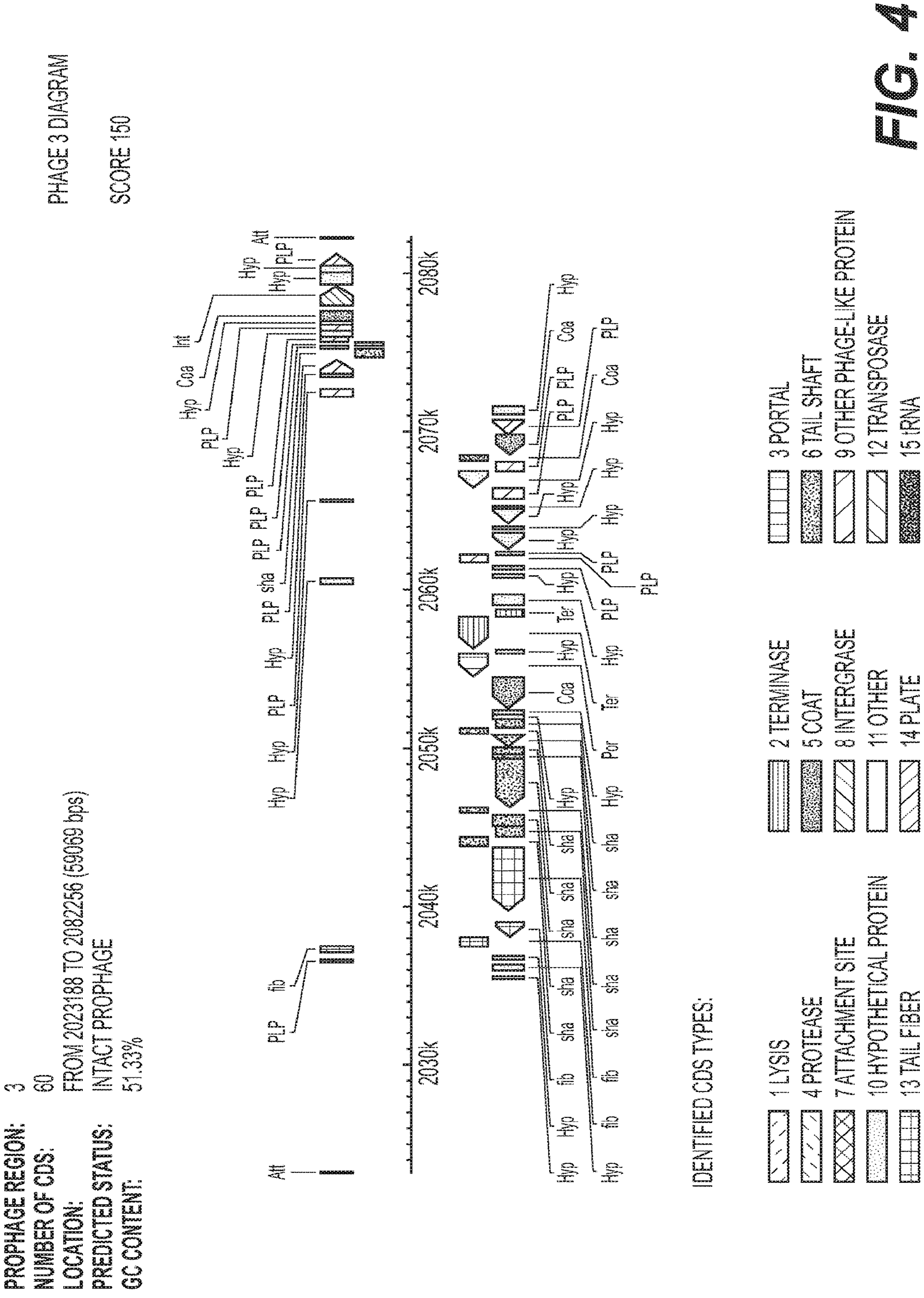
FIG. 4 depicts a schematic showing 1 of 3 high-scoring phage in Nissle using the Phast tool, referred to herein as "Phage 3", and which contains all major components of a phage. Putative genes are labeled Hyp=Hypothetical, PLP=other phage like protein, Oth=Other, RNA=tRNA, TRA=transposase, Lys=Lysis, Ter=Terminase, Coa=Coat, Sha=Tail shaft, Fib=Tail fiber.
Figure 5A:
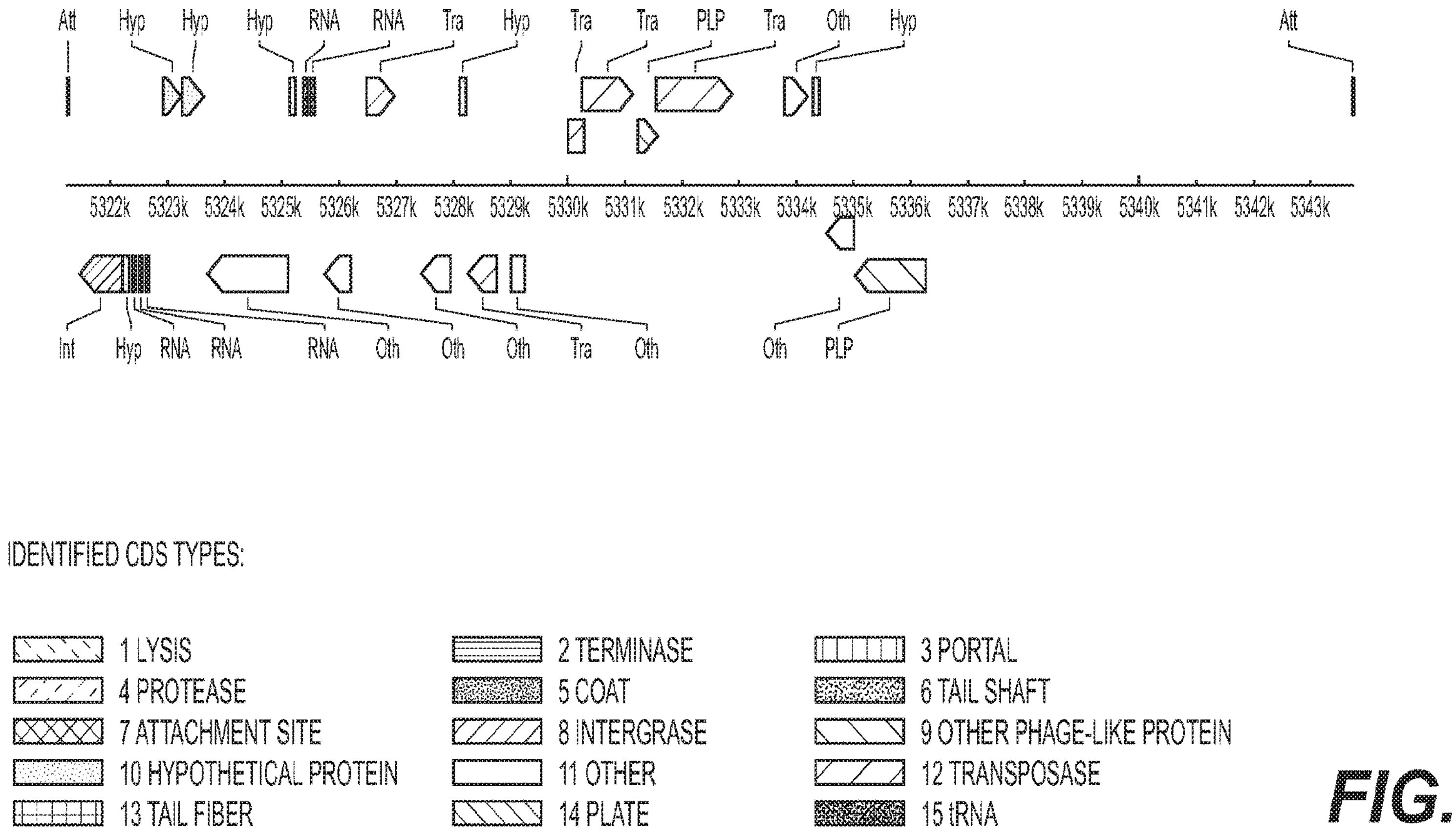
FIG. 5A depicts the first of 2 lower scoring "incomplete" or "questionable" phage identified using the Phast tool. Putative genes are labeled Hyp=Hypothetical, PLP=other phage like protein, Oth=Other, RNA=tRNA, TRA=transposase, int=Integrase, Att=attachment site.
Figure 5B:
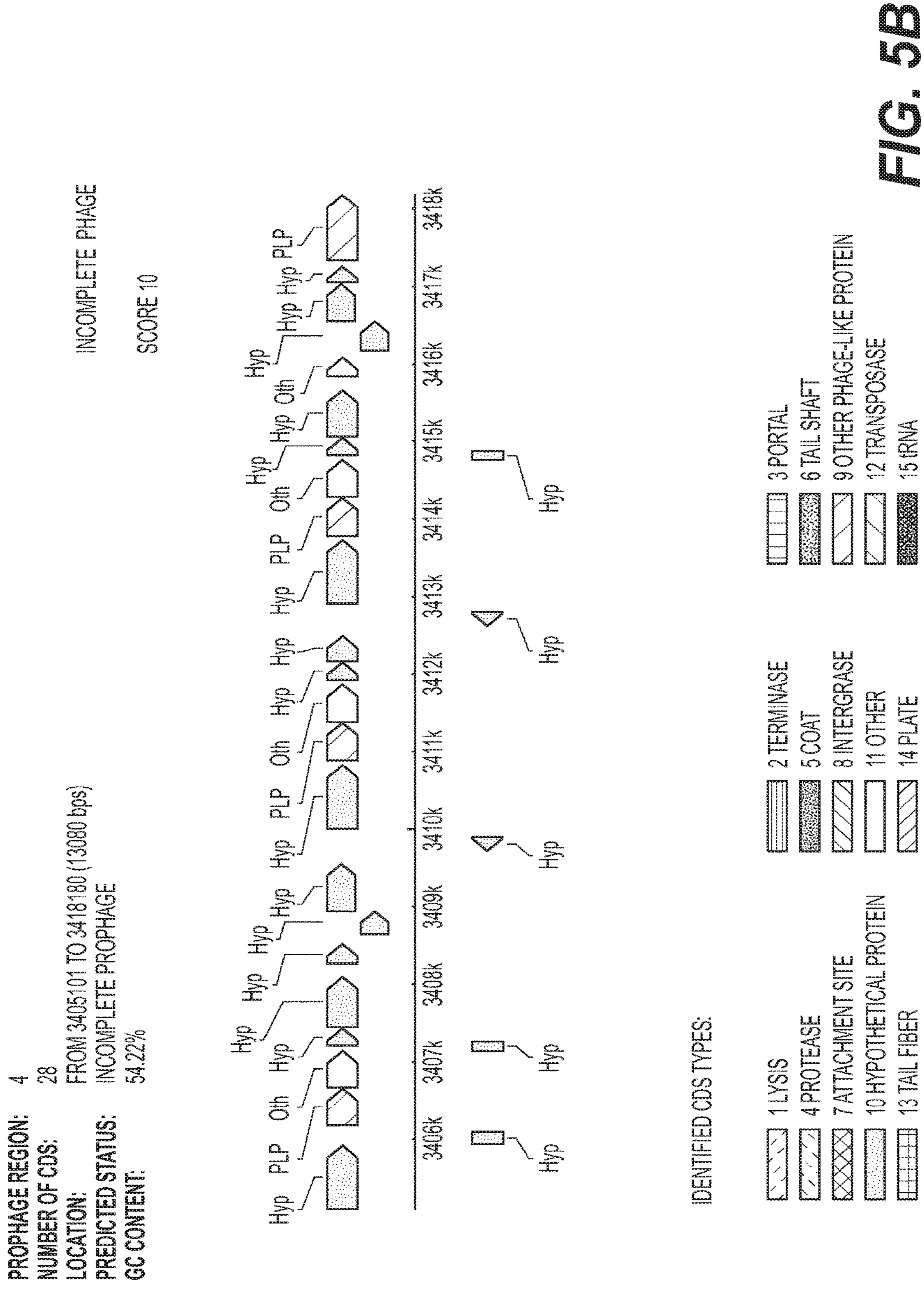
FIG. 5B depicts the second of 2 lower scoring "incomplete" or "questionable" phage identified using the Phast tool. Putative genes are labeled Hyp=Hypothetical, PLP=other phage like protein, Oth=Other.
Figure 6:
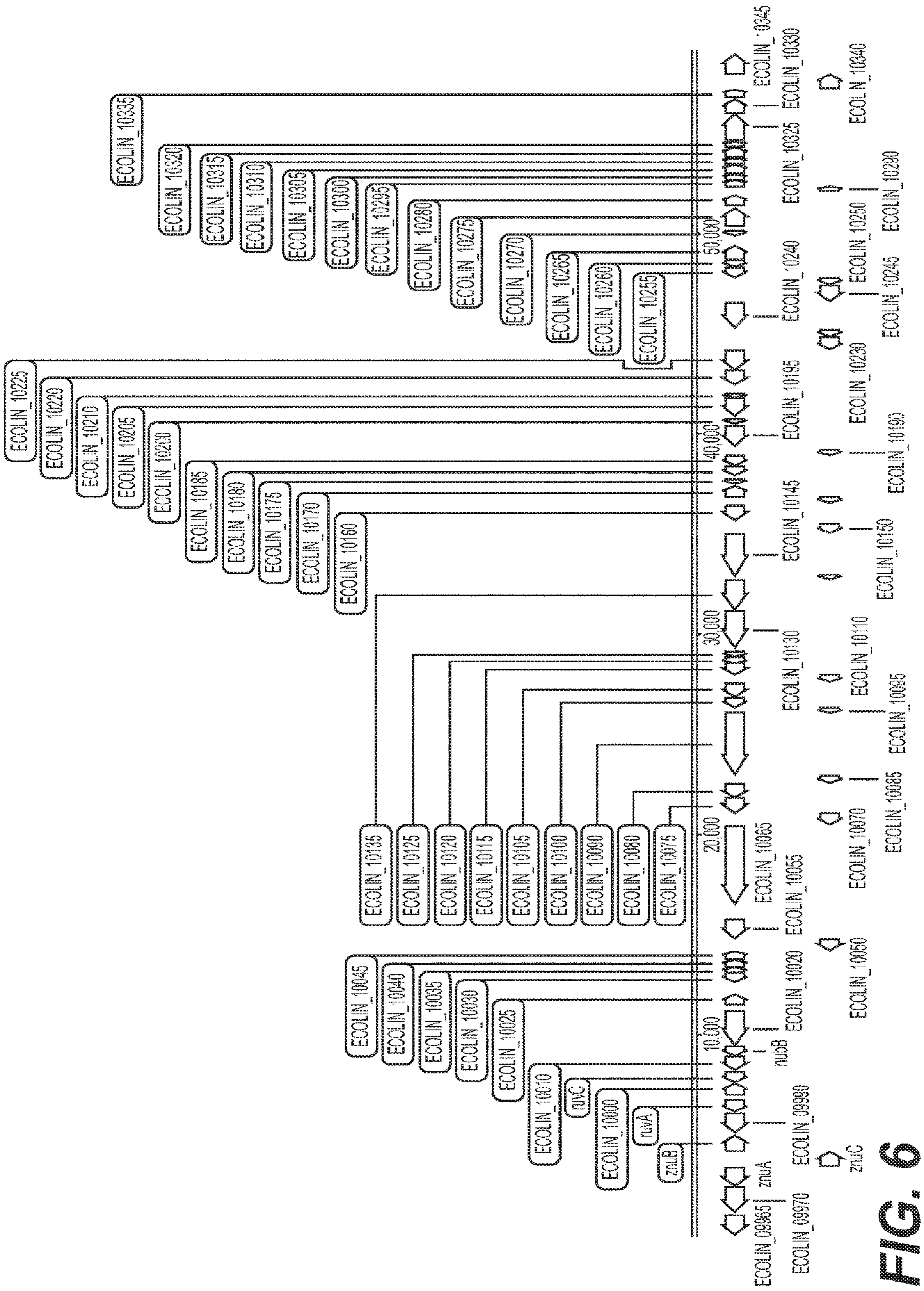
FIG. 6 depicts a schematic of the predicted Nissle Phage 3 sequence (59,056 bp).
Figure 7:
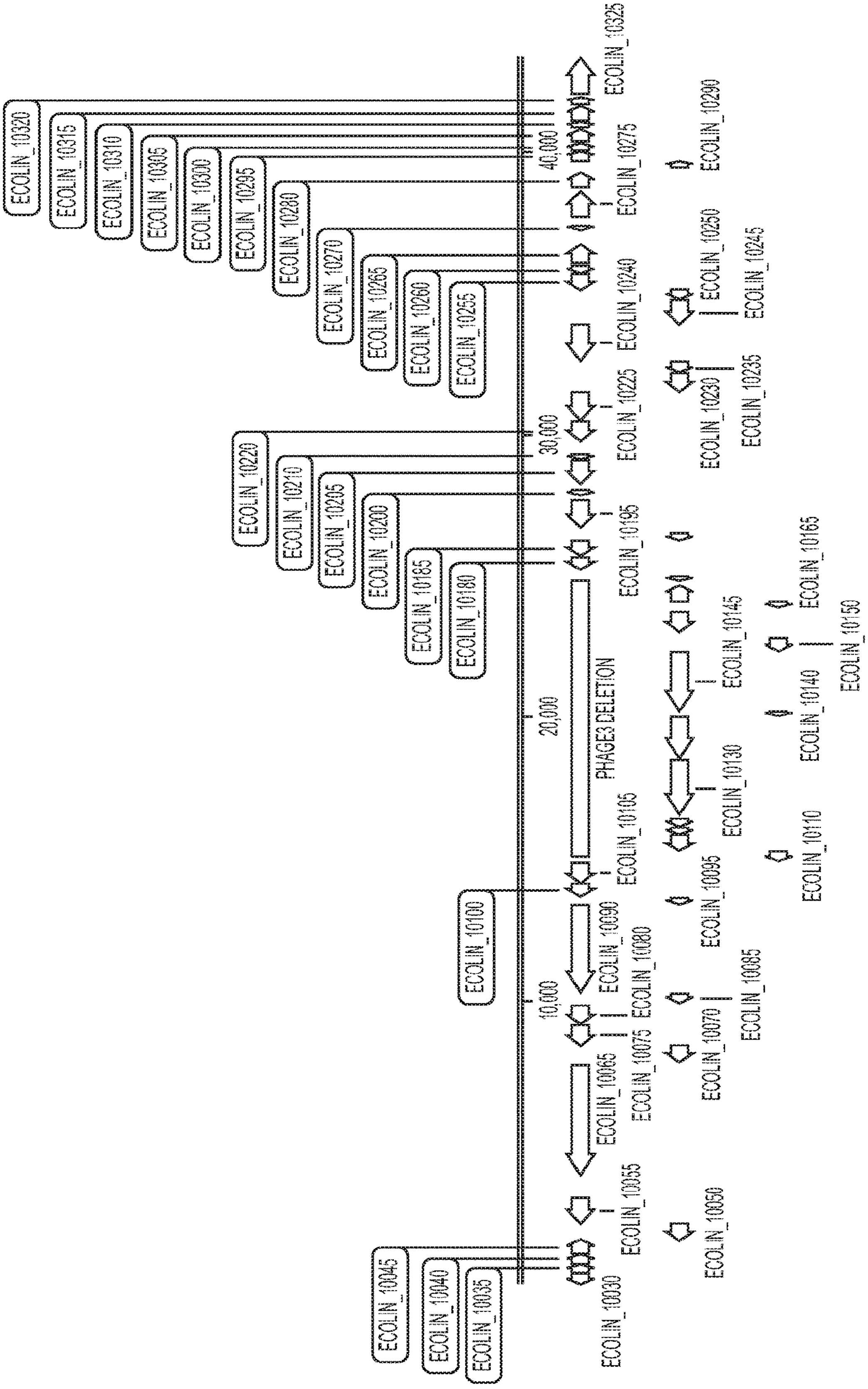
FIG. 7 depicts a schematic of the Phage 3 deletion within the Phage 3 genome used in SYN-PKU-2002.
Figure 8:
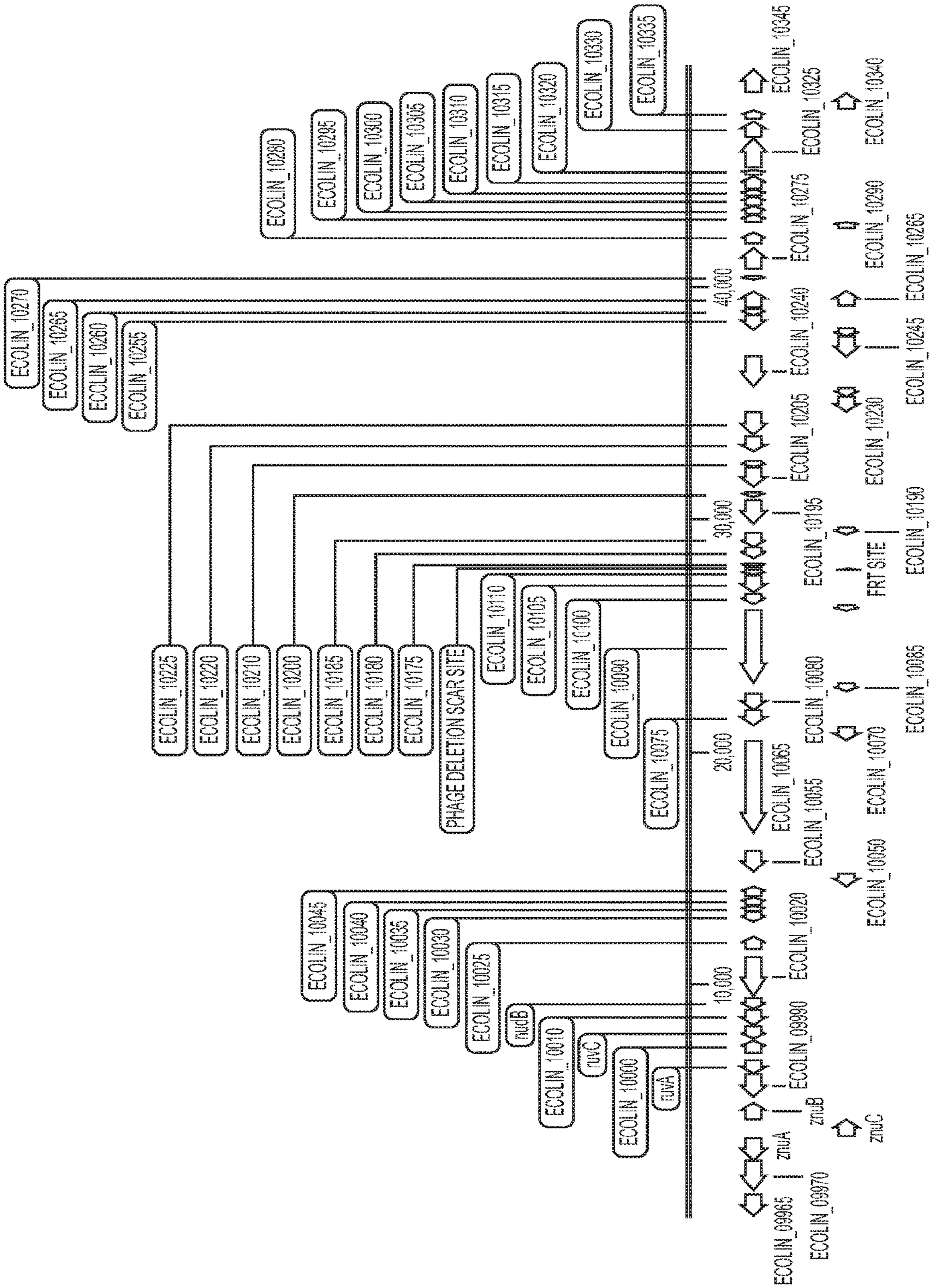
FIG. 8 depicts a schematic showing a 49,496 bp Phage 3 sequence comprising a knockout deletion, e.g., as comprised in SYN-PKU-2002.
Figure 9:
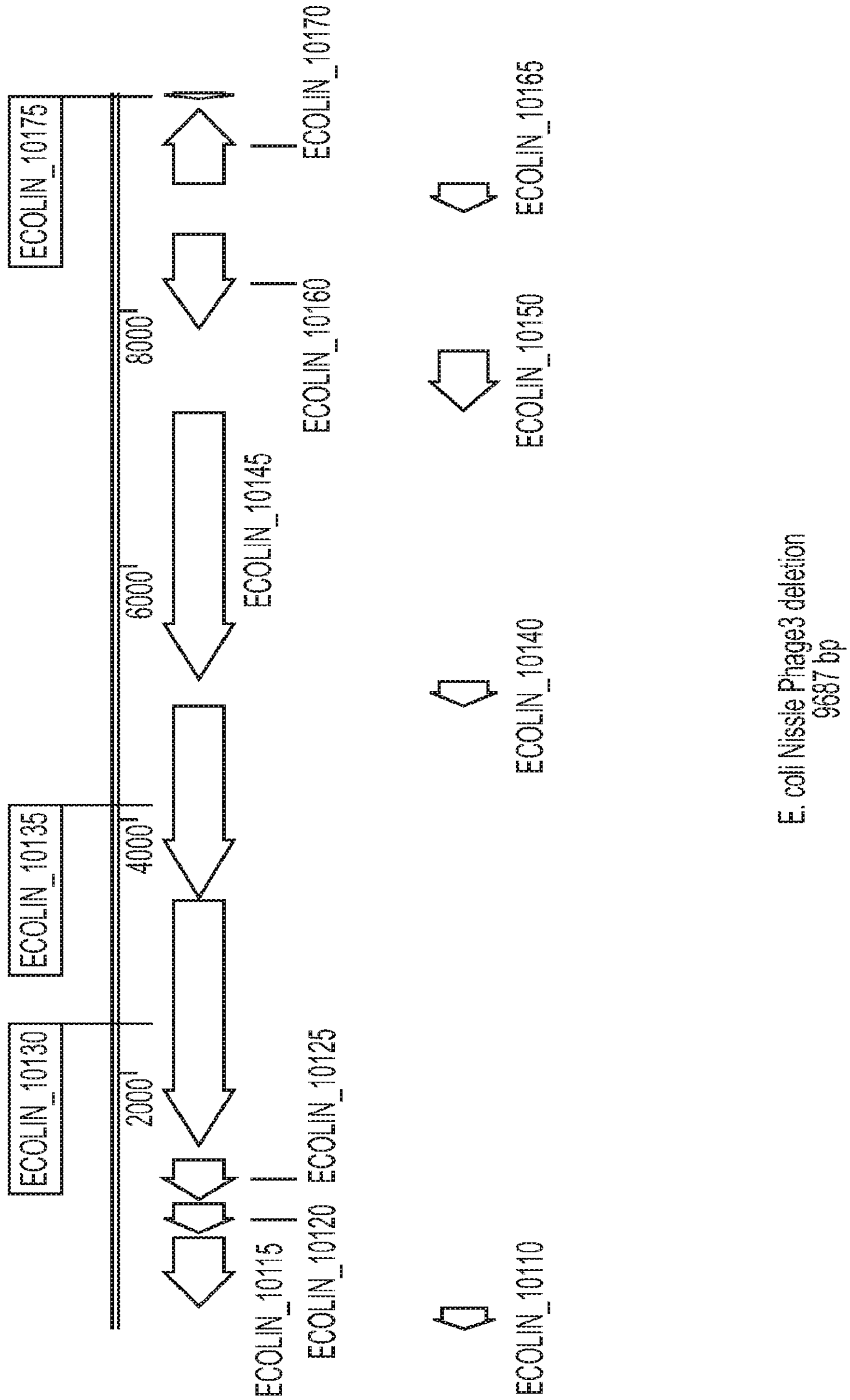
FIG. 9 depicts a schematic of the section of the phage that can be deleted to inactivate the phage, e.g., as deleted in SYN-PKU-2002.

In some embodiments, described herein genetically engineered bacteria are engineered *Escherichia coli* strain Nissle 1917 (*E. coli* Nissle). As described in more detail herein in the examples, routine testing procedures identified bacteriophage production from *Escherichia coli* Nissle 1917 (*E. coli* Nissle; *E. coli* Nissle) and related engineered derivatives. To determine the source of the bacteriophage, a collaborative bioinformatics assessment of the genomes of *E. coli* Nissle, and engineered derivatives was conducted to analyze genomic sequences of the strains for evidence of prophages, to assess any identified prophage elements for the likelihood of producing functional phage, to compare any functional phage elements with other known phage identified among bacterial genomic sequences, and to evaluate the frequency with which prophage elements are found in other sequenced *Escherichia coli* (*E. coli*) genomes. The assessment tools included phage prediction software (PHAST and PHASTER), SPAdes genome assembler software, software for mapping low-divergent sequences against a large reference genome (BWA MEM), genome sequence alignment software (MUMmer), and the National Center for Biotechnology Information (NCBI) nonredundant database. The assessment results show that *E. coli* Nissle and engineered derivatives analyzed contain three candidate prophage elements (FIG. 1), with two of the three (Phage 2 and Phage 3) containing most genetic features characteristic of intact phage genomes (FIG. 2, FIG. 3, and FIG. 4). Two other possible phage elements (FIG. 5A and FIG. 5B) were also identified. Of note, the engineered strains did not contain any additional phage elements that were not identified in parental *E. coli* Nissle, indicating that plaque-forming units produced by these strains originate from one of these endogenous phages. Further analysis described herein identified Phage 3 as the plaque-forming phage (Phage 3). Interestingly, Phage 3 is unique to *E. coli* Nissle among a collection of almost 6000 sequenced *E. coli* genomes, although related sequences limited to short regions of homology with other putative prophage elements are found in a small number of genomes. As described in more detail in the Examples, Phage 3, but not any of the other Phage was found to be inducible and result in bacterial lysis upon induction.

Prophages are very common among *E. coli* strains, with *E. coli* Nissle containing a relatively small number of prophage sequences compared to the average number found in a well-characterized set of sequenced *E. coli* genomes. As such, prophage presence in the engineered strains is part of the natural state of this species and the prophage features of the engineered strains analyzed were consistent with the progenitor strain, *E. coli* Nissle.

Table D lists the genes contained within the genome of Phage 3. Table E. Provides the sequence of Phage 3. Table F provides the sequences of the genes comprised in Phage 3 of *E. coli* Nissle. Table G. provides the sequences of the polypeptides encoded by the genome of *E. coli* Nissle Phage 3.

TABLE D

| Phage 3 Genome | | | | | | |
|---|---|---|---|---|---|---|
| Description | Position | Length | Orientation | GI Number | Protein ID | product |
| ECOLIN_09965 | 27 . . . 998 | 972 | <= | 660511998 | AID78889.1 | lipid A biosynthesis (KDO)2-(lauroyl)-lipid IVA acyltransferase |
| ECOLIN_09970 | 1117 . . . 2439 | 1323 | <= | 660511999 | AID78890.1 | peptidase |
| ECOLIN_09975 | 2455 . . . 3387 | 933 | <= | 660512000 | AID78891.1 | zinc ABC transporter substrate-binding protein |
| ECOLIN_09980 | 3466 . . . 4221 | 756 | => | 660512001 | AID78892.1 | zinc ABC transporter ATPase |
| ECOLIN_09985 | 4218 . . . 5003 | 786 | => | 660512002 | AID78893.1 | high-affinity zinc transporter membrane component |
| ECOLIN_09990 | 5150 . . . 6160 | 1011 | <= | 660512003 | AID78894.1 | ATP-dependent DNA helicase RuvB |
| ECOLIN_09995 | 6169 . . . 6780 | 612 | <= | 660512004 | AID78895.1 | ATP-dependent DNA helicase RuvA |
| ECOLIN_10000 | 7056 . . . 7658 | 603 | => | 660512005 | AID78896.1 | hypothetical protein |
| ECOLIN_10005 | 7660 . . . 8181 | 522 | <= | 660512006 | AID78897.1 | Holliday junction resolvase |
| ECOLIN_10010 | 8216 . . . 8956 | 741 | <= | 660512007 | AID78898.1 | hypothetical protein |
| ECOLIN_10015 | 8985 . . . 9428 | 444 | <= | 660512008 | AID78899.1 | dihydroneopterin triphosphate pyrophosphatase |
| ECOLIN_10020 | 9430 . . . 11,202 | 1773 | <= | 660512009 | AID78900.1 | aspartyl-tRNA synthetase |
| ECOLIN_10025 | 11,512 . . . 12,078 | 567 | => | 660512010 | AID78901.1 | hydrolase |
| ECOLIN_10030 | 12,680 . . . 13,069 | 390 | <= | 660512011 | AID78902.1 | DNA polymerase V ECOLIN_10030 |
| ECOLIN_10035 | 13,148 . . . 13,390 | 243 | => | 660512012 | AID78903.1 | MsgA |
| ECOLIN_10040 | 13,426 . . . 13,806 | 381 | => | 660512013 | AID78904.1 | hypothetical protein |
| ECOLIN_10045 | 13,808 . . . 14,251 | 444 | => | 660512014 | AID78905.1 | hypothetical protein |
| ECOLIN_10050 | 14,223 . . . 14,816 | 594 | <= | 660512015 | AID78906.1 | phage tail protein |
| ECOLIN_10055 | 14,816 . . . 15,748 | 933 | <= | 660512016 | AID78907.1 | tail protein |
| ECOLIN_10065 | 16,519 . . . 20,445 | 3927 | <= | 660512017 | AID78908.1 | host specificity protein |
| ECOLIN_10070 | 20,488 . . . 21,105 | 618 | <= | 660512018 | AID78909.1 | tail protein |
| ECOLIN_10075 | 21,098 . . . 21,817 | 720 | <= | 660512019 | AID78910.1 | peptidase P60 |
| ECOLIN_10080 | 21,820 . . . 22,557 | 738 | <= | 660512020 | AID78911.1 | hypothetical protein |
| ECOLIN_10085 | 22,614 . . . 22,952 | 339 | <= | 660512021 | AID78912.1 | tail protein |
| ECOLIN_10090 | 22,949 . . . 26,086 | 3138 | <= | 660512022 | AID78913.1 | tail protein |
| ECOLIN_10095 | 26,070 . . . 26,342 | 273 | <= | 660512023 | AID78914.1 | tail protein |
| ECOLIN_10100 | 26,393 . . . 26,824 | 432 | <= | 660512024 | AID78915.1 | tail protein |
| ECOLIN_10105 | 26,835 . . . 27,578 | 744 | <= | 660512025 | AID78916.1 | tail fiber protein |
| ECOLIN_10110 | 27,588 . . . 27,989 | 402 | <= | 660512026 | AID78917.1 | Minor tail protein U |
| ECOLIN_10115 | 27,986 . . . 28,558 | 573 | <= | 660512027 | AID78918.1 | tail protein |

TABLE D-continued

| Phage 3 Genome | | | | | | |
|---|---|---|---|---|---|---|
| Description | Position | Length | Orientation | GI Number | Protein ID | product |
| ECOLIN_10120 | 28,574 . . . 28,816 | 243 | <= | 660512028 | AID78919.1 | DNA breaking-rejoining protein |
| ECOLIN_10125 | 28,842 . . . 29,168 | 327 | <= | 660512029 | AID78920.1 | hypothetical protein |
| ECOLIN_10130 | 29,251 . . . 31,197 | 1947 | <= | 660512030 | AID78921.1 | peptidase S14 |
| ECOLIN_10135 | 31,211 . . . 32,710 | 1500 | <= | 660512031 | AID78922.1 | capsid protein |
| ECOLIN_10140 | 32,707 . . . 32,922 | 216 | <= | 660512032 | AID78923.1 | hypothetical protein |
| ECOLIN_10145 | 32,919 . . . 35,021 | 2103 | <= | 660512033 | AID78924.1 | DNA packaging protein |
| ECOLIN_10150 | 35,021 . . . 35,509 | 489 | <= | 660512034 | AID78925.1 | terminase |
| ECOLIN_10160 | 35,693 . . . 36,421 | 729 | <= | 660512035 | AID78926.1 | hypothetical protein |
| ECOLIN_10165 | 36,596 . . . 36,826 | 231 | <= | 660512036 | AID78927.1 | hypothetical protein |
| ECOLIN_10170 | 36,825 . . . 37,421 | 597 | => | 660512037 | AID78928.1 | hypothetical protein |
| ECOLIN_10175 | 37,490 . . . 37,687 | 198 | <= | 660512038 | AID78929.1 | hypothetical protein |
| ECOLIN_10180 | 37,901 . . . 38,380 | 480 | <= | 660512039 | AID78930.1 | hypothetical protein |
| ECOLIN_10185 | 38,401 . . . 38,949 | 549 | <= | 660512040 | AID78931.1 | lysozyme |
| ECOLIN_10190 | 38,921 . . . 39,199 | 279 | <= | 660512041 | AID78932.1 | holin |
| ECOLIN_10195 | 39,345 . . . 40,397 | 1053 | <= | 660512042 | AID78933.1 | DNA adenine methylase |
| ECOLIN_10200 | 40,548 . . . 40,739 | 192 | <= | 660512043 | AID78934.1 | hypothetical protein |
| ECOLIN_10205 | 40,908 . . . 41,807 | 900 | <= | 660512044 | AID78935.1 | serine protease |
| ECOLIN_10210 | 41,820 . . . 42,026 | 207 | <= | 660512045 | AID78936.1 | hypothetical protein |
| ECOLIN_10220 | 42,459 . . . 43,148 | 690 | <= | 660512046 | AID78937.1 | antitermination protein |
| ECOLIN_10225 | 43,170 . . . 44,165 | 996 | <= | 660512047 | AID78938.1 | hypothetical protein |
| ECOLIN_10230 | 44,162 . . . 44,845 | 684 | <= | 660512048 | AID78939.1 | antirepressor |
| ECOLIN_10235 | 44,859 . . . 45,245 | 387 | <= | 660512049 | AID78940.1 | crossover junction endodeoxyribonuclease |
| ECOLIN_10240 | 45,242 . . . 46,561 | 1320 | <= | 660512050 | AID78941.1 | adenine methyltransferase, DNA methyltransferase ECOLIN_10240 |
| ECOLIN_10245 | 46,558 . . . 47,439 | 882 | <= | 660512051 | AID78942.1 | GntR family transcriptional regulator ECOLIN_10245 |
| ECOLIN_10250 | 47,449 . . . 47,787 | 339 | <= | 660512052 | AID78943.1 | hypothetical protein |
| ECOLIN_10255 | 47,784 . . . 48,347 | 564 | <= | 660512053 | AID78944.1 | hypothetical protein, completely unknown |
| ECOLIN_10260 | 48,379 . . . 48,636 | 258 | <= | 660512054 | AID78945.1 | hypothetical protein, cI repressor ECOLIN_10260 |
| ECOLIN_10265 | 48,715 . . . 49,425 | 711 | => | 660512055 | AID78946.1 | hypothetical protein, Domain of unknown function (DUF4222); |

TABLE D-continued

| Phage 3 Genome | | | | | | |
|---|---|---|---|---|---|---|
| Description | Position | Length | Orientation | GI Number | Protein ID | product |
| | | | | | | This short protein is likely to be of phage origin. For example it is found in Enterobacteria phage YYZ-2008. It is largely found in enteric bacteria. The molecular function of this protein is unknown. |
| ECOLIN_10270 | 49,868 . . . 50,065 | 198 | <= | 660512056 | AID78947.1 | hypothetical protein |
| ECOLIN_10275 | 50,378 . . . 51,295 | 918 | => | 660512057 | AID78948.1 | DNA recombinase In *Escherichia coli*, RdgC is required for growth in recombination-deficient exonuclease-depleted strains. Under these conditions, RdgC may act as an exonuclease to remove collapsed replication forks, in the absence of the normal repair mechanisms ECOLIN_10275 |
| ECOLIN_10280 | 51,404 . . . 51,943 | 540 | => | 660512058 | AID78949.1 | hypothetical protein, 5' Deoxynucleotidase YfbR and HD superfamily hydrolases ECOLIN_10280 |
| ECOLIN_10290 | 52,104 . . . 52,358 | 255 | => | 660512059 | AID78950.1 | hypothetical protein Multiple Antibiotic Resistance Regulator (MarR) family of transcriptional regulators |
| ECOLIN_10295 | 52,355 . . . 52,702 | 348 | => | 660512060 | AID78951.1 | hypothetical protein, unknown ead like protein in P22 |
| ECOLIN_10300 | 52,704 . . . 53,012 | 309 | => | 660512061 | AID78952.1 | hypothetical protein, totally unknown |
| ECOLIN_10305 | 53,026 . . . 53,493 | 468 | => | 660512062 | AID78953.1 | hypothetical protein, Protein of unknown function (DUF550); This family is found in a range of |

TABLE D-continued

| Phage 3 Genome | | | | | | |
|---|---|---|---|---|---|---|
| Description | Position | Length | Orientation | GI Number | Protein ID | product |
| | | | | | | Proteobacteria and a few P-22 dsDNA virus particles. The function is currently not known. Similar to P22 EA gene ECOLIN_10305 |
| ECOLIN_10310 | 53,496 . . . 53,750 | 255 | => | 660512063 | AID78954.1 | hypothetical protein, Phage repressor protein C, contains Cro/C1-type HTH and peptisase s24 domains |
| ECOLIN_10315 | 53,772 . . . 54,341 | 570 | => | 660512064 | AID78955.1 | hypothetical protein, 3'-5' exonuclease ECOLIN_10315 |
| ECOLIN_10320 | 54,382 . . . 54,618 | 237 | => | 660512065 | AID78956.1 | excisionase ECOLIN_10320 |
| ECOLIN_10325 | 54,677 . . . 55,990 | 1314 | => | 660512066 | AID78957.1 | integrase, Phage integrase family; Members of this family cleave DNA substrates by a series of staggered XerC |
| ECOLIN_10330 | 56,017 . . . 56,742 | 726 | => | 660512067 | AID78958.1 | hypothetical protein |
| ECOLIN_10335 | 56,795 . . . 57,190 | 396 | => | 660512068 | AID78959.1 | membrane protein |
| ECOLIN_10340 | 57,231 . . . 57,974 | 744 | => | 660512069 | AID78960.1 | tRNA methyltransferase |
| ECOLIN_10345 | 57,971 . . . 58,942 | 972 | => | 660512070 | AID78961.1 | tRNA methyltransferase |

TABLE E

Phage 3 Genome Sequence
SEQ ID NO: 134 aggcctctcctcgcgagaggcatttttatttgatgggataaagatcttt
gcgcttatacggttggatttcgcccggtttgcgagttttcagcaatttta
atatccaggtgtattgttctggtcgcggaccaacaaaaatctcgacttct
tcattcatccgccgcgcaatcgtatgatcatccgcctctaacagatcatc
catcggtgggcgcacctgaatcgtcagacgatgcgtcttgccatcataaa
tcggaaatagcggtacaacgcgcgcacggcacactttcatcaaacgacca
atcgcgggcaacgtcgctttataggtggcaaagaaatcaacaaattcgct
gtgttctgggccatgatcctgatcgggtaaataatatccccagtaaccct
gacgtaccgactggatgaatggtttaataccatcatttctcgcatgcaga
cgaccaccaaagcgacggcgcaccgtgttccagacataatcaaaaaccgg
gttgccctgattatggaacatcgctgccattttctgcccttgcgaggcca
tcagcatggcaggaatatcgacggcccaaccgtgcggcaccagaaaaatc
actttctcgttattacgtcgtatctcttcgatgatctccagcccttgcca
gtcaacgcgcggctgaattttctccggcccgcgtattgccaactcagcca
tcattaccatcgcttgcggcgcggtggcaaacatctcatctacaatcgct
tcgcgttcagcttcactacgttctggaaagcagagcgacagattgattaa
cgcacgacggcgtgagctttttcccagtcgtccggcaaaacgtcccagcc
gtgccagaatgggatcacggaactttggcggcgttaaagcgatacccgcc
atcgctgctacgcccagccatgctccccagtagcgcgggtggcgaaagga
tttatcaaactcaggaatgtattcgctattatttttttcgtttccatgc
ttttccagtttcggataaggcaaaaatcaatctggtgatagtgtagcggc
gcaacttgccccgcaccaaataaaaaagccggtactgactgcgtaccggc
tgcgaatggatgttaattaatcaaaccgtagctgcggcacaatctctttg
gcctgtgccaggaattcgcgacgatcggagccggtcagcccttcggtacg
cggcagttttgccgtcagcgggtttacggcctgctggtttatccatactt
catagtgcagatgcggcccggttgaacgtccggtattaccggaaagcgcg TABLE E-continued Phage 3 Genome Sequence
SEQ ID NO: 134 atacggtcgccacgtttcaccttctgtcccggtttcaccaggatcttgcg
caagtgcatataacgcgtggtgtagctgcgaccatgacgaatagccacat
aataacctgctgcgccactacgtttggcaaccaccacttcaccgtcaccc
actgaaagcactggcgtaccttgtggcatggcaaaatcaacacctctgtg
tggcgcaacgcgaccggtcaccggattagtacgacgcgggttaaagttag
atgagatacggaactgtttcgccgtcgggaatcgcaagaatcctttcgcc
agaccagtaccgttacgatcgtagaatttgccatcttcagcgcggattgc
gtaataatctttaccttctgaacgcaaacgtacgcccagcagctggcttt
gctcacgtttaccatcaagcatttctcgtgacattaacaccgcaaattca
tcgccttttttcagtttgcggaaatccatttgccactgcatggctttaat
cactgcgctcacttcggcgctggttaaaccggcgtttctggcgctggcaa
caaagcttcccccgacggtacctttcagcagattgttgacccactctcct
tgctgcatttcgctggtcattttaaaaccgttagcggcagtacggtcata
ggttcgggtttcacgacgagacacttcccaggtgaggcgctgcagttcgc
cgtccgcggttaatgtccaggagagttgttgaccgattttcaggttacgc
aattctttgtcggcagcagccagttgggtgatatcacccatatcaatacc
atactgattgagaatgctgcttagcgtatcgccagtggaaacaacatatt
catgcacgcccgcttcaccggcgattttgtcatccagttcgtcctgggga
atggcttcatcttcttgtgcagcttgatcaatcggctcactggcttcagg
taagagcgaacgaatttcgttctgttccagctcaatggttttgacaattg
gcgtggcatcgcggtgataaacatagggccgccagacagcgacggccaga
gtaagaacggtgagcgaccccaacataacgcggtgtggtcgcggtaaatt
attaaacgccagggcgacagagcgggctatctgttgcacgtaatcacttc
ctcattaatctcctttcaggcagctcgcatactggttggctaattgattc
aggaattctgaatagcttgttttacccagtttgatattcgtccccagggg
atccaacgttcccatacgaacggatgtccctcgtgcgacgctctcaacga TABLE E-continued Phage 3 Genome Sequence
SEQ ID NO: 134 ccgctggcctgaactgtggctcagcaaaaacgcaggttgcttttgctca
accaactgtgttcttatttcatgtaaacgctgcgcgccaggttgaatctc
agggttaacggtaaaatgaccaagcggtgtcagtccgaactgttttcga
aatagccgtaagcatcgtgaaaaacgaaataacctttccccttgagcggc
gcgagctcgttaccaacctgcttttcggttgaggctaattgtgcctcaaa
atccttcaggttggcgtcaagtttggctcgactttgcggcataagttcca
ctaattttccatggattgcaaccgctgtagcccgcgctatctctggggaa
agccaaagatgcatgttgaaatcgccgtgatggtgatcttcgtcactttt
ttccgcgtggtcgtgatcatcatcatcgccgtgaatacttttcatcagca
gcggtttcacattctctagctgcgcaatcgttacctgtttcgcttcaggt
aatttacttaccggtttttgcatgaacgcttccatctccgggccaaccca
aacgactaagtccgcgttctgtaagcgttttacatctgatggacgcagtg
aataatcatgttctgaagcccgtcaggtagtaaaacctccgtttctgtt
accccatcagcaatggcagaagcgatgaacccaacgggtttaagcgaagc
gacaacggcagcatctgcggcctgtgttgcaccgccccagagagcggcgg
ataatgctgcgaaaagaagcgtttttttatgtaacataatgcgaccaatc
atcgtaatgaatatgagaagtgtgatattataacatttcatgactactgc
aagactaaaattaacatgacaagtctggtttccctggaaaatgtctcggt
ttcttttggccaacgccgcgtcctctctgatgtgtcgctggaacttaaac
ctggaaaaatttgactttacttgggccaaacggcgcaggtaagtcgaca
ctggtacgggtagtgctcgggctggtaacacccgatgaaggggttatcaa
gcgcaacggaaaactgcgcatcggctatgtaccgcagaagctgtatctcg
acaccacgttgccactgaccgtaaaccgttttttacgcttacgccctggc
acacataaagaagatatttgcctgcactgaaacgtgtccaggccgggca
tctgattaacgcaccgatgcaaaagctctcgggtggcgaaacgcagcgtg
tactgttagcgcgagcattgttaaatcgaccgcaattattagtgctggat
gaacccactcagggcgtggatgtgaatggtcaggtggcgttatatgacct
tattgaccaactgcgtcgcgaactggattgtggcgttttaatggtatctc
acgatctgcatctggtaatggcaaaaaccgatgaagtgctttgcctgaat
caccacatttgttgttccggcacaccggaagttgtttccctgcatccgga
gtttatttctatgtttggtcctcgtggtgctgaacaactgggtatctatc
gccatcatcataatcatcgtcacgatttacagggacgaattgttttgcgt
cggggaaatgatcgctcatgattgaattatttatttcccggttggttagcc
gggatcatgctcgcctgtgccgcgggtccgctgggttcgttgtagtctg
gcgtcgtatgtcttatttcggtgatacgctggctcatgcctcattacttg
gcgtcgcgtttggtttgttgctggacgtgaatccattctatgcggtgatt
gccgttacgctgctgctggcgggcggtctggtatggctggagaagcgtcc
acagctggcgatcgacacgttattagggattatggcgcacagtgccctgt
cgctgggcctggtggtcgttagtctgatgtctaatattcgtgttgatttg
atggcttacctgttcggtgatttactggcagtgacgccagaagatctcat
ctctattgcgattggcgtggtcatcgtggtggctattttgttctggcaat
ggcgcaatttgctgtcgatgacgattagcccggatctggcgtttgttgat
ggtgtgaaattacagcgcgtgaaattgttgttgatgctggtgacggcatt
gacgattggtgtagcgatgaaattcgtcggcgcgttgattattacttcac
tgctgattattcctgctgctactgcacgtcgctttgcccgcacgccggaa
cagatggctggtgtcgctgttttggtggggatggtggcagtgactggcgg
tttaaccttttccgcatttacgatacacctgcaggcccgtcggtggtgc
tatgcgcggcactgttatttattatcagtatgatgaaaaagcaggccagc
taatctgtcgctgaacacatttgtcggatgcggcgcgagcgccttatccc
acctgcggttcgctatctctggtaggcctgataagacgcgaacagcgtcg
catcaggcacactgccagtgtcggatgcggctcgagcgaccaatccgact
tacggcatttctggcggcgtgatgccgaagtggttccacgcccgcactgt
cgccatacgcccgcgcggtgtacgctgcaaaaagccttgctgaatcaaat
aaggttccagtacatcctcaatggtttcacgttcttcgccaatggctgcc
gccaggttatccagacctaccggcccaccaaagaacttatcgattaccgc
cagcaacaatttgcggtccatataatcgaaaccttcagcatcgacattca
acatatccagcgcctgagcagcgatatctgccgagatggtgccatcgtgc
ttcacttcagcgaaatcacgcactcgacgcagcagacggttggcaatacg
tggcgtaccgcgcgcacgacgagcaacttccagcgcgccgtcatcactca
tctcaagccccataaagcgtgcgctgcgactgacgatatattgcagatcc
ggcacctgataaaactccagacgttgcacaataccaaaacgatcgcgcaa
cggtgatgtcagcgaacctgcgcgcgtggttgcaccaatcagggtaaacg
gcggcaaatcaattttaatggagcgtgccgccggaccttcaccaatcatg
atatccagttggtaatcttccattgccggatacaacacctcttccaccac
tggtgaaagacggtggatctcatcaataaacagtacatcgtggttcaa
ggttagtgagcattgctgccagatcgcccgccttttccagcaccggacca
gaagtcgtgcgtaaattaacgcccatttcattggcgacaatattggcaag
cgtagttttacccaacccggaggaccaaaaatcaatagatgatcgaggg
catcgccgcgcagtttcgctgctttgatgaaaatctccatctgcgaacga
acctgcggctgaccaacatactcttccagtaatttagggcgaatggcgcg
atctgccacatcttccggcaaagtggtaccggcagaaatcagacggtctg
cttcaatcatcctttacctcataacgcggcgcgtagggcttcgcgaatta
atgtttcactgctggcgtcagggcgagcgattttgctcaccatgcggctt
gcttcttgtggtttatagcccagtgccaccagcgcagcaaccgcttcctg
ttcagcatcgtcggtcgccgggctggcaggagacgtgagtaccaggtcgg
cggctggcgtaaagagatcgccatgcaaacctttaaatcggtctttcatt
tcgacaatcaagcgttcggcggtttttttgccaatacccggcagtttcac TABLE E-continued Phage 3 Genome Sequence
SEQ ID NO: 134 cagtgcccccacttcttcacgctcaacggcattaacgaactgctgcgctg
acattccggagaggatcgccagcgccaacttcgggccgacgccgttggtt
ttgatcaactctttgaacaacgtgcgctcttgtttattgttaaaaccgta
cagcagttgcgcgtcttcacgcaccacaaagtgggtgaaaacgatcgctt
cctgacccgcttcagggagttcataaaaacaggtcatcggcatatgcact
tcatagcctacgccgcccacttcaattaacaccagcgggggttgtttttc
aatgatgatgcctctgagtctgcctatcacatgacgctcctgcgtaatga
atcaaagataatgctgtatgataaaaaaatgctggatagatatccagcga
aggatgaagaaaacttgcgaggtgtctcgatgatctgaaaaatggcgcag
tataatttattctacagattatattggaagcaaatatttaaatattacat
attcagcgaagaaatgtgtaataaaaatacacattgcgacccctgaaaaa
aataaatttttttatgctattacgtatattcatatctatttcaatggaatg
acaacgtgaatattaattatcctgctgaatatgaaattggtgatatcgtc
tttacatgtataagtgctgccttatttggtcaaatatcagctgcatcaaa
ttgctggagtaatcacgtcgggatcattatcggtcataacggtgaagact
ttctggttgcagaaagccgtgttcccctctcaaccatcactacgctatcc
cgttttattaaacgctctgctaatcaacgctatgctataaagcgattaga
cgccggactaacagaacaacaaaatcaacgaattgttgaacaggttcctt
cccggctacgcaaaatttaccacaccggttttaaatacgaatcttcgcgc
cagttctgttcaaaatttgtttttgatatttataaagaggcgctatgtat
tccggtgggtgaaatagagacgtttggagaattgttaaatagcaatccaa
atgcaaaactcactttctggaaattctggttcttaggttctattccgtgg
gagcgtaaaaccgtcacgccagccagtttgtggcatcatccgggtttggt
gttgattcacgcggtgggagttgaaacgcctcagcctgaactgaccgagg
cggtataacttaacgcagtcgccctctcgccaggttcagtcgcgattcgc
tcatttgcatcgcattctgactaacgtggcagtgggtgatggcaatcgcc
agcgcatcggcggcatccgcctgtggattagcgggcagtttcagcaaggt
gcggaccatatgctgcacctggctttttttcggcactaccaatacctacca
ctgtttgctttacctgacgtgccgcatattcaaataccggcaattcctga
ttcaccgccgccacaatcgccacgccgcgcgcctgccccagtttcagggc
tgagtcagcgttcttcgccataaagacctgttcaatggcgaaataatcag
gctggaattgggtgatgatttccgtcacgcccgcatagatgagcttcaga
cgagacggtaaatcatccactttggtgcgtatgcatccgctacccaggta
ggacagttgcctgcctacctggcggatgacgccatagccggtcacgcgcg
aacccgggtcaatgccgagaataatagccatcacgcgtctccgttttgct
gtttagcaggcctcatcagagagtcgctgcaacctcatcagagatttcac
cgttatggtaaacttcctgcacgtcgtcgcaatcttccagcatatcgatc
agacgcatcagtttcggtgcggtttctgcatccatatcagctttggtgga
cgggatcatggaaacttccgcgctgtctgctttcagacctgccgcttcca
gagcgtcgcgtactttgcccatttcttcccatgcagtgtagacatcaatc
gcgccgtcatcataggtcacaacgtcttcagcaccggcttccagggctgc
ttccatgatggtgtcttcatcgcctttctcgaaggagatcacgcctttt
tgctgaacaaataagctacggaaccatcagtaccgaggttaccgccacat
ttgctgaatgcatgacgcacttcagcaacggtacggttgcggttgtcaga
cagacattcaatcatgattgccgtgccgccaggaccgtaaccttcgtaga
tgatggtttccatgtttgcatcatcatcaccgcccacacctcgtgcaatt
gcgcggttcagagtgtcacgggtcatgttgttagacagtgctttatcaat
tgctgcacgcaaacgcgggttagcgtccggatcaccaccgcccagcttag
ccgcggttaccagctcacgaatgattttagtgaagattttaccgcgctta
gcatcctgcgcagctttacgatgtctggtgttggcccatttactatgacc
tgccataaaaatatctccagatagccctgcctgttcaggcagcgttaatt
acaaactgttcaatcgcctgccggttgctccaggacttagtgagcgccgc
cgcagcagacgcatcaagccacttgtaagccagatgttcagtgaaaacga
tctggcgctcgtgcggaagcgcaagacagaaccatgattccgtattacgc
gtcacgcccggcgcatagcgatgacgtaaatgtgaaaaaatttcaaactc
taccgtgcgctgacagtcaattaaggtcagttgttcagcgacaacatcaa
tggtgacctcttcctttacttcgcgcatggcagcttgcggcgcggtttca
ccctcttccacgctgccggttaccgactgccagaaatcgggatcgtcacg
ccgctgcaacatcagcacccgtttcgtatcttgtgcgtagatgaccacta
agatcgaaacgggacgcttataagccatatcagttattctcagccttctt
cacaacctgaatgctcagctcagccagtgcagtcgggttagcaaagctcg
gcgcttcagtcatcaaacacgctgccgccgtggttttcgggaaggcgata
acgtcacggatattgtcggtgccggtcagcagcatcgtcagacggtcaag
accgaatgccaaacctgcgtgcggcggagtaccgtatttcagggcgtcga
gcaggaagccgaatttctcgcgctgttcctcttcgttgatacccagaata
ccaaacaccgtctgctgcatatcaccattatggatacgcacagaaccacc
gcccacttcgtaaccattgatgaccatatcgtaagcgttagccaccgcat
tttccggtgcagctttcagttctgctgccgtcatgtctttcggtgaggtg
aacggatggtgcattgctgtcaggccgccttcaccgtcgtcttcaaacat
cgggaagtcgataacccacagcggtgcccatttgctttcgtcggtcagac
caaggtctttacccactttcaggcgcagtgcgcccatcgcgtcggcaaca
attttcttgttgtcggcaccgaagaaaatcatatcgccatcttgcgcgcc
agtacgctccaggatggcttcgatgatttctgcattaaggaacttcgcta
ccgggctattgataccttccagacctttcgcgcgttcgttaactttgatg
taagccagacctttcgcgccgtagattttaacgaagttaccgtattcgtc
gatctgcttacgggtcaacgatgcgccgcccggaacacgcagagcggcaa
cacggcctttcggatcgttcgccggacctgcaaatactgcaaactcaaca TABLE E-continued Phage 3 Genome Sequence
SEQ ID NO: 134 gatttcagcagatcggcaacgtcggtcagttccatcgggttacgcagatc
cggtttatcagaaccataacggcgttctgcttctgcaaaggtcattaccg
ggaaatcgcccagatccacgcccttcacttccagccacagatgacgcacc
agcgcttccatcacttcacgcacttgcggcgcggtcatgaaagaagtttc
cacatcgatctgagtaaattcaggctgacggtcagcacgcaggtcttcgt
cacggaagcatttaacgatctgatagtagcggtcaaagccggacatcatc
agtagctgtttgaacaactgcggggattgcggcagcgcgtagaatttacc
tttgtgcacacgagaaggcaccaggtagtcacgcgcgccttcaggcgtgg
ctttggtcagcatcggagtttcgatgtcgaggaagccgtggtcatccata
aaacggcgcaccaggctggtgattttagcgcgggttttcaggcgctgagc
catttccgggcgacgcaggtcgaggtagcggtatttcagacgcgcttctt
cggtgttgacgtggttagagtcaagcggcagaacatctgcacggttgatg
atagtcagcgaggacgccagtacttcgatttcgccagtcgccatatcgcg
gttaatatttttttcgtcacgcgcacgtacggtgcccgtgacctgaatgc
agaactcattacgcagttcagaggccagctttaacgcgtccgcacgatcc
ggatcgaaaaatacctgcacgataccttcgcggtcgcgcatatcgatgaa
gatcaggctaccaagatcacgacgacggttgacccaaccacacagagtca
cctgctgccccacgtgggacaaacggagctgtccacaatattctgtacgc
atgagatatcccttaacttagctgccggcggatgccccctgctgcgcagg
tgaccaagtcgcagcgttagctgtatgtcacaactgaatgaaaaaaggcg
gctattatactggaaattctgccgcaccgtaagagcctggcccgcgctgg
aacgcctcgttaccactttatatcgggcctgaaatcagactctacgccag
tttgctataaaggtgttgcccgaactcataaaaattaacaaaatttgtcg
ttccgccatcggctaatcgcattaaggtgagaggcacgattttgttttgt
caggagtcatcatgcttgaacttaatgctaaaaccaccgcgctggtggtg
attgatttacaagaaggcatcttgccttttgccggaggtccacatactgc
cgatgaggtggttaatcgcgccgggaagctggcggcgaaatttcgcgcca
gcggtcagcccgtgtttctggtgcgcgttggctggtctgccgattacgcc
gaagcattaaaacagccggttgatgcccctcccccgcaaaagtgttgcc
cgaaaactggtggcaacatcctgctgcattaggtgcaaccgacagcgata
tcgaaatcatcaaacgtcaatggggtgcgttttacggtacggatctggag
ttgcaattacgccgccggggtatcgatacaatagtgttatgtgggatctc
gaccaatatcggtgttgaatccaccgcccgcaatgcctgggaactcggtt
ttaatctggtgattgccgaagatgcctgtagcgccgctagcgccgagcag
cacaataacagcattaatcatatctacccgcgcatcgcccgtgtgcgtag
cgttgaagagatcctcaacgcgttatgatttacatcggtttgccacaatg
gtcgcatcctaaatgggtgcggttggggatcaccagccttgaagagtatg
cccgccactttaactgcgtgacgcgggcattttaaaaatcactaaagaac
gcccaagagcatgtgttttctttagtttattcaatgcattaaaaaatagt
ttcgcatgaaattcggtaaacttcatgtgtgcaataatgtcccattcatg
ccccaaaatgccccaaagcagacattttgccccaagtatgccccacaag
tcacgtcttcaagtcgtctatatccatagcacaccgagttacattcttgc
atccggggtgtcgacaatacctactttattgagtgtgcgagaattaccag
gaacctttccacaatgtagtagtctaatagtcgaatccatctaacattaa
gaagcgttatgatcactagcctctcattgatatcttctgtaatagtcact
ctatgtatcatggtgttcgctacagtaaaggtagggattggtttgtctaa
caatccagacagaaatgataattaacctcaaccacgtaaccacacttcat
acttcatacttcacttaacagtgaagtgctcacatcaccgggcagtcatc
aaactccgcattcctggcatcattaatgatgtacgtgatcactccaaata
tagcgggtgcagaactgtaaccatcatcatctgctggcagcgcttccctt
ctcccgttatccagattaaccaggtgcggctgaggatgagtccgatatcg
cttgatcctgaattccccgtcgattgcacatatcagcagtgaaccatcgc
aggcagtaagtgacgcatccacaacaagcaacgctccctggattatccct
tccctgaaatgtgaacgcgatgcccgcatgaaataagtcgctgcgggctg
actgattagctgctgatcgagggagattcgtgtttcaacataatctgccg
caggtgaaggaaatcccatgtttacgccctctcttgaataccggataaaa
acacagtataaatactgtatatccatccagcaaagaggcaatgagcaatg
ttcgtggaactcgtttatgacaaaaggaattttgatggtctgcccggtgc
aaaagatatcattctgggcgagttaactaagagagttcaccggatcttcc
ccgatgctgatgttcgggttaaaccgatgatgacactgccggcgatcaac
actgacgccagcaagcatgagaaggaacagataagccgtactgttcagga
aatgtttgaagaggctgaattctggttagtgagtgagtaaagattttcaa
tgcccgccacagttacgtattgattatgctgtggaggatattcattttcg
taaacgttggtttgggagaagcggcaaaacggaatgtgggaacaggggaa
aatcagataccagatatgtctgcatttccatctggcaataactggtttca
gttaccaagtggacatatcgttcagatatttccatgaacgttcttggtg
cagatgctaatggcacgtcagctaattaccccattgcttttccaacaacg
atgattgctgtcagtgctctatggtctgatgggactgtagcaaatgcacc
gacatacaagatgatggggaacacgactaacagaacaactttgacgataa
aagtatcagccagctcaggtacttacgggacaatgattattgcggtggga
cgataaatatgaataaatacagttactctccttcagaaaatgccttttatg
ctgttgcgttaaaaaatacctatgaattgagtggcacatggccagctgat
gcattagatattcctgatgacatttctgtaaaatatatggcggaaccgcc
acaagggaaaatccgagttgcaggggaaaatggttttcccacatgggctg
aaatacctccaccatcacatgaggaacttattgaacaggccgaatcagag
aggcaattattgattaaccaggccaacgaatacatgaacagtaaacaatg
gcccggtaaagccgctattggtcgtctgaaaggcgaggaactggcacaat TABLE E-continued Phage 3 Genome Sequence
SEQ ID NO: 134 ataattcgtggctggattatctggacgcactggaactggtcgatacttcc
ggtacgcccgatattgaatggcctacgcctccggcagttcaggccagatg
acatccggcgcggtgctggtatctgttgcagtcaccgcgtcaatgtaatc
cagcacggcgttaagtcgggttgtttctgcctgagtcagtttccgtccgg
cctgtaatttcagctgaatcagactaatggaagccattgctgcatcaatc
agtgattggcgctgtgcttctgccgcttctactgaggcaccgtgttgtgc
ctcagtatctgtcacccatttctcaccatcccatttatcatatggcgtta
acggtgaaagcgtgacataaccgtttttgatggcaccgatataatccact
gtaacagctgcgccattttcgattgagtaaacagtctcattgcgatggtc
ttcctcatggctccatcccttacctgtaaatactgccactcttcccggaa
tgttttcgtccgggtcaataccagtggaacaggcgggcatacttacgcca
gtattaatatattcatcagaccagcccgtatattcagacgttactgcatc
ataataaaaacaacgcatatcacccggcactgcagccagcccattttcat
caaaaacaggtttcattatttagccctcaccagaaagttaaatgcaatat
ttcgcggtctgacagcaacaaaattcacaccatcacccacagagttactg
ttgaaattaaatcgtgaaaatcctggctgatttccggcgatgccatcatg
aaagttaattgcgtgtccagcacctccgcctatattcccggcaaactgag
aaaagtttgtagcttcctgccagcttaataattcgcgaccaccatctgca
cctcgcccgtcatcccagacacgaatgaaatcaccgcgggcttcaggtaa
taccagcgaaggaaacactttcgccagcacaggataatcagtggcagaga
atttcgcgccgttgaacttcaaaaacaccatactggaccagctgtcgatt
acagtatttggcattgcagcggacggccagaagaacggaacgccaatagc
tggagaaccttctcccaaaccaaggtttgtgcgagcgtctgcggcattcg
ttgcgccggttccgccgtctgcgacagtaaccgcaccgttgctccctttc
tgcgcaagtttaccgatgcctgggatggttacggcggtgccgttgatggt
aactgtgatgctttggtttgctgaggtggtggcgaacgtctcccacgcgc
caatattctcgtcgtactctttgatgagctgtgacatggcctgcgccagg
ccgtcgactgagatattgtccgacacaaggattccatacttctggccgct
cagcgccggggaaactgctggcgtaaccgtcattgacgtggcgctgttca
cggatgaaatctgaaacagctgcaccgggttagacatcacgataatcgtc
tggccagcgcggacctggctggcgggagctgtccagtttgtgccggagcc
ggttgcggtatttccgttaatagagatagttccggtgctataaatcataa
caactcctaaatttagacaacatgaagcccggagaggtatataaccctca
ccagaaataatttctgaattggtttttaatacatgttgggcaacgccagt
gttggcatagctatagttgtatcaaatgccattgaccacccacccaaata
ataattgccgactactttattcctttctgctctgacattcccacctgtca
ttacaattcctttatacctaatatttccgtaaccaccaacgtgtcgacag
ttagccccggtataaacaatctggcaaaattcatcaccaatattcaggtt
cgcattggcgatatttattgtcccatcaaaaatgaatggcttcgtgcaag
taagaagacgtttgcgttgacgattggtttattcaatccatcaactaaaa
tatcatgtaaacgaattgccataacatttcccactttattttacttactc
aacacaacaagtatattaaaattgaaccttgtcaacaacacaaaggagtc
ccaatgaaactcgctctaattatgctgccattatgtctgtccctcactgc
atgtggtaatggtttaaataccggtaaaccaaattccggtgtcattccaa
aacctttggatcgagatggtaacggttctttaatttatgataccgaaaac
cttccaatgacggggcagtggtgtcacgagattgatcacgaataccgacg
aatcggtagcccttctaactgtgttatagactactaaatattaacccctc
aaaagaggggttaatattttaacctgtgaatgaaccagatccgtgtgata
ctatgatagtaggcgaagaaattgacgcacccctgttattttgagcggac
actttaatacgcactgttacgtttggacctgttacaaccgcagaatgcat
gataagtctctccatgtcttgcacggatgaaccactctcattgccgttaa
tgtcgattgttcctgcaccattacctttaacgtttgctataacacagacg
tgtcttgcgtgcccagaactggatgaatcattataagtcattacctttc
taaatatccgtcactagaccgactcacattcgtccctgtgtgcatatttg
caatgtccccgataaaactttgggcttccacagtccctttgaatttaccg
cttgttgcttggatctcaccagtaaagctaccgccactagcatatactac
acctctgacggtcacattgttgaattcagcatctccagctttattcaact
tccaaccagcagaaccagctgcatagttgttggactggatatagttaccg
atttttgcgttctcaatggtgccgtcctggatgaagctggcccggatgaa
tgtctgcccgttctggatcacgaacggcaaagctacgctatttccggctg
ccgtggtgacggcgaagcggtcagccaggaagataacctgcgactgcatg
ccggatggcgtattctccacgccgatacccatccccgcggcgtaatactg
cccgttgctggagacaccaaccttgatgttgtacatcgcgctgagttcgc
cattaacgttggctatagcctgagcgttagtggtgatggcggaggtatgc
ccgttcacggtcgccgtgatgccgtttatctgcgtggcggtggcctgctg
atagtcggagagcgtctgattcaggctgttgatggatgccttgttgccgt
tgacgtccgtctgcaggctcagcaatgaacgtgctgtggcttccttctca
ctgacgatcacctcgtcgagacggtccagattcgcgctgttgccggcgac
cgatgcagaaagggttttacgcgtggccacctgagcgaggttggcctgga
ttatcgcaattgcagagttcttcaccccgcccgtcatgccgtccatagaa
acgctgatgttgtcgattcgctggcccagggcggtatcagccgtcgcaac
ggtctgctcaagctgactgagtgaagacgaaacattcccgaccgtgctgg
aaagctcattaacgctggtctgaaccttcccgacgtcctgggcattttg
gcgatatctttcgcttgctgctccagttcgtcgttggcctgtttgatatc
gttagccatgccagcaatttttcgttgctgtccaccgcgttctcgatca
ggtctttgaacgtttccgactctttcatatcctccagaatgtcattagtt
atttcgctgacatctatcgaggacgtgcccatgatccagtcggtccagtc TABLE E-continued

| Phage 3 Genome Sequence SEQ ID NO: 134 |
|---|
| cccggcgttaccgatacggtcaatcaggcgcgcgcggtaccactggcgaa |
| cgccggcaggcatggggccatgctgataatctgcagccgggtacggcacc |
| aggaccagcagttcaggattggcgtagtcggcagttgtggcgcgctgaat |
| ctctgtataggccgtgtcgcctgagccatccggaaatttccaggtcaggt |
| cgatatgccagaccacatcttcggtcgccaggaagttgagcggagtaccc |
| ggttttcccgttttaccggagagataagttgtttcaccgtatccccatgg |
| tgacgacgtatcctgcgcattcagcgcccgtacgcgcacgtcatagctgc |
| ccgaataaatgccctgaaccgagaaaccctgcgcgctggtaaccggaacg |
| tttatccagtccccgttgtccttacgccactgggcaacataccggattgc |
| gccctctaccttatcccatgacacgtccaggcttgctacagtcagcccct |
| gagacacatgatcgctctcagtcaccacgatattcttcggagcagacagg |
| acgcttatcggcgtgacggtgatcgggggagactcgacccgaacgccgtc |
| atcgatgtaacgatatttgtttggatcgtgctgaacggccgtaatagtga |
| aaccgcctgtactgtcgtcgttagccgcgattgaggtgaccctgaagtac |
| tgtattgcgaggttatcactgtctatcgcccaaacagcgcccgccacagg |
| aacctgactgaatgccgtagccaccgtcaccgtttttttatcggcgctca |
| ccgcgctgattgtccgcgtctgggcttttccgtcgggaaggttaaccacc |
| agccggtctttcgccgcgtagtctatttctcgatcgagggtaatttggcg |
| gccgttggccgcgcttatacggccccccgttctccttaccagagcggaaag |
| gatcggcgacaccgataatttcagcgggcaaagggatataaccgtccagc |
| cccacgccaaacgatacggtcccgtctttggcattggagagcaataccca |
| gcgaccgcgtcggtgcgcttcactttgcgaggtgagccgattgcggtca |
| gggacgtctgccggacgtcgtaacgttctacaagcgccgaatcgtaaacc |
| ccctcaacggtatcgctgtaatggttctgcggatcggaccaggacaccag |
| gcaggagctgtagcgattcttgtatgagccgcccgcataagtaaacagcc |
| catcgataacgtttgagacgttataaacccagtcaacatcgtcctgcggg |
| acgtctgcctggacataaatctgatcgtttccccagaacgttattccacg |
| aaataccgcggcgagatcgttaagtacctgccaggcgtcctcctggctct |
| gaatgaaaacgttgcaggtgaaacgcggttcggtgccaccggcccccgtcg |
| gaaaccatttcgtcacagtactgggcgattgaatacagcgcccacttatc |
| caccatggacgcatccacgcgcgtgcccatgccgtaaatttcatccagaa |
| ccagatcgtaaaagatccaggcagggttattggaccatgccatttgaac |
| ccgccggaccatgaaccagaataggttcgggttttcggatcgtaattatc |
| cggaaccttaatcagcttgccttttatcttacaggtcactttcggcgcgc |
| tgccgttgaattggctgctgtccacttcgacatacaggagcgctgttaaa |
| ggataacgaagcttgctgtcgatgacttccgcatacgaaaacaccttgaa |
| ggcgttaaccagtttcgaatttgatccgctggcatcagccgtaatacgcc |
| tgaccctgacagaccagccggacgtggattttggcagatcgatacggtgg |
| tcacgctgatattccgtcgtggtctttccgtcaaacttgccgtttacaac |
| cgttttccaggcgccgccgtccgttgataaatcgatcgcatactcggtga |
| ccgtgcccaccatatcgccattatctttatagagatactggaccggaagg |
| ctgagcttgatacggatggcatccagggaaaggtttgtaaactggcgcgt |
| ccagggcgcggtggtggtgacagttgtgcccacggccagctcgttgtcga |
| cctggggcatcccggcaatataggtctggtcctgtgtgcccttgcggaac |
| tcccatttcacgccgctgaagttgtattccccgctgtcgtttgccagcgg |
| cgtatcgttgagaaaaatgttctgagcggtcaggtcgccctgtatttccc |
| cctcagaaacggcaatgagcatttttaatttgcgaccgacagcagatcg |
| tcaggctgctcaaccggagtatgtgaactgccacctccccctttggcacc |
| ctgcaggatggtttcttgtttaagaagctgcatttttttcacccataaaaa |
| aaggtgccgaagcacctttaagttagtggccgctggcctactgctgatcg |
| ctcgagtacataccggcgctgactatcgctcccccctgcctcagtcagacc |
| gtaggccagggggacaggatgccccatagcgacggtattgaccggcgccc |
| cgaaggcgtagttaggcgtgttgtccgtgctggaggatttacccgcgccg |
| aaggatggctggggcgtgagcatctggacaacgccccccagcatcatcga |
| cactccgaccccctgtcagaattgacgtggcgctgatagtcgttgcactca |
| tcgccgcgcccccaggctgccatgctcgcaccagcggtaaagaatgcagcg |
| accagcgcaacagccccgacaactatctgcaggacgcccgaacttttggc |
| cccctcataaacgggcacgatccggtacacgcttccaccgcgggtcatat |
| caaactcttccagcccgatattgttgccaccgttaaaaaaggcgaaacgg |
| atccccttcatatgagcttcagacatatatttttttgaatccgggaacctg |
| tgaacacatggccctgagcatctcgcgcaggtcggcaacatcaaactgaa |
| cgcgtttaccgaatttttttgccatttaccttcgagaataagcgtctta |
| accatgcattctgtccttatgcctgaccacccggaccgttctgtcgcgat |
| aatattttccataaggcgttcgcgaagaaaggtgcccgaaaagatgatgg |
| agaatgatgttatcacccacatataccgcggcgtgattagtcaccgatgc |
| ctgcacactcatcatgatgatatctccgggctgcattgcaccggcggcaa |
| tctcaacgaatccctcacgctcccagttgtcgtcgtagagacgctccttg |
| ccgctctcccaccattcgtaaggtactgaataattgccgagaacaatgcc |
| gtattcgcgcagataaaattcacggataagcgaccagcagtcggcgtaac |
| ccagcacccactgccgcccggcataatcccggtcttcacgcggggaaatc |
| gtacaaaaatccccgtccggccaggacatgatcccccactcaatccccga |
| ccagtcgcactggatccggtccagctctgagggcaccagccgaaccacat |
| ccggatgggaatgaatgagcatgatgatctcaccgcgcgcgcgggcagcg |
| agctggtcttccggggagagcgtgaatgtctcctcgggtttatcggcaat |
| gttgcggcagggaataaagatttgttgctggcctgactgaacaatcaggc |
| cgcaggcttctttggggtattcagcagcgacgtgctgacggatagcatcc |
| agcaattttcacgcattttatttcccctgcaggtttgcagccggaaaa |
| ccgccgaacggcagcggcgcatccgggccgtgacgatcctgacaatcctg |
| ccggcggccgccacaaacatctttcgacgggtcatcggtcggtgtaccgt |
| ctttggtaaagtatttcgtgccgttgtaatcgcatccggtcccgcttcgg |
| taccagccccgcatacaccaggtgcagacaggcgtaatctgccgtgtcgg |
| cagctgcaggctctgaatatcgaaaggagaacacagctcgaaatcaacct |
| gtacccgcgtctctgcggttttagcattgacgtaaaagagctgtaagcgc |
| tcatcggccgggctggcacccggattaccgtttttccagttggcggcatc |
| gagatacttcgaaagcgtggtatggattttgaccttagccctgaccatat |
| cgtcatattcaagacacagcgcggtgacatagtttccgacgttcccgacg |
| gacagcgtgggcgttggctgggaacctgtactcgataactccatcccctt |
| aagttcgtagggatggggatcgtactggtttccctgccagataatggcgg |
| gcagattttctgcggcgaaggctgcccacccctcttcctgaatattgtgc |
| gcatgaaaacgcagcacctgatccataccgaattcagtgccgtcgatctc |
| aatcagctgaataacgctgccgggctcaagctgttgtatgtctgccgtaa |
| aactcatactccccccataaaaaaaagccgcccggaggcagctttcagtg |
| tttttcgagaaaatcagggcgcgaacgcctgttcaaaagtgaaggccaca |
| gtggctttttttcccggtagggaaagaaacgctgaacgaatcggccttcat |
| tctgaacagctttttttcaccccatggagtggtccaccagaacgatttag |
| taacgtgagacatcaggaaagcgcgcagcgcagccgcctcctgtctggtg |
| cccgtccagtccaggttccacgtttcctgtttgtcgttgatccccatccc |
| cgctatctgtttgtagccatccccgaactgggcctgcagcgttcgggctg |
| tttcagtgccctgcgctgtttttcgcgtgcgccaggtaaacgtgtccgtc |
| actgtgtcctcctcgaataaagcacgccgcccgcggacatttcttttttc |
| agtcgctcggtgattgtctgctgaacaatcgcctgcagctgtttcgccgt |
| ccccgtggcgttcgcctgatttatgcttccgtcactcccctgctggctga |
| tgctgactggggcataaacactgatcccgcccatgccagcaccggctgcg |
| ttcccgccgccgaccagaccacccgaggcatacccgcgcatcaggcgata |
| gagattagccacgccgatgcggctggttgattctttggtgaagacgaatt |
| ccccgcggtgaacgataccggctggctcgtacttgccgccgtgcccggta |
| aaaccgcccacgtcaaaaccctgtggccggtatgacgggaccgcgaatga |
| ctgaccggcagaggaggttttcgccccgccgctaacccagcccattgcac |
| tctggatggtgtaagccaccagcagctggttgataacggacacaatcatt |
| ttaaggatcgagctggtgaattccctgaagctcgccttcccggttgtcgt |
| caggctggtaagctggcccgccaacccgctgaacgtagcctgagaaatct |
| gctgaacggagctgaaaacgtttgtcgctgaatcctgatattcggcccaa |
| ccctgtttcgcaccggccagccagtttgcacgcagggcatcttcagcttc |
| gaacgtcgccctttgctcttccagaaccttttgctgcgcctgagggttgt |
| acgaatagctttcgctgagacgctgcagcgtagtttgtcgcccggcttcc |
| cgggtggataacccctcagactgagcctgcaggcccgccctggcggcttt |
| ttgctgctgctcaaacttcacggcctgatcggccagctggttgagctttt |
| gctggctggcaaccttatcgcccaggtcggccagctgccgcttgtactcg |
| agcgtttcttctttgtgcgccagcagggatttttcctgcgccgtaagctg |
| acgacgcccagcggcctcctgcagaacggtgaactgattttcagtttgcc |
| agagatcctgacgctgtttacttatgacgtcgttcacgctggtatgctgc |
| tcaagcgttttaagctgggcctgaagggtgagaagttcggcctgcgcctt |
| ttcctcggctttgtccccggcgggcgttgagtagcttttgcctttcggtg |
| tttttggatccttccactgcttttcaatcccggcgcgggccgcggcaatg |
| tccttttcagtccacagcgtggcgacaccgtctttcgcatcctggcggtt |
| tttctcaataagctgactgagctttttctctgctgaagcccgcttttctg |
| ccgccgtcgcgccggactccaccagctggttaaactgctgctggctgcgg |
| attgcctgagcctgctggtccgttcgcatttttttcccgcgcggctgccag |
| cccttcctgggcgtattgctgatcggcaagatcgtaagcctgctttttca |
| gctccacctgctggcgcgcgtttctcagcctttccgcatccgctttctgc |
| agaacgttgttaccggcataatccgggtcgaccttaagattgctggacag |
| cgcgcggtactctttctctgctgcctgccactcagcaaaagagtcctggc |
| gcttcatcgcggtgtcaggattacgcccgacgcccagcatcgcatcccac |
| gcaccggaggcggcattcttcacccagttccaggctttttcgagggatcc |
| gagattatcctcgaccgcaccggcgcgctgaatgaccgcgtcggaatatg |
| cccgcatggccagctcggcagccttctgagaatcccccagcgcctgagca |
| gaagctatctgttcatactgggtggctgtcagaaaatgaagggaatcgtt |
| gagcgtcgcgaccgcgttaaccggatcatccttcaggcgtttaaactgat |
| ttatggtttcgtcaacggcctgcccggtagcctgctgcagcctggcggca |
| acattgctgaccatgctgacgtcattaccgctgaacgcgccgctgccaac |
| gacctgcgccagcacgcctgcagcggcatgctgagtgatgccattacctg |
| ccagcgagcgcgccagcgcctgcagctgccctgacgttttccccgcgtag |
| ttcccggtcaggatcagctgcctgttaaattcctcagactctttgctgcc |
| gtcgtaccaggccttacccaacccgaataccgccgcggcaatccctccga |
| ccatgctggcgatcccaagaccgcgcagtgacagaagctggtctatccac |
| cctgcccggttagccagcgtgatcccggagccgcgcagcgcgccgaagtt |
| accgcgcatgacctcgccgatcagtattcccagttcctgccgggcggcgg |
| cactttgcagccccagaccgtgcgtggcgactttggcagcttcgagcttg |
| cggatatagacttcagccgcatcgctggcaccgacctgcgccgccttcat |
| gcgcagtagctcggtaccggagagcttttgctctgcaacctgttgcttca |
| gctggctgaggaatcgcgtgcgcgctgcggccgatttttcctccacgatc |
| tgcagttctttttgacgggccgtggtgcgggaaataagggcgagataatc |
| ctgctgggttatgttgccctgtgccctcgctgcgcgaaagcgcgcctgca |
| cgttcgcaagcgactgtgtttcaccattgagctggcgtacgccgtcgatc |

TABLE E-continued

Phage 3 Genome Sequence
SEQ ID NO: 134

```
tggcggaaaaatgatgccgcaagttcatcctgtcgacgggcaagcgcagc
ggcctgcccgtcattctcacgcatgcgctgattaagctcggtcacgcggc
ggtgagtttcatcaacggactttgaaacgttctgccagtctttggtaagc
ccttccgttgcggccgactggcgggatttcatatctgcggcagccgccgc
gccagcgtcacccacggttttaaacgcagccgcctgccgctctgaagcgc
gctgcattcgcgtctggactttttcagagtcctcagccatcccggttagc
tggccctttatgcgggcaacctgctcactaaacgtggcgctgtcgacgtc
aaggttgatgaccagatcgctaatctgctgggccatatcggatacctcct
gttatcccctcagctgcggccatcagcgcatcatcatccggctcgtcatc
gctgatgacgataccggaaggagaaagcaggctgaaatgtgcgggggtaa
gttccgggtcgcggaagaaaagagtggagatggaataaagcagctctgag
aaatgcgcatcgagctgagcgtcctgaaaataatgctcccggtagaactg
gtgccagtcgcccagctcagtggaagtcattccagccagcatggcgcgcc
agtcgggtcgcccgaactcgcgcgccagattcaggacaaacttcagctcg
ctggcaagggcttttccgccgcaacgggttctgcgctttcggcctccgct
ggggcatccggatcggcagctttgtcatcctcaaccggaacgagcatgcc
ggagagcagctttatttccatttctgctttaccgatcgcctccggcggcc
agccgctaagcacctgctggtaaagcgtctccacatccgtgccagccgga
tcgttatgccacaaagacatcgcaatcaaacgcgcaccgcagcgaatatt
tgagccaatcagcctggccgtcatttcctgatcgctgatgccgtcgctgt
cagcgctgacggccttttcctctgcggccataaacgtgatgtactcaata
cgctgaagcgccgacagctcgaagatggtcagtgattctttttgccaggt
gaacttctctttttcagaaacatgcgtccttccttacgctgcagttacg
gtaactttgcagaccgcaacgaaattaccgtcgctggtcataacaataac
gtcagcggtgcctgccgccacgccggtgacggtgatcgcattaccgctaa
cggtgaccgttgcttttgccccgtctgaggttgccacacggaacgaggta
tctgaggcactggctgggttaaccgtcacattgagcgttgtggttgcgcc
gacggccacgcttgccgtggctttatcgagcgtaacgcctgtcacgggga
tattcggggtcccgctttcttctgccagttccggcttgccggtattggta
attttcgctgtacgggttatgacctcttttgccggaatggctttacccag
gctgctgcaccagccgcggaaaacgtcgacggtaccgttcgggtatttga
ttttgtaatagcgtactgagccatcaataaaccatgcgacaaggtctttt
tgcccttcttcgcccggcttccaggcgagggtgaacgaggtatcgccagc
agattttgccccctgggccgtcgcgttccagtcggcatcctcgtcgtcga
ggtaagtgtcgtcatacgattcggcggtcatttcgcccggcgtcagctct
ttaattttcgccaggcggttccagtcgatatccgagagtgggttagcgaa
agcgttgcccgttccggtgtaaagccagagggtggtaccggcacctttca
caggggccagcgggtttggagtaggcataagtacctcttaaattgaatag
gtgattaagtacgtgaaatcgactgaaccccaggtggccatttcatcatc
ccgctgatagtcataaccctgcggggtgaacgtctcgaccagttcggtca
gacctgggatgaaggccattgccggatacactttctcttccatccaggaa
tcaagcgcgctgtcggggctggaggctttaagaaatacctcgatgtgaac
aaccgcctgccacgaatcttcgtcaagcgaatcgccggtgtactccgcgt
cagaaaggtatacagccacggcagggagatcctgctcttcaagaaaaaca
gggcgcccgtcaaaccaggtgaccgtgtcggtgatctcggctttcagttt
ggccagaatggctgcacgaattgcgctgtgtctgttcatcgcttcaggtg
gatcctcagttggtttttcagggctgcggaaagttctttgggcatatcgc
tttcaataaggcgctttgaaatagcggtgaaggccacggtgagcggtgtc
tcaagaggaactttgaccacatcaatcggataacgggcctgacctacgcg
ccgcatgacctgccagcgcccgttcgcaagctgttggataaaagcgttac
gaaaggtatagggcccgatttaaggacgctgcccgctccgtttctggcc
ccttttttacgcgagagcctgacgcgcgccgtgccgagctttatcgcagg
aagattaccgcggttgatttttatcgacgcgaccgggcgatcgtgacggg
ccttgcgcagacgggaacgctggcggaccagacgaaccggaagcccctttt
ttccggttatcatcaactgttgcttctttcgctacagctttgctcccctg
gcttatcgttcttctggccaccctgttaagtgcttttgcggttgcctcag
gaacgattaaccggctgaggctgttcaggttctgaatagccctttccagt
cctttcacagacatagcgcctcctcattcgagatggatgcggggttttcc
gttgaacatgtcatagcgggtaacgatcaggttcttaccgtcgtagtcga
cgctgtcgtttcggcgtggctggtaaagctcagagaaaccaccagcgaa
gtacctgttcccgacaatggccccatttcctcgagttgctcggcgggaac
aacgtcatagctgctgccattgatgatcgctgtctttcccatctttttta
tagtggccgcgtccatgcgcgccgccatccggtcaaaggagttaggcatt
gatcttaacttcaacaacggtggtgtttgcccctgcatcttcccaggcga
tgcccgcggcaacggcgtccgtttcttcgatcgtgattttgccgtccttc
agatacacctgcgccccggcagtaaccgcatctgcggatacttttggcag
gaggaaaacaccctcagtaaaaccgtccccggtatcgccagccgggatat
cggtaattgccaccgcgataagttttccaacaacaaccgggtcgccgctg
tgaacatcggttgcaccactgtttaccagagggatcgttttcccgtcctg
cgcatagttcttagccataacttctccattcagcccctttcgaggctggt
ttcaggtataaaaaaagcccttacgggcgtctgtttgtcaggactgtttt
ttactgaccagaggatttggtcatgccgcgatagtccagcggcgccacgc
cagcatcaatacgcactttcgtggcgataccatcagtggtgaagccttcc
tgctgatcgatgtatggcgtgtcgacgccgttgagataagcgacctcaat
ggtgtcggtgcccttcgcggcagccagataccaggctttcgcatcagctt
catccagacgtggttcggcaatgacttctgcaaagttctggataggtta
acgatcccggcattgatgtctgcacctttaacactggccgacttgatggt
```

TABLE E-continued

Phage 3 Genome Sequence
SEQ ID NO: 134

```
ctgatttgccagagtttccagggcgacgggcaccagcatgtaggccggac
ggatattcagggttcgctccccctccttctgcagacgcatcagcttgcgc
gattcgtccaggctggccacagaaattgcacccgagctcaggttcttgtg
atcggcatggaacagcgcctttccgtctgagagtttcgggttttttggtca
gaatggcgtaaaccagatcgccaatcgttgattcgccgcgcgccccatct
tcatcggtacgtcggtaagctggttcagatcgtcgttgatgatcgcctgg
cgagttactgagaagatttcaccatacgtggcaagcgcgatggtttcgcc
tttgtcactggtagtgatgtacttgtactcagccccttcgcgaacctgtc
gcagagaagggaacccacccataccgacacgatgcgccgttttgaagtcc
gacagctggcctttttttggtccactgctcgaaggtttcctgcgcctcgtc
ccagccctgaatcagcgctttgttcgcaacatcaagcagaatgttgccaa
agtcagaggtgctgtgggtcagcgccaggccaaccatctgcatcgggttg
tagctggccacgccgatacctttttctgtcagggccatacgcgcatactc
gcgcagcgtcataccgttataaacgttatcccgctcctgaccttcgaacc
cggcacgcgccatcagtgcctggcgaataccatccgcgacgaagttaccg
ttgcccgcatgaatatgcggctgagtggttttattggacggcgtggccgt
tttaccgagttctgccagcagcaaatctttcgccttatcgacggagcaat
cagggtcggccacacactgattctgcagttccatgtgcttattaccgaac
atggcaaagagatcgccgatagcgttaacacgggttttctgctcagccaa
cacctgcgcgcggatcgcattttcatccggtgccgggtctgttttgcct
gcggtgcctgaggctgggtaataaccgggtcacgctgggtagtgttgcgc
ggcggggtgatcatgttgcgaatgcttttggcatttttcaaattcctc
aatacgttttgaatgaatacaggccatagcctgaaggatggtgtcacct
ggtcggcaaaacccagttcaaggcactcgctgccgttcatccaggtttcg
tcctccagcattaccgcaatttcttcggtggatttccggttttctgtgc
ataagccgggataagaacggattcaaccttgtcgagaagatccgcatagt
cgcgcatatcgctcgcgtcaccaccagcaaaccccccagggcttatggatc
atcatcatcgtgttttcaggcatgatgaccggattgcctaccatcgcaat
caccgaggccatggaggccgccagaccgtcgatatgtacggtaatcgccg
cgccgtggtgcttcagcgcgttataaatagcaattccgtcgaagacatca
ccaccgggcgagttgatataaaggttgatgtgggtgacgtccccaagtgc
ccggagatcattgacgaactgtttcgccgttacgcccccagtacccgattt
cgtcataaataaaaatgtcggcctcactgttattgctggcctgcatgcgg
aaccacgaattactttttgcgctggctttcggacggtggcgcgcccggtt
ctttggcttcggcactggtgcctcctttatcattggcggggtcggtgtca
aacaccaggccctgttcacggttctcgtcaacctcagctttacggcgtga
cttaacatcatcccgggttgcgaccgctggcacgtatccagtcggattcag
tagcagcaccgccgcggatctgcgttttccaggcattcgcttctttaacg
ggatcaatccacggcataacgggcccccgaataaaccgcgttataaagcga
gtccatatcaatgcctctcggcagcttgatttctccggcagcaatagcca
tcttgagccaggctcggtacatgggccgggtcactgaaccgatgaaccag
tcctgaagaatcagatagccgtcggttgactcgacaagctcctgccgctg
ggcactgtacgttccgttgtagtttctggatgtgctggaaaagctgaggc
gactgccggcggacacggcacgcagctgtccgttacgaaaagattcgagg
ttagggttcgggcgatcggatttaatcatcccgatttcttccccggcctg
cagttcgtcatagagcataccgggctgaatcatcagctcgcggtcatcgc
tgcttgaatcagaatcgaagctctgtccgtcgcctttttgatatacatg
ccgagtgccgcagcaattctggcagcagtaagctccgagtcctcgtattc
tttcagcgcgctcagacgcatcagaacaccagacaaaagagacgttccgc
gggtctggtgcaggcgtcgggtgaatttgagatgcagcatgttctctgca
tctatctctttggtatcaaactgacgcccggatactggcaggcttttata
gacctgatatttttttcgggcgtccccagttatcgacaaaaaacgccctgat
tgagctgggtggcagcatcgctgttcatcggcacaaagtccggctccagc
gcttccagccagaacggcacgccagcaaccggctgaagaccatttccggt
accgcgaaccagctgagcaaatacctcaccgtcccggagccacgttcgca
gcatcagccgctccagcattgggcgggtaaactgggttgtgacatctggc
cttacggaccattcgcccccactttcggcggatatcagtggccagcttttt
agcgatcttcccgttactcagcatcggatgcggttcaactatgatgccct
tcgcacccaccaccctttcttccagcttgtcgaaaacgccgatcaccaga
tcgtggttgttatccagccagcgcctgctgcctcagcgaaaccgcccc
catctggctgagctgatcggctgaacgatttccttctgggctttgtggg
tacgcgtttgctttaccgcctcatacgctttaataactgcgcgggcacgc
aggcgtgaggctttccagcctggtgaaaacaggccaatcgcatcatctaa
aaaactcatccaaacctcgccagcctgtagccgggtcgcccacggcgttt
gttattgagcgttgccagtcgtcgctcccattcctgacggcctttctga
tttccgacaggttttcgagcgtcatctgctgcccgttgaaagtgattgat
ttcccctccagaacagacagctcggctgcagcatagcggtcgatcatgtt
ttgaatatctgctggattcacacccaacctcctgacgaagaccacggatt
agcctgctcggttacgggcttctcacgttttggtttggtttagatttcg
gcgcaggcggcggggatggcatttcgccagcttccgtctgcgtgtcctcg
atccacgtttcccgccgtgcccactcaggagctgacggccatttgatttt
ttcgtaaccactaaggatggcgagcgcgtcggcataaacgagcaggtcaa
atgcttcgtttgcgccccggccgggcttactccatttcccttcattcgag
cgttcctcatacgtcagttcgtcatagaaccagctgcccagccaggcggg
gaaatgcacatagccagggccgggtgaatcacgccacagcgcattattca
cccggtctttaagggcatcggtctggagaagataaagaggcacatcacca
gtcgcctgtgcgcggcgcgttgatctgcccgtgttgtcgggaaacgttcg
```

TABLE E-continued

| Phage 3 Genome Sequence<br>SEQ ID NO: 134 |
|---|
| ctggataagtttgctgcgcctgacgctgtcccctttgaagagatagatac |
| gcttacccagcccctcacggcgacatctgcgccagaacttgtaggcatta |
| tccgtcacgccatcttcgcccctgagtccacggccatcgacatcagccg |
| catgccctttgatgggtcagctgcgagcggccacgttttatcaaagacgt |
| cagtgagtaaaagatcccagtcctccggatagctcgccggatccacctga |
| atgctttcaccgttgccgtcgcagcgcagcgaatgccggatgttgtaacg |
| gtcaactatccagcgctcacccatacttccataacccgtaatctgcacaa |
| caaagcgccggttgcgcccggcctgcacgtccacggtcgcagtgagaaac |
| tgcacgccgttcggtaccgaacgttttgggacgtcttcggcacgctgctc |
| gagcaattcacttttacgctgctccatgctggctcgcggcaaatagggcc |
| tgccgaaatcggtgttgatcaccgtcttcagggtttcttcgctgcgcgtg |
| gattcatattcctgctcggcggtcagaaacttataaataagctgcgccca |
| ggtctggtaagcagctgccggaccttccatccagaaggaggcaatacggg |
| aacgacggccatcaccgctaaccaggcctttcctgtcgatggtttgcccg |
| tcccggagccagacacatttcatgttaagcgcacgcttcatgtccggtgt |
| gatcctgcctttacaggcagggcactgaagaaacgccgcttcgctggcaa |
| gcacaggatcgctgctgtcgcggtatccggtcatattgtccatttccggc |
| tggaaatattcgccgcaatgcgggcatggccagtaaagacgacggcggtc |
| accacggttatagagcgataaaattccggtggtcggaggggcttcatggg |
| gcgtggagcgccgccattttgtgtctctgatatccctcccgggcgagctc |
| tcaaccagcgtcatcccggaggacatgaatgtcgtggttcgtttcgatgc |
| cagtgaaaaagcatcccctccccgtcgatatcttccggaaagcggtcat |
| aatccgtcagcgccacacttttatagtccgaggacgacatgatattgacg |
| gatggccagcccagcttcagatagttaccggcgcggaatgtacggtcgta |
| gacgttgttatcgttacgtcttgggcttagccgggttttaacttcagggc |
| tacagcgaaaagtacggtccaggcgtttttggaatgctcgcgcgctttt |
| tcctcagatacctgaattacaagcatatctgccggatcgcagacaatgtt |
| ataaacgatccagccgtcaatcagcccgatggttttacccgttcgcgctg |
| ggcccacaaacacaaccgcatcgtattcacgcgatgccagacagttcatc |
| ggctcaatcacatagggtgccagatccggatcccacggaactgagtttcc |
| cgcccccattggcacgcgcatataagtactgaccgcatcggccaccggca |
| tacgacgcggggctcgtaaaataccggaaacatcgcggcggatgtccctg |
| gcggatgcccgctttgccatcagtcctcctcaggctgctcctcctctttt |
| ccagcgtcctgcaccttctccgccatctggtcgcgcagatcatcgataac |
| gctttgcacacgaactaccgcagcaggcgttaaagcacagtcgcgctcga |
| gcacatccgggagggtttcaagtaccatgacgacggctttcgccatcaat |
| gagaattctcgcgccacttcatctgcgggtattaactgccccgtatcctg |
| ttcgaacttcagcctctcgttctctgctttccagtgggacagcctgtcag |
| aagggggcatatcgtcgatgttggccgaaacggtagggatcatcagttcg |
| gtcagaatgtcggtcaccagatagagctttaacttgctattgctgcctgg |
| agcaggttcaacattttcagtctcgcggcaaccgtctgacggtgtacgc |
| cggttatccctgccagctggttgatattgagttttaaagtggcaatttcc |
| tggtccatgatggtgaacacttttgaacgattcgacatgttgcgaaaat |
| ggcctctaattaaatcaaagacctgcgcacatgatgatgatgaccctgga |
| tccgaaaaactagccgtttcccgcgagcacgccgccccgtggcagggtcc |
| ccctccgggagtaccttttgataataattatcaattgcacactatcgacg |
| gcactgctgccagataacaccaccggggaaacattccatcatgatggccg |
| tgcggacataggaagccagttcatccatcgctttcttgtctgctgccatt |
| tgctttgtgacatccagcgccgcacattcagcagcgtttttcagcgcgtt |
| ttcgatcaacgtttcaatgttggtatcaacaccaggtttaactttgaact |
| tatcggcactgacggttaccttgttctgcgctggctcatcacgctggata |
| ccaaggctgatgttgtagatattggtcaccggctgaggtgtttcgattgc |
| cgctgcgtggatagcaccatttgcgatagcggcgtccttgatgaatgaca |
| ctccattgcgaataagttcgaaggagacggtgtcacgaatgcgctggtcc |
| agctcgtcgattgccttttgtgcagcagaggtatcaatctcaacgccaag |
| cgtcatcgaagcgcaatattgctgctcaccaaaacgcgtattgaccaggt |
| gttcaacggcaaatttctgcccttctgatgtcagaaaggtaaagtgattt |
| tctttctggtattcagttgctgtgtgtctggtttcagcaaaaccaagctc |
| gcgcaattcggctgtgccagatttagaaggcagatcaccagacagcaacg |
| cgccacggaaaaacagcgcataaagcacttcattagcagcgccagatagc |
| gtaatgatttgttactcatggaatatttccttttaggcgtgagcctgtc |
| gcacggcaatgccgcccgagaggtaaacgcaacctaacggcatcacccag |
| gctcactactgaaagactctctttgatgtgcgcgtgcgatgcgcgtagaa |
| gactgatttatcaacctgtctttatatcaggattcattacctgactattt |
| gtgggtaaagttcgtagtgcgctgatcgtgcaaaatgatttttagttggga |
| acagttcgcaactctgtcccataaaaatcagcatattcccatctatccca |
| tatccagcgcattgaccatcgggatactgaagggagattccatcatctct |
| tagaaagatcaccatctcttttgtttcaatttgcatatagctacctggag |
| gatttatgaatgcaaggattttcatggactattaccatgagattgatttt |
| ccatctttattcgcgagagcagtggaaagcgatgacgatgtgggtactac |
| attgcgcattcacctactttgtgagcgcatggtcgaagcatggatatgcg |
| catgctgtgactgccaagatctctttggaagagataaaaacaaactttta |
| atcgaatgtaatactaaaatatccatggcgggaaacctgggaatcccccc |
| ggaacttatgaaatcacttaaaaccatcaactcaatgcgtaatgaccttg |
| cacacaatccatcaatacaaagcattgctgattcaaggatccagagcctg |
| aaggatactctgactgaatactttaaacagcatccaacggaacccagcat |
| ggaagaatcaaaactgggtatttttaacgccgagaatcaattaaccgaag |
| aagtttccttagatagtgacagttcaaaaaacagacttaagttaatcttg |
| ctgttcagcaagttaatgcaggcgttaatgcaattagttgcagctaatca |
| taatgggcgctgggataaccaatttagccaattcgtttaccatgtgacca |
| tgaacgcaacaaagagataaatccaagcccgttttgtacgggctgttgca |
| ttatcacaggcactcagtgaatgcctgctgtaatgccgctagtcgtcgag |
| ttgcaacacaccgtgatccagtgattctgaataggcgataagtccggtat |
| aaccggggataatctcaccattatcagcttcaaattcaggaattgtgccg |
| gtggtgatggtgtattgaggctggccatcttccttcgcgaaggctgccag |
| gtcttcaatctgcttagctgtaagaactactgtcatgctcattcctcagt |
| tgtaaaaaagccccgcgagtgcgaggcgatttgattgaattctcggctct |
| tatctcagcgcagccccttactgcgtgccggttgctcggtgatgagcatc |
| agcgatgagacattaaagccgaccgaaggccagcggcgttcctcatgttg |
| ccgacagagccatatcgacaagaggacgaaaactagcagcatgaatcgcc |
| tattggttattcgacagtcgcactgattcgtaaatccgctcacacgtcat |
| tcctgcccggtagctttcgtcagatcgtccagcataatatcgagctgctt |
| ctgcaaggcttccgagcatgtcggcaagcattgctgcgttggctccggct |
| gttttgcttctgacggaagtggcgagatctgcggtgtgctttgcggcgtc |
| catgtgggtagcgagttttgttgcttcggcgcgcagctgcttaacagtgg |
| tagccaggccagcagaagtaacggcagcgctcgctgcttgagcttgagca |
| tctttaacggcctcatcccgggcgattgttcgcccttgttcaatcatacg |
| agctgcggtctgtgcattcgcttcctgtgaagattccgcgctatcccggt |
| cagcccactttatttccagctgcggttcgtccactcactgccagcgaga |
| aacgaacctaccaacgcaacaatcacaatgatgcagatgccacccggctt |
| cactggtctatcccccagcacgtcagtgcgctttcctggtcccgccgttc |
| tacctgcccataacatccatccttctggcccttggtcaggcggcaatcgc |
| ggccaccgtctttaatccaccagcggatagcttcacaggctcctttcgta |
| tcgccagcattaattcgcttatagaacgtagacgggaaacattttccggg |
| gccgatgttatatgggcagaaagaagcgatacccgctttctgtggttcgg |
| tcagtggtactttgatatttcggtcaacccacgccagcgccttgtcgcgt |
| tcaatggcgtttacctgggcgcatttctcagctgacagcttcatgccctg |
| tactactggcttgccatcaaccattgttgcaccacggcaaatggtccaga |
| gtccgccgccgtcgcgatatgctgtcaagctgttaccctctttctcatcc |
| agaaactgatcgagaatcacgggtgcggaagccccggcaagaatcaaacc |
| aacgaccgctgcgctcaatttattcttcagctttagagacatagccattg |
| cgccgatcctcccgttctttccagcggaaataccagttcactgcacaggt |
| gattaccgtgcatgcgataccgacaataattgcccagtcgctcaggctta |
| accctgcaattctgtcggccaacatccaggacacctcttttgctgtttta |
| gctgtttcggcatatgccttcgctgatacaccgcagccggcaagcgtggt |
| tcctgatccatatgaaagtctgctgtaaatggtgctcattctggtcatag |
| cctcacctccgatagttcggatggcgctgtgtgtgattgaaggggatcag |
| gcaaccgggctcttatgttcaagtaaaaattaaggatgattcccggtgcc |
| tgaagatggtgatcaccacagcaacgggggagcgtggtgatcgttatgat |
| tttttcagtttttccacctcttcggtggtctgtataaacctgtctgcctc |
| cagttctacgccgatcgcccgacggccaagttctattgcagctttcacag |
| ttgaaccagagcccataaagaaatcggcaacgatatcccccggtctgctg |
| ctggcgctaatgatctgtttcagcatgtcggcaggttttcgcatggatg |
| tttgcctggataaaactgaacaggcttatgtgtccatacgtcggtataag |
| gaacaagagcggaaacagagaagcagcgccgaaggattttgtattcctcc |
| agcaattctgaatacttgcggtttaatgactggtaggtagccaccagctg |
| gtggtgaggatgttcaagcttttgctgaatatgtttatcgatggcgatcc |
| gcgtgaacagttcctgcaattttcgatagtccacttcattcggtagttgc |
| cattggcttgcaccaaaccagtgtgacgccatgtttttctttccggttgc |
| ctcagctatttctttcgagctgacacccagtgattcacgggcattacgga |
| agtaatcaatcagcggcgtcataatgtgctgctttagctctgtgcttttc |
| ctttcgtaaacatcctctttacctgtatacggtccaagatagtgctcagc |
| aaacaaaatccgttccgtagatggaaagtacgcacgcaggctttcttat |
| tacatccattccagcggcccgatggtttgcccaaatgatgtgattcaaa |
| acgttgaatcgggcgcgcatcataatctctatatctgaggccagtcggtg |
| accgcaaaacaggtagatgctgccagcaggtttaagaacgcgagcatact |
| cagccaggcagctatcaagccagcgtaagtagtcctcgtccccccttccat |
| tggttgtcccagccgttgggcttcactttgaagtacggaggatccgtaac |
| tataagatcaatagagttatccgggagggtggcgacgtaatgcagactat |
| cagcgttgattaactcaacactgtttatttttacagtatttttcatagat |
| cagtaagcgtaactctgataggctcacgttgcttttgcgctaaagcagtg |
| ggccttggttagcttgtgacctgaaagcatgagctgatggctggccgggt |
| gcgctaacacccaccagccgcccatttccacagcagaaaaccccccattac |
| tggaggcgtttataacatccgaactggtaatcagataaccccgccatcac |
| cagctgcgtaagtatgagctggcaacgttcgtggctgaggtgggtattct |
| gtgcaatctccccagccgttgctggtttatcgcttaattcattgaaaaca |
| gcctttgccgtttctgtcatatcttcctgatttagcatgtcttttaccta |
| aaattagttgcgtgacatacagataactctggttggtgataccagcaaga |
| gaagaatttgattctgcaaccaacaaggcctttaggcatcaggcaggaat |
| gagatgcaataaaaaaaccacccgaaggtggtcttatatgaatctttaac |
| gcggacttagcaaatattccacatcgtactaccgttatggttttcga |
| taatttttgcggctgggctagtaccaaaagagtgcatatagcaatgatga |
| atagtaaggaccagatcctgcaacgtttggtcactctctagctccatgat |
| atttaaaccaatattttgagctttgtccaaatgaatatgtctggcatgtg |

TABLE E-continued

| Phage 3 Genome Sequence SEQ ID NO: 134 |
|---|
| catacgttgcttggtggttgtttaactcatcacatatacgcttagcctta |
| gcttcagcgtcagcctgacctgcgaacataccagtacaaagccatttctg |
| gacaatttcgttcgcccagagaattgcttttttcacactcgccaatcaacg |
| ttggatttagttttggaacgtaaattgccaccattgcagctgcagcaggg |
| ttggcaaaaatttccgcttttgctctctcatactcctcaataattgcatg |
| agatgataacccattaaactgtggatcaattggccccaagttcgactgtt |
| tacctaaaacgatctgctcagcacaacaagcaagcattgtgccacaactc |
| attgaaatcataggtacaatcgctcggatattggttccgaactttgaacg |
| aagataatgaccaattgattctagagctgcgatatcgcctccaggagtat |
| ggagtaagatatccaatcccagactcgtatctaacccattgatagcagac |
| ataagaccatttttatcatcatctgacatctggatcagatgttgaaaccc |
| aggcccccctttttgaaggaagcctgagtaataagaaattacatttcggc |
| cagtatgtttcgataaatcacgtaagtacttgtggcgaacctcatccgct |
| ggtgtacgttgagcgatagtacccatctcacccaatacgtctatccaatt |
| tggcatgttatcaatttatcagtatgagtacagttggtgagattgctgac |
| cgttctgctcagtagtatttggtgttactgtgctgtatgaatagagcaca |
| ccacttctcacattcagatcgttttgctgagcgagaacacgcatagcaaa |
| atgctgtacggattcgccttttgaaactcttggggttgtatgcccattt |
| tttcgtaaaattcagcagcgctcatgatatgtccctcgtttttttctaca |
| tctatgcaattccaggagccatcaacacaagatgtagtagttagcagtcg |
| tcaaatacacgaaaagcctcaagatgaggcttaaaaagattctttttgat |
| aaagatttagccaaactatagcggtcaaaatgcagatttgacaagtataa |
| aaagcacttaaagcctataaataggcagtttttgagaattaaagcatctt |
| taatgaggttgaacaaaatgcagtcttgacgctgaacaggactttactgg |
| aacgtagagctaaatggttcgatttcatgaaccagttacaaaaaaacccg |
| ctcatcggcgggtttataaaacttggcaacatatcaaatatgcttcaaa |
| tatggcttatttttgttgcatttttgcaagcgtgtttgaaggagatggtgaa |
| atttacttcacatttctgccactttgagggcttcttcttcctcatagtat |
| tcaagagccatggccaacgcagattcatcaagctgggtaaaagcggcctt |
| taacccagcccagtgccctgaatagacacgcaaccatgtcgaacggtcaa |
| cgctaaccatgcgggccaacgctgcaccagcatagtctttataggtttca |
| ttatttctggttgcggcaatttcctgccctgccagccataccaggcctat |
| cagtttctttactacgcgctcctgaagggagttatcacccaggcatttct |
| gataagttttccagacgtattcacacatcatcacctggtgcttatagcta |
| aggtcaaaaccgtagcagtaccgcaaccaggcctgctggtatccactaag |
| cgcggacactgccctacgccacggcgcggactcaaattccgcatcttta |
| tcggcggcattggcctgcggcggctgcgtgtttccagcacatacagtggc |
| gcggaaagtgagttaacaaagcgtggccccttctctccttcgagttcgac |
| gagatgaattccacggcgaggggtggcatttttgtctgctggtgggtgtt |
| cactgaaagcctcaagctgccctttttgttccccccagacaggtcaggtagc |
| gcgcggcgcaattctattcttacaaaattcaggtcttgttgattcatgct |
| tctttgcgctccatacacttaagctttcgcaattacgccgatcgccagcg |
| cccgatccataaaacgcagtagcagctcaagctgcgtaccatgcttctgc |
| tcgaatgccggtacatcggcgtgtaactcgtcgtggcactctctgcacag |
| agggatcacgaagagatcatgggcttttgttgctgtcccccccataccgt |
| gccctacgatatggtgcggatcatctgctggccgtcggcaacactcacag |
| ggttgtgttttaacccagcgggtgtacgtctcatttatccagcggcgtcg |
| ctttggcctgagcatgaaagattctggagactccggatcaacagagagcg |
| tgaggatcttcttcgccttctcctgcacgaggctggttgcagaagcggaa |
| ggcacaatgtcgctttccctcatgaccgagcggatcttatcatccggaag |
| gcgtagccccttgtgcgcaacgctttccggaataacatcagccaggtcgt |
| ttctgaccatccaccagcacagttccggaagcgtcaggatatgcgactcg |
| ggaaaaccagaatcacgccgaatgacttccagaatccaggataccaggtt |
| tcctgccgctatacctgcaagctgttcggtatgctgccccgacaaagtgt |
| gatcgcaatgccagcacaggcgaatacttcctggtggtgccgcattgtt |
| gtgaagttcttgtcgtgccacgatgaatgtggccactggcattcaaaccg |
| attactcaaccattgctcaagggaaggaagcccaccagcacgctgaataa |
| cccgatcattctcgaagacctgccgcattaccggatcatcagccagcggc |
| tgaatggcggcgggaacagctcctgtactgaatgacgccattcttctgg |
| ttcaggctcaagcagaacgcgaccgcgcataaagaggtgcatcagttccg |
| cgccgggacgaaacaacacaatccccatacgatgggcgatctcggggggta |
| agcagagctctcacgcgacctgccccctggcaatgtgttctgcccacagt |
| ccaccaatccagcgcacgcctttcgccgtgaaacgtgcctggctgaatgc |
| atgatttgaggttacggatgtgccggtttcacttcaaaacggcccgcat |
| caatatgctgatgccgtggggtcatcgttccgccaagacgatacatgatg |
| tcgttctcaaggaggaataaccgcagatcggctctttggccttaagcag |
| ttttgccacctggcggaatgacattgacccactggctgtacagtaccgat |
| caacaaacgctaccttcggcgccgcggcagccagttcgttagtcaactgc |
| tgtttttgttctgcaaggtcagctgcaagacgtagggcttcagagaatga |
| ttgaggaatcgtctgctgctgtgcctgctcaagctcctgccagcgatcaa |
| ccagacgcgcggtaaactccggcgacagctgcgcgacaacgatataactg |
| tcccgcttccctatcagataaaccgataccgactgattgaggtgattttt |
| aacttcccccattgggggagttcaataacaccgcgctctgccaggcgtt |
| caatggaccgtttaacatggtcatgtcttgattccaccagctcagcaata |
| tcgctgctggacatggttaacgctgttgttgctaactggctcatactttt |
| ctccatatcaggcggctgcacccgccggttcatatctgctgattgttatc |
| tctacccgacctttcggcacaacgggtccccattccaccagcatgcgctt |

TABLE E-continued

| Phage 3 Genome Sequence SEQ ID NO: 134 |
|---|
| aatctggctgtcgtcttcccagacacccgcatgcgtcagcgcgtcaaaca |
| gggctttgttgtaattatcgatatcccggcggcgcgcatccggcgggtac |
| agagtgatttctaccgctgccagttcagtcgatggcttcgggagacgtcg |
| taattgctcaatgatcgccacgcaggcagcgctctggtatttacggccag |
| cggcgctaatgaggtgacgaccggccagcggccccttgttaggggcgcgc |
| cagtaagtgttcacgctcggaggaaaaggcaggatcagtttcacgcggcc |
| tctccccgcatattgcgaacaagttcagaagcagcagtaatgatttcgct |
| ggtggcagtccgctccagccagagttgattgatattggctttcagcttgt |
| gttgcagtgactcatccagcatgtcagcaccatccacctggtcgaataca |
| attctaacctccagcggccagatacgggactcgggaagcggatccgatac |
| tggtttagctttctcacgaatgtgcatgcggatctggcgaatattggacc |
| aactggaaacatccaggcttcccatggctgcaatgaagtcagtgctgttc |
| atgccatattcaccggatgcttcaagggcaacagtgcgaatacgttccga |
| catatccaggcgcacagcagcgtcatcgaattcaatcgacaacagccact |
| catccacaccgaacaaaatactctcacgaataagcagcttcgctttgtcg |
| atcgttaaaggtgatacctgagtgaattccggtgcttcgacagaatccgc |
| cgcccaggtatgcccaaacttcgattcactgaatgtgtattcttctttat |
| cgccaaacgcagctctaacgcatgcccacgcctcgacaccgctgatagca |
| aaaatatctttctgggtgagtggcaactctgcttctggcttatcagctgc |
| aggaggtgtggcagttacaggttgagacttgctggcagcaaattgtgcca |
| aagccataaacgcccgcccttttgcctccagttctgtgcggttgatatag |
| ctgaaccgctcgccacgccatgacttatcgaatacagctatggcaccggc |
| aaaaaacgcgctggtgggtttctgtttttcgtcagcaggtacaaaccaca |
| caggcagatcgaacccaatgcgcccgcgaatgaatacaatgtgatcggca |
| tcttccggccaccacgtttcactcggcgcggcttttatcaggaatacata |
| gcgaccgcccttctcgcgctgggctgctgcgtagttcatgatgtgcgtca |
| tgccggtgatcgcctgcttctcgtggtactgcgaacggctatacggtggg |
| ttgccatagccagcgccacccagttcagccagacgttcagaccagtcctg |
| cgtcagcgcgttatcttcggcggtgtaccatgccgggcatttcgcgttgt |
| cgtcgtcagcaaacaaatccagaactaatggaccaaatagcgcgttgatc |
| ccccaaaaaagcagatccggtgtccgccactgatcgccaacctctttcaa |
| ttcgtgagctggtttgctacgcagtgccgccagcgcctggcaatatttat |
| tggtcatcatgaacggaaccccgaatttctggcagtgagtaatcaacac |
| tctggaagtttgcgcggctggctgagttagtctcccatttgccgttaacg |
| cgttcaggccggccagcactggaccatttggtcgcgctttgcaggtaacc |
| agggaagtttttggaatgaacagagttgccgggcggaggtattgcgcct |
| gctcgctatcacgccaatcggcatttttgtaatccactaccaagcacagg |
| tcatcaacagtgaattgttcccgaagacgggcgcgaatattctccagcga |
| cgtgctgcatacctggtagcgtgagccagtagtctgattcaggtaagaca |
| aaacctgtctggcctgatcagtaatcacaacctcagggtcgggttgcgcc |
| gcaaccggacaagagggttttgaagttacttgtggttcttgttttgattt |
| tactgacggatccccaccagattctgacgggtcaaaaccgcctttttttgc |
| tggatttcgacgcctcaaattttgacgggtcggattttgatgcatcagat |
| tttgatgggtcagattttgatgcgtcagattctgacaggtgagaaaaagc |
| agcctctcgcaacttaacgacgttaagctgatatacgttcgatgcgttac |
| ggttcccattacggcgctgcttacgggaaagccagccatccttctcaagc |
| tgagcaagggccgtccttaccgtactttctccagcaccgatttgacgtgc |
| gatcgtgccaatagacggccagctaacaccctcatcactactgaagtcgg |
| ccagacgcgccatgatggcaacgctggataacttcatgcctgacgaagcg |
| catgcatcccatacgtaaccggttaatttagtgctcatggtcgtccttta |
| attctgtaaatttacgctggaattgttcaagagggctgaagcactcatga |
| tcgtacccttcgcgaaggtatataacgcgctgtgtatctggctcccagcg |
| gacaactctgacgggaactccgtagtgatctctgaaccgccggttaactt |
| cagccattcctcgcgccccttctcgttcatctgaacaaatgcttctacca |
| tcaagtctgctggctggtagttgcctccatcagccgcgttatttatgatt |
| tccacatagccgaactgggcatctttacccaccagcggcaaacatctgaa |
| ttgcttagctggtctgaatcggtttacactgttcatgcgttagtttctcc |
| actgatacgacacgccaaggcgcccggagctgcacactcgcgggcgtcac |
| cttttctgcctgttgaaacgaatacgtcaatcgcctgatctgaaacacca |
| accccataaagcgccataaatcccaggaacccgtgaatctggtggcggag |
| cttcttactgaataattctgaaagcattttgcgctctgatgaatcaatta |
| ccccatcagccgctgctgccatcttggcattagccagctcaccagatgct |
| gctgccgctttcatctcaatgctgtacagctcaacgttatccaggctctc |
| agcagttggaacatccaccagccatttcccttttcggttcgcctggtact |
| cggccaagtaacaagaaccagacaggtcctccatccgttccagttctgcc |
| aaggtaaagaaccgactgccacacttctggtacaggtggttgtggaactg |
| gtcgatagtcatccctaaatcggaagccatacctaagcgaccatgcttgt |
| gtgccttacacatcaggcggattgctgtatttatgctgtctaccatgttg |
| atttccctctggtagttaataatcaacttaaagttgactattgttgttag |
| cggaaggtatgccgtcattttttgttcggataaatatcaggtcgtaattga |
| tggggagttactacccatccgccccattggcagagttgaataactctttc |
| agaaggtactcggttctttgcaatccagttcgcaacagattgaactgatt |
| ggaattcaaaccgccttgatacctctgaaatcgacccgatcgccttcaca |
| gctttagctgttacattcttgtgttgagatgacatgtgttctcctatgac |
| taagcctgcatcaatactacttatagtagcaattattagcaacttaaaat |
| agaaatgacaactatgccttgtgcgcttaatcttctacttatggtggaaa |
| atgctaaatacaaagactttgccgaaaggctaaacaggtctctccaagag |

TABLE E-continued

Phage 3 Genome Sequence
SEQ ID NO: 134 caatctattggagttaaagaattgtcagagttcagtggtgtctcgtatga
gatggcgcggcgctacactcttggtactgcaaagccgagagatgagaaga
tgattcgaattgcagaaagacttgccgtctcaccggcttatcttgattat
ggtgtgcctgttaatggtggcgacgcgccagccaaaggcacggtcagaat
agagcaattggatgttcatgcttcagccggttccggatatataaaccaac
cattccctacaatagtgagctcaatagagattccagaagagaggatcttc
gagttgtttggtcgtagaagccttgatggcatcgtcatgataaatgttga
tggcgatagcatgatgcccacgctttgcccaaaggacctgcttttcatag
acagcaaggttgaacaattcagcggcgacggcgtttatgtgttcaatttt
gaagacagtacgttcgttaaacgtttgcagaaggtaaaagggcgccgact
ggcagttctttcagacaatgaacattacccgcccttcttcatagaggagc
atgaaatgaatgaactatacatattcggcaagctaatcagatgcttacct
ctaaaaatgatagagtttggctaataattaattcatcaagaaaccggcga
aagccggtttttttacgcctccaattcctcacctcataacactacacta
ctaaaaatttcattttctacttttgttgttgcaattatctacttaaagt
agctatagtcattgcatcgaaagcgaacaggcaggacgcccacgaagtag
ccgccggtggcatatgaataaccggatgattcgctgacagaaaacttagg
ttgggggtagaggtttacatgaatcatttattcacatgctcattttgcgg
agcaaccgaactgggagcgataaagatcgtcgcaaaaggtggtaaggacg
aacctgccatctgttcggaatgcgtagtcacatgtgtagaaaaaatgatc
ctgactaaaaaatcagaggctgaaaaaccaacctctgataacgaaataat
atcagtcgataaaaaactatttaaagagcttcttcagcttgtcctcaacc
ttcctgatttcggaagtaagctggctgctgttgacattgatagtagctcc
acatcgacaagtgaaacttttgttcgacttgagccaagcgattttcttct
tcgtcttagtgccgcacttagggcatgcgggtaacgtaatttcctggtta
tcaaaagcgcccataaacatccctcttggttgtgtgagaacaccaagata
ccaccgcgcctgatgtggttaaaagcaggctaaagcaataacaagtaact
ccctgttctggcggcccggtgttttcccgtgtatttccggtaaccgccag
cctttttcagggcacaacagaaaagggcatcaccgggcgacgggctcata
acccaatccacccgggcaaaaagaaagcggtctctgcaagccgccgacca
atgcaggtgcccttctctgttgtgtatggagaaactaacttttttagcgtc
tgtgcagatgcgctgaggaaccgagaatgaataatccgtttttcaaaaat
atgttggtgtatcgcattagtcgcgatttcaccatcaaccaggaagagct
ggaacagcagcttgaactatttcgcttcactccatgcggtagccaggata
tggcaaaaaccggttgggtatcaccacttggtcagctgtcagatcgcttg
catcacactgtcaataatcaagtgttgttggttattcgccgggaagaaaa
aatactgccatctcctgtcattactgaagaactgcgcaagcgtgtgtcgc
gtctagaatccgatcaggggcgtcgcctcaaaaaaactgagaaagattcg
ctgcgtgatgaagtgttgcactccctgcttcctcgggcgttctccaaaaa
ctcgactgttggtttgtggatcaacgtcaccgacggtctgatcatggttg
atgcagccagcgctaaacgtgccgaagactcactggccctgcttcgtaaa
actctcggttctctcccggtggtaccgctgactatggaaacgccgatcga
actaactatgaccgactgggttcgttccggtagtgcgcctgctggctttg
gcctgggtgatgaagccgaactgaaagctattcttgaagatggcggtatt
ggacgctttaaaaaacagactctggtcagtgacgaaattcatgtgcatct
ggaagctggcaaagtagttacaaagctgtctatcgactggcaacagcgca
ttcagttcgttctttgcgatgacggcagcatcaaacgccttaagttctct
aatgagattacagaacaaaacgacgatatcgaccgtgaggatgcggctca
gcggttcgacgctgactttgttctgatgaccggcgagcttatctctctca
ttaacggattaacaacctctctcggcggcgaagccaagcgataaacacca
ggcaacaattacccccataagcatgggttgggttgctgcacgctaaattc
agcaattcattaatttaatggcgcggtgcagcgcgccaatatggagaaaa
ccatgagctacattcagacattatccggcaaacattttaattacctcgat
atccaacaggacgatatcgtgatcgaggatattgctaccgcgttgtctca
tatctgccgctttgcagggcatcttcctgagtttacagtgtcggccagc
atagcgttttaaccagccacctcgttccgcaggagtttgcattagaagca
ctgcttcatgatgctgctgaagcctacctgcaggacatcccctccccact
taagcgcctgcttccggattaccaggcaatcgaagctcgtgtggacgcag
ccattcggcagaagttcggtctaccaactgagcaacacccaaccgtgaaa
tatgccgacctggtgatgctcgccagcgaacgccgcgattttgagattga
cgaaggttccatttggccatgcctcgagggagttgtcccaacggatttat
tcattatcaacccagttcgtcctggccagtcatacggcatgttcatcaat
cgctttaacgagttgatggagcagcgccaatgcgccgcatgaaggtaaaa
gaactcgtagcggaggcgtttgcctccgttgctgaattgccaccaaagca
tgcgccgcttatgcgcgaagtcgccaccagactggacgctacgttcgcag
cattaaaagagtctctggtgcaactggaacaggaacgtaaagataaaacg
ccatgaccgtatttgaatatctccaggctcatccgaataccaccagcggt
gaaatcgccaaaggtatgaacaaaaagaccccagcggtcgccggagcatt
atctcagctctatggcaccggtcggatcgtgaagtctggtgttcgcaagg
gtattccaacataccgcattaacgatatgccgtttggttgcagtaacagc
ctaaccatgatgtttaaccagctcttgagcagagccagacaaggagcagc
ccaatgacagcactcaacaaacaggcgctgcgtgaagaattccagttcat
gcaggacaactatagcgacccggcagaccacgatcggcaggtgatttaca
tcgaggcggaggcgctgctggatgagttggaagccaaagactcaacgata
gcagcacaacaacatgagatccgtatgttgctgaatgcgcttgaggaaaa
accatgcccgaaatgcaacgacacaggaatgactgatagtggcggcacgc
agccatggggcgagccgattgagattgaatgcgactgccgacagcaggat TABLE E-continued Phage 3 Genome Sequence
SEQ ID NO: 134 gccaacaccgcagaacttgtagccgctggcattggcgtgaaggggggagtg
agatggataaattaatcaaacctaccgccaaaggtaaatatgacggttca
tgtgattatctttgctcggaagatgcgcgattcatcgttatgcgcggcga
ttatacggaagcggaaataattcaggcttctgtgtctcaagatgtaatcg
actcggatggtgcggctgattttgcaagtagcgcccgctattatcagtgc
tggtacaaagttagcccaataggtggtcaggatggctattcaggctggca
tcatcctcgtgattcgccgtgtcgcggtgcatatttcgcatcagttttgc
aatgggattaaggaggactaacccatgacaactaacaaccacccggcgca
cggtcctgtatcactcgatcgcctgcaccagatacgcgaacacctgctgc
atgatacccaatactcaaacggcgggaacagagcctacattctcgctgat
gtattgaaggtgattgatggggctattgcccgcgagctggtacgccgtga
gcatgcagcgtggtcacaggctactttcggcgatgtcggtccagttggtc
cgctgaagcacctttccaaagaagcgctcgaggctgctgctgaaccaggc
gaccttagcgaatgggctgacatgcaattcctgttatgggatgcgcaacg
tcgtgccggtatcagtgatgagcagattacccaggcaatgataaaaaagc
tggctataaataaggttcgccaatggcctgagccgaaagacggggaacct
cgattgcatatcaaagaacagtcagagcaggagaaaaaataagaatgttt
agcctgattcggcgcggtcaaatctacacggacagtagcaactggcccgt
aattatccatagctgtagtgatcactcggtccgaattaaacgcaatgatg
gcgagctgagaacgattagcatcaaacgctttaacgaagattttgaacga
gtggagcatgatgagtatcgcaaaatatgtgccgaaatagagcaggaaac
aaacctgaaaaacctacgtgcgatgcgtcgcggcaagattactgaatagc
caaacaggagaatatttaacgtgaacaacttaatgatcgaccttgagtcc
atgggcaaaaaaccgaatgcccctattgtctccattggtgccgtattctt
cgatccgcaaagcggtgaactgggtcaggagttttacaccgctgttaatc
ttgaaagcgctatggagcagggagcggtgccggatggtgacactattctg
tggtggttaagacaaagctcagaagcacgatcagcaatctgtgttgatga
tgcgatgccgatatcatctgccctatctgaactgagccatttcattaatc
ggcattctgataaccctaaatatttaaaagtttggggcaatggagctact
ttcgacaacgttatattgcgcggcgcatatgagcgtgccggccaggtttg
cccgtggcaattttggaatgatcacgacgtcagaaccatcgtcacattag
gcagatctgtaggtttcgatcctaagcgtgatatgccatttgatggggtt
gcacataacgcactggctgatgcccgccaccaggcgaaatatgtttcagc
gatttggcagaaactaatcccaaccaccagcaacagctaaagttttcccc
gggtgcagccgggataatggagaaataactatgagcaatattttccagtt
agctcccaacgattgggtttgtgaaagcgttttgatcgcggttactgggc
tcaaacccggaaccatcctccgtgccagaaaagaatgctggatgattggg
agggagtatatccacgtatcgcctgacggaaatcctaaaccttccagtga
gtgcatgtataacagaaaggctgtagatgcctgggtcgcttcaatgaaaa
gcaagcaaccagggtgatttgatgccatgaaaaaggtaagctcgtatcgc
tcttgggcgtctggaggtaacaccaatggataaagtcacatatccaacag
gcgtcgaaaaccacggtggcacattacgcatctggtttaattttaaaggt
aagcgtgtcagggaaagtctcggtgtccctgacaccgctaagaacaggaa
gatagccggggaactgcggacatcagtatgttttgccatccgcacaggaa
cctttgattatgcaacccagtttcctgactcccctaacctcaaggctttt
ggtgtaagtaaaaaagacattacagtgaaagaacttgaagaaaaatggct
ggatctgaaacggatggaaatctgcgcgaacgcatttaatcgctatgaat
ctgtcgcaaggaatatggtgccgaggatcggaggtaatcgcctggtgtca
gcagtaaccaaagaggaattgctgtatctgaggaaatatttgctaactgg
ttatcagaatccgacgaaaaacaaagccccggcaaaagggcgaagcgttg
ttactgtgaactattacatgacgacaatggccggaatgtttcagtttgct
gcggatcacggttacttagaggtgaacccattcgagggaattaagcctct
gaaaaaagccagggcagaaccagatcctctgtctcgtgatgaatttattc
gcctgatagatgcatgccggcatcagcagacgaaaaacctgtggtcatta
gcagtgtacacaggaatgcgtcacggggaactggtctccctggcctggga
agatatcgacctgaaggctggaacaattaccgtcagacgtaattatacga
aacttggtgagttcactctaccgaaaaccgaggcaagcacagatcgagtg
gtgcatcttatccagcccgcaatcagtatcctgaaaaatcaggctgaaat
gacaaggctgggcaggcaatatcacattgaagtgcagttacgtgagtacg
gccgttcggtgaaccatgagtgtacattcgtctttaatccgcatgtggtc
agacgcagtaagcaggtcggatttatctaccgggtcgattcagtaggcga
ctcatgggaagcggcacttaagcgtgcggggatcagacacagaaaggcgt
accagtcacgacacacctatgcgtgctggtcattatcagctggtgcaaac
cctagttttattgccagtcagatggggcatgcgagcgcgcagatggtgtt
caatgtttacggtgcatggatggctgacagcagcgcagagcagatcgcaa
tgctgaatcagaagctggcagattttgccccattgatgccccatagccac
gagaacagtacgggaggattattaaaatcagtaagttaacccctaacgcc
cgtcatgttaactgtgtggagggtaacaccacgctttatgccctgccgaa
acccgaggttgtcctgcgctggcgtgagcagaccacagatgacttccgct
tctgttttaagtttccggcgaccatttcgcatcaggcagcattacggcat
tgcgatgatttagtgactgaatttttgacccgcatgtcaccgttggctcc
gcgcattggacaatactggctgcaactgcctgccacattcggcccacggg
agctgcctgcgctttggcattttctcgattctcttcccggtgaatttaat
tatggggtggaagtccgccatccacagtttttcgccaaaggggaagagga
acaaacgcttaatcgcggtttacatcagcgcggcgttaatcgggtgattt
tagacagccgcccggttcatgcagcacgtccatacagtgaagctattcgc
gacgctcaacgaaaaaaacctaaagttccggtacatgctgtactgacggc TABLE E-continued

| Phage 3 Genome Sequence SEQ ID NO: 134 |
|---|
| gaaaaatccactgatccgttttatcggtagtgatgatatgacgcaaaacc<br>gggaattatttcaggtctggttacaaaaattagcgcagtggcatcagacc<br>actacgccttatctttttttacatacgccagatattgcccaggccccgga<br>actggtacataccctgtgggaagacttacgtaaaacgcttccagagatcg<br>gagcagttccggctattccacagcaatcttctcttttctgaatttgccac<br>ctatcatagacaggtgccatcggccattttaaagggagtttgtatggtaa<br>gcgcgctgtatgccgttttaagtgcgttgttattaatgaagttctctttt<br>gatgtcgttcgcctgcgaatgcagtaccgcgttgcctatggcgacggcgg<br>ttttagcgaactgcaaagcgctattcgcattcatggtaacgcggtggaat<br>atattcctatcgcgattgtgttgatgctgtttatggaaatgaatggcgca<br>gaaacctggatggtgcatatttgcggcatcgttttgcttgctggtcgtct<br>gatgcattattacggttttcatcaccgtctgttccgctggcgacgttctg<br>gcatgagcgccacctggtgtgcgctgttgctgatggtgctggcgaatctt<br>tggtatatgccctgggagttggttttctccctgcgttagcgcacaatacg<br>ccactttctttttcccggattttacgttatgtctcaccgcgacacgcta<br>ttttctgcccctatcgccagactgggcgactggacctttgatgaacgggt<br>agctgaagtcttcccggatatgatccagcgttccgttcccggctattcca<br>atattatttccatgattggtatgttagccgagcgcttcgttcaacctggt<br>acgcaggtttacgatctgggttgttctctgggcgcggcgacgctctcggt<br>gcgtcgcaacattcatcatgataattgcaaaattattgccatcgacaact<br>ccccggcgatgattgaacgctgccgtcgtcatattgacgcctataaagcc<br>cctacgccagtagacgttattgaaggtgatattcgcgatatcgccattga<br>aaacgcatcgatggtggtgctgaattttaccctgcaattcctggaacctt<br>ccgagcgccaggcgttactggataaaatttatcaagggctgaacccgggc<br>ggtgcgctggtgctttcggaaaaattcagtttcgaagatgccaaagttgg<br>tgaactgctgttcaacatgcaccacgactttaaacgtgccaacggttaca<br>gcgaactggagatcagccagaaacgcagcatgctggaaaacgtgatgctg<br>accgattccgtggaaacccataaagcacgcctgcataaagccggttttga<br>gcatagcgagctgtggttccagtgctttaactttggttcactggtggcat<br>taaaagcagaggacgctgcatgatcgactttggtaacttttattctctga<br>ttgccaaaaatcatctttcacactggctcgaaacgctgcccgcgcagatt<br>gctaactggcagcgcgagcagcagcacgggctgtttaagcagtggtccaa<br>cgcggtggaatttctgcctgaaattaaaccgtatcgtctggatttattgc<br>atagcgtaaccgccgaaagcgaagagccactgagcgccgggcaaattaag<br>cgcattgaaacgctgatgcgcaacctgatgccgtggcgcaaagggccgtt<br>ctcactgtatggcgtcaacatcgataccgaatggcgttccgactggaaat<br>gggatcgcgttatgccccatctttctgatttaaccgggcgcaccattctt<br>gatgtcggctgtggcagcggttatcacatgtggcgcatgattggcgcagg<br>ggcgcatctggcggtgggtatcgatcccacgcagctattcctctgccagt<br>ttgaagcagtgcgtaaactgctgggtaacgatcagcgcgcacatttgtta<br>ccgttaggtattgaacaacttccggcactgaaagcctttgataccgtctt<br>ttcgatgggcgtgctttatcatcgtcgttcaccgctggagcatctctggc<br>agttaaaagaccaactggtgaatgaaggcgaactggtgctggaaacgctg<br>gttattgatggcgacgaaaacacggtgctggtgccgggcgatcgttacgc<br>tcaaatgcgtaatgtctatttcattccttccgcgctggcgctgaaaaact<br>ggctgaagaagtgtggttttgttgatattcgcattgcagatgtgagcgtt<br>accaccacagaagagcagcgacgcaccgaatggatggtcaccgagtctct<br>ggccgattttctcgacccgcatgatccgggtaaaacggtggaaggttatc<br>ctgcgcctaaacgcgcggtgctgattgcgcgcaagccgtaaaggtctggt<br>aatactgccggatgcggcgtgaacgccttatccggcctacaaagtcttgc<br>taattcaatatattgcaggggctatgtaggcctgataagcatagcgcatc<br>aggca |

TABLE F

Sequences of the genes comprised in Phage 3 of *E. coli* Nissle

| Description | Sequence | SEQ ID NO |
|---|---|---|
| ECOLIN_09965 | ttatttgatgggataaagatctttgcgcttatacggttggatttcgcccggtttgcgagttttca<br>gcaattttaatatccaggtgtattgttctggtcgcggaccaacaaaaatctcgacttcttcatt<br>catccgccgcgcaatcgtatgatcatccgcctctaacagatcatccatcggtgggcgcac<br>ctgaatcgtcagacgatgcgtcttgccatcataaatcggaaatagcggtacaacgcgcgc<br>acggcacactttcatcaaacgaccaatcgcgggcaacgtcgctttataggtggcaaagaa<br>atcaacaaattcgctgtgttctgggccatgatcctgatcgggtaaataatatccccagtaac<br>cctgacgtaccgactggatgaatggtttaataccatcatttctcgcatgcagacgaccacc<br>aaagcgacggcgcaccgtgttccagacataatcaaaaaccgggttgccctgattatgga<br>acatcgctgccattttctgcccttgcgaggccatcagcatggcaggaatatcgacggccc<br>aaccgtgcggcaccagaaaaatcactttctcgttattacgtcgtatctcttcgatgatctcca<br>gcccttgccagtcaacgcgcggctgaattttctccggcccgcgtattgccaactcagccat<br>cattaccatcgcttgcggcgcggtggcaaacatctcatctacaatcgcttcgcgttcagctt<br>cactacgttctggaaagcagagcgacagattgattaacgcacgacggcgtgagctttttc<br>ccagtcgtccggcaaaacgtcccagccgtgccagaatgggatcacggaactttggcgg<br>cgttaaagcgatacccgccatcgctgctacgcccagccatgctccccagtagcgcgggt<br>ggcgaaaggatttatcaaactcaggaatgtattcgctattatttttttcgtttccat | 135 |
| ECOLIN_09970 | ttaatcaaaccgtagctgcggcacaatctctttggcctgtgccaggaattcgcgacgatcg<br>gagccggtcagcccttcggtacgcggcagttttgccgtcagcgggtttacggcctgctgg<br>tttatccatacttcatagtgcagatgcggcccggttgaacgtccggtattaccggaaagcg<br>cgatacggtcgccacgtttcaccttctgtcccggtttcaccaggatcttgcgcaagtgcata<br>taacgcgtggtgtagctgcgaccatgacgaatagccacataataacctgctgcgccacta<br>cgtttggcaaccaccacttcaccgtcacccactgaaagcactggcgtaccttgtggcatg<br>gcaaaatcaacacctctgtgtggcgcaacgcgaccggtcaccggattagtacgacgcg<br>ggttaaagttagatgagatacggaactgtttcgccgtcgggaatcgcaagaatcctttcgc<br>cagaccagtaccgttacgatcgtagaatttgccatcttcagcgcggattgcgtaataatcttt<br>accttctgaacgcaaacgtacgcccagcagctggctttgctcacgtttaccatcaagcattt<br>ctcgtgacattaacaccgcaaattcatcgcctttttcagtttgcggaaatccatttgccactg<br>catggctttaatcactgcgctcacttcggcgctggttaaaccggcgtttctggcgctggca<br>acaaagcttcccccgacggtacctttcagcagattgttgacccactctccttgctgcatttcg<br>ctggtcattttaaaaccgttagcggcagtacggtcataggttcgggtttcacgacgagaca<br>cttcccaggtgaggcgctgcagttcgccgtccgcggttaatgtccaggagagttgttgac<br>cgattttcaggttacgcaattctttgtcggcagcagccagttgggtgatatcacccatatcaa<br>taccatactgattgagaatgctgcttagcgtatcgccagtggaaacaacatattcatgcacg<br>cccgcttcaccggcgattttgtcatccagttcgtcctggggaatggcttcatcttcttgtgca<br>gcttgatcaatcggctcactggcttcaggtaagagcgaacgaatttcgttctgttccagctc<br>aatggttttgacaattggcgtggcatcgcggtgataaacatagggccgccagacagcga<br>cggccagagtaagaacggtgagcgaccccaacataacgcggtgtggtcgcggtaaatt<br>attaaacgccagggcgacagagcgggctatctgttgcac | 136 |

TABLE F-continued

| Sequences of the genes comprised in Phage 3 of *E. coli* Nissle | | |
|---|---|---|
| Description | Sequence | SEQ ID NO |
| ECOLIN_09975 | ttaatctcctttcaggcagctcgcatactggttggctaattgattcaggaattctgaatagctt gttttacccagtttgatattcgtccccaggggatccaacgttcccatacgaacggatgtccc tcgtgcgacgctctcaacgaccgctggcctgaactgtggctcagcaaaaacgcaggttg ctttttgctcaaccaactgtgttcttatttcatgtaaacgctgcgcgccaggttgaatctcagg gttaacggtaaaatgaccaagcggtgtcagtccgaactgtttttcgaaatagccgtaagca tcgtgaaaaacgaaataacctttccccttgagcggcgcgagctcgttaccaacctgcttttc ggttgaggctaattgtgcctcaaaatccttcaggttggcgtcaagtttggctcgactttgcg gcataagttccactaattttccatggattgcaaccgctgtagcccgcgctatctctggggaa agccaaagatgcatgttgaaatcgccgtgatggtgatcttcgtcactttttttccgcgtggtcg tgatcatcatcatcgccgtgaatacttttcatcagcagcggtttcacattctctagctgcgca atcgttacctgtttcgcttcaggtaatttacttaccggtttttgcatgaacgcttccatctccgg gccaacccaaacgactaagtccgcgttctgtaagcgttttacatctgatggacgcagtgaa taatcatgttctgaagccccgtcaggtagtaaaacctccgtttctgttaccccatcagcaatg gcagaagcgatgaacccaacgggtttaagcgaagcgacaacggcagcatctgcggcct gtgttgcaccgccccagagagcggcggataatgctgcgaaaagaagcgtttttttatgtaa cat | 137 |
| ECOLIN_09980 | atgacaagtctggtttccctggaaaatgtctcggtttcttttggccaacgccgcgtcctctct gatgtgtcgctggaacttaaacctggaaaaattttgactttacttgggccaaacggcgcag gtaagtcgacactggtacgggtagtgctcgggctggtaacacccgatgaaggggttatc aagcgcaacggaaaactgcgcatcggctatgtaccgcagaagctgtatctcgacaccac gttgccactgaccgtaaaccgtttttttacgcttacgccctggcacacataaagaagatatttt gcctgcactgaaacgtgtccaggccgggcatctgattaacgcaccgatgcaaaagctct cgggtggcgaaacgcagcgtgtactgttagcgcgagcattgttaaatcgaccgcaattatt agtgctggatgaacccactcagggcgtggatgtgaatggtcaggtggcgttatatgacctt attgaccaactgcgtcgcgaactggattgtggcgttttaatggtatctcacgatctgcatctg gtaatggcaaaaaccgatgaagtgctttgcctgaatcaccacatttgttgttccggcacacc ggaagttgtttccctgcatccggagtttatttctatgtttggtcctcgtggtgctgaacaactg ggtatctatcgccatcatcataatcatcgtcacgatttacagggacgaattgttttgcgtcgg ggaaatgatcgctcatga | 138 |
| ECOLIN_09985 | atgattgaattattatttcccggttggttagccgggatcatgctcgcctgtgccgcgggtcc gctgggttcgtttgtagtctggcgtcgtatgtcttatttcggtgatacgctggctcatgcctca ttacttggcgtcgcgtttggtttgttgctggacgtgaatccattctatgcggtgattgccgtta cgctgctgctggcgggcggtctggtatggctggagaagcgtccacagctggcgatcga cacgttattagggattatggcgcacagtgccctgtcgctgggcctggtggtcgttagtctg atgtctaatattcgtgttgatttgatggcttacctgttcggtgatttactggcagtgacgccag aagatctcatctctattgcgattggcgtggtcatcgtggtggctattttgttctggcaatggc gcaatttgctgtcgatgacgattagcccggatctggcgtttgttgatggtgtgaaattacag cgcgtgaaattgttgttgatgctggtgacggcattgacgattggtgtagcgatgaaattcgt cggcgcgttgattattacttcactgctgattattcctgctgctactgcacgtcgctttgcccgc acgccggaacagatggctggtgtcgctgttttggtggggatggtggcagtgactggcgg tttaaccttttccgcattttacgatacacctgcaggcccgtcggtggtgctatgcgcggcac tgttatttattatcagtatgatgaaaaagcaggccagctaa | 139 |
| ECOLIN_09990 | ttacggcatttctggcggcgtgatgccgaagtggttccacgcccgcactgtcgccatacg cccgcgcggtgtacgctgcaaaaagccttgctgaatcaaataaggttccagtacatcctc aatggtttcacgttcttcgccaatggctgccgccaggttatccagacctaccggcccacca aagaacttatcgattaccgccagcaacaatttgcggtccatataatcgaaaccttcagcatc gacattcaacatatccagcgcctgagcagcgatatctgccgagatggtgccatcgtgcttc acttcagcgaaatcacgcactcgacgcagcagacggttggcaatacgtggcgtaccgc gcgcacgacgagcaacttccagcgcgccgtcatcactcatctcaagccccataaagcgt gcgctgcgactgacgatatattgcagatccggcacctgataaaactccagacgttgcaca ataccaaaacgatcgcgcaacggtgatgtcagcgaacctgcgcgcgtggttgcaccaat cagggtaaacggcggcaaatcaattttaatggagcgtgccgccggaccttcaccaatcat gatatccagttggtaatcttccattgccggatacaacacctcttccaccactggtgaaagac ggtggatctcatcaataaacagtacatcgtgtggttcaaggttagtgagcattgctgccag atcgcccgccttttccagcaccggaccagaagtcgtgcgtaaattaacgcccatttcattg gcgacaatattggcaagcgtagttttacccaaccccggaggaccaaaaatcaatagatga tcgagggcatcgccgcgcagtttcgctgctttgatgaaaatctccatctgcgaacgaacct gcggctgaccaacatactcttccagtaatttagggcgaatggcgcgatctgccacatcttc cggcaaagtggtaccggcagaaatcagacggtctgcttcaatcat | 140 |
| ECOLIN_09995 | tcataacgcggcgcgtagggcttcgcgaattaatgtttcactgctggcgtcagggcgagc gattttgctcaccatgcggcttgcttcttgtggtttatagcccagtgccaccagcgcagcaa ccgcttcctgttcagcatcgtcggtcgccgggctggcaggagacgtgagtaccaggtcg gcggctggcgtaaagagatcgccatgcaaacctttaaatcggtctttcatttcgacaatcaa gcgttcggcggtttttttgccaatacccggcagtttcaccagtgcccccacttcttcacgctc aacggcattaacgaactgctgcgctgacattccggagaggatcgccagcgccaacttcg ggccgacgccgttggttttgatcaactctttgaacaacgtgcgctcttgtttattgttaaaacc gtacagcagttgcgcgtcttcacgcaccacaaagtgggtgaaaacgatcgcttcctgacc cgcttcagggagttcataaaaacaggtcatcggcatatgcacttcatagcctacgccgcc cacttcaattaacaccagcgggggttgtttttcaatgatgatgcctctgagtctgcctatcac | 141 |

TABLE F-continued

| Sequences of the genes comprised in Phage 3 of *E. coli* Nissle | | |
|---|---|---|
| Description | Sequence | SEQ ID NO |
| ECOLIN_10000 | gtgaatattaattatcctgctgaatatgaaattggtgatatcgtctttacatgtataagtgctgc<br>cttatttggtcaaatatcagctgcatcaaattgctggagtaatcacgtcgggatcattatcgg<br>tcataacggtgaagactttctggttgcagaaagccgtgttcccctctcaaccatcactacgc<br>tatcccgttttattaaacgctctgctaatcaacgctatgctataaagcgattagacgccggac<br>taacagaacaacaaaatcaacgaattgttgaacaggttccttcccggctacgcaaaattta<br>ccacaccggttttaaatacgaatcttcgcgccagttctgttcaaaatttgtttttgatatttataa<br>agaggcgctatgtattccggtgggtgaaatagagacgtttggagaattgttaaatagcaat<br>ccaaatgcaaaactcactttctggaaattctggttcttaggttctattccgtgggagcgtaaa<br>accgtcacgccagccagtttgtggcatcatccgggtttggtgttgattcacgcggtgggag<br>ttgaaacgcctcagcctgaactgaccgaggcggtataa | 142 |
| ECOLIN_10005 | ttaacgcagtcgccctctcgccaggttcagtcgcgattcgctcatttgcatcgcattctgact<br>aacgtggcagtgggtgatggcaatcgccagcgcatcggcggcatccgcctgtggattag<br>cgggcagtttcagcaaggtgcggaccatatgctgcacctggctttttcggcactaccaat<br>acctaccactgtttgctttacctgacgtgccgcatattcaaataccggcaattcctgattcac<br>cgccgccacaatcgccacgccgcgcgcctgccccagtttcagggctgagtcagcgttct<br>tcgccataaagacctgttcaatggcgaaataatcaggctggaattgggtgatgatttccgtc<br>acgcccgcatagatgagcttcagacgagacggtaaatcatccactttggtgcgtatgcatc<br>cgctacccaggtaggacagttgcctgcctacctggcggatgacgccatagccggtcacg<br>cgcgaacccgggtcaatgccgagaataatagccat | 143 |
| ECOLIN_10010 | tcagagagtcgctgcaacctcatcagagatttcaccgttatggtaaacttcctgcacgtcgt<br>cgcaatcttccagcatatcgatcagacgcatcagtttcggtgcggtttctgcatccatatca<br>gctttggtggacgggatcatggaaacttccgcgctgtctgctttcagacctgccgcttcca<br>gagcgtcgcgtactttgcccatttcttcccatgcagtgtagacatcaatcgcgccgtcatca<br>taggtcacaacgtcttcagcaccggcttccagggctgcttccatgatggtgtcttcatcgcc<br>tttctcgaaggagatcacgcctttttttgctgaacaaataagctacggaaccatcagtaccga<br>ggttaccgccacatttgctgaatgcatgacgcacttcagcaacggtacggttgcggttgtc<br>agacagacattcaatcatgattgccgtgccgccaggaccgtaaccttcgtagatgatggtt<br>tccatgtttgcatcatcatcaccgcccacacctcgtgcaattgcgcggttcagagtgtcacg<br>ggtcatgttgttagacagtgctttatcaattgctgcacgcaaacgcgggttagcgtccggat<br>caccaccgcccagcttagccgcggttaccagctcacgaatgattttagtgaagattttacc<br>gcgcttagcatcctgcgcagattacgatgtctggtgaggcccatttactatgacctgccat | 144 |
| nudB | tcaggcagcgttaattacaaactgttcaatcgcctgccggttgctccaggacttagtgagc<br>gccgccgcagcagacgcatcaagccacttgtaagccagatgttcagtgaaaacgatctg<br>gcgctcgtgcggaagcgcaagacagaaccatgattccgtattacgcgtcacgcccggc<br>gcatagcgatgacgtaaatgtgaaaaaatttcaaactctaccgtgcgctgacagtcaatta<br>aggtcagttgttcagcgacaacatcaatggtgacctcttcctttacttcgcgcatggcagctt<br>gcggcgcggtttcaccctcttccacgctgccggttaccgactgccagaaatcgggatcgt<br>cacgccgctgcaacatcagcacccgtttcgtatcttgtgcgtagatgaccactaagatcga<br>aacgggacgcttataagccat | 145 |
| ECOLIN_10020 | tcagttattctcagccttcttcacaacctgaatgctcagctcagccagtgcagtcgggttag<br>caaagctcggcgcttcagtcatcaaacacgctgccgccgtggttttcgggaaggcgataa<br>cgtcacggatattgtcggtgccggtcagcagcatcgtcagacggtcaagaccgaatgcc<br>aaacctgcgtgcggcggagtaccgtatttcagggcgtcgagcaggaagccgaatttctc<br>gcgctgacctatcgttgatacccagaataccaaacaccgtctgctgcatatcaccattatg<br>gatacgcacagaaccaccgcccacttcgtaaccattgatgaccatatcgtaagcgttagc<br>caccgcattttccggtgcagctttcagttctgctgccgtcatgtctttcggtgaggtgaacg<br>gatggtgcattgctgtcaggccgccttcaccgtcgtcttcaaacatcgggaagtcgataac<br>ccacagcggtgcccatttgctttcgtcggtcagaccaaggtctttacccactttcaggcgc<br>agtgcgcccatcgcgtcggcaacaattttcttgttgtcggcaccgaagaaaatcatatcgc<br>catcttgcgcgccagtacgctccaggatggcttcgatgatttctgcattaaggaacttcgct<br>accgggctattgataccttccagacctttcgcgcgttcgttaactttgatgtaagccagacct<br>ttcgcgccgtagattttaacgaagttaccgtattcgtcgatctgcttacgggtcaacgatgc<br>gccgcccggaacacgcagagcggcaacacggcctttcggatcgttcgccggacctgca<br>aatactgcaaactcaacagatttcagcagatcggcaacgtcggtcagttccatcgggttac<br>gcagatccggtttatcagaaccataacggcgttctgcttctgcaaaggtcattaccgggaa<br>atcgcccagatccacgcccttcacttccagccacagatgacgcaccagcgcttccatcac<br>ttcacgcacttgcggcgcggtcatgaaagaagtttccacatcgatctgagtaaattcaggc<br>tgacggtcagcacgcaggtcttcgtcacggaagcatttaacgatctgatagtagcggtca<br>aagccggacatcatcagtagctgtttgaacaactgcggggattgcggcagcgcgtagaa<br>tttacctttgtgcacacgagaaggcaccaggtagtcacgcgcgccttcaggcgtggctttg<br>gtcagcatcggagtttcgatgtcgaggaagccgtggtcatccataaaacggcgcaccag<br>gctggtgattttagcgcgggttttcaggcgctgagccatttccgggcgacgcaggtcgag<br>gtagcggtatttcagacgcgcttcttcggtgttgacgtggttagagtcaagcggcagaaca<br>tctgcacggttgatgatagtcagcgaggacgccagtacttcgatttcgccagtcgccatat<br>cgcggttaatatttttttcgtcacgcgcacgtacggtgcccgtgacctgaatgcagaactca<br>ttacgcagttcagaggccagctttaacgcgtccgcacgatccggatcgaaaaatacctgc<br>acgataccttcgcggtcgcgcatatcgatgaagatcaggctaccaagatcacgacgacg<br>gttgacccaaccacacagagtcacctgctgccccacgtgggacaaacggagctgtcca<br>caatattctgtacgcat | 146 |

TABLE F-continued

Sequences of the genes comprised in Phage 3 of *E. coli* Nissle

| Description | Sequence | SEQ ID NO |
|---|---|---|
| ECOLIN_10025 | atgcttgaacttaatgctaaaaccaccgcgctggtggtgattgatttacaagaaggcatcttgccttttgccggaggtccacatactgccgatgaggtggttaatcgcgccgggaagctggcggcgaaatttcgcgccagcggtcagcccgtgtttctggtgcgcgttggctggtctgccgattacgccgaagcattaaaacagccggttgatgccccctcccccgcaaaagtgttgcccgaaaactggtggcaacatcctgctgcattaggtgcaaccgacagcgatatcgaaatcatcaaacgtcaatggggtgcgttttacggtacggatctggagttgcaattacgccgccggggtatcgatacaatagtgttatgtgggatctcgaccaatatcggtgttgaatccaccgcccgcaatgcctgggaactcggttttaatctggtgattgccgaagatgcctgtagcgccgctagcgccgagcagcacaataacagcattaatcatatctacccgcgcatcgcccgtgtgcgtagcgttgaagagatcctcaacgcgttatga | 147 |
| ECOLIN_10030 | tcacatcaccgggcagtcatcaaactccgcattcctggcatcattaatgatgtacgtgatcactccaaatatagcgggtgcagaactgtaaccatcatcatctgctggcagcgcttcccttctcccgttatccagattaaccaggtgcggctgaggatgagtccgatatcgcttgatcctgaattccccgtcgattgcacatatcagcagtgaaccatcgcaggcagtaagtgacgcatccacaacaagcaacgctccctggattatcccttccctgaaatgtgaacgcgatgcccgcatgaaataagtcgctgcgggctgactgattagctgctgatcgagggagattcgtgtttcaacataatctgccgcaggtgaaggaaatcccat | 148 |
| ECOLIN_10035 | atgttcgtggaactcgtttatgacaaaaggaattttgatggtctgcccggtgcaaaagatatcattctgggcgagttaactaagagagttcaccggatcttccccgatgctgatgttcgggttaaaccgatgatgacactgccggcgatcaacactgacgccagcaagcatgagaaggaacagataagccgtactgttcaggaaatgtttgaagaggctgaattctggttagtgagtgagtaa | 149 |
| ECOLIN_10040 | atgctgtggaggatattcattttcgtaaacgttggtttgggagaagcggcaaaacggaatgtgggaacaggggaaaatcagataccagatatgtctgcatttccatctggcaataactggtttcagttaccaagtggacatatcgttcagatattttccatgaacgttcttggtgcagatgctaatggcacgtcagctaattaccccattgcttttccaacaacgatgattgctgtcagtgctctatggtctgatgggactgtagcaaatgcaccgacatacaagatgatggggaacacgactaacagaacaactttgacgataaaagtatcagccagctcaggtacttacgggacaatgattattgcggtgggacgataa | 150 |
| ECOLIN_10045 | atgaataaatacagttactctccttcagaaaatgccttttatgctgttgcgttaaaaaatacctatgaattgagtggcacatggccagctgatgcattagatattcctgatgacatttctgtaaaatatatggcggaaccgccacaagggaaaatccgagttgcaggggaaaatggttttcccacatgggctgaaatacctccaccatcacatgaggaacttattgaacaggccgaatcagagaggcaattattgattaaccaggccaacgaatacatgaacagtaaacaatggcccggtaaagccgctattggtcgtctgaaaggcgaggaactggcacaatataattcgtggctggattatctggacgcactggaactggtcgatacttccggtacgcccgatattgaatggcctacgcctccggcagttcaggccagatga | 151 |
| ECOLIN_10050 | ctacgcctccggcagttcaggccagatgacatccggcgcggtgctggtatctgttgcagtcaccgcgtcaatgtaatccagcacggcgttaagtcgggttgtttctgcctgagtcagtttccgtccggcctgtaatttcagctgaatcagactaatggaagccattgctgcatcaatcagtgattggcgctgtgcttctgccgcttctactgaggcaccgtgttgtgcctcagtatctgtcacccatttctcaccatcccatttatcatatggcgttaacggtgaaagcgtgacataaccgtttttgatggcaccgatataatccactgtaacagctgcgccattttcgattgagtaaacagtctcattgcgatggtcttcctcatggctccatcccttacctgtaaatactgccactcttcccggaatgttttcgtccgggtcaataccagtggaacaggcgggcatacttacgccagtattaatatattcatcagaccagcccgtatattcagacgttactgcatcataataaaaacaacgcatatcacccggcactgcagccagcccattttcatcaaaaacaggtttcat | 152 |
| ECOLIN_10055 | ttatttagccctcaccagaaagttaaatgcaatatttcgcggtctgacagcaacaaaattcacaccatcacccacagagttactgttgaaattaaatcgtgaaaatcctggctgatttccggcgatgccatcatgaaagttaattgcgtgtccagcacctccgcctatattcccggcaaactgagaaaagtttgtagcttcctgccagcttaataattcgcgaccaccatctgcacctcgcccgtcatcccagacacgaatgaaatcaccgcgggcttcaggtaataccagcgaaggaaacactttcgccagcacaggataatcagtggcagagaatttcgcgccgttgaacttcaaaaacaccatactggaccagctgtcgattacagtatttggcattgcagcggacggccagaagaacggaacgccaatagctggagaaccttctcccaaaccaaggtttgtgcgagcgtctgcggcattcgttgcgccggttccgccgtctgcgacagtaaccgcaccgttgctccctttctgcgcaagtttaccgatgcctgggatggttacggcggtgccgttgatggtaactgtgatgctttggtttgctgaggtggtggcgaacgtctcccacgcgccaatattctcgtcgtactctttgatgagctgtgacatggcctgcgccaggccgtcgactgagatattgtccgacacaaggattccatacttctggccgctcagcgccggggaaactgctggcgtaaccgtcattgacgtggcgctgttcacggatgaaatctgaaacagctgcaccgggttagacatcacgataatcgtctggccagcgcggacctggctggcgggagctgtccagtttgtgccggagccggttgcggtatttccgttaatagagatagttccggtgctataaatcat | 153 |
| ECOLIN_10065 | ttaacctgtgaatgaaccagatccgtgtgatactatgatagtaggcgaagaaattgacgcacccctgttattttgagcggacactttaatacgcactgttacgtttggacctgttacaaccgcagaatgcatgataagtctctccatgtcttgcacggatgaaccactctcattgccgttaatgtcgattgttcctgcaccattacctttaacgtttgctataacacagacgtgtcttgcgtgcccagaactggatgaatcattataagtcattaccttttctaaatatccgtcactagaccgactcacattcgtccctgtgtgcatatttgcaatgtccccgataaaactttgggcttccacagtccctttgaatttaccgcttgttgcttggatctcaccagtaaagctaccgccactagcatatactacacctctga | 154 |

TABLE F-continued

Sequences of the genes comprised in Phage 3 of *E. coli* Nissle

| Description | Sequence | SEQ ID NO |
|---|---|---|
| | cggtcacattgttgaattcagcatctccagctttattcaacttccaaccagcagaaccagct<br>gcatagttgttggactggatatagttaccgattttgcgttctcaatggtgccgtcctggatga<br>agctggcccggatgaatgtctgcccgttctggatcacgaacggcaaagctacgctatttc<br>cggctgccgtggtgacggcgaagcggtcagccaggaagataacctgcgactgcatgcc<br>ggatggcgtattctccacgccgatacccatccccgcggcgtaatactgcccgttgctgga<br>gacaccaaccttgatgttgtacatcgcgctgagttcgccattaacgttggctatagcctgag<br>cgttagtggtgatggcggaggtatgcccgttcacggtcgccgtgatgccgtttatctgcgt<br>ggcggtggcctgctgatagtcggagagcgtctgattcaggctgttgatggatgccttgttg<br>ccgttgacgtccgtctgcaggctcagcaatgaacgtgctgtggcttccttctcactgacgat<br>cacctcgtcgagacggtccagattcgcgctgttgccggcgaccgatgcagaaagggtttt<br>acgcgtggccacctgagcgaggttggcctggattatcgcaattgcagagttcttcacccc<br>gcccgtcatgccgtccatagaaacgctgatgttgtcgattcgctggcccagggcggtatc<br>agccgtcgcaacggtctgctcaagctgactgagtgaagacgaaacattcccgaccgtgc<br>tggaaagctcattaacgctggtctgaaccttcccgacgtcctgggcatttttggcgatatctt<br>tcgcttgctgctccagttcgtcgttggcctgtttgatatcgttagccatgccagcaatttttttcg<br>ttgctgtccaccgcgttctcgatcaggtctttgaacgtttccgactctttcatatcctccagaa<br>tgtcattagttatttcgctgacatctatcgaggacgtgcccatgatccagtcggtccagtccc<br>cggcgttaccgatacggtcaatcaggcgcgcgcggtaccactggcgaacgccggcag<br>gcatggggccatgctgataatctgcagccgggtacggcaccaggaccagcagttcagg<br>attggcgtagtcggcagttgtggcgcgctgaatctctgtataggccgtgtcgcctgagcca<br>tccggaaatttccaggtcaggtcgatatgccagaccacatcttcggtcgccaggaagttg<br>agcggagtacccggttttcccgttttaccggagagataagttgtttcaccgtatccccatgg<br>tgacgacgtatcctgcgcattcagcgcccgtacgcgcacgtcatagctgcccgaataaat<br>gccctgaaccgagaaaccctgcgcgctggtaaccggaacgtttatccagtccccgttgtc<br>cttacgccactgggcaacataccggattgcgccctctaccttatcccatgacacgtccagg<br>cttgctacagtcagcccctgagacacatgatcgctctcagtcaccacgatattcttcggag<br>cagacaggacgcttatcggcgtgacggtgatcgggggagactcgacccgaacgccgtc<br>atcgatgtaacgatatttgtttggatcgtgctgaacggccgtaatagtgaaaccgcctgtac<br>tgtcgtcgttagccgcgattgaggtgaccctgaagtactgtattgcgaggttatcactgtct<br>atcgcccaaacagcgcccgccacaggaacctgactgaatgccgtagccaccgtcaccg<br>ttttttttatcggcgctcaccgcgctgattgtccgcgtctgggcttttccgtcgggaaggttaa<br>ccaccagccggtctttcgccgcgtagtctatttctcgatcgagggtaatttggcggccgttg<br>gccgcgcttatacggcccccgttctccttaccagagcggaaaggatcggcgacaccgat<br>aatttcagcgggcaaagggatataaccgtccagccccacgccaaacgatacggtcccgt<br>ctttggcattggagagcaatacccagcgaccgcgtcggtgcgcttcactttgcgaggtgc<br>agccgattgcggtcagggacgtctgccggacgtcgtaacgttctacaagcgccgaatcg<br>taaacccccctcaacggtatcgctgtaatggttctgcggatcggaccaggacaccaggca<br>ggagctgtagcgattcttgtatgagccgcccgcataagtaaacagcccatcgataacgttt<br>gagacgttataaacccagtcaacatcgtcctgcgggacgtctgcctggacataaatctgat<br>cgtttccccagaacgttattccacgaaataccgcggcgagatcgttaagtacctgccagg<br>cgtcctcctggctctgaatgaaaacgttgcaggtgaaacgcggttcggtgccaccggcc<br>ccgtcggaaaccatttcgtcacagtactgggcgattgaatacagcgcccacttatccacca<br>tggacgcatccacgcgcgtgcccatgccgtaaatttcatccagaaccagatcgtaaaaga<br>tccaggcagggttattggaccatgccattttgaacccgccggaccatgaaccagaatagg<br>ttcgggttttcggatcgtaattatccggaaccttaatcagcttgccttttatctttacaggtcact<br>ttcggcgcgctgccgttgaattggctgctgtccacttcgacatacaggagcgctgttaaag<br>gataacgaagcttgctgtcgatgacttccgcatacgaaaacaccttgaaggcgttaacca<br>gtttcgaatttgatccgctggcatcagccgtaatacgcctgaccctgacagaccagccgg<br>acgtggatttggcagatcgatacggtggtcacgctgatattccgtcgtggtctttccgtca<br>aacttgccgtttacaaccgttttccaggcgccgccgtccgttgataaatcgatcgcatactc<br>ggtgaccgtgcccaccatatcgccattatctttatagagatactggaccggaaggctgag<br>cttgatacggatggcatccagggaaaggtttgtaaactggcgcgtccagggcgcggtgg<br>tggtgacagttgtgcccacggccagctcgttgtcgacctggggcatcccggcaatatagg<br>tctggtcctgtgtgcccttgcggaactcccatttcacgccgctgaagttgtattccccgctgt<br>cgtttgccagcggcgtatcgttgagaaaaatgttctgagcggtcaggtcgccctgtatttcc<br>ccctcagaaacggcaatgagcatttttaattttgcgaccgacagcagatcgtcaggctgct<br>caaccggagtatgtgaactgccacctccccctttggcaccctgcaggatggtttcttgttta<br>agaagctgcattttttcacccat | |
| ECOLIN_10070 | ctactgctgatcgctcgagtacataccggcgctgactatcgctccccctgcctcagtcaga<br>ccgtaggccaggggacaggatgccccatagcgacggtattgaccggcgccccgaag<br>gcgtagttaggcgtgttgtccgtgctggaggatttacccgcgccgaaggatggctgggg<br>cgtgagcatctggacaacgcccccagcatcatcgacactccgacccctgtcagaattg<br>acgtggcgctgatagctgttgcactcatcgccgcgccccaggctgccatgctcgcacca<br>gcggtaaagaatgcagcgaccagcgcaacagccccgacaactatctgcaggacgccc<br>gaacttttggccccctcataaacgggcacgatccggtacacgcttccaccgcgggtcata<br>tcaaactcttccagcccgatattgttgccaccgttaaaaaggcgaaacggatccccttcat<br>atgagcttcagacatatattttttgaatccgggaacctgtgaacacatggccctgagcatct<br>cgcgcaggtcggcaacatcaaactgaacgcgtttaccgaatttttttgccattttaccttcga<br>gaataagcgtcttaaccat | 155 |
| ECOLIN_10075 | ttaaccatgcattctgtccttatgcctgaccacccggaccgttctgtcgcgataatattttcca<br>taaggcgttcgcgaagaaaggtgcccgaaaagatgatggagaatgatgttatcacccac<br>atataccgcggcgtgattagtcaccgatgcctgcacactcatcatgatgatatctccgggc<br>tgcattgcaccggcggcaatctcaacgaatccctcacgctcccagttgtcgtcgtagaga<br>cgctccttgccgctctcccaccattcgtaaggtactgaataattgccgagaacaatgccgt | 156 |

TABLE F-continued

| Sequences of the genes comprised in Phage 3 of *E. coli* Nissle | | |
|---|---|---|
| Description | Sequence | SEQ ID NO |
| | attcgcgcagataaaattcacggataagcgaccagcagtcggcgtaacccagcacccac<br>tgccgcccggcataatcccggtcttcacgcggggaaatcgtacaaaaatccccgtccgg<br>ccaggacatgatcccccactcaatccccgaccagtcgcactggatccggtccagctctg<br>agggcaccagccgaaccacatccggatgggaatgaatgagcatgatgatctcaccgcg<br>cgcgcgggcagcgagctggtcttccggggagagcgtgaatgtctcctcgggtttatcgg<br>caatgttgcggcagggaataaagatttgttgctggcctgactgaacaatcaggccgcagg<br>cttctttggggtattcagcagcgacgtgctgacggatagcatccagcaatttttcacgcat | |
| ECOLIN_10080 | ttatttcccctgcaggtttgcagccggaaaaccgccgaacggcagcggcgcatccgggc<br>cgtgacgatcctgacaatcctgccggcggccgccacaaacatctttcgacgggtcatcg<br>gtcggtgtaccgtctttggtaaagtatttcgtgccgttgtaatcgcatccggtcccgcttcgg<br>taccagccccgcatacaccaggtgcagacaggcgtaatctgccgtgtcggcagctgca<br>ggctctgaatatcgaaaggagaacacagctcgaaatcaacctgtacccgcgtctctgcg<br>gttttagcattgacgtaaaagagctgtaagcgctcatcggccgggctggcacccggatta<br>ccgtttttccagttggcggcatcgagatacttcgaaagcgtggtatggattttgaccttagcc<br>ctgaccatatcgtcatattcaagacacagcgcggtgacatagtttccgacgttcccgacgg<br>acagcgtgggcgttggctgggaacctgtactcgataactccatccccttaagttcgtaggg<br>atggggatcgtactggtttccctgccagataatggcgggcagattttctgcggcgaaggct<br>gcccacccctcttcctgaatattgtgcgcatgaaaacgcagcacctgatccataccgaatt<br>cagtgccgtcgatctcaatcagctgaataacgctgccgggctcaagctgttgtatgtctgc<br>cgtaaaactcat | 157 |
| ECOLIN_10085 | tcagggcgcgaacgcctgttcaaaagtgaaggccacagtggctttttcccggtagggaa<br>agaaacgctgaacgaatcggccttcattctgaacagctttttttcaccccatggagtggtcc<br>accagaacgatttagtaacgtgagacatcaggaaagcgcgcagcgcagccgcctcctgt<br>ctggtgcccgtccagtccaggttccacgtttcctgtttgtcgttgatccccatccccgctatc<br>tgtttgtagccatccccgaactgggcctgcagcgttcgggctgtttcagtgccctgcgctgt<br>ttttcgcgtgcgccaggtaaacgtgtccgtcac | 158 |
| ECOLIN_10090 | tcactgtgtcctcctcgaataaagcacgccgcccgcggacatttctttttcagtcgctcggt<br>gattgtctgctgaacaatcgcctgcagctgtttcgccgtccccgtggcgttcgcctgatttat<br>gcttccgtcactcccctgctggctgatgctgactggggcataaacactgatcccgcccatg<br>ccagcaccggctgcgttcccgccgccgaccagaccacccgaggcatacccgcgcatc<br>aggcgatagagattagccacgccgatgcggctggttgattctttggtgaagacgaattcc<br>ccgcggtgaacgataccggctggctcgtacttgccgccgtgcccggtaaaaccgccca<br>cgtcaaaaccctgtggccggtatgacgggaccgcgaatgactgaccggcagaggaggt<br>tttcgccccgccgctaacccagcccattgcactctggatggtgtaagccaccagcagctg<br>gttgataacggacacaatcattttaaggatcgagctggtgaattccctgaagctcgccttcc<br>cggttgtcgtcaggctggtaagctggcccgccaacccgctgaacgtagcctgagaaatc<br>tgctgaacggagctgaaaacgtttgtcgctgaatcctgatattcggcccaaccctgtttcgc<br>accggccagccagtttgcacgcagggcatcttcagcttcgaacgtcgccctttgctcttcc<br>agaacctttttgctgcgcctgagggttgtacgaatagctttcgctgagacgctgcagcgtag<br>tttgtcgcccggcttcccgggtggataacccctcagactgagcctgcaggcccgccctg<br>gcggctttttgctgctgctcaaacttcacggcctgatcggccagctggttgagcttttgctg<br>gctggcaaccttatcgcccaggtcggccagctgccgcttgtactcgagcgtttcttctttgt<br>gcgccagcagggatttttcctgcgccgtaagctgacgacgcccagcggcctcctgcaga<br>acggtgaactgattttcagtttgccagagatcctgacgctgtttacttatgacgtcgttcacg<br>ctggtatgctgctcaagcgttttaagctgggcctgaagggtgagaagttcggcctgcgcct<br>tttcctcggctttgtccccggcgggcgttgagtagcttttgcctttcggtgtttttggatccttc<br>cactgcttttcaatcccggcgcgggccgcggcaatgtccttttcagtccacagcgtggcg<br>acaccgtctttcgcatcctggcggtttttctcaataagctgactgagctttttctctgctgaag<br>cccgcttttctgccgccgtcgcgccggactccaccagctggttaaactgctgctggctgc<br>ggattgcctgagcctgctggtccgttcgcatttttttcccgcgcggctgccagcccttcctgg<br>gcgtattgctgatcggcaagatcgtaagcctgcttttttcagctccacctgctggcgcgcgtt<br>tctcagcctttccgcatccgctttctgcagaacgttgttaccggcataatccgggtcgacctt<br>aagattgctggacagcgcgcggtactctttctctgctgcctgccactcagcaaaagagtcc<br>tggcgcttcatcgcggtgtcaggattacgcccgacgcccagcatcgcatcccacgcacc<br>ggaggcggcattcttcacccagttccaggctttttcgagggatccgagattatcctcgacc<br>gcaccggcgcgctgaatgaccgcgtcggaatatgcccgcatggccagctcggcagcct<br>tctgagaatcccccagcgcctgagcagaagctatctgttcatactgggtggctgtcagaa<br>aatgaagggaatcgttgagcgtcgcgaccgcgttaaccggatcatccttcaggcgtttaa<br>actgatttatggtttcgtcaacggcctgcccggtagcctgctgcagcctggcggcaacatt<br>gctgaccatgctgacgtcattaccgctgaacgcgccgctgccaacgacctgcgccagca<br>cgcctgcagcggcatgctgagtgatgccattacctgccagcgagcgcgccagcgcctg<br>cagctgccctgacgttttccccgcgtagttcccggtcaggatcagctgcctgttaaattcct<br>cagactctttgctgccgtcgtaccaggccttacccaacccgaataccgccgcggcaatcc<br>ctccgaccatgctggcgatcccaagaccgcgcagtgacagaagctggtctatccaccct<br>gcccggttagccagcgtgatcccggagccgcgcagcgcgccgaagttaccgcgcatg<br>acctcgccgatcagtattcccagttcctgccgggcggcggcactttgcagccccagacc<br>gtgcgtggcgactttggcagcttcgagcttgcggatatagacttcagccgcatcgctggc<br>accgacctgcgccgccttcatgcgcagtagctcggtaccggagagcttttgctctgcaac<br>ctgttgcttcagctggctgaggaatcgcgtgcgcgctgcggccgatttttcctccacgatct<br>gcagttctttttgacgggccgtggtgcgggaaataagggcgagataatcctgctgggttat<br>gttgccctgtgccctcgctgcgcgaaagcgcgcctgcacgttcgcaagcgactgtgtttc<br>accattgagctggcgtacgccgtcgatctggcggaaaaatgatgccgcaagttcatcctg<br>tcgacgggcaagcgcagcggcctgcccgtcattctcacgcatgcgctgattaagctcgg | 159 |

TABLE F-continued

Sequences of the genes comprised in Phage 3 of *E. coli* Nissle

| Description | Sequence | SEQ ID NO |
|---|---|---|
| | tcacgcggcggtgagtttcatcaacggactttgaaacgttctgccagtctttggtaagccct tccgttgcggccgactggcgggatttcatatctgcggcagccgccgcgccagcgtcacc cacggttttaaacgcagccgcctgccgctctgaagcgcgctgcattcgcgtctggactttttt cagagtcctcagccatcccggttagctggccctttatgcgggcaacctgctcactaaacgt ggcgctgtcgacgtcaaggttgatgaccagatcgctaatctgctgggccat | |
| ECOLIN_10095 | ctaatctgctgggccatatcggatacctcctgttatcccctcagctgcggccatcagcgcat catcatccggctcgtcatcgctgatgacgataccggaaggagaaagcaggctgaaatgt gcgggggtaagttccgggtcgcggaagaaaagagtggagatggaataaagcagctctg agaaatgcgcatcgagctgagcgtcctgaaaataatgctcccggtagaactggtgccagt cgcccagctcagtggaagtcattccagccagcat | 160 |
| ECOLIN_10100 | tcagctcgctggcaagggcttttccgccgcaacgggttctgcgctttcggcctccgctgg ggcatccggatcggcagctttgtcatcctcaaccggaacgagcatgccggagagcagct ttatttccatttctgctttaccgatcgcctccggcggccagccgctaagcacctgctggtaa agcgtctccacatccgtgccagccggatcgttatgccacaaagacatcgcaatcaaacg cgcaccgcagcgaatatttgagccaatcagcctggccgtcatttcctgatcgctgatgccg tcgctgtcagcgctgacggccttttcctctgcggccataaacgtgatgtactcaatacgctg aagcgccgacagctcgaagatggtcagtgattctttttgccaggtgaacttctctttttttcag aaacat | 161 |
| ECOLIN_10105 | ttacgctgcagttacggtaactttgcagaccgcaacgaaattaccgtcgctggtcataaca ataacgtcagcggtgcctgccgccacgccggtgacggtgatcgcattaccgctaacggt gaccgttgcttttgccccgtctgaggttgccacacggaacgaggtatctgaggcactggc tgggttaaccgtcacattgagcgttgtggttgcgccgacggccacgcttgccgtggcttta tcgagcgtaacgcctgtcacggggatattcggggtcccgctttcttctgccagttccggctt gccggtattggtaattttcgctgtacgggttatgacctcttttgccggaatggctttacccag gctgctgcaccagccgcggaaaacgtcgacggtaccgttcgggtatttgattttgtaatag cgtactgagccatcaataaaccatgcgacaaggtctttttgcccttcttcgcccggcttcca ggcgagggtgaacgaggtatcgccagcagattttgcccccctgggccgtcgcgttccagt cggcatcctcgtcgtcgaggtaagtgtcgtcatacgattcggcggtcatttcgcccggcgt cagctctttaattttcgccaggcggttccagtcgatatccgagagtgggttagcgaaagcg ttgcccgttccggtgtaaagccagagggtggtaccggcacctttcacaggggccagcgg gtttggagtaggcat | 162 |
| ECOLIN_10110 | ttaaattgaataggtgattaagtacgtgaaatcgactgaaccccaggtggccatttcatcat cccgctgatagtcataaccctgcggggtgaacgtctcgaccagttcggtcagacctggg atgaaggccattgccggatacactttctcttccatccaggaatcaagcgcgctgtcgggg ctggaggctttaagaaatacctcgatgtgaacaaccgcctgccacgaatcttcgtcaagc gaatcgccggtgtactccgcgtcagaaaggtatacagccacggcagggagatcctgctc ttcaagaaaaacagggcgcccgtcaaaccaggtgaccgtgtcggtgatctcggctttcag tttggccagaatggctgcacgaattgcgctgtgtctgttcat | 163 |
| ECOLIN_10115 | tcatcgcttcaggtggatcctcagttggtttttcagggctgcggaaagttctttgggcatatc gctttcaataaggcgctttgaaatagcggtgaaggccacggtgagcggtgtctcaagag gaactttgaccacatcaatcggataacgggcctgacctacgcgccgcatgacctgccag cgcccgttcgcaagctgttggataaaagcgttacgaaaggtatagggcccgattttaagg acgctgcccgctccgtttctggcccctttttttacgcgagagcctgacgcgcgccgtgccg agctttatcgcaggaagattaccgcggttgatttttatcgacgcgaccgggcgatcgtgac gggccttgcgcagacgggaacgctggcggaccagacgaaccggaagccccttttttccg gttatcatcaactgttgcttctttcgctacagctttgctcccctggcttatcgttcttctggccac cctgttaagtgcttttgcggttgcctcaggaacgattaaccggctgaggctgttcaggttct gaatagccctttccagtcctttcac | 164 |
| ECOLIN_10120 | tcattcgagatggatgcggggttttccgttgaacatgtcatagcgggtaacgatcaggttct taccgtcgtagtcgacgctgtcgtttcggcgtggctggtaaagctcagagaaaaccacca gcgaagtacctgttcccgacaatggccccatttcctcgagttgctcggcgggaacaacgt catagctgctgccattgatgatcgctgtctttcccatctttttttatagtggccgcgtccat | 165 |
| ECOLIN_10125 | ttaggcattgatcttaacttcaacaacggtggtgtttgcccctgcatcttcccaggcgatgcc cgcggcaacggcgtccgtttcttcgatcgtgattttgccgtccttcagatacacctgcgccc cggcagtaaccgcatctgcggatacttttggcaggaggaaaacaccctcagtaaaaccg tccccggtatcgccagccgggatatcggtaattgccaccgcgataagttttccaacaaca accgggtcgccgctgtgaacatcggttgcaccactgtttaccagagggatcgttttcccgt cctgcgcatagttcttagccat | 166 |
| ECOLIN_10130 | ttactgaccagaggatttggtcatgccgcgatagtccagcggcgccacgccagcatcaat acgcactttcgtggcgataccatcagtggtgaagccttcctgctgatcgatgtatggcgtgt cgacgccgttgagataagcgacctcaatggtgtcggtgcccttcgcggcagccagatac caggctttcgcatcagcttcatccagacgtggttcggcaatgacttctgcaaagttctggat agggttaacgatcccggcattgatgtctgcacctttaacactggccgacttgatggtctgat ttgccagagtttccagggcgacgggcaccagcatgtaggccggacggatattcagggtt cgctccccctccttctgcagacgcatcagcttgcgcgattcgtccaggctggccacagaa attgcacccgagctcaggttcttgtgatcggcatggaacagcgcctttccgtctgagagttt cgggtttttggtcagaatggcgtaaaccagatcgccaatcgttgctttcgccgcgcgcccc atcttcatcggtacgtcggtaagctggttcagatcgtcgttgatgatcgcctggcgagttac | 167 |

TABLE F-continued

Sequences of the genes comprised in Phage 3 of *E. coli* Nissle

| Description | Sequence | SEQ ID NO |
| --- | --- | --- |
| | tgagaagatttcaccatacgtggcaagcgcgatggtttcgcctttgtcactggtagtgatgt<br>acttgtactcagccccttcgcgaacctgtcgcagagaagggaacccacccataccgaca<br>cgatgcgccgttttgaagtccgacagctggcctttttggtccactgctcgaaggtttcctgc<br>gcctcgtcccagccctgaatcagcgctttgttcgcaacatcaagcagaatgttgccaaagt<br>cagaggtgctgtgggtcagcgccaggccaaccatctgcatcgggttgtagctggccacg<br>ccgataccttttttctgtcagggccatacgcgcatactcgcgcagcgtcataccgttataaac<br>gttatcccgctcctgaccttcgaacccggcacgcgccatcagtgcctggcgaataccatc<br>cgcgacgaagttaccgttgcccgcatgaatatgcggctgagtggttttattggacggcgtg<br>gccgttttaccgagttctgccagcagcaaatctttcgccttatcgacggagcaatcagggt<br>cggccacacactgattctgcagttccatgtgcttattaccgaacatggcaaagagatcgcc<br>gatagcgttaacacgggttttctgctcagccaacacctgcgcgcggatcgcattttcatcc<br>ggtgccgggtctgtttttgcctgcggtgcctgaggctgggtaataaccgggtcacgctgg<br>gtagtgttgcgcggcggggtgatcatgttgcgaatgctttttggcatttttttcaaattcctcaa<br>tacgttttgaatgaatacaggccatagcctgaagggatggtgtcacctggtcggcaaaac<br>ccagttcaaggcactcgctgccgttcatccaggtttcgtcctccagcattaccgcaatttctt<br>cggtggattttccggttttctgtgcataagccgggataagaacggattcaaccttgtcgaga<br>agatccgcatagtcgcgcatatcgctcgcgtcaccaccagcaaaccccccagggcttatg<br>gatcatcatcatcgtgttttcaggcatgatgaccggattgcctaccatcgcaatcaccgag<br>gccatggaggccgccagaccgtcgatatgtacggtaatcgccgcgccgtggtgcttcag<br>cgcgttataaatagcaattccgtcgaagacatcaccaccgggcgagttgatataaaggttg<br>atgtgggtgacgtccccaagtgcccggagatcattgacgaactgtttcgccgttacgccc<br>cagtacccgatttcgtcataaataaaaatgtcggcctcactgttattgctggcctgcat | |
| ECOLIN_10135 | ttacttttgcgctggctttcggacggtggcgcgcccggttctttggcttcggcactggtgc<br>ctcctttatcattggcggggtcggtgtcaaacaccaggccctgttcacggttctcgtcaacc<br>tcagctttacggcgtgacttaacatcatccgggttgcgaccgctggcacgtatccagtcgg<br>attcagtagcagcaccgccgcggatctgcgttttccaggcattcgcttctttaacgggatca<br>atccacggcataacgggccccgaataaaccgcgttataaagcgagtccatatcaatgcct<br>ctcggcagcttgatttctccggcagcaatagccatcttgagccaggctcggtacatgggc<br>cgggtcactgaaccgatgaaccagtcctgaagaatcagatagccgtcggttgactcgac<br>aagctcctgccgctgggcactgtacgttccgttgtagtttctggatgtgctggaaaagctga<br>ggcgactgccggcggacacggcacgcagctgtccgttacgaaaagattcgaggttagg<br>gttcgggcgatcggatttaatcatcccgatttcttccccggcctgcagttcgtcatagagca<br>taccgggctgaatcatcagctcgcggtcatcgctgcttgaatcagaatcgaagctctgtcc<br>gtcgcctttttttgatatacatgccgagtgccgcagcaattctggcagcagtaagctccgagt<br>cctcgtattctttcagcgcgctcagacgcatcagaacaccagacaaaagagacgttccgc<br>gggtctggtgcaggcgtcgggtgaatttgagatgcagcatgttctctgcatctatctcttg<br>gtatcaaactgacgcccggatactggcaggcttttatagacctgatattttttcgggcgtcc<br>ccagttatcgacaaaaacgccctgattgagctgggtggcagcatcgctgttcatcggcac<br>aaagtccggctccagcgcttccagccagaacggcacgccagcaaccggctgaagacc<br>atttccggtaccgcgaaccagctgagcaaatacctcaccgtcccggagccacgttcgca<br>gcatcagccgctccagcattgggcgggtaaactggttgtgacatctggccttacggacc<br>attcgccccactttcggcggatatcagtggccagctttttagcgatcttcccgttactcagca<br>tcggatgcggttcaactatgatgcccttcgcacccaccaccctttcttccagcttgtcgaaa<br>acgccgatcaccagatcgtggttgttatccagccagcgcgcctgctgcctcagcgaaac<br>cgcccccatctggctgagctgatcggctgaacgattttccttctgggctttgtgggtacgcg<br>tttgctttaccgcctcatacgctttaataactgcgcgggcacgcaggcgtgaggctttccag<br>cctggtgaaaacaggccaatcgcatcatctaaaaaactcat | 168 |
| ECOLIN_10140 | tcatccaaacctcgccagcctgtagccgggtcgcccacggcgtttgttattgagcgttgcc<br>agtcgtcgctcccattcctgacggccttttctgatttccgacaggttttcgagcgtcatctgct<br>gcccgttgaaagtgattgatttcccctccagaacagacagctcggctgcagcatagcggt<br>cgatcatgttttgaatatctgctggattcac | 169 |
| ECOLIN_10145 | tcacacccaacctcctgacgaagaccacggattagcctgctcggttacgggcttctcacg<br>ttttggttttggtttagatttcggcgcaggcggcggggatggcatttcgccagcttccgtctg<br>cgtgtcctcgatccacgtttcccgccgtgcccactcaggagctgacggccatttgatttttc<br>gtaaccactaaggatggcgagcgcgtcggcataaacgagcaggtcaaatgcttcgtttg<br>cgccccggccgggcttactccatttcccttcattcgagcgttcctcatacgtcagttcgtcat<br>agaaccagctgcccagccaggcggggaaatgcacatagccagggccgggtgaatcac<br>gccacagcgcattattcacccggtctttaagggcatcggtctggagaagataaagaggca<br>catcaccagtcgcctgtgcgcggcgcgttgatctgcccgtgttgtcgggaaacgttcgct<br>ggataagtttgctgcgcctgacgctgtccccttgaagagatagatacgcttacccagccc<br>ctcacggcgacatctgcgccagaacttgtaggcattatccgtcacgccatcttcgcccccct<br>gagtccacggccatcgacatcagccgcatgccctttgatgggtcagctgcgagcggcca<br>cgttttatcaaagacgtcagtgagtaaaagatcccagtcctccggatagctcgccggatcc<br>acctgaatgctttcaccgttgccgtcgcagcgcagcgaatgccggatgttgtaacggtca<br>actatccagcgctcacccatacttccataacccgtaatctgcacaacaaagcgccggttgc<br>gcccggcctgcacgtccacggtcgcagtgagaaactgcacgccgttcggtaccgaacg<br>ttttgggacgtcttcggcacgctgctcgagcaattcacttttacgctgctccatgctggctcg<br>cggcaaatagggcctgccgaaatcggtgttgatcaccgtcttcagggtttcttcgctgcgc<br>gtggattcatattcctgctcggcggtcagaaacttataaataagctgcgcccaggtctggta<br>agcagctgccggaccttccatccagaaggaggcaatacgggaacgacggccatcacc<br>gctaaccaggcctttcctgtcgatggtttgcccgtcccggagccagacacatttcatgttaa<br>gcgcacgcttcatgtccggtgtgatcctgcctttacaggcagggcactgaagaaacgcc<br>gcttcgctggcaagcacaggatcgctgctgtcgcggtatccggtcatattgtccatttccg | 170 |

TABLE F-continued

Sequences of the genes comprised in Phage 3 of *E. coli* Nissle

| Description | Sequence | SEQ ID NO |
|---|---|---|
| | gctggaaatattcgccgcaatgcgggcatggccagtaaagacgacggcggtcaccacg gttatagagcgataaaattccggtggtcggaggggcttcatggggcgtggagcgccgcc attttgtgtctctgatatccctcccgggcgagctctcaaccagcgtcatcccggaggacat gaatgtcgtggttcgtttcgatgccagtgaaaaagcatccccctccccgtcgatatcttccg gaaagcggtcataatccgtcagcgccacacttttatagtccgaggacgacatgatattgac ggatggccagcccagcttcagatagttaccggcgcggaatgtacggtcgtagacgttgtt atcgttacgtcttgggcttagccgggttttaacttcagggctacagcgaaaagtacggtcc aggcgtttttggaatgctcgcgcgctttttcctcagatacctgaattacaagcatatctgcc ggatcgcagacaatgttataaacgatccagccgtcaatcagcccgatggttttacccgttc gcgctgggcccacaaacacaaccgcatcgtattcacgcgatgccagacagttcatcggc tcaatcacatagggtgccagatccggatcccacggaactgagtttcccgcccccattggc acgcgcatataagtactgaccgcatcggccaccggcatacgacgcggggctcgtaaaat accggaaacatcgcggcggatgtccctggcggatgcccgctttgccat | |
| ECOLIN_10150 | tcagtcctcctcaggctgctcctcctcttttccagcgtcctgcaccttctccgccatctggtc gcgcagatcatcgataacgctttgcacacgaactaccgcagcaggcgttaaagcacagt cgcgctcgagcacatccgggagggtttcaagtaccatgacgacggctttcgccatcaatg agaattctcgcgccacttcatctgcgggtattaactgccccgtatcctgttcgaacttcagc ctctcgttctctgctttccagtgggacagcctgtcagaaggggcatatcgtcgatgttggc cgaaacggtagggatcatcagttcggtcagaatgtcggtcaccagatagagctttaacttg ctattgctgcctggagcaggttcaacatttttcagtctcgcggcaaccgtctgacggtgtac gccggttatccctgccagctggttgatattgagttttaaagtggcaatttcctggtccat | 171 |
| ECOLIN_10160 | ctatcgacggcactgctgccagataacaccaccggggaaacattccatcatgatggccgt gcggacataggaagccagttcatccatcgctttcttgtctgctgccatttgctttgtgacatc cagcgccgcacattcagcagcgtttttcagcgcgttttcgatcaacgtttcaatgttggtatc aacaccaggtttaactttgaacttatcggcactgacggttaccttgttctgcgctggctcatc acgctggataccaaggctgatgttgtagatattggtcaccggctgaggtgtttcgattgcc gctgcgtggatagcaccatttgcgatagcggcgtccttgatgaatgacactccattgcgaa taagttcgaaggagacggtgtcacgaatgcgctggtccagctcgtcgattgccttttgtgc agcagaggtatcaatctcaacgccaagcgtcatcgaagcgcaatattgctgctcaccaaa acgcgtattgaccaggtgttcaacggcaaatttctgcccttctgatgtcagaaaggtaaagt gattttctttctggtattcagttgctgtgtgtctggtttcagcaaaaccaagctcgcgcaattc ggctgtgccagatttagaaggcagatcaccagacagcaacgcgccacggaaaaacag cgcataaagcacttcattagcagcgccagatagcgtaatgattttgttactcat | 172 |
| ECOLIN_10165 | ctatttgtgggtaaagttcgtagtgcgctgatcgtgcaaaatgattttagttgggaacagttc gcaactctgtcccataaaaatcagcatattcccatctatcccatatccagcgcattgaccat cgggatactgaagggagattccatcatctcttagaaagatcaccatctcttttgtttcaatttg catatagctacctggaggatttatgaatgcaaggattttcat | 173 |
| ECOLIN_10170 | atggactattaccatgagattgattttccatctttattcgcgagagcagtggaaagcgatga cgatgtgggtactacattgcgcattcacctactttgtgagcgcatggtcgaagcatggatat gcgcatgctgtgactgccaagatctctttggaagagataaaaacaaacttttaatcgaatgt aatactaaaatatccatggcgggaaacctgggaatcccccggaacttatgaaatcactta aaaccatcaactcaatgcgtaatgaccttgcacacaatccatcaatacaaagcattgctgat tcaaggatccagagcctgaaggatactctgactgaatactttaaacagcatccaacggaa cccagcatggaagaatcaaaactgggtatttttaacgccgagaatcaattaaccgaagaa gtttccttagatagtgacagttcaaaaaacagacttaagttaatcttgctgttcagcaagttaa tgcaggcgttaatgcaattagttgcagctaatcataatgggcgctgggataaccaatttagc caattcgtttaccatgtgaccatgaacgcaacaaagagataa | 174 |
| ECOLIN_10175 | ctagtcgtcgagttgcaacacaccgtgatccagtgattctgaataggcgataagtccggta taaccggggataatctcaccattatcagcttcaaattcaggaattgtgccggtggtgatggt gtattgaggctggccatcttccttcgcgaaggctgccaggtcttcaatctgcttagctgtaa gaactactgtcat | 175 |
| ECOLIN_10180 | ctattggttattcgacagtcgcactgattcgtaaatccgctcacacgtcattcctgcccggta gctttcgtcagatcgtccagcataatatcgagctgcttctgcaaggcttccgagcatgtcgg caagcattgctgcgttggctccggctgttttgcttctgacggaagtggcgagatctgcggt gtgctttgcggcgtccatgtgggtagcgagttttgttgcttcggcgcgcagctgcttaacag tggtagccaggccagcagaagtaacggcagcgctcgctgcttgagcttgagcatctttaa cggcctcatcccgggcgattgttcgcccttgttcaatcatacgagctgcggtctgtgcattc gcttcctgtgaagattccgcgctatcccggtcagcccactttattttccagctgcggttcgtc cactcactgccagcgagaaacgaacctaccaacgcaacaatcacaat | 176 |
| ECOLIN_10185 | tcactggtctatcccccagcacgtcagtgcgctttcctggtcccgccgttctacctgcccat aacatccatccttctggcccttggtcaggcggcaatcgcggccaccgtctttaatccacca gcggatagcttcacaggctcctttcgtatcgccagcattaattcgcttatagaacgtagacg ggaaacattttccggggccgatgttatatgggcagaaagaagcgatacccgctttctgtg gttcggtcagtggtactttgatatttcggtcaacccacgccagcgccttgtcgcgttcaatg gcgtttacctgggcgcatttctcagctgacagcttcatgccctgtactactggcttgccatca accattgttgcaccacggcaaatggtccagagtccgccgccgtcgcgatatgctgtcaag ctgttaccctctttctcatccagaaactgatcgagaatcacgggtgcggaagccccggca agaatcaaaccaacgaccgctgcgctcaatttattcttcagctttagagacatagccat | 177 |

TABLE F-continued

Sequences of the genes comprised in Phage 3 of *E. coli* Nissle

| Description | Sequence | SEQ ID NO |
|---|---|---|
| ECOLIN_10190 | ttattcttcagctttagagacatagccattgcgccgatcctcccgttctttccagcggaaata<br>ccagttcactgcacaggtgattaccgtgcatgcgataccgacaataattgcccagtcgctc<br>aggcttaaccctgcaattctgtcggccaacatccaggacacctcttttgctgttttagctgttt<br>cggcatatgccttcgctgatacaccgcagccggcaagcgtggttcctgatccatatgaaa<br>gtctgctgtaaatggtgctcattctggtcat | 178 |
| ECOLIN_10195 | ttatgatttttttcagtttttccacctcttcggtggtctgtataaacctgtctgcctccagttctacg<br>ccgatcgcccgacggccaagttctattgcagctttcacagttgaaccagagcccataaag<br>aaatcggcaacgatatcccccggtctgctgctggcgctaatgatctgtttcagcatgtcgg<br>caggtttttcgcatggatgtttgcctggataaaactgaacaggcttatgtgtccatacgtcgg<br>tataaggaacaagagcggaaacagagaagcagcgccgaaggattttgtattcctccagc<br>aattctgaatacttgcggtttaatgactggtaggtagccaccagctggtggtgaggatgttc<br>aagcttttgctgaatatgtttatcgatggcgatccgcgtgaacagttcctgcaattttcgatag<br>tccacttcattcggtagttgccattggcttgcaccaaaccagtgtgacgccatgtttttctttc<br>cggttgcctcagctatttctttcgagctgacacccagtgattcacgggcattacggaagtaa<br>tcaatcagcggcgtcataatgtgctgctttagctctgtgcttttcctttcgtaaacatcctcttta<br>cctgtatacggtccaagatagtgctcagcaaacaaaatccgttccgtagatggaaagtac<br>gcacgcaggctttctttattacatccattccagcggcccgatggttttgcccaaatgatgtga<br>ttcaaaacgttgaatcgggcgcgcatcataatctctatatctgaggccagtcggtgaccgc<br>aaaacaggtagatgctgccagcaggtttaagaacgcgagcatactcagccaggcagcta<br>tcaagccagcgtaagtagtcctcgtccccccttccattggttgtcccagccgttgggcttcac<br>tttgaagtacggaggatccgtaactataagatcaatagagttatccgggagggtggcgac<br>gtaatgcagactatcagcgttgattaactcaacactgtttatttttacagtatttttcat | 179 |
| ECOLIN_10200 | ttactggaggcgtttataacatccgaactggtaatcagataaccccgccatcaccagctgc<br>gtaagtatgagctggcaacgttcgtggctgaggtgggtattctgtgcaatctccccagccg<br>ttgctggtttatcgcttaattcattgaaaacagcctttgccgtttctgtcatatcttcctgatttag<br>cat | 180 |
| ECOLIN_10205 | ttagcaaatattccacatcatcgtactaccgttatggttttcgataatttttgcggctgggctag<br>taccaaaagagtgcatatagcaatgatgaatagtaaggaccagatcctgcaacgtttggtc<br>actctctagctccatgatatttaaaccaatattttgagctttgtccaaatgaatatgtctggcat<br>gtgcatacgttgcttggtggttgtttaactcatcacatatacgcttagccttagcttcagcgtc<br>agcctgacctgcgaacataccagtacaaagccatttctggacaatttcgttcgcccagaga<br>attgctttttcacactcgccaatcaacgttggatttagtttttggaacgtaaattgccaccattg<br>cagtgcagcagggttggcaaaaatttccgcttttgctctctcatactcctcaataattgcatg<br>agatgataacccattaaactgtggatcaattggccccaagttcgactgtttacctaaaacga<br>tctgctcagcacaacaagcaagcattgtgccacaactcattgaaatcataggtacaatcgc<br>tcggatattggttccgaactttgaacgaagataatgaccaattgattctagagctgcgatatc<br>gcctccaggagtatggagtaagatatccaatcccagactcgtatctaacccattgatagca<br>gacataagaccatttttatcatcatctgacatctggatcagatgttgaaacccaggcccccc<br>tttttgaaggaagcctgagtaataagaaattacatttcggccagtatgtttcgataaatcacg<br>taagtacttgtggcgaacctcatccgctggtgtacgttgagcgatagtacccatctcaccc<br>aatacgtctatccaatttggcat | 181 |
| ECOLIN_10210 | tcagtatgagtacagttggtgagattgctgaccgttctgctcagtagtatttggtgttactgtg<br>ctgtatgaatagagcacaccacttctcacattcagatcgttttgctgagcgagaacacgcat<br>agcaaaatgctgtacggattcgcctttttgaaactcttggggttgtatgcccatttttttcgtaa<br>aattcagcagcgctcat | 182 |
| ECOLIN_10220 | tcacatttctgccactttgagggcttcttcttcctcatagtattcaagagccatggccaacgc<br>agattcatcaagctgggtaaaagcggcctttaacccagcccagtgccctgaatagacacg<br>caaccatgtcgaacggtcaacgctaaccatgcgggccaacgctgcaccagcatagtcttt<br>ataggtttcattatttctggttgcggcaatttcctgccctgccagccataccaggcctatcag<br>tttctttactacgcgctcctgaagggagttatcacccaggcatttctgataagttttccagac<br>gtattcacacatcatcacctggtgcttatagctaaggtcaaaaccgtagcagtaccgcaac<br>caggcctgctggtatccactaagcgcggacactgccctacgccacggcgcggactcaa<br>attccgcatcttttatcggcggcattggcctgcggcggctgcgtgtttccagcacatacagt<br>ggcgcggaaagtgagttaacaaagcgtggccccttctctccttcgagttcgacgagatga<br>attccacggcgaggggtggcatttttgtctgctggtgggtgttcactgaaagcctcaagct<br>gccctttttgttcccccagacaggtcaggtagcgcgcggcgcaattctattcttacaaaattc<br>aggtcttgttgattcat | 183 |
| ECOLIN_10225 | ttaagctttcgcaattacgccgatcgccagcgcccgatccataaaacgcagtagcagctc<br>aagctgcgtaccatgcttctgctcgaatgccggtacatcggcgtgtaactcgtcgtggcac<br>tctctgcacagagggatcacgaagagatcatgggcttttgttgctgtccccccccataccgt<br>gccctacgatatggtgcggatcatctgctggccgtcggcaacactcacagggttgtgtttt<br>aacccagcgggtgtacgtctcatttatccagcggcgtcgctttggcctgagcatgaaagat<br>tctggagactccggatcaacagagagcgtgaggatcttcttcgccttctcctgcacgagg<br>ctggttgcagaagcggaaggcacaatgtcgctttccctcatgaccgagcggatcttatcat<br>ccggaaggcgtagccccttgtgcgcaacgctttccggaataacatcagccaggtcgtttc<br>tgaccatccaccagcacagttccggaagcgtcaggatatgcgactcgggaaaaccaga<br>atcacgccgaatgacttccagaatccaggataccaggtttcctgccgctatacctgcaagc<br>tgttcggtatgctgccccgacaaagtgtgatcgcaatgccagcacaggcgaatacttcct<br>ggtgggtgccgcattgttgtgaagttcttgtcgtgccacgatgaatgtggccactggcattc<br>aaaccgattactcaaccattgctcaagggaaggaagcccaccagcacgctgaataaccc | 184 |

TABLE F-continued

Sequences of the genes comprised in Phage 3 of *E. coli* Nissle

| Description | Sequence | SEQ ID NO |
|---|---|---|
| | gatcattctcgaagacctgccgcattaccggatcatcagccagcggctgaatggcggcg<br>ggaacagctcctgtactgaatgacgccatttcttctggttcaggctcaagcagaacgcgac<br>cgcgcataaagaggtgcatcagttccgcgccgggacgaaacaacacaatccccatacg<br>atgggcgatctcgggggtaagcagagctctcac | |
| ECOLIN_10230 | tcacgcgacctgccccctggcaatgtgttctgcccacagtccaccaatccagcgcacgc<br>ctttcgccgtgaaacgtgcctggctgaatgcatgatttgaggttacggatgtgccggttttc<br>acttcaaaacggcccgcatcaatatgctgatgccgtggggtcatcgttccgccaagacga<br>tacatgatgtcgttctcaaggaggaataaccgcagatcgggctctttggccttaagcagttt<br>tgccacctggcggaatgacattgacccactggctgtacagtaccgatcaacaaacgctac<br>cttcggcgccgcggcagccagttcgttagtcaactgctgtttttgttctgcaaggtcagctg<br>caagacgtagggcttcagagaatgattgaggaatcgtctgctgctgtgcctgctcaagctc<br>ctgccagcgatcaaccagacgcgcggtaaactccggcgacagctgcgcgacaacgat<br>ataactgtcccgcttccctatcagataaaccgataccgactgattgaggtgattttaacttc<br>ccccattgggggagttcaataacaccgcgctctgccaggcgttcaatggaccgtttaac<br>atggtcatgtcttgattccaccagctcagcaatatcgctgctggacatggttaacgctgttgt<br>tgctaactggctcat | 185 |
| ECOLIN_10235 | tcaggcggctgcacccgccggttcatatctgctgattgttatctctacccgacctttcggca<br>caacgggtccccattccaccagcatgcgcttaatctggctgtcgtcttcccagacacccgc<br>atgcgtcagcgcgtcaaacagggctttgttgtaattatcgatatcccggcggcgcgcatcc<br>ggcgggtacagagtgatttctaccgctgccagttcagtcgatggcttcgggagacgtcgt<br>aattgctcaatgatcgccacgcaggcagcgctctggtatttacggccagcggcgctaatg<br>aggtgacgaccggccagcggccccttgttaggggcgcgccagtaagtgttcacgctcg<br>gaggaaaaggcaggatcagtttcac | 186 |
| ECOLIN_10240 | tcacgcggcctctccccgcatattgcgaacaagttcagaagcagcagtaatgatttcgctg<br>gtggcagtccgctccagccagagttgattgatattggctttcagcttgtgttgcagtgactc<br>atccagcatgtcagcaccatccacctggtcgaatacaattctaacctccagcggccagat<br>acgggactcgggaagcggatccgatactggtttagctttctcacgaatgtgcatgcggat<br>ctggcgaatattggaccaactggaaacatccaggcttcccatggctgcaatgaagtcagt<br>gctgttcatgccatattcaccggatgcttcaagggcaacagtgcgaatacgttccgacata<br>tccaggcgcacagcagcgtcatcgaattcaatcgacaacagccactcatccacaccgaa<br>caaaatactctcacgaataagcagcttcgctttgtcgatcgttaaaggtgatacctgagtga<br>attccggtgcttcgacagaatccgccgcccaggtatgcccaaacttcgattcactgaatgt<br>gtattcttctttatcgccaaacgcagctctaacgcatgcccacgcctcgacaccgctgata<br>gcaaaaatatctttctgggtgagtggcaactctgcttctggcttatcagctgcaggaggtgt<br>ggcagttacaggttgagacttgctggcagcaaattgtgccaaagccataaacgcccgcc<br>cttttgcctccagttctgtgcggttgatatagctgaaccgctcgccacgccatgacttatcga<br>atacagctatggcaccggcaaaaaacgcgctggtgggtttctgtttttcgtcagcaggtac<br>aaaccacacaggcagatcgaacccaatgcgcccgcgaatgaatacaatgtgatcggcat<br>cttccggccaccacgtttcactcggcgcggcttttatcaggaatacatagcgaccgccctt<br>ctcgcgctgggctgctgcgtagttcatgatgtgcgtcatgccggtgatcgcctgcttctcgt<br>ggtactgcgaacggctatacggtgggttgccatagccagcgccacccagttcagccaga<br>cgttcagaccagtcctgcgtcagcgcgttatcttcggcggtgtaccatgccgggcatttcg<br>cgttgtcgtcgtcagcaaacaaatccagaactaatggaccaaatagcgcgttgatccccc<br>aaaaaagcagatccggtgtccgccactgatcgccaacctctttcaattcgtgagctggttt<br>gctacgcagtgccgccagcgcctggcaatatttattggtcatcat | 187 |
| ECOLIN_10245 | tcatgaacggaaccccgaattttctggcagtgagtaatcaacactctggaagtttgcgcgg<br>ctggctgagttagtctcccatttgccgttaacgcgttcaggccggccagcactggaccattt<br>ggtcgcgctttgcaggtaaccagggaagtttttttggaatgaacagagttgccgggcggag<br>gtattgcgcctgctcgctatcacgccaatcggcatttttgtaatccactaccaagcacaggt<br>catcaacagtgaattgttcccgaagacgggcgcgaatattctccagcgacgtgctgcata<br>cctggtagcgtgagccagtagtctgattcaggtaagacaaaacctgtctggcctgatcagt<br>aatcacaacctcagggtcgggttgcgccgcaaccggacaagagggttttgaagttacttg<br>tggttcttgttttgattttactgacggatccccaccagattctgacgggtcaaaaccgcctttttt<br>tgctggatttcgacgcctcaaattttgacgggtcggattttgatgcatcagattttgatgggtc<br>agattttgatgcgtcagattctgacaggtgagaaaaagcagcctctcgcaacttaacgacg<br>ttaagctgatatacgttcgatgcgttacggttcccattacggcgctgcttacgggaaagcca<br>gccatccttctcaagctgagcaagggccgtccttaccgtactttctccagcaccgatttgac<br>gtgcgatcgtgccaatagacggccagctaacaccctcatcactactgaagtcggccaga<br>cgcgccatgatggcaacgctggataacttcatgcctgacgaagcgcatgcatcccatac<br>gtaaccggttaatttagtgctcat | 188 |
| ECOLIN_10250 | ttaattctgtaaatttacgctggaattgttcaagagggctgaagcactcatgatcgtaccctt<br>cgcgaaggtatataacgcgctgtgtatctggctcccagcggacaactctgacgggaactc<br>cgtagtgatctctgaaccgccggttaacttcagccattcctcgcgccccttctcgttcatctg<br>aacaaatgcttctaccatcaagtctgctggctggtagttgcctccatcagccgcgttatttat<br>gatttccacatagccgaactgggcatctttacccaccagcggcaaacatctgaattgctta<br>gctggtctgaatcggtttacactgttcat | 189 |
| ECOLIN_10255 | tcatgcgttagtttctccactgatacgacacgccaaggcgcccggagctgcacactcgcg<br>ggcgtcaccttttctgcctgttgaaacgaatacgtcaatcgcctgatctgaaacaccaacc<br>ccataaagcgccataaatcccaggaacccgtgaatctggtggcggagcttcttactgaat<br>aattctgaaagcattttgcgctctgatgaatcaattaccccatcagccgctgctgccatcttg | 190 |

TABLE F-continued

| Sequences of the genes comprised in Phage 3 of *E. coli* Nissle | | |
|---|---|---|
| Description | Sequence | SEQ ID NO |
| | gcattagccagctcaccagatgctgctgccgctttcatctcaatgctgtacagctcaacgtt<br>atccaggctctcagcagttggaacatccaccagccatttccctttcggttcgcctggtact<br>cggccaagtaacaagaaccagacaggtcctccatccgttccagttctgccaaggtaaag<br>aaccgactgccacacttctggtacaggtggttgtggaactggtcgatagtcatccctaaat<br>cggaagccatacctaagcgaccatgcttgtgtgccttacacatcaggcggattgctgtattt<br>atgctgtctaccat | |
| ECOLIN_10260 | ttaaagttgactattgttgttagcggaaggtatgccgtcatttttgttcggataaatatcaggtc<br>gtaattgatggggagttactacccatccgccccattggcagagttgaataactctttcagaa<br>ggtactcggttctttgcaatccagttcgcaacagattgaactgattggaattcaaaccgcctt<br>gatacctctgaaatcgacccgatcgccttcacagctttagctgttacattcttgtgttgagat<br>gacat | 191 |
| ECOLIN_10265 | atgccttgtgcgcttaatcttctacttatggtggaaaatgctaaatacaaagactttgccgaa<br>aggctaaacaggtctctccaagagcaatctattggagttaaagaattgtcagagttcagtg<br>gtgtctcgtatgagatggcgcggcgctacactcttggtactgcaaagccgagagatgaga<br>agatgattcgaattgcagaaagacttgccgtctcaccggcttatcttgattatggtgtgcctg<br>ttaatggtggcgacgcgccagccaaaggcacggtcagaatagagcaattggatgttcat<br>gcttcagccggttccggatatataaaccaaccattccctacaatagtgagctcaatagaga<br>ttccagaagagaggatcttcgagttgtttggtcgtagaagccttgatggcatcgtcatgata<br>aatgttgatggcgatagcatgatgcccacgctttgcccaaaggacctgcttttcatagaca<br>gcaaggttgaacaattcagcggcgacggcgtttatgtgttcaattttgaagacagtacgttc<br>gttaaacgtttgcagaaggtaaaagggcgccgactggcagttctttcagacaatgaacatt<br>acccgcccttcttcatagaggagcatgaaatgaatgaactatacatattcggcaagctaat<br>cagatgcttacctctaaaaatgatagagtttggctaa | 192 |
| ECOLIN_10270 | ctatttaaagagcttcttcagcttgtcctcaaccttcctgatttcggaagtaagctggctgctg<br>ttgacattgatagtagctccacatcgacaagtgaaacttttgttcgacttgagccaagcgatt<br>ttcttcttcgtcttagtgccgcacttagggcatgcgggtaacgtaatttcctggttatcaaaag<br>cgcccat | 193 |
| ECOLIN_10275 | atgaataatccgtttttcaaaaatatgttggtgtatcgcattagtcgcgatttcaccatcaacc<br>aggaagagctggaacagcagcttgaactatttcgcttcactccatgcggtagccaggata<br>tggcaaaaaccggttgggtatcaccacttggtcagctgtcagatcgcttgcatcacactgt<br>caataatcaagtgttgttggttattcgccgggaagaaaaaatactgccatctcctgtcattac<br>tgaagaactgcgcaagcgtgtgtcgcgtctagaatccgatcaggggcgtcgcctcaaaa<br>aaactgagaaagattcgctgcgtgatgaagtgttgcactccctgcttcctcgggcgttctcc<br>aaaaactcgactgttggtttgtggatcaacgtcaccgacggtctgatcatggttgatgcag<br>ccagcgctaaacgtgccgaagactcactggccctgcttcgtaaaactctcggttctctccc<br>ggtggtaccgctgactatggaaacgccgatcgaactaactatgaccgactgggttcgttc<br>cggtagtgcgcctgctggctttggcctgggtgatgaagccgaactgaaagctattcttgaa<br>gatggcggtattggacgctttaaaaaacagactctggtcagtgacgaaattcatgtgcatct<br>ggaagctggcaaagtagttacaaagctgtctatcgactggcaacagcgcattcagttcgtt<br>ctttgcgatgacggcagcatcaaacgccttaagttctctaatgagattacagaacaaaacg<br>acgatatcgaccgtgaggatgcggctcagcggttcgacgctgactttgttctgatgaccg<br>gcgagcttatctctctcattaacggattaacaacctctctcggcggcgaagccaagcgata<br>a | 194 |
| ECOLIN_10280 | atgagctacattcagacattatccggcaaacattttaattacctcgatatccaacaggacga<br>tatcgtgatcgaggatattgctaccgcgttgtctcatatctgccgctttgcagggcatcttcct<br>gagttttacagtgtcggccagcatagcgttttaaccagccacctcgttccgcaggagtttgc<br>attagaagcactgcttcatgatgctgctgaagcctacctgcaggacatcccctccccactt<br>aagcgcctgcttccggattaccaggcaatcgaagctcgtgtggacgcagccattcggca<br>gaagttcggtctaccaactgagcaacacccaaccgtgaaatatgccgacctggtgatgct<br>cgccagcgaacgccgcgatttttgagattgacgaaggttccatttggccatgcctcgaggg<br>agttgtcccaacggatttattcattatcaacccagttcgtcctggccagtcatacggcatgtt<br>catcaatcgctttaacgagttgatggagcagcgccaatgcgccgcatga | 195 |
| ECOLIN_10290 | atgaccgtatttgaatatctccaggctcatccgaataccaccagcggtgaaatcgccaaag<br>gtatgaacaaaaagaccccagcggtcgccggagcattatctcagctctatggcaccggt<br>cggatcgtgaagtctggtgttcgcaagggtattccaacataccgcattaacgatatgccgtt<br>tggttgcagtaacagcctaaccatgatgtttaaccagctcttgagcagagccagacaagg<br>agcagcccaatga | 196 |
| ECOLIN_10295 | atgacagcactcaacaaacaggcgctgcgtgaagaattccagttcatgcaggacaactat<br>agcgacccggcagaccacgatcggcaggtgatttacatcgaggcggaggcgctgctg<br>gatgagttggaagccaaagactcaacgatagcagcacaacaacatgagatccgtatgtt<br>gctgaatgcgcttgaggaaaaaccatgcccgaaatgcaacgacacaggaatgactgata<br>gtggcggcacgcagccatggggcgagccgattgagattgaatgcgactgccgacagc<br>aggatgccaacaccgcagaacttgtagccgctggcattggcgtgaagggggagtga | 197 |
| ECOLIN_10300 | atggataaattaatcaaacctaccgccaaaggtaaatatgacggttcatgtgattatctttgc<br>tcggaagatgcgcgattcatcgttatgcgcggcgattatacggaagcggaaataattcag<br>gcttctgtgtctcaagatgtaatcgactcggatggtgcggctgattttgcaagtagcgcccg | 198 |

TABLE F-continued

Sequences of the genes comprised in Phage 3 of *E. coli* Nissle

| Description | Sequence | SEQ ID NO |
|---|---|---|
| | ctattatcagtgctggtacaaagttagcccaataggtggtcaggatggctattcaggctgg catcatcctcgtgattcgccgtgtcgcggtgcatatttcgcatcagttttgcaatgggattaa | |
| ECOLIN_10305 | atgacaactaacaaccacccggcgcacggtcctgtatcactcgatcgcctgcaccagata cgcgaacacctgctgcatgatacccaatactcaaacggcgggaacagagcctacattct cgctgatgtattgaaggtgattgatggggctattgcccgcgagctggtacgccgtgagca tgcagcgtggtcacaggctactttcggcgatgtcggtccagttggtccgctgaagcacctt tccaaagaagcgctcgaggctgctgctgaaccaggcgaccttagcgaatgggctgacat gcaattcctgttatgggatgcgcaacgtcgtgccggtatcagtgatgagcagattacccag gcaatgataaaaaagctggctataaataaggttcgccaatggcctgagccgaaagacgg ggaacctcgattgcatatcaaagaacagtcagagcaggagaaaaaataa | 199 |
| ECOLIN_10310 | atgtttagcctgattcggcgcggtcaaatctacacggacagtagcaactggcccgtaatta tccatagctgtagtgatcactcggtccgaattaaacgcaatgatggcgagctgagaacga ttagcatcaaacgctttaacgaagattttgaacgagtggagcatgatgagtatcgcaaaat atgtgccgaaatagagcaggaaacaaacctgaaaaacctacgtgcgatgcgtcgcggc aagattactgaatag | 200 |
| ECOLIN_10315 | gtgaacaacttaatgatcgaccttgagtccatgggcaaaaaaccgaatgcccctattgtct ccattggtgccgtattcttcgatccgcaaagcggtgaactgggtcaggagttttacaccgc tgttaatcttgaaagcgctatggagcagggagcggtgccggatggtgacactattctgtg gtggttaagacaaagctcagaagcacgatcagcaatctgtgttgatgatgcgatgccgat atcatctgccctatctgaactgagccatttcattaatcggcattctgataaccctaaatatttaa aagtttggggcaatggagctactttcgacaacgttatattgcgcggcgcatatgagcgtgc cggccaggtttgcccgtggcaattttggaatgatcacgacgtcagaaccatcgtcacatta ggcagatctgtaggtttcgatcctaagcgtgatatgccatttgatggggttgcacataacgc actggctgatgcccgccaccaggcgaaatatgtttcagcgatttggcagaaactaatccc aaccaccagcaacagctaa | 201 |
| ECOLIN_10320 | atgagcaatattttccagttagctcccaacgattgggtttgtgaaagcgttttgatcgcggtt actgggctcaaacccggaaccatcctccgtgccagaaaagaatgctggatgattgggag ggagtatatccacgtatcgcctgacggaaatcctaaaccttccagtgagtgcatgtataac agaaaggctgtagatgcctgggtcgcttcaatgaaaagcaagcaaccagggtga | 202 |
| ECOLIN_10325 | atggataaagtcacatatccaacaggcgtcgaaaaccacggtggcacattacgcatctgg tttaattttaaaggtaagcgtgtcagggaaagtctcggtgtccctgacaccgctaagaaca ggaagatagccggggaactgcggacatcagtatgttttgccatccgcacaggaacctttg attatgcaacccagtttcctgactcccctaacctcaaggcttttggtgtaagtaaaaaagac attacagtgaaagaacttgaagaaaaatggctggatctgaaacggatggaaatctgcgcg aacgcatttaatcgctatgaatctgtcgcaaggaatatggtgccgaggatcggaggtaatc gcctggtgtcagcagtaaccaaagaggaattgctgtatctgaggaaatatttgctaactgg ttatcagaatccgacgaaaaacaaagccccggcaaaagggcgaagcgttgttactgtga actattacatgacgacaatggccggaatgtttcagtttgctgcggatcacggttacttagag gtgaacccattcgagggaattaagcctctgaaaaaagccagggcagaaccagatcctct gtctcgtgatgaatttattcgcctgatagatgcatgccggcatcagcagacgaaaaacctg tggtcattagcagtgtacacaggaatgcgtcacggggaactggtctccctggcctgggaa gatatcgacctgaaggctggaacaattaccgtcagacgtaattatacgaaacttggtgagt tcactctaccgaaaaccgaggcaagcacagatcgagtggtgcatcttatccagcccgca atcagtatcctgaaaaatcaggctgaaatgacaaggctgggcaggcaatatcacattgaa gtgcagttacgtgagtacggccgttcggtgaaccatgagtgtacattcgtctttaatccgca tgtggtcagacgcagtaagcaggtcggatttatctaccgggtcgattcagtaggcgactc atgggaagcggcacttaagcgtgcggggatcagacacagaaaggcgtaccagtcacg acacacctatgcgtgctggtcattatcagctggtgcaaaccctagttttattgccagtcagat ggggcatgcgagcgcgcagatggtgttcaatgtttacggtgcatggatggctgacagca gcgcagagcagatcgcaatgctgaatcagaagctggcagatttgccccattgatgcccc atagccacgagaacagtacgggaggattattaaaatcagtaagttaa | 203 |
| ECOLIN_10330 | gtggagggtaacaccacgctttatgccctgccgaaacccgaggttgtcctgcgctggcgt gagcagaccacagatgacttccgcttctgttttaagtttccggcgaccatttcgcatcaggc agcattacggcattgcgatgatttagtgactgaatttttgacccgcatgtcaccgttggctcc gcgcattggacaatactggctgcaactgcctgccacattcggcccacgggagctgcctg cgctttggcattttctcgattctcttcccggtgaatttaattatggggtggaagtccgccatcc acagtttttcgccaaaggggaagaggaacaaacgcttaatcgcggtttacatcagcgcgg cgttaatcgggtgattttagacagccgcccggttcatgcagcacgtccatacagtgaagct attcgcgacgctcaacgaaaaaaacctaaagttccggtacatgctgtactgacggcgaaa aatccactgatccgttttatcggtagtgatgatatgacgcaaaaccgggaattatttcaggtc tggttacaaaaattagcgcagtggcatcagaccactacgccttatctttttttacatacgcca gatattgcccaggccccggaactggtacataccctgtgggaagacttacgtaaaacgctt ccagagatcggagcagttccggctattccacagcaatcttctcttttctga | 204 |
| ECOLIN_10335 | atggtaagcgcgctgtatgccgttttaagtgcgttgttattaatgaagttctcttttgatgtcgtt cgcctgcgaatgcagtaccgcgttgcctatggcgacggcggttttagcgaactgcaaag cgctattcgcattcatggtaacgcggtggaatatattcctatcgcgattgtgttgatgctgttt | 205 |

TABLE F-continued

Sequences of the genes comprised in Phage 3 of *E. coli* Nissle

| Description | Sequence | SEQ ID NO |
|---|---|---|
| | atggaaatgaatggcgcagaaacctggatggtgcatatttgcggcatcgttttgcttgctg gtcgtctgatgcattattacggttttcatcaccgtctgttccgctggcgacgttctggcatga gcgccacctggtgtgcgctgttgctgatggtgctggcgaatctttggtatatgccctggga gttggttttctccctgcgttag | |
| ECOLIN_10340 | atgtctcaccgcgacacgctattttctgcccctatcgccagactgggcgactggacctttg atgaacgggtagctgaagtcttcccggatatgatccagcgttccgttcccggctattccaat attatttccatgattggtatgttagccgagcgcttcgttcaacctggtacgcaggtttacgatc tgggttgttctctgggcgcggcgacgctctcggtgcgtcgcaacattcatcatgataattgc aaaattattgccatcgacaactccccggcgatgattgaacgctgccgtcgtcatattgacg cctataaagcccctacgccagtagacgttattgaaggtgatattcgcgatatcgccattgaa aacgcatcgatggtggtgctgaattttaccctgcaattcctggaaccttccgagcgccagg cgttactggataaaatttatcaagggctgaacccgggcggtgcgctggtgctttcggaaa aattcagtttcgaagatgccaaagttggtgaactgctgttcaacatgcaccacgactttaaa cgtgccaacggttacagcgaactggagatcagccagaaacgcagcatgctggaaaacg tgatgctgaccgattccgtggaaacccataaagcacgcctgcataaagccggttttgagc atagcgagctgtggttccagtgctttaactttggttcactggtggcattaaaagcagaggac gctgcatga | 206 |
| ECOLIN_10345 | atgatcgactttggtaacttttattctctgattgccaaaaatcatctttcacactggctcgaaac gctgcccgcgcagattgctaactggcagcgcgagcagcagcacgggctgtttaagcag tggtccaacgcggtggaatttctgcctgaaattaaaccgtatcgtctggatttattgcatagc gtaaccgccgaaagcgaagagccactgagcgccgggcaaattaagcgcattgaaacg ctgatgcgcaacctgatgccgtggcgcaaagggccgttctcactgtatggcgtcaacatc gataccgaatggcgttccgactggaaatgggatcgcgttatgccccatctttctgatttaac cgggcgcaccattcttgatgtcggctgtggcagcggttatcacatgtggcgcatgattggc gcaggggcgcatctggcggtgggtatcgatcccacgcagctattcctctgccagtttgaa gcagtgcgtaaactgctgggtaacgatcagcgcgcacatttgttaccgttaggtattgaac aacttccggcactgaaagcctttgataccgtcttttcgatgggcgtgctttatcatcgtcgttc accgctggagcatctctggcagttaaaagaccaactggtgaatgaaggcgaactggtgc tggaaacgctggttattgatggcgacgaaaacacggtgctggtgccgggcgatcgttac gctcaaatgcgtaatgtctatttcattccttccgcgctggcgctgaaaaactggctgaagaa gtgtggttttgttgatattcgcattgcagatgtgagcgttaccaccacagaagagcagcga cgcaccgaatggatggtcaccgagtctctggccgatttctcgacccgcatgatccgggt aaaacggtggaaggttatcctgcgcctaaacgcgcggtgctgattgcgcgcaagccgta a | 207 |

TABLE G

Polypeptide sequences encoded by the genome of *E. coli* Nissle Phage 3.

| | | |
|---|---|---|
| ECOLIN_09965 | METKKNNSEYIPEFDKSFRHPRYWGAWLGVAAMAGIALTPPKFRD PILARLGRFAGRLGKSSRRRALINLSLCFPERSEAEREAIVDEMFAT APQAMVMMAELAIRGPEKIQPRVDWQGLEIIEEIRRNNEKVIFLVP HGWAVDIPAMLMASQGQKMAAMFHNQGNPVFDYVWNTVRRRF GGRLHARNDGIKPFIQSVRQGYWGYYLPDQDHGPEHSEFVDFFAT YKATLPAIGRLMKVCRARVVPLFPIYDGKTHRLTIQVRPPMDDLLE ADDHTIARRMNEEVEIFVGPRPEQYTWILKLLKTRKPGEIQPYKRK DLYPIK* | 208 |
| ECOLIN_09970 | MQQIARSVALAFNNLPRPHRVMLGSLTVLTLAVAVWRPYVYHRD ATPIVKTIELEQNEIRSLLPEASEPIDQAAQEDEAIPQDELDDKIAGE AGVHEYVVSTGDTLSSILNQYGIDMGDITQLAAADKELRNLKIGQ QLSWTLTADGELQRLTWEVSRRETRTYDRTAANGFKMTSEMQQG EWVNNLLKGTVGGSFVASARNAGLTSAEVSAVIKAMQWQMDFR KLKKGDEFAVLMSREMLDGKREQSQLLGVRLRSEGKDYYAIRAE DGKFYDRNGTGLAKGFLRFPTAKQFRISSNFNPRRTNPVTGRVAPH RGVDFAMPQGTPVLSVGDGEVVVAKRSGAAGYYVAIRHGRSYTT RYMHLRKILVKPGQKVKRGDRIALSGNTGRSTGPHLHYEVWINQQ AVNPLTAKLPRTEGLTGSDRREFLAQAKEIVPQLRFD* | 209 |
| ECOLIN_09975 | MLHKKTLLFAALSAALWGGATQAADAAVVASLKPVGFIASAIAD GVTETEVLLPDGASEHDYSLRPSDVKRLQNADLVVWVGPEMEAF MQKPVSKLPEAKQVTIAQLENVKPLLMKSIHGDDDDHDHAEKSDE DHHHGDFNMHLWLSPEIARATAVAIHGKLVELMPQSRAKLDANL KDFEAQLASTEKQVGNELAPLKGKGYFVFHDAYGYFEKQFGLTPL GHFTVNPEIQPGAQRLHEIRTQLVEQKATCVFAEPQFRPAVVESVA RGTSVRMGTLDPLGTNIKLGKTSYSEFLNQLANQYASCLKGD* | 210 |
| ECOLIN_09980 | MTSLVSLENVSVSFGQRRVLSDVSLELKPGKILTLLGPNGAGKSTL VRVVLGLVTPDEGVIKRNGKLRIGYVPQKLYLDTTLPLTVNRFLRL RPGTHKEDILPALKRVQAGHLINAPMQKLSGGETQRVLLARALLN | 211 |

TABLE G-continued

| Polypeptide sequences encoded by the genome of *E. coli* Nissle Phage 3. | | |
|---|---|---|
| | RPQLLVLDEPTQGVDVNGQVALYDLIDQLRRELDCGVLMVSHDL HLVMAKTDEVLCLNHHICCSGTPEVVSLHPEFISMFGPRGAEQLGI YRHHHNHRHDLQGRIVLRRGNDRS* | |
| ECOLIN_09985 | MIELLFPGWLAGIMLACAAGPLGSFVVWRRMSYFGDTLAHASLLG VAFGLLLDVNPFYAVIAVTLLLAGGLVWLEKRPQLAIDTLLGIMA HSALSLGLVVVSLMSNIRVDLMAYLFGDLLAVTPEDLISIAIGVVIV VAILFWQWRNLLSMTISPDLAFVDGVKLQRVKLLLMLVTALTIGV AMKFVGALIITSLLIIPAATARRFARTPEQMAGVAVLVGMVAVTG GLTFSAFYDTPAGPSVVLCAALLFIISMMKKQAS* | 212 |
| ECOLIN_09990 | MIEADRLISAGTTLPEDVADRAIRPKLLEEYVGQPQVRSQMEIFIKA AKLRGDALDHLLIFGPPGLGKTTLANIVANEMGVNLRTTSGPVLE KAGDLAAMLTNLEPHDVLFIDEIHRLSPVVEEVLYPAMEDYQLDI MIGEGPAARSIKIDLPPFTLIGATTRAGSLTSPLRDRFGIVQRLEFYQ VPDLQYIVSRSARFMGLEMSDDGALEVARRARGTPRIANRLLRRV RDFAEVKHDGTISADIAAQALDMLNVDAEGFDYMDRKLLLAVID KFFGGPVGLDNLAAAIGEERETIEDVLEPYLIQQGFLQRTPRGRMA TVRAWNHFGITPPEMP* | 213 |
| ECOLIN_09995 | MIGRLRGIIIEKQPPLVLIEVGGVGYEVHMPMTCFYELPEAGQEAIV FTHFVVREDAQLLYGFNNKQERTLFKELIKTNGVGPKLALAILSGM SAQQFVNAVEREEVGALVKLPGIGKKTAERLIVEMKDRFKGLHGD LFTPAADLVLTSPASPATDDAEQEAVAALVALGYKPQEASRMVSK IARPDASSETLIREALRAAL* | 214 |
| ECOLIN_10000 | MNINYPAEYEIGDIVFTCISAALFGQISAASNCWSNHVGIIIGHNGE DFLVAESRVPLSTITTLSRFIKRSANQRYAIKRLDAGLTEQQNQRIV EQVPSRLRKIYHTGFKYESSRQFCSKFVFDIYKEALCIPVGEIETFGE LLNSNPNAKLTFWKFWFLGSIPWERKTVTPASLWHHPGLVLIHAV GVETPQPELTEAV* | 215 |
| ECOLIN_10005 | MAIILGIDPGSRVTGYGVIRQVGRQLSYLGSGCIRTKVDDLPSRLKL IYAGVTEIITQFQPDYFAIEQVFMAKNADSALKLGQARGVAIVAAV NQELPVFEYAARQVKQTVVGIGSAEKSQVQHMVRTLLKLPANPQ ADAADALAIAITHCHVSQNAMQMSESRLNLARGRLR* | 216 |
| ECOLIN_10010 | MAGHSKWANTRHRKAAQDAKRGKIFTKIIRELVTAAKLGGGDPD ANPRLRAAIDKALSNNMTRDTLNRAIARGVGGDDDANMETIIYEG YGPGGTAIMIECLSDNRNRTVAEVRHAFSKCGGNLGTDGSVAYLF SKKGVISFEKGDEDTIMEAALEAGAEDVVTYDDGAIDVYTAWEE MGKVRDALEAAGLKADSAEVSMIPSTKADMDAETAPKLMRLIDM LEDCDDVQEVYHNGEISDEVAATL* | 217 |
| ECOLIN_10015 | MAYKRPVSILVVIYAQDTKRVLMLQRRDDPDFWQSVTGSVEEGET APQAAMREVKEEVTIDVVAEQLTLIDCQRTVEFEIFSHLRHRYAPG VTRNTESWFCLALPHERQIVFTEHLAYKWLDASAAAALTKSWSNR QAIEQFVINAA* | 218 |
| ECOLIN_10020 | MRTEYCGQLRLSHVGQQVTLCGWVNRRRDLGSLIFIDMRDREGIV QVFFDPDRADALKLASELRNEFCIQVTGTVRARDEKNINRDMATG EIEVLASSLTIINRADVLPLDSNHVNTEEARLKYRYLDLRRPEMAQ RLKTRAKITSLVRRFMDDHGFLDIETPMLTKATPEGARDYLVPSRV HKGKFYALPQSPQLFKQLLMMSGFDRYYQIVKCFRDEDLRADRQP EFTQIDVETSFMTAPQVREVMEALVRHLWLEVKGVDLGDFPVMT FAEAERRYGSDKPDLRNPMELTDVADLLKSVEFAVFAGPANDPKG RVAALRVPGGASLTRKQIDEYGNFVKIYGAKGLAYIKVNERAKGL EGINSPVAKFLNAEIIEAILERTGAQDGDMIFFGADNKKIVADAMG ALRLKVGKDLGLTDESKWAPLWVIDFPMFEDDGEGGLTAMHHPF TSPKDMTAAELKAAPENAVANAYDMVINGYEVGGGSVRIHNGD MQQTVFGILGINEEEQREKFGFLLDALKYGTPPHAGLAFGLDRLT MLLTGTDNIRDVIAFPKTTAAACLMTEAPSFANPTALAELSIQVVK KAENN* | 219 |
| ECOLIN_10025 | MLELNAKTTALVVIDLQEGILPFAGGPHTADEVVNRAGKLAAKFR ASGQPVFLVRVGWSADYAEALKQPVDAPSPAKVLPENWWQHPA ALGATDSDIEIIKRQWGAFYGTDLELQLRRRGIDTIVLCGISTNIGVE STARNAWELGFNLVIAEDACSAASAEQHNNSINHIYPRIARVRSVE EILNAL* | 220 |
| ECOLIN_10030 | MGFPSPAADYVETRISLDQQLISQPAATYFMRASRSHFREGIIQGAL LVVDASLTACDGSLLICAIDGEFRIKRYRTHPQPHLVNLDNGRREA LPADDDGYSSAPAIFGVITYIINDARNAEFDDCPVM* | 221 |
| ECOLIN_10035 | MFVELVYDKRNFDGLPGAKDIILGELTKRVHRIFPDADVRVKPMM TLPAINTDASKHEKEQISRTVQEMFEEAEFWLVSE* | 222 |

TABLE G-continued

| Polypeptide sequences encoded by the genome of *E. coli* Nissle Phage 3. | | |
|---|---|---|
| ECOLIN_10040 | MLWRIFIFVNVGLGEAAKRNVGTGENQIPDMSAFPSGNNWFQLPS GHIVQIFSMNVLGADANGTSANYPIAFPTTMIAVSALWSDGTVAN APTYKMMGNTTNRTTLTIKVSASSGTYGTMIIAVGR* | 223 |
| ECOLIN_10045 | MNKYSYSPSENAFYAVALKNTYELSGTWPADALDIPDDISVKYMA EPPQGKIRVAGENGFPTWAEIPPPSHEELIEQAESERQLLINQANEY MNSKQWPGKAAIGRLKGEELAQYNSWLDYLDALELVDTSGTPDIE WPTPPAVQAR* | 224 |
| ECOLIN_10050 | MKPVFDENGLAAVPGDMRCFYYDAVTSEYTGWSDEYINTGVSMP ACSTGIDPDENIPGRVAVFTGKGWSHEEDHRNETVYSIENGAAVT VDYIGAIKNGYVTLSPLTPYDKWDGEKWVTDTEAQHGASVEAAE AQRQSLIDAAMASISLIQLKLQAGRKLTQAETTRLNAVLDYIDAVT ATDTSTAPDVIWPELPEA* | 225 |
| ECOLIN_10055 | MIYSTGTISINGNTATGSGTNWTAPASQVRAGQTIIVMSNPVQLFQI SSVNSATSMTVTPAVSPALSGQKYGILVSDNISVDGLAQAMSQLIK EYDENIGAWETFATTSANQSITVTINGTAVTIPGIGKLAQKGSNGA VTVADGGTGATNAADARTNLGLGEGSPAIGVPFFWPSAAMPNTVI DSWSSMVFLKFNGAKFSATDYPVLAKVFPSLVLPEARGDFIRVWD DGRGADGGRELLSWQEATNFSQFAGNIGGGAGHAINFHDGIAGNQ PGFSRFNFNSNSVGDGVNFVAVRPRNIAFNFLVRAK* | 226 |
| ECOLIN_10065 | MGEKMQLLKQETILQGAKGGGGSSHTPVEQPDDLLSVAKLKMLIA VSEGEIQGDLTAQNIFLNDTPLANDSGEYNFSGVKWEFRKGTQDQ TYIAGMPQVDNELAVGTTVTTTAPWTRQFTNLSLDAIRIKLSLPVQ YLYKDNGDMVGTVTEYAIDLSTDGGAWKTVVNGKFDGKTTTEY QRDHRIDLPKSTSGWSVRVRRITADASGSNSKLVNAFKVFSYAEVI DSKLRYPLTALLYVEVDSSQFNGSAPKVTCKIKGKLIKVPDNYDPK TRTYSGSWSGGFKMAWSNNPAWIFYDLVLDEIYGMGTRVDASMV DKWALYSIAQYCDEMVSDGAGGTEPRFTCNVFIQSQEDAWQVLN DLAAVFRGITFWGNDQIYVQADVPQDDVDWVYNVSNVIDGLFTY AGGSYKNRYSSCLVSWSDPQNHYSDTVEGVYDSALVERYDVRQT SLTAIGCTSQSEAHRRGRWVLLSNAKDGTVSFGVGLDGYIPLPAEII GVADPFRSGKENGGRISAANGRQITLDREIDYAAKDRLVVNLPDG KAQTRTISAVSADKKTVTVATAFSQVPVAGAVWAIDSDNLAIQYF RVTSIAANDDSTGGFTITAVQHDPNKYRYIDDGVRVESPPITVTPIS VLSAPKNIVVTESDHVSQGLTVASLDVSWDKVEGAIRYVAQWRK DNGDWINVPVTSAQGFSVQGIYSGSYDVRVRALNAQDTSSPWGY GETTYLSGKTGKPGTPLNFLATEDVVWHIDLTWKFPDGSGDTAYT EIQRATTADYANPELLVLVPYPAADYQHGPMPAGVRQWYRARLI DRIGNAGDWTDWIMGTSSIDVSEITNDILEDMKESETFKDLIENAV DSNEKIAGMANDIKQANDELEQQAKDIAKNAQDVGKVQTSVNEL SSTVGNVSSSLSQLEQTVATADTALGQRIDNISVSMDGMTGGVKN SAIAIIQANLAQVATRKTLSASVAGNSANLDRLDEVIVSEKEATAR SLLSLQTDVNGNKASINSLNQTLSDYQQATATQINGITATVNGHTS AITTNAQAIANVNGELSAMYNIKVGVSSNGQYYAAGMGIGVENTP SGMQSQVIFLADRFAVTTAAGNSVALPFVIQNGQTFIRASFIQDGTI ENAKIGNYIQSNNYAAGSAGWKLNKAGDAEFNNVTVRGVVYASG GSFTGEIQATSGKFKGTVEAQSFIGDIANMHTGTNVSRSSDGYLEK VMTYNDSSSSGHARHVCVIANVKGNGAGTIDINGNESGSSVQDME RLIMHSAVVTGPNVTVRIKVSAQNNRGASISSPTIIVSHGSGSFTG* | 227 |
| ECOLIN_10070 | MVKTLILEGKMAKKFGKRVQFDVADLREMLRAMCSQVPGFKKY MSEAHMKGIRFAFFNGGNNIGLEEFDMTRGGSVYRIVPVYEGAKS SGVLQIVVGAVALVAAFFTAGASMAAWGAAMSATAISATSILTGV GVSMMLGGVVQMLTPQPSFGAGKSSSTDNTPNYAFGAPVNTVAM GHPVPLAYGLTEAGGAIVSAGMYSSDQQ* | 228 |
| ECOLIN_10075 | MREKLLDAIRQHVAAEYPKEACGLIVQSGQQQIFIPCRNIADKPEET FTLSPEDQLAARARGEIIMLIHSHPDVVRLVPSELDRIQCDWSGIEW GIMSWPDGDFCTISPREDRDYAGRQWVLGYADCWSLIREFYLREY GIVLGNYSVPYEWWESGKERLYDDNWEREGFVEIAAGAMQPGDII MMSVQASVTNHAAVYVGDNIILHHLFGHLSSRTPYGKYYRDRTV RVVRHKDRMHG* | 229 |
| ECOLIN_10080 | MSFTADIQQLEPGSVIQLIEIDGTEFGMDQVLRFHAHNIQEEGWAA FAAENLPAIIWQGNQYDPHPYELKGMELSSTGSQPTPTLSVGNVGN YVTALCLEYDDMVRAKVKIHTTLSKYLDAANWKNGNPGASPADE RLQLFYVNAKTAETRVQVDFELCSPFDIQSLQLPTRQITPVCTWCM RGWYRSGTGCDYNGTKYFTKDGTPTDDPSKDVCGGRRQDCQDR HGPDAPLPFGGFPAANLQGK* | 230 |
| ECOLIN_10085 | MTDTFTWRTRKTAQGTETARTLQAQFGDGYKQIAGMGINDKQET WNLDWTGTRQEAAALRAFLMSHVTKSFWWTTPWGEKKLFRMK ADSFSVSFPTGKKATVAFTFEQAFAP* | 231 |

TABLE G-continued

Polypeptide sequences encoded by the genome of *E. coli* Nissle Phage 3.

| | | |
|---|---|---|
| ECOLIN_10090 | MAQQISDLVINLDVDSATFSEQVARIKGQLTGMAEDSEKVQTRMQ RASERQAAAFKTVGDAGAAAAADMKSRQSAATEGLTKDWQNVS KSVDETHRRVTELNQRMRENDGQAAALARRQDELAASFFRQIDG VRQLNGETQSLANVQARFRAARAQGNITQQDYLALISRTTARQKE LQIVEEKSAAARTRFLSQLKQQVAEQKLSGTELLRMKAAQVGASD AAEVYIRKLEAAKVATHGLGLQSAAARQELGILIGEVMRGNFGAL RGSGITLANRAGWIDQLLSLRGLGIASMVGGIAAAVFGLGKAWYD GSKESEEFNRQLILTGNYAGKTSGQLQALARSLAGNGITQHAAAG VLAQVVGSGAFSGNDVSMVSNVAARLQQATGQAVDETINQFKRL KDDPVNAVATLNDSLHFLTATQYEQIASAQALGDSQKAAELAMR AYSDAVIQRAGAVEDNLGSLEKAWNWVKNAASGAWDAMLGVG RNPDTAMKRQDSFAEWQAAEKEYRALSSNLKVDPDYAGNNVLQ KADAERLRNARQQVELKKQAYDLADQQYAQEGLAAAREKMRTD QQAQAIRSQQQFNQLVESGATAAEKRASAEKKLSQLIEKNRQDAK DGVATLWTEKDIAAARAGIEKQWKDPKTPKGKSYSTPAGDKAEE KAQAELLTLQAQLKTLEQHTSVNDVISKQRQDLWQTENQFTVLQE AAGRRQLTAQEKSLLAHKEETLEYKRQLADLGDKVASQQKLNQL ADQAVKFEQQQKAARAGLQAQSEGLSTREAGRQTTLQRLSESYSY NPQAQQKVLEEQRATFEAEDALRANWLAGAKQGWAEYQDSATN VFSSVQQISQATFSGLAGQLTSLTTTGKASFREFTSSILKMIVSVINQ LLVAYTIQSAMGWVSGGAKTSSAGQSFAVPSYRPQGFDVGGFTGH GGKYEPAGIVHRGEFVFTKESTSRIGVANLYRLMRGYASGGLVGG GNAAGAGMGGISVYAPVSISQQGSDGSINQANATGTAKQLQAIVQ QTITERLKKEMSAGGVLYSRRTQ* | 232 |
| ECOLIN_10095 | MLAGMTSTELGDWHQFYREHYFQDAQLDAHFSELLYSISTLFFRD PELTPAHFSLLSPSGIVISDDEPDDDALMAAAEGITGGIRYGPAD* | 233 |
| ECOLIN_10100 | MFLKKEKFTWQKESLTIFELSALQRIEYITFMAAEEKAVSADSDGIS DQEMTARLIGSNIRCGARLIAMSLWHNDPAGTDVETLYQQVLSG WPPEAIGKAEMEIKLLSGMLVPVEDDKAADPDAPAEAESAEPVAA EKPLPAS* | 234 |
| ECOLIN_10105 | MPTPNPLAPVKGAGTTLWLYTGTGNAFANPLSDIDWNRLAKIKEL TPGEMTAESYDDTYLDDEDADWNATAQGAKSAGDTSFTLAWKP GEEGQKDLVAWFIDGSVRYYKIKYPNGTVDVFRGWCSSLGKAIPA KEVITRTAKITNTGKPELAEESGTPNIPVTGVTLDKATASVAVGATT TLNVTVNPASASDTSFRVATSDGAKATVTVSGNAITVTGVAAGTA DVIVMTSDGNFVAVCKVTVTAA* | 235 |
| ECOLIN_10110 | MNRHSAIRAAILAKLKAEITDTVTWFDGRPVFLEEQDLPAVAVYLS DAEYTGDSLDEDSWQAVVHIEVFLKASSPDSALDSWMEEKVYPA MAFIPGLTELVETFTPQGYDYQRDDEMATWGSVDFTYLITYSI* | 236 |
| ECOLIN_10115 | MKGLERAIQNLNSLSRLIVPEATAKALNRVARRTISQGSKAVAKEA TVDDNRKKGLPVRLVRQRSRLRKARHDRPVASIKINRGNLPAIKLG TARVRLSRKKGARNGAGSVLKIGPYTFRNAFIQQLANGRWQVMR RVGQARYPIDVVKVPLETPLTVAFTAISKRLIESDMPKELSAALKN QLRIHLKR* | 237 |
| ECOLIN_10120 | MDAATIKKMGKTAIINGSSYDVVPAEQLEEMGPLSGTGTSLVVFSE LYQPRRNDSVDYDGKNLIVTRYDMFNGKPRIHLE* | 238 |
| ECOLIN_10125 | MAKNYAQDGKTIPLVNSGATDVHSGDPVVVGKLIAVAITDIPAGD TGDGFTEGVFLLPKVSADAVTAGAQVYLKDGKITIEETDAVAAGI AWEDAGANTTVVEVKINA* | 239 |
| ECOLIN_10130 | MQASNNSEADIFIYDEIGYWGVTAKQFVNDLRALGDVTHINLYINS PGGDVFDGIAIYNALKHHGAAITVHIDGLAASMASVIAMVGNPVI MPENTMMMIHKPWGFAGGDASDMRDYADLLDKVESVLIPAYAQ KTGKSTEEIAVMLEDETWMNGSECLELGFADQVTPSLQAMACIHS KRIEEFEKMPKSIRNMITPPRNTTQRDPVITQPQAPQAKTDPAPDEN AIRAQVLAEQKTRVNAIGDLFAMFGNKHMELQNQCVADPDCSVD KAKDLLLAELGKTATPSNKTTQPHIHAGNGNFVADGIRQALMARA GFEGQERDNVYNGMTLREYARMALTEKGIGVASYNPMQMVGLA LTHSTSDFGNILLDVANKALIQGWDEAQETFEQWTKKGQLSDFKT AHRVGMGGFPSLRQVREGAEYKYITTSDKGETIALATYGEIFSVTR QAIINDDLNQLTDVPMKMGRAAKATIGDLVYAILTKNPKLSDGKA LFHADHKNLSSGAISVASLDESRKLMRLQKEGERTLNIRPAYMLVP VALETLANQTIKSASVKGADINAGIVNPIQNFAEVIAEPRLDEADAK AWYLAAAKGTDTIEVAYLNGVDTPYIDQQEGFTTDGIATKVRIDA GVAPLDYRGMTKSSGQ* | 240 |
| ECOLIN_10135 | MSFLDDAIGLFSPGWKASRLRARAVIKAYEAVKQTRTHKAQKENR SADQLSQMGAVSLRQQARWLDNNHDLVIGVFDKLEERVVGAKGI IVEPHPMLSNGKIAKKLATDIRRKWGEWSVRPDVTTQFTRPMLER LMLRTWLRDGEVFAQLVRGTGNGLQPVAGVPFWLEALEPDFVPM NSDAATQLNQGVFVDNWGRPKKYQVYKSLPVSGRQFDTKEIDAE | 241 |

TABLE G-continued

| Polypeptide sequences encoded by the genome of *E. coli* Nissle Phage 3. | | |
|---|---|---|
| | NMLHLKFTRRLHQTRGTSLLSGVLMRLSALKEYEDSELTAARIAA<br>ALGMYIKKGDGQSFDSDSSSDDRELMIQPGMLYDELQAGEEIGMI<br>KSDRPNPNLESFRNGQLRAVSAGSRLSFSSTSRNYNGTYSAQRQEL<br>VESTDGYLILQDWFIGSVTRPMYRAWLKMAIAAGEIKLPRGIDMD<br>SLYNAVYSGPVMPWIDPVKEANAWKTQIRGGAATESDWIRASGR<br>NPDDVKSRRKAEVDENREQGLVFDTDPANDKGGTSAEAKEPGAP<br>PSESQRKK* | |
| ECOLIN_10140 | MNPADIQNMIDRYAAAELSVLEGKSITFNGQQMTLENLSEIRKGRQ<br>EWERRLATLNNKRRGRPGYRLARFG* | 242 |
| ECOLIN_10145 | MAKRASARDIRRDVSGILRAPRRMPVADAVSTYMRVPMGAGNSV<br>PWDPDLAPYVIEPMNCLASREYDAVVFVGPARTGKTIGLIDGWIV<br>YNIVCDPADMLVIQVSEEKAREHSKKRLDRTFRCSPEVKTRLSPRR<br>NDNNVYDRTFRAGNYLKLGWPSVNIMSSSDYKSVALTDYDRFPE<br>DIDGEGDAFSLASKRTTTFMSSGMTLVESSPGRDIRDTKWRRSTPH<br>EAPPTTGILSLYNRGDRRRLYWPCPHCGEYFQPEMDNMTGYRDSS<br>DPVLASEAAFLQCPACKGRITPDMKRALNMKCVWLRDGQTIDRK<br>GLVSGDGRRSRIASFWMEGPAAAYQTWAQLIYKFLTAEQEYESTR<br>SEETLKTVINTDFGRPYLPRASMEQRKSELLEQRAEDVPKRSVPNG<br>VQFLTATVDVQAGRNRRFVVQITGYGSMGERWIVDRYNIRHSLRC<br>DGNGESIQVDPASYPEDWDLLLTDVFDKTWPLAADPSKGMRLMS<br>MAVDSGGEDGVTDNAYKFWRRCRREGLGKRIYLFKGDSVRRSKL<br>IQRTFPDNTGRSTRRAQATGDVPLYLLQTDALKDRVNNALWRDSP<br>GPGYVHFPAWLGSWFYDELTYEERSNEGKWSKPGRGANEAFDLL<br>VYADALAILSGYEKIKWPSAPEWARRETWIEDTQTEAGEMPSPPPA<br>PKSKPKPKREKPVTEQANPWSSSGGWV* | 243 |
| ECOLIN_10150 | MDQEIATLKLNINQLAGITGVHRQTVAARLKNVEPAPGSNSKLKL<br>YLVTDILTELMIPTVSANIDDMPPSDRLSHWKAENERLKFEQDTGQ<br>LIPADEVAREFSLMAKAVVMVLETLPDVLERDCALTPAAVVRVQS<br>VIDDLRDQMAEKVQDAGKEEEQPEED* | 244 |
| ECOLIN_10160 | MSNKIITLSGAANEVLYALFFRGALLSGDLPSKSGTAELRELGFAET<br>RHTATEYQKENHFTFLTSEGQKFAVEHLVNTRFGEQQYCASMTLG<br>VEIDTSAAQKAIDELDQRIRDTVSFELIRNGVSFIKDAAIANGAIHA<br>AAIETPQPVTNIYNISLGIQRDEPAQNKVTVSADKFKVKPGVDTNIE<br>TLIENALKNAAECAALDVTKQMAADKKAMDELASYVRTAIMMEC<br>FPGGVIWQQCRR* | 245 |
| ECOLIN_10165 | MKILAFINPPGSYMQIETKEMVIFLRDDGISLQYPDGQCAGYGIDG<br>NMLIFMGQSCELFPTKIILHDQRTTNFTHK* | 246 |
| ECOLIN_10170 | MDYYHEIDFPSLFARAVESDDDVGTTLRIHLLCERMVEAWICACC<br>DCQDLFGRDKNKLLIECNTKISMAGNLGIPPELMKSLKTINSMRND<br>LAHNPSIQSIADSRIQSLKDTLTEYFKQHPTEPSMEESKLGIFNAENQ<br>LTEEVSLDSDSSKNRLKLILLFSKLMQALMQLVAANHNGRWDNQF<br>SQFVYHVTMNATKR* | 247 |
| ECOLIN_10175 | MTVVLTAKQIEDLAAFAKEDGQPQYTITTGTIPEFEADNGEIIPGYT<br>GLIAYSESLDHGVLQLDD* | 248 |
| ECOLIN_10180 | MVIVALVGSFLAGSEWTNRSWKIKWADRDSAESSQEANAQTAAR<br>MIEQGRTIARDEAVKDAQAQAASAAVTSAGLATTVKQLRAEATK<br>LATHMDAAKHTADLATSVRSKTAGANAAMLADMLGSLAEAARY<br>YAGRSDESYRAGMTCERIYESVRLSNNQ* | 249 |
| ECOLIN_10185 | MAMSLKLKNKLSAAVVGLILAGASAPVILDQFLDEKEGNSLTAYR<br>DGGGLWTICRGATMVDGKPVVQGMKLSAEKCAQVNAIERDKAL<br>AWVDRNIKVPLTEPQKAGIASFCPYNIGPGKCFPSTFYKRINAGDT<br>KGACEAIRWWIKDGGRDCRLTKGQKDGCYGQVERRDQESALTC<br>WGIDQ* | 250 |
| ECOLIN_10190 | MTRMSTIYSRLSYGSGTTLAGCGVSAKAYAETAKTAKEVSWMLA<br>DRIAGLSLSDWAIIVGIACTVITCAVNWYFRWKEREDRRNGYVSK<br>AEE* | 251 |
| ECOLIN_10195 | MKNTVKINSVELINADSLHYVATLPDNSIDLIVTDPPYFKVKPNGW<br>DNQWKGDEDYLRWLDSCLAEYARVLKPAGSIYLFCGHRLASDIEI<br>MMRARFNVLNHIIWAKPSGRWNGCNKESLRAYFPSTERILFAEHY<br>LGPYTGKEDVYERKSTELKQHIMTPLIDYFRNARESLGVSSKEIAE<br>ATGKKNMASHWFGASQWQLPNEVDYRKLQELFTRIAIDKHIQQK<br>LEHPHHQLVATYQSLNRKYSELLEEYKILRRCFSVSALVPYTDVW<br>THKPVQFYPGKHPCEKPADMLKQIISASSRPGDIVADFFMGSGSTV<br>KAAIELGRRAIGVELEADRFIQTTEEVEKLKKS* | 252 |
| ECOLIN_10200 | MLNQEDMTETAKAVFNELSDKPATAGEIAQNTHLSHERCQLILTQ<br>LVMAGLSDYQFGCYKRLQ* | 253 |

TABLE G-continued

| Polypeptide sequences encoded by the genome of *E. coli* Nissle Phage 3. | | |
|---|---|---|
| ECOLIN_10205 | MPNWIDVLGEMGTIAQRTPADEVRHKYLRDLSKHTGRNVISYYSG FLQKGGPGFQHLIQMSDDDKNGLMSAINGLDTSLGLDILLHTPGG DIAALESIGHYLRSKFGTNIRAIVPMISMSCGTMLACCAEQIVLGKQ SNLGPIDPQFNGLSSHAIIEEYERAKAEIFANPAALQWWQFTFQKL NPTLIGECEKAILWANEIVQKWLCTGMFAGQADAEAKAKRICDEL NNHQATYAHARHIHLDKAQNIGLNIMELESDQTLQDLVLTIHHCY MHSFGTSPAAKIIENHNGSTMMWNIC* | 254 |
| ECOLIN_10210 | MSAAEFYEKMGIQPQEFQKGESVQHFAMRVLAQQNDLNVRSGVL YSYSTVTPNTTEQNGQQSHQLYSY* | 255 |
| ECOLIN_10220 | MNQQDLNFVRIELRRALPDLSGGTKGQLEAFSEHPPADKNATPRR GIHLVELEGEKGPRFVNSLSAPLYVLETRSRRRPMPPIKDAEFESAP WRRAVSALSGYQQAWLRYCYGFDLSYKHQVMMCEYVWKTYQK CLGDNSLQERVVKKLIGLVWLAGQEIAATRNNETYKDYAGAALA RMVSVDRSTWLRVYSGHWAGLKAAFTQLDESALAMALEYYEEE EALKVAEM* | 256 |
| ECOLIN_10225 | MRALLTPEIAHRMGIVLFRPGAELMHLFMRGRVLLEPEPEEMASFS TGAVPAAIQPLADDPVMRQVFENDRVIQRAGGLPSLEQWLSNRFE CQWPHSSWHDKNFTTMRHPPGSIRLCWHCDHTLSGQHTEQLAGIA AGNLVSWILEVIRRDSGFPESHILTLPELCWWMVRNDLADVIPESV AHKGLRLPDDKIRSVMRESDIVPSASATSLVQEKAKKILTLSVDPES PESFMLRPKRRRWINETYTRWVKTQPCECCRRPADDPHHIVGHGM GGTATKAHDLFVIPLCRECHDELHADVPAFEQKHGTQLELLLRFM DRALAIGVIAKA* | 257 |
| ECOLIN_10230 | MSQLATTALTMSSSDIAELVESRHDHVKRSIERLAERGVIELPPMG EVKNHLNQSVSVYLIGKRDSYIVVAQLSPEFTARLVDRWQELEQA QQQTIPQSFSEALRLAADLAEQKQQLTNELAAAAPKVAFVDRYCT ASGSMSFRQVAKLLKAKEPDLRLFLLENDIMYRLGGTMTPRHQHI DAGRFEVKTGTSVTSNHAFSQARFTAKGVRWIGGLWAEHIARGQ VA* | 258 |
| ECOLIN_10235 | MKLILPFPPSVNTYWRAPNKGPLAGRHLISAAGRKYQSAACVAIIE QLRRLPKPSTELAAVEITLYPPDARRRDIDNYNKALFDALTHAGV WEDDSQIKRMLVEWGPVVPKGRVEITISRYEPAGAAA* | 259 |
| ECOLIN_10240 | MMTNKYCQALAALRSKPAHELKEVGDQWRTPDLLFWGINALFGP LVLDLFADDDNAKCPAWYTAEDNALTQDWSERLAELGGAGYGN PPYSRSQYHEKQAITGMTHIMNYAAAQREKGGRYVFLIKAAPSET WWPEDADHIVFIRGRIGFDLPVWFVPADEKQKPTSAFFAGAIAVFD KSWRGERFSYINRTELEAKGRAFMALAQFAASKSQPVTATPPAAD KPEAELPLTQKDIFAISGVEAWACVRAAFGDKEEYTFSESKFGHTW AADSVEAPEFTQVSPLTIDKAKLLIRESILFGVDEWLLSIEFDDAAV RLDMSERIRTVALEASGEYGMNSTDFIAAMGSLDVSSWSNIRQIRM HIREKAKPVSDPLPESRIWPLEVRIVFDQVDGADMLDESLQHKLKA NINQLWLERTATSEIITAASELVRNMRGEAA* | 260 |
| ECOLIN_10245 | MSTKLTGYVWDACASSGMKLSSVAIMARLADFSSDEGVSWPSIGT IARQIGAGESTVRTALAQLEKDGWLSRKQRRNGNRNASNVYQLN VVKLREAAFSHLSESDASKSDPSKSDASKSDPSKFEASKSSKKGGF DPSESGGDPSVKSKQEPQVTSKPSCPVAAQPDPEVVITDQARQVLS YLNQTTGSRYQVCSTSLENIRARLREQFTVDDLCLVVDYKNADWR DSEQAQYLRPATLFIPKNFPGYLQSATKWSSAGRPERVNGKWETN SASRANFQSVDYSLPENSGFRS* | 261 |
| ECOLIN_10250 | MNSVNRFRPAKQFRCLPLVGKDAQFGYVEIINNAADGGNYQPADL MVEAFVQMNEKGREEWLKLTGGSEITTEFPSELSAGSQIHSALYTF AKGTIMSASALLNNSSVNLQN* | 262 |
| ECOLIN_10255 | MVDSINTAIRLMCKAHKHGRLGMASDLGMTIDQFHNHLYQKCGS RFFTLAELERMEDLSGSCYLAEYQANRKGKWLVDVPTAESLDNV ELYSIEMKAAAASGELANAKMAAAADGVIDSSERKMLSELFSKKL RHQIHGFLGFMALYGVGVSDQAIDVFVSTGRKGDARECAAPGAL ACRISGETNA* | 263 |
| ECOLIN_10260 | MSSQHKNVTAKAVKAIGSISEVSRRFEFQSVQSVANWIAKNRVPSE RVIQLCQWGGWVVTPHQLRPDIYPNKNDGIPSANNNSQL* | 264 |
| ECOLIN_10265 | MPCALNLLLMVENAKYKDFAERLNRSLQEQSIGVKELSEFSGVSY EMARRYTLGTAKPRDEKMIRIAERLAVSPAYLDYGVPVNGGDAPA KGTVRIEQLDVHASAGSGYINQPFPTIVSSIEIPEERIFELFGRRSLDG IVMINVDGDSMMPTLCPKDLLFIDSKVEQFSGDGVYVFNFEDSTFV KRLQKVKGRRLAVLSDNEHYPPPFIEEHEMNELYIFGKLIRCLPLK MIEFG* | 265 |

TABLE G-continued

| Polypeptide sequences encoded by the genome of *E. coli* Nissle Phage 3. | | |
|---|---|---|
| ECOLIN_10270 | MGAFDNQEITLPACPKCGTKTKKKIAWLKSNKSFTCRCGATINVN SSQLTSEIRKVEDKLKKLFK* | 266 |
| ECOLIN_10275 | MNNPFFKNMLVYRISRDFTINQEELEQQLELFRFTPCGSQDMAKTG WVSPLGQLSDRLHHTVNNQVLLVIRREEKILPSPVITEELRKRVSRL ESDQGRRLKKTEKDSLRDEVLHSLLPRAFSKNSTVGLWINVTDGLI MVDAASAKRAEDSLALLRKTLGSLPVVPLTMETPIELTMTDWVRS GSAPAGFGLGDEAELKAILEDGGIGRFKKQTLVSDEIHVHLEAGKV VTKLSIDWQQRIQFVLCDDGSIKRLKFSNEITEQNDDIDREDAAQRF DADFVLMTGELISLINGLTTSLGGEAKR* | 267 |
| ECOLIN_10280 | MSYIQTLSGKHFNYLDIQQDDIVIEDIATALSHICRFAGHLPEFYSV GQHSVLTSHLVPQEFALEALLHDAAEAYLQDIPSPLKRLLPDYQAI EARVDAAIRQKFGLPTEQHPTVKYADLVMLASERRDFEIDEGSIWP CLEGVVPTDLFIINPVRPGQSYGMFINRFNELMEQRQCAA* | 268 |
| ECOLIN_10290 | MTVFEYLQAHPNTTSGEIAKGMNKKTPAVAGALSQLYGTGRIVKS GVRKGIPTYRINDMPFGCSNSLTMMFNQLLSRARQGAAQ* | 269 |
| ECOLIN_10295 | MTALNKQALREEFQFMQDNYSDPADHDRQVIYIEAEALLDELEAK DSTIAAQQHEIRMLLNALEEKPCPKCNDTGMTDSGGTQPWGEPIEI ECDCRQQDANTAELVAAGIGVKGE* | 270 |
| ECOLIN_10300 | MDKLIKPTAKGKYDGSCDYLCSEDARFIVMRGDYTEAEIIQASVSQ DVIDSDGAADFASSARYYQCWYKVSPIGGQDGYSGWHHPRDSPC RGAYFASVLQWD* | 271 |
| ECOLIN_10305 | MTTNNHPAHGPVSLDRLHQIREHLLHDTQYSNGGNRAYILADVLK VIDGAIARELVRREHAAWSQATFGDVGPVGPLKHLSKEALEAAAE PGDLSEWADMQFLLWDAQRRAGISDEQITQAMIKKLAINKVRQW PEPKDGEPRLHIKEQSEQEKK* | 272 |
| ECOLIN_10310 | MFSLIRRGQIYTDSSNWPVIIHSCSDHSVRIKRNDGELRTISIKRFNE DFERVEHDEYRKICAEIEQETNLKNLRAMRRGKITE* | 273 |
| ECOLIN_10315 | MNNLMIDLESMGKKPNAPIVSIGAVFFDPQSGELGQEFYTAVNLES AMEQGAVPDGDTILWWLRQSSEARSAICVDDAMPISSALSELSHFI NRHSDNPKYLKVWGNGATFDNVILRGAYERAGQVCPWQFWNDH DVRTIVTLGRSVGFDPKRDMPFDGVAHNALADARHQAKYVSAIW QKLIPTTSNS* | 274 |
| ECOLIN_10320 | MSNIFQLAPNDWVCESVLIAVTGLKPGTILRARKECWMIGREYIHV SPDGNPKPSSECMYNRKAVDAWVASMKSKQPG* | 275 |
| ECOLIN_10325 | MDKVTYPTGVENHGGTLRIWFNFKGKRVRESLGVPDTAKNRKIA GELRTSVCFAIRTGTFDYATQFPDSPNLKAFGVSKKDITVKELEEK WLDLKRMEICANAFNRYESVARNMVPRIGGNRLVSAVTKEELLYL RKYLLTGYQNPTKNKAPAKGRSVVTVNYYMTTMAGMFQFAADH GYLEVNPFEGIKPLKKARAEPDPLSRDEFIRLIDACRHQQTKNLWS LAVYTGMRHGELVSLAWEDIDLKAGTITVRRNYTKLGEFTLPKTE ASTDRVVHLIQPAISILKNQAEMTRLGRQYHIEVQLREYGRSVNHE CTFVFNPHVVRRSKQVGFIYRVDSVGDSWEAALKRAGIRHRKAYQ SRHTYACWSLSAGANPSFIASQMGHASAQMVFNVYGAWMADSS AEQIAMLNQKLADFAPLMPHSHENSTGGLLKSVS* | 276 |
| ECOLIN_10330 | MEGNTTLYALPKPEVVLRWREQTTDDFRFCFKFPATISHQAALRH CDDLVTEFLTRMSPLAPRIGQYWLQLPATFGPRELPALWHFLDSLP GEFNYGVEVRHPQFFAKGEEEQTLNRGLHQRGVNRVILDSRPVHA ARPYSEAIRDAQRKKPKVPVHAVLTAKNPLIRFIGSDDMTQNRELF QVWLQKLAQWHQTTTPYLFLHTPDIAQAPELVHTLWEDLRKTLPE IGAVPAIPQQSSLF* | 277 |
| ECOLIN_10335 | MVSALYAVLSALLLMKFSFDVVRLRMQYRVAYGDGGFSELQSAI RIHGNAVEYIPIAIVLMLFMEMNGAETWMVHICGIVLLAGRLMHY YGFHHRLFRWRRSGMSATWCALLLMVLANLWYMPWELVFSLR* | 278 |
| ECOLIN_10340 | MSHRDTLFSAPIARLGDWTFDERVAEVFPDMIQRSVPGYSNIISMIG MLAERFVQPGTQVYDLGCSLGAATLSVRRNIHHDNCKIIAIDNSPA MIERCRRHIDAYKAPTPVDVIEGDIRDIAIENASMVVLNFTLQFLEP SERQALLDKIYQGLNPGGALVLSEKFSFEDAKVGELLFNMHHDFK RANGYSELEISQKRSMLENVMLTDSVETHKARLHKAGFEHSELWF QCFNFGSLVALKAEDAA* | 279 |

TABLE G-continued

| Polypeptide sequences encoded by the genome of *E. coli* Nissle Phage 3. | | |
|---|---|---|
| ECOLIN_10345 | MIDFGNFYSLIAKNHLSHWLETLPAQIANWQREQQHGLFKQWSNA VEFLPEIKPYRLDLLHSVTAESEEPLSAGQIKRIETLMRNLMPWRK GPFSLYGVNIDTEWRSDWKWDRVMPHLSDLTGRTILDVGCGSGY HMWRMIGAGAHLAVGIDPTQLFLCQFEAVRKLLGNDQRAHLLPL GIEQLPALKAFDTVFSMGVLYHRRSPLEHLWQLKDQLVNEGELVL ETLVIDGDENTVLVPGDRYAQMRNVYFIPSALALKNWLKKCGFV DIRIADVSVTTTEEQRRTEWMVTESLADFLDPHDPGKTVEGYPAPK RAVLIARKP* | 280 |

In any of these embodiments, the bacteria described herein comprise one or more modifications or mutations within the *E. coli* Nissle Phage 3 genome. In some embodiments, the modifications alter the properties or behavior of the Phage 3. In some embodiments, the modifications or mutations prevent Phage 3 from entering or completing the lytic process. In some embodiments, the modifications or mutations reduce the ability of Phage 3 to enter the lytic process. In some embodiments, the modifications or mutations prevent the *E. coli* Nissle Phage 3 from infecting other bacteria of the same or a different type.

In some embodiments, the modifications or mutations alter, e.g., increase or reduce, the fitness of the bacterial host. In some embodiments, the modifications or mutations essentially have no effect on bacterial fitness, and the bacterial fitness is essentially the same as the fitness of the isogenic strain without the modifications or mutations. In some embodiments, the modifications or mutations alter, e.g., increase or reduce, the desired effector function, e.g., of a genetically engineered bacterium. In some embodiments, the modifications or mutations improve the desired effector function, e.g., of a genetically engineered bacterium. In some embodiments, the modifications or mutations essentially have no effect on effector function, and the effector function is essentially the same as effector function of the isogenic strain without the modifications or mutations. In some embodiments, the effector circuits are engineered into the genome first and then the phage is modified. In some embodiments, a new chassis with a modified Phage 3 is generated prior the engineering of the effector function(s).

In some embodiments, the bacteria comprise at least about 1 to 2, at least about 2 to 3, at least about 3 to 4, at least about 4 to 5, at least about 5 to 6, at least about 6 to 7, at least about 7 to 8, at least about 8 to 9, at least about 9 to 10, at least about 10 to 11, at least about 11 to 12, at least about 12 to 13, at least about 13 to 14, at least about 14 to 15, at least about 15 to 16, at least about 16 to 17, at least about 17 to 18, at least about 18 to 19, at least about 19 to 20, at least about 20 to 21, at least about 21 to 22, at least about 22 to 23, at least about 23 to 24, at least about 24 to 25, at least about 25 to 26, at least about 26 to 27, at least about 27 to 28, at least about 28 to 29, at least about 29 to 30, at least about 30 to 31, at least about 31 to 32, at least about 32 to 33, at least about 33 to 34, at least about 34 to 35, at least about 35 to 36, at least about 36 to 37, at least about 37 to 38, at least about 38 to 39, at least about 39 to 40, at least about 40 to 41, at least about 41 to 42, at least about 42 to 43, at least about 43 to 44, at least about 44 to 45, at least about 45 to 46, at least about 46 to 47, at least about 47 to 48, at least about 48 to 49, at least about 49 to 50, at least about 50 to 51, at least about 51 to 52, at least about 52 to 53, at least about 53 to 54, at least about 54 to 55, at least about 55 to 56, at least about 56 to 57, at least about 57 to 58, at least about 58 to 59, at least about 59 to 60, at least about 60 to 61, at least about 61 to 62, at least about 62 to 63, at least about 63 to 64, at least about 64 to 65, at least about 65 to 66, at least about 66 to 67, at least about 67 to 68, at least about 68 to 69, at least about 69 to 70, at least about 70 to 71, at least about 71 to 72, at least about 72 to 73, at least about 73 to 74, at least about 74 to 75, at least about 75 to 76, at least about 76 to 77, at least about 77 to 78, at least about 78 to 79, at least about 79 to 80, at least about 80 to 81, at least about 81 to 82, at least about 82 to 83, at least about 83 to 84, at least about 84 to 85, at least about 85 to 86, at least about 86 to 87, at least about 87 to 88, at least about 88 to 89, at least about 89 to 90, at least about 90 to 91, at least about 91 to 92, at least about 92 to 93, at least about 93 to 94, at least about 94 to 95, at least about 95 to 96, at least about 96 to 97, at least about 97 to 98, at least about 98 to 99, at least about 99 to 100, or at least about 100 or more modifications or mutations.

In some embodiments, the modifications or mutations reduce entry or completion of Phage 3 lytic process by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold. In some embodiments, the modifications or mutations reduce entry or completion of Phage 3 lytic process completely.

In some embodiments, the modifications or mutations reduce entry or completion of Phage 3 lytic process by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100%.

In some embodiments, the modifications or mutations prevent *E. coli* Nissle Phage 3 genome from infecting other bacteria of the same or a different by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold. In some embodiments, the modifications or mutations prevent the *E. coli* Nissle Phage 3 from infecting other bacteria of the same or a different type completely. In some embodiments, the modifications or mutations prevent the *E. coli* Nissle Phage 3 from infecting other bacteria of the same or a different type by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100%.

In some embodiments, the modifications or mutations alters, increases or reduces, the fitness of the bacterial host by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold as compared to the same isogenic strain without the phage modification. In some embodiments, the modifications or mutations alters, increases or reduces, the fitness of the bacterial host by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% as compared to the same isogenic strain without the phage modification.

In some embodiments, the modifications or mutations alters, e.g., increases or reduces, the desired effector function, e.g., of a genetically engineered bacterium by at least about 1- to 2-fold, at least about 2- to 3-fold, at least about 3- to 4-fold, at least about 4- to 5-fold, at least about 5- to 10-fold, at least about 10 to 100-fold, at least about 100- to 1000-fold as compared to the same isogenic strain without the phage modification. In some embodiments, the modifications or mutations alter, e.g., increase or reduce, the desired effector function, e.g., of a genetically engineered bacterium by at least about 1% to 10%, at least about 10% to 20%, at least about 20% to 30%, at least about 30% to 40%, at least about 40% to 50%, at least about 50% to 60%, at least about 60% to 70%, at least about 70% to 80%, at least about 80% to 90%, or at least about 90% to 100% as compared to the same isogenic strain without the phage modification.

In some embodiments, the mutations include one or more deletions within the *E. coli* Nissle Phage 3 genome sequence. In some embodiments, the mutations include one or more insertions into the *E. coli* Nissle Phage 3 genome sequence. In some embodiments, an antibiotic cassette can be inserted into one or more positions within the *E. coli* Nissle Phage 3 genome sequence. In some embodiments, the mutations include one or more substitutions within the *E. coli* Nissle Phage 3 genome sequence. In some embodiments, the mutations include one or more inversions within the *E. coli* Nissle Phage 3 genome sequence. In some embodiments, the inversion may be governed by a specific flippase. Exemplary circuitry comprising multiple levels of control are exemplified herein and are also described in co-owned pending International Patent Application PCT/US2016/039434, the contents of which is herein incorporated by reference in its entirety.

In some embodiments, the modifications within the *E. coli* Nissle Phage 3 genome are combinations of two or more of insertions, deletions, substitutions, or inversions within one or more *E. coli* Nissle Phage 3 genome genes.

In any of the embodiments described herein, the modifications may result in one or more frameshift mutations in one or more genes within the *E. coli* Nissle Phage 3 genome. In any of the embodiments described herein, the modifications may result in one or more missense mutation in one or more genes within the *E. coli* Nissle Phage 3 genome. In any of the embodiments described herein, the modifications may result in one or more nonsense mutations in one or more genes within the *E. coli* Nissle Phage 3 genome.

In some embodiments, the modifications within the *E. coli* Nissle Phage 3 genome are combinations of two or more frameshift, nonsense or missense mutations within one or more *E. coli* Nissle Phage 3 genome genes.

Mutations

In some embodiments, the one or more mutations comprise at least about 1-500 bp of the *E. coli* Nissle Phage 3 genome. In some embodiments, the one or more mutations comprise at least about 500-1000 bp of the *E. coli* Nissle Phage 3 genome. In some embodiments, the one or more mutations comprise at least about 1000-2000 bp of the *E. coli* Nissle Phage 3 genome. In some embodiments, the one or more mutations comprise at least about 1000-2000 bp of the *E. coli* Nissle Phage 3 genome. In some embodiments, the one or more mutations comprise at least about 2000-3000 bp of the *E. coli* Nissle Phage 3 genome. In some embodiments, the one or more mutations comprise at least about 3000-4000 bp of the *E. coli* Nissle Phage 3 genome. In some embodiments, the one or more mutations comprise at least about 4000-5000 bp of the *E. coli* Nissle Phage 3 genome. In some embodiments, the one or more mutations comprise at least about 5,000-6,000 bp of the *E. coli* Nissle Phage 3 genome. In some embodiments, the one or more mutations comprise at least about 6,000-7,000 bp of the *E. coli* Nissle Phage 3 genome. In some embodiments, the one or more mutations comprise at least about 7,000-8,000 bp of the *E. coli* Nissle Phage 3 genome. In some embodiments, the one or more mutations comprise at least about 8,000-9,000 bp of the *E. coli* Nissle Phage 3 genome. In some embodiments, the one or more mutations comprise at least about 9,000-10,000 bp of the *E. coli* Nissle Phage 3 genome. In some embodiments, the one or more mutations comprise at least about 10,000-15,000 bp of the *E. coli* Nissle Phage 3 genome. In some embodiments, the one or more mutations comprise at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In one specific embodiment, 9687 bp of the *E. coli* Nissle Phage 3 genome are mutated. In some embodiments, the mutated nucleotides are interspersed. In some embodiments, the mutated nucleotides are consecutive.

In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome is mutated. In some embodiments, at least about 30-40% of the *E. coli* Nissle Phage 3 genome is mutated. In some embodiments, at least about 40-50% of the *E. coli* Nissle Phage 3 genome is mutated. In some embodiments, at least about 50-60% of the *E. coli* Nissle Phage 3 genome is mutated. In some embodiments, at least about 60-70% of the *E. coli* Nissle Phage 3 genome is mutated. In some embodiments, at least about 70-80% of the *E. coli* Nissle Phage 3 genome is mutated. In some embodiments, at least about 80-90% of the *E. coli* Nissle Phage 3 genome is mutated. In some embodiments, 90-100% of the *E. coli* Nissle Phage 3 genome is mutated.

In some embodiments, at least about 1, 2, 3, 4, 5, 6, 7, 8, 9, 10, 11, 12, 13, 14, 15, 16, 17, 18, 19, or 20 genes are mutated. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are mutated. In some embodiments, 13 genes are completely or partially mutated. In one embodiment, 74 genes are completely or partially mutated.

In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the *E. coli* Nissle Phage 3 genome are completely or partially mutated.

In some embodiments, the one or more mutations are located at the beginning or 5' end of the *E. coli* Nissle Phage 3 genome. In some embodiments, the one or more mutations are located at the end or 3' end of the *E. coli* Nissle Phage 3 genome. In some embodiments, the one or more mutations are located in the middle of the *E. coli* Nissle Phage 3 genome. In some embodiments, the *E. coli* Nissle Phage 3 genes are interspersed within the bacterial genome and the mutation are located in one or more of the interspersed positions.

In some embodiments, the mutations are located within or encompass one or more genes encoding lytic genes. In some embodiments, the mutations are located within or encompass one or more genes encoding one or more proteases or lysins. In some embodiments, the mutations are located within or encompass one or more genes encoding one or more toxins. In some embodiments, the mutations are located within or encompass one or more genes encoding one or more antibiotic resistance related proteins. In some embodiments, the mutations are located within or encompass one or more genes encoding one or phage translation related proteins. In some embodiments, the one or more mutations are located within or encompass one or more genes encoding structural proteins. Such structural genes include genes encoding polypeptides of the head, tail, collar, or coat. In some embodiments, the one or more mutations are located within or encompass one or more genes encoding head proteins. In some embodiments, the one or more mutations are located within or encompass one or more genes encoding tail proteins. In some embodiments, the one or more mutations are located within or encompass one or more genes encoding collar proteins. In some embodiments, the one or more mutations are located within or encompass one or more genes encoding coat proteins. In some embodiments, the mutations are located within or encompass one or more genes encoding one or more plate proteins. In some embodiments, the mutations are located within or encompass one or more genes encoding one or more proteins require for assembly of the bacteriophage. In some embodiments, the mutations are located within or encompass one or more genes encoding one or more portal proteins. In some embodiments, the mutations are located within or encompass one or more genes encoding one or more polypeptides involved in recombination. In some embodiments, the mutations are located within or encompass one or more genes encoding one or more integrases. In some embodiments, the mutations are located within or encompass one or more genes encoding one or more invertases. In some embodiments, the mutations are located within or encompass one or more genes encoding one or more transposases. In some embodiments, the mutations are located with within or encompass one or more genes encoding one or more polypeptides involved in replication or translation. In some embodiments, the mutations are located within or encompass one or more genes encoding one or more primases. In some embodiments, the mutations are located within or encompass one or more genes encoding one or more tRNA related proteins. In some embodiments, the mutations are located within or encompass one or more genes encoding one or more polypeptides involved in phage insertion. In some embodiments, the mutations are located within or encompass one or more genes encoding an attachment site. In some embodiments, the mutations are located within or encompass one or more genes encoding one or more polypeptides involved in packaging. In some embodiments, the mutations are located within or encompass one or more genes encoding one or more terminases. In some embodiments, the mutations are located within or encompass one or more genes encoding one or more host genes.

In some embodiments, the mutations are located withinor encompass genes encoding one or more polypeptides involved in one or more of cell lysis, phage structure, phage assembly, phage packaging recombination, replication or translation, phage insertion, or are host proteins, and combinations thereof.

In some embodiments, the mutations are located withinor encompass genes encoding one or more polypeptides involved in one or more of cell lysis, phage structure, phage assembly, phage packaging recombination, replication or translation, phage insertion, and combinations thereof.

In some embodiments, the mutations are located withinor encompass 1 genes encoding polypeptides involved in cell lysis, phage structure, phage assembly, phage packaging recombination, replication or translation, phage insertion, and combinations thereof. In some embodiments, the mutations are located withinor encompass 2 genes encoding polypeptides involved in cell lysis, phage structure, phage assembly, phage packaging recombination, replication or translation, phage insertion, and combinations thereof. In some embodiments, the mutations are located withinor encompass 3 genes encoding polypeptides involved in cell lysis, phage structure, phage assembly, phage packaging recombination, replication or translation, phage insertion, and combinations thereof. In some embodiments, the mutations are located withinor encompass 4 genes encoding polypeptides involved in cell lysis, phage structure, phage assembly, phage packaging recombination, replication or translation, phage insertion, and combinations thereof. In some embodiments, the mutations are located withinor encompass 2 genes encoding polypeptides involved in cell lysis, phage structure, phage assembly, phage packaging recombination, replication or translation, phage insertion, and combinations thereof. In some embodiments, the mutations are located withinor encompass 5 genes encoding polypeptides involved in cell lysis, phage structure, phage assembly, phage packaging recombination, replication or translation, phage insertion, and combinations thereof. In some embodiments, the mutations are located withinor encompass 6 genes encoding polypeptides involved in cell lysis, phage structure, phage assembly, phage packaging recombination, replication or translation, phage insertion, and combinations thereof. In some embodiments, the mutations are located withinor encompass 7 genes encoding polypeptides involved in cell lysis, phage structure, phage assembly, phage packaging recombination, replication or translation, phage insertion, and combinations thereof. In some embodiments, the mutations are located withinor encompass 8 genes encoding polypeptides involved in cell lysis, phage structure, phage assembly, phage packaging recombination, replication or translation, phage insertion, and combinations thereof. In some embodiments, the mutations are located withinor encompass 9 genes encoding polypeptides involved in cell lysis, phage structure, phage assembly, phage packaging recombination, replication or translation, phage insertion, and combinations thereof. In some embodiments, the mutations are located withinor encompass 10 genes encoding polypeptides involved in cell lysis, phage structure, phage assembly, phage packaging recombination, replication or translation, phage insertion, and combinations thereof. In some embodiments, the mutations are located withinor encompass 11 genes encoding polypeptides involved in cell lysis, phage structure, phage assembly, phage packaging recombination, replication or translation, phage insertion, and combinations thereof. In some embodiments, the mutations are located withinor encompass 12 genes encoding polypeptides involved in cell lysis, phage structure, phage assembly, phage packaging recombination, replication or translation, phage insertion, and combinations thereof. In some embodiments, the mutations are located withinor encompass 13 genes encoding polypeptides involved in cell lysis, phage structure, phage assembly, phage packaging recombination, replication or translation, phage insertion, and combinations thereof. In some embodiments, the mutations are located withinor encompass 14 genes encoding polypeptides involved in cell lysis, phage structure, phage assembly, phage packaging recombination, replication or translation, phage insertion, and combinations thereof. In some embodiments, the mutations are located withinor encompass 15 genes encoding polypeptides involved in cell lysis, phage structure, phage assembly, phage packaging recombination, replication or translation, phage insertion, and combinations thereof. In some embodiments, the mutations are located withinor encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the mutations are located withinor encompass one or more host proteins within the phage genome.

In any of the embodiments described herein, the modifications encompass are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more mutations encompass or are located in ECOLIN_09965. In some embodiments, one or more mutations encompass or are located in ECOLIN_09970. In some embodiments, one or more mutations encompass or are located in ECOLIN_09975. In some embodiments, one or more mutations encompass or are located in ECOLIN_09980. In some embodiments, one or more mutations encompass or are located in ECOLIN_09985. In some embodiments, one or more mutations encompass or are located in ECOLIN_09990. In some embodiments, one or more mutations encompass or are located in ECOLIN_09995. In some embodiments, one or more mutations encompass or are located in ECOLIN_10000. In some embodiments, one or more mutations encompass or are located in ECOLIN_10005. In some embodiments, one or more mutations encompass or are located in ECOLIN_10010. In some embodiments, one or more mutations encompass or are located in ECOLIN_10015. In some embodiments, one or more mutations encompass or are located in ECOLIN_10020. In some embodiments, one or more mutations encompass or are located in ECOLIN_10025. In some embodiments, one or more mutations encompass or are located in ECOLIN_10030. In some embodiments, one or more mutations encompass or are located in ECOLIN_10035. In some embodiments, one or more mutations encompass or are located in ECOLIN_10040. In some embodiments, one or more mutations encompass or are located in ECOLIN_10045. In some embodiments, one or more mutations encompass or are located in ECOLIN_10050. In some embodiments, one or more mutations encompass or are located in ECOLIN_10055. In some embodiments, one or more mutations encompass or are located in ECOLIN_10065. In some embodiments, one or more mutations encompass or are located in ECOLIN_10070. In some embodiments, one or more mutations encompass or are located in ECOLIN_10075. In some embodiments, one or more mutations encompass or are located in ECOLIN_10080. In some embodiments, one or more mutations encompass or are located in ECOLIN_10085. In some embodiments, one or more mutations encompass or are located in ECOLIN_10090. In some embodiments, one or more mutations encompass or are located in ECOLIN_10095. In some embodiments, one or more mutations encompass or are located in ECOLIN_10100. In some embodiments, one or more mutations encompass or are located in ECOLIN_10105. In some embodiments, one or more mutations encompass or are located in ECOLIN_10110. In some embodiments, one or more mutations encompass or are located in ECOLIN_10115. In some embodiments, one or more mutations encompass or are located in ECOLIN_10120. In some embodiments, one or more mutations encompass or are located in ECOLIN_10125. In some embodiments, one or more mutations encompass or are located in ECOLIN_10130. In some embodiments, one or more mutations encompass or are located in ECOLIN_10135. In some embodiments, one or more mutations encompass or are located in ECOLIN_10140. In some embodiments, one or more mutations encompass or are located in ECOLIN_10145. In some embodiments, one or more mutations encompass or are located in ECOLIN_10150. In some embodiments, one or more mutations encompass or are located in ECOLIN_10160. In some embodiments, one or more mutations encompass or are located in ECOLIN_10165. In some embodiments, one or more mutations encompass or are located in ECOLIN_10170. In some embodiments, one or more mutations encompass or are located in ECOLIN_10175. In some embodiments, one or more mutations encompass or are located in ECOLIN_10180. In some embodiments, one or more mutations encompass or are located in ECOLIN_10185. In some embodiments, one or more mutations encompass or are located in ECOLIN_10190. In some embodiments, one or more mutations encompass or are located in ECOLIN_10195. In some embodiments, one or more mutations encompass or are located in ECOLIN_10200. In some embodiments, one or more mutations encompass or are located in ECOLIN_10205. In some embodiments, one or more mutations encompass or are located in ECOLIN_10210. In some embodiments, one or more mutations encompass or are located in ECOLIN_10220. In some embodiments, one or more mutations encompass or are located in ECOLIN_10225. In some embodiments, one or more mutations encompass or are located in ECOLIN_10230. In some embodiments, one or more mutations encompass or are located in ECOLIN_10235. In some embodiments, one or more mutations encompass or are located in ECOLIN_10240. In some embodiments, one or more mutations encompass or are located in ECOLIN_10245. In some embodiments, one or more mutations encompass or are located in ECOLIN_10250. In some embodiments, one or more mutations encompass or are located in ECOLIN_10255. In some embodiments, one or more mutations encompass or are located in ECOLIN_10260. In some embodiments, one or more mutations encompass or are located in ECOLIN_10265. In some embodiments, one or more mutations encompass or are located in ECOLIN_10270. In some embodiments, one or more mutations encompass or are located in ECOLIN_10275. In some embodiments, one or more mutations encompass or are located in ECOLIN_10280. In some embodiments, one or more mutations encompass or are located in ECOLIN_10290. In some embodiments, one or more mutations encompass or are located in ECOLIN_10295. In some embodiments, one or more mutations encompass or are located in ECOLIN_10300. In some embodiments, one or more mutations encompass or are located in ECOLIN_10305. In some embodiments, one or more mutations encompass or are located in ECOLIN_10310. In some embodiments, one or more mutations encompass or are located in ECOLIN_10315. In some embodiments, one or more mutations encompass or are located in ECOLIN_10320. In some embodiments, one or more mutations encompass or are located in ECOLIN_10325. In some embodiments, one or more mutations encompass or are located in ECOLIN_10330. In some embodiments, one or more mutations encompass or are located in ECOLIN_10335. In some embodiments, one or more mutations encompass or are located in ECOLIN_10340. In some embodiments, one or more mutations encompass or are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase are mutated.

In one embodiment, the mutation is a complete or partial mutation of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the mutation is a complete or partial mutation of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the mutation is a complete mutation of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial mutation of ECOLIN_10175. In one embodiment, the sequence of SEQ ID NO: 130 is mutated from the Phage 3 genome. In one embodiment, a sequence comprising SEQ ID NO: 130 is mutated from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Deletions

In some embodiments, the one or more deletions comprise at least about 1-500 bp of the *E. coli* Nissle Phage 3 genome. In some embodiments, the one or more deletions comprise at least about 500-1000 bp of the *E. coli* Nissle Phage 3 genome. In some embodiments, the one or more deletions comprise at least about 1000-2000 bp of the *E. coli* Nissle Phage 3 genome. In some embodiments, the one or more deletions comprise at least about 1000-2000 bp of the *E. coli* Nissle Phage 3 genome. In some embodiments, the one or more deletions comprise at least about 2000-3000 bp of the *E. coli* Nissle Phage 3 genome. In some embodiments, the one or more deletions comprise at least about 3000-4000 bp of the *E. coli* Nissle Phage 3 genome. In some embodiments, the one or more deletions comprise at least about 4000-5000 bp of the *E. coli* Nissle Phage 3 genome. In some embodiments, the one or more deletions comprise at least about 5,000-6,000 bp of the *E. coli* Nissle Phage 3 genome. In some embodiments, the one or more deletions comprise at least about 6,000-7,000 bp of the *E. coli* Nissle Phage 3 genome. In some embodiments, the one or more deletions comprise at least about 7,000-8,000 bp of the *E. coli* Nissle Phage 3 genome. In some embodiments, the one or more deletions comprise at least about 8,000-9,000 bp of the *E. coli* Nissle Phage 3 genome. In some embodiments, the one or more deletions comprise at least about 9,000-10,000 bp of the *E. coli* Nissle Phage 3 genome. In some embodiments, the one or more deletions comprise at least about 10,000-15,000 bp of the *E. coli* Nissle Phage 3 genome. In some embodiments, the one or more deletions comprise at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In one specific embodiment, 9687 bp of the *E. coli* Nissle Phage 3 genome are deleted. In some embodiments, the deleted nucleotides are interspersed. In some embodiments, the deleted nucleotides are consecutive.

In some embodiments, at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome is deleted. In some embodiments, at least about 30-40% of the *E. coli* Nissle Phage 3 genome is deleted. In some embodiments, at least about 40-50% of the *E. coli* Nissle Phage 3 genome is deleted. In some embodiments, at least about 50-60% of the *E. coli* Nissle Phage 3 genome is deleted. In some embodiments, at least about 60-70% of the *E. coli* Nissle Phage 3 genome is deleted. In some embodiments, at least about 70-80% of the *E. coli* Nissle Phage 3 genome is deleted. In some embodiments, at least about 80-90% of the *E. coli* Nissle Phage 3 genome is deleted. In some embodiments, at least about 90-100% of the *E. coli* Nissle Phage 3 genome is deleted.

In some embodiments, one or more genes are partially or completely deleted within the *E. coli* Nissle Phage 3 genome. In some embodiments, one or more genes are completely deleted and one or more genes are partially deleted. In one embodiment, there is one deletion within the *E. coli* Nissle Phage 3 genome and one or two genes at the ends of the deletion are partially deleted and the rest of the genes are completely deleted. In some embodiments, the deleted genes are adjacent to each other. In some embodiments, the deleted genes are not adjacent to each other.

In some embodiments, at least about 1, 2, 3, 4, 5, 6, 7, 8, 9, 10, 11, 12, 13, 14, 15, 16, 17, 18, 19, or 20 genes are deleted. In some embodiments, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes are deleted. In some embodiments, 13 genes are completely or partially deleted. In one embodiment, 74 genes are completely or partially deleted.

In some embodiments, at least about 1% to 2%, at least about 2% to 3%, at least about 3% to 4%, at least about 4% to 5%, at least about 5% to 6%, at least about 6% to 7%, at least about 7% to 8%, at least about 8% to 9%, at least about 9% to 10%, at least about 10% to 11%, at least about 11% to 12%, at least about 12% to 13%, at least about 13% to 14%, at least about 14% to 15%, at least about 15% to 16%, at least about 16% to 17%, at least about 17% to 18%, at least about 18% to 19%, at least about 19% to 20%, at least about 20% to 21%, at least about 21% to 22%, at least about 22% to 23%, at least about 23% to 24%, at least about 24% to 25%, at least about 25% to 26%, at least about 26% to 27%, at least about 27% to 28%, at least about 28% to 29%, at least about 29% to 30%, at least about 30% to 31%, at least about 31% to 32%, at least about 32% to 33%, at least about 33% to 34%, at least about 34% to 35%, at least about 35% to 36%, at least about 36% to 37%, at least about 37% to 38%, at least about 38% to 39%, at least about 39% to 40%, at least about 40% to 41%, at least about 41% to 42%, at least about 42% to 43%, at least about 43% to 44%, at least about 44% to 45%, at least about 45% to 46%, at least about 46% to 47%, at least about 47% to 48%, at least about 48% to 49%, at least about 49% to 50%, at least about 50% to 51%, at least about 51% to 52%, at least about 52% to 53%, at least about 53% to 54%, at least about 54% to 55%, at least about 55% to 56%, at least about 56% to 57%, at least about 57% to 58%, at least about 58% to 59%, at least about 59% to 60%, at least about 60% to 61%, at least about 61% to 62%, at least about 62% to 63%, at least about 63% to 64%, at least about 64% to 65%, at least about 65% to 66%, at least about 66% to 67%, at least about 67% to 68%, at least about 68% to 69%, at least about 69% to 70%, at least about 70% to 71%, at least about 71% to 72%, at least about 72% to 73%, at least about 73% to 74%, at least about 74% to 75%, at least about 75% to 76%, at least about 76% to 77%, at least about 77% to 78%, at least about 78% to 79%, at least about 79% to 80%, at least about 80% to 81%, at least about 81% to 82%, at least about 82% to 83%, at least about 83% to 84%, at least about 84% to 85%, at least about 85% to 86%, at least about 86% to 87%, at least about 87% to 88%, at least about 88% to 89%, at least about 89% to 90%, at least about 90% to 91%, at least about 91% to 92%, at least about 92% to 93%, at least about 93% to 94%, at least about 94% to 95%, at least about 95% to 96%, at least about 96% to 97%, at least about 97% to 98%, at least about 98% to 99%, at least about 99% to 100%, or at least about 100% of genes within the *E. coli* Nissle Phage 3 genome are completely or partially deleted.

In some embodiments, the one or more deletions are located at the beginning or 5' end of the *E. coli* Nissle Phage 3 genome. In some embodiments, the one or more deletions are located at the end or 3' end of the *E. coli* Nissle Phage 3 genome. In some embodiments, the one or more deletions are located in the middle of the *E. coli* Nissle Phage 3 genome. In some embodiments, the *E. coli* Nissle Phage 3 genes are interspersed within the bacterial genome and the deletion are located in one or more of the interspersed positions.

In some embodiments, the region for an optimal deletion, i.e., to achieve a desired effect, can be determined through analysis of homology with other phages in other bacteria, e.g., other *E. coli* strains. Homologous conserved regions in *E. coli* Nissle Phage 3 may be suitable for deletion, as these are conserved and may comprise one or more essential genes. In some embodiments, regulatory elements, such as promoters, are deleted. In some embodiments, coding sequences are deleted. In some embodiments, the one or more deleted regions contain one or more genes essential for the lytic cycle.

In some embodiments, the deletions are located within or encompass one or more genes encoding lytic genes. In some embodiments, the deletions are located within or encompass one or more genes encoding one or more proteases or lysins. In some embodiments, the deletions are located within or encompass one or more genes encoding one or more toxins. In some embodiments, the deletions are located within or encompass one or more genes encoding one or more antibiotic resistance related proteins. In some embodiments, the deletions are located within or encompass one or more genes encoding one or phage translation related proteins. In some embodiments, the one or more deletions are located within or encompass one or more genes encoding structural proteins. Such structural genes include genes encoding polypeptides of the head, tail, collar, or coat. In some embodiments, the deletions are located within or encompass one or more genes encoding one or more head proteins. In some embodiments, the deletions are located within or encompass one or more genes encoding one or more tail proteins. In some embodiments, the deletions are located within or encompass one or more genes encoding one or more collar proteins. In some embodiments, the deletions are located within or encompass one or more genes encoding one or more coat proteins. In some embodiments, the deletions are located within or encompass one or more genes encoding one or more plate proteins. In some embodiments, the deletions are located within or encompass one or more genes encoding one or more proteins require for assembly of the bacteriophage. In some embodiments, the deletions are located within or encompass one or more genes encoding one or more portal proteins. In some embodiments, the deletions are located within or encompass one or more genes encoding one or more polypeptides involved in recombination. In some embodiments, the deletions are located within or encompass one or more genes encoding one or more integrases. In some embodiments, the deletions are located within or encompass one or more genes encoding one or more invertases. In some embodiments, the deletions are located within or encompass one or more genes encoding one or more transposases. In some embodiments, the deletions are located with within or encompass one or more genes encoding one or more polypeptides involved in replication or translation. In some embodiments, the deletions are located within or encompass one or more genes encoding one or more primases. In some embodiments, the deletions are located within or encompass one or more genes encoding one or more tRNA related proteins. In some embodiments, the deletions are located within or encompass one or more genes encoding one or more polypeptides involved in phage insertion. In some embodiments, the deletions are located within or encompass one or more genes encoding an attachment site. In some embodiments, the deletions are located within or encompass one or more genes encoding one or more polypeptides involved in packaging. In some embodiments, the deletions are located within or encompass one or more genes encoding one or more terminases. In some embodiments, the deletions are located within or encompass one or more genes encoding one or more host genes.

In some embodiments, the deletions are located withinor encompass genes encoding one or more polypeptides involved in one or more of cell lysis, phage structure, phage assembly, phage packaging recombination, replication or translation, phage insertion, or are host proteins, and combinations thereof.

In some embodiments, the deletions are located withinor encompass genes encoding one or more polypeptides involved in one or more of cell lysis, phage structure, phage assembly, phage packaging recombination, replication or translation, phage insertion, and combinations thereof.

In some embodiments, the deletions are located withinor encompass 1 genes encoding polypeptides involved in cell lysis, phage structure, phage assembly, phage packaging recombination, replication or translation, phage insertion, and combinations thereof. In some embodiments, the deletions are located withinor encompass 2 genes encoding polypeptides involved in cell lysis, phage structure, phage assembly, phage packaging recombination, replication or translation, phage insertion, and combinations thereof. In some embodiments, the deletions are located withinor encompass 3 genes encoding polypeptides involved in cell lysis, phage structure, phage assembly, phage packaging recombination, replication or translation, phage insertion, and combinations thereof. In some embodiments, the deletions are located withinor encompass 4 genes encoding polypeptides involved in cell lysis, phage structure, phage assembly, phage packaging recombination, replication or translation, phage insertion, and combinations thereof. In some embodiments, the deletions are located withinor encompass 2 genes encoding polypeptides involved in cell lysis, phage structure, phage assembly, phage packaging recombination, replication or translation, phage insertion, and combinations thereof. In some embodiments, the deletions are located within or encompass 5 genes encoding polypeptides involved in cell lysis, phage structure, phage assembly, phage packaging recombination, replication or translation, phage insertion, and combinations thereof. In some embodiments, the deletions are located within or encompass 6 genes encoding polypeptides involved in cell lysis, phage structure, phage assembly, phage packaging recombination, replication or translation, phage insertion, and combinations thereof. In some embodiments, the deletions are located within or encompass 7 genes encoding polypeptides involved in cell lysis, phage structure, phage assembly, phage packaging recombination, replication or translation, phage insertion, and combinations thereof. In some embodiments, the deletions are located within or encompass 8 genes encoding polypeptides involved in cell lysis, phage structure, phage assembly, phage packaging recombination, replication or translation, phage insertion, and combinations thereof. In some embodiments, the deletions are located within or encompass 9 genes encoding polypeptides involved in cell lysis, phage structure, phage assembly, phage packaging recombination, replication or translation, phage insertion, and combinations thereof. In some embodiments, the deletions are located within or encompass 10 genes encoding polypeptides involved in cell lysis, phage structure, phage assembly, phage packaging recombination, replication or translation, phage insertion, and combinations thereof. In some embodiments, the deletions are located within or encompass 11 genes encoding polypeptides involved in cell lysis, phage structure, phage assembly, phage packaging recombination, replication or translation, phage insertion, and combinations thereof. In some embodiments, the deletions are located within or encompass 12 genes encoding polypeptides involved in cell lysis, phage structure, phage assembly, phage packaging recombination, replication or translation, phage insertion, and combinations thereof. In some embodiments, the deletions are located within or encompass 13 genes encoding polypeptides involved in cell lysis, phage structure, phage assembly, phage packaging recombination, replication or translation, phage insertion, and combinations thereof. In some embodiments, the deletions are located within or encompass 14 genes encoding polypeptides involved in cell lysis, phage structure, phage assembly, phage packaging recombination, replication or translation, phage insertion, and combinations thereof. In some embodiments, the deletions are located within or encompass 15 genes encoding polypeptides involved in cell lysis, phage structure, phage assembly, phage packaging recombination, replication or translation, phage insertion, and combinations thereof. In some embodiments, the deletions are located within or encompass at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the deletions are located within or encompass one or more host proteins within the phage genome.

In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more deletions encompass (completely or partially) or are located in ECOLIN_09965. In some embodiments, one or more deletions encompass (completely or partially) or are located in ECOLIN_09970. In some embodiments, one or more deletions encompass (completely or partially) or are located in ECOLIN_09975. In some embodiments, one or more deletions encompass (completely or partially) or are located in ECOLIN_09980. In some embodiments, one or more deletions encompass (completely or partially) or are located in ECOLIN_09985. In some embodiments, one or more deletions encompass (completely or partially) or are located in ECOLIN_09990. In some embodiments, one or more deletions encompass (completely or partially) or are located in ECOLIN_09995. In some embodiments, one or more deletions encompass (completely or partially) or are located in ECOLIN_10000. In some embodiments, one or more deletions encompass (completely or partially) or are located in ECOLIN_10005. In some embodiments, one or more deletions encompass (completely or partially) or are located in ECOLIN_10010. In some embodiments, one or more deletions encompass (completely or partially) or are located in ECOLIN_10015. In some embodiments, one or more deletions encompass (completely or partially) or are located in ECOLIN_10020. In some embodiments, one or more deletions encompass (completely or partially) or are located in ECOLIN_10025. In some embodiments, one or more deletions encompass (completely or partially) or are located in ECOLIN_10030. In some embodiments, one or more deletions encompass (completely or partially) or are located in ECOLIN_10035. In some embodiments, one or more deletions encompass (completely or partially) or are located in ECOLIN_10040. In some embodiments, one or more deletions encompass (completely or partially) or are located in ECOLIN_10045. In some embodiments, one or more deletions encompass (completely or partially) or are located in ECOLIN_10050. In some embodiments, one or more deletions encompass (completely or partially) or are located in ECOLIN_10055. In some embodiments, one or more deletions encompass (completely or partially) or are located in ECOLIN_10065. In some embodiments, one or more deletions encompass (completely or partially) or are located in ECOLIN_10070. In some embodiments, one or more deletions encompass (completely or partially) or are located in ECOLIN_10075. In some embodiments, one or more deletions encompass (completely or partially) or are located in ECOLIN_10080. In some embodiments, one or more deletions encompass (completely or partially) or are located in ECOLIN_10085. In some embodiments, one or more deletions encompass (completely or partially) or are located in ECOLIN_10090. In some embodiments, one or more deletions encompass (completely or partially) or are located in ECOLIN_10095. In some embodiments, one or more deletions encompass (completely or partially) or are located in ECOLIN_10100. In some embodiments, one or more deletions encompass (completely or partially) or are located in ECOLIN_10105. In some embodiments, one or more deletions encompass (completely or partially) or are located in ECOLIN_10110. In some embodiments, one or more deletions encompass (completely or partially) or are located in ECOLIN_10115. In some embodiments, one or more deletions encompass (completely or partially) or are located in ECOLIN_10120. In some embodiments, one or more deletions encompass (completely or partially) or are located in ECOLIN_10125. In some embodiments, one or more deletions encompass (completely or partially) or are located in ECOLIN_10130. In some embodiments, one or more deletions encompass (completely or partially) or are located in ECOLIN_10135. In some embodiments, one or more deletions encompass (completely or partially) or are located in ECOLIN_10140. In some embodiments, one or more deletions encompass (completely or partially) or are located in ECOLIN_10145. In some embodiments, one or more deletions encompass (completely or partially) or are located in ECOLIN_10150. In some embodiments, one or more deletions encompass (completely or partially) or are located in ECOLIN_10160. In some embodiments, one or more deletions encompass (completely or partially) or are located in ECOLIN_10165. In some embodiments, one or more deletions encompass (completely or partially) or are located in ECOLIN_10170. In some embodiments, one or more deletions encompass (completely or partially) or are located in ECOLIN_10175. In some embodiments, one or more deletions encompass (completely or partially) or are located in ECOLIN_10180. In some embodiments, one or more deletions encompass (completely or partially) or are located in ECOLIN_10185. In some embodiments, one or more deletions encompass (completely or partially) or are located in ECOLIN_10190. In some embodiments, one or more deletions encompass (completely or partially) or are located in ECOLIN_10195. In some embodiments, one or more deletions encompass (completely or partially) or are located in ECOLIN_10200. In some embodiments, one or more deletions encompass (completely or partially) or are located in ECOLIN_10205. In some embodiments, one or more deletions encompass (completely or partially) or are located in ECOLIN_10210. In some embodiments, one or more deletions encompass (completely or partially) or are located in ECOLIN_10220. In some embodiments, one or more deletions encompass (completely or partially) or are located in ECOLIN_10225. In some embodiments, one or more deletions encompass (completely or partially) or are located in ECOLIN_10230. In some embodiments, one or more deletions encompass (completely or partially) or are located in ECOLIN_10235. In some embodiments, one or more deletions encompass (completely or partially) or are located in ECOLIN_10240. In some embodiments, one or more deletions encompass (completely or partially) or are located in ECOLIN_10245. In some embodiments, one or more deletions encompass (completely or partially) or are located in ECOLIN_10250. In some embodiments, one or more deletions encompass (completely or partially) or are located in ECOLIN_10255. In some embodiments, one or more deletions encompass (completely or partially) or are located in ECOLIN_10260. In some embodiments, one or more deletions encompass (completely or partially) or are located in ECOLIN_10265. In some embodiments, one or more deletions encompass (completely or partially) or are located in ECOLIN_10270. In some embodiments, one or more deletions encompass (completely or partially) or are located in ECOLIN_10275. In some embodiments, one or more deletions encompass (completely or partially) or are located in ECOLIN_10280. In some embodiments, one or more deletions encompass (completely or partially) or are located in ECOLIN_10290. In some embodiments, one or more deletions encompass (completely or partially) or are located in ECOLIN_10295. In some embodiments, one or more deletions encompass (completely or partially) or are located in ECOLIN_10300. In some embodiments, one or more deletions encompass (completely or partially) or are located in ECOLIN_10305. In some embodiments, one or more deletions encompass (completely or partially) or are located in ECOLIN_10310. In some embodiments, one or more deletions encompass (completely or partially) or are located in ECOLIN_10315. In some embodiments, one or more deletions encompass (completely or partially) or are located in ECOLIN_10320. In some embodiments, one or more deletions encompass (completely or partially) or are located in ECOLIN_10325. In some embodiments, one or more deletions encompass (completely or partially) or are located in ECOLIN_10330. In some embodiments, one or more deletions encompass (completely or partially) or are located in ECOLIN_10335. In some embodiments, one or more deletions encompass (completely or partially) or are located in ECOLIN_10340. In some embodiments, one or more deletions encompass (completely or partially) or are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase are deleted.

In one specific embodiment, a Minor tail protein U, a tail protein, a DNA breaking-rejoining protein, a peptidase S14, a capsid protein, a DNA packaging protein, and a terminase are deleted. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Insertions

In some embodiments, the insertion is in a coding region of the *E. coli* Nissle Phage 3 genome. In some embodiments, the insertion is inserted into a regulatory region of the *E. coli* Nissle Phage 3 genome. In some embodiments, the inserted polynucleotides comprise one or more antibiotic cassette(s). Suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more inserted polynucleotides comprise at least about 1-500 bp in length. In some embodiments, the one or more inserted polynucleotides comprise at least about 500-1000 bp in length. In some embodiments, the one or more inserted polynucleotides comprise at least about 1000-2000 bp in length. In some embodiments, the one or more inserted polynucleotides comprise at least about 1000-2000 bp in length. In some embodiments, the one or more inserted polynucleotides comprise at least about 2000-3000 bp in length. In some embodiments, the one or more inserted polynucleotides comprise at least about 3000-4000 bp in length. In some embodiments, the one or more inserted polynucleotides comprise at least about 4000-5000 bp in length. In some embodiments, the one or more inserted polynucleotides comprise at least about 5,000-6,000 bp in length. In some embodiments, the one or more inserted polynucleotides comprise at least about 6,000-7,000 bp in length. In some embodiments, the one or more inserted polynucleotides comprise at least about 7,000-8,000 bp in length. In some embodiments, the one or more inserted polynucleotides comprise at least about 8,000-9,000 bp in length. In some embodiments, the one or more inserted polynucleotides comprise at least about 9,000-10,000 bp in length. In some embodiments, the one or more inserted polynucleotides comprise at least about 10,000-15,000 bp in length. In some embodiments, the one or more inserted polynucleotides comprise at least about 10,000-15,000 bp in length, at least about 15,000-20,000 bp in length, at least about 20,000-25,000 bp in length, at least about 25,000-30,000 bp in length, at least about 30,000-35,000 bp in length, at least about 35,000-40,000 bp in length, at least about 40,000-45,000 bp in length, at least about 45,000-50,000 bp in length, at least about 50,000-55,000 bp in length, at least about 55,000-60,000 bp in length, at least about 60,000-65,000 bp in length, at least about 65,000-70,000 bp in length, at least about 70,000-75,000 bp in length, at least about 75,000-80,000 bp in length, at least about 80,000-85,000 bp in length, at least about 85,000-90,000 bp in length, at least about 90,000-95,000 bp in length, 95,000-100,000 bp in length, at least about 100,000-110,000 bp in length, at least about 110,000-120,000 bp in length, at least about 120,000-130,000 bp in length, at least about 130,000-140,000 bp in length, at least about 140,000-150,000 bp in length, at least about 150,000-200,000 bp in length, or more than at least about 200,000 bp in length. In one specific embodiment, at least about 9687 bp in length are inserted.

In some embodiments, the one or more insertions are located within at least about 1-500 bp of the *E. coli* Nissle Phage 3 genome. In some embodiments, the one or more insertions are located within at least about 500-1000 bp of the *E. coli* Nissle Phage 3 genome. In some embodiments, the one or more insertions are located within at least about 1000-2000 bp of the *E. coli* Nissle Phage 3 genome. In some embodiments, the one or more insertions are located within at least about 1000-2000 bp of the *E. coli* Nissle Phage 3 genome. In some embodiments, the one or more insertions are located within at least about 2000-3000 bp of the *E. coli* Nissle Phage 3 genome. In some embodiments, the one or more insertions are located within at least about 3000-4000 bp of the *E. coli* Nissle Phage 3 genome. In some embodiments, the one or more insertions are located within at least about 4000-5000 bp of the *E. coli* Nissle Phage 3 genome. In some embodiments, the one or more insertions are located within at least about 5,000-6,000 bp of the *E. coli* Nissle Phage 3 genome. In some embodiments, the one or more insertions are located within at least about 6,000-7,000 bp of the *E. coli* Nissle Phage 3 genome. In some embodiments, the one or more insertions are located within at least about 7,000-8,000 bp of the *E. coli* Nissle Phage 3 genome. In some embodiments, the one or more insertions are located within at least about 8,000-9,000 bp of the *E. coli* Nissle Phage 3 genome. In some embodiments, the one or more insertions are located within at least about 9,000-10,000 bp of the *E. coli* Nissle Phage 3 genome. In some embodiments, the one or more insertions are located within at least about 10,000-15,000 bp of the *E. coli* Nissle Phage 3 genome. In some embodiments, the one or more insertions are located within at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In one specific embodiment, 9687 bp of the *E. coli* Nissle Phage 3 genome are inserted. In some embodiments, the inserted nucleotides are interspersed. In some embodiments, the inserted nucleotides are consecutive.

In some embodiments, the insertions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome. In some embodiments, at least about 30-40% of the *E. coli* Nissle Phage 3 genome is inserted. In some embodiments, the insertions are located within at least about 40-50% of the *E. coli* Nissle Phage 3 genome. In some embodiments, the insertions are located within at least about 50-60% of the *E. coli* Nissle Phage 3 genome. In some embodiments, the insertions are located within at least about 60-70% of the *E. coli* Nissle Phage 3 genome. In some embodiments, the insertions are located within at least about 70-80% of the *E. coli* Nissle Phage 3 genome. In some embodiments, the insertions are located within at least about 80-90% of the *E. coli* Nissle Phage 3 genome. In some embodiments, the insertions are located within at least about 90-100% of the *E. coli* Nissle Phage 3 genome.

In some embodiments, at least about 1, 2, 3, 4, 5, 6, 7, 8, 9, 10, 11, 12, 13, 14, 15, 16, 17, 18, 19, or 20 genes comprise insertions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise insertions. In some embodiments, 13 genes comprise insertions. In one embodiment, 74 genes comprise insertions.

In some embodiments, the one or more insertions are located at the beginning or 5' end of the *E. coli* Nissle Phage 3 genome. In some embodiments, the one or more insertions are located at the end or 3' end of the *E. coli* Nissle Phage 3 genome. In some embodiments, the one or more insertions are located in the middle of the *E. coli* Nissle Phage 3 genome. In some embodiments, the *E. coli* Nissle Phage 3 genes are interspersed within the bacterial genome and the insertion are located in one or more of the interspersed positions.

In some embodiments, the region for an optimal insertion, i.e., to achieve a desired effect, can be determined through analysis of homology with other phages in other bacteria. Homologous conserved regions in phages may be suitable for insertion, as these are conserved and may comprise one or more essential genes. In some embodiments, regulatory elements, such as promoters, are inserted. In some embodiments, coding sequences are inserted. In some embodiments, the one or more inserted regions contain one or more genes essential for the lytic cycle.

In some embodiments, the insertions are located within one or more genes encoding lytic genes. In some embodiments, the insertions are located within one or more genes encoding one or more proteases or lysins. In some embodiments, the insertions are located within one or more genes encoding one or more toxins. In some embodiments, the insertions are located within one or more genes encoding one or more antibiotic resistance related proteins. In some embodiments, the insertions are located within one or more genes encoding one or phage translation related proteins. In some embodiments, the one or more insertions are located within one or more genes encoding structural proteins. Such structural genes include genes encoding polypeptides of the head, tail, collar, or coat. In some embodiments, the one or more mutations are located within or encompass one or more genes encoding head proteins. In some embodiments, the one or more mutations are located within or encompass one or more genes encoding tail proteins. In some embodiments, the one or more mutations are located within or encompass one or more genes encoding collar proteins. In some embodiments, the one or more mutations are located within or encompass one or more genes encoding coat proteins. In some embodiments, the insertions are located within one or more genes encoding one or more plate proteins. In some embodiments, the insertions are located within one or more genes encoding one or more proteins require for assembly of the bacteriophage. In some embodiments, the insertions are located within one or more genes encoding one or more portal proteins. In some embodiments, the insertions are located within one or more genes encoding one or more polypeptides involved in recombination. In some embodiments, the insertions are located within one or more genes encoding one or more integrases. In some embodiments, the insertions are located within one or more genes encoding one or more invertases. In some embodiments, the insertions are located within one or more genes encoding one or more transposases. In some embodiments, the insertions are located with within one or more genes encoding one or more polypeptides involved in replication or translation. In some embodiments, the insertions are located within one or more genes encoding one or more primases. In some embodiments, the insertions are located within one or more genes encoding one or more tRNA related proteins. In some embodiments, the insertions are located within one or more genes encoding one or more polypeptides involved in phage insertion. In some embodiments, the insertions are located within one or more genes encoding an attachment site. In some embodiments, the insertions are located within one or more genes encoding one or more polypeptides involved in packaging. In some embodiments, the insertions are located within one or more genes encoding one or more terminases. In some embodiments, the insertions are located within one or more genes encoding one or more host genes.

In some embodiments, the insertions are located within genes encoding one or more polypeptides involved in one or more of cell lysis, phage structure, phage assembly, phage packaging recombination, replication or translation, phage insertion, or are host proteins, and combinations thereof.

In some embodiments, the insertions are located within genes encoding one or more polypeptides involved in one or more of cell lysis, phage structure, phage assembly, phage packaging recombination, replication or translation, phage insertion, and combinations thereof.

In some embodiments, the insertions are located within 1 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 3 genes encoding polypeptides involved in cell lysis, phage structure, phage assembly, phage packaging recombination, replication or translation, phage insertion, and combinations thereof. In some embodiments, the insertions are located within 4 genes encoding polypeptides involved in cell lysis, phage structure, phage assembly, phage packaging recombination, replication or translation, phage insertion, and combinations thereof. In some embodiments, the insertions are located within 2 genes encoding polypeptides involved in cell lysis, phage structure, phage assembly, phage packaging recombination, replication or translation, phage insertion, and combinations thereof. In some embodiments, the insertions are located within 5 genes encoding polypeptides involved in cell lysis, phage structure, phage assembly, phage packaging recombination, replication or translation, phage insertion, and combinations thereof. In some embodiments, the insertions are located within 6 genes encoding polypeptides involved in cell lysis, phage structure, phage assembly, phage packaging recombination, replication or translation, phage insertion, and combinations thereof. In some embodiments, the insertions are located within 7 genes encoding polypeptides involved in cell lysis, phage structure, phage assembly, phage packaging recombination, replication or translation, phage insertion, and combinations thereof. In some embodiments, the insertions are located within 8 genes encoding polypeptides involved in cell lysis, phage structure, phage assembly, phage packaging recombination, replication or translation, phage insertion, and combinations thereof. In some embodiments, the insertions are located within 9 genes encoding polypeptides involved in cell lysis, phage structure, phage assembly, phage packaging recombination, replication or translation, phage insertion, and combinations thereof. In some embodiments, the insertions are located within 10 genes encoding polypeptides involved in cell lysis, phage structure, phage assembly, phage packaging recombination, replication or translation, phage insertion, and combinations thereof. In some embodiments, the insertions are located within 11 genes encoding polypeptides involved in cell lysis, phage structure, phage assembly, phage packaging recombination, replication or translation, phage insertion, and combinations thereof. In some embodiments, the insertions are located within 12 genes encoding polypeptides involved in cell lysis, phage structure, phage assembly, phage packaging recombination, replication or translation, phage insertion, and combinations thereof. In some embodiments, the insertions are located within 13 genes encoding polypeptides involved in cell lysis, phage structure, phage assembly, phage packaging recombination, replication or translation, phage insertion, and combinations thereof. In some embodiments, the insertions are located within 14 genes encoding polypeptides involved in cell lysis, phage structure, phage assembly, phage packaging recombination, replication or translation, phage insertion, and combinations thereof. In some embodiments, the insertions are located within 15 genes encoding polypeptides involved in cell lysis, phage structure, phage assembly, phage packaging recombination, replication or translation, phage insertion, and combinations thereof. In some embodiments, the insertions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage insertion, and combinations thereof. In some embodiments, the insertions are located within one or more host proteins within the phage genome.

In any of the embodiments described herein, the insertions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more insertions are located in ECOLIN_09965. In some embodiments, one or more insertions are located in ECOLIN_09970. In some embodiments, one or more insertions are located in ECOLIN_09975. In some embodiments, one or more insertions are located in ECOLIN_09980. In some embodiments, one or more insertions are located in ECOLIN_09985. In some embodiments, one or more insertions are located in ECOLIN_09990. In some embodiments, one or more insertions are located in ECOLIN_09995. In some embodiments, one or more insertions are located in ECOLIN_10000. In some embodiments, one or more insertions are located in ECOLIN_10005. In some embodiments, one or more insertions are located in ECOLIN_10010. In some embodiments, one or more insertions are located in ECOLIN_10015. In some embodiments, one or more insertions are located in ECOLIN_10020. In some embodiments, one or more insertions are located in ECOLIN_10025. In some embodiments, one or more insertions are located in ECOLIN_10030. In some embodiments, one or more insertions are located in ECOLIN_10035. In some embodiments, one or more insertions are located in ECOLIN_10040. In some embodiments, one or more insertions are located in ECOLIN_10045. In some embodiments, one or more insertions are located in ECOLIN_10050. In some embodiments, one or more insertions are located in ECOLIN_10055. In some embodiments, one or more insertions are located in ECOLIN_10065. In some embodiments, one or more insertions are located in ECOLIN_10070. In some embodiments, one or more insertions are located in ECOLIN_10075. In some embodiments, one or more insertions are located in ECOLIN_10080. In some embodiments, one or more insertions are located in ECOLIN_10085. In some embodiments, one or more insertions are located in ECOLIN_10090. In some embodiments, one or more insertions are located in ECOLIN_10095. In some embodiments, one or more insertions are located in ECOLIN_10100. In some embodiments, one or more insertions are located in ECOLIN_10105. In some embodiments, one or more insertions are located in ECOLIN_10110. In some embodiments, one or more insertions are located in ECOLIN_10115. In some embodiments, one or more insertions are located in ECOLIN_10120. In some embodiments, one or more insertions are located in ECOLIN_10125. In some embodiments, one or more insertions are located in ECOLIN_10130. In some embodiments, one or more insertions are located in ECOLIN_10135. In some embodiments, one or more insertions are located in ECOLIN_10140. In some embodiments, one or more insertions are located in ECOLIN_10145. In some embodiments, one or more insertions are located in ECOLIN_10150. In some embodiments, one or more insertions are located in ECOLIN_10160. In some embodiments, one or more insertions are located in ECOLIN_10165. In some embodiments, one or more insertions are located in ECOLIN_10170. In some embodiments, one or more insertions are located in ECOLIN_10175. In some embodiments, one or more insertions are located in ECOLIN_10180. In some embodiments, one or more insertions are located in ECOLIN_10185. In some embodiments, one or more insertions are located in ECOLIN_10190. In some embodiments, one or more insertions are located in ECOLIN_10195. In some embodiments, one or more insertions are located in ECOLIN_10200. In some embodiments, one or more insertions are located in ECOLIN_10205. In some embodiments, one or more insertions are located in ECOLIN_10210. In some embodiments, one or more insertions are located in ECOLIN_10220. In some embodiments, one or more insertions are located in ECOLIN_10225. In some embodiments, one or more insertions are located in ECOLIN_10230. In some embodiments, one or more insertions are located in ECOLIN_10235. In some embodiments, one or more insertions are located in ECOLIN_10240. In some embodiments, one or more insertions are located in ECOLIN_10245. In some embodiments, one or more insertions are located in ECOLIN_10250. In some embodiments, one or more insertions are located in ECOLIN_10255. In some embodiments, one or more insertions are located in ECOLIN_10260. In some embodiments, one or more insertions are located in ECOLIN_10265. In some embodiments, one or more insertions are located in ECOLIN_10270. In some embodiments, one or more insertions are located in ECOLIN_10275. In some embodiments, one or more insertions are located in ECOLIN_10280. In some embodiments, one or more insertions are located in ECOLIN_10290. In some embodiments, one or more insertions are located in ECOLIN_10295. In some embodiments, one or more insertions are located in ECOLIN_10300. In some embodiments, one or more insertions are located in ECOLIN_10305. In some embodiments, one or more insertions are located in ECOLIN_10310. In some embodiments, one or more insertions are located in ECOLIN_10315. In some embodiments, one or more insertions are located in ECOLIN_10320. In some embodiments, one or more insertions are located in ECOLIN_10325. In some embodiments, one or more insertions are located in ECOLIN_10330. In some embodiments, one or more insertions are located in ECOLIN_10335. In some embodiments, one or more insertions are located in ECOLIN_10340. In some embodiments, one or more insertions are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase contain one or more insertions. In one specific embodiment, a Minor tail protein U, a tail protein, a DNA breaking-rejoining protein, a peptidase S14, a capsid protein, a DNA packaging protein, and a terminase contain one or more insertions.

In one embodiment one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175 comprise an insertion.

Inversions

In some embodiments, the inversion is in a coding region of the *E. coli* Nissle Phage 3 genome. In some embodiments, the inversion is inverted into a regulatory region of the *E. coli* Nissle Phage 3 genome. In some embodiments, the inversions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more inversions comprise 1-500 bp. In some embodiments, the one or more inversions comprise at least about 500-1000 bp. In some embodiments, the one or more inversions comprise at least about 1000-2000 bp. In some embodiments, the one or more inversions comprise at least about 1000-2000 bp. In some embodiments, the one or more inversions comprise at least about 2000-3000 bp. In some embodiments, the one or more inversions comprise at least about 3000-4000 bp. In some embodiments, the one or more inversions comprise at least about 4000-5000 bp. In some embodiments, the one or more inversions comprise at least about 5,000-6,000 bp. In some embodiments, the one or more inversions comprise at least about 6,000-7,000 bp. In some embodiments, the one or more inversions comprise at least about 7,000-8,000 bp. In some embodiments, the one or more inversions comprise at least about 8,000-9,000 bp. In some embodiments, the one or more inversions comprise at least about 9,000-10,000 bp. In some embodiments, the one or more inversions comprise at least about 10,000-15,000 bp. In some embodiments, the one or more inversions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, or at least about 55,000-60,000 bp. In one specific embodiment, 9687 bp are inverted. In some embodiments, the inverted nucleotides are interspersed. In some embodiments, the inverted nucleotides are consecutive.

In some embodiments, the one or more inversions are located within at least about 1-500 bp of the *E. coli* Nissle Phage 3 genome. In some embodiments, the one or more inversions are located within at least about 500-1000 bp of the *E. coli* Nissle Phage 3 genome. In some embodiments, the one or more inversions are located within at least about 1000-2000 bp of the *E. coli* Nissle Phage 3 genome. In some embodiments, the one or more inversions are located within at least about 1000-2000 bp of the *E. coli* Nissle Phage 3 genome. In some embodiments, the one or more inversions are located within at least about 2000-3000 bp of the *E. coli* Nissle Phage 3 genome. In some embodiments, the one or more inversions are located within at least about 3000-4000 bp of the *E. coli* Nissle Phage 3 genome. In some embodiments, the one or more inversions are located within at least about 4000-5000 bp of the *E. coli* Nissle Phage 3 genome. In some embodiments, the one or more inversions are located within at least about 5,000-6,000 bp of the *E. coli* Nissle Phage 3 genome. In some embodiments, the one or more inversions are located within at least about 6,000-7,000 bp of the *E. coli* Nissle Phage 3 genome. In some embodiments, the one or more inversions are located within at least about 7,000-8,000 bp of the *E. coli* Nissle Phage 3 genome. In some embodiments, the one or more inversions are located within at least about 8,000-9,000 bp of the *E. coli* Nissle Phage 3 genome. In some embodiments, the one or more inversions are located within at least about 9,000-10,000 bp of the *E. coli* Nissle Phage 3 genome. In some embodiments, the one or more inversions are located within at least about 10,000-15,000 bp of the *E. coli* Nissle Phage 3 genome. In some embodiments, the one or more inversions are located within at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, at least about 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome. In some embodiments, the inverted nucleotides are interspersed. In some embodiments, the inverted nucleotides are consecutive.

In some embodiments, the inversions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome. In some embodiments, at least about 30-40% of the *E. coli* Nissle Phage 3 genome is inverted. In some embodiments, the inversions are located within at least about 40-50% of the *E. coli* Nissle Phage 3 genome. In some embodiments, the inversions are located within at least about 50-60% of the *E. coli* Nissle Phage 3 genome. In some embodiments, the inversions are located within at least about 60-70% of the *E. coli* Nissle Phage 3 genome. In some embodiments, the inversions are located within at least about 70-80% of the *E. coli* Nissle Phage 3 genome. In some embodiments, the inversions are located within at least about 80-90% of the *E. coli* Nissle Phage 3 genome. In some embodiments, the inversions are located within at least about 90-100% of the *E. coli* Nissle Phage 3 genome.

In some embodiments, at least about 1, 2, 3, 4, 5, 6, 7, 8, 9, 10, 11, 12, 13, 14, 15, 16, 17, 18, 19, or 20 genes comprise inversions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise inversions. In some embodiments, 13 genes comprise inversions. In one embodiment, 74 genes comprise inversions.

In some embodiments, the one or more inversions are located at the beginning or 5' end of the *E. coli* Nissle Phage 3 genome. In some embodiments, the one or more inversions are located at the end or 3' end of the *E. coli* Nissle Phage 3 genome. In some embodiments, the one or more inversions are located in the middle of the *E. coli* Nissle Phage 3 genome. In some embodiments, the *E. coli* Nissle Phage 3 genes are interspersed within the bacterial genome and the inversion are located in one or more of the interspersed positions.

In some embodiments, the region for an optimal inversion, i.e., to achieve a desired effect, can be determined through analysis of homology with other phages in other bacteria. Homologous conserved regions in phages may be suitable for inversion, as these are conserved and may comprise one or more essential genes. In some embodiments, regulatory elements, such as promoters, are inverted. In some embodiments, coding sequences are inverted. In some embodiments, the one or more inverted regions contain one or more genes essential for the lytic cycle.

In some embodiments, the inversions are located within one or more genes encoding lytic genes. In some embodiments, the inversions are located within one or more genes encoding one or more proteases or lysins. In some embodiments, the inversions are located within one or more genes encoding one or more toxins. In some embodiments, the inversions are located within one or more genes encoding one or more antibiotic resistance related proteins. In some embodiments, the inversions are located within one or more genes encoding one or phage translation related proteins. In some embodiments, the one or more inversions are located within one or more genes encoding structural proteins. Such structural genes include genes encoding polypeptides of the head, tail, collar, or coat. In some embodiments, the one or more mutations are located within or encompass one or more genes encoding head proteins. In some embodiments, the one or more mutations are located within or encompass one or more genes encoding tail proteins. In some embodiments, the one or more mutations are located within or encompass one or more genes encoding collar proteins. In some embodiments, the one or more mutations are located within or encompass one or more genes encoding coat proteins. In some embodiments, the inversions are located within one or more genes encoding one or more plate proteins. In some embodiments, the inversions are located within one or more genes encoding one or more proteins require for assembly of the bacteriophage. In some embodiments, the inversions are located within one or more genes encoding one or more portal proteins. In some embodiments, the inversions are located within one or more genes encoding one or more polypeptides involved in recombination. In some embodiments, the inversions are located within one or more genes encoding one or more integrases. In some embodiments, the inversions are located within one or more genes encoding one or more invertases. In some embodiments, the inversions are located within one or more genes encoding one or more transposases. In some embodiments, the inversions are located with within one or more genes encoding one or more polypeptides involved in replication or translation. In some embodiments, the inversions are located within one or more genes encoding one or more primases. In some embodiments, the inversions are located within one or more genes encoding one or more tRNA related proteins. In some embodiments, the inversions are located within one or more genes encoding one or more polypeptides involved in phage inversion. In some embodiments, the inversions are located within one or more genes encoding an attachment site. In some embodiments, the inversions are located within one or more genes encoding one or more polypeptides involved in packaging. In some embodiments, the inversions are located within one or more genes encoding one or more terminases. In some embodiments, the inversions are located within one or more genes encoding one or more host genes.

In some embodiments, the inversions are located within genes encoding one or more polypeptides involved in one or more of cell lysis, phage structure, phage assembly, phage packaging recombination, replication or translation, phage inversion, or are host proteins, and combinations thereof.

In some embodiments, the inversions are located within genes encoding one or more polypeptides involved in one or more of cell lysis, phage structure, phage assembly, phage packaging recombination, replication or translation, phage inversion, and combinations thereof.

In some embodiments, the inversions are located within 1 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 3 genes encoding polypeptides involved in cell lysis, phage structure, phage assembly, phage packaging recombination, replication or translation, phage inversion, and combinations thereof. In some embodiments, the inversions are located within 4 genes encoding polypeptides involved in cell lysis, phage structure, phage assembly, phage packaging recombination, replication or translation, phage inversion, and combinations thereof. In some embodiments, the inversions are located within 2 genes encoding polypeptides involved in cell lysis, phage structure, phage assembly, phage packaging recombination, replication or translation, phage inversion, and combinations thereof. In some embodiments, the inversions are located within 5 genes encoding polypeptides involved in cell lysis, phage structure, phage assembly, phage packaging recombination, replication or translation, phage inversion, and combinations thereof. In some embodiments, the inversions are located within 6 genes encoding polypeptides involved in cell lysis, phage structure, phage assembly, phage packaging recombination, replication or translation, phage inversion, and combinations thereof. In some embodiments, the inversions are located within 7 genes encoding polypeptides involved in cell lysis, phage structure, phage assembly, phage packaging recombination, replication or translation, phage inversion, and combinations thereof. In some embodiments, the inversions are located within 8 genes encoding polypeptides involved in cell lysis, phage structure, phage assembly, phage packaging recombination, replication or translation, phage inversion, and combinations thereof. In some embodiments, the inversions are located within 9 genes encoding polypeptides involved in cell lysis, phage structure, phage assembly, phage packaging recombination, replication or translation, phage inversion, and combinations thereof. In some embodiments, the inversions are located within 10 genes encoding polypeptides involved in cell lysis, phage structure, phage assembly, phage packaging recombination, replication or translation, phage inversion, and combinations thereof. In some embodiments, the inversions are located within 11 genes encoding polypeptides involved in cell lysis, phage structure, phage assembly, phage packaging recombination, replication or translation, phage inversion, and combinations thereof. In some embodiments, the inversions are located within 12 genes encoding polypeptides involved in cell lysis, phage structure, phage assembly, phage packaging recombination, replication or translation, phage inversion, and combinations thereof. In some embodiments, the inversions are located within 13 genes encoding polypeptides involved in cell lysis, phage structure, phage assembly, phage packaging recombination, replication or translation, phage inversion, and combinations thereof. In some embodiments, the inversions are located within 14 genes encoding polypeptides involved in cell lysis, phage structure, phage assembly, phage packaging recombination, replication or translation, phage inversion, and combinations thereof. In some embodiments, the inversions are located within 15 genes encoding polypeptides involved in cell lysis, phage structure, phage assembly, phage packaging recombination, replication or translation, phage inversion, and combinations thereof. In some embodiments, the inversions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage inversion, and combinations thereof. In some embodiments, the inversions are located within one or more host proteins within the phage genome.

In any of the embodiments described herein, the inversions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more inversions encompass (completely or partially) or are located in ECOLIN_09965. In some embodiments, one or more inversions encompass (completely or partially) or are located in ECOLIN_09970. In some embodiments, one or more inversions encompass (completely or partially) or are located in ECOLIN_09975. In some embodiments, one or more inversions encompass (completely or partially) or are located in ECOLIN_09980. In some embodiments, one or more inversions encompass (completely or partially) or are located in ECOLIN_09985. In some embodiments, one or more inversions encompass (completely or partially) or are located in ECOLIN_09990. In some embodiments, one or more inversions encompass (completely or partially) or are located in ECOLIN_09995. In some embodiments, one or more inversions encompass (completely or partially) or are located in ECOLIN_10000. In some embodiments, one or more inversions encompass (completely or partially) or are located in ECOLIN_10005. In some embodiments, one or more inversions encompass (completely or partially) or are located in ECOLIN_10010. In some embodiments, one or more inversions encompass (completely or partially) or are located in ECOLIN_10015. In some embodiments, one or more inversions encompass (completely or partially) or are located in ECOLIN_10020. In some embodiments, one or more inversions encompass (completely or partially) or are located in ECOLIN_10025. In some embodiments, one or more inversions encompass (completely or partially) or are located in ECOLIN_10030. In some embodiments, one or more inversions encompass (completely or partially) or are located in ECOLIN_10035. In some embodiments, one or more inversions encompass (completely or partially) or are located in ECOLIN_10040. In some embodiments, one or more inversions encompass (completely or partially) or are located in ECOLIN_10045. In some embodiments, one or more inversions encompass (completely or partially) or are located in ECOLIN_10050. In some embodiments, one or more inversions encompass (completely or partially) or are located in ECOLIN_10055. In some embodiments, one or more inversions encompass (completely or partially) or are located in ECOLIN_10065. In some embodiments, one or more inversions encompass (completely or partially) or are located in ECOLIN_10070. In some embodiments, one or more inversions encompass (completely or partially) or are located in ECOLIN_10075. In some embodiments, one or more inversions encompass (completely or partially) or are located in ECOLIN_10080. In some embodiments, one or more inversions encompass (completely or partially) or are located in ECOLIN_10085. In some embodiments, one or more inversions encompass (completely or partially) or are located in ECOLIN_10090. In some embodiments, one or more inversions encompass (completely or partially) or are located in ECOLIN_10095. In some embodiments, one or more inversions encompass (completely or partially) or are located in ECOLIN_10100. In some embodiments, one or more inversions encompass (completely or partially) or are located in ECOLIN_10105. In some embodiments, one or more inversions encompass (completely or partially) or are located in ECOLIN_10110. In some embodiments, one or more inversions encompass (completely or partially) or are located in ECOLIN_10115. In some embodiments, one or more inversions encompass (completely or partially) or are located in ECOLIN_10120. In some embodiments, one or more inversions encompass (completely or partially) or are located in ECOLIN_10125. In some embodiments, one or more inversions encompass (completely or partially) or are located in ECOLIN_10130. In some embodiments, one or more inversions encompass (completely or partially) or are located in ECOLIN_10135. In some embodiments, one or more inversions encompass (completely or partially) or are located in ECOLIN_10140. In some embodiments, one or more inversions encompass (completely or partially) or are located in ECOLIN_10145. In some embodiments, one or more inversions encompass (completely or partially) or are located in ECOLIN_10150. In some embodiments, one or more inversions encompass (completely or partially) or are located in ECOLIN_10160. In some embodiments, one or more inversions encompass (completely or partially) or are located in ECOLIN_10165. In some embodiments, one or more inversions encompass (completely or partially) or are located in ECOLIN_10170. In some embodiments, one or more inversions encompass (completely or partially) or are located in ECOLIN_10175. In some embodiments, one or more inversions encompass (completely or partially) or are located in ECOLIN_10180. In some embodiments, one or more inversions encompass (completely or partially) or are located in ECOLIN_10185. In some embodiments, one or more inversions encompass (completely or partially) or are located in ECOLIN_10190. In some embodiments, one or more inversions encompass (completely or partially) or are located in ECOLIN_10195. In some embodiments, one or more inversions encompass (completely or partially) or are located in ECOLIN_10200. In some embodiments, one or more inversions encompass (completely or partially) or are located in ECOLIN_10205. In some embodiments, one or more inversions encompass (completely or partially) or are located in ECOLIN_10210. In some embodiments, one or more inversions encompass (completely or partially) or are located in ECOLIN_10220. In some embodiments, one or more inversions encompass (completely or partially) or are located in ECOLIN_10225. In some embodiments, one or more inversions encompass (completely or partially) or are located in ECOLIN_10230. In some embodiments, one or more inversions encompass (completely or partially) or are located in ECOLIN_10235. In some embodiments, one or more inversions encompass (completely or partially) or are located in ECOLIN_10240. In some embodiments, one or more inversions encompass (completely or partially) or are located in ECOLIN_10245. In some embodiments, one or more inversions encompass (completely or partially) or are located in ECOLIN_10250. In some embodiments, one or more inversions encompass (completely or partially) or are located in ECOLIN_10255. In some embodiments, one or more inversions encompass (completely or partially) or are located in ECOLIN_10260. In some embodiments, one or more inversions encompass (completely or partially) or are located in ECOLIN_10265. In some embodiments, one or more inversions encompass (completely or partially) or are located in ECOLIN_10270. In some embodiments, one or more inversions encompass (completely or partially) or are located in ECOLIN_10275. In some embodiments, one or more inversions encompass (completely or partially) or are located in ECOLIN_10280. In some embodiments, one or more inversions encompass (completely or partially) or are located in ECOLIN_10290. In some embodiments, one or more inversions encompass (completely or partially) or are located in ECOLIN_10295. In some embodiments, one or more inversions encompass (completely or partially) or are located in ECOLIN_10300. In some embodiments, one or more inversions encompass (completely or partially) or are located in ECOLIN_10305. In some embodiments, one or more inversions encompass (completely or partially) or are located in ECOLIN_10310. In some embodiments, one or more inversions encompass (completely or partially) or are located in ECOLIN_10315. In some embodiments, one or more inversions encompass (completely or partially) or are located in ECOLIN_10320. In some embodiments, one or more inversions encompass (completely or partially) or are located in ECOLIN_10325. In some embodiments, one or more inversions encompass (completely or partially) or are located in ECOLIN_10330. In some embodiments, one or more inversions encompass (completely or partially) or are located in ECOLIN_10335. In some embodiments, one or more inversions encompass (completely or partially) or are located in ECOLIN_10340. In some embodiments, one or more inversions encompass (completely or partially) or are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase are inverted. In one specific embodiment, a Minor tail protein U, a tail protein, a DNA breaking-rejoining protein, a peptidase S14, a capsid protein, a DNA packaging protein, and a terminase are inverted.

In one embodiment, the inversion is a complete or partial inversion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the inversion is a complete or partial inversion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the inversion is a complete inversion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial inversion of ECOLIN_10175. In one embodiment, the sequence of SEQ ID NO: 130 is inverted from the Phage 3 genome. In one embodiment, a sequence comprising SEQ ID NO: 130 is inverted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Substitutions

In some embodiments, the substitution is in a coding region of the *E. coli* Nissle Phage 3 genome. In some embodiments, the substitution is substituted into a regulatory region of the *E. coli* Nissle Phage 3 genome. In some embodiments, the substitutions comprise one or more antibiotic cassette(s). suitable antibiotic cassettes are known in the art, and non-limiting examples of such antibiotic cassettes are described herein. In some embodiments, the antibiotic is chloramphenicol. In some embodiments, the antibiotic is kanamycin. In some embodiments, the antibiotic is ampicillin. In some embodiments, the antibiotic is chloramphenicol and kanamycin. In some embodiments, the one or more substitutions comprise at least about 1-500 bp. In some embodiments, the one or more substitutions comprise at least about 500-1000 bp. In some embodiments, the one or more substitutions comprise at least about 1000-2000 bp. In some embodiments, the one or more substitutions comprise at least about 1000-2000 bp. In some embodiments, the one or more substitutions comprise at least about 2000-3000 bp. In some embodiments, the one or more substitutions comprise at least about 3000-4000 bp. In some embodiments, the one or more substitutions comprise at least about 4000-5000 bp. In some embodiments, the one or more substitutions comprise at least about 5,000-6,000 bp. In some embodiments, the one or more substitutions comprise at least about 6,000-7,000 bp. In some embodiments, the one or more substitutions comprise at least about 7,000-8,000 bp. In some embodiments, the one or more substitutions comprise at least about 8,000-9,000 bp. In some embodiments, the one or more substitutions comprise at least about 9,000-10,000 bp. In some embodiments, the one or more substitutions comprise at least about 10,000-15,000 bp. In some embodiments, the one or more substitutions comprise at least about 10,000-15,000 bp, at least about 15,000-20,000 bp, at least about 20,000-25,000 bp, at least about 25,000-30,000 bp, at least about 30,000-35,000 bp, at least about 35,000-40,000 bp, at least about 40,000-45,000 bp, at least about 45,000-50,000 bp, at least about 50,000-55,000 bp, at least about 55,000-60,000 bp, at least about 60,000-65,000 bp, at least about 65,000-70,000 bp, at least about 70,000-75,000 bp, at least about 75,000-80,000 bp, at least about 80,000-85,000 bp, at least about 85,000-90,000 bp, at least about 90,000-95,000 bp, at least about 95,000-100,000 bp, at least about 100,000-110,000 bp, at least about 110,000-120,000 bp, at least about 120,000-130,000 bp, at least about 130,000-140,000 bp, at least about 140,000-150, 000 bp, at least about 150,000-200,000 bp, or more than at least about 200,000 bp. In one specific embodiment, 9687 bp are substituted. In some embodiments, the substituted nucleotides are interspersed. In some embodiments, the substituted nucleotides are consecutive.

In some embodiments, the one or more substitutions are located within 1-500 bp of the *E. coli* Nissle Phage 3 genome. In some embodiments, the one or more substitutions are located within 500-1000 bp of the *E. coli* Nissle Phage 3 genome. In some embodiments, the one or more substitutions are located within at least about 1000-2000 bp of the *E. coli* Nissle Phage 3 genome. In some embodiments, the one or more substitutions are located within at least about 1000-2000 bp of the *E. coli* Nissle Phage 3 genome. In some embodiments, the one or more substitutions are located within at least about 2000-3000 bp of the *E. coli* Nissle Phage 3 genome. In some embodiments, the one or more substitutions are located within at least about 3000-4000 bp of the *E. coli* Nissle Phage 3 genome. In some embodiments, the one or more substitutions are located within at least about 4000-5000 bp of the *E. coli* Nissle Phage 3 genome. In some embodiments, the one or more substitutions are located within at least about 5,000-6,000 bp of the *E. coli* Nissle Phage 3 genome. In some embodiments, the one or more substitutions are located within at least about 6,000-7,000 bp of the *E. coli* Nissle Phage 3 genome. In some embodiments, the one or more substitutions are located within at least about 7,000-8,000 bp of the *E. coli* Nissle Phage 3 genome. In some embodiments, the one or more substitutions are located within at least about 8,000-9,000 bp of the *E. coli* Nissle Phage 3 genome. In some embodiments, the one or more substitutions are located within at least about 9,000-10,000 bp of the *E. coli* Nissle Phage 3 genome. In some embodiments, the one or more substitutions are located within at least about 10,000-15,000 bp of the *E. coli* Nissle Phage 3 genome. In some embodiments, the one or more substitutions are located within at least about 10,000-15,000 bp of the *E. coli* Nissle Phage 3 genome, at least about 15,000-20,000 bp of the *E. coli* Nissle Phage 3 genome, at least about 20,000-25,000 bp of the *E. coli* Nissle Phage 3 genome, at least about 25,000-30,000 bp of the *E. coli* Nissle Phage 3 genome, at least about 30,000-35,000 bp of the *E. coli* Nissle Phage 3 genome, at least about 35,000-40,000 bp of the *E. coli* Nissle Phage 3 genome, 40,000-45,000 bp of the *E. coli* Nissle Phage 3 genome, at least about 45,000-50,000 bp of the *E. coli* Nissle Phage 3 genome, at least about 50,000-55,000 bp of the *E. coli* Nissle Phage 3 genome, or at least about 55,000-60,000 bp of the *E. coli* Nissle Phage 3 genome In one specific embodiment, 9687 bp of the *E. coli* Nissle Phage 3 genome are substituted. In some embodiments, the substituted nucleotides are interspersed. In some embodiments, the substituted nucleotides are consecutive.

In some embodiments, the substitutions are located within at least about 0.1 to 1%, at least about 1 to 2%, at least about 2 to 3%, at least about 3 to 4%, at least about 4 to 5%, at least about 5 to 6%, at least about 6 to 7%, at least about 7 to 8%, at least about 8 to 9%, at least about 9 to 10%, at least about 10 to 11%, at least about 11 to 12%, at least about 12 to 13%, at least about 13 to 14%, at least about 14 to 15%, at least about 15 to 16, 16 to 17%, at least about 17 to 18%, at least about 18 to 19%, at least about 19 to 20%, at least about 20 to 21%, at least about 21 to 22%, at least about 22 to 23%, at least about 23 to 24%, at least about 24 to 25%, at least about 25 to 26%, at least about 26 to 27%, at least about 27 to 28%, at least about 28 to 29%, at least about or 29 to 30% of the *E. coli* Nissle Phage 3 genome. In some embodiments, at least about 30-40% of the *E. coli* Nissle Phage 3 genome is substituted. In some embodiments, the substitutions are located within at least about 40-50% of the *E. coli* Nissle Phage 3 genome. In some embodiments, the substitutions are located within at least about 50-60% of the *E. coli* Nissle Phage 3 genome. In some embodiments, the substitutions are located within at least about 60-70% of the *E. coli* Nissle Phage 3 genome. In some embodiments, the substitutions are located within at least about 70-80% of the *E. coli* Nissle Phage 3 genome. In some embodiments, the substitutions are located within at least about 80-90% of the *E. coli* Nissle Phage 3 genome. In some embodiments, the substitutions are located within at least about 90-100% of the *E. coli* Nissle Phage 3 genome.

In some embodiments, at least about 1, 2, 3, 4, 5, 6, 7, 8, 9, 10, 11, 12, 13, 14, 15, 16, 17, 18, 19, or 20 genes comprise substitutions. In some embodiments, at least about 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 genes comprise substitutions. In some embodiments, 13 genes comprise substitutions. In one embodiment, 74 genes comprise substitutions.

In some embodiments, the one or more substitutions are located at the beginning or 5' end of the *E. coli* Nissle Phage 3 genome. In some embodiments, the one or more substitutions are located at the end or 3' end of the *E. coli* Nissle Phage 3 genome. In some embodiments, the one or more substitutions are located in the middle of the *E. coli* Nissle Phage 3 genome. In some embodiments, the *E. coli* Nissle Phage 3 genes are interspersed within the bacterial genome and the substitution are located in one or more of the interspersed positions.

In some embodiments, the region for an optimal substitution, i.e., to achieve a desired effect, can be determined through analysis of homology with other phages is other bacteria. Homologous conserved regions in phages may be suitable for substitution, as these are conserved and may comprise one or more essential genes. In some embodiments, regulatory elements, such as promoters, are substituted. In some embodiments, coding sequences are substituted. In some embodiments, the one or more substituted regions contain one or more genes essential for the lytic cycle.

In some embodiments, the substitutions are located within one or more genes encoding lytic genes. In some embodiments, the substitutions are located within one or more genes encoding one or more proteases or lysins. In some embodiments, the substitutions are located within one or more genes encoding one or more toxins. In some embodiments, the substitutions are located within one or more genes encoding one or more antibiotic resistance related proteins. In some embodiments, the substitutions are located within one or more genes encoding one or phage translation related proteins. In some embodiments, the one or more substitutions are located within one or more genes encoding structural proteins. Such structural genes include genes encoding polypeptides of the head, tail, collar, or coat. In some embodiments, the substitutions are located within one or more genes encoding one or more plate proteins. In some embodiments, the substitutions are located within one or more genes encoding one or more proteins require for assembly of the bacteriophage. In some embodiments, the substitutions are located within one or more genes encoding one or more portal proteins. In some embodiments, the substitutions are located within one or more genes encoding one or more polypeptides involved in recombination. In some embodiments, the substitutions are located within one or more genes encoding one or more integrases. In some embodiments, the substitutions are located within one or more genes encoding one or more invertases. In some embodiments, the substitutions are located within one or more genes encoding one or more transposases. In some embodiments, the substitutions are located with within one or more genes encoding one or more polypeptides involved in replication or translation. In some embodiments, the substitutions are located within one or more genes encoding one or more primases. In some embodiments, the substitutions are located within one or more genes encoding one or more tRNA related proteins. In some embodiments, the substitutions are located within one or more genes encoding one or more polypeptides involved in phage substitution. In some embodiments, the substitutions are located within one or more genes encoding an attachment site. In some embodiments, the substitutions are located within one or more genes encoding one or more polypeptides involved in packaging. In some embodiments, the substitutions are located within one or more genes encoding one or more terminases. In some embodiments, the substitutions are located within one or more genes encoding one or more host genes.

In some embodiments, the substitutions are located within genes encoding one or more polypeptides involved in one or more of cell lysis, phage structure, phage assembly, phage packaging recombination, replication or translation, phage substitution, or are host proteins, and combinations thereof.

In some embodiments, the substitutions are located within genes encoding one or more polypeptides involved in one or more of cell lysis, phage structure, phage assembly, phage packaging recombination, replication or translation, phage substitution, and combinations thereof.

In some embodiments, the substitutions are located within 1 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 3 genes encoding polypeptides involved in cell lysis, phage structure, phage assembly, phage packaging recombination, replication or translation, phage substitution, and combinations thereof. In some embodiments, the substitutions are located within 4 genes encoding polypeptides involved in cell lysis, phage structure, phage assembly, phage packaging recombination, replication or translation, phage substitution, and combinations thereof. In some embodiments, the substitutions are located within 2 genes encoding polypeptides involved in cell lysis, phage structure, phage assembly, phage packaging recombination, replication or translation, phage substitution, and combinations thereof. In some embodiments, the substitutions are located within 5 genes encoding polypeptides involved in cell lysis, phage structure, phage assembly, phage packaging recombination, replication or translation, phage substitution, and combinations thereof. In some embodiments, the substitutions are located within 6 genes encoding polypeptides involved in cell lysis, phage structure, phage assembly, phage packaging recombination, replication or translation, phage substitution, and combinations thereof. In some embodiments, the substitutions are located within 7 genes encoding polypeptides involved in cell lysis, phage structure, phage assembly, phage packaging recombination, replication or translation, phage substitution, and combinations thereof. In some embodiments, the substitutions are located within 8 genes encoding polypeptides involved in cell lysis, phage structure, phage assembly, phage packaging recombination, replication or translation, phage substitution, and combinations thereof. In some embodiments, the substitutions are located within 9 genes encoding polypeptides involved in cell lysis, phage structure, phage assembly, phage packaging recombination, replication or translation, phage substitution, and combinations thereof. In some embodiments, the substitutions are located within 10 genes encoding polypeptides involved in cell lysis, phage structure, phage assembly, phage packaging recombination, replication or translation, phage substitution, and combinations thereof. In some embodiments, the substitutions are located within 11 genes encoding polypeptides involved in cell lysis, phage structure, phage assembly, phage packaging recombination, replication or translation, phage substitution, and combinations thereof. In some embodiments, the substitutions are located within 12 genes encoding polypeptides involved in cell lysis, phage structure, phage assembly, phage packaging recombination, replication or translation, phage substitution, and combinations thereof. In some embodiments, the substitutions are located within 13 genes encoding polypeptides involved in cell lysis, phage structure, phage assembly, phage packaging recombination, replication or translation, phage substitution, and combinations thereof. In some embodiments, the substitutions are located within 14 genes encoding polypeptides involved in cell lysis, phage structure, phage assembly, phage packaging recombination, replication or translation, phage substitution, and combinations thereof. In some embodiments, the substitutions are located within 15 genes encoding polypeptides involved in cell lysis, phage structure, phage assembly, phage packaging recombination, replication or translation, phage substitution, and combinations thereof. In some embodiments, the substitutions are located within at least about 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more genes encoding polypeptides involved in cell lysis, phage structure, phage assembly, phage packaging recombination, replication or translation, phage substitution, and combinations thereof. In some embodiments, the substitutions are located within one or more host proteins within the phage genome.

In any of the embodiments described herein, the substitutions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

In some embodiments, one or more substitutions are located in ECOLIN_09965. In some embodiments, one or more substitutions are located in ECOLIN_09970. In some embodiments, one or more substitutions are located in ECOLIN_09975. In some embodiments, one or more substitutions are located in ECOLIN_09980. In some embodiments, one or more substitutions are located in ECOLIN_09985. In some embodiments, one or more substitutions are located in ECOLIN_09990. In some embodiments, one or more substitutions are located in ECOLIN_09995. In some embodiments, one or more substitutions are located in ECOLIN_10000. In some embodiments, one or more substitutions are located in ECOLIN_10005. In some embodiments, one or more substitutions are located in ECOLIN_10010. In some embodiments, one or more substitutions are located in ECOLIN_10015. In some embodiments, one or more substitutions are located in ECOLIN_10020. In some embodiments, one or more substitutions are located in ECOLIN_10025. In some embodiments, one or more substitutions are located in ECOLIN_10030. In some embodiments, one or more substitutions are located in ECOLIN_10035. In some embodiments, one or more substitutions are located in ECOLIN_10040. In some embodiments, one or more substitutions are located in ECOLIN_10045. In some embodiments, one or more substitutions are located in ECOLIN_10050. In some embodiments, one or more substitutions are located in ECOLIN_10055. In some embodiments, one or more substitutions are located in ECOLIN_10065. In some embodiments, one or more substitutions are located in ECOLIN_10070. In some embodiments, one or more substitutions are located in ECOLIN_10075. In some embodiments, one or more substitutions are located in ECOLIN_10080. In some embodiments, one or more substitutions are located in ECOLIN_10085. In some embodiments, one or more substitutions are located in ECOLIN_10090. In some embodiments, one or more substitutions are located in ECOLIN_10095. In some embodiments, one or more substitutions are located in ECOLIN_10100. In some embodiments, one or more substitutions are located in ECOLIN_10105. In some embodiments, one or more substitutions are located in ECOLIN_10110. In some embodiments, one or more substitutions are located in ECOLIN_10115. In some embodiments, one or more substitutions are located in ECOLIN_10120. In some embodiments, one or more substitutions are located in ECOLIN_10125. In some embodiments, one or more substitutions are located in ECOLIN_10130. In some embodiments, one or more substitutions are located in ECOLIN_10135. In some embodiments, one or more substitutions are located in ECOLIN_10140. In some embodiments, one or more substitutions are located in ECOLIN_10145. In some embodiments, one or more substitutions are located in ECOLIN_10150. In some embodiments, one or more substitutions are located in ECOLIN_10160. In some embodiments, one or more substitutions are located in ECOLIN_10165. In some embodiments, one or more substitutions are located in ECOLIN_10170. In some embodiments, one or more substitutions are located in ECOLIN_10175. In some embodiments, one or more substitutions are located in ECOLIN_10180. In some embodiments, one or more substitutions are located in ECOLIN_10185. In some embodiments, one or more substitutions are located in ECOLIN_10190. In some embodiments, one or more substitutions are located in ECOLIN_10195. In some embodiments, one or more substitutions are located in ECOLIN_10200. In some embodiments, one or more substitutions are located in ECOLIN_10205. In some embodiments, one or more substitutions are located in ECOLIN_10210. In some embodiments, one or more substitutions are located in ECOLIN_10220. In some embodiments, one or more substitutions are located in ECOLIN_10225. In some embodiments, one or more substitutions are located in ECOLIN_10230. In some embodiments, one or more substitutions are located in ECOLIN_10235. In some embodiments, one or more substitutions are located in ECOLIN_10240. In some embodiments, one or more substitutions are located in ECOLIN_10245. In some embodiments, one or more substitutions are located in ECOLIN_10250. In some embodiments, one or more substitutions are located in ECOLIN_10255. In some embodiments, one or more substitutions are located in ECOLIN_10260. In some embodiments, one or more substitutions are located in ECOLIN_10265. In some embodiments, one or more substitutions are located in ECOLIN_10270. In some embodiments, one or more substitutions are located in ECOLIN_10275. In some embodiments, one or more substitutions are located in ECOLIN_10280. In some embodiments, one or more substitutions are located in ECOLIN_10290. In some embodiments, one or more substitutions are located in ECOLIN_10295. In some embodiments, one or more substitutions are located in ECOLIN_10300. In some embodiments, one or more substitutions are located in ECOLIN_10305. In some embodiments, one or more substitutions are located in ECOLIN_10310. In some embodiments, one or more substitutions are located in ECOLIN_10315. In some embodiments, one or more substitutions are located in ECOLIN_10320. In some embodiments, one or more substitutions are located in ECOLIN_10325. In some embodiments, one or more substitutions are located in ECOLIN_10330. In some embodiments, one or more substitutions are located in ECOLIN_10335. In some embodiments, one or more substitutions are located in ECOLIN_10340. In some embodiments, one or more substitutions are located in ECOLIN_10345.

In some embodiments, the mutations are located in or encompass one or more polypeptides selected from lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, and tRNA methyltransferase. In one embodiment, one or more of a Minor tail protein U, a tail protein, a DNA breaking-rejoining protein, a peptidase S14, a capsid protein, a DNA packaging protein, and a terminase contain one or more substitutions. In one specific embodiment, a Minor tail protein U, a tail protein, a DNA breaking-rejoining protein, a peptidase S14, a capsid protein, a DNA packaging protein, and a terminase contain one or more substitutions.

In one embodiment, the substitution is a complete or partial substitution of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the substitution is a complete or partial substitution of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the substitution is a complete substitution of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial substitution of ECOLIN_10175. In one embodiment, the sequence of SEQ ID NO: 130 is substituted from the Phage 3 genome. In one embodiment, a sequence comprising SEQ ID NO: 130 is substituted from the Phage 3 genome.

Regulation of Effector Molecules and Payloads Expression

In some embodiments, the bacterial cell which comprises a mutated endogenous phage further comprises a stably maintained plasmid or chromosome carrying the gene(s) encoding payload (s), such that the payload(s) can be expressed in the host cell, and the host cell is capable of survival and/or growth in vitro, e.g., in medium, and/or in vivo, e.g., in the gutor the tumor microenvironment. In some embodiments, bacterial cell comprises two or more distinct payloads or operons, e.g., two or more payload genes. In some embodiments, bacterial cell comprises three or more distinct transporters or operons, e.g., three or more payload genes. In some embodiments, bacterial cell comprises at least about 4, 5, 6, 7, 8, 9, 10, or more distinct payloads or operons, e.g., at least about 4, 5, 6, 7, 8, 9, 10, or more payload genes.

In one embodiment, the genetically engineered bacteria of the invention comprise a gene encoding a phenylalanine-metabolizing enzyme (PME). In some embodiments, the genetically engineered bacteria comprise a gene encoding a phenylalanine-metabolizing enzyme (PME) and are capable of reducing hyperphenylalaninemia.

Examples of phenylalanine metabolizing enzymes include, but are not limited to, phenylalanine hydroxylase (PAH), phenylalanine ammonia lyase (PAL), aminotransferases, L-amino acid deaminase (LAAD), and phenylalanine dehydrogenases. Reactions with phenylalanine hydroxylases, phenylalanine dehydrogenases or aminotransferases require cofactors, while LAAD and PAL do not require any extra cofactor. Without wishing to be bound by theory, the lack of need for a cofactor means that phenylalanine degradation by the enzyme encoded by the genetically engineered bacteria is dependent on the availability of the substrate and is not limited by the availability of the cofactor.

In some embodiments, the engineered bacteria comprise gene sequence encoding one or more phenylalanine hydroxylase (PAH) polypeptides. In some embodiments, the engineered bacteria comprise gene sequence encoding one or more phenylalanine ammonia lyase (PAL) polypeptides. Phenylalanine ammonia lyase (PAL; EC 4.3.1.24) is an enzyme that catalyzes a reaction converting L-phenylalanine to ammonia and trans-cinnamic acid. Phenylalanine ammonia lyase is specific for L-Phe, and to a lesser extent, L-Tyrosine. The reaction catalyzed by PAL is the spontaneous, non-oxidative deamination of L-phenylalanine to yield trans-cinnamic acid and ammonia. Unlike the mammalian enzyme (PAH), PAL is a monomer and requires no cofactors (MacDonald et al., Biochem Cell Biol 2007; 85:273-82. A modern view of phenylalanine ammonia lyase). In microorganisms, it has a catabolic role, allowing them to utilize L-phenylalanine (L-Phe) as a sole source of carbon and nitrogen. In one embodiment, the genetically engineered bacteria of the invention comprise a PAL gene. PAL is capable of converting phenylalanine to non-toxic levels of transcinnamic acid and ammonia. Trans-cinnamic acid (TCA) can further be converted to TCA metabolites benzoic and hippuric acids (Sarkissian et al., J Mass Spectrom. 2007 June; 42(6):811-7; Quantitation of phenylalanine and its trans-cinnamic, benzoic and hippuric acid metabolites in biological fluids in a single GC-MS analysis). PAL enzyme activity does not require THB cofactor activity.

In some embodiments, PAL is encoded by a PAL gene derived from a bacterial species, including but not limited to, *Achromobacter xylosoxidans, Pseudomonas aeruginosa, Photorhabdus luminescens, Anabaena variabilis*, and *Agrobacterium tumefaciens*. In some embodiments, the bacterial species is *Photorhabdus luminescens*. In some embodiments, the bacterial species is *Anabaena variabilis*. In some embodiments, PAL is encoded by a PAL gene derived from a eukaryotic species, e.g., a yeast species, a plant species. Multiple distinct PAL proteins are known in the art. The genetically engineered bacteria convert more phenylalanine when the PAL gene is expressed than unmodified bacteria of the same bacterial subtype under the same conditions. Thus, the genetically engineered bacteria comprising PAL may be used to metabolize phenylalanine in the body into non-toxic molecules in order to treat conditions associated with hyperphenylalaninemia, including PKU. In some embodiments, the genetically engineered bacteria express *Anabaena variabilis* PAL ("PAL1"). In some embodiments, the genetically engineered bacteria express *Photorhabdus luminescens* PAL ("PAL3"). Non-limiting examples of PAL sequences of interest are shown in Table 2.

In some embodiments, the engineered bacteria comprise gene sequence encoding one or more LAAD polypeptides. In some embodiments, the engineered bacteria comprise gene sequence encoding one or more PAL polypeptides and one or more LAAD polypeptides. LAAD catalyzes the stereospecific oxidative, i.e., oxygen consuming, deamination of L-amino acids to α-keto acids along with the production of ammonia and hydrogen peroxide via an imino acid intermediate. LAADs are found in snake venoms, and in many bacteria (Bifulco et al. 2013), specifically in the cytomembranes of the *Proteus, Providencia*, and *Morgan-*

*ella* bacteria. LAADs (EC 1.4.3.2) are flavoenzymes with a dimeric structure. Each subunit contains a non-covalently-bound flavin adenine dinucleotide (FAD) cofactor) and do not require any external cofactors. *Proteus mirabilis* contains two types of LAADs (Duerre and Chakrabarty 1975). One has broad substrate specificity and catalyzes the oxidation of aliphatic and aromatic L-amino acids to keto acids, typically L-phenylalanine (GenBank: U35383.1) (Baek et al., Journal of Basic Microbiology 2011, 51, 129-135; "Expression and characterization of a second L-amino acid deaminase isolated from *Proteus mirabilis* in *Escherichia coli*"). The other type acts mainly on basic L-amino acids (GenBank: EU669819.1). LAADs from bacterial, fungal, and plant sources appear to be involved in the utilization of L-amino acids (i.e., ammonia produced by the enzymatic activity) as a nitrogen source. Most eukaryotic and prokaryotic L-amino acid deaminases are extracellularly secreted, with the exception of from *Proteus* species LAADs, which are membrane-bound. In *Proteus mirabilis*, LAADs have been reported to be located in the plasma membrane, facing outward into the periplasmic space, in which the enzymatic activity resides (Pelmont J et al., (1972) "L-amino acid oxidases of *Proteus mirabilis*: general properties" Biochimie 54: 1359-1374).

In one embodiment, the genetically engineered bacteria of the invention comprise a LAAD gene. LAAD is capable of converting phenylalanine to non-toxic levels of phenylpyruvate, which can also further be degraded, e.g., by liver enzymes, to phenyllactate. Phenylpyruvate cannot cross the blood brain barrier, which allows LAAD to reduce the levels of phenylalanine in the brain without allowing the accumulation of another potentially toxic metabolite. In some embodiments, LAAD is encoded by a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the genetically engineered bacteria express *Proteus mirabilis* LAAD enzyme GenBank: U35383.1. Non-limiting examples of LAAD sequences of interest are shown in Table 2. In some embodiments, the LAAD enzyme is derived from snake venom. According to the invention, genetically engineered bacteria convert more phenylalanine when the LAAD gene is expressed than unmodified bacteria of the same bacterial subtype under the same conditions. Thus, the genetically engineered bacteria comprising LAAD may be used to metabolize phenylalanine in the body into non-toxic molecules in order to treat conditions associated with hyperphenylalaninemia, including PKU.

In some embodiments, the genetically engineered bacteria encode a wild type enzyme as it occurs in nature. In some embodiments, the genetically engineered bacteria encode an enzyme which comprises mutations relative to the wild type sequence. In some embodiments, the mutations increase stability of the enzyme. In some embodiments, the mutations increase the catalytic activity of the enzyme. In some embodiments, the genetically engineered bacteria comprise a gene encoding one or more of the proteins listed in Table 2. In some embodiments, the genetically engineered bacteria comprise gene sequence(s) encoding one or more of the polypeptides comprising sequence of any of SEQ ID Nos: 1-8. In some embodiments, the genetically engineered bacteria comprise gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 1-8. In some embodiments, the genetically engineered bacteria encode one or more enzymes from Table 2, which comprise a mutation. In some embodiments, the genetically engineered bacteria comprise a gene encoding wild type PAH. In some embodiments, the genetically engineered bacteria encode a mutated PAH with increased stability and/or activity. In some embodiments, the genetically engineered bacteria comprise a gene encoding wild type PAL. In some embodiments, the genetically engineered bacteria encode a mutated PAL with increased stability and/or activity. In some embodiments, the genetically engineered bacteria comprise a gene encoding wild type LAAD. In some embodiments, the genetically engineered bacteria encode a mutated LAAD with increased stability and/or activity. Methods for screening for enzymes with desirable properties are known in the art and described herein.

TABLE 2

Sequences of Phenylalanine Metabolizing Enzymes

| Description | Sequence | SEQ ID NO |
|---|---|---|
| Phenylalanine ammonia-lyase (*Anabaena variabilis*) Acc. No.: Q3M5Z3.1 | MKTLSQAQSKTSSQQFSFTGNSSANVIIGNQKLTINDVA<br>RVARNGTLVSLTNNTDILQGIQASCDYINNAVESGEPIY<br>GVTSGFGGMANVAISREQASELQTNLVWFLKTGAGNKL<br>PLADVRAAMLLRANSHMRGASGIRLELIKRMEIFLNAG<br>VTPYVYEFGSIGASGDLVPLSYITGSLIGLDPSFKVDFNG<br>KEMDAPTALRQLNLSPLTLLPKEGLAMMNGTSVMTGIA<br>ANCVYDTQILTAIAMGVHALDIQALNGTNQSFHPFIHNS<br>KPHPGQLWAADQMISLLANSQLVRDELDGKHDYRDHE<br>LIQDRYSLRCLPQYLGPIVDGISQIAKQIEIEINSVTDNPLI<br>DVDNQASYHGGNFLGQYVGMGMDHLRYYIGLLAKHL<br>DVQIALLASPEFSNGLPPSLLGNRERKVNMGLKGLQICG<br>NSIMPLLTFYGNSIADRFPTHAEQFNQNINSQGYTSATLA<br>RRSVDIFQNYVAIALMFGVQAVDLRTYKKTGHYDARA<br>CLSPATERLYSAVRHVVGQKPTSDRPYIWNDNEQGLDE<br>HIARISADIAAGGVIVQAVQDILPCLH | SEQ ID NO: 1 |
| histidine ammonia-lyase [*Anabaena variabilis* ATCC 29413] | MKTLSQAQSKTSSQQFSFTGNSSANVIIGNQKLTINDVA<br>RVARNGTLVSLTNNTDILQGIQASCDYINNAVESGEPIY<br>GVTSGFGGMANVAISREQASELQTNLVWFLKTGAGNKL<br>PLADVRAAMLLRANSHMRGASGIRLELIKRMEIFLNAG<br>VTPYVYEFGSIGASGDLVPLSYITGSLIGLDPSFKVDFNG<br>KEMDAPTALRQLNLSPLTLLPKEGLAMMNGTSVMTGIA | SEQ ID NO: 2 |

TABLE 2-continued

Sequences of Phenylalanine Metabolizing Enzymes

| Description | Sequence | SEQ ID NO |
|---|---|---|
| (Acc. NO:<br>ABA23593.1) | ANCVYDTQILTAIAMGVHALDIQALNGTNQSFHPFIHNS<br>KPHPGQLWAADQMISLLANSQLVRDELDGKHDYRDHE<br>LIQDRYSLRCLPQYLGPIVDGISQIAKQIEIEINSVTDNPLI<br>DVDNQASYHGGNFLGQYVGMGMDHLRYYIGLLAKHL<br>DVQIALLASPEFSNGLPPSLLGNRERKVNMGLKGLQICG<br>NSIMPLLTFYGNSIADRFPTHAEQFNQNINSQGYTSATLA<br>RRSVDIFQNYVAIALMFGVQAVDLRTYKKTGHYDARA<br>CLSPATERLYSAVRHVVGQKPTSDRPYIWNDNEQGLDE<br>HIARISADIAAGGVIVQAVQDILPCLH | |
| histidine<br>ammonia-<br>lyase<br>[*Photorhabdus*<br>*luminescens*]<br>(WP_011146484) | MKAKDVQPTIIINKNGLISLEDIYDIAIKQKKVEISTEITEL<br>LTHGREKLEEKLNSGEVIYGINTGFGGNANLVVPFEKIA<br>EHQQNLLTFLSAGTGDYMSKPCIKASQFTMLLSVCKGW<br>SATRPIVAQAIVDHINHDIVPLVPRYGSVGASGDLIPLSYI<br>ARALCGIGKVYYMGAEIDAAEAIKRAGLTPLSLKAKEG<br>LALINGTRVMSGISAITVIKLEKLFKASISAIALAVEALLA<br>SHEHYDARIQQVKNHPGQNAVASALRNLLAGSTQVNLL<br>SGVKEQANKACRHQEITQLNDTLQEVYSIRCAPQVLGIV<br>PESLATARKILEREVISANDNPLIDPENGDVLHGGNFMG<br>QYVARTMDALKLDIALIANHLHAIVALMMDNRFSRGLP<br>NSLSPTPGMYQGFKGVQLSQTALVAAIRHDCAASGIHTL<br>ATEQYNQDIVSLGLHAAQDVLEMEQKLRNIVSMTILVV<br>CQAIHLRGNISEIAPETAKFYHAVREISSPLITDRALDEDII<br>RIADAIINDQLPLPEIMLEE | SEQ ID<br>NO: 3 |
| Histidine<br>ammonia<br>lyase<br>(*Photorhabdus*<br>*luminescens*)<br>Acc. NO:<br>CAE15566 | MKQLTIYPGKLTLDELRQVYLQPVKITLDSQIFPAIERSV<br>ECVNAILAENRTAYGINTGFGLLASTRIEEDNLEKLQRSL<br>VVSHAAGVGKALDDNMTRLIMVLKINSLSRGYSGIRLA<br>VIQALIALVNAEIYPHIPCKGSVGASGDLAPLAHMSLLLL<br>GEGQARYQGEWLPAKEALAKANLQPITLAAKEGLALLN<br>GTQVSTAFALRGLFEAEDLLAAAIVCGSLSVEAALGSRK<br>PFDARVHVVRGQQGQIDVAALYRHVLEESSELSDSHINC<br>PKVQDPYSLRCQPQVMGACLTQLRHAADVILTEANAVS<br>DNPLVFAEQGEVISGGNFHAEPVAMASDNLALVLAEIG<br>ALSERRIALLMDSHMSQLPPFLVENGGVNSGFMIAQVTA<br>AALASENKALAHPASVDSLPTSANQEDHVSMAPAAGRR<br>LWEMAENTRGILAIEWLSACQGIDFRNGLKSSPILEEAR<br>VILRAKVDYYDQDRFFAPDIDAAVKLLAEQHLSSLLPSG<br>QILQRKNNR | SEQ ID<br>NO: 4 |
| amino acid<br>deaminase<br>(*Proteus*<br>*mirabilis*)<br>Acc. No:<br>ACD36582 | MAISRRKFILGGTVVAVAAGAGVLTPMLTREGRFVPGT<br>PRHGFVEGTGGPLPKQDDVVVIGAGILGIMTAINLAERG<br>LSVTIVEKGNIAGEQSSRFYGQAISYKMPDETFLLHHLG<br>KHRWREMNAKVGIDTTYRTQGRVEVPLDEEDLENVRK<br>WIDAKSKDVGSDIPFRTKMIEGAELKQRLRGATTDWKI<br>AGFEEDSGSFDPEVATFVMAEYAKKMGIKIFTNCAARG<br>LETQAGVISDVVTEKGPIKTSRVVVAGGVGSRLFMQNL<br>NVDVPTLPAYQSQQLISAAPNAPGGNVALPGGIFFRDQA<br>DGTYATSPRVIVAPVVKESFTYGYKYLPLLALPDFPVHIS<br>LNEQLINSFMQSTHWDLNEESPFEKYRDMTALPDLPELN<br>ASLEKLKKEFPAFKESTLIDQWSGAMAIAPDENPIISDVK<br>EYPGLVINTATGWGMTESPVSAEITADLLLGKKPVLDAK<br>PFSLYRF | SEQ ID<br>NO: 5 |
| amino acid<br>deaminase<br>[*Proteus*<br>*mirabilis*<br>HI4320])<br>Acc. No.:<br>AAA86752.1 | MNISRRKLLLGVGAAGVLAGGAALVPMVRRDGKFVEA<br>KSRASFVEGTQGALPKEADVVIIGAGIQGIMTAINLAERG<br>MSVTILEKGQIAGEQSGRAYSQIISYQTSPEIFPLHHYGKI<br>LWRGMNEKIGADTSYRTQGRVEALADEKALDKAQAWI<br>KTAKEAAGFDTPLNTRIIKGEELSNRLVGAQTPWTVAAF<br>EEDSGSVDPETGTPALARYAKQIGVKIYTNCAVRGIETA<br>GGKISDVVSEKGAIKTSQVVLAGGIWSRLFMGNMGIDIP<br>TLNVYLSQQRVSGVPGAPRGNVHLPNGIHFREQADGTY<br>AVAPRIFTSSIVKDSFLLGPKFMHLLGGGELPLEFSIGEDL<br>FNSFKMPTSWNLDEKTPFEQFRVATATQNTQHLDAVFQ<br>RMKTEFPVFEKSEVVERWGAVVSPTFDELPIISEVKEYP<br>GLVINTATVWGMTEGPAAGEVTADIVMGKKPVIDPTPF<br>SLDRFKK | SEQ ID<br>NO: 6 |
| LAAD from<br>*Proteus*<br>*vulgaris*;<br>(Acc. NO:<br>BAA90864) | MAISRRKFIIGGTVVAVAAGAGILTPMLTREGRFVPGTP<br>RHGFVEGTEGALPKQADVVVVGAGILGIMTAINLVERG<br>LSVVIVEKGNIAGEQSSRFYGQAISYKMPDETFLLHHLG<br>KHRWREMNAKVGIDTTYRTQGRVEVPLDEEDLVNVRK<br>WIDERSKNVGSDIPFKTRIIEGAELNQRLRGATTDWKIAG<br>FEEDSGSFDPEVATFVMAEYAKKMGVRIYTQCAARGLE<br>TQAGVISDVVTEKGAIKTSQVVVAGGVWSRLFMQNLN | SEQ ID<br>NO: 7 |

TABLE 2-continued

| Sequences of Phenylalanine Metabolizing Enzymes | | |
|---|---|---|
| Description | Sequence | SEQ ID NO |
| | VDVPTLPAYQSQQLISGSPTAPGGNVALPGGIFFREQAD GTYATSPRVIVAPVVKESFTYGYKYLPLLALPDFPVHISL NEQLINSFMQSTHWNLDEVSPFEQFRNMTALPDLPELNA SLEKLKAEFPAFKESKLIDQWSGAMAIAPDENPIISEVKE YPGLVINTATGWGMTESPVSAELTADLLLGKKPVLDPK PFSLYRF | |
| Phenylalanine hydroxylase [*Homo sapiens*] (Acc. No. AAH26251] | MSTAVLENPGLGRKLSDFGQETSYIEDNCNQNGAISLIFS LKEEVGALAKVLRLFEENDVNLTHIESRPSRLKKDEYEF FTHLDKRSLPALTNIIKILRHDIGATVHELSRDKKKDTVP WFPRTIQELDRFANQILSYGAELDADHPGFKDPVYRARR KQFADIAYNYRHGQPIPRVEYMEEGKKTWGTVFKTLKS LYKTHACYEYNHIFPLLEKYCGFHEDNIPQLEDVSQFLQ TCTGFRLRPVAGLLSSRDFLGGLAFRVFHCTQYIRHGSK PMYTPEPDICHELLGHVPLFSDRSFAQFSQEIGLASLGAP DEYIEKLATIYWFTVEFGLCKQGDSIKAYGAGLLSSFGE LQYCLSEKPKLLPLELEKTAIQNYTVTEFQPLYYVAESF NDAKEKVRNFAATIPRPFSVRYDPYTQRIEVLDNTQQLK ILADSINSEIGILCSALQKIK | SEQ ID NO: 8 |

The PME, e.g., PAL, LAAD, or PAH, gene(s) may be present on a plasmid or chromosome in the genetically engineered bacteria. In some embodiments, the PME gene sequence(s) are expressed under the control of one or more constitutive promoter(s). In some embodiments, the PME gene is expressed under the control of a promoter that is directly or indirectly induced by exogenous environmental conditions, as described herein. In some embodiments, the PME gene is expressed under the control of a promoter that is directly or indirectly induced by exogenous environmental conditions, such as in the presence of molecules or metabolites specific to the gut of a mammal. In one embodiment, the PME gene is expressed under the control of a promoter that is directly or indirectly induced by low-oxygen, microaerobic, or anaerobic conditions, wherein expression of the PME gene, e.g., the PAL gene, is activated under low-oxygen or anaerobic environments, such as the environment of the mammalian gut.

In some embodiments, the genetically engineered bacteria comprise gene sequence encoding one or more PAL polypeptide sequence(s). In some embodiments, the engineered bacteria comprise gene sequence encoding one or more PAL polypeptide sequence(s) in which the gene sequence(s) is directly or indirectly induced by low-oxygen or anaerobic conditions, such as the mammalian gut. In some embodiments, the engineered bacteria comprise gene sequence encoding one or more LAAD polypeptides. In some embodiments, the engineered bacteria comprise gene sequence encoding one or more LAAD polypeptides, in which the gene sequence(s) is directly or indirectly induced by oxygenated, low oxygen, or microaerobic conditions, such as conditions found in the proximal intestine, including but not limited to the stomach, duodenum, and ileum. In other embodiments, the engineered bacteria comprise gene sequence(s) encoding one or more PME polypeptide sequences(s) in which the gene sequene(s) is directly or indirectly induced by an environmental factor that is naturally present in a mammalian gut. In other embodiments, the genetically engineered bacteria encode one or more PME gene sequences(s) which are directly or indirectly induced by an environmental factor that is not naturally present in a mammalian gut, e.g., arabinose or IPTG. In other embodiments, the genetically engineered bacteria encode one or more PME gene sequences(s) which are directly or indirectly induced by an environmental factor that is naturally present in a mammalian gut under inflammatory conditions. In some embodiments, the engineered bacteria comprise gene sequence(s) encoding one or more PAL polypeptides and gene sequence(s) encoding one or more LAAD polypeptides in which the gene sequences are under the control of the same promoter or a different copy of the same promoter, which is directly or indirectly induced by exogenous environmental conditions, such as any of the environmental conditions discussed herein and such as any of the promoters discussed herein. In some embodiments, the engineered bacteria comprise gene sequence(s) encoding one or more PAL polypeptides and gene sequence(s) encoding one or more LAAD polypeptides in which the gene sequences are under the control of a different promoter, which is directly or indirectly induced by exogenous environmental conditions, such as any of the environmental conditions discussed herein and such as any of the promoters discussed herein. In some embodiments, the engineered bacteria comprise gene sequence(s) encoding one or more PAL polypeptides and gene sequence(s) encoding one or more LAAD polypeptides in which the gene sequences are under the control of a constitutive promoter. In some embodiments, the engineered bacteria comprise gene sequence(s) encoding one or more PAL polypeptides and gene sequence(s) encoding one or more LAAD polypeptides in which the PAL gene sequences are under the control of a constitutive promoter and the LAAD gene sequence(s) are under the control of an inducible promoter. In some embodiments, the engineered bacteria comprise gene sequence(s) encoding one or more PAL polypeptides and gene sequence(s) encoding one or more LAAD polypeptides in which the LAAD gene sequences are under the control of a constitutive promoter and the PAL gene sequence(s) are under the control of an inducible promoter. In any of these embodiments, the bacteria may further comprise gene sequence encoding one or more Phe transporter polypeptides, which gene sequence(s) may be under the control of a constitutive or inducible promoter and may be the same or different promoter from the promoter controlling the Pal and/or LAAD gene sequence(s).

In other embodiments, the engineered bacteria encode one or more PME gene sequence(s) which are directly or indirectly induced prior to in vivo administration during bacterial cell culture; i.e., one or more PME gene sequence(s) are expressed under the control of an inducible promoter that is responsive to specific molecules or metabolites, temperature, oxygen levels or other parameters provided in the culture of the bacterium as it is grown in a flask, fermenter, or other culture vessel. In some embodiments, the engineered bacteria encode one or more PME gene sequence(s) which are directly or indirectly induced prior to in vivo administration during bacterial cell culture; wherein the one or more PME gene sequence(s) are expressed under low oxygen or anaerobic conditions. In some embodiments, the engineered bacteria encode one or more PME gene sequence(s) which are directly or indirectly induced prior to in vivo administration during bacterial cell culture; wherein the one or more PME gene sequence(s) are expressed under aerobic conditions. In some embodiments, the engineered bacteria encode one or more PME gene sequence(s) which are directly or indirectly induced prior to in vivo administration during bacterial cell culture; wherein the one or more PME gene sequence(s) are expressed under microaerobic conditions. In some embodiments, the engineered bacteria encode one or more PME gene sequence(s) which are directly or indirectly induced prior to in vivo administration during bacterial cell culture; wherein the one or more PME gene sequence(s) are expressed in the presence of arabinose. In some embodiments, the engineered bacteria encode one or more PME gene sequence(s) which are directly or indirectly induced prior to in vivo administration during bacterial cell culture; wherein the one or more PME gene sequence(s) are expressed in the presence of IPTG.

Payload (and/or polypeptides of interest and/or proteins of interest and/or therapeutic polypeptides and/or therapeutic proteins and/or therapeutic peptides and/or effector and/or effector molecules) include any of the metabolites described herein and/or any of the enzyme(s) or polypeptide(s) which function as enzymes for the production or catabolism of such effector molecules. Effector molecules and payloads include but are not limited to anti-cancer molecules, immune modulators, gut barrier enhancer molecules, anti-inflammatory molecules, satiety molecules or neuromodulatory effectors. Non-limiting examples of payloads are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

As used herein, the term "gene of interest" or "gene sequence of interest" includes any or a plurality of any of the gene(s) an/or gene sequence(s) and or gene cassette(s) encoding one or more effector molecules and payloads include but are not limited to anti-cancer molecules, immune modulators, gut barrier enhancer molecules, anti-inflammatory molecules, satiety molecules or effectors, neuromodulatory molecules described herein, e.g., kynureninase, tryptophan production enzymes, tryptophan degradation enzymes, one or more kynurenine production enzymes, serotonin or melatonin production or degradation enzymes, indole metabolite production or degradation enzymes (described herein) KP metabolite production or degradation enzymes. Non-limiting examples of additional genes of interest are described in Non-limiting examples of payloads are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

In some embodiments, the genetically engineered bacteria comprise multiple copies of the same payload gene(s). In some embodiments, the gene encoding the payload is present on a plasmid and operably linked to a directly or indirectly inducible promoter. In some embodiments, the gene encoding the payload is present on a plasmid and operably linked to a constitutive promoter. In some embodiments, the gene encoding the payload is present on a plasmid and operably linked to a promoter that is induced under low-oxygen or anaerobic conditions. In some embodiments, the gene encoding the payload is present on plasmid and operably linked to a promoter that is induced by exposure to tetracycline or arabinose, or another chemical or nutritional inducer described herein.

In some embodiments, the gene encoding the payload is present on a chromosome and operably linked to a directly or indirectly inducible promoter. In some embodiments, the gene encoding the payload is present on a chromosome and operably linked to a constitutive promoter. In some embodiments, the gene encoding the payload is present in the chromosome and operably linked to a promoter that is induced under low-oxygen or anaerobic conditions. In some embodiments, the gene encoding the payload is present on chromosome and operably linked to a promoter that is induced by exposure to tetracycline or arabinose, or another chemical or nutritional inducer described herein.

In some embodiments, the genetically engineered bacteria comprise two or more payloads, all of which are present on the chromosome. In some embodiments, the genetically engineered bacteria comprise two or more payloads, all of which are present on one or more same or different plasmids. In some embodiments, the genetically engineered bacteria comprise two or more payloads, some of which are present on the chromosome and some of which are present on one or more same or different plasmids.

In any of the nucleic acid embodiments, described above, the one or more payload(s) for producing a polypeptide of interest combinations are operably linked to one or more directly or indirectly inducible promoter(s). In some embodiments, the one or more payload(s) are operably linked to a directly or indirectly inducible promoter that is induced under exogeneous environmental conditions, e.g., conditions found in the gut, the tumor microenvironment, or other tissue specific conditions. In some embodiments, the one or more payload(s) are operably linked to a directly or indirectly inducible promoter that is induced by metabolites found in the gut, the tumor microenvironment, or other specific conditions. In some embodiments, the one or more payload(s) are operably linked to a directly or indirectly inducible promoter that is induced under low-oxygen or anaerobic conditions. In some embodiments, the one or more payload(s) are operably linked to a directly or indirectly inducible promoter that is induced under inflammatory conditions (e.g., RNS, ROS), as described herein. In some embodiments, the one or more payload(s) are operably linked to a directly or indirectly inducible promoter that is induced under immunosuppressive conditions, e.g., as found in the tumor, or other specific tissues, as described herein. In some embodiments, the two or more gene sequence(s) are linked to a directly or indirectly inducible promoter that is induced by exposure a chemical or nutritional inducer, which may or may not be present under in vivo conditions and which may be present during in vitro conditions (such as strain culture, expansion, manufacture), such as tetracycline or arabinose, or others described herein. In some embodiments, the two or more payloads are all linked to a constitutive promoter.

In a non-limiting example, the genetically engineered bacteria may comprise two payloads, one of which is linked to a constitutive promoter, and one of which is linked to a directly or indirectly inducible promoter. In a non-limiting example, the genetically engineered bacteria may comprise three payloads, one of which is linked to a constitutive promoter, and one of which is linked to a directly or indirectly inducible promoter and one of which is linked to a second, different directly or indirectly inducible promoter.

In some embodiments, the promoter is induced under in vivo conditions, e.g., the gut, as described herein. In some embodiments, the promoters are induced under in vitro conditions, e.g., various cell culture and/or cell manufacturing conditions, as described herein. In some embodiments, the promoter is induced under in vivo conditions, e.g., the gut, as described herein, and under in vitro conditions, e.g., various cell culture and/or cell production and/or manufacturing conditions, as described herein.

In some embodiments, the promoter that is operably linked to the gene encoding the payload is directly induced by exogenous environmental conditions (e.g., in vivo and/or in vitro and/or production/manufacturing conditions). In some embodiments, the promoter that is operably linked to the gene encoding the payload is indirectly induced by exogenous environmental conditions (e.g., in vivo and/or in vitro and/or production/manufacturing conditions).

In some embodiments, the promoter is directly or indirectly induced by exogenous environmental conditions specific to the gut of a mammal. In some embodiments, the promoter is directly or indirectly induced by exogenous environmental conditions specific to the hypoxic environment of a tumor and/or the small intestine of a mammal. In some embodiments, the promoter is directly or indirectly induced by low-oxygen or anaerobic conditions such as the hypoxic environment of a tumor and/or the environment of the mammalian gut. In some embodiments, the promoter is directly or indirectly induced by molecules or metabolites that are specific to the tumor, a particular tissue, or the gut of a mammal. In some embodiments, the promoter is directly or indirectly induced by a molecule that is co-administered with the bacterial cell.

FNR Dependent Regulation

The genetically engineered bacteria of the invention comprise a gene or gene cassette for producing a polypeptide of interest, wherein the gene or gene cassette is operably linked to a directly or indirectly inducible promoter that is controlled by exogenous environmental condition(s). In some embodiments, the inducible promoter is an oxygen level-dependent promoter and a polypeptide of interest is expressed in low-oxygen, microaerobic, or anaerobic conditions. For example, in low oxygen conditions, the oxygen level-dependent promoter is activated by a corresponding oxygen level-sensing transcription factor, thereby driving production of the polypeptide of interest.

Bacteria have evolved transcription factors that are capable of sensing oxygen levels. Different signaling pathways may be triggered by different oxygen levels and occur with different kinetics. An oxygen level-dependent promoter is a nucleic acid sequence to which one or more oxygen level-sensing transcription factors is capable of binding, wherein the binding and/or activation of the corresponding transcription factor activates downstream gene expression. In one embodiment, the genetically engineered bacteria comprise a gene or gene cassette for producing a payload under the control of an oxygen level-dependent promoter. In a more specific aspect, the genetically engineered bacteria comprise a gene or gene cassette for producing a payload under the control of an oxygen level-dependent promoter that is activated under low-oxygen or anaerobic environments, such as the hypoxic environment of a tumor and/or the environment of the mammalian gut, and/or other specific tissues.

In certain embodiments, the bacterial cell comprises a gene encoding a payload expressed under the control of a fumarate and nitrate reductase regulator (FNR) responsive promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. FNR responsive promoters include, but are not limited to, the FNR responsive promoters listed in Table 3 below. Underlined sequences are predicted ribosome binding sites, and bolded sequences are restriction sites used for cloning.

TABLE 3

FNR Promoter Sequences

| FNR Responsive Promoter | Sequence |
|---|---|
| SEQ ID NO: 1A | GTCAGCATAACACCCTGACCTCTCATTAATTGTTCATGCCGGGCG<br>GCACTATCGTCGTCCGGCCTTTTCCTCTCTTACTCTGCTACGTAC<br>ATCTATTTCTATAAATCCGTTCAATTTGTCTGTTTTTTGCACAAAC<br>ATGAAATATCAGACAATTCCGTGACTTAAGAAAATTTATACAAA<br>TCAGCAATATACCCCTTAAGGAGTATATAAAGGTGAATTTGATT<br>TACATCAATAAGCGGGGTTGCTGAATCGTTAAGGTAGGCGGTAA<br>TAG<u>AAAAGAAATCGAGGCAAAA</u> |
| SEQ ID NO: 2A | ATTTCCTCTCATCCCATCCGGGGTGAGAGTCTTTTCCCCCGACTT<br>ATGGCTCATGCATGCATCAAAAAAGATGTGAGCTTGATCAAAAA<br>CAAAAAATATTTCACTCGACAGGAGTATTTATATTGCGCCCGTT<br>ACGTGGGCTTCGACTGTAAATC<u>AGAAAGGAGAAAACACCT</u> |

TABLE 3-continued

FNR Promoter Sequences

| FNR Responsive Promoter | Sequence |
|---|---|
| SEQ ID NO: 3A | GTCAGCATAACACCCTGACCTCTCATTAATTGTTCATGCCGGGCG<br>GCACTATCGTCGTCCGGCCTTTTCCTCTCTTACTCTGCTACGTAC<br>ATCTATTTCTATAAATCCGTTCAATTTGTCTGTTTTTTGCACAAAC<br>ATGAAATATCAGACAATTCCGTGACTTAAGAAAATTTATACAAA<br>TCAGCAATATACCCCTTAAGGAGTATATAAAGGTGAATTTGATT<br>TACATCAATAAGCGGGGTTGCTGAATCGTTAA**GGATCC**CTCTAG<br>AAATAATTTTGTTTAACTTTAAGAAGGAGATATACAT |
| SEQ ID NO: 4A | CATTTCCTCTCATCCCATCCGGGGTGAGAGTCTTTTCCCCCGACT<br>TATGGCTCATGCATGCATCAAAAAAGATGTGAGCTTGATCAAAA<br>ACAAAAAATATTTCACTCGACAGGAGTATTTATATTGCGCCC**GG**<br>**ATCC**CTCTAGAAATAATTTTGTTTAACTTTAAGAAGGAGATATA<br>CAT |
| SEQ ID NO: 5A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGTAAAGTTTGAGCGAAGTCAATAAACTCTCTACCCATTC<br>AGGGCAATATCTCTCTT**GGATCC**CTCTAGAAATAATTTTGTTTA<br>ACTTTAAGAAGGAGATATACAT |
| SEQ ID NO: 6A | ATCCCCATCACTCTTGATGGAGATCAATTCCCCAAGCTGCTAGAG<br>CGTTACCTTGCCCTTAAACATTAGCAATGTCGATTTATCAGAGGG<br>CCGACAGGCTCCCACAGGAGAAAACCG |
| SEQ ID NO: 7A | CTCTTGATCGTTATCAATTCCCACGCTGTTTCAGAGCGTTACCTT<br>GCCCTTAAACATTAGCAATGTCGATTTATCAGAGGGCCGACAGG<br>CTCCCACAGGAGAAAACCG |
| nirB1<br>SEQ ID NO: 8A | GTCAGCATAACACCCTGACCTCTCATTAATTGTTCATGCCGGGCG<br>GCACTATCGTCGTCCGGCCTTTTCCTCTCTTACTCTGCTACGTACA<br>TCTATTTCTATAAATCCGTTCAATTTGTCTGTTTTTTGCACAAACA<br>TGAAATATCAGACAATTCCGTGACTTAAGAAAATTTATACAAAT<br>CAGCAATATACCCCTTAAGGAGTATATAAAGGTGAATTTGATTT<br>ACATCAATAAGCGGGGTTGCTGAATCGTTAAGGTAGGCGGTAAT<br>AGAAAAGAAATCGAGGCAAAA |
| nirB2<br>SEQ ID NO: 9A | CGGCCCGATCGTTGAACATAGCGGTCCGCAGGCGGCACTGCTTA<br>CAGCAAACGGTCTGTACGCTGTCGTCTTTGTGATGTGCTTCCTGT<br>TAGGTTTCGTCAGCCGTCACCGTCAGCATAACACCCTGACCTCTC<br>ATTAATTGCTCATGCCGGACGGCACTATCGTCGTCCGGCCTTTTC<br>CTCTCTTCCCCCGCTACGTGCATCTATTTCTATAAACCCGCTCATT<br>TTGTCTATTTTTTGCACAAACATGAAATATCAGACAATTCCGTGA<br>CTTAAGAAAATTTATACAAATCAGCAATATACCCATTAAGGAGT<br>ATATAAAGGTGAATTTGATTTACATCAATAAGCGGGGTTGCTGA<br>ATCGTTAAGGTAGGCGGTAATAGAAAAGAAATCGAGGCAAAAat<br>gtttgtttaactttaagaaggagatatacat |
| nirB3<br>SEQ ID NO: 10A | GTCAGCATAACACCCTGACCTCTCATTAATTGCTCATGCCGGACG<br>GCACTATCGTCGTCCGGCCTTTTCCTCTCTTCCCCCGCTACGTGC<br>ATCTATTTCTATAAACCCGCTCATTTTGTCTATTTTTTGCACAAAC<br>ATGAAATATCAGACAATTCCGTGACTTAAGAAAATTTATACAAA<br>TCAGCAATATACCCATTAAGGAGTATATAAAGGTGAATTTGATT<br>TACATCAATAAGCGGGGTTGCTGAATCGTTAAGGTAGGCGGTAA<br>TAGAAAAGAAATCGAGGCAAAA |
| ydfZ<br>SEQ ID NO: 11A | ATTTCCTCTCATCCCATCCGGGGTGAGAGTCTTTTCCCCCGACTT<br>ATGGCTCATGCATGCATCAAAAAAGATGTGAGCTTGATCAAAAA<br>CAAAAAATATTTCACTCGACAGGAGTATTTATATTGCGCCCGTTA<br>CGTGGGCTTCGACTGTAAATCAGAAAGGAGAAAACACCT |
| nirB + RBS<br>SEQ ID NO: 12A | GTCAGCATAACACCCTGACCTCTCATTAATTGTTCATGCCGGGCG<br>GCACTATCGTCGTCCGGCCTTTTCCTCTCTTACTCTGCTACGTACA<br>TCTATTTCTATAAATCCGTTCAATTTGTCTGTTTTTTGCACAAACA<br>TGAAATATCAGACAATTCCGTGACTTAAGAAAATTTATACAAAT<br>CAGCAATATACCCCTTAAGGAGTATATAAAGGTGAATTTGATTT<br>ACATCAATAAGCGGGGTTGCTGAATCGTTAA**GGATCC**CTCTAGA<br>AATAATTTTGTTTAACTTTAAGAAGGAGATATACAT |
| ydfZ + RBS<br>SEQ ID NO: 13A | CATTTCCTCTCATCCCATCCGGGGTGAGAGTCTTTTCCCCCGACT<br>TATGGCTCATGCATGCATCAAAAAAGATGTGAGCTTGATCAAAA<br>ACAAAAAATATTTCACTCGACAGGAGTATTTATATTGCGCCC**GG**<br>**ATCC**CTCTAGAAATAATTTTGTTTAACTTTAAGAAGGAGATATA<br>CAT |

TABLE 3-continued

| FNR Promoter Sequences | |
|---|---|
| FNR Responsive Promoter | Sequence |
| fnrS1<br>SEQ ID NO: 14A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGTAAAGTTTGAGCGAAGTCAATAAACTCTCTACCCATTC<br>AGGGCAATATCTCTCTT**GGATCC**CTCTAGAAATAATTTTGTTTAA<br>CTTTAAGAAGGAGATATACAT |
| fnrS2<br>SEQ ID NO: 15A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGCAAAGTTTGAGCGAAGTCAATAAACTCTCTACCCATTC<br>AGGGCAATATCTCTCTTGGATCCAAAGTGAACTCTAGAAATAAT<br>TTTGTTTAACTTTAAGAAGGAGATATACAT |
| nirB + crp<br>SEQ ID NO: 16A | TCGTCTTTGTGATGTGCTTCCTGTTAGGTTTCGTCAGCCGTCACC<br>GTCAGCATAACACCCTGACCTCTCATTAATTGCTCATGCCGGACG<br>GCACTATCGTCGTCCGGCCTTTTCCTCTCTTCCCCCGCTACGTGC<br>ATCTATTTCTATAAACCCGCTCATTTTGTCTATTTTTTGCACAAAC<br>ATGAAATATCAGACAATTCCGTGACTTAAGAAAATTTATACAAA<br>TCAGCAATATACCCATTAAGGAGTATATAAAGGTGAATTTGATT<br>TACATCAATAAGCGGGGTTGCTGAATCGTTAAGGTAGaaatgtgatcta<br>gttcacatttGCGGTAATAGAAAAGAAATCGAGGCAAAA*atgtttgtttaacttta*<br>*agaaggagatatacat* |
| fnrS + crp<br>SEQ ID NO: 17A | AGTTGTTCTTATTGGTGGTGTTGCTTTATGGTTGCATCGTAGTAA<br>ATGGTTGTAACAAAAGCAATTTTTCCGGCTGTCTGTATACAAAA<br>ACGCCGCAAAGTTTGAGCGAAGTCAATAAACTCTCTACCCATTC<br>AGGGCAATATCTCTCaaatgtgatctagttcacattt*ttgtttaactttaagaaggagatatac*<br>*at* |

FNR promoter sequences are known in the art, and any suitable FNR promoter sequence(s) may be used in the genetically engineered bacteria of the invention. Any suitable FNR promoter(s) may be combined with any suitable payload.

Non-limiting FNR promoter sequences are provided in Table 3, which depicts the nucleic acid sequences of exemplary regulatory region sequences comprising a FNR-responsive promoter sequence. Underlined sequences are predicted ribosome binding sites, and bolded sequences are restriction sites used for cloning. In some embodiments, the genetically engineered bacteria of the invention comprise one or more of: SEQ ID NO: 1A, SEQ ID NO: 2A, SEQ ID NO: 3A, SEQ ID NO: 4A, SEQ ID NO: 5A, SEQ ID NO: 6A, SEQ ID NO: 7A, nirBi1 promoter (SEQ ID NO: 8A), nirB2 promoter (SEQ ID NO: 9A), nirB3 promoter (SEQ ID NO: 10A), ydfZ promoter (SEQ ID NO: 11A), nirB promoter fused to a strong ribosome binding site (SEQ ID NO: 12A), ydfZ promoter fused to a strong ribosome binding site (SEQ ID NO: 13A), fnrS, an anaerobically induced small RNA gene (fnrS1 promoter SEQ ID NO: 14A or fnrS2 promoter SEQ ID NO: 15A), nirB promoter fused to a crp binding site (SEQ ID NO: 16A), and fnrS fused to a crp binding site (SEQ ID NO: 17A). In some embodiments, the FNR-responsive promoter is at least about 80%, at least about 85%, at least about 90%, at least about 95%, or at least about 99% homologous to the sequence of any one of SEQ ID NOs: 1A-17A.

In some embodiments, multiple distinct FNR nucleic acid sequences are inserted in the genetically engineered bacteria. In alternate embodiments, the genetically engineered bacteria comprise a gene encoding a payload (e.g. PME e.g. PAL) expressed under the control of an alternate oxygen level-dependent promoter, e.g., DNR (Trunk et al., 2010) or ANR (Ray et al., 1997). In these embodiments, expression of the payload gene is particularly activated in a low-oxygen or anaerobic environment, such as in the gut. In some embodiments, gene expression is further optimized by methods known in the art, e.g., by optimizing ribosomal binding sites and/or increasing mRNA stability. In one embodiment, the mammalian gut is a human mammalian gut.

Any suitable FNR promoter(s) may be combined with any suitable PAL. Non-limiting FNR promoter sequences are provided in Table 3, and non-limiting PAL sequences are also provided herein. In some embodiments, the genetically engineered bacteria of the invention comprise one or more of the following SEQ ID NOs disclosed in WO2017087580, the contents of which are herein incorporated by reference in their entirety: SEQ ID NO: 9, SEQ ID NO: 10, nirB1 promoter (SEQ ID NO: 11), nirB2 promoter (SEQ ID NO: 12), nirB3 promoter (SEQ ID NO: 13), ydfZ promoter (SEQ ID NO: 14), nirB promoter fused to a strong ribosome binding site (SEQ ID NO: 15), ydfZ promoter fused to a strong ribosome binding site (SEQ ID NO: 16), fnrS, an anaerobically induced small RNA gene (fnrS1 promoter SEQ ID NO: 9 or fnrS2 promoter SEQ ID NO: 17), nirB promoter fused to a crp binding site (SEQ ID NO: 18), andffnrS fused to a crp binding site (SEQ ID NO: 19).

In another embodiment, the genetically engineered bacteria comprise the gene or gene cassette for producing the payload expressed under the control of anaerobic regulation of arginine deiminiase and nitrate reduction transcriptional regulator (ANR). In *P. aeruginosa*, ANR is "required for the expression of physiological functions which are inducible under oxygen-limiting or anaerobic conditions" (Winteler et al., 1996; Sawers 1991). *P. aeruginosa* ANR is homologous with *E. coli* FNR, and "the consensus FNR site (TTGATATCAA) was recognized efficiently by ANR and FNR" (Winteler et al., 1996). Like FNR, in the anaerobic state, ANR activates numerous genes responsible for adapting to anaerobic growth. In the aerobic state, ANR is inactive. Pseudomonasfluorescens, *Pseudomonas putida, Pseudomonas syringae*, and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcriptional regulator which is required in conjunction with ANR for "anaerobic nitrate respiration of *Pseudomonas aeruginosa*" (Hasegawa et al., 1998). For certain genes, the FNR-binding motifs "are probably recognized only by DNR" (Hasegawa et al., 1998). Any suitable transcriptional regulator that is controlled by exogenous environmental conditions and corresponding regulatory region may be used. Non-limiting examples include ArcA/B, ResD/E, NreA/B/C, and AirSR, and others are known in the art.

In other embodiments, the one or more gene sequence(s) for producing a payload (e.g. a PME e.g. PAL) are expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism, and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stilke, 2008). In some embodiments, the gene or gene cassette for producing a payload molecule is controlled by an oxygen level-dependent promoter fused to a CRP binding site. In some embodiments, the one or more gene sequence(s) for a payload are controlled by an FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the gene or gene cassette by recruiting RNA polymerase to the FNR promoter via direct protein-protein interactions. In the presence of glucose, cyclic AMP does not bind to CRP and transcription of the gene or gene cassette for producing a payload is repressed. In some embodiments, an oxygen level-dependent promoter (e.g., an FNR promoter) fused to a binding site for a transcriptional activator is used to ensure that the gene or gene cassette for producing a payload is not expressed under anaerobic conditions when sufficient amounts of glucose are present, e.g., by adding glucose to growth media in vitro.

In some embodiments, the genetically engineered bacteria comprise an oxygen level-dependent promoter from a different species, strain, or substrain of bacteria. In some embodiments, the genetically engineered bacteria comprise an oxygen level-sensing transcription factor, e.g., FNR, ANR or DNR, from a different species, strain, or substrain of bacteria. In some embodiments, the genetically engineered bacteria comprise an oxygen level-sensing transcription factor and corresponding promoter from a different species, strain, or substrain of bacteria. The heterologous oxygen-level dependent transcriptional regulator and/or promoter increases the transcription of genes operably linked to said promoter, e.g., one or more gene sequence(s) for producing the payload(s) in a low-oxygen or anaerobic environment, as compared to the native gene(s) and promoter in the bacteria under the same conditions. In certain embodiments, the non-native oxygen-level dependent transcriptional regulator is an FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., the gene encoding the payload, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., the gene encoding the payload, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., (2006). In some embodiments, both the oxygen level-sensing transcriptional regulator and corresponding promoter are mutated relative to the wild-type sequences from bacteria of the same subtype in order to increase expression of the payload in low-oxygen conditions.

In some embodiments, the bacterial cells comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding the payload are present on different plasmids. In some embodiments, the gene encoding the oxygen level-sensing transcriptional regulator and the gene encoding the payload are present on the same plasmid.

In some embodiments, the gene encoding the oxygen level-sensing transcriptional regulator is present on a chromosome. In some embodiments, the gene encoding the oxygen level-sensing transcriptional regulator and the gene encoding the payload are present on different chromosomes. In some embodiments, the gene encoding the oxygen level-sensing transcriptional regulator and the gene encoding the payload are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the payload. In some embodiments, expression of the transcriptional regulator is controlled by the same promoter that controls expression of the payload. In some embodiments, the transcriptional regulator and the payload are divergently transcribed from a promoter region.

Oxygen Level Independent Inducible Promoters

Oxygen Level Independent Inducible Promoters systems, such as systems including FNRS24Y, are described in PCT/US2016/062369, filed Nov. 16, 2016 and published as WO2017087580, the contents of which is herein incorporated by reference in its entirety.

In addition to promoters that are induced in response to oxygen levels, the PME gene(s) and/or Phe transporter gene(s) can be regulated by promoters that are induced in response to inflammatory conditions, such as in presence of reactive nitrogen species or in the presence of reactive oxygen species. Examples of such inducible promoters are found in co-pending, co-owned International Application PCT/US2016/050836, filed Sep. 8, 2016, the contents of which are hereby incorporated by reference in their entirety.

In any of the embodiments described herein, the genetically engineered bacteria comprising one or more PME and/or one or more phe transporters under control of an oxygen independent promoter further comprise one or more bacteriophages. In some embodiments, the bacteriophages have been mutated in one or more genes within the bacteriophage genome. Such mutations include deletions, insertions, substitutions and inversions and are located in or encompass one or more bacteriophage genes.

In some embodiments, the genetically engineered bacteria comprise one or more *E. coli* In some embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

RNS-Dependent Regulation

In some embodiments, the genetically engineered bacteria or genetically engineered virus comprise a gene encoding a payload that is expressed under the control of an inducible promoter. In some embodiments, the genetically engineered bacterium or genetically engineered virus that expresses a payload under the control of a promoter that is activated by inflammatory conditions. In one embodiment, the gene for producing the payload is expressed under the control of an inflammatory-dependent promoter that is activated in inflammatory environments, e.g., a reactive nitrogen species or RNS promoter. In some embodiments, the genetically engineered bacteria of the invention comprise a tunable regulatory region that is directly or indirectly controlled by a transcription factor that is capable of sensing at least one reactive nitrogen species. Suitable RNS inducible promoters, e.g., inducible by reactive nitrogen species are described in International Patent Application PCT/US2016/062369, filed Nov. 16, 2016 and published as WO2017087580, published as WO2017/123675, the contents of which is herein incorporated by reference in its entirety.

ROS-Dependent Regulation

In some embodiments, the genetically engineered bacteria or genetically engineered virus comprise a gene for producing a payload that is expressed under the control of an inducible promoter. In some embodiments, the genetically engineered bacterium or genetically engineered virus that expresses a payload under the control of a promoter that is activated by conditions of cellular damage. In one embodiment, the gene for producing the payload is expressed under the control of a cellular damaged-dependent promoter that is activated in environments in which there is cellular or tissue damage, e.g., a reactive oxygen species or ROS promoter. In some embodiments, the genetically engineered bacteria of the invention comprise a tunable regulatory region that is directly or indirectly controlled by a transcription factor that is capable of sensing at least one reactive oxygen species. Suitable ROS inducible promoters, e.g., inducible by reactive oxygen species are described in International Patent Application PCT/US2017/013072, filed Jan. 11, 2017, published as WO2017/123675, International Patent Applications PCT/US2016/032562, filed—May 13, 2016, published as WO2016183531, and PCT/US2016/062369, filed Nov. 16, 2016 and published as WO2017087580, the contents of each of which are herein incorporated by reference in their entireties.

TABLE 17

Nucleotide sequences of exemplary OxyR-regulated regulatory regions

| Regulatory Sequence | Sequence |
|---|---|
| katG (SEQ ID NO: 18C) | TGTGGCTTTTATGAAAATCACACAGTGATCACAAATTTTAAACAGAGC ACAAAATGCTGCCTCGAAATGAGGGCGGGAAAATAAGGTTATCAGCC TTGTTTTCTCCCTCATTACTTGAAGGATATGAAGCTAAAACCCTTTTTT ATAAAGCATTTGTCCGAATTCGGACATAATCAAAAAAGCTTAATTAAG ATCAATTTGATCTACATCTCTTTAACCAACAATATGTAAGATCTCAACT ATCGCATCCGTGGATTAATTCAATTATAACTTCTCTCTAACGCTGTGTA |

TABLE 17-continued

Nucleotide sequences of exemplary OxyR-regulated regulatory regions

| Regulatory Sequence | Sequence |
|---|---|
| | TCGTAACGGTAACACTGTAGAGGGGAGCACATTGATGCGAATTCATTA AAGAGGAGAAAGGTACC |
| dps (SEQ ID NO: 19C) | TTCCGAAAATTCCTGGCGAGCAGATAAATAAGAATTGTTCTTATCAAT ATATCTAACTCATTGAATCTTTATTAGTTTTGTTTTTCACGCTTGTTACC ACTATTAGTGTGATAGGAACAGCCAGAATAGCGGAACACATAGCCGG TGCTATACTTAATCTCGTTAATTACTGGGACATAACATCAAGAGGATA TGAAATTCGAATTCATTAAAGAGGAGAAAGGTACC |
| ahpC (SEQ ID NO: 20C) | GCTTAGATCAGGTGATTGCCCTTTGTTTATGAGGGTGTTGTAATCCATG TCGTTGTTGCATTTGTAAGGGCAACACCTCAGCCTGCAGGCAGGCACT GAAGATACCAAAGGGTAGTTCAGATTACACGGTCACCTGGAAAGGGG GCCATTTTACTTTTTATCGCCGCTGGCGGTGCAAAGTTCACAAAGTTGT CTTACGAAGGTTGTAAGGTAAAACTTATCGATTTGATAATGGAAACGC ATTAGCCGAATCGGCAAAAATTGGTTACCTTACATCTCATCGAAAACA CGGAGGAAGTATAGATGCGAATTCATTAAAGAGGAGAAAGGTACC |
| oxyS (SEQ ID NO: 21C) | CTCGAGTTCATTATCCATCCTCCATCGCCACGATAGTTCATGGCGATA GGTAGAATAGCAATGAACGATTATCCCTATCAAGCATTCTGACTGATA ATTGCTCACACGAATTCATTAAAGAGGAGAAAGGTACC |

In some embodiments, the regulatory region sequence is at least about 80%, at least about 85%, at least about 90%, at least about 95%, or at least about 99% homologous to the sequence of SEQ ID NO: 18C, SEQ ID NO: 19C, SEQ ID NO: 20C, and/or SEQ ID NO: 21C.

Propionate and Other Promoters

In some embodiments, the genetically engineered bacteria comprise the gene or gene cassette for producing one or more payload genes expressed under the control of an inducible promoter that is responsive to specific molecules or metabolites in the environment, e.g., the tumor microenvironment, a specific tissue, or the mammalian gut. For example, the short-chain fatty acid propionate is a major microbial fermentation metabolite localized to the gut (Hosseini et al., 2011). In one embodiment, the gene or gene cassette for producing a payload is under the control of a propionate-inducible promoter. In a more specific embodiment, the gene or gene cassette for producing the payload is under the control of a propionate-inducible promoter that is activated by the presence of propionate in the mammalian gut. Any molecule or metabolite found in the mammalian gut, in a healthy and/or disease state, may be used to induce payload expression. Non-limiting examples of inducers include propionate, bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese. In alternate embodiments, the gene or gene cassette for producing therapeutic polypeptide is under the control of a pAraBAD promoter, which is activated in the presence of the sugar arabinose.

In some embodiments, the gene or gene cassette for producing the polypeptide of interest is present on a plasmid and operably linked to a promoter that is induced under low-oxygen or anaerobic conditions. In some embodiments, the gene or gene cassette for producing polypeptide of interest is present in the chromosome and operably linked to a promoter that is induced under low-oxygen or anaerobic conditions. In some embodiments, the gene or gene cassette for producing a polypeptide of interest is present on a plasmid and operably linked to a promoter that is induced by molecules or metabolites that are specific to the to the tumor and/or the mammalian gut. In some embodiments, the gene or gene cassette for producing polypeptide of interest is present on a chromosome and operably linked to a promoter that is induced by molecules or metabolites that are specific to the tumor and/or the mammalian gut. In some embodiments, the gene or gene cassette for producing polypeptide of interest is present on a chromosome and operably linked to a promoter that is induced by exposure to tetracycline. In some embodiments, the gene or gene cassette for producing polypeptide of interest is present on a plasmid and operably linked to a promoter that is induced by exposure to tetracycline.

In some embodiments, gene expression is further optimized by methods known in the art, e.g., by optimizing ribosomal binding sites (RBS), manipulating transcriptional regulators, and/or increasing mRNA stability. Bioinformatics tools for the fine tuning and optimization of RBS are known in the art.

In any of the embodiments described herein above (and elsewhere herein), the engineered bacteria may additionally comprise gene sequence(s) encoding one or more gene sequence(s) under the control of any of the promoters discussed herein. In some embodiments, the genetically engineered bacteria comprise a stably maintained plasmid or chromosome carrying the gene or gene cassette for producing the polypeptide of interest, such that the gene or gene cassette can be expressed in the host cell, and the host cell is capable of survival and/or growth in vitro, e.g., in medium, and/or in vivo, e.g., in the gut or the tumor microenvironment. In some embodiments, a bacterium may comprise multiple copies of the gene or gene cassette for producing a polypeptide of interest. In some embodiments, gene or gene cassette for producing the payload is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, gene or gene cassette for producing a polypeptide of interest is expressed on a high-copy plasmid. In some embodiments, the high-copy plasmid may be useful for increasing gene or gene cassette expression. In some embodiments, gene or gene cassette for producing a polypeptide of interest is expressed on a chromosome.

Other Inducible Promoters

In some embodiments, the gene encoding a polypeptide of interest is present on a plasmid and operably linked to a promoter that is induced by one or more nutritional and/or chemical inducer(s) and/or metabolite(s). In some embodiments, the gene encoding a polypeptide of interest is present in the chromosome and operably linked to a promoter that is induced by one or more nutritional and/or chemical inducer(s) and/or metabolite(s).

In some embodiments, the bacterial cell comprises a stably maintained plasmid or chromosome carrying the one or more gene sequences(s), inducible by one or more nutritional and/or chemical inducer(s) and/or metabolite(s), encoding a polypeptide of interest, such that a polypeptide of interest can be expressed in the host cell, and the host cell is capable of survival and/or growth in vitro, e.g., in medium, and/or in vivo, e.g., in the tumor or in the gut. In some embodiments, bacterial cell comprises two or more distinct copies of the one or more gene sequences(s) encoding a polypeptide of interest, which is controlled by a promoter inducible one or more nutritional and/or chemical inducer(s) and/or metabolite(s). In some embodiments, the genetically engineered bacteria comprise multiple copies of the one or more gene sequences(s) encoding a polypeptide of interest, which is controlled by a promoter inducible by one or more nutritional and/or chemical inducer(s) and/or metabolite(s). In some embodiments, the one or more gene sequences(s) encoding a polypeptide of interest(s), is present on a plasmid and operably linked to a directly or indirectly inducible promoter inducible by one or more nutritional and/or chemical inducer(s) and/or metabolite(s). In some embodiments, the one or more gene sequences(s) encoding a polypeptide of interest, is present on a chromosome and operably linked to a directly or indirectly inducible promoter. In some embodiments, the one or more gene sequence(s) encoding a polypeptide of interest is induced by one or more nutritional and/or chemical inducer(s) and/or metabolites.

In some embodiments, one or more gene sequence(s) encoding polypeptides of interest described herein is present on a plasmid and operably linked to promoter a directly or indirectly inducible by one or more nutritional and/or chemical inducer(s) and/or metabolite(s). In some embodiments, the bacterial cell comprises a stably maintained plasmid or chromosome carrying the gene encoding a polypeptide of interest, which is induced by one or more nutritional and/or chemical inducer(s) and/or metabolite(s), such that a polypeptide of interest can be expressed in the host cell, and the host cell is capable of survival and/or growth in vitro, e.g., under culture conditions, and/or in vivo, e.g., in the gut or the tumor microenvironment. In some embodiments, bacterial cell comprises two or more gene sequence(s) for the production of a polypeptide of interest, one or more of which are induced by one or more nutritional and/or chemical inducer(s) and/or metabolite(s). In some embodiments, the genetically engineered bacteria comprise multiple copies of the same gene sequence(s) for the production of a polypeptide of interest which are induced by one or more nutritional and/or chemical inducer(s) and/or metabolite(s). In some embodiments, the genetically engineered bacteria comprise multiple copies of different gene sequence(s) for the production of a polypeptide of interest, one or more of which are induced by one or more nutritional and/or chemical inducer(s) and/or metabolite(s).

In some embodiments, the gene sequence(s) for the production of a polypeptide of interest is present on a plasmid and operably linked to a promoter that is induced by one or more nutritional and/or chemical inducer(s) and/or metabolite(s). In some embodiments, gene sequence(s) for the production of a polypeptide of interest is present in the chromosome and operably linked to a promoter that is induced by one or more nutritional and/or chemical inducer(s) and/or metabolite(s).

In some embodiments, the genetically engineered bacteria comprise two or more distinct PAL genes. In some embodiments, the genetically engineered bacteria comprise multiple copies of the same PAL gene. In some embodiments, the PAL gene is present on a plasmid and operably linked to a directly or indirectly inducible promoter. In some embodiments, the PAL gene is present on a plasmid and operably linked to a promoter that is induced under low-oxygen or anaerobic conditions. In some embodiments, the PAL gene is present on a chromosome and operably linked to a directly or indirectly inducible promoter. In some embodiments, the PAL gene is present in the chromosome and operably linked to a promoter that is induced under low-oxygen or anaerobic conditions. In some embodiments, the PAL gene is present on a plasmid and operably linked to a promoter that is induced by exposure to tetracycline. In some embodiments, the PAL gene is present on a plasmid and operably linked to a promoter that is induced by exposure to arabinose. In some embodiments, the PAL gene is present on a plasmid and operably linked to a promoter that is induced by exposure to IPTG or another LacI inducer. In some embodiments, the PAL gene is present on a plasmid and operably linked to a promoter that is induced by exposure to rhamnose. In some embodiments, the PAL gene is present on a plasmid and operably linked to a promoter that is induced by exposure to tetracycline. In some embodiments, the PAL gene is present on a plasmid and operably linked to a promoter that is induced by change in temperature from a non-permissive temperature to a permissive temperature. In some embodiments, the PAL gene is present on a chromosome and operably linked to a promoter that is induced by exposure to arabinose. In some embodiments, the PAL gene is present on a chromosome and operably linked to a promoter that is induced by exposure to IPTG or another LacI inducer. In some embodiments, the PAL gene is present on a chromosome and operably linked to a promoter that is induced by exposure to rhamnose. In some embodiments, the PAL gene is present on a chromosome and operably linked to a promoter that is induced by exposure to tetracycline. In some embodiments, the PAL gene is present on a chromosome and operably linked to a promoter that is induced by change in temperature from a non-permissive temperature to a permissive temperature.

In some embodiments, the genetically engineered bacteria comprise a stably maintained plasmid or chromosome carrying the LAAD gene, such that LAAD can be expressed in the host cell, and the host cell is capable of survival and/or growth in vitro, e.g., in medium, and/or in vivo, e.g., in the gut. In some embodiments, the genetically engineered bacteria comprise two or more distinct LAAD genes. In some embodiments, the genetically engineered bacteria comprise multiple copies of the same LAAD gene. In some embodiments, the LAAD gene is present on a plasmid and operably linked to a directly or indirectly inducible promoter. In some embodiments, the LAAD gene is present on a plasmid and operably linked to a promoter that is inducible, e.g., by arabinose or tetracycline. In some embodiments, the LAAD gene is present on a chromosome and operably linked to a directly or indirectly inducible promoter. In some embodiments, the LAAD gene is present in the chromosome and operably linked to a promoter that is induced, e.g., by arabinose or tetracycline. In some embodiments, the LAAD gene is present on a plasmid and operably linked to a promoter that is induced by exposure to tetracycline. In some embodiments, the LAAD gene is present on a plasmid and operably linked to a promoter that is induced by exposure to arabinose. In some embodiments, the LAAD gene is present on a plasmid and operably linked to a promoter that is induced by exposure to IPTG or another LacI inducer. In some embodiments, the LAAD gene is present on a plasmid and operably linked to a promoter that is induced by exposure to rhamnose. In some embodiments, the LAAD gene is present on a plasmid and operably linked to a promoter that is induced by change in temperature from a non-permissive temperature to a permissive temperature. In some embodiments, the LAAD gene is present on a plasmid and operably linked to a constitutive promoter. In some embodiments, the LAAD gene is present on a plasmid and operably linked to a promoter that is induced by exposure to tetracycline. In some embodiments, the LAAD gene is present on a chromosome and operably linked to a promoter that is induced by exposure to arabinose. In some embodiments, the LAAD gene is present on a chromosome and operably linked to a promoter that is induced by exposure to IPTG or another LacI inducer. In some embodiments, the LAAD gene is present on a chromosome and operably linked to a promoter that is induced by exposure to rhamnose. In some embodiments, the LAAD gene is present on a chromosome and operably linked to a promoter that is induced by change in temperature from a non-permissive temperature to a permissive temperature. In some embodiments, the LAAD gene is present on a chromosome and operably linked to a constitutive promoter.

In any of these embodiments of bacteria comprising PME gene(s), e.g., PAL, PAH, and/or LAAD, the bacteria may further comprise gene sequence encoding one or more Phe transporters, which Phe transporter gene sequence(s) may be present on a plasmid or chromosome, which may be the same or a different plasmid or chromosome from the location of the PME gene. The Phe transporter gene sequence(s) may be under the control of the same or a different promoter from the PMR gene sequence(s).

In some embodiments, the genetically engineered bacteria comprise an oxygen-level dependent transcriptional regulator, e.g., FNR, ANR, or DNR, and corresponding promoter from a different bacterial species. The non-native oxygen-level dependent transcriptional regulator and promoter increase the transcription of genes operably linked to said promoter, e.g., PAL or PAH, in a low-oxygen or anaerobic environment, as compared to the native transcriptional regulator and promoter in the bacteria under the same conditions. PAL or PAH, in a low-oxygen or anaerobic environment, as compared to the wild-type promoter under the same conditions. PAL or PAH, in a low-oxygen or anaerobic environment, as compared to the wild-type transcriptional regulator under the same conditions. 2006).

In some embodiments, the genetically engineered bacteria of the invention comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding PAL are present on different plasmids. In some embodiments, the gene encoding the oxygen level-sensing transcriptional regulator and the gene encoding PAL are present on the same plasmid. In some embodiments, the gene encoding the oxygen level-sensing transcriptional regulator is present on a chromosome. In some embodiments, the gene encoding the oxygen level-sensing transcriptional regulator and the gene encoding PAL are present on different chromosomes. In some embodiments, the gene encoding the oxygen level-sensing transcriptional regulator and the gene encoding PAL are present on the same chromosome.

In one embodiment, LAAD expression is under the control of the ParaBAD promoter. In one embodiment, expression of LAAD occurs under aerobic or microaerobic conditions. In one embodiment, PAL expression is under the control of the ParaBAD promoter. In one embodiment, PAL expression occurs under aerobic or microaerobic conditions. In one embodiment, PAL expression occurs under anaerobic or low oxygen conditions and LADD expression occurs under aerobic or microaerobic conditions. In one embodiment, PAL expression occurs under anaerobic or low oxygen conditions and LADD expression is under the control of the ParaBAD promoter.

In some embodiments, one or more gene(s) or gene cassette(s) for producing polypeptide(s) of interest (e.g., PAL and LAAD gene) are present, and each gene is expressed under the control of different promoters, such as any of the promoters discussed in this paragraph and elsewhere herein.

In some embodiments, the one or more PME genes, e.g., PAL and/or LAAD gene are expressed under the control of a promoter that is induced by exposure to arabinose. In some embodiments, the one or more PME genes, e.g., PAL and/or LAAD gene are expressed under the control of a promoter that is induced by exposure to IPTG or other LacI inducer. In some embodiments, the one or more PME genes, e.g., PAL and/or LAAD gene are expressed under the control of a promoter that is induced by exposure to rhamnose. In some embodiments, the one or more PME genes, e.g., PAL and/or LAAD gene are expressed under the control of a promoter that is induced by a change in temperature from a non-permissive temperature to a permissive temperature.

In some embodiments, the promoter that is operably linked to the gene encoding polypeptide of interest is directly or indirectly induced by one or more nutritional and/or chemical inducer(s) and/or metabolite(s).

In some embodiments, one or more inducible promoter(s) are useful for or induced during in vivo expression of the one or more protein(s) of interest. In some embodiments, the promoters are induced during in vivo expression of one or more anti-cancer, satiety, gut barrier enhancer, immune modulatory and/or neuromodulatory molecules and/or other polypeptide(s) of interest. In some embodiments, expression of one or more a polypeptide of interest(s) and/or other polypeptide(s) of interest is driven directly or indirectly by one or more arabinose inducible promoter(s) in vivo. In some embodiments, the promoter is directly or indirectly induced by a chemical and/or nutritional inducer and/or metabolite which is co-administered with the genetically engineered bacteria of the invention.

In some embodiments, expression of one or more a polypeptide of interest and/or other polypeptide(s) of interest, is driven directly or indirectly by one or more promoter(s) induced by a chemical and/or nutritional inducer and/or metabolite during in vitro growth, preparation, or manufacturing of the strain prior to in vivo administration. In some embodiments, the promoter(s) induced by a chemical and/or nutritional inducer and/or metabolite are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with a polypeptide of interest(s) and/or other polypeptide(s) of interest prior to administration. In some embodiments, the cultures, which are induced by a chemical and/or nutritional inducer and/or metabolite, are grown aerobically. In some embodiments, the cultures, which are induced by a chemical and/or nutritional inducer and/or metabolite, are grown anaerobically.

The genes of arabinose metabolism are organized in one operon, AraBAD, which is controlled by the PAraBAD promoter. The PAraBAD (or Para) promoter suitably fulfills the criteria of inducible expression systems. PAraBAD displays tighter control of payload gene expression than many other systems, likely due to the dual regulatory role of AraC, which functions both as an inducer and as a repressor. Additionally, the level of ParaBAD-based expression can be modulated over a wide range of L-arabinose concentrations to fine-tune levels of expression of the payload. However, the cell population exposed to sub-saturating L-arabinose concentrations is divided into two subpopulations of induced and uninduced cells, which is determined by the differences between individual cells in the availability of L-arabinose transporter (Zhang et al., Development and Application of an Arabinose-Inducible Expression System by Facilitating Inducer Uptake in *Corynebacterium glutamicum*; Appl. Environ. Microbiol. August 2012 vol. 78 no. 16 5831-5838). Alternatively, inducible expression from the ParaBad can be controlled or fine-tuned through the optimization of the ribosome binding site (RBS), as described herein.

In one embodiment, expression of one or more polypeptides of interest, e.g., one or more therapeutic polypeptide(s), is driven directly or indirectly by one or more arabinose inducible promoter(s).

In some embodiments, the arabinose inducible promoter is useful for or induced during in vivo expression of the one or more protein(s) of interest. In some embodiments, expression of one or more protein(s) of interest is driven directly or indirectly by one or more arabinose inducible promoter(s) in vivo. In some embodiments, the promoter is directly or indirectly induced by a molecule that is co-administered with the genetically engineered bacteria of the invention, e.g., arabinose.

In some embodiments, expression of one or more protein(s) of interest, is driven directly or indirectly by one or more arabinose inducible promoter(s) during in vitro growth, preparation, or manufacturing of the strain prior to in vivo administration. In some embodiments, the arabinose inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., arabinose. In some embodiments, the cultures, which are induced by arabinose, are grown aerobically. In some embodiments, the cultures, which are induced by arabinose, are grown anaerobically.

In one embodiment, the arabinose inducible promoter drives the expression of a construct comprising one or more protein(s) of interest, jointly with a second promoter, e.g., a second constitutive or inducible promoter. In some embodiments, two promoters are positioned proximally to the construct and drive its expression, wherein the arabinose inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., arabinose and IPTG). In another non-limiting example, the first inducing conditions may be culture conditions, e.g., including arabinose presence, and the second inducing conditions may be in vivo conditions. Such in vivo conditions include low-oxygen, microaerobic, or anaerobic conditions, presence of gut metabolites, and/or metabolites administered in combination with the bacterial strain. In some embodiments, the one or more arabinose promoters drive expression of one or more protein(s) of interest, in combination with the FNR promoter driving the expression of the same gene sequence(s).

In some embodiments, the arabinose inducible promoter drives the expression of one or more protein(s) of interest from a low-copy plasmid or a high copy plasmid or a biosafety system plasmid described herein. In some embodiments, the arabinose inducible promoter drives the expression of one or more protein(s) of interest from a construct which is integrated into the bacterial chromosome. Exemplary insertion sites are described herein.

In some embodiments, one or more protein(s) of interest are knocked into the arabinose operon and are driven by the native arabinose inducible promoter In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 23 of Table 18. In some embodiments, the arabinose inducible construct further comprises a gene encoding AraC, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 24 of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 25 of Table 18.

In some embodiments, the genetically engineered bacteria comprise one or more gene sequence(s) which are inducible through a rhamnose inducible system. The genes rhaBAD are organized in one operon which is controlled by the rhaP BAD promoter. The rhaP BAD promoter is regulated by two activators, RhaS and RhaR, and the corresponding genes belong to one transcription unit which divergently transcribed in the opposite direction of rhaBAD. In the presence of L-rhamnose, RhaR binds to the rhaP RS promoter and activates the production of RhaR and RhaS. RhaS together with L-rhamnose then bind to the rhaP BAD and the rhaP T promoter and activate the transcription of the structural genes. In contrast to the arabinose system, in which AraC is provided and divergently transcribed in the gene sequence(s), it is not necessary to express the regulatory proteins in larger quantities in the rhamnose expression system because the amounts expressed from the chromosome are sufficient to activate transcription even on multicopy plasmids. Therefore, only the rhaP BAD promoter is cloned upstream of the gene that is to be expressed. Full induction of rhaBAD transcription also requires binding of the CRP-cAMP complex, which is a key regulator of catabolite repression. Alternatively, inducible expression from the rhaBAD can be controlled or fine-tuned through the optimization of the ribosome binding site (RBS), as described herein. In one embodiment, expression of one or more protein(s) of interest is driven directly or indirectly by one or more rhamnose inducible promoter(s). In one embodiment, expression of the payload is driven directly or indirectly by a rhamnose inducible promoter.

In some embodiments, the rhamnose inducible promoter is useful for or induced during in vivo expression of the one or more protein(s) of interest. In some embodiments, expression of one or more protein(s) of interest is driven directly or indirectly by one or more rhamnose inducible promoter(s) in vivo. In some embodiments, the promoter is directly or indirectly induced by a molecule that is co-administered with the genetically engineered bacteria of the invention, e.g., rhamnose In some embodiments, expression of one or more protein(s) of interest, is driven directly or indirectly by one or more rhamnose inducible promoter(s) during in vitro growth, preparation, or manufacturing of the strain prior to in vivo administration. In some embodiments, the rhamnose inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., rhamnose. In some embodiments, the cultures, which are induced by rhamnose, are grown aerobically. In some embodiments, the cultures, which are induced by rhamnose, are grown anaerobically.

In one embodiment, the rhamnose inducible promoter drives the expression of a construct comprising one or more protein(s) of interest jointly with a second promoter, e.g., a second constitutive or inducible promoter. In some embodiments, two promoters are positioned proximally to the construct and drive its expression, wherein the rhamnose inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., rhamnose and arabinose). In another non-limiting example, the first inducing conditions may be culture conditions, e.g., including rhamnose presence, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more rhamnose promoters drive expression of one or more protein(s) of interest and/or transcriptional regulator(s), e.g., FNRS24Y, in combination with the FNR promoter driving the expression of the same gene sequence(s).

In some embodiments, the rhamnose inducible promoter drives the expression of one or more protein(s) of interest, from a low-copy plasmid or a high copy plasmid or a biosafety system plasmid described herein. In some embodiments, the rhamnose inducible promoter drives the expression of one or more protein(s) of interest, from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 26 of Table 18.

In some embodiments, the genetically engineered bacteria comprise one or more gene sequence(s) which are inducible through an Isopropyl β-D-1-thiogalactopyranoside (IPTG) inducible system or other compound which induced transcription from the Lac Promoter. IPTG is a molecular mimic of allolactose, a lactose metabolite that activates transcription of the lac operon. In contrast to allolactose, the sulfur atom in IPTG creates a non-hydrolyzable chemical blond, which prevents the degradation of IPTG, allowing the concentration to remain constant. IPTG binds to the lac repressor and releases the tetrameric repressor (lacd) from the lac operator in an allosteric manner, thereby allowing the transcription of genes in the lac operon. Since IPTG is not metabolized by *E. coli*, its concentration stays constant and the rate of expression of Lac promoter-controlled is tightly controlled, both in vivo and in vitro. IPTG intake is independent on the action of lactose permease, since other transport pathways are also involved. Inducible expression from the PLac can be controlled or fine-tuned through the optimization of the ribosome binding site (RBS), as described herein. Other compounds which inactivate Lacd, can be used instead of IPTG in a similar manner.

In one embodiment, expression of one or more protein(s) of interest is driven directly or indirectly by one or more IPTG inducible promoter(s).

In some embodiments, the IPTG inducible promoter is useful for or induced during in vivo expression of the one or more protein(s) of interest. In some embodiments, expression of one or more protein(s) of interest is driven directly or indirectly by one or more IPTG inducible promoter(s) in vivo. In some embodiments, the promoter is directly or indirectly induced by a molecule that is co-administered with the genetically engineered bacteria of the invention, e.g., IPTG.

In some embodiments, expression of one or more protein(s) of interest is driven directly or indirectly by one or more IPTG inducible promoter(s) during in vitro growth, preparation, or manufacturing of the strain prior to in vivo administration. In some embodiments, the IPTG inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., IPTG. In some embodiments, the cultures, which are induced by IPTG, are grown arerobically. In some embodiments, the cultures, which are induced by IPTG, are grown anaerobically.

In one embodiment, the IPTG inducible promoter drives the expression of a construct comprising one or more protein(s) of interest jointly with a second promoter, e.g., a second constitutive or inducible promoter. In some embodiments, two promoters are positioned proximally to the construct and drive its expression, wherein the IPTG inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., arabinose and IPTG). In another non-limiting example, the first inducing conditions may be culture conditions, e.g., including IPTG presence, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more IPTG inducible promoters drive expression of one or more protein(s) of interest in combination with the FNR promoter driving the expression of the same gene sequence(s).

In some embodiments, the IPTG inducible promoter drives the expression of one or more protein(s) of interest from a low-copy plasmid or a high copy plasmid or a biosafety system plasmid described herein. In some embodiments, the IPTG inducible promoter drives the expression of one or more protein(s) of interest from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 27 of Table 18. In some embodiments, the IPTG inducible construct further comprises a gene encoding lacI, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 28 of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 29 of Table 18.

In some embodiments, the genetically engineered bacteria comprise one or more gene sequence(s) which are inducible through a tetracycline inducible system. The initial system Gossen and Bujard (Tight control of gene expression in mammalian cells by tetracycline-responsive promoters. (Gossen M & Bujard H. *PNAS,* 1992 Jun. 15; 89(12):5547-51) developed is known as tetracycline off: in the presence of tetracycline, expression from a tet-inducible promoter is reduced. Tetracycline-controlled transactivator (tTA) was created by fusing tetR with the C-terminal domain of VP16 (virion protein 16) from herpes simplex virus. In the absence of tetracycline, the tetR portion of tTA will bind tetO sequences in the tet promoter, and the activation domain promotes expression. In the presence of tetracycline, tetracycline binds to tetR, precluding tTA from binding to the tetO sequences. Next, a reverse Tet repressor (rTetR), was developed which created a reliance on the presence of tetracycline for induction, rather than repression. The new transactivator rtTA (reverse tetracycline-controlled transactivator) was created by fusing rTetR with VP16. The tetracycline on system is also known as the rtTA-dependent system.

In one embodiment, expression of one or more protein(s) of interest is driven directly or indirectly by one or more tetracycline inducible promoter(s). In some embodiments, the tetracycline inducible promoter is useful for or induced during in vivo expression of the one or more protein(s) of interest. In some embodiments, expression of one or more protein(s) of interest and/or transcriptional regulator(s), e.g., FNRS24Y, is driven directly or indirectly by one or more tetracycline inducible promoter(s) in vivo. In some embodiments, the promoter is directly or indirectly induced by a molecule that is co-administered with the genetically engineered bacteria of the invention, e.g., tetracycline In some embodiments, expression of one or more protein(s) of interest is driven directly or indirectly by one or more tetracycline inducible promoter(s) during in vitro growth, preparation, or manufacturing of the strain prior to in vivo administration. In some embodiments, the tetracycline inducible promoter(s) are induced in culture, e.g., grown in a flask, fermenter or other appropriate culture vessel, e.g., used during cell growth, cell expansion, fermentation, recovery, purification, formulation, and/or manufacture. In some embodiments, the promoter is directly or indirectly induced by a molecule that is added to in the bacterial culture to induce expression and pre-load the bacterium with the payload prior to administration, e.g., tetracycline. In some embodiments, the cultures, which are induced by tetracycline, are grown arerobically. In some embodiments, the cultures, which are induced by tetracycline, are grown anaerobically.

In one embodiment, the tetracycline inducible promoter drives the expression of a construct comprising one or more protein(s) of interest jointly with a second promoter, e.g., a second constitutive or inducible promoter. In some embodiments, two promoters are positioned proximally to the construct and drive its expression, wherein the tetracycline inducible promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., tetracycline and IPTG). In another non-limiting example, the first inducing conditions may be culture conditions, e.g., including tetracycline presence, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more tetracycline promoters drive expression of one or more protein(s) of interest in combination with the FNR promoter driving the expression of the same gene sequence(s).

In some embodiments, the tetracycline inducible promoter drives the expression of one or more protein(s) of interest from a low-copy plasmid or a high copy plasmid or a biosafety system plasmid described herein. In some embodiments, the tetracycline inducible promoter drives the expression of one or more protein(s) of interest from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the bolded sequences of SEQ ID NO: 34 (tet promoter is in bold) of Table 18. In some embodiments, the tetracycline inducible construct further comprises a gene encoding AraC, which is divergently transcribed from the same promoter as the one or more one or more protein(s) of interest In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 34 in italics (Tet repressor is in italics) of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 34 in italics (Tet repressor is in italics) of Table 18.

In some embodiments, the genetically engineered bacteria comprise one or more gene sequence(s) whose expression is controlled by a temperature sensitive mechanism. Thermoregulators are advantageous because of strong transcriptional control without the use of external chemicals or specialized media (see, e.g., Nemani et al., Magnetic nanoparticle hyperthermia induced cytosine deaminase expression in microencapsulated *E. coli* for enzyme-prodrug therapy; J Biotechnol. 2015 Jun. 10; 203: 32-40, and references therein). Thermoregulated protein expression using the mutant cI857 repressor and the pL and/or pR phage λ promoters have been used to engineer recombinant bacterial strains. The gene of interest cloned downstream of the λ promoters can then be efficiently regulated by the mutant thermolabile cI857 repressor of bacteriophage λ. At temperatures below 37° C., cI857 binds to the oL or oR regions of the pR promoter and blocks transcription by RNA polymerase. At higher temperatures, the functional cI857 dimer is destabilized, binding to the oL or oR DNA sequences is abrogated, and mRNA transcription is initiated. An exemplary construct is depicted in FIG. 88A of WO2017087580, the contents of which are herein incorporated by reference in their entirety. Inducible expression from the ParaBad can be controlled or further fine-tuned through the optimization of the ribosome binding site (RBS), as described herein.

In one embodiment, expression of one or more protein(s) of interest is driven directly or indirectly by one or more thermoregulated promoter(s). In some embodiments, thermoregulated promoter is useful for or induced during in vivo expression of the one or more protein(s) of interest. In some embodiments, expression of one or more protein(s) of interest is driven directly or indirectly by one or more thermoregulated promoter(s) in vivo. In some embodiments, the promoter is directly or indirectly induced by a molecule that is co-administered with the genetically engineered bacteria of the invention, e.g., temperature.

In some embodiments, expression of one or more protein(s) of interest is driven directly or indirectly by one or more thermoregulated promoter(s) during in vitro growth, preparation, or manufacturing of the strain prior to in vivo administration. In some embodiments, it may be advantageous to shut off production of the one or more protein(s) of interest. This can be done in a thermoregulated system by growing the strain at lower temperatures, e.g., 30 C. Expression can then be induced by elevating the temperature to 37 C and/or 42 C. In some embodiments, thermoregulated promoter(s) are induced in culture, e.g., grown in a flask, fermenter or other appropriate culture vessel, e.g., used during cell growth, cell expansion, fermentation, recovery, purification, formulation, and/or manufacture. In some embodiments, the cultures, which are induced by temperatures between 37 C and 42 C, are grown arerobically. In some embodiments, the cultures, which are induced by induced by temperatures between 37 C and 42 C, are grown anaerobically.

In one embodiment, thermoregulated promoter drives the expression of a construct comprising one or more protein(s) of interest jointly with a second promoter, e.g., a second constitutive or inducible promoter. In some embodiments, two promoters are positioned proximally to the construct and drive its expression, wherein thermoregulated promoter drives expression under a first set of exogenous conditions, and the second promoter drives the expression under a second set of exogenous conditions. In a non-limiting example, the first and second conditions may be two sequential culture conditions (i.e., during preparation of the culture in a flask, fermenter or other appropriate culture vessel, e.g., thermoregulation and arabinose). In another non-limiting example, the first inducing conditions may be culture conditions, e.g., permissive temperature, and the second inducing conditions may be in vivo conditions. Such in vivo conditions include low-oxygen, microaerobic, or anaerobic conditions, conditions of the tumor microenvironment, presence of gut metabolites, and/or metabolites administered in combination with the bacterial strain. In some embodiments, the one or more thermoregulated promoters drive expression of one or more protein(s) of interest in combination with the FNR promoter driving the expression of the same gene sequence(s).

In some embodiments, thermoregulated promoter drives the expression of one or more protein(s) of interest from a low-copy plasmid or a high copy plasmid or a biosafety system plasmid described herein. In some embodiments, thermoregulated promoter drives the expression of one or more protein(s) of interest from a construct which is integrated into the bacterial chromosome. Exemplary insertion sites are described herein.

In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 30 of Table 18. In some embodiments, thermoregulated construct further comprises a gene encoding mutant cI857 repressor, which is divergently transcribed from the same promoter as the one or more one or more protein(s) of interest. In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 31 of Table 18. In some embodiments, the genetically engineered bacteria comprise one or more gene sequence(s) encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% identity with the polypeptide encoded by any of the sequences of SEQ ID NO: 33 of Table 18.

In some embodiments, the genetically engineered bacteria comprise one or more gene sequence(s) which are indirectly inducible through a system driven by the PssB promoter. The Pssb promoter is active under aerobic conditions, and shuts off under anaerobic conditions.

This promoter can be used to express a gene of interest under aerobic conditions. This promoter can also be used to tightly control the expression of a gene product such that it is only expressed under anaerobic conditions. In this case, the oxygen induced PssB promoter induces the expression of a repressor, which represses the expression of a gene of interest. As a result, the gene of interest is only expressed in the absence of the repressor, i.e., under anaerobic conditions. This strategy has the advantage of an additional level of control for improved fine-tuning and tighter control. FIG. 89A of WO2017087580, the contents of which are herein incorporated by reference in their entirety depicts a schematic of the gene organization of a PssB promoter.

In one embodiment, expression of one or more protein(s) of interest is indirectly regulated by a repressor expressed under the control of one or more PssB promoter(s).

In some embodiments, induction of the PssB promoter(s) indirectly drives the in vivo expression of one or more protein(s) of interest. In some embodiments, induction of the PssB promoter(s) indirectly drives the expression of one or more protein(s) of interest during in vitro growth, preparation, or manufacturing of the strain prior to in vivo administration. In some embodiments, conditions for induction of the PssB promoter(s) are provided in culture, e.g., in a flask, fermenter or other appropriate culture vessel, e.g., used during cell growth, cell expansion, fermentation, recovery, purification, formulation, and/or manufacture.

In some embodiments, the PssB promoter indirectly drives the expression of one or more protein(s) of interest from a low-copy plasmid or a high copy plasmid or a biosafety system plasmid described herein. In some embodiments, the PssB promoter indirectly drives the expression of one or more protein(s) of interest from a construct which is integrated into the bacterial chromosome. Exemplary insertion sites are described herein.

In another non-limiting example, this strategy can be used to control expression of thyA and/or dapA, e.g., to make a conditional auxotroph. The chromosomal copy of dapA or ThyA is knocked out. Under anaerobic conditions, dapA or thyA—as the case may be—are expressed, and the strain can grow in the absence of dap or thymidine. Under aerobic conditions, dapA or thyA expression is shut off, and the strain cannot grow in the absence of dap or thymidine. Such a strategy can, for example be employed to allow survival of bacteria under anaerobic conditions, e.g., the gut and/or conditions of the tumor microenvironment, but prevent survival under aerobic conditions (biosafety switch). In some embodiments, the genetically engineered bacteria comprise one or more gene sequence(s) having at least 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID NO: 35 of Table 18.

Sequences useful for expression from inducible promoters are listed in Table 18.

TABLE 18

Inducible promoter construct sequences

| Description | Sequence |
|---|---|
| Arabinose Promoter region SEQ ID NO: 23 | CAGACATTGCCGTCACTGCGTCTTTTACTGGCTCTTCTCGCTAAC CCAACCGGTAACCCCGCTTATTAAAAGCATTCTGTAACAAAGCG GGACCAAAGCCATGACAAAAACGCGTAACAAAAGTGTCTATAA TCACGGCAGAAAAGTCCACATTGATTATTTGCACGGCGTCACAC TTTGCTATGCCATAGCATTTTTATCCATAAGATTAGCGGATCCA GCCTGACGCTTTTTTTCGCAACTCTCTACTGTTTCTCCATACCTC TAGAAATAATTTTGTTTAACTTTAAGAAGGAGATATACAT |
| AraC (reverse orientation) SEQ ID NO: 24 | TTATTCACAACCTGCCCTAAACTCGCTCGGACTCGCCCCGGTGC ATTTTTTAAATACTCGCGAGAAATAGAGTTGATCGTCAAAACCG ACATTGCGACCGACGGTGGCGATAGGCATCCGGGTGGTGCTCA AAAGCAGCTTCGCCTGACTGATGCGCTGGTCCTCGCGCCAGCTT AATACGCTAATCCCTAACTGCTGGCGGAACAAATGCGACAGAC GCGACGGCGACAGGCAGACATGCTGTGCGACGCTGGCGATATC AAAATTACTGTCTGCCAGGTGATCGCTGATGTACTGACAAGCCT CGCGTACCCGATTATCCATCGGTGGATGGAGCGACTCGTTAATC GCTTCCATGCGCCGCAGTAACAATTGCTCAAGCAGATTTATCGC CAGCAATTCCGAATAGCGCCCTTCCCCTTGTCCGGCATTAATGA TTTGCCCAAACAGGTCGCTGAAATGCGGCTGGTGCGCTTCATCC GGGCGAAAGAAACCGGTATTGGCAAATATCGACGGCCAGTTAA GCCATTCATGCCAGTAGGCGCGCGGACGAAAGTAAACCCACTG GTGATACCATTCGTGAGCCTCCGGATGACGACCGTAGTGATGA ATCTCTCCAGGCGGGAACAGCAAAATATCACCCGGTCGGCAGA CAAATTCTCGTCCCTGATTTTTCACCACCCCCTGACCGCGAATG GTGAGATTGAGAATATAACCTTTCATTCCCAGCGGTCGGTCGAT AAAAAAATCGAGATAACCGTTGGCCTCAATCGGCGTTAAACCC GCCACCAGATGGGCGTTAAACGAGTATCCCGGCAGCAGGGGAT CATTTTGCGCTTCAGCCATACTTTTCATACTCCCGCCATTCAGAG AAGAAACCAATTGTCCATATTGCAT |
| AraC polypeptide SEQ ID NO: 25 | MQYGQLVSSLNGGSMKSMAEAQNDPLLPGYSFNAHLVAGLTPIE ANGYLDFFIDRPLGMKGYILNLTIRGQGVVKNQGREFVCRPGDILL FPPGEIHHYGRHPEAHEWYHQWVYFRPRAYWHEWLNWPSIFANT GFFRPDEAHQPHFSDLFGQIINAGQGEGRYSELLAINLLEQLLLRRM EAINESLHPPMDNRVREACQYISDHLADSNFDIASVAQHVCLSPSR LSHLFRQQLGISVLSWREDQRISQAKLLLSTTRMPIATVGRNVGFD DQLYFSRVFKKCTGASPSEFRAGCE* |

TABLE 18-continued

| Inducible promoter construct sequences | |
|---|---|
| Description | Sequence |
| Region comprising rhamnose inducible promoter SEQ ID NO: 26 | CGGTGAGCATCACATCACCACAATTCAGCAAATTGTGAACATC ATCACGTTCATCTTTCCCTGGTTGCCAATGGCCCATTTTCCTGTC AGTAACGAGAAGGTCGCGAATCAGGCGCTTTTTAGACTGGTCG TAATGAAATTCAGCTGTCACCGGATGTGCTTTCCGGTCTGATGA GTCCGTGAGGACGAAACAGCCTCTACAAATAATTTTGTTTAAAA CAACACCCACTAAGATAACTCTAGAAATAATTTTGTTTAACTTT AAGAAGGAGATATACAT |
| Lac Promoter region SEQ ID NO: 27 | ATTCACCACCCTGAATTGACTCTCTTCCGGGCGCTATCATGCCA TACCGCGAAAGGTTTTGCGCCATTCGATGGCGCGCCGCTTCGTC AGGCCACATAGCTTTCTTGTTCTGATCGGAACGATCGTTGGCTG TGTTGACAATTAATCATCGGCTCGTATAATGTGTGGAATTGTGA GCGCTCACAATTAGCTGTCACCGGATGTGCTTTCCGGTCTGATG AGTCCGTGAGGACGAAACAGCCTCTACAAATAATTTTGTTTAA ACAACACCCACTAAGATAACTCTAGAAATAATTTTGTTTAACTT TAAGAAGGAGATATACAT |
| LacO | GGAATTGTGAGCGCTCACAATT |
| LacI (in reverse orientation) SEQ ID NO: 28 | TCACTGCCCGCTTTCCAGTCGGGAAACCTGTCGTGCCAGCTGCA TTAATGAATCGGCCAACGCGCGGGGAGAGGCGGTTTGCGTATT GGGCGCCAGGGTGGTTTTTCTTTTCACCAGTGAGACTGGCAACA GCTGATTGCCCTTCACCGCCTGGCCCTGAGAGAGTTGCAGCAAG CGGTCCACGCTGGTTTGCCCCAGCAGGCGAAAATCCTGTTTGAT GGTGGTTAACGGCGGGATATAACATGAGCTATCTTCGGTATCGT CGTATCCCACTACCGAGATATCCGCACCAACGCGCAGCCCGGA CTCGGTAATGGCGCGCATTGCGCCCAGCGCCATCTGATCGTTGG CAACCAGCATCGCAGTGGGAACGATGCCCTCATTCAGCATTTGC ATGGTTTGTTGAAAACCGGACATGGCACTCCAGTCGCCTTCCCG TTCCGCTATCGGCTGAATTTGATTGCGAGTGAGATATTTATGCC AGCCAGCCAGACGCAGACGCGCCGAGACAGAACTTAATGGGCC CGCTAACAGCGCGATTTGCTGGTGACCCAATGCGACCAGATGCT CCACGCCCAGTCGCGTACCGTCCTCATGGGAGAAAATAATACT GTTGATGGGTGTCTGGTCAGAGACATCAAGAAATAACGCCGGA ACATTAGTGCAGGCAGCTTCCACAGCAATGGCATCCTGGTCATC CAGCGGATAGTTAATGATCAGCCCACTGACGCGTTGCGCGAGA AGATTGTGCACCGCCGCTTTACAGGCTTCGACGCCGCTTCGTTC TACCATCGACACCACCACGCTGGCACCCAGTTGATCGGCGCGA GATTTAATCGCCGCGACAATTTGCGACGGCGCGTGCAGGGCCA GACTGGAGGTGGCAACGCCAATCAGCAACGACTGTTTGCCCGC CAGTTGTTGTGCCACGCGGTTGGGAATGTAATTCAGCTCCGCCA TCGCCGCTTCCACTTTTTCCCGCGTTTTCGCAGAAACGTGGCTG GCCTGGTTCACCACGCGGGAAACGGTCTGATAAGAGACACCGG CATACTCTGCGACATCGTATAACGTTACTGGTTTCAT |
| LacI polypeptide sequence SEQ ID NO: 29 | MKPVTLYDVAEYAGVSYQTVSRVVNQASHVSAKTREKVEAAMA ELNYIPNRVAQQLAGKQSLLIGVATSSLALHAPSQIVAAIKSRADQ LGASVVVSMVERSGVEACKAAVHNLLAQRVSGLIINYPLDDQDAI AVEAACTNVPALFLDVSDQTPINSIIFSHEDGTRLGVEHLVALGHQ QIALLAGPLSSVSARLRLAGWHKYLTRNQIQPIAEREGDWSAMSG FQQTMQMLNEGIVPTAMLVANDQMALGAMRAITESGLRVGADIS VVGYDDTEDSSCYIPPLTTIKQDFRLLGQTSVDRLLQLSQGQAVKG NQLLPVSLVKRKTTLAPNTQTASPRALADSLMQLARQVSRLESGQ |
| Region comprising Temperature sensitive promoter SEQ ID NO: 30 | ACGTTAAATCTATCACCGCAAGGGATAAATATCTAACACCGTGC GTGTTGACTATTTTACCTCTGGCGGTGATAATGGTTGCATAGCT GTCACCGGATGTGCTTTCCGGTCTGATGAGTCCGTGAGGACGAA ACAGCCTCTACAAATAATTTTGTTTAAAACAACACCCACTAAGA TAACTCTAGAAATAATTTTGTTTAACTTTAAGAAGGAGATATAC AT |
| mutant cI857 repressor SEQ ID NO: 31 | TCAGCCAAACGTCTCTTCAGGCCACTGACTAGCGATAACTTTCC CCACAACGGAACAACTCTCATTGCATGGGATCATTGGGTACTGT GGGTTTAGTGGTTGTAAAAACACCTGACCGCTATCCCTGATCAG TTTCTTGAAGGTAAACTCATCACCCCCAAGTCTGGCTATGCAGA AATCACCTGGCTCAACAGCCTGCTCAGGGTCAACGAGAATTAA CATTCCGTCAGGAAAGCTTGGCTTGGAGCCTGTTGGTGCGGTCA TGGAATTACCTTCAACCTCAAGCCAGAATGCAGAATCACTGGCT TTTTTGGTTGTGCTTACCCATCTCTCCGCATCACCTTTGGTAAAG GTTCTAAGCTTAGGTGAGAACATCCCTGCCTGAACATGAGAAA AAACAGGGTACTCATACTCACTTCTAAGTGACGGCTGCATACTA ACCGCTTCATACATCTCGTAGATTTCTCTGGCGATTGAAGGGCT AAATTCTTCAACGCTAACTTTGAGAATTTTTGTAAGCAATGCGG CGTTATAAGCATTTAATGCATTGATGCCATTAAATAAAGCACCA ACGCCTGACTGCCCCATCCCCATCTTGTCTGCGACAGATTCCTG |

TABLE 18-continued

Inducible promoter construct sequences

| Description | Sequence |
|---|---|
| | GGATAAGCCAAGTTCATTTTTCTTTTTTTCATAAATTGCTTTAAG<br>GCGACGTGCGTCCTCAAGCTGCTCTTGTGTTAATGGTTTCTTTTT<br>TGTGCTCAT |
| RBS and leader region SEQ ID NO: 32 | CTCTAGAAATAATTTTGTTTAACTTTAAGAAGGAGATATACAT |
| mutant cI857 repressor polypeptide sequence SEQ ID NO: 33 | MSTKKKPLTQEQLEDARRLKAIYEKKKNELGLSQESVADKMGMG<br>QSGVGALFNGINALNAYNAALLTKILKVSVEEFSPSIAREIYEMYE<br>AVSMQPSLRSEYEYPVFSHVQAGMFSPKLRTFTKGDAERWVSTTK<br>KASDSAFWLEVEGNSMTAPTGSKPSFPDGMLILVDPEQAVEPGDF<br>CIARLGGDEFTFKKLIRDSGQVFLQPLNPQYPMIPCNESCSVVGKVI<br>ASQWPEETFG |
| TetR-Tet promoter construct SEQ ID NO: 34 | *Ttaagacccactttcacatttaagttgtattctaatccgcatatgatcaattcaaggccgaataagaagg*<br>*ctggctctgcaccttggtgatcaaataattcgatagcttgtcgtaataatggcggcatactatcagtagta*<br>*ggtgtttccctttcttctttagcgacttgatgctcttgatcttccaatacgcaacctaaagtaaaatgcccca*<br>*cagcgctgagtgcatataatgcattctctagtgaaaaaccttgttggcataaaaaggctaattgattttcg*<br>*agagtttcatactgttatctgtaggccgtgtacctaaatgtacttttgctccatcgcgatgacttagtaaag*<br>*cacatctaaaacttttagcgttattacgtaaaaaatcttgccagctttccccttctaaagggcaaaagtga*<br>*gtatggtgcctatctaacatctcaatggctaaggcgtcgagcaaagcccgcttattttttacatgccaata*<br>*caatgtaggctgctctacacctagcttctgggcgagtttacgggttgttaaaccttcgattccgacctcatt*<br>*aagcagctctaatgcgctgttaatcactttactttt atctaatctagacat*cattaattcctaattttt**gttgaca**<br>**ctctatcattgatagagttattttaccactccctatcagtgatagagaa**aagtgaa*ctctagaaataatt*<br>*ttgtttaactttaagaaggagatatacat* |
| PssB promoter SEQ ID NO: 35 | tcacctttcccggattaaacgctttttttgcccggtggcatggtgctaccggcgatcacaaacggttaattatg<br>acacaaattgacctgaatgaatatacagtattggaatgcattacccggagtgttgtgtaacaatgtctggcca<br>ggtttgtttcccggaaccgaggtcacaacatagtaaaagcgctattggtaatggtacaatcgcgcgtttaca<br>cttattc |

Constitutive Promoters

In some embodiments, the gene encoding the payload is present on a plasmid and operably linked to a constitutive promoter. In some embodiments, the gene encoding the payload is present on a chromosome and operably linked to a promoter that is induced by change in temperature from a non-permissive temperature to a permissive temperature. In some embodiments, the gene encoding the payload is present on a chromosome and operably linked to a constitutive promoter.

In some embodiments, the constitutive promoter is active under in vivo conditions, e.g., the gut and/or conditions of the tumor microenvironment, as described herein. In some embodiments, the promoters are active under in vitro conditions, e.g., various cell culture and/or cell manufacturing conditions, as described herein. In some embodiments, the constitutive promoter is active under in vivo conditions, e.g., the gut and/or conditions of the tumor microenvironment, as described herein, and under in vitro conditions, e.g., various cell culture and/or cell production and/or manufacturing conditions, as described herein.

In some embodiments, the constitutive promoter that is operably linked to the gene encoding the payload is active in various exogenous environmental conditions (e.g., in vivo and/or in vitro and/or production/manufacturing conditions). In some embodiments, the constitutive promoter is active in exogenous environmental conditions specific to the gut of a mammal and/or specific to conditions of the tumor microenvironment. In some embodiments, the constitutive promoter is active in exogenous environmental conditions specific to the small intestine of a mammal. In some embodiments, the constitutive promoter is active in low-oxygen or anaerobic conditions such as the environment of the mammalian gut and/or conditions of the tumor microenvironment. In some embodiments, the constitutive promoter is active in the presence of molecules or metabolites that are specific to the gut of a mammal and/or conditions of the tumor microenvironment. In some embodiments, the constitutive promoter is directly or indirectly induced by a molecule that is co-administered with the bacterial cell. In some embodiments, the constitutive promoter is active in the presence of molecules or metabolites or other conditions, that are present during in vitro culture, cell production and/or manufacturing conditions.

Bacterial constitutive promoters are known in the art and are described in International Patent Application PCT/US2017/013072, filed Jan. 11, 2017, published as WO2017/123675, the contents of which is herein incorporated by reference in its entirety.

Ribosome Binding Sites

In some embodiments, ribosome binding sites are added, switched out or replaced. By testing a few ribosome binding sites, expression levels can be fine-tuned to the desired level. Non-limiting examples of RBS are listed at Registry of standard biological parts and are described in are described in International Patent Application PCT/US2017/013072, filed Jan. 11, 2017, published as WO2017/123675, the contents of which is herein incorporated by reference in its entirety.

Induction of Payloads During Strain Culture

Induction of payloads during culture is described in International Patent Application PCT/US2017/013072, filed Jan. 11, 2017, published as WO2017/123675, International Patent Applications PCT/US2016/032562, filed—May 13, 2016, published as WO2016183531, and PCT/US2016/062369, filed Nov. 16, 2016 and published as WO2017087580, the contents of each of which are herein incorporated by reference in their entireties.

In some embodiments, it is desirable to pre-induce payload or protein of interest expression and/or payload activity prior to administration. Such payload or protein of interest may be an effector intended for secretion or may be an enzyme which catalyzes a metabolic reaction to produce an effector. In other embodiments, the protein of interest is an enzyme which catabolizes a harmful metabolite. In such situations, the strains are pre-loaded with active payload or protein of interest. In such instances, the genetically engineered bacteria of the invention express one or more protein(s) of interest, under conditions provided in bacterial culture during cell growth, expansion, purification, fermentation, and/or manufacture prior to administration in vivo. Such culture conditions can be provided in a flask, fermenter or other appropriate culture vessel, e.g., used during cell growth, cell expansion, fermentation, recovery, purification, formulation, and/or manufacture. As used herein, the term "bacterial culture" or bacterial cell culture" or "culture" refers to bacterial cells or microorganisms, which are maintained or grown in vitro during several production processes, including cell growth, cell expansion, recovery, purification, fermentation, and/or manufacture. As used herein, the term "fermentation" refers to the growth, expansion, and maintenance of bacteria under defined conditions. Fermentation may occur under a number of cell culture conditions, including anaerobic or low oxygen or oxygenated conditions, in the presence of inducers, nutrients, at defined temperatures, and the like.

Culture conditions are selected to achieve optimal activity and viability of the cells, while maintaining a high cell density (high biomass) yield. A number of cell culture conditions and operating parameters are monitored and adjusted to achieve optimal activity, high yield and high viability, including oxygen levels (e.g., low oxygen, microaerobic, aerobic), temperature of the medium, and nutrients and/or different growth media, chemical and/or nutritional inducers and other components provided in the medium.

In some embodiments, the one or more protein(s) of interest and are directly or indirectly induced, while the strains is grown up for in vivo administration. Without wishing to be bound by theory, pre-induction may boost in vivo activity, e.g., in the gut or a tumor. If the bacterial residence time in a particular gut compartment is relatively short, the bacteria may pass through the small intestine without reaching full in vivo induction capacity. In contrast, if a strain is pre-induced and preloaded, the strains are already fully active, allowing for greater activity more quickly as the bacteria reach the intestine. Ergo, no transit time is "wasted", in which the strain is not optimally active. As the bacteria continue to move through the intestine, in vivo induction occurs under environmental conditions of the gut (e.g., low oxygen, or in the presence of gut metabolites). Similarly, if a tumor targeting or other bacterium is pre-induced and preloaded, this may allow for greater activity more quickly as the bacteria reach the gut or the tumor, either through systemic administration or intratumor injection, as described herein. Once in the gut or the tumor, in vivo induction occurs, e.g., under conditions of the tumor microenvironment.

In one embodiment, expression of one or more payload(s), is induced during cell growth, cell expansion, fermentation, recovery, purification, formulation, and/or manufacture. In one embodiment, expression of several different proteins of interest is induced during cell growth, cell expansion, fermentation, recovery, purification, formulation, and/or manufacture.

In some embodiments, the strains are administered without any pre-induction protocols during strain growth prior to in vivo administration.

Anaerobic Induction

In some embodiments, cells are induced under anaerobic or low oxygen conditions in culture. In such instances, cells are grown (e.g., for 1.5 to 3 hours) until they have reached a certain OD, e.g., ODs within the range of 0.1 to 10, indicating a certain density e.g., ranging from 1×10^8 to 1×10^11, and exponential growth and are then switched to anaerobic or low oxygen conditions for approximately 3 to 5 hours. In some embodiments, strains are induced under anaerobic or low oxygen conditions, e.g. to induce FNR promoter activity and drive expression of one or more payload(s) and/or transporters under the control of one or more FNR promoters.

In one embodiment, expression of one or more payload(s), is under the control of one or more FNR promoter(s) and is induced during cell growth, cell expansion, fermentation, recovery, purification, formulation, and/or manufacture under anaerobic or low oxygen conditions. In one embodiment, expression of several different proteins of interest is under the control of one or more FNR promoter(s) and is induced during cell growth, cell expansion, fermentation, recovery, purification, formulation, and/or manufacture under anaerobic or low oxygen conditions.

Without wishing to be bound by theory, strains that comprise one or more payload(s) under the control of an FNR promoter, may allow expression of payload(s) from these promoters in vitro, under anaerobic or low oxygen culture conditions, and in vivo, under the low oxygen conditions found in the gut and/or conditions of the tumor microenvironment.

In some embodiments, promoters linked to the payload of interest may be inducible by arabinose, cumate, and salicylate, IPTG, rhamnose, tetracycline, and/or other chemical and/or nutritional inducers can be induced under anaerobic or low oxygen conditions in the presence of the chemical and/or nutritional inducer. In particular, strains may comprise a combination of gene sequence(s), some of which are under control of FNR promoters and others which are under control of promoters induced by chemical and/or nutritional inducers. In some embodiments, strains may comprise one or more payload gene sequence(s) and/or under the control of one or more FNR promoter(s), and one or more payload gene sequence(s) under the control of a one or more constitutive promoter(s) described herein.

Aerobic Induction

In some embodiments, it is desirable to prepare, pre-load and pre-induce the strains under aerobic conditions. This allows more efficient growth and viability, and, in some cases, reduces the build-up of toxic metabolites. In such instances, cells are grown (e.g., for 1.5 to 3 hours) until they have reached a certain OD, e.g., ODs within the range of 0.1 to 10, indicating a certain density e.g., ranging from 1×10^8 to 1×10^11, and exponential growth and are then induced through the addition of the inducer or through other means, such as shift to a permissive temperature, for approximately 3 to 5 hours.

In some embodiments, promoters inducible by arabinose, cumate, and salicylate, IPTG, rhamnose, tetracycline, and/or other chemical and/or nutritional inducers described herein or known in the art can be induced under aerobic conditions in the presence of the chemical and/or nutritional inducer during cell growth, cell expansion, fermentation, recovery, purification, formulation, and/or manufacture. In one embodiment, expression of one or more payload(s) is under the control of one or more promoter(s) regulated by chemical and/or nutritional inducers and is induced during cell growth, cell expansion, fermentation, recovery, purification, formulation, and/or manufacture under aerobic conditions.

In some embodiments, genetically engineered strains comprise gene sequence(s) which are induced under aerobic culture conditions. In some embodiments, these strains further comprise FNR inducible gene sequence(s) for in vivo activation in the gut and/or conditions of the tumor microenvironment. In some embodiments, these strains do not further comprise FNR inducible gene sequence(s) for in vivo activation in the gut and/or conditions of the tumor microenvironment.

Microaerobic Induction

In some embodiments, viability, growth, and activity are optimized by pre-inducing the bacterial strain under microaerobic conditions. In some embodiments, microaerobic conditions are best suited to "strike a balance" between optimal growth, activity and viability conditions and optimal conditions for induction; in particular, if the expression of the one or more payload(s) are driven by an anaerobic and/or low oxygen promoter, e.g., a FNR promoter. In such instances, cells are for example grown (e.g., for 1.5 to 3 hours) until they have reached a certain OD, e.g., ODs within the range of 0.1 to 10, indicating a certain density e.g., ranging from 1×10^8 to 1×10^11, and exponential growth and are then induced through the addition of the inducer or through other means, such as shift to at a permissive temperature, for approximately 3 to 5 hours.

In one embodiment, expression of one or more payload(s) is under the control of one or more FNR promoter(s) and is induced during cell growth, cell expansion, fermentation, recovery, purification, formulation, and/or manufacture under microaerobic conditions.

Without wishing to be bound by theory, strains that comprise one or more payload(s) under the control of an FNR promoter, may allow expression of payload(s) from these promoters in vitro, under microaerobic culture conditions, and in vivo, under the low oxygen conditions found in the gut and/or conditions of the tumor microenvironment.

In some embodiments, promoters inducible by arabinose, cumate, and salicylate, IPTG, rhamnose, tetracycline, and/or other chemical and/or nutritional inducers can be induced under microaerobic conditions in the presence of the chemical and/or nutritional inducer. In particular, strains may comprise a combination of gene sequence(s), some of which are under control of FNR promoters and others which are under control of promoters induced by chemical and/or nutritional inducers. In some embodiments, strains may comprise one or more payload gene sequence(s) under the control of one or more FNR promoter(s), and one or more payload gene sequence(s) under the control of a one or more constitutive promoter(s) described herein.

In one embodiment, expression of one or more payload(s) is under the control of one or more promoter(s) regulated by chemical and/or nutritional inducers and is induced during cell growth, cell expansion, fermentation, recovery, purification, formulation, and/or manufacture under microaerobic conditions.

In some embodiments, it is desirable to pre-induce payload or protein of interest expression and/or payload activity prior to administration. Such payload or protein of interest may be an effector intended for secretion or may be an enzyme which catalyzes a metabolic reaction to produce an effector. In other embodiments, the protein of interest is an enzyme which catabolizes a harmful metabolite. In such situations, the strains are pre-loaded with active payload or Generation of Bacterial Strains with Enhanced Ability to Transport Biomolecules Due to their ease of culture, short generation times, very high population densities and small genomes, microbes can be evolved to unique phenotypes in abbreviated timescales. Adaptive laboratory evolution (ALE) is the process of passaging microbes under selective pressure to evolve a strain with a preferred phenotype. Most commonly, this is applied to increase utilization of carbon/energy sources or adapting a strain to environmental stresses (e.g., temperature, pH), whereby mutant strains more capable of growth on the carbon substrate or under stress will outcompete the less adapted strains in the population and will eventually come to dominate the population.

This same process can be extended to any essential metabolite by creating an auxotroph. An auxotroph is a strain incapable of synthesizing an essential metabolite and must therefore have the metabolite provided in the media to grow. In this scenario, by making an auxotroph and passaging it on decreasing amounts of the metabolite, the resulting dominant strains should be more capable of obtaining and incorporating this essential metabolite.

For example, if the biosynthetic pathway for producing an amino acid is disrupted a strain capable of high-affinity capture of said amino acid can be evolved via ALE. First, the strain is grown in varying concentrations of the auxotrophic amino acid, until a minimum concentration to support growth is established. The strain is then passaged at that concentration, and diluted into lowering concentrations of the amino acid at regular intervals. Over time, cells that are most competitive for the amino acid—at growth-limiting concentrations—will come to dominate the population. These strains will likely have mutations in their amino acid-transporters resulting in increased ability to import the essential and limiting amino acid.

Similarly, by using an auxotroph that cannot use an upstream metabolite to form an amino acid, a strain can be evolved that not only can more efficiently import the upstream metabolite, but also convert the metabolite into the essential downstream metabolite. These strains will also evolve mutations to increase import of the upstream metabolite, but may also contain mutations which increase expression or reaction kinetics of downstream enzymes, or that reduce competitive substrate utilization pathways.

In the previous examples, a metabolite innate to the microbe was made essential via mutational auxotrophy and selection was applied with growth-limiting supplementation of the endogenous metabolite. However, phenotypes capable of consuming non-native compounds can be evolved by tying their consumption to the production of an essential compound. For example, if a gene from a different organism is isolated which can produce an essential compound or a precursor to an essential compound this gene can be recombinantly introduced and expressed in the heterologous host. This new host strain will now have the ability to synthesize an essential nutrient from a previously non-metabolizable substrate. Hereby, a similar ALE process can be applied by creating an auxotroph incapable of converting an immediately downstream metabolite and selecting in growth-limiting amounts of the non-native compound with concurrent expression of the recombinant enzyme. This will result in mutations in the transport of the non-native substrate, expression and activity of the heterologous enzyme and expression and activity of downstream native enzymes. It should be emphasized that the key requirement in this process is the ability to tether the consumption of the non-native metabolite to the production of a metabolite essential to growth.

Once the basis of the selection mechanism is established and minimum levels of supplementation have been established, the actual ALE experimentation can proceed. Throughout this process several parameters must be vigilantly monitored. It is important that the cultures are maintained in an exponential growth phase and not allowed to reach saturation/stationary phase. This means that growth rates must be check during each passaging and subsequent dilutions adjusted accordingly. If growth rate improves to such a degree that dilutions become large, then the concentration of auxotrophic supplementation should be decreased such that growth rate is slowed, selection pressure is increased and dilutions are not so severe as to heavily bias subpopulations during passaging. In addition, at regular intervals cells should be diluted, grown on solid media and individual clones tested to confirm growth rate phenotypes observed in the ALE cultures.

Predicting when to halt the stop the ALE experiment also requires vigilance. As the success of directing evolution is tied directly to the number of mutations "screened" throughout the experiment and mutations are generally a function of errors during DNA replication, the cumulative cell divisions (CCD) acts as a proxy for total mutants which have been screened. Previous studies have shown that beneficial phenotypes for growth on different carbon sources can be isolated in about $10^{11.2}$ CCD[1]. This rate can be accelerated by the addition of chemical mutagens to the cultures—such as N-methyl-N-nitro-N-nitrosoguanidine (NTG)—which causes increased DNA replication errors. However, when continued passaging leads to marginal or no improvement in growth rate the population has converged to some fitness maximum and the ALE experiment can be halted.

At the conclusion of the ALE experiment, the cells should be diluted, isolated on solid media and assayed for growth phenotypes matching that of the culture flask. Best performers from those selected are then prepped for genomic DNA and sent for whole genome sequencing. Sequencing with reveal mutations occurring around the genome capable of providing improved phenotypes, but will also contain silent mutations (those which provide no benefit but do not detract from desired phenotype). In cultures evolved in the presence of NTG or other chemical mutagen, there will be significantly more silent, background mutations. If satisfied with the best performing strain in its current state, the user can proceed to application with that strain. Otherwise the contributing mutations can be deconvoluted from the evolved strain by reintroducing the mutations to the parent strain by genome engineering techniques. See Lee, D.-H., Feist, A. M., Barrett, C. L. & Palsson, B. Ø. Cumulative Number of Cell Divisions as a Meaningful Timescale for Adaptive Laboratory Evolution of *Escherichia coli. PLoS ONE* 6, e26172 (2011).

Metabolite Transport

In some embodiments, the genetically engineered bacteria further comprise a gene encoding a transporter. Transporters may be expressed or modified in the genetically engineered bacteria of the invention in order to enhance phenylalanine transport into the cell. Non-limiting examples of such transporters are described in pending International Patent Application PCT/US2016/032565, the contents of which is herein incorporated by reference in its entirety.

Such transporters are membrane transport protein that is capable of transporting metabolites into bacterial cells. In some embodiments, the gene encoding the transporter in the genetically modified bacteria of the invention is not modified. In some embodiments, the genetically engineered bacteria of the invention comprise multiple copies of the transporter gene. In some embodiments, the genetically engineered bacteria of the invention comprise multiple copies of a non-native transporter gene. In some embodiments, the genetically engineered bacteria of the invention comprise a transporter gene that is controlled by its native promoter, an inducible promoter, a promoter that is stronger than the native promoter, e.g., the GlnRS promoter or the P(Bla) promoter, or a constitutive promoter. In some embodiments, the promoter is induced under conditions during manufacture or other in vitro conditions. In some embodiments, expression of the transporter gene is controlled by a different promoter than the promoter that controls expression of the gene encoding the one or more effector molecule. In some embodiments, expression of the transporter gene is controlled by the same promoter that controls expression of the one or more effector molecules. In some embodiments, the transporter gene and the one or more effector molecules are divergently transcribed from a promoter region.

In some embodiments, the native transporter gene is mutagenized, mutants exhibiting increased transport are selected, and the mutagenized transporter gene is isolated and inserted into the genetically engineered bacteria (see, e.g., Pi et al., 1996; Pi et al., 1998).

In some embodiments, the genetically engineered bacteria of the invention produce PAL under exogenous environmental conditions, such as the low-oxygen environment of the mammalian gut, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. In some embodiments, the genetically engineered bacteria of the invention produce PAL under exogenous environmental conditions, such as the low-oxygen environment of the mammalian gut, and increase hippuric acid in the urine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing to hippurate. In embodiments using genetically modified forms of these bacteria, PAL-mediated processing of phenylalanine will be appreciable under exogenous environmental conditions.

Figure 16A:
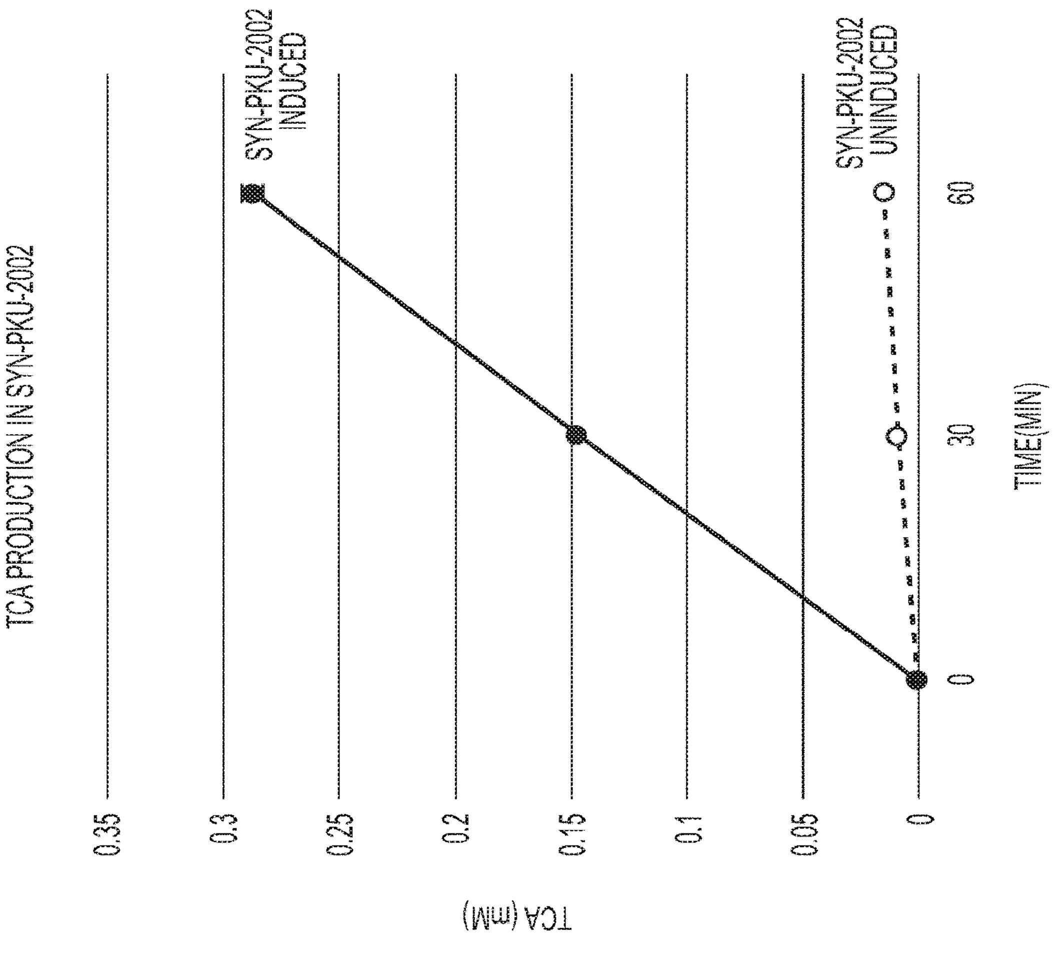
FIG. 16A and FIG. 16B depict line graphs showing TCA production (FIG. 16A) and Phenylpyruvate production (FIG. 16B) in SYN-PKU-2002. Both are measures of the degradation of phenylalanine in vitro by SYN-PKU-2002. SYN-PKU-2002 was prepared by growth in Lysogeny Broth (LB) either aerobically (the uninduced state) or anaerobically with the addition of IPTG and arabinose (the induced state). In vitro, incubation of activated SYN-PKU-2002 in the presence of phenylalanine results in the production of TCA and PP over time, demonstrating that SYN-PKU-2002 is capable of metabolizing phenylalanine.
Figure 16B:
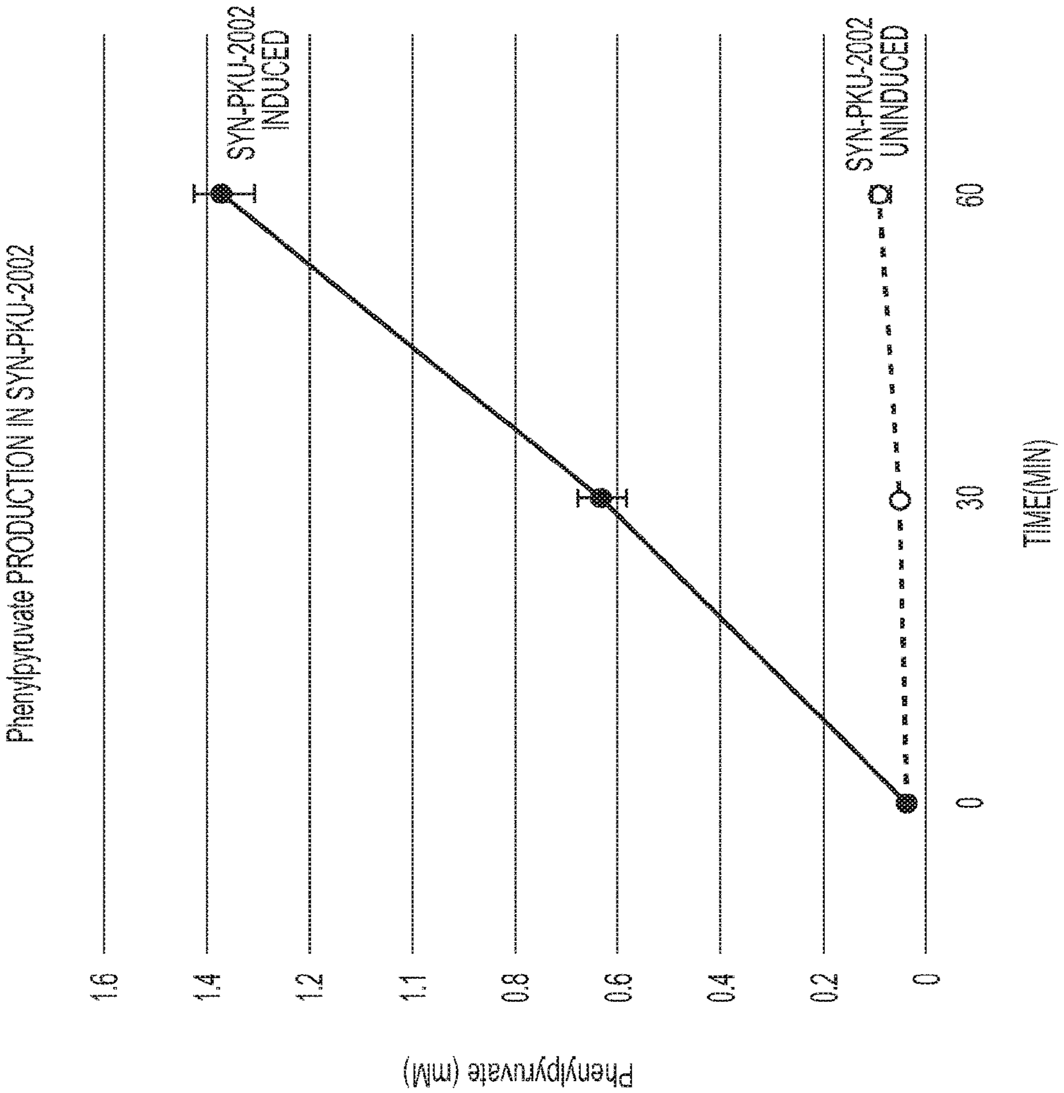

In some embodiments, the genetically engineered bacteria of the invention produce PAL under exogenous environmental conditions, such as under bacterial culture conditions in vitro, and increase transcinnamic acid in the media by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Phenylalanine may be measured by methods known in the art, e.g., blood sampling and mass spectrometry. In some embodiments, cinnamate is measured by methods known in the art to assess PAL activity. Cinnamate production is directly correlated with phenylalanine degradation, and in some embodiments, that cinnamate may be used as an alternative biomarker for strain activity (FIG. 16B). Cinnamate can be further degraded to hippuric acid by liver enzymes; both can be measured as described in Example 24-26. As shown herein, TCA is rapidly converted to hippuric acid in vivo, and hippuric acid subsequently accumulates in the urine. Therefore, hippurate, in blood and in particular in the urine, may be an even better biomarker for phenylalanine degradation in vivo. In some embodiments, PAL expression is measured by methods known in the art, e.g., measurement of blood phenylalanine levels. Hippuric acid may be measured according to methods described herein in the Examples, and methods known in the art.

In some embodiments, the genetically engineered bacteria of the invention produce LAAD, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing. In embodiments using genetically modified forms of these bacteria, LAAD-mediated processing of phenylalanine will be appreciable under exogenous environmental conditions. Phenylalanine may be measured by methods known in the art, e.g., blood sampling and mass spectrometry. Pyruvic acid and phenylpyruvate, the LAAD generated degradation products can be measured using mass spectrometry as described in Examples 24-26, and can be used as an additional readout of LAAD activity.

In some embodiments, the genetically engineered bacteria of the invention produce more than one PME, e.g., PAL, PAH, and/or LAAD, under exogenous environmental conditions, such as in vivo or under bacterial culture conditions in vitro, and reduce blood phenylalanine and/or increase transcinnamic acid in the media by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. In any of these embodiments, the bacteria may further comprise gene sequence(s) encoding one or more Phe transporter polypeptides.

In some embodiments, one or more PME(s), e.g., PAL, LAAD, and/or PAH, are expressed on a low-copy plasmid.

In some embodiments, the gene(s) encoding the one or more transporter(s) is located on a plasmid or in the chromosome and expression may be regulated by any of the promoters disclosed herein.

In other embodiments, the genetically engineered bacteria encode one or more transporter(s) which are directly or indirectly induced in vivo administration, e.g., are expressed under the control of an inducible promoter that is responsive conditions or to specific molecules or metabolites in the exogenous in vivo environment, e.g., the gut. In some embodiments, the promoter is induced by gut specific molecules, or low oxygen conditions. In some embodiments, the bacterial strains are administered in combination with a chemical and/or nutritional inducer.

Figure 15:
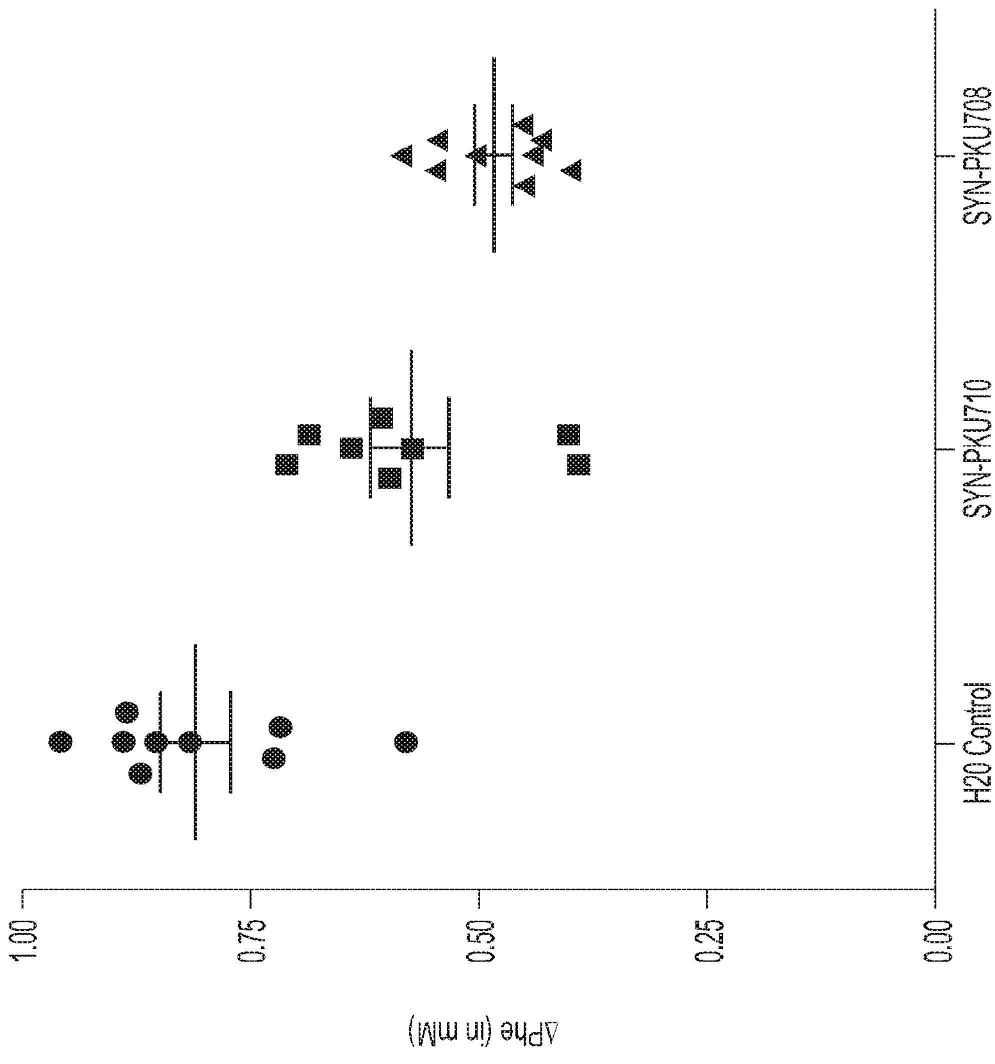
FIG. 15 depicts blood phenylalanine concentrations relative to baseline at 4 hours post SC phenylalanine injection, comparing strains SYN-PKU710 and SYN-PKU708. Mice were administered single dose of phenylalanine by subcutaneous injection at 0.1 mg per gram body weight. At 1, 2 and 3 h post Phe challenge, the bacteria (or water) were administered to mice by oral gavage (300 ul/dose, total of 3×e10 cfu/mouse). The percentage decrease in deltaPhe SYN-PKU710 and SYN-PKU708 were calculated to be 29% and 40%, respectively.

In some embodiments, one or more PME(s), e.g., PAL, LAAD, and/or PAH, are expressed on a high-copy plasmid. In some embodiments, the high-copy plasmid may be useful for increasing the PME, e.g., PAL, LAAD, and/or PAH, expression, thereby increasing the metabolism of phenylalanine and reducing hyperphenylalaninemia. In some embodiments, a genetically engineered bacterium comprising a the PME, e.g., PAL, LAAD, and/or PAH, expressed on a high-copy plasmid does not increase phenylalanine metabolism or decrease phenylalanine levels as compared to a genetically engineered bacterium comprising the same PME, e.g., PAL, LAAD, and/or PAH, expressed on a low-copy plasmid in the absence of heterologous pheP and additional copies of a native pheP. Genetically engineered bacteria comprising the same the PME gene(s), e.g., PAL, LAAD, and/or PAH gene(s) on high and low copy plasmids were generated. For example, either PAL1 or PAL3 on a high-copy plasmid and a low-copy plasmid were generated, and each metabolized and reduced phenylalanine to similar levels (FIG. 15). Thus, in some embodiments, the rate-limiting step of phenylalanine metabolism is phenylalanine availability (see, e.g., FIG. 16). In these embodiments, it may be advantageous to increase phenylalanine transport into the cell, thereby enhancing phenylalanine metabolism. In conjunction with pheP, even low-copy PAL plasmids are capable of almost completely eliminating Phe from a test sample (see, e.g., FIG. 16A). Furthermore, in some embodiments, that incorporate pheP, there may be additional advantages to using a low-copy PAL-expressing plasmid in conjunction in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

In some embodiments, a transporter may not increase phenylalanine degradation. For example, *Proteus mirabilis* LAAD is localized to the plasma membrane, with the enzymatic catalysis occurring in the periplasm. Phenylalanine can readily traverse the outer membrane without the need of a transporter. Therefore, in embodiments, in which the genetically engineered bacteria express LAAD, a transporter may not be needed or improve phenylalanine metabolism.

In some embodiments, the PME(s), e.g., PAL, LAAD, and/or PAH, gene(s) are expressed on a chromosome. In some embodiments, expression from the chromosome may be useful for increasing stability of expression of the PME. In some embodiments, the PME gene, e.g., PAL, LAAD, and/or PAH gene(s), is integrated into the bacterial chromosome at one or more integration sites in the genetically engineered bacteria. In some embodiments, the PME gene, e.g., PAL, LAAD, and/or PAH gene(s) is inserted into the bacterial genome at one or more of the following insertion sites in *E. coli* Nissle: malE/K, insB/I, araC/BAD, lacZ, agal/rsml, thyA, and malP/T. Any suitable insertion site may be used (see, e.g., FIG. 66 of WO2017087580, the contents of which are herein incorporated by reference in their entirety). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. In some embodiments, more than one copy, e.g., two, three, four, five, six, seven, eight, nine, ten or more copies of the PME gene, e.g., PAL, PAH, and/or LAAD is integrated into the bacterial chromosome at one or more integration sites in the genetically engineered bacteria. The more than one copy of a PME gene may be more than one copy of the same PME gene or more than one copy of different PME genes.

Exemplary constructs are shown in Tables 4-13 below. Table 4 shows the sequence of an exemplary construct comprising a gene encoding PheP and an FNR promoter sequence for chromosomal insertion (SEQ ID NO: 21B), with the pheP sequence underlined and the FNR promoter sequence bolded. Table 5 shows the sequence of an exemplary construct comprising a gene encoding PAL1 and an FNR promoter sequence on a high-copy plasmid (SEQ ID NO: 22B), with the PAL1 sequence underlined and the FNR promoter sequence bolded. Table 6 shows the sequence of an exemplary construct comprising a gene encoding PAL3 and an FNR promoter sequence on a high-copy plasmid (SEQ ID NO: 23B), with the PAL3 sequence underlined and the FNR promoter sequence bolded. Table 7 shows the sequence of an exemplary construct comprising a gene encoding PAL1 and a Tet promoter sequence on a high-copy plasmid (SEQ ID NO: 24B), with the PAL1 sequence underlined and the Tet promoter sequence bolded. Table 8 shows the sequence of an exemplary construct comprising a gene encoding PAL3 and a Tet promoter sequence on a high-copy plasmid (SEQ ID NO: 25B), with the PAL3 sequence underlined and the Tet promoter sequence bolded. Table 9 shows the sequence of an exemplary construct comprising a gene encoding PAL1 and an FNR promoter sequence on a low-copy plasmid (SEQ ID NO: 26B), with the PAL1 sequence underlined and the FNR promoter sequence bolded. Table 10 shows the sequence of an exemplary construct comprising a gene encoding PAL3 and an FNR promoter sequence on a low-copy plasmid (SEQ ID NO: 27B), with the PAL3 sequence underlined and the FNR promoter sequence bolded. Table 11 shows the sequence of an exemplary construct comprising a gene encoding PAL1 and a Tet promoter sequence on a low-copy plasmid (SEQ ID NO: 28B), with the PAL1 sequence underlined and the Tet promoter sequence bolded. Table 12 shows the sequence of an exemplary construct comprising a gene encoding PAL3 and a Tet promoter sequence on a low-copy plasmid (SEQ ID NO: 29B), with the PAL3 sequence underlined and the Tet promoter sequence bolded. Table 13 shows the sequence of an exemplary construct comprising a gene encoding PheP, a gene coding TetR, and a Tet promoter sequence for chromosomal insertion (SEQ ID NO: 30B), with the pheP sequence underlined, the TetR sequence boxed, and the FNR promoter sequence bolded.

TABLE 4

| Nucleotide sequences of FNR promoter-PheP construct (SEQ ID NO: 21B) |
|---|
| **CTCTTGATCGTTATCAATTCCCACGCTGTTTCAGAGCGTTACCTTGCCCTT** |
| **AAACATTAGCAATGTCGATTTATCAGAGGGCCGACAGGCTCCCACAGGAGA** |
| **AAACCG**ATGAAAAACGCGTCAACCGTATCGGAAGATACTGCGTCGAATCAA |
| GAGCCGACGCTTCATCGCGGATTACATAACCGTCATATTCAACTGATTGCG |
| TTGGGTGGCGCAATTGGTACTGGTCTGTTTCTTGGCATTGGCCCGGCGATT |
| CAGATGGCGGGTCCGGCTGTATTGCTGGGCTACGGCGTCGCCGGGATCATC |
| GCTTTCCTGATTATGCGCCAGCTTGGCGAAATGGTGGTTGAGGAGCCGGTA |

TABLE 4-continued

| Nucleotide sequences of FNR promoter-PheP construct (SEQ ID NO: 21B) |
|---|
| TCCGGTTCATTTGCCCACTTTGCCTATAAATACTGGGGACCGTTTGCGGGC |
| TTCCTCTCTGGCTGGAACTACTGGGTAATGTTCGTGCTGGTGGGAATGGCA |
| GAGCTGACCGCTGCGGGCATCTATATGCAGTACTGGTTCCCGGATGTTCCA |
| ACGTGGATTTGGGCTGCCGCCTTCTTTATTATCATCAACGCCGTTAACCTG |
| GTGAACGTGCGCTTATATGGCGAAACCGAGTTCTGGTTTGCGTTGATTAAA |
| GTGCTGGCAATCATCGGTATGATCGGCTTTGGCCTGTGGCTGCTGTTTTCT |
| GGTCACGGCGGCGAGAAAGCCAGTATCGACAACCTCTGGCGCTACGGTGGT |
| TTCTTCGCCACCGGCTGGAATGGGCTGATTTTGTCGCTGGCGGTAATTATG |
| TTCTCCTTCGGCGGTCTGGAGCTGATTGGGATTACTGCCGCTGAAGCGCGC |
| GATCCGGAAAAAAGCATTCCAAAAGCGGTAAATCAGGTGGTGTATCGCATC |
| CTGCTGTTTTACATCGGTTCACTGGTGGTTTTACTGGCGCTCTATCCGTGG |
| GTGGAAGTGAAATCCAACAGTAGCCCGTTTGTGATGATTTTCCATAATCTC |
| GACAGCAACGTGGTAGCTTCTGCGCTGAACTTCGTCATTCTGGTAGCATCG |
| CTGTCAGTGTATAACAGCGGGGTTTACTCTAACAGCCGCATGCTGTTTGGC |
| CTTTCTGTGCAGGGTAATGCGCCGAAGTTTTTGACTCGCGTCAGCCGTCGC |
| GGTGTGCCGATTAACTCGCTGATGCTTTCCGGAGCGATCACTTCGCTGGTG |
| GTGTTAATCAACTATCTGCTGCCGCAAAAAGCGTTTGGTCTGCTGATGGCG |
| CTGGTGGTAGCAACGCTGCTGTTGAACTGGATTATGATCTGTCTGGCGCAT |
| CTGCGTTTTCGTGCAGCGATGCGACGTCAGGGGCGTGAAACACAGTTTAAG |
| GCGCTGCTCTATCCGTTCGGCAACTATCTCTGCATTGCCTTCCTCGGCATG |
| ATTTTGCTGCTGATGTGCACGATGGATGATATGCGCTTGTCAGCGATCCTG |
| CTGCCGGTGTGGATTGTATTCCTGTTTATGGCATTTAAAACGCTGCGTCGG |
| AAATAA |

TABLE 5

| Nucleotide sequences of FNR promoter-PAL1 construct, high-copy (SEQ ID NO: 22B) |
|---|
| **CTCTTGATCGTTATCAATTCCCACGCTGTTTCAGAGCGTTACCTTGCCCTT** |
| **AAACATTAGCAATGTCGATTTATCAGAGGGCCGACAGGCTCCCACAGGAGA** |
| **AAACCG**ATGAAAACACTATCACAGGCCCAATCTAAAACTTCTTCACAGCAA |
| TTCAGCTTTACCGGGAACTCGTCTGCGAATGTAATTATCGGCAATCAAAAG |
| CTGACCATTAATGATGTAGCTCGCGTTGCCCGGAATGGCACTTTGGTGTCA |
| CTGACGAACAATACCGACATTCTGCAAGGTATTCAAGCTAGCTGCGATTAT |
| ATCAATAACGCCGTTGAATCTGGCGAGCCAATCTACGGGGTAACAAGCGGT |
| TTTGGTGGGATGGCGAACGTTGCCATTAGCCGTGAACAGGCGAGCGAACTT |
| CAGACCAACCTCGTTTGGTTCCTAAAGACAGGAGCTGGTAATAAGTTACCT |
| CTGGCTGACGTAAGAGCCGCGATGCTGCTTCGCGCTAATAGTCACATGCGC |
| GGCGCCAGTGGTATCCGTCTTGAGCTTATCAAGAGGATGGAAATCTTCCTC |
| AACGCGGGTGTCACACCATATGTTTATGAGTTTGGTAGTATCGGAGCCAGT |

TABLE 5-continued

| Nucleotide sequences of FNR promoter-PAL1 construct, high-copy (SEQ ID NO: 22B) |
|---|
| GGTGATCTTGTTCCCCTGAGTTATATTACGGGTTCATTGATTGGTTTAGAC |
| CCGTCCTTTAAAGTGGATTTTAACGGGAAAGAAATGGACGCCCCGACCGCT |
| TTACGACAGCTTAATCTGAGCCCACTTACTTTGCTCCCTAAAGAAGGTCTT |
| GCCATGATGAATGGCACCTCTGTGATGACTGGAATTGCCGCGAATTGTGTG |
| TATGACACGCAGATCCTAACGGCCATTGCCATGGGTGTTCACGCGTTGGAC |
| ATTCAAGCCCTGAATGGTACAAACCAGTCGTTTCATCCGTTTATCCATAAT |
| TCAAAACCCCATCCGGGACAGCTTTGGGCTGCTGATCAGATGATCTCACTC |
| CTGGCCAATAGTCAACTGGTTCGGGACGAGCTCGACGGCAAACATGATTAT |
| CGCGATCATGAGCTCATCCAGGACCGGTATTCACTTCGTTGTCTCCCACAA |
| TACCTGGGGCCTATCGTTGATGGTATATCTCAAATTGCGAAGCAAATTGAA |
| ATTGAGATCAATAGCGTAACCGACAACCCGCTTATCGATGTTGATAATCAG |
| GCCTCTTATCACGGTGGCAATTTTCTGGGCCAGTATGTTGGTATGGGGATG |
| GATCACCTGCGGTACTATATTGGGCTTCTGGCTAAACATCTTGATGTGCAG |
| ATTGCCTTATTAGCTTCACCAGAATTTTCAAATGGACTGCCGCCATCATTG |
| CTCGGTAACAGAGAAAGGAAAGTAAATATGGGCCTTAAGGGCCTTCAGATA |
| TGTGGTAACTCAATCATGCCCCTCCTGACCTTTTATGGGAACTCAATTGCT |
| GATCGTTTTCCGACACATGCTGAACAGTTTAACCAAAACATTAACTCACAG |
| GGCTATACATCCGCGACGTTAGCGCGTCGGTCCGTGGATATCTTCCAGAAT |
| TATGTTGCTATCGCTCTGATGTTCGGCGTACAGGCCGTTGATTTGCGCACT |
| TATAAAAAAACCGGTCACTACGATGCTCGGGCTTGCCTGTCGCCTGCCACC |
| GAGCGGCTTTATAGCGCCGTACGTCATGTTGTGGGTCAGAAACCGACGTCG |
| GACCGCCCCTATATTTGGAATGATAATGAACAAGGGCTGGATGAACACATC |
| GCCCGGATATCTGCCGATATTGCCGCCGGAGGTGTCATCGTCCAGGCGGTA |
| CAAGACATACTTCCTTGCCTGCATTAAGCTTGGCGTAATCATGGTCATAGC |
| TGTTTCCTGTGTGAAATTGTTATCCGCTCACAATTCCACACAACATACGAG |
| CCGGAAGCATAAAGTGTAAAGCCTGGGGTGCCTAATGAGTGAGCTAACTCA |
| CATTAATTGCGTTGCGCTCACTGCCCGCTTTCCAGTCGGGAAACCTGTCGT |
| GCCAGCTGCATTAATGAATCGGCCAACGCGCGGGGAGAGGCGGTTTGCGTA |
| TTGGGCGCTCTTCCGCTTCCTCGCTCACTGACTCGCTGCGCTCGGTCGTTC |
| GGCTGCGGCGAGCGGTATCAGCTCACTCAAAGGCGGTAATACGGTTATCCA |
| CAGAATCAGGGGATAACGCAGGAAAGAACATGTGAGCAAAAGGCCAGCAAA |
| AGGCCAGGAACCGTAAAAAGGCCGCGTTGCTGGCGTTTTTCCATAGGCTCC |
| GCCCCCCTGACGAGCATCACAAAAATCGACGCTCAAGTCAGAGGTGGCGAA |
| ACCCGACAGGACTATAAAGATACCAGGCGTTTCCCCCTGGAAGCTCCCTCG |
| TGCGCTCTCCTGTTCCGACCCTGCCGCTTACCGGATACCTGTCCGCCTTTC |
| TCCCTTCGGGAAGCGTGGCGCTTTCTCATAGCTCACGCTGTAGGTATCTCA |
| GTTCGGTGTAGGTCGTTCGCTCCAAGCTGGGCTGTGTGCACGAACCCCCCG |
| TTCAGCCCGACCGCTGCGCCTTATCCGGTAACTATCGTCTTGAGTCCAACC |

TABLE 5-continued

| Nucleotide sequences of FNR promoter-PAL1 construct, high-copy (SEQ ID NO: 22B) |
|---|
| CGGTAAGACACGACTTATCGCCACTGGCAGCAGCCACTGGTAACAGGATTA |
| GCAGAGCGAGGTATGTAGGCGGTGCTACAGAGTTCTTGAAGTGGTGGCCTA |
| ACTACGGCTACACTAGAAGAACAGTATTTGGTATCTGCGCTCTGCTGAAGC |
| CAGTTACCTTCGGAAAAAGAGTTGGTAGCTCTTGATCCGGCAAACAAACCA |
| CCGCTGGTAGCGGTGGTTTTTTTGTTTGCAAGCAGCAGATTACGCGCAGAA |
| AAAAAGGATCTCAAGAAGATCCTTTGATCTTTTCTACGGGGTCTGACGCTC |
| AGTGGAACGAAAACTCACGTTAAGGGATTTTGGTCATGAGATTATCAAAAA |
| GGATCTTCACCTAGATCCTTTTAAATTAAAAATGAAGTTTTAAATCAATCT |
| AAAGTATATATGAGTAAACTTGGTCTGACAGTTACCAATGCTTAATCAGTG |
| AGGCACCTATCTCAGCGATCTGTCTATTTCGTTCATCCATAGTTGCCTGAC |
| TCCCCGTCGTGTAGATAACTACGATACGGGAGGGCTTACCATCTGGCCCCA |
| GTGCTGCAATGATACCGCGAGACCCACGCTCACCGGCTCCAGATTTATCAG |
| CAATAAACCAGCCAGCCGGAAGGGCCGAGCGCAGAAGTGGTCCTGCAACTT |
| TATCCGCCTCCATCCAGTCTATTAATTGTTGCCGGGAAGCTAGAGTAAGTA |
| GTTCGCCAGTTAATAGTTTGCGCAACGTTGTTGCCATTGCTACAGGCATCG |
| TGGTGTCACGCTCGTCGTTTGGTATGGCTTCATTCAGCTCCGGTTCCCAAC |
| GATCAAGGCGAGTTACATGATCCCCCATGTTGTGCAAAAAAGCGGTTAGCT |
| CCTTCGGTCCTCCGATCGTTGTCAGAAGTAAGTTGGCCGCAGTGTTATCAC |
| TCATGGTTATGGCAGCACTGCATAATTCTCTTACTGTCATGCCATCCGTAA |
| GATGCTTTTCTGTGACTGGTGAGTACTCAACCAAGTCATTCTGAGAATAGT |
| GTATGCGGCGACCGAGTTGCTCTTGCCCGGCGTCAATACGGGATAATACCG |
| CGCCACATAGCAGAACTTTAAAAGTGCTCATCATTGGAAAACGTTCTTCGG |
| GGCGAAAACTCTCAAGGATCTTACCGCTGTTGAGATCCAGTTCGATGTAAC |
| CCACTCGTGCACCCAACTGATCTTCAGCATCTTTTACTTTCACCAGCGTTT |
| CTGGGTGAGCAAAAACAGGAAGGCAAAATGCCGCAAAAAAGGGAATAAGGG |
| CGACACGGAAATGTTGAATACTCATACTCTTCCTTTTTCAATATTATTGAA |
| GCATTTATCAGGGTTATTGTCTCATGAGCGGATACATATTTGAATGTATTT |
| AGAAAAATAAACAAATAGGGGTTCCGCGCACATTTCCCCGAAAAGTGCCAC |
| CTGACGTCTAAGAAACCATTATTATCATGACATTAACCTATAAAAATAGGC |
| GTATCACGAGGCCCTTTCGTCTCGCGCGTTTCGGTGATGACGGTGAAAACC |
| TCTGACACATGCAGCTCCCGGAGACGGTCACAGCTTGTCTGTAAGCGGATG |
| CCGGGAGCAGACAAGCCCGTCAGGGCGCGTCAGCGGGTGTTGGCGGGTGTC |
| GGGGCTGGCTTAACTATGCGGCATCAGAGCAGATTGTACTGAGAGTGCACC |
| ATATGCGGTGTGAAATACCGCACAGATGCGTAAGGAGAAAATACCGCATCA |
| GGCGCCATTCGCCATTCAGGCTGCGCAACTGTTGGGAAGGGCGATCGGTGC |
| GGGCCTCTTCGCTATTACGCCAGCTGGCGAAAGGGGGATGTGCTGCAAGGC |
| GATTAAGTTGGGTAACGCCAGGGTTTTCCCAGTCACGACGTT |

TABLE 6

Nucleotide sequences of FNR promoter-PAL3 construct, high-copy (SEQ ID NO: 23B)

**CTCTTGATCGTTATCAATTCCCACGCTGTTTCAGAGCGTTACCTTGCCCTT
AAACATTAGCAATGTCGATTTATCAGAGGGCCGACAGGCTCCCACAGGAGA
AAACCG**ATGAAAGCTAAAGATGTTCAGCCAACCATTATTATTAATAAAAAT
GGCCTTATCTCTTTGGAAGATATCTATGACATTGCGATAAAACAAAAAAA
GTAGAAATATCAACGGAGATCACTGAACTTTTGACGCATGGTCGTGAAAAA
TTAGAGGAAAAATTAAATTCAGGAGAGGTTATATATGGAATCAATACAGGA
TTTGGAGGGAATGCCAATTTAGTTGTGCCATTTGAGAAAATCGCAGAGCAT
CAGCAAAATCTGTTAACTTTTCTTTCTGCTGGTACTGGGGACTATATGTCC
AAACCTTGTATTAAAGCGTCACAATTTACTATGTTACTTTCTGTTTGCAAA
GGTTGGTCTGCAACCAGACCAATTGTCGCTCAAGCAATTGTTGATCATATT
AATCATGACATTGTTCCTCTGGTTCCTCGCTATGGCTCAGTGGGTGCAAGC
GGTGATTTAATTCCTTTATCTTATATTGCACGAGCATTATGTGGTATCGGC
AAAGTTTATTATATGGGCGCAGAAATTGACGCTGCTGAAGCAATTAAACGT
GCAGGGTTGACACCATTATCGTTAAAAGCCAAAGAAGGTCTTGCTCTGATT
AACGGCACCCGGGTAATGTCAGGAATCAGTGCAATCACCGTCATTAAACTG
GAAAAACTATTTAAAGCCTCAATTTCTGCGATTGCCCTTGCTGTTGAAGCA
TTACTTGCATCTCATGAACATTATGATGCCCGGATTCAACAAGTAAAAAAT
CATCCTGGTCAAAACGCGGTGGCAAGTGCATTGCGTAATTTATTGGCAGGT
TCAACGCAGGTTAATCTATTATCTGGGGTTAAAGAACAAGCCAATAAAGCT
TGTCGTCATCAAGAAATTACCCAACTAAATGATACCTTACAGGAAGTTTAT
TCAATTCGCTGTGCACCACAAGTATTAGGTATAGTGCCAGAATCTTTAGCT
ACCGCTCGGAAAATATTGGAACGGGAAGTTATCTCAGCTAATGATAATCCA
TTGATAGATCCAGAAAATGGCGATGTTCTACACGGTGGAAATTTTATGGGG
CAATATGTCGCCCGAACAATGGATGCATTAAAACTGGATATTGCTTTAATT
GCCAATCATCTTCACGCCATTGTGGCTCTTATGATGGATAACCGTTTCTCT
CGTGGATTACCTAATTCACTGAGTCCGACACCCGGCATGTATCAAGGTTTT
AAAGGCGTCCAACTTTCTCAAACCGCTTTAGTTGCTGCAATTCGCCATGAT
TGTGCTGCATCAGGTATTCATACCCTCGCCACAGAACAATACAATCAAGAT
ATTGTCAGTTTAGGTCTGCATGCCGCTCAAGATGTTTTAGAGATGGAGCAG
AAATTACGCAATATTGTTTCAATGACAATTCTGGTAGTTTGTCAGGCCATT
CATCTTCGCGGCAATATTAGTGAAATTGCGCCTGAAACTGCTAAATTTTAC
CATGCAGTACGCGAAATCAGTTCTCCTTTGATCACTGATCGTGCGTTGGAT
GAAGATATAATCCGCATTGCGGATGCAATTATTAATGATCAACTTCCTCTG
CCAGAAATCATGCTGGAAGAATAAGCTTGGCGTAATCATGGTCATAGCTGT
TTCCTGTGTGAAATTGTTATCCGCTCACAATTCCACACAACATACGAGCCG
GAAGCATAAAGTGTAAAGCCTGGGGTGCCTAATGAGTGAGCTAACTCACAT
TAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTG
GGCGCTCTTCCGCTTCCTCGCTCACTGACTCGCTGCGCTCGGTCGTTCGGC

TABLE 6-continued

Nucleotide sequences of FNR promoter-PAL3 construct, high-copy (SEQ ID NO: 23B)

TGCGGCGAGCGGTATCAGCTCACTCAAAGGCGGTAATACGGTTATCCACAG
AATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACC
CGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGG
TAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGT
GGAACGAAAACTCACGTTAAGGGATTTTGGTCATGAGATTATCAAAAAGGA
TCTTCACCTAGATCCTTTTAAATTAAAAATGAAGTTTTAAATCAATCTAAA
GTATATATGAGTAAACTTGGTCTGACAGTTACCAATGCTTAATCAGTGAGG
CACCTATCTCAGCGATCTGTCTATTTCGTTCATCCATAGTTGCCTGACTCC
CCGTCGTGTAGATAACTACGATACGGGAGGGCTTACCATCTGGCCCCAGTG
CTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCT
TCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGAT
GCTTTTCTGTGACTGGTGAGTACTCAACCAAGTCATTCTGAGAATAGTGTA
TGCGGCGACCGAGTTGCTCTTGCCCGGCGTCAATACGGGATAATACCGCGC
CACATAGCAGAACTTTAAAAGTGCTCATCATTGGAAAACGTTCTTCGGGGC
GAAAACTCTCAAGGATCTTACCGCTGTTGAGATCCAGTTCGATGTAACCCA
CTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGA
CACGGAAATGTTGAATACTCATACTCTTCCTTTTTCAATATTATTGAAGCA
TTTATCAGGGTTATTGTCTCATGAGCGGATACATATTTGAATGTATTTAGA
AAAATAAACAAATAGGGGTTCCGCGCACATTTCCCCGAAAAGTGCCACCTG
ACGTCTAAGAAACCATTATTATCATGACATTAACCTATAAAAATAGGCGTA

TABLE 6-continued

| Nucleotide sequences of FNR promoter-PAL3 construct, high-copy (SEQ ID NO: 23B) |
|---|
| TCACGAGGCCCTTTCGTCTCGCGCGTTTCGGTGATGACGGTGAAAACCTCT |
| GACACATGCAGCTCCCGGAGACGGTCACAGCTTGTCTGTAAGCGGATGCCG |
| GGAGCAGACAAGCCCGTCAGGGCGCGTCAGCGGGTGTTGGCGGGTGTCGGG |
| GCTGGCTTAACTATGCGGCATCAGAGCAGATTGTACTGAGAGTGCACCATA |
| TGCGGTGTGAAATACCGCACAGATGCGTAAGGAGAAAATACCGCATCAGGC |
| GCCATTCGCCATTCAGGCTGCGCAACTGTTGGGAAGGGCGATCGGTGCGGG |
| CCTCTTCGCTATTACGCCAGCTGGCGAAAGGGGGATGTGCTGCAAGGCGAT |
| TAAGTTGGGTAACGCCAGGGTTTTCCCAGTCACGACGTT |

TABLE 7

| Nucleotide sequences of Tet promoter-PAL1 construct, high-copy (SEQ ID NO: 24B) |
|---|
| CTCTAGAAATAATTTTGTTTAACTTTAAGAAGGAGATATACATATGAAAAC |
| ACTATCACAGGCCCAATCTAAAACTTCTTCACAGCAATTCAGCTTTACCGG |
| GAACTCGTCTGCGAATGTAATTATCGGCAATCAAAAGCTGACCATTAATGA |
| TGTAGCTCGCGTTGCCCGGAATGGCACTTTGGTGTCACTGACGAACAATAC |
| CGACATTCTGCAAGGTATTCAAGCTAGCTGCGATTATATCAATAACGCCGT |
| TGAATCTGGCGAGCCAATCTACGGGGTAACAAGCGGTTTTGGTGGGATGGC |
| GAACGTTGCCATTAGCCGTGAACAGGCGAGCGAACTTCAGACCAACCTCGT |
| TTGGTTCCTAAAGACAGGAGCTGGTAATAAGTTACCTCTGGCTGACGTAAG |
| AGCCGCGATGCTGCTTCGCGCTAATAGTCACATGCGCGGCGCCAGTGGTAT |
| CCGTCTTGAGCTTATCAAGAGGATGGAAATCTTCCTCAACGCGGGTGTCAC |
| ACCATATGTTTATGAGTTTGGTAGTATCGGAGCCAGTGGTGATCTTGTTCC |
| CCTGAGTTATATTACGGGTTCATTGATTGGTTTAGACCCGTCCTTTAAAGT |
| GGATTTTAACGGGAAAGAAATGGACGCCCCGACCGCTTTACGACAGCTTAA |
| TCTGAGCCCACTTACTTTGCTCCCTAAAGAAGGTCTTGCCATGATGAATGG |
| CACCTCTGTGATGACTGGAATTGCCGCGAATTGTGTGTATGACACGCAGAT |
| CCTAACGGCCATTGCCATGGGTGTTCACGCGTTGGACATTCAAGCCCTGAA |
| TGGTACAAACCAGTCGTTTCATCCGTTTATCCATAATTCAAAACCCCATCC |
| GGGACAGCTTTGGGCTGCTGATCAGATGATCTCACTCCTGGCCAATAGTCA |
| ACTGGTTCGGGACGAGCTCGACGGCAAACATGATTATCGCGATCATGAGCT |
| CATCCAGGACCGGTATTCACTTCGTTGTCTCCCACAATACCTGGGGCCTAT |
| CGTTGATGGTATATCTCAAATTGCGAAGCAAATTGAAATTGAGATCAATAG |
| CGTAACCGACAACCCGCTTATCGATGTTGATAATCAGGCCTCTTATCACGG |
| TGGCAATTTTCTGGGCCAGTATGTTGGTATGGGGATGGATCACCTGCGGTA |
| CTATATTGGGCTTCTGGCTAAACATCTTGATGTGCAGATTGCCTTATTAGC |
| TTCACCAGAATTTTCAAATGGACTGCCGCCATCATTGCTCGGTAACAGAGA |
| AAGGAAAGTAAATATGGGCCTTAAGGGCCTTCAGATATGTGGTAACTCAAT |
| CATGCCCCTCCTGACCTTTTATGGGAACTCAATTGCTGATCGTTTTCCGAC |

TABLE 7-continued

| Nucleotide sequences of Tet promoter-PAL1 construct, high-copy (SEQ ID NO: 24B) |
|---|
| ACATGCTGAACAGTTTAACCAAAACATTAACTCACAGGGCTATACATCCGC |
| GACGTTAGCGCGTCGGTCCGTGGATATCTTCCAGAATTATGTTGCTATCGC |
| TCTGATGTTCGGCGTACAGGCCGTTGATTTGCGCACTTATAAAAAAACCGG |
| TCACTACGATGCTCGGGCTTGCCTGTCGCCTGCCACCGAGCGGCTTTATAG |
| CGCCGTACGTCATGTTGTGGGTCAGAAACCGACGTCGGACCGCCCCTATAT |
| TTGGAATGATAATGAACAAGGGCTGGATGAACACATCGCCCGGATATCTGC |
| CGATATTGCCGCCGGAGGTGTCATCGTCCAGGCGGTACAAGACATACTTCC |
| TTGCCTGCATTAAGCTTGGCGTAATCATGGTCATAGCTGTTTCCTGTGTGA |
| AATTGTTATCCGCTCACAATTCCACACAACATACGAGCCGGAAGCATAAAG |
| TGTAAAGCCTGGGGTGCCTAATGAGTGAGCTAACTCACATTAATTGCGTTG |
| CGCTCACTGCCCGCTTTCCAGTCGGGAAACCTGTCGTGCCAGCTGCATTAA |
| TGAATCGGCCAACGCGCGGGGAGAGGCGGTTTGCGTATTGGGCGCTCTTCC |
| GCTTCCTCGCTCACTGACTCGCTGCGCTCGGTCGTTCGGCTGCGGCGAGCG |
| GTATCAGCTCACTCAAAGGCGGTAATACGGTTATCCACAGAATCAGGGGAT |
| AACGCAGGAAAGAACATGTGAGCAAAAGGCCAGCAAAAGGCCAGGAACCGT |
| AAAAAGGCCGCGTTGCTGGCGTTTTTCCATAGGCTCCGCCCCCCTGACGAG |
| CATCACAAAAATCGACGCTCAAGTCAGAGGTGGCGAAACCCGACAGGACTA |
| TAAAGATACCAGGCGTTTCCCCCTGGAAGCTCCCTCGTGCGCTCTCCTGTT |
| CCGACCCTGCCGCTTACCGGATACCTGTCCGCCTTTCTCCCTTCGGGAAGC |
| GTGGCGCTTTCTCATAGCTCACGCTGTAGGTATCTCAGTTCGGTGTAGGTC |
| GTTCGCTCCAAGCTGGGCTGTGTGCACGAACCCCCCGTTCAGCCCGACCGC |
| TGCGCCTTATCCGGTAACTATCGTCTTGAGTCCAACCCGGTAAGACACGAC |
| TTATCGCCACTGGCAGCAGCCACTGGTAACAGGATTAGCAGAGCGAGGTAT |
| GTAGGCGGTGCTACAGAGTTCTTGAAGTGGTGGCCTAACTACGGCTACACT |
| AGAAGAACAGTATTTGGTATCTGCGCTCTGCTGAAGCCAGTTACCTTCGGA |
| AAAAGAGTTGGTAGCTCTTGATCCGGCAAACAAACCACCGCTGGTAGCGGT |
| GGTTTTTTTGTTTGCAAGCAGCAGATTACGCGCAGAAAAAAAGGATCTCAA |
| GAAGATCCTTTGATCTTTTCTACGGGGTCTGACGCTCAGTGGAACGAAAAC |
| TCACGTTAAGGGATTTTGGTCATGAGATTATCAAAAAGGATCTTCACCTAG |
| ATCCTTTTAAATTAAAAATGAAGTTTTAAATCAATCTAAAGTATATATGAG |
| TAAACTTGGTCTGACAGTTACCAATGCTTAATCAGTGAGGCACCTATCTCA |
| GCGATCTGTCTATTTCGTTCATCCATAGTTGCCTGACTCCCCGTCGTGTAG |
| ATAACTACGATACGGGAGGGCTTACCATCTGGCCCCAGTGCTGCAATGATA |
| CCGCGAGACCCACGCTCACCGGCTCCAGATTTATCAGCAATAAACCAGCCA |
| GCCGGAAGGGCCGAGCGCAGAAGTGGTCCTGCAACTTTATCCGCCTCCATC |
| CAGTCTATTAATTGTTGCCGGGAAGCTAGAGTAAGTAGTTCGCCAGTTAAT |
| AGTTTGCGCAACGTTGTTGCCATTGCTACAGGCATCGTGGTGTCACGCTCG |
| TCGTTTGGTATGGCTTCATTCAGCTCCGGTTCCCAACGATCAAGGCGAGTT |

TABLE 7-continued

| Nucleotide sequences of Tet promoter-PAL1 construct, high-copy (SEQ ID NO: 24B) |
|---|
| ACATGATCCCCCATGTTGTGCAAAAAAGCGGTTAGCTCCTTCGGTCCTCCG |
| ATCGTTGTCAGAAGTAAGTTGGCCGCAGTGTTATCACTCATGGTTATGGCA |
| GCACTGCATAATTCTCTTACTGTCATGCCATCCGTAAGATGCTTTTCTGTG |
| ACTGGTGAGTACTCAACCAAGTCATTCTGAGAATAGTGTATGCGGCGACCG |
| AGTTGCTCTTGCCCGGCGTCAATACGGGATAATACCGCGCCACATAGCAGA |
| ACTTTAAAAGTGCTCATCATTGGAAAACGTTCTTCGGGGCGAAAACTCTCA |
| AGGATCTTACCGCTGTTGAGATCCAGTTCGATGTAACCCACTCGTGCACCC |
| AACTGATCTTCAGCATCTTTTACTTTCACCAGCGTTTCTGGGTGAGCAAAA |
| ACAGGAAGGCAAAATGCCGCAAAAAAGGGAATAAGGGCGACACGGAAATGT |
| TGAATACTCATACTCTTCCTTTTTCAATATTATTGAAGCATTTATCAGGGT |
| TATTGTCTCATGAGCGGATACATATTTGAATGTATTTAGAAAAATAAACAA |
| ATAGGGGTTCCGCGCACATTTCCCCGAAAAGTGCCACCTGACGTCTAAGAA |
| ACCATTATTATCATGACATTAACCTATAAAAATAGGCGTATCACGAGGCCC |
| TTTCGTCTCGCGCGTTTCGGTGATGACGGTGAAAACCTCTGACACATGCAG |
| CTCCCGGAGACGGTCACAGCTTGTCTGTAAGCGGATGCCGGGAGCAGACAA |
| GCCCGTCAGGGCGCGTCAGCGGGTGTTGGCGGGTGTCGGGGCTGGCTTAAC |
| TATGCGGCATCAGAGCAGATTGTACTGAGAGTGCACCATATGCGGTGTGAA |
| ATACCGCACAGATGCGTAAGGAGAAAATACCGCATCAGGCGCCATTCGCCA |
| TTCAGGCTGCGCAACTGTTGGGAAGGGCGATCGGTGCGGGCCTCTTCGCTA |
| TTACGCCAGCTGGCGAAAGGGGGATGTGCTGCAAGGCGATTAAGTTGGGTA |
| ACGCCAGGGTTTTCCCAGTCACGACGTTGTAAAACGACGGCCAGTGAATTC |
| GTTAAGACCCACTTTCACATTTAAGTTGTTTTTCTAATCCGCATATGATCA |
| ATTCAAGGCCGAATAAGAAGGCTGGCTCTGCACCTTGGTGATCAAATAATT |
| CGATAGCTTGTCGTAATAATGGCGGCATACTATCAGTAGTAGGTGTTTCCC |
| TTTCTTCTTTAGCGACTTGATGCTCTTGATCTTCCAATACGCAACCTAAAG |
| TAAAATGCCCCACAGCGCTGAGTGCATATAATGCATTCTCTAGTGAAAAAC |
| CTTGTTGGCATAAAAAGGCTAATTGATTTTCGAGAGTTTCATACTGTTTTT |
| CTGTAGGCCGTGTACCTAAATGTACTTTTGCTCCATCGCGATGACTTAGTA |
| AAGCACATCTAAAACTTTTAGCGTTATTACGTAAAAAATCTTGCCAGCTTT |
| CCCCTTCTAAAGGGCAAAAGTGAGTATGGTGCCTATCTAACATCTCAATGG |
| CTAAGGCGTCGAGCAAAGCCCGCTTATTTTTTACATGCCAATACAATGTAG |
| GCTGCTCTACACCTAGCTTCTGGGCGAGTTTACGGGTTGTTAAACCTTCGA |
| TTCCGACCTCATTAAGCAGCTCTAATGCGCTGTTAATCACTTTACTTTTAT |
| CTAATCTAGACATCATTAATTCCTAATTTTT**GTTGACACTCTATCATTGAT** |
| **AGAGTTATTTTACCACTCCCTATCAGTGATAGAGAA**AAGTGAA |

TABLE 8

| Nucleotide sequences of Tet promoter-PAL3, high-copy construct (SEQ ID NO: 25B) |
|---|
| CTCTAGAAATAATTTTGTTTAACTTTAAGAAGGAGATATACATATGAAAGC |
| TAAAGATGTTCAGCCAACCATTATTATTAATAAAAATGGCCTTATCTCTTT |
| GGAAGATATCTATGACATTGCGATAAAACAAAAAAAAGTAGAAATATCAAC |
| GGAGATCACTGAACTTTTGACGCATGGTCGTGAAAAATTAGAGGAAAAATT |
| AAATTCAGGAGAGGTTATATATGGAATCAATACAGGATTTGGAGGGAATGC |
| CAATTTAGTTGTGCCATTTGAGAAAATCGCAGAGCATCAGCAAAATCTGTT |
| AACTTTTCTTTCTGCTGGTACTGGGGACTATATGTCCAAACCTTGTATTAA |
| AGCGTCACAATTTACTATGTTACTTTCTGTTTGCAAAGGTTGGTCTGCAAC |
| CAGACCAATTGTCGCTCAAGCAATTGTTGATCATATTAATCATGACATTGT |
| TCCTCTGGTTCCTCGCTATGGCTCAGTGGGTGCAAGCGGTGATTTAATTCC |
| TTTATCTTATATTGCACGAGCATTATGTGGTATCGGCAAAGTTTATTATAT |
| GGGCGCAGAAATTGACGCTGCTGAAGCAATTAAACGTGCAGGGTTGACACC |
| ATTATCGTTAAAAGCCAAAGAAGGTCTTGCTCTGATTAACGGCACCCGGGT |
| AATGTCAGGAATCAGTGCAATCACCGTCATTAAACTGGAAAAACTATTTAA |
| AGCCTCAATTTCTGCGATTGCCCTTGCTGTTGAAGCATTACTTGCATCTCA |
| TGAACATTATGATGCCCGGATTCAACAAGTAAAAAATCATCCTGGTCAAAA |
| CGCGGTGGCAAGTGCATTGCGTAATTTATTGGCAGGTTCAACGCAGGTTAA |
| TCTATTATCTGGGGTTAAAGAACAAGCCAATAAAGCTTGTCGTCATCAAGA |
| AATTACCCAACTAAATGATACCTTACAGGAAGTTTATTCAATTCGCTGTGC |
| ACCACAAGTATTAGGTATAGTGCCAGAATCTTTAGCTACCGCTCGGAAAAT |
| ATTGGAACGGGAAGTTATCTCAGCTAATGATAATCCATTGATAGATCCAGA |
| AAATGGCGATGTTCTACACGGTGGAAATTTTATGGGGCAATATGTCGCCCG |
| AACAATGGATGCATTAAAACTGGATATTGCTTTAATTGCCAATCATCTTCA |
| CGCCATTGTGGCTCTTATGATGGATAACCGTTTCTCTCGTGGATTACCTAA |
| TTCACTGAGTCCGACACCCGGCATGTATCAAGGTTTTAAAGGCGTCCAACT |
| TTCTCAAACCGCTTTAGTTGCTGCAATTCGCCATGATTGTGCTGCATCAGG |
| TATTCATACCCTCGCCACAGAACAATACAATCAAGATATTGTCAGTTTAGG |
| TCTGCATGCCGCTCAAGATGTTTTAGAGATGGAGCAGAAATTACGCAATAT |
| TGTTTCAATGACAATTCTGGTAGTTTGTCAGGCCATTCATCTTCGCGGCAA |
| TATTAGTGAAATTGCGCCTGAAACTGCTAAATTTTACCATGCAGTACGCGA |
| AATCAGTTCTCCTTTGATCACTGATCGTGCGTTGGATGAAGATATAATCCG |
| CATTGCGGATGCAATTATTAATGATCAACTTCCTCTGCCAGAAATCATGCT |
| GGAAGAATAAGCTTGGCGTAATCATGGTCATAGCTGTTTCCTGTGTGAAAT |
| TGTTATCCGCTCACAATTCCACACAACATACGAGCCGGAAGCATAAAGTGT |
| AAAGCCTGGGGTGCCTAATGAGTGAGCTAACTCACATTAATTGCGTTGCGC |
| TCACTGCCCGCTTTCCAGTCGGGAAACCTGTCGTGCCAGCTGCATTAATGA |
| ATCGGCCAACGCGCGGGGAGAGGCGGTTTGCGTATTGGGCGCTCTTCCGCT |
| TCCTCGCTCACTGACTCGCTGCGCTCGGTCGTTCGGCTGCGGCGAGCGGTA |
| TCAGCTCACTCAAAGGCGGTAATACGGTTATCCACAGAATCAGGGGATAAC |

TABLE 8-continued

| Nucleotide sequences of Tet promoter-PAL3, high-copy construct (SEQ ID NO: 25B) |
|---|
| GCAGGAAAGAACATGTGAGCAAAAGGCCAGCAAAAGGCCAGGAACCGTAAA |
| AAGGCCGCGTTGCTGGCGTTTTTCCATAGGCTCCGCCCCCCTGACGAGCAT |
| CACAAAAATCGACGCTCAAGTCAGAGGTGGCGAAACCCGACAGGACTATAA |
| AGATACCAGGCGTTTCCCCCTGGAAGCTCCCTCGTGCGCTCTCCTGTTCCG |
| ACCCTGCCGCTTACCGGATACCTGTCCGCCTTTCTCCCTTCGGGAAGCGTG |
| GCGCTTTCTCATAGCTCACGCTGTAGGTATCTCAGTTCGGTGTAGGTCGTT |
| CGCTCCAAGCTGGGCTGTGTGCACGAACCCCCCGTTCAGCCCGACCGCTGC |
| GCCTTATCCGGTAACTATCGTCTTGAGTCCAACCCGGTAAGACACGACTTA |
| TCGCCACTGGCAGCAGCCACTGGTAACAGGATTAGCAGAGCGAGGTATGTA |
| GGCGGTGCTACAGAGTTCTTGAAGTGGTGGCCTAACTACGGCTACACTAGA |
| AGAACAGTATTTGGTATCTGCGCTCTGCTGAAGCCAGTTACCTTCGGAAAA |
| AGAGTTGGTAGCTCTTGATCCGGCAAACAAACCACCGCTGGTAGCGGTGGT |
| TTTTTTGTTTGCAAGCAGCAGATTACGCGCAGAAAAAAAGGATCTCAAGAA |
| GATCCTTTGATCTTTTCTACGGGGTCTGACGCTCAGTGGAACGAAAACTCA |
| CGTTAAGGGATTTTGGTCATGAGATTATCAAAAAGGATCTTCACCTAGATC |
| CTTTTAAATTAAAAATGAAGTTTTAAATCAATCTAAAGTATATATGAGTAA |
| ACTTGGTCTGACAGTTACCAATGCTTAATCAGTGAGGCACCTATCTCAGCG |
| ATCTGTCTATTTCGTTCATCCATAGTTGCCTGACTCCCCGTCGTGTAGATA |
| ACTACGATACGGGAGGGCTTACCATCTGGCCCCAGTGCTGCAATGATACCG |
| CGAGACCCACGCTCACCGGCTCCAGATTTATCAGCAATAAACCAGCCAGCC |
| GGAAGGGCCGAGCGCAGAAGTGGTCCTGCAACTTTATCCGCCTCCATCCAG |
| TCTATTAATTGTTGCCGGGAAGCTAGAGTAAGTAGTTCGCCAGTTAATAGT |
| TTGCGCAACGTTGTTGCCATTGCTACAGGCATCGTGGTGTCACGCTCGTCG |
| TTTGGTATGGCTTCATTCAGCTCCGGTTCCCAACGATCAAGGCGAGTTACA |
| TGATCCCCCATGTTGTGCAAAAAAGCGGTTAGCTCCTTCGGTCCTCCGATC |
| GTTGTCAGAAGTAAGTTGGCCGCAGTGTTATCACTCATGGTTATGGCAGCA |
| CTGCATAATTCTCTTACTGTCATGCCATCCGTAAGATGCTTTTCTGTGACT |
| GGTGAGTACTCAACCAAGTCATTCTGAGAATAGTGTATGCGGCGACCGAGT |
| TGCTCTTGCCCGGCGTCAATACGGGATAATACCGCGCCACATAGCAGAACT |
| TTAAAAGTGCTCATCATTGGAAAACGTTCTTCGGGGCGAAAACTCTCAAGG |
| ATCTTACCGCTGTTGAGATCCAGTTCGATGTAACCCACTCGTGCACCCAAC |
| TGATCTTCAGCATCTTTTACTTTCACCAGCGTTTCTGGGTGAGCAAAAACA |
| GGAAGGCAAAATGCCGCAAAAAAGGGAATAAGGGCGACACGGAAATGTTGA |
| ATACTCATACTCTTCCTTTTTCAATATTATTGAAGCATTTATCAGGGTTAT |
| TGTCTCATGAGCGGATACATATTTGAATGTATTTAGAAAAATAAACAAATA |
| GGGGTTCCGCGCACATTTCCCCGAAAAGTGCCACCTGACGTCTAAGAAACC |
| ATTATTATCATGACATTAACCTATAAAAATAGGCGTATCACGAGGCCCTTT |
| CGTCTCGCGCGTTTCGGTGATGACGGTGAAAACCTCTGACACATGCAGCTC |
| CCGGAGACGGTCACAGCTTGTCTGTAAGCGGATGCCGGGAGCAGACAAGCC |
| CGTCAGGGCGCGTCAGCGGGTGTTGGCGGGTGTCGGGGCTGGCTTAACTAT |
| GCGGCATCAGAGCAGATTGTACTGAGAGTGCACCATATGCGGTGTGAAATA |
| CCGCACAGATGCGTAAGGAGAAAATACCGCATCAGGCGCCATTCGCCATTC |
| AGGCTGCGCAACTGTTGGGAAGGGCGATCGGTGCGGGCCTCTTCGCTATTA |
| CGCCAGCTGGCGAAAGGGGGATGTGCTGCAAGGCGATTAAGTTGGGTAACG |
| CCAGGGTTTTCCCAGTCACGACGTTGTAAAACGACGGCCAGTGAATTCGTT |
| AAGACCCACTTTCACATTTAAGTTGTTTTTCTAATCCGCATATGATCAATT |
| CAAGGCCGAATAAGAAGGCTGGCTCTGCACCTTGGTGATCAAATAATTCGA |
| TAGCTTGTCGTAATAATGGCGGCATACTATCAGTAGTAGGTGTTTCCCTTT |
| CTTCTTTAGCGACTTGATGCTCTTGATCTTCCAATACGCAACCTAAAGTAA |
| AATGCCCCACAGCGCTGAGTGCATATAATGCATTCTCTAGTGAAAAACCTT |
| GTTGGCATAAAAAGGCTAATTGATTTTCGAGAGTTTCATACTGTTTTTCTG |
| TAGGCCGTGTACCTAAATGTACTTTTGCTCCATCGCGATGACTTAGTAAAG |
| CACATCTAAAACTTTTAGCGTTATTACGTAAAAAATCTTGCCAGCTTTCCC |
| CTTCTAAAGGGCAAAAGTGAGTATGGTGCCTATCTAACATCTCAATGGCTA |
| AGGCGTCGAGCAAAGCCCGCTTATTTTTTACATGCCAATACAATGTAGGCT |
| GCTCTACACCTAGCTTCTGGGCGAGTTTACGGGTTGTTAAACCTTCGATTC |
| CGACCTCATTAAGCAGCTCTAATGCGCTGTTAATCACTTTACTTTTATCTA |
| ATCTAGACATCATTAATTCCTAATTTTT**GTTGACACTCTATCATTGATAGA** |
| **GTTATTTTACCACTCCCTATCAGTGATAGAGAA**AAGTGAA |

TABLE 9

| Nucleotide sequences of FNR promoter-PAL1 construct, low-copy (SEQ ID NO: 26B) |
|---|
| **CTCTTGATCGTTATCAATTCCCACGCTGTTTCAGAGCGTTACCTTGCCCTT** |
| **AAACATTAGCAATGTCGATTTATCAGAGGGCCGACAGGCTCCCACAGGAGA** |
| **AAACCG**ATGAAAACACTATCACAGGCCCAATCTAAAACTTCTTCACAGCAA |
| TTCAGCTTTACCGGGAACTCGTCTGCGAATGTAATTATCGGCAATCAAAAG |
| CTGACCATTAATGATGTAGCTCGCGTTGCCCGGAATGGCACTTTGGTGTCA |
| CTGACGAACAATACCGACATTCTGCAAGGTATTCAAGCTAGCTGCGATTAT |
| ATCAATAACGCCGTTGAATCTGGCGAGCCAATCTACGGGGTAACAAGCGGT |
| TTTGGTGGGATGGCGAACGTTGCCATTAGCCGTGAACAGGCGAGCGAACTT |
| CAGACCAACCTCGTTTGGTTCCTAAAGACAGGAGCTGGTAATAAGTTACCT |
| CTGGCTGACGTAAGAGCCGCGATGCTGCTTCGCGCTAATAGTCACATGCGC |
| GGCGCCAGTGGTATCCGTCTTGAGCTTATCAAGAGGATGGAAATCTTCCTC |
| AACGCGGGTGTCACACCATATGTTTATGAGTTTGGTAGTATCGGAGCCAGT |
| GGTGATCTTGTTCCCCTGAGTTATATTACGGGTTCATTGATTGGTTTAGAC |
| CCGTCCTTTAAAGTGGATTTTAACGGGAAAGAAATGGACGCCCCGACCGCT |

TABLE 9-continued

Nucleotide sequences of FNR promoter-PAL1 construct, low-copy (SEQ ID NO: 26B)

TTACGACAGCTTAATCTGAGCCCACTTACTTTGCTCCCTAAAGAAGGTCTT
GCCATGATGAATGGCACCTCTGTGATGACTGGAATTGCCGCGAATTGTGTG
TATGACACGCAGATCCTAACGGCCATTGCCATGGGTGTTCACGCGTTGGAC
ATTCAAGCCCTGAATGGTACAAACCAGTCGTTTCATCCGTTTATCCATAAT
TCAAAACCCCATCCGGGACAGCTTTGGGCTGCTGATCAGATGATCTCACTC
CTGGCCAATAGTCAACTGGTTCGGGACGAGCTCGACGGCAAACATGATTAT
CGCGATCATGAGCTCATCCAGGACCGGTATTCACTTCGTTGTCTCCCACAA
TACCTGGGGCCTATCGTTGATGGTATATCTCAAATTGCGAAGCAAATTGAA
ATTGAGATCAATAGCGTAACCGACAACCCGCTTATCGATGTTGATAATCAG
GCCTCTTATCACGGTGGCAATTTTCTGGGCCAGTATGTTGGTATGGGGATG
GATCACCTGCGGTACTATATTGGGCTTCTGGCTAAACATCTTGATGTGCAG
ATTGCCTTATTAGCTTCACCAGAATTTTCAAATGGACTGCCGCCATCATTG
CTCGGTAACAGAGAAAGGAAAGTAAATATGGGCCTTAAGGGCCTTCAGATA
TGTGGTAACTCAATCATGCCCCTCCTGACCTTTTATGGGAACTCAATTGCT
GATCGTTTTCCGACACATGCTGAACAGTTTAACCAAAACATTAACTCACAG
GGCTATACATCCGCGACGTTAGCGCGTCGGTCCGTGGATATCTTCCAGAAT
TATGTTGCTATCGCTCTGATGTTCGGCGTACAGGCCGTTGATTTGCGCACT
TATAAAAAAACCGGTCACTACGATGCTCGGGCTTGCCTGTCGCCTGCCACC
GAGCGGCTTTATAGCGCCGTACGTCATGTTGTGGGTCAGAAACCGACGTCG
GACCGCCCCTATATTTGGAATGATAATGAACAAGGGCTGGATGAACACATC
GCCCGGATATCTGCCGATATTGCCGCCGGAGGTGTCATCGTCCAGGCGGTA
CAAGACATACTTCCTTGCCTGCATTAAGCTTGGCGTAATCATGGTCATAGC
TGTTTCCTGTGTGAAATTGTTATCCGCTCACAATTCCACACAACATACGAG
CCGGAAGCATAAAGTGTAAAGCCTGGGGTGCCTAATGAGTGAGCTAACTCA
CATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTA
TTGGGCGCTCTTCCGCTTCCTCGCTCACTGACTCGCTGCGCTCGGTCGTTC
GGCTGCGGCGAGCGGTATCAGCTCACTCAAAGGCGGTAGTACGGGTTTTGC
TGCCCGCAAACGGGCTGTTCTGGTGTTGCTAGTTTGTTATCAGAATCGCAG
ATCCGGCTTCAGGTTTGCCGGCTGAAAGCGCTATTTCTTCCAGAATTGCCA
TGATTTTTTCCCCACGGGAGGCGTCACTGGCTCCCGTGTTGTCGGCAGCTT
TGATTCGATAAGCAGCATCGCCTGTTTCAGGCTGTCTATGTGTGACTGTTG
AGCTGTAACAAGTTGTCTCAGGTGTTCAATTTCATGTTCTAGTTGCTTTGT
TTTACTGGTTTCACCTGTTCTATTAGGTGTTACATGCTGTTCATCTGTTAC
ATTGTCGATCTGTTCATGGTGAACAGCTTTAAATGCACCAAAAACTCGTAA
AAGCTCTGATGTATCTATCTTTTTTACACCGTTTTCATCTGTGCATATGGA
CAGTTTTCCCTTTGATATCTAACGGTGAACAGTTGTTCTACTTTTGTTTGT
TAGTCTTGATGCTTCACTGATAGATACAAGAGCCATAAGAACCTCAGATCC

TABLE 9-continued

Nucleotide sequences of FNR promoter-PAL1 construct, low-copy (SEQ ID NO: 26B)

TTCCGTATTTAGCCAGTATGTTCTCTAGTGTGGTTCGTTGTTTTTGCGTGA
GCCATGAGAACGAACCATTGAGATCATGCTTACTTTGCATGTCACTCAAAA
ATTTTGCCTCAAAACTGGTGAGCTGAATTTTTGCAGTTAAAGCATCGTGTA
GTGTTTTTCTTAGTCCGTTACGTAGGTAGGAATCTGATGTAATGGTTGTTG
GTATTTTGTCACCATTCATTTTTATCTGGTTGTTCTCAAGTTCGGTTACGA
GATCCATTTGTCTATCTAGTTCAACTTGGAAAATCAACGTATCAGTCGGGC
GGCCTCGCTTATCAACCACCAATTTCATATTGCTGTAAGTGTTTAAATCTT
TACTTATTGGTTTCAAAACCCATTGGTTAAGCCTTTTAAACTCATGGTAGT
TATTTTCAAGCATTAACATGAACTTAAATTCATCAAGGCTAATCTCTATAT
TTGCCTTGTGAGTTTTCTTTTGTGTTAGTTCTTTTAATAACCACTCATAAA
TCCTCATAGAGTATTTGTTTTCAAAAGACTTAACATGTTCCAGATTATATT
TTATGAATTTTTTTAACTGGAAAAGATAAGGCAATATCTCTTCACTAAAAA
CTAATTCTAATTTTTCGCTTGAGAACTTGGCATAGTTTGTCCACTGGAAAA
TCTCAAAGCCTTTAACCAAAGGATTCCTGATTTCCACAGTTCTCGTCATCA
GCTCTCTGGTTGCTTTAGCTAATACACCATAAGCATTTTCCCTACTGATGT
TCATCATCTGAGCGTATTGGTTATAAGTGAACGATACCGTCCGTTCTTTCC
TTGTAGGGTTTTCAATCGTGGGGTTGAGTAGTGCCACACAGCATAAAATTA
GCTTGGTTTCATGCTCCGTTAAGTCATAGCGACTAATCGCTAGTTCATTTG
CTTTGAAAACAACTAATTCAGACATACATCTCAATTGGTCTAGGTGATTTT
AATCACTATACCAATTGAGATGGGCTAGTCAATGATAATTACTAGTCCTTT
TCCTTTGAGTTGTGGGTATCTGTAAATTCTGCTAGACCTTTGCTGGAAAAC
TTGTAAATTCTGCTAGACCCTCTGTAAATTCCGCTAGACCTTTGTGTGTTT
TTTTTGTTTATATTCAAGTGGTTATAATTTATAGAATAAAGAAAGAATAAA
AAAAGATAAAAAGAATAGATCCCAGCCCTGTGTATAACTCACTACTTTAGT
CAGTTCCGCAGTATTACAAAAGGATGTCGCAAACGCTGTTTGCTCCTCTAC
AAAACAGACCTTAAAACCCTAAAGGCTTAAGTAGCACCCTCGCAAGCTCGG
GCAAATCGCTGAATATTCCTTTTGTCTCCGACCATCAGGCACCTGAGTCGC
TGTCTTTTTCGTGACATTCAGTTCGCTGCGCTCACGGCTCTGGCAGTGAAT
GGGGGTAAATGGCACTACAGGCGCCTTTTATGGATTCATGCAAGGAAACTA
CCCATAATACAAGAAAAGCCCGTCACGGGCTTCTCAGGGCGTTTTATGGCG
GGTCTGCTATGTGGTGCTATCTGACTTTTTGCTGTTCAGCAGTTCCTGCCC
TCTGATTTTCCAGTCTGACCACTTCGGATTATCCCGTGACAGGTCATTCAG
ACTGGCTAATGCACCCAGTAAGGCAGCGGTATCATCAACAGGCTTACCCGT
CTTACTGTCTTTTCTACGGGGTCTGACGCTCAGTGGAACGAAAACTCACGT
TAAGGGATTTTGGTCATGAGATTATCAAAAAGGATCTTCACCTAGATCCTT
TTAAATTAAAAATGAAGTTTTAAATCAATCTAAAGTATATATGAGTAAACT
TGGTCTGACAGTTACCAATGCTTAATCAGTGAGGCACCTATCTCAGCGATC
TGTCTATTTCGTTCATCCATAGTTGCCTGACTCCCCGTCGTGTAGATAACT
ACGATACGGGAGGGCTTACCATCTGGCCCCAGTGCTGCAATGATACCGCGA

TABLE 9-continued

| Nucleotide sequences of FNR promoter-PAL1 construct, low-copy (SEQ ID NO: 26B) |
|---|
| GACCCACGCTCACCGGCTCCAGATTTATCAGCAATAAACCAGCCAGCCGGA |
| AGGGCCGAGCGCAGAAGTGGTCCTGCAACTTTATCCGCCTCCATCCAGTCT |
| ATTAATTGTTGCCGGGAAGCTAGAGTAAGTAGTTCGCCAGTTAATAGTTTG |
| CGCAACGTTGTTGCCATTGCTACAGGCATCGTGGTGTCACGCTCGTCGTTT |
| GGTATGGCTTCATTCAGCTCCGGTTCCCAACGATCAAGGCGAGTTACATGA |
| TCCCCCATGTTGTGCAAAAAAGCGGTTAGCTCCTTCGGTCCTCCGATCGTT |
| GTCAGAAGTAAGTTGGCCGCAGTGTTATCACTCATGGTTATGGCAGCACTG |
| CATAATTCTCTTACTGTCATGCCATCCGTAAGATGCTTTTCTGTGACTGGT |
| GAGTACTCAACCAAGTCATTCTGAGAATAGTGTATGCGGCGACCGAGTTGC |
| TCTTGCCCGGCGTCAATACGGGATAATACCGCGCCACATAGCAGAACTTTA |
| AAAGTGCTCATCATTGGAAAACGTTCTTCGGGGCGAAAACTCTCAAGGATC |
| TTACCGCTGTTGAGATCCAGTTCGATGTAACCCACTCGTGCACCCAACTGA |
| TCTTCAGCATCTTTTACTTTCACCAGCGTTTCTGGGTGAGCAAAAACAGGA |
| AGGCAAAATGCCGCAAAAAAGGGAATAAGGGCGACACGGAAATGTTGAATA |
| CTCATACTCTTCCTTTTTCAATATTATTGAAGCATTTATCAGGGTTATTGT |
| CTCATGAGCGGATACATATTTGAATGTATTTAGAAAAATAAACAAATAGGG |
| GTTCCGCGCACATTTCCCCGAAAAGTGCCACCTGACGTCTAAGAAACCATT |
| ATTATCATGACATTAACCTATAAAAATAGGCGTATCACGAGGCCCTTTCGT |
| CTCGCGCGTTTCGGTGATGACGGTGAAAACCTCTGACACATGCAGCTCCCG |
| GAGACGGTCACAGCTTGTCTGTAAGCGGATGCCGGGAGCAGACAAGCCCGT |
| CAGGGCGCGTCAGCGGGTGTTGGCGGGTGTCGGGGCTGGCTTAACTATGCG |
| GCATCAGAGCAGATTGTACTGAGAGTGCACCATATGCGGTGTGAAATACCG |
| CACAGATGCGTAAGGAGAAAATACCGCATCAGGCGCCATTCGCCATTCAGG |
| CTGCGCAACTGTTGGGAAGGGCGATCGGTGCGGGCCTCTTCGCTATTACGC |
| CAGCTGGCGAAAGGGGGATGTGCTGCAAGGCGATTAAGTTGGGTAACGCCA |
| GGGTTTTCCCAGTCACGACGTTGTAAAACGACGGCCAGTGAATTCG |

TABLE 10

| Nucleotide sequences of FNR promoter-PAL3 construct, low-copy (SEQ ID NO: 27B) |
|---|
| **CTCTTGATCGTTATCAATTCCCACGCTGTTTCAGAGCGTTACCTTGCCCTT** |
| **AAACATTAGCAATGTCGATTTATCAGAGGGCCGACAGGCTCCCACAGGAGA** |
| **AAACCG**ATGAAAGCTAAAGATGTTCAGCCAACCATTATTATTAATAAAAAT |
| GGCCTTATCTCTTTGGAAGATATCTATGACATTGCGATAAAACAAAAAAAA |
| GTAGAAATATCAACGGAGATCACTGAACTTTTGACGCATGGTCGTGAAAAA |
| TTAGAGGAAAAATTAAATTCAGGAGAGGTTATATATGGAATCAATACAGGA |
| TTTGGAGGGAATGCCAATTTAGTTGTGCCATTTGAGAAAATCGCAGAGCAT |
| CAGCAAAATCTGTTAACTTTTCTTTCTGCTGGTACTGGGGACTATATGTCC |

TABLE 10-continued

| Nucleotide sequences of FNR promoter-PAL3 construct, low-copy (SEQ ID NO: 27B) |
|---|
| AAACCTTGTATTAAAGCGTCACAATTTACTATGTTACTTTCTGTTTGCAAA |
| GGTTGGTCTGCAACCAGACCAATTGTCGCTCAAGCAATTGTTGATCATATT |
| AATCATGACATTGTTCCTCTGGTTCCTCGCTATGGCTCAGTGGGTGCAAGC |
| GGTGATTTAATTCCTTTATCTTATATTGCACGAGCATTATGTGGTATCGGC |
| AAAGTTTATTATATGGGCGCAGAAATTGACGCTGCTGAAGCAATTAAACGT |
| GCAGGGTTGACACCATTATCGTTAAAAGCCAAAGAAGGTCTTGCTCTGATT |
| AACGGCACCCGGGTAATGTCAGGAATCAGTGCAATCACCGTCATTAAACTG |
| GAAAAACTATTTAAAGCCTCAATTTCTGCGATTGCCCTTGCTGTTGAAGCA |
| TTACTTGCATCTCATGAACATTATGATGCCCGGATTCAACAAGTAAAAAAT |
| CATCCTGGTCAAAACGCGGTGGCAAGTGCATTGCGTAATTTATTGGCAGGT |
| TCAACGCAGGTTAATCTATTATCTGGGGTTAAAGAACAAGCCAATAAAGCT |
| TGTCGTCATCAAGAAATTACCCAACTAAATGATACCTTACAGGAAGTTTAT |
| TCAATTCGCTGTGCACCACAAGTATTAGGTATAGTGCCAGAATCTTTAGCT |
| ACCGCTCGGAAAATATTGGAACGGGAAGTTATCTCAGCTAATGATAATCCA |
| TTGATAGATCCAGAAAATGGCGATGTTCTACACGGTGGAAATTTTATGGGG |
| CAATATGTCGCCCGAACAATGGATGCATTAAAACTGGATATTGCTTTAATT |
| GCCAATCATCTTCACGCCATTGTGGCTCTTATGATGGATAACCGTTTCTCT |
| CGTGGATTACCTAATTCACTGAGTCCGACACCCGGCATGTATCAAGGTTTT |
| AAAGGCGTCCAACTTTCTCAAACCGCTTTAGTTGCTGCAATTCGCCATGAT |
| TGTGCTGCATCAGGTATTCATACCCTCGCCACAGAACAATACAATCAAGAT |
| ATTGTCAGTTTAGGTCTGCATGCCGCTCAAGATGTTTTAGAGATGGAGCAG |
| AAATTACGCAATATTGTTTCAATGACAATTCTGGTAGTTTGTCAGGCCATT |
| CATCTTCGCGGCAATATTAGTGAAATTGCGCCTGAAACTGCTAAATTTTAC |
| CATGCAGTACGCGAAATCAGTTCTCCTTTGATCACTGATCGTGCGTTGGAT |
| GAAGATATAATCCGCATTGCGGATGCAATTATTAATGATCAACTTCCTCTG |
| CCAGAAATCATGCTGGAAGAATAAGCTTGGCGTAATCATGGTCATAGCTGT |
| TTCCTGTGTGAAATTGTTATCCGCTCACAATTCCACACAACATACGAGCCG |
| GAAGCATAAAGTGTAAAGCCTGGGGTGCCTAATGAGTGAGCTAACTCACAT |
| TAATTGCGTTGCGCTCACTGCCCGCTTTCCAGTCGGGAAACCTGTCGTGCC |
| AGCTGCATTAATGAATCGGCCAACGCGCGGGGAGAGGCGGTTTGCGTATTG |
| GGCGCTCTTCCGCTTCCTCGCTCACTGACTCGCTGCGCTCGGTCGTTCGGC |
| TGCGGCGAGCGGTATCAGCTCACTCAAAGGCGGTAGTACGGGTTTTGCTGC |
| CCGCAAACGGGCTGTTCTGGTGTTGCTAGTTTGTTATCAGAATCGCAGATC |
| CGGCTTCAGGTTTGCCGGCTGAAAGCGCTATTTCTTCCAGAATTGCCATGA |
| TTTTTTCCCCACGGGAGGCGTCACTGGCTCCCGTGTTGTCGGCAGCTTTGA |
| TTCGATAAGCAGCATCGCCTGTTTCAGGCTGTCTATGTGTGACTGTTGAGC |
| TGTAACAAGTTGTCTCAGGTGTTCAATTTCATGTTCTAGTTGCTTTGTTTT |
| ACTGGTTTCACCTGTTCTATTAGGTGTTACATGCTGTTCATCTGTTACATT |
| GTCGATCTGTTCATGGTGAACAGCTTTAAATGCACCAAAAACTCGTAAAAG |

TABLE 10-continued

| Nucleotide sequences of FNR promoter-PAL3 construct, low-copy (SEQ ID NO: 27B) |
|---|
| CTCTGATGTATCTATCTTTTTTACACCGTTTTCATCTGTGCATATGGACAG |
| TTTTCCCTTTGATATCTAACGGTGAACAGTTGTTCTACTTTTGTTTGTTAG |
| TCTTGATGCTTCACTGATAGATACAAGAGCCATAAGAACCTCAGATCCTTC |
| CGTATTTAGCCAGTATGTTCTCTAGTGTGGTTCGTTGTTTTTGCGTGAGCC |
| ATGAGAACGAACCATTGAGATCATGCTTACTTTGCATGTCACTCAAAAATT |
| TTGCCTCAAAACTGGTGAGCTGAATTTTTGCAGTTAAAGCATCGTGTAGTG |
| TTTTTCTTAGTCCGTTACGTAGGTAGGAATCTGATGTAATGGTTGTTGGTA |
| TTTTGTCACCATTCATTTTTATCTGGTTGTTCTCAAGTTCGGTTACGAGAT |
| CCATTTGTCTATCTAGTTCAACTTGGAAAATCAACGTATCAGTCGGGCGGC |
| CTCGCTTATCAACCACCAATTTCATATTGCTGTAAGTGTTTAAATCTTTAC |
| TTATTGGTTTCAAAACCCATTGGTTAAGCCTTTTAAACTCATGGTAGTTAT |
| TTTCAAGCATTAACATGAACTTAAATTCATCAAGGCTAATCTCTATATTTG |
| CCTTGTGAGTTTTCTTTTGTGTTAGTTCTTTTAATAACCACTCATAAATCC |
| TCATAGAGTATTTGTTTTCAAAAGACTTAACATGTTCCAGATTATATTTTA |
| TGAATTTTTTTAACTGGAAAAGATAAGGCAATATCTCTTCACTAAAAACTA |
| ATTCTAATTTTTCGCTTGAGAACTTGGCATAGTTTGTCCACTGGAAAATCT |
| CAAAGCCTTTAACCAAAGGATTCCTGATTTCCACAGTTCTCGTCATCAGCT |
| CTCTGGTTGCTTTAGCTAATACACCATAAGCATTTTCCCTACTGATGTTCA |
| TCATCTGAGCGTATTGGTTATAAGTGAACGATACCGTCCGTTCTTTCCTTG |
| TAGGGTTTTCAATCGTGGGGTTGAGTAGTGCCACACAGCATAAAATTAGCT |
| TGGTTTCATGCTCCGTTAAGTCATAGCGACTAATCGCTAGTTCATTTGCTT |
| TGAAAACAACTAATTCAGACATACATCTCAATTGGTCTAGGTGATTTTAAT |
| CACTATACCAATTGAGATGGGCTAGTCAATGATAATTACTAGTCCTTTTCC |
| TTTGAGTTGTGGGTATCTGTAAATTCTGCTAGACCTTTGCTGGAAAACTTG |
| TAAATTCTGCTAGACCCTCTGTAAATTCCGCTAGACCTTTGTGTGTTTTTT |
| TTGTTTATATTCAAGTGGTTATAATTTATAGAATAAAGAAAGAATAAAAAA |
| AGATAAAAAGAATAGATCCCAGCCCTGTGTATAACTCACTACTTTAGTCAG |
| TTCCGCAGTATTACAAAAGGATGTCGCAAACGCTGTTTGCTCCTCTACAAA |
| ACAGACCTTAAAACCCTAAAGGCTTAAGTAGCACCCTCGCAAGCTCGGGCA |
| AATCGCTGAATATTCCTTTTGTCTCCGACCATCAGGCACCTGAGTCGCTGT |
| CTTTTTCGTGACATTCAGTTCGCTGCGCTCACGGCTCTGGCAGTGAATGGG |
| GGTAAATGGCACTACAGGCGCCTTTTATGGATTCATGCAAGGAAACTACCC |
| ATAATACAAGAAAAGCCCGTCACGGGCTTCTCAGGGCGTTTTATGGCGGGT |
| CTGCTATGTGGTGCTATCTGACTTTTTGCTGTTCAGCAGTTCCTGCCCTCT |
| GATTTTCCAGTCTGACCACTTCGGATTATCCCGTGACAGGTCATTCAGACT |
| GGCTAATGCACCCAGTAAGGCAGCGGTATCATCAACAGGCTTACCCGTCTT |
| ACTGTCTTTTCTACGGGGTCTGACGCTCAGTGGAACGAAAACTCACGTTAA |
| GGGATTTTGGTCATGAGATTATCAAAAAGGATCTTCACCTAGATCCTTTTA |
| AATTAAAAATGAAGTTTTAAATCAATCTAAAGTATATATGAGTAAACTTGG |
| TCTGACAGTTACCAATGCTTAATCAGTGAGGCACCTATCTCAGCGATCTGT |
| CTATTTCGTTCATCCATAGTTGCCTGACTCCCCGTCGTGTAGATAACTACG |
| ATACGGGAGGGCTTACCATCTGGCCCCAGTGCTGCAATGATACCGCGAGAC |
| CCACGCTCACCGGCTCCAGATTTATCAGCAATAAACCAGCCAGCCGGAAGG |
| GCCGAGCGCAGAAGTGGTCCTGCAACTTTATCCGCCTCCATCCAGTCTATT |
| AATTGTTGCCGGGAAGCTAGAGTAAGTAGTTCGCCAGTTAATAGTTTGCGC |
| AACGTTGTTGCCATTGCTACAGGCATCGTGGTGTCACGCTCGTCGTTTGGT |
| ATGGCTTCATTCAGCTCCGGTTCCCAACGATCAAGGCGAGTTACATGATCC |
| CCCATGTTGTGCAAAAAAGCGGTTAGCTCCTTCGGTCCTCCGATCGTTGTC |
| AGAAGTAAGTTGGCCGCAGTGTTATCACTCATGGTTATGGCAGCACTGCAT |
| AATTCTCTTACTGTCATGCCATCCGTAAGATGCTTTTCTGTGACTGGTGAG |
| TACTCAACCAAGTCATTCTGAGAATAGTGTATGCGGCGACCGAGTTGCTCT |
| TGCCCGGCGTCAATACGGGATAATACCGCGCCACATAGCAGAACTTTAAAA |
| GTGCTCATCATTGGAAAACGTTCTTCGGGGCGAAAACTCTCAAGGATCTTA |
| CCGCTGTTGAGATCCAGTTCGATGTAACCCACTCGTGCACCCAACTGATCT |
| TCAGCATCTTTTACTTTCACCAGCGTTTCTGGGTGAGCAAAAACAGGAAGG |
| CAAAATGCCGCAAAAAAGGGAATAAGGGCGACACGGAAATGTTGAATACTC |
| ATACTCTTCCTTTTTCAATATTATTGAAGCATTTATCAGGGTTATTGTCTC |
| ATGAGCGGATACATATTTGAATGTATTTAGAAAAATAAACAAATAGGGGTT |
| CCGCGCACATTTCCCCGAAAAGTGCCACCTGACGTCTAAGAAACCATTATT |
| ATCATGACATTAACCTATAAAAATAGGCGTATCACGAGGCCCTTTCGTCTC |
| GCGCGTTTCGGTGATGACGGTGAAAACCTCTGACACATGCAGCTCCCGGAG |
| ACGGTCACAGCTTGTCTGTAAGCGGATGCCGGGAGCAGACAAGCCCGTCAG |
| GGCGCGTCAGCGGGTGTTGGCGGGTGTCGGGGCTGGCTTAACTATGCGGCA |
| TCAGAGCAGATTGTACTGAGAGTGCACCATATGCGGTGTGAAATACCGCAC |
| AGATGCGTAAGGAGAAAATACCGCATCAGGCGCCATTCGCCATTCAGGCTG |
| CGCAACTGTTGGGAAGGGCGATCGGTGCGGGCCTCTTCGCTATTACGCCAG |
| CTGGCGAAAGGGGGATGTGCTGCAAGGCGATTAAGTTGGGTAACGCCAGGG |
| TTTTCCCAGTCACGACGTTGTAAAACGACGGCCAGTGAATTCG |

TABLE 11

| Nucleotide sequences of Tet promoter-PAL1 construct, low-copy (SEQ ID NO: 28B) |
|---|
| **ACCACTCCCTATCAGTGATAGAGAA**AAGTGAACTCTAGAAATAATTTTGTT |
| TAACTTTAAGAAGGAGATATACATATGAAAACACTATCACAGGCCCAATCT |
| AAAACTTCTTCACAGCAATTCAGCTTTACCGGGAACTCGTCTGCGAATGTA |
| ATTATCGGCAATCAAAAGCTGACCATTAATGATGTAGCTCGCGTTGCCCGG |
| AATGGCACTTTGGTGTCACTGACGAACAATACCGACATTCTGCAAGGTATT |

TABLE 11-continued

| Nucleotide sequences of Tet promoter-PAL1 construct, low-copy (SEQ ID NO: 28B) |
|---|
| CAAGCTAGCTGCGATTATATCAATAACGCCGTTGAATCTGGCGAGCCAATC |
| TACGGGGTAACAAGCGGTTTTGGTGGGATGGCGAACGTTGCCATTAGCCGT |
| GAACAGGCGAGCGAACTTCAGACCAACCTCGTTTGGTTCCTAAAGACAGGA |
| GCTGGTAATAAGTTACCTCTGGCTGACGTAAGAGCCGCGATGCTGCTTCGC |
| GCTAATAGTCACATGCGCGGCGCCAGTGGTATCCGTCTTGAGCTTATCAAG |
| AGGATGGAAATCTTCCTCAACGCGGGTGTCACACCATATGTTTATGAGTTT |
| GGTAGTATCGGAGCCAGTGGTGATCTTGTTCCCCTGAGTTATATTACGGGT |
| TCATTGATTGGTTTAGACCCGTCCTTTAAAGTGGATTTTAACGGAAAGAA |
| ATGGACGCCCCGACCGCTTTACGACAGCTTAATCTGAGCCCACTTACTTTG |
| CTCCCTAAAGAAGGTCTTGCCATGATGAATGGCACCTCTGTGATGACTGGA |
| ATTGCCGCGAATTGTGTGTATGACACGCAGATCCTAACGGCCATTGCCATG |
| GGTGTTCACGCGTTGGACATTCAAGCCCTGAATGGTACAAACCAGTCGTTT |
| CATCCGTTTATCCATAATTCAAAACCCCATCCGGGACAGCTTTGGGCTGCT |
| GATCAGATGATCTCACTCCTGGCCAATAGTCAACTGGTTCGGGACGAGCTC |
| GACGGCAAACATGATTATCGCGATCATGAGCTCATCCAGGACCGGTATTCA |
| CTTCGTTGTCTCCCACAATACCTGGGGCCTATCGTTGATGGTATATCTCAA |
| ATTGCGAAGCAAATTGAAATTGAGATCAATAGCGTAACCGACAACCCGCTT |
| ATCGATGTTGATAATCAGGCCTCTTATCACGGTGGCAATTTTCTGGGCCAG |
| TATGTTGGTATGGGGATGGATCACCTGCGGTACTATATTGGGCTTCTGGCT |
| AAACATCTTGATGTGCAGATTGCCTTATTAGCTTCACCAGAATTTTCAAAT |
| GGACTGCCGCCATCATTGCTCGGTAACAGAGAAAGGAAAGTAAATATGGGC |
| CTTAAGGGCCTTCAGATATGTGGTAACTCAATCATGCCCCTCCTGACCTTT |
| TATGGGAACTCAATTGCTGATCGTTTTCCGACACATGCTGAACAGTTTAAC |
| CAAAACATTAACTCACAGGGCTATACATCCGCGACGTTAGCGCGTCGGTCC |
| GTGGATATCTTCCAGAATTATGTTGCTATCGCTCTGATGTTCGGCGTACAG |
| GCCGTTGATTTGCGCACTTATAAAAAAACCGGTCACTACGATGCTCGGGCT |
| TGCCTGTCGCCTGCCACCGAGCGGCTTTATAGCGCCGTACGTCATGTTGTG |
| GGTCAGAAACCGACGTCGGACCGCCCCTATATTTGGAATGATAATGAACAA |
| GGGCTGGATGAACACATCGCCCGGATATCTGCCGATATTGCCGCCGGAGGT |
| GTCATCGTCCAGGCGGTACAAGACATACTTCCTTGCCTGCATTAAGCTTGG |
| CGTAATCATGGTCATAGCTGTTTCCTGTGTGAAATTGTTATCCGCTCACAA |
| TTCCACACAACATACGAGCCGGAAGCATAAAGTGTAAAGCCTGGGGTGCCT |
| AATGAGTGAGCTAACTCACATTAATTGCGTTGCGCTCACTGCCCGCTTTCC |
| AGTCGGGAAACCTGTCGTGCCAGCTGCATTAATGAATCGGCCAACGCGCGG |
| GGAGAGGCGGTTTGCGTATTGGGCGCTCTTCCGCTTCCTCGCTCACTGACT |
| CGCTGCGCTCGGTCGTTCGGCTGCGGCGAGCGGTATCAGCTCACTCAAAGG |
| CGGTAGTACGGGTTTTGCTGCCCGCAAACGGGCTGTTCTGGTGTTGCTAGT |
| TTGTTATCAGAATCGCAGATCCGGCTTCAGGTTTGCCGGCTGAAAGCGCTA |

TABLE 11-continued

| Nucleotide sequences of Tet promoter-PAL1 construct, low-copy (SEQ ID NO: 28B) |
|---|
| TTTCTTCCAGAATTGCCATGATTTTTTCCCCACGGGAGGCGTCACTGGCTC |
| CCGTGTTGTCGGCAGCTTTGATTCGATAAGCAGCATCGCCTGTTTCAGGCT |
| GTCTATGTGTGACTGTTGAGCTGTAACAAGTTGTCTCAGGTGTTCAATTTC |
| ATGTTCTAGTTGCTTTGTTTTACTGGTTTCACCTGTTCTATTAGGTGTTAC |
| ATGCTGTTCATCTGTTACATTGTCGATCTGTTCATGGTGAACAGCTTTAAA |
| TGCACCAAAAACTCGTAAAAGCTCTGATGTATCTATCTTTTTTACACCGTT |
| TTCATCTGTGCATATGGACAGTTTTCCCTTTGATATCTAACGGTGAACAGT |
| TGTTCTACTTTTGTTTGTTAGTCTTGATGCTTCACTGATAGATACAAGAGC |
| CATAAGAACCTCAGATCCTTCCGTATTTAGCCAGTATGTTCTCTAGTGTGG |
| TTCGTTGTTTTTGCGTGAGCCATGAGAACGAACCATTGAGATCATGCTTAC |
| TTTGCATGTCACTCAAAAATTTTGCCTCAAAACTGGTGAGCTGAATTTTTG |
| CAGTTAAAGCATCGTGTAGTGTTTTTCTTAGTCCGTTACGTAGGTAGGAAT |
| CTGATGTAATGGTTGTTGGTATTTTGTCACCATTCATTTTTATCTGGTTGT |
| TCTCAAGTTCGGTTACGAGATCCATTTGTCTATCTAGTTCAACTTGGAAAA |
| TCAACGTATCAGTCGGGCGGCCTCGCTTATCAACCACCAATTTCATATTGC |
| TGTAAGTGTTTAAATCTTTACTTATTGGTTTCAAAACCCATTGGTTAAGCC |
| TTTTAAACTCATGGTAGTTATTTTCAAGCATTAACATGAACTTAAATTCAT |
| CAAGGCTAATCTCTATATTTGCCTTGTGAGTTTTCTTTTGTGTTAGTTCTT |
| TTAATAACCACTCATAAATCCTCATAGAGTATTTGTTTTCAAAAGACTTAA |
| CATGTTCCAGATTATATTTTATGAATTTTTTTAACTGGAAAAGATAAGGCA |
| ATATCTCTTCACTAAAAACTAATTCTAATTTTTCGCTTGAGAACTTGGCAT |
| AGTTTGTCCACTGGAAAATCTCAAAGCCTTTAACCAAAGGATTCCTGATTT |
| CCACAGTTCTCGTCATCAGCTCTCTGGTTGCTTTAGCTAATACACCATAAG |
| CATTTTCCCTACTGATGTTCATCATCTGAGCGTATTGGTTATAAGTGAACG |
| ATACCGTCCGTTCTTTCCTTGTAGGGTTTTCAATCGTGGGGTTGAGTAGTG |
| CCACACAGCATAAAATTAGCTTGGTTTCATGCTCCGTTAAGTCATAGCGAC |
| TAATCGCTAGTTCATTTGCTTTGAAAACAACTAATTCAGACATACATCTCA |
| ATTGGTCTAGGTGATTTTAATCACTATACCAATTGAGATGGGCTAGTCAAT |
| GATAATTACTAGTCCTTTTCCTTTGAGTTGTGGGTATCTGTAAATTCTGCT |
| AGACCTTTGCTGGAAAACTTGTAAATTCTGCTAGACCCTCTGTAAATTCCG |
| CTAGACCTTTGTGTGTTTTTTTTGTTTATATTCAAGTGGTTATAATTTATA |
| GAATAAAGAAAGAATAAAAAAAGATAAAAAGAATAGATCCCAGCCCTGTGT |
| ATAACTCACTACTTTAGTCAGTTCCGCAGTATTACAAAAGGATGTCGCAAA |
| CGCTGTTTGCTCCTCTACAAAACAGACCTTAAAACCCTAAAGGCTTAAGTA |
| GCACCCTCGCAAGCTCGGGCAAATCGCTGAATATTCCTTTTGTCTCCGACC |
| ATCAGGCACCTGAGTCGCTGTCTTTTTCGTGACATTCAGTTCGCTGCGCTC |
| ACGGCTCTGGCAGTGAATGGGGGTAAATGGCACTACAGGCGCCTTTTATGG |
| ATTCATGCAAGGAAACTACCCATAATACAAGAAAAGCCCGTCACGGGCTTC |
| TCAGGGCGTTTTATGGCGGGTCTGCTATGTGGTGCTATCTGACTTTTTGCT |

TABLE 11-continued

| Nucleotide sequences of Tet promoter-PAL1 construct, low-copy (SEQ ID NO: 28B) |
|---|
| GTTCAGCAGTTCCTGCCCTCTGATTTTCCAGTCTGACCACTTCGGATTATC |
| CCGTGACAGGTCATTCAGACTGGCTAATGCACCCAGTAAGGCAGCGGTATC |
| ATCAACAGGCTTACCCGTCTTACTGTCTTTTCTACGGGGTCTGACGCTCAG |
| TGGAACGAAAACTCACGTTAAGGGATTTTGGTCATGAGATTATCAAAAAGG |
| ATCTTCACCTAGATCCTTTTAAATTAAAAATGAAGTTTTAAATCAATCTAA |
| AGTATATATGAGTAAACTTGGTCTGACAGTTACCAATGCTTAATCAGTGAG |
| GCACCTATCTCAGCGATCTGTCTATTTCGTTCATCCATAGTTGCCTGACTC |
| CCCGTCGTGTAGATAACTACGATACGGGAGGGCTTACCATCTGGCCCCAGT |
| GCTGCAATGATACCGCGAGACCCACGCTCACCGGCTCCAGATTTATCAGCA |
| ATAAACCAGCCAGCCGGAAGGGCCGAGCGCAGAAGTGGTCCTGCAACTTTA |
| TCCGCCTCCATCCAGTCTATTAATTGTTGCCGGGAAGCTAGAGTAAGTAGT |
| TCGCCAGTTAATAGTTTGCGCAACGTTGTTGCCATTGCTACAGGCATCGTG |
| GTGTCACGCTCGTCGTTTGGTATGGCTTCATTCAGCTCCGGTTCCCAACGA |
| TCAAGGCGAGTTACATGATCCCCCATGTTGTGCAAAAAAGCGGTTAGCTCC |
| TTCGGTCCTCCGATCGTTGTCAGAAGTAAGTTGGCCGCAGTGTTATCACTC |
| ATGGTTATGGCAGCACTGCATAATTCTCTTACTGTCATGCCATCCGTAAGA |
| TGCTTTTCTGTGACTGGTGAGTACTCAACCAAGTCATTCTGAGAATAGTGT |
| ATGCGGCGACCGAGTTGCTCTTGCCCGGCGTCAATACGGGATAATACCGCG |
| CCACATAGCAGAACTTTAAAAGTGCTCATCATTGGAAAACGTTCTTCGGGG |
| CGAAAACTCTCAAGGATCTTACCGCTGTTGAGATCCAGTTCGATGTAACCC |
| ACTCGTGCACCCAACTGATCTTCAGCATCTTTTACTTTCACCAGCGTTTCT |
| GGGTGAGCAAAAACAGGAAGGCAAAATGCCGCAAAAAAGGGAATAAGGGCG |
| ACACGGAAATGTTGAATACTCATACTCTTCCTTTTTCAATATTATTGAAGC |
| ATTTATCAGGGTTATTGTCTCATGAGCGGATACATATTTGAATGTATTTAG |
| AAAAATAAACAAATAGGGGTTCCGCGCACATTTCCCCGAAAAGTGCCACCT |
| GACGTCTAAGAAACCATTATTATCATGACATTAACCTATAAAAATAGGCGT |
| ATCACGAGGCCCTTTCGTCTCGCGCGTTTCGGTGATGACGGTGAAAACCTC |
| TGACACATGCAGCTCCCGGAGACGGTCACAGCTTGTCTGTAAGCGGATGCC |
| GGGAGCAGACAAGCCCGTCAGGGCGCGTCAGCGGGTGTTGGCGGGTGTCGG |
| GGCTGGCTTAACTATGCGGCATCAGAGCAGATTGTACTGAGAGTGCACCAT |
| ATGCGGTGTGAAATACCGCACAGATGCGTAAGGAGAAAATACCGCATCAGG |
| CGCCATTCGCCATTCAGGCTGCGCAACTGTTGGGAAGGGCGATCGGTGCGG |
| GCCTCTTCGCTATTACGCCAGCTGGCGAAAGGGGGATGTGCTGCAAGGCGA |
| TTAAGTTGGGTAACGCCAGGGTTTTCCCAGTCACGACGTTGTAAAACGACG |
| GCCAGTGAATTCGTTAAGACCCACTTTCACATTTAAGTTGTTTTTCTAATC |
| CGCATATGATCAATTCAAGGCCGAATAAGAAGGCTGGCTCTGCACCTTGGT |
| GATCAAATAATTCGATAGCTTGTCGTAATAATGGCGGCATACTATCAGTAG |
| TAGGTGTTTCCCTTTCTTCTTTAGCGACTTGATGCTCTTGATCTTCCAATA |
| CGCAACCTAAAGTAAAATGCCCCACAGCGCTGAGTGCATATAATGCATTCT |
| CTAGTGAAAAACCTTGTTGGCATAAAAAGGCTAATTGATTTTCGAGAGTTT |
| CATACTGTTTTTCTGTAGGCCGTGTACCTAAATGTACTTTTGCTCCATCGC |
| GATGACTTAGTAAAGCACATCTAAAACTTTTAGCGTTATTACGTAAAAAAT |
| CTTGCCAGCTTTCCCCTTCTAAAGGGCAAAAGTGAGTATGGTGCCTATCTA |
| ACATCTCAATGGCTAAGGCGTCGAGCAAAGCCCGCTTATTTTTTACATGCC |
| AATACAATGTAGGCTGCTCTACACCTAGCTTCTGGGCGAGTTTACGGGTTG |
| TTAAACCTTCGATTCCGACCTCATTAAGCAGCTCTAATGCGCTGTTAATCA |
| CTTTACTTTTATCTAATCTAGACATCATTAATTCCTAATTTTT**GTTGACAC** |
| **TCTATCATTGATAGAGTTATTTT** |

TABLE 12

| Nucleotide sequences of Tet promoter-PAL3 construct, low-copy (SEQ ID NO: 29B) |
|---|
| **ACCACTCCCTATCAGTGATAGAGAA**AAGTGAACTCTAGAAATAATTTTGTT |
| TAACTTTAAGAAGGAGATATACATATGAAAGCTAAAGATGTTCAGCCAACC |
| ATTATTATTAATAAAAATGGCCTTATCTCTTTGGAAGATATCTATGACATT |
| GCGATAAAACAAAAAAAAGTAGAAATATCAACGGAGATCACTGAACTTTTG |
| ACGCATGGTCGTGAAAAATTAGAGGAAAAATTAAATTCAGGAGAGGTTATA |
| TATGGAATCAATACAGGATTTGGAGGGAATGCCAATTTAGTTGTGCCATTT |
| GAGAAAATCGCAGAGCATCAGCAAAATCTGTTAACTTTTCTTTCTGCTGGT |
| ACTGGGGACTATATGTCCAAACCTTGTATTAAAGCGTCACAATTTACTATG |
| TTACTTTCTGTTTGCAAAGGTTGGTCTGCAACCAGACCAATTGTCGCTCAA |
| GCAATTGTTGATCATATTAATCATGACATTGTTCCTCTGGTTCCTCGCTAT |
| GGCTCAGTGGGTGCAAGCGGTGATTTAATTCCTTTATCTTATATTGCACGA |
| GCATTATGTGGTATCGGCAAAGTTTATTATATGGGCGCAGAAATTGACGCT |
| GCTGAAGCAATTAAACGTGCAGGGTTGACACCATTATCGTTAAAAGCCAAA |
| GAAGGTCTTGCTCTGATTAACGGCACCCGGGTAATGTCAGGAATCAGTGCA |
| ATCACCGTCATTAAACTGGAAAAACTATTTAAAGCCTCAATTTCTGCGATT |
| GCCCTTGCTGTTGAAGCATTACTTGCATCTCATGAACATTATGATGCCCGG |
| ATTCAACAAGTAAAAAATCATCCTGGTCAAAACGCGGTGGCAAGTGCATTG |
| CGTAATTTATTGGCAGGTTCAACGCAGGTTAATCTATTATCTGGGGTTAAA |
| GAACAAGCCAATAAAGCTTGTCGTCATCAAGAAATTACCCAACTAAATGAT |
| ACCTTACAGGAAGTTTATTCAATTCGCTGTGCACCACAAGTATTAGGTATA |
| GTGCCAGAATCTTTAGCTACCGCTCGGAAAATATTGGAACGGGAAGTTATC |
| TCAGCTAATGATAATCCATTGATAGATCCAGAAAATGGCGATGTTCTACAC |
| GGTGGAAATTTTATGGGGCAATATGTCGCCCGAACAATGGATGCATTAAAA |
| CTGGATATTGCTTTAATTGCCAATCATCTTCACGCCATTGTGGCTCTTATG |
| ATGGATAACCGTTTCTCTCGTGGATTACCTAATTCACTGAGTCCGACACCC |

TABLE 12-continued

| Nucleotide sequences of Tet promoter-PAL3 construct, low-copy (SEQ ID NO: 29B) |
| --- |

GGCATGTATCAAGGTTTTAAAGGCGTCCAACTTTCTCAAACCGCTTTAGTT
GCTGCAATTCGCCATGATTGTGCTGCATCAGGTATTCATACCCTCGCCACA
GAACAATACAATCAAGATATTGTCAGTTTAGGTCTGCATGCCGCTCAAGAT
GTTTTAGAGATGGAGCAGAAATTACGCAATATTGTTTCAATGACAATTCTG
GTAGTTTGTCAGGCCATTCATCTTCGCGGCAATATTAGTGAAATTGCGCCT
GAAACTGCTAAATTTTACCATGCAGTACGCGAAATCAGTTCTCCTTTGATC
ACTGATCGTGCGTTGGATGAAGATATAATCCGCATTGCGGATGCAATTATT
AATGATCAACTTCCTCTGCCAGAAATCATGCTGGAAGAATAAGCTTGGCGT
AATCATGGTCATAGCTGTTTCCTGTGTGAAATTGTTATCCGCTCACAATTC
CACACAACATACGAGCCGGAAGCATAAAGTGTAAAGCCTGGGGTGCCTAAT
GAGTGAGCTAACTCACATTAATTGCGTTGCGCTCACTGCCCGCTTTCCAGT
CGGGAAACCTGTCGTGCCAGCTGCATTAATGAATCGGCCAACGCGCGGGGA
GAGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCGG
TAGTACGGGTTTTGCTGCCCGCAAACGGGCTGTTCTGGTGTTGCTAGTTTG
TTATCAGAATCGCAGATCCGGCTTCAGGTTTGCCGGCTGAAAGCGCTATTT
CTTCCAGAATTGCCATGATTTTTTCCCCACGGGAGGCGTCACTGGCTCCCG
TGTTGTCGGCAGCTTTGATTCGATAAGCAGCATCGCCTGTTTCAGGCTGTC
TATGTGTGACTGTTGAGCTGTAACAAGTTGTCTCAGGTGTTCAATTTCATG
TTCTAGTTGCTTTGTTTTACTGGTTTCACCTGTTCTATTAGGTGTTACATG
CTGTTCATCTGTTACATTGTCGATCTGTTCATGGTGAACAGCTTTAAATGC
ACCAAAAACTCGTAAAAGCTCTGATGTATCTATCTTTTTTACACCGTTTTC
ATCTGTGCATATGGACAGTTTTCCCTTTGATATCTAACGGTGAACAGTTGT
TCTACTTTTGTTTGTTAGTCTTGATGCTTCACTGATAGATACAAGAGCCAT
AAGAACCTCAGATCCTTCCGTATTTAGCCAGTATGTTCTCTAGTGTGGTTC
GTTGTTTTTGCGTGAGCCATGAGAACGAACCATTGAGATCATGCTTACTTT
GCATGTCACTCAAAAATTTTGCCTCAAAACTGGTGAGCTGAATTTTTGCAG
TTAAAGCATCGTGTAGTGTTTTTCTTAGTCCGTTACGTAGGTAGGAATCTG
ATGTAATGGTTGTTGGTATTTTGTCACCATTCATTTTTATCTGGTTGTTCT
CAAGTTCGGTTACGAGATCCATTTGTCTATCTAGTTCAACTTGGAAAATCA
ACGTATCAGTCGGGCGGCCTCGCTTATCAACCACCAATTTCATATTGCTGT
AAGTGTTTAAATCTTTACTTATTGGTTTCAAAACCCATTGGTTAAGCCTTT
TAAACTCATGGTAGTTATTTTCAAGCATTAACATGAACTTAAATTCATCAA
GGCTAATCTCTATATTTGCCTTGTGAGTTTTCTTTTGTGTTAGTTCTTTTA
ATAACCACTCATAAATCCTCATAGAGTATTTGTTTTCAAAAGACTTAACAT
GTTCCAGATTATATTTTATGAATTTTTTTAACTGGAAAAGATAAGGCAATA
TCTCTTCACTAAAAACTAATTCTAATTTTTCGCTTGAGAACTTGGCATAGT
TTGTCCACTGGAAAATCTCAAAGCCTTTAACCAAAGGATTCCTGATTTCCA

TABLE 12-continued

| Nucleotide sequences of Tet promoter-PAL3 construct, low-copy (SEQ ID NO: 29B) |
| --- |

CAGTTCTCGTCATCAGCTCTCTGGTTGCTTTAGCTAATACACCATAAGCAT
TTTCCCTACTGATGTTCATCATCTGAGCGTATTGGTTATAAGTGAACGATA
CCGTCCGTTCTTTCCTTGTAGGGTTTTCAATCGTGGGGTTGAGTAGTGCCA
CACAGCATAAAATTAGCTTGGTTTCATGCTCCGTTAAGTCATAGCGACTAA
TCGCTAGTTCATTTGCTTTGAAAACAACTAATTCAGACATACATCTCAATT
GGTCTAGGTGATTTTAATCACTATACCAATTGAGATGGGCTAGTCAATGAT
AATTACTAGTCCTTTTCCTTTGAGTTGTGGGTATCTGTAAATTCTGCTAGA
CCTTTGCTGGAAAACTTGTAAATTCTGCTAGACCCTCTGTAAATTCCGCTA
GACCTTTGTGTGTTTTTTTTGTTTATATTCAAGTGGTTATAATTTATAGAA
TAAAGAAAGAATAAAAAAAGATAAAAAGAATAGATCCCAGCCCTGTGTATA
ACTCACTACTTTAGTCAGTTCCGCAGTATTACAAAAGGATGTCGCAAACGC
TGTTTGCTCCTCTACAAAACAGACCTTAAAACCCTAAAGGCTTAAGTAGCA
CCCTCGCAAGCTCGGGCAAATCGCTGAATATTCCTTTTGTCTCCGACCATC
AGGCACCTGAGTCGCTGTCTTTTTCGTGACATTCAGTTCGCTGCGCTCACG
GCTCTGGCAGTGAATGGGGGTAAATGGCACTACAGGCGCCTTTTATGGATT
CATGCAAGGAAACTACCCATAATACAAGAAAAGCCCGTCACGGGCTTCTCA
GGGCGTTTTATGGCGGGTCTGCTATGTGGTGCTATCTGACTTTTTGCTGTT
CAGCAGTTCCTGCCCTCTGATTTTCCAGTCTGACCACTTCGGATTATCCCG
TGACAGGTCATTCAGACTGGCTAATGCACCCAGTAAGGCAGCGGTATCATC
AACAGGCTTACCCGTCTTACTGTCTTTTCTACGGGGTCTGACGCTCAGTGG
AACGAAAACTCACGTTAAGGGATTTTGGTCATGAGATTATCAAAAAGGATC
TTCACCTAGATCCTTTTAAATTAAAAATGAAGTTTTAAATCAATCTAAAGT
ATATATGAGTAAACTTGGTCTGACAGTTACCAATGCTTAATCAGTGAGGCA
CCTATCTCAGCGATCTGTCTATTTCGTTCATCCATAGTTGCCTGACTCCCC
GTCGTGTAGATAACTACGATACGGGAGGGCTTACCATCTGGCCCCAGTGCT
GCAATGATACCGCGAGACCCACGCTCACCGGCTCCAGATTTATCAGCAATA
AACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCA
AGGCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCATG
GTTATGGCAGCACTGCATAATTCTCTTACTGTCATGCCATCCGTAAGATGC
TTTTCTGTGACTGGTGAGTACTCAACCAAGTCATTCTGAGAATAGTGTATG
CGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGA
AAACTCTCAAGGATCTTACCGCTGTTGAGATCCAGTTCGATGTAACCCACT
CGTGCACCCAACTGATCTTCAGCATCTTTTACTTTCACCAGCGTTTCTGGG
TGAGCAAAAACAGGAAGGCAAAATGCCGCAAAAAAGGGAATAAGGGCGACA

TABLE 12-continued

| Nucleotide sequences of Tet promoter-PAL3 construct, low-copy (SEQ ID NO: 29B) |
|---|
| CGGAAATGTTGAATACTCATACTCTTCCTTTTTCAATATTATTGAAGCATT |
| TATCAGGGTTATTGTCTCATGAGCGGATACATATTTGAATGTATTTAGAAA |
| AATAAACAAATAGGGGTTCCGCGCACATTTCCCCGAAAAGTGCCACCTGAC |
| GTCTAAGAAACCATTATTATCATGACATTAACCTATAAAAATAGGCGTATC |
| ACGAGGCCCTTTCGTCTCGCGCGTTTCGGTGATGACGGTGAAAACCTCTGA |
| CACATGCAGCTCCCGGAGACGGTCACAGCTTGTCTGTAAGCGGATGCCGGG |
| AGCAGACAAGCCCGTCAGGGCGCGTCAGCGGGTGTTGGCGGGTGTCGGGGC |
| TGGCTTAACTATGCGGCATCAGAGCAGATTGTACTGAGAGTGCACCATATG |
| CGGTGTGAAATACCGCACAGATGCGTAAGGAGAAAATACCGCATCAGGCGC |
| CATTCGCCATTCAGGCTGCGCAACTGTTGGGAAGGGCGATCGGTGCGGGCC |
| TCTTCGCTATTACGCCAGCTGGCGAAAGGGGGATGTGCTGCAAGGCGATTA |
| AGTTGGGTAACGCCAGGGTTTTCCCAGTCACGACGTTGTAAAACGACGGCC |
| AGTGAATTCGTTAAGACCCACTTTCACATTTAAGTTGTTTTTCTAATCCGC |
| ATATGATCAATTCAAGGCCGAATAAGAAGGCTGGCTCTGCACCTTGGTGAT |
| CAAATAATTCGATAGCTTGTCGTAATAATGGCGGCATACTATCAGTAGTAG |
| GTGTTTCCCTTTCTTCTTTAGCGACTTGATGCTCTTGATCTTCCAATACGC |
| AACCTAAAGTAAAATGCCCCACAGCGCTGAGTGCATATAATGCATTCTCTA |
| GTGAAAAACCTTGTTGGCATAAAAAGGCTAATTGATTTTCGAGAGTTTCAT |
| ACTGTTTTTCTGTAGGCCGTGTACCTAAATGTACTTTTGCTCCATCGCGAT |
| GACTTAGTAAAGCACATCTAAAACTTTTAGCGTTATTACGTAAAAAATCTT |
| GCCAGCTTTCCCCTTCTAAAGGGCAAAAGTGAGTATGGTGCCTATCTAACA |
| TCTCAATGGCTAAGGCGTCGAGCAAAGCCCGCTTATTTTTTACATGCCAAT |
| ACAATGTAGGCTGCTCTACACCTAGCTTCTGGGCGAGTTTACGGGTTGTTA |
| AACCTTCGATTCCGACCTCATTAAGCAGCTCTAATGCGCTGTTAATCACTT |
| TACTTTTATCTAATCTAGACATCATTAATTCCTAATTTTT**GTTGACACTCT** |
| **ATCATTGATAGAGTTATTTT** |

TABLE 13

| Nucleotide sequences of TetR-PheP construct, low-copy (SEQ ID NO: 30B) |
|---|
| ccagtgaattcgttaagacccactttcacatttaagttgtttttctaatccgcatatgatcaattcaaggccgaataagaaggctggctctgcaccttg |
| gtgatcaaataattcgatagcttgtcgtaataatggcggcatactatcagtagtaggtgtttccctttcttctttagcgacttgatgctcttgatcttcca |
| atacgcaacctaaagtaaaatgccccacagcgctgagtgcatataatgcattctctagtgaaaaaccttgttggcataaaaaggctaattgattttc |
| gagaggtttcatactgtttttctgtaggccgtgtacctaaatgtacttttgctccatcgcgatgacttagtaaagcacatctaaaacttttagcgttattac |
| gtaaaaaatcttgccagctttccccttctaaagggcaaaagtgagtatggtgcctatctaacatctcaatggctaaggcgtcgagcaaagcccgc |
| ttattttttacatgccaatacaatgtaggctgctctacacctagcttctgggcgagtttacgggttgttaaaccttcgattccgacctcattaagcagct |
| ctaatgcgctgttaatcactttacttttatctaatctagacatcattaattcctaattttt**gttgacactctatcattgatagagttattttaccactccc** |
| **tatcagtgatagagaa**aagtgaactctagaaataattttgtttaactttaagaaggagatatacatATGAAAAACGCGTCAACC |
| GTATCGGAAGATACTGCGTCGAATCAAGAGCCGACGCTTCATCGCGGATTACATAACCGTCATATTCAACTGA |
| TTGCGTTGGGTGGCGCAATTGGTACTGGTCTGTTTCTTGGCATTGGCCCGGCGATTCAGATGGCGGGTCCGGCTGTATTGCTGGG |
| CTACGGCGTCGCCGGGATCATCGCTTTCCTGATTATGCGCCAGCTTGGCGAAATGGTGGTTGAGG |
| AGCCGGTATCCGGTTCATTTGCCCACTTTGCCTATAAATACTGGGGACCGTTTGCGGGCTTCCTCTCTGGCTGGAACTACTGGG |
| TAATGTTCGTGCTGGTGGGAATGGCAGAGCTGACCGCTGCGGGCATCTATATGCAGTACTGGTTCC |
| CGGATGTTCCAACGTGGATTTGGGCTGCCGCCTTCTTTATTATCATCAACGCCGTTAACCTGGTGAACGTGCGCTTA |
| TATGGCGAAACCGAGTTCTGGTTTGCGTTGATTAAAGTGCTGGCAATCATCGGTATGATCGGCTTTGGCCTGT |
| GGCTGCTGTTTTCTGGTCACGGCGGCGAGAAAGCCAGTATCGACAACCTCTGGCGCTACGGTGGTTTCTTCGC |
| CACCGGCTGGAATGGGCTGATTTTGTCGCTGGCGGTAATTATGTTCTCCTTCGGCGGTCTGGAGCTGATTGGGATTA |
| CTGCCGCTGAAGCGCGCGATCCGGAAAAAAGCATTCCAAAAGCGGTAAATCAGGTGGTGTATCGCATCCTGCTGTTTTACAT |
| CGGTTCACTGGTGGTTTTACTGGCGCTCTATCCGTGGGTGGAAGTGAAATCCAACAGTAGCCCGTTTG |

TABLE 13-continued

| Nucleotide sequences of TetR-PheP construct, low-copy (SEQ ID NO: 30B) |
|---|
| TGATGATTTTCCATAATCTCGACAGCAACGTGGTAGCTTCTGCGCTGAACTTCGTCATTCTGGTAGCATCGCTGTCAGTG |
| TATAACAGCGGGGTTTACTCTAACAGCCGCATGCTGTTTGGCCTTTCTGTGCAGGGTAATGCGCCGAAGT |
| TTTTGACTCGCGTCAGCCGTCGCGGTGTGCCGATTAACTCGCTGATGCTTTCCGGAGCGATCACTTCGCTGGTGGTGTTAATC |
| AACTATCTGCTGCCGCAAAAAGCGTTTGGTCTGCTGATGGCGCTGGTGGTAGCAACGCTGCTGTTGA |
| ACTGGATTATGATCTGTCTGGCGCATCTGCGTTTTCGTGCAGCGATGCGACGTCAGGGGCGTGAAACACAGTTTA |
| AGGCGCTGCTCTATCCGTTCGGCAACTATCTCTGCATTGCCTTCCTCGGCATGATTTTGCTGCTGATGTGCACGA |
| TGGATGATATGCGCTTGTCAGCGATCCTGCTGCCGGTGTGGATTGTATTCCTGTTTATGGCATTTAAAACGCTGCGTCGGAAATAA |

In some embodiments, the genetically engineered bacteria contain gene sequence(s) comprising one or more sequence(s) of any of SEQ ID Nos: 21B-30B. In some embodiments, the genetically engineered bacteria contain gene sequence(s) comprising one or more sequence(s) having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 21B-30B.

In any of the embodiments described herein, the genetically engineered bacteria comprising one or more genes encoding one or more PME(s) further comprise one or more endogenous bacteriophage genomes. In some embodiments, the bacteriophage has been mutated in one or more genes within the bacteriophage genome. Such mutations include deletions, insertions, substitutions and inversions and may be located in or encompass one or more bacteriophage genes.

In one embodiment, *E. coli* Nissle is used as a starting point, parental strain or "chassis" for the genetically engineered bacteria comprising one or more PME(s). In one embodiment, the bacteriophage which is modified is a phage which is endogenous to *E. coli* Nissle in its natural state.

In some embodiments, the genetically engineered bacteria comprise one or more *E. coli*. Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some of the preceding embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one embodiment, the genetically engineered bacteria comprise a complete or partial deletion of one or more ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Oxygen Consuming Enzymes

LAAD catalytic activity is dependent on oxygen, and therefore may not be active in anaerobic and/or low oxygen environments in the intestine, e.g., the colon. Oxygen is present in more proximal compartments of the GI tract.

The oxygen tension as measured in healthy mice is shown in Table 17A. He et al., Proc Natl Acad Sci USA. 1999 Apr. 13; 96(8):4586-91; "Noninvasive measurement of anatomic structure and intraluminal oxygenation in the gastrointestinal tract of living mice with spatial and spectral EPR imaging", the contents of which is herein incorporated by reference in its entirety. A marked oxygen gradient from the proximal to the distal GI tract. As noted by He, the observed oxygen gradient seen along the GI tract can be explained by a combination of processes. Without wishing to be bound by theory, food, when swallowed, is initially equilibrated with the oxygen tension of ambient room air. On passage to the stomach and later the small intestine, the oxygen levels may fall as oxygen diffuses across the mucosal membrane. A gradual process of equilibration with the capillary levels of oxygen (i.e., 5-10 torr; ref. 9) may occur. On passage to the colon, with its heavy bacterial colonization, further decreases in oxygenation occur. Finally, the lumen of the distal colon displays marked hypoxia, as expected, based on the abundance of anaerobic bacteria at this site.

TABLE 17A

Oxygen Tension in Gastrointestinal Tract Compartments

| Compartment | Oxygen Tension |
|---|---|
| Ambient Air | 159 Torr |
| stomach | ~60 torr |
| duodenum and first part of jejunum | (~30 torr); ~20% oxygen in ambient air |
| Ileum | (~10 torr); ~6% oxygen in ambient air |
| colon | (<2 torr) |

As shown in FIG. 25B, LAAD activity is retained in microaerobic conditions, albeit at lower levels than under aerobic conditions (FIG. 25A and FIG. 25B). LAAD therefore may be active in the more proximal areas of the intestine, such as stomach, duodenum, jejunum, and ileum. It is contemplated as part of this disclosure that LAAD expressed by the genetically engineered bacteria may advantageously be active in a different compartment than PAL, which may be expressed in the colon if under the control of an FNR promoter. In one embodiment, the genetically engineered bacteria express two enzymes, which have different oxygen requirements and/or are induced under different oxygen conditions, such that an PME is expressed and active throughout the entire gastrointestinal system. For example, the first enzyme, e.g., LAAD, which is dependent on the presence of oxygen, is expressed in one or more of stomach, duodenum and ileum under the control of a constitutive or inducible promoter (such as ParaBAD), and the second enzyme, e.g., PAL, is expressed in the colon under the control of an FNR promoter. In some embodiments, PAL is expressed under the conditions found in the small intestine, e.g. under the control of an FNR promoter, constitutive promoter, or a different inducible promoter described herein. In some embodiments, PAL and/or LAAD are pre-induced prior to in vivo administration, and are expressed and active in the proximal part of the intestine. In some embodiments, PAL and/or LAAD are pre-induced (aerobically or anaerobically, or with or without chemical and/or nutritional inducer, as described herein) prior to in vivo administration, and are expressed and active in the distal part of the intestine.

Several strategies can be employed to further increase LAAD activity under oxygen limiting conditions. For example, the activity of other enzymes that consume large amounts of oxygen can be reduced or extinguished. One such enzyme is NADH dehydrogenase. *E. coli* has two NADH dehydrogenases; nuo and ndh2, and is has been shown that knock out of both of these enzymes reduces oxygen consumption by 80%. In some embodiments, additional measures are taken to conserve limiting oxygen, i.e., to allow LAAD to function under lower exogenous oxygen conditions in the genetically engineered bacteria expressing LAAD. In some embodiments, the genetically engineered bacteria further comprise a mutation in one or more genes involved in oxygen consumption. In some embodiments, one or both *E. coli* NADH dehydrogenases are knocked out. In some embodiments, the knocked out NADH dehydrogenase is nuo. In some embodiments, the knocked out NADH dehydrogenase is ndh2. In some embodiments nuo and ndh2 are knocked out. Other enzymes involved in *E. coli* oxygen metabolism may also be knocked out, including enzymes in the respiratory chain, such as cydB (a subunit of high affinity terminal oxidase), cydD (an enzyme required to make cytochrome D), and cyoABC (subunits of low affinity cytochrome oxidase). In some embodiments, the genetically engineered bacteria harbor a knock out mutation/deletion in one more genes selected from cydB, cydD, and cyoABC.

In one embodiment, the one or more PME encoded by the genetically engineered bacteria are expressed and show activity in the stomach. In one embodiment, the one or more PME encoded by the genetically engineered bacteria are expressed and show activity in the duodenum. In one embodiment, the one or more PME encoded by the genetically engineered bacteria are expressed and show activity in the jejunum. In one embodiment, the one or more PME encoded by the genetically engineered bacteria are expressed and show activity in the ileum. In one embodiment, the one or more PME encoded by the genetically engineered bacteria are expressed and show activity in the colon.

Phenylalanine Transport

In some embodiments wherein the bacterium comprises a gene encoding a PME, the bacterium may further comprise a gene encoding a phenylalanine transporter. Phenylalanine transporters may be expressed or modified in the genetically engineered bacteria of the invention in order to enhance phenylalanine transport into the cell.

PheP is a membrane transport protein that is capable of transporting phenylalanine into bacterial cells (see, e.g., Pi et al., 1991). In some embodiments, the native pheP gene in the genetically modified bacteria of the invention is not modified. In some embodiments, the genetically engineered bacteria of the invention comprise multiple copies of the native pheP gene. In some embodiments, the genetically engineered bacteria of the invention comprise multiple copies of a non-native pheP gene. In some embodiments, the genetically engineered bacteria of the invention comprise a pheP gene that is controlled by its native promoter, an inducible promoter, a promoter that is stronger than the native promoter, e.g., the GlnRS promoter or the P(Bla) promoter, or a constitutive promoter. In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP. The phenylalanine transporter modifications described herein may be present on a plasmid or chromosome.

In some embodiments, the genetically engineered bacterium is *E. coli* Nissle, and the native pheP gene in *E. coli* Nissle is not modified; one or more additional copies the native *E. coli* Nissle pheP genes are inserted into the *E. coli* Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium is inserted into the *E. coli* Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is *E. coli* Nissle, and the native pheP gene in *E. coli* Nissle is not modified; one or more additional copies the native *E. coli* Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

In other embodiments, the gene(s) encoding the one or more Phe transporter(s) may be located on a plasmid or in the chromosome and the gene expression may be regulated by any of the promoters disclosed herein, which may be the same or different from the promoters regulating the PME gene(s).

It has been reported that *Escherichia coli* has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient *E. coli* strain (AaroP ApheP Amtr Atna AtyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in *Escherichia coli* K-12).

In some embodiments, the genetically engineered bacteria comprise an aroP gene. In some embodiments, the genetically engineered bacterium is *E. coli* Nissle, and the native aroP gene in *E. coli* Nissle is not modified; one or more additional copies of the native *E. coli* Nissle aroP genes are present in the bacterium on a plasmid or in the chromosome and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in *E. coli* Nissle is not modified, and a copy of a non-native aroP gene from a different bacterium, are present in the bacterium on a plasmid or in the chromosome and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in *E. coli* Nissle: malE/K, insB/I, araC/BAD, lacZ, agal/rsml, thyA, and malP/T. Any suitable insertion site may be used (see, e.g., FIG. 66 of WO2017087580, the contents of which are herein incorporated by reference in their entirety). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacteria encode one or more Phe transporter(s) which are directly or indirectly pre-induced prior to in vivo administration, e.g., are expressed under the control of an inducible promoter that is responsive to specific molecules or metabolites in the provided in the culture of the bacterium in a flask, fermenter, or other culture vessel, during production of the strain prior to in vivo administration.

In other embodiments, the genetically engineered bacteria encode one or more Phe transporter(s) which are directly or indirectly induced in vivo administration, e.g., are expressed under the control of an inducible promoter that is responsive conditions or to specific molecules or metabolites in the exogenous in vivo environment, e.g., the gut. In some embodiments, the promoter is induced by gut specific molecules, or low oxygen conditions. In some embodiments, the bacterial strains are administered in combination with a chemical and/or nutritional inducer.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS/nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

In any of the embodiments described herein, the genetically engineered bacteria comprising one or more genes encoding one or more phenylalanine transporters further comprise one or more endogenous bacteriophages. In some embodiments, the bacteriophage(s) have been mutated in one or more genes within the bacteriophage genome. Such mutations include deletions, insertions, substitutions and inversions and are located in or encompass one or more bacteriophage genes.

In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP The phenylalanine transporter modifications described herein may be present on a plasmid or chromosome.

In some embodiments, the genetically engineered bacterium is *E. coli* Nissle, and the native pheP gene in *E. coli* Nissle is not modified; one or more additional copies the native *E. coli* Nissle pheP genes are inserted into the *E. coli* Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium is inserted into the *E. coli* Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is *E. coli* Nissle, and the native pheP gene in *E. coli* Nissle is not modified; one or more additional copies the native *E. coli* Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

In other embodiments, the gene(s) encoding the one or more Phe transporter(s) may be located on a plasmid or in the chromosome and the gene expression may be regulated by any of the promoters disclosed herein, which may be the same or different from the promoters regulating the PME gene(s).

It has been reported that *Escherichia coli* has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient *E. coli* strain (ΔaroP ΔpheP Δmtr Δtna ΔtyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in *Escherichia coli* K-12).

In some embodiments, the genetically engineered bacteria comprise an aroP gene. In some embodiments, the genetically engineered bacterium is *E. coli* Nissle, and the native aroP gene in *E. coli* Nissle is not modified; one or more additional copies of the native *E. coli* Nissle aroP genes are present in the bacterium on a plasmid or in the chromosome and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in *E. coli* Nissle is not modified, and a copy of a non-native aroP gene from a different bacterium, are present in the bacterium on a plasmid or in the chromosome and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in *E. coli* Nissle: malE/K, insB/I, araC/BAD, lacZ, agal/rsml, thyA, and malP/T. Any suitable insertion site may be used (see, e.g., FIG. 66 of WO2017087580, the contents of which are herein incorporated by reference in their entirety). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacteria encode one or more Phe transporter(s) which are directly or indirectly pre-induced prior to in vivo administration, e.g., are expressed under the control of an inducible promoter that is responsive to specific molecules or metabolites in the provided in the culture of the bacterium in a flask, fermenter, or other culture vessel, during production of the strain prior to in vivo administration.

In other embodiments, the genetically engineered bacteria encode one or more Phe transporter(s) which are directly or indirectly induced in vivo administration, e.g., are expressed under the control of an inducible promoter that is responsive conditions or to specific molecules or metabolites in the exogenous in vivo environment, e.g., the gut. In some embodiments, the promoter is induced by gut specific molecules, or low oxygen conditions. In some embodiments, the bacterial strains are administered in combination with a chemical and/or nutritional inducer.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS/nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

In any of the embodiments described herein, the genetically engineered bacteria comprising one or more genes encoding one or more phenylalanine transporters further comprise one or more endogenous bacteriophages. In some embodiments, the bacteriophage(s) have been mutated in one or more genes within the bacteriophage genome. Such mutations include deletions, insertions, substitutions and inversions and are located in or encompass one or more bacteriophage genes.

In one embodiment, *E. coli* Nissle is used as a starting point, parental strain or "chassis" for the genetically engineered bacteria. In one embodiment, the bacteriophage which is modified is a phage which is endogenous to *E. coli* Nissle in its natural state.

In some embodiments, the genetically engineered bacteria comprise one or more *E. coli* Nissle bacteriophage, e.g., Phage 1, Phage2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some embodiments, the mutation is a deletion. In some embodiments, the genetically engineered bacteria comprise one or more deletions Multiple Mechanisms of Action In some embodiments of the disclosure, modifications to the genome of EcN have been made to enhance phenylalanine degradation under the low oxygen conditions found in the gut while augmenting biologic containment through diaminopimelate auxotrophy. These genetically engineered bacteria further comprise one or more modifications to endogenous EcN phage 3.

Figure 13:
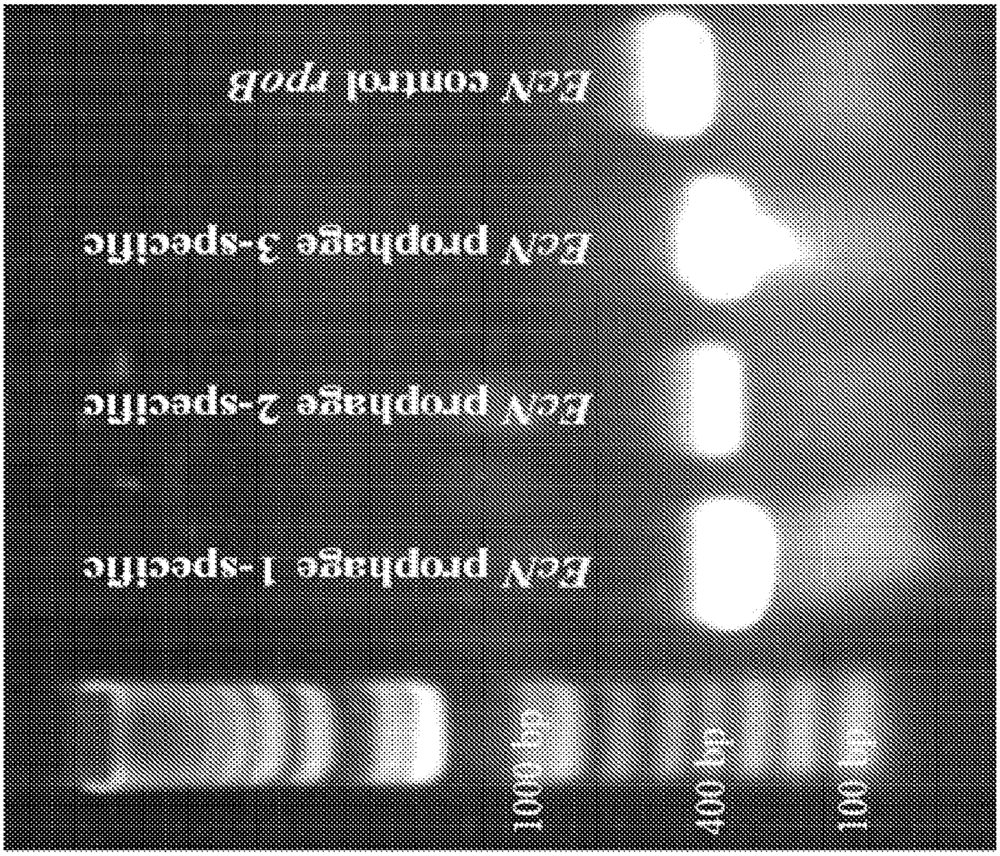
FIG. 13 depicts an DNA gel electrophoresis study verifying phage-specific PCR Primers. The performance of PCR primer pairs for Phages 1, 2 and 3 and rpoB against EcN genomic DNA is shown. Abbreviations: bp=base pair; EcN=*E. coli* Nissle; rpoB=3 subunit of bacterial RNA polymerase.

In some embodiments, the bacteria are genetically engineered to include multiple mechanisms of action (MoAs), e.g., circuits producing multiple copies of the same product (e.g., to enhance copy number) or circuits performing multiple different functions. Examples of insertion sites include, but are not limited to, malE/K, yicS/nepI, insB/I, araC/BAD, lacZ, agal/rsml, thyA, malP/T, dapA, and cea, and others shown in FIG. 66 of WO2017087580, the contents of which are herein incorporated by reference in their entirety. For example, the genetically engineered bacteria may include four copies of a payload inserted at four different insertion sites, e.g., malE/K, insB/I, araC/BAD, and lacZ. The genetically engineered bacteria may also include four copies of the same or different payload inserted at four different insertion sites, e.g., malE/K, yicS/nepI, agaI/rsmI, and cea, and one copy a third same or different gene inserted at a different insertion site, e.g., lacZ (FIG. 13B of WO2017087580, the contents of which are herein incorporated by reference in their entirety). Alternatively, the genetically engineered bacteria may include three copies of a payload inserted at three different insertion sites, e.g., malE/K, insB/I, and lacZ.

In some embodiments, the genetically engineered bacteria are capable of expressing any one or more of the described circuits in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

In some embodiments, under conditions where the gene sequence(s) for producing the payload(s), are expressed, the bacterium produces an effector or metabolizes a substrate at levels at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold greater as compared to unmodified bacteria of the same subtype under the same conditions.

In any of these embodiments, the genetically engineered bacteria further contain one or more mutations or modifications to an endogenous phage genome. In some embodiments, the mutations are deletion, insertion, substitution or inversions within the phage genome. IN some embodiments, the mutations are deletions. In some embodiments, the deletions comprise one or more phage genes. In some embodiments, phage genes are partially deleted. In some embodiments, the mutations are insertions. In some embodiments, the insertion comprises an antibiotic cassette as described herein. IN some embodiments, one or more genes are substituted. In some embodiments, the substitution comprises an antibiotic cassette. In some embodiments, one or more phage genes are inverted. In some embodiments parts or one or more phage genes are inverted.

In one embodiment, the *E. coli* Nissle bacteria described herein comprise one or more modifications or mutations, e.g., deletion, insertion, substitution or inversion, within the *E. coli* Nissle Phage 3 genome. In some embodiments, the mutation is an insertion. In some embodiments, the insertion comprises an antibiotic cassette as described herein. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Induction of PMEs and/or Phe Transporters During Strain Culture

For induction and preinduction of PME's and/or Phe Transporters described herein, protocols and strategies were employed as described in PCT/WO2017/087580 A1, the entire contents of which are expressly incorporated herein by reference in its entirety.

In any of the embodiments described herein, the genetically engineered bacteria comprise one or more PMEs and/or one or more transporters which are induced under manufacturing conditions (e.g., aerobic, anaerobic, low-oxygen, or microaerobic) comprise one or more endogenous bacteriophage genomes. In some embodiments, the bacteriophage(s) have been mutated in one or more genes within the bacteriophage genome. Such mutations include deletions, insertions, substitutions and inversions and are located in or encompass one or more bacteriophage genes.

In some embodiments, the genetically engineered bacteria comprise one or more *E. coli* Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Measurement of Pre-Induction

In some embodiments, such culture conditions, in which expression of the PME(s) and or PheP are induced result in the reduction of phenylalanine in the culture by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions, or as compared to the baseline levels. In some embodiments, such culture conditions, in which expression of the PME(s) and or PheP are induced result in the production of transcinnamic acid (TCA) in the culture by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions, or as compared to the baseline levels.

In some embodiments, cinnamate accumulation in the bacterial cultures is measured by methods known in the art and described herein. Cinnamate production is directly correlated with phenylalanine degradation, and in some embodiments, cinnamate may be used as an indicator for strain activity during strain growth, production and manufacture. Measurement of a reduction in phenylalanine and or the production of TCA therefore may be used to measure and monitor, and fine tune the induction of a therapeutic strain prior to administration in vivo.

Phage 3

PAL inserted at four different insertion sites, e.g., malE/K, insB/I, araC/BAD, and lacZ. The genetically engineered bacteria may also include four copies of PAL inserted at four different insertion sites, e.g., malE/K, yicS/nepI, agaI/rsmI, and cea, and one copy of a phenylalanine transporter gene inserted at a different insertion site, e.g., lacZ (FIG. 13B). Alternatively, the genetically engineered bacteria may include three copies of PAL inserted at three different insertion sites, e.g., malE/K, insB/I, and lacZ, and three copies of a phenylalanine transporter gene inserted at three different insertion sites, e.g., dapA, cea, and araC/BAD. In any of these embodiments, the genetically engineered bacteria further contain one or more mutations or modifications to EcN endogenous Phage 3.

In some embodiments, the genetically engineered bacteria comprise one or more gene sequence(s) encoding one or more of (1) PAL, PAH, and/or LAAD for degradation of phenylalanine, in wild type or in a mutated form (for increased stability or metabolic activity) (2) transporter PheP and/or AroP for uptake of phenylalanine, in wild type or in mutated form (for increased stability or metabolic activity) (3) PAL, PAH, LAAD, and/or PheP for secretion and extracellular phenylalanine degradation, (4) components of secretion machinery, as described herein (5) Auxotrophy, e.g., deltaThyA and/or deltadapA (6) antibiotic resistance, including but not limited to, kanamycin or chloramphenicol resistance (7) mutations/deletions in genes involved in oxygen metabolism, as described herein and (8) mutations/deletions in genes of the endogenous Nissle phenylalanine synthesis pathway (e.g., delta PheA for Phe auxotrophy) (9) one or more biosafety systems constructs and/or kill switches (10) one or more other regulatory factors, e.g., FNRS24Y (11) one or more modifications or mutations, e.g., deletion, insertion, substitution or inversion, within the *E. coli* Nissle Phage 3 genome.

In any of the embodiments described herein, the genetically engineered bacteria for the consumption of phenylalanine further comprise one or more endogenous bacteriophage genomes. In some embodiments, the bacteriophage(s) have been mutated in one or more genes within the bacteriophage genome. Such mutations include deletions, insertions, substitutions and inversions and are located in or encompass one or more bacteriophage genes.

In some embodiments, the genetically engineered bacteria comprise one or more *E. coli* Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, under conditions where the gene sequence(s) for producing the payload(s), e.g., the PME(s), Phe tranporter(s), and/or transcriptional regulator(s) are expressed, the genetically engineered bacteria of the disclosure both degrade phenylalanine and generate TCA at levels at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold greater as compared to unmodified bacteria of the same subtype under the same conditions.

In some embodiments, under conditions where the gene sequence(s) for producing the payload(s), e.g., the PME(s), Phe tranporter(s), and/or transcriptional regulator(s) are expressed, the genetically engineered bacteria of the disclosure both degrade phenylalanine and generate hippurate at levels at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold greater as compared to unmodified bacteria of the same subtype under the same conditions.

In some embodiments, the gene sequence(s) encoding the PME(s) and/or Phe transporters, e.g., PheP, and/or other regulatory proteins, e.g., FNRS24Y_are expressed under the control of a constitutive promoter. In another embodiment, the gene sequence(s) encoding the one or more PME(s) and/or Phe transporters, e.g., PheP, and/or other regulatory proteins, e.g., FNRS24Y are expressed under the control of an inducible promoter. In some embodiments, the gene sequence(s) encoding the one or more PME(s) and/or Phe transporters, e.g., PheP, and/or other regulatory proteins, e.g., FNRS24Y, are expressed under the control of a promoter that is directly or indirectly induced by exogenous environmental conditions. In one embodiment, the gene sequence(s) encoding the one or more PME(s) and/or Phe transporters, e.g., PheP, and/or other regulatory proteins, e.g., FNRS24Y, are expressed under the control of a promoter that is directly or indirectly induced by low-oxygen or anaerobic conditions, wherein expression of the gene sequence(s) encoding the PME(s) and/or Phe transporters, e.g., PheP, and/or other regulatory proteins, e.g., FNRS24Y, are activated under low-oxygen or anaerobic environments, such as the environment of the mammalian gut. Exemplary inducible promoters described herein include oxygen level-dependent promoters (e.g., FNR-inducible promoter) arabinose, tetracycline, IPTG, rhamnose, and other chemical and/or nutritional inducers. In some embodiments, such inducible promoters described herein, are induced under in vitro culture conditions, as strains are prepared prior to in vivo administration, as described herein. Examples of inducible promoters include, but are not limited to, an FNR responsive promoter, a $P_{araBAD}$ promoter, and a $P_{TetR}$ promoter, Plac promoter, the rhaP BAD (rhamnose) promoter, each of which are described in more detail herein. Inducible promoters are described in more detail infra.

The at least one gene encoding the one or more PME(s) and/or Phe transporters, e.g., PheP, and/or other regulatory proteins, e.g., FNRS24Y, may be present on a plasmid or chromosome in the bacterial cell. In one embodiment, the gene sequence(s) encoding the one or more PME(s) and/or Phe transporters, e.g., PheP, and/or other regulatory proteins, e.g., FNRS24Y, are located on a plasmid in the bacterial cell. In another embodiment, the gene sequence(s) encoding the one or more PME(s) and/or Phe transporters, e.g., PheP, and/or other regulatory proteins, e.g., FNRS24Y, are located in the chromosome of the bacterial cell. In yet another embodiment, a native copy of the gene sequence(s) encoding the one or more PME(s) and/or Phe transporters, e.g., PheP, and/or other regulatory proteins, e.g., FNRS24Y, are located in the chromosome of the bacterial cell, and one or more gene(s) encoding one or more PME(s) and/or Phe transporters, e.g., PheP, and/or other regulatory proteins, e.g., FNRS24Y, are located on a plasmid in the bacterial cell. In yet another embodiment, a native copy of the gene sequence(s) encoding the one or more PME(s) and/or Phe transporters, e.g., PheP, and/or other regulatory proteins, e.g., FNRS24Y, are located on a plasmid in the bacterial cell, and at least one gene encoding the at least one or more PME(s) and/or Phe transporters, e.g., PheP, and/or other regulatory proteins, e.g., FNRS24Y, from a different species of bacteria are located on a plasmid in the bacterial cell. In yet another embodiment, a native copy of the gene sequence(s) encoding the one or more PME(s) and/or Phe transporters, e.g., PheP, and/or other regulatory proteins, e.g., FNRS24Y, are located in the chromosome of the bacterial cell, and the one or more gene(s) encoding the one or more PME(s) and/or Phe transporters, e.g., PheP, and/or other regulatory proteins, e.g., FNRS24Y, from a different species of bacteria are located in the chromosome of the bacterial cell. In some embodiments, the gene sequence(s) encoding the one or more PME(s) and/or Phe transporters, e.g., PheP, and/or other regulatory proteins, e.g., FNRS24Y, are expressed on a low-copy plasmid. In some embodiments, the gene sequence(s) encoding the one or more PME(s) and/or Phe transporters, e.g., PheP, and/or other regulatory proteins, e.g., FNRS24Y, are expressed on a high-copy plasmid. In some embodiments, the high-copy plasmid may be useful for increasing expression of the at least one PME(s) and/or Phe transporters, e.g., PheP, and/or other regulatory proteins, e.g., FNRS24Y. In some embodiments, the genetically engineered bacteria described above further comprise one or more of the modifications, mutations, and/or deletions in endogenous genes described herein. In any of the embodiments described herein, the genetically engineered bacteria comprise one or more endogenous bacteriophage genomes. In some embodiments, the bacteriophage(s) have been mutated in one or more genes within the bacteriophage genome. Such mutations include deletions, insertions, substitutions and inversions and may be located in or encompass one or more bacteriophage genes.

In some embodiments, the genetically engineered bacteria comprise one or more *E. coli* Nissle bacteriophage, e.g., Phage 1, Phage2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one embodiment, the genetically engineered bacterial strain comprises three chromosomal insertions of FNR driven PAL3 (3×fnrS-PAL (malP/T, yicS/nepI, malE/K), e.g., SEQ ID NO: 38 of WO2017087580, the contents of which are herein incorporated by reference in their entirety) and two copies of FNR driven pheP (2×fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y The strain further comprises one copy of LAAD knocked into the arabinose operon with expression driven by the native Para promoter (Para::FNRS24Y, e.g., SEQ ID NO: 64 of WO2017087580, the contents of which are herein incorporated by reference in their entirety). In one embodiment, the genetically engineered bacterial strain is SYN-PKU707.

In one embodiment, the genetically engineered bacterial strain comprises three chromosomal insertions of FNR driven PAL3 (3×fnrS-PAL (malP/T, yicS/nepI, malE/K), e.g., SEQ ID NO: 38 of WO2017087580, the contents of which are herein incorporated by reference in their entirety) and two copies of FNR driven pheP (2×fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y knocked into the arabinose operon with expression driven by the native Para promoter (Para::FNRS24Y e.g., SEQ ID NO: 64 of WO2017087580, the contents of which are herein incorporated by reference in their entirety). The genome is further engineered to include a dapA auxotrophy, in which the dapA gene is deleted. In one embodiment, the genetically engineered bacterial strain is SYN-PKU712.

In one embodiment, the genetically engineered bacterial strain comprises a bacterial chromosome with three chromosomal insertions of FNR driven PAL3 (3×fnrS-PAL (malP/T, yicS/nepI, malE/K), e.g., SEQ ID NO: 38 of WO2017087580, the contents of which are herein incorporated by reference in their entirety) and two copies of FNR driven pheP (2×fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y knocked into the arabinose operon with expression driven by the native Para promoter and one copy of LAAD inserted at the same insertion site (Para::FNRS24Y-LAAD, e.g., SEQ ID NO: 73 of WO2017087580, the contents of which are herein incorporated by reference in their entirety), which is transcribed as a bicistronic message from the endogenous arabinose promoter. The genome is further engineered to include a dapA auxotrophy, in which the dapA gene is deleted. In one embodiment, the genetically engineered bacterial strain is SYN-PKU708.

In one embodiment, the genetically engineered bacterial strain comprises a bacterial chromosome with three chromosomal insertions of FNR driven PAL3 (3×fnrS-PAL (malP/T, yicS/nepI, malE/K), e.g., SEQ ID NO: 38 of WO2017087580, the contents of which are herein incorporated by reference in their entirety) and two copies of FNR driven pheP (2×fnrS-pheP (lacZ, agaI/rsmI), e.g., SEQ ID NO: 62 of WO2017087580, the contents of which are herein incorporated by reference in their entirety). The strain further comprises one copy of the mutated FNR transcription factor FNRS24Y knocked into the arabinose operon with expression driven by the native Para promoter and one copy of LAAD inserted at the same insertion site (Para::FNRS24Y-LAAD, e.g., SEQ ID NO: 73 of WO2017087580, the contents of which are herein incorporated by reference in their entirety), which is transcribed as a bicistronic message from the endogenous arabinose promoter. In one embodiment, the genetically engineered bacterial strain is SYN-PKU711.

In one embodiment, the genetically engineered bacterial strain comprises a bacterial chromosome comprising three chromosomal insertions of FNR driven PAL3 (3×fnrS-PAL (malP/T, yicS/nepI, malE/K), e.g., SEQ ID NO: 38 of WO2017087580, the contents of which are herein incorporated by reference in their entirety) and two copies of FNR driven pheP (2×fnrS-pheP (lacZ, agaI/rsmI), e.g., SEQ ID NO: 62 of WO2017087580, the contents of which are herein incorporated by reference in their entirety). The strain further comprises one copy of LAAD knocked into the arabinose operon with expression driven by the native Para promoter (Para::LAAD, e.g., SEQ ID NO: 40 of WO2017087580, the contents of which are herein incorporated by reference in their entirety). The genome is further engineered to include a dapA auxotrophy, in which the dapA gene is deleted. In one embodiment, the genetically engineered bacterial strain is SYN-PKU709.

In one embodiment, the genetically engineered bacterial strain comprises a bacterial chromosome comprising three chromosomal insertions of FNR driven PAL3 (3×fnrS-PAL (malP/T, yicS/nepI, malE/K), e.g., SEQ ID NO: 38 of WO2017087580, the contents of which are herein incorporated by reference in their entirety) and two copies of FNR driven pheP (2×fnrS-pheP (lacZ, agaI/rsmI), e.g., SEQ ID NO: 62 of WO2017087580, the contents of which are herein incorporated by reference in their entirety). The strain further comprises one copy of the LAAD knocked into the arabinose operon with expression driven by the native Para promoter (Para::LAAD, e.g., SEQ ID NO: 40 of WO2017087580, the contents of which are herein incorporated by reference in their entirety). SYN-PKU710 further comprises two copies of IPTG inducible PAL3 (2×LacIPAL, exo/cea and rhtC/rhtB, e.g., SEQ ID NO: 74 of WO2017087580, the contents of which are herein incorporated by reference in their entirety), a dapA auxotrophy and is cured of all antibiotic resistances. In one embodiment, the genetically engineered bacterial strain is SYN-PKU710.

In any of these embodiments, the any of the genetically engineered described herein and depicted in FIG. 47 of WO2017087580, the contents of which are herein incorporated by reference in their entirety further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In one embodiment, the genetically engineered bacteria comprise two additional copies of PheP (in addition to the wild type gene). This provides redundancy, in case one of the PheP genes acquires a mutation. In one embodiment, the PheP genes are inserted at lacZ and agal/rsml. In one embodiment, the two copies of PheP are under the control of the $P_{fnrS}$ promoter. In one embodiment, the genetically engineered bacteria comprise three copies of PAL3. In one embodiment, the genetically engineered bacteria comprise three copies of PAL3, inserted at malEK, malPT, yicS/nepl. In one embodiment, the expression of the three copies of PAL3 is under the control of the $P_{fnrS}$ promoter. In one embodiment, the genetically engineered bacteria comprise one or more copies of LAAD. In one embodiment, the genetically engineered bacteria comprise one copy of LAAD, inserted in the arabinose operon. In one embodiment, LAAD is under the control of the endogenous ParaBAD promoter. In one embodiment, the genetically engineered bacteria comprise an auxotrophy, e.g., deltaThyA. In one embodiment, the genetically engineered bacteria comprise an antibiotic resistance. In one embodiment, the genetically engineered bacteria comprise an antibiotic resistance and an auxotrophy, e.g., deltaThyA. In one embodiment, the genetically engineered bacteria do not comprise an auxotrophy, e.g., deltaThyA. In one embodiment, the genetically engineered bacteria do not comprise an antibiotic resistance. In one embodiment, the genetically engineered bacteria comprise neither an antibiotic resistance nor an auxotrophy, e.g., deltaThyA.

In one embodiment, the genetically engineered bacteria comprise three copies of PAL, e.g., PAL3, 2 copies of PheP (in addition to the endogenous PheP), and one copy of LAAD. In one embodiment, the genetically engineered bacteria comprise three copies of PAL, e.g., PAL3, 2 copies of PheP (in addition to the endogenous PheP), and one copy of LAAD, and an auxotrophy, e.g., delta ThyA. In one embodiment, the genetically engineered bacteria comprise three copies of PAL, 2 copies of PheP (in addition to the endogenous PheP), and one copy of LAAD, and an antibiotic resistance gene. In one embodiment, the genetically engineered bacteria comprise three copies of PAL, 2 copies of PheP (in addition to the endogenous PheP), and one copy of LAAD, and an antibiotic resistance gene and an auxotrophy, e.g., delta ThyA.

In one embodiment, the genetically engineered bacteria comprise three copies of PAL (each under control of a $P_{fnrS}$ promoter), 2 copies of PheP (each under control of a $P_{fnrS}$ promoter), and one copy of LAAD (under the control of the endogenous ParaBAD promoter). In one embodiment, the genetically engineered bacteria comprise three copies of PAL (each under control of a $P_{fnrS}$ promoter), 2 copies of PheP (each under control of a $P_{fnrS}$ promoter), and one copy of LAAD (under the control of the endogenous ParaBAD promoter), and an antibiotic resistance. In one embodiment, the genetically engineered bacteria comprise three copies of PAL (each under control of a $P_{fnrS}$ promoter), 2 copies of PheP (each under control of a $P_{fnrS}$ promoter), and one copy of LAAD (under the control of the endogenous ParaBAD promoter), and an auxotrophy, e.g., delta dapA. In one embodiment, the genetically engineered bacteria comprise three copies of PAL (each under control of a $P_{fnrS}$ promoter), 2 copies of PheP (each under control of a $P_{fnrS}$ promoter), and one copy of LAAD (under the control of the endogenous ParaBAD promoter), and an antibiotic resistance and an auxotrophy, e.g., deltadapA.

In one embodiment, the genetically engineered bacteria comprise three copies of PAL (each under control of a $P_{fnrS}$ promoter and inserted at the malEK, malPT, and yicS/nepl sites), 2 copies of PheP (each under control of a $P_{fnrS}$ promoter and inserted at the LacZ and agal/rsml sites), and one copy of LAAD (under the control of the endogenous ParaBAD promoter, and inserted in the endogenous arabinose operon). In one embodiment, the genetically engineered bacteria comprise three copies of PAL (each under control of a $P_{fnrS}$ promoter and inserted at the malEK, malPT, and yicS/nepl sites), 2 copies of PheP (each under control of a $P_{fnrS}$ promoter and inserted at the LacZ and agal/rsml sites), and one copy of LAAD (under the control of the endogenous ParaBAD promoter, and inserted in the endogenous arabinose operon), and further comprise an antibiotic resistance. In one embodiment, the genetically engineered bacteria comprise three copies of PAL (each under control of a $P_{fnrS}$ promoter and inserted at the malEK, malPT, and yicS/nepl sites), 2 copies of PheP (each under control of a $P_{fnrS}$ promoter and inserted at the LacZ and agal/rsml sites), and one copy of LAAD (under the control of the endogenous ParaBAD promoter, and inserted in the endogenous arabinose operon) and further comprise an auxotrophy, e.g., deltadapA. In one embodiment, the genetically engineered bacteria comprise three copies of PAL (each under control of a $P_{fnrS}$ promoter and inserted at the malEK, malPT, and yicS/nepl sites), 2 copies of PheP (each under control of a $P_{fnrS}$ promoter and inserted at the LacZ and agal/rsml sites), and one copy of LAAD (under the control of the endogenous ParaBAD promoter, and inserted in the endogenous arabinose operon), and further comprise an antibiotic resistance and an auxotrophy, e.g., deltadapA.

In one embodiment, the genetically engineered bacteria are SYN-PKU705. In one embodiment, SYN-PKU705 further comprises an antibiotic resistance. In one embodiment, SYN-PKU705 further comprises an auxotrophy, e.g., deltaThyA. In one embodiment, SYN-PKU705 further comprises an antibiotic resistance and auxotrophy, e.g., deltaThyA. In any of these embodiments, the any of the genetically engineered described in the preceeding paragraphs further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1001.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO:98 of WO2017087580, the contents of which are herein incorporated by reference in their entirety). In one embodiment, the strain is SYN-PKU1002.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1003.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1004.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1005

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1006.

In one embodiment, the genetically engineered bacterium comprises two chromosomal copies of pheP (lacZ::PfnrS-pheP, agaI/rsmI::PfnrS-pheP) and a construct shown in FIG.

61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1007.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1008.

In one embodiment, the genetically engineered bacterium a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1009.

In one embodiment, the genetically engineered bacterium a construct shown in FIG. 61C of WO2017087580, the contents of which are herein incorporated by reference in their entirety knocked into the dapA locus on the bacterial chromosome (low copy RBS;dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1010.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1011.

In one embodiment, the genetically engineered bacterium a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1012.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1013.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lacI-Ptac-PAL-PAL, e.g., SEQ ID NO: 98 of WO2017087580, the contents of which are herein incorporated by reference in their entirety). In one embodiment, the strain is SYN-PKU1014.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65B of WO2017087580, the contents of which are herein incorporated by reference in their entirety (LacI Fnrs-Ptac-PAL-PAL, e.g., SEQ ID NO: 97 of WO2017087580, the contents of which are herein incorporated by reference in their entirety). In one embodiment, the strain is SYN-PKU1015.

In one embodiment, the genetically engineered bacterium comprises a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65D of WO2017087580, the contents of which are herein incorporated by reference in their entirety (lac-Ptac-PAL-PAL, e.g., SEQ ID NO: 98 of WO2017087580, the contents of which are herein incorporated by reference in their entirety). In one embodiment, the strain is SYN-PKU1016.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65A of WO2017087580, the contents of which are herein incorporated by reference in their entirety (Lac Fnrs-Ptac-PAL-PAL-PheP, e.g., SEQ ID NO: 95 of WO2017087580, the contents of which are herein incorporated by reference in their entirety). In one embodiment, the strain is SYN-PKU1017.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65C of WO2017087580, the contents of which are herein incorporated by reference in their entirety (Lac Fnrs-Ptac-PAL-PAL-PheP, e.g., SEQ ID NO: 96 of WO2017087580, the contents of which are herein incorporated by reference in their entirety). In one embodiment, the strain is SYN-PKU1018.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1019.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1020.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1021.

In one embodiment, the genetically engineered bacterium comprises two chromosomal copies of pheP (lacZ::PfnrS-pheP, agaI/rsmI::PfnrS-pheP) and a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1022.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1023.

In one embodiment, the genetically engineered bacterium comprises two chromosomal copies of pheP (lacZ::PfnrS-pheP, agaI/rsmI::PfnrS-pheP) and a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1024.

In one embodiment, the genetically engineered bacterium a construct shown in FIG. 61C of WO2017087580, the contents of which are herein incorporated by reference in their entirety knocked into the dapA locus on the bacterial chromosome (low copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1025.

In one embodiment, the genetically engineered bacterium a construct shown in FIG. 61C of WO2017087580, the contents of which are herein incorporated by reference in their entirety knocked into the dapA locus on the bacterial chromosome (low copy RBS;dapA::constitutive prom1 (BBA_J26100)-Pi(R6K)-constitutive promoter 2(P1)-Kis antitoxin). The strain further comprises a plasmid shown in FIG. 61A of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1026.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1027.

In one embodiment, the genetically engineered bacterium a construct shown in FIG. 61D of WO2017087580, the contents of which are herein incorporated by reference in their entirety knocked into the dapA locus on the bacterial chromosome (medium copy RBS; dapA::constitutive prom1 (BBA_J26100)-Pi(R6K)-constitutive promoter 2(P1)-Kis antitoxin). The strain further comprises a plasmid shown in FIG. 61A, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1028.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1029.

In one embodiment, the genetically engineered bacterium comprises a construct shown in FIG. 61C of WO2017087580, the contents of which are herein incorporated by reference in their entirety knocked into the thyA locus on the bacterial chromosome (low copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1030.

In one embodiment, the genetically engineered bacterium comprises a construct shown in FIG. 61D of WO2017087580, the contents of which are herein incorporated by reference in their entirety knocked into the dapA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65A of WO2017087580, the contents of which are herein incorporated by reference in their entirety (LacI Fnrs-Ptac-PAL-PAL-PheP, e.g., SEQ ID NO: 95 of WO2017087580, the contents of which are herein incorporated by reference in their entirety). In one embodiment, the strain is SYN-PKU1032.

In one embodiment, the genetically engineered bacterium comprises a construct shown in FIG. 61D of WO2017087580, the contents of which are herein incorporated by reference in their entirety knocked into the thyA locus on the bacterial chromosome (medium copy RBS; thyA::constitutive prom1 (BBA_J26100)-Pi(R6K)-constitutive promoter 2(P1)-Kis antitoxin). The strain further comprises a plasmid shown in FIG. 61B of WO2017087580, the contents of which are herein incorporated by reference in their entirety, except that the bla gene is replaced with the construct of FIG. 65C of WO2017087580, the contents of which are herein incorporated by reference in their entirety (LacI Fnrs-Ptac-PAL-PAL-PheP, e.g., SEQ ID NO: 96 of WO2017087580, the contents of which are herein incorporated by reference in their entirety). In one embodiment, the strain is SYN-PKU1032. In any of these embodiments, the any of the genetically engineered described herein comprising an AIPS system further comprise a bacteriophage genome described herein, which further comprises one or more mutations described herein.

In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In any of the preceeding embodiments, the bacteria described herein comprise one or more modifications or mutations, e.g., deletion, insertion, substitution or inversion, within the *E. coli* Nissle Phage 3 genome. In some embodiments, the mutation is an insertion. In some embodiments, the insertion comprises an antibiotic cassette as described herein. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one embodiment, the genetically engineered bacteria comprise one or more copies of PAL3, (e.g., under the control of a Pfnr promoter) and one or more copies of PAL1 (e.g. under the control of a Pfnr promoter). In one embodiment, the genetically engineered bacteria comprise one or more copies of PAL3, (e.g., under the control of a Pfnr promoter) and one or more copies of PAL1 (e.g. under the control of a Pfnr promoter); and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of LAAD (e.g., under the control of the ParaBAD promoter). In one embodiment, the genetically engineered bacteria comprise one or more copies of PAL3, (e.g., under the control of a Pfnr promoter) and one or more copies of LAAD (e.g., under the control of the ParaBAD promoter); and are derived from *E. coli* Nissle and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of PAH. In one embodiment, the genetically engineered bacteria comprise one or more copies of PAL3, (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAL1, (e.g., under the control of a Pfnr promoter) and one or more copies of LAAD (e.g., under the control of the ParaBAD promoter). In one embodiment, the genetically engineered bacteria comprise one or more copies of PAL1, (e.g., under the control of a Pfnr promoter) and one or more copies of LAAD (e.g., under the control of the ParaBAD promoter); and further comprises one or more copies of a phenylalanine transporter (e.g., PheP and/or AroP, e.g., under the control of a Pfnr promoter). In one embodiment, the genetically engineered bacteria comprise one or more copies of PAL1 (e.g., under the control of a Pfnr promoter) and one or more copies of PAH. In one embodiment, the genetically engineered bacteria comprise one or more copies of PAL1 (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAH and one or more copies of LAAD (e.g., under the control of the ParaBAD promoter). In one embodiment, the genetically engineered bacteria comprise one or more copies of PAH and one or more copies of LAAD (e.g., under the control of the ParaBAD promoter); and further comprises one or more copies of a phenylalanine transporter (e.g., PheP and/or AroP, e.g., under the control of a Pfnr promoter). PMEs and transporters may be integrated into any of the insertion sites described herein. In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter); and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH. In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter); and further comprise one or more copies of a phenylalanine transporter (e.g., PheP and/or AroP, e.g., under the control of a Pfnr promoter). PMEs and/or transporters may be integrated into any of the insertion sites described herein. Alternatively, PMEs and/or transporters may be comprised on low or high copy plasmids. PMEs and/or transporters may be integrated into any of the insertion sites described herein in combination with PMEs and/or transporters that are comprised on low or high copy plasmids. In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). PMEs and transporters may be integrated into any of the insertion sites described herein. Alternatively, PMEs and/or transporters may be comprised on low or high copy plasmids. In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). PMEs and transporters may be integrated into any of the insertion sites described herein. Alternatively, located PMEs and/or transporters may be comprised on low or high copy plasmids. In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise two copies of PAL (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and one copy of LAAD (e.g., under the control of the ParaBAD promoter). In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In any of these embodiments, the any of the genetically engineered described in the preceding paragraph further comprise a bacteriophage genome described herein, which further comprises one or more mutations described herein. In any of these embodiments, the genetically engineered bacteria are derived from *E. coli* Nissle and further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted. In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In any of these embodiments, the genetically engineered bacteria further comprise a bacteriophage genome described herein, which further comprises one or more mutations described herein. In a non-limiting example, the phage genome is Phage 3 and one or more genes are partially deleted. In a non-limiting example, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170 are partially or completely deleted.

In any of these embodiments, the bacteria described herein comprise one or more modifications or mutations, e.g., deletion, insertion, substitution or inversion, within the *E. coli* Nissle Phage 3 genome. In some embodiments, the mutation is an insertion. In some embodiments, the insertion comprises an antibiotic cassette as described herein. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:

a) One or more additional copies of an endogenous Nissle gene encoding a high affinity phenylalanine transporter (PheP);
b) One more copies of a gene encoding phenylalanine ammonia lyase (PAL) derived from *Photorhabdus;*
c) One or more gene encoding L-amino acid deaminase (LAAD) derived from *Proteus mirabilis;*
d) One or more deletion of endogenous genes to generate an auxotrophy, e.g., dapA or ThyA;
e) Antibiotic resistance; and
f) One or more modifications or mutations, e.g., deletion, insertion, substitution or inversion, within the *E. coli* Nissle Phage 3 genome In any of the preceding embodiments, the mutation in Phage 3 is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:

a) One or more additional copies of an endogenous Nissle gene encoding a high affinity phenylalanine transporter (PheP);
b) One more copies of a gene encoding phenylalanine ammonia lyase (PAL) derived from *Photorhabdus;*
c) One or more gene encoding L-amino acid deaminase (LAAD) derived from *Proteus mirabilis;*
d) One or more deletion of endogenous genes to generate an auxotrophy, e.g., dapA or ThyA; and
e) One or more modifications or mutations, e.g., deletion, insertion, substitution or inversion, within the *E. coli* Nissle Phage 3 genome.

In any of the preceding embodiments, the mutation in Phage 3 is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise the following elements:

a) One or more additional copies of an endogenous Nissle gene encoding a high affinity phenylalanine transporter (PheP);
b) One more copies of a gene encoding phenylalanine ammonia lyase (PAL) derived from *Photorhabdus;*
c) One or more gene encoding L-amino acid deaminase (LAAD) derived from *Proteus mirabilis;*
d) One or more deletion of endogenous genes to generate an auxotrophy, e.g., dapA or ThyA; and
e) One or more modifications or mutations, e.g., deletion, insertion, substitution or inversion, within the *E. coli* Nissle Phage 3 genome.

In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:

a) One or more additional copies of an endogenous Nissle gene encoding a high affinity phenylalanine transporter (PheP) under the regulatory control of an promoter inducible under exogenous environmental conditions;
b) One more copies of a gene encoding phenylalanine ammonia lyase (PAL) derived from *Photorhabdus luminescens* inducible under exogenous environmental conditions;
c) One or more copies of the gene encoding PAL under the regulatory control of a promoter inducible by a chemical or nutritional inducer;
d) One or more gene encoding L-amino acid deaminase (LAAD) derived from *Proteus mirabilis* under the regulatory control of a promoter inducible by a chemical inducer, which is the same or different from the chemical inducer that induces expression of PAL;
e) One or more deletion of endogenous genes to generate an auxotrophy, e.g., dapA or ThyA; and
f) One or more modifications or mutations, e.g., deletion, insertion, substitution or inversion, within the *E. coli* Nissle Phage 3 genome In any of the preceding embodiments, the mutation in Phage 3 is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise the following elements:

a) One or more additional copies of an endogenous Nissle gene encoding a high affinity phenylalanine transporter (PheP) under the regulatory control of an promoter inducible under exogenous environmental conditions;
b) One more copies of a gene encoding phenylalanine ammonia lyase (PAL) derived from *Photorhabdus luminescens* inducible under exogenous environmental conditions;

c) One or more copies of the gene encoding PAL under the regulatory control of a promoter inducible by a chemical or nutritional inducer;
d) One or more gene encoding L-amino acid deaminase (LAAD) derived from *Proteus mirabilis* under the regulatory control of a promoter inducible by a chemical inducer, which is the same or different from the chemical inducer that induces expression of PAL;
e) One or more deletion of endogenous genes to generate an auxotrophy, e.g., dapA or ThyA; and
f) One or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise the following elements:

a) Two additional copies of an endogenous Nissle gene encoding a high affinity phenylalanine transporter (PheP) under the regulatory control of an promoter inducible under exogenous environmental conditions;
b) Three copies of a gene encoding phenylalanine ammonia lyase (PAL) derived from *Photorhabdus luminescens* inducible under exogenous environmental conditions;
c) Two copies of the gene encoding PAL under the regulatory control of a promoter inducible by a chemical or nutritional inducer;
d) One copy of the gene encoding L-amino acid deaminase (LAAD) derived from *Proteus mirabilis* under the regulatory control of a promoter inducible by a chemical inducer, which is the same or different from the chemical inducer that induces expression of PAL;
e) One or more deletion of endogenous dapA to generate an auxotrophy; and
f) one or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacteria comprise one or more of the following elements:

a) One or more additional copies of an endogenous Nissle gene encoding a high affinity phenylalanine transporter (PheP) under the regulatory control of an anaerobic-inducible promoter (PfnrS) and the anaerobic-responsive transcriptional activator FNR;
b) One more copies of a gene encoding phenylalanine ammonia lyase (PAL) derived from *Photorhabdus luminescens* under the regulatory control of PfnrS and FNR;
c) One or more copies of the gene encoding PAL under the regulatory control of a synthetic promoter (Ptac) and the lactose-responsive transcriptional repressor LacI;
d) One or more gene encoding L-amino acid deaminase (LAAD) derived from *Proteus mirabilis* under the regulatory control of the arabinose-inducible promoter (PBAD) and the arabinose-responsive transcriptional activator AraC;
c) One or more deletion of endogenous genes to generate an auxotrophy, e.g., dapA or ThyA; and
f) one or more modifications or mutations, e.g., deletion, insertion, substitution or inversion, within the *E. coli* Nissle Phage 3 genome.

In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In some embodiments, the genetically engineered bacterium comprises the following elements:

a) One or more additional copies of an endogenous Nissle gene encoding a high affinity phenylalanine transporter (PheP) under the regulatory control of an anaerobic-inducible promoter (PfnrS) and the anaerobic-responsive transcriptional activator FNR;
b) One more copies of a gene encoding phenylalanine ammonia lyase (PAL) derived from *Photorhabdus luminescens* under the regulatory control of PfnrS and FNR;
c) One or more copies of the gene encoding PAL under the regulatory control of a synthetic promoter (Ptac) and the lactose-responsive transcriptional repressor LacI;
d) One or more gene encoding L-amino acid deaminase (LAAD) derived from *Proteus mirabilis* under the regulatory control of the arabinose-inducible promoter (PBAD) and the arabinose-responsive transcriptional activator AraC;
e) One or more deletion of endogenous genes to generate an auxotrophy, e.g., dapA or ThyA; and
f) one or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one specific embodiment, the genetically engineered bacteria comprise each of the following elements:

a) two additional copies of the endogenous Nissle gene encoding the high affinity phenylalanine transporter (PheP) under the regulatory control of an anaerobic-inducible promoter (PfnrS) and the anaerobic-responsive transcriptional activator FNR, inserted into the chromosome at the lacZ and the agal/rsml loci;
b) three copies of a gene encoding phenylalanine ammonia lyase (PAL) derived from *Photorhabdus luminescens* under the regulatory control of PfnrS and FNR, inserted into the chromosome at the malEK, malPT, and yicS/nepI loci;
c) two additional copies of the gene encoding PAL under the regulatory control of a synthetic promoter (Plac) and the lactose-responsive transcriptional repressor LacI, inserted at the exo/cea and the rhtC/rhtB loci;
d)
e) one copy of a gene encoding L-amino acid deaminase (LAAD) derived from *Proteus mirabilis* under the regulatory control of the arabinose-inducible promoter (PBAD) and the arabinose-responsive transcriptional activator AraC, with LAAD under the native arabinose promoter;
f) a deletion of the dapA gene that encodes 4-hydroxy-tetrahydropicolinate synthase to create a diaminopimelate auxotroph; and One or more modifications or mutations, e.g., deletion, insertion, substitution or inversion, within the *E. coli* Nissle Phage 3 genome In some of the preceding embodiments, the mutation is an insertion. In some embodiments, the insertion comprises an antibiotic cassette. In some of the preceding embodiments, the mutation is a deletion. In any one the of the preceding embodiments, the deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

In one specific embodiment, the genetically engineered bacteria comprise each of the following elements:

a) Two additional copies of the endogenous Nissle gene encoding the high affinity phenylalanine transporter (PheP) under the regulatory control of an anaerobic-inducible promoter (PfnrS) and the anaerobic-responsive transcriptional activator FNR, inserted into the chromosome at the lacZ and the agal/rsml loci;
b) Three copies of a gene encoding phenylalanine ammonia lyase (PAL) derived from *Photorhabdus lumine-*

*scens* under the regulatory control of PfnrS and FNR, inserted into the chromosome at the malEK, malPT, and yicS/nepI loci;

c) Two additional copies of the gene encoding PAL under the regulatory control of a synthetic promoter (Plac) and the lactose-responsive transcriptional repressor LacI, inserted at the exo/cea and the rhtC/rhtB loci;

d) One copy of a gene encoding L-amino acid deaminase (LAAD) derived from *Proteus mirabilis* under the regulatory control of the arabinose-inducible promoter (PBAD) and the arabinose-responsive transcriptional activator AraC, with LAAD under the native arabinose promoter;

e) A deletion of the dapA gene that encodes 4-hydroxy-tetrahydropicolinate synthase to create a diaminopimelate auxotroph; and f) A deletion of a region within the *E. coli* Nissle Phage 3 genome, wherein deleted region comprises ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, and partially ECOLIN_10165.

In one specific embodiment, the genetically engineered bacteria comprise each of the following elements:

a) two additional copies of the endogenous Nissle gene encoding the high affinity phenylalanine transporter (PheP) under the regulatory control of an anaerobic-inducible promoter (PfnrS) and the anaerobic-responsive transcriptional activator FNR, inserted into the chromosome at the lacZ and the agal/rsml loci;

b) three copies of a gene encoding phenylalanine ammonia lyase (PAL) derived from *Photorhabdus luminescens* under the regulatory control of PfnrS and FNR, inserted into the chromosome at the malEK, malPT, and yicS/nepI loci;

c) two additional copies of the gene encoding PAL under the regulatory control of a synthetic promoter (Plac) and the lactose-responsive transcriptional repressor LacI, inserted at the exo/cea and the rhtC/rhtB loci;

d) one copy of a gene encoding L-amino acid deaminase (LAAD) derived from *Proteus mirabilis* under the regulatory control of the arabinose-inducible promoter (PBAD) and the arabinose-responsive transcriptional activator AraC, with LAAD under the native arabinose promoter;

e) a deletion of the dapA gene that encodes 4-hydroxy-tetrahydropicolinate synthase to create a diaminopimelate auxotroph; and g) a deletion of a region within the *E. coli* Nissle Phage 3 genome, wherein deleted region consists of SEQ ID NO: 130.

In one embodiment, the genetically engineered bacterium is *E. coli* Nissle. In some embodiments, the strain comprises the same modifications as SYN-PKU-2002. In some embodiments, the strain is SYN-PKU-2002.

Table 14 contains non-limiting examples of the genetically engineered bacteria of the disclosure. In certain embodiments, the genetically engineered bacteria of Table 14 further contain a PME for secretion.

TABLE 14

Non-limiting Examples of Embodiments of the Disclosure

| Strain Name | Genotype |
|---|---|
| SYN-PKU101 | Low copy pSC101-Ptet::PAL1, ampicillin resistant |
| SYN-PKU102 | High copy pColE1-Ptet::PAL1, ampicillin resistant, |
| SYN-PKU201 | Low copy pSC101-Ptet::PAL3, ampicillin resistant |
| SYN-PKU202 | High copy pColE1-Ptet::PAL3, ampicillin resistant, |
| SYN-PKU203 | lacZ::Ptet-pheP::cam |

TABLE 14-continued

Non-limiting Examples of Embodiments of the Disclosure

| Strain Name | Genotype |
|---|---|
| SYN-PKU401 | Low copy pSC101-Ptet::PAL1, ampicillin resistant, chromosomal lacZ::Ptet-pheP::cam |
| SYN-PKU402 | High copy pColE1-Ptet::PAL1, ampicillin resistant, chromosomal lacZ::Ptet-pheP::cam |
| SYN-PKU302 | Low Copy pSC101-Ptet::PAL3, ampicillin resistant; chromosomal lacZ::Ptet-pheP::cam |
| SYN-PKU303 | High copy pColE1-Ptet::PAL3, ampicillin resistant, chromosomal lacZ::Ptet-pheP::cam |
| SYN-PKU304 | Low Copy pSC101-PfnrS-PAL3, ampicillin resistant; chromosomal lacZ::PfnrS-pheP::cam |
| SYN-PKU305 | Low Copy pSC101-PfnrS-PAL3, kanamycin resistant; chromosomal lacZ::PfnrS-pheP::cam |
| SYN-PKU306 | Low Copy pSC101-PfnrS-PAL3, kanamycin resistant; thyA |
| SYN-PKU307 | Low Copy pSC101-PfnrS-PAL3, ampicillin resistant; |
| SYN-PKU308 | Low Copy pSC101-PfnrS-PAL3, kanamycin resistant; |
| SYN-PKU401 | High Copy pUC57-Ptet-LAAD; kanamycin resistant |
| SYN-PKU501 | malPT::PfnrS-PAL3::kan |
| SYN-PKU502 | malPT::PfnrS-PAL3::kan; bicistronic lacZ::PfnrS-PAL3-pheP::cam |
| SYN-PKU503 | malEK::PfnrS-PAL3::cam |
| SYN-PKU504 | agaI/rsmI::PfnrS-PAL3 |
| SYN-PKU505 | cea::PfnrS-PAL3 |
| SYN-PKU506 | malEK::PfnrS-PAL3; agaI/rsmI::PfnrS-PAL3; cea::PfnrS-PAL3 |
| SYN-PKU507 | malEK::PfnrS-PAL3; agaI/rsmI::PfnrS-PAL3; cea::PfnrS-PAL3; lacZ::PfnrS-pheP::cam |
| SYN-PKU508 | malEK::PfnrS-PAL3; pheA auxotroph |
| SYN-PKU509 | malEK::PfnrS-PAL3; agaI/rsmI::PfnrS-PAL3; cea::PfnrS-PAL3; lacZ::PfnrS-pheP::cam |
| SYN-PKU601 | malPT::PfnrS-INT5::kan, rrnBUP-[PAL3]; lacZ::PfnrS-pheP::cam (recombinase based strain) |
| SYN-PKU510 | malEK::PfnrS-PAL3; agaI/rsmI::PfnrS-PAL3; cea::PfnrS-PAL3; |
| SYN-PKU511 | malEK::PfnrS-PAL3; agaI/rsmI::PfnrS-PAL3; cea::PfnrS-PAL3; yicS/nepI::PfnrS-PAL3::kan; malPT::PfnrS-PAL3; lacZ::PfnrS-pheP; ΔthyA |
| SYN-PKU204 | lacZ::PfnrS-pheP::cam |
| SYN-PKU512 | malEK::PfnrS-PAL3; agaI/rsmI::PfnrS-PAL3; cea::PfnrS-PAL3; malPT::PfnrS-PAL3; lacZ::PfnrS-pheP::cam; ΔthyA |
| SYN-PKU513 | malEK::PfnrS-PAL3; agaI/rsmI::PfnrS-PAL3; cea::PfnrS-PAL3; lacZ::PfnrS-pheP; ΔthyA |
| SYN-PKU514 | malEK::PfnrS-PAL3; agaI/rsmI:PfnrS-PAL3; cea::PfnrS-PAL3; malPT::PfnrS-PAL3; ΔthyA |
| SYN-PKU515 | malEK::PfnrS-PAL3; agaI/rsmI::PfnrS-PAL3; cea::PfnrS-PAL3; ΔthyA |
| SYN-PKU516 | agaI/rsmI::PfnrS-PAL3::kan |
| SYN-PKU517 | malEK::PfnrS-PAL3::cam; malPT::PfnrS-PAL3::kan; lacZ::PfnrS-pheP; ΔthyA |
| SYN-PKU518 | malEK-PfnrS-PAL3::cam; PfnrS::pheP::kan |
| SYN-PKU519 | ParaBC-PAL3::cam; PfnrS-pheP::kan |
| SYN-PKU520 | agaI/rsmI:PfnrS-PAL3::kan; PfnrS-PheP::cam |
| SYN-PKU801 | ΔargR; thyA::cam |
| SYN-PKU701 | ParaBC-LAAD::cam; malEK-PfnrS-PAL3; malPT::PfnrS-PAL3::kan; PfnrS-pheP |
| SYN-PKU521 | yicS/nepI::PfnrS-PAL3::kan; lacZ::PfnrS-pheP::cam |
| SYN-PKU522 | cea::PfnrS-PAL3::kan; lacZ::PfnrS-pheP::cam |
| SYN-PKU523 | malPT::PfnrS-PAL3::kan; lacZ::PfnrS-pheP::cam |
| SYN-PKU524 | malEK::PfnrS-PAL3; malPT::PfnrS-PAL3; lacZ::PfnrS-pheP |
| SYN-PKU702 | malEK::PfnrS-PAL3; lacZ::PfnrS-pheP; Para::LAAD |
| SYN-PKU703 | malEK::PfnrS-PAL3; malPT::PfnrS-PAL3; lacZ::PfnrS-pheP; agaI/rsmI:PfnrS::pheP; Para::LAAD |
| SYN-PKU704 | malEK::PfnrS-PAL3; malPT::PfnrS-PAL3; yicS/nepI::PfnrS-PAL3; lacZ::PfnrS-pheP; Para::LAAD |
| SYN-PKU705 | malEK::PfnrS-PAL3; malPT::PfnrS-PAL3; yicS/nepI::PfnrS-PAL3::kan; lacZ::PfnrS-pheP; agaI/rsmI::PfnrS::pheP Para::LAAD |
| SYN-PKU602 | malEK::PT7::PAL3; Para::INT5::cam (recombinase); lacZ::PfnrS-pheP; malPT::Pconstitutive::T7 polymerase (unflipped); |
| SYN-PKU901 | Nissle with streptomycin resistance |
| SYN001 | WT Nissle |

TABLE 14-continued

| Non-limiting Examples of Embodiments of the Disclosure | |
|---|---|
| Strain Name | Genotype |
| SYN-902 | WT nissle that has the pKD46 plasmid |
| SYN-903 | WT nissle that has the pKD46 plasmid and with phage knockout |
| SYN-PKU713 | LacZ::PfnrS-PAL3::pheP |
| SYN-PKU706 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD, ΔdapA::cm |
| SYN-PKU707 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y::cm |
| SYN-PKU708 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y-LAAD; ΔdapA |
| SYN-PKU-709 | malEK::PfnrS-PAL3; malPT::PfnrS-PAL3; yicS/nepI::PfnrS-PAL3; lacZ::PfnrS-pheP, agaI/rsmI::PfnrS-pheP; Para-LAAD; ΔdapA |
| SYN-PKU-710 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA |
| SYN-PKU711 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y-LAAD; |
| SYN-PKU-712 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y; ΔDapA |
| SYN-PKU-713 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3:cm; rhtC/rhtB::LacIPAL3:kn; ΔdapA (chloramphenicol and kanamycin resistance) |
| SYN-PKU-2002 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA; phage free (deletion of SEQ ID NO: 130) |
| SYN-PKU-2001 | Parental strain of SYN2002 with insertion of phage3 KO frag::cm and cured of pKD46 (not cured of chloramphenicol resistance); malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA) with insertion of phage3 KO frag::cm and cured of pKD46 (not cured of chloramphenicol resistance) |
| SYN3282 | *E. coli* Nissle 1917, lacZ::$P_{fnrS}$-PheP, ΔlacZ, malEK::$P_{fnrs}$-PAL, araBC::$P_{BAD}$-LAAD, malPT::$P_{fnrS}$-PAL, yicS/nepI::$P_{fnrS}$-PAL, agaI/rsmI::$P_{fnrS}$-PheP, exo/cea::$P_{tac}$-PAL, rhtBC::$P_{tac}$-PAL, ΔΦ, chloramphenicol resistant<br>Note: DAP prototrophic strain genetically engineered to encode Phe-degrading activity |
| SYN766 | *E. coli* Nissle 1917, ΔdapA, chloramphenicol resistant. |

In any of the embodiments, described herein, in which the genetically engineered organism, e.g., engineered bacteria or engineered OV, produces a protein, polypeptide, peptide, or other anti-cancer, gut barrier enhancer, anti-inflammatory, neuromodulatory, satiety effector, DNA, RNA, small molecule or other molecule intended to be secreted from the microorganism, the engineered microorganism may comprise a secretion mechanism and corresponding gene sequence(s) encoding the secretion system.

| | |
|---|---|
| SYN-PKU-1035 | SYN-PKU-1033 cured entirely |
| SYN-PKU-1036 | SYN-PKU-1034 cured entirely |

In one embodiment, the genetically engineered bacteria comprise one or more PMEs for metabolizing phenylalanine in combination with one or more PMEs for secretion. In one embodiment, the genetically engineered bacteria comprise one or more PMEs for metabolizing phenylalanine and a phenylalanine transporter in combination with one or more PMEs for secretion. In one embodiment, the genetically engineered bacteria comprise one or more PMEs for metabolizing phenylalanine and a phenylalanine transporter in combination with one or more PMEs for secretion, and also include an auxotrophy and/or an antibiotic resistance. Secretion systems described herein are utilized to secrete the PMEs in the genetically engineered bacteria with multiple mechanisms of action.

In any of these embodiments, the bacteria described herein comprise one or more modifications or mutations, e.g., deletion, insertion, substitution or inversion, within the *E. coli* Nissle Phage 3 genome. In some embodiments, the mutation is an insertion. In some embodiments, the mutation is a deletion. In any of the embodiments described herein, the deletions encompass (completely or partially) or are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the deletion is a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281.

Secretion

In any of the embodiments described herein, in which the genetically engineered microorganism produces a protein, polypeptide, peptide, or other anti-cancer, immune modulatory, DNA, RNA, small molecule or other molecule intended to be secreted from the microorganism, the engineered microorganism may comprise a secretion mechanism and corresponding gene sequence(s) encoding the secretion system.

In some embodiments, the genetically engineered bacteria further comprise a native secretion mechanism or non-native secretion mechanism that is capable of secreting the anti-cancer molecule from the bacterial cytoplasm in the extracellular environment. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes.

In order to translocate a protein, e.g., therapeutic polypeptide, to the extracellular space, the polypeptide must first be translated intracellularly, mobilized across the inner membrane and finally mobilized across the outer membrane. Many effector proteins (e.g., therapeutic polypeptides)—particularly those of eukaryotic origin—contain disulphide bonds to stabilize the tertiary and quaternary structures. While these bonds are capable of correctly forming in the oxidizing periplasmic compartment with the help of periplasmic chaperones, in order to translocate the polypeptide across the outer membrane the disulphide bonds must be reduced and the protein unfolded again.

Suitable secretion systems for secretion of heterologous polypeptides, e.g., effector molecules, from gram negative and gram positive bacteria are described in pending, co-owned International Patent Applications PCT/US2016/34200, filed May 25, 2016, PCT/US2017/013072, filed Jan. 11, 2017, PCT/US2017/016603, filed Feb. 3, 2017, PCT/US2017/016609, filed Feb. 4, 2016, PCT/US2017/017563, filed Feb. 10, 2017, PCT/US2017/017552, filed Feb. 10, 2017, PCT/US2016/044922, filed Jul. 29, 2016, PCT/US2016/049781, filed Aug. 31, 2016, PCT/US2016/37098, filed Jun. 10, 2016, PCT/US2016/069052, filed Dec. 28, 2016, PCT/US2016/32562, filed May 13, 2016, PCT/US2016/062369, filed Nov. 16, 2016, and PCT/US2017/013072, the contents of which are herein incorporated by reference in their entireties.

Surface Display

In some embodiments, the genetically engineered bacteria and/or microorganisms encode one or more gene(s) and/or gene cassette(s) encoding a polypeptide of interest described herein which is anchored or displayed on the surface of the bacteria and/or microorganisms. Examples of the payload molecules which are displayed or anchored to the bacteria and/or microorganism, are any of the payload molecules or other effectors described herein, and include but are not limited to enzymes (e.g., PME(s) or kynureninase), antibodies, e.g., scFv fragments, and tumor-specific antigens or neoantigens.

Suitable systems for surface display of heterologous polypeptides, e.g., effector molecules, on the surface of gram negative and gram positive bacteria are described in International Patent Application PCT/US2017/013072, filed Jan. 11, 2017, published as WO2017/123675, the contents of which is herein incorporated by reference in its entirety The Essential Genes and Auxotrophs As used herein, the term "essential gene" refers to a gene that is necessary for cell growth and/or survival. Bacterial essential genes are well known to one of ordinary skill in the art, and can be identified by directed deletion of genes and/or random mutagenesis and screening (see, e.g., Zhang and Lin, "DEG 5.0, a database of essential genes in both prokaryotes and eukaryotes," Nucl Acids Res, 2009; 37:D455-D458 and Gerdes et al., "Essential genes on metabolic maps," Curr Opin Biotechnol, 2006; 17(5):448-456, the entire contents of each of which are expressly incorporated herein by reference).

An "essential gene" may be dependent on the circumstances and environment in which an organism lives. For example, a mutation of, modification of, or excision of an essential gene may result in the genetically engineered bacteria of the disclosure becoming an auxotroph. An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, ginA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thiI, as long as the corresponding wild-type gene product is not produced in the bacteria. Table 18A lists exemplary bacterial genes which may be disrupted or deleted to produce an auxotrophic strain. These include, but are not limited to, genes required for oligonucleotide synthesis, amino acid synthesis, and cell wall synthesis.

TABLE 18A

Non-limiting Examples of Bacterial Genes Useful for Generation of an Auxotroph

| Amino Acid | Oligonucleotide | Cell Wall |
|---|---|---|
| cysE | thyA | dapA |
| glnA | uraA | dapB |
| ilvD | | dapD |
| leuB | | dapE |
| lysA | | dapF |
| serA | | |
| metA | | |
| glyA | | |
| hisB | | |
| ilvA | | |
| pheA | | |
| proA | | |
| thrC | | |
| trpC | | |
| tyrA | | |

Table 19A shows the survival of various amino acid auxotrophs in the mouse gut, as detected 24 hrs and 48 hrs post-gavage. These auxotrophs were generated using BW25113, a non-Nissle strain of *E. coli*.

TABLE 19A

Survival of amino acid auxotrophs in the mouse gut

| Gene | AA Auxotroph | Pre-Gavage | 24 hours | 48 hours |
|---|---|---|---|---|
| argA | Arginine | Present | Present | Absent |
| cysE | Cysteine | Present | Present | Absent |
| glnA | Glutamine | Present | Present | Absent |
| glyA | Glycine | Present | Present | Absent |
| hisB | Histidine | Present | Present | Present |
| ilvA | Isoleucine | Present | Present | Absent |
| leuB | Leucine | Present | Present | Absent |
| lysA | Lysine | Present | Present | Absent |
| metA | Methionine | Present | Present | Present |
| pheA | Phenylalanine | Present | Present | Present |
| proA | Proline | Present | Present | Absent |
| serA | Serine | Present | Present | Present |
| thrC | Threonine | Present | Present | Present |
| trpC | Tryptophan | Present | Present | Present |
| tyrA | Tyrosine | Present | Present | Present |
| ilvD | Valine/Isoleucine/Leucine | Present | Present | Absent |
| thyA | Thiamine | Present | Absent | Absent |
| uraA | Uracil | Present | Absent | Absent |
| flhD | FlhD | Present | Present | Present |

For example, thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro, or in the presence of high DAP levels found naturally in the human gut in vivo. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro, or in the presence of high uracil levels found naturally in the human gut in vivo. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to, yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, lgt, fbaA, pgk, yqgD, metK, yqgF, plsC, ygiT, pare, ribB, cca, ygjD, tdcF, yraL, yihA, ftsN, murl, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, ispA, ispH, dapB, folA, imp, yabQ, ftsL, ftsl, murE, murF, mraY, murD, ftsW, murG, murC, ftsQ, ftsA, ftsZ, lpxC, secM, secA, can, folK, hemL, yadR, dapD, map, rpsB, injB, nusA, ftsH, obgE, rpmA, rplU, ispB, murA, yrbB, yrbK, yhbN, rpsl, rplm, degS, mreD, mreC, mreB, accB, accC, yrdC, def, fint, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf, pyrH, olA, rlpB, leuS, lnt, glnS, fidA, cydA, infA, cydC, ftsK, lolA, serS, rpsA, msbA, lpxK, kdsB, mukF, mukE, mukB, asnS, *fabA*, mviN, me, yceQ, fabD, fabG, acpP, tmk, holB, lolC, lolD, oE, purB, ymfK, minE, mind, pth, rsA, ispE, lolB, hemA, prfA, prmC, kdsA, topA, ribA, fabL, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson, "Synthetic Auxotrophs with Ligand-Dependent Essential Genes for a BL21 (DE3) Biosafety Strain," ACS Synth Biol 2015; 4(12):1279-1286, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L5I, and L6G. In some embodiments, the essential gene is adk comprising the mutations I4L, L51, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid, or L-histidine methyl ester. Bacterial cells comprising mutations in dnaN (H191N, R240C, I317S, F319V, L340T, V347I, and S345C) are complemented by benzothiazole, indole, or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system shown in FIGS. 85-86 of WO2017087580.

In some embodiments, the genetically engineered bacterium of the disclosure is an auxotroph and also comprises kill switch circuitry, such as any of the kill switch components and systems described herein. For example, the genetically engineered bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synth Biol, 2015; 4(3):307-316, the entire contents of which are expressly incorporated herein by reference). In some embodiments, the genetically engineered bacterium of the disclosure is an auxotroph and also comprises kill switch circuitry, such as any of the kill switch components and systems described herein, as well as another biosecurity system, such a conditional origin of replication (Wright et al., 2015). In one embodiment, a genetically engineered bacterium, comprises one or more AIPS constructs integrated into the bacterial chromosome in combination with one or more biosafety plasmid(s). In some embodiments, the plasmid comprises a conditional origin of replication (COR), for which the plasmid replication initiator protein is provided in trans, i.e., is encoded by the chromosomally integrated biosafety construct. In some embodiments, the chromosomally integrated construct is further introduced into the host such that an auxotrophy results (e.g., dapA or thyA auxotrophy), which in turn is complemented by a gene product expressed from the biosafety plasmid construct. In some embodiments, the biosafety plasmid further encodes a broad-spectrum toxin (e.g., Kis), while the integrated biosafety construct encodes an anti-toxin (e.g., anti-Kis), permitting propagation of the plasmid in the bacterial cell containing both constructs. Without wishing to be bound by theory, this mechanism functions to select against plasmid spread by making the plasmid DNA itself disadvantageous to maintain by a wild-type bacterium. A non-limiting example of such a biosafety system is shown in FIG. 61A, FIG. 61B, FIG. 61C, and FIG. 61D of WO2017087580, the contents of which are herein incorporated by reference in their entirety.

In some embodiments, the genetically engineered bacteria comprise a chromosomally inserted biosafety construct nucleic acid sequence (to be combined with a plasmid based biosafety construct) that is at least about 80%, at least about 85%, at least about 90%, at least about 95%, or at least about 99% homologous to the DNA sequence of SEQ ID NO: 81, 82, 83, 84, 85 of WO2017087580, the contents of which are herein incorporated by reference in their entirety, or a functional fragment thereof. In some embodiments, the genetically engineered bacteria comprise a chromosomally inserted biosafety construct nucleic acid sequence (to be combined with a plasmid based biosafety construct) encoding a polypeptide sequence that is at least about 80%, at least about 85%, at least about 90%, at least about 95%, or at least about 99% homologous to the polypeptide sequence of SEQ ID NO: 86, 87, 88 of WO2017087580, the contents of which are herein incorporated by reference in their entirety, or a functional fragment thereof.

In some embodiments, the genetically engineered bacteria comprise a chromosome based biosafety construct nucleic acid sequence (to be combined with a plasmid based biosafety construct) that is at least about 80%, at least about 85%, at least about 90%, at least about 95%, or at least about 99% homologous to the DNA sequence of SEQ ID NO: 89, 90, 91, 92, 93, 94 of WO2017087580, the contents of which are herein incorporated by reference in their entirety or a functional fragment thereof. In some embodiments, the genetically engineered bacteria comprise a chromosome based biosafety construct nucleic acid sequence (to be combined with a plasmid based biosafety construct) encoding a polypeptide sequence that is at least about 80%, at least about 85%, at least about 90%, at least about 95%, or at least about 99% homologous to the polypeptide sequence encoded by the DNA sequence of SEQ ID NO: 89, 90, 91, 92, 93, 94 of WO2017087580, the contents of which are herein incorporated by reference in their entirety or a functional fragment thereof.

In some embodiments, the genetically engineered bacteria comprise a plasmid based biosafety construct payload nucleic acid sequence at least about 80%, at least about 85%, at least about 90%, at least about 95%, or at least about 99% homologous to the DNA sequence of SEQ ID NO: 36, 37, 74, 95, 96, 98, 99, 100, 113 of WO2017087580, the contents of which are herein incorporated by reference in their entirety or a functional fragment thereof. In some embodiments, the genetically engineered bacteria comprise a plasmid based biosafety construct payload nucleic acid sequence encoding a polypeptide which is at least about 80%, at least about 85%, at least about 90%, at least about 95%, or at least about 99% homologous to the polypeptide encoded by the DNA sequence of SEQ ID NO: 36, 37, 74, 95, 96, 98, 99, 100, 113 of WO2017087580, the contents of which are herein incorporated by reference in their entirety or a functional fragment thereof. In some embodiments, the plasmid based construct comprises one or more copies of PAL. In some embodiments, the plasmid based construct comprises one or more copies of PheP. In some embodiments, the plasmid based construct comprises one or more copies of LAAD. In some embodiments, the plasmid based construct comprises one or more copies of PAL and one or more copies of PheP. In some embodiments, the plasmid based construct comprises one or more copies of PAL and one or more copies of LAAD. In some embodiments, the plasmid based construct comprises one or more copies of LAAD and one or more copies of PheP. In some embodiments, the plasmid based construct comprises one or more copies of PAL and one or more copies of PheP and one or more copies of LAAD. In some embodiments, the phenylalanine catabolizing plasmid payload(s) (i.e., PAL, PheP, and/or LAAD) are under the control of one or more constitutive or inducible promoter(s) as described herein (e.g., low oxygen, arabinose, IPTG inducible, or a combination thereof). In some embodiments, the promoter is useful for pre-induction. In some embodiments, the promoter is useful for in vivo activation. In some embodiments, the promoter is useful for pre-induction and in vivo activity. In some embodiments, the construct comprises two or more promoters, some of which are useful for pre0induction, and some of which are useful for in vivo activity.

In some embodiments, the genetically engineered bacteria comprise a plasmid based biosafety construct nucleic acid sequence (to be combined with a chromosome based biosafety construct), e.g., that comprises a payload construct for the catabolism of phenylalanine. In some embodiments, the plasmid based construct comprises one or more copies of PAL. In some embodiments, the plasmid based construct comprises one or more copies of PheP. In some embodiments, the plasmid based construct comprises one or more copies of LAAD. In some embodiments, the plasmid based construct comprises one or more copies of PAL and one or more copies of PheP. In some embodiments, the plasmid based construct comprises one or more copies of PAL and one or more copies of LAAD. In some embodiments, the plasmid based construct comprises one or more copies of LAAD and one or more copies of PheP. In some embodiments, the plasmid based construct comprises one or more copies of PAL and one or more copies of PheP and one or more copies of LAAD. In some embodiments, the phenylalanine catabolizing plasmid payload(s) (i.e., PAL, PheP, and/or LAAD) are under the control of one or more constitutive or inducible promoter(s) as described herein (e.g., low oxygen, arabinose, IPTG inducible, or a combination thereof). In some embodiments, the promoter is useful for pre-induction. In some embodiments, the promoter is useful for in vivo activation. In some embodiments, the promoter is useful for pre-induction and in vivo activity. In some embodiments, the construct comprises two or more promoters, some of which are useful for pre0induction, and some of which are useful for in vivo activity.

In any of these embodiments, the genetically engineered bacteria comprising an auxotrophy contain one or more mutations or modifications to an endogenous phage genome. In some embodiments, the modifications to the endogenous phage genome are one or more deletion(s), insertion(s), substitution(s) or inversions(s) or combinations thereof within the phage genome. In some embodiments, the mutations are deletions. In some embodiments, the deletions comprise one or more phage genes. In some embodiments, phage genes are partially deleted. In some embodiments, the mutations are insertions. In some embodiments, the insertion comprises an antibiotic cassette as described herein. In some embodiments, one or more genes are substituted. In some embodiments, the substitution comprises an antibiotic cassette. In some embodiments, one or more phage genes are inverted. In some embodiments parts of one or more phage genes are inverted.

In some embodiments, the genetically engineered bacteria are derived from *E. coli* Nissle and comprise one or more *E. coli* Nissle bacteriophage, e.g., Phage 1, Phage 2, and Phage 3. In some embodiments, the genetically engineered bacteria comprise one or mutations in Phage 3. Such mutations include deletions, insertions, substitutions and inversions and are located in or encompass one or more Phage 3 genes. In some embodiments, the insertion comprises an antibiotic cassette. In some of the preceding embodiments, the mutation is a deletion. In some embodiments, the genetically engineered bacteria comprise one or more deletions are located in one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the genetically engineered bacteria comprise a complete or partial deletion of one or more of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. In one specific embodiment, the deletion is a complete deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, and ECOLIN_10170, and a partial deletion of ECOLIN_10175. In one embodiment, the sequence of SEQ ID NO: 130 is deleted from the Phage 3 genome. In one embodiment, a sequence comprising SEQ ID NO: 130 is deleted from the Phage 3 genome. In one embodiment, the genetically engineered bacteria comprise modified phage genome sequence comprising SEQ ID NO: 281. In one embodiment, the genetically engineered bacteria comprise modified phage genome sequence consisting of SEQ ID NO: 281. In some embodiments, the genetically engineered bacteria further comprise one or more circuits comprising one or more gene(s) encoding one or more effector molecules. In some embodiments, the genetically engineered bacteria are capable of expressing any one or more of the circuits in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

The addition of a Phe-auxotrophy may also have utility for increasing the rate of phenylalanine degradation. For example, the deletion of the pheA gene confers phenylalanine auxotrophy. By turning off endogenous bacterial phenylalanine production, this may drive increased uptake from the environment and also result in increased degradation of phenylalanine taken up from the environment.

Genetic Regulatory Circuits

In some embodiments, the genetically engineered bacteria comprise multi-layered genetic regulatory circuits for expressing the constructs described herein. Suitable multi-layered genetic regulatory circuits are described in International Patent Application PCT/US2016/39434, filed on Jun. 24, 2016, published as WO2016/210378, the contents of which is herein incorporated by reference in its entirety. The genetic regulatory circuits are useful to screen for mutant bacteria that produce an anti-cancer molecule or rescue an auxotroph. In certain embodiments, the invention provides methods for selecting genetically engineered bacteria that produce one or more genes of interest.

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is an antibiotic independent plasmid system (AIPS) (Wright et al., 2015). These and other systems and platforms are described in International Patent Application PCT/US2017/013072, filed Jan. 11, 2017, published as WO2017/123675, the contents of which is herein incorporated by reference in its entirety. Kill Switch In some embodiments, the genetically engineered bacteria of the invention also comprise a kill switch. The kill switch is intended to actively kill genetically engineered bacteria in response to external stimuli. As opposed to an auxotrophic mutation where bacteria die because they lack an essential nutrient for survival, the kill switch is triggered by a particular factor in the environment that induces the production of toxic molecules within the microbe that cause cell death. Suitable kill switches are described in PCT/US2016/039427, filed Jun. 24, 2016 and published as WO2016210373, the contents of which is herein incorporated by reference in its entirety.

Pharmaceutical Compositions and Formulations

Pharmaceutical compositions comprising the genetically engineered bacteria of the invention may be used to treat, manage, ameliorate, and/or prevent diseases associated with hyperphenylalaninemia, e.g., PKU. Pharmaceutical compositions of the invention comprising one or more genetically engineered bacteria, alone or in combination with prophylactic agents, therapeutic agents, and/or and pharmaceutically acceptable carriers are provided. In certain embodiments, the pharmaceutical composition comprises one species, strain, or subtype of bacteria that are engineered to comprise the genetic modifications described herein. In alternate embodiments, the pharmaceutical composition comprises two or more species, strains, and/or subtypes of bacteria that are each engineered to comprise the genetic modifications described herein.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, PA). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, PA. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria described herein.

In one embodiment, the genetically engineered bacteria of the disclosure may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered bacteria may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the disclosure provides methods of treating a disease comprising administering to a subject in need thereof a composition comprising an engineered bacteria disclosed herein. In some embodiments, the disclosure provides a method for treating a disease comprising administering to a subject in need thereof a composition comprising an engineered bacteria comprising a modification in an endogenous or native phage genome.

Another aspect of the disclosure provides methods of treating a disease associated with hyperphenylalaninemia or symptom(s) associated with hyperphenylalaninemia. In some embodiments, the disclosure provides a method for treating a disease associated with hyperphenylalaninemia or symptom(s) associated with hyperphenylalaninemia comprising administering to a subject in need thereof a composition comprising an engineered bacteria disclosed herein. In some embodiments, the disclosure provides a method for treating a disease associated with hyperphenylalaninemia or symptom(s) associated with hyperphenylalaninemia comprising administering to a subject in need thereof a composition comprising an engineered bacteria comprising gene sequence encoding one or PMEs, e.g., PAH and/or PAH, and/or LAAD. In some embodiments, the engineered bacteria may comprise a modification in an endogenous or native phage genome. In some embodiments, the genetically engineered bacteria further comprise one or more circuits comprising one or more gene(s) encoding one or more effector molecules (e.g. one or more PMEs, e.g., PAH and/or PAH, and/or LAAD and/or gene sequence encoding one or more Phe transporters). In some embodiments, the genetically engineered bacteria are capable of expressing any one or more of the circuits in low-oxygen conditions, in the presence of disease or tissue specific molecules or metabolites, in the presence of molecules or metabolites associated with inflammation or an inflammatory response or immune suppression, liver damage, metabolic disease, or in the presence of some other metabolite that may or may not be present in the gut or the tumor microenvironment, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits. In any of these embodiments, the modifications to the endogenous phage genome are one or more deletion(s), insertion(s), substitution(s) or inversions(s) or combinations thereof within the phage genome. In some embodiments, the mutations are deletions. In some embodiments, the deletions comprise one or more phage genes. In some embodiments, phage genes are partially deleted. In some embodiments, the mutations are insertions. In some embodiments, the insertion comprises an antibiotic cassette as described herein. IN some embodiments, one or more genes are substituted. In some embodiments, the substitution comprises an antibiotic cassette. In some embodiments, one or more phage genes are inverted. In some embodiments parts of one or more phage genes are inverted.

In some embodiments, the disclosure provides a method for treating a disease associated with hyperphenylalaninemia or symptom(s) associated with hyperphenylalaninemia comprising administering to a subject in need thereof a composition comprising an engineered bacteria comprising gene sequence encoding one or more PMEs, e.g., PAH and/or PAH, and/or LAAD and optionally gene sequence encoding one or more Phe transporters, wherein the gene sequence(s) encoding the one or more PMES are under the control of an inducible promoter, and the gene sequence encoding the one or more Phe transporters are under the control of an inducible promoter, such as any of the inducible promoters disclosed herein. The gene sequence(s) may be under the control of the same or different inducible promoters. In some embodiments, one or more of the gene sequence encoding the one or more PMEs, e.g., PAH and/or PAH, and/or LAAD are under the control of constitutive promoter. In some embodiments, one or more of the gene sequence encoding the one or more Phe transporters are under the control of constitutive promoter. In other embodiments, the bacteria may comprise one or more of the following: one or more auxotrophies, one or more kill-switches, gene guard components, and/or antibiotic resistance. In some embodiments, the insertion comprises an antibiotic cassette as described herein.

In some embodiments, the disease is selected from the group consisting of: classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, autoimmune disorders, cancer, tumors, metabolic disease (e.g., type 2 diabetes, obesity, hepatic encephalopathy, non-alcoholic fatty liver diease, and associated or related disorders), Segawa's disease, and rare disorders of metabolism. Non-limiting examples of such rare disorder of metabolism include maple sirup urine disease, isovereric acidemia, methylmalonic acidemia, propionic acidemia, hyperoxalurea, phenylketonuria, and hyperammonemia). In some embodiments, hyperphenylalaninemia is secondary to other conditions, e.g., liver diseases. In some embodiments, the invention provides methods for reducing, ameliorating, or eliminating one or more symptom(s) associated with these diseases, including but not limited to neurological deficits, mental retardation, encephalopathy, epilepsy, eczema, reduced growth, microcephaly, tremor, limb spasticity, and/or hypopigmentation. In some embodiments, the subject to be treated is a human patient.

In certain embodiments, the genetically engineered bacteria are capable of metabolizing a meabolite in the diet in order to treat a disease or disorder associated with accumulation of the metabolite (e.g., hyperphenylalaninemia, e.g., PKU). In some embodiments, the genetically engineered bacteria are delivered simultaneously with dietary protein. In other embodiments, the genetically engineered bacteria are not delivered simultaneously with dietary protein. Studies have shown that pancreatic and other glandular secretions into the intestine contain high levels of proteins, enzymes, and polypeptides, and that the amino acids produced as a result of their catabolism are reabsorbed back into the blood in a process known as "enterorecirculation" (Chang, 2007; Sarkissian et al., 1999). Thus, high intestinal levels of phenylalanine may be partially independent of food intake, and are available for breakdown by PAL. In some embodiments, the genetically engineered bacteria and dietary protein are delivered after a period of fasting or phenylalanine-restricted dieting. In these embodiments, a patient suffering from hyperphenylalaninemia may be able to resume a substantially normal diet, or a diet that is less restrictive than a phenylalanine-free diet. In some embodiments, the genetically engineered bacteria may be capable of metabolizing phenylalanine from additional sources, e.g., the blood, in order to treat a disease associated with hyperphenylalaninemia, e.g., PKU. In these embodiments, the genetically engineered bacteria need not be delivered simultaneously with dietary protein, and a phenylalanine gradient is generated, e.g., from blood to gut, and the genetically engineered bacteria metabolize phenylalanine and reduce phenylalaninemia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, the pharmaceutical composition described herein is administered to reduce levels of a certain metabolite or other type of biomarker molecule or molecule associated with or causative of the disorder in a subject. In some embodiments, the methods of the present disclosure reduce the phenylalanine levels in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the phenylalanine level in a subject before and after administration of the pharmaceutical composition. In some embodiments, the method of treating or ameliorating hyperphenylalaninemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, levels of a certain metabolite or other type of biomarker molecule or molecule associated with or causative of the disorder (e.g. phenylalanine) in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce levels of a certain metabolite (e.g. phenylalanine) or other type of biomarker molecule or molecule associated with or causative of the disorder. In some embodiments, the methods may include administration of the compositions of the invention to reduce the metabolite or other type of molecule to undetectable levels in a subject. In some embodiments, the methods may include administration of the compositions of the invention to reduce concentrations of the metabolite or other type of molecule to undetectable levels, or to less than about 1%, 2%, 5%, 10%, 20%, 25%, 30%, 40%, 50%, 60%, 70%, 75%, or 80% of the subject's levels prior to treatment.

Levels of a metabolite or other type of molecule that accumulates in response to the administration of the genetically engineered bacteria upon induction of the circuitry in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods described herein may include administration of the compositions of the invention to reduce levels of a certain metabolite or other type of biomarker molecule or molecule associated with or causative of the disorder and resulting in increased levels of a metabolite or other type of molecule which accumulates as a result of the administration of the genetically engineered bacteria. In some embodiments, the methods may include administration of the compositions of the invention to reduce one metabolite or other type of molecule to undetectable levels in a subject, and concurrently and proportionately increase levels of another metabolite or other type of molecule. In some embodiments, the methods may include administration of the compositions of the invention, leading to an increase concentrations of a metabolite or other type of molecule to more than about 1%, 2%, 5%, 10%, 20%, 25%, 30%, 40%, 50%, 60%, 70%, 75%, 80%, 90%, 95%, or up to 99% or up to 100% of the subject's levels of the metabolite prior to treatment. Such increases may be measured for example in the urine, the blood, the feces, or in a tumor.

In some embodiments, the activity of genetically engineered bacteria expressing PAL (e.g., phenylalanine degrading activity) can be detected in the urine of a mammalian subject, e.g., an animal model or a human, by measuring the amounts of hippurate produced and the rate of its accumulation. Hippurate is a PAL specific breakdown product, and is normally present in human urine at low concentrations. It is the end product of metabolism of phenylalanine via the PAL pathway. Phenylalanine ammonia lyase mediates the conversion of phenylalanine to cinnamate. When cinnamate is produced in the gut, is absorbed and quickly converted to hippurate in the liver and excreted in the liver (Hoskins JA and Gray Phenylalanine ammonia lyase in the management of phenylketonuria: the relationship between ingested cinnamate and urinary hippurate in humans. J Res Commun Chem Pathol Pharmacol. 1982 February; 35(2):275-82). Phenylalanine is converted to hippurate in a 1:1 ratio, i.e., 1 mole of Phe is converted into 1 mol of hippurate. Thus, changes in urinary hippurate levels can be used as a non-invasive measure of the effect of therapies that utilize this mechanism.

Hippuric acid thus has the potential to function as a biomarker allowing monitoring of dietary adherence and treatment effect in patients receiving PAL-based regimens. It can be used as an adjunct to measurement of blood Phe levels in the management of patients and because it is a urinary biomarker, it can have advantages particularly in children to adjust protein intake—which can be challenging as needs vary based on growth.

In some embodiments, the methods of the present disclosure increase the hippurate levels in the urine of a subject by at least about 10%, 20%, 25%, 30%, 40%, 50%, 60%, 70%, 75%, 80%, 85%, 90%, 95%, 96%, 97%, 98%, 99% or more as compared to levels in an untreated or control subject. In some embodiments, the increase is measured by comparing the hippurate level in a subject before and after administration of the pharmaceutical composition of the disclosure.

In this section, the term "PAL-based drug" refers to any drug, polypeptide, biologic, or treatment regimen that has PAL activity, for example, PEG-PAL, Kuvan, a composition comprising a bacteria of the present disclosure, e.g., bacteria encoding PAL and optionally PheP transporter. In some embodiments, the disclosure provides a method for measuring PAL activity in vivo by administering to a subject, e.g., a mammalian subject, a PAL-based drug and measuring the amount of hippurate produced in the subject as a measure of PAL activity. In some embodiments, the disclosure provides a method for monitoring the therapeutic activity of a PAL-based drug by administering to a subject, e.g., a mammalian subject, the PAL-based drug and measuring the amount of hippurate produced in the subject as a measure of PAL therapeutic activity. In some embodiments, the disclosure provides a method for adjusting the dosage of a PAL-based drug by administering to a subject, e.g., a mammalian subject, the PAL-based drug, measuring the amount of hippurate produced in the subject to determine PAL activity, and adjusting (e.g., increasing or decreasing) the dosage of the drug to increase or decrease the PAL activity in the subject. In some embodiments, the disclosure provides a method for adjusting the protein intake and/or diet of a subject having hyperphenylalanemia comprising administering to the subject a PAL-based drug, measuring the amount of hippurate produced in the subject, and adjusting (e.g., increasing or decreasing) the protein intake or otherwise adjusting the diet of the subject to increase or decrease the PAL activity in the subject. In some embodiments, the disclosure provides a method for confirming adherence to a protein intake and/or diet regimen of a subject having hyperphenylalanemia comprising administering to the subject a PAL-based drug, measuring the amount of hippurate produced in the subject, and measuring PAL activity in the subject.

In some embodiments of the methods disclosed herein, both blood phenylalanine levels and urine hippurate levels are monitored in a subject. In some embodiments, blood phenylalanine and hippurate in the urine are measured at multiple time points, to determine the rate of phenylalanine breakdown. In some embodiments, hippurate levels in the urine are used evaluate PAL activity or strain activity in animal models.

In some embodiments, hippuric acid measurements in the urine, alone or in combination with blood phenylalanine measurements, are used to the strain prove mechanism of action. In some embodiments, hippuric acid measurements in the urine, alone or in combination with blood phenylalanine measurements, are used as a tool to differentiate between PAL and LAAD activity in a strain, and allow to determine the contribution of each enzyme to the overall strain activity.

In some embodiments, hippuric acid measurements in the urine, alone or in combination with blood phenylalanine measurements, are used evaluate safety in animal models and human subjects. In some embodiments, hippuric acid measurements in the urine, alone or in combination with blood phenylalanine measurements, are used in the evaluation of dose-response and optimal regimen for the desired pharmacologic effect and safety. In some embodiments, hippuric acid measurements in the urine, alone or in combination with blood phenylalanine measurements, are used as surrogate endpoint for efficacy and/or toxicity. In some embodiments, hippuric acid measurements in the urine, alone or in combination with blood phenylalanine measurements, are used to predict patients' response to a regimen comprising a therapeutic strain. In some embodiments, hippuric acid measurements in the urine, alone or in combination with blood phenylalanine measurements, are used for the identification of certain patient populations that are more likely to respond to the drug therapy. In some embodiments, hippuric acid measurements in the urine, alone or in combination with blood phenylalanine measurements, are used to avoid specific adverse events. In some embodiments, hippuric acid measurements in the urine, alone or in combination with blood phenylalanine measurements, are useful for patient selection.

In some embodiments, hippuric acid measurements in the urine, alone or in combination with blood phenylalanine measurements, are used as one method for adjusting protein intake/diet of PKU patient on a regimen which includes the administration of a therapeutic PKU strain expressing PAL.

In some embodiments, measurement of urine levels of hippuric acid, alone or in combination with blood phenylalanine measurements, is used to measure and/or monitor the activity of recombinant PAL. In some embodiments, measurement of urine levels of hippuric acid is used to measure and/or monitor the activity of recombinant pegylated PAL (Peg-PAL). In some embodiments, measurement of urine levels of hippuric acid, alone or in combination with blood phenylalanine measurements, is used to measure and/or monitor the activity of recombinant PAL administered in combination with a therapeutic strain as described herein.

In some embodiments, hippuric acid measurements in the urine, alone or in combination with blood phenylalanine measurements, are used in combination with other biomarkers, e.g., clinical safety biomarkers. In some embodiments, measurement of increases and/or decreases in certain metabolites or other types of molecules are used their combination with measurements of other biomarkers, e.g., clinical safety biomarkers. Non-limiting examples of such safety markers include physical examination, vital signs, and electrocardiogram (ECG). Other non-limiting examples include liver safety tests known in the art, e.g., serum aspartate transaminase (AST), alanine transaminase (ALT), alkaline phosphatase (ALP), gamma-glutamyl transferase (GGT), and bilirubin. Such biosafety markers also include renal safety tests, e.g., those known in the art, e.g., blood urea nitrogen (BUN), serum creatinine, glomerular filtration rate (GFR), creatinine clearance, serum electrolytes (sodium, potassium, chloride, and bicarbonate), and complete urine analysis (color, pH, specific gravity, glucose, proteins, ketone bodies, and microscopic exam for blood, leukocytes, casts), as well as Cystatin-c, β 2-microglobulin, uric acid, clusterin, N-acetyl-beta-dglucosaminidase, neutrophil gelatinase-associated lipocalin (NGAL), N-acetyl-β-dglucosaminidase (NAG), and kidney injury molecule-1 (KIM-1). Other non-limiting examples include Hematology safety biomarkers known in the art, e.g., Complete blood count, total hemoglobin, hematocrit, red cell count, mean red cell volume, mean cell hemoglobin, red cell distribution width %, mean cell hemoglobin concentration, total white cell count, differential white cell count (Neutrophils, lymphocytes, basophils, esinophils, and monocytes), and platelets. Other no-liming examples include bone safety markers known in the art, e.g., Serum calcium and inorganic phosphates. Other non-limiting examples include basic metabolic safety biomarkers known in the art, e.g., blood glucose, triglycerides (TG), total cholesterol, low density lipoprotein cholesterol (LDLc), and high density lipoprotein cholesterol (HDL-c). Other specific safety biomarkers known in the art include, e.g., serum immunoglobulin levels, C-reactive protein (CRP), fibrinogen, thyroid stimulating hormone (TSH), thyroxine, testosterone, insulin, lactate dehydrogenase (LDH), creatine kinase (CK) and its isoenzymes, cardiac troponin (cTn), and methemoglobin.

In some embodiments, the activity of genetically engineered bacteria expressing LAAD can be specifically detected in the feces and differentiated from other *E. coli* strains. A Phenylalanine Deaminase Test "Phenylalanine Agar Slant" can be used for this purpose. Phenylalanine agar used to determine whether the microbe can use phenylalanine and convert it to phenyl pyruvate. When the test chemicals are added to the tube containing the sample on the phenylalanine agar, phenylpyruvate is converted to a green compound, indicating a positive test. Wild type *E. coli* does not produce phenylpyruvate, since they do not encode an enzyme, which can produce phenylpyruvate from phenylalanine, allowing differentiation from other *E. coli* strains. The genetically engineered bacteria can be differentiated from other bacterial species which are able to produce phenylpyruvate by PCR-based tests known in the art. For example, species specific sequences can be amplified. For example, universal PCR that amplifies conserved regions in various bacteria is ideal to detect any pathogen in screening of specimens. For this purpose, the conserved region of the 16S rRNA gene can be used as a target gene for the universal PCR; the 16S rRNA gene contains species-specific regions by which a large number of bacterial species can be differentiated.

In some embodiments, the Phenylalanine Deaminase Test can be used to detect the genetically engineered bacteria in a feces sample. In some embodiments, PCR-based tests can be conducted to differentiate the genetically engineered bacteria from other bacterial species.

In some embodiments, quantitative PCR (qPCR) is used to amplify, detect, and/or quantify mRNA expression levels of the gene, gene(s), or gene cassettes for producing the payloads, e.g., PME(s) and/or PheP. Primers may be designed and used to detect mRNA in a sample according to methods known in the art. In some embodiments, a fluorophore is added to a sample reaction mixture that may contain payload RNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the payload(s).

In some embodiments, quantitative PCR (qPCR) is used to amplify, detect, and/or quantify mRNA expression levels of the payload(s). Primers may be designed and used to detect mRNA in a sample according to methods known in the art. In some embodiments, a fluorophore is added to a sample reaction mixture that may contain payload, payloads, e.g., PME(s) and/or PheP and/or FNRS24Y, mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the payload(s) e.g., PME(s) and/or PheP and/or FNRS24Y.

In certain embodiments, the genetically engineered bacteria are *E. coli* Nissle in which endogenous or native *E. coli* Nissle Phage 3 has been modified as described herein. In some embodiments, Phage 3 can no longer undergo the lytic cycle due to the modification. In some embodiments, the lytic cycle is reduced or less frequent due to the modification. The genetically engineered bacteria may be destroyed, e.g., by defense factors in the gut or blood serum (Sonnenborn et al., 2009) or by activation of a kill switch, several hours or days after administration. Thus, the pharmaceutical composition comprising the genetically engineered bacteria may be re-administered at a therapeutically effective dose and frequency. Length of Nissle residence in vivo in mice is shown in FIG. 68 of WO2017087580, the contents of which are herein incorporated by reference in their entirety. In alternate embodiments, the genetically engineered bacteria are not destroyed within hours or days after administration and may propagate and colonize the gut.

The methods of the invention may comprise administration of the pharmaceutical composition alone or in combination with one or more additional therapeutic agents. In some embodiments for the treatment of hyperphenylalaninemia, the pharmaceutical composition may be administered in conjunction with the cofactor tetrahydrobiopterin (e.g., Kuvan/sapropterin), large neutral amino acids (e.g., tyrosine, tryptophan), glycomacropeptides, a probiotic (e.g., VSL3), an enzyme (e.g., pegylated-PAL), and/or other agents used in the treatment of phenylketonuria (Al Hafid and Christodoulou, 2015). See, e.g., WO2017087580 A1, the entire contents of which are incorporated by reference in its entirety.

An important consideration in the selection of the one or more additional therapeutic agents is that the agent(s) should be compatible with the genetically engineered bacteria of the invention, e.g., the agent(s) must not interfere with or kill the bacteria. In some embodiments, the pharmaceutical composition is administered with food. In alternate embodiments, the pharmaceutical composition is administered before or after eating food. The pharmaceutical composition may be administered in combination with one or more dietary modifications, e.g., low-phenylalanine diet. The dosage of the pharmaceutical composition and the frequency of administration may be selected based on the severity of the symptoms and the progression of the disease. The appropriate therapeutically effective dose and/or frequency of administration can be selected by a treating clinician. The methods of the invention also include kits comprising the pharmaceutical composition described herein. The kit can include one or more other elements including, but not limited to: instructions for use; other reagents, e.g., a label, an additional therapeutic agent; devices or materials for measuring levels of metabolites or other types of molecules associated with the disorder, in a subject; devices or other materials for preparing the pharmaceutical composition of the invention for administration; and devices or other materials for administration to a subject. Instructions for use can include guidance for therapeutic application, such as suggested dosages and/or modes of administration, e.g., in a patient with the disorder. The kit can further contain at least one additional therapeutic agent, and/or one or more additional genetically engineered bacterial strains of the invention, formulated as appropriate, in one or more separate pharmaceutical preparations.

In some embodiments, the kit is used for administration of the pharmaceutical composition to a subject. In some embodiments, the kit is used for administration of the pharmaceutical composition, alone or in combination with one or more additional therapeutic agents, to a subject. In some embodiments, the kit is used for measuring levels of metabolites or other types of molecules in a subject before, during, or after administration of the pharmaceutical composition to the subject. In certain embodiments, the kit is used for administration and/or re-administration of the pharmaceutical composition, alone or in combination with one or more additional therapeutic agents, when levels of metabolites or other types of molecules are increased or abnormally high. In some embodiments involving hyperphenylalaninemia, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL.

In some embodiments, the genetically engineered bacteria achieve a target degradation rate of about 0.15 to about 8.01 μmol/$10^9$ CFUs/hr. In some embodiments, the genetically engineered bacteria achieve a target degradation rate of about 0.15 to about 2 μmol/$10^9$ CFUs/hr. In some embodiments, the genetically engineered bacteria achieve a target degradation rate of about 0.6 to about 8.01 μmol/$10^9$ CFUs/hr. In some embodiments, the genetically engineered bacteria achieve a target degradation rate of about 0.2 to about 2.67 μmol/$10^9$ CFUs/hr.

In some embodiments, the genetically engineered bacteria achieve a target degradation rate of about 0.15 to about 0.6 μmol/$10^9$ CFUs/hr. In some embodiments, the genetically engineered bacteria achieve a target degradation rate of about 0.22 to about 0.9 μmol/$10^9$ CFUs/hr. In some embodiments, the genetically engineered bacteria achieve a target degradation rate of about 0.3 to about 1.21 μmol/$10^9$ CFUs/hr. In some embodiments, the genetically engineered bacteria achieve a target degradation rate of about 0.54 to about 2.16 μmol/$10^9$ CFUs/hr. In some embodiments, the genetically engineered bacteria achieve a target degradation rate of about 1.13 to about 4.53 mol/$10^9$ CFUs/hr. In some embodiments, the genetically engineered bacteria achieve a target degradation rate of about 1.84 to about 7.38 μmol/$10^9$ CFUs/hr. In some embodiments, the genetically engineered bacteria achieve a target degradation rate of about 1.61 to about 6.43 mol/$10^9$ CFUs/hr. In some embodiments, the genetically engineered bacteria achieve a target degradation rate of about 2 to about 8.01 μmol/$10^9$ CFUs/hr.

In some embodiments, the genetically engineered bacteria achieve a target degradation rate of about 0.1 to about 1 μmol/$10^9$ CFUs/hr. In some embodiments, the genetically engineered bacteria achieve a target degradation rate of about 1 to about 2 μmol/$10^9$ CFUs/hr. In some embodiments, the genetically engineered bacteria achieve a target degradation rate of about 2 to about 3 μmol/$10^9$ CFUs/hr. In some embodiments, the genetically engineered bacteria achieve a target degradation rate of about 3 to about 4 μmol/$10^9$ CFUs/hr. In some embodiments, the genetically engineered bacteria achieve a target degradation rate of about 4 to about 5 μmol/$10^9$ CFUs/hr. In some embodiments, the genetically engineered bacteria achieve a target degradation rate of about 5 to about 6 μmol/$10^9$ CFUs/hr. In some embodiments, the genetically engineered bacteria achieve a target degradation rate of about 6 to about 7 μmol/$10^9$ CFUs/hr. In some embodiments, the genetically engineered bacteria achieve a target degradation rate of about 7 to about 8 mol/$10^9$ CFUs/hr.

In some embodiments, the genetically engineered bacteria achieve a target reduction rate of less than 0.15 μmol/$10^9$ CFUs/hr. In some embodiments, the genetically engineered bacteria achieve a target degradation rate of greater than 8.01 μmol/$10^9$ CFUs/hr.

In some embodiments, the genetically engineered bacteria achieve a target reduction of between about 178 mg and 2382 mg. In some embodiments, the genetically engineered bacteria achieve a target reduction of 1.08 mmol to 14.42 mmol. In some embodiments, the reduction is less than 1.08 mmol. In some embodiments, the reduction is greater than 14.42 mmol.

In some embodiments, target reduction and target degradation rates are based on classical PKU phenylalanine levels. In some embodiments, the target reduction and target degradation rates are based on phenylalanine levels observed in mild PKU. In some embodiments, target reduction and target degradation rates are based on phenylalanine levels observed in mild hyperphenylalaninemia.

Figure 28:
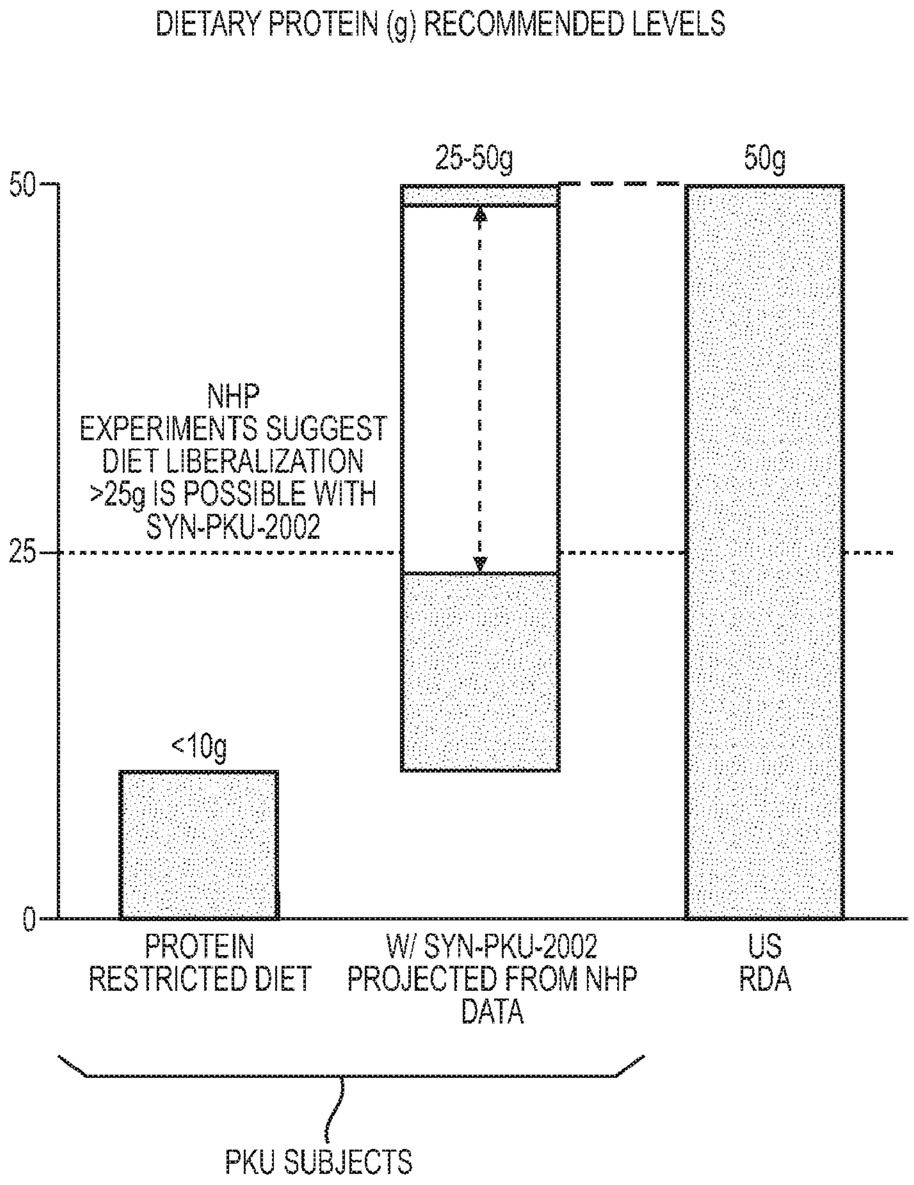
FIG. 28 depicts a graph showing SYN-PKU-2002 conversion of Phe in an NHP resulting in an increase in protein intake, which would correspond to a 2.5 fold increase in protein intake in a PKU patient.
Figure 29:
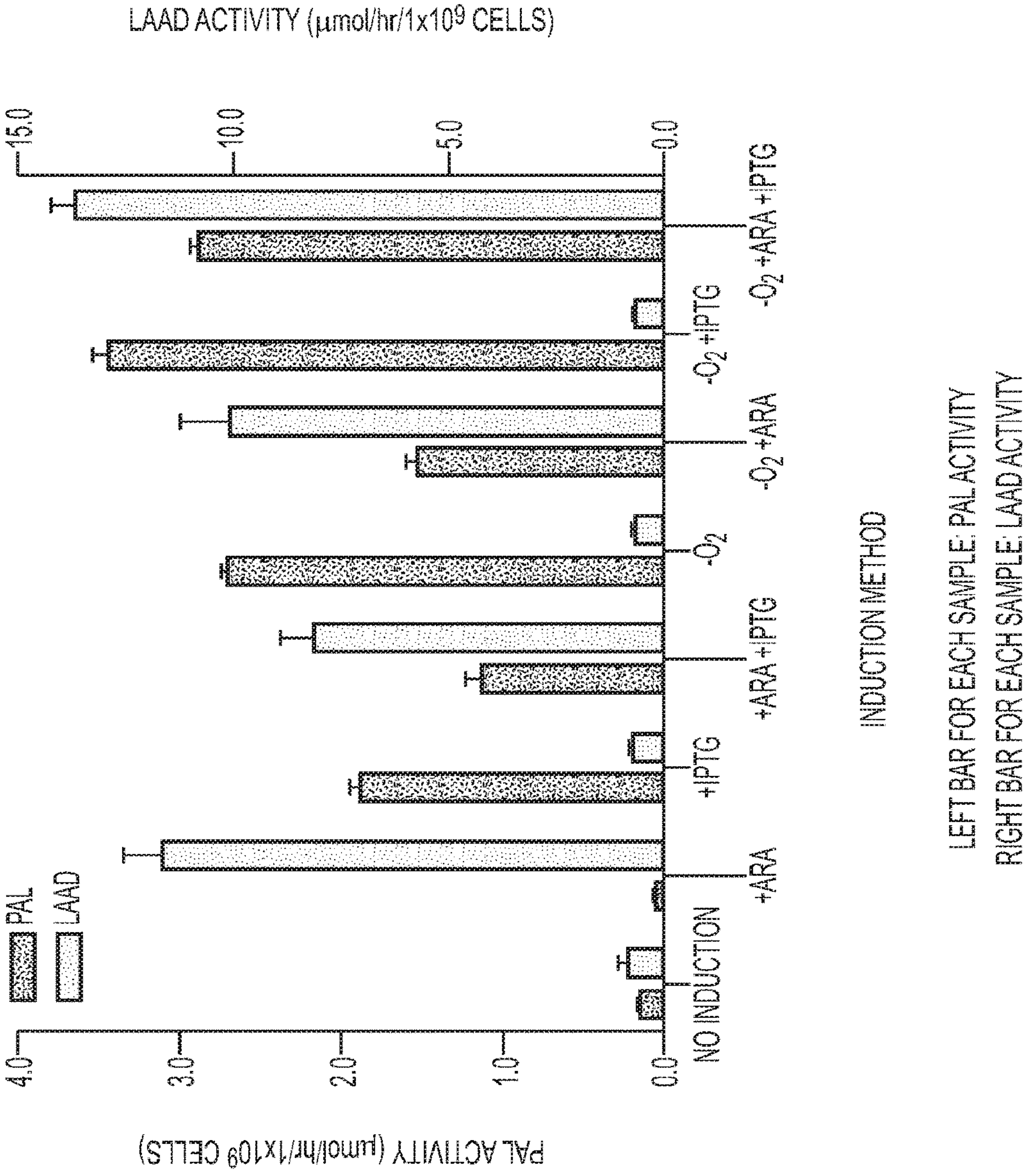
FIG. 29 depicts a graph showing in vitro activity of SYN-PKU-2002. $1\times10^8$ activated cells were analyzed in 50 mM Phe assay buffer for PAL (dark blue bars, left y-axis) and LAAD (light blue bars, right y-axis) activity. Cells were pre-induced with L-arabinose (+ara), IPTG (+IPTG) or in an anaerobic chamber (—$O_2$) and rates of TCA and PP were calculated by linear regression of TCA and PP production over time. The graph displays the average and standard deviation of three biological replicates.
Figure 30:
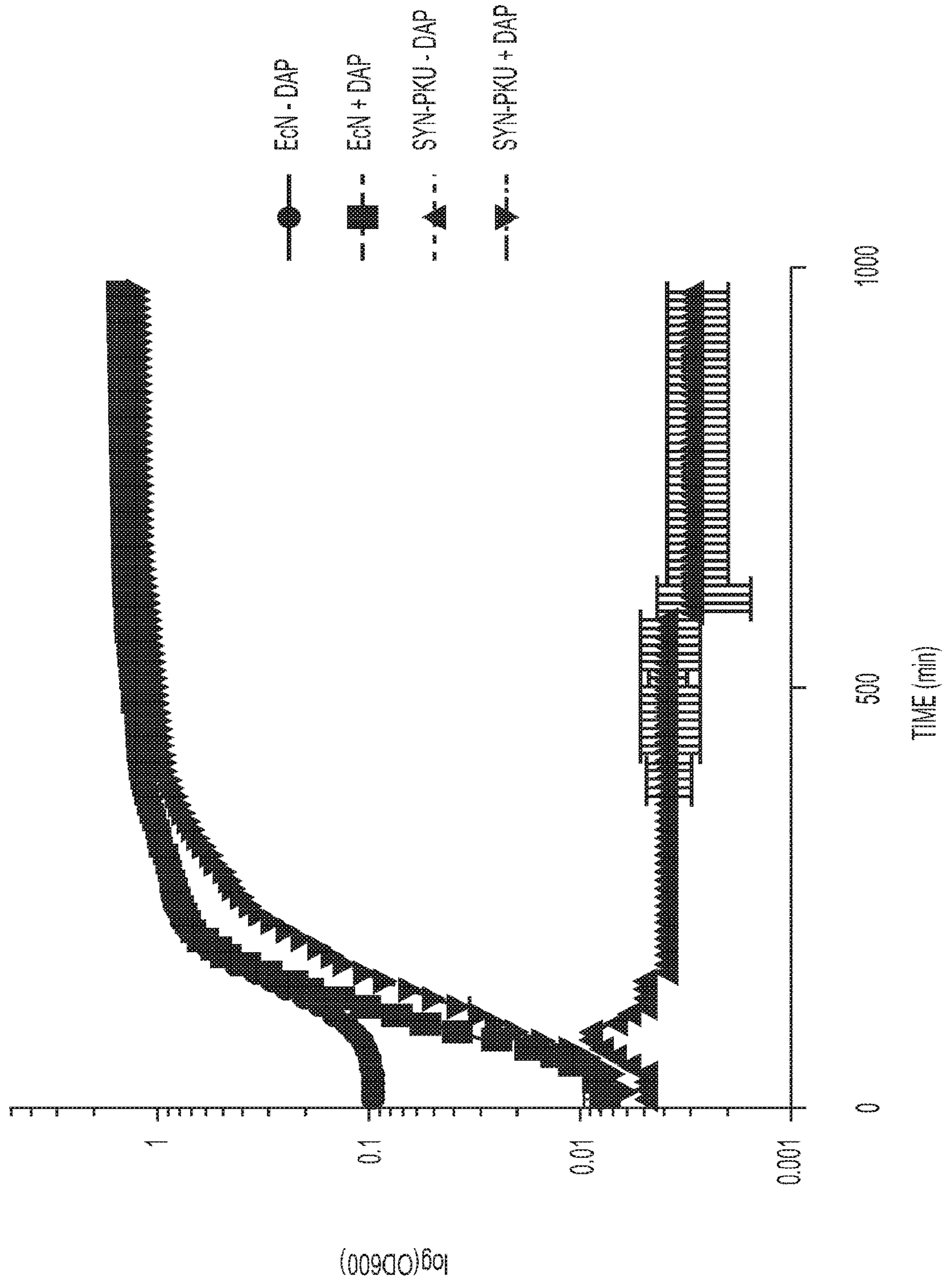
FIG. 30 depicts a graph showing the effect of dapA deletion on SYN-PKU-2002 growth in vitro. To characterize the growth of *E. coli* Nissle (EcN) and SYN-PKU-2002, which contains a mutation in the dapA gene, both strains were incubated in LB that did (+) or did not (−) contain diaminopimelic acid (DAP; 100 μg/mL) at 37° C. for 960 minutes under constant shaking. The OD600 was measured every 10 minutes to assess cell growth over time. The average of three biological replicates and two technical replicates is plotted for each time point. Data shows that SYN-PKU-2002 is unable to grow without the addition of exogenous DAP to the growth media.

In some embodiments, administration of the genetically engineered bacteria allow for diet liberalization (partial or complete) (see FIG. 28).

Treatment In Vivo

The genetically engineered bacteria of the invention may be evaluated in vivo, e.g., in an animal model. Any suitable animal model of the disease or condition may be used. In some embodiments, the animal model is a mouse model. See e.g. WO2017/087580 A1, the entire contents of which are incorporated by reference in its entirety.

In some embodiments, pharmacokinetics and pharmacodynamic studies may be conducted in non-human primates to determine any potential toxicities arising from administration of the genetically engineered bacteria. Non-limiting examples of such studies are described in Examples 30 and 31.

Screening Methods

In some embodiments, of the disclosure a genetically engineered strain may be improved upon by using screening and selection methods, e.g., to increase activity of an effector (e.g. to increase PME enzymatic activity) or to increase the ability of a strain to take up a metabolite (e.g. increased ability to take up phenylalanine). In some embodiments, the screen serves to generate a bacterial strain with improved effector activity. In some embodiments, the screen serves to generate a bacterial strain which has improved ability to take up a metabolite. In some embodiments, the screen may identify a bacterial strain with both improved effector activity and enhanced substrate import. Non-limiting examples of methods of screening which can be used are described herein.

Generation of Bacterial Strains with Enhance Ability to Transport Biomolecules

In some embodiments, the ALE method can be used to identify genetically engineered bacteria with improved phenylalanine uptake.

Specific Screen to Improve PME Activity

Screens using genetic selection are conducted to improve phenylalanine consumption in the genetically engineered bacteria. Toxic phenylalanine analogs exert their mechanism of action (MOA) by being incorporated into cellular protein, causing cell death. These compounds, such as paralog p-fluoro-DL-phenylalanine and ortholog o-fluoro-DL-phenylalanine have utility in an untargeted approach to select PAL enzymes with increased activity. Assuming that these toxic compounds can be metabolized by PAL into a non-toxic metabolite, rather than being incorporated into cellular protein, genetically engineered bacteria which have improved phenylalanine degradation activity can tolerate higher levels of these compounds and can be screened for and selected on this basis.

REFERENCES

Al Hafid N, Christodoulou J. Phenylketonuria: a review of current and future treatments. Transl Pediatr. 2015 October; 4(4):304-317. PMID: 26835392;

Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-229. PMID: 15039098;

Andersen et al. Uracil uptake in *Escherichia coli* K-12: isolation of uraA mutants and cloning of the gene. J Bacteriol. 1995 April; 177(8):2008-2013. PMID: 7721693;

Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-76. PMID: 7664887;

Arthur et al. Intestinal inflammation targets cancer-inducing activity of the microbiota. Science. 2012 Oct. 5; 338 (6103):120-123. PMID: 22903521;

Callura et al. Tracking, Tuning and terminating microbial physiology using synthetic riboregulators. Proc Natl Acad Sci USA. 2010; 27(36):15898-15903. PMID: 20713708;

Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-2844. PMID: 19477902;

Chang, ed. (2007) "Use of Enzyme Artificial Cells for Genetic Enzyme Defects." In Artificial Cells: Biotechnology, Nanomedicine, Regenerative Medicine, Blood Substitutes, Bioencapsulation, and Cell/Stem Cell Therapy. World Scientific Publishing, pp. 147-159;
Clarkson et al. Diaminopimelic acid and lysine auxotrophs of *Pseudomonas aeruginosa* 8602. J Gen Microbiol. 1971 May; 66(2):161-169. PMID: 4999073;
Cuevas-Ramos et al. *Escherichia coli* induces DNA damage in vivo and triggers genomic instability in mammalian cells. Proc Natl Acad Sci USA. 2010 Jun. 22; 107(25): 11537-11542. PMID: 20534522;
Danino et al. Programmable probiotics for detection of cancer in urine. Sci Transl Med. 2015 May 27; 7(289): 289ra84. PMID: 26019220;
Deutscher. The mechanisms of carbon catabolite repression in bacteria. Curr Opin Microbiol. 2008 April; 11(2):87-93. PMID: 18359269;
Dinleyici et al. *Saccharomyces boulardii* CNCM 1-745 in different clinical conditions. Expert Opin Biol Ther. 2014 November; 14(11):1593-1609. PMID: 24995675;
Dobbelaere et al. Evaluation of nutritional status and pathophysiology of growth retardation in patients with phenylketonuria. J Inherit Metab Dis. 2003; 26(1):1-11. PMID: 12872834;
Eiglmeier et al. Molecular genetic analysis of FNR-dependent promoters. Mol Microbiol. 1989 July; 3(7):869-878. PMID: 2677602;
Estrem et al. Identification of an UP element consensus sequence for bacterial promoters. Proc Natl Acad Sci USA. 1998 Aug. 18; 95(17):9761-9766. PMID: 9707549;
Galimand et al. Positive FNR-like control of anaerobic arginine degradation and nitrate respiration in *Pseudomonas aeruginosa*. J Bacteriol. 1991 March; 173(5):1598-1606. PMID: 1900277;
Gardner et al. Construction of a genetic toggle switch in *Escherichia coli*. Nature. 2000; 403:339-342. PMID: 10659857;
Gerdes et al. Essential genes on metabolic maps. Curr Opin Biotechnol. 2006 October; 17(5):448-456. PMID: 16978855;
Gilbert et al. Molecular cloning of the phenylalanine ammonia lyase gene from *Rhodosporidium toruloides* in *Escherichia coli* K-12. J Bacteriol. 1985 January; 161(1): 314-320. PMID: 2981805;
Görke B, Stulke J. Carbon catabolite repression in bacteria: many ways to make the most out of nutrients. Nat Rev Microbiol. 2008 August; 6(8):613-624. PMID: 18628769;
Hasegawa et al. Activation of a consensus FNR-dependent promoter by DNR of *Pseudomonas aeruginosa* in response to nitrite. FEMS Microbiol Lett. 1998 Sep. 15; 166(2):213-217. PMID: 9770276;
Hoeks et al. Adult issues in phenylketonuria. Neth J Med. 2009 January; 67(1):2-7. PMID: 19155540;
Hoeren et al. Sequence and expression of the gene encoding the respiratory nitrous-oxide reductase from *Paracoccus denitrificans*. Eur J Biochem. 1993 Nov. 15; 218(1):49-57. PMID: 8243476;
Hosseini et al. Propionate as a health-promoting microbial metabolite in the human gut. Nutr Rev. 2011 May; 69(5): 245-258. PMID: 21521227;
Isabella et al. Deep sequencing-based analysis of the anaerobic stimulon in *Neisseria gonorrhoeae*. BMC Genomics. 2011 Jan. 20; 12:51. PMID: 21251255;
Ivanovska et al. Pediatric drug formulations: a review of challenges and progress. Pediatrics. 2014 August; 134(2): 361-372. PMID: 25022739; Kobe et al. Regulation and crystallization of phosphorylated and dephosphorylated forms of truncated dimeric phenylalanine hydroxylase. Protein Sci. 1997 June; 6(6):1352-1357. PMID: 9194198;
Kwok et al. Nucleotide sequence of a full-length complementary DNA clone and amino acid sequence of human phenylalanine hydroxylase. Biochemistry 1985 Jan. 29; 24(3):556-561. PMID: 2986678;
Leonard J V (2006). Disorders of the urea cycle and related enzymes. Inborn Metabolic Diseases, $4^{th}$ ed (pp. 263-272). Springer Medizin Verlag Heidelberg;
Longo et al. Phase 1 Trial of Subcutaneous rAvPAL-PEG in Subjects with Phenylketonuria. Lancet. 2014 Jul. 5; 384 (9937):37-44;
Lopez G, Anderson J C. Synthetic Auxotrophs with Ligand-Dependent Essential Genes for a BL21(DE3) Biosafety Strain. ACS Synth Biol. 2015 Dec. 18; 4(12):1279-1286. PMID: 26072987;
Macleod et al. Nutritional Management of Phenylketonuria. Ann Nestle Eng. 2010 June; 68(2):58-69. PMID: 22475869;
Meadow et al. Biosynthesis of diaminopimelic acid and lysine in *Escherichia coli*. Biochem J. 1959 July; 72(3): 396-400. PMID: 16748796;
Miller (1972) Experiments in Molecular Genetics. Cold Spring Harbor Laboratory Press, Cold Spring Harbor, NY;
Moffitt et al. Discovery of two cyanobacterial phenylalanine ammonia lyases: kinetic and structural characterization. Biochemistry. 2007 Jan. 30; 46(4):1004-1012. PMID: 17240984;
Moore et al. Regulation of FNR dimerization by subunit charge repulsion. J Biol Chem. 2006 Nov. 3; 281(44): 33268-33275. PMID: 16959764;
Nougayrede et al. *Escherichia coli* induces DNA double-strand breaks in eukaryotic cells. Science. 2006 Aug. 11; 313(5788):848-51. PMID: 16902142;
Olier et al. Genotoxicity of *Escherichia coli* Nissle 1917 strain cannot be dissociated from its probiotic activity. Gut Microbes. 2012 November-December; 3(6):501-509. PMID: 22895085;
Pi et al. Cloning and sequencing of the pheP gene, which encodes the phenylalanine-specific transport system of *Escherichia coli*. J Bacteriol. 1991 June; 173(12):3622-3629. PMID: 1711024;
Pi et al. Topology of the phenylalanine-specific permease of *Escherichia coli*. J Bacteriol. 1996 May; 178(9):2650-2655. PMID: 8626334;
Pi et al. Functional consequences of changing proline residues in the phenylalanine-specific permease of *Escherichia coli*. J Bacteriol. 1998 November; 180(21):5515-5519. PMID: 9791098;
Purcell et al. Towards a whole-cell modeling approach for synthetic biology. Chaos. 2013 June; 23(2):025112. PMID: 23822510;
Ray et al. The effects of mutation of the anr gene on the aerobic respiratory chain of *Pseudomonas aeruginosa*. FEMS Microbiol Lett. 1997 Nov. 15; 156(2):227-232. PMID: 9513270;
Reister et al. Complete genome sequence of the Gram-negative probiotic *Escherichia coli* strain Nissle 1917. J Biotechnol. 2014 Oct. 10; 187:106-107. PMID: 25093936;
Rembacken et al. Non-pathogenic *Escherichia coli* versus mesalazine for the treatment of ulcerative colitis: a randomised trial. Lancet. 1999 Aug. 21; 354(9179):635-639. PMID: 10466665;
Remington's Pharmaceutical Sciences (2012), $22^{nd}$ ed. Mack Publishing Co, Easton, PA.

Salmon et al. Global gene expression profiling in *Escherichia coli* K12. The effects of oxygen availability and FNR. J Biol Chem. 2003 Aug. 8; 278(32):29837-29855. PMID: 12754220;

Sarkissian et al. A different approach to treatment of phenylketonuria: phenylalanine degradation with recombinant phenylalanine ammonia lyase. Proc Natl Acad Sci USA. 1999 Mar. 2; 96(5):2339-2344. PMID: 10051643;

Sat et al. The *Escherichia coli* mazEF suicide module mediates thymineless death. J Bacteriol. 2003 March; 185(6):1803-1807. PMID: 12618443;

Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-1481. PMID: 1787797;

Schultz. Clinical use of *E. coli* Nissle 1917 in inflammatory bowel disease. Inflamm Bowel Dis. 2008 July; 14(7): 1012-1018. PMID: 18240278;

Sonnenborn et al. The non-pathogenic *Escherichia coli* strain Nissle 1917—features of a versatile probiotic. Microbial Ecology in Health and Disease. 2009; 21:122-158;

Trunk et al. Anaerobic adaptation in *Pseudomonas aeruginosa*: definition of the Anr and Dnr regulons. Environ Microbiol. 2010 June; 12(6):1719-1733. PMID: 20553552;

Ukena et al. Probiotic *Escherichia coli* Nissle 1917 inhibits leaky gut by enhancing mucosal integrity. PLoS One. 2007 Dec. 12; 2(12):e1308. PMID: 18074031;

Unden et al. Alternative respiratory pathways of *Escherichia coli*: energetics and transcriptional regulation in response to electron acceptors. Biochim Biophys Acta. 1997 Jul. 4; 1320(3):217-234. PMID: 9230919;

Vockley et al. Phenylalanine hydroxylase deficiency: diagnosis and management guideline. Genet Med. 2014 February; 16(2):188-200. PMID: 24385074;

Wanner et al. The phenylalanine ammonia-lyase gene family in *Arabidopsis thaliana*. Plant Mol Biol. 1995 January; 27(2):327-338. PMID: 7888622;

Williams et al. The gene stlA encodes a phenylalanine ammonia-lyase that is involved in the production of a stilbene antibiotic in *Photorhabdus luminescens* TTO1. Microbiology. 2005 August; 151(Pt 8):2543-2550. PMID: 16079333.

Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-693. PMID: 8868444;

Wright et al. GeneGuard: A Modular Plasmid System Designed for Biosafety. ACS Synth Biol. 2015 Mar. 20; 4(3):307-316. PMID: 24847673;

Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598;

Xiang L, Moore B S. Biochemical characterization of a prokaryotic phenylalanine ammonia lyase. J Bacteriol. 2005 June; 187(12):4286-4289. PMID: 15937191;

Zhang R, Lin Y. DEG 5.0, a database of essential genes in both prokaryotes and eukaryotes. Nucleic Acids Res. 2009 January; 37(Database issue):D455-D458. PMID: 18974178;

Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-1490. PMID: 1787798.

EXAMPLES

Example 3. Metabolite Measurements

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Phenylalanine Quantification (Dansyl-Chloride Derivatization)

For in vitro and in vivo assays described herein, which assess the ability of the genetically engineered bacteria to degrade phenylalanine and which require quantification of phenylalanine levels in the sample, a dansyl-chloride derivatization protocol was employed as described in co-owned, pending International Patent Applications PCT/US2016/032562, filed May 13, 2016 and PCT/US2016/062369, the contents of each of which is herein incorporated by reference in its entirety.

Trans-Cinnamic Acid Quantification (Trifluoroethylamine Derivatization)

For in vitro and in vivo assays described herein, which assess the ability of the genetically engineered bacteria to degrade phenylalanine and which require quantification of Trans-cinnamic acid levels in the sample, a trifluoroethylamine derivatization protocol was employed as as described in co-owned, pending PCT/US2016/032562, filed May 13, 2016 and PCT/US2016/062369, the contents of each of which is herein incorporated by reference in its entirety.

Phenylalanine, Trans-Cinnamic Acid, Phenylacetic Acid, Phenylpyruvic Acid, Phenyllactic Acid, Hippuric Acid and Benzoic Acid Quantification (2-Hydrazinoquinoline Derivatization)

For in vitro and in vivo assays described herein, which assess the ability of the genetically engineered bacteria to degrade phenylalanine and which require quantification of phenylalanine, trans-cinnamic acid, phenylacetic acid, phenylpyruvic acid, phenyllactic acid, hippuric acid, and benzoic acid levels in the sample, a 2-Hydrazinoquinoline derivatization protocol was employed as as described in co-owned, pending International Patent Applications PCT/US2016/032562, filed May 13, 2016 and PCT/US2016/062369, the contents of each of which is herein incorporated by reference in its entirety.

Hippuric Acid, Trans-Cinnamic Acid, Phenylalanine, and Phenylpyruvate Quantification in Plasma and Urine by LC-MS/MS Hippuric acid, Trans-cinnamic acid, Phenylalanine, and Phenylpyruvate Quantification in Plasma and Urine by LC-MS/MS were measured as described in in co-owned, pending International Patent Applications PCT/US2016/032562, filed May 13, 2016 and PCT/US2016/062369, the contents of each of which is herein incorporated by reference in its entirety.

Examples 1-55 of PCT/US2016/062369, filed Nov. 16, 2016, the contents of each of which is herein incorporated by reference in its entirety describe the construction and activity of various Phe consuming strains.

Example 27. In Vitro Activity of SYN-PKU-710

SYN-PKU-710 is an engineered bacterium derived from *Escherichia coli* Nissle 1917 (EcN) (ref) that has been designed to treat hyperphenylalaninemia by consuming and converting phenylalanine to the non-toxic metabolites trans-cinnamate (TCA) and phenylpyruvate (PP). It works by intercepting and degrading phenylalanine found in the intestine, which decreases the flux of phenylalanine into the blood. SYN-PKU-710 was created by a series of genetic manipulations that allowed for the degradation of phenylalanine in the microaerobic (low oxygen) environment of the human gut. The following modifications to the genome of EcN have been made to enhance phenylalanine degradation under the low oxygen conditions found in the gut while augmenting biologic containment through diaminopimelate auxotrophy:

a. Insertion of two additional copies of an endogenous Nissle gene encoding a high affinity phenylalanine transporter (PheP) under the regulatory control of an anaerobic-inducible promoter ($P_{fnrS}$) and the anaerobic-responsive transcriptional activator FNR
b. Insertion of three copies of a gene encoding phenylalanine ammonia lyase (PAL) derived from *Photorhabdus luminescens* under the regulatory control of $P_{fnrS}$ and FNR
c. Insertion of two additional copies of the gene encoding PAL under the regulatory control of a synthetic promoter (Plac) and the lactose-responsive transcriptional repressor LacI
d. Insertion of the gene encoding L-amino acid deaminase (LAAD) derived from *Proteus mirabilis* under the regulatory control of the arabinose-inducible promoter (PBAD) and the arabinose-responsive transcriptional activator AraC
e. Deletion of the dapA gene that encodes 4-hydroxy-tetrahydropicolinate synthase to create a diaminopimelate auxotroph SYN-PKU-710 was derived from EcN in a series of genetic manipulations designed to allow degradation of phenylalanine in the microaerobic (low oxygen) environment of the human gut. Genomic insertions of two additional copies of the endogenous gene encoding PheP, a high affinity phenylalanine transporter, were made within the EcN chromosome. This transporter allows the uptake of environmental phenylalanine into the bacterial cell. In addition, three copies of a gene encoding phenylalanine ammonia lyase (PAL), derived from the organism *Photorhabdus luminescens*, were chromosomally integrated. PAL catalyzes the conversion of phenylalanine into the non-toxic product trans-cinnamate. The genes encoding PheP and PAL were placed under the regulatory control of an anaerobic-inducible promoter (PfnrS) and the anaerobic-responsive transcriptional activator FNR. These regulatory components ensure that phenylalanine degradation machinery are produced in the anoxic environment of the human gut. Additional copies of the gene encoding PAL were inserted into the Nissle chromosome under the control of a synthetic promoter (Plac) and the LacI transcriptional repressor. These copies may be induced for expression when lactose or a lactose analog is used to alleviate transcriptional repression, and are envisioned to be utilized for the induction of phenylalanine degradation activity during the production of drug material. In this manner, initial strain potency from LacI-mediated induction will allow for immediate activity upon SYN-PKU-710 administration, while PfnrS-mediated induction will allow for de novo potency induction post-administration. A second pathway of phenylalanine degradation in SYN-PKU-710 was introduced through the chromosomal insertion of the gene encoding L-amino acid deaminase (LAAD), derived from the organism *Proteus mirabilis*, which converts phenylalanine into phenylpyruvate in the presence of oxygen. This gene was inserted downstream of the endogenous Nissle araC gene in a manner that allows the expression of LAAD to be induced by AraC in response to arabinose during production of drug material. The activity of PAL and LAAD have shown to be additive. The inclusion of LAAD is a mechanism to capitalize on the available oxygen expected to be found in greater abundance in the proximal GI tract.

SYN-PKU-710 was also modified with a deletion of the diaminopimelate (dapA) gene that encodes 4-hydroxy-tetrahydropicolinate synthase, which is essential for bacterial growth. This deletion renders SYN-PKU-710 unable to synthesize diaminopimelate, thereby preventing the proper formation of bacterial cell wall unless the strain is supplemented with diaminopimelate exogenously. For external manufacturing purposes, SYN-PKU-710 was also modified with a deletion of a portion of its endogenous prophage (Φ) which removes its ability to express phage particles. The strain comprising the deletion of a portion of its endogenous prophage is referred to herein as SYN-PKU-2002.

Sequences and additional details relating toe SYN-PKU-710 are described in International Patent Applications PCT/US2016/032562, filed—May 13, 2016 and PCT/US2016/062369, filed Nov. 16, 2016, the contents of each of which are herein incorporated by reference in their entireties.

To measure in vitro activity, overnight cultures were diluted 1:100 in LB and grown with shaking (250 rpm) at 37° C. After 1.5 hrs of growth, cultures were placed in a Coy anaerobic chamber supplying 90% $N_2$, 5% $CO_2$, 5% $H_2$. After 4 hrs of induction, bacteria were pelleted, washed in PBS, and resuspended in assay buffer (M9 minimal media with 0.5% glucose, 8.4% sodium bicarbonate, and 4 mM Phe). Rates of phenylalanine degradation (i.e., disappearance from the assay solution) or cinnamate accumulation from 30 to 90 min were normalized to 1e9 cells. Table 59 shows the normalized rates for all strains and describes genotypes and the activities of non-limiting examples of engineered plasmid-bearing strains and engineered strains comprising chromosomal insertions.

TABLE 59

Genotype and Activity of engineered plasmid-bearing strains and engineered strains comprising chromosomal insertions.

| Strain Name | Genotype | PAL Activity (umol/hr./10^9 cells) | LAAD activity (umol/hr./10^9 cells) |
|---|---|---|---|
| | Plasmid-based strains | | |
| SYN-PKU101 | Low copy pSC101-Ptet::PAL1, ampicillin resistant | ND | NA |
| SYN-PKU102 | High copy pColE1-Ptet::PAL1, ampicillin resistant, | ND | NA |
| SYN-PKU201 | Low copy pSC101-Ptet::PAL3, ampicillin resistant | ND | NA |
| SYN-PKU202 | High copy pColE1-Ptet::PAL3, ampicillin resistant, | ND | NA |

TABLE 59-continued

Genotype and Activity of engineered plasmid-bearing strains and engineered strains comprising chromosomal insertions.

| Strain Name | Genotype | PAL Activity (umol/hr./10^9 cells) | LAAD activity (umol/hr./10^9 cells) |
|---|---|---|---|
| SYN-PKU203 | lacZ::Ptet-pheP::cam | 0 | NA |
| SYN-PKU401 | Low copy pSC101-Ptet::PAL1, ampicillin resistant, chromosomal lacZ::Ptet-pheP::cam | 1.1 | NA |
| SYN-PKU402 | High copy pColE1-Ptet::PAL1, ampicillin resistant, chromosomal lacZ::Ptet-pheP::cam | 0.8 | NA |
| SYN-PKU302 | Low Copy pSC101-Ptet::PAL3, ampicillin resistant; chromosomal lacZ::Ptet-pheP::cam | 2.2 | NA |
| SYN-PKU303 | High copy pColE1-Ptet::PAL3, ampicillin resistant, chromosomal lacZ::Ptet-pheP::cam | 7.1 | NA |
| SYN-PKU304 | Low Copy pSC101-PfnrS-PAL3, ampicillin resistant; chromosomal lacZ::PfnrS-pheP::cam | 3 | NA |
| SYN-PKU305 | Low Copy pSC101-PfnrS-PAL3, kanamycin resistant; chromosomal lacZ::PfnrS-pheP::cam | 3 | NA |
| SYN-PKU306 | Low Copy pSC101-PfnrS-PAL3, kanamycin resistant; thyA | 0.3 | NA |
| SYN-PKU307 | Low Copy pSC101-PfnrS-PAL3, ampicillin resistant; | 0.3 | NA |
| SYN-PKU308 | Low Copy pSC101-PfnrS-PAL3, kanamycin resistant; | 0.3 | NA |
| SYN-PKU401 | High Copy pUC57-Ptet::LAAD; kanamycin resistant | NA | 50 ($^{+}O_2$), 0 ($^{-}O_2$) |
| | Integrated strains | | |
| SYN-PKU501 | malPT::PfnrS-PAL3::kan | 0.3 | NA |
| SYN-PKU502 | malPT::PfnrS-PAL3::kan; bicistronic lacZ::PfnrS-PAL3-pheP::cam | ND | NA |
| SYN-PKU503 | malEK::PfnrS-PAL3::cam | 0.3 | NA |
| SYN-PKU504 | agaI/rsmI::PfnrS-PAL3 | 0.3 | NA |
| SYN-PKU505 | cea::PfnrS-PAL3 | 0.3 | NA |
| SYN-PKU506 | malEK::PfnrS-PAL3::agaI/rsmI::PfnrS-PAL3; cea::PfnrS-PAL3 | 0.7 | NA |
| SYN-PKU507 | malEK::PfnrS-PAL3; agaI/rsmI::PfnrS-PAL3; cea::PfnrS-PAL3; lacZ::PfnrS-pheP::cam | 5.2 | NA |
| SYN-PKU508 | malEK::PfnrS-PAL3; pheA auxotroph | 0.4 | NA |
| SYN-PKU509 | malEK::PfnrS-PAL3; agaI/rsmI::PfnrS-PAL3; cea::PfnrS-PAL3; lacZ::PfnrS-pheP::cam | 4.9 | NA |
| SYN-PKU601 | malPT::PfrnS::INT5::kan, rrnBUP-[PAL3]; lacZ::PfnrS-pheP::cam (recombinase based strain) | 0.9 | NA |
| SYN-PKU510 | malEK::PfnrS-PAL3; agaI/rsmI::PfnrS-PAL3; cea::PfnrS-PAL3; | 0.6 | NA |
| SYN-PKU511 | malEK::PfnrS-PAL3; agaI/rsmI::PfnrS-PAL3; cea::PfnrS-PAL3; yicS/nepI::PfnrS-PAL3::kan; malPT::PfnrS-PAL3; lacZ::PfnrS-pheP; ΔthyA | 7.7 | NA |
| SYN-PKU204 | lacZ::PfnrS-pheP::cam | ND | NA |
| SYN-PKU512 | malEK::PfnrS-PAL3; agaI/rsmI::PfnrS-PAL3; cea::PfnrS-PAL3; malPT::PfnrS-PAL3::lacZ::PfnrS-pheP::cam; ΔthyA | 6.7 | NA |
| SYN-PKU513 | malEK::PfnrS-PAL3; agaI/rsmI::PfnrS-PAL3; cea::PfnrS-PAL3; lacZ::PfnrS-pheP; ΔthyA | 4.9 | NA |
| SYN-PKU514 | malEK::PfnrS-PAL3; agaI/rsmI::PfnrS-PAL3; cea::PfnrS-PAL3; malPT::PfnrS-PAL3::ΔthyA | 0.8 | NA |
| SYN-PKU515 | malEK::PfnrS-PAL3; agaI/rsmI::PfnrS-PAL3; cea::PfnrS-PAL3; ΔthyA | 0.7 | NA |
| SYN-PKU516 | agaI/rsmI::PfnrS-PAL3::kan | 0.3 | NA |
| SYN-PKU517 | malEK::PfnrS-PAL3::cam; malPT::PfnrS-PAL3::kan, lacZ::PfnrS-pheP; ΔthyA | 2.9 | NA |
| SYN-PKU518 | malEK-PfnrS-PAL3::cam; PfnrS::pheP::kan | 1.7 | NA |
| SYN-PKU519 | ParaBC-PAL3::cam; PfnrS-pheP::kan | 1.3 | NA |
| SYN-PKU520 | agaI/rsmI::PfnrS-PAL3::kan; PfnrS-PheP::cam | 2.0 | NA |
| SYN-PKU801 | ΔargR; thyA::cam | ND | NA |
| SYN-PKU701 | ParaBC-LAAD::cam; malEK-PfnrS-PAL3; malPT::PfnrS-PAL3::kan; PfnrS-pheP | 2.7 | 28 ($^{+}O_2$), 0 ($^{-}O_2$) |
| SYN-PKU521 | yicS/nepI::PfrnS-PAL3::kan; lacZ::PfnrS-pheP::cam | 2.4 | NA |
| SYN-PKU522 | cea::PfnrS-PAL3::kan; lacZ::PfnrS-pheP::cam | ND | NA |
| SYN-PKU523 | malPT::PfrnS-PAL3::kan; lacZ::PfnrS-pheP::cam | 0.5 | NA |
| SYN-PKU524 | malEK::PfnrS-PAL3; malPT::PfnrS-PAL3; lacZ::PfnrS-pheP | 2.9 | NA |
| SYN-PKU702 | malEK::PfnrS-PAL3; lacZ::PfnrS-pheP; Para::LAAD | 1.5 | ND |

TABLE 59-continued

Genotype and Activity of engineered plasmid-bearing strains and engineered strains comprising chromosomal insertions.

| Strain Name | Genotype | PAL Activity (umol/hr./10^9 cells) | LAAD activity (umol/hr./10^9 cells) |
|---|---|---|---|
| SYN-PKU703 | malEK::PfnrS-PAL3; malPT::PfnrS-PAL3; lacZ::PfnrS-pheP; agaI/rsmI::PfnrS::pheP; Para::LAAD | 3.1 | ND |
| SYN-PKU704 | malEK::PfnrS-PAL3; malPT::PfnrS-PAL3; yicS/nepI::PfnrS-PAL3; lacZ::PfnrS-pheP; Para::LAAD | 3.5 | ND |
| SYN-PKU705 | malEK::PfnrS-PAL3; malPT::PfnrS-PAL3; yicS/nepI::PfnrS-PAL3::kan; lacZ::PfnrS-pheP; agaI/rsmI::PfnrS::pheP Para::LAAD | 3.7 | ND |
| SYN-PKU602 | malEK::PT7::PAL3; Para::INT5::cam (recombinase); lacZ::PfnrS-pheP; malPT::Pconstitutive::T7 polymerase (unflipped); | 2.4 | NA |
| SYN-PKU901 | Nissle with streptomycin resistance | NA | NA |
| SYN-PKU713 | LacZ::PfnrS-PAL3::pheP | NA | NA |
| SYN-PKU706 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD, ΔdapA::cm | ND | ND |
| SYN-PKU707 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y::cm | 4.0 | NA |
| SYN-PKU708 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y-LAAD; ΔdapA | 4.0 | 44 ($^{+}O_2$), 0 ($^{-}O_2$) |
| SYN-PKU-709 | malEK::PfnrS-PAL3; malPT::PfnrS-PAL3; yicS/nepI::PfnrS-PAL3; lacZ::PfnrS-pheP, agaI/rsmI::PfnrS-pheP; Para-LAAD; ΔdapA | ND | NA |
| SYN-PKU-710 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA | 4.4 | 40 ($^{+}O_2$), 0 ($^{-}O_2$) |
| SYN-PKU711 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y-LAAD; | ND | ND |
| SYN-PKU-712 | malEK::PfnrS-PAL3; malPT::PfnrS-PAL3; yicS/nepI::PfnrS-PAL3; lacZ::PfnrS-pheP, agaI/rsmI::PfnrS-pheP; Para::FNRS24Y; ΔDapA | ND | ND |
| SYN-PKU-714 | lacZ::PfnrS-pheP, agaI/rsmI::PfnrS-pheP | ND | ND |

| Description | Sequence | SEQ ID NO |
|---|---|---|
| FNRS24Y (bold) driven by the arabinose inducible promoter (underlined) and araC in reverse direction (italic). RBS is underlined and bolded (see FIG. 48A of WO2017087580) | *TTATTCACAACCTGCCCTAAACTCGCTCGGACTCGCCCCGGTGCATT*<br>*TTTTAAATACTCGCGAGAAATAGAGTTGATCGTCAAAACCGACATTG*<br>*CGACCGACGGTGGCGATAGGCATCCGGGTGGTGCTCAAAAGCAGC*<br>*TTCGCCTGACTGATGCGCTGGTCCTCGCGCCAGCTTAATACGCTAAT*<br>*CCCTAACTGCTGGCGGAACAAATGCGACAGACGCGACGGCGACAG*<br>*GCAGACATGCTGTGCGACGCTGGCGATATCAAAATTACTGTCTGCC*<br>*AGGTGATCGCTGATGTACTGACAAGCCTCGCGTACCCGATTATCCAT*<br>*CGGTGGATGGAGCGACTCGTTAATCGCTTCCATGCGCCGCAGTAAC*<br>*AATTGCTCAAGCAGATTTATCGCCAGCAATTCCGAATAGCGCCCTTC*<br>*CCCTTGTCCGGCATTAATGATTTGCCCAAACAGGTCGCTGAAATGCG*<br>*GCTGGTGCGCTTCATCCGGGCGAAAGAAACCGGTATTGGCAAATAT*<br>*CGACGGCCAGTTAAGCCATTCATGCCAGTAGGCGCGCGGACGAAA*<br>*GTAAACCCACTGGTGATACCATTCGTGAGCCTCCGGATGACGACCG*<br>*TAGTGATGAATCTCTCCAGGCGGGAACAGCAAAATATCACCCGGTC*<br>*GGCAGACAAATTCTCGTCCCTGATTTTTCACCACCCCCTGACCGCGA*<br>*ATGGTGAGATTGAGAATATAACCTTTCATTCCCAGCGGTCGGTCGAT*<br>*AAAAAAATCGAGATAACCGTTGGCCTCAATCGGCGTTAAACCCGCCA*<br>*CCAGATGGGCGTTAAACGAGTATCCCGGCAGCAGGGGATCATTTTG*<br>*CGCTTCAGCCATACTTTTCATACTCCCGCCATTCAGAGAAGAAACCA*<br>*ATTGTCCATATTGCAT*CAGACATTGCCGTCACTGCGTCTTTTACTG<br>GCTCTTCTCGCTAACCCAACCGGTAACCCCGCTTATTAAAAGCA<br>TTCTGTAACAAAGCGGGACCAAAGCCATGACAAAAACGCGTAA | 64 |

-continued

| Description | Sequence | SEQ ID NO |
|---|---|---|
| | CAAAAGTGTCTATAATCACGGCAGAAAAGTCCACATTGATTATT<br>TGCACGGCGTCACACTTTGCTATGCCATAGCATTTTTATCCATA<br>AGATTAGCGGATCCAGCCTGACGCTTTTTTTCGCAACTCTCTAC<br>TGTTTCTCCATAC**CTCTAGAAATAATTTTGTTTAACTTTAAGA<br>AGGAGATATACATATGATCCCGGAAAAGCGAATTATACGGC<br>GCATTCAGTCTGGCGGTTGTGCTATCCATTGCCAGGATTGC<br>TATATCAGCCAGCTTTGCATCCCGTTCACACTCAACGAACAT<br>GAGCTTGATCAGCTTGATAATATCATTGAGCGGAAGAAGCC<br>TATTCAGAAAGGCCAGACGCTGTTTAAGGCTGGAGATGAAC<br>TTAAATCGCTTTATGCCATCCGCTCCGGTACGATTAAAAGTT<br>ATACCATCACTGAGCAAGGCGACGAGCAAATCACTGGTTTC<br>CATTTAGCAGGCGATCTGGTGGGATTTGATGCCATCGGCAG<br>CGGTCATCACCCGAGTTTCGCGCAGGCGCTGGAAACCTCGA<br>TGGTATGTGAAATCCCGTTCGAAACGCTGGACGATTTGTCT<br>GGTAAAATGCCGAATCTGCGTCAGCAGATGATGCGTCTGAT<br>GAGCGGTGAAATCAAAGGCGATCAGGACATGATCCTGCTGT<br>TGTCGAAGAAAAATGCCGAGGAACGTCTGGCTGCATTCATC<br>TACAACCTGTCCCGTCGTTTTGCCCAACGCGGCTTCTCCCCT<br>CGTGAATTCCGCCTGACGATGACTCGTGGTGATATCGGTAA<br>CTATCTGGGCCTGACGGTTGAAACCATCAGCCGTCTGCTGG<br>GTCGCTTCCAGAAAAGCGGTATGCTGGCAGTCAAAGGTAAA<br>TACATCACTATCGAAAATAACGATGCGCTGGCCCAGCTTGC<br>TGGTCATACGCGTAACGTTGCCTGA** | |
| FNRS24Y | ATGATCCCGGAAAAGCGAATTATACGGCGCATTCAGTCTGGCG<br>GTTGTGCTATCCATTGCCAGGATTGCTATATCAGCCAGCTTTGC<br>ATCCCGTTCACACTCAACGAACATGAGCTTGATCAGCTTGATAA<br>TATCATTGAGCGGAAGAAGCCTATTCAGAAAGGCCAGACGCTG<br>TTTAAGGCTGGAGATGAACTTAAATCGCTTTATGCCATCCGCTC<br>CGGTACGATTAAAAGTTATACCATCACTGAGCAAGGCGACGAG<br>CAAATCACTGGTTTCCATTTAGCAGGCGATCTGGTGGGATTTGA<br>TGCCATCGGCAGCGGTCATCACCCGAGTTTCGCGCAGGCGCTGG<br>AAACCTCGATGGTATGTGAAATCCCGTTCGAAACGCTGGACGA<br>TTTGTCTGGTAAAATGCCGAATCTGCGTCAGCAGATGATGCGTC<br>TGATGAGCGGTGAAATCAAAGGCGATCAGGACATGATCCTGCT<br>GTTGTCGAAGAAAAATGCCGAGGAACGTCTGGCTGCATTCATCT<br>ACAACCTGTCCCGTCGTTTTGCCCAACGCGGCTTCTCCCCTCGT<br>GAATTCCGCCTGACGATGACTCGTGGTGATATCGGTAACTATCT<br>GGGCCTGACGGTTGAAACCATCAGCCGTCTGCTGGGTCGCTTCC<br>AGAAAAGCGGTATGCTGGCAGTCAAAGGTAAATACATCACTAT<br>CGAAAATAACGATGCGCTGGCCCAGCTTGCTGGTCATACGCGT<br>AACGTTGCCTGA | 65 |
| AraC (reverse orientation) | TTATTCACAACCTGCCCTAAACTCGCTCGGACTCGCCCCGGTGC<br>ATTTTTTAAATACTCGCGAGAAATAGAGTTGATCGTCAAAACCG<br>ACATTGCGACCGACGGTGGCGATAGGCATCCGGGTGGTGCTCA<br>AAAGCAGCTTCGCCTGACTGATGCGCTGGTCCTCGCGCCAGCTT<br>AATACGCTAATCCCTAACTGCTGGCGGAACAAATGCGACAGAC<br>GCGACGGCGACAGGCAGACATGCTGTGCGACGCTGGCGATATC<br>AAAATTACTGTCTGCCAGGTGATCGCTGATGTACTGACAAGCCT<br>CGCGTACCCGATTATCCATCGGTGGATGGAGCGACTCGTTAATC<br>GCTTCCATGCGCCGCAGTAACAATTGCTCAAGCAGATTTATCGC<br>CAGCAATTCCGAATAGCGCCCTTCCCCTTGTCCGGCATTAATGA<br>TTTGCCCAAACAGGTCGCTGAAATGCGGCTGGTGCGCTTCATCC<br>GGGCGAAAGAAACCGGTATTGGCAAATATCGACGGCCAGTTAA<br>GCCATTCATGCCAGTAGGCGCGCGGACGAAAGTAAACCCACTG<br>GTGATACCATTCGTGAGCCTCCGGATGACGACCGTAGTGATGA<br>ATCTCTCCAGGCGGGAACAGCAAAATATCACCCGGTCGGCAGA<br>CAAATTCTCGTCCCTGATTTTTCACCACCCCCTGACCGCGAATG<br>GTGAGATTGAGAATATAACCTTTCATTCCCAGCGGTCGGTCGAT<br>AAAAAAATCGAGATAACCGTTGGCCTCAATCGGCGTTAAACCC<br>GCCACCAGATGGGCGTTAAACGAGTATCCCGGCAGCAGGGGAT<br>CATTTTGCGCTTCAGCCATACTTTTCATACTCCCGCCATTCAGAG<br>AAGAAACCAATTGTCCATATTGCAT | 66 |
| Promoter region | CAGACATTGCCGTCACTGCGTCTTTTACTGGCTCTTCTCGCTAAC<br>CCAACCGGTAACCCCGCTTATTAAAAGCATTCTGTAACAAAGCG<br>GGACCAAAGCCATGACAAAAACGCGTAACAAAAGTGTCTATAA<br>TCACGGCAGAAAAGTCCACATTGATTATTTGCACGGCGTCACAC<br>TTTGCTATGCCATAGCATTTTTATCCATAAGATTAGCGGATCCA<br>GCCTGACGCTTTTTTTCGCAACTCTCTACTGTTTCTCCATACCTC<br>TAGAAATAATTTTGTTTAACTTTAAGAAGGAGATATACAT | 67 |
| RBS and Leader Region | CTCTAGAAATAATTTTGTTTAACTTTAAGAAGGAGATATACAT | 68 |

-continued

| Description | Sequence | SEQ ID NO |
|---|---|---|
| FNRS24Y Polypeptide | MIPEKRIIRRIQSGGCAIHCQDCYISQLCIPFTLNEHELDQLDNIIERK KPIQKGQTLFKAGDELKSLYAIRSGTIKSYTITEQGDEQITGFHLAG DLVGFDAIGSGHHPSFAQALETSMVCEIPFETLDDLSGKMPNLRQQ MMRLMSGEIKGDQDMILLLSKKNAEERLAAFIYNLSRRFAQRGFS PREFRLTMTRGDIGNYLGLTVETISRLLGRFQKSGMLAVKGKYITIE NNDALAQLAGHTRNVA | 69 |
| AraC polypeptide | MQYGQLVSSLNGGSMKSMAEAQNDPLLPGYSFNAHLVAGLTPIE ANGYLDFFIDRPLGMKGYILNLTIRGQGVVKNQGREFVCRPGDILL FPPGEIHHYGRHPEAHEWYHQWVYFRPRAYWHEWLNWPSIFANT GFFRPDEAHQPHFSDLFGQIINAGQGEGRYSELLAINLLEQLLLRRM EAINESLHPPMDNRVREACQYISDHLADSNFDIASVAQHVCLSPSR LSHLFRQQLGISVLSWREDQRISQAKLLLSTTRMPIATVGRNVGFD DQLYFSRVFKKCTGASPSEFRAGCE* | 70 |
| Wild Type FNR | ATGATCCCGGAAAAGCGAATTATACGGCGCATTCAGTCTGGCG GTTGTGCTATCCATTGCCAGGATTGCACGATCAGCCAGCTTTGC ATCCCGTTCACACTCAACGAACATGAGCTTGATCAGCTTGATAA TATCATTGAGCGGAAGAAGCCTATTCAGAAAGGCCAGACGCTG TTTAAGGCTGGAGATGAACTTAAATCGCTTTATGCCATCCGCTC CGGTACGATTAAAAGTTATACCATCACTGAGCAAGGCGACGAG CAAATCACTGGTTTCCATTTAGCAGGCGATCTGGTGGGATTTGA TGCCATCGGCAGCGGTCATCACCCGAGTTTCGCGCAGGCGCTGG AAACCTCGATGGTATGTGAAATCCCGTTCGAAACGCTGGACGA TTTGTCTGGTAAAATGCCGAATCTGCGTCAGCAGATGATGCGTC TGATGAGCGGTGAAATCAAAGGCGATCAGGACATGATCCTGCT GTTGTCGAAGAAAAATGCCGAGGAACGTCTGGCTGCATTCATCT ACAACCTGTCCCGTCGTTTTGCCCAACGCGGCTTCTCCCCTCGT GAATTCCGCCTGACGATGACTCGTGGTGATATCGGTAACTATCT GGGCCTGACGGTTGAAACCATCAGCCGTCTGCTGGGTCGCTTCC AGAAAAGCGGTATGCTGGCAGTCAAAGGTAAATACATCACTAT CGAAAATAACGATGCGCTGGCCCAGCTTGCTGGTCATACGCGT AACGTTGCCTGA | 71 |
| Wild Type FNR polypeptide | MIPEKRIIRRIQSGGCAIHCQDCSISQLCIPFTLNEHELDQLDNIIERK KPIQKGQTLFKAGDELKSLYAIRSGTIKSYTITEQGDEQITGFHLAG DLVGFDAIGSGHHPSFAQALETSMVCEIPFETLDDLSGKMPNLRQQ MMRLMSGEIKGDQDMILLLSKKNAEERLAAFIYNLSRRFAQRGFS PREFRLTMTRGDIGNYLGLTVETISRLLGRFQKSGMLAVKGKYITIE NNDALAQLAGHTRNVA | 72 |

TABLE 77

Biosafety System Constructs and Sequence Components

| Description | Sequence | SEQ ID NO |
|---|---|---|
| Biosafety Plasmid System Component-dap A Biosafety Plasmid System Vector sequences, comprising dapA, Kid Toxin and R6K minimal ori, and promoter elements driving expression of these components, as shown in FIG. 61A of WO2017087580, | ACTCTTCCTTTTTCAATATTATTGAAGCATTTATCAGGGT TATTGTCTCATGAGCGGATACATATTTGAATGTATTTAG AAAAATAAACAAATAGGGGAATTAAAAAAAAGCCCGCT CATTAGGCGGGCTACTACCTAGGCCGCGGCCGCGCGAAT TCGAGCTCGGTACCCGGGGATCCTCTAGAGTCGACCTGC AGGCATGCAAGCTTGCGGCCGCGTCGTGACTGGGAAAA CCCTGGCGACTAGTCTTGGACTCCTGTTGATAGATCCAG TAATGACCTCAGAACTCCATCTGGATTTGTTCAGAACGC TCGGTTGCCGCCGGGCGTTTTTTATTGGTGAGAATCCAG GGGTCCCCAATAATTACGATTTAAATCACAGCAAACACC ACGTCGGCCCTATCAGCTGCGTGCTTTCTATGAGTCGTTG CTGCATAACTTGACAATTAACATCCGGCTCGTAGGGTTT GTGGAGGGCCCAAGTTCACTTAAAAAGGAGATCAACAA TGAAAGCAATTTTCGTACTGAAACATCTTAATCATGCTG GGGAGGGTTTCTAATGTTCACGGGAAGTATTGTCGCGAT TGTTACTCCGATGGATGAAAAAGGTAATGTCTGTCGGGC TAGCTTGAAAAAACTGATTGATTATCATGTCGCCAGCGG TACTTCGGCGATCGTTTCTGTTGGCACCACTGGCGAGTC CGCTACCTTAAATCATGACGAACATGCTGATGTGGTGAT GATGACGCTGGATCTGGCTGATGGGCGCATTCCGGTAAT TGCCGGGACCGGCGCTAACGCTACTGCGGAAGCCATTAG CCTGACGCAGCGCTTCAATGACAGTGGTATCGTCGGCTG CCTGACGGTAACCCCTTACTACAATCGTCCGTCGCAAGA AGGTTTGTATCAGCATTTCAAAGCCATCGCTGAGCATAC | 81 |

TABLE 77-continued

Biosafety System Constructs and Sequence Components

| Description | Sequence | SEQ ID NO |
|---|---|---|
| | TGACCTGCCGCAAATTCTGTATAATGTGCCGTCCCGTAC<br>TGGCTGCGATCTGCTCCCGGAAACGGTGGGCCGTCTGGC<br>GAAAGTAAAAAATATTATCGGAATCAAAGAGGCAACAG<br>GGAACTTAACGCGTGTAAACCAGATCAAAGAGCTGGTTT<br>CAGATGATTTTGTTCTGCTGAGCGGCGATGATGCGAGCG<br>CGCTGGACTTCATGCAATTGGGCGGTCATGGGGTTATTT<br>CCGTTACGGCTAACGTCGCAGCGCGTGATATGGCCCAGA<br>TGTGCAAACTGGCAGCAGAAGGGCATTTTGCCGAGGCA<br>CGCGTTATTAATCAGCGTCTGATGCCATTACACAACAAA<br>CTATTTGTCGAACCCAATCCAATCCCGGTGAAATGGGCA<br>TGTAAGGAACTGGGTCTTGTGGCGACCGATACGCTGCGC<br>CTGCCAATGACACCAATCACCGACAGTGGCCGTGAGAC<br>GGTCAGAGCGGCGCTTAAACATGCCGGTTTGCTGTAAGA<br>CTTTTGTCAGGTTCCTACTGTGACGACTACCACCGATAG<br>ACTGGAGTGTTGCTGCGAAAAAACCCCGCCGAAGCGGG<br>GTTTTTTGCGAGAAGTCACCACGATTGTGCTTTACACGG<br>AGTAGTCGGCAGTTCCTTAAGTCAGAATAGTGGACAGGC<br>GGCCAAGAACTTCGTTCATGATAGTCTCCGGAACCCGTT<br>CGAGTCGTTTTCCGCCCCGTGCTTTCATATCAATTGTCCG<br>GGGTTGATCGCAACGTACAACACCTGTGGTACGTATGCC<br>AACACCATCCAACGACACCGCAAAGCCGGCAGTGCGGG<br>CAAAATTGCCTCCGCTGGTTACGGGCACAACAACAGGCA<br>GGCGGGTCACGCGATTAAAGGCCGCCGGTGTGACAATC<br>AGCACCGGCCGCGTTCCCTGCTGCTCATGACCTGCGGTA<br>GGATCAAGCGAGACAAGCCAGATTTCCCCTCTTTCCATC<br>TAGTATAACTATTGTTTCTCTAGTAACATTTATTGTACAA<br>CACGAGCCCATTTTTGTCAAATAAATTTTAAATTATATCA<br>ACGTTAATAAGACGTTGTCAATAAAATTATTTTGACAAA<br>ATTGGCCGGCCGGCGCGCCGATCTGAAGATCAGCAGTTC<br>AACCTGTTGATAGTACGTACTAAGCTCTCATGTTTCACGT<br>ACTAAGCTCTCATGTTTAACGTACTAAGCTCTCATGTTTA<br>ACGAACTAAACCCTCATGGCTAACGTACTAAGCTCTCAT<br>GGCTAACGTACTAAGCTCTCATGTTTCACGTACTAAGCT<br>CTCATGTTTGAACAATAAAATTAATATAAATCAGCAACT<br>TAAATAGCCTCTAAGGTTTTAAGTTTTATAAGAAAAAAA<br>AGAATATATAAGGCTTTTAAAGCCTTTAAGGTTTAACGG<br>TTGTGGACAACAAGCCAGGGATGTAACGCACTGAGAAG<br>CCCTTAGAGCCTCTCAAAGCAATTTTGAGTGACACAGGA<br>ACACTTAACGGCTGACATGGGGCGCGCCCAGCTGTCTAG<br>GGCGGCGGATTTGTCCTACTCAGGAGAGCGTTCACCGAC<br>AAACAACAGATAAAACGAAAGGCCCAGTCTTTCGACTG<br>AGCCTTTCGTTTTATTTGATGCCT | |
| Biosafety Plasmid System Component-ThyA<br>Biosafety Plasmid System Vector sequences, comprising ThyA, Kid Toxin and R6K minimal ori, and promoter elements driving expression of these components, as shown in FIG. 61B of WO2017087580 | ACTCTTCCTTTTTCAATATTATTGAAGCATTTATCAGGGT<br>TATTGTCTCATGAGCGGATACATATTTGAATGTATTTAG<br>AAAAATAAACAAATAGGGGAATTAAAAAAAAGCCCGCT<br>CATTAGGCGGGCTACTACCTAGGCCGCGGCCGCGCGAAT<br>TCGAGCTCGGTACCCGGGGATCCTCTAGAGTCGACCTGC<br>AGGCATGCAAGCTTGCGGCCGCGTCGTGACTGGGAAAA<br>CCCTGGCGACTAGTCTTGGACTCCTGTTGATAGATCCAG<br>TAATGACCTCAGAACTCCATCTGGATTTGTTCAGAACGC<br>TCGGTTGCCGCCGGGCGTTTTTTATTGGTGAGAATCCAG<br>GGGTCCCCAATAATTACGATTTAAATCACAGCAAACACC<br>ACGTCGGCCCTATCAGCTGCGTGCTTTCTATGAGTCGTTG<br>CTGCATAACTTGACAATTAATCATCCGGCTCGTAGGGTT<br>TGTGGAGGGCCCAAGTTCACTTAAAAAGGAGATCAACA<br>ATGAAAGCAATTTTCGTACTGAAACATCTTAATCATGCT<br>GGGGAGGGTTTCTAATGAAACAGTATTTAGAACTGATGC<br>AAAAAGTGCTCGACGAAGGCACACAGAAAAACGACCGT<br>ACCGGAACCGGAACGCTTTCCATTTTTGGTCATCAGATG<br>CGTTTTAACCTGCAAGATGGATTCCCGCTGGTGACAACT<br>AAACGTTGCCACCTGCGTTCCATCATCCATGAACTGCTG<br>TGGTTTCTTCAGGGCGACACTAACATTGCTTATCTACAC<br>GAAAACAATGTCACCATCTGGGACGAATGGGCCGATGA<br>AAACGGCGACCTCGGGCCAGTGTATGGTAAACAGTGGC<br>GTGCCTGGCCAACGCCAGATGGTCGTCATATTGACCAGA<br>TCACTACGGTACTGAACCAGCTGAAAAACGACCCGGATT<br>CGCGCCGCATTATTGTTTCAGCGTGGAACGTAGGCGAAC<br>TGGATAAAATGGCGCTGGCACCGTGCCATGCATTCTTCC<br>AGTTCTATGTGGCAGACGGCAAACTCTCTTGCCAGCTTT<br>ATCAGCGCTCCTGTGACGTCTTCCTCGGCCTGCCGTTCAA<br>CATTGCCAGCTACGCGTTATTGGTGCATATGATGGCGCA<br>GCAGTGCGATCTGGAAGTGGGTGATTTTGTCTGGACCGG<br>TGGCGACACGCATCTGTACAGCAACCATATGGATCAAAC<br>TCATCTGCAATTAAGCCGCGAACCGCGTCCGCTGCCGAA | 82 |

TABLE 77-continued

| Biosafety System Constructs and Sequence Components | | |
|---|---|---|
| Description | Sequence | SEQ ID NO |
| | GTTGATTATCAAACGTAAACCCGAATCCATCTTCGACTA CCGTTTCGAAGACTTTGAGATTGAAGGCTACGATCCGCA TCCGGGCATTAAAGCGCCGGTGGCTATCTAAGACTTTTG TCAGGTTCCTACTGTGACGACTACCACCGATAGACTGGA GTGTTGCTGCGAAAAAACCCCGCCGAAGCGGGGTTTTTT GCGAGAAGTCACCACGATTGTGCTTTACACGGAGTAGTC GGCAGTTCCTTAAGTCAGAATAGTGGACAGGCGGCCAA GAACTTCGTTCATGATAGTCTCCGGAACCCGTTCGAGTC GTTTTCCGCCCCGTGCTTTCATATCAATTGTCCGGGGTTG ATCGCAACGTACAACACCTGTGGTACGTATGCCAACACC ATCCAACGACACCGCAAAGCCGGCAGTGCGGGCAAAAT TGCCTCCGCTGGTTACGGGCACAACAACAGGCAGGCGG GTCACGCGATTAAAGGCCGCCGGTGTGACAATCAGCACC GGCCGCGTTCCCTGCTGCTCATGACCTGCGGTAGGATCA AGCGAGACAAGCCAGATTTCCCCTCTTTCCATCTAGTAT AACTATTGTTTCTCTAGTAACATTTATTGTACAACACGAG CCCATTTTTGTCAAATAAATTTTAAATTATATCAACGTTA ATAAGACGTTGTCAATAAAATTATTTTGACAAAATTGGC CGGCCGGCGCGCCGATCTGAAGATCAGCAGTTCAACCTG TTGATAGTACGTACTAAGCTCTCATGTTTCACGTACTAA GCTCTCATGTTTAACGTACTAAGCTCTCATGTTTAACGAA CTAAACCCTCATGGCTAACGTACTAAGCTCTCATGGCTA ACGTACTAAGCTCTCATGTTTCACGTACTAAGCTCTCATG TTTGAACAATAAAATTAATATAAATCAGCAACTTAAATA GCCTCTAAGGTTTTAAGTTTTATAAGAAAAAAAAGAATA TATAAGGCTTTTAAAGCCTTTAAGGTTTAACGGTTGTGG ACAACAAGCCAGGGATGTAACGCACTGAGAAGCCCTTA GAGCCTCTCAAAGCAATTTTGAGTGACACAGGAACACTT AACGGCTGACATGGGGCGCGCCCAGCTGTCTAGGGCGG CGGATTTGTCCTACTCAGGAGAGCGTTCACCGACAAACA ACAGATAAAACGAAAGGCCCAGTCTTTCGACTGAGCCTT TCGTTTTATTTGATGCCT | |
| Kid toxin (reverse orientation) | TTAAGTCAGAATAGTGGACAGGCGGCCAAGAACTTCGTT CATGATAGTCTCCGGAACCCGTTCGAGTCGTTTTCCGCC CCGTGCTTTCATATCAATTGTCCGGGGTTGATCGCAACG TACAACACCTGTGGTACGTATGCCAACACCATCCAACGA CACCGCAAAGCCGGCAGTGCGGGCAAAATTGCCTCCGCT GGTTACGGGCACAACAACAGGCAGGCGGGTCACGCGAT TAAAGGCCGCCGGTGTGACAATCAGCACCGGCCGCGTTC CCTGCTGCTCATGACCTGCGGTAGGATCAAGCGAGACAA GCCAGATTTCCCCTCTTTCCAT | 83 |
| dapA | ATGTTCACGGGAAGTATTGTCGCGATTGTTACTCCGATG GATGAAAAAGGTAATGTCTGTCGGGCTAGCTTGAAAAA ACTGATTGATTATCATGTCGCCAGCGGTACTTCGGCGAT CGTTTCTGTTGGCACCACTGGCGAGTCCGCTACCTTAAA TCATGACGAACATGCTGATGTGGTGATGATGACGCTGGA TCTGGCTGATGGGCGCATTCCGGTAATTGCCGGGACCGG CGCTAACGCTACTGCGGAAGCCATTAGCCTGACGCAGCG CTTCAATGACAGTGGTATCGTCGGCTGCCTGACGGTAAC CCCTTACTACAATCGTCCGTCGCAAGAAGGTTTGTATCA GCATTTCAAAGCCATCGCTGAGCATACTGACCTGCCGCA AATTCTGTATAATGTGCCGTCCCGTACTGGCTGCGATCT GCTCCCGGAAACGGTGGGCCGTCTGGCGAAAGTAAAAA ATATTATCGGAATCAAAGAGGCAACAGGGAACTTAACG CGTGTAAACCAGATCAAAGAGCTGGTTTCAGATGATTTT GTTCTGCTGAGCGGCGATGATGCGAGCGCGCTGGACTTC ATGCAATTGGGCGGTCATGGGGTTATTTCCGTTACGGCT AACGTCGCAGCGCGTGATATGGCCCAGATGTGCAAACTG GCAGCAGAAGGGCATTTTGCCGAGGCACGCGTTATTAAT CAGCGTCTGATGCCATTACACAACAAACTATTTGTCGAA CCCAATCCAATCCCGGTGAAATGGGCATGTAAGGAACTG GGTCTTGTGGCGACCGATACGCTGCGCCTGCCAATGACA CCAATCACCGACAGTGGCCGTGAGACGGTCAGAGCGGC GCTTAAACATGCCGGTTTGCTGTAA | 84 |
| thyA | ATGAAACAGTATTTAGAACTGATGCAAAAAGTGCTCGAC GAAGGCACACAGAAAAACGACCGTACCGGAACCGGAAC GCTTTCCATTTTTGGTCATCAGATGCGTTTTAACCTGCAA GATGGATTCCCGCTGGTGACAACTAAACGTTGCCACCTG CGTTCCATCATCCATGAACTGCTGTGGTTTCTTCAGGGCG ACACTAACATTGCTTATCTACACGAAAACAATGTCACCA TCTGGGACGAATGGGCCGATGAAAACGGCGACCTCGGG CCAGTGTATGGTAAACAGTGGCGTGCCTGGCCAACGCCA | 85 |

TABLE 77-continued

Biosafety System Constructs and Sequence Components

| Description | Sequence | SEQ ID NO |
|---|---|---|
| | GATGGTCGTCATATTGACCAGATCACTACGGTACTGAAC<br>CAGCTGAAAAACGACCCGGATTCGCGCCGCATTATTGTT<br>TCAGCGTGGAACGTAGGCGAACTGGATAAAATGGCGCT<br>GGCACCGTGCCATGCATTCTTCCAGTTCTATGTGGCAGA<br>CGGCAAACTCTCTTGCCAGCTTTATCAGCGCTCCTGTGA<br>CGTCTTCCTCGGCCTGCCGTTCAACATTGCCAGCTACGC<br>GTTATTGGTGCATATGATGGCGCAGCAGTGCGATCTGGA<br>AGTGGGTGATTTTGTCTGGACCGGTGGCGACACGCATCT<br>GTACAGCAACCATATGGATCAAACTCATCTGCAATTAAG<br>CCGCGAACCGCGTCCGCTGCCGAAGTTGATTATCAAACG<br>TAAACCCGAATCCATCTTCGACTACCGTTTCGAAGACTT<br>TGAGATTGAAGGCTACGATCCGCATCCGGGCATTAAAGC<br>GCCGGTGGCTATCTAA | |
| Kid toxin polypeptide | MERGEIWLVSLDPTAGHEQQGTRPVLIVTPAAFNRVTRLPV<br>VVPVTSGGNFARTAGFAVSLDGVGIRTTGVVRCDQPRTID<br>MKARGGKRLERVPETIMNEVLGRLSTILT* | 86 |
| dapA polypeptide | MFTGSIVAIVTPMDEKGNVCRASLKKLIDYHVASGTSAIVS<br>VGTTGESATLNHDEHADVVMMTLDLADGRIPVIAGTGAN<br>ATAEAISLTQRFNDSGIVGCLTVTPYYNRPSQEGLYQHFKAI<br>AEHTDLPQILYNVPSRTGCDLLPETVGRLAKVKNIIGIKEAT<br>GNLTRVNQIKELVSDDFVLLSGDDASALDFMQLGGHGVIS<br>VTANVAARDMAQMCKLAAEGHFAEARVINQRLMPLHNK<br>LFVEPNPIPVKWACKELGLVATDTLRLPMTPITDSGRETVR<br>AALKHAGLL | 87 |
| ThyA polypeptide | MKQYLELMQKVLDEGTQKNDRTGTGTLSIFGHQMRFNLQ<br>DGFPLVTTKRCHLRSIIHELLWFLQGDTNIAYLHENNVTIW<br>DEWADENGDLGPVYGKQWRAWPTPDGRHIDQITTVLNQL<br>KNDPDSRRIIVSAWNVGELDKMALAPCHAFFQFYVADGKL<br>SCQLYQRSCDVFLGLPFNIASYALLVHMMAQQCDLEVGDF<br>VWTGGDTHLYSNHMDQTHLQLSREPRPLPKLIIKRKPESIF<br>DYRFEDFEIEGYDPHPGIKAPVAI* | 88 |

I. Example 55. Prophage Bioinformatic Analysis of *Escherichia coli* Nissle 1917 and Its Engineered Derivatives A. Synopsis Objective: Routine testing procedures identified bacteriophage production from *Escherichia coli* Nissle 1917 (*E. coli* Nissle; *E. coli* Nissle) and related engineered derivatives. In an effort to determine the source of the bacteriophage, a collaborative bioinformatics assessment of the genomes of *E. coli* Nissle, and engineered derivatives was conducted to analyze genomic sequences of the strains for evidence of prophages, to assess any identified prophage elements for the likelihood of producing functional phage, to compare any functional phage elements with other known phage identified among bacterial genomic sequences, and to evaluate the frequency with which prophage elements are found in other sequenced *Escherichia coli* (*E. coli*) genomes.

Experimental Procedures

1. Bioanalytical Methods a. Phage Prediction

The phage prediction software (PHAST) (Zhou, et al., "PHAST: A Fast Phage Search Tool" Nucl. Acids Res. (2011) 39(suppl 2): W347-W352) was used to search for prophage within the published and publicly available *E. coli* Nissle genome (Genbank accession NZ_CP007799.1) (Reister et al., Complete genome sequence of the gram-negative probiotic *Escherichia coli* strain Nissle 1917; J Biotechnol. 2014 Oct. 10; 187:106-7), as well as within SYN001—*E. coli* Nissle 1917, a research cell bank produced from a single expansion of *E. coli* Nissle derived from DSM 6601, lot #Jul91 (DSMZ, Braunschweig, Germany), and the genome of the genetically engineered strains.

b. DNA Sequencing and Assembly

The genome sequences of the genetically engineered strains were generated by an external resource (GENEWIZ, Boston MA) using an Illumina MiSeq DNA sequencer. To examine the sequences for phage sequences, it was first necessary to assemble the genomic sequencing reads using genome assembler software (SPAdes) version 3.9.1, using default parameters (Nurk et al., Assembling single-cell genomes and mini-metagenomes from chimeric MDA products; J Comput Biol. 2013 October; 20(10):714-37). Scaffolds with lengths less than 500 nucleotides were discarded.

c. Identification of Potential Sequence Regions Specific to a Genetically Engineered Strain In order to identify any sequences which could be potentially present in the engineered strains but not present in the original *E. coli* Nissle strain, the raw read data were aligned to each of three reference genomes using software for mapping low-divergent sequences against a large reference genome (BWA MEM) (Li and Durbin, Fast and accurate short read alignment with Burrows-Wheeler transform; Bioinformatics. 2009 Jul. 15; 25(14):1754-60). The three reference genomes were the published sequences and publicly available *E. coli* Nissle genome (Genbank accession NZ_CP007799.1) (Reister et al., Complete genome sequence of the gram-negative probiotic *Escherichia coli* strain Nissle 1917; J Biotechnol. 2014 Oct. 10; 187:106-7), the SYN001 (wild type *E. coli* Nissle) version of the *E. coli* Nissle genome that was sequenced by Genewiz, and the expected sequence for the genome of engineered strain which was based on the sequence of SYN001 along with changes resulting from specific engineering steps used to create the engineered strain. To focus on those sequences that did not correspond to the expected sequence of the engineered strain, the reads were aligned to each reference, and those that aligned to each reference separately according to the software Samtools (Li et al., The Sequence Alignment/Map format and SAMtools; Bioinformatics. 2009 Aug. 15; 25(16):2078-9) were discarded, and the remaining reads that did not align to each reference genome were further analyzed. The same process was used to identify unique sequences in the engineered strains.

The reads that did not map to each of the three references were assembled using the genome assembler software SPAdes version 3.9.1, with default parameters (Nurk et al., Assembling single-cell genomes and mini-metagenomes from chimeric MDA products; J Comput Biol. 2013 October; 20(10):714-37). These assembled scaffolds were used to check for the presence of phage-related sequences by comparing them against the nonredundant database in the National Center for Biotechnology Information (NCBI) using the Blast tool (Altschul et al., Basic local alignment search tool; J Mol Biol. 1990 Oct. 5; 215(3):403-10).

To verify these results, a whole-genome alignment was performed between the entire assembly of the genetically engineered strain and the publicly available CP007799.1 reference genome using genome sequence alignment software (MUMmer) (Delcher et al., Fast algorithms for large-scale genome alignment and comparison; Nucleic Acids Res. 2002 Jun. 1; 30(11):2478-83). These alignments identified unique sequences from the new assembly that did not map to the reference assembly. The unique sequences were again compared against the non-redundant database in NCBI using the Blast tool (Altschul et al., Basic local alignment search tool; J Mol Biol. 1990 Oct. 5; 215(3):403-10) to check for the presence of phage-related sequence. The approach resulted in the identification of three potential phages.

d. Search for Matches to Phage 3 in Other Genomes

To further refine the size of the Phage 3 sequence identified by the PHAST bioinformatic tool, the core region of the Phage 3 sequence was determined by aligning the 59 kilobase (kb) region of Phage 3 in *E. coli* Nissle to the closely-related genome of *E. coli* BW25113, which does not contain Phage 3. Regions at the left- and right-hand ends of the 59 kb Phage 3 sequence from *E. coli* Nissle matched the genomic organization of genes in *E. coli* BW25113 which likely corresponded to host chromosomal (non-phage) sequences; however a 43 kb region in the middle of the Phage 3 sequence from *E. coli* Nissle was not present in *E. coli* BW25113 and appeared as an insertion between two host chromosomal genes present in *E. coli* BW25113. Therefore, by this alignment, a 43 kb core Phage 3 region was observed which was unique to *E. coli* Nissle and likely contains the true limits of Phage 3. This 43 kb core Phage 3 sequence was then compared for alignment against a comprehensive set of 5691 *E. coli* and *Shigella* assemblies downloaded from NCBI using the MUMmer alignment software DElcher et al., Fast algorithms for large-scale genome alignment and comparison; Nucleic Acids Res. 2002 Jun. 1; 30(11):2478-83). To identify instances of Phage 3 outside of *E. coli*, the entire 43 kb core Phage 3 region was compared against the nonredundant NCBI database using the Blast tool (Altschul et al., Basic local alignment search tool; J Mol Biol. 1990 Oct. 5; 215(3):403-10).

To determine whether partial hits to Phage 3 in other genomes were part of larger phage elements, the scaffolds with partial matches to Phage 3 were extracted from the other genomes and PHAST (Zhou, et al., "PHAST: A Fast Phage Search Tool" Nucl. Acids Res. (2011) 39(suppl 2): W347-W352) was used to predict the presence of prophage within these regions.

e. Large-Scale Phage Prediction Across *E. coli*

To assess the frequency with which prophages of any type are found among sequenced *E. coli* strains, a newly published, more efficient version of PHAST (PHASTER) Arndt D., et al., PHASTER: a better, faster version of the PHAST phage search tool. Nucleic Acids Res. 44, W16-W21(2016)) was used to search for the presence of any prophage elements within a large set of *E. coli* genomes. Because the accuracy of phage prediction algorithms is dependent on the use of high-quality genomes, a set of 287 high-quality reference sequence (Refseq) *E. coli* genomes was used for this search.

B. Results

1. Phage Content of *E. coli* Nissle

Three high-confidence, predicted prophage sequences were found within each version of the *E. coli* Nissle genome, referred herein to as Phage 1, Phage 2, and Phage 3 (FIG. 1). All three of these high-scoring phage were designated by PHAST as "intact" phage, indicating that they contain all of the major components of a phage (FIG. 1). The longest predicted phage in *E. coli* Nissle (Phage 3) contains a total of 68 proteins, and includes a phage tail, head, portal, terminase, lysin, capsid, and integrase, all of which appear to be intact. Phage 2 contains a total of 69 proteins, and includes phage transposase, lysis, terminase, head, portal, capsid, and tail proteins. Closer inspection of Phage 2 revealed that the int/xis gene pair have been disrupted by a mobile genetic element, and that the cI repressor has been fragmented into separate DNA-binding and sensing peptides, which would be expected to prevent induction of this phage. The shortest of the intact phages predicted in *E. coli* Nissle, Phage 1, contains a total of 32 proteins, and includes lysis and transposase functionality. However, the absence of many structural genes within the putative prophage element termed Phage 1 calls into question its potential to release viable phage particles. Features of Phage 1-3 are summarized in Table 84.

TABLE 84 i. Summary of Putative Phage Features

| Feature | Phage 1 | Phage 2 | Phage 3 |
|---|---|---|---|
| Nissle coordinates | 241563-260441 | 1325883-1378287 | 2023188-2082243 |
| Phast score | 110 | 150 | 150 |
| Intact designation (score greater or equal 90) | "intact" | "intact" | "intact" |

TABLE 84-continued

| i. Summary of Putative Phage Features | | | |
|---|---|---|---|
| Feature | Phage 1 | Phage 2 | Phage 3 |
| Length | 18.8 kb, | 52.4 kb | 59 kb |
| Top hit | PHAGE_Stx2_c_1717_NC_011357 | PHAGE_Entero_lambda_NC_001416 | PH AGE_Entero_c_1_NC_019706 |
| Encoded essential phage genes | Contains a lysin and a transposase | Contains transposase, lysis, terminase, head, portal, capsid, tail | Contains tail, head, portal, terminase, lysin, capsid, integrase |
| Total number of Proteins | 32 | 69 | 68 |
| Number of proteins classified as phage | 18 | 52 | 59 |
| Number of proteins which are "hypothetical" | 12 | 12 | 8 |

2. Engineered Strain has the Same Phage Content as *E. coli* Nissle

Within the assembled genome of the engineered strain, PHAST predicted the same phage content as had been predicted in the original *E. coli* Nissle genome. All three of the phage that were identified as "intact" phage within *E. coli* Nissle were also identified within the genome of the engineered strain (Phages 1-3).

3. Engineered Strain Contains No Additional Prophage Elements

The vast majority of the raw sequencing reads of the engineered strain mapped to the reference genomes, and there were very few sequences that were unique to the engineered strain genome. There was no evidence for phage sequence within the small amount of unique sequence. When assembled, these unique sequences resulted in only 3 scaffolds, each with length <2 kb, and no similarity to known phage sequence. This result was confirmed by performing a whole-genome alignment of the complete engineered strain assembly to the *E. coli* Nissle reference genome, and identifying regions within the engineered strain which did not map to the reference. Using this procedure, two of the same short sequences were identified. None of these short sequences had any similarity to any known phage sequence. These very short sequences unique to the engineered strain likely represent spurious DNA in the samples, and not phage.

4. Phage 3 is Specific to *E. coli* Nissle

Figure 10:
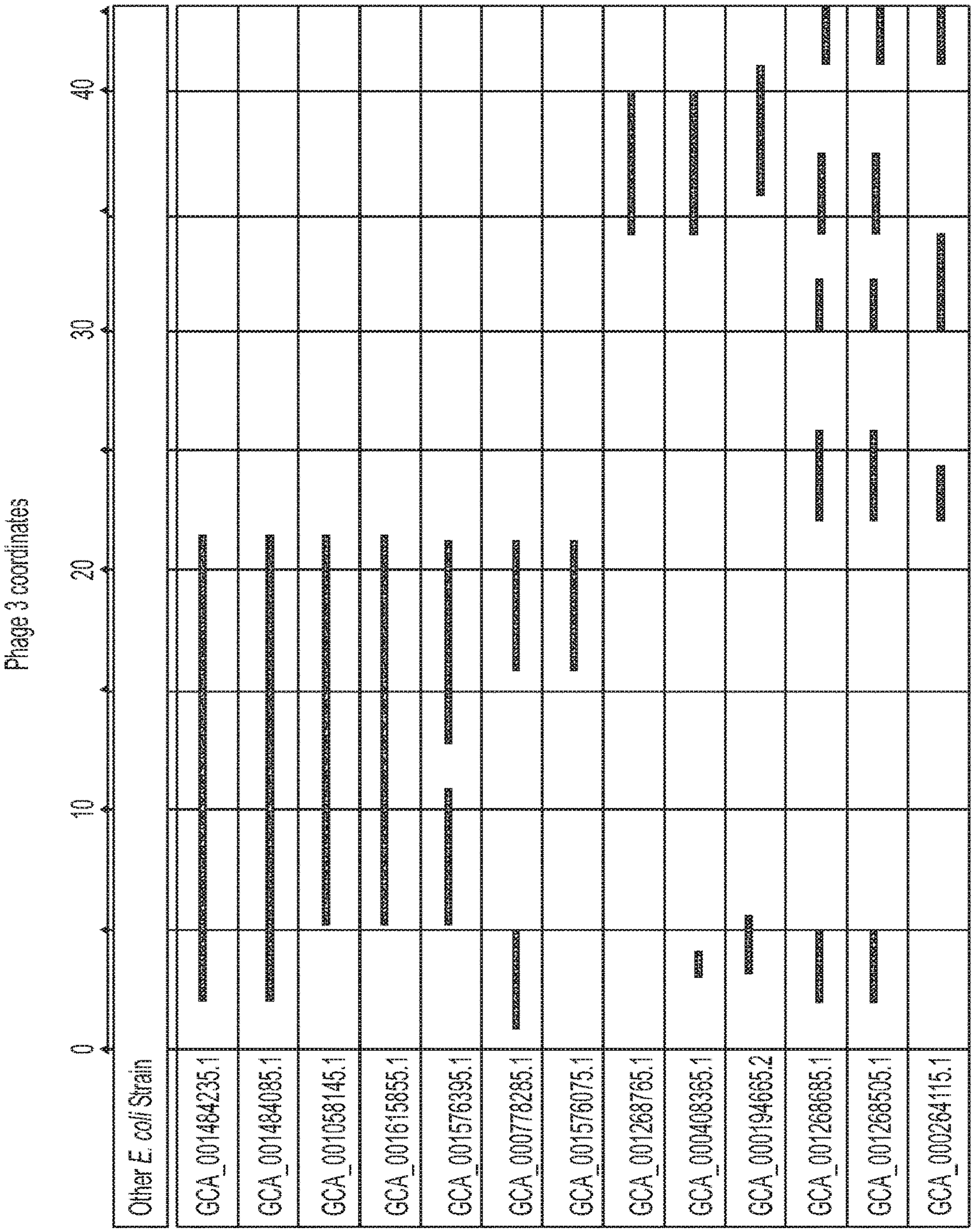
FIG. 10 depicts a schematic showing partial regions within the 43 kb Phage 3 sequence that align to sequence in other *E. coli* strains. The sequence identified as Phage 3 was compared against 5691 *E. coli* and *Shigella* genome assemblies downloaded from NCBI. Listed in the column on the left are the accession numbers of the *E. coli* genomes that were positive in the analysis. Across the top of the Figure are the coordinates of the DNA sequence according to the number of kb from the start of the sequence. The lines depict the sequence from each specific *E. coli* genome that align with the DNA sequence of Phage 3. Abbreviations: *E. coli=Escherichia coli*; kb=kilobase; NCBI=National Center for Biotechnology Information; DNA=deoxyribonucleic acid.
Figure 11:
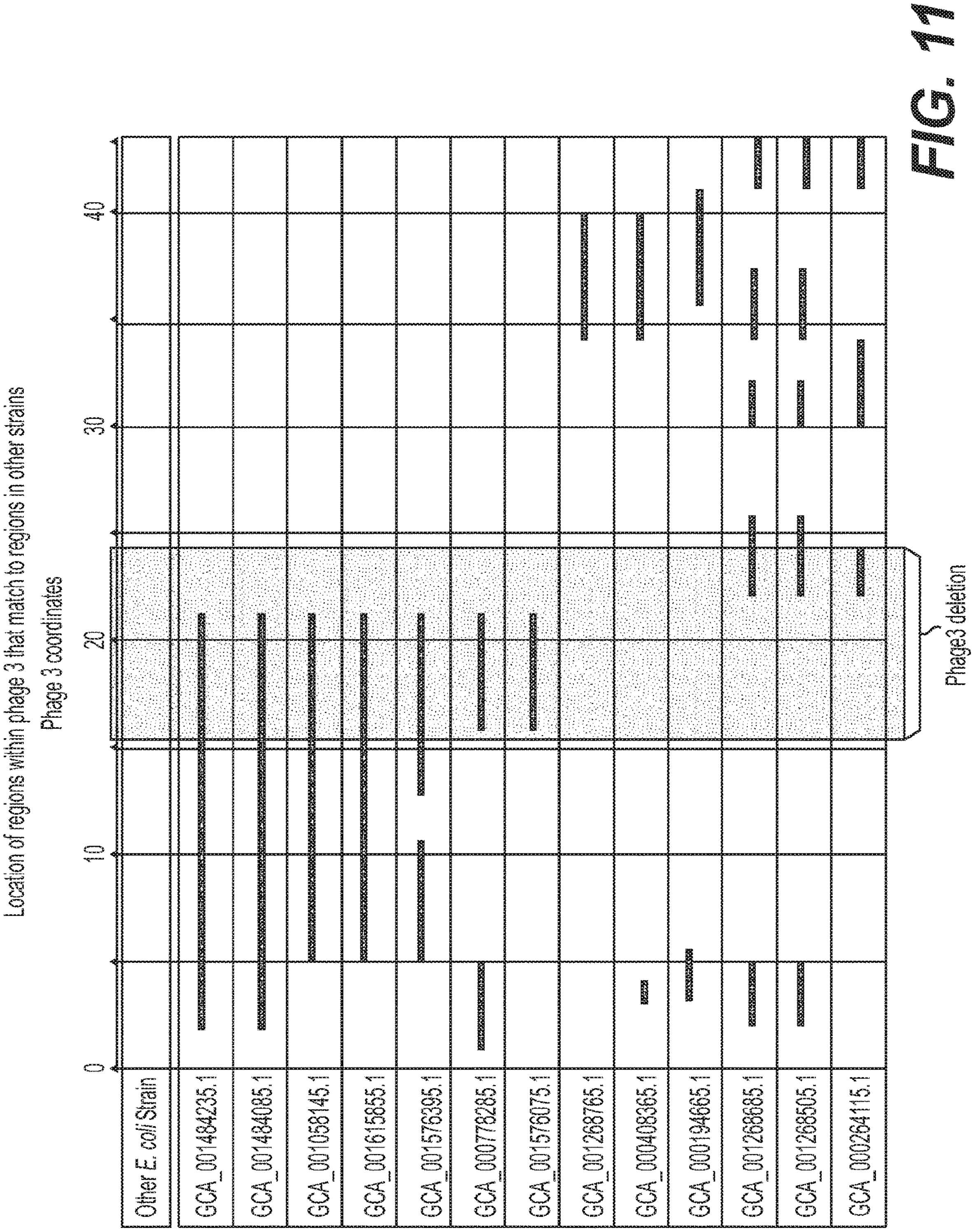
FIG. 11 depicts a schematic showing partial regions within the 43 kb Phage 3 sequence that align to sequence in other *E. coli* strains. The area in the shaded box was chosen as a site for deletion in the Phage 3 knockout strategy.

Laboratory studies have determined that the plaque-forming phage particles released by *E. coli* Nissle, and the engineered strain were exclusively derived from Phage 3 (SYN-17.002). Therefore, an assessment of the presence of Phage 3 (as a prophage) in other *E. coli* genomes was conducted. Within an extensive data set of 5691 *E. coli* and *Shigella* genome assemblies downloaded from NCBI, full-length Phage 3 was only found in *E. coli* Nissle. There were only two full-length, 43 kb matches covering the entire length of Phage 3 with 100% identity, and both of these corresponded to different versions of the *E. coli* Nissle genome (GCA_000333215.1 and GCA_000714595.1). There were five additional long partial matches (14-20 kb, with 97-99.6% identity), and four other shorter partial matches (5-10 kb, 95-98% identity) in other *E. coli* genomes within the data set (FIG. 10). Several other shorter fragments, split between multiple scaffolds of the same assembly, were also identified. The partial matches map to different regions of Phage 3 and are displayed in FIG. 10.

The scaffolds containing these partial matches in other genomes were extracted and used to determine that each partial match to Phage 3 comprises a fragment of a longer prophage within the other genome that had no other similarity to Phage 3. These regions were always part of a longer, high-scoring, "intact" phage prediction in the other genomes. These phage outside of *E. coli* Nissle corresponded to "hybrid" phage, where part of the sequence matches to Phage 3, and the rest corresponds to phage sequence which are different from Phage 3. These results indicate that the closest related phage present in *E. coli* share up to approximately half of their genome with the Phage 3 DNA sequence. Outside of *E. coli*, several partial matches were identified within more distantly related *Enterobacter,* 10-18 kb long, with 96-97% identity.

5. Distribution of Predicted Phage Across *E. coli*

Phage are very common in *E. coli*. Almost all of the *E. coli* genomes in the Refseq database contained at least one "intact", high-scoring phage as assessed using the PHASTER phage prediction software tool, and some have up to 20 (FIG. 12). The average number of predicted phage in an *E. coli* genome is 6.4, which is substantially higher than the number predicted for *E. coli* Nissle by PHASTER. Using this newer phage prediction tool, only the two longer phage are identified in *E. coli* Nissle (those referred to herein as Phage 2 and Phage 3). Therefore, *E. coli* Nissle has substantially fewer predicted phage than most other *E. coli*.

C. Conclusions

Conclusions of the bioinformatics analyses are as follows: First, *E. coli* Nissle and the engineered derivatives contain three candidate prophage elements, with two of the three (Phage 2 and Phage 3) containing most genetic features characteristic of intact phage genomes. Additionally, Phage 3 is unique to *E. coli* Nissle among a collection of almost 6000 sequenced *E. coli* genomes, although related sequences limited to short regions of homology with other putative prophage elements are found in a small number of genomes. Fourth, prophages are very common among *E. coli* strains, with *E. coli* Nissle containing a relatively small number as compared to the average found in a well-characterized set of sequenced *E. coli* genomes. These data support the conclusion that prophage presence in an engineered strain of *E. coli* Nissle is a consequence of the natural state of this species and the prophage features of such the engineered strains analyzed were consistent with the progenitor strain, *E. coli* Nissle.

Example 56. General Protocol for the Detection and Characterization of Bacteriophage from *E. coli* Nissle and Genetically Engineered Derivatives

*Escherichia coli* Nissle 1917 (*E. coli* Nissle) and engineered derivatives test positive for a low level presence of phage 3 in a validated bacteriophage plaque assay. Bacteriophage plaque assays were conducted to determine presence and levels of bacteriophage. In brief, supernatants from cultures of test bacteria that were grown overnight were mixed with a phage-sensitive indicator strain and plated in soft agar to detect the formation of plaques, indicative of the presence of bacteriophage. Polymerase chain reaction (PCR) primers were designed to detect the three different endogenous prophages identified in the bioinformatics analyses, and were used to assess plaques for the presence of phage-specific DNA.

D. Experimental Procedures

1. Phage Testing Protocol: Plaque Assay of Bacterial Virus from *Escherichia coli* Using Mitomycin C Induction Data Analysis The cell lines were analyzed for the production of phage using the mitomycin C phage induction procedure (Method STM-V-708, Plaque Assay of Bacterial Virus from *Escherichia coli* (*E. coli*). Using Mitomycin C Induction, as described in Sinsheimer R L. Purification and Properties of Bacteriophage X174. J. Mol. Biol. 1959; 1:37-42, and Clowes, R C and Hayes, W. Experiments in microbial genetics. John Wiley & Sons, NY. 1968, the contents of each of which is herein incorporated by reference in its entireties). Briefly, sample (with thymidine supplemented media to support cell expansion, as appropriate) and control cells were grown overnight. A portion of the sample, positive control (*E. coli*, EMG 2: K (lambda), ATCC 23716, or equivalent) and negative control (*E. coli*, ATCC 13706, or equivalent) were removed and centrifuged, and each supernatant examined in a plaque assay for the presence of bacteriophage. Mitomycin C, at a final concentration of 2 μg/mL, was added to the remaining sample, positive and negative bacterial cultures. The cultures were then placed at 37±2° C. and shaken at 300-400 RPM until lysis occurred in the positive control (−4.5 hours). Each culture was treated with chloroform, centrifuged, and a 0.1 mL aliquot of the supernatant was examined for the presence of bacteriophage. To accomplish this, supernatants were mixed with phage-sensitive *E. coli* strain ATCC 13706, mixed with 0.7% agarose solution, and plated as a lawn atop lysogeny broth (LB) agar. The test was considered valid if plaques were present in the positive control and no plaques were present in the negative control.

2. PCR Detection of Specific Bacteriophage a. Selection of Phage-Specific PCR Primers Oligonucleotide polymerase chain reaction (PCR) primers were designed with specificity to each of the three putative prophage regions of *E. coli* Nissle, and ordered from Integrated DNA Technologies (IDT, Skokie, IL). The primers were selected after careful examination of the Nissle genome, and designed to bind completely within unique regions predicted to encode phage-specific proteins (Table 85).

TABLE 85

Phage-specific and Control Primers for *E. coli* Nissle

| Primer Descrip-tion: | Primer Sequence: | Predicted Fragment Size: | SEQ ID NO |
|---|---|---|---|
| Putative Prophage 1 Forward | 5'-agtgcctgtacca gacgttc-3' | 366 bp | SEQ ID NO: 118 |
| Putative Prophage 1 Reverse | 5'-agaaatgacaacc agagagc-3' | | SEQ ID NO: 119 |
| Putative Prophage 2 Forward | 5'-ttgagtttaatat ggcagaac-3' | 379 bp | SEQ ID NO: 120 |
| Putative Prophage 2 Reverse | 5'-aaatgatcatcgc gtcatc-3' | | SEQ ID NO: 121 |
| Putative Prophage 3 Forward | 5'-gcatcaatcagtg attggc-3' | 349 bp | SEQ ID NO: 122 |
| Putative Prophage 3 Reverse | 5'-acgtctgaatata cgggctg-3' | | SEQ ID NO: 123 |
| Control rpoB Forward | 5'-tccagcttgactc gtttcag-3' | 424 bp | SEQ ID NO: 124 |
| Control rpoB Reverse | 5'-agcaccttacccg aagagt-3' | | SEQ ID NO: 125 |

Abbreviations:
bp = basepair;
*E. coli* Nissle = *Escherichia coli* Nissle 1917;
rpoB = β subunit of bacterial RNA polymerases An additional pair of oligonucleotide PCR primers was designed that specifically bound to rpoB, an essential bacterial-specific gene found within the *E. coli* Nissle genome and related strains but located outside of the three phage elements. The primer set that bound to rpoB served as a positive control for both the quality of the genomic DNA preparations, and the effectiveness of the PCR protocol. Additionally, phage DNA should not contain the rpoB gene, therefore these primers also served as a control for the purity of the phage-plaque picking technique. It was determined that while 25 PCR reaction cycles was sufficient to produce a strong band with a specific Phage PCR primer pair for plaques produced by that corresponding phage, only a weak or often no band, was observed with the rpoB primers using the same plaque DNA with 25 cycles (data not shown). For this reason, PCR analysis of plaque samples was conducted for 25 cycles.

b. PCR Reaction Conditions and Confirmation of Primer Specificity

Using the oligonucleotide primers described supra, PCR was performed against *E. coli* Nissle genomic DNA (gDNA) to determine whether the expected PCR products for Phage 1, 2, and 3 as well as the rpoB host genomic control were produced. The phage-negative strain ATCC 13706 served as a negative control for the PCR reaction. To prepare gDNA template for the PCR reaction, *E. coli* Nissle was grown in LB medium at 37±2° C. and shaken at 250 rotations per minute (rpm) overnight. One hundred (100) p L of stationary phase culture was added to a 1.5 mL microcentrifuge tube and spun at >20,000×g (15,000 rpm) in a microcentrifuge for 30 seconds. The supernatant was removed and the cell pellet was resuspended in 100 μL of sterile water. This 100 μL suspension was moved to a 0.2 mL thin wall tube and heated at 98° C. in an Eppendorf Mastercycler Pro thermocycler for 10 minutes. The resulting solution contained gDNA that was suitable for a PCR reaction. Polymerase chain reaction was performed using MyTaq™ Red Mix (Bioline) as the source of DNA nucleotides and polymerase to support DNA amplification, with *E. coli* Nissle gDNA as the DNA template, and mixed according to the conditions in Table 86. Polymerase chain reactions were performed in an Eppendorf Mastercycler Pro thermocycler as described in Table 87. Upon completion of PCR, 5 μL of reactions or DNA standard (1 $kB^+$ ladder, Invitrogen) were loaded onto a 0.8% agarose gel for separation by electrophoresis and visualization using a Syngene ultra violet (UV) transilluminator.

TABLE 86

PCR Preparation to Amplify Putative Prophage Regions from *E. coli* Nissle

| Reagent | Per Reaction (μL) | Final Concentration |
|---|---|---|
| Nuclease-free sterile water | 23 | N/A |
| Forward primer (100 μM) | 0.5 | 1 μM |
| Reverse primer (100 μM) | 0.5 | 1 μM |
| gDNA template | 1 | N/A |
| 2X MyTaq ™ Red Mix | 25 | 0.2 U/μL |

Abbreviation:
*E. coli* Nissle = *Escherichia coli*;
gDNA = genomic deoxyribonucleic acid;
N/A = not applicable;
PCR = polymerase chain reaction;
U = unit;
μL = microliter;
μM = micromolar

TABLE 87

PCR Reaction Cycle for Amplifying Prophage Regions from *E. coli* Nissle

| Stage | Temperature (° C.) | Time (min:sec) |
|---|---|---|
| 1 | 95 | 1:00 |
| 2 | 95 | 0:15 |
| | 58 | 0:15 |
| | 72 | 0:10 |
| 3 | Repeat Stage 2: 30x | NA |
| 4 | 72 | 1:00 |
| 5 | 4 | Infinity |

Abbreviation:
° C. = degrees Celsius;
*E. coli* Nissle = *Escherichia coli*;
min = minute;
PCR = polymerase chain reaction;
sec = second(s);
NA = not applicable 3. Testing of Individual Plaques for Specific Phages Bacteriophage titer assays were performed using a validated method. PCR analysis was conducted on supernatants of resulting phage titer plates that contained enumerable bacteriophage plaques (when applicable) derived from *E. coli* Nissle, or an engineered strain. The identity of the phage that generated the plaques was determined by PCR. Agar plugs of individual plaques were removed from the culture plates with 2 μL pipet tips. Each plug was resuspended in 0.5 mL of sterile distilled water. The plug resuspensions were vortexed for 15 seconds, then 1 μL was added to PCR reactions as the DNA template. The phage-specific PCR reactions were performed with MyTaq™ Red Mix (Bioline) as the source of DNA nucleotides and polymerase to support DNA amplification, with the plug resuspensions as the DNA template, and mixed according to the conditions in Table 5. Each set of primers from Table 85, supra was used in a separate PCR reaction to identify each of the three putative phage, with *E. coli* Nissle and ATCC 13706 gDNAs serving as positive and negative controls. The PCR reactions were performed according to the conditions in Table 89, and were performed for a limiting number of cycles (25 cycles) to prevent the amplification of any residual host chromosomal DNA present in the plaques. Upon completion of PCR, 5 μL of reactions or DNA standard (1 kB+ ladder, Invitrogen) were loaded onto a 0.8% agarose gel for separation by electrophoresis and visualization using a Syngene UV transilluminator.

TABLE 88

PCR Reaction Conditions to Amplify *E. coli* Nissle Specific Phage from Plaque Plugs

| Reagent | Per Reaction (μL) | Final Concentration |
|---|---|---|
| Nuclease-free sterile water | 23 | N/A |
| Forward primer (100 μM) | 0.5 | 1 μM |
| Reverse primer (100 μM) | 0.5 | 1 μM |
| plaque plug or gDNA template (control) | 1 | N/A |
| 2X MyTaq ™ Red Mix | 25 | 0.2 U/gL |

Abbreviation:
*E. coli* Nissle = *Escherichia coli*;
gDNA = genomic deoxyribonucleic acid;
N/A = not applicable;
PCR = polymerase chain reaction;
rxn = reaction;
U = unit;
μL = microliter;
μM = micromolar

TABLE 89

PCR Reaction Cycle for Amplifying Prophage Regions from Plaque Plugs

| Stage | Temperature (° C.) | Time (min:sec) |
|---|---|---|
| 1 | 95 | 5:00 |
| 2 | 95 | 0:15 |
| | 58 | 0:15 |
| | 72 | 0:10 |
| 3 | Repeat Stage 2: 24x | NA |
| 4 | 72 | 1:00 |
| 5 | 4 | Infinity |

Abbreviation:
° C. = degrees Celsius;
min = minute(s);
PCR = polymerase chain reaction;
sec = second(s);
NA = not applicable

Example 57. Testing of *E. coli* Nissle and Mutaflor for Presence of Phage

4. Summary of Phage Testing Data

Independent analyses to detect the presence of phage in several samples was conducted. The analyses showed that the Cell bank sample of *E. coli* Nissle from the German Collection of Microorganisms and Cell Culture (referred to herein as SYN001), and capsules of Mutaflor which contain *E. coli* Nissle, variably express a low level of phage under the uninduced and induced (mitomycin C treatment) conditions (Table 90).

Interestingly, *E. coli* Nissle strains are not always inducible as seen by the CTM lot demonstrating no phage in either condition. Additionally, even when inducible *E. coli* Nissle cells (Mutaflor and SYN001) express detectable phage, the levels are similar to the maximum levels seen under uninduced or induced conditions for other *E. coli* Nissle strains. In contrast, a positive control strain, ATCC 23716,[2] which is an *E. coli* K-12 strain that contains a bacteriophage lambda prophage, produced 5-6 orders of magnitude more phage than *E. coli* Nissle or its derivatives following induction. This demonstrates an obvious lack of inducibility of *E. coli* Nissle strains, for reasons that are not yet understood.

TABLE 90

Summary of Phage Plaque Assay Testing Results

| Strain | Phage Titer Uninduced (pfu/mL) | Phage Titer Induced (pfu/mL) |
|---|---|---|
| *E. coli* Nissle- Mutaflor capsule | 0 | $2.5 \times 10^4$ |
| *E. coli* Nissle- SYN001 | 0 | $2.0 \times 10^4$ |
| ATCC 23716 (positive control) | $3.0 \times 10^4$ | $3.2 \times 10^9$ |

Abbreviations:
CTM = clinical trial material;
*E. coli* Nissle = *Escherichia coli* Nissle 1917;
MCB = master cell bank;
pfu = plaque forming unit;
SYN001 = *Escherichia coli* Nissle 1917 from the German Collection of Microorganisms and Cell Cultures.
Note that most strains were evaluated in separate experiments, and that the ATCC 23716 positive control strain was run as a control in each assay. The data above for ATCC23716 are the average of positive control strain for these assays.

5. Verification of Phage-Specific Primers Against *E. coli* Nissle Genomic DNA

To verify that the PCR analysis method could identify plaque-producing phage, PCR analysis was performed against *E. coli* Nissle gDNA using the primers specific for either Prophage 1, 2, 3, or the host rpoB gene (Table 85). Although not shown here, a similar analysis with the same primers against the indicator strain ATCC 13706 gave no band for the Phage primers and faint band for rpoB, consistent with this strain lacking the three *E. coli* Nissle prophages but containing an rpoB gene with some sequence similarity to the *E. coli* Nissle gene. Each primer set produced a single DNA product of the correct size as judged by agarose gel electrophoresis, which is displayed in FIG. 13. Based on this result, these primer pairs were used to assess phage DNA from individual plaques from the analyses summarized in Table 90 for the presence of the different phages.

6. Analysis of Individual Plaques for the Presence of Phages 1, 2, and 3

Figure 14:
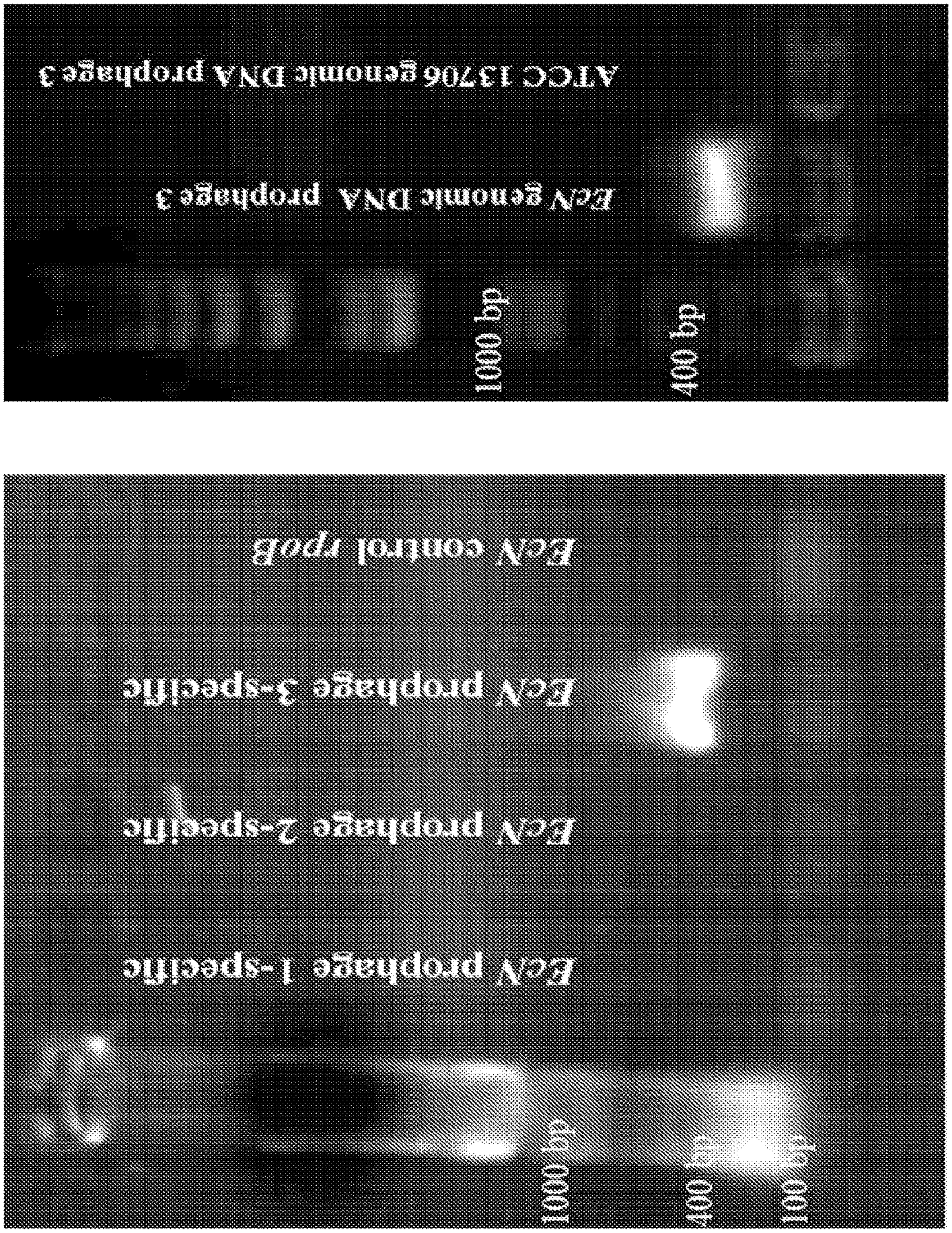
FIG. 14 depicts DNA gel electrophoresis study showing EcN Prophage Regions Amplified from ATCC 13706 Plaque Plugs. Abbreviations: bp=base pairs; EcN=*Escherichia coli* Nissle 1917; rpoB=3 subunit of bacterial RNA polymerase.

Plates with enumerable plaques from the plaque assays were analyzed by PCR analysis. Polymerase chain reaction analysis was performed against ten plaques from plates with enumerable plaques using the primers specific for either prophage 1, 2, 3, or the host rpoB gene to determine the identity of the phage that created the plaques. In some cases, plates with clearly enumerable plaques contained fewer than ten plaques, in which case all plaques were used. However, at least 6 plaques were tested for every analysis. In every PCR reaction that was run, only the primers specific for prophage 3 produced a PCR product, and this was true in all cases for each test strain and batch listed in Table 90. A representative gel analysis of this data is displayed in FIG. 14; the left panel of FIG. 14 shows a representative set of PCR reactions visualized for an individual plaque plug taken from an assay of *E. coli* Nissle-Mutaflor. The right panel shows a control experiment using gDNA from either *E. coli* Nissle or ATCC13706, the phage-negative indicator strain used in the CRL phage assay, and which does not contain a resident prophage 3. This latter finding confirms that the positive results observed in the phage plaque PCR analysis is not the result of a cross-reaction with sequences in the ATCC13706 plating strain.

E. Conclusions

In conclusion, these data demonstrate that an expressible prophage element resides in the *E. coli* Nissle and Mutaflor strains evaluated. This indicates that an expressible prophage is present in *E. coli* Nissle. In the uninduced state, *E. coli* Nissle and Mutaflor produce no or low-level detectable plaques. The levels of phage produced in all cases was 5-6 orders of magnitude lower than for the positive control strain ATCC23716. Based on bioinformatics analyses of these bacterial genomes, PCR assays were developed to determine if any of the three endogenous prophage elements identified in these strains were the source of the active phage particles. The results show that the plaques derived from *E. coli* Nissle result from only one of the three prophage elements identified bioinformatically, referred to herein as Phage 3, as this prophage genome was uniquely amplified from plaques formed on the phage-sensitive *E. coli* strain ATCC 13706 (which does not natively contain the Phage 3 sequence). Taken together, these data strongly support the conclusions that Phage 3 is the responsible agent for positive phage test results, and that there appear to be no observable differences in phage production among these strains. This information also establishes that the phage produced by these strains is the result of a prophage element native to *E. coli* Nissle, including commercial Mutaflor capsules.

1. Summary of Results and Conclusions:

In conclusion, these data demonstrate that an expressible prophage element is endogenous to *E. coli* Nissle. The frequencies with which phage particles were produced by the tested strains, as determined by the validated plaque assay, were quantitatively at a similar low level, indicating that a generally expressible prophage is present in *E. coli* Nissle. Based on bioinformatics analyses of these bacterial genomes (Example 55), PCR assays were developed to determine if any of the three endogenous prophage elements identified in *E. coli* Nissle were the source of the plaque-forming phage particles. The results show that the plaques, when expressed from *E. coli* Nissle result from only one of the three prophage elements identified bioinformatically, prophage 3. This prophage genome was uniquely amplified by PCR from plaques formed on the phage-sensitive *Escherichia coli* (*E. coli*) strain ATCC 13706 (which does not natively contain the prophage 3 sequence). Taken together, these data strongly support the conclusions that prophage 3 is the responsible agent for positive phage test results, and that there appear to be no observable differences in phage production among these strains. This information also establishes that the phage produced by these strains is the result of a prophage element native to *E. coli* Nissle, including commercial Mutaflor.

Example 58. Phage Testing of SYN001, SYN-PKU-710, SYN-PKU1033, and SYN-PKU1034

In this study, plaque assays on *E. coli* Nissle, and engineered strains comprising phenylalanine consuming circuitry, SYN-PKU-710, SYN-PKU1033 and SYN-PKU1034, were conducted to determine levels of phage produced by each strain. Table 91 provides descriptions of the strains used in this study.

TABLE 91

| Strain Descriptions | |
|---|---|
| Stain Designation | Strain Description |
| SYN-PKU-710 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA. |
| SYN-PKU1033 | Phenylalanine consuming strain which has an Antibiotic Independent Plasmid System (AIPS) comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU1034 has a weaker RBS upstream of the pheP portion of the PAL-pheP gene cassette in the AIP plasmid compared to SYN-PKU1033 |
| SYN-PKU1034 | phenylalanine consuming strain which has an AIPS comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU1034 has a weaker RBS upstream of the pheP portion of the PAL-pheP gene cassette in the AIP plasmid compared to SYN-PKU1033 |

Each strain was tested with and without mitomycin C in log phase, and without mitomycin C from stationary overnights. CFU counts were determined before supernatants were processed for the plaque assay, in order to determine the amount of plaques produced per cell.

The following test strains were grown overnight in LB (with DAP 100 ug/mL where appropriate), 3 mL in a 14 mL culture tube shaking at 250 rpm at 37 C: SYN01 (Nissle); ATC13706 (negative control); SYN-PKU-710; SYN-PKU1033, and SYN-PKU1034. An additional 20 mL culture of ATCC13706 was grown in LB in a 125 mL baffled flask (37 C, 250 rpm) for use as the sensitive plaque indicator strain. These overnight cultures were used to inoculate 10 mL cultures in LB at a 1:100 dilution (DAP 100 ug/mL where appropriate) in 125 mL baffled flasks in duplicate. For each strain, one flask contained 2 ug/mL of mitomycin C and the other culture was used as a log phase uninduced control. All flasks were grown at 37 C shaking (250 rpm) for 4.5 hours. Next, cultures and stationary uninduced overnight cultures were diluted 10-fold in PBS in a 96-well plate and plated for determination of cell counts. Ten ul of spot dilutions spanning the 10^−3 to the 10^−8 dilutions were plated per plate (LB plates—DAP 100 ug/mL where appropriate), in duplicate, for each strain.

After counting the cells, 1 mL from each culture (3 cultures per strain) was transferred into 1.5 mL microcentrifuge tubes and 50 μL of chloroform was added. Tubes were vortexed for 15-30 seconds, cells were spun down in a microcentrifuge for 2 minutes at maximum speed.

Supernatants were diluted in 96-well plates containing 180 μL of LB per well. 200 μL of neat supernatant for each strain was added to a first well, and 10-fold dilutions were performed with a multichannel pipette. To prepare sensitive control strain, 10 mL ATCC13706 were spun down at 4000×g in a 15 mL falcon tube, supernatant was decanted, and cells were resuspended in an equal volume of 10 mM magnesium sulfate.

Fourteen mL culture tubes containing 100 ul of ATCC13706 cell suspension were prepared for the appropriate strains and dilution of supernatants. Neat supernatant and supernatant dilutions were added to the tubes and the cell/supernatant mixture was incubated for a minimum of 5 min.

After incubation, 3 mL of liquid top agar composed of 7 g/L agar in LB media lacking yeast extract was added to tubes and the mixture was immediately poured evenly onto appropriately labelled LB plate. After plates dried, they were moved the 37C static incubator, inverted, and incubated overnight. Plaque counts are shown in Table 92.

TABLE 92

Plaque Counts

| | supernatant dilution | | | | | |
|---|---|---|---|---|---|---|
| | 0 | −1 | −2 | −3 | −4 | |
| | final dilution (for calculating pfu/mL) | | | | | cfu/mL |
| | −1 | −2 | −3 | −4 | −5 | culture |
| ATCC13706 uninduced stationary | N | N | | | | 3.1 x 10^9 |
| ATCC13706 uninduced log | N | N | | | | 3.2 x 10^9 |
| ATCC13706 + MC log | N | N | | | | 2.4 x 10^8 |
| SYN001 uninduced stationary | 4 | 1 | N | | | 2.4 x 10^9 |
| SYN001 uninduced log | 16 | N | N | | | 4.7 x 10^9 |
| SYN001 + MC log | TMTC | 46 | 1 | | | 0 |
| SYN-PKU-710 uninduced stationary | TMTC | 39 | 4 | N | N | 1.45 x 10^9 |
| SYN-PKU-710 uninduced log | TMTC | 118 | 13 | N | N | 3.0 x 10^9 |
| SYN-PKU-710 + MC log | TMTC | TMTC | 261 | 34 | 3 | 0 |
| SYN-PKU1033 uninduced stationary | 27 | 2 | N | N | N | 7.5 x 10^8 |
| SYN-PKU1033 uninduced log | 4 | N | N | N | N | 7.4 x 10^8 |
| SYN-PKU1033 + MC log | 30 | 4 | 1 | N | N | 0 |
| SYN-PKU1034 uninduced stationary | 6 | 1 | N | N | N | 1.2 x 10^9 |
| SYN-PKU1034 uninduced log | 6 | 1 | N | N | N | 5.5 x 10^8 |
| SYN-PKU1034 + MC log | 31 | 3 | N | N | N | 0 |

TMTC = too many to count;
N = none

Colony counting showed that 2 ug/mL of mitomycin C was completely lethal for all Nissle strains but not for ATCC13706, in which 2 ug/mL killed approximately 90% of cells.

PCR analysis was conducted to confirm that phage 3 DNA was present using primers specific to Phage 3 (not shown).

Example 59. Deactivating Phage Production from *E. coli* Nissle Using Chromosomal Insertion of an Antibiotic Cassette Bioinformatic approaches helped identify 3 regions of the genome putatively containing active phage (see Example 55). Using an in-house developed PCR method, it was shown that the active phage originated from a genomic locus between bases 2,035,867 and 2,079,177 of the *E. coli* Nissle genome.

F. Knock-Out Primer Design

To inactivate the phage, lambda red recombineering was used to make a 9,687 base pair deletion. Lambda red recombineering is a procedure using recombination enzymes from a bacteriophage lambda to insert a piece of custom DNA into the chromosome of *E. coli* directed by flanking homology. First, primers were designed and synthesized to amplify a chloramphenicol acetyltransferase (CAT) gene flanked by flippase recognition sites (FRT) from the plasmid pKD3 (Table 93). When introduced into Nissle, this cassette provides resistance to the antibiotic chloramphenicol. In addition, these primers contain 60 base pairs of homology to the genome which directs the antibiotic cassette into the Phage loci. The Phage3 KO FWD and Phage3 KO REV primers were used to PCR amplify a 1178 base pair linear DNA fragment, which was PCR purified. The resulting DNA template was used in recombineering.

TABLE 93

Primers used in the inactivation of Phage3

| Primer Name | Sequence | SEQ ID NO |
|---|---|---|
| Phage3 KO FWD | **TGGAGGCTTTAAGAAATACCTCGATGTGAACAACCGCCTGCCACGAATCTTCGTCAAGCG***ATTACACGTCTTGAGCGAT* | SEQ ID NO: 126 |
| Phage3 KO REV | **GATAATGGTGAGATTATCCCCGGTTATACCGGACTTATCGCCTATTCAGAATCACTGGAT***CTGACATGGGAATTAGCCA* | SEQ ID NO: 127 |

Bold = Homology to Nissle genome;
Italicized = Homology to pKD3

G. Introduction of Lambda Red System

To prepare a strain of Nissle for deletion of phage, first the lambda red system was introduced, by transforming a pKD46 plasmid into the *E. coli* Nissle host strain. *E. coli* Nissle cells were grown overnight in LB media. The overnight culture was diluted 1:100 in 5 mL of LB media and grown until it reached an $OD_{600}$ of 0.4-0.6. All tubes, solutions, and cuvettes were pre-chilled to 4° C. The *E. coli* cells were centrifuged at 2,000 rpm for 5 min. at 4° C., the supernatant was removed, and the cells were resuspended in 1 mL of 4° C. water. The *E. coli* cells were centrifuged at 2,000 rpm for 5 min. at 4° C., the supernatant was removed, and the cells were resuspended in 0.5 mL of 4° C. water. The *E. coli* cells were centrifuged at 2,000 rpm for 5 min. at 4° C., the supernatant is removed, and the cells are resuspended in 0.1 mL of 4° C. water. The electroporator was set to 2.5 kV. One ng of pKD46 plasmid DNA was added to the *E. coli* cells, mixed by pipetting, and pipetted into a sterile, chilled cuvette. The dry cuvette was placed into the sample chamber, and the electric pulse was applied. One mL of room-temperature SOC media was immediately added, and the mixture was transferred to a culture tube and incubated at 30° C. for 1 hr. The cells were spread out on a selective media plate and incubated overnight at 30° C.

H. Lambda Red Inactivation of Phage in Nissle

The recombineering construct was transformed into *E. coli* Nissle comprising pKD46 to delete the phage sequence. All tubes, solutions, and cuvettes were pre-chilled to 4° C. An overnight culture was diluted 1:100 in 5 mL of LB media containing carbenicillin and grown until it reached an OD600 of 0.1. Next, 0.05 mL of 100× L-arabinose stock solution was added to induce pKD46 lambda red expression. The culture was grown until it reached an OD600 of 0.4-0.6. The *E. coli* cells were then centrifuged at 2,000 rpm for 5 min. at 4° C., the supernatant was removed, and the cells were resuspended in 1 mL of 4° C. water. The *E. coli* cells were centrifuged at 2,000 rpm for 5 min. at 4° C., the supernatant was removed, and the cells were resuspended in 0.5 mL of 4° C. water. The *E. coli* were centrifuged at 2,000 rpm for 5 min. at 4° C., the supernatant was removed, and the cells were resuspended in 0.1 mL of 4° C. water. The electroporator was set to 2.5 kV, and 0.5 μg of the recombineering construct was added to the cells, mixed by pipetting, and pipetted into a sterile, chilled cuvette. The dry cuvette was placed into the sample chamber, and the electric pulse was applied. 1 mL of room-temperature SOC media was immediately added, and the mixture was transferred to a culture tube and incubated at 37° C. for 1 hr. The cells were spread out on an LB plate containing 35 μg/mL chloramphenicol and incubated overnight.

L. Verification of Mutation

The presence of the mutation was verified by colony PCR. Colonies were picked with a pipette tip and resuspended in 20 μl of cold ddH2O by pipetting up and down. Three μl of the suspension was pipetted onto an index plate with appropriate antibiotic for later use. The index plate was grown at 37° C. overnight. A PCR master mix was made using 5 μl of 10×PCR buffer, 0.6 μl of 10 mM dNTPs, 0.4 μl of 50 mM $Mg_2SO_4$, 6.0 μl of 10× enhancer, and 3.0 μl of ddH2O (15 μl of master mix per PCR reaction). A 10 μM primer mix was made by mixing 2 μL of a primer unique to the CAT gene (100 μM stock) or genomic sequence neighboring the inserted CAT gene (100 μM stock) into 16 μL of ddH2O. Sequence of primers used is shown in Table 94. For each 20 μl reaction, 15 μL of the PCR master mix, 2.0 μL of the colony suspension (template), 2.0 μL of the primer mix, and 1.0 μL of Pfx Platinum DNA Pol were mixed in a PCR tube. The PCR thermocycler was programmed as follows, with steps 2-4 repeating 34 times: 1) 94° C. at 5:00 min., 2) 94° C. at 0:15 min., 3) 55° C. at 0:30 min., 4) 68° C. at 2:00 min., 5) 68° C. at 7:00 min., and then cooled to 4° C. The PCR products were analyzed by gel electrophoresis using 10 L of each amplicon and 2.5 μL 5× dye. The PCR product only forms if the CAT gene has inserted into the genome (thereby deleting and inactivating the Phage).

TABLE 94

Primers for Verifying Deletion of Phage3

| Primer Name | Sequence | SEQ ID NO |
|---|---|---|
| Phage3 KO verify FWD | TGGAGGCTTTAAGAAATACC | SEQ ID NO: 128 |
| Phage3 KO verify REV | GCTGGCGATTCAGGTTCATC | SEQ ID NO: 129 |

J. Removal of Antibiotic Resistances from Mutant

The antibiotic resistance gene was removed with the plasmid pCP20. Plasmid pCP20 is a temperature-sensitive plasmid that expresses the Flippase recombinase that will recombine the FRT-sites thereby removing the CAT gene. The strain with deleted phage sequence was grown in LB media containing antibiotics at 37° C. until it reached an OD600 of 0.4-0.6. All tubes, solutions, and cuvettes were pre-chilled to 4° C. The cells were centrifuged at 2,000 rpm for 5 min. at 4° C., the supernatant was removed, and the cells were resuspended in 1 mL of 4° C. water. Cells were centrifuged at 2,000 rpm for 5 min. at 4° C., the supernatant was removed, and the cells were resuspended in 0.5 mL of 4° C. water. Cells were centrifuged at 2,000 rpm for 5 min. at 4° C., the supernatant was removed, and the cells were resuspended in 0.1 mL of 4° C. water. The electroporator was set to 2.5 kV, and 1 ng of pCP20 plasmid DNA was added to the cells, mixed by pipetting, and pipetted into a sterile, chilled cuvette. The dry cuvette was placed into the sample chamber, and the electric pulse was applied. One mL of room-temperature SOC media was immediately added, and the mixture was transferred to a culture tube and incubated at 30° C. for 1-3 hrs. Next, 200 μL of cells were spread on carbenicillin plates, 200 μL of cells were spread on chloramphenicol plates, and both were grown at 37° C. overnight. The carbenicillin plate contain cells with pCP20. The cells were incubated overnight, and colonies that did not grow to a sufficient OD600 overnight were further incubated for an additional 24 hrs. The chloramphenicol plate provides an indication of how many cells survived the electroporation. Transformants from the carbenicillin plate were purified non-selectively at 43° C. and allowed to grow overnight.

The purified transformants were tested for sensitivity to carbenicillin and chloramphenicol. A colony from the plate grown at 43° C. was picked and resuspended in 10 μL of LB media. Three μL of the cell suspension was pipetted onto each of three plates: 1) an LB plate with chloramphenicol incubated at 37° C., which tests for the presence or absence of the CAT gene in the genome of the host strain; 2) an LB plate with carbenicillin incubated at 30° C., which tests for the presence or absence of the beta-lactamase (CarbR) gene from the pCP20 plasmid; and 3) an LB plate without antibiotic incubated at 37° C. If no growth was observed on the chloramphenicol or carbenicillin plates for a colony, then both the CAT gene and the pCP20 plasmid were lost, and the colony was saved for further analysis. The saved colonies were restreaked onto an LB plate to obtain single colonies and grown overnight at 37° C. The deletion of the phage sequence was confirmed by sequencing the phage loci region of the genome and, more importantly, by phenotypically verifying the absence of plaque formation (essentially following the protocol as described in Examples 57 or 58, and as described for example in Example 60).

Table 95. lists the portion of the *E. coli* Nissle Phage 3 removed for inactivation of the Phage 3.

TABLE 95

| Sequence removed from Phage 3<br>SEQ ID NO: 130 |
|---|
| aatcgccggtgtactccgcgtcagaaaggtatacagccacggcagggagatcctgctcttcaagaaaaacagggcgcccgtcaaaccag |
| gtgaccgtgtcggtgatctcggctttcagtttggccagaatggctgcacgaattgcgctgtgtctgttcatcgcttcaggtggatcctcagttggt |
| ttttcagggctgcggaaagttctttgggcatatcgctttcaataaggcgctttgaaatagcggtgaaggccacggtgagcggtgtctcaagag |
| gaactttgaccacatcaatcggataacgggcctgacctacgcgccgcatgacctgccagcgcccgttcgcaagctgttggataaaagcgtta |
| cgaaaggtatagggcccgattttaaggacgctgcccgctccgtttctggcccctttttttacgcgagagcctgacgcgcgccgtgccgagcttt |
| atcgcaggaagattaccgcggttgatttttatcgacgcgaccgggcgatcgtgacgggccttgcgcagacgggaacgctggcggaccaga |
| cgaaccggaagccccttttttccggttatcatcaactgttgcttctttcgctacagctttgctcccctggcttatcgttcttctggccaccctgttaagt |
| gcttttgcggttgcctcaggaacgattaaccggctgaggctgttcaggttctgaatagccctttccagtcctttcacagacatagcgcctcctca |
| ttcgagatggatgcggggttttccgttgaacatgtcatagcgggtaacgatcaggttcttaccgtcgtagtcgacgctgtcgtttcggcgtggct |
| ggtaaagctcagagaaaaccaccagcgaagtacctgttcccgacaatggccccatttcctcgagttgctcggcgggaacaacgtcatagct |
| gctgccattgatgatcgctgtctttcccatctttttttatagtggccgcgtccatgcgcgccgccatccggtcaaaggagttaggcattgatcttaa |
| cttcaacaacggtggtgtttgcccctgcatcttcccaggcgatgcccgcggcaacggcgtccgtttcttcgatcgtgattttgccgtccttcaga |
| tacacctgcgccccggcagtaaccgcatctgcggatacttttggcaggaggaaaacaccctcagtaaaaccgtccccggtatcgccagccg |
| ggatatcggtaattgccaccgcgataagttttccaacaacaaccgggtcgccgctgtgaacatcggttgcaccactgtttaccagagggatcg |
| ttttcccgtcctgcgcatagttcttagccataacttctccattcagcccctttcgaggctggtttcaggtataaaaaaagcccttacgggcgtctgt |
| ttgtcaggactgtttttttactgaccagaggatttggtcatgccgcgatagtccagcggcgccacgccagcatcaatacgcactttcgtggcgat |
| accatcagtggtgaagccttcctgctgatcgatgtatggcgtgtcgacgccgttgagataagcgacctcaatggtgtcggtgcccttcgcggc |
| agccagataccaggctttcgcatcagcttcatccagacgtggttcggcaatgacttctgcaaagttctggatagggttaacgatcccggcattg |
| atgtctgcacctttaacactggccgacttgatggtctgatttgccagagtttccagggcgacgggcaccagcatgtaggccggacggatattc |
| agggttcgctccccctccttctgcagacgcatcagcttgcgcgattcgtccaggctggccacagaaattgcacccgagctcaggttcttgtga |
| tcggcatggaacagcgcctttccgtctgagagtttcgggtttttggtcagaatggcgtaaaccagatcgccaatcgttgctttcgccgcgcgcc |
| ccatcttcatcggtacgtcggtaagctggttcagatcgtcgttgatgatcgcctggcgagttactgagaagatttcaccatacgtggcaagcgc |
| gatggtttcgcctttgtcactggtagtgatgtacttgtactcagccccttcgcgaacctgtcgcagagaagggaacccacccataccgacacg |
| atgcgccgttttgaagtccgacagctggcctttttttggtccactgctcgaaggtttcctgcgcctcgtcccagccctgaatcagcgctttgttcgc |
| aacatcaagcagaatgttgccaaagtcagaggtgctgtgggtcagcgccaggccaaccatctgcatcgggttgtagctggccacgccgata |
| cctttttctgtcagggccatacgcgcatactcgcgcagcgtcataccgttataaacgttatcccgctcctgaccttcgaacccggcacgcgcca |
| tcagtgcctggcgaataccatccgcgacgaagttaccgttgcccgcatgaatatgcggctgagtggttttattggacggcgtggccgttttacc |
| gagttctgccagcagcaaatctttcgccttatcgacggagcaatcagggtcggccacacactgattctgcagttccatgtgcttattaccgaac |
| atggcaaagagatcgccgatagcgttaacacgggttttctgctcagccaacacctgcgcgcggatcgcattttcatccggtgccgggtctgtt |
| tttgcctgcggtgcctgaggctgggtaataaccgggtcacgctgggtagtgttgcgcggcggggtgatcatgttgcgaatgctttttggcatttt |
| ttcaaattcctcaatacgttttgaatgaatacaggccatagcctgaagggatggtgtcacctggtcggcaaaacccagttcaaggcactcgctg |
| ccgttcatccaggtttcgtcctccagcattaccgcaatttcttcggtggattttccggttttctgtgcataagccgggataagaacggattcaacct |
| tgtcgagaagatccgcatagtcgcgcatatcgctcgcgtcaccaccagcaaacccccagggcttatggatcatcatcatcgtgttttcaggca |
| tgatgaccggattgcctaccatcgcaatcaccgaggccatggaggccgccagaccgtcgatatgtacggtaatcgccgcgccgtggtgctt |
| cagcgcgttataaatagcaattccgtcgaagacatcaccaccgggcgagttgatataaaggttgatgtgggtgacgtccccaagtgcccgga |
| gatcattgacgaactgtttcgccgttacgccccagtacccgatttcgtcataaataaaaatgtcggcctcactgttattgctggcctgcatgcgg |
| aaccacgaattacttttttgcgctggctttcggacggtggcgcgcccggttctttggcttcggcactggtgcctcctttatcattggcggggtcgg |

TABLE 95-continued

| Sequence removed from Phage 3 SEQ ID NO: 130 |
|---|
| tgtcaaacaccaggccctgttcacggttctcgtcaacctcagctttacggcgtgacttaacatcatccgggttgcgaccgctggcacgtatcca |
| gtcggattcagtagcagcaccgccgcggatctgcgttttccaggcattcgcttctttaacgggatcaatccacggcataacgggccccgaata |
| aaccgcgttataaagcgagtccatatcaatgcctctcggcagcttgatttctccggcagcaatagccatcttgagccaggctcggtacatggg |
| ccgggtcactgaaccgatgaaccagtcctgaagaatcagatagccgtcggttgactcgacaagctcctgccgctgggcactgtacgttccgt |
| tgtagtttctggatgtgctggaaaagctgaggcgactgccggcggacacggcacgcagctgtccgttacgaaaagattcgaggttagggttc |
| gggcgatcggatttaatcatcccgatttcttccccggcctgcagttcgtcatagagcataccgggctgaatcatcagctcgcggtcatcgctgc |
| ttgaatcagaatcgaagctctgtccgtcgcctttttttgatatacatgccgagtgccgcagcaattctggcagcagtaagctccgagtcctcgtat |
| tctttcagcgcgctcagacgcatcagaacaccagacaaaagagacgttccgcgggtctggtgcaggcgtcgggtgaatttgagatgcagca |
| tgttctctgcatctatctctttggtatcaaactgacgcccggatactggcaggcttttatagacctgatattttttcgggcgtccccagttatcgaca |
| aaaacgccctgattgagctgggtggcagcatcgctgttcatcggcacaaagtccggctccagcgcttccagccagaacggcacgccagca |
| accggctgaagaccatttccggtaccgcgaaccagctgagcaaatacctcaccgtcccggagccacgttcgcagcatcagccgctccagc |
| attgggcgggtaaactgggttgtgacatctggccttacggaccattcgccccactttcggcggatatcagtggccagctttttagcgatcttccc |
| gttactcagcatcggatgcggttcaactatgatgcccttcgcacccaccaccctttcttccagcttgtcgaaaacgccgatcaccagatcgtgg |
| ttgttatccagccagcgcgcctgctgcctcagcgaaaccgcccccatctggctgagctgatcggctgaacgattttccttctgggctttgtggg |
| tacgcgtttgctttaccgcctcatacgctttaataactgcgcgggcacgcaggcgtgaggctttccagcctggtgaaaacaggccaatcgcat |
| catctaaaaaactcatccaaacctcgccagcctgtagccgggtcgcccacggcgtttgttattgagcgttgccagtcgtcgctcccattcctga |
| cggccttttctgatttccgacaggttttcgagcgtcatctgctgcccgttgaaagtgattgatttcccctccagaacagacagctcggctgcagc |
| atagcggtcgatcatgttttgaatatctgctggattcacacccaacctcctgacgaagaccacggattagcctgctcggttacgggcttctcac |
| gttttggttttggtttagatttcggcgcaggcggcggggatggcatttcgccagcttccgtctgcgtgtcctcgatccacgtttcccgccgtgcc |
| cactcaggagctgacggccatttgattttttcgtaaccactaaggatggcgagcgcgtcggcataaacgagcaggtcaaatgcttcgtttgcg |
| ccccggccgggcttactccatttcccttcattcgagcgttcctcatacgtcagttcgtcatagaaccagctgcccagccaggcggggaaatgc |
| acatagccagggccgggtgaatcacgccacagcgcattattcacccggtctttaagggcatcggtctggagaagataaagaggcacatcac |
| cagtcgcctgtgcgcggcgcgttgatctgcccgtgttgtcgggaaacgttcgctggataagtttgctgcgcctgacgctgtcccctttgaaga |
| gatagatacgcttacccagcccctcacggcgacatctgcgccagaacttgtaggcattatccgtcacgccatcttcgccccctgagtccacg |
| gccatcgacatcagccgcatgccctttgatgggtcagctgcgagcggccacgttttatcaaagacgtcagtgagtaaaagatcccagtcctc |
| cggatagctcgccggatccacctgaatgctttcaccgttgccgtcgcagcgcagcgaatgccggatgttgtaacggtcaactatccagcgct |
| cacccatacttccataacccgtaatctgcacaacaaagcgccggttgcgcccggcctgcacgtccacggtcgcagtgagaaactgcacgc |
| cgttcggtaccgaacgttttgggacgtcttcggcacgctgctcgagcaattcacttttacgctgctccatgctggctcgcggcaaatagggcct |
| gccgaaatcggtgttgatcaccgtcttcagggtttcttcgctgcgcgtggattcatattcctgctcggcggtcagaaacttataaataagctgcg |
| cccaggtctggtaagcagctgccggaccttccatccagaaggaggcaatacgggaacgacggccatcaccgctaaccaggcctttcctgt |
| cgatggtttgcccgtcccggagccagacacatttcatgttaagcgcacgcttcatgtccggtgtgatcctgcctttacaggcagggcactgaa |
| gaaacgccgcttcgctggcaagcacaggatcgctgctgtcgcggtatccggtcatattgtccatttccggctggaaatattcgccgcaatgcg |
| ggcatggccagtaaagacgacggcggtcaccacggttatagagcgataaaattccggtggtcggaggggcttcatggggcgtggagcgc |
| cgccattttgtgtctctgatatccctcccgggcgagctctcaaccagcgtcatcccggaggacatgaatgtcgtggttcgtttcgatgccagtg |
| aaaaagcatccccctccccgtcgatatcttccggaaagcggtcataatccgtcagcgccacacttttatagtccgaggacgacatgatattga |
| cggatggccagcccagcttcagatagttaccggcgcggaatgtacggtcgtagacgttgttatcgttacgtcttgggcttagccgggttttaac |
| ttcagggctacagcgaaaagtacggtccaggcgtttttttggaatgctcgcgcgctttttcctcagatacctgaattacaagcatatctgccggat |
| cgcagacaatgttataaacgatccagccgtcaatcagcccgatggttttacccgttcgcgctgggcccacaaacacaaccgcatcgtattcac |
| gcgatgccagacagttcatcggctcaatcacatagggtgccagatccggatcccacggaactgagtttcccgcccccattggcacgcgcat |

TABLE 95-continued

| Sequence removed from Phage 3<br>SEQ ID NO: 130 |
|---|
| ataagtactgaccgcatcggccaccggcatacgacgcggggctcgtaaaataccggaaacatcgcggcggatgtccctggcggatgccc |
| gctttgccatcagtcctcctcaggctgctcctcctcttttccagcgtcctgcaccttctccgccatctggtcgcgcagatcatcgataacgctttg |
| cacacgaactaccgcagcaggcgttaaagcacagtcgcgctcgagcacatccgggagggtttcaagtaccatgacgacggctttcgccat |
| caatgagaattctcgcgccacttcatctgcgggtattaactgccccgtatcctgttcgaacttcagcctctcgttctctgctttccagtgggacag |
| cctgtcagaaggggcatatcgtcgatgttggccgaaacggtagggatcatcagttcggtcagaatgtcggtcaccagatagagctttaactt |
| gctattgctgcctggagcaggttcaacatttttcagtctcgcggcaaccgtctgacggtgtacgccggttatccctgccagctggttgatattga |
| gttttaaagtggcaatttcctggtccatgatggtgaacactttttgaacgattcgacatgttgcgaaaatggcctctaattaaatcaaagacctgc |
| gcacatgatgatgatgaccctggatccgaaaaactagccgtttcccgcgagcacgccgccccgtggcagggtccccctccgggagtacctt |
| ttgataataattatcaattgcacactatcgacggcactgctgccagataacaccaccggggaaacattccatcatgatggccgtgcggacata |
| ggaagccagttcatccatcgctttcttgtctgctgccatttgctttgtgacatccagcgccgcacattcagcagcgtttttcagcgcgttttcgatc |
| aacgtttcaatgttggtatcaacaccaggtttaactttgaacttatcggcactgacggttaccttgttctgcgctggctcatcacgctggatacca |
| aggctgatgttgtagatattggtcaccggctgaggtgtttcgattgccgctgcgtggatagcaccatttgcgatagcggcgtccttgatgaatg |
| acactccattgcgaataagttcgaaggagacggtgtcacgaatgcgctggtccagctcgtcgattgccttttgtgcagcagaggtatcaatctc |
| aacgccaagcgtcatcgaagcgcaatattgctgctcaccaaaacgcgtattgaccaggtgttcaacggcaaatttctgcccttctgatgtcag |
| aaaggtaaagtgatttctttctggtattcagttgctgtgtgtctggtttcagcaaaaccaagctcgcgcaattcggctgtgccagatttagaagg |
| cagatcaccagacagcaacgcgccacggaaaaacagcgcataaagcacttcattagcagcgccagatagcgtaatgattttgttactcatgg |
| aatatttccttttaggcgtgagcctgtcgcacggcaatgccgcccgagaggtaaacgcaacctaacggcatcacccaggctcactactgaaa |
| gactctctttgatgtgcgcgtgcgatgcgcgtagaagactgatttatcaacctgtctttatatcaggattcattacctgactatttgtgggtaaagtt |
| cgtagtgcgctgatcgtgcaaaatgattttagttgggaacagttcgcaactctgtcccataaaaatcagcatattcccatctatcccatatccagc |
| gcattgaccatcgggatactgaagggagattccatcatctcttagaaagatcaccatctcttttgtttcaatttgcatatagctacctggaggattt |
| atgaatgcaaggattttcatggactattaccatgagattgattttccatctttattcgcgagagcagtggaaagcgatgacgatgtgggtactaca |
| ttgcgcattcacctactttgtgagcgcatggtcgaagcatggatatgcgcatgctgtgactgccaagatctctttggaagagataaaaacaaac |
| ttttaatcgaatgtaatactaaaatatccatggcgggaaacctgggaatcccccggaacttatgaaatcacttaaaaccatcaactcaatgcgt |
| aatgaccttgcacacaatccatcaatacaaagcattgctgattcaaggatccagagcctgaaggatactctgactgaatactttaaacagcatc |
| caacggaacccagcatggaagaatcaaaactgggtatttttaacgccgagaatcaattaaccgaagaagtttccttagatagtgacagttcaa |
| aaaacagacttaagttaatcttgctgttcagcaagttaatgcaggcgttaatgcaattagttgcagctaatcataatgggcgctgggataaccaa |
| tttagccaattcgtttaccatgtgaccatgaacgcaacaaagagataaatccaagcccgttttgtacgggctgttgcattatcacaggcactcag |
| tgaatgcctgctgtaatgccgctagtcgtcgagttgcaacacaccgtg |

Table E. lists the Phage 3 genes that were inactivated by the deletion.

TABLE E

| Phage 3 Genes inactivated by the deletion | | | |
|---|---|---|---|
| ECOLIN_10110 | 1 . . . 160 | Minor tail protein U | GI: 660512026 |
| ECOLIN_10115 | 157 . . . 729 | tail protein | GI: 660512027 |
| ECOLIN_10120 | 745 . . . 987 | DNA breaking-rejoining protein | GI: 660512028 |
| ECOLIN_10125 | 1013 . . . 1339 | hypothetical protein | GI: 660512029 |

TABLE E-continued

| Phage 3 Genes inactivated by the deletion | | | |
|---|---|---|---|
| ECOLIN_10130 | 1422 . . . 3368 | peptidase S14 | GI: 660512030 |
| ECOLIN_10135 | 3382 . . . 4881 | capsid protein | GI: 660512031 |
| ECOLIN_10140 | 4878 . . . 5093 | hypothetical protein | GI: 660512032 |
| ECOLIN_10145 | 5090 . . . 7192 | DNA packaging protein | GI: 660512033 |
| ECOLIN_10150 | 7192 . . . 7680 | terminase | GI: 660512034 |
| ECOLIN_10160 | 7864 . . . 8592 | hypothetical protein | GI: 660512035 |

TABLE E-continued

| Phage 3 Genes inactivated by the deletion | | | |
|---|---|---|---|
| ECOLIN_10165 | 8767 . . . 8997 | hypothetical protein | GI: 660512036 |
| ECOLIN_10170 | 8996 . . . 9592 | hypothetical protein | GI: 660512037 |
| ECOLIN_10175 | 9661 . . . 9687 | hypothetical protein | GI: 660512038 |

Table F. shows the sequence of Phage 3 comprising the deletion.

TABLE F

| Phage 3 sequence with Deletion SEQ ID NO: 281 |
|---|
| aggcctctcctcgcgagaggcatttttatttgatgggataaagatctttgcgcttatacggttggatttcgcccggtttgcgagttttcagcaattttta |
| atatccaggtgtattgttctggtcgcggaccaacaaaaatctcgacttcttcattcatccgccgcgcaatcgtatgatcatccgcctctaacagatca |
| tccatcggtgggcgcacctgaatcgtcagacgatgcgtcttgccatcataaatcggaaatagcggtacaacgcgcgcacggcacactttcatca |
| aacgaccaatcgcgggcaacgtcgctttataggtggcaaagaaatcaacaaattcgctgtgttctgggccatgatcctgatcgggtaaataatat |
| ccccagtaaccctgacgtaccgactggatgaatggtttaataccatcatttctcgcatgcagacgaccaccaaagcgacggcgcaccgtgttcc |
| agacataatcaaaaaccgggttgccctgattatggaacatcgctgccattttctgcccttgcgaggccatcagcatggcaggaatatcgacggcc |
| caaccgtgcggcaccagaaaaatcactttctcgttattacgtcgtatctcttcgatgatctccagcccttgccagtcaacgcgcggctgaattttctc |
| cggcccgcgtattgccaactcagccatcattaccatcgcttgcggcgcggtggcaaacatctcatctacaatcgcttcgcgttcagcttcactacg |
| ttctggaaagcagagcgacagattgattaacgcacgacggcgtgagctttttcccagtcgtccggcaaaacgtcccagccgtgccagaatggg |
| atcacggaactttggcggcgttaaagcgatacccgccatcgctgctacgcccagccatgctccccagtagcgcgggtggcgaaaggatttatc |
| aaactcaggaatgtattcgctattatttttttttcgtttccatgcttttccagtttcggataaggcaaaaatcaatctggtgatagtgtagcggcgcaactt |
| gccccgcaccaaataaaaaagccggtactgactgcgtaccggctgcgaatggatgttaattaatcaaaccgtagctgcggcacaatctctttgg |
| cctgtgccaggaattcgcgacgatcggagccggtcagcccttcggtacgcggcagttttgccgtcagcgggtttacggcctgctggtttatccat |
| acttcatagtgcagatgcggcccggttgaacgtccggtattaccggaaagcgcgatacggtcgccacgtttcaccttctgtcccggtttcaccag |
| gatcttgcgcaagtgcatataacgcgtggtgtagctgcgaccatgacgaatagccacataataacctgctgcgccactacgtttggcaaccacc |
| acttcaccgtcacccactgaaagcactggcgtaccttgtggcatggcaaaatcaacacctctgtgtggcgcaacgcgaccggtcaccggatta |
| gtacgacgcgggttaaagttagatgagatacggaactgtttcgccgtcgggaatcgcaagaatcctttcgccagaccagtaccgttacgatcgta |
| gaatttgccatcttcagcgcggattgcgtaataatctttaccttctgaacgcaaacgtacgcccagcagctggctttgctcacgtttaccatcaagc |
| atttctcgtgacattaacaccgcaaattcatcgcctttttttcagtttgcggaaatccatttgccactgcatggctttaatcactgcgctcacttcggcgc |
| tggttaaaccggcgtttctggcgctggcaacaaagcttcccccgacggtacctttcagcagattgttgacccactctccttgctgcatttcgctggt |
| cattttaaaaccgttagcggcagtacggtcataggttcgggtttcacgacgagacacttcccaggtgaggcgctgcagttcgccgtccgcggtta |
| atgtccaggagagttgttgaccgattttcaggttacgcaattctttgtcggcagcagccagttgggtgatatcacccatatcaataccatactgattg |
| agaatgctgcttagcgtatcgccagtggaaacaacatattcatgcacgcccgcttcaccggcgattttgtcatccagttcgtcctggggaatggct |
| tcatcttcttgtgcagcttgatcaatcggctcactggcttcaggtaagagcgaacgaatttcgttctgttccagctcaatggttttgacaattggcgtg |
| gcatcgcggtgataaacatagggccgccagacagcgacggccagagtaagaacggtgagcgaccccaacataacgcggtgtggtcgcggt |
| aaattattaaacgccagggcgacagagcgggctatctgttgcacgtaatcacttcctcattaatctcctttcaggcagctcgcatactggttggcta |
| attgattcaggaattctgaatagcttgttttacccagtttgatattcgtccccaggggatccaacgttcccatacgaacggatgtccctcgtgcgacg |
| ctctcaacgaccgctggcctgaactgtggctcagcaaaaacgcaggttgctttttgctcaaccaactgtgttcttatttcatgtaaacgctgcgcgc |
| caggttgaatctcagggttaacggtaaaatgaccaagcggtgtcagtccgaactgtttttcgaaatagccgtaagcatcgtgaaaaacgaaataa |
| cctttccccttgagcggcgcgagctcgttaccaacctgcttttcggttgaggctaattgtgcctcaaaatccttcaggttggcgtcaagtttggctcg |
| actttgcggcataagttccactaattttccatggattgcaaccgctgtagcccgcgctatctctggggaaagccaaagatgcatgttgaaatcgcc |

TABLE F-continued

| Phage 3 sequence with Deletion SEQ ID NO: 281 |
|---|
| gtgatggtgatcttcgtcactttttccgcgtggtcgtgatcatcatcatcgccgtgaatacttttcatcagcagcggtttcacattctctagctgcgca |
| atcgttacctgtttcgcttcaggtaatttacttaccggtttttgcatgaacgcttccatctccgggccaacccaaacgactaagtccgcgttctgtaag |
| cgttttacatctgatggacgcagtgaataatcatgttctgaagccccgtcaggtagtaaaacctccgtttctgttaccccatcagcaatggcagaag |
| cgatgaacccaacgggtttaagcgaagcgacaacggcagcatctgcggcctgtgttgcaccgccccagagagcggcggataatgctgcgaa |
| aagaagcgtttttttatgtaacataatgcgaccaatcatcgtaatgaatatgagaagtgtgatattataacatttcatgactactgcaagactaaaatta |
| acatgacaagtctggtttccctggaaaatgtctcggtttcttttggccaacgccgcgtcctctctgatgtgtcgctggaacttaaacctggaaaaatt |
| ttgactttacttgggccaaacggcgcaggtaagtcgacactggtacgggtagtgctcgggctggtaacacccgatgaaggggttatcaagcgc |
| aacggaaaactgcgcatcggctatgtaccgcagaagctgtatctcgacaccacgttgccactgaccgtaaaccgtttttacgcttacgccctgg |
| cacacataaagaagatattttgcctgcactgaaacgtgtccaggccgggcatctgattaacgcaccgatgcaaaagctctcgggtggcgaaac |
| gcagcgtgtactgttagcgcgagcattgttaaatcgaccgcaattattagtgctggatgaacccactcagggcgtggatgtgaatggtcaggtgg |
| cgttatatgaccttattgaccaactgcgtcgcgaactggattgtggcgttttaatggtatctcacgatctgcatctggtaatggcaaaaaccgatgaa |
| gtgctttgcctgaatcaccacatttgttgttccggcacaccggaagttgtttccctgcatccggagtttatttctatgtttggtcctcgtggtgctgaac |
| aactgggtatctatcgccatcatcataatcatcgtcacgatttacagggacgaattgttttgcgtcggggaaatgatcgctcatgattgaattattattt |
| cccggttggttagccgggatcatgctcgcctgtgccgcgggtccgctgggttcgtttgtagtctggcgtcgtatgtcttatttcggtgatacgctgg |
| ctcatgcctcattacttggcgtcgcgtttggtttgttgctggacgtgaatccattctatgcggtgattgccgttacgctgctgctggcgggcggtctg |
| gtatggctggagaagcgtccacagctggcgatcgacacgttattagggattatggcgcacagtgccctgtcgctgggcctggtggtcgttagtc |
| tgatgtctaatattcgtgttgatttgatggcttacctgttcggtgatttactggcagtgacgccagaagatctcatctctattgcgattggcgtggtcat |
| cgtggtggctatttgttctggcaatggcgcaatttgctgtcgatgacgattagcccggatctggcgtttgttgatggtgtgaaattacagcgcgtga |
| aattgttgttgatgctggtgacggcattgacgattggtgtagcgatgaaattcgtcggcgcgttgattattacttcactgctgattattcctgctgctac |
| tgcacgtcgctttgcccgcacgccggaacagatggctggtgtcgctgttttggtggggatggtggcagtgactggcggtttaaccttttccgcatt |
| ttacgatacacctgcaggcccgtcggtggtgctatgcgcggcactgttatttattatcagtatgatgaaaaagcaggccagctaatctgtcgctga |
| acacatttgtcggatgcggcgcgagcgccttatcccacctgcggttcgctatctctggtaggcctgataagacgcgaacagcgtcgcatcaggc |
| acactgccagtgtcggatgcggctcgagcgaccaatccgacttacggcatttctggcggcgtgatgccgaagtggttccacgcccgcactgtc |
| gccatacgcccgcgcggtgtacgctgcaaaaagccttgctgaatcaaataaggttccagtacatcctcaatggtttcacgttcttcgccaatggct |
| gccgccaggttatccagacctaccggcccaccaaagaacttatcgattaccgccagcaacaatttgcggtccatataatcgaaaccttcagcatc |
| gacattcaacatatccagcgcctgagcagcgatatctgccgagatggtgccatcgtgcttcacttcagcgaaatcacgcactcgacgcagcaga |
| cggttggcaatacgtggcgtaccgcgcgcacgacgagcaacttccagcgcgccgtcatcactcatctcaagccccataaagcgtgcgctgcg |
| actgacgatatattgcagatccggcacctgataaaactccagacgttgcacaataccaaaacgatcgcgcaacggtgatgtcagcgaacctgc |
| gcgcgtggttgcaccaatcagggtaaacggcggcaaatcaattttaatggagcgtgccgccggaccttcaccaatcatgatatccagttggtaat |
| cttccattgccggatacaacacctcttccaccactggtgaaagacggtggatctcatcaataaacagtacatcgtgtggttcaaggttagtgagca |
| ttgctgccagatcgcccgccttttccagcaccggaccagaagtcgtgcgtaaattaacgcccatttcattggcgacaatattggcaagcgtagtttt |
| acccaaccccggaggaccaaaaatcaatagatgatcgagggcatcgccgcgcagtttcgctgctttgatgaaaatctccatctgcgaacgaac |
| ctgcggctgaccaacatactcttccagtaatttagggcgaatggcgcgatctgccacatcttccggcaaagtggtaccggcagaaatcagacgg |
| tctgcttcaatcatcctttacctcataacgcggcgcgtagggcttcgcgaattaatgtttcactgctggcgtcagggcgagcgattttgctcaccat |
| gcggcttgcttcttgtggtttatagcccagtgccaccagcgcagcaaccgcttcctgttcagcatcgtcggtcgccgggctggcaggagacgtg |
| agtaccaggtcggcggctggcgtaaagagatcgccatgcaaacctttaaatcggtctttcatttcgacaatcaagcgttcggcggtttttttgccaa |
| tacccggcagtttcaccagtgcccccacttcttcacgctcaacggcattaacgaactgctgcgctgacattccggagaggatcgccagcgccaa |
| cttcgggccgacgccgttggttttgatcaactctttgaacaacgtgcgctcttgtttattgttaaaaccgtacagcagttgcgcgtcttcacgcacca |
| caaagtgggtgaaaacgatcgcttcctgacccgcttcagggagttcataaaaacaggtcatcggcatatgcacttcatagcctacgccgcccac |

TABLE F-continued

| Phage 3 sequence with Deletion SEQ ID NO: 281 |
|---|
| ttcaattaacaccagcggggggttgtttttcaatgatgatgcctctgagtctgcctatcacatgacgctcctgcgtaatgaatcaaagataatgctgtat |
| gataaaaaaatgctggatagatatccagcgaaggatgaagaaaacttgcgaggtgtctcgatgatctgaaaaatggcgcagtataatttattctac |
| agattatattggaagcaaatatttaaatattacatattcagcgaagaaatgtgtaataaaaatacacattgcgacccctgaaaaaaataaatttttttatg |
| ctattacgtatattcatatctatttcaatggaatgacaacgtgaatattaattatcctgctgaatatgaaattggtgatatcgtctttacatgtataagtgct |
| gccttatttggtcaaatatcagctgcatcaaattgctggagtaatcacgtcgggatcattatcggtcataacggtgaagactttctggttgcagaaa |
| gccgtgttcccctctcaaccatcactacgctatcccgttttattaaacgctctgctaatcaacgctatgctataaagcgattagacgccggactaac |
| agaacaacaaaatcaacgaattgttgaacaggttccttcccggctacgcaaaatttaccacaccggttttaaatacgaatcttcgcgccagttctgt |
| tcaaaatttgtttttgatatttataaagaggcgctatgtattccggtgggtgaaatagagacgtttggagaattgttaaatagcaatccaaatgcaaaa |
| ctcactttctggaaattctggttcttaggttctattccgtgggagcgtaaaaccgtcacgccagccagtttgtggcatcatccgggtttggtgttgatt |
| cacgcggtgggagttgaaacgcctcagcctgaactgaccgaggcggtataacttaacgcagtcgccctctcgccaggttcagtcgcgattcgc |
| tcatttgcatcgcattctgactaacgtggcagtgggtgatggcaatcgccagcgcatcggcggcatccgcctgtggattagcgggcagtttcag |
| caaggtgcggaccatatgctgcacctggctttttttcggcactaccaatacctaccactgtttgctttacctgacgtgccgcatattcaaataccggc |
| aattcctgattcaccgccgccacaatcgccacgccgcgcgcctgccccagtttcagggctgagtcagcgttcttcgccataaagacctgttcaat |
| ggcgaaataatcaggctggaattgggtgatgatttccgtcacgcccgcatagatgagcttcagacgagacggtaaatcatccactttggtgcgta |
| tgcatccgctacccaggtaggacagttgcctgcctacctggcggatgacgccatagccggtcacgcgcgaacccgggtcaatgccgagaata |
| atagccatcacgcgtctccgttttgctgtttagcaggcctcatcagagagtcgctgcaacctcatcagagatttcaccgttatggtaaacttcctgca |
| cgtcgtcgcaatcttccagcatatcgatcagacgcatcagtttcggtgcggtttctgcatccatatcagctttggtggacgggatcatggaaacttc |
| cgcgctgtctgctttcagacctgccgcttccagagcgtcgcgtactttgcccatttcttcccatgcagtgtagacatcaatcgcgccgtcatcatag |
| gtcacaacgtcttcagcaccggcttccagggctgcttccatgatggtgtcttcatcgcctttctcgaaggagatcacgcctttttttgctgaacaaata |
| agctacggaaccatcagtaccgaggttaccgccacatttgctgaatgcatgacgcacttcagcaacggtacggttgcggttgtcagacagacat |
| tcaatcatgattgccgtgccgccaggaccgtaaccttcgtagatgatggtttccatgtttgcatcatcatcaccgcccacacctcgtgcaattgcgc |
| ggttcagagtgtcacgggtcatgttgttagacagtgctttatcaattgctgcacgcaaacgcgggttagcgtccggatcaccaccgcccagctta |
| gccgcggttaccagctcacgaatgattttagtgaagattttaccgcgcttagcatcctgcgcagctttacgatgtctggtgttggcccatttactatg |
| acctgccataaaaatatctccagatagccctgcctgttcaggcagcgttaattacaaactgttcaatcgcctgccggttgctccaggacttagtga |
| gcgccgccgcagcagacgcatcaagccacttgtaagccagatgttcagtgaaaacgatctggcgctcgtgcggaagcgcaagacagaacca |
| tgattccgtattacgcgtcacgcccggcgcatagcgatgacgtaaatgtgaaaaaatttcaaactctaccgtgcgctgacagtcaattaaggtca |
| gttgttcagcgacaacatcaatggtgacctcttcctttacttcgcgcatggcagcttgcggcgcggtttcaccctcttccacgctgccggttaccga |
| ctgccagaaatcgggatcgtcacgccgctgcaacatcagcacccgtttcgtatcttgtgcgtagatgaccactaagatcgaaacgggacgcttat |
| aagccatatcagttattctcagccttcttcacaacctgaatgctcagctcagccagtgcagtcgggttagcaaagctcggcgcttcagtcatcaaa |
| cacgctgccgccgtggttttcgggaaggcgataacgtcacggatattgtcggtgccggtcagcagcatcgtcagacggtcaagaccgaatgcc |
| aaacctgcgtgcggcggagtaccgtatttcagggcgtcgagcaggaagccgaatttctcgcgctgttcctcttcgttgatacccagaataccaaa |
| caccgtctgctgcatatcaccattatggatacgcacagaaccaccgcccacttcgtaaccattgatgaccatatcgtaagcgttagccaccgcatt |
| ttccggtgcagctttcagttctgctgccgtcatgtctttcggtgaggtgaacggatggtgcattgctgtcaggccgccttcaccgtcgtcttcaaac |
| atcgggaagtcgataacccacagcggtgcccatttgctttcgtcggtcagaccaaggtctttacccactttcaggcgcagtgcgcccatcgcgtc |
| ggcaacaattttcttgttgtcggcaccgaagaaaatcatatcgccatcttgcgcgccagtacgctccaggatggcttcgatgatttctgcattaagg |
| aacttcgctaccgggctattgataccttccagacctttcgcgcgttcgttaactttgatgtaagccagacctttcgcgccgtagattttaacgaagtta |
| ccgtattcgtcgatctgcttacgggtcaacgatgcgccgcccggaacacgcagagcggcaacacggcctttcggatcgttcgccggacctgca |
| aatactgcaaactcaacagatttcagcagatcggcaacgtcggtcagttccatcgggttacgcagatccggtttatcagaaccataacggcgttct |

TABLE F-continued

| Phage 3 sequence with Deletion SEQ ID NO: 281 |
|---|
| gcttctgcaaaggtcattaccgggaaatcgcccagatccacgcccttcacttccagccacagatgacgcaccagcgcttccatcacttcacgca |
| cttgcggcgcggtcatgaaagaagtttccacatcgatctgagtaaattcaggctgacggtcagcacgcaggtcttcgtcacggaagcatttaacg |
| atctgatagtagcggtcaaagccggacatcatcagtagctgtttgaacaactgcggggattgcggcagcgcgtagaatttacctttgtgcacacg |
| agaaggcaccaggtagtcacgcgcgccttcaggcgtggctttggtcagcatcggagtttcgatgtcgaggaagccgtggtcatccataaaacg |
| gcgcaccaggctggtgattttagcgcgggttttcaggcgctgagccatttccgggcgacgcaggtcgaggtagcggtatttcagacgcgcttct |
| tcggtgttgacgtggttagagtcaagcggcagaacatctgcacggttgatgatagtcagcgaggacgccagtacttcgatttcgccagtcgccat |
| atcgcggttaatatttttttcgtcacgcgcacgtacggtgcccgtgacctgaatgcagaactcattacgcagttcagaggccagctttaacgcgtc |
| cgcacgatccggatcgaaaaatacctgcacgataccttcgcggtcgcgcatatcgatgaagatcaggctaccaagatcacgacgacggttgac |
| ccaaccacacagagtcacctgctgccccacgtgggacaaacggagctgtccacaatattctgtacgcatgagatatcccttaacttagctgccg |
| gcggatgccccctgctgcgcaggtgaccaagtcgcagcgttagctgtatgtcacaactgaatgaaaaaaggcggctattatactggaaattctg |
| ccgcaccgtaagagcctggcccgcgctggaacgcctcgttaccactttatatcgggcctgaaatcagactctacgccagtttgctataaaggtgt |
| tgcccgaactcataaaaattaacaaaatttgtcgttccgccatcggctaatcgcattaaggtgagaggcacgattttgttttgtcaggagtcatcatg |
| cttgaacttaatgctaaaaccaccgcgctggtggtgattgatttacaagaaggcatcttgccttttgccggaggtccacatactgccgatgaggtg |
| gttaatcgcgccgggaagctggcggcgaaatttcgcgccagcggtcagcccgtgtttctggtgcgcgttggctggtctgccgattacgccgaa |
| gcattaaaacagccggttgatgcccccctcccccgcaaaagtgttgcccgaaaactggtggcaacatcctgctgcattaggtgcaaccgacagc |
| gatatcgaaatcatcaaacgtcaatggggtgcgttttacggtacggatctggagttgcaattacgccgccggggtatcgatacaatagtgttatgt |
| gggatctcgaccaatatcggtgttgaatccaccgcccgcaatgcctgggaactcggttttaatctggtgattgccgaagatgcctgtagcgccgc |
| tagcgccgagcagcacaataacagcattaatcatatctacccgcgcatcgcccgtgtgcgtagcgttgaagagatcctcaacgcgttatgattta |
| catcggtttgccacaatggtcgcatcctaaatgggtgcggttggggatcaccagccttgaagagtatgcccgccactttaactgcgtgacgcgg |
| gcattttaaaaatcactaaagaacgcccaagagcatgtgttttctttagtttattcaatgcattaaaaaatagtttcgcatgaaattcggtaaacttcat |
| gtgtgcaataatgtcccattcatgccccaaaatgccccaaagcagacatttttgccccaagtatgccccacaagtcacgtcttcaagtcgtctatat |
| ccatagcacaccgagttacattcttgcatccggggtgtcgacaatacctactttattgagtgtgcgagaattaccaggaacctttccacaatgtagt |
| agtctaatagtcgaatccatctaacattaagaagcgttatgatcactagcctctcattgatatcttctgtaatagtcactctatgtatcatggtgttcgct |
| acagtaaaggtagggattggtttgtctaacaatccagacagaaatgataattaacctcaaccacgtaaccacacttcatacttcatacttcacttaac |
| agtgaagtgctcacatcaccgggcagtcatcaaactccgcattcctggcatcattaatgatgtacgtgatcactccaaatatagcgggtgcagaa |
| ctgtaaccatcatcatctgctggcagcgcttcccttctcccgttatccagattaaccaggtgcggctgaggatgagtccgatatcgcttgatcctga |
| attccccgtcgattgcacatatcagcagtgaaccatcgcaggcagtaagtgacgcatccacaacaagcaacgctccctggattatcccttccctg |
| aaatgtgaacgcgatgcccgcatgaaataagtcgctgcgggctgactgattagctgctgatcgagggagattcgtgtttcaacataatctgccgc |
| aggtgaaggaaatcccatgtttacgccctctcttgaataccggataaaaacacagtataaatactgtatatccatccagcaaagaggcaatgagc |
| aatgttcgtggaactcgtttatgacaaaaggaattttgatggtctgcccggtgcaaaagatatcattctgggcgagttaactaagagagttcaccg |
| gatcttccccgatgctgatgttcgggttaaaccgatgatgacactgccggcgatcaacactgacgccagcaagcatgagaaggaacagataag |
| ccgtactgttcaggaaatgtttgaagaggctgaattctggttagtgagtgagtaaagattttcaatgcccgccacagttacgtattgattatgctgtg |
| gaggatattcattttcgtaaacgttggtttgggagaagcggcaaaacggaatgtgggaacaggggaaaatcagataccagatatgtctgcatttc |
| catctggcaataactggtttcagttaccaagtggacatatcgttcagatattttccatgaacgttcttggtgcagatgctaatggcacgtcagctaatt |
| accccattgcttttccaacaacgatgattgctgtcagtgctctatggtctgatgggactgtagcaaatgcaccgacatacaagatgatggggaaca |
| cgactaacagaacaactttgacgataaaagtatcagccagctcaggtacttacgggacaatgattattgcggtgggacgataatatgaataaata |
| cagttactctccttcagaaaatgccttttatgctgttgcgttaaaaaatacctatgaattgagtggcacatggccagctgatgcattagatattcctgat |
| gacatttctgtaaaatatatggcggaaccgccacaagggaaaatccgagttgcaggggaaaatggttttcccacatgggctgaaatacctccac |
| catcacatgaggaacttattgaacaggccgaatcagagaggcaattattgattaaccaggccaacgaatacatgaacagtaaacaatggcccg |

TABLE F-continued

| Phage 3 sequence with Deletion<br>SEQ ID NO: 281 |
|---|

gtaaagccgctattggtcgtctgaaaggcgaggaactggcacaatataattcgtggctggattatctggacgcactggaactggtcgatacttcc ggtacgcccgatattgaatggcctacgcctccggcagttcaggccagatgacatccggcgcggtgctggtatctgttgcagtcaccgcgtcaat gtaatccagcacggcgttaagtcgggttgtttctgcctgagtcagtttccgtccggcctgtaatttcagctgaatcagactaatggaagccattgct gcatcaatcagtgattggcgctgtgcttctgccgcttctactgaggcaccgtgttgtgcctcagtatctgtcacccatttctcaccatcccatttatcat atggcgttaacggtgaaagcgtgacataaccgtttttgatggcaccgatataatccactgtaacagctgcgccattttcgattgagtaaacagtctc attgcgatggtcttcctcatggctccatcccttacctgtaaatactgccactcttcccggaatgttttcgtccgggtcaataccagtggaacaggcg ggcatacttacgccagtattaatatattcatcagaccagcccgtatattcagacgttactgcatcataataaaaacaacgcatatcacccggcactg cagccagcccattttcatcaaaaacaggtttcattatttagccctcaccagaaagttaaatgcaatatttcgcggtctgacagcaacaaaattcaca ccatcacccacagagttactgttgaaattaaatcgtgaaaatcctggctgatttccggcgatgccatcatgaaagttaattgcgtgtccagcacctc cgcctatattcccggcaaactgagaaaagtttgtagcttcctgccagcttaataattcgcgaccaccatctgcacctcgcccgtcatcccagacac gaatgaaatcaccgcgggcttcaggtaataccagcgaaggaaacactttcgccagcacaggataatcagtggcagagaatttcgcgccgttga acttcaaaaacaccatactggaccagctgtcgattacagtatttggcattgcagcggacggccagaagaacggaacgccaatagctggagaac cttctcccaaaccaaggtttgtgcgagcgtctgcggcattcgttgcgccggttccgccgtctgcgacagtaaccgcaccgttgctccctttctgcg caagtttaccgatgcctgggatggttacggcggtgccgttgatggtaactgtgatgctttggtttgctgaggtggtggcgaacgtctcccacgcg ccaatattctcgtcgtactctttgatgagctgtgacatggcctgcgccaggccgtcgactgagatattgtccgacacaaggattccatacttctggc cgctcagcgccggggaaactgctggcgtaaccgtcattgacgtggcgctgttcacggatgaaatctgaaacagctgcaccgggttagacatca cgataatcgtctggccagcgcggacctggctggcgggagctgtccagtttgtgccggagccggttgcggtatttccgttaatagagatagttcc ggtgctataaatcataacaactcctaaatttagacaacatgaagcccggagaggtatataaccctcaccagaaataatttctgaattggtttttaata catgttgggcaacgccagtgttggcatagctatagttgtatcaaatgccattgaccacccacccaaataataattgccgactactttattcctttctgc tctgacattcccacctgtcattacaattcctttatacctaatatttccgtaaccaccaacgtgtcgacagttagccccggtataaacaatctggcaaaa ttcatcaccaatattcaggttcgcattggcgatatttattgtcccatcaaaaatgaatggcttcgtgcaagtaagaagacgtttgcgttgacgattggt ttattcaatccatcaactaaaatatcatgtaaacgaattgccataacatttcccactttattttacttactcaacacaacaagtatattaaaattgaacctt gtcaacaacacaaaggagtcccaatgaaactcgctctaattatgctgccattatgtctgtccctcactgcatgtggtaatggtttaaataccggtaa accaaattccggtgtcattccaaaacctttggatcgagatggtaacggttctttaatttatgataccgaaaaccttccaatgacggggcagtggtgt cacgagattgatcacgaataccgacgaatcggtagcccttctaactgtgttatagactactaaatattaacccctcaaaagaggggttaatattttaa cctgtgaatgaaccagatccgtgtgatactatgatagtaggcgaagaaattgacgcacccctgttattttgagcggacactttaatacgcactgtta cgtttggacctgttacaaccgcagaatgcatgataagtctctccatgtcttgcacggatgaaccactctcattgccgttaatgtcgattgttcctgca ccattacctttaacgtttgctataacacagacgtgtcttgcgtgcccagaactggatgaatcattataagtcattaccttttctaaatatccgtcactag accgactcacattcgtccctgtgtgcatatttgcaatgtccccgataaaactttgggcttccacagtccctttgaatttaccgcttgttgcttggatctc accagtaaagctaccgccactagcatatactacacctctgacggtcacattgttgaattcagcatctccagctttattcaacttccaaccagcagaa ccagctgcatagttgttggactggatatagttaccgattttgcgttctcaatggtgccgtcctggatgaagctggcccggatgaatgtctgcccgtt ctggatcacgaacggcaaagctacgctatttccggctgccgtggtgacggcgaagcggtcagccaggaagataacctgcgactgcatgccg gatggcgtattctccacgccgatacccatccccgcggcgtaatactgcccgttgctggagacaccaaccttgatgttgtacatcgcgctgagttc gccattaacgttggctatagcctgagcgttagtggtgatggcggaggtatgcccgttcacggtcgccgtgatgccgtttatctgcgtggcggtgg cctgctgatagtcggagagcgtctgattcaggctgttgatggatgccttgttgccgttgacgtccgtctgcaggctcagcaatgaacgtgctgtgg cttccttctcactgacgatcacctcgtcgagacggtccagattcgcgctgttgccggcgaccgatgcagaaagggttttacgcgtggccacctga gcgaggttggcctggattatcgcaattgcagagttcttcaccccgcccgtcatgccgtccatagaaacgctgatgttgtcgattcgctggcccag ggcggtatcagccgtcgcaacggtctgctcaagctgactgagtgaagacgaaacattcccgaccgtgctggaaagctcattaacgctggtctg TABLE F-continued

| Phage 3 sequence with Deletion SEQ ID NO: 281 |
|---|
| aaccttcccgacgtcctgggcatttttggcgatatctttcgcttgctgctccagttcgtcgttggcctgtttgatatcgttagccatgccagcaatttttt |
| cgttgctgtccaccgcgttctcgatcaggtctttgaacgtttccgactctttcatatcctccagaatgtcattagttatttcgctgacatctatcgagga |
| cgtgcccatgatccagtcggtccagtccccggcgttaccgatacggtcaatcaggcgcgcgcggtaccactggcgaacgccggcaggcatg |
| gggccatgctgataatctgcagccgggtacggcaccaggaccagcagttcaggattggcgtagtcggcagttgtggcgcgctgaatctctgta |
| taggccgtgtcgcctgagccatccggaaatttccaggtcaggtcgatatgccagaccacatcttcggtcgccaggaagttgagcggagtaccc |
| ggttttcccgttttaccggagagataagttgtttcaccgtatccccatggtgacgacgtatcctgcgcattcagcgcccgtacgcgcacgtcatag |
| ctgcccgaataaatgccctgaaccgagaaaccctgcgcgctggtaaccggaacgtttatccagtccccgttgtccttacgccactgggcaacat |
| accggattgcgccctctaccttatcccatgacacgtccaggcttgctacagtcagcccctgagacacatgatcgctctcagtcaccacgatattct |
| tcggagcagacaggacgcttatcggcgtgacggtgatcgggggagactcgacccgaacgccgtcatcgatgtaacgatatttgtttggatcgt |
| gctgaacggccgtaatagtgaaaccgcctgtactgtcgtcgttagccgcgattgaggtgaccctgaagtactgtattgcgaggttatcactgtcta |
| tcgcccaaacagcgcccgccacaggaacctgactgaatgccgtagccaccgtcaccgtttttttatcggcgctcaccgcgctgattgtccgcgt |
| ctgggcttttccgtcgggaaggttaaccaccagccggtctttcgccgcgtagtctatttctcgatcgagggtaatttggcggccgttggccgcgct |
| tatacggccccccgttctccttaccagagcggaaaggatcggcgacaccgataatttcagcgggcaaagggatataaccgtccagccccacgc |
| caaacgatacggtcccgtctttggcattggagagcaatacccagcgaccgcgtcggtgcgcttcactttgcgaggtgcagccgattgcggtca |
| gggacgtctgccggacgtcgtaacgttctacaagcgccgaatcgtaaacccccctcaacggtatcgctgtaatggttctgcggatcggaccagg |
| acaccaggcaggagctgtagcgattcttgtatgagccgcccgcataagtaaacagcccatcgataacgtttgagacgttataaacccagtcaac |
| atcgtcctgcgggacgtctgcctggacataaatctgatcgtttccccagaacgttattccacgaaataccgcggcgagatcgttaagtacctgcc |
| aggcgtcctcctggctctgaatgaaaacgttgcaggtgaaacgcggttcggtgccaccggccccgtcggaaaccatttcgtcacagtactggg |
| cgattgaatacagcgcccacttatccaccatggacgcatccacgcgcgtgcccatgccgtaaatttcatccagaaccagatcgtaaaagatcca |
| ggcagggttattggaccatgccattttgaacccgccggaccatgaaccagaataggttcgggttttcggatcgtaattatccggaaccttaatcag |
| cttgccttttatcttacaggtcactttcggcgcgctgccgttgaattggctgctgtccacttcgacatacaggagcgctgttaaaggataacgaagc |
| ttgctgtcgatgacttccgcatacgaaaacaccttgaaggcgttaaccagtttcgaatttgatccgctggcatcagccgtaatacgcctgaccctg |
| acagaccagccggacgtggattttggcagatcgatacggtggtcacgctgatattccgtcgtggtctttccgtcaaacttgccgtttacaaccgttt |
| tccaggcgccgccgtccgttgataaatcgatcgcatactcggtgaccgtgcccaccatatcgccattatctttatagagatactggaccggaagg |
| ctgagcttgatacggatggcatccagggaaaggtttgtaaactggcgcgtccagggcgcggtggtggtgacagttgtgcccacggccagctc |
| gttgtcgacctggggcatcccggcaatataggtctggtcctgtgtgcccttgcggaactcccatttcacgccgctgaagttgtattccccgctgtc |
| gtttgccagcggcgtatcgttgagaaaaatgttctgagcggtcaggtcgccctgtatttccccctcagaaacggcaatgagcattttttaattttgcg |
| accgacagcagatcgtcaggctgctcaaccggagtatgtgaactgccacctccccctttggcaccctgcaggatggtttcttgtttaagaagctg |
| catttttttcacccataaaaaaaggtgccgaagcacctttaagttagtggccgctggcctactgctgatcgctcgagtacataccggcgctgactat |
| cgctccccctgcctcagtcagaccgtaggccaggggggacaggatgccccatagcgacggtattgaccggcgccccgaaggcgtagttaggc |
| gtgttgtccgtgctggaggatttacccgcgccgaaggatggctggggcgtgagcatctggacaacgcccccccagcatcatcgacactccgac |
| ccctgtcagaattgacgtggcgctgatagctgttgcactcatcgccgcgccccaggctgccatgctcgcaccagcggtaaagaatgcagcgac |
| cagcgcaacagccccgacaactatctgcaggacgcccgaacttttggccccctcataaacgggcacgatccggtacacgcttccaccgcggg |
| tcatatcaaactcttccagcccgatattgttgccaccgttaaaaaaggcgaaacggatccccttcatatgagcttcagacatatatttttttgaatccg |
| ggaacctgtgaacacatggccctgagcatctcgcgcaggtcggcaacatcaaactgaacgcgtttaccgaatttttttgccattttaccttcgaga |
| ataagcgtcttaaccatgcattctgtccttatgcctgaccacccggaccgttctgtcgcgataatattttccataaggcgttcgcgaagaaaggtgc |
| ccgaaaagatgatggagaatgatgttatcacccacatataccgcggcgtgattagtcaccgatgcctgcacactcatcatgatgatatctccggg |
| ctgcattgcaccggcggcaatctcaacgaatccctcacgctcccagttgtcgtcgtagagacgctccttgccgctctcccaccattcgtaaggta |
| ctgaataattgccgagaacaatgccgtattcgcgcagataaaattcacggataagcgaccagcagtcggcgtaacccagcacccactgccgcc |

TABLE F-continued

| Phage 3 sequence with Deletion SEQ ID NO: 281 |
| --- |

cggcataatcccggtcttcacgcggggaaatcgtacaaaaatccccgtccggccaggacatgatcccccactcaatccccgaccagtcgcact ggatccggtccagctctgagggcaccagccgaaccacatccggatgggaatgaatgagcatgatgatctcaccgcgcgcgcgggcagcga gctggtcttccggggagagcgtgaatgtctcctcgggtttatcggcaatgttgcggcagggaataaagatttgttgctggcctgactgaacaatc aggccgcaggcttctttggggtattcagcagcgacgtgctgacggatagcatccagcaatttttcacgcatttttatttcccctgcaggtttgcagc cggaaaaccgccgaacggcagcggcgcatccgggccgtgacgatcctgacaatcctgccggcggccgccacaaacatctttcgacgggtc atcggtcggtgtaccgtctttggtaaagtatttcgtgccgttgtaatcgcatccggtcccgcttcggtaccagccccgcatacaccaggtgcagac aggcgtaatctgccgtgtcggcagctgcaggctctgaatatcgaaaggagaacacagctcgaaatcaacctgtacccgcgtctctgcggtttta gcattgacgtaaaagagctgtaagcgctcatcggccgggctggcacccggattaccgtttttccagttggcggcatcgagatacttcgaaagcg tggtatggattttgaccttagccctgaccatatcgtcatattcaagacacagcgcggtgacatagtttccgacgttcccgacggacagcgtgggc gttggctgggaacctgtactcgataactccatccccttaagttcgtagggatggggatcgtactggtttccctgccagataatggcgggcagatttt ctgcggcgaaggctgcccacccctcttcctgaatattgtgcgcatgaaaacgcagcacctgatccataccgaattcagtgccgtcgatctcaatc agctgaataacgctgccgggctcaagctgttgtatgtctgccgtaaaactcatactcccccataaaaaaaagccgcccggaggcagctttcag tgtttttcgagaaaatcagggcgcgaacgcctgttcaaaagtgaaggccacagtggctttttttcccggtagggaaagaaacgctgaacgaatcg gccttcattctgaacagctttttttcaccccatggagtggtccaccagaacgatttagtaacgtgagacatcaggaaagcgcgcagcgcagccgc ctcctgtctggtgcccgtccagtccaggttccacgtttcctgtttgtcgttgatccccatccccgctatctgtttgtagccatccccgaactgggcct gcagcgttcgggctgtttcagtgccctgcgctgtttttcgcgtgcgccaggtaaacgtgtccgtcactgtgtcctcctcgaataaagcacgccgcc cgcggacatttctttttttcagtcgctcggtgattgtctgctgaacaatcgcctgcagctgtttcgccgtccccgtggcgttcgcctgatttatgcttcc gtcactcccctgctggctgatgctgactggggcataaacactgatcccgcccatgccagcaccggctgcgttcccgccgccgaccagaccac ccgaggcatacccgcgcatcaggcgatagagattagccacgccgatgcggctggttgattctttggtgaagacgaattccccgcggtgaacga taccggctggctcgtacttgccgccgtgcccggtaaaaccgcccacgtcaaaaccctgtggccggtatgacgggaccgcgaatgactgaccg gcagaggaggttttcgccccgccgctaacccagcccattgcactctggatggtgtaagccaccagcagctggttgataacggacacaatcattt taaggatcgagctggtgaattccctgaagctcgccttcccggttgtcgtcaggctggtaagctggcccgccaacccgctgaacgtagcctgaga aatctgctgaacggagctgaaaacgtttgtcgctgaatcctgatattcggcccaaccctgtttcgcaccggccagccagtttgcacgcagggcat cttcagcttcgaacgtcgcccctttgctctttccagaaccttttgctgcgcctgagggttgtacgaatagctttcgctgagacgctgcagcgtagtttgt cgcccggcttcccgggtggataacccctcagactgagcctgcaggcccgccctggcggctttttgctgctgctcaaacttcacggcctgatcgg ccagctggttgagcttttgctggctggcaaccttatcgcccaggtcggccagctgccgcttgtactcgagcgtttcttctttgtgcgccagcaggg atttttcctgcgccgtaagctgacgacgcccagcggcctcctgcagaacggtgaactgattttcagtttgccagagatcctgacgctgtttacttat gacgtcgttcacgctggtatgctgctcaagcgttttaagctgggcctgaagggtgagaagttcggcctgcgccttttcctcggctttgtccccggc gggcgttgagtagcttttgcctttcggtgtttttggatccttccactgcttttcaatcccggcgcgggccgcggcaatgtccttttcagtccacagcgt ggcgacaccgtctttcgcatcctggcggtttttctcaataagctgactgagctttttctctgctgaagcccgcttttctgccgccgtcgcgccggact ccaccagctggttaaactgctgctggctgcggattgcctgagcctgctggtccgttcgcatttttttcccgcgcggctgccagcccttcctgggcgt attgctgatcggcaagatcgtaagcctgctttttcagctccacctgctggcgcgcgtttctcagcctttccgcatccgctttctgcagaacgttgtta ccggcataatccgggtcgaccttaagattgctggacagcgcgcggtactctttctctgctgcctgccactcagcaaaagagtcctggcgcttcat cgcggtgtcaggattacgcccgacgcccagcatcgcatcccacgcaccggaggcggcattcttcacccagttccaggctttttcgagggatcc gagattatcctcgaccgcaccggcgcgctgaatgaccgcgtcggaatatgcccgcatggccagctcggcagccttctgagaatcccccagcg cctgagcagaagctatctgttcatactgggtggctgtcagaaaatgaagggaatcgttgagcgtcgcgaccgcgttaaccggatcatccttcag gcgtttaaactgatttatggtttcgtcaacggcctgcccggtagcctgctgcagcctggcggcaacattgctgaccatgctgacgtcattaccgct gaacgcgccgctgccaacgacctgcgccagcacgcctgcagcggcatgctgagtgatgccattacctgccagcgagcgcgccagcgcctg TABLE F-continued

| Phage 3 sequence with Deletion<br>SEQ ID NO: 281 |
|---|
| cagctgccctgacgttttccccgcgtagttcccggtcaggatcagctgcctgttaaattcctcagactctttgctgccgtcgtaccaggccttaccc |
| aacccgaataccgccgcggcaatccctccgaccatgctggcgatcccaagaccgcgcagtgacagaagctggtctatccaccctgcccggtt |
| agccagcgtgatcccggagccgcgcagcgcgccgaagttaccgcgcatgacctcgccgatcagtattcccagttcctgccgggcggcggca |
| ctttgcagccccagaccgtgcgtggcgactttggcagcttcgagcttgcggatatagacttcagccgcatcgctggcaccgacctgcgccgcct |
| tcatgcgcagtagctcggtaccggagagcttttgctctgcaacctgttgcttcagctggctgaggaatcgcgtgcgcgctgcggccgatttttcct |
| ccacgatctgcagttctttttgacgggccgtggtgcgggaaataagggcgagataatcctgctgggttatgttgccctgtgccctcgctgcgcga |
| aagcgcgcctgcacgttcgcaagcgactgtgtttcaccattgagctggcgtacgccgtcgatctggcggaaaaatgatgccgcaagttcatcct |
| gtcgacgggcaagcgcagcggcctgcccgtcattctcacgcatgcgctgattaagctcggtcacgcggcggtgagtttcatcaacggactttg |
| aaacgttctgccagtctttggtaagcccttccgttgcggccgactggcgggatttcatatctgcggcagccgccgcgccagcgtcacccacggt |
| tttaaacgcagccgcctgccgctctgaagcgcgctgcattcgcgtctggactttttcagagtcctcagccatcccggttagctggccctttatgcg |
| ggcaacctgctcactaaacgtggcgctgtcgacgtcaaggttgatgaccagatcgctaatctgctgggccatatcggatacctcctgttatcccct |
| cagctgcggccatcagcgcatcatcatccggctcgtcatcgctgatgacgataccggaaggagaaagcaggctgaaatgtgcgggggtaagt |
| tccgggtcgcggaagaaaagagtggagatggaataaagcagctctgagaaatgcgcatcgagctgagcgtcctgaaaataatgctcccggta |
| gaactggtgccagtcgcccagctcagtggaagtcattccagccagcatggcgcgccagtcgggtcgcccgaactcgcgcgccagattcagg |
| acaaacttcagctcgctggcaagggcttttccgccgcaacgggttctgcgctttcggcctccgctggggcatccggatcggcagctttgtcatcc |
| tcaaccggaacgagcatgccggagagcagctttatttccatttctgctttaccgatcgcctccggcggccagccgctaagcacctgctggtaaa |
| gcgtctccacatccgtgccagccggatcgttatgccacaaagacatcgcaatcaaacgcgcaccgcagcgaatatttgagccaatcagcctgg |
| ccgtcatttcctgatcgctgatgccgtcgctgtcagcgctgacggccttttcctctgcggccataaacgtgatgtactcaatacgctgaagcgccg |
| acagctcgaagatggtcagtgattctttttgccaggtgaacttctctttttttcagaaacatgcgtccttccttacgctgcagttacggtaactttgcaga |
| ccgcaacgaaattaccgtcgctggtcataacaataacgtcagcggtgcctgccgccacgccggtgacggtgatcgcattaccgctaacggtga |
| ccgttgcttttgccccgtctgaggttgccacacggaacgaggtatctgaggcactggctgggttaaccgtcacattgagcgttgtggttgcgccg |
| acggccacgcttgccgtggctttatcgagcgtaacgcctgtcacggggatattcggggtcccgctttcttctgccagttccggcttgccggtattg |
| gtaattttcgctgtacgggttatgacctcttttgccggaatggctttacccaggctgctgcaccagccgcggaaaacgtcgacggtaccgttcgg |
| gtatttgattttgtaatagcgtactgagccatcaataaaccatgcgacaaggtctttttgcccttcttcgcccggcttccaggcgagggtgaacgag |
| gtatcgccagcagattttgccccctgggccgtcgcgttccagtcggcatcctcgtcgtcgaggtaagtgtcgtcatacgattcggcggtcatttcg |
| cccggcgtcagctctttaattttcgccaggcggttccagtcgatatccgagagtgggttagcgaaagcgttgcccgttccggtgtaaagccagag |
| ggtggtaccggcacctttcacaggggccagcgggtttggagtaggcataagtacctcttaaattgaataggtgattaagtacgtgaaatcgactg |
| aaccccaggtggccatttcatcatcccgctgatagtcataaccctgcggggtgaacgtctcgaccagttcggtcagacctgggatgaaggccat |
| tgccggatacactttctcttccatccaggaatcaagcgcgctgtcggggctggaggctttaagaaatacctcgatgtgaacaaccgcctgccac |
| gaatcttcgtcaagcgattacacgtcttgagcgattgtgtaggctggagctgcttcgaagttcctatactttctagagaataggaacttcggaatag |
| gaactaaggaggatattcatatggaccatggctaattcccatgtcagtccagtgattctgaataggcgataagtccggtataaccggggataatct |
| caccattatcagcttcaaattcaggaattgtgccggtggtgatggtgtattgaggctggccatcttccttcgcgaaggctgccaggtcttcaatctg |
| cttagctgtaagaactactgtcatgctcattcctcagttgtaaaaaagccccgcgagtgcgaggcgatttgattgaattctcggctcttatctcagcg |
| cagccccttactgcgtgccggttgctcggtgatgagcatcagcgatgagacattaaagccgaccgaaggccagcggcgttcctcatgttgccg |
| acagagccatatcgacaagaggacgaaaactagcagcatgaatcgcctattggttattcgacagtcgcactgattcgtaaatccgctcacacgtc |
| attcctgcccggtagctttcgtcagatcgtccagcataatatcgagctgcttctgcaaggcttccgagcatgtcggcaagcattgctgcgttggctc |
| cggctgttttgcttctgacggaagtggcgagatctgcggtgtgctttgcggcgtccatgtgggtagcgagttttgttgcttcggcgcgcagctgctt |
| aacagtggtagccaggccagcagaagtaacggcagcgctcgctgcttgagcttgagcatctttaacggcctcatcccgggcgattgttcgccct |
| tgttcaatcatacgagctgcggtctgtgcattcgcttcctgtgaagattccgcgctatcccggtcagcccactttattttccagctgcggttcgtcca |

TABLE F-continued

| Phage 3 sequence with Deletion SEQ ID NO: 281 |
| --- |

ctcactgccagcgagaaacgaacctaccaacgcaacaatcacaatgatgcagatgccacccggcttcactggtctatcccccagcacgtcagt
gcgctttcctggtcccgccgttctacctgcccataacatccatccttctggcccttggtcaggcggcaatcgcggccaccgtctttaatccaccag
cggatagcttcacaggctcctttcgtatcgccagcattaattcgcttatagaacgtagacgggaaacattttccggggccgatgttatatgggcag
aaagaagcgatacccgctttctgtggttcggtcagtggtactttgatatttcggtcaacccacgccagcgccttgtcgcgttcaatggcgtttacct
gggcgcatttctcagctgacagcttcatgccctgtactactggcttgccatcaaccattgttgcaccacggcaaatggtccagagtccgccgccg
tcgcgatatgctgtcaagctgttaccctctttctcatccagaaactgatcgagaatcacgggtgcggaagccccggcaagaatcaaaccaacga
ccgctgcgctcaatttattcttcagctttagagacatagccattgcgccgatcctcccgttctttccagcggaaataccagttcactgcacaggtgat
taccgtgcatgcgataccgacaataattgcccagtcgctcaggcttaaccctgcaattctgtcggccaacatccaggacacctcttttgctgtttta
gctgtttcggcatatgccttcgctgatacaccgcagccggcaagcgtggttcctgatccatatgaaagtctgctgtaaatggtgctcattctggtca
tagcctcacctccgatagttcggatggcgctgtgtgtgattgaaggggatcaggcaaccgggctcttatgttcaagtaaaaattaaggatgattcc
cggtgcctgaagatggtgatcaccacagcaacgggggagcgtggtgatcgttatgatttttttcagtttttccacctcttcggtggtctgtataaacct
gtctgcctccagttctacgccgatcgcccgacggccaagttctattgcagctttcacagttgaaccagagcccataaagaaatcggcaacgatat
cccccggtctgctgctggcgctaatgatctgtttcagcatgtcggcaggtttttcgcatggatgtttgcctggataaaactgaacaggcttatgtgtc
catacgtcggtataaggaacaagagcggaaacagagaagcagcgccgaaggattttgtattcctccagcaattctgaatacttgcggtttaatga
ctggtaggtagccaccagctggtggtgaggatgttcaagcttttgctgaatatgtttatcgatggcgatccgcgtgaacagttcctgcaattttcgat
agtccacttcattcggtagttgccattggcttgcaccaaaccagtgtgacgccatgtttttctttccggttgcctcagctatttctttcgagctgacacc
cagtgattcacgggcattacggaagtaatcaatcagcggcgtcataatgtgctgctttagctctgtgcttttcctttcgtaaacatcctctttacctgta
tacggtccaagatagtgctcagcaaacaaaatccgttccgtagatggaaagtacgcacgcaggctttctttattacatccattccagcggcccgat
ggttttgcccaaatgatgtgattcaaaacgttgaatcgggcgcgcatcataatctctatatctgaggccagtcggtgaccgcaaaacaggtagat
gctgccagcaggtttaagaacgcgagcatactcagccaggcagctatcaagccagcgtaagtagtcctcgtccccccttccattggttgtcccag
ccgttgggcttcactttgaagtacggaggatccgtaactataagatcaatagagttatccgggagggtggcgacgtaatgcagactatcagcgtt
gattaactcaacactgtttatttttacagtatttttcatagatcagtaagcgtaactctgataggctcacgttgcttttgcgctaaagcagtgggccttg
gttagcttgtgacctgaaagcatgagctgatggctggccgggtgcgctaacacccaccagccgcccatttccacagcagaaaccccccattact
ggaggcgtttataacatccgaactggtaatcagataaccccgccatcaccagctgcgtaagtatgagctggcaacgttcgtggctgaggtgggt
attctgtgcaatctccccagccgttgctggtttatcgcttaattcattgaaaacagcctttgccgtttctgtcatatcttcctgatttagcatgtcttttacc
taaaattagttgcgtgacatacagataactctggttggtgataccagcaagagaagaatttgattctgcaaccaacaaggcctttaggcatcaggc
aggaatgagatgcaataaaaaaaccacccgaaggtggtcttatatgaatctttaacgcggacttagcaaatattccacatcatcgtactaccgttat
ggttttcgataatttttgcggctgggctagtaccaaaagagtgcatatagcaatgatgaatagtaaggaccagatcctgcaacgtttggtcactctc
tagctccatgatatttaaaccaatattttgagctttgtccaaatgaatatgtctggcatgtgcatacgttgcttggtggttgtttaactcatcacatatac
gcttagccttagcttcagcgtcagcctgacctgcgaacataccagtacaaagccatttctggacaatttcgttcgcccagagaattgctttttcaca
ctcgccaatcaacgttggatttagtttttggaacgtaaattgccaccattgcagtgcagcagggttggcaaaaatttccgcttttgctctctcatactc
ctcaataattgcatgagatgataacccattaaactgtggatcaattggccccaagttcgactgtttacctaaaacgatctgctcagcacaacaagca
agcattgtgccacaactcattgaaatcataggtacaatcgctcggatattggttccgaactttgaacgaagataatgaccaattgattctagagctg
cgatatcgcctccaggagtatggagtaagatatccaatcccagactcgtatctaacccattgatagcagacataagaccattttttatcatcatctga
catctggatcagatgttgaaacccaggcccccctttttgaaggaagcctgagtaataagaaattacatttcggccagtatgtttcgataaatcacgt
aagtacttgtggcgaacctcatccgctggtgtacgttgagcgatagtacccatctcacccaatacgtctatccaatttggcatgttatcaatttatca
gtatgagtacagttggtgagattgctgaccgttctgctcagtagtatttggtgttactgtgctgtatgaatagagcacaccacttctcacattcagatc
gttttgctgagcgagaacacgcatagcaaaatgctgtacggattcgccttttgaaactcttggggttgtatgcccatttttttcgtaaaattcagcagc TABLE F-continued

| Phage 3 sequence with Deletion<br>SEQ ID NO: 281 |
|---|
| gctcatgatatgtccctcgtttttttctacatctatgcaattccaggagccatcaacacaagatgtagtagttagcagtcgtcaaatacacgaaaagc |
| ctcaagatgaggcttaaaaagattctttttgataaagatttagccaaactatagcggtcaaaatgcagatttgacaagtataaaaagcacttaaagc |
| ctataaataggcagtttttgagaattaaagcatctttaatgaggttgaacaaaatgcagtcttgacgctgaacaggactttactggaacgtagagct |
| aaatggttcgatttcatgaaccagttacaaaaaaacccgctcatcggcgggtttataaaactttggcaacatatcaaatatgcttcaaatatggctta |
| ttttgttgcattttgcaagcgtgtttgaaggagatggtgaaatttacttcacatttctgccactttgagggcttcttcttcctcatagtattcaagagccat |
| ggccaacgcagattcatcaagctgggtaaaagcggcctttaacccagcccagtgccctgaatagacacgcaaccatgtcgaacggtcaacgc |
| taaccatgcgggccaacgctgcaccagcatagtctttataggtttcattatttctggttgcggcaatttcctgccctgccagccataccaggcctatc |
| agtttctttactacgcgctcctgaagggagttatcacccaggcatttctgataagttttccagacgtattcacacatcatcacctggtgcttatagcta |
| aggtcaaaaccgtagcagtaccgcaaccaggcctgctggtatccactaagcgcggacactgccctacgccacggcgcggactcaaattccgc |
| atcttttatcggcggcattggcctgcggcggctgcgtgtttccagcacatacagtggcgcggaaagtgagttaacaaagcgtggccccttctctc |
| cttcgagttcgacgagatgaattccacggcgaggggtggcatttttgtctgctggtgggtgttcactgaaagcctcaagctgcccttttgttccccc |
| agacaggtcaggtagcgcgcggcgcaattctattcttacaaaattcaggtcttgttgattcatgcttctttgcgctccatacacttaagctttcgcaat |
| tacgccgatcgccagcgcccgatccataaaacgcagtagcagctcaagctgcgtaccatgcttctgctcgaatgccggtacatcggcgtgtaa |
| ctcgtcgtggcactctctgcacagagggatcacgaagagatcatgggcttttgttgctgtccccccataccgtgccctacgatatggtgcggat |
| catctgctggccgtcggcaacactcacagggttgtgttttaacccagcgggtgtacgtctcatttatccagcggcgtcgctttggcctgagcatga |
| aagattctggagactccggatcaacagagagcgtgaggatcttcttcgccttctcctgcacgaggctggttgcagaagcggaaggcacaatgtc |
| gctttccctcatgaccgagcggatcttatcatccggaaggcgtagccccttgtgcgcaacgctttccggaataacatcagccaggtcgtttctgac |
| catccaccagcacagttccggaagcgtcaggatatgcgactcgggaaaaccagaatcacgccgaatgacttccagaatccaggataccaggt |
| ttcctgccgctatacctgcaagctgttcggtatgctgccccgacaaagtgtgatcgcaatgccagcacaggcgaatacttcctggtgggtgccgc |
| attgttgtgaagttcttgtcgtgccacgatgaatgtggccactggcattcaaaccgattactcaaccattgctcaagggaaggaagcccaccagc |
| acgctgaataacccgatcattctcgaagacctgccgcattaccggatcatcagccagcggctgaatggcggcgggaacagctcctgtactgaa |
| tgacgccatttcttctggttcaggctcaagcagaacgcgaccgcgcataaagaggtgcatcagttccgcgccgggacgaaacaacacaatccc |
| catacgatgggcgatctcgggggtaagcagagctctcacgcgacctgccccctggcaatgtgttctgcccacagtccaccaatccagcgcac |
| gcctttcgccgtgaaacgtgcctggctgaatgcatgatttgaggttacggatgtgccggttttcacttcaaaacggcccgcatcaatatgctgatg |
| ccgtggggtcatcgttccgccaagacgatacatgatgtcgttctcaaggaggaataaccgcagatcgggctctttggccttaagcagttttgcca |
| cctggcggaatgacattgacccactggctgtacagtaccgatcaacaaacgctaccttcggcgccgcggcagccagttcgttagtcaactgctg |
| tttttgttctgcaaggtcagctgcaagacgtagggcttcagagaatgattgaggaatcgtctgctgctgtgcctgctcaagctcctgccagcgatc |
| aaccagacgcgcggtaaactccggcgacagctgcgcgacaacgatataactgtcccgcttccctatcagataaaccgataccgactgattgag |
| gtgattttaacttcccccattgggggagttcaataacaccgcgctctgccaggcgttcaatggaccgtttaacatggtcatgtcttgattccacca |
| gctcagcaatatcgctgctggacatggttaacgctgttgttgctaactggctcatacttttctccatatcaggcggctgcacccgccggttcatatct |
| gctgattgttatctctacccgacctttcggcacaacgggtccccattccaccagcatgcgcttaatctggctgtcgtcttcccagacacccgcatgc |
| gtcagcgcgtcaaacagggctttgttgtaattatcgatatcccggcggcgcgcatccggcgggtacagagtgatttctaccgctgccagttcagt |
| cgatggcttcgggagacgtcgtaattgctcaatgatcgccacgcaggcagcgctctggtatttacggccagcggcgctaatgaggtgacgacc |
| ggccagcggccccttgttaggggcgcgccagtaagtgttcacgctcggaggaaaaggcaggatcagtttcacgcggcctctccccgcatattg |
| cgaacaagttcagaagcagcagtaatgatttcgctggtggcagtccgctccagccagagttgattgatattggctttcagcttgtgttgcagtgact |
| catccagcatgtcagcaccatccacctggtcgaatacaattctaacctccagcggccagatacgggactcgggaagcggatccgatactggttt |
| agctttctcacgaatgtgcatgcggatctggcgaatattggaccaactggaaacatccaggcttcccatggctgcaatgaagtcagtgctgttcat |
| gccatattcaccggatgcttcaagggcaacagtgcgaatacgttccgacatatccaggcgcacagcagcgtcatcgaattcaatcgacaacag |
| ccactcatccacaccgaacaaaatactctcacgaataagcagcttcgctttgtcgatcgttaaaggtgatacctgagtgaattccggtgcttcgac |

TABLE F-continued

| Phage 3 sequence with Deletion SEQ ID NO: 281 |
|---|
| agaatccgccgcccaggtatgcccaaacttcgattcactgaatgtgtattcttctttatcgccaaacgcagctctaacgcatgcccacgcctcgac |
| accgctgatagcaaaaatatctttctgggtgagtggcaactctgcttctggcttatcagctgcaggaggtgtggcagttacaggttgagacttgct |
| ggcagcaaattgtgccaaagccataaacgcccgcccttttgcctccagttctgtgcggttgatatagctgaaccgctcgccacgccatgacttatc |
| gaatacagctatggcaccggcaaaaaacgcgctggtgggtttctgtttttcgtcagcaggtacaaaccacacaggcagatcgaacccaatgcg |
| cccgcgaatgaatacaatgtgatcggcatcttccggccaccacgtttcactcggcgcggcttttatcaggaatacatagcgaccgcccttctcgc |
| gctgggctgctgcgtagttcatgatgtgcgtcatgccggtgatcgcctgcttctcgtggtactgcgaacggctatacggtgggttgccatagcca |
| gcgccacccagttcagccagacgttcagaccagtcctgcgtcagcgcgttatcttcggcggtgtaccatgccgggcatttcgcgttgtcgtcgtc |
| agcaaacaaatccagaactaatggaccaaatagcgcgttgatcccccaaaaaagcagatccggtgtccgccactgatcgccaacctctttcaat |
| tcgtgagctggtttgctacgcagtgccgccagcgcctggcaatatttattggtcatcatgaacggaaccccgaattttctggcagtgagtaatcaa |
| cactctggaagtttgcgcggctggctgagttagtctcccatttgccgttaacgcgttcaggccggccagcactggaccatttggtcgcgctttgca |
| ggtaaccagggaagtttttttggaatgaacagagttgccgggcggaggtattgcgcctgctcgctatcacgccaatcggcatttttgtaatccacta |
| ccaagcacaggtcatcaacagtgaattgttcccgaagacgggcgcgaatattctccagcgacgtgctgcatacctggtagcgtgagccagtag |
| tctgattcaggtaagacaaaacctgtctggcctgatcagtaatcacaacctcagggtcgggttgcgccgcaaccggacaagagggttttgaagtt |
| acttgtggttcttgttttgattttactgacggatccccaccagattctgacgggtcaaaaccgcctttttttgctggatttcgacgcctcaaattttgacg |
| ggtcggattttgatgcatcagattttgatgggtcagattttgatgcgtcagattctgacaggtgagaaaaagcagcctctcgcaacttaacgacgtt |
| aagctgatatacgttcgatgcgttacggttcccattacggcgctgcttacgggaaagccagccatccttctcaagctgagcaagggccgtcctta |
| ccgtactttctccagcaccgatttgacgtgcgatcgtgccaatagacggccagctaacaccctcatcactactgaagtcggccagacgcgccat |
| gatggcaacgctggataacttcatgcctgacgaagcgcatgcatcccatacgtaaccggttaatttagtgctcatggtcgtcctttaattctgtaaat |
| ttacgctggaattgttcaagagggctgaagcactcatgatcgtacccttcgcgaaggtatataacgcgctgtgtatctggctcccagcggacaac |
| tctgacgggaactccgtagtgatctctgaaccgccggttaacttcagccattcctcgcgcccccttctcgttcatctgaacaaatgcttctaccatcaa |
| gtctgctggctggtagttgcctccatcagccgcgttatttatgatttccacatagccgaactgggcatctttacccaccagcggcaaacatctgaat |
| tgcttagctggtctgaatcggtttacactgttcatgcgttagtttctccactgatacgacacgccaaggcgcccggagctgcacactcgcgggcgt |
| caccttttctgcctgttgaaacgaatacgtcaatcgcctgatctgaaacaccaaccccataaagcgccataaatcccaggaacccgtgaatctgg |
| tggcggagcttcttactgaataattctgaaagcattttgcgctctgatgaatcaattaccccatcagccgctgctgccatcttggcattagccagctc |
| accagatgctgctgccgctttcatctcaatgctgtacagctcaacgttatccaggctctcagcagttggaacatccaccagccatttccccttttcggt |
| tcgcctggtactcggccaagtaacaagaaccagacaggtcctccatccgttccagttctgccaaggtaaagaaccgactgccacacttctggta |
| caggtggttgtggaactggtcgatagtcatccctaaatcggaagccatacctaagcgaccatgcttgtgtgccttacacatcaggcggattgctgt |
| atttatgctgtctaccatgttgatttccctctggtagttaataatcaacttaaagttgactattgttgttagcggaaggtatgccgtcatttttgttcggata |
| aatatcaggtcgtaattgatggggagttactacccatccgccccattggcagagttgaataactctttcagaaggtactcggttctttgcaatccagt |
| tcgcaacagattgaactgattggaattcaaaccgccttgatacctctgaaatcgacccgatcgccttcacagctttagctgttacattcttgtgttga |
| gatgacatgtgttctcctatgactaagcctgcatcaatactacttatagtagcaattattagcaacttaaaatagaaatgacaactatgccttgtgcgc |
| ttaatcttctacttatggtggaaaatgctaaatacaaagactttgccgaaaggctaaacaggtctctccaagagcaatctattggagttaaagaattg |
| tcagagttcagtggtgtctcgtatgagatggcgcggcgctacactcttggtactgcaaagccgagagatgagaagatgattcgaattgcagaaa |
| gacttgccgtctcaccggcttatcttgattatggtgtgcctgttaatggtggcgacgcgccagccaaaggcacggtcagaatagagcaattggat |
| gttcatgcttcagccggttccggatatataaaccaaccattccctacaatagtgagctcaatagagattccagaagagaggatcttcgagttgtttg |
| gtcgtagaagccttgatggcatcgtcatgataaatgttgatggcgatagcatgatgcccacgctttgcccaaaggacctgcttttcatagacagca |
| aggttgaacaattcagcggcgacggcgtttatgtgttcaattttgaagacagtacgttcgttaaacgtttgcagaaggtaaaagggcgccgactg |
| gcagttctttcagacaatgaacattacccgcccttcttcatagaggagcatgaaatgaatgaactatacatattcggcaagctaatcagatgcttac |

TABLE F-continued

| Phage 3 sequence with Deletion SEQ ID NO: 281 |
|---|
| ctctaaaaatgatagagtttggctaataattaattcatcaagaaaccggcgaaagccggtttttttttacgcctccaattcctcacctcataacactaca |
| ctactaaaaatttcattttctactttttgttgttgcaattatctacttaaagtagctatagtcattgcatcgaaagcgaacaggcaggacgccccacgaa |
| gtagccgccggtggcatatgaataaccggatgattcgctgacagaaaacttaggttgggggtagaggtttacatgaatcatttattcacatgctca |
| ttttgcggagcaaccgaactgggagcgataaagatcgtcgcaaaaggtggtaaggacgaacctgccatctgttcggaatgcgtagtcacatgt |
| gtagaaaaaaatgatcctgactaaaaaatcagaggctgaaaaaccaacctctgataacgaaataatatcagtcgataaaaaactatttaaagagctt |
| cttcagcttgtcctcaaccttcctgatttcggaagtaagctggctgctgttgacattgatagtagctccacatcgacaagtgaaacttttgttcgactt |
| gagccaagcgattttcttcttcgtcttagtgccgcacttagggcatgcgggtaacgtaatttcctggttatcaaaagcgcccataaacatccctcttg |
| gttgtgtgagaacaccaagataccaccgcgcctgatgtggttaaaagcaggctaaagcaataacaagtaactccctgttctggcggcccggtgt |
| tttcccgtgtatttccggtaaccgccagcctttttcagggcacaacagaaaagggcatcaccgggcgacgggctcataacccaatccacccgg |
| gcaaaaagaaagcggtctctgcaagccgccgaccaatgcaggtgcccttctctgttgtgtatggagaaactaactttttagcgtctgtgcagatg |
| cgctgaggaaccgagaatgaataatccgtttttcaaaaatatgttggtgtatcgcattagtcgcgatttcaccatcaaccaggaagagctggaaca |
| gcagcttgaactatttcgcttcactccatgcggtagccaggatatggcaaaaaccggttgggtatcaccacttggtcagctgtcagatcgcttgca |
| tcacactgtcaataatcaagtgttgttggttattcgccgggaagaaaaaatactgccatctcctgtcattactgaagaactgcgcaagcgtgtgtcg |
| cgtctagaatccgatcaggggcgtcgcctcaaaaaaactgagaaagattcgctgcgtgatgaagtgttgcactccctgcttcctcgggcgttctc |
| caaaaactcgactgttggtttgtggatcaacgtcaccgacggtctgatcatggttgatgcagccagcgctaaacgtgccgaagactcactggcc |
| ctgcttcgtaaaactctcggttctctcccggtggtaccgctgactatggaaacgccgatcgaactaactatgaccgactgggttcgttccggtagt |
| gcgcctgctggctttggcctgggtgatgaagccgaactgaaagctattcttgaagatggcggtattggacgctttaaaaaacagactctggtcag |
| tgacgaaattcatgtgcatctggaagctggcaaagtagttacaaagctgtctatcgactggcaacagcgcattcagttcgttctttgcgatgacgg |
| cagcatcaaacgccttaagttctctaatgagattacagaacaaaacgacgatatcgaccgtgaggatgcggctcagcggttcgacgctgactttg |
| ttctgatgaccggcgagcttatctctctcattaacggattaacaacctctctcggcggcgaagccaagcgataaacaccaggcaacaattacccc |
| cataagcatgggttgggttgctgcacgctaaattcagcaattcattaatttaatggcgcggtgcagcgcgccaatatggagaaaaccatgagcta |
| cattcagacattatccggcaaacattttaattacctcgatatccaacaggacgatatcgtgatcgaggatattgctaccgcgttgtctcatatctgcc |
| gctttgcagggcatcttcctgagttttacagtgtcggccagcatagcgttttaaccagccacctcgttccgcaggagtttgcattagaagcactgct |
| tcatgatgctgctgaagcctacctgcaggacatcccctccccacttaagcgcctgcttccggattaccaggcaatcgaagctcgtgtggacgca |
| gccattcggcagaagttcggtctaccaactgagcaacacccaaccgtgaaatatgccgacctggtgatgctcgccagcgaacgccgcgatttt |
| gagattgacgaaggttccatttggccatgcctcgagggagttgtcccaacggatttattcattatcaacccagttcgtcctggccagtcatacggc |
| atgttcatcaatcgctttaacgagttgatggagcagcgccaatgcgccgcatgaaggtaaaagaactcgtagcggaggcgtttgcctccgttgct |
| gaattgccaccaaagcatgcgccgcttatgcgcgaagtcgccaccagactggacgctacgttcgcagcattaaaagagtctctggtgcaactg |
| gaacaggaacgtaaagataaaacgccatgaccgtatttgaatatctccaggctcatccgaataccaccagcggtgaaatcgccaaaggtatga |
| acaaaaagaccccagcggtcgccggagcattatctcagctctatggcaccggtcggatcgtgaagtctggtgttcgcaagggtattccaacata |
| ccgcattaacgatatgccgtttggttgcagtaacagcctaaccatgatgtttaaccagctcttgagcagagccagacaaggagcagcccaatga |
| cagcactcaacaaacaggcgctgcgtgaagaattccagttcatgcaggacaactatagcgacccggcagaccacgatcggcaggtgatttac |
| atcgaggcggaggcgctgctggatgagttggaagccaaagactcaacgatagcagcacaacaacatgagatccgtatgttgctgaatgcgctt |
| gaggaaaaaccatgcccgaaatgcaacgacacaggaatgactgatagtggcggcacgcagccatggggcgagccgattgagattgaatgc |
| gactgccgacagcaggatgccaacaccgcagaacttgtagccgctggcattggcgtgaagggggagtgagatggataaattaatcaaaccta |
| ccgccaaaggtaaatatgacggttcatgtgattatctttgctcggaagatgcgcgattcatcgttatgcgcggcgattatacggaagcggaaataa |
| ttcaggcttctgtgtctcaagatgtaatcgactcggatggtgcggctgattttgcaagtagcgcccgctattatcagtgctggtacaaagttagccc |
| aataggtggtcaggatggctattcaggctggcatcatcctcgtgattcgccgtgtcgcggtgcatatttcgcatcagttttgcaatgggattaagga |
| ggactaacccatgacaactaacaaccacccggcgcacggtcctgtatcactcgatcgcctgcaccagatacgcgaacacctgctgcatgatac |

TABLE F-continued

| Phage 3 sequence with Deletion SEQ ID NO: 281 |
|---|
| ccaatactcaaacggcgggaacagagcctacattctcgctgatgtattgaaggtgattgatggggctattgcccgcgagctggtacgccgtgag |
| catgcagcgtggtcacaggctactttcggcgatgtcggtccagttggtccgctgaagcacctttccaaagaagcgctcgaggctgctgctgaac |
| caggcgaccttagcgaatgggctgacatgcaattcctgttatgggatgcgcaacgtcgtgccggtatcagtgatgagcagattacccaggcaat |
| gataaaaaagctggctataaataaggttcgccaatggcctgagccgaaagacggggaacctcgattgcatatcaaagaacagtcagagcagg |
| agaaaaaataagaatgtttagcctgattcggcgcggtcaaatctacacggacagtagcaactggcccgtaattatccatagctgtagtgatcactc |
| ggtccgaattaaacgcaatgatggcgagctgagaacgattagcatcaaacgctttaacgaagattttgaacgagtggagcatgatgagtatcgc |
| aaaatatgtgccgaaatagagcaggaaacaaacctgaaaaacctacgtgcgatgcgtcgcggcaagattactgaatagccaaacaggagaat |
| atttaacgtgaacaacttaatgatcgaccttgagtccatgggcaaaaaaccgaatgcccctattgtctccattggtgccgtattcttcgatccgcaa |
| agcggtgaactgggtcaggagttttacaccgctgttaatcttgaaagcgctatggagcagggagcggtgccggatggtgacactattctgtggt |
| ggttaagacaaagctcagaagcacgatcagcaatctgtgttgatgatgcgatgccgatatcatctgccctatctgaactgagccatttcattaatcg |
| gcattctgataaccctaaatatttaaaagtttggggcaatggagctactttcgacaacgttatattgcgcggcgcatatgagcgtgccggccaggtt |
| tgcccgtggcaattttggaatgatcacgacgtcagaaccatcgtcacattaggcagatctgtaggtttcgatcctaagcgtgatatgccatttgatg |
| gggttgcacataacgcactggctgatgcccgccaccaggcgaaatatgtttcagcgatttggcagaaactaatcccaaccaccagcaacagct |
| aaagttttccccgggtgcagccgggataatggagaaataactatgagcaatattttccagttagctcccaacgattgggtttgtgaaagcgttttga |
| tcgcggttactgggctcaaacccggaaccatcctccgtgccagaaaagaatgctggatgattgggagggagtatatccacgtatcgcctgacg |
| gaaatcctaaaccttccagtgagtgcatgtataacagaaaggctgtagatgcctgggtcgcttcaatgaaaagcaagcaaccagggtgatttgat |
| gccatgaaaaaggtaagctcgtatcgctcttgggcgtctggaggtaacaccaatggataaagtcacatatccaacaggcgtcgaaaaccacgg |
| tggcacattacgcatctggtttaattttaaaggtaagcgtgtcagggaaagtctcggtgtccctgacaccgctaagaacaggaagatagccggg |
| gaactgcggacatcagtatgttttgccatccgcacaggaacctttgattatgcaacccagtttcctgactcccctaacctcaaggcttttggtgtaag |
| taaaaaagacattacagtgaaagaacttgaagaaaaatggctggatctgaaacggatggaaatctgcgcgaacgcatttaatcgctatgaatctg |
| tcgcaaggaatatggtgccgaggatcggaggtaatcgcctggtgtcagcagtaaccaaagaggaattgctgtatctgaggaaatatttgctaact |
| ggttatcagaatccgacgaaaaacaaagccccggcaaaagggcgaagcgttgttactgtgaactattacatgacgacaatggccggaatgtttc |
| agtttgctgcggatcacggttacttagaggtgaacccattcgagggaattaagcctctgaaaaaagccagggcagaaccagatcctctgtctcgt |
| gatgaatttattcgcctgatagatgcatgccggcatcagcagacgaaaaacctgtggtcattagcagtgtacacaggaatgcgtcacggggaac |
| tggtctccctggcctgggaagatatcgacctgaaggctggaacaattaccgtcagacgtaattatacgaaacttggtgagttcactctaccgaaa |
| accgaggcaagcacagatcgagtggtgcatcttatccagcccgcaatcagtatcctgaaaaatcaggctgaaatgacaaggctgggcaggca |
| atatcacattgaagtgcagttacgtgagtacggccgttcggtgaaccatgagtgtacattcgtctttaatccgcatgtggtcagacgcagtaagca |
| ggtcggatttatctaccgggtcgattcagtaggcgactcatgggaagcggcacttaagcgtgcggggatcagacacagaaaggcgtaccagt |
| cacgacacacctatgcgtgctggtcattatcagctggtgcaaaccctagttttattgccagtcagatggggcatgcgagcgcgcagatggtgttc |
| aatgtttacggtgcatggatggctgacagcagcgcagagcagatcgcaatgctgaatcagaagctggcagattttgccccattgatgccccata |
| gccacgagaacagtacgggaggattattaaaatcagtaagttaacccctaacgcccgtcatgttaactgtgtggagggtaacaccacgctttatg |
| ccctgccgaaacccgaggttgtcctgcgctggcgtgagcagaccacagatgacttccgcttctgttttaagtttccggcgaccatttcgcatcag |
| gcagcattacggcattgcgatgatttagtgactgaatttttgacccgcatgtcaccgttggctccgcgcattggacaatactggctgcaactgcctg |
| ccacattcggcccacgggagctgcctgcgctttggcattttctcgattctcttcccggtgaatttaattatggggtggaagtccgccatccacagttt |
| ttcgccaaaggggaagaggaacaaacgcttaatcgcggtttacatcagcgcggcgttaatcgggtgattttagacagccgcccggttcatgcag |
| cacgtccatacagtgaagctattcgcgacgctcaacgaaaaaaacctaaagttccggtacatgctgtactgacggcgaaaaatccactgatccg |
| ttttatcggtagtgatgatatgacgcaaaaccgggaattatttcaggtctggttacaaaaattagcgcagtggcatcagaccactacgccttatctttt |
| tttacatacgccagatattgcccaggccccggaactggtacatacctgtgggaagacttacgtaaaacgcttccagagatcggagcagttccg |

TABLE F-continued

| Phage 3 sequence with Deletion SEQ ID NO: 281 |
|---|
| gctattccacagcaatcttctcttttctgaatttgccacctatcatagacaggtgccatcggccattttaaagggagtttgtatggtaagcgcgctgta |
| tgccgttttaagtgcgttgttattaatgaagttctcttttgatgtcgttcgcctgcgaatgcagtaccgcgttgcctatggcgacggcggttttagcga |
| actgcaaagcgctattcgcattcatggtaacgcggtggaatatattcctatcgcgattgtgttgatgctgtttatggaaatgaatggcgcagaaacc |
| tggatggtgcatatttgcggcatcgttttgcttgctggtcgtctgatgcattattacggttttcatcaccgtctgttccgctggcgacgttctggcatga |
| gcgccacctggtgtgcgctgttgctgatggtgctggcgaatctttggtatatgccctgggagttggttttctccctgcgttagcgcacaatacgcca |
| ctttctttttcccggattttacgttatgtctcaccgcgacacgctattttctgcccctatcgccagactgggcgactggacctttgatgaacgggtag |
| ctgaagtcttcccggatatgatccagcgttccgttcccggctattccaatattatttccatgattggtatgttagccgagcgcttcgttcaacctggta |
| cgcaggtttacgatctgggttgttctctgggcgcggcgacgctctcggtgcgtcgcaacattcatcatgataattgcaaaattattgccatcgacaa |
| ctccccggcgatgattgaacgctgccgtcgtcatattgacgcctataaagcccctacgccagtagacgttattgaaggtgatattcgcgatatcgc |
| cattgaaaacgcatcgatggtggtgctgaattttaccctgcaattcctggaaccttccgagcgccaggcgttactggataaaatttatcaagggct |
| gaacccgggcggtgcgctggtgctttcggaaaaattcagtttcgaagatgccaaagttggtgaactgctgttcaacatgcaccacgactttaaac |
| gtgccaacggttacagcgaactggagatcagccagaaacgcagcatgctggaaaacgtgatgctgaccgattccgtggaaacccataaagca |
| cgcctgcataaagccggttttgagcatagcgagctgtggttccagtgctttaactttggttcactggtggcattaaaagcagaggacgctgcatga |
| tcgactttggtaacttttattctctgattgccaaaaatcatctttcacactggctcgaaacgctgcccgcgcagattgctaactggcagcgcgagca |
| gcagcacgggctgtttaagcagtggtccaacgcggtggaatttctgcctgaaattaaaccgtatcgtctggatttattgcatagcgtaaccgccga |
| aagcgaagagccactgagcgccgggcaaattaagcgcattgaaacgctgatgcgcaacctgatgccgtggcgcaaagggccgttctcactgt |
| atggcgtcaacatcgataccgaatggcgttccgactggaaatgggatcgcgttatgccccatctttctgatttaaccgggcgcaccattcttgatgt |
| cggctgtggcagcggttatcacatgtggcgcatgattggcgcaggggcgcatctggcggtgggtatcgatcccacgcagctattcctctgcca |
| gtttgaagcagtgcgtaaactgctgggtaacgatcagcgcgcacatttgttaccgttaggtattgaacaacttccggcactgaaagcctttgatac |
| cgtcttttcgatgggcgtgctttatcatcgtcgttcaccgctggagcatctctggcagttaaaagaccaactggtgaatgaaggcgaactggtgct |
| ggaaacgctggttattgatggcgacgaaaacacggtgctggtgccgggcgatcgttacgctcaaatgcgtaatgtctatttcattccttccgcgct |
| ggcgctgaaaaactggctgaagaagtgtggttttgttgatattcgcattgcagatgtgagcgttaccaccacagaagagcagcgacgcaccgaa |
| tggatggtcaccgagtctctggccgatttctcgacccgcatgatccgggtaaaacggtggaaggttatcctgcgcctaaacgcgcggtgctgat |
| tgcgcgcaagccgtaaaggtctggtaatactgccggatgcggcgtgaacgccttatccggcctacaaagtcttgctaattcaatatattgcaggg |
| gctatgtaggcctgataagcatagcgcatcaggca |

Example 60. Testing of a Phage 3 Knockout of Wild Type *E. coli* Nissle (Prior to Removal of Chloramphenicol Cassette)

As described in Example 59, primers with 40 bp overhangs and homology to pKID3 had been used to create a knock out targeting a 10 kB region of the phage genome (lambda red recombineering followed by selecting for chloramphenicol resistance). Four clones obtained were selected. Using primers for to screen for the presence of an insertion of a chloramphenicol cassette in the phage 3 genome, the expected the 200 bp band was seen for all four clones indicating a positive insertion specific to the phage 3 genome.

The same 4 chloramphenicol resistant colonies were resuspended in 1 mL of LB in 14 mL culture tubes. Tubes were grown shaking at 37 C, 250 rpm. When cells reached early log phase, the cultures were split into two 500 ul aliquots; one aliquot was treated with mitomycin C (2 ug/mL); the other was left untreated. After 3.5 hrs, 400 ul of each culture was removed and 20 ul of chloroform was added. Samples were vortexed for 15 seconds and spun down in a centrifuge at max speed for 1 min. Table 96 shows the number of plaques counted. SYN-902 is WT Nissle comprising the pKD46 plasmid.

TABLE 96

| i. Plaque Counts | | | |
|---|---|---|---|
| supernatant dilution | 0 | −1 | −2 |
| SYN-902 Φ3 knockout 1 no induction | 0 | | |
| SYN-902 Φ3 knockout 1 + MC | 0 | | |
| SYN-902 Φ3 knockout 2 no induction | 0 | | |
| SYN-902 Φ3 knockout 2 + MC | 0 | | |
| SYN-902 Φ3 knockout 3 no induction | 0 | | |
| SYN-902 Φ3 knockout 3 + MC | 0 | | |
| SYN-902 Φ3 knockout 4 no induction | 0 | | |
| SYN-902 Φ3 knockout 4 + MC | 0 | | |
| ATCC13706 (negative control) | 0 | | |
| SYN-PKU-710 + MC (positive control) | TMTC | not plated | TMTC |

TMTC: too many to count

In conclusion, no plaques were observed in any of the knock out strains, while the positive control produced a large number of plaques. These results indicate that deletion of a 10 kb internal region of phage 3 in wild type *E. coli* Nissle prevents the formation of plaques following mitomycin C treatment.

Example 61. Phage Detection Assay in a Phage 3 Knockout Strain (Wild Type Nissle and SYN-PKU-1034)

This study was conducted to test whether A phage 3 knockout in wild type Nissle and in SYN-PKU-1034 results in a negative test in a plaque assay. Table 97 describes the strains used in this study.

TABLE 97

Strain Descriptions

| Strain Name | Description |
|---|---|
| SYN-PKU-1034 | Phenylalanine consuming strain which has a AIPS comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin) |
| SYN-PKU-1034d"phi"3 | SYN-PKU-1034 with phage knockout |
| SYN001 | Wild type *E. coli* Nissle |
| SYN-903 | SYN001 with phage knockout |

In this study, supernatants from *E. coli* Nissle (SYN01), SYN-903 (the phage 3 knockout in the Nissle background), SYN-PKU-1034d"phi"3 (phage 3 knockout in negative strain), SYN-PKU-710 (positive control), and ATCC13706 (negative control) were tested for the presence of phage.

PCR analysis using a primer set specific to a chloramphenicol (cm) cassette on one end and Phage 3 on the other had previously shown that the clone SYN-PKU-1034 phage 3 KO tested positive for the correct insertion of the chloramphenicol cassette (data not shown). Insertion of the CM cassette was performed as described above in Example 59.

For phage testing, strains (SYN01 (Nissle), ATC13706 (negative control), SYN-PKU-710, SYN-PKU-1033, SYN-PKU-1034, ATCC13706 (sensitive plaque indicator strain) were grown overnight in LB (with DAP 100 ug/mL where appropriate), 3 mL in a 14 mL culture tube shaking at 250 rpm at 37 C. Top agar composed of 7 g/L agar in LB media lacking yeast extract is prepared, melted, and kept at 45 C to maintain liquid.

Overnight cultures were used to inoculate 10 LB with DAP 100 ug/mL where appropriate in 125 mL baffled flasks at a 1:100 dilution. Each test strain was inoculated into 2 10 mL cultures: one flask with 2 ug/mL of mitomycin C to induce the phage and the second flask as a log phase uninduced control. All flasks were grown at 37 C shaking (250 rpm). All cultures were grown for 4.5 hours, diluted 10-fold in PBS in a 96-well plate, and plated for determination of cell counts. Spot dilutions (10 ul) spanning the 10^−3 to the 10^−8 dilutions were plated per plate (LB plates—DAP 100 ug/mL where appropriate), in duplicate, for each strain.

After completion of the cell counts, 1 mL from each culture (3 cultures per strain) was removed and placed in a 1.5 mL Eppendorf, 50 μL of chloroform was added, and tubes were vortexed for 15-30 seconds. Cells were spun down in a microcentrifuge for 2 minutes at maximum speed. Meanwhile, a 96-well plate was prepared to contain 180 μL of LB per well in columns 2-5 and 8-11. Dilutions of supernatant were performed in this plate. 200 μL of neat supernatant for each strain was added to column 1 for samples 1-8 and column 7 for samples 9-15. 10-fold dilutions were performed with a multi-channel pipette from columns 2-5 and 8-11.

To prepare sensitive control strain, 10 mL ATCC13706 was spun down at 4000×g in 15 mL falcon tube, supernatant was decanted and cells were resuspended in an equal volume of 10 mM magnesium sulfate. 14 mL culture tubes were set up and labelled for the appropriate strain and dilution of supernatant was added. To each tube, 100 ul of ATCC13706 cell suspension was added. Neat supernatant and its dilutions were added to the appropriate tubes and the cell/supernatant mixture was incubated for a minimum of 5 min.

After incubation, 3 mL of top agar was added to tubes and the mixture was immediately spread (by pouring) onto labelled LB plates. Plates were allowed to dry and then moved to a 37C static incubator, inverted, and incubated overnight. Results are shown in Table 987.

TABLE 98

| Plaque Counts | | | | | | |
|---|---|---|---|---|---|---|
| | Supernatant dilution | | | | | |
| | 0 | −1 | −2 | −3 | −4 | |
| | Final dilution (for calculating pfu/mL) | | | | | cfu/mL |
| | −1 | −2 | −3 | −4 | −5 | culture |
| ATCC13706 uninduced stationary | 0 | 0 | | | | 3.3 × 10^9 |
| ATCC13706 + MC log | 0 | 0 | 0 | | | 1.8 × 10^7 |
| SYN001 uninduced stationary | 20 | 3 | | | | 1.8 × 10^ |
| SYN001 + MC log | 249 | 18 | 2 | | | 0 |
| SYN-903 uninduced stationary | 0 | 0 | | | | 3.5e9 |
| SYN-903 + MC log | 0 | 0 | 0 | | | 1.5 × 10^4 |
| SYN-PKU-1034dphi3 uninduced stationary | 0 | 0 | | | | 1.8 × 10^9 |
| SYN-PKU-1034dphi3 + MC log | 0 | 0 | 0 | | | 0 |
| SYN-PKU-710 uninduced stationary | TMTC | 65 | 2 | | | 2.1 × 10^9 |
| SYN-PKU-710 + MC log | TMTC | TMTC | 289 | 72 | 3 | 0 |

TMTC = too many to count

As seen in the Table above, phage 3 is responsible for plaque formation, and a deletion in central genes within the phage chromosome can inhibit the formation of plaques. Gross observation did not suggest any sort of growth defect caused by deletion of the phage sequences.

Example 62. Phage Testing of SYN-PKU-2001, SYN-PKU-1035, and SYN-PKU-1036

This study was conducted to assess the phage production in various phenylalanine strains in which the antibiotic cassette has been removed from the plasmid background, and to confirm that removal of this cassette does not allow for reformation of phage particles.

Additionally, a phage-3 knockout version of SYN-PKU-710, but still containing the cm cassette was tested. Table 99 describes the strains used in this study and related background strains.

TABLE 99

| Strain Descriptions | |
|---|---|
| Name | Description |
| SYN-PKU-710 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA. |
| SYN-PKU-2001 | SYN-PKU-710 with deltaphage3::cm |
| SYN-PKU1033 | Phenylalanine consuming strain which has a kill switch system comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU-1034has a weaker RBS upstream of the pheP portion of the PAL-pheP gene cassette in the AIP plasmid compared to SYN-PKU1033 |
| SYN-PKU-1035 | SYN-PKU1033deltaphage 3 cured entirely |
| SYN-PKU-1034 | Phenylalanine consuming strain which has a kill switch system comprising the plasmid and genomic components shown in FIG. 61 of WO2017087580, the contents of which are herein incorporated by reference in their entirety. The plasmid comprising the toxin is medium copy, and in lieu of the bla gene, the plasmid contains pLac pFNR PAL and PheP (IPTG and low oxygen inducible PAL and PheP in tandem). The antitoxin is integrated into dapA gene, causing a dapA auxotrophy. The strain further contains LAAD integrated into the genomic Ara locus and also has a thyA auxotrophy (Para::LAAD; ΔthyA; dapA::antitoxin); Note: SYN-PKU-1034has a weaker RBS upstream of the pheP portion of the PAL-pheP gene cassette in the AIP plasmid compared to SYN-PKU1033 |
| SYN-PKU-1036 | SYN-PKU-1034deltaphage 3 cured entirely |

Cultures of ATCC13706 control, SYN-PKU-2001, SYN-PKU-1035, and SYN-PKU-1036 were grown overnight in 3 mL cultures in 14 mL tubes shaking at 37 C. Cells were then diluted into fresh media with mitomycin C (2 ug/mL). Plaque assays were performed essentially as described in Example 58. Plaque counts are shown in Table 100.

TABLE 100

| Plaque Counts | | | | | |
|---|---|---|---|---|---|
| | Supernatant Dilution | | | | |
| | 0 | −1 | −2 | −3 | −4 |
| | Final Dilution (for calculating pfu/mL) | | | | |
| | −1 | −2 | −3 | −4 | −5 |
| ATCC13706 uninduced stationary | 0 | 0 | N/T | N/T | N/T |
| ATCC13706 + MC log | 0 | 0 | N/T | N/T | N/T |
| SYN-PKU-2001 uninduced stationary | 0 | 0 | N/T | N/T | N/T |
| SYN-PKU-2001 + MC log | 0 | 0 | N/T | N/T | N/T |
| SYN-PKU-1035 uninduced stationary | 0 | 0 | N/T | N/T | N/T |
| SYN-PKU-1035 + MC log | 0 | 0 | N/T | N/T | N/T |
| SYN-PKU-1036 uninduced stationary | 0 | 0 | N/T | N/T | N/T |
| SYN-PKU-1036 + MC log | 0 | 0 | N/T | N/T | N/T |
| SYN-PKU-710 uninduced stationary | TMTC | 57 | 3 | 0 | N/T |
| SYN-PKU-710 + MC log | TMTC | TMTC | 42 | 4 | 1 |

N/T—not tested;
MC—mitomycin C at 2 ug/mL

These results show that the knockout of phage 3 in SYN-PKU-710 resulted in no pfu from supernatant. Curing cassette from phage 3 knockout in plasmid strains also led to no pfu formation in supernatant.

Example 63. Generation and Analysis of SYN-PKU-2002

A version of the phenylalanine consuming strain SYN-PKU-710 in which phage 3 has been knocked out and the chloramphenicol cassette has been cured was analyzed. First, plaque formation was assessed in a plaque assay. Next, the ability of the strain to produce transcinnamic acid (TCA) was compared with SYN-PKU-710 to determine whether removal of the phage would cause any changes in phenylalanine consumption activity in vitro. Sanger sequencing of the relevant Phe degrading regions was performed to confirm that phenylalanine consuming circuitry.

First, to cure the chloramphenicol cassette, SYN-PKU-2001 (SYN-PKU-7103 with a delta phage 3::cm insertion) was transformed with pCP20, and 4 carbenicillin resistant transformants were selected for analysis. Removal of the chloramphenicol cassette was first confirmed by PCR. These transformants were grown overnight at 42 degrees to cure the pCP20 plasmid and were then streaked on LB plates (plain LB plates as control to ensure no growth, LB plus carbenicillin to confirm loss of plasmid and LB chloramphenicol to confirm removal of the chromosomal Cm cassette respectively, and LB Dap, on which the strains grow (dap auxotrophy)). Cells were also streaked on Phe agar and spotted ferric chloride to ensure LAAD activity was still present. All 4 clones turned dark green immediately, signifying a positive LAAD result. One clone was maintained for further analysis and named SYN-PKU-2002.

Next SYN-PKU-2002 was prepared for phage testing using ATCC13706 as a negative control and SYN-PKU-710 as a positive control. Plaque assay was carried out essentially as described in Example 58. Phage testing results showed no plaques in uninduced and mitomycin C induced supernatants from SYN-PKU-2002 (data not shown).

Next, flasks were prepared for testing activity of SYN-PKU-2002. Activity was tested with or without IPTG induction (aerobically), and with anaerobic induction. To perform this assay, an overnight culture of SYN-PKU-2002 was back-diluted 1:100 in 10 mL cultures in 125 mL baffled flasks (3 flasks inoculated, 1 for each condition). Cells were allowed to grow for 1 hr and 40 minutes, at which point they had entered early log phase. One flask remained untouched, the other received IPTG at 1 mM final concentration, and third flask was moved to the anaerobic chamber supplying 90% $N_2$, 5% $CO_2$, and 5% $H_2$. The cells were allowed to induce for 4.5 hours. The TCA production assay was then performed according to the standard protocol as described elsewhere herein. Essentially, bacteria were resuspended in assay buffer containing 50 mM phenylalanine. Aliquots were removed from cell assays every 20 min for 1.5 hrs for trans-cinnamate quantification by absorbance at 290 nm.

As seen in Table 101, both IPTG and anaerobic induction of SYN-PKU-2002 was observed.

TABLE 101

| In vitro Activity Measurements | | | | |
|---|---|---|---|---|
| Strain | CFU/ ASSAY | 30 | 60 | rate (umol/hr/ 1e9cells) |
| SYN-PKU-2002 − IPTG A | 8.16E+07 | 0.00488 | 0.015122 | 0.19 |
| SYN-PKU-2002 − IPTG B | 8.57E+07 | 0.00267 | 0.009158 | 0.11 |
| SYN-PKU-2002 + IPTG A | 8.00E+07 | 0.1345 | 0.273565 | 3.42 |
| SYN-PKU-2002 + IPTG B | 8.93E+07 | 0.13411 | 0.263227 | 2.95 |
| SYN-PKU-2002 − O2 A | 7.25E+07 | 0.09474 | 0.170983 | 2.36 |
| SYN-PKU-2002 − O2 B | 8.62E+07 | 0.08878 | 0.176152 | 2.04 |

All samples were sent for Sanger sequencing and confirmed that all of the Phe-degrading relevant regions in SYN-PKU-2002 were sequence accurate.

In conclusion, SYN-PKU-2002 does not produce plaque forming units (pfus) against ATCC13706, when supernatant was used form cultures that were uninduced or induced with mitomycin C. SYN-PKU-2002 contains no antibiotic markers and no plasmids. It also has phenylalanine degrading activity both with IPTG and anaerobic induction. All of the relevant regions involved in phenylalanine degradation were sequenced. Therefore, SYN-PKU-2002 appears functionally equivalent to SYN2619 except that it does not produce phage.

Example 64. SYN-PKU-2002 In Vitro Activity Measurements

A 1:100 back-dilution from overnight culture of SYN-PKU-2002 was grown to early log phase for 1.5 h before moving to the anaerobic chamber for 4 hours in the presence of 1 mM IPTG and 0.1% arabinose for induction as described herein. To perform activity assay, 1e8 cells were resuspended and incubated in assay buffer (M9 media with 0.5% glucose, 50 mM Phe, and 50 mM MOPS with 50 mM phenylalanine). Supernatant samples were taken over time and TCA (the product of PAL) was measured by absorbance at 290 nm to determine the rate of TCA production/PAL activity. Phenylpyruvate was measured using LCMS methods described herein. Results are shown in FIG. 16A and FIG. 16B.

Example 65. Analysis of Activity of SYN-PKU-2002 In Vivo—the Effect of Phage 3 Deletion from SYN-PKU-710 on In Vivo Activity in the Enterorecirculaton Model of Phenylketonuria (PKU)

The activity of SYN-PKU-2002 to produce hippurate in vivo is assessed. In this study, SYN-PKU-710 and SYN-PKU-2002 are grown in flasks and induced anaerobically, and the effect of the phage deletion on the ability of the SYN-PKU-2002 to produce hippurate and reduce serum Phe is assessed through comparison with the isogenic phage containing strain SYN-PKU-710 in vivo.

SYN-PKU-710 and SYN-PKU-2002 overnight cultures are each used to inoculate 4 2 L flasks containing 500 mL of LB with DAP 100 ug/mL. These cultures are grown for 1 hr and 45 min and then moved to the anaerobic chamber supplying 90% $N_2$, 5% $CO_2$, and 5% $H_2$ for 4 hours. Cells are then spun down at 4600×G for 12 min and resuspended in 10 mL of formulation buffer (Glycerol: 15% (v/v), Sucrose: 10% (w/v) (100 g/L), MOPS: 10 mM (2.1 g/L), NaCl: 25 mM (1.46 g/L)). Several 40 ul aliquots are removed to be used for cell counting and activity determination. Activity is determined essentially as described in Example 63 and is measured for SYN-PKU-710 and SYN-PKU-2002, respectively. The viability as determined by cellometer count for SYN-PKU-710 and SYN-PKU-2002. SYN-PKU901 (streptomycin resistant Nissle, 8e10 cfu/ml) is used as a control. Cells are brought up to 10 ml with PBS, and then mixed 9:1 with 1 M bicarbonate to achieve a final concentration of 100 mM bicarbonate, in preparation for daily gavage of 4e10 cells (3×300 ul doses).

To compare the efficacy of phage positive SYN-PKU-710 vs isogenic phageless strain SYN-PKU-2002 in vivo, strains are administered to in enu2 mice. SYN-PKU901 is administered as a control. Female BTBR-Pah enu2 mice (20-35 g) from CRL (GEMS) within 6-18 wks of age are allowed to acclimate to facility for at least 2 days. Animals are placed on phenylalanine deficient diet (Teklad TD.97152) and are given a phenylalanine enriched water at 0.5 g/L of L-Phenylalanine (Sigma) and 5% sucrose/L (Sigma) at least 2 days prior to starting study. Phenylalanine enriched water is removed for duration of study and is replaced with normal water.

On the day of the study, mice are randomized into treatment groups according to weight as follows: Group 1: H2O (n=9); Group 2: SYN-PKU901 (n=9); Group 3: SYN-PKU-710 (n=9); Group 4: SYN-PKU-2002 (n=9). Blood samples are collected by sub-mandibular skin puncture to determine baseline phenylalanine levels. Mice are then administered single dose of phenylalanine by subcutaneous injection at 0.1 mg per gram body weight, according to the average group weight. At 1, 2 and 3 h post Phe challenge, the bacteria (or water) are administered to mice by oral gavage (3×300 ul). Animals are bled and urine is collected from all animals up to 4 h post Phe challenge. Blood samples are kept on ice until processing for plasma in a centrifuge (2000 g for 10 min at 4 C) within 20 min of collection. Plasma is then transferred into a 96-well plate for MS analysis. Urine is collected in 5 mL tubes and volumes are recorded before transferring samples to MS for hippurate analysis.

Example 66. In Vivo Serum Phe and Hippurate Measurements Upon Administration of SYN-PKU-2002

The activity of SYN-PKU-2002 was assessed in vivo. To prepare the cells for the study, SYN-PKU901 and SYN-PKU-2002 overnight cultures were each used to inoculate 4 2 L flasks containing 500 mL of LB with DAP 100 ug/mL. These cultures were grown for 1 hr and 45 min and then moved to the anaerobic chamber supplying 90% $N_2$, 5% $CO_2$, and 5% $H_2$ for 4 hours. Cells were then spun down at 4600×G for 12 min and resuspended in 10 mL of formulation buffer (Glycerol: 15% (v/v), Sucrose: 10% (w/v) (100 g/L), MOPS: 10 mM (2.1 g/L), NaCl: 25 mM (1.46 g/L)). Several 40 ul aliquots were removed to be used for cell counting and activity determination. The viability as determined by cellometer count (in quadruplicate) 6.94e10 cfu/ml (+/−5.78e9).

Activity was determined using a plate based assay. Briefly, $1\times10^8$ cfu as determined by cellometer were added to 1 ml of prewarmed assay buffer (1×M9 minimal media containing 0.5% glucose, 50 mM MOPS, and 50 mM phenylalanine) in a microfuge tube, vortexed briefly, and immediately placed in a heat block or water bath at 37 degrees Celsius for static incubation (t=0). Supernatant samples from cells re-suspended in assay buffer were analyzed for the abundance of TCA over several time points using spectrophotometer at an absorbance of 290 nm. The accurate $OD_{290}$ window for TCA detection occurs in a relatively narrow concentration range. For this reason, supernatant samples were diluted to ensure that the absorbance measurement fell into the linear range for detection. Measurements were compared to a TCA standard curve. Activity was determined to be 2.72 umol/hr/1e9 cfu (+/−0.15 umol/hr/1e9 cfu).

Beginning 4 days prior to the study (i.e., Days −4-1), Pah ENU2/2 mice (~11-15 weeks of age) were maintained on phenylalanine-free chow and water that was supplemented with 0.5 grams/L phenylalanine. On the day of the study, mice were randomized into treatment groups according to weight as follows: Group 1: SYN-PKU901 (n=9); Group 2: Group 2: SYN-PKU-2002 (n=9). Blood samples were collected by sub-mandibular skin puncture to determine baseline phenylalanine levels. Mice were then administered single dose of phenylalanine by subcutaneous injection at 0.1 mg per gram body weight, according to the average group weight. At 1, 2 and 3 h post Phe challenge, the bacteria (or water) were administered to mice by oral gavage (3×250 ul). Whole blood was collected via submandibular bleed at each time point. Urine collection in metabolic caging commenced immediately after the 1$^{st}$ bacterial dose and continued to be collected for the duration of the study (4 hours).

Figure 17A:
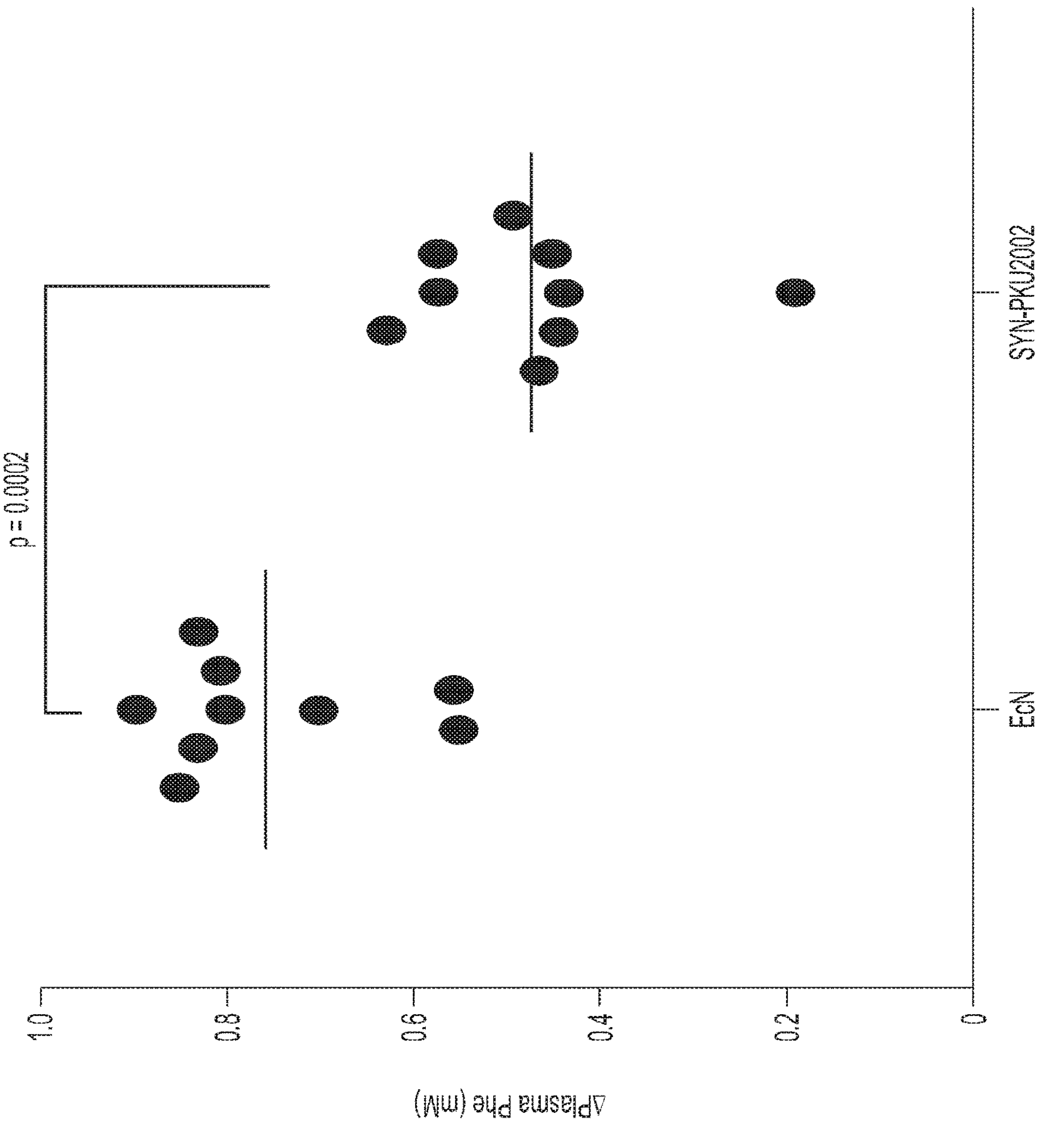
FIG. 17A and FIG. 17B depict the change in phenylalanine levels and hippurate recovery in mice gavaged with either streptomycin resistant Nissle or phage free strain SYN-PKU-2002 (which is phage free SYN-PKU-710). Mice were administered a single dose of phenylalanine (0.1 mg per gram body weight) by subcutaneous injection. At 1, 2 and 3 h post Phe challenge, the bacteria (or water no shown) were administered to mice by oral gavage (3×250 ul). Whole blood was collected via submandibular bleed at each time point and analyzed for phenylalanine levels. Urine collection in metabolic caging commenced immediately after the 1st bacterial dose and continued to be collected for the duration of the study and analyzed for hippurate levels.
Figure 17B:
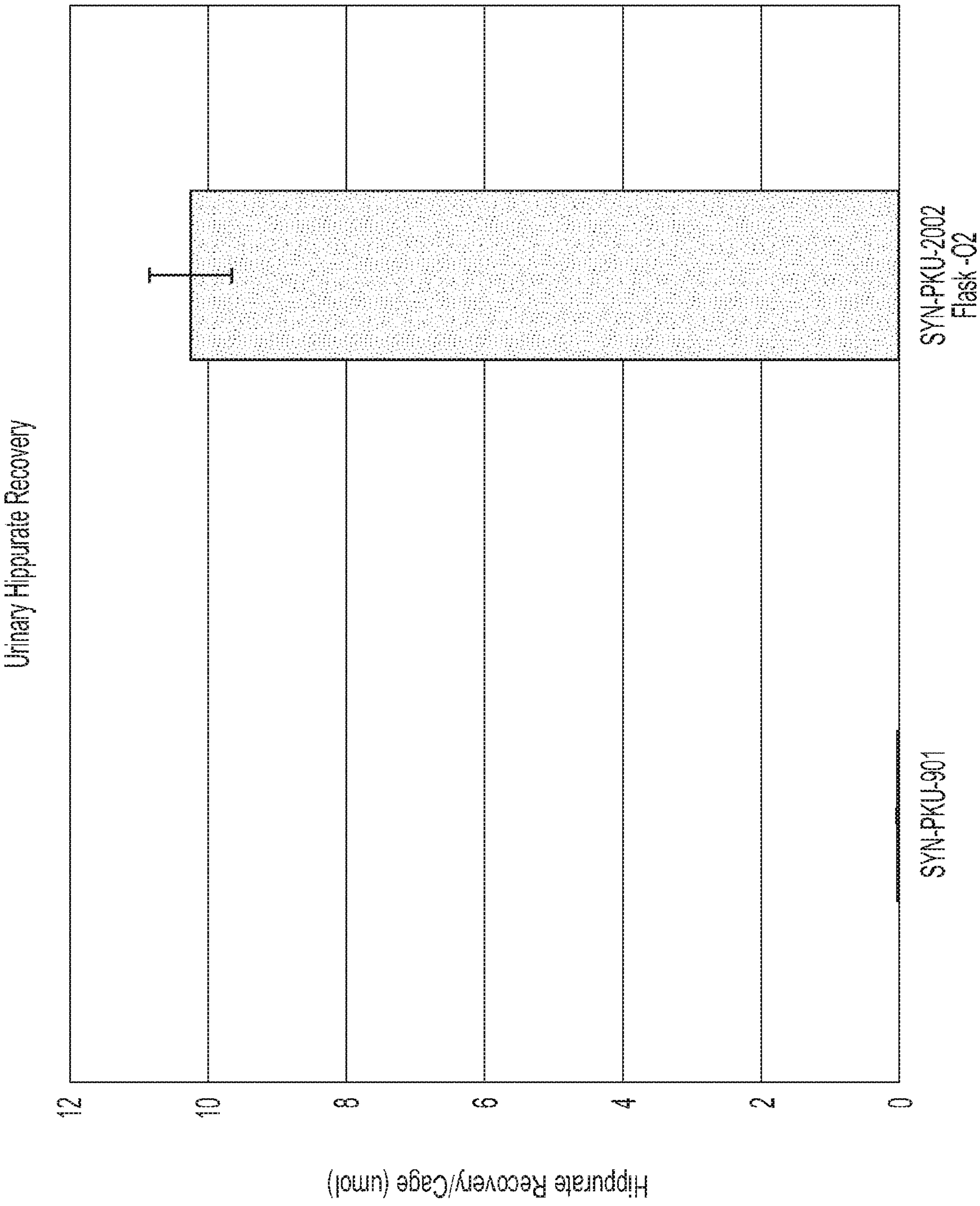

Blood samples were kept on ice until processing for plasma in a centrifuge (2000 g for 10 min at 4 C) within 20 min of collection. Plasma was then transferred into a 96-well plate for MS analysis. Urine was collected in 5 mL tubes and volumes were recorded before transferring samples to MS for analysis. Results are shown in FIG. 17A and FIG. 17B and show that SYN-PKU-2002 causes decreased changes in phenylalanine post-Phe injection and produces hippurate, in a similar manner as SYN-PKU-710.

Example 67. Efficacy of SYN-PKU-2002 in the ENU2 Murine Model of Phenylketonuria The objective of this study was to examine the dose dependent in vivo activity of the phenylalanine (Phe)-degrading probiotic SYN-PKU-2002 in the ENU2 murine model of phenylketonuria (PKU), as measured by the generation of urinary hippurate (HA), trans-cinnamate (TCA), and phenylalanine (Phe) following oral SYN-PKU-2002 administration. Efficacy of SYN-PKU-2002 as it relates to PKU was measured by the ability of orally administered SYN-PKU-2002 to decrease plasma Phe levels in $Pah^{enu2/enu2}$ mice independent of dietary Phe intake, in conjunction with the appearance of plasma TCA and HA, and was also assessed by measuring these metabolites in the plasma following Phe administration by subcutaneous (SQ) injection.

In the initial study, female $Pah^{enu2/enu2}$ mice maintained on Phe-deficient diet were weighed and then randomized by weight into 2 treatment groups (n=9 each). Blood (lithium heparin used as anticoagulant) was obtained from each mouse via submandibular bleed (T=0 h). Mice then received an SQ injection of Phe (0.1 mg/g) and were immediately placed in metabolic cages (3 mice/cage) for collection of urine. At 1, 2, and 3 h post Phe injection, mice were gavaged orally with either control SYN-PKU901 (Group 1) or SYN-PKU-2002 (Group 2) cells that had been grown and pre-induced in shake flasks ($5\times10^{10}$ cells total dose, evenly split across the 3 hourly gavages). At 4 h post-injection, plasma (lithium heparin used as anticoagulant) was obtained by submandibular bleed and the urine was collected. Liquid chromatography-tandem mass spectroscopy (LC-MS/MS) was used to measure concentrations of Phe, TCA, and HA in plasma and urine.

The study was performed similarly to the study described in Example 65 with the exception that the SYN-PKU-2002 test article used to gavage mice was grown and activated in a bioreactor using a process similar to the one intended for scale up of drug substance. Female ENU2 mice (n=63) maintained on Phe deficient diet were weighed and then randomized by weight into 7 treatment groups (n=9 each). Mice were then given a SQ injection with Phe (0.1 mg/g) and immediately placed in metabolic cages for urine collection. SYN-PKU-2002 was gavaged orally at 1, 2, and 3 h post Phe injection to 6 dose groups (n=9/dose group split into 3 metabolic cages of 3 mice/cage). Dose groups received $1\times10^{11}$, $5\times10^{10}$, $2.5\times10^{10}$, $1.25\times10^{10}$, $6.25\times10^{9}$, or $3.13\times10^{9}$ cells in total, equally split across the 3 hourly gavages. SYN-PKU901 was gavaged to a control group (n=9) at the highest dose of $1\times10^{11}$ cells. Urine was collected over 4 h. Plasma (lithium heparin used as anticoagulant). was obtained by submandibular bleed at T=0 h and at T=4 h at the highest dose group ($1\times10^{11}$ cells) for both SYN-PKU-2002 and SYN-PKU901-treated mice for the determination of plasma Phe changes. LC-MS/MS was used to measure plasma and urinary Phe, HA, and TCA. A quantitative LC-MS/MS method was not available to measure phenylpyruvate in plasma or urine.

Figure 18A:
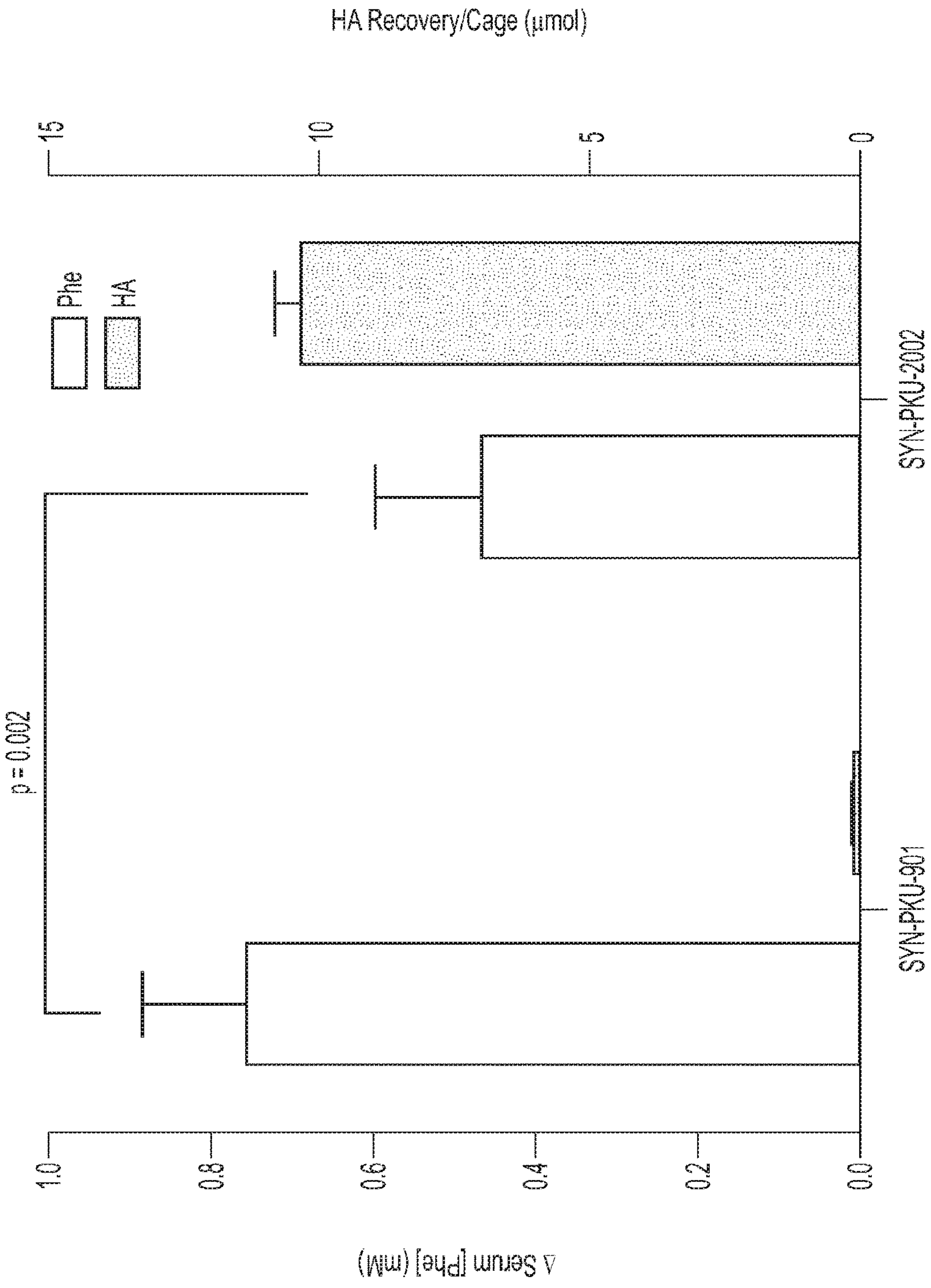
FIG. 18A and FIG. 18B depicts a graph showing changes in phenylalanine levels post Phe challenge (FIG. 18A) and hippurate recovery (FIG. 18B) from urine collected from animals treated with the indicated doses of SYN-PKU-2002. In brief, animals were transferred to metabolic cages (3 mice per cage, 2 cages per group) and administered single dose of phenylalanine by subcutaneous injection (0.1 mg per gram body weight). At 1, 2 and 3 h post Phe challenge, bacteria were administered to mice by oral gavage at the doses $1\times10^{11}$, $5\times10^{10}$, $2.5\times10^{10}$, $1.25\times10^{10}$, $6.25\times10^{9}$, or $3.13\times10^{9}$ cells. SYN-PKU901 was gavaged to a control group (n=9) at the highest dose of $1\times10^{11}$ cells. Urine was collected from all animals up to 4 h post Phe challenge. Blood was obtained by submandibular bleed at T=0 h and at T=4 h at the highest dose group ($1\times10^{11}$ cells) for both SYN-PKU-2002 and SYN-PKU901-treated mice for the determination of changes in serum Phe.
Figure 18B:
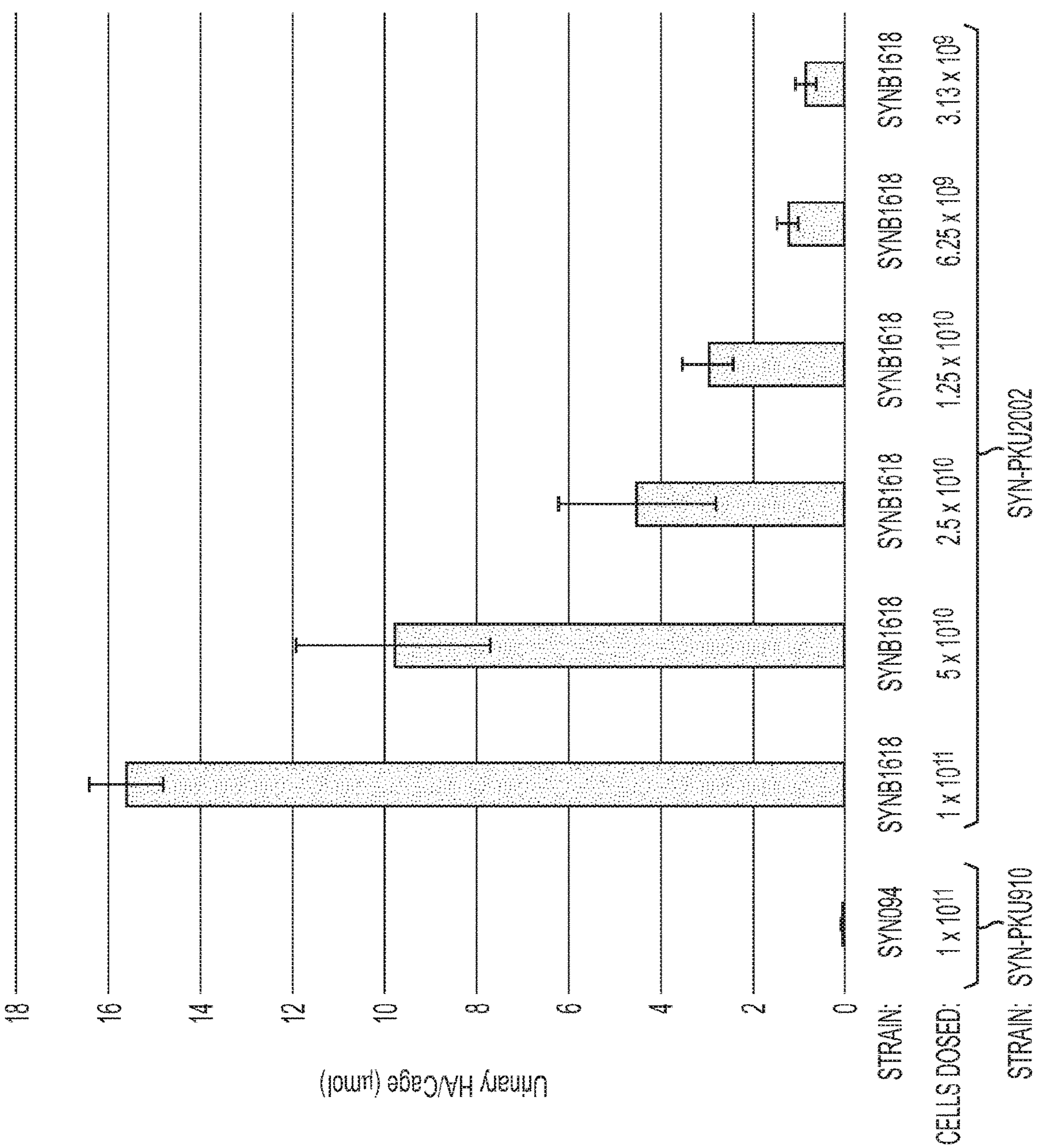

Results are shown in FIG. 17A and FIG. 18B. In the first study, following SQ Phe injection (0.1 mg/g), a plasma Phe increase was significantly blunted in ENU2 mice that received an oral dose of $5\times10^{10}$ SYN-PKU-2002 cells compared to an equal dose of the control strain SYN-PKU901 (37.7% decrease, p=0.0002). The quantity of urinary HA excreted during the 0-4 h sampling period of the study was determined by multiplying the urinary HA concentration by the volume of urine collected. Urinary HA concentrations were below the lower limit of quantitation (BLLOQ; <0.04 mM) in mice treated with the control strain SYN-PKU901, while concentrations in mice administered SYN-PKU-2002 were high (ranging from 6.59-7.97 mM), resulting in measurable HA excretion over 4 hours (10.24±0.59 μmol). TCA and HA were not observed in the plasma of any of the mice at T=0 but were detected 4 h post administration in the group receiving SYN-PKU-2002. TCA and HA were not measurable in the plasma of mice treated with the control strain SYN-PKU901 at any time point, indicating that TCA increases were due to SYN-PKU-2002 activity and demonstrating SYN-PKU-2002 function in vivo. Urinary concentrations of Phe and TCA were BLLOQ in all samples.

In the second study, efficacy was also observed when SYN-PKU-2002 was grown in a bioreactor under conditions similar to the process used for scale-up of drug substance. Following SQ Phe injection (0.1 mg/g) in ENU2 mice, a plasma Phe increase was significantly blunted in the group that received an oral dose of $1\times10^{11}$ SYN-PKU-2002 cells compared to an equal dose of SYN-PKU901 cells (29.3% decrease, p=0.02). Additionally, increases in urinary HA excretion were observed in mice treated with SYN-PKU-2002 in a dose-dependent manner (15.61±0.81, 9.81±2.11, 4.52±1.70, 2.97±0.55, 1.24±0.23, and 0.86±0.25 μmol of HA were excreted in mice dosed with $1\times10^{11}$, $5\times10^{10}$, $2.5\times10^{10}$, $1.25\times10^{10}$, $6.25\times10^{9}$, or $3.13\times10^{9}$ SYN-PKU-2002 cells, respectively). Mice treated with $1\times10^{11}$ SYN-PKU901 cells, the highest dose used for SYN-PKU-2002, did not excrete a large amount of HA (0.08±0.02 μmol). Similar to the first study, TCA and HA were not observed in the plasma of any of the mice at T=0, but were detected at 4 h post-administration in the group receiving SYN-PKU-2002 and not in animals receiving SYN-PKU901. HA excretion in urine correlated well with the amount of SYN-PKU-2002 cells dosed, indicating that the metabolite HA is a promising biomarker of in vivo SYN-PKU-2002 activity.

In conclusion, these data demonstrate the Phe-metabolizing activity of SYN-PKU-2002 in vivo by increasing the circulation of plasma TCA and HA and greatly increasing the amount SYN-PKU-2002 activity in the ENU2 mouse model. The second part of the study showed that SYN-PKU-2002 grown in a bioreactor using a process intended for the scale-up of drug substance was active in vivo. In this experiment, plasma Phe levels increased in mice when given an SQ injection of Phe along with orally administered control strain SYN-PKU901; however, mice orally dosed with SYN-PKU-2002 had a significantly blunted spike in plasma Phe concentrations following SQ Phe injection. Importantly, this result indicates that systemically circulating Phe reaches the intestine through enterorecirculation and is subsequently broken down by orally administered SYN-PKU-2002 in the gastrointestinal (GI) tract. This experiment demonstrated that SYN-PKU-2002 can decrease circulating Phe levels in blood, independent of the dietary intake of protein

Example 68. Viability Comparison Between Phage Containing and Phage Free Phenylalanine Consuming Strains In Vivo To identify potential differences in viability, transit or colonization between the phage containing phenylalanine strain SYN-PKU-710 and its phage-free counterpart SYN-PKU-2002, an in vivo competition study was conducted and a competitive index of SYN-PKU-710 vs the isogenic phageless SYN-PKU-2002 strain was generated. Because neither SYN-PKU-710 or SYN-PKU-2002 have antibiotic cassettes, marked strains that are uncured of antibiotic resistance were used in this study. For SYN-PKU-710, the chloramphenicol/kanamycin (cm/kan) marked strain SYN-PKU-713 was used. For SYN-PKU-2002, the chloramphenicol (cm) marked strain SYN-PKU-2001 was used. Table 102 lists strains relevant to this study.

TABLE 102

| Strain Descriptions | |
|---|---|
| Strain Name | Description |
| SYN-PKU-710 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA. |
| SYN-PKU-713 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3:cm; rhtC/rhtB::LacIPAL3:kn; ΔdapA (chloramphenicol and kanamycin resistance) |
| SYN-PKU-2002 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA; with phage3 KO, cured of cm resistance |
| SYN-PKU-2001 | malEK::PfnrS-PAL3; malPT::PfnrS-PAL3; yicS/nepI::PfnrS-PAL3; lacZ::PfnrS-pheP, agaI/rsmI::PfnrS-pheP; Para::LAAD; exo/cea::LacIPAL3; rhtC/rhtB::LacIPAL3; ΔdapA; with insertion of phage3 KO frag::cm and cured of pKD46 (not cured of chloramphenicol resistance; with chloraphenico resistance |

Briefly, overnight cultures of SYN-PKU-713 and SYN-PKU-2001 were used to inoculate 100 mL of LB (also containing DAP 100 ug/mL and appropriate antibiotics) in 500 mL baffled flasks. The cultures were grown for 6 h, at which point they were spun down in a centrifuge at 4000×g for 15 minutes for collection. Supernatant was discarded. Cells were resuspended in approximately 7 mL of formulation buffer (Glycerol: 15% (v/v), Sucrose: 10% (w/v) (100 g/L), MOPS: 10 mM (2.1 g/L), NaCl: 25 mM (1.46 g/L)). Cells were aliquoted into 650 μL aliquots and frozen at −80 C. Smaller aliquots were removed for cell plating and viability determination. Using a cellometer, viability was shown to be very high, and cell numbers fairly comparable between the strains.

All cell counts for this study (including input) were obtained by plating so that input (gavage) and output (feces) could be consistently compared. The two 650 μL aliquots were thawed on ice, mixed 1:1, diluted in sodium bicarbonate (9 parts cells:1 part 1M bicarbonate (144 uL), and then plated out in quadruplicate for quantitation on kan/cm and cm (from −8->−10 dilution by 10-fold 10 uL spot plating).

On Day 1, wild type B6 mice (n=6) were gavaged with 200 ul cells (approximately 3×10^9 of each strain). Fecal pellets were collected 6 hours prior and 6 hours post gavage. On days 2 and 3, mice were gavaged with 200 ul cells and fecal pellets were collected 6 hours prior and 6 hours post gavage. On days 4 and 5, fecal pellets were collected.

Each day, collected fecal pellets were weighed in tubes containing 1 ml PBS and homogenized. To determine the CFU of Nissle in the fecal pellet, the homogenized fecal pellet was serially diluted, and each sample was plated onto LB plates containing chloramphenicol and plates containing kanamycin. The plates were incubated at 37° C. overnight, and colonies were counted. To determine the amount of the two strains in the feces, total recombinant Nissle was counted on cm plates, and the number of SYN-PKU-713 obtained on kan plates was subtracted from the total amount to determine the number of SYN-PKU-2001 CFUs.

Figure 19:
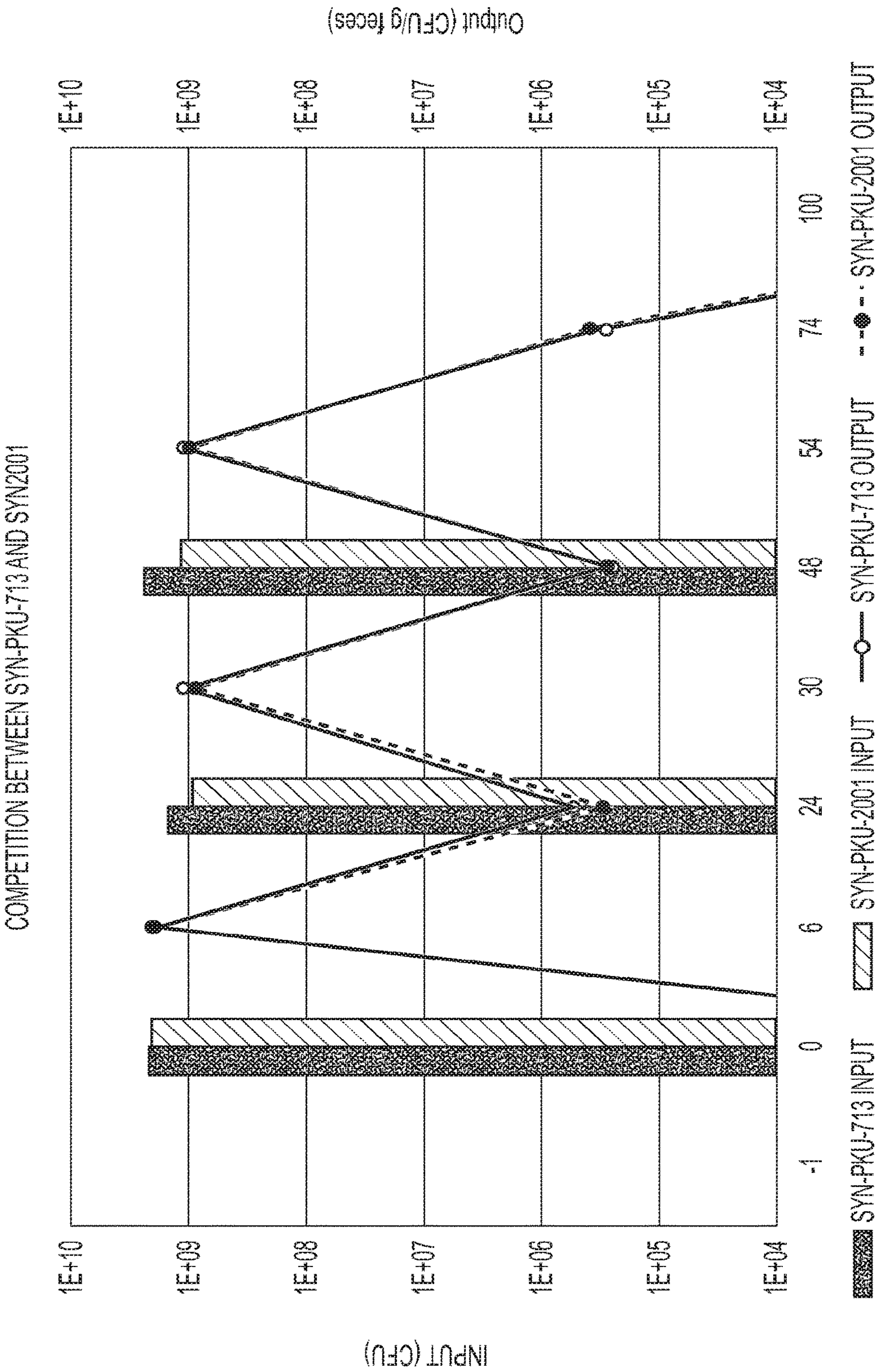
FIG. 19 depicts a graph showing the outcome of an in vivo competition study between phage containing and phage free strains SYN-PKU-713 and SYN-PKU-2001. Mice were administered equal amounts (approx. 3×10ˆ9 of cells) daily for three days. Each day fecal pellets were collected and CFUs determined in plating assay based on the different antibiotic resistances of the two strains, as described in the Examples. Results indicate that there is no large difference in transit or colonization between the phage-free PKU strain of Nissle SYN-PKU-713 and SYN-PKU-2001.

Results are shown in FIG. 19 and the competitive index (SYN-PKU-713 input/SYN-PKU-2001 output are shown in Table 103.

TABLE 103

| Competitive Index of Output<br>Competitive index of output (SYN-PKU-713 output/SYN-PKU-2001 output): | | | | | | | |
|---|---|---|---|---|---|---|---|
| Time (h) | M1 | M2 | M3 | M4 | M5 | M6 | AVG |
| 6 | 0.6 | 1.1 | 2.1 | 1.6 | 1.8 | 1.4 | 1.4 |
| 24 | 1.7 | 1.2 | 1.2 | 22.5 | 2.9 | 1 | 5.1 |
| 30 | 1.2 | 1 | 0.9 | 1.5 | 1.8 | 0.9 | 1.2 |
| 48 | 1.5 | 1.1 | 1 | 1.1 | 1.5 | 0.1 | 1.1 |
| 54 | 1 | 1.2 | 0.9 | 1.1 | 1.2 | 1.8 | 1.2 |
| 74 | 0.4 | 0.4 | 0.8 | 1.8 | 1.6 | 0.7 | 0.9 |
| 100 | NA | NA | NA | NA | NA | NA | NA |

Results indicate that there is no large difference in transit or colonization between the phage-free PKU strain of Nissle SYN-PKU-713 and SYN-PKU-2001.

Example 69. General Bacteriophage Testing Protocol for Strains Derived from *E. coli* Nissle The following procedure detects a DNA sequence found in EcN prophage/phage. It amplifies phage and prophage DNA within the EcN genome in SYN-PKU-2002 as the primers amplify outside of the region of prophage deleted to generate the bacterial strain for SYN-PKU-2002.

The validated bacteriophage (phage) method, GP-V708, Plaque Assay of Bacterial Virus from *E. coli* Using Mitomycin C Induction, measures the presence of phage using a plaque assay. Testing confirms that phage detected is from the endogenous EcN prophage and not from a contaminating phage, or adventitious agent.

The plaque assay starts with a loopful or scrape of frozen sample, negative and positive bacterial cultures which are grown in enriched medium supplemented with 10 mM thymidine at 37±2° C. and shaken at 200-300 RPM overnight. A portion of the sample, positive control (*E. coli*, EMG 2: K [lambda], ATCC 23716, or equivalent) and negative control (*E. coli*, ATCC 13706, or equivalent) is removed and centrifuged, and each supernatant examined in a plaque assay for the presence of bacteriophage. Mitomycin C, at a final concentration of 2 μg/mL, is added to the remaining sample, positive and negative bacterial cultures. The cultures are then placed at 37±2° C. and shaken at 300-400 RPM until lysis occurs in the positive control (~4.5 hours). Each culture is treated with chloroform, centrifuged, and a 0.1 mL aliquot of the supernatant is examined for the presence of bacteriophage. To accomplish this, supernatants are mixed with phage-sensitive *E. coli* strain ATCC 13706, mixed with 0.7% agarose solution, and plated as a lawn atop LB agar. The test is considered valid if plaques are present in the positive control and no plaques are present in the negative control.

Plates containing the strain of interest that contain enumerable plaques are identity tested by end point PCR to confirm that plaques are from phage generated from the endogenous EcN prophage. This is accomplished by first creating an agar plug of individual plaques with a 2 μL pipet tip and resuspending each plug in 0.5 mL of deionized water. Plug resuspensions are vortexed for 15 sec and 1 μL is used as template for PCR. As a negative control, an agar plug from the same plates is created from an area which does not contain plaques. A total of 10 plaques are tested per sample, when available. In cases when less than 10 plaques are formed per sample, all plaques are analyzed. One (1) negative control plug is tested per sample. As additional controls, pure broth cultures of EcN and ATCC 13706 are grown overnight in enriched medium at 37±2° C. with shaking at 200-300 RPM. One hundred (100) μL of stationary cultures are added to 0.2 mL thin wall tubes and heated at 98° C. in an Eppendorf Mastercycler Pro thermocycler for 10 min to prepare genomic lysate to be used as template for PCR.

Overall samples and controls used as template for each PCR assay were:

a. Sample: 1 μL of up to 10 resuspended plaques picked from an enumerable plate
b. Negative control: 1 μL of 1 plug picked from a non-plaque area from the enumerable sample plate
c. Negative control: 1 μL from lysed stationary culture of *E. coli*, ATCC 13706, or equivalent strain (plaque indicator strain)
d. Positive control: 1 μL from lysed stationary culture of the strain of interest cells PCR is used to amplify a region of EcN-specific phage followed by detection of PCR amplified fragment at the endpoint of the reaction via gel electrophoresis. Primers (Integrated DNA Technologies, Skokie, IL) used for the amplification of EcN-specific phage are shown in Table 104. The primers were selected after careful examination of the EcN phage and amplify a region within the EcN-specific phage but do not bind to any region in the genomic DNA within the phage-sensitive *E. coli* strain ATCC 13706 that is used for plaque detection.

TABLE 104

EcN-Phage-specific PCR Primers

| Primer description | Primer sequence | SEQ ID NO |
|---|---|---|
| EcN phage forward primer | 5-gcatcaatcagtgattggc-3 | SEQ ID NO: 132 |
| EcN phage reverse primer | 5-ACGTCTGAATATACGGGCTG-3 | SEQ ID NO: 133 |

Abbreviations:
EcN = *E. coli* Nissle 1917

The reactions are carried out in 0.2 mL thin wall tubes using an Eppendorf Mastercycler Pro PCR machine. A master mix is prepared for the phage-specific primers. Primers are reconstituted to a final concentration of 100 μM in nuclease-free sterile water. Master mixes are prepared per the recipe in Table 105.

TABLE 105

PCR Master Mix Preparation

| Reagent | Per rxn (μL) | Final Concentration |
|---|---|---|
| Nuclease-free sterile water | 8.8 | N/A |
| Forward primer (10 μM) | 0.1 | 0.12 μM |
| Reverse primer (10 μM) | 0.1 | 0.12 μM |
| 2X MyTaq ™ Red Mix | 10 | 0.2 U/μL |

Abbreviations:
N/A = not applicable;
PCR = polymerase chain reaction;
rxn = reaction Nineteen (19) L of PCR master mix is added to each 0.2 mL PCR tube followed by addition of 1 μL of PCR template into individual tubes. The tubes are capped, placed in the PCR machine, and the reaction cycle run following parameters in Table 106.

TABLE 106

PCR Reaction Cycle

| Stage | Temperature (° C.) | Time (min:sec) |
|---|---|---|
| 1 | 95 | 5:00 |
| 2 | 95 | 0:15 |
| | 58 | 0:15 |
| | 72 | 0:10 |
| 3 | Repeat Stage 2: 25 cycles | N/A |
| 4 | 72 | 1:00 |
| 5 | 45 | N/A |

Abbreviations:
° C. = degrees Celsius;
min = minute(s);
PCR = polymerase chain reaction;
sec = second(s)

Five μL of each standard, sample, or control reaction are loaded onto a 0.8% agarose gel for separation by electrophoresis and visualization using a Syngene UV transilluminator. The approximate size of the amplified band is 350 bp for the presence of EcN-specific phage while the negative control does not produce any bands.

Example 70. SYN-PKU-2002 Toxicology Study

The dosing duration for the GLP toxicology study is 28 days in male and female CD-1 mice with BID dosing (twice daily). Doses cover an approximate range of 1×109, 1×1010, and 1×1011 CFUs. The highest concentration is the maximum feasible dose. Mice are assessed for test article related mortality, clinical observations, body weight, hematology, clinical chemistry, and macroscopic and microscopic pathology. Following cessation of dosing, fecal samples are taken from mice for several days to assay for the presence of SYN-PKU-2002 DNA using qPCR analysis to determine the decrease in SYN-PKU-2002 over time. Blood also is evaluated for the presence of SYN-PKU-2002 DNA using qPCR. The design of the 28-Day Mouse GLP Toxicology Study is outlined in Table 107.

TABLE 107

Design for 28-Day Mouse GLP Toxicology Study
4-Week GLP Toxicity Study of SYN-PKU-2002 in Mice with 2-Week Recovery Phase

| | | | | |
|---|---|---|---|---|
| Purpose | Determine subchronic toxicity of test compound<br>Determine reversibility of test compound effects<br>Determine TK profile and exposures associated with findings<br>Determine excretion/clearance of SYN-PKU-2002 in feces | | | |
| GLP Status | GLP | | | |
| Species, Strain | Mouse, CD1 | | | |
| Test Article | SYN-PKU-2002 | | | |
| Route/Number Doses | Oral (PO)/twice daily (BID, 6-8 hours between the doses) | | | |
| Treatment Duration | 28 days | | | |
| Recovery | 14 days | | | |
| | | Dose/day | Numbers of Animals | |
| Study Design | Group | (CFU)* | M | F |
| | 1 (Control) | 0 | 12 MS + 6 Rec | 12 MS + 6 Rec |
| | 2 | ~2 × $10^9$ CFU | 12 MS + 6 Rec | 12 MS + 6 Rec |
| | 3 | ~2 × $10^{10}$ CFU | 12 MS | 12 MS |
| | 4 | ~2 × $10^{11}$ CFU (maximum feasible dose) | 12 MS | 12 MS |
| | MS = main study; Rec = recovery<br>*draft doses estimated based on prior programs<br>CFU = colony forming units | | | |
| Mortality | All animals, 2X daily (AM, PM) | | | |
| Clinical Observation | MS animals, 1X daily, detailed observations | | | |
| Body Weight | All animals- pretest, weekly, and prior to necropsy (fasted) | | | |
| Food Consumption | MS animals, weekly | | | |
| Veterinary Exams | MS animals, standard assessments | | | |
| Ophthalmology | All animals- pretest and prior to necropsy (Main study animals. Recovery animals if significant ophthalmic changes are noted at end-of-dosing. | | | |
| Hematology/Serum Chemistry | MS animals- at least 3/sex/group for hematology<br>MS animals- at least 3/sex/group for clinical chemistry<br>Recovery- at least 3/sex/group for hematology<br>Recovery- at least 3/sex/group for clinical chemistry | | | |
| Urinalysis | Main study and recovery animals (Week 4 and Week 6) | | | |
| Necropsy | Day 28 (Main study animals) and Day 42 (Recovery animals) | | | |
| Fecal Excretion of SYN-PKU-2002 (non-GLP) | Fecal samples will be collected from all animals predose, Days 7, 14, 21, 28, and from recovery animals Days 30, 35 and 40 and SYN-PKU-2002 DNA will be quantified using a qPCR method (Taqman chemistry) that uses primers specific for SYN-PKU-2002 | | | |
| Gross Necropsy/Organ Weights | All animals, standard organ list | | | |
| Histopathology | All animals, standard tissue list, evaluate control and high dose animals, read down when findings are seen. | | | |
| Toxicokinetics | A sample of blood will be collected on Day 28 just prior to necropsy and analyzed for the presence of SYN-PKU-2002 DNA using a qPCR method (Taqman chemistry) that uses primers specific for SYN-PKU-2002 | | | |

24. Example 71 Assessment of Gastric Phenylpyruvate in a Pig Model

Levels of gastric phenylpyruvate in two pigs (which had a duodenal cannula) at various times prior and post administration of SYN-PKU-2002.

Two days prior to administration of SYN-PKU-2002, two pigs were put on liquid diet with protein shake/apple juice for 2 days. On day 0, pigs were anesthetized and intubated, and ~250 ml (~50 g) Peptone, 3×10e12 bacteria (SYN-PKU-2001 in 30 ml)+24 ml 1M bicarbonate flush (2 g) were instilled at T=0.

Figure 20:
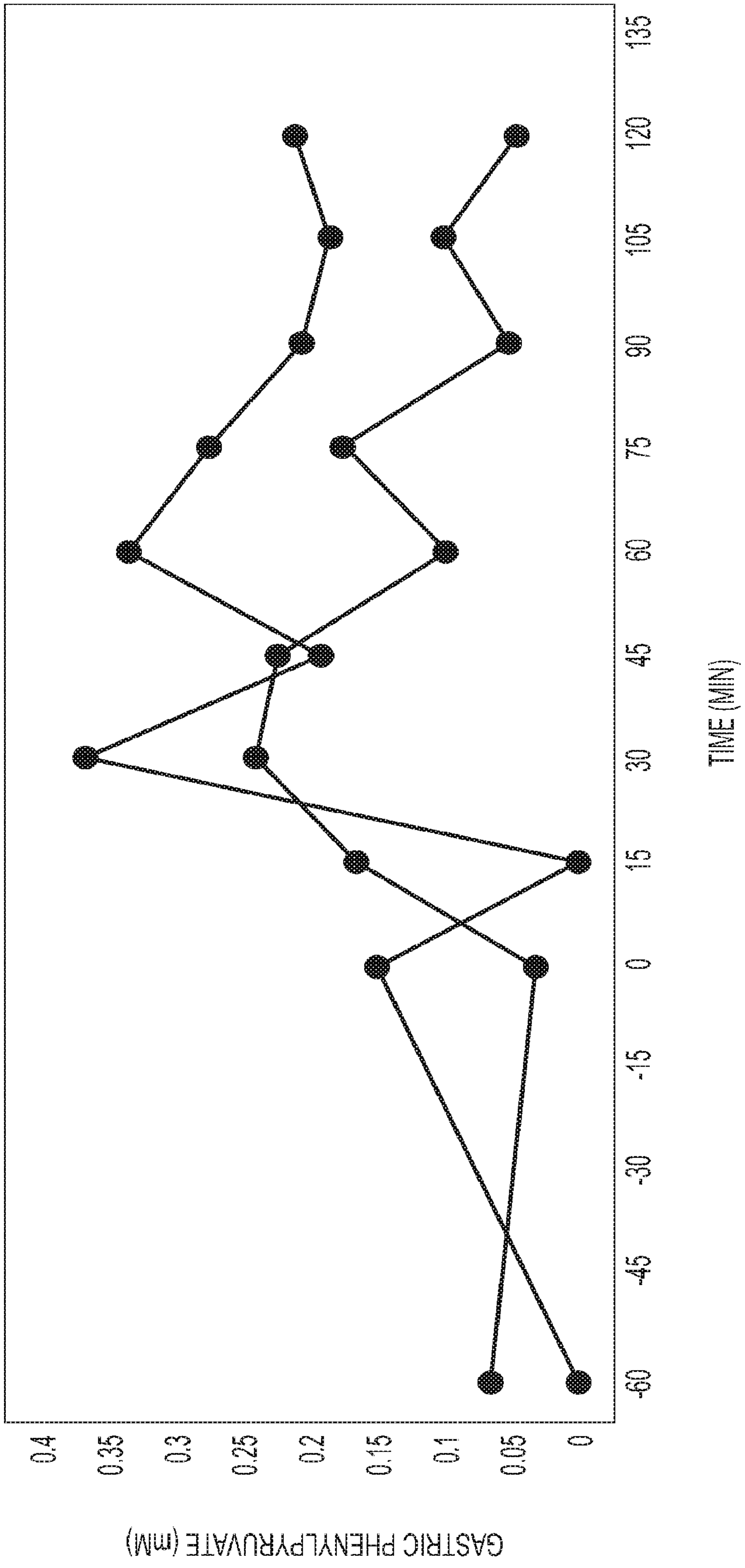
FIG. 20 depicts a graph showing measurements of gastric phenylpyruvate in two pigs at various times prior and post administration of SYN-PKU-2001.

Next, 1 ml gastric samples were taken at T=0, 15 min, 30 min, 45 min, 60 min, 75 min, 90 min, 105 min, 120 min. Samples were immediately spun down, the supernatant frozen and the tube with the pellet put at 4 C. Additionally, 1 ml blood samples were taken at T=0, 30 min, 60 min, 90 min, and 120 min, collected in heparinized tubes, spun, plasma collected and frozen. When possible, urine was collected and frozen. Results are shown in FIG. 20 and indicate that LAAD is active in the stomach.

Example 72. Conversion Efficiency of Oral Trans-Cinnamate to Urinary Hippurate in Non-Human Primates Studies of SYN-PKU-2002 activity and efficacy were next extended to fasted healthy non-human primates (NHPs), a translational model with more relevant metabolism and GI physiology to the human. A cohort of 6 Cynomolgus monkeys (2.5-4 kg) was used. Though not a PKU phenotype, healthy NHP physiology is helpful for informing future clinical studies that will likely initially be performed in healthy humans.

All NHP studies described herein were performed at Charles River Labs (Shrewsbury, MA) in compliance with all applicable sections of the Final Rules of the Animal Welfare Act regulations (Code of Federal Regulations, Title 9), the *Public Health Service Policy on Humane Care and Use of Laboratory Animals* from the Office of Laboratory Animal Welfare, and the *Guide for the Care and Use of Laboratory Animals* from the National Research Council. Six male NHP subjects aged 2 to 5 years were used (2.5-4 kg), and were maintained on International Certified Primate Chow (PMI nutrition, 5048). Subjects were fasted overnight (16 h) before initiation of all studies. For all studies, immediately prior to dosing, animals were separated into individual cages and an angled pan was inserted at the bottom of each cage to aid in the collection of urine. Orogastric tubes were used for all oral dosing.

Figure 21:
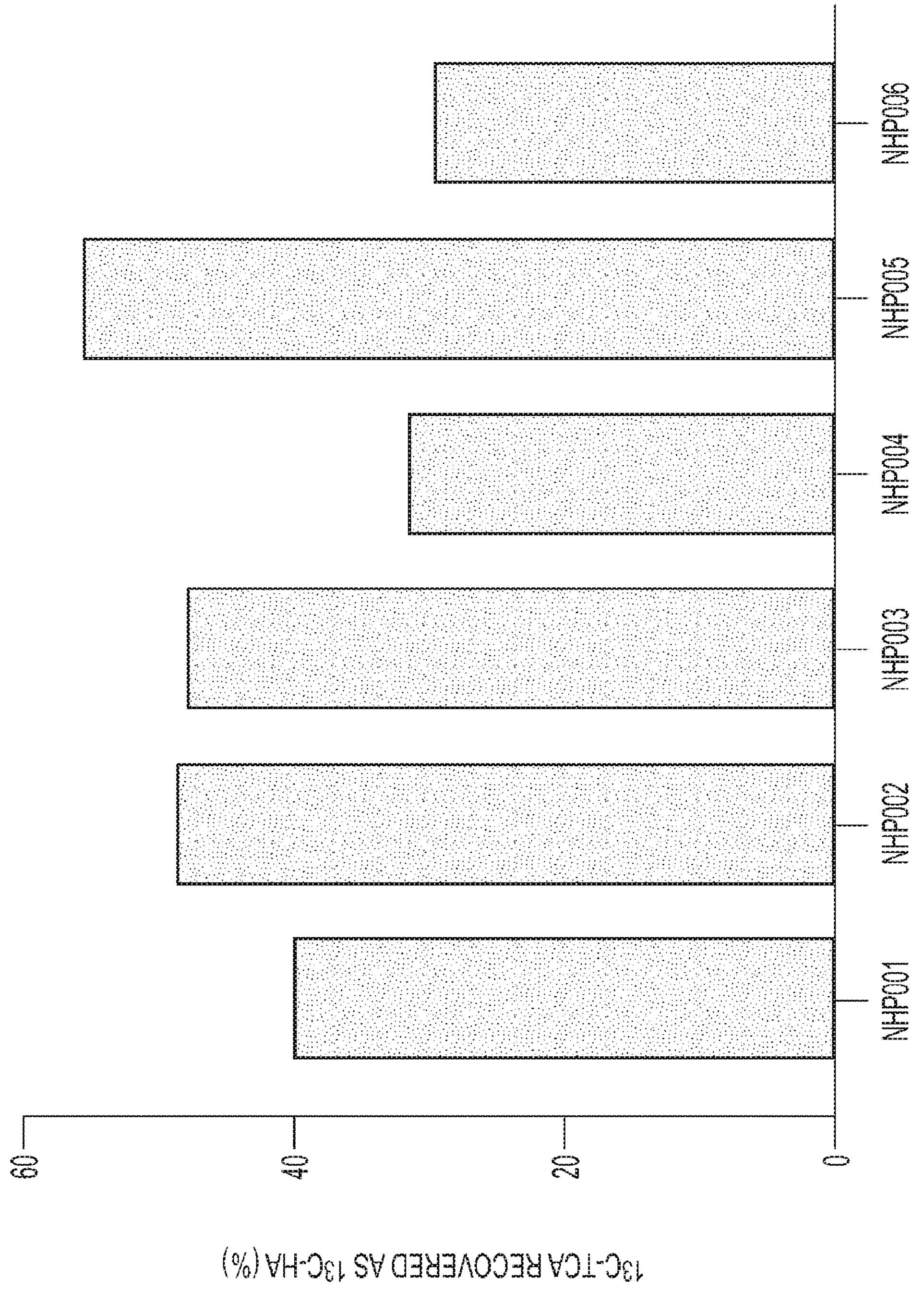
FIG. 21 depicts a graph showing conversion efficiency of oral trans-cinnamate to urinary hippurate in non-human primates. NHPs (n=6) were orally administered $^{13}$C-trans-cinnamate ($^{13}$C-TCA) and urine was collected over 6 h. $^{13}$C-Hippurate ($^{13}$C-HA) was measured by mass spectroscopy. The percentage of urinary $^{13}$C-HA recovered as a function of $^{13}$C-TCA administered was calculated and used as a normalization factor for HA recovery in subsequent experiments. This factor accounts for TCA that is not converted to HA or that is lost to incomplete urinary collection, thus allowing a more accurate description of strain activity.

First, the conversion efficiency of orally administered TCA to urinary HA in monkeys was measured for calculation of a normalization factor to use in subsequent experiments. Each NHP was orally administered 10 mL of Peptone from meat (500 g/L; Sigma, 70174) and 15 mL of $^{13}$C-TCA (12.5 mg/mL; Cambridge Isotopes Lab, CLM-7498-PK) dissolved in 120 mM sodium bicarbonate, followed by a 2 mL water flush. In this manner, the in vivo PAL/Phe degradation activity of SYN-PKU could be inferred from urinary HA recovery. Isotopically labeled $^{13}$C-TCA was orally administered and urinary $^{13}$C-HA was measured. An average of 41.9±10.3% of the orally administered $^{13}$C-TCA was recovered as urinary $^{13}$C-HA (FIG. 21).

Example 73. Profiling and Efficacy in Non-Human Primates (NHPs)

Efficacy of SYN-PKU-2002 in a non-human primate model was assessed.

In all studies described herein animals were separated into individual cages and an angled pan was inserted at the bottom of each cage to aid in the collection of urine immediately prior to dosing. Orogastric tubes were used for all oral dosing.

NHPs were orally administered 10 mL of Peptone from meat (500 g/mL) or water as a mock. Next, NHPs were administered 10 mL of SYN-PKU-2002 resuspended in formulation buffer (previously grown in activated in a bioreactor and thawed on ice) or formulation buffer alone as a mock. Finally, NHPs were administered 5 mL of 0.36M sodium bicarbonate followed by a flush with 2 mL of water. Where applicable, 1 h post dosing regimen, animals were injected intravenously with 12.5 mL of $^{13}$C-Phe (20 mg/mL). Animals were bled at 0, 0.5, 1, 2, 4, and 6 h by venipuncture. Where applicable, animals were given 3.5 mL of $d_5$-Phe (20 mg/mL; CDN Isotopes, D-1589) following mock protein dose. At 6 h post dosing, the urine collection pan was removed and the contents poured into a graduated cylinder for volume measurement. All samples were stored at −80° C. until LC-MS/MS analysis.

Phe area under the curves (AUC) were calculated with the linear-trapezoidal method using R and the PKNCA package (Denny W, D. S., and Buckeridge C. Simple, automatic, noncompartmental analysis: The PKNCA R package. *J Pharmk PharmD* 42.1, 11-107, doi:10.1007/s10928-015-9432-2 (2015)), and models to describe the AUCs were estimated with the rstanarm package. AUC0-last for $d_5$-Phe were calculated with the linear-up/log-down method. Mean and credible intervals for labeled Phe AUC and the treatment difference were calculated using a hierarchical Bayesian model with a fixed effect for treatment (vehicle or cells) and a random effect per animal.

For growth and induction of strains in bioreactors, a sterile loop was used to inoculate cells in 50 mL of FM2 medium (Supplementary Table 2) in a 500 mL Ultra-Yield™ flask (Thomson). Cells were grown at 37° C. with shaking at 350 rpm until an $OD_{600}$ of ~5 was reached, at which point 30 mL of the culture was used to inoculate 4 L of FM2 in an Eppendorf BioFlow 115 bioreactor (starting $OD_{600}$ of ~0.02). The fermenter was controlled at 60% dissolved oxygen with agitation, air, and oxygen supplementation, and controlled to pH 7 using ammonium hydroxide. At $OD_{600}$ of ~1.5, cells were activated by creation of a low oxygen environment (10% dissolved oxygen), and the addition of IPTG (1 mM). At $OD_{600}$ of ~20, L-arabinose (0.15% final concentration) was added and the cells were grown for an additional hour. Cells were harvested by centrifugation at 4,500×G for 30 min at 4° C., resuspended in formulation buffer, and stored at −80° C. until the day of testing.

Figure 22A:
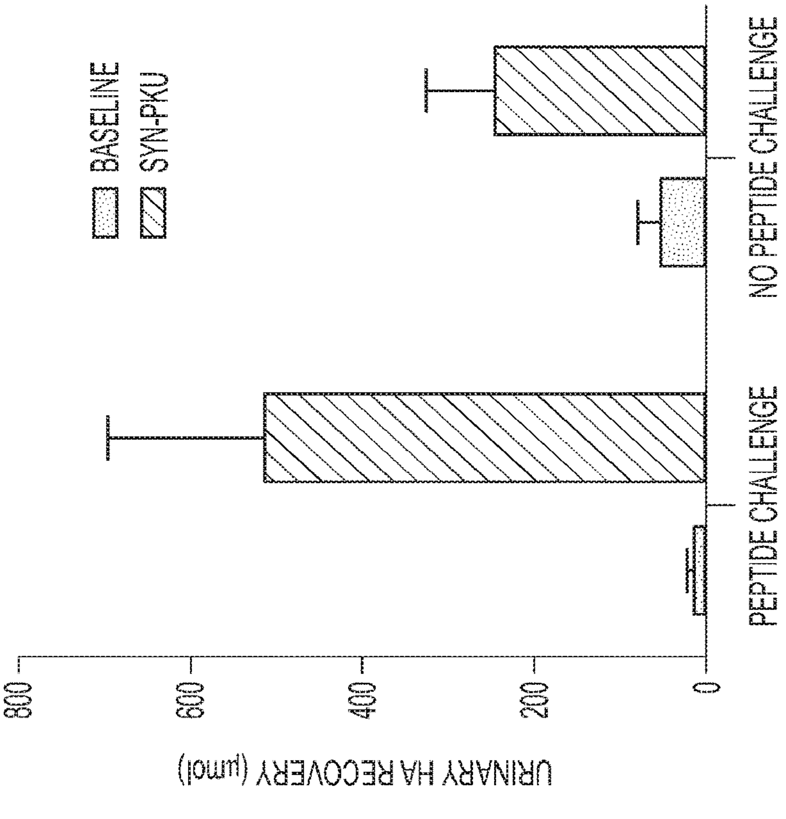
FIGS. 22A, 22B, 22C, 22D, and 22E depict graphs showing profiling and efficacy in non-human primates (NHPs).
Figure 22B:
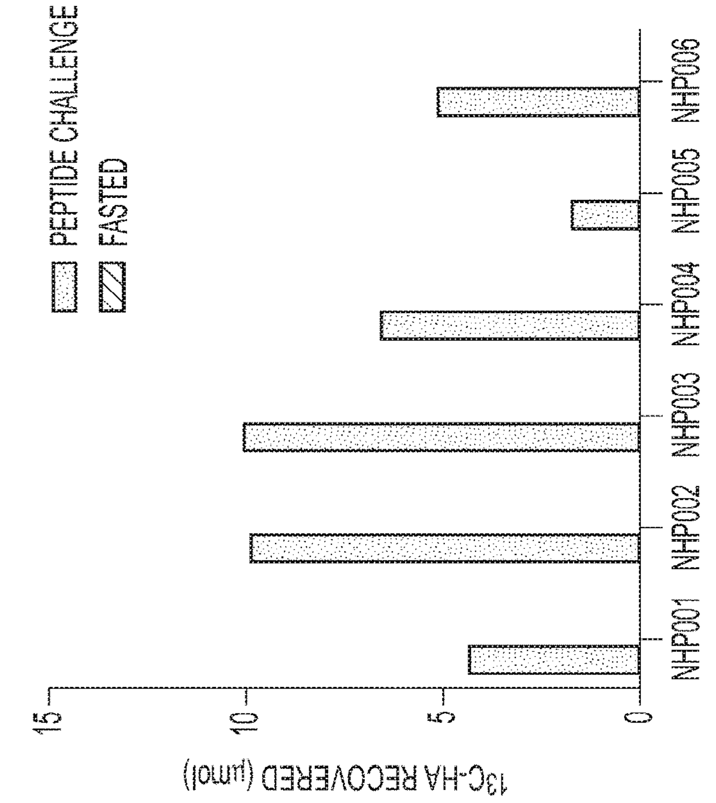
Figure 22D:
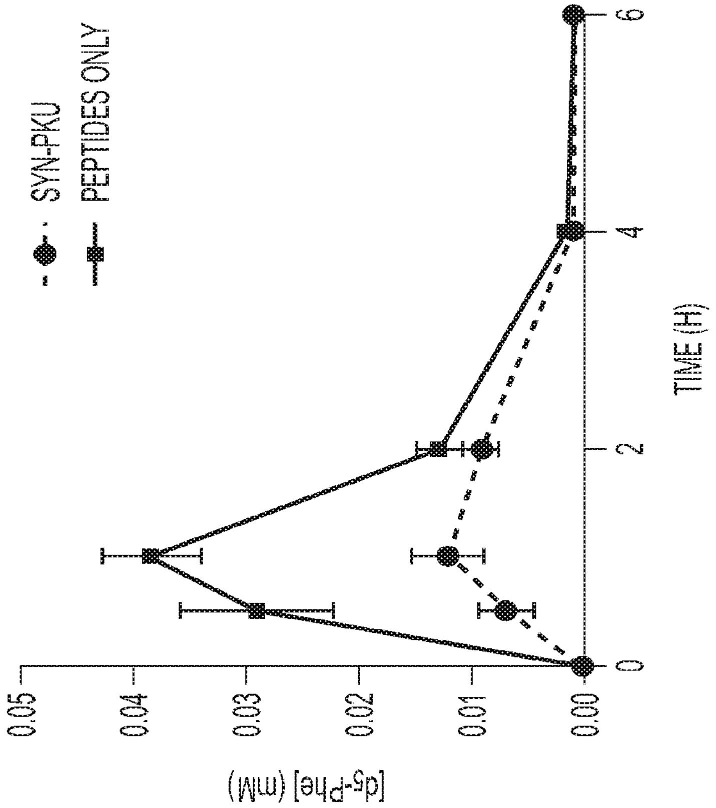

First, fasted monkeys were administered a 5 g peptide challenge with and without SYN-PKU-2002 administration and urinary HA was measured. All animals showed a significant HA response when treated with SYN-PKU-2002 compared to baseline levels without cell administration (FIG. 22A, left). Interestingly, significant HA was recovered in fasted monkeys that did not receive a peptide challenge (FIG. 22A, right), suggesting that, the primate GI tract may be a reservoir for Phe. In both preceding experiments (FIG. 22A), to examine the process of enterorecirculation in monkeys, subjects that received SYN-PKU-2002 were also injected with $^{13}$C-Phe intravenously 1 h following peptide challenge and $^{13}$C-HA was measured in urine (FIG. 22B). No $^{13}$C-HA was detected in the group that did not receive peptide, however, $^{13}$C-HA was detected in the group administered a peptide challenge, demonstrating that enterorecirculation occurs in primates, is associated with protein intake, and can provide Phe that can be consumed by SYN-PKU-2002.

Figure 22C:
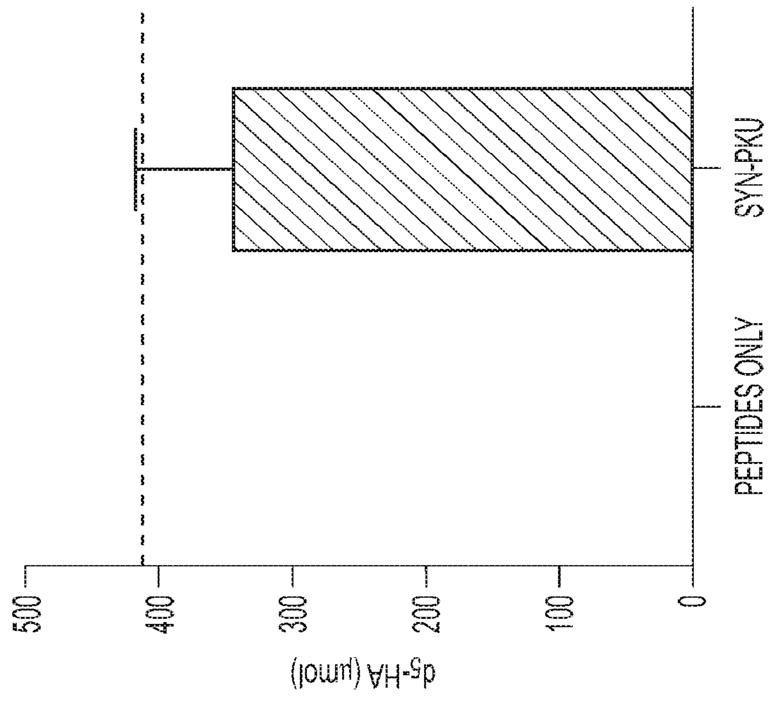
Figure 22E:
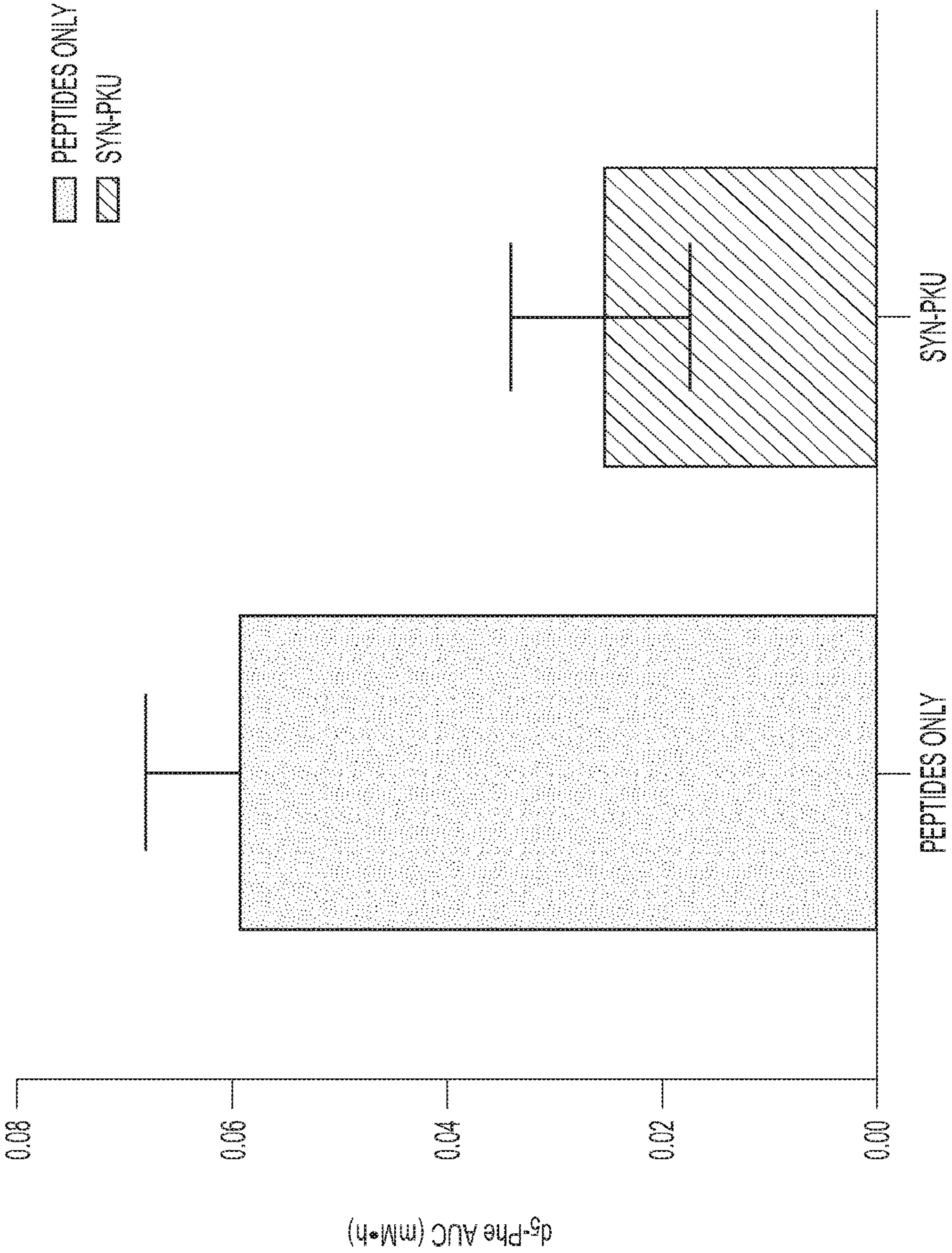
Figure 23B:
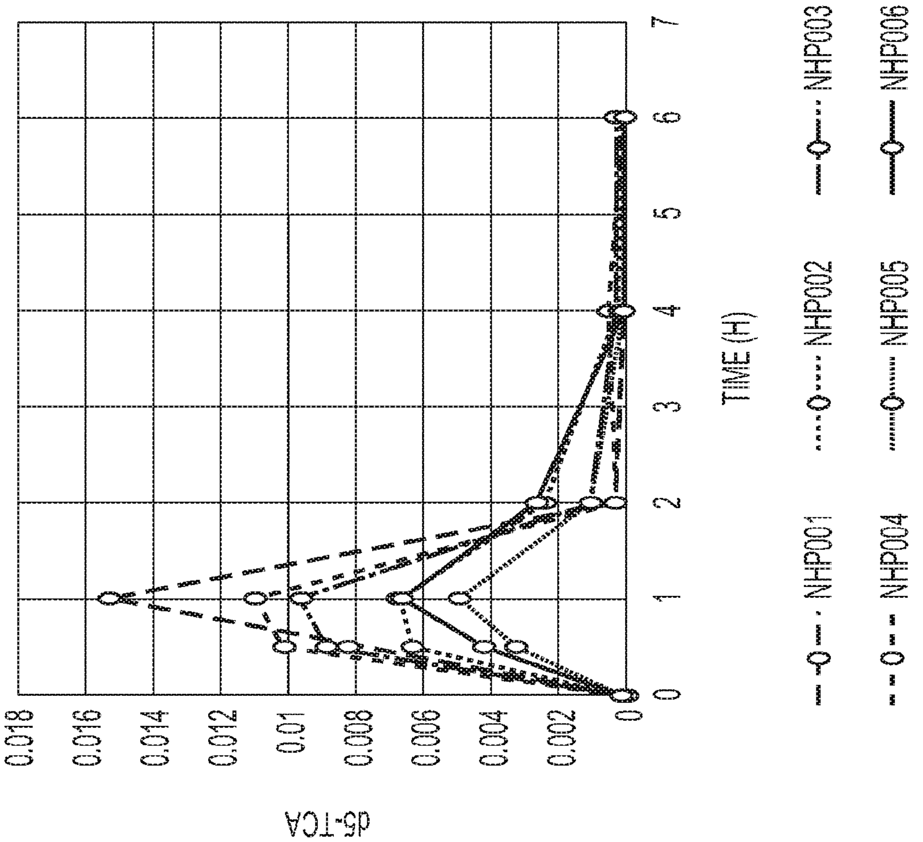
FIG. 23A and FIG. 23B depict graphs showing SYN-PKU-2002 specific metabolite detection in serum of non-human primates. Using LC-MS/MS, serum concentrations of d5-HA (FIG. 23A) and d5-TCA (FIG. 23B) were determined in non-human primates administered d5-Phe and SYN-PKU-2002 orally. No detectable d5-HA or d5-TCA was detected when d5-Phe was administered in the absence of SYN-PKU-2002 (data not shown). The presence of these metabolites demonstrates SYN-PKU-2002-specific activity in these animals.
Figure 23A:
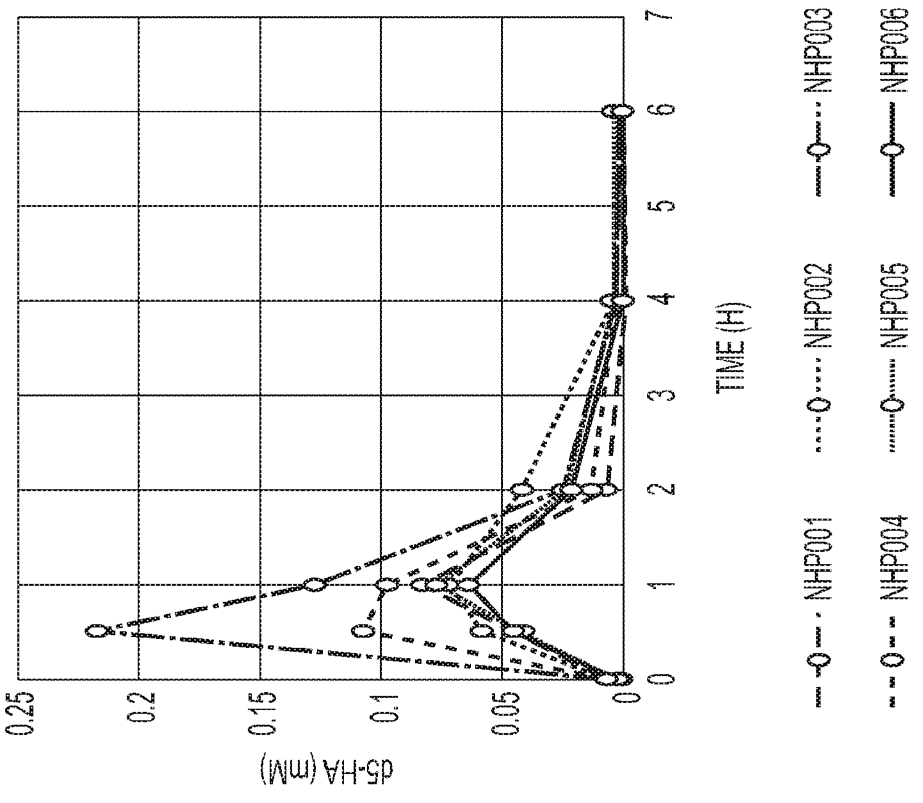

In the definitive study, the ability of SYN-PKU-2002 to lower serum Phe in monkeys was determined. However, this is difficult in healthy subjects (non-PKU), as high concentrations of protein are required to even slightly elevate serum Phe levels (by body mass, the 5 g peptide challenge used in monkeys equates to ~100 g challenge in an average adult male). Baseline Phe levels and its low dynamic response in serum post peptide challenge due to a functional PAH enzyme obfuscates detection of serum Phe lowering by SYN-PKU-2002. For these reasons, an oral deuterated Phe ($d_5$-Phe) challenge was performed. The quantity of $d_5$-Phe administered (70 mg) equated by body mass to the Phe contained in ~30 g protein for an average adult human male, consistent with an amount that may be present in a typical meal (Layman, D. K. Dietary Guidelines should reflect new understandings about adult protein needs. *Nutr Metab* (*Lond*) 6, 12, doi:10.1186/1743-7075-6-12 (2009)). As expected, baseline $d_5$-Phe was undetectable in urine and serum but could be detected in blood following its administration (FIGS. 22C and D). Following SYN-PKU-2002 administration, normalized $d_5$-HA recovery in the urine demonstrate that the majority of the $d_5$-Phe administered was metabolized to $d_5$-HA (FIG. 22C). SYN-PKU-2002-specific metabolites $d_5$-HA and $d_5$-TCA were also detected in serum (FIGS. 23A and B). Most importantly, an increase in serum $d_5$-Phe was remarkably blunted upon SYN-PKU administration (FIG. 22B), concomitant with a highly significant decrease in the AUC of serum $d_5$-Phe (FIG. 22C; 58% decrease with a 90% credible level between 29.4 and 57.8%).

High resting Phe levels in the GI tract of monkeys can also be inferred from the significant HA recovery observed in fasted animals that received SYN-PKU-2002 but no peptide challenge. Enterorecirculation was also shown to exist in monkeys, though difficulty working in a non-PKU background and inability to sample intestinal effluents easily in these animals indicates that more work must be performed to understand the mechanistic basis of this process. Regardless, maintenance of a reservoir of substrate may increase the therapeutic utility of SYN-PKU-2002, and impose less constraints on the timing of therapeutic administration with meals in PKU patients.

Example 74. Assessment of LAAD in Expression of Phe in Non-Human Primates

Efficacy of of LAAD expression and determination of any negative effects on PAL metabolism of Phe was assessed.

Figure 24B:
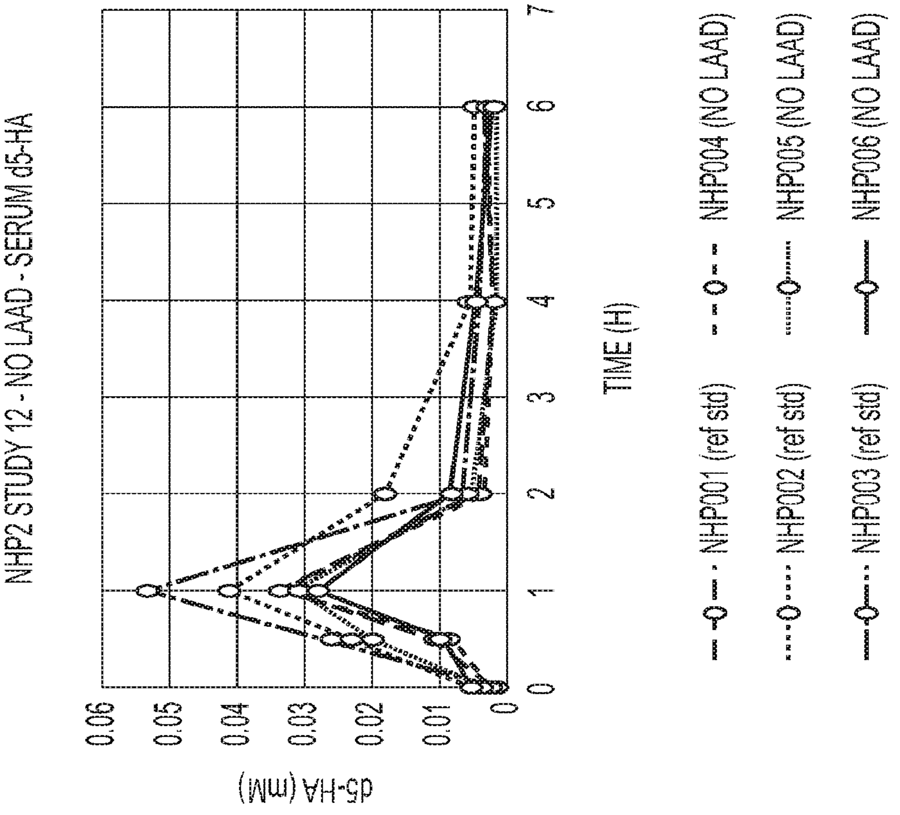
FIG. 24A and FIG. 24B depict the conversion of trans-cinnamate to urinary hippurate in NHPs.
Figure 24A:
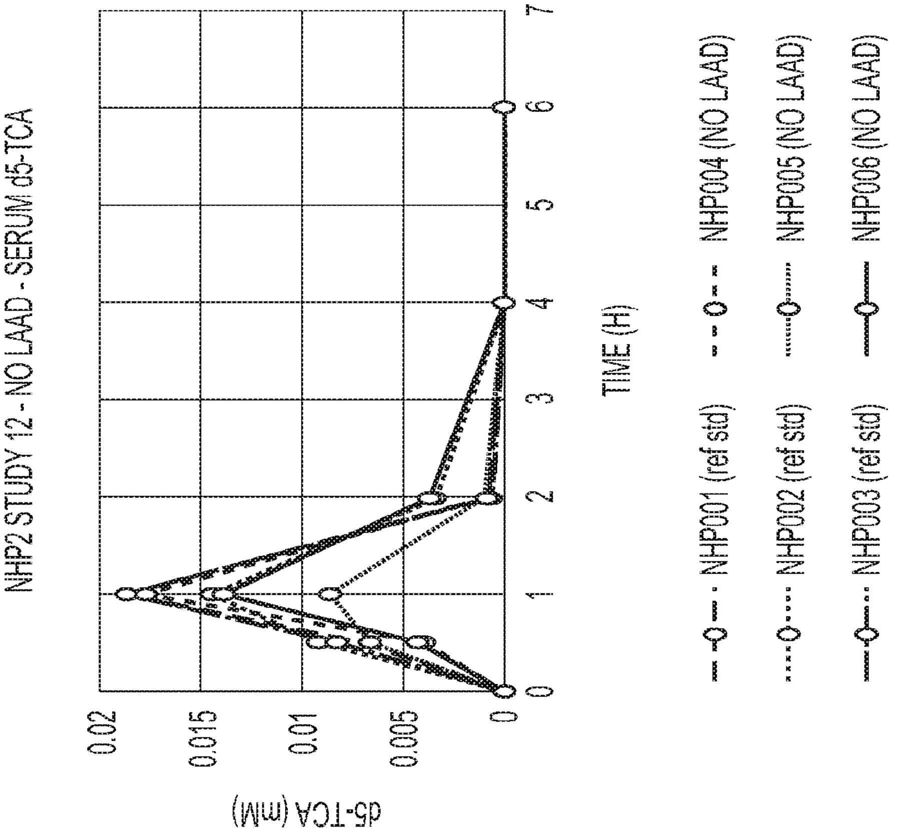

At T=0, the urine pan was emptied, and Non-Human Primates (NHPs) were orally administered 5.5 g of Peptone from meat in 11 mL, and 10 mL of an oral gavage bacteria. A SYN-PKU-2001 ($5\times10^{11}$ CFU) oral gavage bacteria strain was administered to NHP's 1-3. A SYN-PKU-2001 ($5\times10^{11}$ CFU) without LAAD was administered to NHP's 4-6. Both strains were suspended in formulation buffer (previously grown in activated in a bioreactor and thawed on ice) or formulation buffer alone as a mock. Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. Results are shown in FIG. 24A and FIG. 24B confirm that expression of LAAD did not have a negative effect on PAL metabolism of Phe.

Example 75. Oral Tracer Studies with Non-Human Primates (NHPs)

Figure 25:
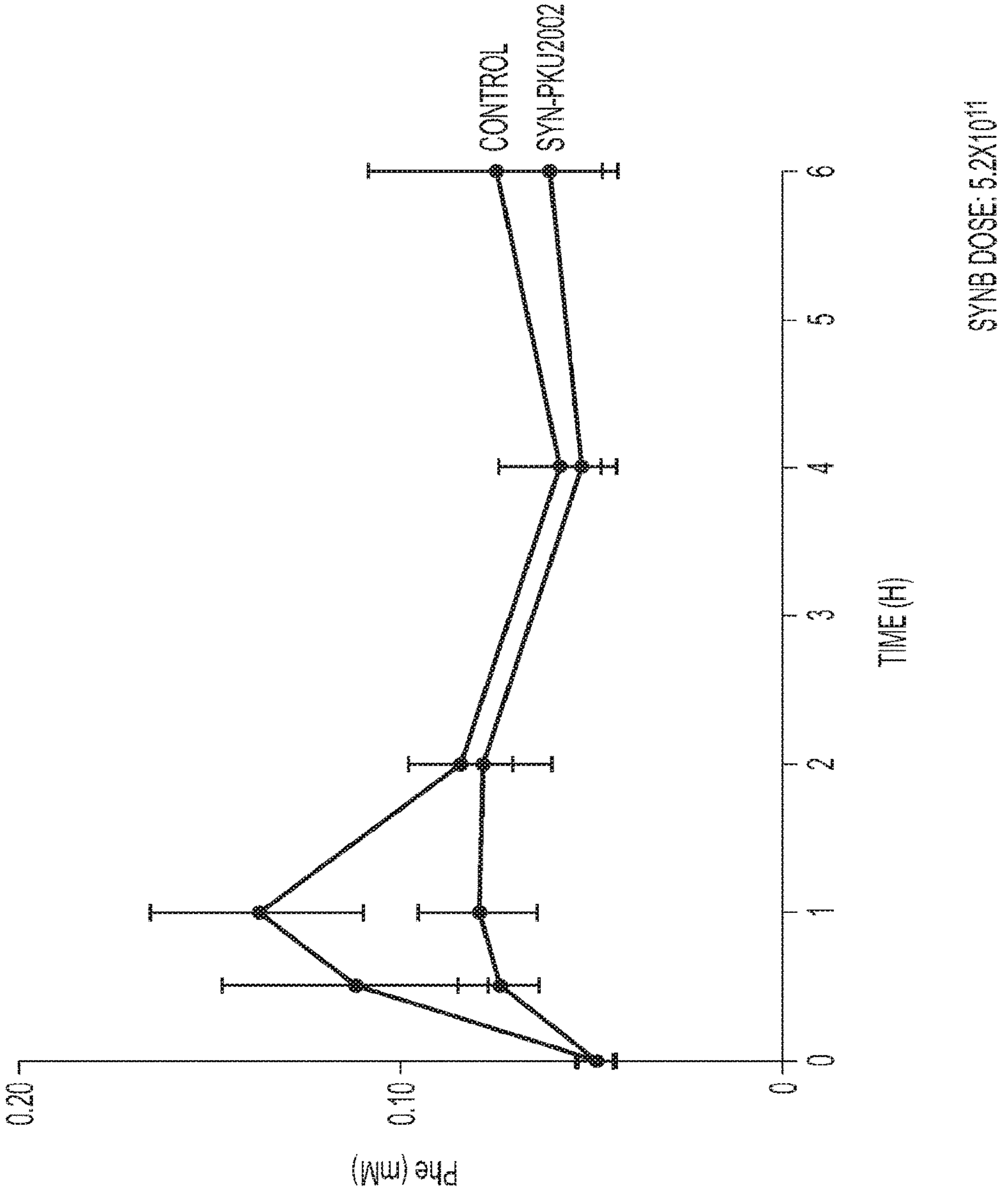
FIG. 25 depicts a graph showing that SYN-PKU-2002 metabolizes Phe when administered orally in healthy non-human primates (NHPs). Gavage with SYN-PKU-2002 reduces the spike in blood phe levels observed upon administration of protein challenge together with radio-labelled Phe.

Oral Tracer studies were conducted to further characterize activity. At T=0, the urine pan was emptied, and NHPs were administered an oral gavage of 5.5 g of Peptone from meat in 11 mL, 4 mL D5-phenylalanine (20 mg/mL), and 10 mL of bacteria ($5.2\times10^{11}$ CFU SYN-PKU-2001). Concurrently, NHP's 1-10 were all administered 5 mL of 0.36M sodium bicarbonate followed by a flush with 2 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. FIG. 25 shows the large spike in blood Phe levels upon administration.

For the oral tracer study control, at T=0, the urine pan was emptied, and NHPs were administered an oral gavage of 5.5 g of Peptone from meat in 11 mL, 4 mL D5-phenylalaline (20 mg/mL), and 10 mL formulation buffer. Concurrently, all NHP's were administered 5 mL of 0.36M sodium bicarbonate followed by a flush with 2 mL of water. Animals were bled at 0, 0.5, 1, 2, 4, and 6 h by venipuncture. At 6 h post dosing, the urine collection pan was removed and the contents poured into a graduated cylinder for volume measurement of 5 mL.

Results in FIG. 25 show administration of the oral gavage with the SYN-PKU-2002 effectively metabolizes Phe and reduces the spike in blood Phe levels observed in the control dosage.

Example 76. Dose Dependent Responses of SYN-PKU-2002

Four studies confirmed successful dose dependent conversions of Phe and production of plasma biomarkers t-cinnamic acid (TCA) and hippuric acid (HA) in non-human primates (NHPs) after single dose administration of SYN-PKU-2002 after a protein rich meal.

Study 1: At T=0, the urine pan was emptied, and ten NHPs were orally administered 5.5 g of peptone from meat in 11 mL of water. NHP's 1-5 were administered an oral gavage of 4 ml of SYN-PKU-2002 ($3.6\times10^{11}$ CFU). NHPs 6-10 were administered an oral gavage of 4 mL formulation buffer, 2 mL of SYN-PKU-2002 ($1.8\times10^{11}$ CFU) followed by an oral gavage of 6 mL of formulation buffer. Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL.

Study 2: Ten NHP's were orally administered 5.5 g of Peptone from meat in 11 mL. NHP's 1-5 were gavaged with 8 ml of SYN-PKU-2002 ($7.2\times10^{11}$ CFU) bacteria strain. NHP's 6-10 were gavaged with 1 mL of SYN-PKU-2002 ($9.0\times10^{10}$ CFU) followed 7 mL of formulation buffer. Concurrently, NHP's 1-10 were all administered 5 mL of 0.36M sodium bicarbonate followed by a flush with water. Animals were bled at 0, 0.5, 1, 2, 4, and 6 h by venipuncture. At 6 h post dosing, the urine collection pan was removed, and the contents poured into a graduated cylinder for volume measurement of 5 mL.

Study 3: Ten NHP's were orally administered 5.5 g of Peptone from meat in 11 mL. NHP's 1-5 were gavaged with 8 ml of SYN-PKU-2002 diluted in formulation buffer ($2.3\times10^{10}$ CFU). NHP's 6-10 were gavaged with 8 mL of diluted SYN-PKU-2002 diluted in formulation buffer ($4.5\times10^{10}$ CFU). Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. NHP's 1-10 all fasted the previous night.

Study 4: Ten NHP's were orally administered 5.5 g of Peptone from meat in 11 mL. NHP's 1-5 were gavaged with 8 ml of diluted SYN-PKU-2002 ($3.3\times10^{9}$ CFU). NHP's 6-10 were gavaged with 8 mL of diluted SYN-PKU-2002 ($1.1\times10^{10}$ CFU). Concurrently, NHP's 1-10 were all administered 5 mL of 0.36M sodium bicarbonate followed by a flush with 5 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. NHP's 1-10 all fasted the previous night.

Results shown in FIGS. 117A, 117B, 117C, and 117D show that Phe metabolism was evident at doses of $9\times10^{10}$ CFU and higher. Additionally, dose-dependent conversion of Phe and production of biomarkers TCA and hippuric acid were observed.

Example 77. Casein Study in Non-Human Primates with SYN-PKU-2002

Efficacy of replacing peptones (composed of small peptides) with casein (a whole protein) for expressing Phe, TCA, and HA consumption was evaluated.

At T=0, urine pans were emptied, and NHPs were administered an oral gavage of 28 mL of casein (4.5 g)/biocarbonate/D5-phenylalanine (25 mg; 8 mg/kg). NHPs 1-5 were further administered an oral gavage of 3.5 mL SYN-PKU-2002 ($5\times10^{11}$ CFU), and NHPs 6-10 were administered 3.5 mL formulation buffer via oral gavage. Concurrently, the NHPs were administered a flush with 2 mL of water. Animals were bled at 0, 0.5, 1, 2, 4, and 6 h by venipuncture. At 6 h post dosing, the urine collection pan was removed and the contents poured into a graduated cylinder for volume measurement of 5 mL. Results are shown in FIGS. 118A-118C.

The results from this study demonstrate that the genetically engineered bacterial strains of the disclosure can consume Phe that is naturally digested and can prevent a spike in blood Phe observed in the control upon D5-Phe consumption.

Example 78. Phe Metabolism is Clinically Relevant

The disclosed studies in non-human primates demonstrate the relevancy of Phe metabolism and the profound effect it could have on the diet of patients with PKU. The Institute of Medicine has established dietary reference intakes that establish a phenylalanine is assumed to be 80-90 mg/g whole protein. The recommended intake of protein for a human is 50 g (for a 2000 calorie diet). An unrestricted American diet provides approximately 100 g of whole protein (males) and 70 g (female) on average. An unrestricted diet will therefore provide approximately 6-9 g of phenylalanine.

The recommended phenylalanine consumption for patients with PKU>4 years of age is 200-1100 mg (Vockley, et al. 2014, the entire contents of which are incorporated herein by reference), or about <10 g protein/day. Based on the studies above, the highest dosage of SYN-PKU-2002 can be extrapolated (assuming 35% recovery of urinary HA in NHP's) to three $5\times10^{11}$ doses per day in patients. Said dosage predicts the daily metabolism of Phe to support a ~25 g of dietary protein intake in humans (25 mg/kg=1.7 g for a 70 kg person). Therefore, the dose of Phe is about 25% of the Phe intake that a PKU patient following an unrestricted diet would receive in 24 hours (FIG. 28). This is ~50% of the daily recommended protein intake (see US RDA; assuming an unrestricted American diet provides on average approximately 100 g (males) and 70 g (females) of whole protein). For PKU patients, this results an a 2.5-fold increase in protein uptake, a result which would liberate the diet and lifestyle of PKU patients.

In some embodiments, upon treatment with the bacteria of the disclosure, PKU patients may increase their dietary protein intake per day to greater than 10 g; from about 10 g to about 30 g, from about 10 g to about 25 g, from about 10 g to about 20 g, from about 10 g to about 15 g. In some embodiments, upon treatment with the bacteria of the disclosure, PKU patients may increase their dietary protein intake per day to about 15 g, about 20 g, or about 25 g.

In some embodiments, upon treatment with the genetically engineered bacteria of the disclosure, PKU patients may increase their daily protein intake by about 2.5 fold. In some embodiments, upon treatment with the genetically engineered bacteria, PKU patients may increase their daily protein intake by about 2.0 fold. In some embodiments, upon treatment with the genetically engineered bacteria, PKU patients may increase their daily protein intake by about 1.5 fold In some embodiments, upon treatment with the genetically engineered bacteria, PKU patients may increase their daily protein intake by about 1.0 fold. In some embodiments, upon treatment with the genetically engineered bacteria, PKU patients may increase their daily protein intake by about 3 fold, 3.5 fold or 4 fold. In some embodiments, upon treatment with the genetically engineered bacteria, PKU patients may increase their daily protein intake by about 50%. In some embodiments, upon treatment with the genetically engineered bacteria, PKU patients may increase their daily protein intake by about 5% to 10%, 10% to 20%, 20% to 30%, 30% to 40%, 40% to 50%, 50% to 60%, 60% to 70%, 70% to 80%, 80% to 90%, 90% to 100%. In some embodiments, upon treatment with the genetically engineered bacteria, PKU patients may increase their daily protein intake by about 5%, 10%, 20%, 30%, 40%, 50%, 60%, 70%, 80%, and 90% to 100%.

Example 79: Characterization of the Growth of SYN766, an *Escherichia coli* Nissle 1917 DAP Auxotroph in Varying Concentrations of Diaminopimelate To determine the minimum amount of DAP required for bacterial growth and division, the growth of SYN766, an EcN DAP auxotroph, was characterized by incubation in a range of DAP concentrations.

All bacterial cultures were started from glycerol stocks stored at ≤−65° C. Bacteria were grown in 14 mL culture tubes overnight with shaking at 250 rpm at 37° C. in LB broth supplemented with DAP at 100 μg/mL. Overnight cultures were then diluted 1:100 in wells of 96-well plates containing 100 μL of LB with various DAP concentrations.

In all experiments, the 96-well plates were sealed with parafilm and analyzed on a Synergy™ Neo Microplate Reader (BioTek Instruments, Inc., Winooski, VT). The plate was incubated at 37° C. with shaking for 960 minutes, and the $OD_{600}$ was measured every 10 minutes.

The data were collected in Gen5™ software version 2.06 (BioTek Instruments, Inc., Winooski, VT), exported to Microsoft® Excel to calculate the mean and standard error, and processed in GraphPad Prism version 7.03 (GraphPad Software, Inc., San Diego, CA).

Figure 32:
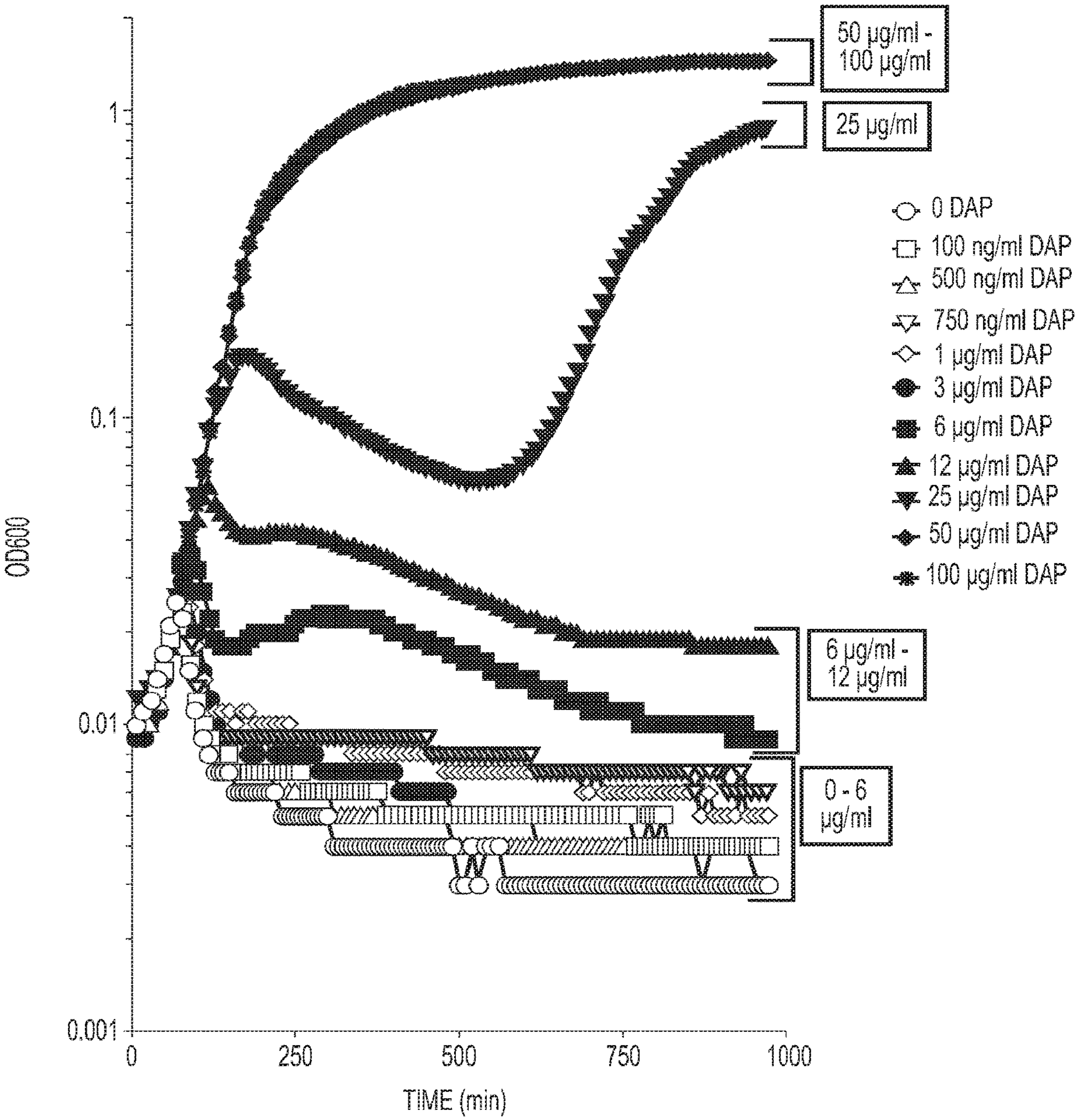
FIG. 32 depicts a graph showing the growth characteristics of SYN766, a diaminopimelate auxotroph in various concentrations of diaminopimelate. SYN766 (*E. coli* Nissle 1917, ΔdapA) was incubated in growth media which contained decreasing concentrations of DAP at 37° C. for 960 minutes under constant shaking. The OD600 was measured every 10 minutes in order to assess cell growth over time. The average of three biological replicates is plotted for each time point.

SYN766, a DAP auxotroph strain of EcN, was analyzed to determine the concentration of DAP required for growth; the data are displayed in FIG. 32. In liquid media with DAP at concentrations of 50 μg/mL and 100 μg/mL, SYN766 grew exponentially for 350 minutes before entering stationary phase at an $OD_{600}$ of approximately 1. At a DAP concentration of 25 μg/mL, cells grew for 200 min, reaching an $OD_{600}$ of 0.15 before declining. Growth resumed after 600 min and reached a final $OD_{600}$ of approximately 0.8, which was significantly less total cell mass than when the DAP concentration was at least 50 μg/mL. At 6 μg/mL and 12 μg/mL DAP, SYN766 grew exponentially for approximately 180 minutes before displaying a declining $OD_{600}$ for the remainder of the experiment. When DAP concentrations were below 6 μg/mL, SYN766 showed growth for approximately 100 min before displaying a declining $OD_{600}$ for the remainder of the experiment.

Figure 33:
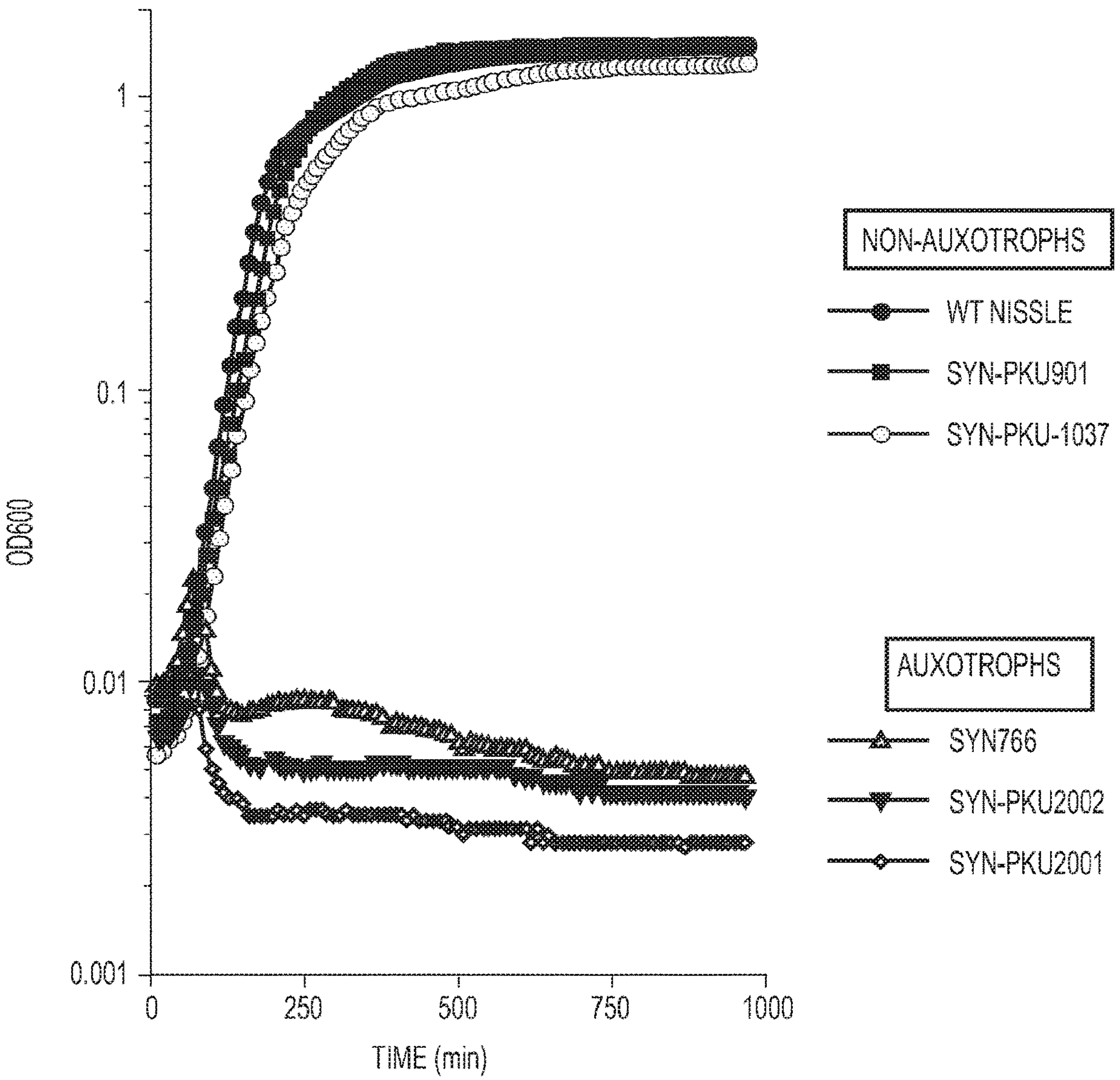
FIG. 33 depicts a graph showing the growth characteristics of various strains of *E. coli* Nissle in LB growth media without diaminopimelate. To characterize the growth characteristics of various modified strains of EcN in absence of DAP, cultures were incubated in LB that did not contain DAP at 37° C. for 960 minutes under constant shaking. The OD600 was measured every 10 minutes to assess cell growth over time. The average of three biological replicates and two technical replicates is plotted for each time point.

Example 80: Characterization of the Growth of Various Strains of *Escherichia coli* Nissle 1917 in LB Growth Media without Diaminopimelate Various modified strains of EcN were grown in media without DAP to confirm the growth characteristics of DAP auxotrophs and prototrophs. Similar growth conditions were used to those described in Example 79. Various strains of EcN that have been modified to consume phenylalanine were analyzed for their ability to grow in the absence and presence of DAP. Results are shown in FIG. 33. The non-auxotrophic strains, SYN001, SYN-PKU901 and SYN3282, grew exponentially for approximately 400 minutes before entering stationary phase at an OD600 of approximately 1.2. Under similar conditions, the DAP auxotroph strains, SYN766, SYN-PKU-2001, and SYN-PKU-2002, stayed within the inoculation OD600 of approximately 0.010 for the first 90 min before starting to show a decline, concluding the experiment at an OD600 of approximately 0.005. This shows that the deletion of dapA results in a cessation of growth in the absence of an external source of DAP. The presence of genes involved in Phe degradation in SYN3282 had no effect on growth compared to wild type strains. The combination of DAP auxotrophy with genes involved in Phe degradation in SYN-PKU-2001 and SYN-PKU-2002 had no effect on the growth impairment observed with DAP auxotrophy alone (SYN766). These results show that DAP auxotrophy is the main factor regulating growth and survival of these engineered strains.

Figure 34:
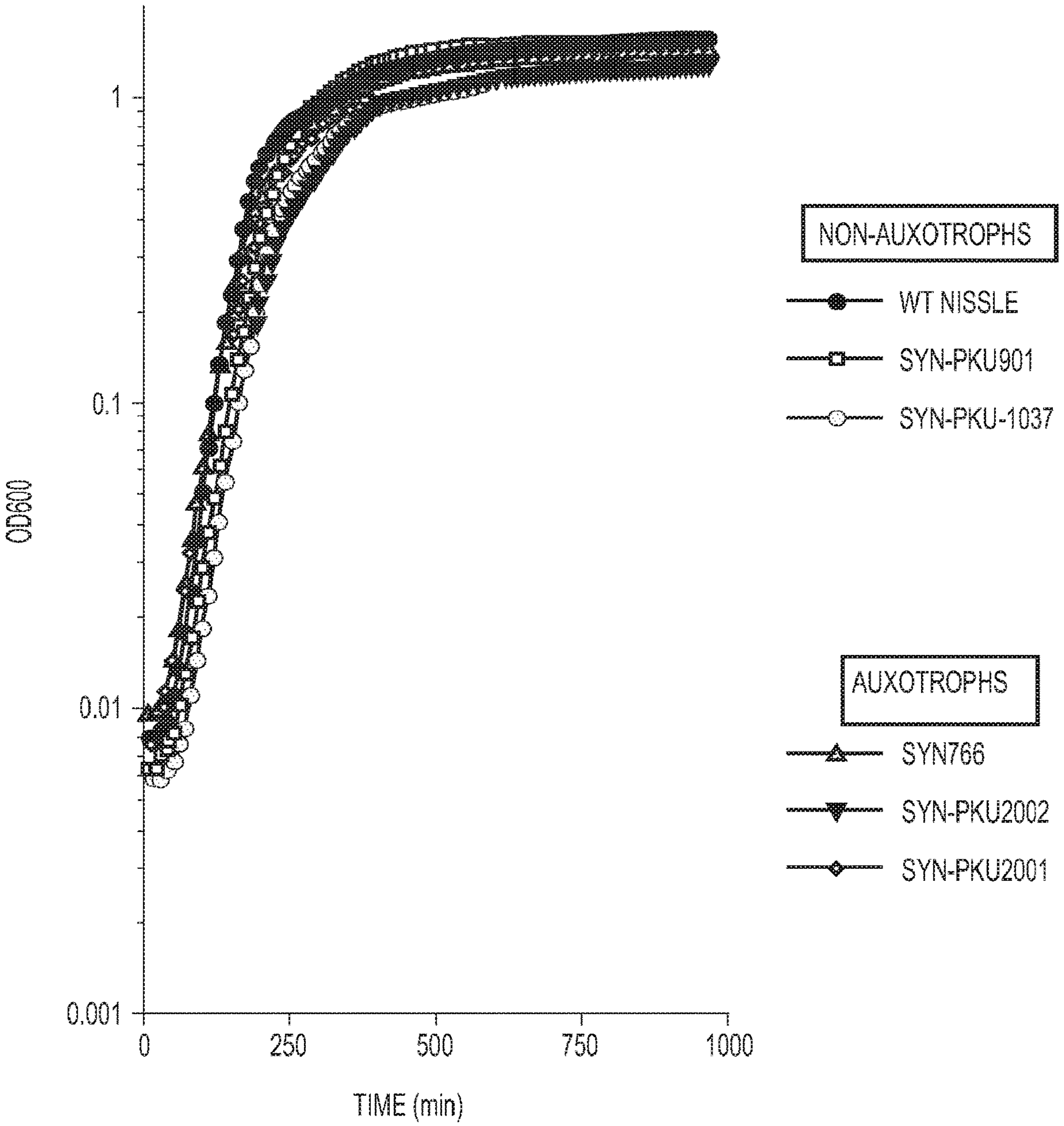
FIG. 34 depicts a graph showing the growth characteristics of various strains of EcN in LB growth media with 100 µg/mL diaminopimelate. To characterize the growth characteristics of various modified strains of EcN in the presence of DAP, they were incubated in growth media with 100 µg/mL DAP, at 37° C. for 960 minutes, constantly shaking. The OD600 was measured every 10 minutes to assess cell growth over time. The average of three biological replicates is plotted for each time point.

Example 81. Characterization of the Growth of Various Strains of *Escherichia coli* Nissle 1917 in LB Growth Media with 100 μg/mL Diaminopimelate Various modified strains of EcN were grown in media with 100 μg/mL DAP, using identical growth conditions to those described in Example 79. In contrast to the results in example 80, when grown in LB supplemented with 100 μg/mL DAP, all of the tested strains of EcN exhibited comparable growth (see FIG. 34). The non-auxotrophic strains SYN001, SYN-PKU901 and SYN3282 and the auxotrophic strains SYN766, SYN-PKU-2001 and SYN-PKU-2002 grew exponentially for approximately 400 minutes before entering stationary phase at an $OD_{600}$ of approximately 1.4.

Example 82. Fecal Excretion and Clearance of Engineered *Escherichia coli* Nissle 1917 in C57BL/6 Mice Following Oral Administration The major objective of this experiment was to determine the kinetics of fecal excretion of strains containing DAP auxotrophy and/or the Phe-degradation activity compared to wild type EcN. EcN strains utilized for this study included wild type (SYN-PKU901), a DAP auxotroph (SYN766), a strain genetically engineered to encode Phe-degrading activity (SYN3282), and a strain with both DAP auxotropy and Phe-degrading activity (SYN-PKU-2001). SYN-PKU-2001 is a surrogate for the clinical candidate strain SYN-PKU-2002, but contains a chloramphenicol resistance cassette that allows it to be isolated from other microbial flora in intestinal contents and biological tissues by plating on selective media. SYN3282 is identical to SYN-PKU-2001, but does not have DAP auxotrophy. For this purpose, female C57BL/6 mice were weighed and randomized by weight into 3 treatment groups (n=5 each). Each group would receive a single oral dose containing 2 mixed strains of bacteria at approximately $3\times10^9$ CFU/strain (200 μL/dose). Group 1 received SYN-PKU901 and SYN766 to examine the effect of DAP auxotrophy, group 2 received SYN-PKU901 and SYN3282 to examine the effect of Phe-degradation activity, and group 3 received SYN-PKU-2001 and SYN3282 to examine the combined effects of both DAP auxotrophy and Phe-degradation activity.

Before dosing, fecal samples were collected from each individual mouse at T=0 and processed by serial microdilution plating to determine the baseline level of viable CFUs, if any, on LB agar plates selective for the bacterial strains to be dosed within the group. Bacterial doses were then administered immediately after the T=0 h fecal collection. For collection of feces at designated time points, each mouse was isolated in a small empty pipet tip box until a recoverable fecal sample was produced. Samples were moved into 2 mL microcentrifuge tubes. If no sample was produced within 30 minutes of isolation, the time point for that animal was excluded from analysis. Fecal pellets were collected and weighed from each mouse at 4, 6, 8, 24, 30, and 48 h post-dose.

For processing of weighed fecal pellets, 1 mL of PBS was added to each sample and disposable pellet pestles (Kimble, 749521-150) were used for manual homogenization. The samples were then vortexed at maximum speed for 10-20 s. The 10 μL microdilution was used to dilute samples 1:10 across 6 orders of magnitude. Ten (10) μL of these dilutions and the undiluted fecal homogenate were plated on the appropriate selective LB agar plates. Dilutions were plated on LB agar supplemented with antibiotics or DAP where appropriate (SYN-PKU901=streptomycin 300 μg/mL; SYN3282=chloramphenicol 30 μg/mL; SYN766/SYN-PKU-2001=chloramphenicol 30 μg/mL and DAP 100 μg/mL). Plates were incubated overnight at 37° C. and colonies were counted manually the following day. Plates were incubated overnight at 37° C.±2° C. Colonies were counted manually in a dilution that contained at least 10 but no more than 200 individual colonies. The final CFU count was determined by back-calculation using the dilution factor multiplied by the number of colonies counted for calculation of CFU/mL of fecal homogenate. This value was divided by the weight of fecal pellets for calculation of CFU/mg feces.

Next, the effect, if any, of mutation/engineering in modified EcN strains compared to their isogenic parents was examined. The amount of each strain excreted at each time point was divided by the number of CFUs of that strain in the initial dose. Using this normalization, the two strains within a study group could be directly compared for excretion and clearance kinetics.

Figure 35A:
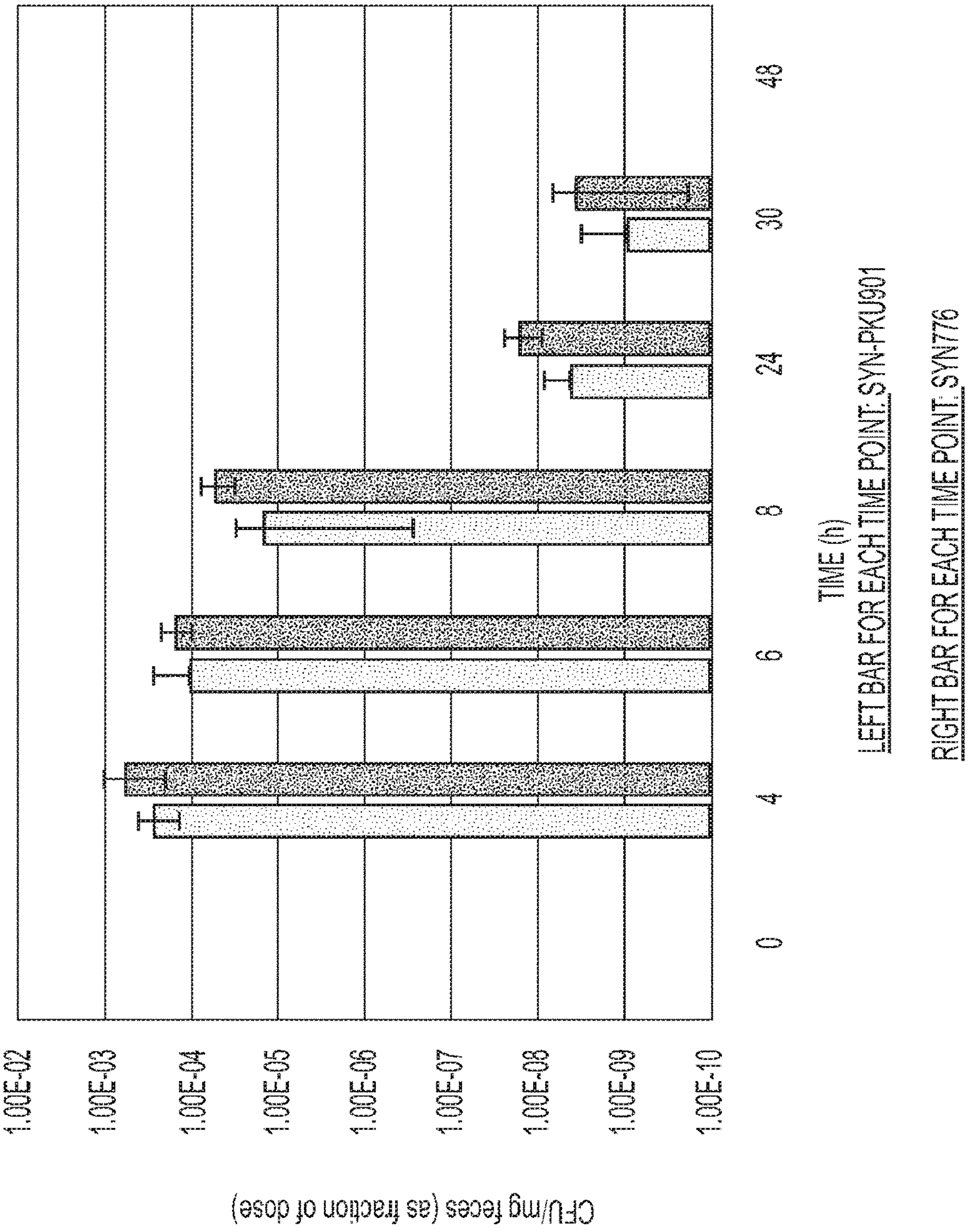
FIGS. 35A, 35B, and 35C depict the effect of DAP auxotrophy and Phe degradation activity on EcN survival and transit in C57BL/6 Mice.
Figure 35B:
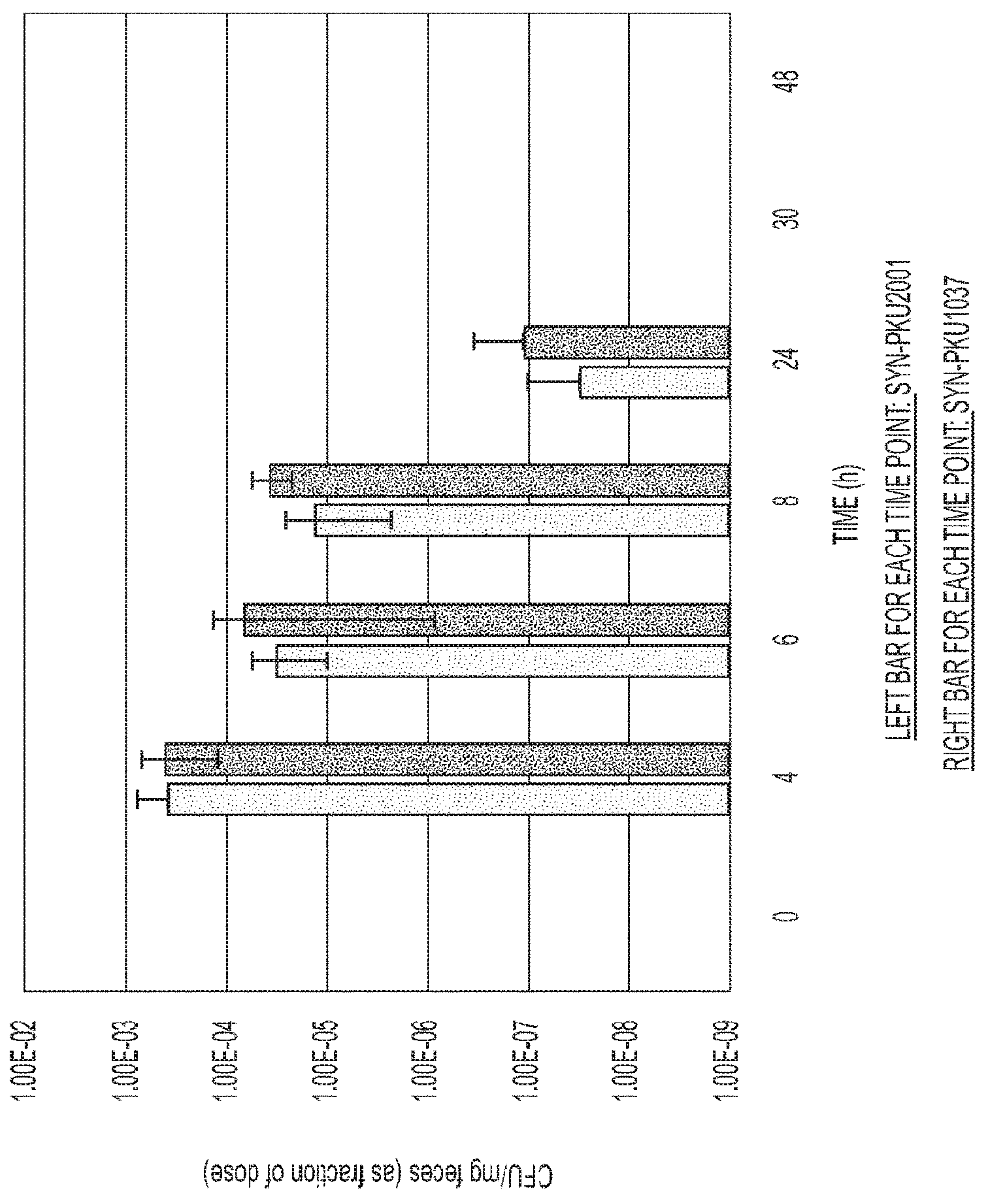
Figure 35C:
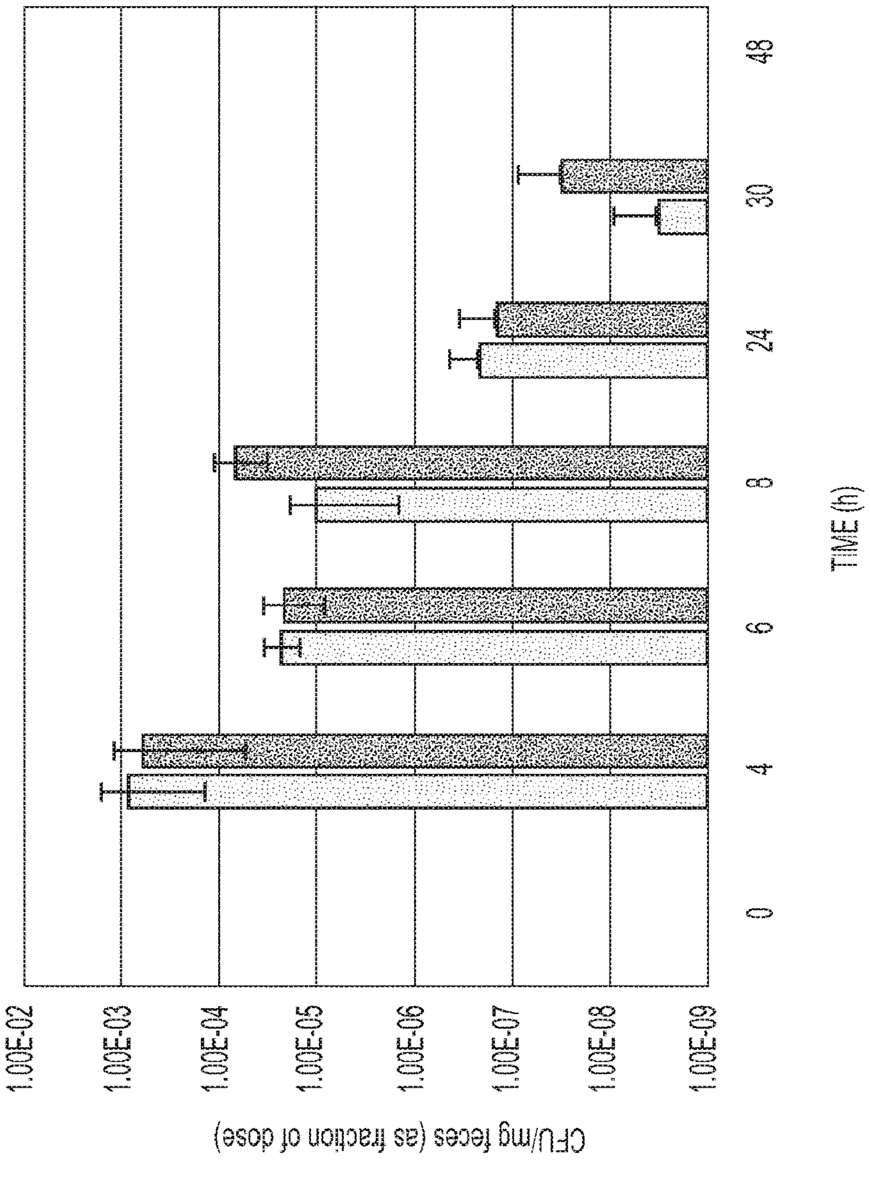
Figure 36A:
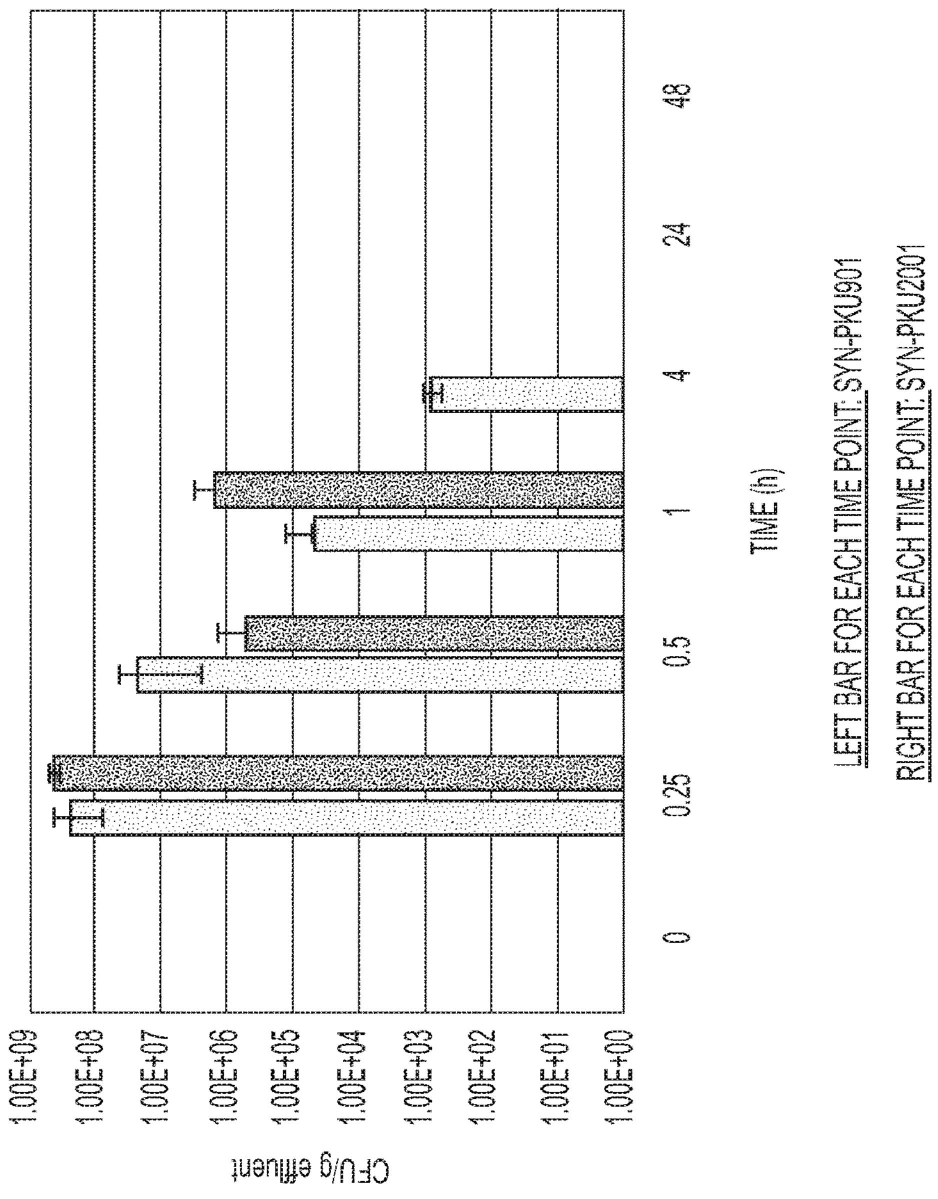
FIGS. 36A-36F depicts the effect of DAP auxotrophy and Phe degradation activity on EcN transit and clearance in C57BL/6 mice. SYN-PKU901 or SYN-PKU-2001 were orally administered to C57BL/6 mice (9×109 CFU/dose, n=3/time point). At the indicated times, effluents from the stomach (A), upper small intestine (B), middle small intestine (C), lower small intestine (D), cecum (E) and colon (F) were collected and plated for CFU counts. CFU determination was performed by microdilution on antibiotic selective media. For each time point, data represent the CFUs determined from 3 effluent samples±standard deviation. No CFUs were determined in any sample at 48 h post-dose, indicating complete bacterial clearance.
Figure 36B:
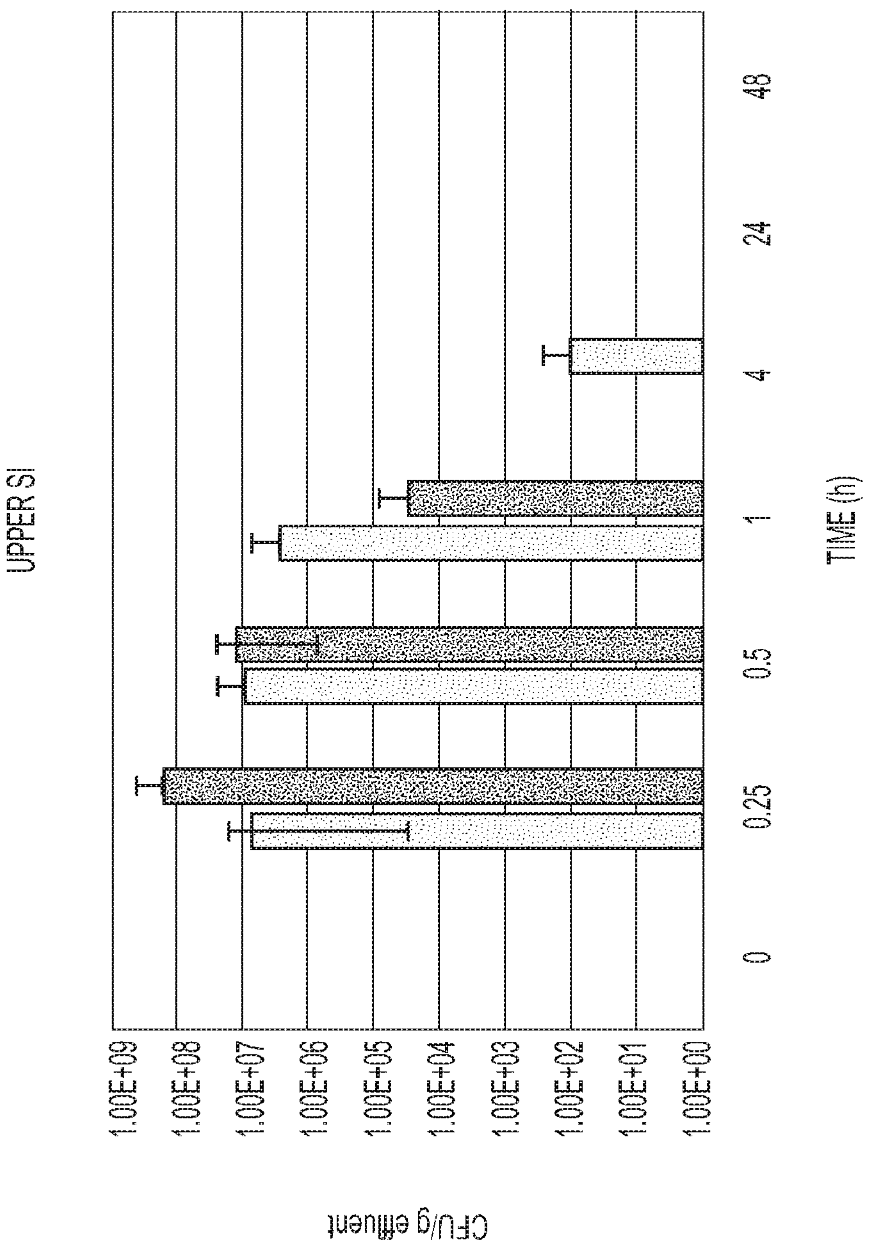
Figure 36C:
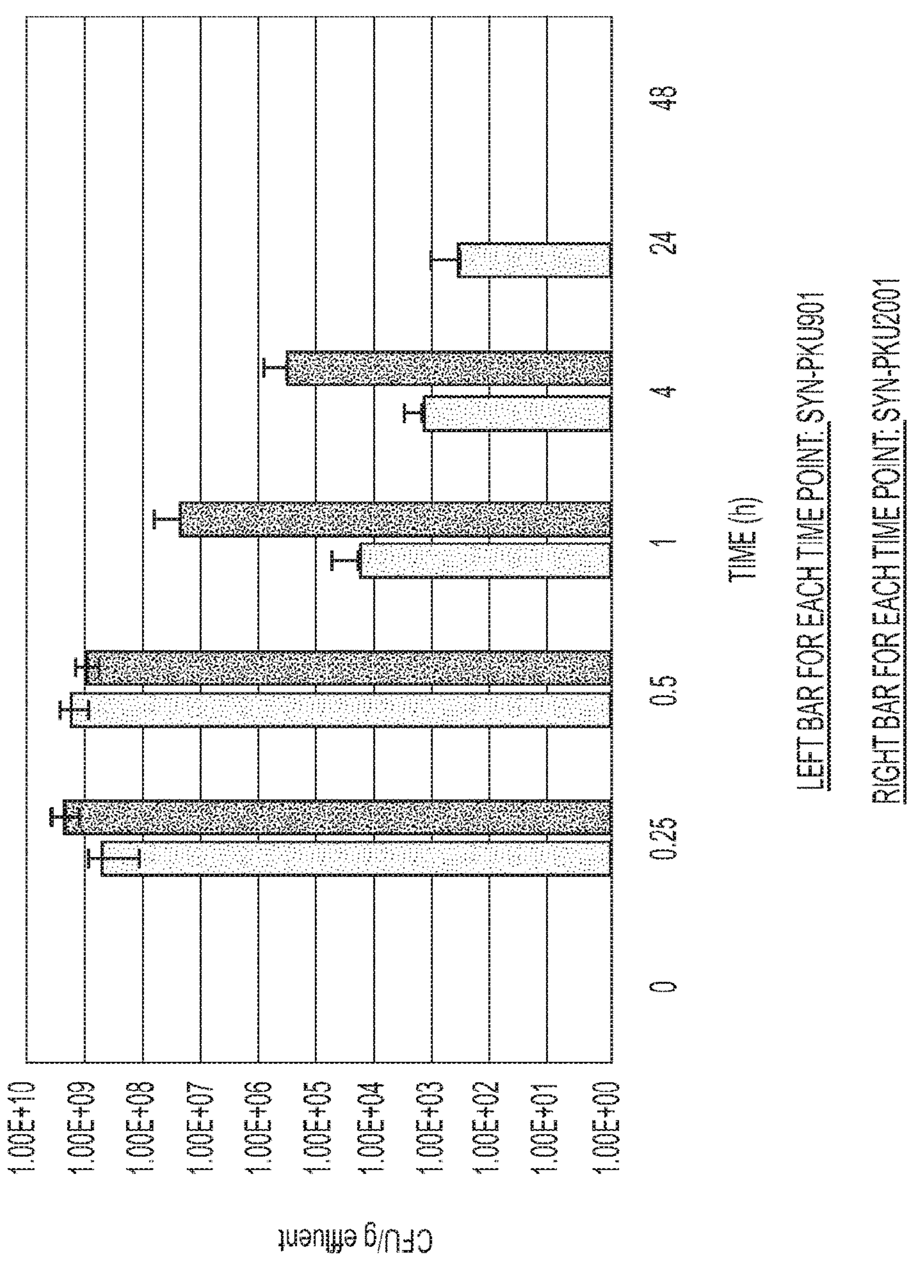
Figure 36D:
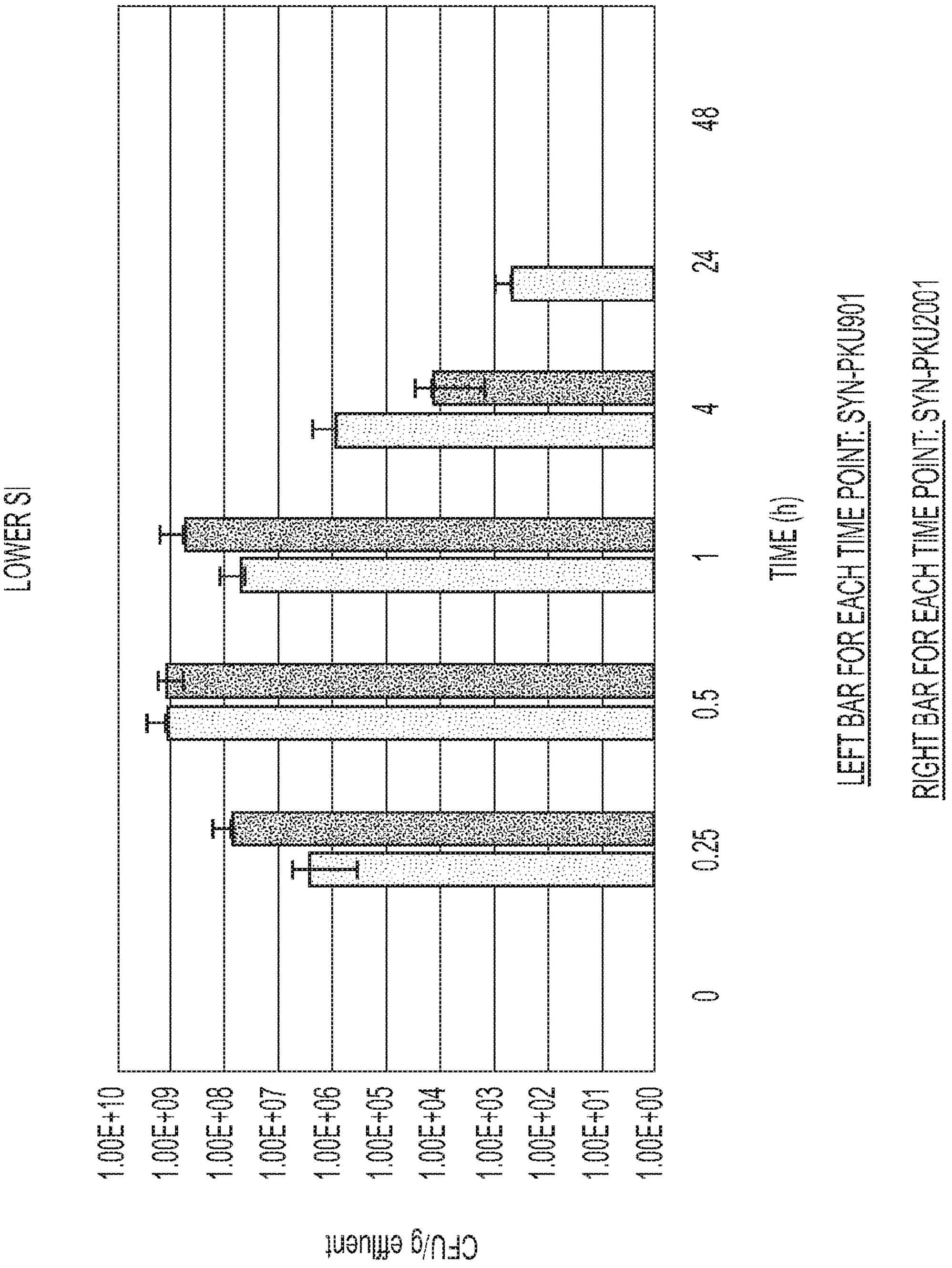
Figure 36E:
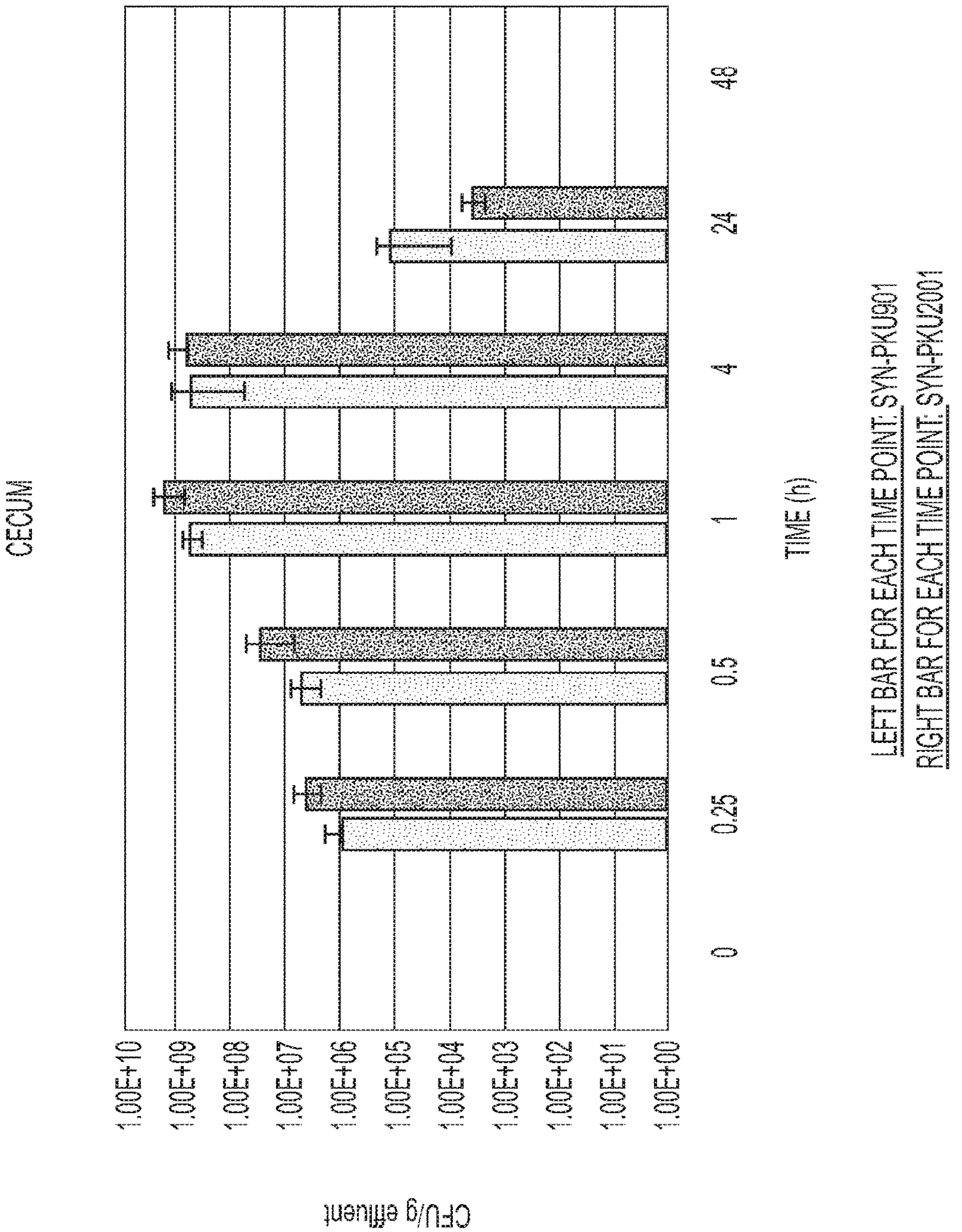
Figure 36F:
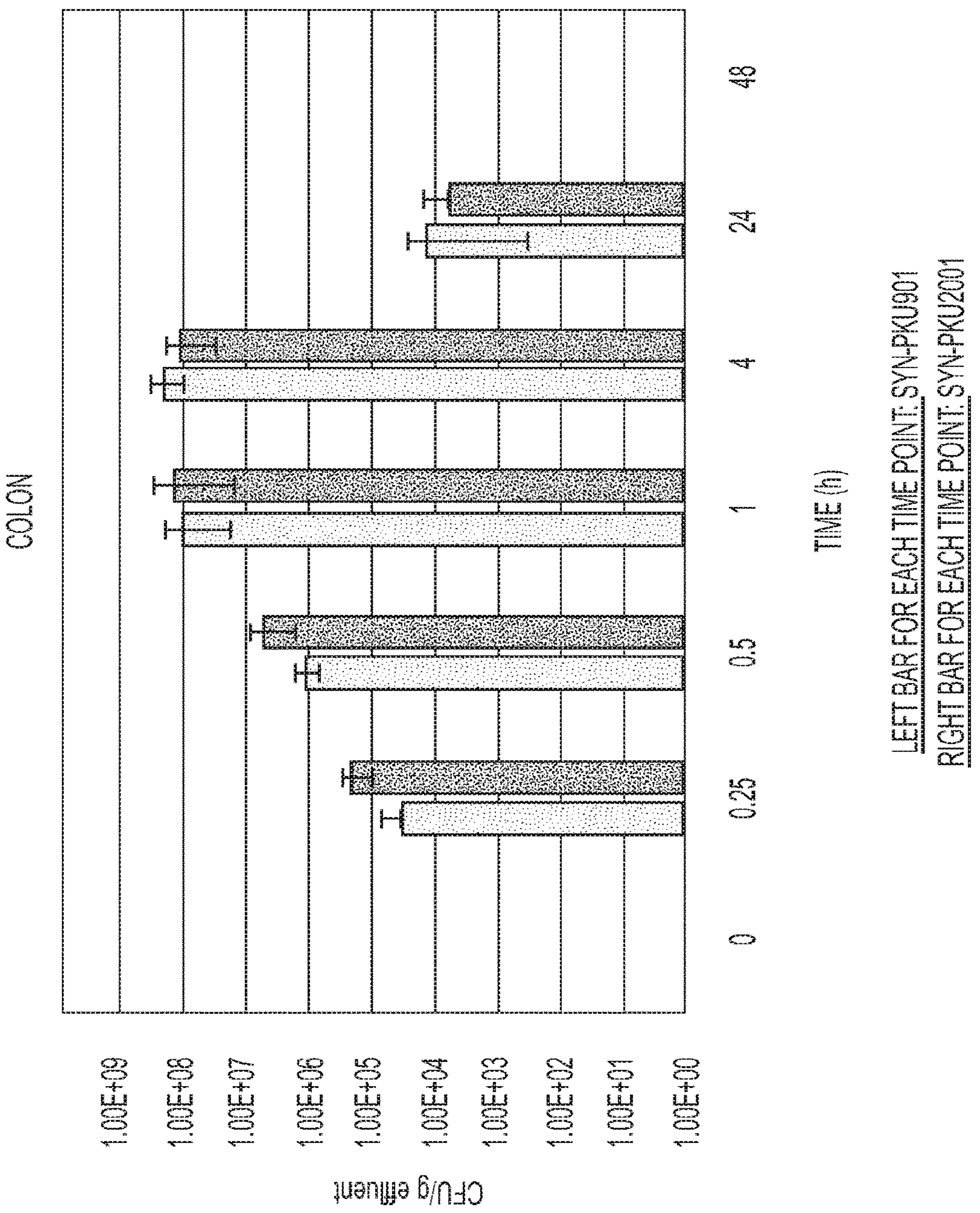
Figure 37:
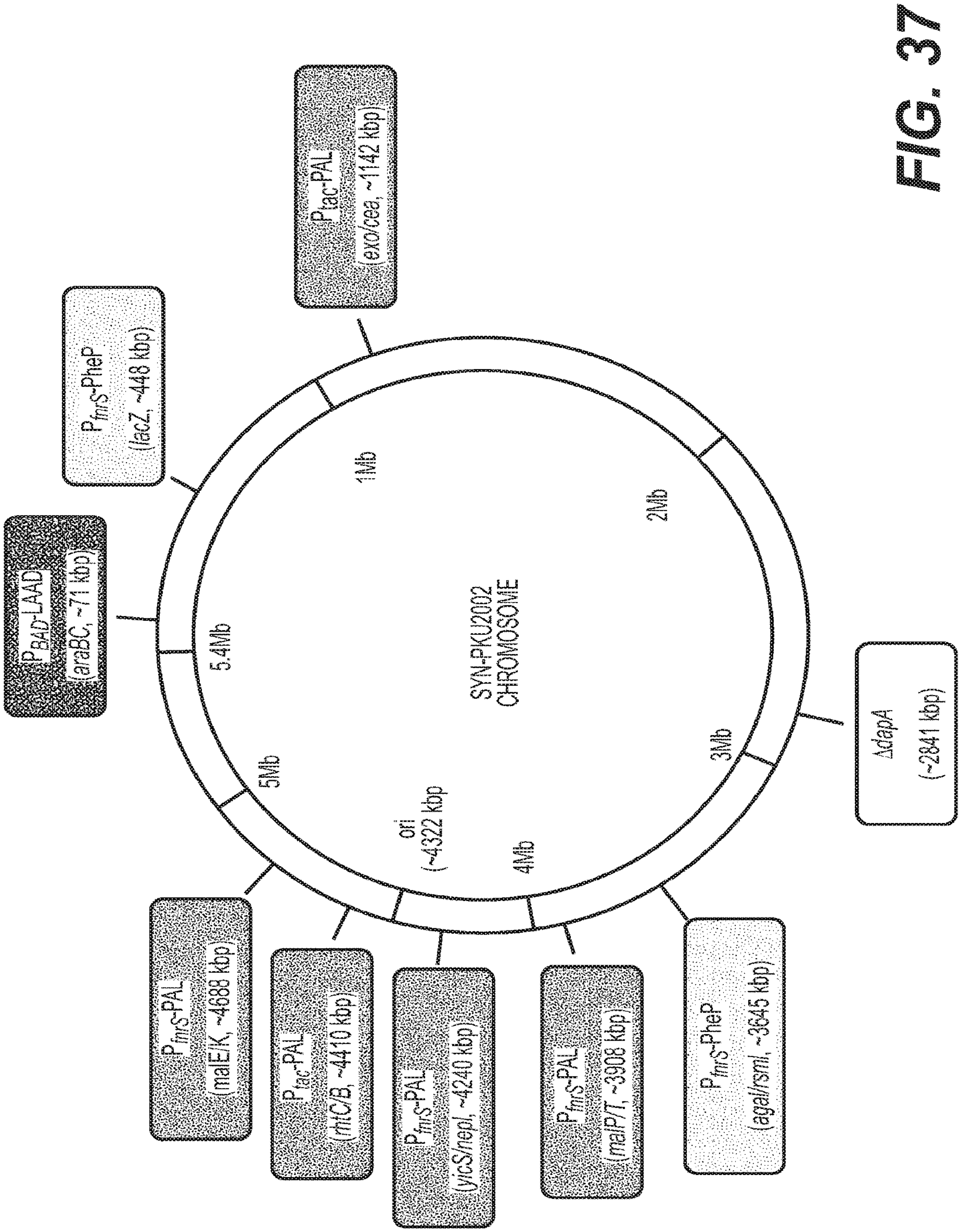
FIG. 37 depicts a schematic of the SYN-PKU-2002 genome. The locations of the genomic modification sites in SYN-PKU-2002 are shown, with kbp designation indicating the chromosomal position relative to the 0/5.4 Mb reference marker. The chromosomal origin of replication is shown as a red line. Green text boxes designate PheP gene insertions, purple text boxes designate PAL gene insertions, orange text box designates LAAD gene insertion, and grey text boxes with Δ symbol designates the location of the dapA and Φ deletion. Italicized gene names in parenthesis refer to the upstream and downstream genes surrounding the inserted genes.

Results are shown in FIG. 35A-35C. There were no CFUs detected on selective media in the pre-dose (T=0 h) fecal samples for any of the mice, demonstrating that CFUs detected post-dosing were attributable to EcN-derived strains and not due to background growth from the microbiome. In all 3 groups, all strains of bacteria had reached peak amounts in the feces at 4 h post dose and steadily declined over time. By 24 h, bacterial counts in the feces dropped by 3-4 orders of magnitude for all strains. By 30 h, at least 2 mice from groups 1 and 3, and all mice in group 2, contained no detectable EcN-derived bacteria in the feces. By 48 h, all EcN-derived bacteria were cleared from the feces. There were no apparent differences in the kinetics of excretion in the modified EcN strains, as similar rates of elimination were observed for all bacteria, showing that neither DAP auxotropy (SYN766, group 1), Phe-degradation activity (SYN3282, group 2), nor their combination (SYN-PKU-2001, group 3), had any significant effect on intestinal transit time or strain survival in the mouse model compared to the wild type SYN-PKU901 strain.

In conclusion, DAP auxotrophy and/or Phe degradation activity in EcN did not change the survival or disappearance of bacteria from the feces of C57BL/6 mice over time. All orally administered EcN-derived bacterial strains, regardless of genotype, were cleared from the feces of mice within 48 h, suggesting that EcN and its derivatives are not viable long term.

Example 83. In Vivo Survival of *Escherichia coli* Nissle 1917 Derivatives SYN-PKU901 and SYN-PKU-2001 in Healthy Mice The objective of this pharmacology study was to evaluate in female C57BL/6 mice any differences in survival, gastrointestinal (GI) distribution or time to complete clearance of *Escherichia coli* Nissle (EcN) wild type strain SYN-PKU901 compared to the genetically engineered EcN derivative SYN-PKU-2001, a surrogate strain for SYN-PKU-2002, which contained identical diaminopimelate (DAP) auxotrophy and phenylalanine (Phe) degradation elements. GI distribution, transit and clearance kinetics were measured by enumerating colony forming units (CFUs) over a 48-h time period in multiple GI segments of female C57BL/6 mice following a single oral dose of 9×109 CFUs of SYN-PKU901 or SYN-PKU-2001.

EcN strains utilized for this study included SYN-PKU901, a wild type control, and SYN-PKU-2001, a strain genetically engineered to encode Phe-degrading activity and DAP auxotrophy. SYN-PKU-2001 is a surrogate for the clinical candidate strain SYN-PKU-2002, but contains a chloramphenicol resistance cassette that allows for selection plating from biological tissues.

Female C57BL/6 mice were weighed and randomized by weight into 12 treatment groups (n=3 each) and a control group (n=3). The mice in the control group (T=0) were sacrificed by carbon dioxide asphyxiation followed by cervical dislocation. The stomach, small intestine (SI), cecum, and colon were carefully excised. The SI was further divided into 3 equal length sections (upper, middle, and lower). Each organ section was flushed with 0.5 mL of ice cold phosphate-buffered saline (PBS) and effluents were collected into separate 1.5 mL microcentrifuge tubes. The PBS/effluent samples were weighed and maintained on ice until processing by serial dilution plating on selective media to determine viable CFUs in the effluent of each intestinal segment. In formulations containing 100 mM sodium bicarbonate, animals in the treatment groups received an oral dose of 9×109 CFUs of SYN-PKU901 (6 groups) or SYN-PKU-2001 (6 groups). At 0.25, 0.5, 1, 4, 24, and 48 h post dose, a SYN-PKU901- and a SYN-PKU-2001-treated group were sacrificed and tissues were processed in a manner identical to the control group.

To calculate CFUs/mL, 10 μL of each weighed effluent sample was used in a 10-fold microdilution series performed in PBS in a sterile 96-well plate. Ten (10) μL of the undiluted effluent and of the dilutions were plated on LB agar supplemented with antibiotics or DAP where appropriate (SYN-PKU901=streptomycin 300 μg/mL; SYN-PKU-2001=chloramphenicol 30 μg/mL and DAP 100 μg/mL). Plates were incubated overnight at 37° C. and colonies were counted manually the following day.

For CFU determination, counts were collected by the manual counting of colonies in a dilution that contained at least 10 but no more than 200 individual colonies. In cases where colonies were only observed at the lowest dilution (the plating of undiluted effluent), all colonies were counted and scored, even when less than 10. The final CFU count was determined by back-calculation using the dilution factor multiplied by both the number of colonies counted and the volume of effluent collected.

See results in FIG. 36A-F. No CFUs were detected on selective media in the effluent samples of mice that did not receive cells, demonstrating that CFUs detected in effluents post-dosing were attributable to EcN-derived strains and not due to background growth from the microbiota. In the effluents obtained from the stomach, upper small intestine, middle small intestine, lower small intestine, cecum and colon of mice dosed with either SYN-PKU-2001 or SYN-PKU901 (control), survival and GI distribution over time were highly similar over the first 24 hours. No CFUs were found for either bacteria at 48 h post-dose, demonstrating complete clearance by this time point.

In conclusion, DAP auxotrophy and/or the phenylalanine-degradation activity of SYN-PKU-2001 did not change the survival, GI distribution or time to complete clearance from the GI tract of C57BL/6 mice compared to the SYN-PKU901 control strain. The complete clearance of all orally administered EcN-derived strains within 48 h suggests that EcN and its derivatives were not viable long term.

Example 84. Phenylalanine Degradation to Trans-Cinnamate and Phenylpyruvate in Bioreactor-Grown *Escherichia coli* Strain SYN-PKU-2002

The conversion of phenylalanine (Phe) into the metabolites trans-cinnamate (TCA) and phenylpyruvate (PP) in modified *Escherichia coli* Nissle 1917 (EcN) strain SYN-PKU-2002 that was grown and activated in a bioreactor was determined as a measure of phenylalanine ammonia lyase (PAL) and L-amino acid deaminase (LAAD) activity. Additional objectives included determining if bioreactor-activated SYN-PKU-2002 could use complex mixtures of Phe-containing peptides or whole protein as substrates for Phe degradation.

EcN-derived strain SYN-PKU-2002, a Phe-degrading strain intended for the therapeutic treatment of phenylketonuria (PKU), was grown and activated in a bioreactor following a process intended to be used for the scale-up of SYN-PKU-2002 for clinical trials. This process, performed on a 5 L scale, included the creation of a low dissolved oxygen (DO) environment that was achieved through control of culture agitation rate. Low DO activated expression of chromosomally integrated copies of genes encoding PAL and high affinity phenylalanine transporter, PheP. Following the drop to low DO, isopropyl β-D-1-thiogalactopyranoside (IPTG; 1 mM) was added to activate expression of additional copies of PAL, and L-arabinose (0.15% final concentration) was added to activate expression of LAAD. Following high density growth, cells were concentrated and frozen at ≤65 C in glycerol-based formulation buffer.

1×108 activated cells were incubated aerobically at 37 C in assay media containing 50 mM Phe, Phe-Pro, Phe-Gly-Gly, Phe-Val, Phe-Ala, or Gly-Phe peptides, or in 20 g/L of peptone from meat, tryptone, or whole casein powder. Supernatant samples were removed at 30 and 60 min and the concentrations of Phe, TCA, and PP were determined by LC MS/MS.

Figure 31A:
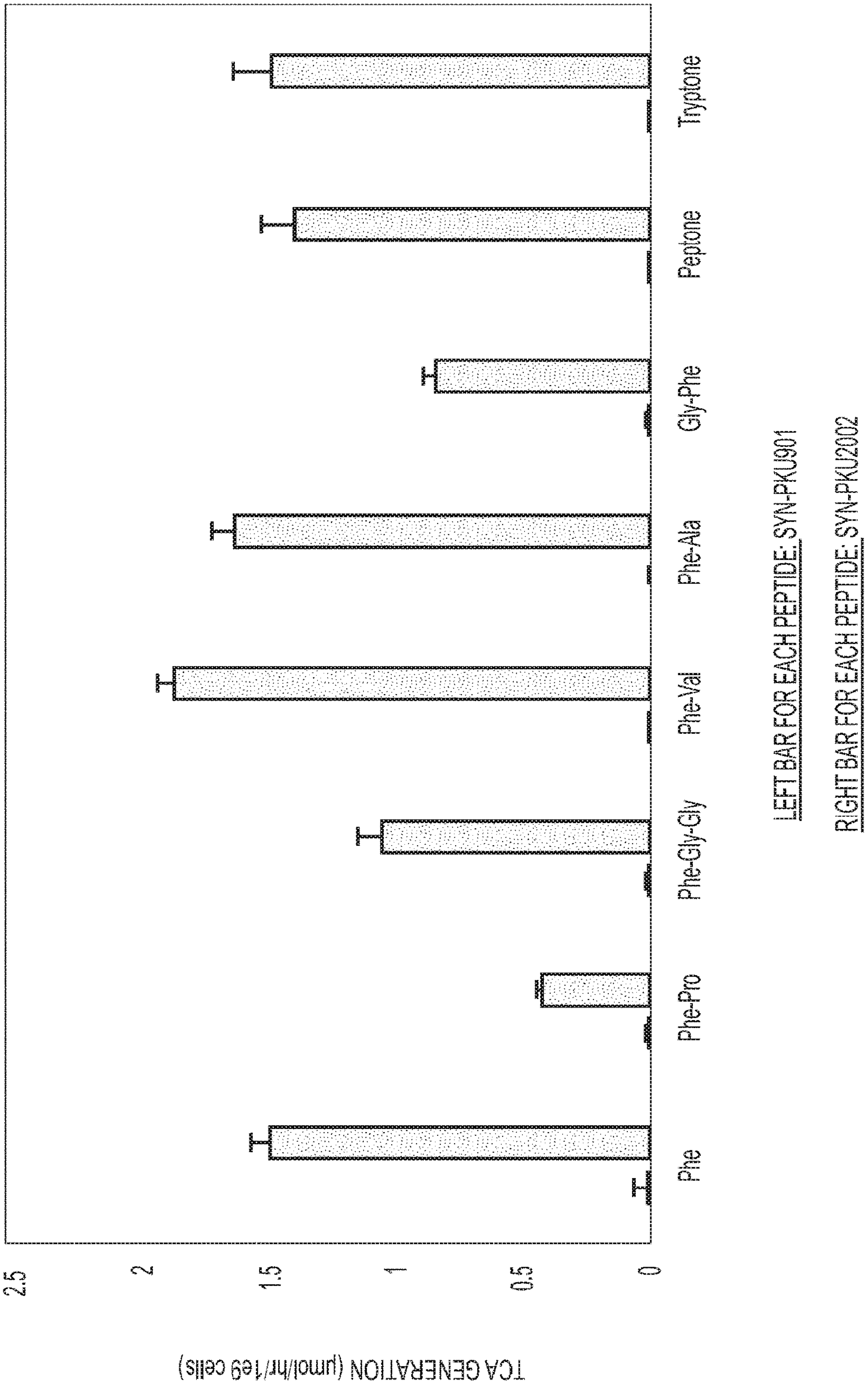
FIG. 31A and FIG. 31B depict graphs showing PAL activity of SYN-PKU-2002 against peptides. SYN-PKU-2002 was grown in a bioreactor and induced for PAL and LAAD activity. Activated cells were incubated for 60 min at 37° C. in Phe assay media containing 50 mM Phe in the form of free Phe, Phe-Pro, Phe-Gly-Gly, Phe-Val, Gly-Phe, or in 5 g/L peptone, or tryptone. The total concentration of trans-cinnamate (FIG. 31A) or phenylpyruvate (FIG. 31B) produced was determined by LC-MS/MS over time, and rates of TCA and PP production were calculated by linear regression. Significant PAL activity was observed with all substrates. LAAD activity was observed only when free Phe was used as a substrate, with a lesser amount of activity when complex substrates peptone or tryptone were used. The graph displays the average and standard deviation of three biological replicates.
Figure 31B:
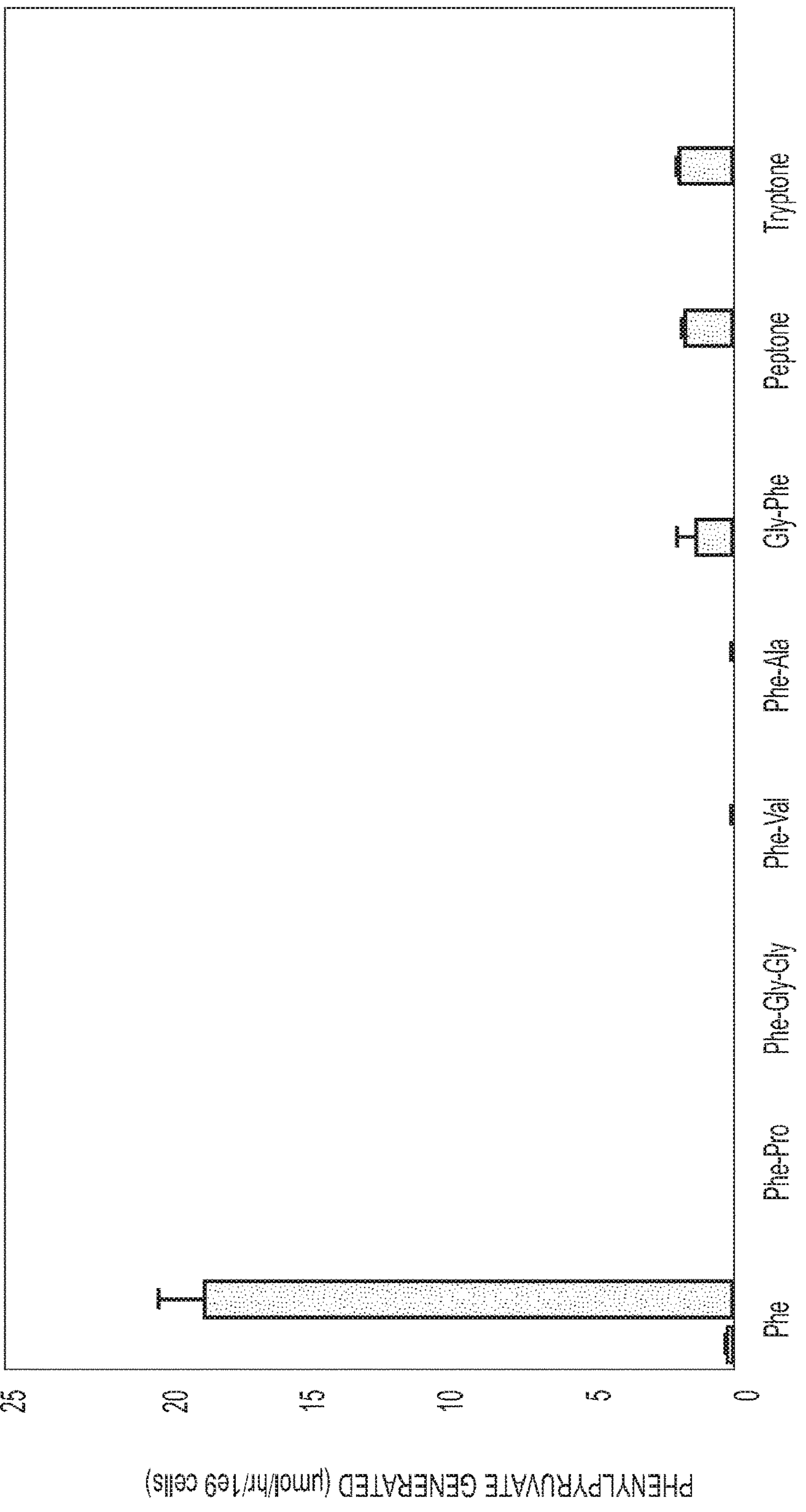

See results in FIGS. 31A and B. Although both PAL and LAAD activities in SYN-PKU-2002 could be detected in vitro when free Phe was used as the substrate, only PAL activity was observed when the provided substrate came in the form of Phe-containing peptides, demonstrating that LAAD may be better at accessing free amino acid than other sources of Phe. No PAL or LAAD activity was observed when undigested casein protein was used as a substrate.

These data demonstrate that SYN-PKU-2002 grown in a bioreactor is capable of growth and activation of both the PAL and LAAD Phe degrading pathways, suggesting that SYN-PKU-2002 is amenable to the production of activated bulk drug at higher volumes. Additionally, it was demonstrated that complex mixtures of Phe-containing peptides, likely to be produced in addition to free Phe during normal digestive processes in the mammalian gastrointestinal tract, are metabolized by the PAL component of SYN-PKU-2002 but not the LAAD component.

Example 85. Dose Response Study of SYN-PKU-2002 in Healthy Non-Human Primates

The phenylalanine-metabolizing activity of SYN-PKU-2002 in healthy male cynomolgus monkeys was characterized by measuring the levels of phenylalanine (Phe) and its metabolites in plasma and urine following administration of SYN-PKU-2002 at dose levels ranging from 3.3×109 to $7.2\times10^{11}$ colony forming units (CFUs).

In this study, healthy male cynomolgus monkeys (2.8-4.5 kg) were fasted overnight. Prior to dosing, plasma samples (heparin) were taken to establish a baseline for unlabeled Phe and downstream metabolites. Animals were dosed, by oral gavage, consecutive solutions of 11 mL of peptone (5.5 g), SYN-PKU-2002 (doses ranging from $3.3\times10^{9}$ to $7.2\times10^{11}$ CFU/dose), and 5 mL of 0.36 M sodium bicarbonate. Plasma was collected 0.5, 1, 2, 4, and 6 hours post dose and frozen until analysis. Plasma samples collected during the study arms were analyzed for the presence of Phe, phenylpyruvate (PP), trans-cinnamate (TCA), and hippurate (HA) using liquid chromatography-tandem mass spectrometry (LC-MS/MS). Urine was collected over the 6-hour post-dose period, the volume measured, and a 5-mL aliquot was frozen and stored until LC-MS/MS analysis.

Figure 26B:
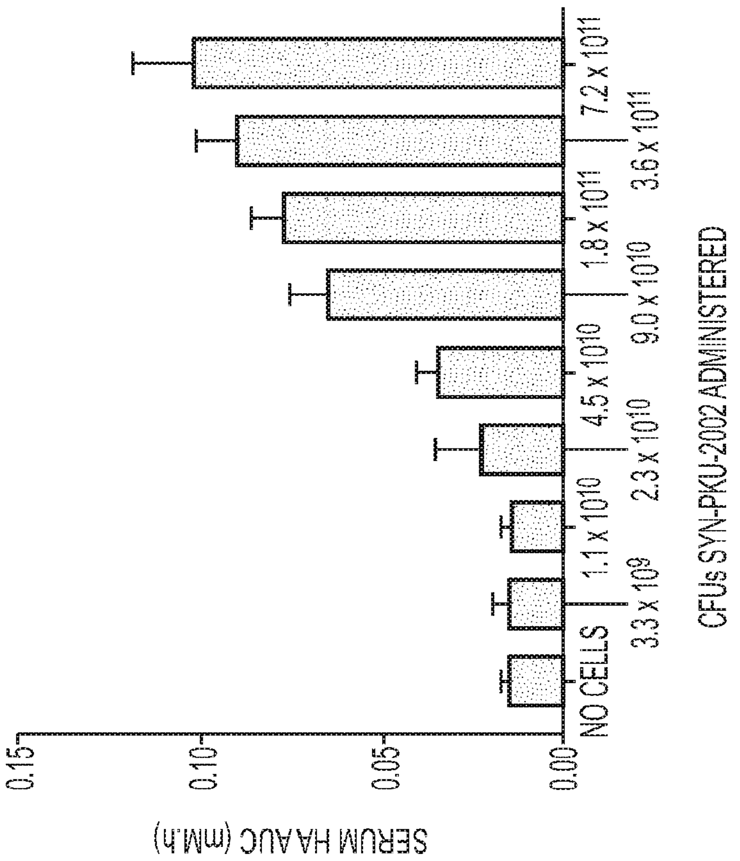
FIG. 26A, FIG. 26B, FIG. 26C, and FIG. 26D depict graphs showing SYN-PKU-2002 dose-dependent conversion of Phe and production of plasma biomarkers in non human primates upon single dose of SYN-PKU-2002 with protein meal, illustrating significant activity and efficacy of of SYN-PKU-2002 in the NHP model. Fasted NHPs (n=5 per dose group) were administered a 5 g peptide bolus with the indicated dose (CFUs) of SYN-PKU-2002. Urine was collected over 6 h and serum at 0, 0.5, 1, 2, 4, and 6 h.
Figure 26A:
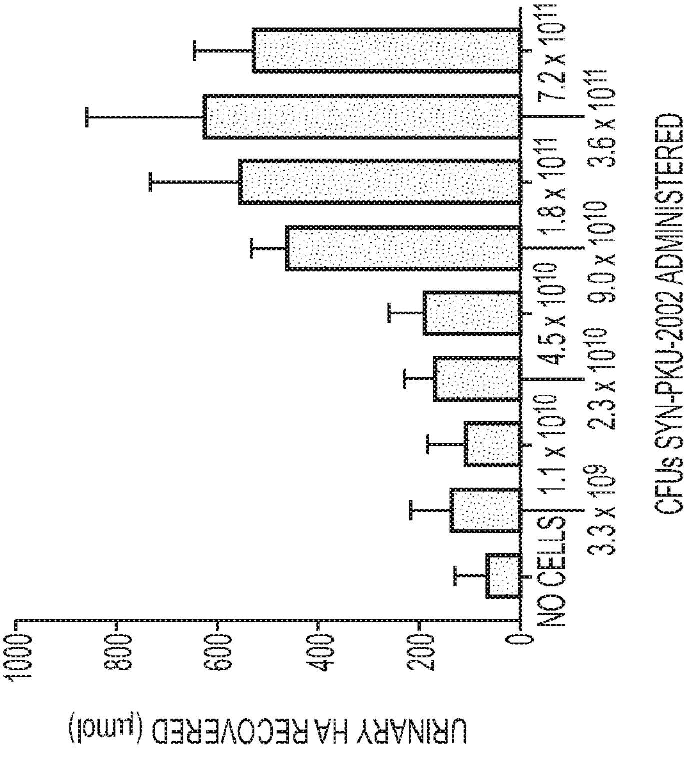
Figure 26C:
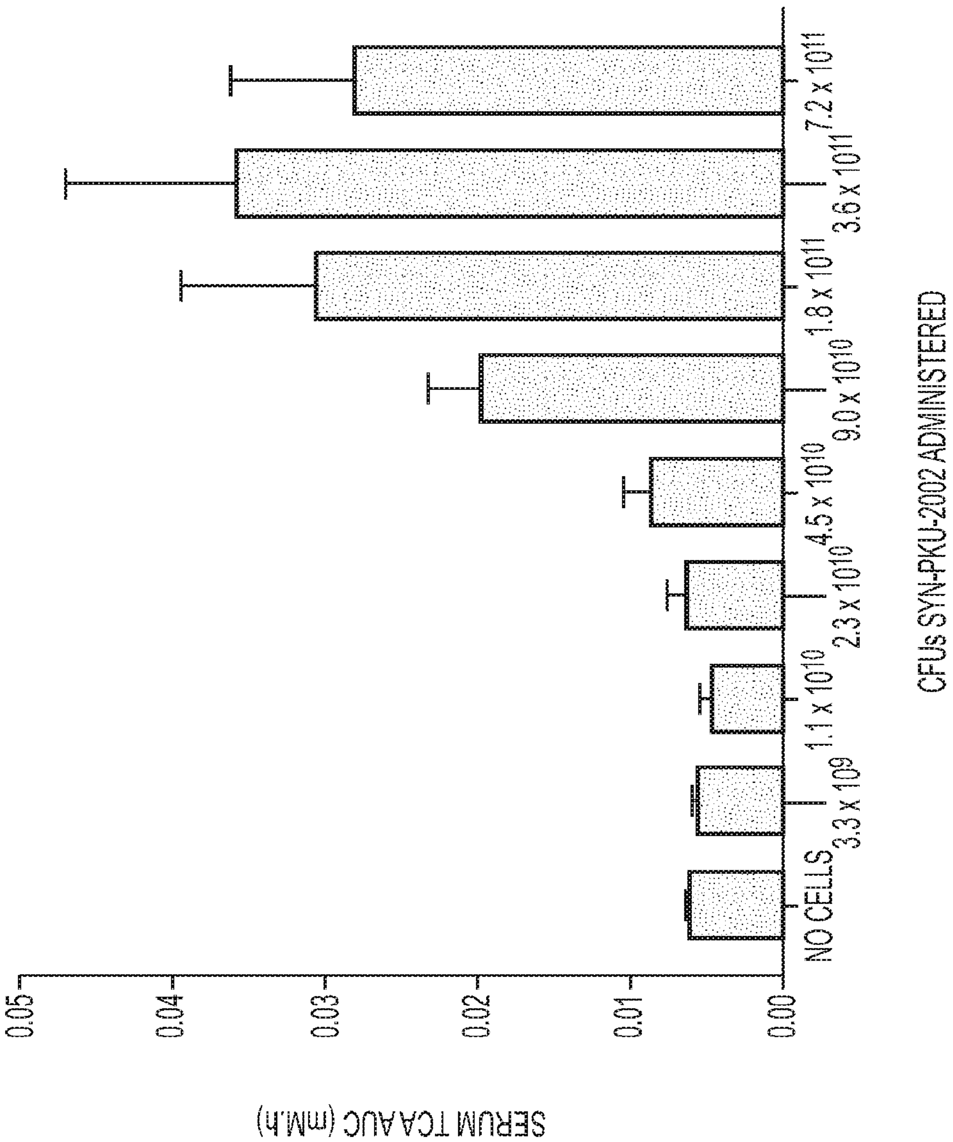
Figure 26D:
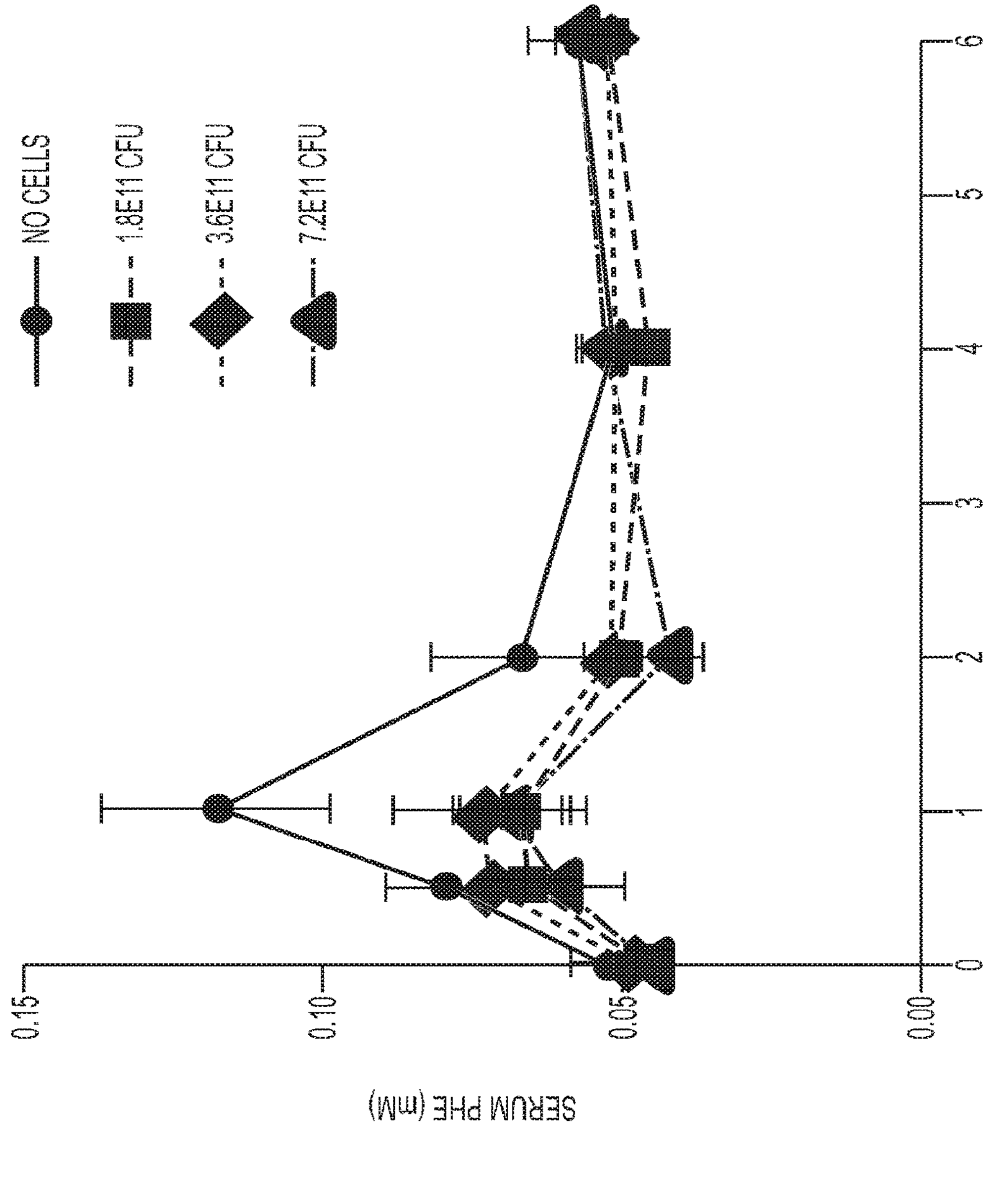
Figure 27A:
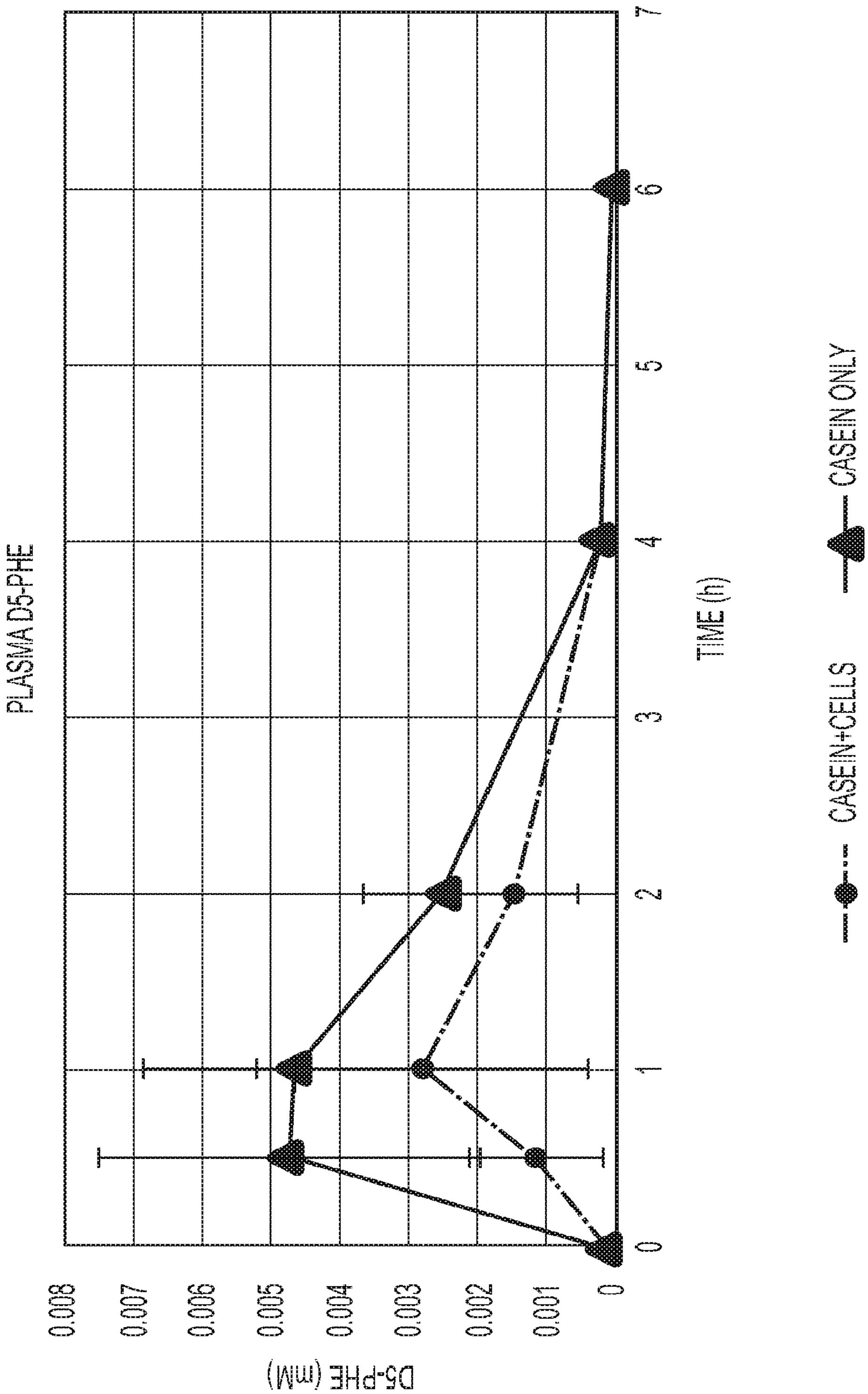
FIG. 27A, FIG. 27B, and FIG. 27C depicts graphs showing SYN-PKU-2002 dose dependent conversion of Phe from casein (FIG. 27A) TCA levels (FIG. 27B), and hippuric acid (FIG. 27C) in NHP's. Blood metabolites were collected for 6 hours.
Figure 27B:
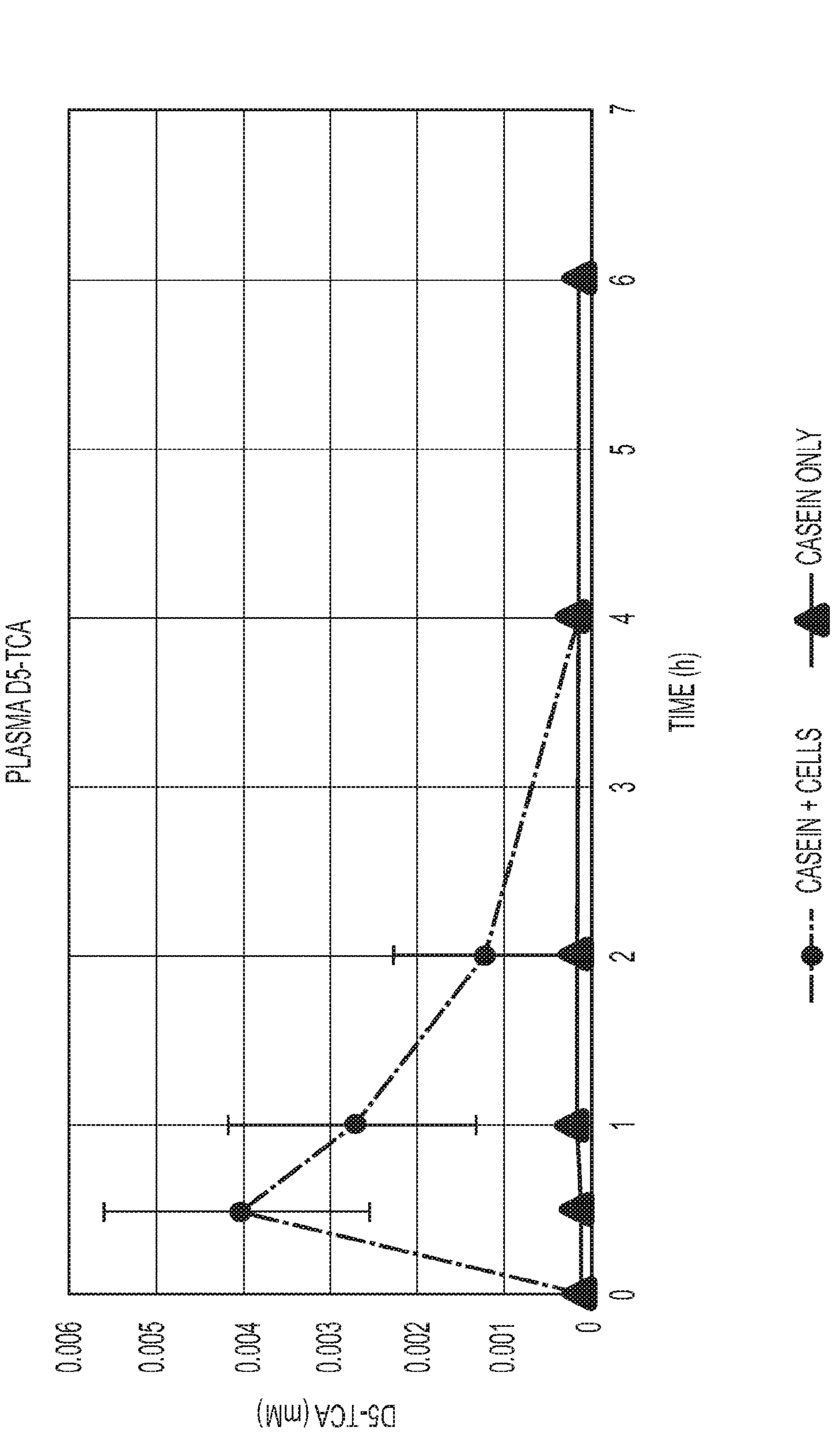
Figure 27C:
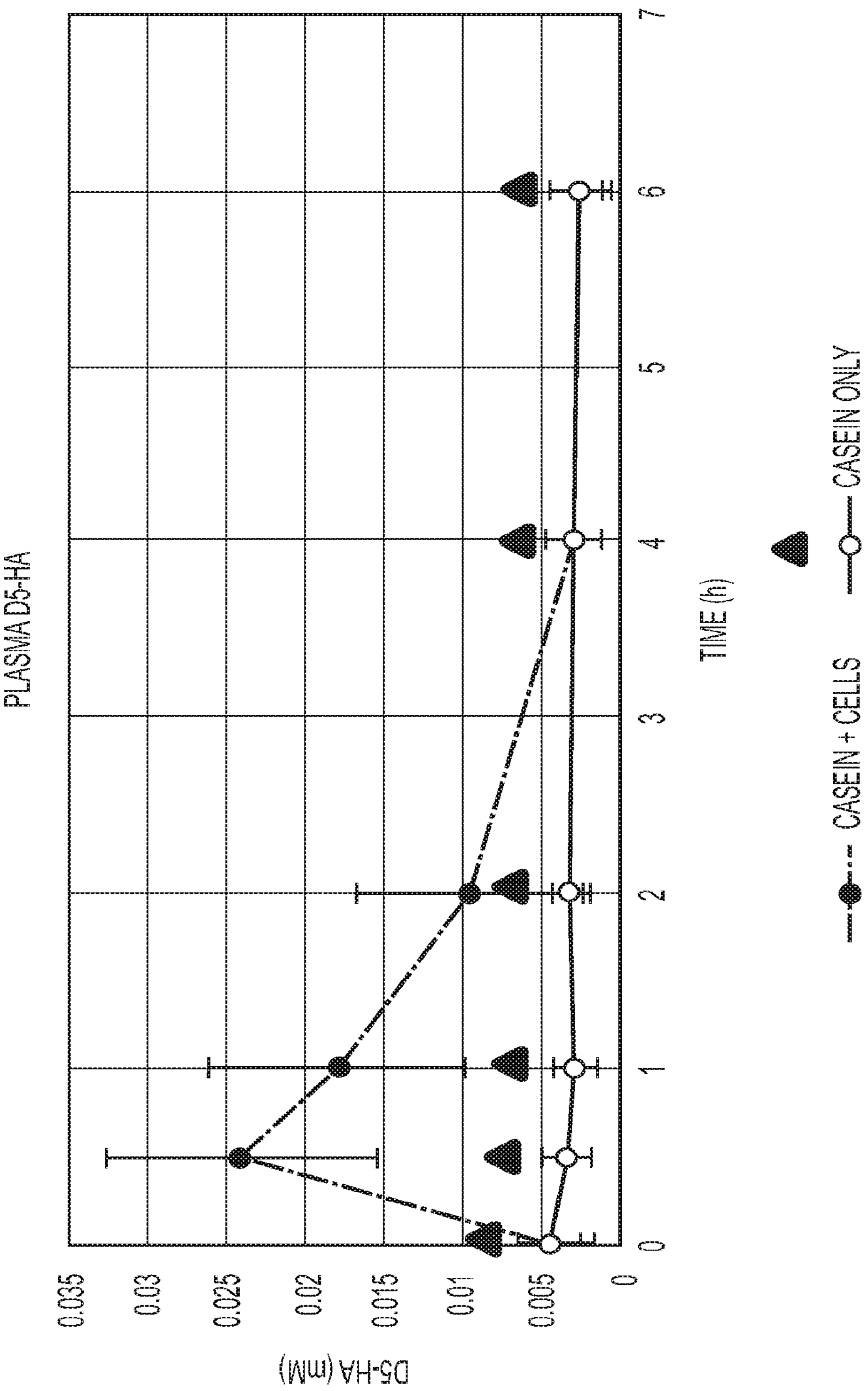

Administration of peptone to healthy monkeys resulted in a spike in plasma Phe concentrations peaking around 1 hour post-administration (see FIG. 26D). Oral dosing of SYN-PKU-2002 to healthy monkeys receiving 5.5 g of peptone resulted in a blunting of this Phe spike. Although not completely dose-proportional over the entire range, plasma concentrations of Phe were generally lower in the SYN-PKU-2002-dosed groups, particularly at or above the dose level of $9\times10^{10}$ CFUs. Concurrent with decreases in Phe following SYN-PKU-2002 dosing, plasma concentrations of TCA (the direct product of phenylalanine ammonia lyase metabolism of Phe, see FIG. 26C) and HA (a metabolite of TCA, see FIG. 26B and FIG. 38) increased in a dose-dependent manner; however, there were no detectable plasma concentrations of PP (the direct product of L-amino acid deaminase metabolism of Phe) in monkeys treated with the highest dose (lower doses not measured). Hippurate is known to be rapidly excreted in urine and consistent with increased plasma TCA and HA concentrations, urinary HA excretion increased in a generally dose dependent manner (see FIG. 26A, no PP was detected in urine of the highest dose monkeys).

These studies demonstrate that SYN-PKU-2002 is able to metabolize Phe in male cynomolgus monkeys. PP was not detected in plasma and urine of monkeys treated with the highest dose. There was a dose-dependent increase in the plasma concentrations of the phenylalanine metabolites TCA and HA as well as dose-dependent increases in urinary HA excretion over 6 hours. This indicates that between the two Phe-degrading enzymes in SYN-PKU-2002, PAL is responsible for most of the Phe metabolism in the monkey, with little or no contribution from LAAD in this model. In addition, this study shows that HA and TCA could potentially serve as biomarkers of SYN-PKU-2002 activity in future clinical studies.

Example 86. Gastrointestinal Tract Characterization of SYN-PKU-2001 in Non-Human Primates Two studies were performed to characterize the phenylalanine-metabolizing activity and colonization of SYN-PKU-2001 within different segments of the gastrointestinal tract of healthy cynomolgus monkeys. In the first study, animals were separated into 2 groups of 3 females each, dosed with 5.5 grams of peptone, 5 mL of 0.36 M Sodium Bicarbonate, 25 mg/kg of D5-Phenylalanine, and either SYN-PKU-2001 or a blank control. Two hours after dosing, animals were euthanized and samples collected. In the second study, one group of 3 male monkeys were dosed with 5.5 grams of peptone, 5 mL of 0.36 M Sodium Bicarbonate, 25 mg/kg of D5-Phenylalanine, and SYN-PKU-2001, and animals were euthanized and samples collected 0.5 hours after dosage.

In both studies, animals were administered test articles (see table below) by a single oral gavage on Day 1. The capped bacteria tube was inverted 3 times before each dose administration. Dose formulations were administered by oral gavage using a disposable catheter attached to a plastic syringe. Following dosing, the gavage tube was rinsed with 5 mL of the animal drinking water, into the animal's stomach. Each animal was dosed with a clean gavage tube. The first day of dosing was designated as Day 1. The animals were temporarily restrained for dose administration and were not sedated.

Test and Control Article Identification

| | Test Article | Test Article | Test Article | Test Article | Test Article |
|---|---|---|---|---|---|
| Identification | Peptone | Bacteria | D5-Phenylalanine | Formulation buffer | Sodium Bicarbonate |
| Batch ID | | SYN-PKU-2001 2917-C | | | |
| Concentration | 500 g/L | $5.5\times10^{10}$ CFU/mL | 20 mg/mL | | 0.36M |
| Physical Description | liquid | liquid | liquid | | liquid |
| Storage Conditions | Controlled Room Temperature | −80° C. | 4° C. | 4° C. | Controlled Room Temperature |

Formulation buffer and D5-Phenylalanine (20 mg/mL) were maintained at 4° C. until use, at which point, aliquots were removed and allowed to warm to room temperature for at least 30 minutes before dosing. Sodium Bicarbonate (0.36M) was stored and administered at ambient temperature.

Shown in the table below are the dose volumes and regimens used for each group of animals.

Experimental Design

| Group (Study No.) | No. Animals | Treatment | Dose Volume (mL) | Dose Regimen |
|---|---|---|---|---|
| Group 1 (Study No. 1) | 3 | Peptone | 11 | PO |
| | | Sodium Bicarbonate | 5 | |
| | | D5-Phe | 1.3 | |
| | | Bacteria | 1.8 | |
| Group 2 (Study No. 1) | 3 | Peptone | 11 | |
| | | Sodium Bicarbonate | 5 | |
| | | D5-Phe | 1.3 | |
| | | Formulation buffer | 1.8 | |
| Group 1 (Study No. 3) | 3 | Peptone | 11 | PO |
| | | Sodium Bicarbonate | 5 | |
| | | D5-Phe | 1.3 | |
| | | Bacteria | 1.8 | |

-

The dose of 5.5 grams of Peptone is based on a typical 60 kg individual consuming 100 g of protein per day and we wanted to simulate this so that we could measure Phe in the blood after feeding and metabolites of Phe in the urine. The oral dose of 25 mg/kg of D5-Phenylalanine was chosen because it gives measurable levels of D5-Hippurate in the urine of mice when dosed at this level.

In both studies, animals were fasted overnight, and weighed on day 1 before dosing. Blood samples (5 mL) were collected from the femoral vein using Heparin as the anti-coagulant, and placed on crushed wet ice before centrifugation. Following centrifugation, the resultant plasma was separated, transferred into two aliquots, immediately frozen over dry ice and transferred to a freezer set to −80° C. Samples were shipped on dry ice to a separate facility for analysis.

Animals were euthanized (without sedation) 2 hours (Study 1) or 0.5 hours (Study 2) post dose via intravenous injection via tail vein, using a percutaneous catheter set-up, of a commercially available veterinary euthanasia solution.

Terminal Procedures for Study

| | | Scheduled | Necropsy Procedures | | Histology | | |
|---|---|---|---|---|---|---|---|
| Study No. | No. of Animals | Euthanasia Day[a] | Necropsy | Tissue Collection | Organ Weights | | Histopathology |
| 1<br>2 | 6 (F)<br>3 (M) | 1 | — | X | — | — | — |

Tissues identified in the Tissue Collection and Preservation table were collected from all animals as indicated.

Tissue Collection and Preservation

| Tissue | Weigh | Collect | Microscopic Evaluation | Comment |
|---|---|---|---|---|
| Large intestine, proximal colon | — | X | — | Contents, whole tissue (Studies 1 and 2) and mucus scrappings (study 2 only). |
| Small intestine, duodenum | — | X | — | Contents and whole tissue in 30 cm segments (see below). |
| Small intestine, ileum | — | X | — | |
| Small intestine, jejunum | — | X | — | |
| Stomach | — | X | — | Contents and whole tissue (see below). |

X = Procedure to be conducted;

— = Not applicable.

Following exsanguination, the stomach and colon were clamped. Additional clamps were used to section the small intestine at approximately 30 cm segments. 10 mL of cold sterile saline was injected into the stomach and massaged to loosen contents. The stomach was opened and contents drained into a labeled 50 mL conical tube and volume recorded. Approximately 1 mL of contents was transferred to the analysis facility to plate at time of collection. Remaining stomach contents were separated in 3 different aliquots: 1 mL, 1.6 mL (to which sponsor added glycerol before freezing) and remaining. The remaining stomach tissue (whole and collected into a labeled ziplock bag) was frozen on dry ice until shipped, with contents, via same-day courier (frozen on dry ice) to the analysis facility.

Each approximate 30 cm segment of the small intestine was injected with 15 mL of cold sterile saline and contents collected into a labeled 50 mL conical tube and volume recorded. Approximately 1 mL of contents from each segment was transferred to the analysis facility to plate at time of collection. Remaining contents were separated in 3 different aliquots: 1 mL, 1.6 mL (to which sponsor added glycerol before freezing) and remaining. Small intestine tissue sections (collected into labeled ziplock bags) were frozen on dry ice until shipped, with contents, via same-day courier (frozen on dry ice) to the analysis facility.

In the first study, no more than 20 mL of proximal colon contents were collected (undiluted) into a clean, pre-weighed glass bottle maintained on wet ice. Approximately 1 mL of contents were transferred to the analysis facility to plate at time of collection. Two different aliquots: 1 mL frozen on dry ice and 1.6 mL (to which sponsor added glycerol before freezing) were transferred to pre-identified tubes. The colon was then opened and the remaining content removed and transferred to the glass bottle (if less than 50 mL was previously collected). Tissue was grasped with forceps and gently rinsed in a basin containing sterile saline. The colon tissue was then scraped using a clean spatula to collect mucus into a labeled and pre-weighed glass bottle. The mucus sample was kept on wet ice until transferred to the analysis facility. The tissue was collected (whole) in a ziplock bag and frozen on dry ice until shipped via same-day courier (frozen on dry ice) to the analysis facility.

In the second study, 15 mL of cold sterile saline was injected into the proximal colon and the content was collected into a labeled 50 mL conical tube and the volume recorded. Approximately 1 mL of contents was transferred to the analysis facility to plate at time of collection. Remaining contents were separated into 3 different aliquots: 1 mL, 1.6 mL (to which sponsor added glycerol before freezing) and remaining. Large intestine tissue (collected into labeled ziplock bags) was frozen on dry ice until shipped, with contents, via same-day courier (frozen on dry ice) to the analysis facility at the address below.

Figure 38:
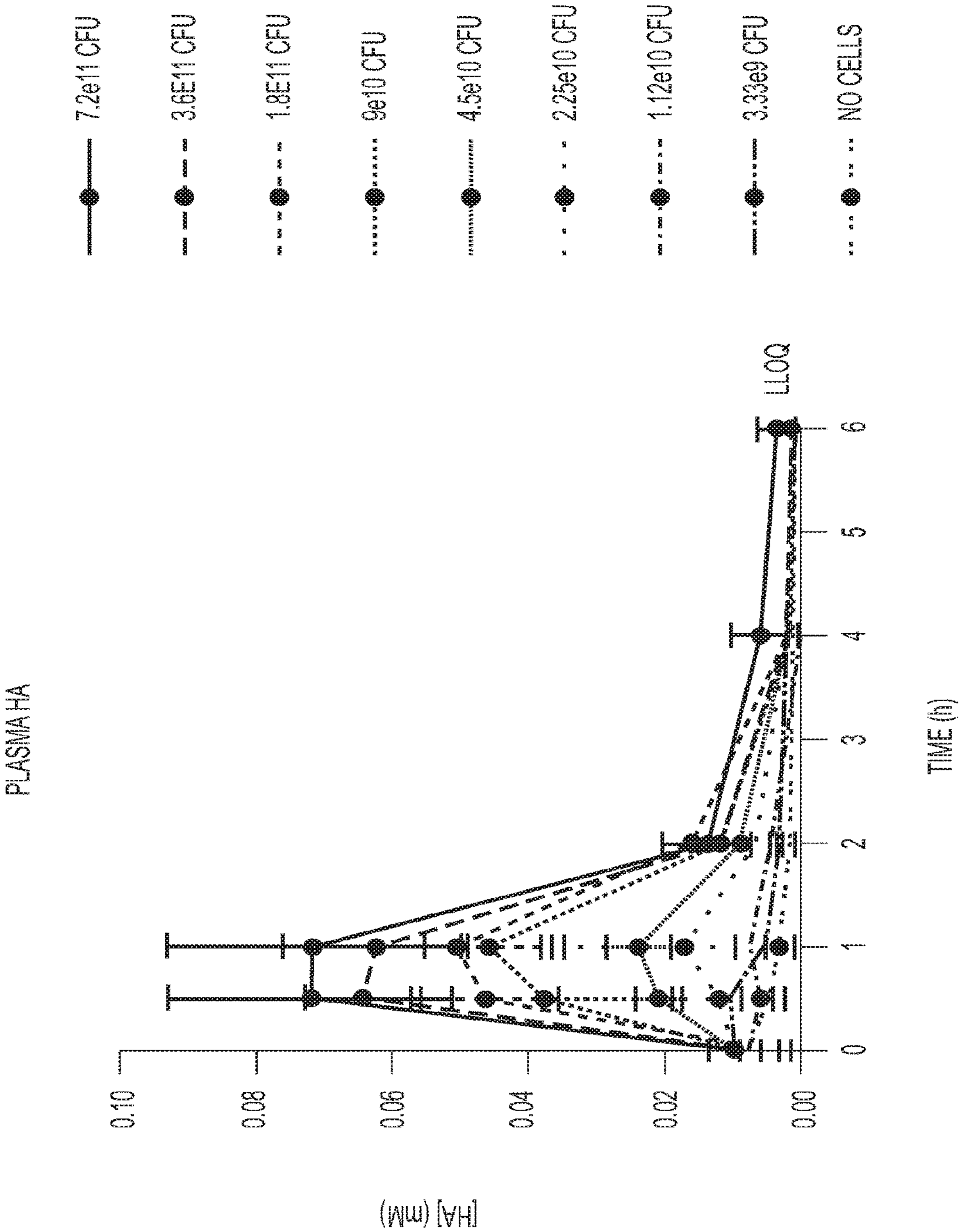
FIG. 38 depicts SYN-PKU-2002 dose-dependent conversion of Phe and production of plasma biomarkers in non-human primates upon single dose of SYN-PKU-2002 with protein meal, illustrating significant activity and efficacy of SYN-PKU-2002 in the NHP model. Fasted NHPs (n=5 per dose group) were administered a 5 g peptide bolus with the indicated dose (CFUs) of SYN-PKU-2002. Plasma was collected at 0, 0.5, 1, 2, 4, and 6 h after dosing at time 0. Each point represents the HA concentration measured in plasma at the time point after dosing. Standard deviations are shown as vertical bars at each point.
Figure 39:
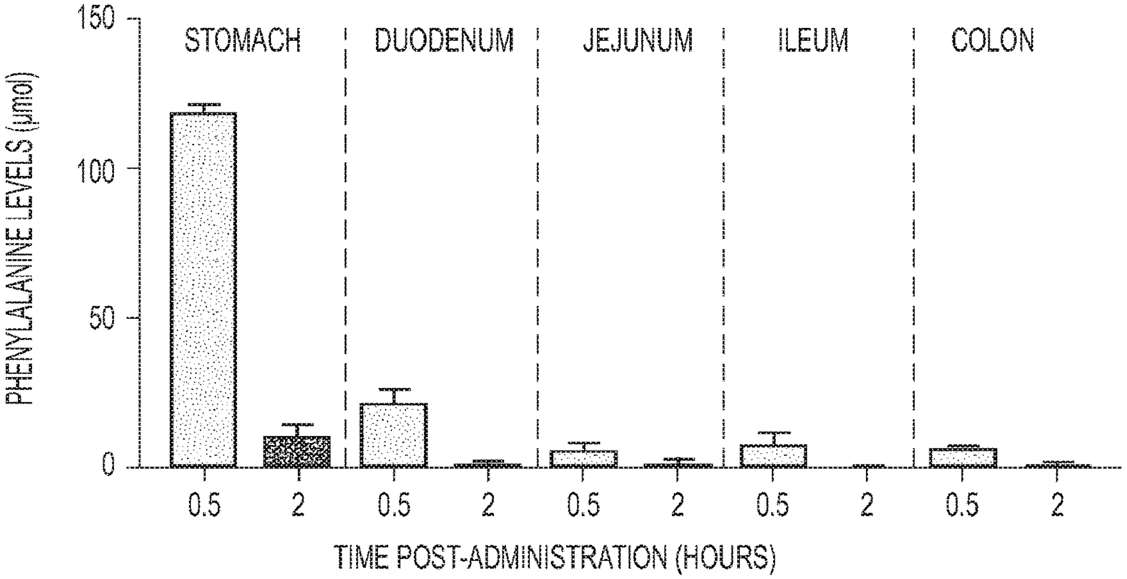
FIG. 39 depicts SYN-PKU-2001 characterization within the gastrointestinal tract of Non-Human Primates. Cynomolgus monkeys were dosed with 5.5 grams of peptone, 5 mL of 0.36 M sodium bicarbonate, 25 mg/kg of D5-Phenylalanine, and SYN-PKU-2001 and euthanized either 0.5 hours or 2 hours after dosing. Following euthanization, tissue samples were collected from various sections of the gastrointestinal tract and analyzed to determine the concentration of Phe and SYN-PKU-2001 in each section.
Figure 39:
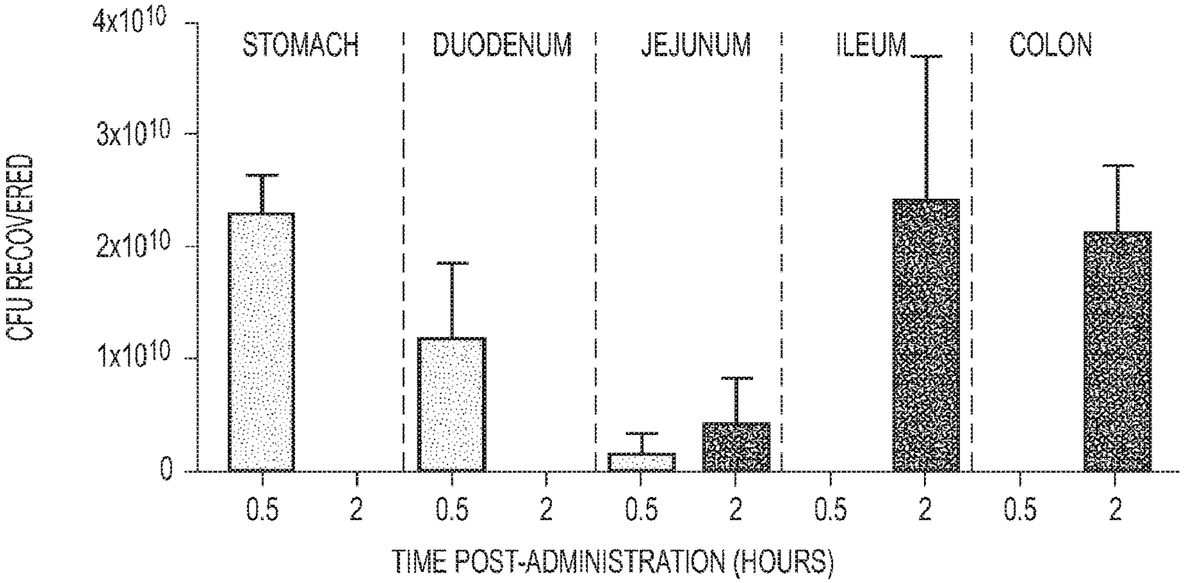

The measured Phe levels and CFU counts for each part of the gastrointestinal tract are displayed in FIG. 38. Both 2 hours, and 0.5 hours after doseage, phenylalanine levels were found to be highest in the stomach and gradually decrease further down the gut. 2 hours after administration, less than 10% of phenylalanine was found in the stomach and duodenum. 2 hours post-dosage, SYN-PKU-2001 was found mainly in the ileum and proximal colon, where very little substrate is available. This suggests that SYN-PKU-2001 activity is limited by substrate availability and should thus be taken with food.

The invention claimed is:

1. An *E. coli* Nissle bacterium, wherein the bacterium comprises (i) one or more gene(s) encoding a phenylalanine ammonia lyase (PAL) enzyme comprising an amino acid sequence having at least 90% identity to SEQ ID NO: 3, and (ii) one or more non-native deletions in one or more phage genes in *E. coli* Nissle Phage 3, wherein the one or more phage genes are selected from the group consisting of ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345.

2. The bacterium of claim 1, wherein the non-native deletions comprise a complete or partial deletion of ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175.

3. The bacterium of claim 1, wherein the non-native deletions are: a complete deletion of ECOLIN_10110, ECOLIN_10115, ECOLIN 10120, ECOLIN_10125, ECOLIN_10130, ECOLIN_10135, ECOLIN_10140, ECOLIN 10145, ECOLIN_10150, ECOLIN_10160, ECOLIN_10165, ECOLIN_10170, and a partial deletion of ECOLIN_10175.

4. The bacterium of claim 3, wherein the deleted phage genes comprise SEQ ID NO: 130, or the deleted phage genes consist of SEQ ID NO: 130.

5. The bacterium of claim 1, wherein the bacterium further comprises an antibiotic resistance gene.

6. The bacterium of claim 1, further comprising one or more gene(s) encoding a phenylalanine transporter.

7. The bacterium of claim 6, wherein the phenylalanine transporter is PheP.

8. The bacterium of claim 6, further comprising one or more gene(s) encoding L-amino acid deaminase (LAAD).

9. The bacterium of claim 8, wherein:

the one or more genes encoding PAL are operably linked to a promoter;

the one or more genes encoding the phenylalanine transporter are operably linked to a promoter; and the one or more genes encoding LAAD are operably linked to a promoter.

10. The bacterium of claim 9, wherein:

the one or more genes encoding PAL are operably linked to an IPTG-inducible promoter; and the one or more genes encoding LAAD are operably linked to an arabinose-inducible promoter.

11. The bacterium of claim 9, wherein:

the one or more genes encoding PAL are operably linked to an IPTG-inducible promoter;

the one or more genes encoding the phenylalanine transporter are operably linked to an IPTG-inducible promoter; and the one or more genes encoding LAAD are operably linked to an arabinose-inducible promoter.

12. The bacterium of claim 9, wherein:

the one or more genes encoding PAL are operably linked to an FNR-responsive promoter;

the one or more genes encoding the phenylalanine transporter are operably linked to an FNR-responsive promoter; and the one or more genes encoding LAAD are operably linked to an arabinose-inducible promoter.

13. The bacterium of claim 9, wherein:

the one or more of the genes encoding PAL are operably linked to an FNR-responsive promoter;

one or more additional genes encoding PAL comprise an amino acid sequence having at least 90% identity to SEQ ID NO: 3 and are operably linked to an IPTG-inducible promoter;

the one or more genes encoding the phenylalanine transporter are operably linked to an FNR-responsive promoter; and the one or more genes encoding LAAD are operably linked to an arabinose-inducible promoter.

14. The bacterium of claim 9, wherein the bacterium comprises:

three copies of the gene encoding PAL each independently comprising an amino acid sequence having at least 90% identity to SEQ ID NO: 3;

two additional copies of the gene encoding PAL each independently comprising an amino acid sequence having at least 90% identity to SEQ ID NO: 3;

two copies of the gene encoding the phenylalanine transporter, wherein the two copies of the gene encoding the phenylalanine transporter are non-native and derived from *Escherichia coli;* one copy of the gene encoding LAAD, wherein the one copy of the gene encoding LAAD is derived from *Proteus mirabilis*; and a mutation in one or more of ThyA or DapA to generate an auxotrophy.

15. The bacterium of claim 14, wherein:

the promoter operably linked to the three copies of the gene encoding PAL is inducible under anaerobic or low-oxygen conditions;

the promoter operably linked to the two additional copies of the gene encoding PAL is an IPTG-inducible promoter;

the promoter operably linked to the two copies of the non-native gene encoding the phenylalanine transporter derived from *Escherichia coli* is inducible under anaerobic or low-oxygen conditions;

the promoter operably linked to the one copy of the gene encoding LAAD derived from *Proteus mirabilis* is an arabinose-inducible promoter; and the mutation in one or more of ThyA or DapA is a mutation in the DapA gene.

16. The bacterium of claim 15, wherein:

the promoter to which the three copies of the gene encoding PAL are operably linked to is an FNR-responsive promoter; and the promoter to which the two copies of the non-native gene encoding the phenylalanine transporter derived from *Escherichia coli* are operably linked to is an FNR-responsive promoter.

17. The bacterium of claim 9, wherein the bacterium comprises:

four copies of the gene encoding PAL;

one copy of the gene encoding PheP phenylalanine transporter, wherein the one copy of the gene encoding PheP phenylalanine transporter is non-native and derived from *Escherichia coli;* one copy of the gene encoding LAAD, wherein the one copy of the gene encoding LAAD is derived from *Proteus mirabilis*; and a mutation in one or more of ThyA or DapA to generate an auxotrophy.

18. The bacterium of claim 17, wherein:

the promoter operably linked to the four copies of the gene encoding PAL is an IPTG-inducible promoter;

the promoter operably linked to the one copy of the non-native gene encoding the phenylalanine transporter derived from *Escherichia coli* is an IPTG-inducible promoter;

the promoter operably linked to the one copy of the gene encoding LAAD derived from *Proteus mirabilis* is an arabinose-inducible promoter; and the mutation in one or more of ThyA or DapA is a mutation in the DapA gene.

19. A pharmaceutically acceptable composition comprising the bacterium of claim 1, and a pharmaceutically acceptable carrier.

20. The composition of claim 19 formulated for oral administration.

* * * * *